US012497365B2

(12) United States Patent
Lian et al.

(10) Patent No.: US 12,497,365 B2
(45) Date of Patent: Dec. 16, 2025

(54) 4-PYRIDINYL FORMAMIDE COMPOUND OR DERIVATIVE THEREOF, PREPARATION METHOD THEREFOR, HERBICIDAL COMPOSITION AND USE THEREOF

(71) Applicant: Qingdao Kingagroot Chemical Compound Co., Ltd., Qingdao (CN)

(72) Inventors: Lei Lian, Qingdao (CN); Rongbao Hua, Qingdao (CN); Xuegang Peng, Qingdao (CN); De Zhao, Qingdao (CN); Qi Cui, Qingdao (CN)

(73) Assignee: Qingdao Kingagroot Chemical Compound Co., Ltd., Qingdao (CN)

( * ) Notice: Subject to any disclaimer, the term of this patent is extended or adjusted under 35 U.S.C. 154(b) by 1190 days.

(21) Appl. No.: 17/420,752

(22) PCT Filed: Jan. 14, 2020

(86) PCT No.: PCT/CN2020/071932

§ 371 (c)(1),
(2) Date: Jul. 6, 2021

(87) PCT Pub. No.: WO2020/147705

PCT Pub. Date: Jul. 23, 2020

(65) Prior Publication Data

US 2023/0087801 A1 Mar. 23, 2023

(30) Foreign Application Priority Data

Jan. 14, 2019 (CN) ......................... 201910031819.7

(51) Int. Cl.

| | |
|---|---|
| ***C07D 213/56*** | (2006.01) |
| ***A01N 43/40*** | (2006.01) |
| ***A01N 43/82*** | (2006.01) |
| ***A01N 43/90*** | (2006.01) |
| ***C07D 401/12*** | (2006.01) |
| ***C07D 401/14*** | (2006.01) |

(Continued)

(52) U.S. Cl.

CPC ........... *C07D 213/56* (2013.01); *A01N 43/40* (2013.01); *A01N 43/82* (2013.01); *A01N 43/90* (2013.01); *C07D 401/12* (2013.01); *C07D 401/14* (2013.01); *C07D 405/14* (2013.01); *C07D 409/14* (2013.01); *C07D 413/12* (2013.01); *C07D 413/14* (2013.01); *C07D 471/04* (2013.01); *C07D 487/04* (2013.01); *C07D 513/04* (2013.01)

(58) Field of Classification Search

None

See application file for complete search history.

(56) References Cited

U.S. PATENT DOCUMENTS 5,013,659 A 5/1991 Bedbrook et al.

FOREIGN PATENT DOCUMENTS

CN 103459386 12/2013
CN 103987701 8/2014

(Continued)

OTHER PUBLICATIONS

"CAS RN: 2158120-95-5", ACS, STN Registry, Dec. 14, 2017.

(Continued)

*Primary Examiner* — Alton N Pryor

(74) *Attorney, Agent, or Firm* — FINNEGAN, HENDERSON, FARABOW, GARRETT & DUNNER LLP

(57) ABSTRACT

The invention belongs to the technical field of pesticides, and specifically relates to a 4-pyridinyl formamide compound or a derivative thereof, a preparation method therefor, a herbicidal composition and the use thereof. The 4-pyridinyl formamide compound is as represented by formula (I), wherein, X and Y each independently represent nitro, halogen, cyano, formyl, thiocyano, mercapto, etc.; and M represents an unsubstituted or substituted structure (II). The compound, and the derivative and the composition thereof have excellent herbicidal activity and a higher crop safety, and establish good selectivity, especially for key crops such as wheat and rice.

(I)

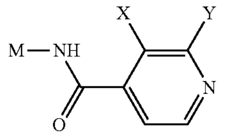

(II)

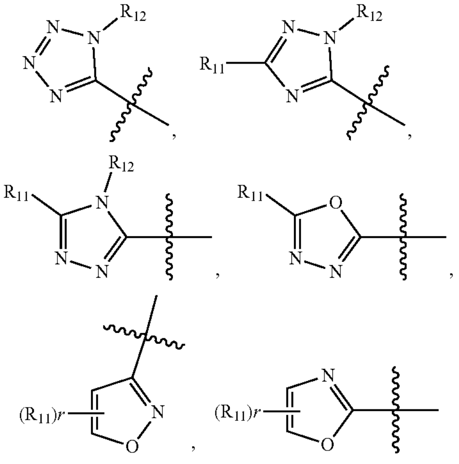

13 Claims, No Drawings

(51) Int. Cl.

| | |
|---|---|
| ***C07D 405/14*** | (2006.01) |
| ***C07D 409/14*** | (2006.01) |
| ***C07D 413/12*** | (2006.01) |
| ***C07D 413/14*** | (2006.01) |
| ***C07D 471/04*** | (2006.01) |
| ***C07D 487/04*** | (2006.01) |
| ***C07D 513/04*** | (2006.01) |

(56) References Cited

FOREIGN PATENT DOCUMENTS

| | | | | |
|---|---|---|---|---|
| CN | 104220434 | | | 12/2014 |
| CN | 104411698 | | | 3/2015 |
| CN | 104854104 | | | 8/2015 |
| CN | 105073719 | | | 11/2015 |
| CN | 105658067 | | | 6/2016 |
| EP | 0131624 | A | | 1/1985 |
| EP | 0142924 | A | | 5/1985 |
| EP | 0193259 | A | | 9/1986 |
| EP | 0221044 | A | | 5/1987 |
| EP | 0242236 | A | | 10/1987 |
| EP | 0242246 | A | | 10/1987 |
| EP | 0257993 | | | 3/1988 |
| JP | 04124108 | A | * | 4/1992 |
| WO | WO91/13972 | | | 9/1991 |
| WO | WO91/19806 | | | 12/1991 |
| WO | WO92/00377 | | | 1/1992 |
| WO | WO92/11376 | | | 7/1992 |
| WO | WO92/14827 | | | 9/1992 |
| WO | WO199835967 | | | 8/1998 |
| WO | WO2011035874 | | | 3/2011 |
| WO | WO2012028579 | | | 3/2012 |
| WO | WO 2012123416 | A1 | | 9/2012 |
| WO | WO2013017559 | | | 2/2013 |
| WO | WO2013/087577 | | | 6/2013 |
| WO | WO2014184074 | | | 11/2014 |
| WO | WO2017055146 | | | 4/2017 |
| WO | WO2018050677 | | | 3/2018 |

OTHER PUBLICATIONS

"CAS RN: 2320606-21-9", ACS, STN Registry, May 30, 2019.
"CAS RN: 2054210-09-8", ACS, STN Registry, Dec. 8, 2017.
"CAS RN: 2150258-78-7", ACS, STN Registry, Dec. 3, 2017.
"CAS RN: 1994473-87-8", ACS, STN Registry, Sep. 16, 2016.
"CAS RN: 1990275-01-8", ACS, STN Registry, Sep. 9, 2016.
"CAS RN: 1983206-31-0", ACS, STN Registry, Aug. 30, 2016.
"CAS RN: 1981525-56-7", ACS, STN Registry, Aug. 28, 2016.
"CAS RN: 1981512-07-5", ACS, STN Registry, Aug. 28, 2016.
"CAS RN: 1981512-01-9", ACS, STN Registry, Aug. 28, 2016.
"CAS RN: 1981497-90-8", ACS, STN Registry, Aug. 28, 2016.
"CAS RN: 1981419-87-7", ACS, STN Registry, Aug. 28, 2016.
"CAS RN: 1981397-34-5", ACS, STN Registry, Aug. 28, 2016.
"CAS RN: 1981395-51-0", ACS, STN Registry, Aug. 28, 2016.
"CAS RN: 1981395-42-9", ACS, STN Registry, Aug. 28, 2016.
"CAS RN: 1981392-81-7", ACS, STN Registry, Aug. 28, 2016.
"CAS RN: 1981372-05-7", ACS, STN Registry, Aug. 28, 2016.
"CAS RN: 1981189-00-7", ACS, STN Registry, Aug. 28, 2016.
"CAS RN: 1981186-17-7", ACS, STN Registry, Aug. 28, 2016.
"CAS RN: 1981173-34-5", ACS, STN Registry, Aug. 28, 2016.
"CAS RN: 1981170-79-9", ACS, STN Registry, Aug. 28, 2016.
"CAS RN: 1981135-59-4", ACS, STN Registry, Aug. 28, 2016.
"CAS RN: 1981004-73-2", ACS, STN Registry, Aug. 28, 2016.
"CAS RN: 1981004-05-0", ACS, STN Registry, Aug. 28, 2016.
"CAS RN: 1981001-84-6", ACS, STN Registry, Aug. 28, 2016.
"CAS RN: 1981001-76-6", ACS, STN Registry, Aug. 28, 2016.
"CAS RN: 1974653-47-8", ACS, STN Registry, Aug. 28, 2016.
"CAS RN: 1974551-12-6", ACS, STN Registry, Aug. 28, 2016.
"CAS RN: 1972455-84-7", ACS, STN Registry, Aug. 28, 2016.
"CAS RN: 1933955-97-5", ACS, STN Registry, Jun. 17, 2016.
"CAS RN: 1931544-41-0", ACS, STN Registry, Jun. 14, 2016.
"CAS RN: 1929905-53-2", ACS, STN Registry, Jun. 12, 2016.
"CAS RN: 1929180-35-7", ACS, STN Registry, Jun. 10, 2016.
"CAS RN: 1915305-47-3", ACS, STN Registry, May 22, 2016.
"CAS RN: 1914838-15-5", ACS, STN Registry, May 20, 2016.
"CAS RN: 1914474-00-2", ACS, STN Registry, May 20, 2016.
"CAS RN: 1798578-76-3", ACS, STN Registry, Jul. 10, 2015.
"CAS RN: 1798480-74-6", ACS, STN Registry, Jul. 10, 2015.
"CAS RN: 1772342-99-0", ACS, STN Registry, Jun. 3, 2015.
"CAS RN: 1711184-58-5", ACS, STN Registry, May 24, 2015.
"CAS RN: 1704011-60-8", ACS, STN Registry, May 14, 2015.
"CAS RN: 1602529-54-3", ACS, STN Registry, May 12, 2014.
"CAS RN: 1595886-66-0", ACS, STN Registry, May 2, 2014.
"CAS RN: 1504812-52-5", ACS, STN Registry, Dec. 27, 2013.
"CAS RN: 1497292-38-2", ACS, STN Registry, Dec. 17, 2013.
"CAS RN: 1487135-99-8", ACS, STN Registry, Dec. 5, 2013.
"CAS RN: 1482249-37-5", ACS, STN Registry, Nov. 27, 2013.
Christou P, Transformation Technology, Trends in Plant Science, 1:423-431 (1996).
Braun et al., The General Mitochondrial Processing Peptidase from Potato Is an Integral Part of Cytochrome C Reductase of The Respiratory Chain, *EMBO J.* 11:3219-3227 (1992).
Wolter et al., Rbcs Genes in Solanum Tuberosum: Conservation of Transit Peptide and Exon Shuffling During Evolution, *Proc. Natl. Acad. Sci. USA*, 85:846-850 (1988).
Sonnewald et al., Transgenic Tobacco Plants Expressing Yeast-Derived Invertase in Either the Cytosol, Vacuole or Apoplast: A Powerful Tool for Studying Sucrose Metabolism and Sink/Source Interactions, *Plant J.* 1:95-106 (1991).
International Search Report of International Application No. PCT/CN2020/071932, dated Apr. 1, 2020.
Extended European Search Report of counterpart European patent application No. EP20741322.0, dated Aug. 2, 2022.

* cited by examiner

4-PYRIDINYL FORMAMIDE COMPOUND OR DERIVATIVE THEREOF, PREPARATION METHOD THEREFOR, HERBICIDAL COMPOSITION AND USE THEREOF

CROSS REFERENCE TO RELATED APPLICATION

This application is a national stage filing under 35 U.S.C. § 371 of International Application No. PCT/CN2020/071932, filed Jan. 14, 2020, and claims the priority to and benefits of Chinese Application No. 201910031819.7, filed Jan. 14, 2019, which is incorporated herein by reference in its entirety.

TECHNICAL FIELD

The invention belongs to the technical field of pesticides, and specifically relates to a 4-pyridinyl formamide compound or derivative thereof, preparation method therefor, herbicidal composition and use thereof.

TECHNICAL BACKGROUND

Weed control is one of the most important links in the course of achieving high-efficiency agriculture. Various herbicides are available in the market, for example, WO2013087577A1 etc. disclose certain arylformamide compounds and their use as herbicides. However, due to the continuous expansion of the market, the resistance of weeds, the service life of chemicals and the economical efficiency of chemicals, as well as the increasing emphasis on the environment, especially the resistance of the mainstream ALS inhibitor and ACCe inhibitor herbicides is becoming more and more serious. In rice fields and wheat fields, more and more efficient, selective herbicides that can solve resistance are needed. This requires scientists to continuously research and develop new high-efficiency, safe, economic herbicides with different action modes.

Invention Contents

The present invention provides a 4-pyridinyl formamide compound or derivative thereof, preparation method therefor, herbicidal composition and use thereof. The compound has excellent herbicidal activity and a higher crop safety, and establishes good selectivity, especially for key crops such as wheat and rice.

The technical solution adopted by the invention is as follows:

A 4-pyridinyl formamide compound or derivative thereof, as shown in Formula I:

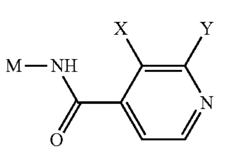

I

Wherein, X, and Y each independently represent nitro, halogen, cyano, formyl, thiocyano, mercapto; alkyl, alkenyl, alkynyl, cycloalkyl, cycloalkenyl, cycloalkylalkyl, or cycloalkenylalkyl, which is with or without halogen; $OR^1$, $COR^1$, $COOR^1$, $OCOR^1$, $OCOOR^1$, $NR^3SO_2R^2$, $OSO_2R^2$, $S(O)_mR^2$, $NR^3COR^1$, $NR^3COOR^1$, $C(O)NR^3OR^1$, $SO_2OR^1$, $C(O)NR^4R^5$, $NR^3C(O)NR^4R^5$, $OC(O)NR^4R^5$, $SO_2NR^4R^5$, $C(S)R^1$, $C(S)OR^1$, $C(S)SR^2$, $C(O)SR^2$, $SC(O)R^1$, $SC(S)R^1$, $OC(S)R^1$, -alkyl-$C(S)R^1$, -alkyl-$C(S)OR^1$, -alkyl-$C(O)SR^1$, -alkyl-$C(S)SR^1$, -alkyl-$SC(O)R^1$, -alkyl-$OC(S)R^1$, -alkyl-$SC(S)R^1$, —O-alkyl-$NR^4R^5$, —S-alkyl-$NR^4R^5$, -alkyl-O-alkyl-$NR^4R^5$, -alkyl-S-alkyl-$NR^4R^5$, -alkyl-$(C{=}S)_n$—$NR^4R^5$, —NH-alkyl-$NR^4R^5$, -alkyl-$OR^1$, -alkyl-$COR^1$, -alkyl-$CO_2R^1$, -alkyl-$OCOR^1$, -alkyl-$NR^3COR^1$, -alkyl-$SO_2OR^1$, -alkyl-$NR^3SO_2R^2$, -alkyl-$OSO_2R^2$, -alkyl-$S(O)_m R^2$, -alkyl-$CONR^4R^5$, -alkyl-$SO_2NR^4R^5$, $NR^4R^5$,

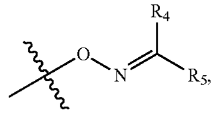

$P(O)(OR^6)_2$, $CH_2P(O)(OR^6)_2$, $SO_2NR^4R^5$-alkyl-$S(O)_mR^2$, -alkyl-CN, -alkylaryl, -alkylheteroaryl, -alkylheterocyclyl, aryl, heteroaryl, or heterocyclyl;

$R^1$, $R^3$, $R^4$, and $R^5$ each independently represent hydrogen, aryl, arylalkyl, heteroaryl, heteroarylalkyl, alkyl, halogenated alkyl, alkenyl, halogenated alkenyl, alkynyl, halogenated alkynyl, cycloalkyl, halogenated cycloalkyl, alkoxyalkyl, or cycloalkylalkyl, wherein the last 10 groups as mentioned are each substituted by s groups selected from the group consisting of cyano, halogen, nitro, thiocyano, $OR^7$, $S(O)_mR^9$, $NR^7R^8$, $NR^8OR^7$, $COR^7$, $OCOR^7$, $SCOR^7$, $NR^8COR^7$, $CO_2R^7$, $COSR^7$, $CONR^7R^8$, and alkoxyalkoxycarbonyl;

$R^2$ represents aryl, arylalkyl, heteroaryl, heteroarylalkyl, alkyl, alkenyl, alkynyl, cycloalkyl, or cycloalkylalkyl, wherein the last 5 groups as mentioned are each substituted by s groups selected from the group consisting of cyano, halogen, nitro, thiocyano, $OR^7$, $S(O)_mR^9$, $NR^7R^8$, $NR^8OR^7$, $COR^7$, $OCOR^7$, $SCOR^7$, $NR^8COR^7$, $CO_2R^7$, $COSR^7$, $CONR^7R^8$, and alkoxyalkoxycarbonyl;

$R^6$ represents methyl, or ethyl;

$R^7$, and $R^8$ each independently represent hydrogen, alkyl, alkenyl, or alkynyl;

$R^9$ represents alkyl, alkenyl, or alkynyl;

M represents

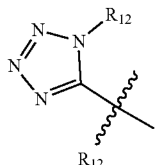 ,

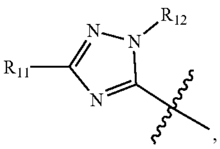 ,

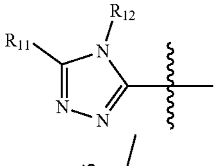 ,

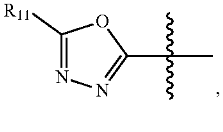 ,

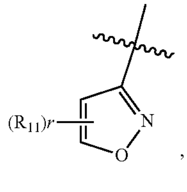 , or

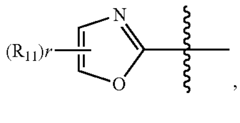 , which is unsubstituted or substituted;

$R_{11}$ represents hydrogen, halogen, cyano, nitro, alkyl which is unsubstituted or substituted with a substituent selected from $R_{13}$, cycloalkyl which is unsubstituted or substituted with a substituent selected from $R_{14}$, alkenyl, halogenated alkenyl, alkynyl, halogenated alkynyl, cycloalkenyl, $NH_2$, aminoacyl, carboxyl, alkoxyalkoxycarbonyl, $OR_{15}$, -alkyl-$OR_{15}$, $C(O)R_{16}$, -alkyl-$C(O)R_{16}$, $C(O)OR_{16}$, -alkyl-$C(O)OR_{16}$, $S(O)_mR_{16}$, -alkyl-$S(O)_mR_{16}$, —$N(R_{16})_2$, —$NHR_{16}$, —$C(O)NHR_{16}$, —$C(O)N(R_{16})_2$, —NHC(O)Rn, heterocyclyl, heterocyclylalkyl, heterocyclyloxy, heterocyclylcarbonyl, aryl, arylalkyl, aryloxy, arylcarbonyl, heteroaryl, heteroarylalkyl, heteroaryloxy, or heteroarylcarbonyl;

$R_{12}$ represents hydrogen, alkyl which is unsubstituted or substituted with a substituent selected from $R_{18}$, cycloalkyl, halogenated cycloalkyl, alkenyl, halogenated alkenyl, alkynyl, halogenated alkynyl, cycloalkenyl, alkoxyalkyl, alkylthioalkyl, alkoxycarbonylalkyl, aryl, or arylalkyl;

when M is

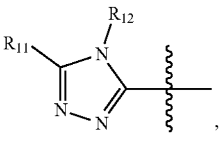

,

—$(CH_2)_4$— or —CH═CH—CH═CH— formed by $R_{11}$ and $R_{12}$, the nitrogen atom bound to $R_{12}$ and the carbon atom bound to $R_{11}$ together form a 6-membered ring;

$R_{15}$ represents alkyl which is unsubstituted or substituted with a substituent selected from $R_{21}$, cycloalkyl, halogenated cycloalkyl, alkenyl, halogenated alkenyl, alkynyl, halogenated alkynyl, cycloalkenyl, or phenyl;

$R_{16}$ represents alkyl, halogenated alkyl, cycloalkyl, alkenyl, halogenated alkenyl, alkynyl, halogenated alkynyl, or cycloalkenyl;

$R_{21}$ represents halogen, cyano, cycloalkyl, hydroxy, mercapto, alkoxy, $C(O)R_{22}$, carboxyl, alkoxycarbonyl, alkoxyalkoxycarbonyl, —$S(O)_m$-alkyl, heteroaryl, heterocyclyl, or phenyl which is unsubstituted or substituted with one or more groups selected from $R_{23}$;

$R_{17}$, and $R_{22}$ each independently represent hydrogen, alkyl, or $N(R_{24})R_{25}$;

$R_{23}$ represents halogen, cyano, nitro, alkyl, alkyl which is unsubstituted or substituted with a substituent selected from $R_{31}$, cycloalkyl, halogenated cycloalkyl, alkenyl, halogenated alkenyl, alkynyl, halogenated alkynyl, cycloalkenyl, alkylcarbonyl, cycloalkylcarbonyl, halogenated alkylcarbonyl, halogenated cycloalkylcarbonyl, alkoxycarbonyl, halogenated alkoxycarbonyl, alkylaminocarbonyl, halogenated alkylaminocarbonyl, bis(alkyl)aminocarbonyl, $OR_{32}$, $S(O)_mR_{33}$, alkylaminosulfonyl, bis(alkyl)aminosulfonyl, $NH_2$, alkylamino, bis(alkyl)amino, aryl, heteroaryl, or heterocyclyl;

$R_{24}$, and $R_{25}$ each independently represent hydrogen, alkyl, or phenyl; or, alkylidene chain formed by $R_{24}$ and $R_{25}$, and the nitrogen atom(s) bound to $R_{24}$ and $R_{25}$ together form a 3-7-membered ring, said alkylidene chain optionally contains one O, S, S(O), $S(O)_2$, NH, or N-alkyl and optionally substituted by oxo or thio group;

$R_{13}$. $R_{14}$, $R_{18}$, and $R_{31}$ each independently represent halogen, cyano, nitro, carboxyl, alkoxycarbonyl, alkoxyalkoxycarbonyl, $S(O)_mR_{41}$, $OR_{42}$, aryl, heteroaryl, or heterocyclyl;

$R_{32}$ represents hydrogen, alkyl, halogenated alkyl, cycloalkyl, halogenated cycloalkyl, alkenyl, halogenated alkenyl, alkynyl, halogenated alkynyl, or cycloalkenyl;

$R_{33}$ represents alkyl, halogenated alkyl, cycloalkyl, alkenyl, halogenated alkenyl, alkynyl, halogenated alkynyl, or cycloalkenyl;

$R_{41}$, and $R_{42}$ each independently represent hydrogen, alkyl, halogenated alkyl, cycloalkyl, halogenated cycloalkyl, alkenyl, halogenated alkenyl, alkynyl, halogenated alkynyl, cycloalkenyl, or phenyl;

r represents 1 or 2;

m represents 0, 1 or 2;

n represents 0, or 1;

s represents 0, 1, 2 or 3.

Preferably, X, and Y each independently represent nitro, halogen, cyano, formyl, thiocyano, mercapto; C1-C8 alkyl, C2-C8 alkenyl, C2-C8 alkynyl, C3-C8 cycloalkyl, C3-C8 cycloalkenyl, C3-C8 cycloalkyl-C1-C6 alkyl, or C3-C8 cycloalkenyl-C1-C6 alkyl, which is with or without halogen; $OR^1$, $COR^1$, $COOR^1$, $OCOR^1$, $OCOOR^1$, $NR^3SO_2R^2$, $OSO_2R^2$, $S(O)_mR^2$, $NR^3COR^1$, $NR^3COOR^1$, $C(O)NR^3OR^1$, $SO_2OR^1$, $C(O)NR^4R^5$, $NR^3C(O)NR^4R^5$, $OC(O)NR^4R^5$, $SO_2NR^4R^5$, $C(S)R^1$, $C(S)OR^1$, $C(S)SR^2$, $C(O)SR^2$, $SC(O)R_2$, $SC(S)R^1$, $OC(S)R_1$, —(C1-C6)alkyl-$C(S)R^1$, —(C1-C6)alkyl-$C(S)OR^1$, —(C1-C6)alkyl-$C(O)SR^1$, —(C1-C6)alkyl-$C(S)SR^1$, —(C1-C6)alkyl-$SC(O)R^1$, —(C1-C6)alkyl-$OC(S)R^1$, —(C1-C6)alkyl-$SC(S)R^1$, —O—(C1-C6)alkyl-$NR^4R^5$, —S—(C1-C6)alkyl-$NR^4R^5$, —(C1-C6)alkyl-O—(C1-C6)alkyl-$NR^4R^5$, —(C1-C6)alkyl-S—(C1-C6)alkyl-$NR^4R^5$, —(C1-C6)alkyl-$(C{=}S)_n$—$NR^4R^5$, —NH—(C1-C6)alkyl-$NR^4R^5$, —(C1-C6)alkyl-$OR^1$, —(C1-C6)alkyl-$COR^1$, —(C1-C6)alkyl-$CO_2R^1$, —(C1-C6)alkyl-$OCOR^1$, —(C1-C6)alkyl-$NR^3COR^1$, —(C1-C6)alkyl-$SO_2OR^1$, —(C1-C6)alkyl-$NR^3SO_2R^2$, —(C1-C6)alkyl-$OSO_2R^2$, -alkyl-$S(O)_mR^2$, —(C1-C6)alkyl-$CONR^4R^5$, —(C1-C6)alkyl-$SO_2NR^4R^5$, $NR^4R^5$,

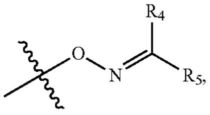

$P(O)(OR^6)_2$, $CH_2P(O)(OR^6)_2$, $SO_2NR^4R^5$—(C1-C6)alkyl-$S(O)_mR^2$, —(C1-C6)alkyl-CN, —(C1-C6)alkylaryl, —(C1-C6)alkylheteroaryl, —(C1-C6)alkylheterocyclyl, aryl, heteroaryl, or heterocyclyl;

$R^1$, $R^3$, $R^4$, and $R^5$ each independently represent hydrogen, aryl, aryl-C1-C6 alkyl, heteroaryl, heteroaryl-C1-C6 alkyl, C1-C8 alkyl, halogenated C1-C8 alkyl, C2-C8 alkenyl, halogenated C2-C8 alkenyl, C2-C8 alkynyl, halogenated C2-C8 alkynyl, C3-C8 cycloalkyl, halogenated C3-C8 cycloalkyl, C1-C8 alkoxy-C1-C6 alkyl, or C3-C8 cycloalkyl-C1-C6 alkyl, wherein the last 10 groups as mentioned are each substituted by s groups selected from the group consisting of cyano, halogen, nitro, thiocyano, $OR^7$, $S(O)_mR^9$, $NR^7R^8$, $NR^8OR^7$, $COR^7$, $OCOR^7$, $SCOR^7$, $NR^8COR^7$, $CO_2R^7$, $COSR^7$, $CONR^7R^8$, and C1-C8 alkoxy-C1-C6 alkoxycarbonyl;

$R^2$ represents aryl, aryl-C1-C6 alkyl, heteroaryl, heteroaryl-C1-C6 alkyl, C1-C8 alkyl, C2-C8 alkenyl, C2-C8 alkynyl, C3-C8 cycloalkyl, or C3-C8 cycloalkyl-C1-C6 alkyl, wherein the last 5 groups as mentioned are each substituted by s groups selected from the group consisting of cyano, halogen, nitro, thiocyano, $OR^7$, $S(O)_mR^9$, $NR^7R^8$, $NR^8OR^7$, $COR^7$, $OCOR^7$, $SCOR^7$, $NR^8COR^7$, $CO_2R^7$, $COSR^7$, $CONR^7R^8$, and C1-C8 alkoxy-C1-C6 alkoxycarbonyl;

$R^6$ represents methyl, or ethyl;

$R^7$, and $R^8$ each independently represent hydrogen, C1-C8 alkyl, C2-C8 alkenyl, or C2-C8 alkynyl;

$R^9$ represents C1-C8 alkyl, C2-C8 alkenyl, or C2-C8 alkynyl;

M represents

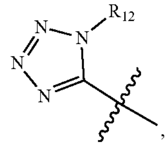
,
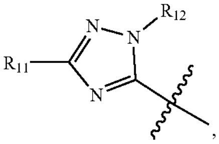
,
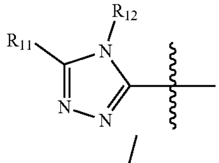
,
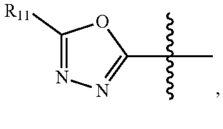
,
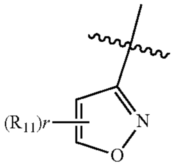
, or
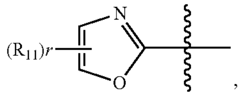
, which is unsubstituted or substituted;

$R_{11}$ represents hydrogen, halogen, cyano, nitro, C1-C8 alkyl which is unsubstituted or substituted with a substituent selected from $R_{13}$, C3-C8 cycloalkyl which is unsubstituted or substituted with a substituent selected from $R_{14}$, C2-C8 alkenyl, halogenated C2-C8 alkenyl, C2-C8 alkynyl, halogenated C2-C8 alkynyl, C3-C8 cycloalkenyl, $NH_2$, aminoacyl, carboxyl, C1-C8 alkoxy-C1-C6 alkoxycarbonyl, $OR_{15}$, —(C1-C6)alkyl-$OR_{15}$, C(O)$R_{16}$, —(C1-C6)alkyl-C(O)$R_{16}$, C(O)O$R_{16}$, —(C1-C6)alkyl-C(O)O$R_{16}$, $S(O)_mR_{16}$, —(C1-C6)alkyl-$S(O)_mR_{16}$, —$N(R_{16})_2$, —$NHR_{16}$, —C(O)N$HR_{16}$, —C(O)$N(R_{16})_2$, —NHC(O)Rn, heterocyclyl, heterocyclyl-C1-C6 alkyl, heterocyclyloxy, heterocyclylcarbonyl, aryl, aryl-C1-C6 alkyl, aryloxy, arylcarbonyl, heteroaryl, heteroaryl-C1-C6 alkyl, heteroaryloxy, or heteroarylcarbonyl;

$R_{12}$ represents hydrogen, C1-C8 alkyl which is unsubstituted or substituted with a substituent selected from $R_{18}$, C3-C8 cycloalkyl, halogenated C3-C8 cycloalkyl, C2-C8 alkenyl, halogenated C2-C8 alkenyl, C2-C8 alkynyl, halogenated C2-C8 alkynyl, C3-C8 cycloalkenyl, C1-C8 alkoxy-C1-C6 alkyl, C1-C8 alkylthio-C1-C6 alkyl, C1-C8 alkoxycarbonyl-C1-C6 alkyl, aryl, or aryl-C1-C6 alkyl;

when M is

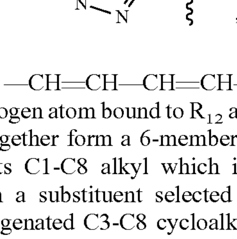
,

—$(CH_2)_4$— or —CH═CH—CH═CH— formed by $R_{11}$ and $R_{12}$, the nitrogen atom bound to $R_{12}$ and the carbon atom bound to $R_{11}$ together form a 6-membered ring;

$R_{15}$ represents C1-C8 alkyl which is unsubstituted or substituted with a substituent selected from $R_{21}$, C3-C8 cycloalkyl, halogenated C3-C8 cycloalkyl, C2-C8 alkenyl, halogenated C2-C8 alkenyl, C2-C8 alkynyl, halogenated C2-C8 alkynyl, C3-C8 cycloalkenyl, or phenyl;

$R_{16}$ represents C1-C8 alkyl, halogenated C1-C8 alkyl, C3-C8 cycloalkyl, C2-C8 alkenyl, halogenated C2-C8 alkenyl, C2-C8 alkynyl, halogenated C2-C8 alkynyl, or C3-C8 cycloalkenyl;

$R_{21}$ represents halogen, cyano, C3-C8 cycloalkyl, hydroxy, mercapto, C1-C8 alkoxy, C(O)$R_{22}$, carboxyl, C1-C8 alkoxy carbonyl, C1-C8 alkoxy-C1-C6 alkoxy carbonyl, —$S(O)_m$—(C1-C8)alkyl, heteroaryl, heterocyclyl, or phenyl which is unsubstituted or substituted with one or more groups selected from $R_{23}$;

$R_{17}$, and $R_{22}$ each independently represent hydrogen, C1-C8 alkyl, or $N(R_{24})R_{25}$;

$R_{23}$ represents halogen, cyano, nitro, C1-C8 alkyl, C1-C8 alkyl which is unsubstituted or substituted with a substituent selected from $R_{31}$, C3-C8 cycloalkyl, halogenated C3-C8 cycloalkyl, C2-C8 alkenyl, halogenated C2-C8 alkenyl, C2-C8 alkynyl, halogenated C2-C8 alkynyl, C3-C8 cycloalkenyl, C1-C8 alkylcarbonyl, C3-C8 cycloalkylcarbonyl, halogenated C1-C8 alkylcarbonyl, halogenated C3-C8 cycloalkylcarbonyl, C1-C8 alkoxy carbonyl, halogenated C1-C8 alkoxy carbonyl, C1-C8 alkylaminocarbonyl, halogenated C1-C8 alkylaminocarbonyl, bis(C1-C8 alkyl)aminocarbonyl, $OR_{32}$, $S(O)_mR_{33}$, C1-C8 alkylaminosulfonyl, bis(C1-C8 alkyl)aminosulfonyl, $NH_2$, C1-C8 alkylamino, bis(C1-C8 alkyl)amino, aryl, heteroaryl, or heterocyclyl;

$R_{24}$, and $R_{25}$ each independently represent hydrogen, C1-C8 alkyl, or phenyl; or, C2-C8 alkylidene chain formed by $R_{24}$ and $R_{25}$, and the nitrogen atom(s) bound to $R_{24}$ and $R_{25}$ together form a 3-7-membered ring, said C2-C8 alkylidene chain optionally contains one O, S, S(O), $S(O)_2$, NH, or N-alkyl and optionally substituted by oxo or thio group;

$R_{13}$, $R_{14}$, $R_{18}$, and $R_{31}$ each independently represent halogen, cyano, nitro, carboxyl, C1-C8 alkoxycarbonyl, C1-C8 alkoxy-C1-C8 alkoxy carbonyl, $S(O)_mR_{41}$, $OR_{42}$, aryl, heteroaryl, or heterocyclyl;

$R_{32}$ represents hydrogen, C1-C8 alkyl, halogenated C1-C8 alkyl, C3-C8 cycloalkyl, halogenated C3-C8 cycloalkyl, C2-C8 alkenyl, halogenated C2-C8 alkenyl, C2-C8 alkynyl, halogenated C2-C8 alkynyl, or C3-C8 cycloalkenyl;

$R_{33}$ represents C1-C8 alkyl, halogenated C1-C8 alkyl, C3-C8 cycloalkyl, C2-C8 alkenyl, halogenated C2-C8 alkenyl, C2-C8 alkynyl, halogenated C2-C8 alkynyl, or C3-C8 cycloalkenyl;

$R_{41}$, and $R_{42}$ each independently represent hydrogen, C1-C8 alkyl, halogenated C1-C8 alkyl, C3-C8 cycloalkyl, halogenated C3-C8 cycloalkyl, C2-C8 alkenyl, halogenated C2-C8 alkenyl, C2-C8 alkynyl, halogenated C2-C8 alkynyl, C3-C8 cycloalkenyl, or phenyl;

r represents 1, or 2;

m represents 0, 1, or 2;

n represents 0, or 1;

s represents 0, 1, 2, or 3.

More preferably, X represents nitro, halogen, cyano, formyl, thiocyano, mercapto; C1-C6 alkyl, C2-C6 alkenyl, C2-C6 alkynyl, C3-C6 cycloalkyl, C3-C6 cycloalkenyl, C3-C6 cycloalkyl-C1-C3 alkyl, or C3-C6 cycloalkenyl-C1-C3 alkyl, which is with or without halogen; $OR^1$, $COR^1$, $COOR^1$, $OCOR^1$, $OCOOR^1$, $NR^3SO_2R^2$, $OSO_2R^2$, $S(O)_mR^2$, $NR^3COR^1$, $NR^3COOR^1$, $C(O)NR^3OR^1$, $SO_2OR^1$, $C(O)NR^4R^5$, $NR^3C(O)NR^4R^5$, $OC(O)NR^4R^5$, $SO_2NR^4R^5$, $C(S)R^1$, $C(S)OR^1$, $C(S)SR^2$, $C(O)SR^2$, $SC(O)R^1$, $SC(S)R^1$, $OC(S)R^1$, —(C1-C3)alkyl-$C(S)R^1$, —(C1-C3)alkyl-$C(S)OR^1$, —(C1-C3)alkyl-$C(O)SR^1$, —(C1-C3)alkyl-$C(S)SR^1$, —(C1-C3)alkyl-$SC(O)R^1$, —(C1-C3)alkyl-$OC(S)R^1$, —(C1-C3)alkyl-$SC(S)R^1$, —O—(C1-C3)alkyl-$NR^4R^5$, —S—(C1-C3)alkyl-$NR^4R^5$, —(C1-C3)alkyl-O—(C1-C3) alkyl-$NR^4R^5$, —(C1-C3)alkyl-S—(C1-C3)alkyl-$NR^4R^5$, —(C1-C3)alkyl-$(C{=}S)_n$—$NR^4R^5$, —NH—(C1-C3)alkyl-$NR^4R^5$, —(C1-C3)alkyl-$OR^1$, —(C1-C3)alkyl-$COR^1$, —(C1-C3)alkyl-$CO_2R^1$, —(C1-C3)alkyl-$OCOR^1$, —(C1-C3)alkyl-$NR^3COR^1$, —(C1-C3)alkyl-$SO_2OR^1$, —(C1-C3) alkyl-$NR^3SO_2R^2$, —(C1-C3)alkyl-$OSO_2R^2$, -alkyl-$S(O)_m R^2$, —(C1-C3)alkyl-$CONR^4R^5$, —(C1-C3)alkyl-$SO_2NR^4R^5$, $NR^4R^5$,

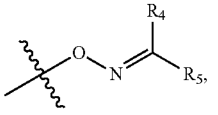

$P(O)(OR^6)_2$, $CH_2P(O)(OR^6)_2$, $SO_2NR^4R^5$—(C1-C3)alkyl-$S(O)_mR^2$, —(C1-C3)alkyl-CN, —(C1-C3)alkylaryl, —(C1-C3)alkylheteroaryl, —(C1-C3)alkylheterocyclyl, aryl, heteroaryl, or heterocyclyl;

Y represents C1-C6 alkyl, C2-C6 alkenyl, C2-C6 alkynyl, C3-C6 cycloalkyl, or C3-C6 cycloalkenyl, which is with or without halogen; $OR^1$, $S(O)_mR^2$, $NR^4R^5$, heterocyclyl, aryl, or heteroaryl;

$R^1$, $R^3$, $R^4$, and $R^5$ each independently represent hydrogen, aryl, aryl-C1-C3 alkyl, heteroaryl, heteroaryl-C1-C3 alkyl, C1-C6 alkyl, halogenated C1-C6 alkyl, C2-C6 alkenyl, halogenated C2-C6 alkenyl, C2-C6 alkynyl, halogenated C2-C6 alkynyl, C3-C6 cycloalkyl, halogenated C3-C6 cycloalkyl, C1-C6 alkoxy-C1-C3 alkyl, or C3-C6 cycloalkyl-C1-C3 alkyl, wherein the last 10 groups as mentioned are each substituted by s groups selected from the group consisting of cyano, halogen, nitro, thiocyano, $OR^7$, $S(O)_m R^9$, $NR^7R^8$, $NR^8OR^7$, $COR^7$, $OCOR^7$, $SCOR^7$, $NR^8COR^7$, $CO_2R^7$, $COSR^7$, $CONR^7R^8$, and C1-C6 alkoxy-C1-C3 alkoxycarbonyl;

$R^2$ represents aryl, aryl-C1-C3 alkyl, heteroaryl, heteroaryl-C1-C3 alkyl, C1-C6 alkyl, C2-C6 alkenyl, C2-C6 alkynyl, C3-C6 cycloalkyl, or C3-C6 cycloalkyl-C1-C3 alkyl, wherein the last 5 groups as mentioned are each substituted by s groups selected from the group consisting of cyano, halogen, nitro, thiocyano, $OR^7$, $S(O)_mR^9$, $NR^7R^8$, $NR^8OR^7$, $COR^7$, $OCOR^7$, $SCOR^7$, $NR^8COR^7$, $CO_2R^7$, $COSR^7$, $CONR^7R^8$, and C1-C6 alkoxy-C1-C3 alkoxycarbonyl;

$R^6$ represents methyl, or ethyl;

$R^7$, and $R^8$ each independently represent hydrogen, C1-C6 alkyl, C2-C6 alkenyl, or C2-C6 alkynyl;

$R^9$ represents C1-C6 alkyl, C2-C6 alkenyl, or C2-C6 alkynyl;

M represents

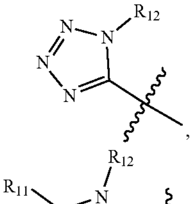
,
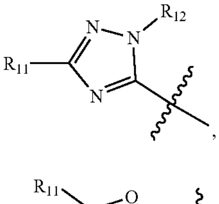
,
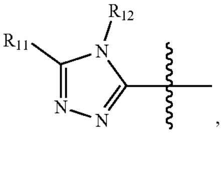
,
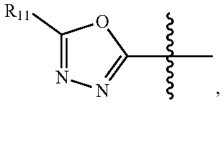
,

-continued

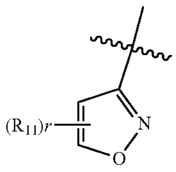
, or
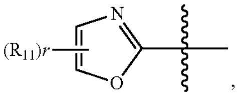
, which is unsubstituted or substituted;

$R_{11}$ represents hydrogen, halogen, cyano, nitro, C1-C6 alkyl which is unsubstituted or substituted with a substituent selected from $R_{13}$, C3-C6 cycloalkyl which is unsubstituted or substituted with a substituent selected from $R_{14}$, C2-C6 alkenyl, halogenated C2-C6 alkenyl, C2-C6 alkynyl, halogenated C2-C6 alkynyl, C3-C6 cycloalkenyl, $NH_2$, aminoacyl, carboxyl, C1-C6 alkoxy-C1-C3 alkoxy carbonyl, $OR_{15}$, —(C1-C3)alkyl-$OR_{15}$, $C(O)R_{16}$, —(C1-C3)alkyl-$C(O)R_{16}$, $C(O)OR_{16}$, —(C1-C3)alkyl-$C(O)OR_{16}$, $S(O)_mR_{16}$, —(C1-C3)alkyl-$S(O)_mR_{16}$, —$N(R_{16})_2$, —$NHR_{16}$, —$C(O)NHR_{16}$, —$C(O)N(R_{16})_2$, —NHC(O)Rn, heterocyclyl, heterocyclyl-C1-C3 alkyl, heterocyclyloxy, heterocyclylcarbonyl, aryl, aryl-C1-C3 alkyl, aryloxy, arylcarbonyl, heteroaryl, heteroaryl-C1-C3 alkyl, heteroaryloxy, or heteroarylcarbonyl;

$R_{12}$ represents hydrogen, C1-C6 alkyl which is unsubstituted or substituted with a substituent selected from $R_{18}$, C3-C6 cycloalkyl, halogenated C3-C6 cycloalkyl, C2-C6 alkenyl, halogenated C2-C6 alkenyl, C2-C6 alkynyl, halogenated C2-C6 alkynyl, C3-C6 cycloalkenyl, C1-C6 alkoxy-C1-C3 alkyl, C1-C6 alkylthio-C1-C3 alkyl, C1-C6 alkoxy-carbonyl-C1-C3 alkyl, aryl, or aryl-C1-C3 alkyl;

when M is

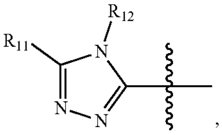
,

—$(CH_2)_4$— or —CH=CH—CH=CH— formed by $R_{11}$ and $R_{12}$, the nitrogen atom bound to $R_{12}$ and the carbon atom bound to Rn together form a 6-membered ring;

$R_{15}$ represents C1-C6 alkyl which is unsubstituted or substituted with a substituent selected from $R_{21}$, C3-C6 cycloalkyl, halogenated C3-C6 cycloalkyl, C2-C6 alkenyl, halogenated C2-C6 alkenyl, C2-C6 alkynyl, halogenated C2-C6 alkynyl, C3-C6 cycloalkenyl, or phenyl;

$R_{16}$ represents C1-C6 alkyl, halogenated C1-C6 alkyl, C3-C6 cycloalkyl, C2-C6 alkenyl, halogenated C2-C6 alkenyl, C2-C6 alkynyl, halogenated C2-C6 alkynyl, or C3-C6 cycloalkenyl;

$R_{21}$ represents halogen, cyano, C3-C6 cycloalkyl, hydroxy, mercapto, C1-C6 alkoxy, $C(O)R_{22}$, carboxyl, C1-C6 alkoxy carbonyl, C1-C6 alkoxy-C1-C3 alkoxy carbonyl, —$S(O)_m$—(C1-C6)alkyl, heteroaryl, heterocyclyl, or phenyl which is unsubstituted or substituted with 1~3 groups selected from $R_{23}$;

$R_{17}$, and $R_{22}$ each independently represent hydrogen, C1-C6 alkyl, or $N(R_{24})R_{25}$;

$R_{23}$ represents halogen, cyano, nitro, C1-C6 alkyl, C1-C6 alkyl which is unsubstituted or substituted with a substituent selected from $R_{31}$, C3-C6 cycloalkyl, halogenated C3-C6 cycloalkyl, C2-C6 alkenyl, halogenated C2-C6 alkenyl, C2-C6 alkynyl, halogenated C2-C6 alkynyl, C3-C6 cycloalkenyl, C1-C6 alkylcarbonyl, C3-C6 cycloalkylcarbonyl, halogenated C1-C6 alkylcarbonyl, halogenated C3-C6 cycloalkylcarbonyl, C1-C6 alkoxycarbonyl, halogenated C1-C6 alkoxycarbonyl, C1-C6 alkylaminocarbonyl, halogenated C1-C6 alkylaminocarbonyl, bis(C1-C6 alkyl)aminocarbonyl, $OR_{32}$, $S(O)_mR_{33}$, C1-C6 alkylaminosulfonyl, bis(C1-C6 alkyl)aminosulfonyl, $NH_2$, C1-C6 alkylamino, bis(C1-C6 alkyl)amino, aryl, heteroaryl, or heterocyclyl;

$R_{24}$, and $R_{25}$ each independently represent hydrogen, C1-C6 alkyl, or phenyl; or, C2-C6 alkylidene chain formed by $R_{24}$ and $R_{25}$, and the nitrogen atom(s) bound to $R_{24}$ and $R_{25}$ together form a 3-7-membered ring, said C2-C6 alkylidene chain optionally contains one O, S, S(O), $S(O)_2$, NH, or N-alkyl and optionally substituted by oxo or thio group;

$R_{13}$, $R_{14}$, $R_{18}$, and $R_{31}$ each independently represent halogen, cyano, nitro, carboxyl, C1-C6 alkoxycarbonyl, C1-C6 alkoxy-C1-C6 alkoxy carbonyl, $S(O)_mR_{41}$, $OR_{42}$, aryl, heteroaryl, or heterocyclyl;

$R_{32}$ represents hydrogen, C1-C6 alkyl, halogenated C1-C6 alkyl, C3-C6 cycloalkyl, halogenated C3-C6 cycloalkyl, C2-C6 alkenyl, halogenated C2-C6 alkenyl, C2-C6 alkynyl, halogenated C2-C6 alkynyl, or C3-C6 cycloalkenyl;

$R_{33}$ represents C1-C6 alkyl, halogenated C1-C6 alkyl, C3-C6 cycloalkyl, C2-C6 alkenyl, halogenated C2-C6 alkenyl, C2-C6 alkynyl, halogenated C2-C6 alkynyl, or C3-C6 cycloalkenyl;

$R_{41}$, and $R_{42}$ each independently represent hydrogen, C1-C6 alkyl, halogenated C1-C6 alkyl, C3-C6 cycloalkyl, halogenated C3-C6 cycloalkyl, C2-C6 alkenyl, halogenated C2-C6 alkenyl, C2-C6 alkynyl, halogenated C2-C6 alkynyl, C3-C6 cycloalkenyl, or phenyl;

r represents 1, or 2;

m represents 0, 1, or 2;

n represents 0, or 1;

s represents 0, 1, 2, or 3.

Further preferably, X represents halogen, nitro, cyano, $OR^1$, $S(O)_mR^2$, NR $COR^1$. $NR^4R^5$,

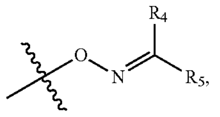

C1-C6 alkoxy-C1-C3 alkyl; C1-C6 alkyl, C2-C6 alkenyl, C2-C6 alkynyl, or C3-C6 cycloalkyl, which is with or without halogen;

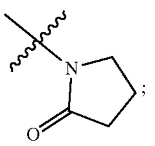 [SMILES: *N1CCCC1=O]

or phenyl which is unsubstituted or substituted with 1, 2, or 3 groups selected from halogen, and C1-C6 alkoxy;

Y represents C1-C6 alkyl, C2-C6 alkenyl, C2-C6 alkynyl, C3-C6 cycloalkyl, or C3-C6 cycloalkenyl, which is with or without halogen; $OR^1$, $S(O)_mR^2$, $NR^4R^5$, heterocyclyl, aryl, or heteroaryl;

$R^1$, $R^3$, $R^4$, and $R^5$ each independently represent hydrogen, C1-C6 alkyl, halogenated C1-C6 alkyl, phenyl; or benzyl which is unsubstituted or substituted with 1, 2, or 3 groups selected from halogen, and C1-C6 alkoxy;

$R^2$ represents C1-C6 alkyl, or halogenated C1-C6 alkyl;

M represents

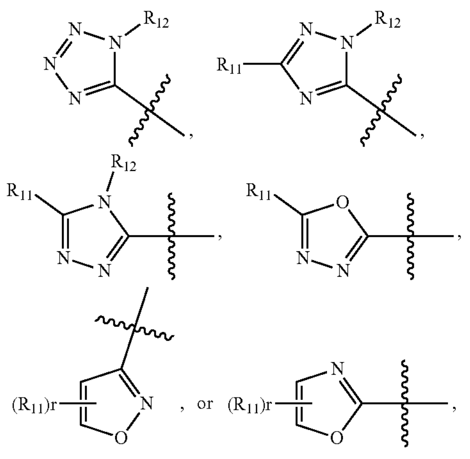

, or which is unsubstituted or substituted;

$R_{11}$ represents hydrogen, C1-C6 alkyl, C3-C6 cycloalkyl, halogenated C1-C6 alkyl, C1-C6 alkoxy, C1-C6 alkylthio, halogen, C1-C6 alkylamino, bis(C1-C6 alkyl)amino, cyano, nitro, C1-C6 alkylcarbonyl, C1-C6 alkoxy carbonyl, C1-C6 alkoxycarbonyl-C1-C3 alkyl, aminocarbonyl, C1-C6 alkylcarbonylamino, C1-C6 alkoxy-C1-C3 alkyl, C1-C6 alkylthio-C1-C3 alkyl, C1-C6 alkylsulfinyl-C1-C3 alkyl, C1-C6 alkylsulfonyl-C1-C3 alkyl; or benzyl, phenoxy, benzoyl, pyridyl,

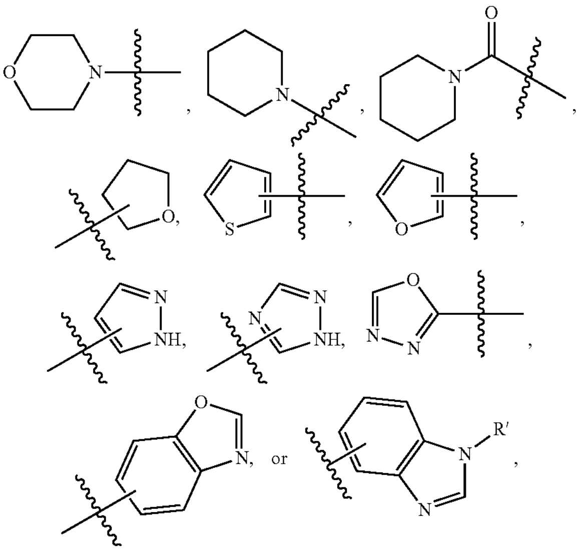

, or which is unsubstituted or substituted with 1, 2, or 3 groups selected from halogen, and C1-C6 alkoxy;

$R_{12}$ represents hydrogen, C1-C6 alkyl, C2-C6 alkenyl, C1-C6 alkoxy-C1-C3 alkyl, C1-C6 alkylthio-C1-C3 alkyl, C1-C6 alkoxycarbonyl-C1-C3 alkyl; or phenyl, or benzyl which is unsubstituted or substituted with at least one group selected from halogen, and halogenated C1-C6 alkyl;

r represents 1, or 2;

m represents 0, 1, or 2;

wherein, the "heterocyclyl" is

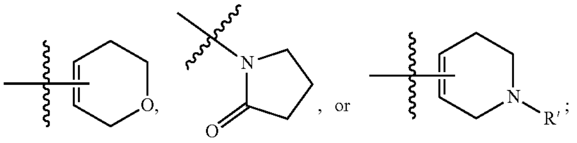

the "aryl" is phenyl, naphthyl, or

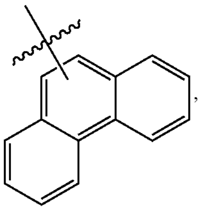

which is unsubstituted or substituted; the "heteroaryl" is

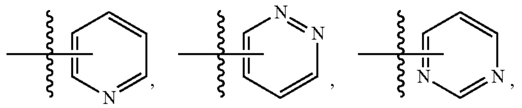

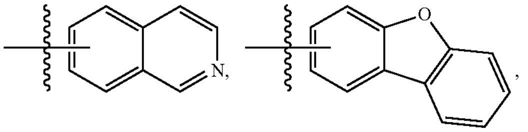

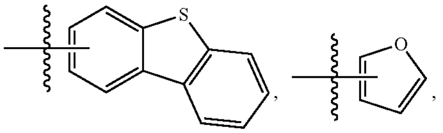

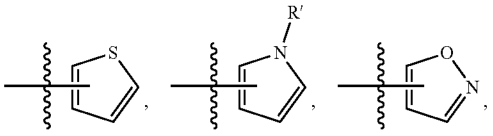

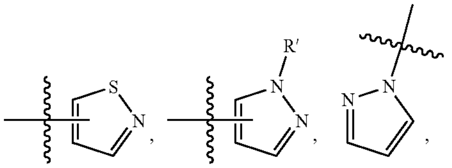

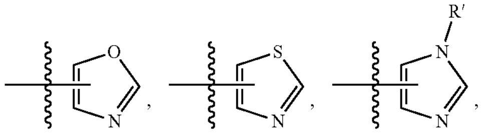

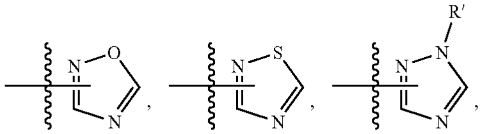

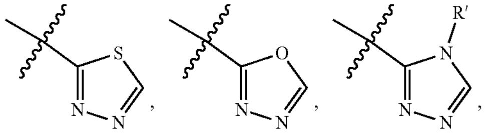

-continued

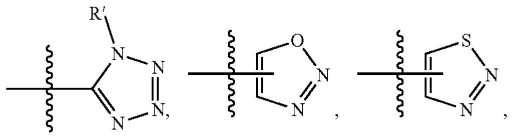

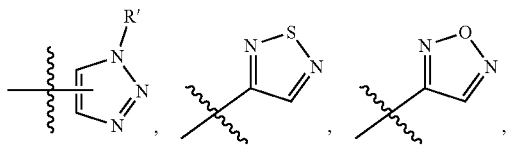

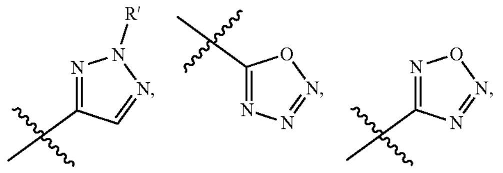

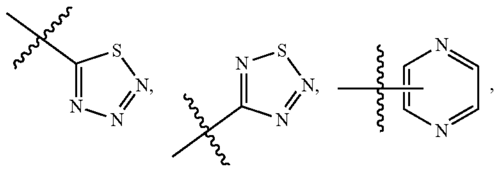

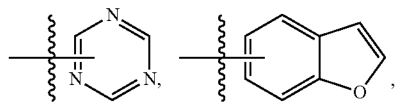

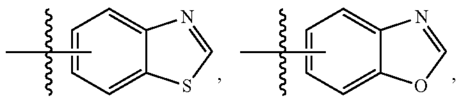

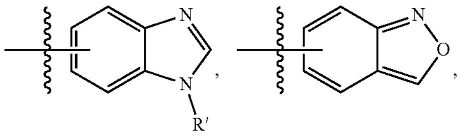

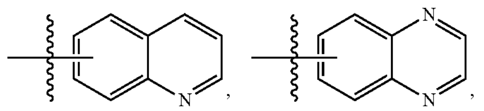

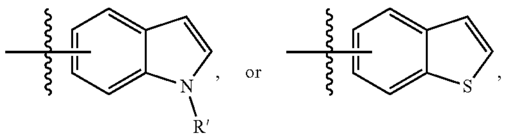

which is unsubstituted or substituted; the aforementioned "substituted" respectively refers to being substituted by 1~3 groups selected from: halogen, nitro, cyano, thiocyano, cyano C1-C3 alkyl, hydroxy, hydroxy C1-C3 alkyl, mercapto, carboxyl, formyl,

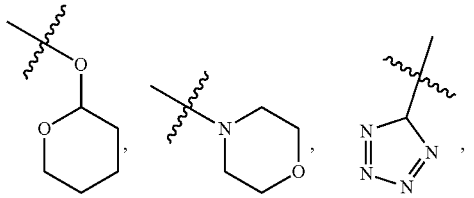

-continued

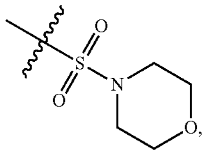,
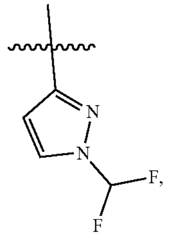

phenyl, phenyl substituted by C1-C6 alkyl, phenoxy, benzyloxy; amino, aminoalkyl, or aminocarbonyl group which is unsubstituted or substituted by one or two groups selected from C1-C6 alkyl, COR", and COOR"; and C1-C6 alkyl, C2-C6 alkenyl, C3-C6 cycloalkyl, C1-C6 alkoxy-C1-C3 alkyl, C1-C6 alkylthio-C1-C3 alkyl, C1-C6 alkylcarbonylthio, C3-C6 cycloalkyl substituted with C1-C6 alkyl, OR", SR", SOR", COR", COOR", or $SO_2R"$, which is with or without halogen; or, two adjacent substitutable positions of the above-mentioned "heterocyclyl", "aryl", "heteroaryl" groups are linked with $—OCH_2CH_2—$, $—OCH_2O—$, $—OCH_2CH_2O—$, or —CH═CH—CH═CH— group to form a ring, wherein the $—OCH_2CH_2—$, $—OCH_2O—$, $—OCH_2CH_2O—$, or —CH═CH—CH═CH— group, which is with or without halogen;

R' each independently represents hydrogen, C1-C6 alkyl, C1-C6 alkylcarbonyl, halogenated C1-C6 alkyl,

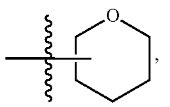

C1-C6 alkoxycarbonyl, C1-C6 alkoxy-C1-C3 alkyl, or benzyl;

R" each independently represents C1-C6 alkyl, or C2-C6 alkenyl.

Further preferably, X represents chlorine, fluorine, bromine, methyl, ethyl, isopropyl, vinyl, allyl, ethynyl, cyclopropyl, trifluoromethyl,

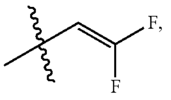 [SMILES: *C=C(F)F]

hydroxy, methoxy, ethyloxy, methylthio, ethylthio,

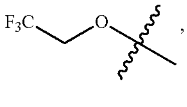,
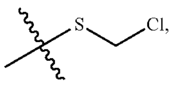

nitro, cyano, methylsulfinyl, ethylsulfinyl, methylsulfonyl, amino, monomethylamino, dimethylamino, acetamido,

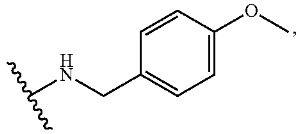
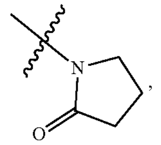
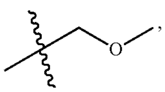
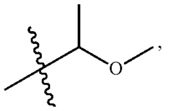
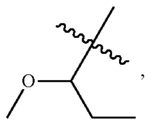
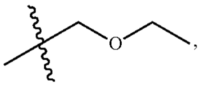
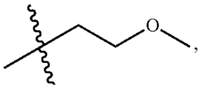
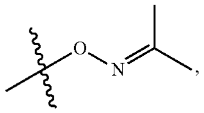

phenyl, phenoxy, or 4-fluorophenyl;

Y represents methyl, ethyl, vinyl, methoxy,

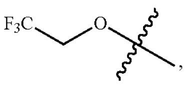

phenoxy, benzyloxy, methylthio, propylthio, tert-butylthio, benzylthio, 4-methoxybenzylthiol, propylsulfinyl, amino, monomethylamino, dimethylamino, anilino, p-methoxybenzylamino, tert-butyl, cyclopropyl, cyclohexyl,

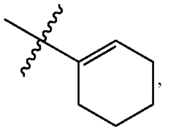 [SMILES: *C1=CCCCC1]

heterocyclyl, aryl, or heteroaryl;

M represents

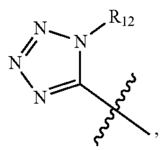
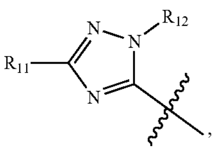
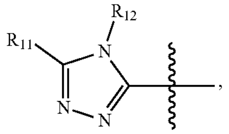
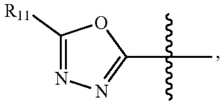
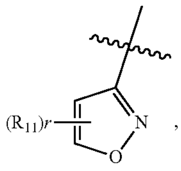
, or
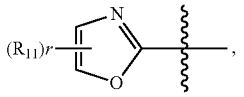

which is unsubstituted or substituted;

$R_{11}$ each independently represents hydrogen, methyl, ethyl, n-propyl, isopropyl, cyclopropyl, monochloromethyl, trifluoromethyl, methoxy, isopropyloxy, methylthio, fluorine, chlorine, bromine, iodine, dimethylamino, ethylamino, cyano, nitro, acetyl, methoxycarbonyl; phenyl which is unsubstituted or substituted by 1, 2, or 3 groups selected from chlorine, and methoxy; pyridyl,

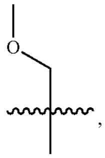, 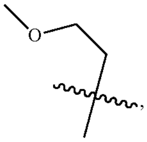, 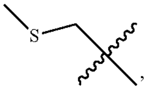,

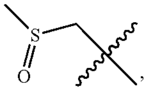, 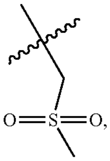, 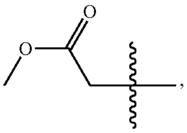,

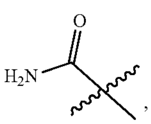, 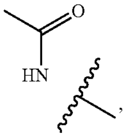, 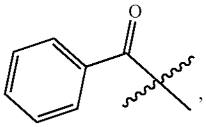,

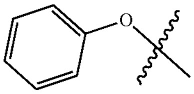, 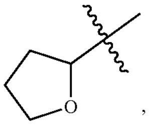, 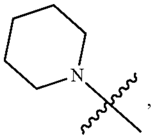,

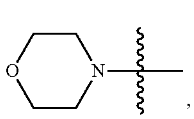, 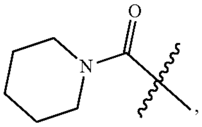, 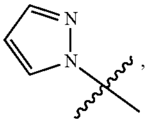,

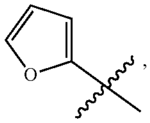, 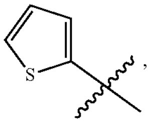, 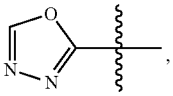,

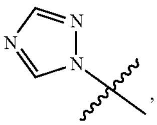, 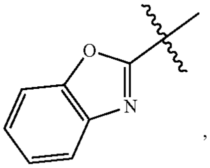, or

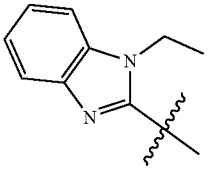;

$R_{12}$ each independently represents hydrogen, methyl, ethyl, n-propyl, isopropyl, allyl,

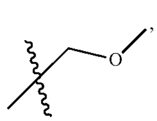, 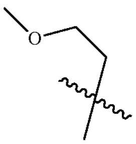, 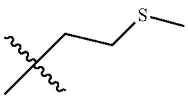,

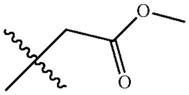;

or phenyl, or benzyl which is unsubstituted or substituted by 1, 2, or 3 groups selected from chlorine, and trifluoromethyl;

r represents 1, or 2:

wherein, the "heterocyclyl" is

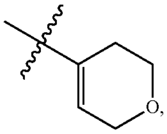, 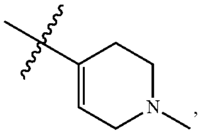,

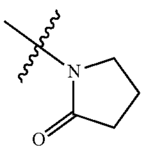, 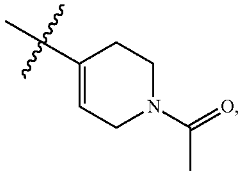, or

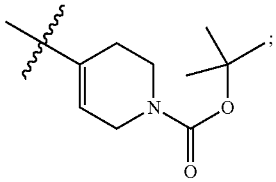;

the "aryl" is phenyl, naphthyl, or

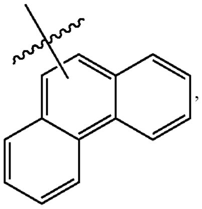, which is unsubstituted or substituted; the "heteroaryl" is

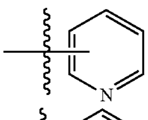, 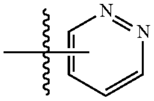, 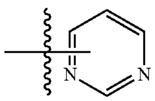,

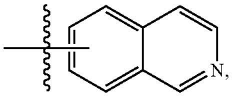, 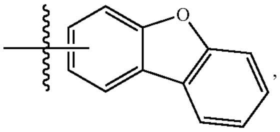,

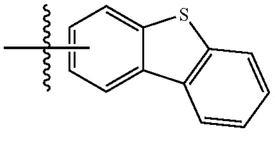, 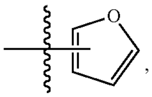,

-continued

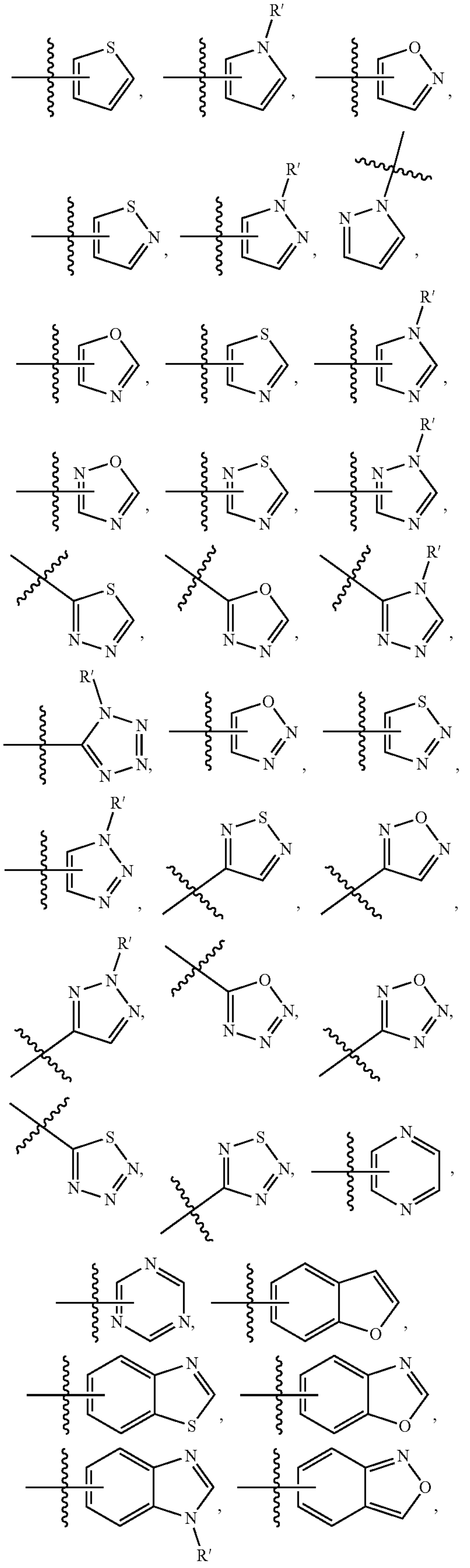

-continued

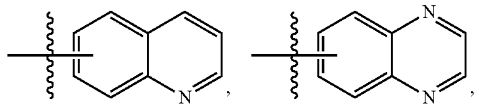

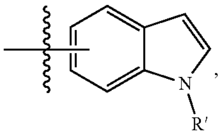, or 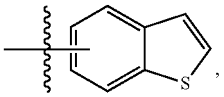, which is unsubstituted or substituted; the aforementioned "substituted" refers to being substituted by 1, 2, or 3 groups selected from: methyl, ethyl, isopropyl, n-butyl, tert-butyl, n-pentyl, vinyl, cyclopropyl,

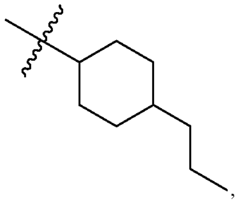 [SMILES: *C1CCC(CCC)CC1], fluorine, chlorine, bromine, iodine, monobromomethyl, difluoromethyl, trifluoromethyl, methoxy, ethoxy, propoxy, butoxy, trifluoromethoxy, hydroxyl, hydroxymethyl, amino, cyano, cyanomethyl, thiocyano, mercapto, nitro, carboxy, formyl, acetyl, methoxycarbonyl, tert-butyloxycarbonyl, methylthio, isopropylthio, methylsulfinyl, methylsulfonyl,

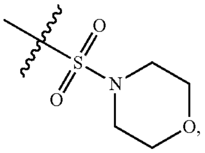 [SMILES: *S(=O)(=O)N1CCOCC1], dimethylamino, aminocarbonyl, dimethylaminocarbonyl, acetylamino,

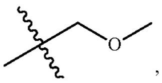, 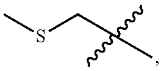, 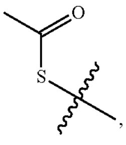,

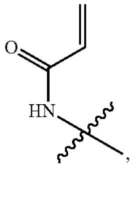, 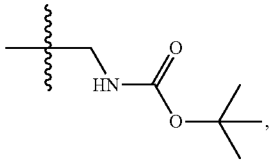, 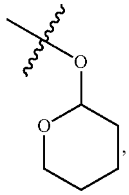,

-continued

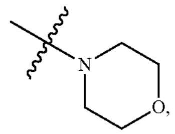, 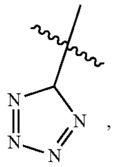, 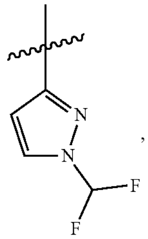, phenyl, 4-ethylphenyl, phenoxy, and benzyloxy; or, two adjacent substitutable positions of the above-mentioned "aryl", "heteroaryl" groups are linked with —$OCH_2CH_2$—, —$OCH_2O$—, —$OCH_2CH_2O$—, or —CH═CH—CH═CH— group to form a ring, wherein the —$OCH_2CH_2$—, —$OCH_2O$—, —$OCH_2CH_2O$—, or —CH═CH—CH═CH— group is with or without halogen;

R' each independently represents hydrogen, methyl, ethyl, n-propyl, isopropyl, difluoromethyl, 3,3,3-trifluoroethyl, benzyl,

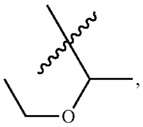, or 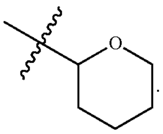.

It should be particularly pointed out that when X is fluorine, Y is not amino, monomethylamino, monoethylamino and monopropylamino; when M is

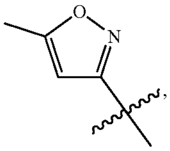 [SMILES: *c1cc(C)on1],

X and Y are not methyl at the same time.

The structural formula of the derivative is

I-1

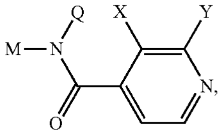

wherein Q represents hydrogen. -alkyl-$Q_1$, $OQ_2$, $SQ_2$, $COQ_2$, $COOQ_2$, $CON(Q_3)_2$, $N(Q_3)_2$, $NQ_4COOQ_2$, $NQ_4CON(Q_3)_2$; alkyl, alkenyl, alkynyl, or cycloalkyl, which is with or without halogen; or arylalkyl, or heteroarylalkyl, which is unsubstituted or substituted;

$Q_1$ each independently represents alkenyl, alkynyl, or cycloalkyl, which is with or without halogen; CN, $OQ_{11}$, $OCOQ_{11}$, $COOQ_{11}$, $COQ_{11}$, —O—(C═O)—O-$Q_{11}$, $OSO_2Q_{12}$, $SO_2OQ_{11}$, —$S(O)_pQ_{12}$, $N(Q_{13})_2$, $CON(Q_{13})_2$, $SO_2N(Q_{13})_2$, $NQ_{14}COQ_{11}$, $NQ_{14}SO_2Q_{12}$, or —O—(C═O)—$N(Q_{13})_2$;

$Q_2$, and $Q_{11}$ each independently represent hydrogen; alkyl, alkenyl, alkynyl, cycloalkyl, cycloalkylalkyl, cycloalkenyl, or alkoxyalkyl, which is with or without halogen; or heterocyclyl, heterocyclylalkyl, heterocyclyloxyalkyl, aryl, arylalkyl, aryloxyalkyl, heteroaryl, heteroarylalkyl, or heteroaryloxyalkyl, which is unsubstituted or substituted;

$Q_{12}$ each independently represents alkyl, alkenyl, alkynyl, cycloalkyl, cycloalkylalkyl, cycloalkenyl, or alkoxyalkyl, which is with or without halogen; or heterocyclyl, heterocyclylalkyl, aryl, arylalkyl, heteroaryl, or heteroarylalkyl, which is unsubstituted or substituted;

$Q_3$, $Q_4$, $Q_{13}$, and $Q_{14}$ each independently represent hydrogen, nitro, alkoxyaminocarbonyl, trialkylsilyl, dialkylphosphonyl, $N(Q_{21})_2$, $CON(Q_{21})_2$, $OQ_{21}$, $COQ_{21}$, $CO_2Q_{21}$, $COSQ_{21}$, $OCOQ_{21}$, $S(O)_pQ_{22}$, alkyl, haloalkyl, alkenyl, haloalkenyl, alkynyl, haloalkynyl, cycloalkyl, cycloalkenyl, halocycloalkyl, alkoxyalkyl, cycloalkylalkyl, aryl, arylalkyl, aryloxy, aryloxyalkyl, arylalkyloxy, arylcarbonyl, arylsulfonyl, heteroaryl, heteroarylalkyl, heteroaryloxy, heteroaryloxyalkyl, heteroarylalkyloxy, heteroarylcarbonyl, heteroarylsulfonyl, heterocyclyl, heterocyclylalkyl, heterocyclyloxy, heterocyclooxyalkyl, heterocyclylalkyloxy, heterocyclylcarbonyl, heterocyclylsulfonyl, aryl-$NQ_{21}$-alkyl, heteroaryl-$NQ_{21}$-alkyl, or heterocyclyl-$NQ_{21}$-alkyl, wherein the last 35 groups as mentioned each are independently substituted by 0, 1, 2, or 3 groups selected from the group consisting of cyano, halogen, nitro, cyanothio, $OQ_{21}$, $S(O)_pQ_{22}$, $N(Q_{21})_2$, $NQ_{21}OQ_{21}$, $COQ_{21}$, $OCOQ_{21}$, $SCOQ_{22}$, $NQ_{21}COQ_{21}$, $NQ_{21}SO_2Q_{22}$, $CO_2Q_{21}$, $COSQ_{21}$, $CON(Q_{21})_2$, and alkoxyalkoxy carbonyl;

$Q_{21}$ each independently represents hydrogen, alkyl, alkenyl, alkynyl, cycloalkyl, or cycloalkylalkyl;

$Q_{22}$ each independently represents alkyl, alkenyl, alkynyl, cycloalkyl, or cycloalkylalkyl;

p each independently represents 0, 1, or 2.

Preferably, Q represents hydrogen, —(C1-C6)alkyl-$Q_1$, $OQ_2$, $SQ_2$, $COQ_2$, $COOQ_2$, $CON(Q_3)_2$, $N(Q_3)_2$, $NQ_4COOQ_2$, $NQ_4CON(Q_3)_2$; C1-C6 alkyl, C2-C6 alkenyl, C2-C6 alkynyl, or C3-C6 cycloalkyl, which is with or without halogen; or aryl-C1-C6 alkyl, or heteroaryl-C1-C6 alkyl, which is unsubstituted or substituted;

$Q_1$ each independently represents C2-C6 alkenyl, C2-C6 alkynyl, or C3-C6 cycloalkyl, which is with or without halogen; CN, $OQ_{11}$, $OCOQ_{11}$, $COOQ_{11}$, $COQ_{11}$, —O—(C═O)—O-$Q_{11}$, $OSO_2Q_{12}$, $SC_2OQ_{11}$, —$S(O)_pQ_{12}$, $N(Q_{13})_2$, $CON(Q_{13})_2$, $SO_2N(Q_{13})_2$, $NQ_{14}COQ_{11}$, $NQ_{14}SO_2Q_{12}$, or —O—(C═O)—$N(Q_{13})_2$;

$Q_2$, and $Q_{11}$ each independently represent hydrogen; C1-C6 alkyl, C2-C6 alkenyl, C2-C6 alkynyl, C3-C6 cycloalkyl, C3-C6 cycloalkyl-C1-C6 alkyl, C3-C6 cycloalkenyl, or C1-C6 alkoxy-C1-C6 alkyl, which is with or without halogen; or heterocyclyl, heterocyclyl-C1-C6 alkyl, heterocyclyloxy-C1-C6 alkyl, aryl, aryl-C1-C6 alkyl, aryloxy-C1-C6 alkyl, heteroaryl, heteroaryl-C1-C6 alkyl, or heteroaryloxy-C1-C6 alkyl, which is unsubstituted or substituted;

$Q_{12}$ each independently represents C1-C6 alkyl, C2-C6 alkenyl, C2-C6 alkynyl, C3-C6 cycloalkyl, C3-C6 cycloalkyl-C1-C6 alkyl, C3-C6 cycloalkenyl, or C1-C6 alkoxy-C1-C6 alkyl, which is with or without halogen; or heterocyclyl, heterocyclyl-C1-C6 alkyl, aryl, aryl-C1-C6 alkyl, heteroaryl, or heteroaryl-C1-C6 alkyl, which is unsubstituted or substituted;

$Q_3$, $Q_4$, $Q_{13}$, and $Q_{14}$ each independently represent hydrogen, nitro, C1-C6 alkoxyaminocarbonyl, tri-C1-C6 alkylsilyl, di-C1-C6 dialkylphosphonyl, $N(Q_{21})_2$, $CON(Q_{21})_2$, $OQ_{21}$, $COQ_{21}$, $CO_2Q_{21}$, $COSQ_{21}$, $OCOQ_{21}$, $S(O)_pQ_{22}$, C1-C6 alkyl, halo-C1-C6 alkyl, C2-C6 alkenyl, halo-C2-C6 alkenyl, C2-C6 alkynyl, halo-C2-C6 alkynyl, C3-C6 cycloalkyl, C3-C6 cycloalkenyl, halo-C3-C6 cycloalkyl, C1-C6 alkoxy-C1-C6 alkyl, C3-C6 cycloalkyl-C1-C6 alkyl, aryl, aryl-C1-C6 alkyl, aryloxy, aryloxy-C1-C6 alkyl, aryl-C1-C6 alkyloxy, arylcarbonyl, arylsulfonyl, heteroaryl, heteroaryl-C1-C6 alkyl, heteroaryloxy, heteroaryloxy-C1-C6 alkyl, heteroaryl-C1-C6 alkyloxy, heteroarylcarbonyl, heteroarylsulfonyl, heterocyclyl, heterocyclyl-C1-C6 alkyl, heterocyclyloxy, heterocyclooxy-C1-C6 alkyl, heterocyclyl-C1-C6 alkyloxy, heterocyclylcarbonyl, heterocyclylsulfonyl, aryl-$NQ_{21}$-(C1-C6)alkyl, heteroaryl-$NQ_{21}$-(C1-C6)alkyl, or heterocyclyl-$NQ_{21}$-(C1-C6)alkyl, wherein the last 35 groups as mentioned each are independently substituted by 0, 1, 2, or 3 groups selected from the group consisting of cyano, halogen, nitro, cyanothio, $OQ_{21}$, $S(O)_pQ_{22}$, $N(Q_{21})_2$, $NQ_{21}OQ_{21}$, $COQ_{21}$, $OCOQ_{21}$, $SCOQ_{22}$, $NQ_{21}COQ_{21}$, $NQ_{21}SO_2Q_{22}$, $CO_2Q_{21}$, $COSQ_{21}$, $CON(Q_{21})_2$, and C1-C6 alkoxy-C1-C6 alkoxycarbonyl;

$Q_{21}$ each independently represents hydrogen, C1-C6 alkyl, C2-C6 alkenyl, C2-C6 alkynyl, C3-C6 cycloalkyl, or C3-C6 cycloalkyl-C1-C6 alkyl;

$Q_{22}$ each independently represents C1-C6 alkyl, C2-C6 alkenyl, C2-C6 alkynyl, C3-C6 cycloalkyl, or C3-C6 cycloalkyl-C1-C6 alkyl;

p each independently represents 0, 1, or 2.

In addition, the derivatives also include salts commonly used in pesticides, for example, it can be processed into an metal salt, an amine salt, a sulfonium salt or a phosphonium salt; or, when a basic moiety is present in the molecule, it can be processed into, for example, a sulfate, a hydrochloride, a nitrate, a phosphate, etc. When these salts are used as herbicides in agriculture or horticulture, they are also included in the present invention. In the present invention, the "metal salt" may be, for example, an alkali metal salt, an alkaline earth metal salt, an aluminum salt or an iron salt; the "alkali metal salt" may be, for example, a sodium salt, a potassium salt or a lithium salt, preferably a sodium salt or a potassium salt. In the present invention, the "alkaline earth metal salt" may be, for example, a calcium salt or a magnesium salt, preferably a calcium salt. In the present invention, the "amine salt" may be, for example, a secondary alkylamine salt, a tertiary alkylamine salt or a quaternary alkylammonium salt; a primary alkanolamine salt, a secondary alkanolamine salt, a tertiary alkanolamine salt or a quaternary alkanoammonium salt; a primary alkylalkanolamine salt, a secondary alkylalkanolamine salt, a tertiary alkylalkanolamine salt or a quaternary alkylalkanolammonium salt; or a primary alkoxyalkanolamine salt, a secondary alkoxyalkanolamine salt, a tertiary alkoxyalkanolamine salt or a quaternary alkoxyalkanolammonium salt, preferably, wherein the alkyl, alkanol and alkoxy are independently saturated and independently contain 1-4 carbon atoms, and may also be substituted by phenyl and/or halogen, more preferably, ethanolamine salt, dimethylethanolamine salt, triethanolamine salt, dimethylamine salt, triethylamine salt, isopropylamine salt, choline salt, diglycolamine salt,

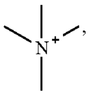,
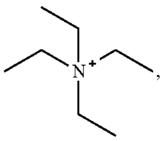,
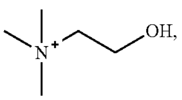

-continued

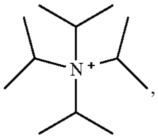,
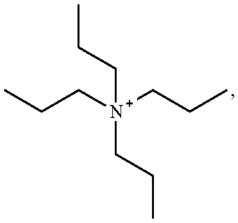,

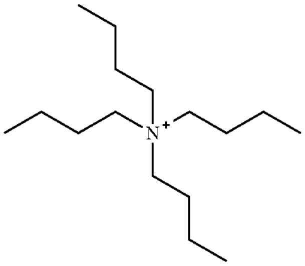
or

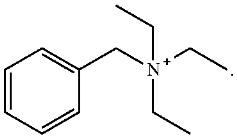.

In the present invention, the "sulfonium salt" and "phosphonium salt" may be, for example, an alkylsulfonium salt, an alkylphosphonium salt or an alkanolphosphonium salt, preferably, wherein the alkyl is independently saturated and independently contain 1-4 carbon atoms, and may also be substituted by phenyl and/or halogen, more preferably,

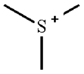
or
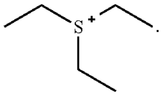.

Solvates of the compounds of the invention are also included in the invention.

Wherein, unless otherwise specified, the "heterocyclyl" of the present invention includes but not limited to,

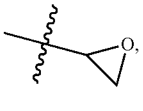,
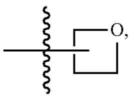,
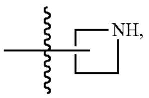,
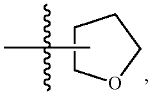,
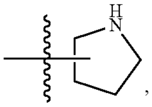,
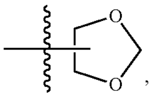,
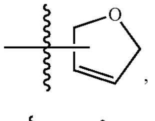,
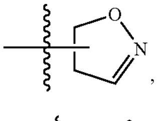,
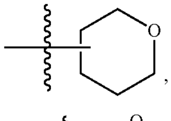,
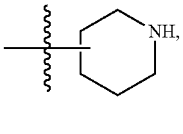,
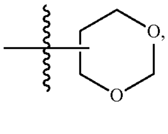,
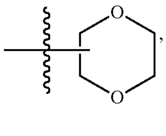

-continued
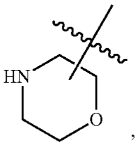
,
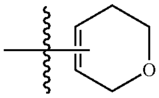
, or
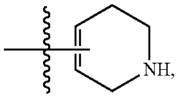
which has 0, 1 or 2 oxo groups; the "aryl" includes but not limited to, phenyl, naphthyl,
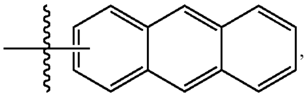
, or
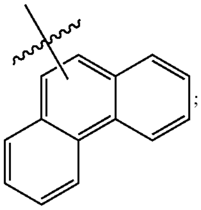
;
the "heteroaryl" is an aromatic cyclic group having, for example, 3 to 6 ring atoms and optionally fused with a benzo ring, 1 to 4 (for example, 1, 2, 3 or 4) of the ring atoms are heteroatoms (for example, oxygen, nitrogen and/or sulfur). For example,
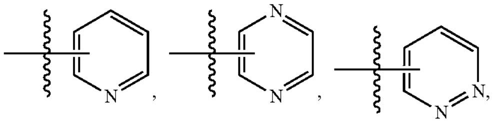
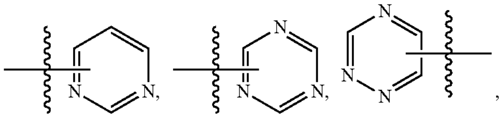
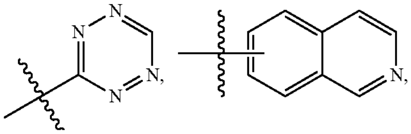
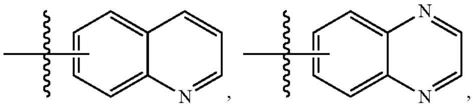
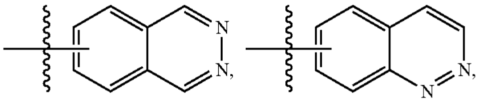
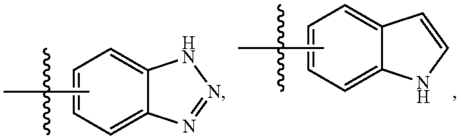
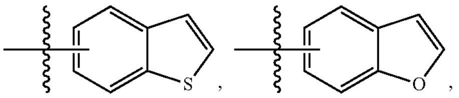
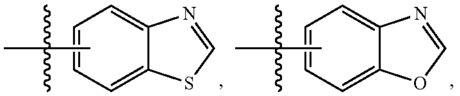
-continued
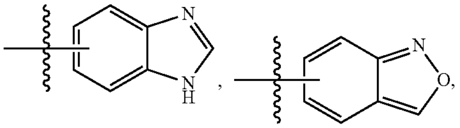
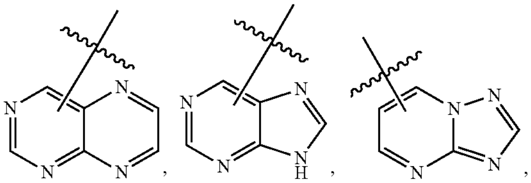
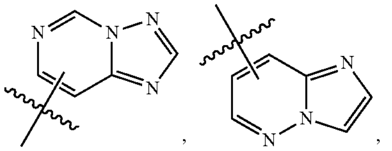
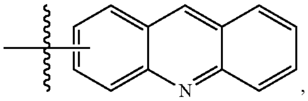
,
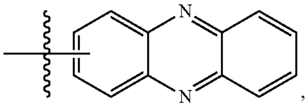
,
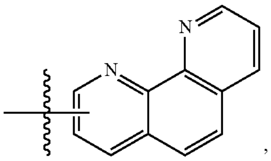
,
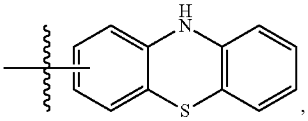
,
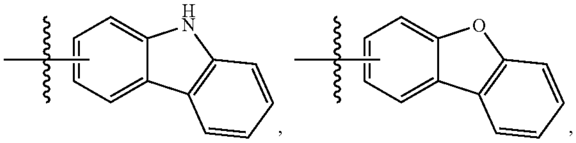
,
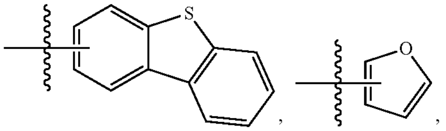
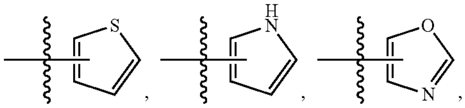
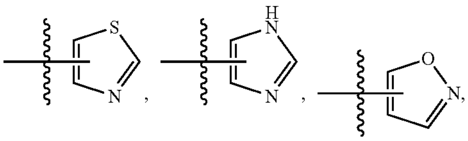
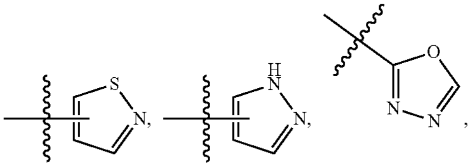

-continued

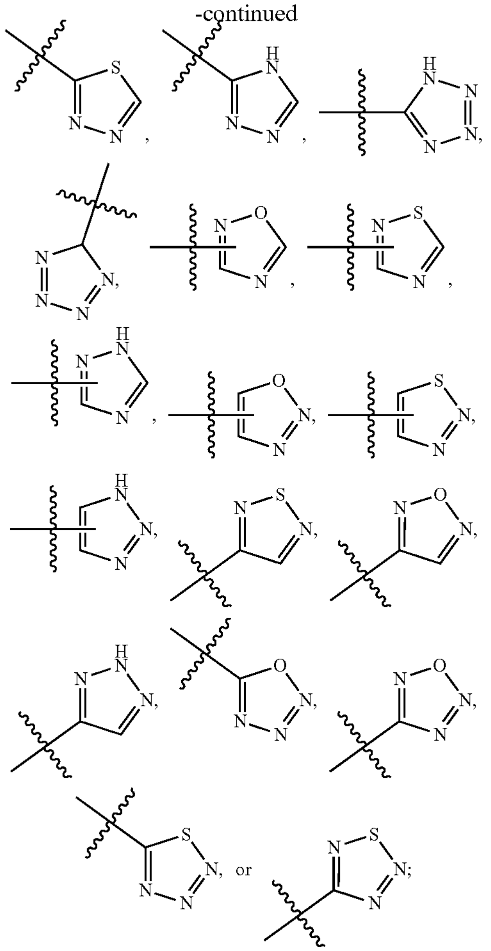

, or ;

the above-mentioned groups are respectively unsubstituted or substituted by at least one group selected from: halogen, nitro, cyano, thiocyano, cyanoalkyl, mercapto, hydroxy, hydroxyalkyl, carboxyl, formyl, trialkylsilyl, dialkylphosphonyl; heterocyclyl, heterocyclylalkyl, aryl, arylalkyl, heteroaryl, or heteroarylalkyl, which is unsubstituted or substituted; alkyl, alkenyl, alkynyl, cycloalkyl, cycloalkenyl, cycloalkylalkyl, cycloalkyl substituted by alkyl, OR", SR", -alkyl-OR", —O-alkyl-OR", -alkyl-SR", COR", -alkyl-COR", —O-alkyl-COR", COOR", -alkyl-COOR", —O-alkyl-COOR", COSR", SOR", $SO_2R$", —O—$SO_2R$", -alkyl-$SO_2R$", OCOR", -alkyl-OCOR", or SCOR" group, which is with or without halogen; and amino, aminoalkyl, aminocarbonyl, aminocarbonylalkyl, or aminosulfonyl group which is unsubstituted or substituted by one or two groups selected from R", COR", COOR", $SO_2R$", and OR", wherein the R", COR", COOR", $SO_2R$", or OR" is with or without halogen; or, two adjacent substitutable positions of the above-mentioned "heterocyclyl", "aryl", "heteroaryl" groups are linked with —$OCH_2CH_2$—, —$OCH_2O$—, —$OCH_2CH_2O$— or —CH═CH—CH═CH— group to form a ring, wherein the —$OCH_2CH_2$—, —$OCH_2O$—, —$OCH_2CH_2O$— or —CH═CH—CH═CH— group is with or without halogen;

R" each independently represents alkyl, alkenyl, alkynyl, cycloalkyl, cycloalkylalkyl, cycloalkenyl; or heterocyclyl, heterocyclylalkyl, aryl, arylalkyl, heteroaryl, or heteroarylalkyl, which is unsubstituted or substituted.

Preferably, the above-mentioned groups are respectively unsubstituted or substituted by at least one group selected from: halogen, nitro, cyano, thiocyano, cyano C1-C6 alkyl, mercapto, hydroxy, hydroxy C1-C6 alkyl, carboxyl, formyl, tri(C1-C6 alkyl)silyl, di(C1-C6 alkyl)phosphonyl; heterocyclyl, heterocyclyl-C1-C6 alkyl, aryl, aryl-C1-C6 alkyl, heteroaryl, or heteroaryl-C1-C6 alkyl, which is unsubstituted or substituted; C1-C6 alkyl, C2-C6 alkenyl, C2-C6 alkynyl, C3-C6 cycloalkyl, C3-C6 cycloalkenyl, C3-C6 cycloalkyl-C1-C6 alkyl, C3-C6 cycloalkyl substituted by C1-C6 alkyl, OR", SR", —(C1-C6 alkyl)-OR", —O—(C1-C6 alkyl)-OR", —(C1-C6 alkyl)-SR", COR", —(C1-C6 alkyl)-COR", —O—(C1-C6 alkyl)-COR", COOR", —(C1-C6 alkyl)-COOR", —O—(C1-C6 alkyl) —COOR", COSR", SOR", $SO_2R$", —O—$SO_2R$", —(C1-C6 alkyl)-$SO_2R$", OCOR", —(C1-C6 alkyl) —OCOR", or SCOR", which is with or without halogen; and amino, amino-C1-C6 alkyl, aminocarbonyl, aminocarbonyl-C1-C6 alkyl, or aminosulfonyl group, which is unsubstituted or substituted by one or two groups selected from R", COR", COOR", $SO_2R$", and OR", wherein the R", COR", COOR", $SO_2R$", or OR" is with or without halogen; or, two adjacent substitutable positions of the above-mentioned "heterocyclyl", "aryl", "heteroaryl" groups are linked with —$OCH_2CH_2$—, —$OCH_2O$—, —$OCH_2CH_2O$—, or —CH═CH—CH═CH— group to form a ring, wherein the —$OCH_2CH_2$—, —$OCH_2O$—, —$OCH_2CH_2O$—, or —CH═CH—CH═CH— group is with or without halogen;

R" each independently represents C1-C6 alkyl, C2-C6 alkenyl, C2-C6 alkynyl, C3-C6 cycloalkyl, C3-C6 cycloalkyl-C1-C6 alkyl, C3-C6 cycloalkenyl; or heterocyclyl, heterocyclyl-C1-C6 alkyl, aryl, aryl-C1-C6 alkyl, heteroaryl, or heteroaryl-C1-C6 alkyl, which is unsubstituted or substituted.

More preferably, the "heterocyclyl" is

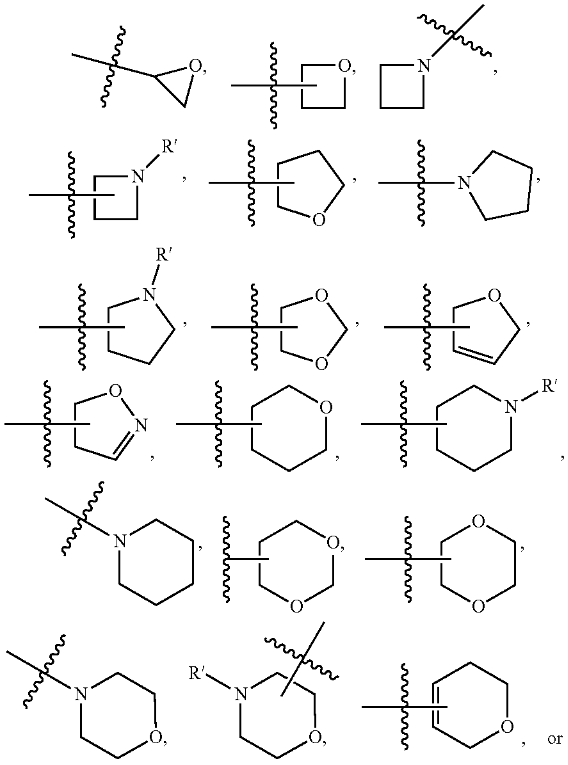

, or

-continued
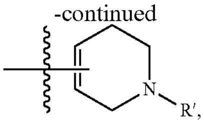,
which has 0, 1, or 2 oxo groups; the “aryl” is phenyl, naphthyl,
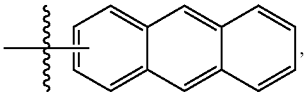, or
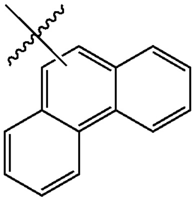;
the “heteroaryl” is
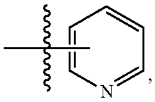, 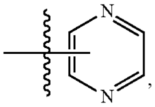, 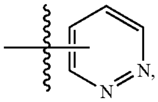
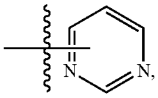 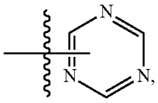 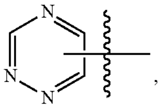,
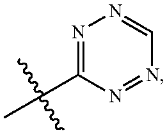 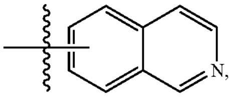
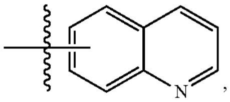, 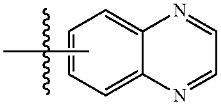,
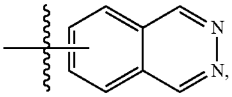 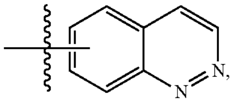
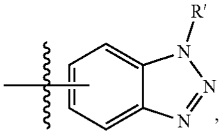, 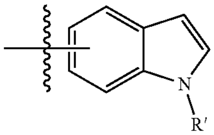,
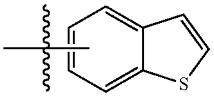, 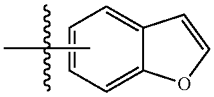,
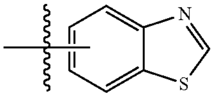, 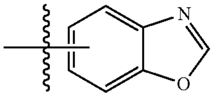,
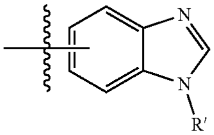, 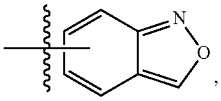,
-continued
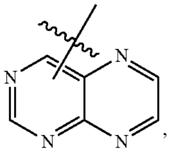, 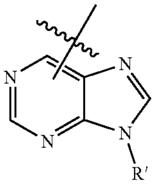, 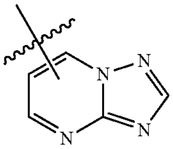,
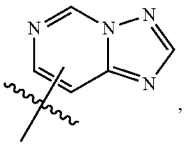, 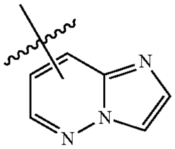,
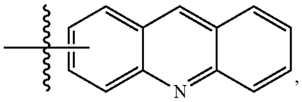
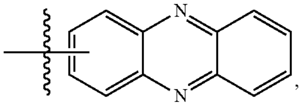, 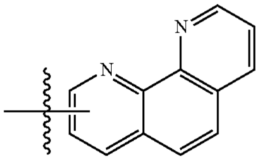,
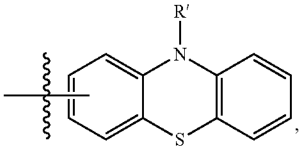
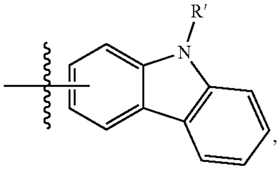, 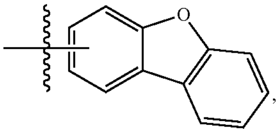,
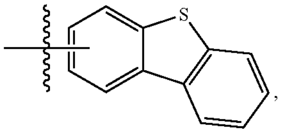, 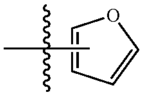,
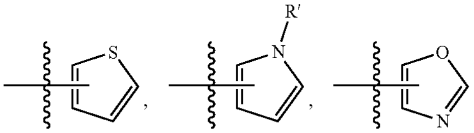,
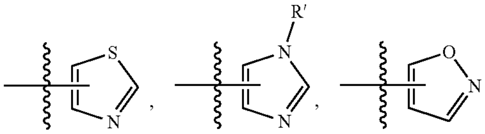,
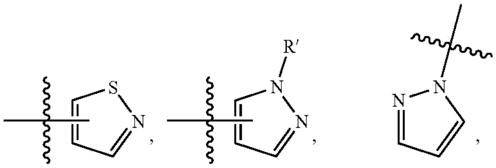,
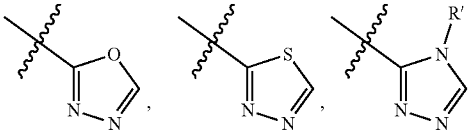, -continued

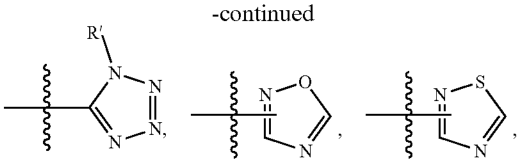

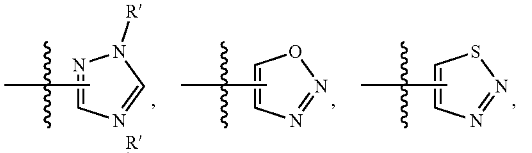

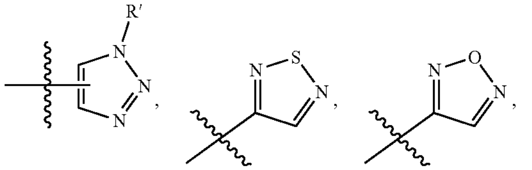

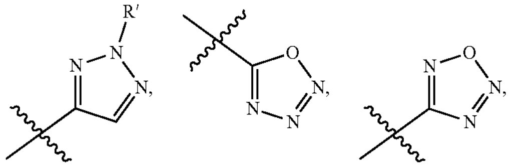

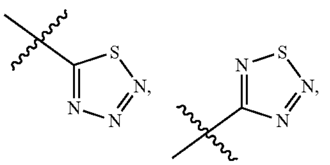

or

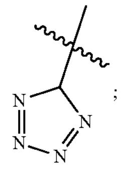

;

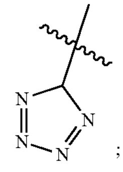

;

the above-mentioned groups are respectively unsubstituted or substituted by 1~3 groups selected from: halogen, nitro, cyano, thiocyano, cyano C1-C6 alkyl, mercapto, hydroxy, hydroxy C1-C6 alkyl, carboxyl, formyl;

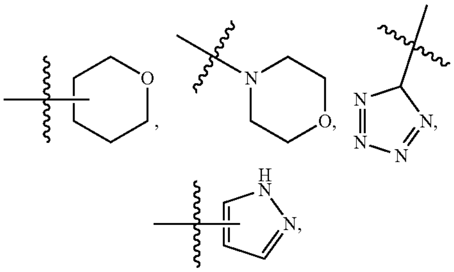

phenyl, or benzyl group, which is unsubstituted or substituted by 1~3 groups selected from halogen, hydroxy, nitro, cyano, amino, carboxyl, C1-C6 alkyl with or without halogen, C2-C6 alkenyl with or without halogen, C2-C6 alkynyl with or without halogen, C3-C6 cycloalkyl with or without halogen, C1-C6 alkoxy with or without halogen, C1-C6 alkoxycarbonyl with or without halogen, C1-C6 alkylacyl with or without halogen, C1-C6 alkylacyloxy with or without halogen, C1-C6 alkylamino with or without halogen, and C1-C6 alkylsulfonyl with or without halogen; C1-C6 alkyl, C2-C6 alkenyl, C2-C6 alkynyl, C3-C6 cycloalkyl, C3-C6 cycloalkyl-C1-C6 alkyl, C3-C6 cycloalkyl substituted by C1-C6 alkyl, OR", SR", —(C1-C6) alkyl —OR", —O—(C1-C6) alkyl —OR", —(C1-C6) alkyl —SR", COR", —(C1-C6) alkyl —COR", —O—(C1-C6) alkyl —COR", COOR", —(C1-C6) alkyl —COOR", —O—(C1-C6) alkyl —COOR", COSR", SOR", $SO_2R$", —O—$SO_2R$", —(C1-C6) alkyl —$SO_2R$", OCOR", —(C1-C6) alkyl —OCOR", or SCOR" group, which is with or without halogen; and amino, aminoalkyl, aminocarbonyl, or aminosulfonyl group, which is unsubstituted or substituted by one or two groups selected from R", COR", COOR", $SO_2R$", and OR", wherein the R", COR", COOR", $SO_2R$", or OR" is with or without halogen; or, two adjacent substitutable positions of the above-mentioned “heterocyclyl”, “aryl”, “heteroaryl” groups are linked with —$OCH_2CH_2$—, —$OCH_2O$—, —$OCH_2CH_2O$—, or —CH═CH—CH═CH— group to form a ring, wherein the —$OCH_2CH_2$—, —$OCH_2O$—, —$OCH_2CH_2O$—, or —CH═CH—CH═CH— group is with or without halogen;

R' each independently represents hydrogen, nitro, hydroxy, amino; C1-C6 alkyl, C2-C6 alkenyl, C2-C6 alkynyl, C3-C6 cycloalkyl, C3-C6 cycloalkenyl, C3-C6 cycloalkyl-C1-C6 alkyl,

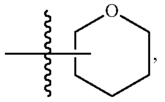

C1-C6 alkoxy, C2-C6 alkenyloxy, C2-C6 alkynyloxy, C3-C6 cycloalkyloxy, C1-C6 alkoxy-C1-C6 alkyl, C1-C6 alkoxy carbonyl, C1-C6 alkylthiocarbonyl, C1-C6 alkylsulfonyl, C1-C6 alkylsulfonyl-C1-C6 alkyl, C1-C6 alkylcarbonyl, C1-C6 alkylcarbonyl-C1-C6 alkyl, C1-C6 alkylacyloxy, C1-C6 alkylamino, C1-C6 alkylaminocarbonyl, C1-C6 alkoxyaminocarbonyl, C1-C6 alkoxycarbonyl-C1-C6 alkyl, C1-C6 alkylaminocarbonyl-C1-C6 alkyl, tri (C1-C6 alkyl)silyl, or di(C1-C6 alkyl)phosphonyl, which is with or without halogen; or phenyl, or benzyl which is unsubstituted or substituted by 1~3 groups selected from halogen, hydroxy, nitro, cyano, amino, carboxyl, C1-C6 alkyl with or without halogen, C2-C6 alkenyl with or without halogen, C2-C6 alkynyl with or without halogen, C3-C6 cycloalkyl with or without halogen, C1-C6 alkoxy with or without halogen, C1-C6 alkoxy carbonyl with or without halogen, C1-C6 alkylacyl with or without halogen, C1-C6 alkylacyloxy with or without halogen, C1-C6 alkylamino with or without halogen, and C1-C6 alkylsulfonyl with or without halogen;

R" each independently represents C1-C6 alkyl, C2-C6 alkenyl, C2-C6 alkynyl, C3-C6 cycloalkyl, C3-C6 cycloalkyl-C1-C6 alkyl, C3-C6 cycloalkenyl; or

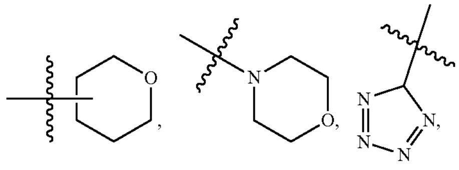

phenyl, or benzyl which is unsubstituted or substituted by 1~3 groups selected from halogen, hydroxy, nitro, cyano, amino, carboxyl, C1-C6 alkyl with or without halogen, C2-C6 alkenyl with or without halogen, C2-C6 alkynyl with or without halogen, C3-C6 cycloalkyl with or without halogen, C1-C6 alkoxy with or without halogen, C1-C6 alkoxy carbonyl with or without halogen, C1-C6 alkylacyl with or without halogen, C1-C6 alkylacyloxy with or without halogen, C1-C6 alkylamino with or without halogen, and C1-C6 alkylsulfonyl with or without halogen.

In the definition of the compound represented by the above Formula and all of the following structural formulas, the technical terms used, whether used alone or used in compound word, represent the following substituents: an alkyl having more than two carbon atoms may be linear or branched. For example, the alkyl in the compound word "-alkyl-OR[1]" may be —$CH_2$—, —$CH_2CH_2$—, —CH($CH_3$)—, —$C(CH_3)_2$—, and the like. The alkyl is, for example, $C_1$ alkyl; methyl; $C_2$ alkyl; ethyl; $C_3$ alkyl; propyl such as n-propyl or isopropyl; $C_4$ alkyl; butyl such as n-butyl, isobutyl, tert-butyl or 2-butyl; $C_5$ alkyl; pentyl such as n-pentyl; $C_6$ alkyl; hexyl such as n-hexyl, isohexyl and 1,3-dimethylbutyl. Similarly, the alkenyl is, for example, allyl, 1-methylprop-2-en-1-yl, 2-methylprop-2-en-1-yl, but-2-en-1-yl, butyl-3-en-1-yl, 1-methylbut-3-en-1-yl and 1-methylbut-2-en-1-yl. The alkynyl is, for example, propargyl, but-2-yn-1-yl, but-3-yn-1-yl, 1-methylbut-3-yn-1-yl. The multiple bond(s) may be placed at any position of each unsaturated group. The cycloalkyl is a carbocyclic saturated ring system having, for example, three to six carbon atoms, such as cyclopropyl, cyclobutyl, cyclopentyl or cyclohexyl. Similarly, the cycloalkenyl is monocycloalkenyl having, for example, three to six carbon ring members, such as cyclopropenyl, cyclobutenyl, cyclopentenyl, and cyclohexenyl, wherein double bond can be at any position. Halogen is fluorine, chlorine, bromine or iodine.

If a group is substituted by a group, which should be understood to mean that the group is substituted by one or more groups, which are same or different groups, selected from the mentioned groups. In addition, the same or different substitution characters contained in the same or different substituents are independently selected, and may be the same or different. This is also applicable to ring systems formed with different atoms and units. Meanwhile, the scope of the claims will exclude those compounds chemically unstable under standard conditions known to those skilled in the art.

In addition, unless specifically defined, the term occurring after multiple juxtaposed substituents (separated by "," or "or") in the present invention has a limiting effect on each of the substituents, such as the term "with or without halogen" in "alkyl, alkenyl, alkynyl, cycloalkyl, cycloalkenyl, cycloalkylalkyl, or cycloalkenylalkyl, which is with or without halogen" has a limiting effect on each of the following groups "alkyl", "alkenyl", "alkynyl", "cycloalkyl", "cycloalkenyl", "cycloalkylalkyl" and "cycloalkenylalkyl"; a group (including heterocyclyl, aryl, heteroaryl, etc.) without being specified a linking site may be attached at any site, including a C or N site; if it is substituted, the substituent may be substituted at any site as long as it comply with the valence bond theory. For example, if the heteroaryl

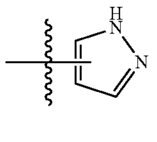

is substituted with one methyl, it can be

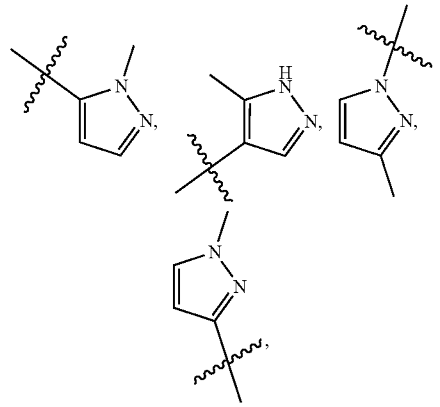

etc.

Depending on the property of substituents and the linkage manner thereof, the compound of Formula I may exist as a stereoisomer. For example, if a compound has one or more asymmetric carbon atoms, it may has enantiomers and diastereomers. The stereoisomer can be obtained from the mixtures obtained in the preparation by conventional separation methods, for example by chromatographic separation. The stereoisomer may also be prepared selectively by using stereoselective reactions and using optically active starting materials and/or auxiliaries. The present invention also relates to all stereoisomers and mixtures thereof which are included in the general Formula I but are not specifically defined.

A method for preparing the 4-pyridinyl formamide compound I, which comprises the following steps:

subjecting the compound of the general formula II and the compound of the general formula III to amidation reaction to obtain the compound of the general formula I, the chemical reaction scheme is as follows:

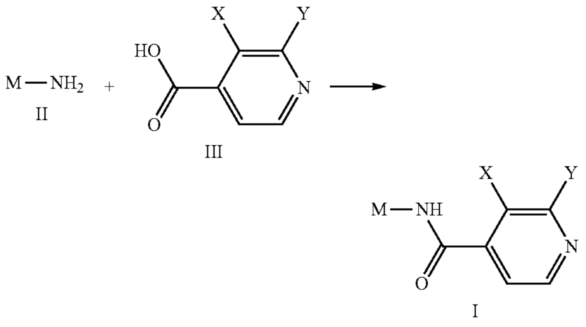

The reaction is carried out in the presence of a halogenating agent, a catalyst and a solvent; preferably, the halogenating agent is $SOCl_2$, the catalyst is 4-dimethylaminopyridine, and the solvent is pyridine;

Or the reaction is carried out in the presence of a condensing agent and a solvent; preferably, the condensing agent is CDI, DCC, DBU or a combination thereof, and the solvent is methylene chloride.

The preparation method of its derivative 1-1 includes the following steps:

subjecting the compound of the general formula I and Hal-Q to reaction to obtain the compound of the general formula I-1, the chemical reaction scheme is as follows:

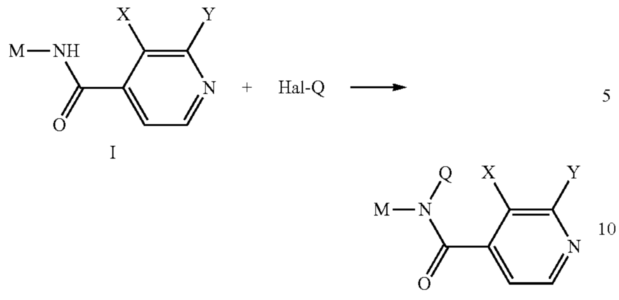

I-1

Wherein, Hal represents halogen, preferably fluorine, chlorine or bromine;

The reaction is carried out in the presence of a base and a solvent; preferably, the base is selected from one or a combination of potassium carbonate and sodium carbonate, and the solvent is one or more selected from the group consisting of DCM, DCE, ACN, THF, and DMF; or the reaction is carried out in the presence of a catalyst and a solvent; preferably, the catalyst is 4-dimethylaminopyridine, and the solvent is pyridine.

In addition, the compound of the general formula II and the compound of the general formula III are known in principle, and can be prepared, for example, by the methods described in WO199835967A2, CN103459386A, CN103987701A, WO2017055146A, WO2013017559A1, WO2012028579A1, WO2011035874A1. Moreover, the compounds of the present invention can also be prepared by referring to the methods described therein.

A herbicidal composition comprising (i) the 4-pyridinyl formamide compound or derivative thereof as shown in general formula I; preferably, further comprising (ii) one or more further herbicides and/or safeners; more preferably, further comprising (iii) agrochemically acceptable formulation auxiliaries.

A method for controlling a weed which comprises applying a herbicidally effective amount of at least one of the 4-pyridinyl formamide compound or derivative thereof or the herbicidal composition as above-described to a plant or a weed area.

Use of at least one of the 4-pyridinyl formamide compound or derivative thereof or the herbicidal composition as above-described for controlling a weed, preferably, wherein the 4-pyridinyl formamide compound or derivative thereof is used for preventing and/or controlling a weed in a useful crop, wherein the useful crop is a transgenic crop or a crop treated by gene editing technique.

The compounds of the formula I according to the invention have an outstanding herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being a restriction to certain species. Examples of weed species on which the active compounds act efficiently are, from amongst the monocotyledons, *Avena, Lolium, Alopecurus, Phalaris, Echinochloa, Digitaria, Setaria* and also *Cyperus* species from the annual sector and from amongst the perennial species *Agropyron, Cynodon, Imperata* and *Sorghum*, and also perennial *Cyperus* species.

In the case of the dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from amongst the annuals, and *Convolvulus, Cirsium, Rumex* and *Artemisia* in the case of the perennial weeds. The active compounds according to the invention also effect outstanding control of harmful plants which occur under the specific conditions of rice growing such as, for example, *Echinochloa, Sagittaria, Alisma, Eleocharis, Scirpus* and *Cyperus*. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. In particular, the compounds according to the invention exhibit excellent activity against *Apera spica venti, Chenopodium album, Lamium purpureum, Polygonum convulvulus, Stellaria media, Veronica* hederifolia, *Veronica persica, Viola* tricolor and against *Amaranthus, Galium* and *Kochia* species.

Although the compounds according to the invention have an excellent herbicidal activity against monocotyledonous and dicotyledonous weeds, crop plants of economically important crops such as, for example, wheat, barley, rye, rice, corn, sugarbeet, cohon and soya, are not damaged at all, or only to a negligible extent. In particular, they have excellent compatibility in cereals, such as wheat, barley and corn, in particular wheat. For these reasons, the present compounds are highly suitable for selectively controlling undesired plant growth in plantings for agricultural use or in plantings of ornamentals.

Owing to their herbicidal properties, these active compounds can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested produce are known.

The use of the compounds of the formula I according to the invention or their derivatives in economically important transgenic crops of useful and ornamental plants, for example of cereal, such as wheat, barley, rye, oats, millet, rice, manIok and corn, or else in crops of sugarbeet, cotton, soya, rapeseed, potato, tomato, pea and other vegetable species is preferred. The compounds of the formula I can preferably be used as herbicides in crops of useful plants which are resistant or which have been made resistant by genetic engineering toward the phytotoxic effects of the herbicides.

Conventional ways for preparing novel plants which have modified properties compared to known plants comprise, for example, traditional breeding methods and the generation of mutants. Alternatively, novel plants having modified properties can be generated with the aid of genetic engineering methods (see, for example, EP-A0 221 044, EP-A0 131 624). For example, there have been described several cases of:

- genetically engineered changes in crop plants in order to modify the starch synthesized in the plants (for example WO 92/11376, WO 92/14827, WO 91/19806),
- transgenic crop plants which are resistant to certain herbicides of the glufosinate- (cf., for example, EP-A 0 242 236, EP-A 0 242 246) or glyphosate-type (WO 92/00377), or of the sulfonylurea-type (EP-A0 257 993, U.S. Pat. No. 5,013,659A),
- transgenic crop plants, for example cohon, having the ability to produce *Bacillus thuringiensis* toxins (Bt toxins) which impart resistance to certain pests to the plants (EP-A 0 142 924, EP-A0 193 259),
- transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim, 2nd edition 1996, or Christou, "Trends in Plant Science" 1 (1996) 423-431). In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the above-mentioned gene product.

To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to whole plants using known techniques. The transgenic plants can in principle be plants of any desired plant species, i.e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants. The invention therefore also provides for the use of the compounds according to the invention as herbicides for controlling harmful plants in transgenic crop plants.

In addition, the substances according to the invention have outstanding growth-regulating properties in crop plants. They engage in the plant metabolism in a regulating manner and can this be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledon and dicotyledon crops because lodging can be reduced hereby, or prevented completely.

The compounds according to the invention can be applied in the customary formulations in the form of wettable powders, emulsifiable concentrates, sprayable solutions, dusts or granules. The invention therefore also provides herbicidal compositions comprising compounds of the formula I. The compounds of the formula I can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil dispersions (OD), oil- or water-based dispersions, oil-miscible solutions, dusts (DP), capsule suspensions (CS), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes. These individual formulation types are known in principle and are described, for example, in Winnacker-Kiichler, "Chemische Technologie" [Chemical Technology], Volume 7, C. Hauser Verlag Munich, 4th. Edition 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzfliichenaktive Athylenoxidaddkte" [Surface-active ethylene oxide adducts], Wiss. Verlagagesell. Stuttgart 1976; Winnacker-Kiichler, "Chemische Technologie" [Chemical Technology], Volume 7, C. Hauser Verlag Munich, 4th Edition 1986.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane-6,6'-disulfonate, sodium dibutyinaphthalenesulfona-te or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth. Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers. Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, pp. 8-57. For further details on the formulation of crop protection products, see for example G. C. Klingman, "Weed Control as a Science", John Wiley and Sons Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations generally contain from 0.1 to 99% by weight, in particular from 0.1 to 95% by weight, of active compound of the formula F In wettable powders the concentration of active compound is, for example, from about 10 to 99% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, the formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Suitable active compounds which can be combined with the active compounds according to the invention in mixed formulations or in a tank mix are, for example, known active compounds as described in for example World Herbicide New Product Technology Handbook, China Agricultural Science and Farming Techniques Press, 2010.9 and in the literature cited therein. For example the following active compounds may be mentioned as herbicides which can be combined with the compounds of the formula I (note: the compounds are either named by the "common name" in accordance with the International Organization for Standardization (ISO) or by the chemical names, if appropriate together with a customary code number): acetochlor, butachlor, alachlor, propisochlor, metolachlor, s-metolachlor, pretilachlor, propachlor, ethachlor, napropamide, R-left handed napropamide, propanil, mefenacet, diphenamid, diflufenican, ethaprochlor, beflubutamid, bromobutide, dimethenamid, dimethenamid-P, etobenzanid, flufenacet, thenylchlor, metazachlor, isoxaben, flamprop-M-methyl, flamprop-M-propyl, allidochlor, pethoxamid, chloranocryl, cyprazine, mefluidide, monalide, delachlor, prynachlor, terbuchlor, xylachlor, dimethachlor, cisanilide, trimexachlor, clomeprop, propyzamide, pentanochlor, carbetamide, benzoylprop-ethyl, cyprazole, butenachlor, tebutam, benzipram, mogrton, dichlofluanid, naproanilide, diethatyl-ethyl, naptalam, flufenacet, EL-177, benzadox, chlorthiamid, chlorophthalimide, isocarbamide, picolinafen, atrazine, simazine, prometryn, cyanatryn, simetryn, ametryn, propazine, dipropetryn, SSH-108, terbutryn, terbuthylazine, triaziflam, cyprazine, proglinazine, trietazine, prometon, simetone, aziprotryne, desmetryn, dimethametryn, procyazine, mesoprazine, sebuthylazine, secbumeton, terbumeton, methoprotryne, cyanatryn, ipazine, chlorazine, atraton, pendimethalin, eglinazine, cyanuric acid, indaziflam, chlorsulfuron, metsulfuron-methyl, bensulfuron methyl, chlorimuron-ethyl, tribenuron-methyl, thifensulfuron-methyl, pyrazosulfuron-ethyl, mesosulfuron, iodosulfuron-methyl sodium, foramsulfuron, cinosulfuron, triasulfuron, sulfometuron methyl, nicosulfuron, ethametsulfuron-methyl, amidosulfuron, ethoxy sulfur on, cyclosulfamuron, rimsulfuron, azimsulfuron, flazasulfuron, monosulfuron, monosulfuron-ester, flucarbazone-sodium, flupyrsulfuron-methyl, halosulfuron-methyl, oxasulfuron, imazosulfuron, primisulfuron, propoxycarbazone, prosulfuron, sulfosulfuron, trifloxysulfuron, triflusulfuron-methyl, tritosulfuron, sodium metsulfuron methyl, flucetosulfuron, HNPC-C, orthosulfamuron, propyrisulfuron, metazosulfuron, acifluorfen, fomesafen, lactofen, fluoroglycofen, oxyfluorfen, chlomitrofen, aclonifen, ethoxyfen-ethyl, bifenox, nitrofluorfen, chlomethoxyfen, fluorodifen, fluoronitrofen, furyloxyfen, nitrofen, TOPE, DMNP, PPG1013, AKH-7088, halosafen, chlortoluron, isoproturon, linuron, diuron, dymron, fluometuron, benzthiazuron, methabenzthiazuron, cumyluron, ethidimuron, isouron, tebuthiuron, buturon, chlorbromuron, methyldymron, phenobenzuron, SK-85, metobromuron, metoxuron, afesin, monuron, siduron, fenuron, fluothiuron, neburon, chloroxuron, noruron, isonoruron, 3-cyclooctyl-1, thiazfluron, tebuthiuron, difenoxuron, parafluron, methylamine tribunil, karbutilate, trimeturon, dimefuron, monisouron, anisuron, methiuron, chloreturon, tetrafluron, phenmedipham, phenmedipham-ethyl, desmedipham, asulam, terbucarb, barban, propham, chlorpropham, rowmate, swep, chlorbufam, carboxazole, chlorprocarb, fenasulam, BCPC, CPPC, carbasulam, butylate, benthiocarb, vemolate, molinate, triallate, dimepiperate, esprocarb, pyributicarb, cycloate, avadex, EPTC, ethiolate, orbencarb, pebulate, prosulfocarb, tiocarbazil, CDEC, dimexano, isopobnate, methiobencarb, 2,4-D butyl ester, MCPA-Na, 2,4-D isooctyl ester, MCPA isooctyl ester, 2,4-D sodium salt, 2,4-D dimethyla mine salt, MCPA-thioethyl, MCPA, 2,4-D propionic acid, high 2,4-D propionic acid salt, 2,4-D butyric acid, MCPA propionic acid, MCPA propionic acid salt, MCPA butyric acid, 2,4,5-D, 2,4,5-D propionic acid, 2,4,5-D butyric acid, MCPA amine salt, dicamba, erbon, chlorfenac, saison, TBA, chloramben, methoxy-TBA, diclofop-methyl, fluazifop-butyl, fluazifop-p-butyl, haloxyfop-methyl, haloxyfop-P, quizalofop-ethyl, quizalofop-p-ethyl, fenoxaprop-ethy, fenoxaprop-p-ethyl, propaquizafop, cyhalofop-butyl, metamifop, clodinafop-propargyl, fenthiaprop-ethyl, chloroazifop-propynyl, poppenate-methyl, trifopsime, isoxapyrifop, paraquat, diquat, oryzalin, ethalfluralin, isopropalin, nitralin, profluralin, prodinamine, benfluralin, fluchloraline, dinitramina, dipropalin, chlomidine, methalpropalin, dinoprop, glyphosate, anilofos, glufosinate ammonium, amiprophos-methyl, sulphosate, piperophos, bialaphos-sodium, bensulide, butamifos, phocarb, 2,4-DEP, H-9201, zytron, imazapyr, imazethapyr, imazaquin, imazamox, imazamox ammonium salt, imazapic, imazamethabenz-methyl, fluroxypyr, fluroxypyr isooctyl ester, clopyralid, picloram, trichlopyr, dithiopyr, haloxydine, 3,5,6-trichloro-2-pyridinol, thiazopyr, fluridone, aminopyralid, diflufenzopyr, triclopyr-butotyl, Cliodinate, sethoxydim, clethodim, cycloxydim, alloxydim, clefoxydim, butroxydim, tralkoxydim, tepraloxydim, buthidazole, metribuzin, hexazinone, metamitron, ethiozin, ametridione, amibuzin, bromoxynil, bromoxynil octanoate, ioxynil octanoate, ioxynil, dichlobenil, diphenatrile, pyraclonil, chloroxynil, iodobonil, flumetsulam, florasulam, penoxsulam, metosulam, cloransulam-methyl, diclosulam, pyroxsulam, benfuresate, bispyribac-sodium, pyribenzoxim, pyriftalid, pyriminobac-methyl, pyrithiobac-sodium, benzobicylon, mesotrione, sulcotrione, tembotrione, tefuryltrione, bicyclopyrone, ketodpiradox, isoxaflutole, clomazone, fenoxasulfone, methiozolin, fluazolate, pyraflufen-ethyl, pyrazolynate, difenzoquat, pyrazoxyfen, benzofenap, nipyraclofen, pyrasulfotole, topramezone, pyroxasulfone, cafenstrole, flupoxam, aminotriazole, amicarbazone, azafenidin, carfentrazone-ethyl, sulfentrazone, bencarbazone, benzfendizone, butafenacil, bromacil, isocil, lenacil, terbacil, flupropacil, cinidon-ethyl, flumiclorac-pentyl, flumioxazin, propyzamide, MK-129, flumezin, pentachlorophenol, dinoseb, dinoterb, dinoterb acetate, dinosam, DNOC, chloronitrophene, medinoterb acetate, dinofenate, oxadiargyl, oxadiazon, pentoxazone, Flufenacet, fluthiacet-methyl, fentrazamide, flufenpyr-ethyl, pyrazon, brompyrazon, metflurazon, kusakira, dimidazon, oxapyrazon, norflurazon, pyridafol, quinclorac, quinmerac, bentazone, pyridate, oxaziclomefone, benazolin, clomazone, cinmethylin, ZJ0702, pyribambenz-propyl, indanofan, sodium chlorate, dalapon, trichloroacetic acid, monochloroacetic acid, hexachloroacetone, flupropanate, cyperquat, bromofenoxim, epronaz, methazole, flurtamone, benfuresate, ethofumesate, tioclorim, chlorthal, fluorochloridone, tavron, acrolein, bentranil, tridiphane, chlorfenpropmethyl, thidiarizonaimin, phenisopham, busoxinone, methoxyphenone, saflufenacil, clacyfos, chloropon, alorac, diethamquat, etnipromid, iprymidam, ipfencarbazone, thiencarbazone-methyl, pyrimisulfan, chlorflurazole, tripropindan, sulglycapin, prosulfalin, cambendichlor, aminocyclopyrachlor, rodethanil, benoxacor, fenclorim, flurazole, fenchlorazole-ethyl, cloquintocet-mexyl, oxabetrinil, MG/91, cyometrinil, DKA-24, mefenpyr-diethyl, furilazole, fluxofenim, isoxadifen-ethyl, dichlormid, halauxifen-methyl, DOW florpyrauxifen, UBH-509, D489, LS 82-556, KPP-300, NC-324, NC-330, KH-218, DPX-N8189, SC-0744, DOWC0535, DK-8910, V-53482, PP-600, MBH-001, KIH-9201, ET-751, KIH-6127 and KIH-2023.

In the context of the present specification, if an abbreviation of a generic name of an active compound is used, it includes in each case all customary derivatives, such as esters and salts, as well as isomers, in particular optical isomers, especially one or more commercially available forms. If the generic name denotes an ester or a salt, it also includes in each case all other conventional derivatives, such as other esters and salts, free acids and neutral compounds, as well as isomers, in particular optical isomers, especially one or more commercially available forms. The chemical name given to a compound means at least one compound encompassed by the generic name, and generally the preferred compound. In the case of sulfonamides such as sulfonylurea, salts also include salts formed by the exchange of cations with hydrogen atoms in the sulfonamide group. For example, 2,4-D or 2,4-DB derivatives include but are not limited to: 2,4-D or 2,4-DB salt such as sodium salt, potassium salt, dimethylammonium salt, triethanolammonium salt, isopropylamine salt, choline, etc., and 2,4-D or 2,4-DB esters such as methyl ester, ethyl ester, butyl ester, isooctyl ester, etc.; 2-methyl-4-chloro derivatives include but are not limited to: 2-methyl-4-chloro sodium salt, -potassium salt, -dimethylammonium salt, -isopropylamine salt, etc., as well as 2-methyl-4-chloro methyl ester, -ethyl ester, -isooctyl ester, -thioethyl, etc.

For use, the formulations which are present in commercially available form are, if appropriate, diluted in the customary manner, for example using water in the case of wettable powders, emulsifiable concentrates, dispersions and water-dispersible granules. Products in the form of dusts, granules for soil application or broadcasting and sprayable solutions are usually not further diluted with other inert substances prior to use. The application rate of the compounds of the formula I required varies with the external conditions, such as temperature, humidity, the nature of the herbicide used and the like. It can vary within wide limits, for example between 0.001 and 1.0 kg a.i./ha or more of active substance, but it is preferably between 0.005 and 750 g a.i./ha, in particular between 0.005 and 500 g a.i./ha.

SPECIFIC MODE FOR CARRYING OUT THE INVENTION

The following embodiments are used to illustrate the present invention in detail and should not be taken as any limit to the present invention. The scope of the invention would be explained through the Claims.

In view of economics and variety of a compound, we preferably synthesized several compounds, part of which are listed in the following Table A1. The structure and information of a certain compound are shown in Table A1. The compounds in Table A1 are listed for further explication of the present invention, other than any limit therefor. The subject of the present invention should not be interpreted by those skilled in the art as being limited to the following compounds.

TABLE A1
Structures and $^{1}H$ NMR data of compounds
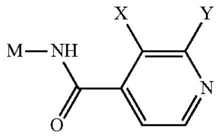
I
| NO. | X | Y | M | $^{1}$HNMR |
|---|---|---|---|---|
| 1-1 | Cl | $CH_3$ | 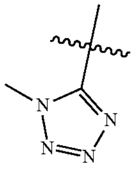 | $^{1}H$ NMR (500 MHz, DMSO-$d_6$) δ 12.05 (s, 1H), 8.52 (d, J = 5.5 Hz, 1H), 7.49 (d, J = 5.5 Hz, 1H), 4.25 (s, 3H), 2.50 (s, 3H). |
| 1-2 | Cl | 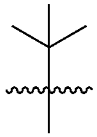 [SMILES: *C(C)(C)C] | 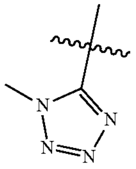 | $^{1}H$ NMR (500 MHz, DMSO-$d_6$) δ 12.05 (s, 1H), 8.47 (d, J = 5.5 Hz, 1H), 7.50 (d, J = 5.5 Hz, 1H), 4.25 (s, 3H), 1.54 (s, 9H). |
| 1-3 | Cl | 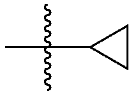 [SMILES: *C1CC1] | 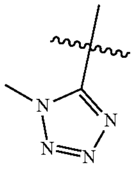 | $^{1}H$ NMR (500 MHz, DMSO-$d_6$) δ 12.04 (s, 1H), 8.45 (d, J = 5.5 Hz, 1H), 7.48 (d, J = 5.5 Hz, 1H), 4.25 (s, 3H), 2.62-2.57 (m, 1H), 1.03-0.94 (m, 2H), 0.95-0.85 (m, 2H). |
| 1-4 | Cl | 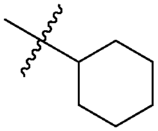 [SMILES: *C1CCCCC1] | 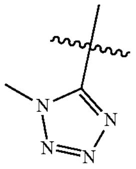 [SMILES: *c1nnnn1C] | $^{1}H$ NMR (500 MHz, DMSO-$d_6$) δ 12.06 (s, 1H), 8.48 ((d, J = 5.5 Hz, 1H), 7.49 (d, J = 5.5 Hz, 1H), 4.25 (s, 3H), 3.05-3.01 (m, 1H), 1.99-1.95 (m, 2H), 1.73-1.70 (m, 2H), 1.60-1.45 (m, 6H). |

TABLE A1-continued
| | | | | |
|---|---|---|---|---|
| 1-5 | Cl | 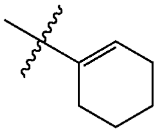 [SMILES: *C1=CCCCC1] | 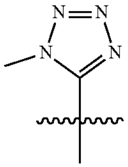 [SMILES: *c1nnnn1C] | $^1$H NMR (500 MHz, DMSO-$d_6$) δ 11.98 (s, 1H), 8.64 (d, J = 5.0 Hz, 1H), 7.63 (d, J = 5.0 Hz, 1H), 6.03 (t, J = 7.0 Hz, 1H), 4.00 (s, 3H), 2.35-2.10 (m, 4H), 1.74 (t, J = 6.0 Hz, 2H), 1.69-1.60 (m, 2H). |
| 1-6 | Cl | 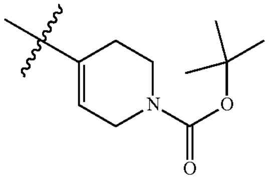 [SMILES: *C1=CCN(C(=O)OC(C)(C)C)CC1] | 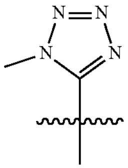 [SMILES: *c1nnnn1C] | $^1$H NMR (500 MHz, DMSO-$d_6$) δ 12.08 (s, 1H), 8.78 (d, J = 5.0 Hz, 1H), 7.23 (d, J = 5.0 Hz, 1H), 6.58-6.53 (m, 1H), 4.32 (s, 3H), 3.55 (t, J = 5.5 Hz, 2H), 3.33 (dt, J = 6.5, 1.5 Hz, 2H), 3.20 (t, J = 5.5, 1.5 Hz, 2H), 1.47 (s, 9H). |
| 1-7 | Cl | 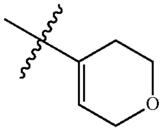 [SMILES: *C1=CCOCC1] | 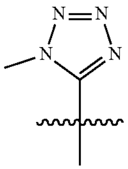 [SMILES: *c1nnnn1C] | $^1$H NMR (500 MHz, DMSO-$d_6$) δ 12.07 (s, 1H), 8.75 (d, J = 5.0 Hz, 1H), 7.38 (d, J = 5.0 Hz, 1H), 6.12-6.09 (m, 1H), 4.31 (s, 3H), 4.20-4.15 (m, 2H), 3.79 (t, J = 5.5 Hz, 2H), 2.16-2.10 (m, 2H). |
| 1-8 | Cl | 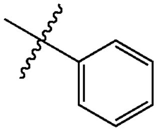 [SMILES: *c1ccccc1] | 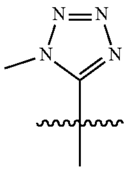 [SMILES: *c1nnnn1C] | 1H NMR (500 MHz, DMSO-d6) δ 12.03 (s, 1H), 8.77 (d, J = 5.0 Hz, 1H), 7.77 (d, J = 5.50 Hz, 1H), 7.69-7.63 (m, 2H), 7.55-7.45 (m, 3H), 3.97 (s, 3H). |
| 1-9 | Cl | 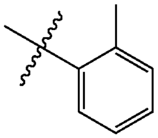 [SMILES: *c1ccccc1C] | 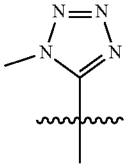 [SMILES: *c1nnnn1C] | 1H NMR (500 MHz, DMSO-d6) δ 12.08 (s, 1H), 8.76 (d, J = 5.0 Hz, 1H), 7.79 (d, J = 5.0 Hz, 1H), 7.33-7.22 (m, 3H), 7.21 (d, J = 7.5 Hz, 1H), 3.99 (s, 3H), 2.07 (s, 3H). |
| 1-10 | Cl | 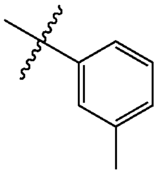 [SMILES: *c1cccc(C)c1] | 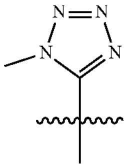 [SMILES: *c1nnnn1C] | $^1$H NMR (500 MHz, DMSO-$d_6$) δ 12.03 (s, 1H), 8.72 (d, J = 5.0 Hz, 1H), 7.89-7.83 (m, 1H), 7.81-7.71 (m, 2H), 7.59 (t, J = 7.5 Hz, 1H), 7.32-7.21 (m, 1H), 4.33 (s, 3H), 2.47 (d, J = 1.5 Hz, 3H). |

TABLE A1-continued
| | | | | |
|---|---|---|---|---|
| 1-11 | Cl | 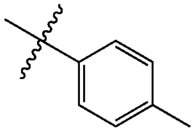 [SMILES: *c1ccc(C)cc1] | 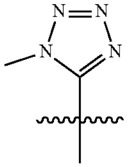 | 1H NMR (500 MHz, DMSO-d6) δ 12.02 (s, 1H), 8.75 (d, J = 5.0 Hz, 1H), 7.73 (d, J = 5.0 Hz, 1H), 7.57 (d, J = 8.0 Hz, 2H), 7.31 (d, J = 8.0 Hz, 2H), 4.00 (s, 3H), 2.37 (s, 3H). |
| 1-12 | Cl | 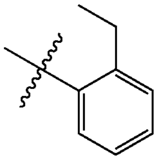 [SMILES: *c1ccccc1CC] | 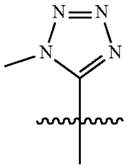 [SMILES: *c1nnnn1C] | $^1$H NMR (500 MHz, DMSO-$d_6$) δ 12.12 (s, 1H), 8.78 (d, J = 5.0 Hz, 1H), 7.89-7.75 (m, 1H), 7.46-7.41 (m, 2H), 7.36-7.27 (m, 1H), 7.20 (d, J = 7.5 Hz, 1H), 4.01 (s, 3H), 3.33 (q, J = 7.5 Hz, 2H), 1.01 (t, J = 7.5 Hz, 3H). |
| 1-13 | Cl | 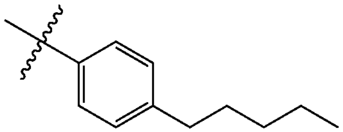 [SMILES: *c1ccc(CCCCC)cc1] | 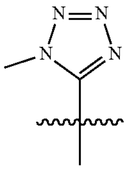 | $^1$H NMR (500 MHz, DMSO-$d_6$) δ 12.04 (s, 1H), 8.74 (d, J = 5.0 Hz, 1H), 7.73 (d, J = 5.0 Hz, 1H), 7.58 (d, J = 8.0 Hz, 2H), 7.32 (d, J = 8.0 Hz, 2H), 3.98 (s, H), 2.62 (t, J = 8.0 Hz, 2H), 1.60-1.29 (m, 6H), 0.85 (t, J = 6.5 Hz, 3H). |
| 1-14 | Cl | 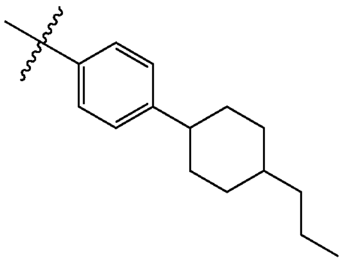 [SMILES: *c1ccc(C2CCC(CCC)CC2)cc1] | 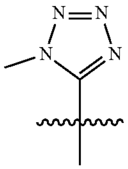 [SMILES: *c1nnnn1C] | $^1$H NMR (500 MHz, DMSO-$d_6$) δ 12.06 (s, 1H), 8.87 (d, J = 5.0 Hz, 1H), 7.78 (d, J = 5.0 Hz, 1H), 7.74-7.69 (m, 2H), 7.52-7.46 (m, 2H), 4.33 (s, 3H), 2.09-1.98 (m, 2H), 1.81-1.67 (m, 4H), 1.35-1.24 (m, 2H), 1.27-1.13 (m, 6H), 0.83 (t, J = 8.0 Hz, 3H). |
| 1-15 | Cl | 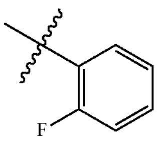 [SMILES: *c1ccccc1F] | 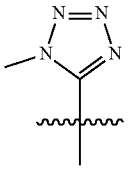 [SMILES: *c1nnnn1C] | $^1$H NMR (500 MHz, DMSO-$d_6$) δ 12.10 (s, 1H), 8.80 (d, J = 4.5 Hz, 1H), 7.85 (d, J = 4.5 Hz, 1H), 7.63-7.55 (m, 1H), 7.51-7.46 (m, 1H), 7.40-7.31 (m, 2H), 3.99 (s, 3H). |

TABLE A1-continued
| | | | | |
|---|---|---|---|---|
| 1-16 | Cl | 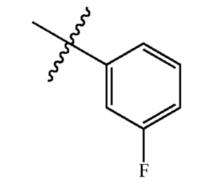 [SMILES: *c1cccc(F)c1] | 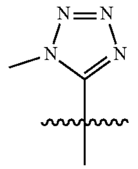 [SMILES: *c1nnnn1C] | $^1$H NMR (500 MHz, DMSO-$d_6$) δ 12.04 (s, 1H), 8.73 (d, J = 5.0 Hz, 1H), 7.87-7.79 (m, 1H), 7.72 (d, J = 5.0 Hz, 1H), 7.69-7.63 (m, 1H), 7.48-7.46 (m, 1H), 7.32-7.20 (m, 1H), 4.33 (s, 3H). |
| 1-17 | Cl | 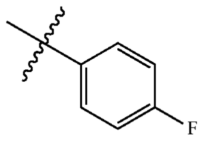 [SMILES: *c1ccc(F)cc1] | 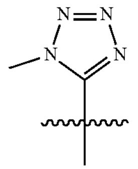 [SMILES: *c1nnnn1C] | 1H NMR (500 MHz, DMSO-d6) δ 12.08 (s, 1H), 8.76 (d, J = 5.0 Hz, 1H), 7.79-7.69 (m, 3H), 7.39-7.26 (m, 2H), 3.99 (s, 3H) |
| 1-18 | Cl | 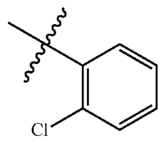 | 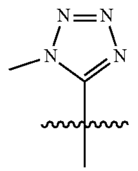 [SMILES: *c1nnnn1C] | $^1$H NMR (500 MHz, DMSO-$d_6$) δ 12.06 (s, 1H), 8.55 (d, J = 5.0 Hz, 1H), 7.85 (dd, J = 7.5, 2.5 Hz, 1H), 7.58 (d, J = 5.0 Hz, 1H), 7.52-7.43 (m, 2H), 7.41-7.37 (m, 1H), 4.26 (s, 3H). |
| 1-19 | Cl | 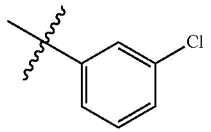 [SMILES: *c1cccc(Cl)c1] | 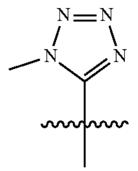 [SMILES: *c1nnnn1C] | $^1$H NMR (500 MHz, DMSO-$d_6$) δ 12.06 (s, 1H), 8.72 (d, J = 5.0 Hz, 1H), 8.02 (t, J = 2.0 Hz, 1H), 7.89-7.71 (m 2H), 7.68 (d, J = 5.0 Hz, 1H), 7.45 (t, J = 7.5 Hz, 1H), 4.33 (s, 3H). |
| 1-20 | Cl | 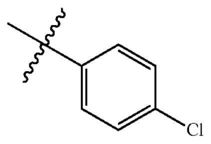 | 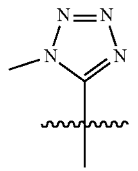 [SMILES: *c1nnnn1C] | 1H NMR (500 MHz, DMSO-d6) δ 12.06 (s, 1H), 8.78 (d, J = 5.0 Hz, 1H), 7.80 (d, J = 5.0 Hz, 1H), 7.70 (d, J = 8.0 Hz, 2H), 7.58 (d, J = 8.0 Hz, 2H), 4.00 (s, 3H). |
| 1-21 | Cl | 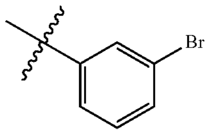 [SMILES: *c1cccc(Br)c1] | 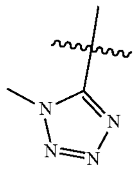 [SMILES: *c1nnnn1C] | $^1$H NMR (500 MHz, DMSO-$d_6$) δ 12.06 (s, 1H), 8.56 (d, J = 5.5 Hz, 1H), 7.96 (t, J = 2.5 Hz, 1H), 7.88-7.86 (m, 1H), 7.61 (d, J = 5.5 Hz, 1H), 7.55-7.52 (m, 1H), 7.45 (t, J = 7.5 Hz, 1H), 4.25 (s, 3H). |

TABLE A1-continued
| | | | | |
|---|---|---|---|---|
| 1-22 | Cl | 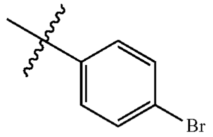 [SMILES: *c1ccc(Br)cc1] | 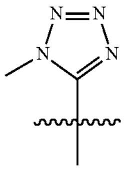 [SMILES: *c1nnnn1C] | 1H NMR (500 MHz, DMSO-d6) δ 12.06 (s, 1H), 8.82 (d, J = 5.0 Hz, 1H), 7.79 (d, J = 5.0 Hz, 1H), 7.72 (d, J = 8.0 Hz, 1H), 7.66-7.60 (m, 2H), 7.56-7.45 (m, 1H), 3.99 (s, 3H). |
| 1-23 | Cl | 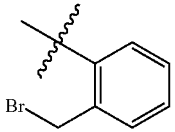 | 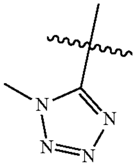 [SMILES: *c1nnnn1C] | $^1$H NMR (500 MHz, DMSO-$d_6$) δ 12.05 (s, 1H), 8.56 (d, J = 5.5 Hz, 1H), 8.06 (dd, J = 7.5, 2.0 Hz, 1H), 7.61 (d, J = 5.5 Hz, 1H), 7.39-7.36 (m, 1H), 7.35-7.29 (m, 2H), 4.73 (s, 2H), 4.25 (s, 3H). |
| 1-24 | Cl | 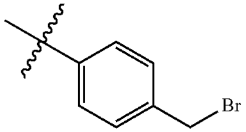 [SMILES: *c1ccc(CBr)cc1] | 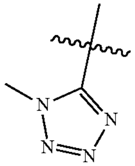 [SMILES: *c1nnnn1C] | $^1$H NMR (500 MHz, DMSO-$d_6$) δ 12.05 (s, 1H), 8.57 (d, J = 5.0 Hz, 1H), 7.96-7.90 (m, 2H), 7.51 (d, J = 5.0 Hz, 1H), 7.3-7.26 (m, 2H), 4.40 (s, 2H), 4.25 (s, 3H). |
| 1-25 | Cl | 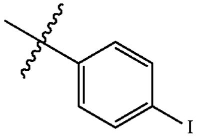 [SMILES: *c1ccc(I)cc1] | 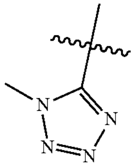 | $^1$H NMR (500 MHz, DMSO-$d_6$) δ 12.04 (s, 1H), 8.57 (d, J = 5.5 Hz, 1H), 7.89-7.82 (m, 2H), 7.72-7.66 (m, 2H), 7.50 (d, J = 5.5 Hz, 1H), 4.26 (s, 3H). |
| 1-26 | Cl | 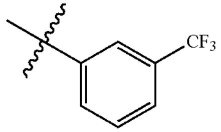 [SMILES: *c1cccc(C(F)(F)F)c1] | 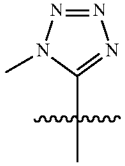 [SMILES: *c1nnnn1C] | $^1$H NMR (500 MHz, DMSO-$d_6$) δ 12.01 (s, 1H), 8.81 (d, J = 5.0 Hz, 1H), 8.06-7.94 (m, 2H), 7.88 (d, J = 8.0 Hz, 1H), 7.84 (s, 1H), 7.80-7.76 (m, 1H), 4.00 (s, 3H). |
| 1-27 | Cl | 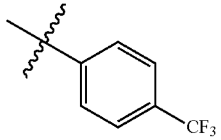 | 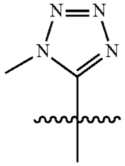 [SMILES: *c1nnnn1C] | $^1$H NMR (500 MHz, DMSO-$d_6$) δ 12.06 (s, 1H), 8.82 (d, J = 5.0 Hz, 1H), 7.98-7.79 (m, 5H), 4.07 (s, 3H). |

TABLE A1-continued
| | | | | |
|---|---|---|---|---|
| 1-28 | Cl | 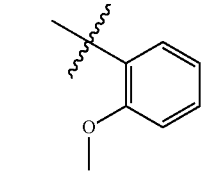 [SMILES: *c1ccccc1OC] | 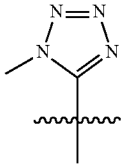 [SMILES: *c1nnnn1C] | $^1$H NMR (500 MHz, DMSO-$d_6$) δ 12.05 (s, 1H), 8.72 (d, J = 5.0 Hz, 1H), 7.75 (d, J = 5.0 Hz, 1H), 7.50-7.42 (m, 1H), 7.26-7.19 (m, 1H), 7.14 (d, J = 8.5 Hz, 1H), 7.06 (t, J = 7.5 Hz, 1H), 3.98 (s, 3H), 3.74 (s, 3H). |
| 1-29 | Cl | 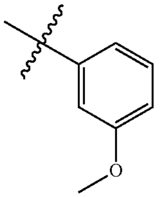 [SMILES: *c1cccc(OC)c1] | 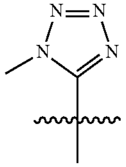 [SMILES: *c1nnnn1C] | $^1$H NMR (500 MHz, DMSO-$d_6$) δ 12.07 (s, 1H), 8.73 (d, J = 5.0 Hz, 1H), 7.73 (d, J = 5.0 Hz, 1H), 7.68-7.57 (m, 1H), 7.33 (t, J = 7.5 Hz, 1H), 7.23 (t, J = 2.0 Hz, 1H), 6.89-6.81 (m, 1H), 4.33 (s, 3H), 3.80 (s, 3H). |
| 1-30 | Cl | 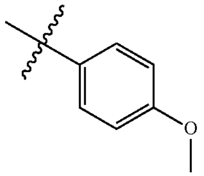 [SMILES: *c1ccc(OC)cc1] | 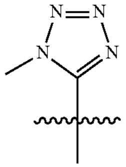 | $^1$H NMR (500 MHz, DMSO-$d_6$) δ 12.02 (s, 1H), 8.73 (d, J = 4.5 Hz, 1H), 7.69 (d, J = 4.5 Hz, 1H), 7.66 (d, J = 8.5 Hz, 2H), 6.88 (d, J = 8.5 Hz, 2H) 3.99 (s, 3H), 3.81 (s, 3H) |
| 1-31 | Cl | 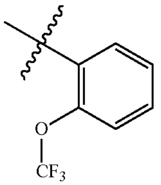 [SMILES: *c1ccccc1OC(F)(F)F] | 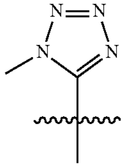 | $^1$H NMR (500 MHz, DMSO-$d_6$) δ 12.13 (s, 1H), 8.79 (d, J = 5.0 Hz, 1H), 7.85 (s, 1H), 7.70-7.65 (m, 1H), 7.58-7.44 (m, 3H), 3.98 (s, 3H). |
| 1-32 | Cl | 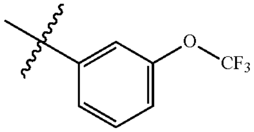 [SMILES: *c1cccc(OC(F)(F)F)c1] | 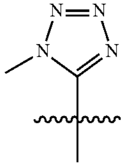 [SMILES: *c1nnnn1C] | $^1$H NMR (500 MHz, DMSO-$d_6$) δ 12.16 (s, 1H), 8.92 (d, J = 5.0 Hz, 1H), 7.94 (d, J = 5.0 Hz, 1H), 7.85 (d, J = 8.0 Hz, 1H), 7.77-7.71 (m, 2H), 7.64 (d, J = 8.0 Hz, 1H), 4.11 (s, 3H). |

TABLE A1-continued
| | | | | |
|---|---|---|---|---|
| 1-33 | Cl | 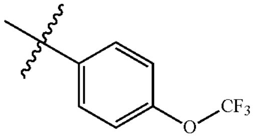 [SMILES: *c1ccc(OC(F)(F)F)cc1] | 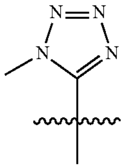 [SMILES: *c1nnnn1C] | $^1$H NMR (500 MHz, DMSO-$d_6$) δ 12.04 (s, 1H), 8.78 (d, J = 4.5 Hz, 1H), 7.82-7.76 (m, 3H), 7.61-7.35 (m, 2H), 4.00 (s, 3H). |
| 1-34 | Cl | 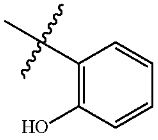 [SMILES: *c1ccccc1O] | 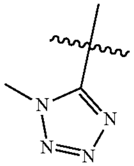 | $^1$H NMR (500 MHz, DMSO-$d_6$) δ 12.05 (s, 1H), 9.74 (s, 1H), 8.54 (d, J = 5.5 Hz, 1H), 8.04 (dd, J = 7.5, 2.0 Hz, 1H), 7.49 (d, J = 5.5 Hz, 1H), 7.32-7.21 (m, 2H), 7.01 (dd, J = 7.5, 2.0 Hz, 1H), 4.25 (s, 3H). |
| 1-35 | Cl | 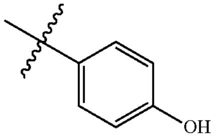 [SMILES: *c1ccc(O)cc1] | 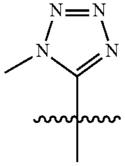 [SMILES: *c1nnnn1C] | 1H NMR (500 MHz, DMSO-d6) δ 12.05 (s, 1H), 9.63 (s, 1H), 8.71 (d, J = 4.5 Hz, 1H), 7.74-7.64 (m, 3H), 6.79-6.73 (m, 2H), 4.33 (s, 3H). |
| 1-36 | Cl | 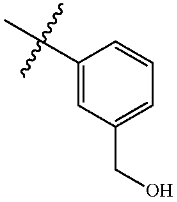 [SMILES: *c1cccc(CO)c1] | 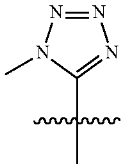 | $^1$H NMR (500 MHz, DMSO-$d_6$) δ 12.05 (s, 1H), 8.75 (d, J = 5.0 Hz, 1H), 7.74 (d, J = 5.0 Hz, 1H), 7.60 (d, J = 7.5 Hz, 1H), 7.52 (d, J = 7.5 Hz, 1H), 7.48-7.35 (m, 2H), 5.28 (s, 1H), 4.56 (s, 2H), 3.98 (s, 3H). |
| 1-37 | Cl | 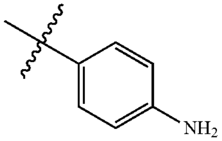 | 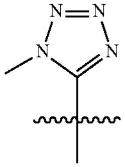 [SMILES: *c1nnnn1C] | 1H NMR (500 MHz, DMSO-d6) δ 12.03 (s, 1H), 8.71 (d, J = 4.5 Hz, 1H), 7.88-7.82 (m, 2H), 7.70 (d, J = 4.5 Hz, 1H), 6.58-6.52 (m, 2H), 6.27 (s, 2H), 4.33 (s, 3H). |
| 1-38 | Cl | 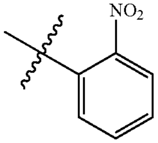 [SMILES: *c1ccccc1[N+](=O)[O-]] | 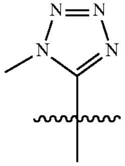 [SMILES: *c1nnnn1C] | $^1$H NMR (500 MHz, DMSO-d6) δ 12.06 (s, 1H), 8.72 (d, J = 5.0 Hz, 1H), 8.10 (dd, J = 6.5, 2.5 Hz, 1H), 7.97 (dd, J = 7.0, 2.5 Hz, 1H), 7.66-7.62 (m, 2H), 7.22 (d, J = 5.0 Hz, 1H), 4.33 (s, 3H). |

TABLE A1-continued
| | | | | |
|---|---|---|---|---|
| 1-39 | Cl | 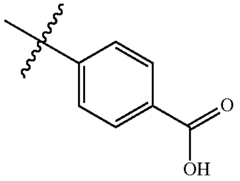 [SMILES: *c1ccc(C(=O)O)cc1] | 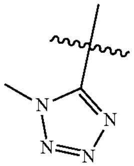 [SMILES: *c1nnnn1C] | $^1$H NMR (500 MHz, DMSO-$d_6$) δ 13.56 (s, 1H), 12.06 (s, 1H), 8.57 (d, J = 5.5 Hz, 1H), 8.07-8.01 (m, 1H), 7.99-7.93 (m, 2H), 7.51 (d, J = 5.5 Hz, 1H), 4.26 (s, 3H). |
| 1-40 | Cl | 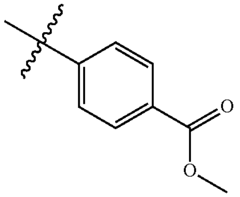 [SMILES: *c1ccc(C(=O)OC)cc1] | 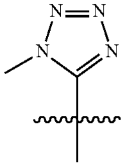 | $^1$H NMR (500 MHz, DMSO-$d_6$) δ 12.07 (s, 1H), 8.80 (d, J = 5.0 Hz, 1H), 8.09 (d, J = 8.0 Hz, 2H), 7.82 (d, J = 8.0 Hz, 2H), 7.32 (d, J = 5.0 Hz, 1H), 4.00 (s, 3H), 3.88 (s, 3H). |
| 1-41 | Cl | 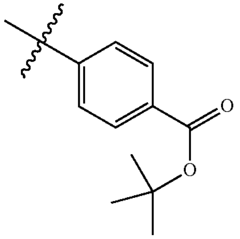 [SMILES: *c1ccc(C(=O)OC(C)(C)C)cc1] | 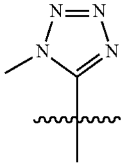 [SMILES: *c1nnnn1C] | $^1$H NMR (500 MHz, DMSO-$d_6$) δ 12.06 (s, 1H), 8.80 (d, J = 5.0 Hz, 1H), 8.03 (d, J = 8.0 Hz, 2H), 7.78 (d, J = 8.0 Hz, 2H), 7.35 (d, J = 5.0 Hz, 1H), 4.00 (s, 3H), 1.56 (s, 9H). |
| 1-42 | Cl | 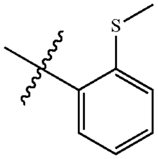 [SMILES: *c1ccccc1SC] | 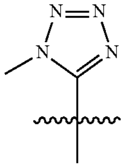 [SMILES: *c1nnnn1C] | $^1$H NMR (500 MHz, DMSO-d6) δ 12.06 (s, 1H), 8.74 (d, J = 5.0 Hz, 1H), 7.81 (dd, J =7.5, 2.0 Hz, 1H), 7.45-7.34 (m, 2H), 7.23-7.18 (m, 1H), 7.10 (d, J = 5.0 Hz, 1H), 4.32 (s, 3H), 2.35 (s, 3H). |
| 1-43 | Cl | 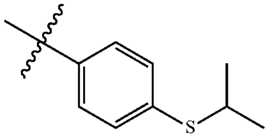 [SMILES: *c1ccc(SC(C)C)cc1] | 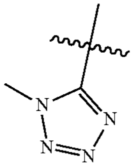 | $^1$H NMR (500 MHz, DMSO-$d_6$) δ 12.04 (s, 1H), 8.57 (d, J = 5.5 Hz, 1H), 7.97-7.91 (m, 2H), 7.54-7.47 (m, 3H), 4.26 (s, 3H), 3.33 (hept, J = 6.5 Hz, 1H), 1.31 (d, J = 6.5 Hz, 6H). |

TABLE A1-continued
| | | | | |
|---|---|---|---|---|
| 1-44 | Cl | 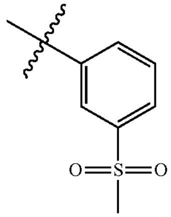 [SMILES: *c1cccc(S(C)(=O)=O)c1] | 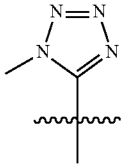 [SMILES: *c1nnnn1C] | $^1$H NMR (500 MHz, DMSO-d6) δ 12.05 (s, 1H), 8.79 (d, J = 4.5 Hz, 1H), 8.39 (t, J = 2.0 Hz, 1H), 8.03-7.95 (m, 2H), 7.63 (t, J = 7.5 Hz, 1H), 7.28 (d, J = 4.5 Hz, 1H), 4.32 (s, 3H), 3.25 (s, 3H). |
| 1-45 | Cl | 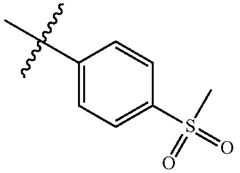 [SMILES: *c1ccc(S(C)(=O)=O)cc1] | 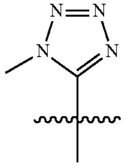 | 1H NMR (500 MHz, DMSO-d6) δ 12.11 (s, 1H), 8.81 (d, J = 5.0 Hz, 1H), 8.01 (d, J = 8.0 Hz, 2H), 7.93 (d, J = 8.0 Hz, 2H), 7.86 (d, J = 5.0 Hz, 1H), 3.98 (s, 3H), 3.18 (s, 3H). |
| 1-46 | Cl | 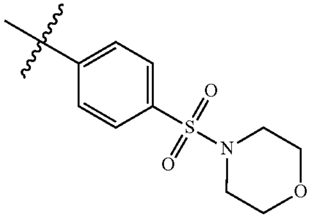 [SMILES: *c1ccc(S(=O)(=O)N2CCOCC2)cc1] | 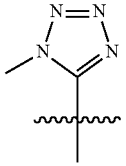 [SMILES: *c1nnnn1C] | $^1$H NMR (500 MHz, DMSO-$d_6$) δ 12.11 (s, 1H), 8.86 (d, J = 5.0 Hz, 1H), 7.98 (d, J = 8.0 Hz, 2H), 7.91 (d, J = 8.0 Hz, 2H), 7.45 (d, J = 5.0 Hz, 1H), 4.03 (s, 3H), 3.73-3.64 (m, 4H), 2.95 (t, J = 4.5 Hz, 4H). |
| 1-47 | Cl | 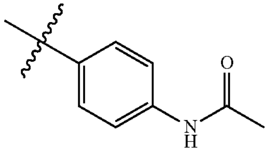 [SMILES: *c1ccc(NC(C)=O)cc1] | 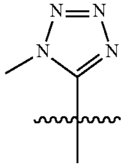 [SMILES: *c1nnnn1C] | 1H NMR (500 MHz, DMSO-d6) δ 12.06 (s, 1H), 10.14 (s, 1H), 8.73 (d, J = 5.0 Hz, 1H), 7.73-7.67 (m, 3H), 7.66-7.61 (m, 2H), 3.98 (s, 3H), 2.06 (s, 3H). |
| 1-48 | Cl | 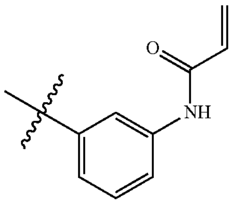 [SMILES: *c1cccc(NC(=O)C=C)c1] | 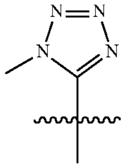 [SMILES: *c1nnnn1C] | $^1$H NMR (500 MHz, DMSO-$d_6$) δ 12.05 (s, 1H), 11.36 (s, 1H), 8.74 (d, J = 5.0 Hz, 1H), 7.86-7.80 (m, 2H), 7.77-7.70 (m, 2H), 7.42 (t, J = 7.0 Hz, 1H), 6.48 (dd, J = 16.5, 10.0 Hz, 1H), 6.29-6.20 (m, 1H), 5.78 (dd, J = 16.5, 10.0 Hz, 1H), 4.33 (s, 3H). |

TABLE A1-continued
| | | | | |
|---|---|---|---|---|
| 1-49 | Cl | 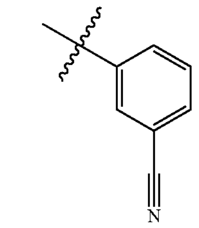 [SMILES: *c1cccc(C#N)c1] | 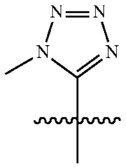 [SMILES: *c1nnnn1C] | $^1$H NMR (500 MHz, DMSO-$d_6$) δ 12.06 (s, 1H), 8.81 (d, J = 5.0 Hz, 1H), 8.12 (s, 1H), 7.99-7.90 (m, 2H), 7.84 (d, J = 5.0 Hz, 1H), 7.74 (t, J = 7.5 Hz, 1H), 3.99 (s, 3H). |
| 1-50 | Cl | 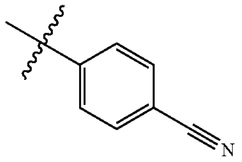 [SMILES: *c1ccc(C#N)cc1] | 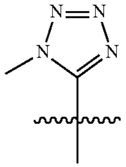 [SMILES: *c1nnnn1C] | $^1$H NMR (500 MHz, DMSO-$d_6$) δ 12.05 (s, 1H), 8.82 (d, J = 5.0 Hz, 1H), 8.00 (d, J = 8.0 Hz, 2H), 7.86 (d, J = 8.0 Hz, 2H), 7.46 (t, J = 5.0 Hz, 1H), 4.00 (s, 3H). |
| 1-51 | Cl | 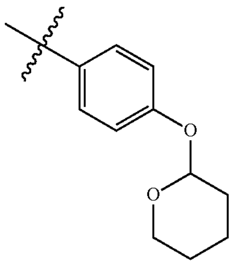 [SMILES: *c1ccc(OC2CCCCO2)cc1] | 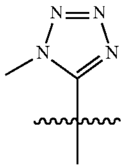 | $^1$H NMR (500 MHz, DMSO-d6) δ 12.09 (s, 1H), 8.94 (d, J = 4.5 Hz, 1H), 7.70-7.64 (m, 2H), 7.35 (d, J = 4.5 Hz, 1H), 7.06-6.99 (m, 2H), 5.33 (t, J = 6.5 Hz, 1H), 4.33 (s, 3H), 3.83-3.81 (m, 1H), 3.52-3.49 (m, 1H), 2.11-1.99 (m, 1H), 1.89-1.77 (m, 2H), 1.61-1.40 (m, 3H). |
| 1-52 | Cl | 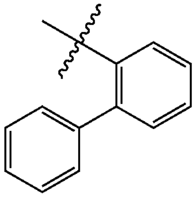 [SMILES: *c1ccccc1-c1ccccc1] | 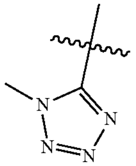 [SMILES: *c1nnnn1C] | $^1$H NMR (500 MHz, DMSO-$d_6$) δ 12.05 (s, 1H), 8.64 (d, J = 5.0 Hz, 1H), 8.00 (dd, J = 7.5, 2.0 Hz, 1H), 7.68-7.64 (m, 3H), 7.63-7.53 (m, 3H), 7.49-7.41 (m, 2H), 7.40-7.35 (m, 1H), 4.25 (s, 3H). |
| 1-53 | Cl | 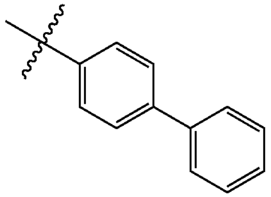 [SMILES: *c1ccc(-c2ccccc2)cc1] | 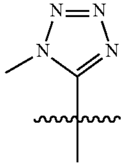 [SMILES: *c1nnnn1C] | $^1$H NMR (500 MHz, DMSO-$d_6$) δ 12.06 (s, 1H), 8.79 (dd, J = 5.0, 2.5 Hz, 1H), 7.92-7.67 (m, 7H), 7.51-7.47 (m, 2H), 7.42-7.34 (m, 1H), 4.00 (s, 3H). |

TABLE A1-continued
| | | | | |
|---|---|---|---|---|
| 1-54 | Cl | 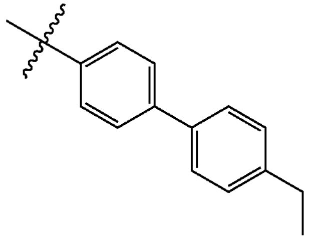 [SMILES: *c1ccc(-c2ccc(CC)cc2)cc1] | 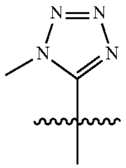 [SMILES: *c1nnnn1C] | $^1$H NMR (500 MHz, DMSO-$d_6$) δ 12.10 (s, 1H), 8.93 (d, J = 5.0 Hz, 1H), 8.14-8.08 (m, 2H), 7.90-7.81 (m, 3H), 7.65-7.59 (m, 2H), 7.40-7.35 (m, 2H), 4.33 (s, 3H), 2.77-2.67 (m, 2H), 1.19 (t, J = 8.0 Hz, 3H). |
| 1-55 | Cl | 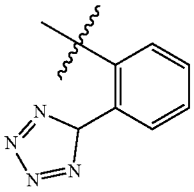 [SMILES: *c1ccccc1C1N=NN=N1] | 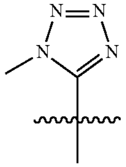 [SMILES: *c1nnnn1C] | $^1$H NMR (500 MHz, DMSO-$d_6$) δ 12.15 (s, 1H), 8.75 (d, J = 5.0 Hz, 1H), 7.75 (d, J = 7.5 Hz, 1H), 7.46 (td, J = 7.5, 2.0 Hz, 1H), 7.38 (td, J = 7.5, 2.0 Hz, 1H), 7.36-7.28 (m, 2H), 4.32 (s, 3H). |
| 1-56 | Cl | 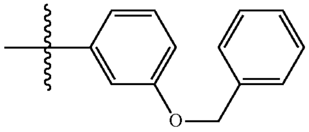 [SMILES: *c1cccc(OCc2ccccc2)c1] | 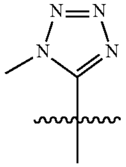 | $^1$H NMR (500 MHz, DMSO-$d_6$) δ 12.02 (s, 1H), 8.88 (d, J = 5.0 Hz, 1H), 7.78 (d, J = 5.0 Hz, 1H), 7.68-7.54 (m, 1H), 7.47-7.43 (m, 2H), 7.41 7.27 (m, 5H), 6.85-6.72 (m, 1H), 5.10 (s, 2H), 4.33 (s, 3H). |
| 1-57 | Cl | 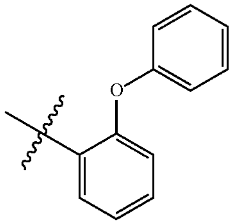 [SMILES: *c1ccccc1Oc1ccccc1] | 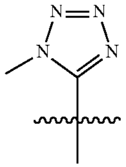 [SMILES: *c1nnnn1C] | 1H NMR (500 MHz, DMSO-d6) δ 12.08 (s, 1H), 8.84 (d, J = 5.0 Hz, 1H), 8.24 (dd, J = 7.5, 2.0 Hz, 1H), 7.73 (d, J = 5.0 Hz, 1H), 7.52-7.48 (m, 1H), 7.43-7.33 (m, 3H), 7.32-7.28 (m, 1H), 7.14-7.10 (m, 1H), 7.09-7.04 (m, 2H), 4.33 (s, 3H). |
| 1-58 | Cl | 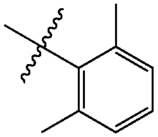 [SMILES: *c1c(C)cccc1C] | 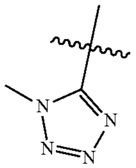 | $^1$H NMR (500 MHz, DMSO-$d_6$) δ 12.08 (s, 1H), 8.51 (d, J = 5.5 Hz, 1H), 7.59 (d, J = 5.5 Hz, 1H), 7.31-7.23 (m, 3H), 4.25 (s, 3H), 2.38 (s, 6H). |

TABLE A1-continued
| | | | | |
|---|---|---|---|---|
| 1-59 | Cl | 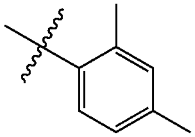 [SMILES: *c1ccc(C)cc1C] | 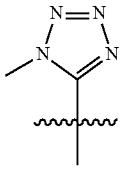 [SMILES: *c1nnnn1C] | $^1$H NMR (500 MHz, DMSO-$d_6$) δ 12.05 (s, 1H), 8.68 (d, J = 5.0 Hz, 1H), 7.77 (d, J = 7.5 Hz, 1H), 7.71 (d, J = 5.0 Hz, 1H), 7.13-7.05 (m, 2H), 4.33 (s, 3H), 2.43 (d, J = 1.0 Hz, 3H), 2.31 (s, 3H). |
| 1-60 | Cl | 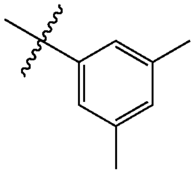 [SMILES: *c1cc(C)cc(C)c1] | 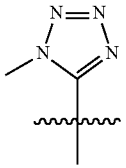 [SMILES: *c1nnnn1C] | $^1$H NMR (500 MHz, DMSO-$d_6$) δ 12.01 (s, 1H), 8.74 (d, J = 5.0 Hz, 1H), 7.73 (s, 1H), 7.24 (s, 2H), 7.11 (d, J = 5.0 Hz, 1H), 3.99 (s, 3H), 2.33 (s, 6H). |
| 1-61 | Cl | 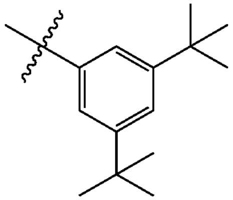 [SMILES: *c1cc(C(C)(C)C)cc(C(C)(C)C)c1] | 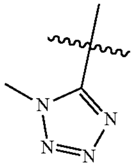 | $^1$H NMR (500 MHz, DMSO-$d_6$) δ 12.04 (s, 1H), 8.74 (d, J = 5.5 Hz, 1H), 7.81-7.78 (m, 2H), 7.56 (d, J = 5.5 Hz, 1H), 7.49 (t J = 2.5 Hz, 1H), 4.26 (s, 3H), 1.31 (s, 18H). |
| 1-62 | Cl | 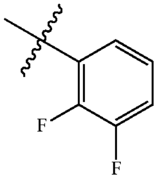 [SMILES: *c1cccc(F)c1F] | 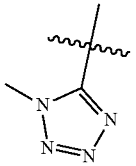 | $^1$H NMR (500 MHz, DMSO-$d_6$) δ 12.04 (s, 1H), 8.50 (d, J = 5.5 Hz, 1H), 7.68-7.65 (m, 1H), 7.59 (d, J = 5.5 Hz, 1H), 7.40-7.27 (m, 2H), 4.26 (s, 3H). |
| 1-63 | Cl | 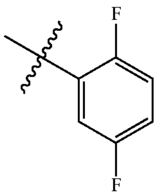 | 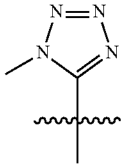 [SMILES: *c1nnnn1C] | $^1$H NMR (500 MHz, DMSO-d6) δ 11.85 (s, 1H), 8.74 (d, J = 4.5 Hz, 1H), 7.64-7.58 (m, 1H), 7.39-7.32 (m, 1H), 7.2-7.15 (m, 1H), 7.08 (d, J = 4.5 Hz, 1H), 4.31 (s, 3H). |

TABLE A1-continued
| | | | | |
|---|---|---|---|---|
| 1-64 | Cl | 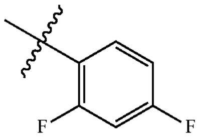 [SMILES: *c1ccc(F)cc1F] | 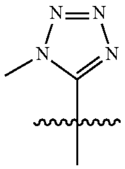 [SMILES: *c1nnnn1C] | $^1$H NMR (500 MHz, DMSO-$d_6$) δ 12.10 (s, 1H), 8.79 (d, J = 5.0 Hz, 1H), 7.86 (d, J = 5.0 Hz, 1H), 7.57-7.52 (m, 1H), 7.44 (t, J = 10.0 Hz, 1H), 7.26 (dd, J = 8.5, 7.0 Hz, 1H), 3.99 (s, 3H). |
| 1-65 | Cl | 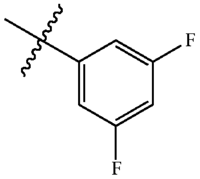 [SMILES: *c1cc(F)cc(F)c1] | 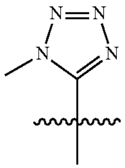 [SMILES: *c1nnnn1C] | $^1$H NMR (500 MHz, DMSO-$d_6$) δ 12.05 (s, 1H), 8.79 (d, J = 5.0 Hz, 1H), 7.84 (d, J = 5.0 Hz, 1H), 7.40 (t, J = 9.0 Hz, 2H), 7.25-7.20 (m, 1H), 3.99 (s, 3H). |
| 1-66 | Cl | 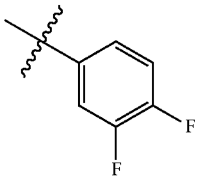 [SMILES: *c1ccc(F)c(F)c1] | 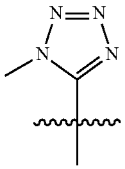 [SMILES: *c1nnnn1C] | 1H NMR (500 MHz, DMSO-d6) δ 12.03 (s, 1H), 8.78 (d, J = 5.5 Hz, 1H), 7.86-7.70 (m, 2H), 7.66-7.49 (m, 2H), 4.00 (s, 3H),. |
| 1-67 | Cl | 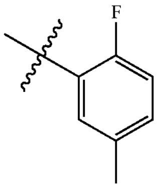 [SMILES: *c1cc(C)ccc1F] | 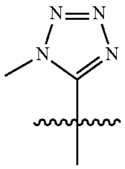 [SMILES: *c1nnnn1C] | 1H NMR (500 MHz, DMSO-d6) δ 12.11 (s, 1H), 8.79 (d, J = 5.0 Hz, 1H), 7.84 (d, J = 5.0 Hz, 1H), 7.29-7.19 (m, 3H), 3.99 (s, 3H), 2.34 (s, 3H). |
| 1-68 | Cl | 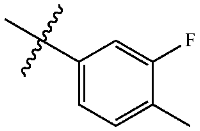 [SMILES: *c1ccc(C)c(F)c1] | 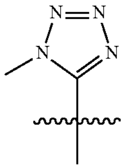 [SMILES: *c1nnnn1C] | $^1$H NMR (500 MHz, DMSO-d6) δ 11.96 (s, 1H), 8.78 (d, J = 4.5 Hz, 1H), 7.54 (d, J = 8.5, 1H), 7.37 (dd, J = 7.5, 2.0 Hz, 1H), 7.26 (d, J = 4.5 Hz, 1H), 7.20-7.16 (m, 1H), 4.32 (s, 3H), 2.29 (s, 3H). |

TABLE A1-continued
| | | | | |
|---|---|---|---|---|
| 1-69 | Cl | 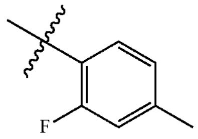 [SMILES: *c1ccc(C)cc1F] | 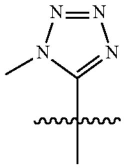 [SMILES: *c1nnnn1C] | $^1$H NMR (500 MHz, DMSO-$d_6$) δ 12.07 (s, 1H), 8.77 (d, J = 5.0 Hz, 1H), 7.80 (s, 1H), 7.35 (t, J = 8.0 Hz, 1H), 7.17 (t, J = 10.5 Hz, 2H), 3.98 (s, 3H), 2.39 (s, 3H),. |
| 1-70 | Cl | 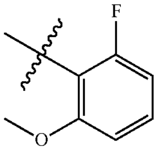 [SMILES: *c1c(F)cccc1OC] | 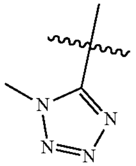 | $^1$H NMR (500 MHz, DMSO-$d_6$) δ 12.06 (s, 1H), 8.51 (d, J = 5.5 Hz, 1H), 7.56 (d, J = 5.5 Hz, 1H), 7.42-7.38 (m, 1H), 7.13-7.10 (m, 1H), 6.82-6.80 (m, 1H), 4.26 (s, 3H), 3.85 (s, 3H). |
| 1-71 | Cl | 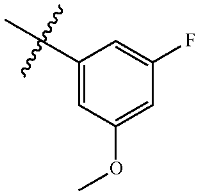 [SMILES: *c1cc(F)cc(OC)c1] | 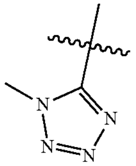 | $^1$H NMR (500 MHz, DMSO-$d_6$) δ 12.06 (s, 1H), 8.48 (d, J = 5.5 Hz, 1H), 7.56-7.49 (m, 2H), 7.17 (t, J = 2.0 Hz, 1H), 6.80-6.75 (m, 1H), 4.26 (s, 3H), 3.80 (s, 3H). |
| 1-72 | Cl | 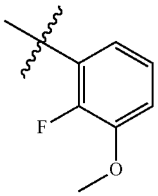 [SMILES: *c1cccc(OC)c1F] | 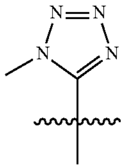 | $^1$H NMR (500 MHz, DMSO-$d_6$) δ 12.10 (s, 1H), 8.79 (d, J = 4.5 Hz, 1H), 7.84 (d, J = 4.5 Hz, 1H), 7.34-7.19 (m, 2H), 6.98-6.95 (m, 1H), 3.99 (s, 3H), 3.88 (s, 3H). |
| 1-73 | Cl | 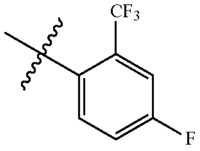 | 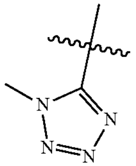 | $^1$H NMR (500 MHz, DMSO-$d_6$) δ 12.06 (s, 1H), 8.55 (d, J = 5.5 Hz, 1H), 7.80 (dd, J = 8.5, 7.5 Hz, 1H), 7.60-7.50 (m, 2H), 7.23-7.20 (m, 1H), 4.25 (s, 3H). |

TABLE A1-continued
| | | | | |
|---|---|---|---|---|
| 1-74 | Cl | 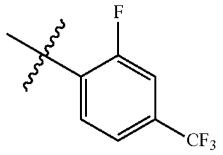 | 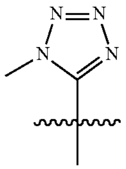 | $^1$H NMR (500 MHz, DMSO-d6) δ 12.06 (s, 1H), 8.81 (d, J = 5.0 Hz, 1H), 7.77 (d, J = 7.5 Hz, 1H), 7.45-7.39 (m, 1H), 7.33-7.23 (m, 2H), 4.32 (s, 3H). |
| 1-75 | Cl | 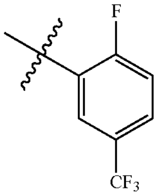 | 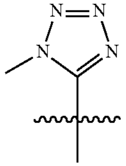 | $^1$H NMR (500 MHz, DMSO-$d_6$) δ 12.14 (s, 1H), 8.82 (d, J = 5.0 Hz, 1H), 7.94-7.84 (m, 3H), 7.65-7.51 (m, 1H), 3.99 (s, 3H). |
| 1-76 | Cl | 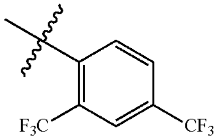 | 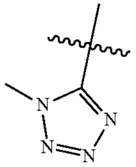 | $^1$H NMR (500 MHz, DMSO-$d_6$) δ 12.04 (s, 1H), 8.55 (d, J = 5.5 Hz, 1H), 8.05 (d, J = 8.5 Hz, 1H), 7.84 (d, J = 2.0 Hz, 1H), 7.74 (dd, J = 8.5, 2.0 Hz, 1H), 7.58 (d, J = 5.5 Hz, 1H), 4.26 (s, 3H). |
| 1-77 | Cl | 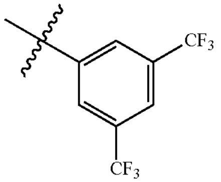 [SMILES: *c1cc(C(F)(F)F)cc(C(F)(F)F)c1] | 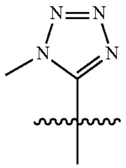 | $^1$H NMR (500 MHz, DMSO-$d_6$) δ 12.19 (s, 1H), 8.97 (d, J = 5.0 Hz, 1H), 8.49 (s, 2H), 8.42 (s, 1H), 8.02 (d, J = 5.0 Hz, 1H), 4.12 (s, 3H). |
| 1-78 | Cl | 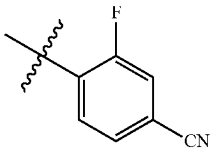 [SMILES: *c1ccc(C#N)cc1F] | 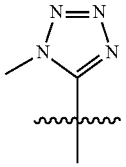 [SMILES: *c1nnnn1C] | $^1$H NMR (500 MHz, DMSO-$d_6$) δ 12.06 (s, 1H), 8.69 (d, J = 5.5 Hz, 1H), 8.05-7.95 (m, 2H), 7.69 (d, J = 5.5 Hz, 1H), 7.51 (dd, J = 13.5, 2.5 Hz, 1H), 4.33 (s, 3H). |

TABLE A1-continued
| | | | | |
|---|---|---|---|---|
| 1-79 | Cl | 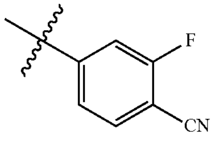 [SMILES: *c1ccc(C#N)c(F)c1] | 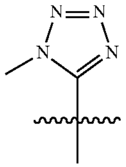 [SMILES: *c1nnnn1C] | $^1$H NMR (500 MHz, DMSO-$d_6$) δ 12.03 (s, 1H), 8.70 (d, J = 5.5 Hz, 1H), 7.96-7.89 (m, 2H), 7.76 (dd, J = 8.0, 7.0 Hz, 1H), 7.71 (d, J = 5.5 Hz, 1H), 4.33 (s, 3H). |
| 1-80 | Cl | 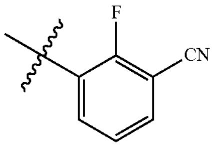 [SMILES: *c1cccc(C#N)c1F] | 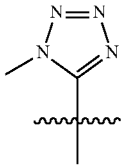 [SMILES: *c1nnnn1C] | $^1$H NMR (500 MHz, DMSO-$d_6$) δ 12.05 (s, 1H), 8.69 (d, J = 5.5 Hz, 1H), 8.12-8.08 (m, 1H), 7.82-7.78 (m, 1H), 7.69 (d, J = 5.5 Hz, 1H), 7.32 (dt, J = 7.5, 2.5 Hz, 1H), 4.33 (s, 3H). |
| 1-81 | Cl | 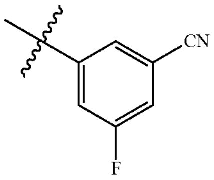 [SMILES: *c1cc(F)cc(C#N)c1] | 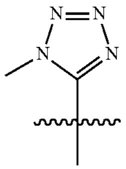 [SMILES: *c1nnnn1C] | $^1$H NMR (500 MHz, DMSO-$d_6$) δ 12.06 (s, 1H), 8.70 (d, J = 5.5 Hz, 1H), 8.06-7.95 (m, 2H), 7.89 (t, J = 2.0 Hz, 1H), 7.70-7.68 (m, 1H), 4.33 (s, 3H). |
| 1-82 | Cl | 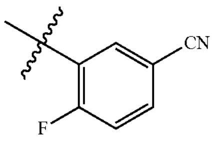 [SMILES: *c1cc(C#N)ccc1F] | 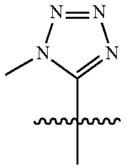 [SMILES: *c1nnnn1C] | $^1$H NMR (500 MHz, DMSO-$d_6$) δ 12.05 (s, 1H), 8.69 (d, J = 5.5 Hz, 1H), 8.07 (dd, J = 7.5, 2.0 Hz, 1H), 7.77-7.73 (m, 1H), 7.70 (d, J = 5.5 Hz, 1H), 7.45 (dd, J = 11.5, 7.5 Hz, 1H), 4.33 (s, 3H). |
| 1-83 | Cl | 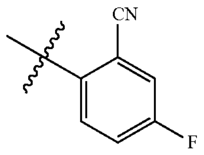 [SMILES: *c1ccc(F)cc1C#N] | 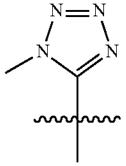 [SMILES: *c1nnnn1C] | $^1$H NMR (500 MHz, DMSO-$d_6$) δ 12.05 (s, 1H), 8.70 (d, J = 5.5 Hz, 1H), 7.99-7.95 (m, 2H), 7.67 (d, J = 5.5 Hz, 1H), 7.49-7.45 (m, 1H), 4.33 (s, 3H). |
| 1-84 | Cl | 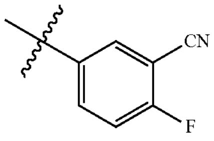 [SMILES: *c1ccc(F)c(C#N)c1] | 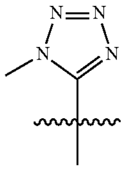 [SMILES: *c1nnnn1C] | $^1$H NMR (500 MHz, DMSO-$d_6$) δ 12.05 (s, 1H), 8.69 (d, J = 5.5 Hz, 1H), 8.26-8.21 (m, 1H), 8.16 (dd, J = 8.0, 2.5 Hz, 1H), 7.70 (d, J = 5.5 Hz, 1H), 7.47 (dd, J = 13.5, 7.5 Hz, 1H), 4.33 (s, 3H). |

TABLE A1-continued
| | | | | |
|---|---|---|---|---|
| 1-85 | Cl | 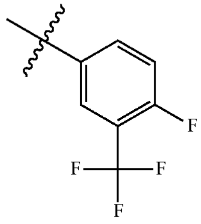 [SMILES: *c1ccc(F)c(C(F)(F)F)c1] | 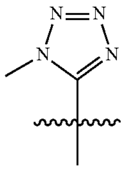 [SMILES: *c1nnnn1C] | $^1$H NMR (500 MHz, DMSO-$d_6$) δ 12.03 (s, 1H), 8.81 (d, J = 5.0 Hz, 1H), 8.17-8.01 (m, 2H), 7.84 (d, J = 7.5 Hz, 1H), 7.69-7.64 (m, 1H), 4.00 (s, 3H),. |
| 1-86 | Cl | 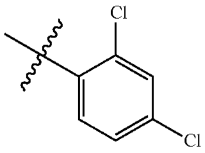 [SMILES: *c1ccc(Cl)cc1Cl] | 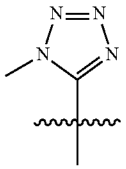 [SMILES: *c1nnnn1C] | 1H NMR (500 MHz, DMSO-d6) δ 12.12 (s, 1H), 8.79 (d, J = 5.0 Hz, 1H), 7.90-7.85 (m, 1H), 7.81 (d, J = 2.0 Hz, 1H), 7.58 (dd, J = 8.5, 2.0 Hz, 1H), 7.48 (d, J = 8.5 Hz, 1H), 3.99 (s, 3H). |
| 1-87 | Cl | 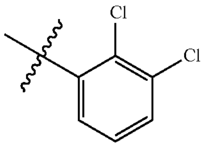 [SMILES: *c1cccc(Cl)c1Cl] | 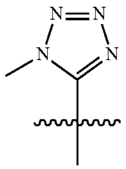 | $^1$H NMR (500 MHz, DMSO-$d_6$) δ 12.18 (s, 1H), 8.81 (d, J = 5.0 Hz, 1H), 7.89 (d, J = 7.0 Hz, 1H), 7.84-7.77 (m, 1H), 7.58-7.51 (m, 1H), 7.44 (d, J = 7.0 Hz, 1H), 4.02 (s, 3H). |
| 1-88 | Cl | 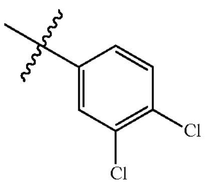 [SMILES: *c1ccc(Cl)c(Cl)c1] | 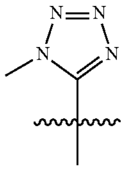 [SMILES: *c1nnnn1C] | $^1$H NMR (500 MHz, DMSO-$d_6$) δ 12.05 (s, 1H), 8.79 (d, J = 5.0 Hz, 1H), 7.92 (d, J = 2.0 Hz, 1H), 7.85-7.77 (m, 2H), 7.70-7.67 (m, 1H), 4.00 (s, 3H). |
| 1-89 | Cl | 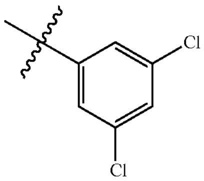 [SMILES: *c1cc(Cl)cc(Cl)c1] | 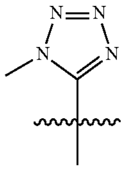 [SMILES: *c1nnnn1C] | 1H NMR (500 MHz, DMSO-d6) δ 12.07 (s, 1H), 8.79 (d, J = 4.5 Hz, 1H), 7.84 (d, J = 4.5 Hz, 1H), 7.78 (t, J = 2.0 Hz, 1H), 7.71 (d, J = 2.0 Hz, 2H), 3.99 (s, 3H). |

TABLE A1-continued
| | | | | |
|---|---|---|---|---|
| 1-90 | Cl | 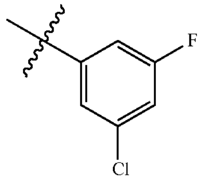 [SMILES: *c1cc(F)cc(Cl)c1] | 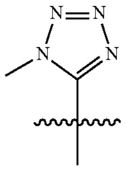 [SMILES: *c1nnnn1C] | 1H NMR (500 MHz, DMSO-d6) δ 12.08 (s, 1H), 8.79 (d, J = 4.5 Hz, 1H), 7.84 (d, J = 4.5 Hz, 1H), 7.62 (dt, J = 9.0, 2.0 Hz, 1H), 7.57 (s, 1H), 7.52 (d, J = 9.0 Hz, 1H), 3.99 (s, 3H). |
| 1-91 | Cl | 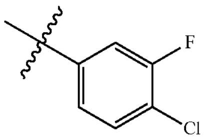 [SMILES: *c1ccc(Cl)c(F)c1] | 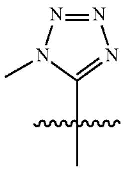 [SMILES: *c1nnnn1C] | $^{1}$H NMR (500 MHz, DMSO-$d_6$) δ 12.06 (s, 1H), 8.79 (d, J = 5.0 Hz, 1H), 7.82 (d, J = 9.0 Hz, 1H), 7.76-7.71 (m, 2H), 7.55 (d, J = 8.5 Hz, 1H), 3.99 (s, 3H). |
| 1-92 | Cl | 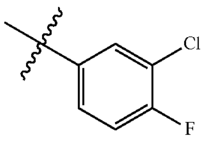 [SMILES: *c1ccc(F)c(Cl)c1] | 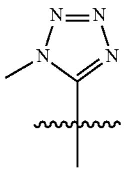 [SMILES: *c1nnnn1C] | $^{1}$H NMR (500 MHz, DMSO-$d_6$) δ 12.06 (s, 1H), 8.69 (d, J = 5.0 Hz, 1H), 7.87-7.81 (m, 2H), 7.68 (d, J = 5.0 Hz, 1H), 7.29-7.22 (m, 1H), 4.33 (s, 3H). |
| 1-93 | Cl | 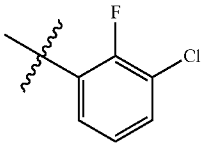 | 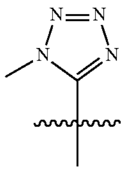 [SMILES: *c1nnnn1C] | 1H NMR (500 MHz, DMSO-d6) δ 12.07 (s, 1H), 8.63 (d, J = 5.0 Hz, 1H), 7.73-7.66 (m, 1H), 7.54-7.42 (m, 1H), 7.48 (d, J = 5.0 Hz, 1H), 7.18 (t, J = 7.5 Hz, 1H), 4.33 (s, 3H). |
| 1-94 | Cl | 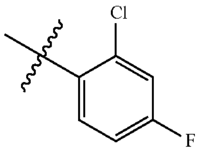 [SMILES: *c1ccc(F)cc1Cl] | 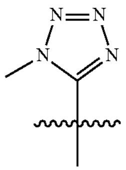 [SMILES: *c1nnnn1C] | 1H NMR (500 MHz, DMSO-d6) δ 12.14 (s, 1H), 8.78 (d, J = 5.0 Hz, 1H), 7.86 (d, J = 5.0 Hz, 1H), 7.64 (dd, J = 9.0, 2.5 Hz, 1H), 7.51 (dd, J = 8.5, 6.0 Hz, 1H), 7.38-7.30 (m, 1H), 3.98 (s, 3H). |
| 1-95 | Cl | 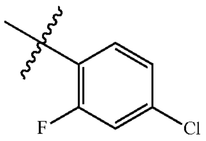 | 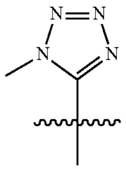 [SMILES: *c1nnnn1C] | $^{1}$H NMR (500 MHz, DMSO-$d_6$) δ 12.10 (s, 1H), 8.80 (d, J = 5.0 Hz, 1H), 7.87 (d, J = 5.0 Hz, 1H), 7.69-7.62 (m, 1H), 7.55 (d, J = 8.0 Hz, 1H), 7.46 (dd, J = 8.0, 2.0 Hz, 1H), 3.99 (s, 3H). |

TABLE A1-continued
| | | | | |
|---|---|---|---|---|
| 1-96 | Cl | 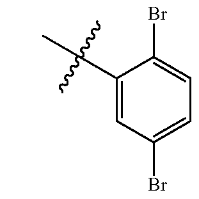 | 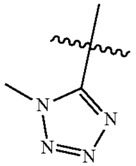 | $^1$H NMR (500 MHz, DMSO-$d_6$) δ 12.10 (s, 1H), 8.62 (d, J = 5.5 Hz, 1H), 7.84 (d, J = 2.0 Hz, 1H), 7.71 (d, J = 8.5 Hz, 1H), 7.62 (d, J = 5.5 Hz, 1H), 7.55 (dd, J = 8.5, 2.0 Hz, 1H), 4.26 (s, 3H). |
| 1-97 | Cl | 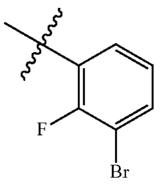 [SMILES: *c1cccc(Br)c1F] | 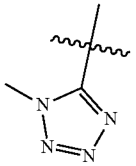 | $^1$H NMR (500 MHz, DMSO-$d_6$) δ 12.05 (s, 1H), 8.54 (d, J = 5.5 Hz, 1H), 7.84-7.80 (m, 1H), 7.65-7.56 (m, 2H), 7.28-7.24 (m, 1H), 4.26 (s, 3H). |
| 1-98 | Cl | 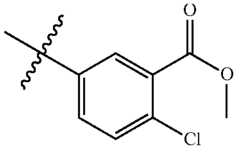 [SMILES: *c1ccc(Cl)c(C(=O)OC)c1] | 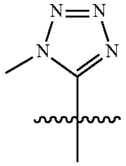 [SMILES: *c1nnnn1C] | $^1$H NMR (500 MHz, DMSO-d6) δ 11.99 (s, 1H), 8.75 (d, J = 4.5 Hz, 1H), 8.14 (d, J = 2.0 Hz, 1H), 7.79 (dd, J = 7.5, 2.0 Hz, 1H), 7.52 (d, J = 7.5 Hz, 1H), 7.09 (d, J = 4.5 Hz, 1H), 4.32 (s, 3H), 3.94 (s, 3H). |
| 1-99 | Cl | 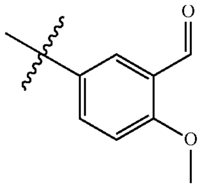 [SMILES: *c1ccc(OC)c(C=O)c1] | 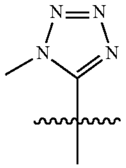 [SMILES: *c1nnnn1C] | $^1$H NMR (500 MHz, DMSO-$d_6$) δ 12.10 (s, 1H), 11.26 (s, 1H), 8.68 (d, J = 5.0 Hz, 1H), 8.38 (d, J = 2.0 Hz, 1H), 8.02 (dd, J = 7.5, 2.0 Hz, 1H), 7.68 (d, J = 5.0 Hz, 1H), 7.09 (d, J = 7.5 Hz, 1H), 4.33 (s, 3H), 3.90 (s, 3H). |
| 1-100 | Cl | 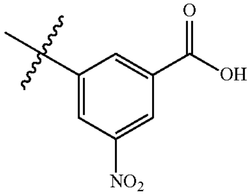 | 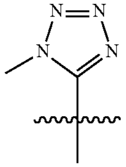 [SMILES: *c1nnnn1C] | $^1$H NMR (500 MHz, DMSO-$d_6$) δ 13.19 (s, 1H), 12.01 (s, 1H), 8.74 (d, J = 5.0 Hz, 1H), 8.70 (s, 1H), 8.66 (s, 1H), 7.88 (s, 1H), 7.63 (d, J = 4.5 Hz, 1H), 4.00 (s, 3H). |

TABLE A1-continued
| | | | | |
|---|---|---|---|---|
| 1-101 | Cl | 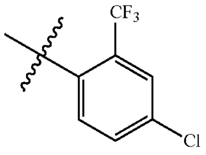 | 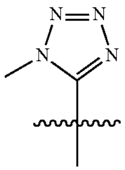 | $^1$H NMR (500 MHz, DMSO-$d_6$) δ 12.07 (s, 1H), 8.76 (d, J = 4.5 Hz, 1H), 7.81 (d, J = 7.5 Hz, 1H), 7.66-7.62 (m, 1H), 7.39 (dd, J = 7.5, 2.0 Hz, 1H), 7.24 (d, J = 4.5 Hz, 1H), 4.33 (s, 3H). |
| 1-102 | Cl | 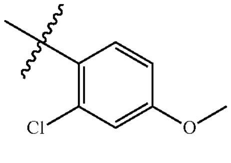 [SMILES: *c1ccc(OC)cc1Cl] | 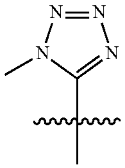 [SMILES: *c1nnnn1C] | $^1$H NMR (500 MHz, DMSO-$d_6$) δ 12.10 (s, 1H), 8.75 (d, J = 4.5 Hz, 1H), 7.81 (d, J = 4.5 Hz, 1H), 7.36-7.30 (m, 1H), 7.17 (d, J = 2.5 Hz, 1H), 7.07-7.01 (m, 1H), 3.98 (s, 3H), 3.83 (s, 3H). |
| 1-103 | Cl | 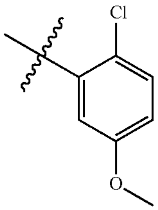 [SMILES: *c1cc(OC)ccc1Cl] | 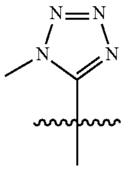 [SMILES: *c1nnnn1C] | $^1$H NMR (500 MHz, DMSO-$d_6$) δ 12.20 (s, 1H), 8.87 (d, J = 5.0 Hz, 1H), 7.69 (d, J = 5.0 Hz, 1H), 7.59 (d, J = 9.0 Hz, 1H), 7.23-7.15 (m, 1H), 7.05 (d, J = 3.0 Hz, 1H), 4.08 (s, 3H), 3.86 (s, 3H). |
| 1-104 | Cl | 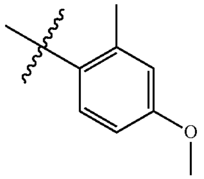 [SMILES: *c1ccc(OC)cc1C] | 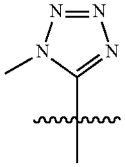 | $^1$H NMR (500 MHz, DMSO-$d_6$) δ 12.09 (s, 1H), 8.76 (d, J = 5.0 Hz, 1H), 7.78 (d, J = 5.0 Hz, 1H), 7.16 (d, J = 8.5 Hz, 1H), 6.92 (d, J = 2.5 Hz, 1H), 6.88 (d, J = 8.5, 2.5 Hz, 1H), 4.01 (s, 3H), 3.81 (s, 3H), 2.09 (s, 3H). |
| 1-105 | Cl | 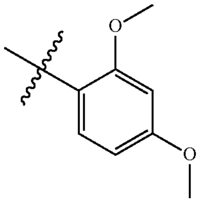 [SMILES: *c1ccc(OC)cc1OC] | 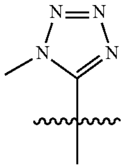 [SMILES: *c1nnnn1C] | 1H NMR (500 MHz, DMSO-d6) δ 12.04 (s, 1H), 8.69 (d, J = 5.0 Hz, 1H), 7.71 (d, J = 5.0 Hz, 1H), 7.14 (d, J = 8.5 Hz, 1H), 6.70-6.59 (m, 2H), 3.97 (s, 3H), 3.81 (s, 3H), 3.73 (s, 3H). |

TABLE A1-continued
| | | | | |
|---|---|---|---|---|
| 1-106 | Cl | 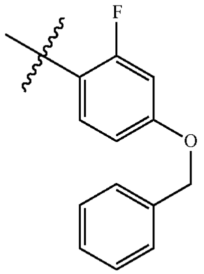 [SMILES: *c1ccc(OCc2ccccc2)cc1F] | 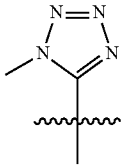 [SMILES: *c1nnnn1C] | 1H NMR (500 MHz, DMSO-d6) δ 12.09 (s, 1H), 8.77 (d, J = 5.0 Hz, 1H), 7.81 (d, J = 5.0 Hz, 1H), 7.41-7.29 (m, 6H), 7.03-6.95 (m, 2H), 5.18 (s, 2H), 3.98 (s, 3H). |
| 1-107 | Cl | 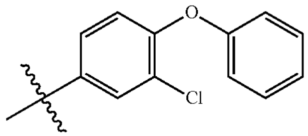 [SMILES: *c1ccc(Oc2ccccc2)c(Cl)c1] | 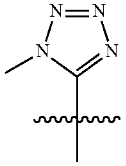 [SMILES: *c1nnnn1C] | $^{1}H$ NMR (500 MHz, DMSO-$d_6$) δ 12.07 (s, 1H), 8.89 (d, J = 5.0 Hz, 1H), 7.84-7.75 (m, 2H), 7.70 (dd, J = 7.5, 2.0 Hz, 1H), 7.50-7.44 (m, 2H), 7.42 (d, J = 7.5 Hz, 1H), 7.41-7.34 (m, 2H), 7.32-7.28 (m, 1H), 4.33 (s, 3H). |
| 1-108 | Cl | 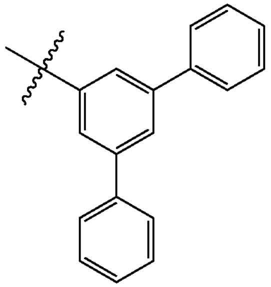 [SMILES: *c1cc(-c2ccccc2)cc(-c2ccccc2)c1] | 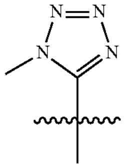 [SMILES: *c1nnnn1C] | $^{1}H$ NMR (500 MHz, DMSO-$d_6$) δ 12.07 (s, 1H), 8.85 (d, J = 5.0 Hz, 1H), 8.13 (d, J = 2.0 Hz, 2H), 7.96 (t, J = 2.0 Hz, 1H), 7.80 (d, J = 5.0 Hz, 1H), 7.73 (dd, J = 7.5, 2.0 Hz, 4H), 7.49 (t, J = 7.5 Hz, 4H), 7.43-7.35 (m, 2H), 4.33 (s, 3H). |
| 1-109 | Cl | 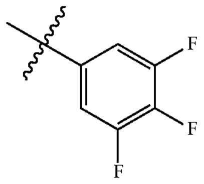 [SMILES: *c1cc(F)c(F)c(F)c1] | 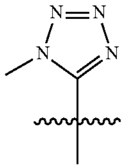 [SMILES: *c1nnnn1C] | 1H NMR (500 MHz, DMSO-d6) δ 12.08 (s, 1H), 8.79 (d, J = 4.5 Hz, 1H), 7.67-7.60 (m, 2H), 7.55-7.42 (m, 1H), 3.99 (s, 3H). |

TABLE A1-continued

| | | | | |
|---|---|---|---|---|
| 1-110 | Cl | 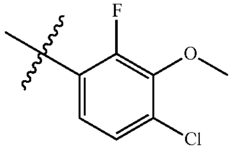 | 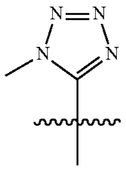 [SMILES: *c1nnnn1C] | 1H NMR (500 MHz, DMSO-d6) δ 12.12 (s, 1H), 8.81 (d, J = 5.0 Hz, 1H), 7.89 (d, J = 5.0 Hz, 1H), 7.48 (dd, J = 7.5, 1.5 Hz, 1H), 7.26 (t, J = 7.5 Hz, 1H), 4.00 (s, 3H), 3.92 (s, 3H). |
| 1-111 | Cl | 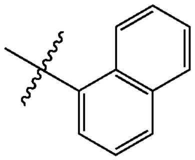 [SMILES: *c1cccc2ccccc12] | 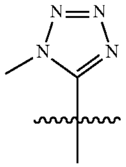 | 1H NMR (500 MHz, DMSO-d6) δ 12.19 (s, 1H), 8.83 (d, J = 5.0 Hz, 1H), 8.04-7.98 (m, 2H), 7.87 (d, J = 5.0 Hz, 1H), 7.64 (t, J = 7.5 Hz, 1H), 7.53-7.42 (m, 3H), 7.36 (d, J = 8.5 Hz, 1H), 3.98 (s, 3H). |
| 1-112 | Cl | 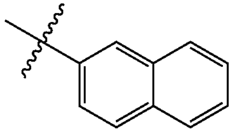 [SMILES: *c1ccc2ccccc2c1] | 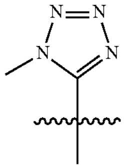 [SMILES: *c1nnnn1C] | $^1$H NMR (500 MHz, DMSO-$d_6$) δ 12.08 (s, 1H), 8.83 (d, J = 5.0 Hz, 1H), 8.13-8.06 (m, 2H), 7.99 (d, J = 7.5 Hz, 1H), 7.82 (d, J = 5.0 Hz, 1H), 7.79-7.73 (m, 2H), 7.62-7.56 (m, 2H), 4.01 (s, 3H). |
| 1-113 | Cl | 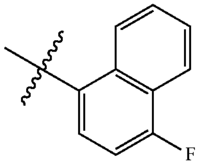 [SMILES: *c1ccc(F)c2ccccc12] | 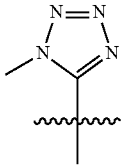 | $^1$H NMR (500 MHz, DMSO-$d_6$) δ 12.07 (s, 1H), 8.91 (d, J = 5.5 Hz, 1H), 8.33 (dd, J = 7.5, 1.5 Hz, 1H), 8.22 (dd, J = 7.5, 1.5 Hz, 1H), 8.03-7.99 (m, 1H), 7.84 (d, J = 5.5 Hz, 1H), 7.53-7.50 (m, 1H), 7.37 (dd, J = 7.5, 8.0 Hz, 1H), 6.63-6.60 (m, 1H), 4.33 (s, 3H). |
| 1-114 | Cl | 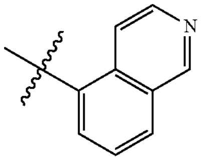 [SMILES: *c1cccc2cnccc12] | 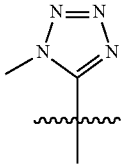 [SMILES: *c1nnnn1C] | $^1$H NMR (500 MHz, DMSO-$d_6$) δ 12.03 (s, 1H), 9.28 (s, 1H), 8.87 (d, J = 5.0 Hz, 1H), 8.60 (d, J = 7.5 Hz, 1H), 8.18-8.10 (m, 2H), 7.88-7.78 (m, 3H), 4.33 (s, 3H). |
| 1-115 | Cl | 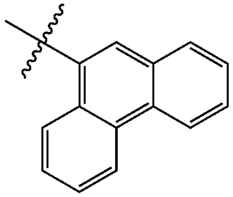 [SMILES: *c1cc2ccccc2c2ccccc12] | 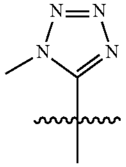 [SMILES: *c1nnnn1C] | $^1$H NMR (500 MHz, DMSO-$d_6$) δ 12.03 (s, 1H), 8.94-8.86 (m, 2H), 8.78 (d, J = 5.5 Hz, 1H), 8.38 (s, 1H), 8.05-7.95 (m, 2H), 7.86 (d, J = 5.0 Hz, 1H), 7.74-7.61 (m, 4H), 4.33 (s, 3H). |

TABLE A1-continued

| | | | | |
|---|---|---|---|---|
| 1-116 | Cl | 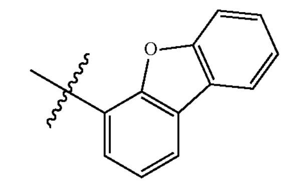 [SMILES: *c1cccc2c1oc1ccccc12] | 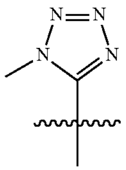 [SMILES: *c1nnnn1C] | 1H NMR (500 MHz, DMSO-d6) δ 12.17 (s, 1H), 8.88 (d, J = 5.0 Hz, 1H), 8.30 (d d, J = 7.5, 1.5 Hz, 1H), 8.22 (d, J = 7.5 Hz, 1H), 7.92 (d, J = 5.0 Hz, 1H), 7.68 (d, J = 8.0 Hz, 1H), 7.64-7.58 (m, 1H), 7.59-7.49 (m, 2H), 7.43 (t, J = 7.5 Hz, 1H), 4.01 (s, 3H). |
| 1-117 | Cl | 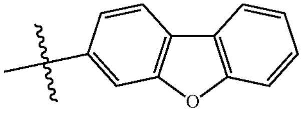 [SMILES: *c1ccc2c(c1)oc1ccccc12] | 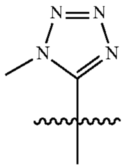 [SMILES: *c1nnnn1C] | $^1$H NMR (500 MHz, DMSO-$d_6$) δ 12.01 (s, 1H), 8.91 (d, J = 5.0 Hz, 1H), 8.13 (d, J = 1.5 Hz, 1H), 8.09-8.01 (m, 2H), 7.95 (dd, J = 7.5, 1.5 Hz, 1H), 7.81 (d, J = 5.0 Hz, 1H), 7.54 (dd, J = 7.5, 1.5 Hz, 1H), 7.48-7.41 (m, 1H), 7.37-7.32 (m, 1H), 4.33 (s, 3H). |
| 1-118 | Cl | 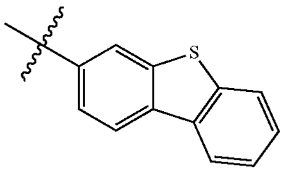 [SMILES: *c1ccc2c(c1)sc1ccccc12] | 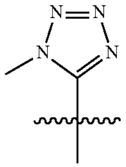 [SMILES: *c1nnnn1C] | 1H NMR (500 MHz, DMSO-d6) δ 12.11 (s, 1H), 8.76 (d, J = 5.0 Hz, 1H), 8.51-8.38 (m, 3H), 7.98 (d, J = 5.0 Hz, 1H), 7.74 (s, 2H), 7.67-7.64 (m, 1H), 7.52 (s, 1H), 3.88 (s, 3H). |
| 1-119 | Cl | 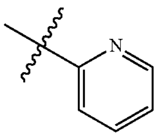 [SMILES: *c1ccccn1] | 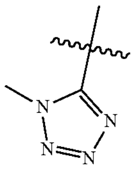 | $^1$H NMR (500 MHz, DMSO-$d_6$) δ 12.05 (s, 1H), 8.69 (d, J = 5.5 Hz, 1H), 8.63 (d, J = 5.5 Hz, 1H), 8.22 (dd, J = 8.0, 2.0 Hz, 1H), 7.82 (t, J = 8.0 Hz, 1H), 7.69 (d, J = 5.5 Hz, 1H), 7.41-7.38 (m, 1H), 4.25 (s, 3H). |
| 1-120 | Cl | 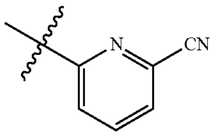 [SMILES: *c1cccc(C#N)n1] | 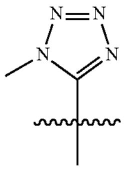 [SMILES: *c1nnnn1C] | $^1$H NMR (500 MHz, DMSO-$d_6$) δ 12.05 (s, 1H), 8.89 (d, J = 7.5, 1H), 8.75 (d, J = 5.5 Hz, 1H), 7.92 (t, J = 7.5 Hz, 1H), 7.82 (d, J = 5.5 Hz, 1H), 7.65 (d, J = 7.5 Hz, 1H), 4.33 (s, 3H). |
| 1-121 | Cl | 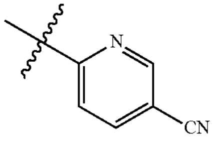 [SMILES: *c1ccc(C#N)cn1] | 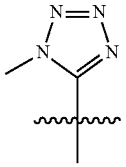 [SMILES: *c1nnnn1C] | $^1$H NMR (500 MHz, DMSO-$d_6$) δ 12.05 (s, 1H), 9.11 (s, 1H), 8.75 (d, J = 5.5 Hz, 1H), 8.54 (d, J = 8.0 Hz, 1H), 8.19 (d, J = 8.0 Hz, 1H), 7.83 (d, J = 5.5 Hz, 1H), 4.33 (s, 3H). |

TABLE A1-continued

| | | | | |
|---|---|---|---|---|
| 1-122 | Cl | 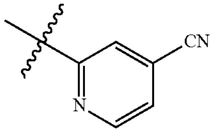 [SMILES: *c1cc(C#N)ccn1] | 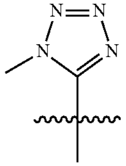 | $^1$H NMR (500 MHz, DMSO-$d_6$) δ 12.05 (s, 1H), 8.80 (d, J = 5.5 Hz, 1H), 8.71 (d, J = 5.5 Hz, 1H), 8.56 (s, 1H), 7.78 (d, J = 5.5 Hz, 1H), 7.53 (d, J = 5.5 Hz, 1H), 4.33 (s, 3H). |
| 1-123 | Cl | 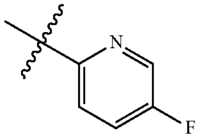 | 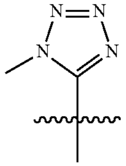 | $^1$H NMR (500 MHz, DMSO-$d_6$) δ 12.04 (s, 1H), 8.76 (d, J = 5.5 Hz, 1H), 8.68 (dd, J = 8.0, 2.5 Hz, 1H), 8.22 (dd, J = 12.5, 2.5 Hz, 1H), 7.80 (d, J = 5.5 Hz, 1H), 7.62-7.58 (m, 1H), 4.33 (s, 3H). |
| 1-124 | Cl | 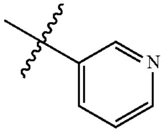 [SMILES: *c1cccnc1] | 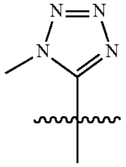 [SMILES: *c1nnnn1C] | $^1$H NMR (500 MHz, DMSO-$d_6$) δ 12.04 (s, 1H), 8.86 (d, J = 2.5 Hz, 1H), 8.82 (d, J = 5.0 Hz, 1H), 8.69-8.68 (m, 1H), 8.11 (d, J = 8.0 Hz, 1H), 7.84 (d, J = 5.0 Hz, 1H), 7.57-7.55 (m, 1H), 4.00 (s, 3H). |
| 1-125 | Cl | 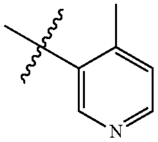 | 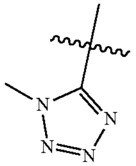 | 1H NMR (500 MHz, DMSO-d6) δ 12.12 (s, 1H), 8.56-8.49 (m, 1H), 8.48 (d, J = 5.0 Hz, 1H), 8.35 (s, 1H), 7.49 (d, J = 5.0 Hz, 1H), 7.36 (d, J = 5.0 Hz, 1H), 3.68 (s, 3H), 2.10 (s, 3H). |
| 1-126 | Cl | 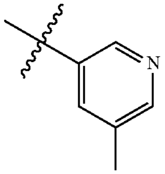 [SMILES: *c1cncc(C)c1] | 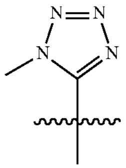 [SMILES: *c1nnnn1C] | $^1$H NMR (500 MHz, DMSO-$d_6$) δ 12.06 (s, 1H), 8.80 (d, J = 5.0 Hz, 1H), 8.65 (s, 1H), 8.52 (s, 1H), 7.90 (s, 1H), 7.81 (d, J = 5.0 Hz, 1H), 3.99 (s, 3H), 2.38 (s, 3H). |
| 1-127 | Cl | 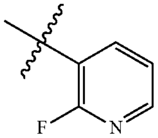 [SMILES: *c1cccnc1F] | 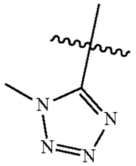 | $^1$H NMR (500 MHz, DMSO-$d_6$) δ 12.05 (s, 1H), 8.73 (d, J = 5.0 Hz, 1H), 8.27 (dd, J = 5.5, 1.5 Hz, 1H), 8.18-8.16 (m, 1H), 7.78-7.75 (m, 1H), 7.72 (d, J = 5.0 Hz, 1H), 4.33 (s, 3H). |

TABLE A1-continued
| | | | | |
|---|---|---|---|---|
| 1-128 | Cl | 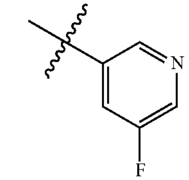 [SMILES: *c1cncc(F)c1] | 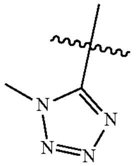 | $^1$H NMR (500 MHz, DMSO-$d_6$) δ 12.05 (s, 1H), 8.77-8.71 (m, 2H), 8.40-8.36 (m, 2H), 7.88 (d, J = 5.0 Hz, 1H), 4.33 (s, 3H). |
| 1-129 | Cl | 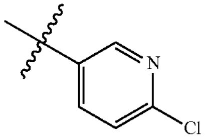 [SMILES: *c1ccc(Cl)nc1] | 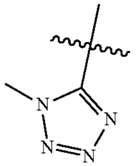 | $^1$H NMR (500 MHz, DMSO-$d_6$) δ 12.09 (s, 1H), 8.80 (d, J = 4.5 Hz, 1H), 8.72 (d, J = 2.5 Hz, 1H), 8.20-8.18 (m, 1H), 7.82 (d, J = 4.5 Hz, 1H), 7.69 (d, J = 8.0 Hz, 1H), 3.97 (s, 3H). |
| 1-130 | Cl | 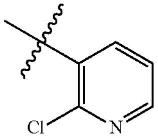 | 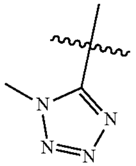 | $^1$H NMR (500 MHz, DMSO-$d_6$) δ 12.05 (s, 1H), 8.74 (d, J = 5.0 Hz, 1H), 8.35 (dd, J = 5.0, 2.0 Hz, 1H), 8.07-8.02 (m, 1H), 7.92-7.85 (m, 2H), 4.33 (s, 3H). |
| 1-131 | Cl | 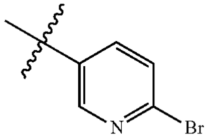 [SMILES: *c1ccc(Br)nc1] | 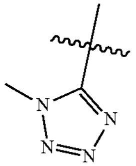 | $^1$H NMR (500 MHz, DMSO-$d_6$) δ 12.04 (s, 1H), 8.81 (d, J = 1.5 Hz, 1H), 8.74 (d, J = 5.0 Hz, 1H), 8.02 (dd, J = 8.0, 1.5 Hz, 1H), 7.88 (d, J = 5.0 Hz, 1H), 7.76 (d, J = 8.0 Hz, 1H), 4.33 (s, 3H). |
| 1-132 | Cl | 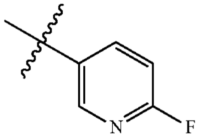 [SMILES: *c1ccc(F)nc1] | 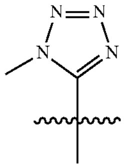 [SMILES: *c1nnnn1C] | $^1$H NMR (500 MHz, DMSO-$d_6$) δ 12.06 (s, 1H), 8.83 (d, J = 5.5 Hz, 1H), 8.75 (d, J = 7.5 Hz, 1H), 8.18 (dd, J = 7.5, 7.5 Hz, 1H), 7.98 (d, J = 5.5 Hz, 1H), 7.18 (dd, J = 12.5, 7.5 Hz, 1H), 4.33 (s, 3H). |
| 1-133 | Cl | 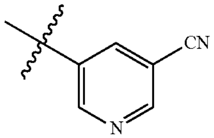 [SMILES: *c1cncc(C#N)c1] | 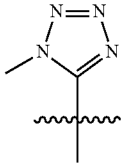 [SMILES: *c1nnnn1C] | $^1$H NMR (500 MHz, DMSO-$d_6$) δ 12.07 (s, 1H), 9.25 (s, 1H), 9.08 (s, 1H), 8.85 (d, J = 5.5 Hz, 1H), 8.68 (s, 1H), 8.00 (d, J = 5.5 Hz, 1H), 4.33 (s, 3H). |

TABLE A1-continued
| | | | | |
|---|---|---|---|---|
| 1-134 | Cl | 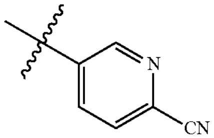 [SMILES: *c1ccc(C#N)nc1] | 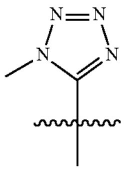 [SMILES: *c1nnnn1C] | $^1$H NMR (500 MHz, DMSO-$d_6$) δ 12.04 (s, 1H), 8.98 (s, 1H), 8.85 (d, J = 5.5 Hz, 1H), 8.24 (d, J = 8.0 Hz, 1H), 7.99 (d, J = 5.5 Hz, 1H), 7.87 (d, J = 8.0 Hz, 1H), 4.33 (s, 3H). |
| 1-135 | Cl | 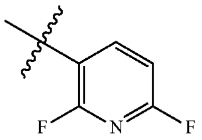 | 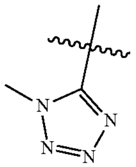 | $^1$H NMR (500 MHz, DMSO-$d_6$) δ 12.06 (s, 1H), 8.73 (d, J = 5.0 Hz, 1H), 8.38-8.33 (m, 1H), 7.88 (d, J = 5.0 Hz, 1H), 7.16-7.11 (m, 1H), 4.33 (s, 3H). |
| 1-136 | Cl | 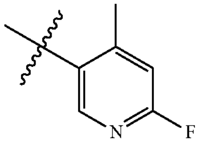 [SMILES: *c1cnc(F)cc1C] | 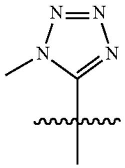 [SMILES: *c1nnnn1C] | 1H NMR (500 MHz, DMSO-d6) δ 12.12 (s, 1H), 8.81 (d, J = 5.0 Hz, 1H), 8.14 (s, 1H), 7.87 (d, J = 5.0 Hz, 1H), 7.26 (d, J = 6.0 Hz, 1H), 3.99 (s, 3H), 2.17 (s, 3H). |
| 1-137 | Cl | 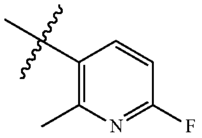 [SMILES: *c1ccc(F)nc1C] | 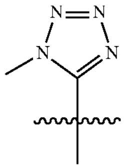 [SMILES: *c1nnnn1C] | $^1$H NMR (500 MHz, DMSO-d6) δ 12.02 (s, 1H), 8.85 (d, J = 4.5 Hz, 1H), 8.28 (dd, J = 11.0, 8.0 Hz, 1H), 7.52 (d, J = 4.5 Hz, 1H), 6.88 (dd, J = 8.0, 7.0 Hz, 1H), 4.32 (s, 3H), 2.79 (s, 3H). |
| 1-138 | Cl | 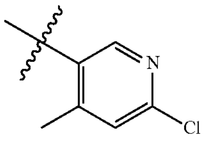 [SMILES: *c1cnc(Cl)cc1C] | 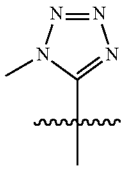 | $^1$H NMR (500 MHz, DMSO-d6) δ 12.03 (s, 1H), 8.88-8.82 (m, 2H), 7.54-7.47 (m, 2H), 4.32 (s, 3H), 2.37 (s, 3H). |
| 1-139 | Cl | 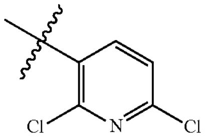 [SMILES: *c1ccc(Cl)nc1Cl] | 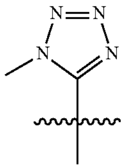 [SMILES: *c1nnnn1C] | $^1$H NMR (500 MHz, DMSO-d6) δ 12.04 (s, 1H), 8.84 (d, J = 4.5 Hz, 1H), 8.36 (d, J = 8.0 Hz, 1H), 7.47 (d, J = 8.0 Hz, 1H), 7.33 (d, J = 4.5 Hz, 1H), 4.32 (s, 3H). |

TABLE A1-continued

| | | | | |
|---|---|---|---|---|
| 1-140 | Cl | 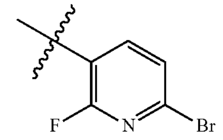 | 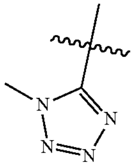 | $^1$H NMR (500 MHz, DMSO-$d_6$) δ 12.04 (s, 1H), 8.73 (d, J = 5.0 Hz, 1H), 8.18 (dd, J = 8.0, 6.0 Hz, 1H), 7.88 (d, J = 5.0 Hz, 1H), 7.74 (d, J = 8.0 Hz, 1H), 4.33 (s, 3H). |
| 1-141 | Cl | 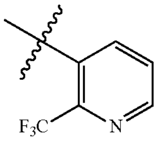 | 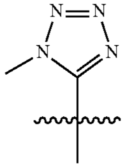 [SMILES: *c1nnnn1C] | $^1$H NMR (500 MHz, DMSO-d6) δ 12.04 (s, 1H), 8.86 (d, J = 4.5 Hz, 1H), 8.69 (dd, J = 5.0, 1.5 Hz, 1H), 8.26 (dd, J = 8.0, 1.5 Hz, 1H), 7.67 (dd, J = 8.0, 5.0 Hz, 1H), 7.36 (d, J = 5.0 Hz, 1H), 4.33 (s, 3H). |
| 1-142 | Cl | 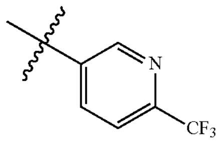 | 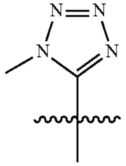 | $^1$H NMR (500 MHz, DMSO-$d_6$) δ 12.10 (s, 1H), 9.07 (d, J = 2.0 Hz, 1H), 8.87 (d, J = 5.0 Hz, 1H), 8.46-8.38 (m, 1H), 8.09 (d, J = 8.0 Hz, 1H), 7.91 (d, J = 5.0 Hz, 1H), 4.00 (s, 3H). |
| 1-143 | Cl | 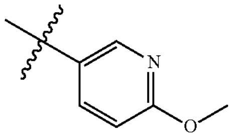 | 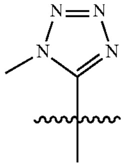 [SMILES: *c1nnnn1C] | $^1$H NMR (500 MHz, DMSO-$d_6$) δ 12.19 (s, 1H), 8.89 (d, J = 5.0 Hz, 1H), 8.63 (d, J = 2.5 Hz, 1H), 8.21-8.08 (m, 1H), 7.88 (d J = 5.0 Hz, 1H), 7.08 (d, J = 8.5 Hz, 1H), 4.11 (s, 3H), 4.03 (s, 3H). |
| 1-144 | Cl | 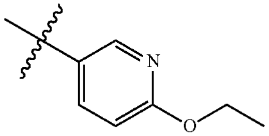 [SMILES: *c1ccc(OCC)nc1] | 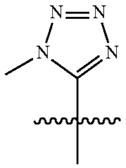 [SMILES: *c1nnnn1C] | $^1$H NMR (500 MHz, DMSO-$d_6$) δ 12.03 (s, 1H), 8.77 (d, J = 5.0 Hz, 1H), 8.59 (d, J = 1.5 Hz, 1H), 8.03 (dd, J = 8.0, 1.5 Hz, 1H), 7.92 (d, J = 5.0 Hz, 1H), 7.09 (d, J = 8.0 Hz, 1H), 4.33 (q, J = 8.0 Hz, 2H), 4.33 (s, 3H), 1.28 (t, J = 8.0 Hz, 3H). |
| 1-145 | Cl | 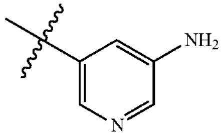 [SMILES: *c1cncc(N)c1] | 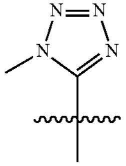 | 1H NMR (500 MHz, DMSO-d6) δ 12.07 (s, 1H), 8.84 (d, J = 4.5 Hz, 1H), 8.38 (d, J = 1.5 Hz, 1H), 8.04-7.95 (m, 2H), 7.46 (t, J = 1.5 Hz, 1H), 6.18 (s, 2H), 4.33 (s, 3H). |

TABLE A1-continued
| | | | | |
|---|---|---|---|---|
| 1-146 | Cl | 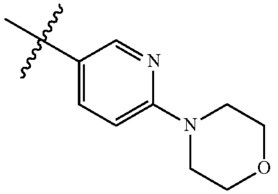 [SMILES: *c1ccc(N2CCOCC2)nc1] | 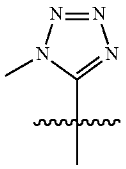 [SMILES: *c1nnnn1C] | $^1$H NMR (500 MHz, DMSO-$d_6$) δ 12.14 (s, 1H), 8.77 (d, J = 5.0 Hz, 1H), 8.53 (d, J = 2.5 Hz, 1H), 8.01 (dd, J = 9.0, 2.5 Hz, 1H), 7.74 (d, J = 5.0 Hz, 1H), 7.03 (d, J = 9.0 Hz, 1H), 4.03 (s, 3H), 3.73 (t, J = 5.0 Hz, 4H), 3.60 (t, J = 5.0 Hz, 4H). |
| 1-147 | Cl | 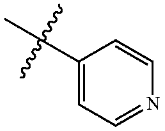 | 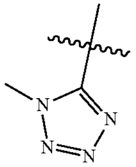 | $^1$H NMR (500 MHz, DMSO-$d_6$) δ 12.05 (s, 1H), 8.75 (d, J = 5.0 Hz, 1H), 8.66 (d, J = 5.0 Hz, 2H), 8.04 (d, J = 5.0 Hz, 1H), 7.90 (d, J = 5.0 Hz, 1H), 4.33 (s, 3H). |
| 1-148 | Cl | 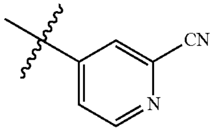 [SMILES: *c1ccnc(C#N)c1] | 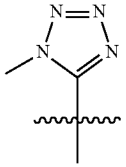 | $^1$H NMR (500 MHz, DMSO-$d_6$) δ 12.05 (s, 1H), 8.85 (d, J = 5.5 Hz, 1H), 8.78 (d, J = 5.5 Hz, 1H), 8.53 (s, 1H), 8.29 (d, J = 5.5 Hz, 1H), 8.00 (d, J = 5.5 Hz, 1H), 4.33 (s, 3H). |
| 1-149 | Cl | 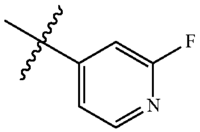 [SMILES: *c1ccnc(F)c1] | 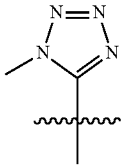 [SMILES: *c1nnnn1C] | $^1$H NMR (500 MHz, DMSO-$d_6$) δ 12.05 (s, 1H), 8.85 (d, J = 5.0 Hz, 1H), 8.27 (d, J = 5.0 Hz, 1H), 8.06-7.97 (m, 2H), 7.84 (dd, J = 5.0, 1.0 Hz, 1H), 4.33 (s, 3H). |
| 1-150 | Cl | 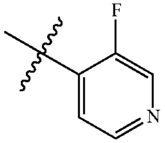 [SMILES: *c1ccncc1F] | 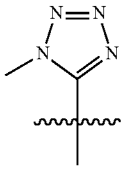 [SMILES: *c1nnnn1C] | $^1$H NMR (500 MHz, DMSO-$d_6$) δ 12.06 (s, 1H), 8.85 (d, J = 5.0 Hz, 1H), 8.41 (d, J = 8.0 Hz, 1H), 8.33 (d, J = 4.5 Hz, 1H), 7.73 (dd, J = 8.0, 4.5 Hz, 1H), 7.51 (d, J = 5.0 Hz, 1H), 4.32 (s, 3H). |

TABLE A1-continued
| | | | | |
|---|---|---|---|---|
| 1-151 | Cl | 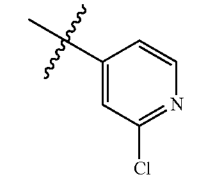 [SMILES: *c1ccnc(Cl)c1] | 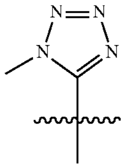 [SMILES: *c1nnnn1C] | $^1$H NMR (500 MHz, DMSO-$d_6$) δ 12.05 (s, 1H), 8.83 (d, J = 5.0 Hz, 1H), 8.42-8.34 (m, 2H), 8.06-7.96 (m, 2H), 4.33 (s, 3H). |
| 1-152 | Cl | 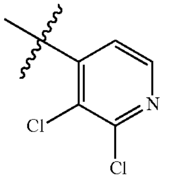 [SMILES: *c1ccnc(Cl)c1Cl] | 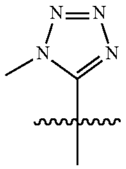 | $^1$H NMR (500 MHz, DMSO-d6) δ 12.07 (s, 1H), 8.86 (d, J = 5.0 Hz, 1H), 8.40 (d, J = 5.0 Hz, 1H), 7.94 (d, J = 5.0 Hz, 1H), 7.51 (d, J = 5.0 Hz, 1H), 4.32 (s, 3H). |
| 1-153 | Cl | 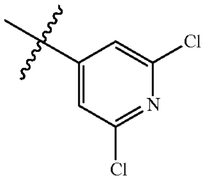 | 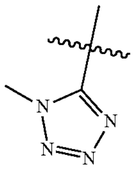 | $^1$H NMR (500 MHz, DMSO-$d_6$) δ 12.04 (s, 1H), 8.76 (d, J = 5.0 Hz, 1H), 8.49 (s, 2H), 8.11 (d, J = 5.0 Hz, 1H), 4.33 (s, 3H). |
| 1-154 | Cl | 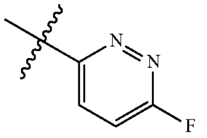 [SMILES: *c1ccc(F)nn1] | 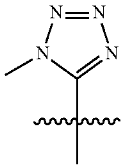 [SMILES: *c1nnnn1C] | $^1$H NMR (500 MHz, DMSO-$d_6$) δ 12.04 (s, 1H), 8.94 (dd, J = 7.5, 7.5 Hz, 1H), 8.89 (d, J = 5.5 Hz, 1H), 8.01 (d, J = 5.5 Hz, 1H), 7.68 (dd, J = 12.0, 7.5 Hz, 1H), 4.33 (s, 3H). |
| 1-155 | Cl | 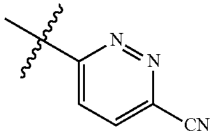 [SMILES: *c1ccc(C#N)nn1] | 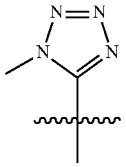 [SMILES: *c1nnnn1C] | $^1$H NMR (500 MHz, DMSO-$d_6$) δ 12.05 (s, 1H), 8.94 (d, J = 7.5 Hz, 1H), 8.89 (d, J = 5.5 Hz, 1H), 8.34 (d, J = 7.5 Hz, 1H), 8.01 (d, J = 5.5 Hz, 1H), 4.33 (s, 3H). |
| 1-156 | Cl | 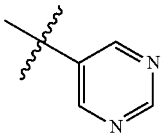 [SMILES: *c1cncnc1] | 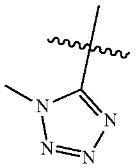 | $^1$H NMR (500 MHz, DMSO-$d_6$) δ 12.10 (s, 1H), 9.40 (s, 2H), 9.35 (s, 1H), 8.79 (d, J = 5.0 Hz, 1H), 7.89 (d, J = 5.0 Hz, 1H), 4.33 (s, 3H). |

TABLE A1-continued
| | | | | |
|---|---|---|---|---|
| 1-157 | Cl | 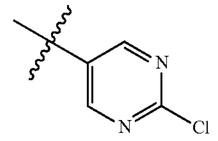 [SMILES: *c1cnc(Cl)nc1] | 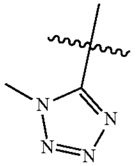 | $^1$H NMR (500 MHz, DMSO-$d_6$) δ 12.06 (s, 1H), 9.27 (s, 2H), 8.79 (d, J = 5.0 Hz, 1H), 8.08 (d, J = 5.0 Hz, 1H), 4.33 (s, 3H). |
| 1-158 | Cl | 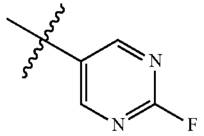 [SMILES: *c1cnc(F)nc1] | 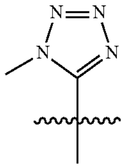 [SMILES: *c1nnnn1C] | $^1$H NMR (500 MHz, DMSO-$d_6$) δ 12.06 (s, 1H), 9.45 (d, J = 7.5 Hz, 2H), 8.89 (d, J = 5.5 Hz, 1H), 7.98 (d, J = 5.5 Hz, 1H), 4.33 (s, 3H). |
| 1-159 | Cl | 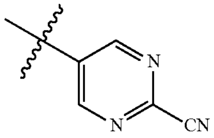 [SMILES: *c1cnc(C#N)nc1] | 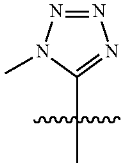 [SMILES: *c1nnnn1C] | $^1$H NMR (500 MHz, DMSO-$d_6$) δ 12.03 (s, 1H), 9.01 (s, 2H), 8.90 (d, J = 5.5 Hz, 1H), 7.96 (d, J = 5.5 Hz, 1H), 4.33 (s, 3H). |
| 1-160 | Cl | 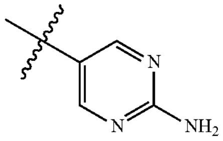 | 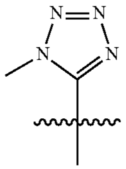 [SMILES: *c1nnnn1C] | $^1$H NMR (500 MHz, DMSO-$d_6$) δ 12.03 (s, 1H), 8.74 (d, J = 5.0 Hz, 1H), 8.63 (s, 2H), 7.70 (d, J = 5.0 Hz, 1H), 7.11 (s, 2H), 4.00 (s, 3H). |
| 1-161 | Cl | 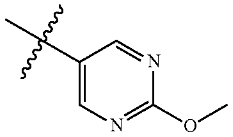 [SMILES: *c1cnc(OC)nc1] | 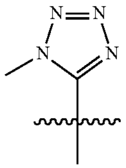 [SMILES: *c1nnnn1C] | $^1$H NMR (500 MHz, DMSO-$d_6$) δ 12.03 (s, 1H), 9.50 (s, 2H), 8.89 (d, J = 5.0 Hz, 1H), 7.96 (d, J = 5.0 Hz, 1H), 4.33 (s, 3H), 3.85 (s, 3H). |

TABLE A1-continued
| | | | | |
|---|---|---|---|---|
| 1-162 | Cl | 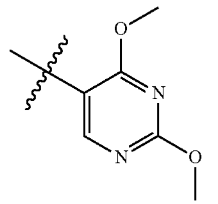 [SMILES: *c1cnc(OC)nc1OC] | 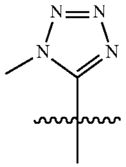 [SMILES: *c1nnnn1C] | $^1$H NMR (500 MHz, DMSO-d6) δ 12.34 (s, 1H), 8.89 (d, J = 5.0 Hz, 1H), 8.74 (s, 1H), 7.31 (d, J = 5.0 Hz, 1H), 4.31 (s, 3H), 3.98 (s, 3H), 3.84 (s, 3H). |
| 1-163 | Cl | 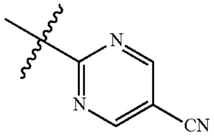 | 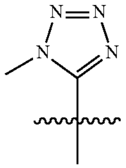 | $^1$H NMR (500 MHz, DMSO-$d_6$) δ 12.06 (s, 1H), 9.25 (s, 2H), 8.86 (d, J = 5.5 Hz, 1H), 8.00 (d, J = 5.5 Hz, 1H), 4.33 (s, 3H). |
| 1-164 | Cl | 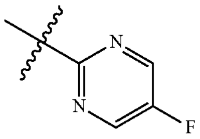 [SMILES: *c1ncc(F)cn1] | 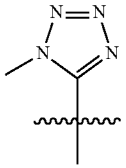 [SMILES: *c1nnnn1C] | $^1$H NMR (500 MHz, DMSO-$d_6$) δ 12.05 (s, 1H), 8.88 (d, J = 5.5 Hz, 1H), 8.84 (d, J = 12.5, 2.5 Hz, 2H), 7.99 (d, J = 5.5 Hz, 1H), 4.33 (s, 3H). |
| 1-165 | Cl | 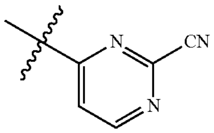 [SMILES: *c1ccnc(C#N)n1] | 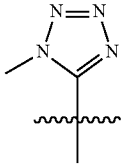 [SMILES: *c1nnnn1C] | $^1$H NMR (500 MHz, DMSO-$d_6$) δ 12.05 (s, 1H), 9.10 (d, J = 5.0 Hz, 1H), 8.88 (d, J = 5.0 Hz, 1H), 8.76 (d, J = 5.0 Hz, 1H), 8.02 (d, J = 5.0 Hz, 1H), 4.33 (s, 3H). |
| 1-166 | Cl | 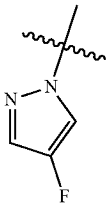 | 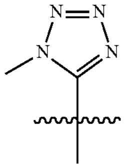 [SMILES: *c1nnnn1C] | $^1$H NMR (500 MHz, DMSO-$d_6$) δ 12.05 (s, 1H), 8.98 (d, J = 5.0 Hz, 1H), 7.95 (d, J = 5.0 Hz, 1H), 7.50 (d, J = 12.5 Hz, 2H), 4.33 (s, 3H). |

TABLE A1-continued
| | | | | |
|---|---|---|---|---|
| 1-167 | Cl | 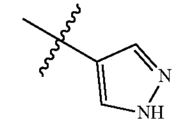 | 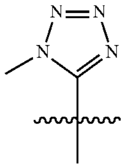 [SMILES: *c1nnnn1C] | 1H NMR (500 MHz, DMSO-d6) δ 13.15 (s, 1H), 8.38 (d, J = 5.0 Hz, 1H), 8.22 (s, 2H), 7.16 (d, J = 5.0 Hz, 1H), 3.70 (s, 3H). |
| 1-168 | Cl | 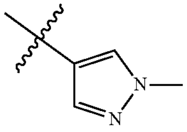 [SMILES: *c1cnn(C)c1] | 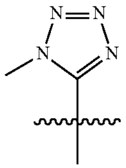 [SMILES: *c1nnnn1C] | $^1$H NMR (500 MHz, DMSO-$d_6$) δ 12.15 (s, 1H), 8.77 (d, J = 5.0 Hz, 1H), 8.63 (s, 1H), 8.25 (s, 1H), 7.68 (d, J = 5.0 Hz, 1H), 4.12 (s, 3H), 4.03 (s, 3H). |
| 1-169 | Cl | 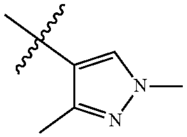 [SMILES: *c1cn(C)nc1C] | 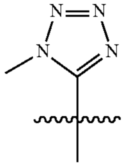 [SMILES: *c1nnnn1C] | $^1$H NMR (500 MHz, DMSO-$d_6$) δ 12.01 (s, 1H), 8.69 (d, J = 5.0 Hz, 1H), 8.20 (s, 1H), 7.59 (d, J = 5.0 Hz, 1H), 3.99 (s, 3H), 3.82 (s, 3H), 2.28 (s, 3H). |
| 1-170 | Cl | 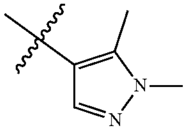 [SMILES: *c1cnn(C)c1C] | 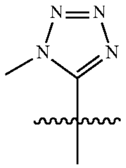 [SMILES: *c1nnnn1C] | $^1$H NMR (500 MHz, DMSO-$d_6$) δ 12.09 (s, 1H), 8.99 (d, J = 5.0 Hz, 1H), 7.67 (s, 1H), 7.52 (d, J = 5.0 Hz, 1H), 4.33 (s, 3H), 3.94 (s, 3H), 2.34 (s, 3H). |
| 1-171 | Cl | 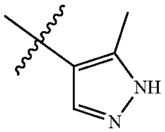 [SMILES: *c1cn[nH]c1C] | 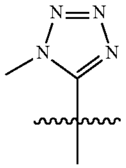 | $^1$H NMR (500 MHz, DMSO-$d_6$) δ 13.53 (s, 1H), 12.03 (s, 1H), 8.91 (d, J = 5.0 Hz, 1H), 7.95 (d, J = 5.0 Hz, 1H), 7.40 (s, 1H), 4.33 (s, 3H), 2.31 (s, 3H). |
| 1-172 | Cl | 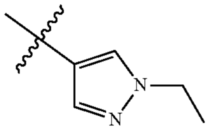 [SMILES: *c1cnn(CC)c1] | 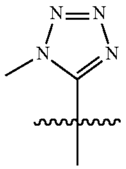 [SMILES: *c1nnnn1C] | $^1$H NMR (500 MHz, DMSO-$d_6$) δ 12.02 (s, 1H), 8.65 (d, J = 5.0 Hz, 1H), 8.53 (s, 1H), 8.15 (s, 1H), 7.56 (d, J = 5.0 Hz, 1H), 4.21-4.15 (m, 2H), 4.00 (s, 3H), 1.40 (t, J = 7.0 Hz, 3H). |

TABLE A1-continued
| | | | | |
|---|---|---|---|---|
| 1-173 | Cl | 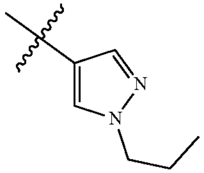 [SMILES: *c1cnn(CCC)c1] | 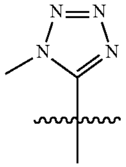 [SMILES: *c1nnnn1C] | $^1$H NMR (500 MHz, DMSO-d6) δ 12.17 (s, 1H), 8.97 (d, J = 5.0 Hz, 1H), 7.86 (d, J = 1.5 Hz, 1H), 7.47 (d, J = 5.0 Hz, 1H), 6.91 (d, J = 1.5 Hz, 1H), 4.33 (s, 3H), 4.20 (t, J = 8.0 Hz, 2H), 2.00 (m, 2H), 0.95 (t, J = 8.0 Hz, 3H). |
| 1-174 | Cl | 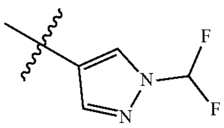 [SMILES: *c1cnn(C(F)F)c1] | 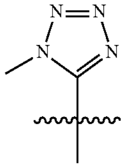 [SMILES: *c1nnnn1C] | $^1$H NMR (500 MHz, DMSO-$d_6$) δ 12.05 (s, 1H), 8.91 (d, J = 5.5 Hz, 1H), 7.95 (t, J = 65.0 Hz, 1H), 7.71 (d, J = 5.5 Hz, 1H), 7.67 (s, 1H), 7.06 (s, 1H)), 4.33 (s, 3H). |
| 1-175 | Cl | 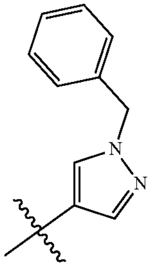 [SMILES: *c1cnn(Cc2ccccc2)c1] | 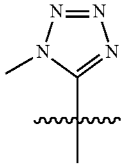 | $^1$H NMR (500 MHz, DMSO-$d_6$) δ 12.13 (s, 1H), 8.95-8.69 (m, 2H), 8.30 (d, J = 5.5 Hz, 1H), 7.68 (s, 1H), 7.42-7.29 (m, 5H), 5.53 (s, 2H), 4.11 (s, 3H). |
| 1-176 | Cl | 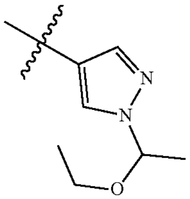 [SMILES: *c1cnn(C(C)OCC)c1] | 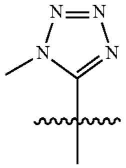 | 1H NMR (500 MHz, DMSO-d6) δ 12.03 (s, 1H), 8.66-8.59 (m, 2H), 8.22 (s, 1H), 7.60 (d, J = 5.5 Hz, 1H), 5.65-5.60 (m, 1H), 4.00 (s, 3H), 3.51-3.41 (m, 2H), 1.63 (d, J = 6.0 Hz, 3H), 1.06-0.97 (m, 3H). |
| 1-177 | Cl | 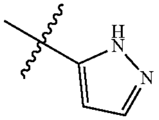 [SMILES: *c1ccn[nH]1] | 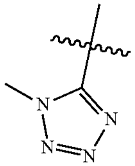 | $^1$H NMR (500 MHz, DMSO-$d_6$) δ 13.56 (s, 1H), 12.13 (s, 1H), 8.82 (d, J = 5.0 Hz, 1H), 8.30 (d, J = 2.5 Hz, 1H), 7.89 (d, J = 2.5 Hz, 1H), 7.61 (d, J = 5.0 Hz, 1H), 4.00 (s, 3H). |

TABLE A1-continued

| | | | | |
|---|---|---|---|---|
| 1-178 | Cl | 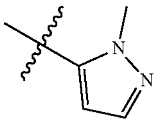 [SMILES: *c1ccnn1C] | 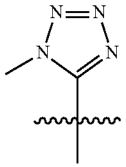 [SMILES: *c1nnnn1C] | $^1$H NMR (500 MHz, DMSO-$d_6$) δ 12.08 (s, 1H), 8.83 (d, J = 5.0 Hz, 1H), 7.84 (d, J = 2.5 Hz, 1H), 7.61-7.44 (m, 1H), 6.67 (d, J = 5.0 Hz, 1H), 3.99 (s, 3H), 3.83 (s, 3H). |
| 1-179 | Cl | 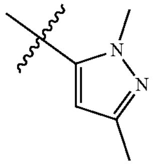 [SMILES: *c1cc(C)nn1C] | 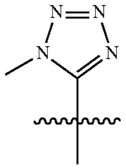 [SMILES: *c1nnnn1C] | $^1$H NMR (500 MHz, DMSO-d6) δ 12.07 (s, 1H), 8.98 (d, J = 4.5 Hz, 1H), 7.51 (d, J = 4.5 Hz, 1H), 6.55 (s, 1H), 4.33 (s, 3H), 4.00 (s, 3H), 2.35 (s, 3H). |
| 1-180 | Cl | 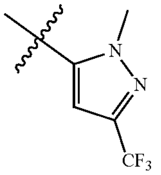 | 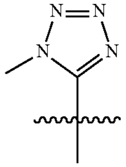 [SMILES: *c1nnnn1C] | $^1$H NMR (500 MHz, DMSO-d6) δ 12.05 (s, 1H), 8.98 (d, J = 5.0 Hz, 1H), 7.51 (d, J = 5.0 Hz, 1H), 6.68 (s, 1H), 4.33 (s, 3H), 4.02 (s, 3H). |
| 1-181 | Cl | 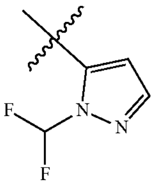 | 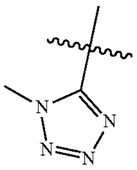 [SMILES: *c1nnnn1C] | $^1$H NMR (500 MHz, DMSO-$d_6$) δ 12.05 (s, 1H), 8.87 (d, J = 5.0 Hz, 1H), 7.96-7.73 (t, J = 6.5 Hz, 1H), 7.70 (d, J = 5.0 Hz, 1H), 7.64 (d, J = 2.5 Hz, 1H), 6.73 (d, J = 2.5 Hz, 1H), 4.33 (s, 3H). |
| 1-182 | Cl | 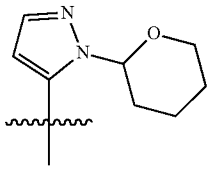 [SMILES: *c1ccnn1C1CCCCO1] | 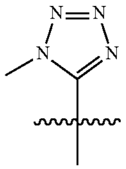 | $^1$H NMR (500 MHz, DMSO-$d_6$) δ 12.05 (s, 1H), 8.76 (d, J = 5.0 Hz, 1H), 8.10 (d, J = 5.0 Hz, 1H), 7.61 (d, J = 2.5 Hz, 1H), 6.68 (d, J = 2.5 Hz, 1H), 6.12 (t, J = 6.5 Hz, 1H), 4.33 (s, 3H), 3.90-3.77 (m, 2H), 2.47-2.36 (m, 1H), 2.08-1.95 (m, 2H), 1.81-1.69 (m, 1H), 1.59-1.55 (m, 2H). |
| 1-183 | Cl | 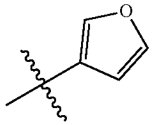 [SMILES: *c1ccoc1] | 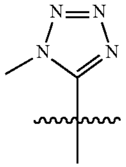 | $^1$H NMR (500 MHz, DMSO-$d_6$) δ 12.16 (s, 1H), 8.84 (d, J = 5.0 Hz, 1H), 8.66 (s, 1H), 7.98-7.88 (m, 1H), 7.78 (d, J = 2.0 Hz, 1H), 7.25 (d, J = 2.0 Hz, 1H), 4.20 (s, 3H). |

TABLE A1-continued
| | | | | |
|---|---|---|---|---|
| 1-184 | Cl | 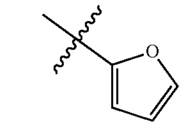 [SMILES: *c1ccco1] | 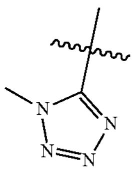 | $^1$H NMR (500 MHz, DMSO-$d_6$) δ 12.05 (s, 1H), 8.87 (d, J = 5.0 Hz, 1H), 8.10-8.04 (m, 2H), 7.25 (d, J = 2.5 Hz, 1H), 6.98 (t, J = 2.5 Hz, 1H), 4.33 (s, 3H). |
| 1-185 | Cl | 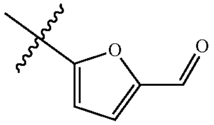 [SMILES: *c1ccc(C=O)o1] | 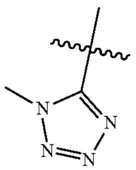 [SMILES: *c1nnnn1C] | $^1$H NMR (500 MHz, DMSO-$d_6$) δ 12.06 (s, 1H), 9.25 (s, 1H), 8.88 (d, J = 5.0 Hz, 1H), 8.08 (d, J = 5.0 Hz, 1H), 7.29 (d, J = 2.5 Hz, 1H), 7.22 (d, J = 2.5 Hz, 1H), 4.33 (s, 3H). |
| 1-186 | Cl | 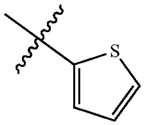 [SMILES: *c1cccs1] | 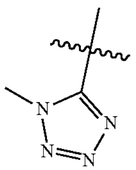 | 1H NMR (500 MHz, DMSO-d6) δ 12.04 (s, 1H), 8.73 (d, J = 5.0 Hz, 1H), 8.20 (dd, J = 3.0, 1.5 Hz, 1H), 7.74-7.58 (m, 3H), 4.01 (s, 3H). |
| 1-187 | Cl | 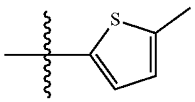 [SMILES: *c1ccc(C)s1] | 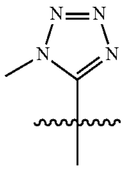 | $^1$H NMR (500 MHz, DMSO-$d_6$) δ 12.04 (s, 1H), 8.64 (d, J = 5.0 Hz, 1H), 7.93 (d, J = 2.5 Hz, 1H), 7.61 (d, J = 5.0 Hz, 1H), 6.92 (d, J = 2.5 Hz, 1H), 4.00 (s, 3H), 2.38 (s, 3H). |
| 1-188 | Cl | 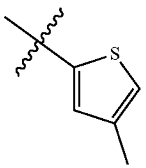 [SMILES: *c1cc(C)cs1] | 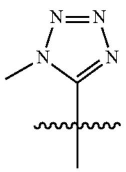 [SMILES: *c1nnnn1C] | $^1$H NMR (500 MHz, DMSO-$d_6$) δ 12.08 (s, 1H), 8.69 (d, J = 5.0 Hz, 1H), 7.97 (s, 1H), 7.67 (d, J = 5.0 Hz, 1H), 7.42 (s, 1H), 4.03 (s, 3H), 2.29 (s, 3H). |
| 1-189 | Cl | 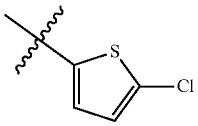 [SMILES: *c1ccc(Cl)s1] | 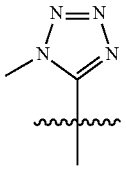 [SMILES: *c1nnnn1C] | $^1$H NMR (500 MHz, DMSO-d6) δ 12.05 (s, 1H), 8.99 (d, J = 5.0 Hz, 1H), 7.53 (d, J = 5.0 Hz, 1H), 7.33 (d, J = 2.5 Hz, 1H), 7.08 (d, J = 2.5 Hz, 1H), 4.33 (s, 3H). |

TABLE A1-continued
| | | | | |
|---|---|---|---|---|
| 1-190 | Cl | 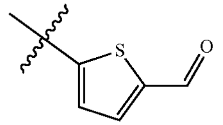 [SMILES: *c1ccc(C=O)s1] | 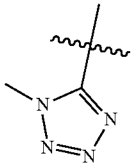 | $^{1}$H NMR (500 MHz, DMSO-$d_6$) δ 12.05 (s, 1H), 9.87 (s, 1H), 8.90 (d, J = 5.0 Hz, 1H), 8.10 (d, J = 5.0 Hz, 1H), 7.95 (d, J = 2.5 Hz, 1H), 7.81 (d, J = 2.5 Hz, 1H), 4.33 (s, 3H). |
| 1-191 | Cl | 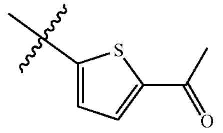 [SMILES: *c1ccc(C(C)=O)s1] | 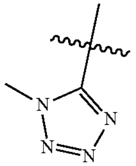 | $^{1}$H NMR (500 MHz, DMSO-$d_6$) δ 12.05 (s, 1H), 8.89 (d, J = 5.0 Hz, 1H), 8.11 (d, J = 2.5 Hz, 1H), 7.82 (d, J = 2.5 Hz, 1H), 7.77 (d, J = 5.0 Hz, 1H), 4.33 (s, 3H), 2.50 (s, 3H). |
| 1-192 | Cl | 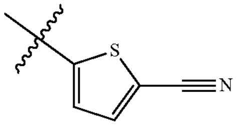 [SMILES: *c1ccc(C#N)s1] | 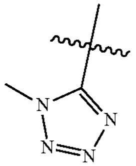 | $^{1}$H NMR (500 MHz, DMSO-$d_6$) δ 12.06 (s, 1H), 8.87 (d, J = 5.0 Hz, 1H), 7.92 (d, J = 5.0 Hz, 1H), 7.59-7.51 (m, 2H), 4.33 (s, 3H), 4.26 (s, 1H). |
| 1-193 | Cl | 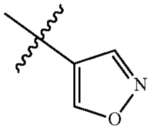 [SMILES: *c1cnoc1] | 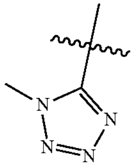 | $^{1}$H NMR (500 MHz, DMSO-$d_6$) δ 12.06 (s, 1H), 8.91 (d, J = 5.5 Hz, 1H), 8.45 (s, 1H), 8.09 (s, 1H), 7.91 (d, J = 5.5 Hz, 1H), 4.33 (s, 3H). |
| 1-194 | $CH_3$ | 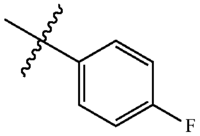 [SMILES: *c1ccc(F)cc1] | 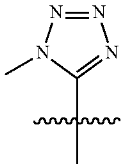 [SMILES: *c1nnnn1C] | $^{1}$H NMR (500 MHz, DMSO-d6) δ 12.31 (s, 1H), 8.69 (d, J = 4.5 Hz, 1H), 7.60-7.52 (m, 2H), 7.14-7.03 (m, 3H), 4.33 (s, 3H), 2.35 (s, 3H). |
| 1-195 | F | 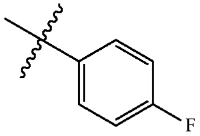 [SMILES: *c1ccc(F)cc1] | 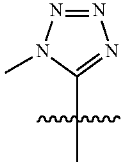 | $^{1}$H NMR (500 MHz, DMSO-$d_6$) δ 12.09 (s, 1H), 8.44 (dd, J = 5.0, 1.5 Hz, 1H), 8.08-8.01 (m, 2H), 7.83 (dd, J = 7.5, 5.0 Hz, 1H), 7.35-7.27 (m, 2H), 4.33 (s, 3H). |

TABLE A1-continued
| | | | | |
|---|---|---|---|---|
| 1-196 | Br | 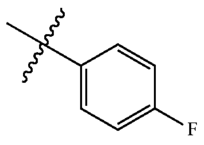 [SMILES: *c1ccc(F)cc1] | 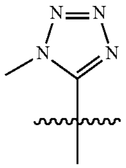 [SMILES: *c1nnnn1C] | $^1$H NMR (500 MHz, DMSO-$d_6$) δ 12.06 (s, 1H), 8.80 (d, J = 5.5 Hz, 1H), 7.96 (dd, J = 7.5, 7.0 Hz, 2H), 7.72 (d, J = 5.5 Hz, 1H), 7.33 (dd, J = 12.0, 7.0 Hz, 2H), 4.33 (s, 3H). |
| 1-197 | 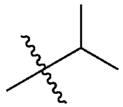 [SMILES: *C(C)C] | 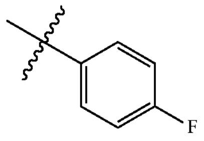 | 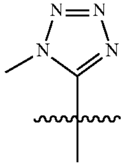 [SMILES: *c1nnnn1C] | $^1$H NMR (500 MHz, DMSO-d6) δ 12.17 (s, 1H), 8.69 (d, J = 5.0 Hz, 1H), 7.54-7.45 (m, 2H), 7.11-7.03 (m, 2H), 7.00 (d, J = 5.0 Hz, 1H), 4.35 (s, 3H), 3.16-3.11 (m, 1H), 1.25 (d, J = 6.5 Hz, 6H). |
| 1-198 | $CF_3$ | 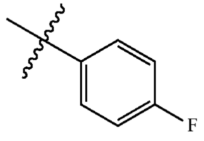 [SMILES: *c1ccc(F)cc1] | 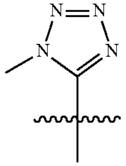 [SMILES: *c1nnnn1C] | $^1$H NMR (500 MHz, DMSO-d6) δ 12.07 (s, 1H), 8.87 (d, J = 4.5 Hz, 1H), 7.64-7.56 (m, 2H), 7.13 (d, J = 4.5 Hz, 1H), 7.11-7.03 (m, 2H), 4.35 (s, 3H). |
| 1-199 | 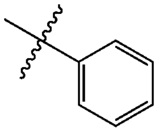 [SMILES: *c1ccccc1] | 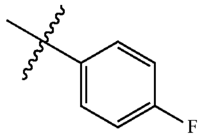 [SMILES: *c1ccc(F)cc1] | 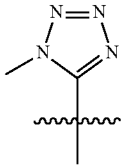 | $^1$H NMR (500 MHz, DMSO-d6) δ 11.98 (s, 1H), 8.66 (d, J = 5.0 Hz, 1H), 7.61-7.53 (m, 4H), 7.42 (t, J = 7.5 Hz, 1H), 7.40 (d, J = 7.5 Hz, 1H), 7.37-7.29 (m, 2H), 7.11-7.03 (m, 2H), 4.29 (s, 3H). |
| 1-200 | 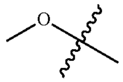 [SMILES: *OC] | 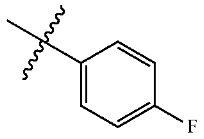 [SMILES: *c1ccc(F)cc1] | 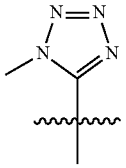 [SMILES: *c1nnnn1C] | $^1$H NMR (500 MHz, DMSO-d6) δ 12.06 (s, 1H), 8.66 (d, J = 5.0 Hz, 1H), 7.71-7.63 (m, 2H), 7.46 (d, J = 5.0 Hz, 1H), 7.11-7.03 (m, 2H) 4.34 (s, 3H), 3.79 (s, 3H). |
| 1-201 | 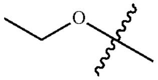 [SMILES: *OCC] | 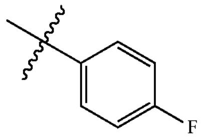 [SMILES: *c1ccc(F)cc1] | 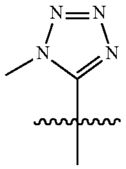 [SMILES: *c1nnnn1C] | $^1$H NMR (500 MHz, DMSO-$d_6$) δ 12.07 (s, 1H), 8.66 (d, J = 5.0 Hz, 1H), 7.71-7.64 (m, 2H), 7.46 (d, J = 5.0 Hz, 1H), 7.11-7.03 (m, 2H), 4.34-4.06 (m, 2H), 4.34 (s, 3H), 1.61 (t, J = 8.0 Hz, 3H). |

TABLE A1-continued
| | | | | |
|---|---|---|---|---|
| 1-202 | 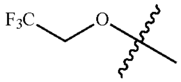 | 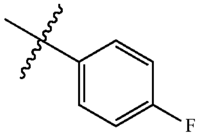 [SMILES: *c1ccc(F)cc1] | 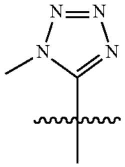 [SMILES: *c1nnnn1C] | $^1$H NMR (500 MHz, DMSO-$d_6$) δ 11.93 (s, 1H), 8.67 (d, J = 4.5 Hz, 1H), 7.72-7.64 (m, 2H), 7.42 (d, J = 4.5 Hz, 1H), 7.11-7.03 (m, 2H), 4.46-4.39 (m, 2H), 4.34 (s, 3H). |
| 1-203 | 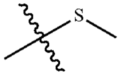 [SMILES: *SC] | 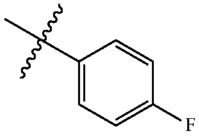 [SMILES: *c1ccc(F)cc1] | 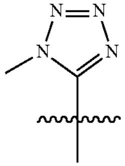 [SMILES: *c1nnnn1C] | $^1$H NMR (500 MHz, DMSO-$d_6$) δ 12.25 (s, 1H), 8.60 (d, J = 5.5 Hz, 1H), 8.02 (dd, J = 7.5, 7.5 Hz, 2H), 7.60 (d, J = 5.5 Hz, 1H), 7.32 (dd, J = 11.5, 7.5 Hz, 2H), 4.33 (s, 3H), 2.21 (s, 3H). |
| 1-204 | 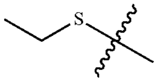 [SMILES: *SCC] | 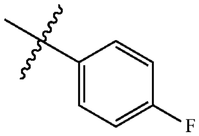 | 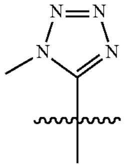 [SMILES: *c1nnnn1C] | $^1$H NMR (500 MHz, DMSO-d6) δ 11.82 (s, 1H), 8.65 (d, J = 5.0 Hz, 1H), 7.64-7.56 (m, 2H), 7.24 (d, J = 5.0 Hz, 1H), 7.11-7.03 (m, 2H), 4.33 (s, 3H), 2.97-2.89 (m, 2H), 1.28 (t, J = 8.0 Hz, 3H). |
| 1-205 | 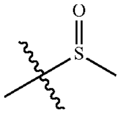 [SMILES: *S(C)=O] | 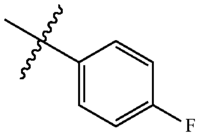 [SMILES: *c1ccc(F)cc1] | 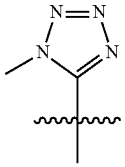 [SMILES: *c1nnnn1C] | $^1$H NMR (500 MHz, DMSO-$d_6$) δ 12.06 (s, 1H), 8.87 (d, J = 5.5 Hz, 1H), 7.98 (dd, J = 7.5, 7.5 Hz, 2H), 7.65 (d, J = 5.5 Hz, 1H), 7.33 (dd, J = 11.5, 7.5 Hz, 2H), 4.33 (s, 3H), 2.61 (s, 3H). |
| 1-206 | 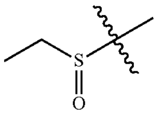 [SMILES: *S(=O)CC] | 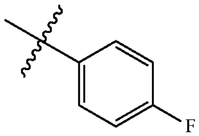 | 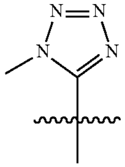 [SMILES: *c1nnnn1C] | $^1$H NMR (500 MHz, DMSO-6) δ 12.02 (s, 1H), 8.90 (d, J = 5.0 Hz, 1H), 7.66-7.59 (m, 2H), 7.28 (d, J = 5.0 Hz, 1H), 7.11-7.03 (m, 2H), 4.30 (s, 3H), 3.25-3.16 (m, 2H), 1.35 (t, J = 8.0 Hz, 3H). |
| 1-207 | 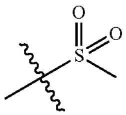 [SMILES: *S(C)(=O)=O] | 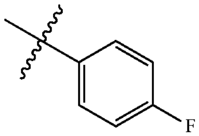 [SMILES: *c1ccc(F)cc1] | 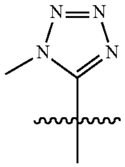 [SMILES: *c1nnnn1C] | $^1$H NMR (500 MHz, DMSO-$d_6$) δ 12.15 (s, 1H), 9.02 (d, J = 5.5 Hz, 1H), 8.12 (dd, J = 7.5, 7.5 Hz, 2H), 7.78 (d, J = 5.5 Hz, 1H), 7.31 (dd, J = 12.0, 7.5 Hz, 2H), 4.33 (s, 3H), 2.94 (s, 3H). |

TABLE A1-continued
| | | | | |
|---|---|---|---|---|
| 1-208 | 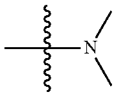 [SMILES: *N(C)C] | 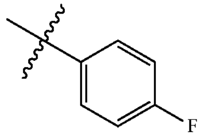 [SMILES: *c1ccc(F)cc1] | 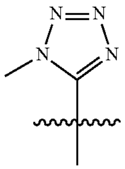 | $^1$H NMR (500 MHz, DMSO-d6) δ 12.08 (s, 1H), 8.48 (d, J = 4.5 Hz, 1H), 7.57-7.47 (m, 3H), 7.11-7.03 (m, 2H), 4.33 (s, 3H), 2.89 (s, 6H). |
| 1-209 | 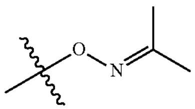 [SMILES: *ON=C(C)C] | 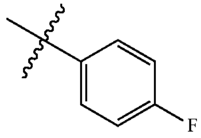 [SMILES: *c1ccc(F)cc1] | 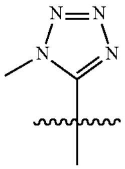 [SMILES: *c1nnnn1C] | $^1$H NMR (500 MHz, DMSO-$d_6$) δ 12.05 (s, 1H), 8.49 (d, J = 5.5 Hz, 1H), 8.05 (dd, J = 7.5, 7.5 Hz, 2H), 7.89 (d, J = 5.5 Hz, 1H), 7.27 (dd, J = 11.5, 7.5 Hz, 2H), 4.33 (s, 3H), 2.35 (s, 6H). |
| 1-210 | Et | 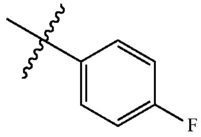 [SMILES: *c1ccc(F)cc1] | 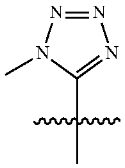 [SMILES: *c1nnnn1C] | $^1$H NMR (500 MHz, DMSO-$d_6$) δ 12.05 (s, 1H), 8.58 (d, J = 5.5 Hz, 1H), 7.96-7.88 (m, 2H), 7.40 (d, J = 5.5 Hz, 1H), 7.35-7.27 (m, 2H), 4.33 (s, 3H), 2.70 (q, J = 8.0 Hz, 2H), 1.07 (t, J = 8.0 Hz, 3H). |
| 1-211 | 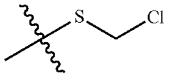 [SMILES: *SCCl] | 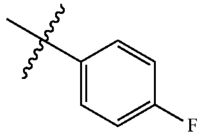 [SMILES: *c1ccc(F)cc1] | 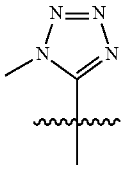 [SMILES: *c1nnnn1C] | $^1$H NMR (500 MHz, DMSO-$d_6$) δ 12.06 (s, 1H), 8.54 (d, J = 5.5 Hz, 1H), 8.06-7.98 (m, 2H), 7.53 (d, J = 5.5 Hz, 1H), 7.35-7.27 (m, 2H), 5.02 (s, 2H), 4.33 (s, 3H). |
| 1-212 | $NO_2$ | 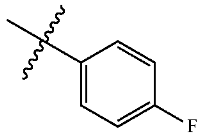 [SMILES: *c1ccc(F)cc1] | 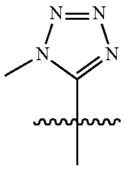 [SMILES: *c1nnnn1C] | $^1$H NMR (500 MHz, DMSO-$d_6$) δ 12.15 (s, 1H), 8.78 (d, J = 5.5 Hz, 1H), 7.92 (dd, J = 7.5, 7.0 Hz, 2H), 7.79 (d, J = 5.5 Hz, 1H), 7.27 (dd, J = 11.0, 7.5 Hz, 2H), 4.33 (s, 3H). |
| 1-213 | CN | 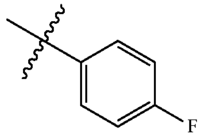 [SMILES: *c1ccc(F)cc1] | 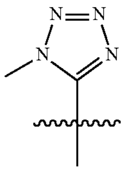 [SMILES: *c1nnnn1C] | $^1$H NMR (500 MHz, DMSO-$d_6$) δ 12.04 (s, 1H), 8.80 (d, J = 5.5 Hz, 1H), 7.98 (dd, J = 7.5, 7.0 Hz, 2H), 7.72 (d, J = 5.5 Hz, 1H), 7.31 (dd, J = 11.5, 7.5 Hz, 2H), 4.33 (s, 3H). |

TABLE A1-continued

| | | | | |
|---|---|---|---|---|
| 1-214 | 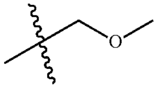 [SMILES: *COC] | 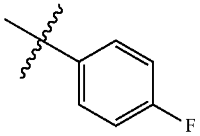 [SMILES: *c1ccc(F)cc1] | 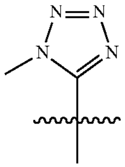 [SMILES: *c1nnnn1C] | $^1$H NMR (500 MHz, DMSO-$d_6$) δ 12.09 (s, 1H), 8.68 (d, J = 5.0 Hz, 1H), 8.04-7.96 (m, 2H), 7.66 (d, J = 5.0 Hz, 1H), 7.35-7.27 (m, 2H), 4.68 (s, 2H), 4.33 (s, 3H), 3.28 (s, 3H). |
| 1-215 | 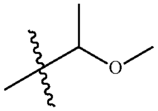 [SMILES: *C(C)OC] | 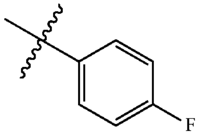 [SMILES: *c1ccc(F)cc1] | 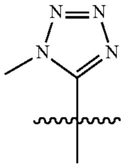 [SMILES: *c1nnnn1C] | $^1$H NMR (500 MHz, DMSO-$d_6$) δ 12.08 (s, 1H), 8.69 (d, J = 5.0 Hz, 1H), 7.97-7.90 (m, 2H), 7.79 (d, J = 5.0 Hz, 1H), 7.35-7.27 (m, 2H), 4.64 (q, J = 7.0 Hz, 1H), 4.33 (s, 3H), 3.23 (s, 3H), 1.36 (d, J = 7.0 Hz, 3H). |
| 1-216 | 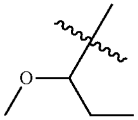 [SMILES: *C(CC)OC] | 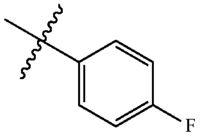 [SMILES: *c1ccc(F)cc1] | 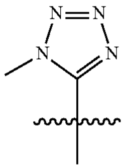 [SMILES: *c1nnnn1C] | $^1$H NMR (500 MHz, DMSO-$d_6$) δ 12.09 (s, 1H), 8.69 (d, J = 5.0 Hz, 1H), 7.97-7.90 (m, 2H), 7.79 (d, J = 5.0 Hz, 1H), 7.35-7.27 (m, 2H), 4.36 (t, J = 8.0 Hz, 1H), 4.33 (s, 3H), 3.22 (s, 3H), 1.77-1.62 (m, 2H), 0.85 (t, J = 8.0 Hz, 3H). |
| 1-217 | 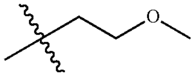 [SMILES: *CCOC] | 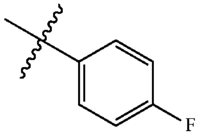 | 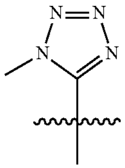 [SMILES: *c1nnnn1C] | $^1$H NMR (500 MHz, DMSO-$d_6$) δ 12.06 (s, 1H), 8.61 (d, J = 5.0 Hz, 1H), 7.93-7.85 (m, 2H), 7.40 (d, J = 5.0 Hz, 1H), 7.35-7.27 (m, 2H), 4.33 (s, 3H), 3.48 (t, J = 7.5 Hz, 2H), 3.23 (s, 3H), 2.75 (t, J = 7.5 Hz, 2H). |
| 1-218 | 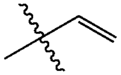 [SMILES: *C=C] | 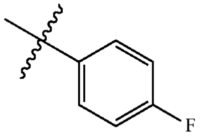 [SMILES: *c1ccc(F)cc1] | 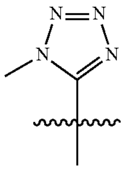 [SMILES: *c1nnnn1C] | $^1$H NMR (500 MHz, DMSO-$d_6$) δ 12.09 (s, 1H), 8.69 (d, J = 5.5 Hz, 1H), 8.0.1 (dd, J = 7.5, 7.0 Hz, 2H), 7.47 (d, J = 5.5 Hz, 1H), 7.27 (dd, J = 12.0, 7.5 Hz, 2H), 6.59 (dd, J = 16.5, 10.5 Hz, 1H), 5.55 (dd, J = 13.5, 10.5 Hz, 1H), 5.36 (dd, J = 16.5, 13.5 Hz, 1H), 4.33 (s, 3H). |
| 1-219 | 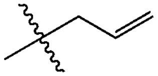 [SMILES: *CC=C] | 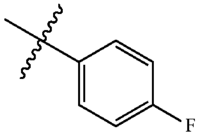 | 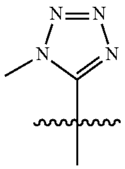 [SMILES: *c1nnnn1C] | $^1$H NMR (500 MHz, DMSO-$d_6$) δ 12.06 (s, 1H), 8.65 (d, J = 5.0 Hz, 1H), 8.01-7.93 (m, 2H), 7.45 (d, J = 5.0 Hz, 1H), 7.35-7.27 (m, 2H), 5.69-5.65 (m, 1H), 5.06-4.92 (m, 2H), 4.33 (s, 3H), 3.33-3.30 (m, 2H). |

TABLE A1-continued

| | | | | |
|---|---|---|---|---|
| 1-220 | 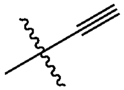 [SMILES: *C#C] | 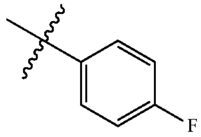 [SMILES: *c1ccc(F)cc1] | 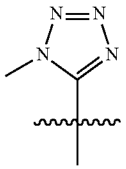 [SMILES: *c1nnnn1C] | $^{1}$H NMR (500 MHz, DMSO-$d_6$) δ 12.08 (s, 1H), 8.72 (d, J = 5.5 Hz, 1H), 8.07 (dd, J = 7.5, 7.5 Hz, 2H), 7.57 (d, J = 5.5 Hz, 1H), 7.35 (dd, J = 11.5, 7.5 Hz, 2H), 4.33 (s, 3H), 4.31 (s, 1H). |
| 1-221 | 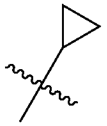 [SMILES: *C1CC1] | 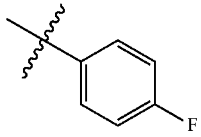 | 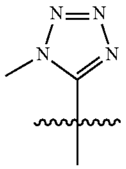 [SMILES: *c1nnnn1C] | $^{1}$H NMR (500 MHz, DMSO-$d_6$) δ 12.05 (s, 1H), 8.77 (d, J = 5.0 Hz, 1H), 8.01-7.93 (m, 2H), 7.51 (d, J = 5.0 Hz, 1H), 7.35-7.27 (m, 2H), 4.33 (s, 3H), 2.25 (p, J = 7.0 Hz, 1H), 0.91-0.81 (m, 2H), 0.70-0.66 (m, 2H). |
| 1-222 | 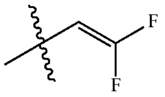 [SMILES: *C=C(F)F] | 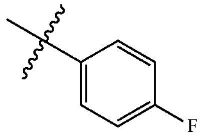 [SMILES: *c1ccc(F)cc1] | 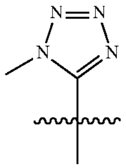 [SMILES: *c1nnnn1C] | $^{1}$H NMR (500 MHz, DMSO-$d_6$) δ 12.06 (s, 1H), 8.56 (d, J = 5.0 Hz, 1H), 8.00-7.92 (m, 2H), 7.35-7.27 (m, 3H), 4.90 (s, 1H), 4.33 (s, 3H). |
| 1-223 | 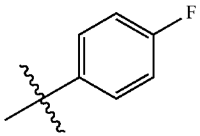 | 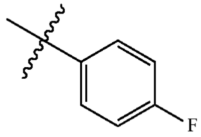 | 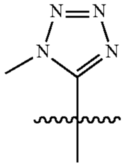 | $^{1}$H NMR (500 MHz, DMSO-$d_6$) δ 12.03 (s, 1H), 9.02 (d, J = 5.5 Hz, 1H), 7.99 (dd, J = 7.5, 7.5 Hz, 2H), 7.78 (d, J = 5.5 Hz, 1H), 7.55 (dd, J = 7.5, 7.0 Hz, 2H), 7.35 (dd, J = 11.5, 7.5 Hz, 2H), 7.23 (dd, J = 11.0, 7.5 Hz, 2H), 4.33 (s, 3H). |
| 1-224 | Cl | 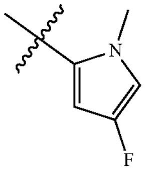 [SMILES: *c1cc(F)cn1C] | 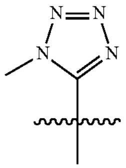 [SMILES: *c1nnnn1C] | $^{1}$H NMR (500 MHz, DMSO-$d_6$) δ 12.15 (s, 1H), 9.17 (d, J = 5.0 Hz, 1H), 8.05 (d, J = 5.0 Hz, 1H), 6.50 (d, J = 2.5 Hz, 1H), 6.10 (d, J = 2.5 Hz, 1H), 4.33 (s, 3H), 3.63 (s, 3H). |
| 1-225 | Cl | 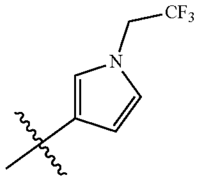 [SMILES: *c1ccn(CC(F)(F)F)c1] | 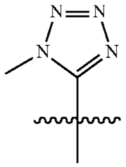 [SMILES: *c1nnnn1C] | $^{1}$H NMR (500 MHz, DMSO-$d_6$) δ 12.25 (s, 1H), 8.92 (d, J = 5.0 Hz, 1H), 7.82 (d, J = 5.0 Hz, 1H), 7.02 (s, 1H), 6.91 (d, J = 2.0 Hz, 1H), 6.61 (d, J = 2.0 Hz, 1H), 4.37 (q, J = 9.0 Hz, 2H), 4.33 (s, 3H). |

TABLE A1-continued
| | | | | |
|---|---|---|---|---|
| 1-226 | Cl | 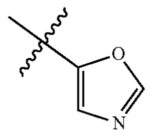 [SMILES: *c1cnco1] | 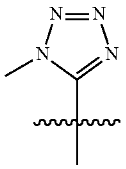 [SMILES: *c1nnnn1C] | $^1H$ NMR (500 MHz, DMSO-$d_6$) δ 12.06 (s, 1H), 8.91 (d, J = 5.0 Hz, 1H), 8.09 (s, 1H), 7.93 (d, J = 5.0 Hz, 1H), 7.70 (s, 1H), 4.33 (s, 3H). |
| 1-227 | Cl | 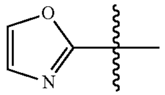 [SMILES: *c1ncco1] | 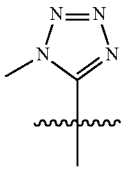 [SMILES: *c1nnnn1C] | $^1H$ NMR (500 MHz, DMSO-$d_6$) δ 12.13 (s, 1H), 8.91 (d, J = 5.0 Hz, 1H), 7.86 (d, J = 2.5 Hz, 1H), 7.78 (d, J = 5.0 Hz, 1H), 7.36 (d, J = 2.5 Hz, 1H), 4.33 (s, 3H). |
| 1-228 | Cl | 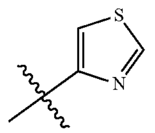 | 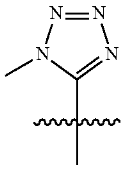 [SMILES: *c1nnnn1C] | $^1H$ NMR (500 MHz, DMSO-$d_6$) δ 12.07 (s, 1H), 9.19 (s, 1H), 8.92 (d, J = 5.5 Hz, 1H), 8.03 (s, 1H), 7.94 (d, J = 5.5 Hz, 1H), 4.33 (s, 3H). |
| 1-229 | Cl | 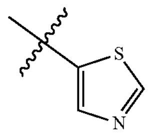 | 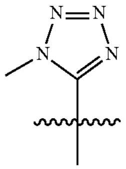 [SMILES: *c1nnnn1C] | $^1H$ NMR (500 MHz, DMSO-$d_6$) δ 12.05 (s, 1H), 9.19 (s, 1H), 8.94 (d, J = 5.0 Hz, 1H), 8.12 (s, 1H), 7.96 (d, J = 5.0 Hz, 1H), 4.33 (s, 3H). |
| 1-230 | Cl | 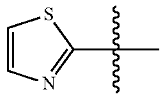 | 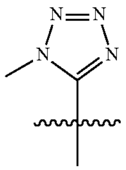 [SMILES: *c1nnnn1C] | $^1H$ NMR (500 MHz, DMSO-$d_6$) δ 12.05 (s, 1H), 8.93 (d, J = 5.5 Hz, 1H), 8.04 (d, J = 2.5 Hz, 1H), 7.96 (d, J = 5.5 Hz, 1H), 7.50 (d, J = 2.5 Hz, 1H), 4.33 (s, 3H). |
| 1-231 | Cl | 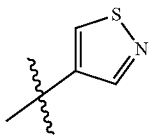 [SMILES: *c1cnsc1] | 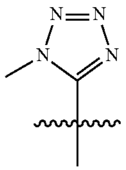 [SMILES: *c1nnnn1C] | $^1H$ NMR (500 MHz, DMSO-$d_6$) δ 12.09 (s, 1H), 8.91 (d, J = 5.0 Hz, 1H), 8.72 (s, 1H), 7.98 (s, 1H), 7.92 (d, J = 5.0 Hz, 1H), 4.33 (s, 3H). |

TABLE A1-continued
| | | | | |
|---|---|---|---|---|
| 1-232 | Cl | 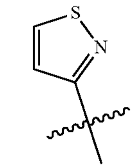 [SMILES: *c1ccsn1] | 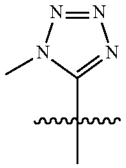 [SMILES: *c1nnnn1C] | $^1H$ NMR (500 MHz, DMSO-$d_6$) δ 12.21 (s, 1H), 8.90 (d, J = 5.0 Hz, 1H), 8.09 (d, J = 2.5 Hz, 1H), 7.75 (d, J = 5.0 Hz, 1H), 7.33 (d, J = 2.5 Hz, 1H), 4.33 (s, 3H). |
| 1-233 | Cl | 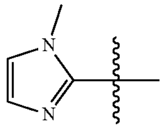 | 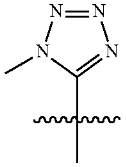 [SMILES: *c1nnnn1C] | $^1H$ NMR (500 MHz, DMSO-$d_6$) δ 12.06 (s, 1H), 8.90 (d, J = 5.5 Hz, 1H), 7.95 (d, J = 2.5 Hz, 1H), 7.39 (d, J = 5.5 Hz, 1H), 7.05 (d, J = 2.5 Hz, 1H), 4.33 (s, 3H), 3.92 (s, 3H). |
| 1-234 | Cl | 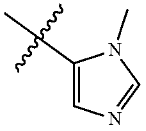 [SMILES: *c1cncn1C] | 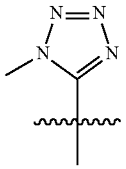 | $^1H$ NMR (500 MHz, DMSO-$d_6$) δ 12.05 (s, 1H), 8.91 (d, J = 5.0 Hz, 1H), 7.93 (d, J = 5.0 Hz, 1H), 7.73 (s, 1H), 7.67 (s, 1H), 4.33 (s, 3H), 3.79 (s, 3H). |
| 1-235 | Cl | 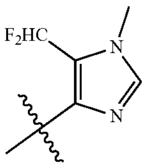 | 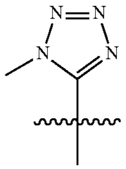 | $^1H$ NMR (500 MHz, DMSO-$d_6$) δ 12.08 (s, 1H), 8.92 (d, J = 5.0 Hz, 1H), 7.77 (d, J = 5.0 Hz, 1H), 7.61 (s, 1H), 6.70 (t, J = 65 Hz, 1H), 4.33 (s, 3H), 3.54 (s, 3H). |
| 1-236 | Cl | 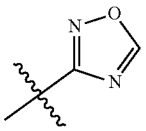 [SMILES: *c1ncon1] | 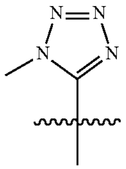 [SMILES: *c1nnnn1C] | $^1H$ NMR (500 MHz, DMSO-$d_6$) δ 12.25 (s, 1H), 8.87 (d, J = 5.0 Hz, 1H), 8.18 (s, 1H), 7.75 (d, J = 5.0 Hz, 1H), 4.33 (s, 3H). |
| 1-237 | Cl | 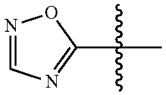 [SMILES: *c1ncno1] | 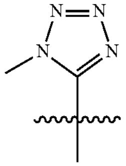 | $^1H$ NMR (500 MHz, DMSO-$d_6$) δ 12.14 (s, 1H), 8.89 (d, J = 5.0 Hz, 1H), 8.45 (s, 1H), 7.77 (d, J = 5.0 Hz, 1H), 4.33 (s, 3H). |

TABLE A1-continued
| | | | | |
|---|---|---|---|---|
| 1-238 | Cl | 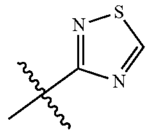 | 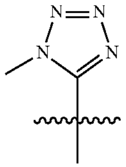 [SMILES: *c1nnnn1C] | $^1$H NMR (500 MHz, DMSO-$d_6$) δ 12.09 (s, 1H), 8.81 (d, J = 5.0 Hz, 1H), 8.32 (s, 1H), 7.69 (d, J = 5.0 Hz, 1H), 4.33 (s, 3H). |
| 1-239 | Cl | 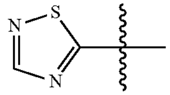 [SMILES: *c1ncns1] | 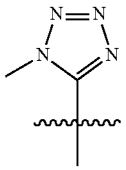 [SMILES: *c1nnnn1C] | $^1$H NMR (500 MHz, DMSO-$d_6$) δ 12.08 (s, 1H), 8.79 (d, J = 5.0 Hz, 1H), 7.74 (s, 1H), 7.65 (d, J = 5.0 Hz, 1H), 4.32 (s, 3H). |
| 1-240 | Cl | 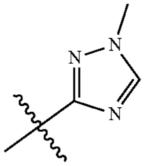 | 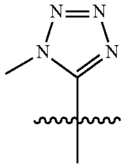 [SMILES: *c1nnnn1C] | $^1$H NMR (500 MHz, DMSO-$d_6$) δ 12.08 (s, 1H), 8.85 (d, J = 5.0 Hz, 1H), 8.27 (s, 1H), 7.86 (d, J = 5.0 Hz, 1H), 4.33 (s, 3H). |
| 1-241 | Cl | 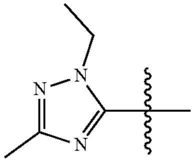 [SMILES: *c1nc(C)nn1CC] | 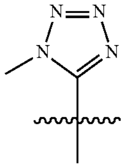 [SMILES: *c1nnnn1C] | $^1$H NMR (500 MHz, DMSO-$d_6$) δ 12.18 (s, 1H), 8.92 (d, J = 5.0 Hz, 1H), 7.96 (d, J = 5.0 Hz, 1H), 4.35-4.25 (m, 5H), 2.51 (s, 3H), 1.39 (t, J = 8.0 Hz, 3H). |
| 1-242 | Cl | 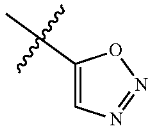 [SMILES: *c1cnno1] | 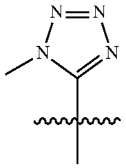 [SMILES: *c1nnnn1C] | $^1$H NMR (500 MHz, DMSO-$d_6$) δ 12.07 (s, 1H), 8.80 (d, J = 5.0 Hz, 1H), 7.82 (s, 1H), 7.65 (d, J = 5.0 Hz, 1H), 4.33 (s, 3H). |
| 1-243 | Cl | 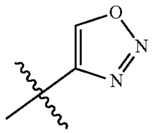 [SMILES: *c1conn1] | 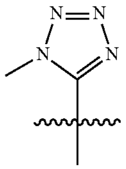 [SMILES: *c1nnnn1C] | $^1$H NMR (500 MHz, DMSO-$d_6$) δ 12.05 (s, 1H), 8.85 (d, J = 5.0 Hz, 1H), 8.19 (s, 1H), 7.73 (d, J = 5.0 Hz, 1H), 4.31 (s, 3H). |

TABLE A1-continued
| | | | | |
|---|---|---|---|---|
| 1-244 | Cl | 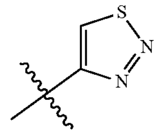 [SMILES: *c1csnn1] | 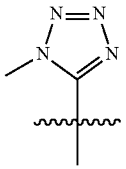 [SMILES: *c1nnnn1C] | $^1$H NMR (500 MHz, DMSO-$d_6$) δ 12.09 (s, 1H), 9.25 (s, 1H), 8.84 (d, J = 5.0 Hz, 1H), 7.73 (d, J = 5.0 Hz, 1H), 4.33 (s, 3H). |
| 1-245 | Cl | 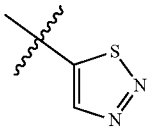 [SMILES: *c1cnns1] | 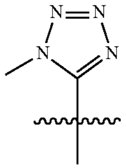 | $^1$H NMR (500 MHz, DMSO-$d_6$) δ 12.05 (s, 1H), 8.86 (d, J = 5.0 Hz, 1H), 8.16 (s, 1H), 7.76 (d, J = 5.0 Hz, 1H), 4.33 (s, 3H). |
| 1-246 | Cl | 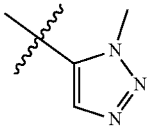 [SMILES: *c1cnnn1C] | 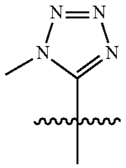 [SMILES: *c1nnnn1C] | $^1$H NMR (500 MHz, DMSO-$d_6$) δ 12.09 (s, 1H), 8.94 (d, J = 5.0 Hz, 1H), 8.36 (s, 1H), 7.96 (d, J = 5.0 Hz, 1H), 4.33 (s, 3H), 4.19 (s, 3H). |
| 1-247 | Cl | 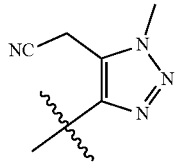 [SMILES: *c1nnn(C)c1CC#N] | 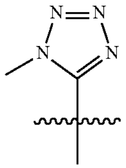 [SMILES: *c1nnnn1C] | $^1$H NMR (500 MHz, DMSO-$d_6$) δ 12.06 (s, 1H), 8.98 (d, J = 5.0 Hz, 1H), 7.80 (d, J = 5.0 Hz, 1H), 4.33 (s, 3H), 4.16 (s, 3H), 3.67 (s, 2H). |
| 1-248 | Cl | 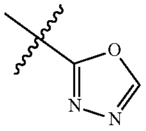 [SMILES: *c1nnco1] | 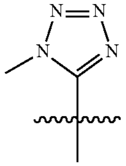 [SMILES: *c1nnnn1C] | $^1$H NMR (500 MHz, DMSO-$d_6$) δ 12.08 (s, 1H), 8.89 (d, J = 5.0 Hz, 1H), 7.91 (s, 1H), 7.78 (d, J = 5.0 Hz, 1H), 4.33 (s, 3H). |
| 1-249 | Cl | 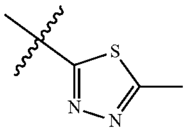 [SMILES: *c1nnc(C)s1] | 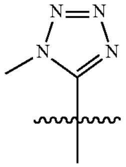 [SMILES: *c1nnnn1C] | $^1$H NMR (500 MHz, DMSO-$d_6$) δ 12.05 (s, 1H), 8.89 (d, J = 5.5 Hz, 1H), 7.93 (d, J = 5.5 Hz, 1H), 4.33 (s, 3H), 2.49 (s, 3H). |

TABLE A1-continued
| | | | | |
|---|---|---|---|---|
| 1-250 | Cl | 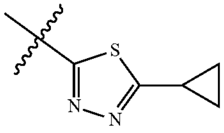 [SMILES: *c1nnc(C2CC2)s1] | 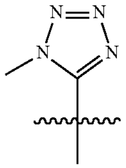 | $^1$H NMR (500 MHz, DMSO-$d_6$) δ 12.15 (s, 1H), 9.17 (d, J = 5.0 Hz, 1H), 8.05 (d, J = 5.0 Hz, 1H), 4.33 (s, 3H), 1.50 (p, J = 8.0 Hz, 1H), 1.19-1.15 (m, 2H), 1.05-1.01 (m, 2H). |
| 1-251 | Cl | 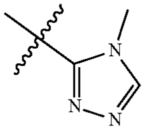 | 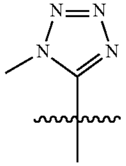 | $^1$H NMR (500 MHz, DMSO-$d_6$) δ 12.08 (s, 1H), 8.87 (d, J = 5.0 Hz, 1H), 8.27 (s, 1H), 7.78 (d, J = 5.0 Hz, 1H), 4.33 (s, 3H). |
| 1-252 | Cl | 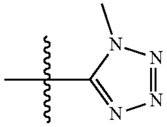 [SMILES: *c1nnnn1C] | 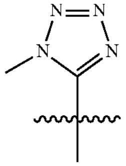 [SMILES: *c1nnnn1C] | $^1$H NMR (500 MHz, DMSO-$d_6$) δ 12.08 (s, 1H), 8.87 (d, J = 5.0 Hz, 1H), 7.78 (d, J = 5.0 Hz, 1H), 4.33 (s, 3H), 4.20 (s, 3H) |
| 1-253 | Cl | 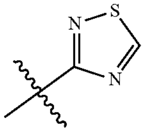 | 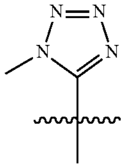 [SMILES: *c1nnnn1C] | $^1$H NMR (500 MHz, DMSO-$d_6$) δ 12.06 (s, 1H), 8.85 (d, J = 5.0 Hz, 1H), 7.96 (s, 1H), 7.72 (d, J = 5.0 Hz, 1H), 4.33 (s, 3H). |
| 1-254 | Cl | 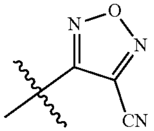 [SMILES: *c1nonc1C#N] | 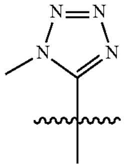 | $^1$H NMR (500 MHz, DMSO-$d_6$) δ 12.05 (s, 1H), 8.66 (d, J = 5.0 Hz, 1H), 7.75 (d, J = 5.0 Hz, 1H), 4.33 (s, 3H). |
| 1-255 | Cl | 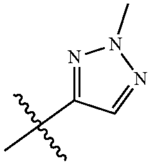 [SMILES: *c1cnn(C)n1] | 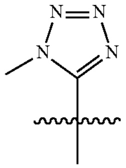 [SMILES: *c1nnnn1C] | $^1$H NMR (500 MHz, DMSO-$d_6$) δ 12.06 (s, 1H), 8.91 (d, J = 5.0 Hz, 1H), 8.30 (s, 1H), 7.67 (d, J = 5.0 Hz, 1H), 4.33 (s, 3H), 4.29 (s, 3H). |

TABLE A1-continued
| | | | | |
|---|---|---|---|---|
| 1-256 | Cl | 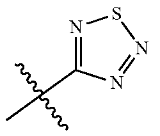 | 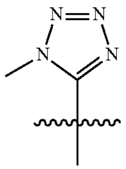 [SMILES: *c1nnnn1C] | $^1$H NMR (500 MHz, DMSO-$d_6$) δ 12.05 (s, 1H), 8.83 (d, J = 5.0 Hz, 1H), 7.88 (d, J = 5.0 Hz, 1H), 4.33 (s, 3H). |
| 1-257 | Cl | 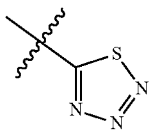 | 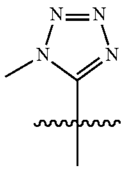 [SMILES: *c1nnnn1C] | $^1$H NMR (500 MHz, DMSO-$d_6$) δ 12.05 (s, 1H), 8.87 (d, J = 5.0 Hz, 1H), 7.90 (d, J = 5.0 Hz, 1H), 4.33 (s, 3H). |
| 1-258 | Cl | 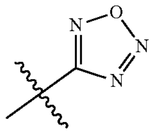 [SMILES: *c1nnon1] | 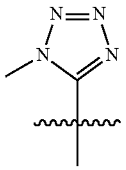 [SMILES: *c1nnnn1C] | $^1$H NMR (500 MHz, DMSO-$d_6$) δ 12.06 (s, 1H), 8.88 (d, J = 5.0 Hz, 1H), 7.90 (d, J = 5.0 Hz, 1H), 4.33 (s, 3H). |
| 1-259 | Cl | 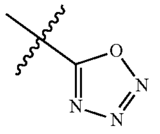 [SMILES: *c1nnno1] | 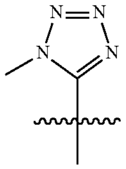 | $^1$H NMR (500 MHz, DMSO-$d_6$) δ 12.06 (s, 1H), 8.92 (d, J = 5.0 Hz, 1H), 7.96 (d, J = 5.0 Hz, 1H), 4.33 (s, 3H). |
| 1-260 | Cl | 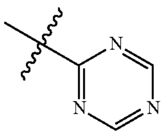 [SMILES: *c1ncncn1] | 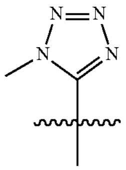 [SMILES: *c1nnnn1C] | $^1$H NMR (500 MHz, DMSO-$d_6$) δ 12.15 (s, 1H), 10.15 (s, 2H), 8.82 (d, J = 5.0 Hz, 1H), 7.79 (d, J = 5.0 Hz, 1H), 4.33 (s, 3H). |
| 1-261 | Cl | 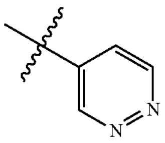 [SMILES: *c1ccnnc1] | 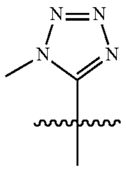 [SMILES: *c1nnnn1C] | $^1$H NMR (500 MHz, DMSO-$d_6$) δ 12.08 (s, 1H), 9.87 (d, J = 1.5 Hz, 1H), 9.50 (d, J = 5.0 Hz, 1H), 8.83 (d, J = 5.0 Hz, 1H), 8.29 (dd, J = 5.0, 1.5 Hz, 1H), 7.76 (d, J = 5.0 Hz, 1H), 4.33 (s, 3H). |

TABLE A1-continued
| | | | | |
|---|---|---|---|---|
| 1-262 | Cl | 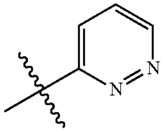 [SMILES: *c1cccnn1] | 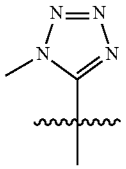 [SMILES: *c1nnnn1C] | $^1$H NMR (500 MHz, DMSO-$d_6$) δ 12.10 (s, 1H), 9.35 (dd, J = 5.0, 1.5 Hz, 1H), 8.82 (d, J = 5.0 Hz, 1H), 8.68 (dd, J = 7.5, 1.5 Hz, 1H), 7.99-7.92 (m, 2H), 4.33 (s, 3H). |
| 1-263 | Cl | 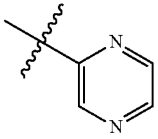 [SMILES: *c1cnccn1] | 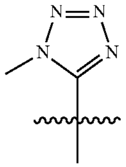 [SMILES: *c1nnnn1C] | $^1$H NMR (500 MHz, DMSO-$d_6$) δ 12.06 (s, 1H), 9.06 (s, 1H), 8.91 (d, J = 5.0 Hz, 1H), 8.85 (d, J = 5.0 Hz, 1H), 8.78 (d, J = 5.0 Hz, 1H), 8.00 (d, J = 5.0 Hz, 1H), 4.33 (s, 3H). |
| 1-264 | Cl | 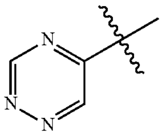 [SMILES: *c1cnncn1] | 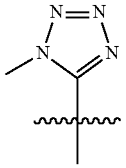 [SMILES: *c1nnnn1C] | |
| 1-265 | Cl | 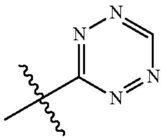 [SMILES: *c1nncnn1] | 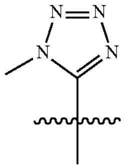 | |
| 1-266 | Cl | 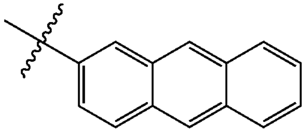 [SMILES: *c1ccc2cc3ccccc3cc2c1] | 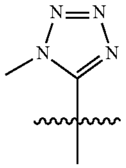 [SMILES: *c1nnnn1C] | |
| 1-267 | Cl | 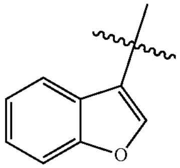 [SMILES: *c1coc2ccccc12] | 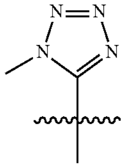 [SMILES: *c1nnnn1C] | $^1$H NMR (500 MHz, DMSO-$d_6$) δ 12.06 (s, 1H), 8.81 (d, J = 5.0 Hz, 1H), 7.94 (dd, J = 7.5, 1.5 Hz, 1H), 7.77 (d, J = 5.0 Hz, 1H), 7.59 (dd, J = 7.5, 1.5 Hz, 1H), 7.53 (s, 1H), 7.40 (td, J = 7.5, 1.5 Hz, 1H), 7.35 (td, J = 7.5, 1.5 Hz, 1H), 4.33 (s, 3H). |

TABLE A1-continued
| | | | | |
|---|---|---|---|---|
| 1-268 | Cl | 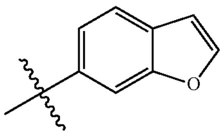 [SMILES: *c1ccc2ccoc2c1] | 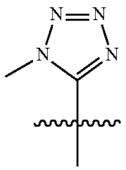 [SMILES: *c1nnnn1C] | $^1$H NMR (500 MHz, DMSO-$d_6$) δ 12.08 (s, 1H), 8.71 (d, J = 5.0 Hz, 1H), 8.09 (d, J = 2.0 Hz, 1H), 7.92 (d, J = 1.5 Hz, 1H), 7.81 (dd, J = 7.5, 1.5 Hz, 1H), 7.76-7.69 (m, 2H), 7.04 (d, J = 2.0, 1H), 4.33 (s, 3H). |
| 1-269 | Cl | 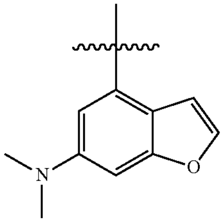 [SMILES: *c1cc(N(C)C)cc2occc12] | 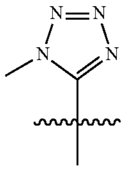 | $^1$H NMR (500 MHz, DMSO-$d_6$) δ 12.05 (s, 1H), 8.71 (d, J = 5.0 Hz, 1H), 7.66 (d, J = 2.0 Hz, 1H), 7.57 (d, J = 5.0 Hz, 1H), 7.47 (d, J = 1.5 Hz, 1H), 7.17 (d, J = 1.5 Hz, 1H), 6.91 (d, J = 2.0 Hz, 1H), 4.33 (s, 3H), 3.02 (s, 6H). |
| 1-270 | Cl | 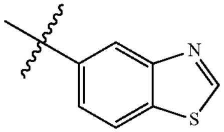 [SMILES: *c1ccc2scnc2c1] | 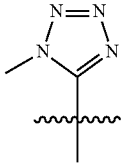 [SMILES: *c1nnnn1C] | $^1$H NMR (500 MHz, DMSO-$d_6$) δ 12.03 (s, 1H), 9.32 (s, 1H), 8.71 (d, J = 5.0 Hz, 1H), 8.60 (d, J = 1.5 Hz, 1H), 8.08 (d, J = 7.5 Hz, 1H), 7.95 (dd, J = 7.5, 1.5 Hz, 1H), 7.72 (d, J = 5.0 Hz, 1H), 4.33 (s, 3H). |
| 1-271 | Cl | 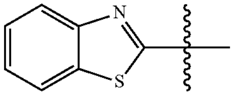 [SMILES: *c1nc2ccccc2s1] | 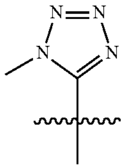 [SMILES: *c1nnnn1C] | $^1$H NMR (500 MHz, DMSO-$d_6$) δ 12.05 (s, 1H), 8.82 (d, J = 5.0 Hz, 1H), 8.18 (dd, J = 7.5, 1.5 Hz, 1H), 8.08 (dd, J = 7.5, 1.5 Hz, 1H), 7.79 (d, J = 5.0 Hz, 1H), 7.58-7.54 (m, 1H), 7.50-7.46 (m, 1H), 4.33 (s, 3H). |
| 1-272 | Cl | 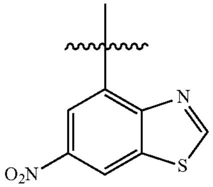 | 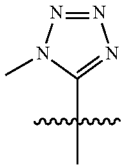 [SMILES: *c1nnnn1C] | $^1$H NMR (500 MHz, DMSO-$d_6$) δ 12.15 (s, 1H), 9.46 (s, 1H), 8.99-8.95 (m, 2H), 8.73 (d, J = 5.0 Hz, 1H), 7.62 (d, J = 5.0 Hz, 1H), 4.33 (s, 3H). |

TABLE A1-continued
| | | | | |
|---|---|---|---|---|
| 1-273 | Cl | 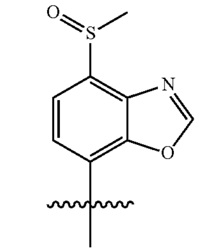 [SMILES: *c1ccc(S(C)=O)c2ncoc12] | 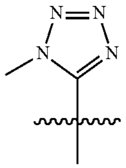 [SMILES: *c1nnnn1C] | $^1$H NMR (500 MHz, DMSO-$d_6$) δ 12.05 (s, 1H), 8.71 (d, J = 5.0 Hz, 1H), 8.58 (s, 1H), 8.10 (d, J = 7.5 Hz, 1H), 7.80 (d, J = 7.5 Hz, 1H), 7.57 (d, J = 5.0 Hz, 1H), 4.33 (s, 3H), 2.84 (s, 3H). |
| 1-274 | Cl | 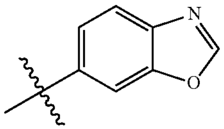 [SMILES: *c1ccc2ncoc2c1] | 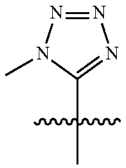 [SMILES: *c1nnnn1C] | $^1$H NMR (500 MHz, DMSO-$d_6$) δ 12.09 (s, 1H), 8.70 (d, J = 5.0 Hz, 1H), 8.53 (s, 1H), 7.98 (d, J = 1.5 Hz, 1H), 7.73 (d, J = 7.5 Hz, 1H), 7.67 (dd, J = 7.5, 1.5 Hz, 1H), 7.54 (d, J = 5.0 Hz, 1H), 4.33 (s, 3H). |
| 1-275 | Cl | 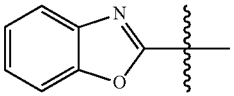 [SMILES: *c1nc2ccccc2o1] | 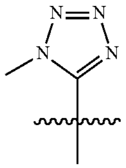 | $^1$H NMR (500 MHz, DMSO-$d_6$) δ 12.09 (s, 1H), 8.83 (d, J = 5.0 Hz, 1H), 7.98-7.89 (m, 2H), 7.87-7.84 (m, 1H), 7.64-7.59 (m, 2H), 4.33 (s, 3H). |
| 1-276 | Cl | 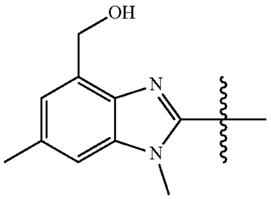 [SMILES: *c1nc2c(CO)cc(C)cc2n1C] | 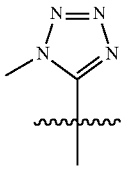 [SMILES: *c1nnnn1C] | $^1$H NMR (500 MHz, DMSO-$d_6$) δ 12.06 (s, 1H), 8.81 (d, J = 5.0 Hz, 1H), 7.79 (d, J = 5.0 Hz, 1H), 7.58 (d, J = 1.5 Hz, 1H), 7.37 (d, J = 1.5 Hz, 1H), 5.32 (s, 1H), 4.50 (s, 2H), 4.33 (s, 3H), 4.02 (s, 3H), 2.34 (s, 3H). |
| 1-277 | Cl | 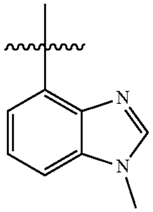 | 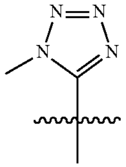 [SMILES: *c1nnnn1C] | $^1$H NMR (500 MHz, DMSO-$d_6$) δ 12.09 (s, 1H), 8.69 (d, J = 5.0 Hz, 1H), 8.32 (s, 1H), 8.17 (dd, J = 7.5, 1.5 Hz, 1H), 7.83 (dd, J = 7.5, 1.5 Hz, 1H), 7.53 (d, J = 5.0 Hz, 1H), 7.37 (t, J = 7.5 Hz, 1H), 4.33 (s, 3H), 3.79 (s, 3H). |

TABLE A1-continued
| | | | | |
|---|---|---|---|---|
| 1-278 | Cl | 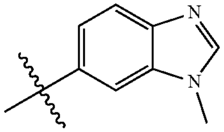 [SMILES: *c1ccc2ncn(C)c2c1] | 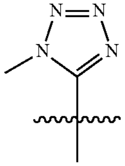 | $^1$H NMR (500 MHz, DMSO-$d_6$) δ 12.08 (s, 1H), 8.70 (d, J = 5.0 Hz, 1H), 8.28 (d, J = 1.5 Hz, 1H), 8.16 (d, J = 7.5, 1.5 Hz, 1H), 8.05 (s, 1H), 7.80 (d, J = 7.5 Hz, 1H), 7.52 (d, J = 5.0 Hz, 1H), 4.33 (s, 3H), 3.79 (s, 3H). |
| 1-279 | Cl | 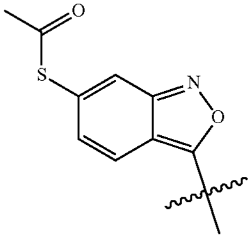 [SMILES: *c1onc2cc(SC(C)=O)ccc12] | 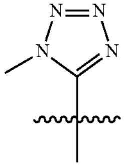 [SMILES: *c1nnnn1C] | $^1$H NMR (500 MHz, DMSO-$d_6$) δ 12.06 (s, 1H), 8.87 (d, J = 5.0 Hz, 1H), 7.83 (d, J = 5.0 Hz, 1H), 7.64-7.54 (m, 2H), 7.47 (d, J = 1.5 Hz, 1H), 4.33 (s, 3H), 2.51 (s, 3H). |
| 1-280 | Cl | 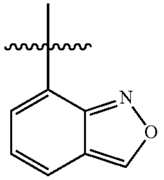 [SMILES: *c1cccc2conc12] | 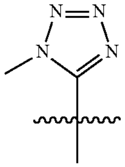 [SMILES: *c1nnnn1C] | $^1$H NMR (500 MHz, DMSO-$d_6$) δ 12.07 (s, 1H), 8.69 (d, J = 5.0 Hz, 1H), 8.39 (s, 1H), 8.07 (dd, J = 7.5, 1.5 Hz, 1H), 7.64 dd, J = 7.5, 1.5 Hz, 1H), 7.55 (d, J = 5.0 Hz, 1H), 7.45 (t, J = 7.5 Hz, 1H), 4.33 (s, 3H). |
| 1-281 | Cl | 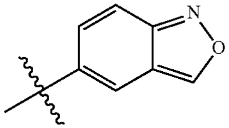 [SMILES: *c1ccc2nocc2c1] | 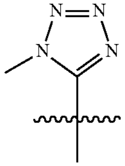 [SMILES: *c1nnnn1C] | $^1$H NMR (500 MHz, DMSO-$d_6$) δ 12.05 (s, 1H), 8.70 (d, J = 5.0 Hz, 1H), 8.39 (d, J = 7.5 Hz, 1H), 7.88-7.79 (m, 2H), 7.64 (d, J = 7.5 Hz, 1H), 7.54 (d, J = 5.0 Hz, 1H), 4.33 (s, 3H). |
| 1-282 | Cl | 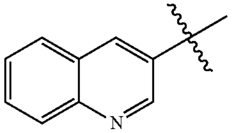 [SMILES: *c1cnc2ccccc2c1] | 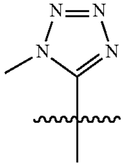 | $^1$H NMR (500 MHz, DMSO-$d_6$) δ 12.05 (s, 1H), 9.27 (d, J = 1.5 Hz, 1H), 8.96 (d, J = 5.0 Hz, 1H), 8.69 (d, J = 1.5 Hz, 1H), 8.15-8.05 (m, 2H), 7.87 (d, J = 5.0 Hz, 1H), 7.69 (td, J = 7.5, 1.5 Hz, 1H), 7.58 (td, J = 7.5, 1.5 Hz, 1H), 4.33 (s, 3H). |

TABLE A1-continued
| | | | | |
|---|---|---|---|---|
| 1-283 | Cl | 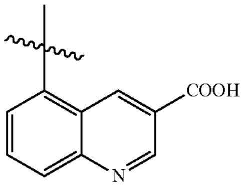 [SMILES: *c1cccc2ncc(C(=O)O)cc12] | 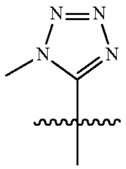 [SMILES: *c1nnnn1C] | $^1$H NMR (500 MHz, DMSO-$d_6$) δ 13.19 (s, 1H), 12.08 (s, 1H), 9.79 (d, J = 1.5 Hz, 1H), 9.21 (d, J = 1.5 Hz, 1H), 8.89 (d, J = 5.0 Hz, 1H), 8.44 (dd, J = 7.5, 1.5 Hz, 1H), 8.33 (dd, J = 7.5, 1.5 Hz, 1H), 8.12 (t, J = 7.5 Hz, 1H), 7.85 (d, J = 5.0 Hz, 1H), 4.33 (s, 3H). |
| 1-284 | Cl | 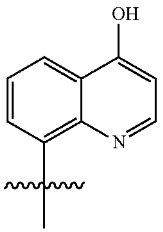 [SMILES: *c1cccc2c(O)ccnc12] | 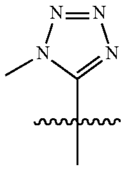 [SMILES: *c1nnnn1C] | $^1$H NMR (500 MHz, DMSO-$d_6$) δ 12.15 (s, 1H), 9.73 (s, 1H), 8.83 (d, J = 5.0 Hz, 1H), 8.49-8.41 (m, 2H), 8.35 (dd, J = 7.5, 1.5 Hz, 1H), 7.93 (d, J = 7.5 Hz, 1H), 7.74 (t, J = 7.5 Hz, 1H), 7.63 (d, J = 5.0 Hz, 1H), 4.33 (s, 3H). |
| 1-285 | Cl | 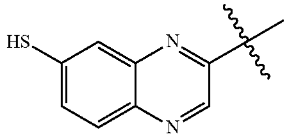 [SMILES: *c1cnc2ccc(S)cc2n1] | 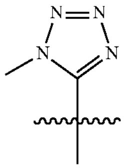 [SMILES: *c1nnnn1C] | $^1$H NMR (500 MHz, DMSO-$d_6$) δ 12.10 (s, 1H), 9.69 (s, 1H), 9.04 (d, J = 5.0 Hz, 1H), 8.43 (d, J = 1.5 Hz, 1H), 8.07-7.97 (m, 3H), 4.33 (s, 3H), 3.85 (s, 1H). |
| 1-286 | Cl | 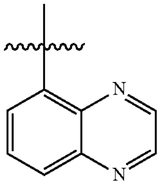 [SMILES: *c1cccc2nccnc12] | 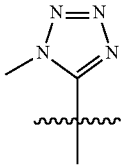 [SMILES: *c1nnnn1C] | $^1$H NMR (500 MHz, DMSO-$d_6$) δ 12.05 (s, 1H), 9.13 (d, J = 5.5 Hz, 1H), 8.91-8.83 (m, 2H), 8.23 (dd, J = 7.5, 1.5 Hz, 2H), 7.93 (t, J = 7.5 Hz, 1H), 7.65 (d, J = 5.5 Hz, 1H), 4.33 (s, 3H). |
| 1-287 | Cl | 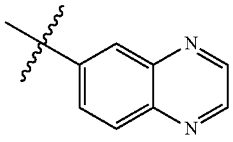 [SMILES: *c1ccc2nccnc2c1] | 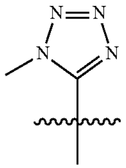 [SMILES: *c1nnnn1C] | $^1$H NMR (500 MHz, DMSO-$d_6$) δ 12.08 (s, 1H), 8.91-8.86 (m, 3H), 8.74 (d, J = 1.5 Hz, 1H), 8.29-8.21 (m, 2H), 7.62 (d, J = 5.0 Hz, 1H), 4.33 (s, 3H). |

TABLE A1-continued

| | | | | |
|---|---|---|---|---|
| 1-288 | Cl | 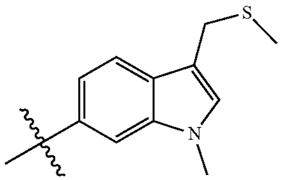 [SMILES: *c1ccc2c(CSC)cn(C)c2c1] | 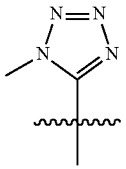 [SMILES: *c1nnnn1C] | $^1$H NMR (500 MHz, DMSO-$d_6$) δ 12.06 (s, 1H), 8.70 (d, J = 5.0 Hz, 1H), 8.28 (dd, J = 7.5, 1.5 Hz, 1H), 7.93 (d, J = 7.5 Hz, 1H), 7.80 (d, J = 1.5 Hz, 1H), 7.53 (d, J = 5.0 Hz, 1H), 7.05 (s, 1H), 4.33 (s, 3H), 3.62 (s, 3H), 3.55 (s, 2H), 2.18 (s, 3H). |
| 1-289 | Cl | 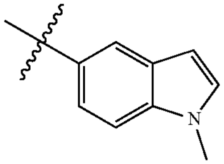 [SMILES: *c1ccc2c(ccn2C)c1] | 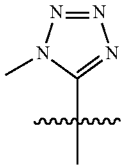 [SMILES: *c1nnnn1C] | $^1$H NMR (500 MHz, DMSO-$d_6$) δ 12.05 (s, 1H), 8.77 (d, J = 1.5 Hz, 1H), 8.71 (d, J = 5.0 Hz, 1H), 8.24 (dd, J = 7.5, 1.5 Hz, 1H), 7.74-7.68 (m, 2H), 7.17 (d, J = 7.5 Hz, 1H), 6.63 (d, J = 2.5 Hz, 1H), 4.33 (s, 3H), 3.79 (s, 3H). |
| 1-290 | Cl | 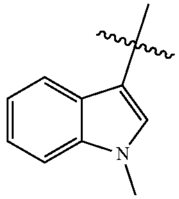 [SMILES: *c1cn(C)c2ccccc12] | 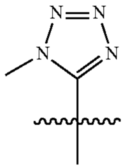 [SMILES: *c1nnnn1C] | $^1$H NMR (500 MHz, DMSO-$d_6$) δ 12.06 (s, 1H), 8.81 (d, J = 5.0 Hz, 1H), 8.00-7.92 (m, 2H), 7.73 (dd, J = 7.5, 1.5 Hz, 1H), 7.47 (td, J = 7.5, 1.5 Hz, 1H), 7.31 (td, J = 7.5, 1.5 Hz, 1H), 7.14 (s, 1H), 4.33 (s, 3H), 3.82 (s, 3H). |
| 1-291 | Cl | 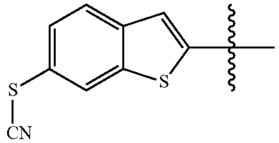 [SMILES: *c1cc2ccc(SC#N)cc2s1] | 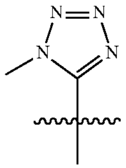 [SMILES: *c1nnnn1C] | $^1$H NMR (500 MHz, DMSO-$d_6$) δ 12.07 (s, 1H), 8.81 (d, J = 5.0 Hz, 1H), 7.97 (d, J = 7.5 Hz, 1H), 7.95-7.88 (m, 3H), 7.39 (dd, J = 7.5, 1.5 Hz, 1H), 4.33 (s, 3H). |
| 1-292 | Cl | 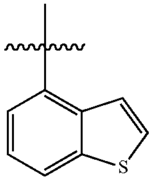 | 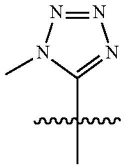 | $^1$H NMR (500 MHz, DMSO-$d_6$) δ 12.06 (s, 1H), 8.73 (d, J = 5.0 Hz, 1H), 8.04 (dd, J = 7.5, 1.5 Hz, 1H), 7.91 (dd, J = 7.5, 1.5 Hz, 1H), 7.76 (d, J = 5.0 Hz, 1H), 7.65 (d, J = 2.5 Hz, 1H), 7.56 (t, J = 7.5 Hz, 1H), 7.44 (d, J = 2.5 Hz, 1H), 4.33 (s, 3H). |

TABLE A1-continued
| | | | | |
|---|---|---|---|---|
| 1-293 | Cl | 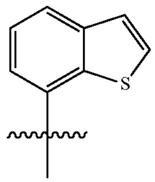 | 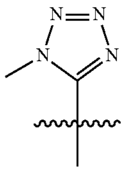 [SMILES: *c1nnnn1C] | $^1$H NMR (500 MHz, DMSO-$d_6$) δ 12.05 (s, 1H), 8.72 (d, J = 5.0 Hz, 1H), 8.07-7.97 (m, 2H), 7.75 (d, J = 5.0 Hz, 1H), 7.66-7.56 (m, 2H), 7.50 (t, J = 7.5 Hz, 1H), 4.33 (s, 3H). |
| 1-294 | Cl | 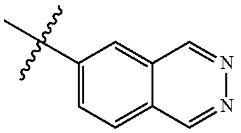 [SMILES: *c1ccc2cnncc2c1] | 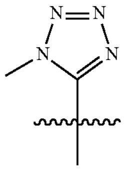 [SMILES: *c1nnnn1C] | |
| 1-295 | Cl | 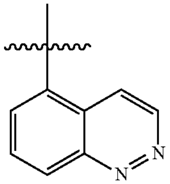 [SMILES: *c1cccc2nnccc12] | 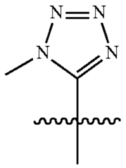 [SMILES: *c1nnnn1C] | |
| 1-296 | Cl | 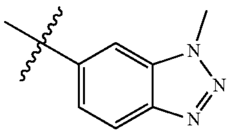 [SMILES: *c1ccc2nnn(C)c2c1] | 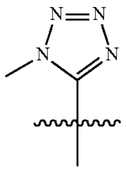 | |
| 1-297 | Cl | 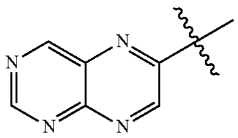 [SMILES: *c1cnc2ncncc2n1] | 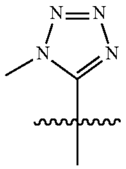 [SMILES: *c1nnnn1C] | |

TABLE A1-continued
| | | | |
|---|---|---|---|
| 1-298 | Cl | 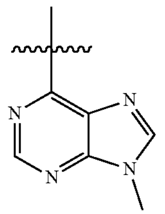 [SMILES: *c1ncnc2c1ncn2C] | 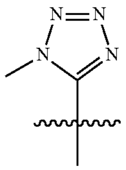 |
| 1-299 | Cl | 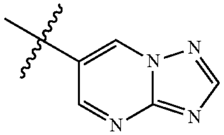 [SMILES: *c1cnc2ncnn2c1] | 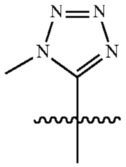 |
| 1-300 | Cl | 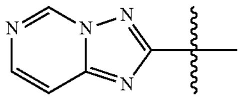 [SMILES: *c1nc2ccncn2n1] | 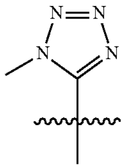 [SMILES: *c1nnnn1C] |
| 1-301 | Cl | 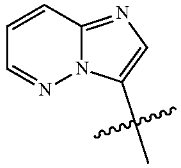 [SMILES: *c1cnc2cccnn12] | 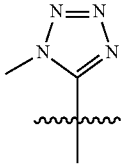 [SMILES: *c1nnnn1C] |
| 1-302 | Cl | 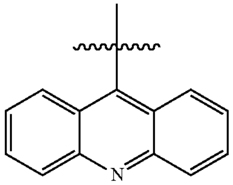 [SMILES: *c1c2ccccc2nc2ccccc12] | 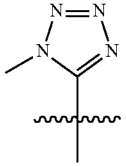 [SMILES: *c1nnnn1C] |

TABLE A1-continued
| | | | | |
|---|---|---|---|---|
| 1-303 | Cl | 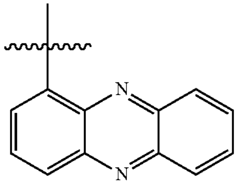 [SMILES: *c1cccc2nc3ccccc3nc12] | 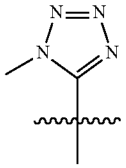 [SMILES: *c1nnnn1C] | |
| 1-304 | Cl | 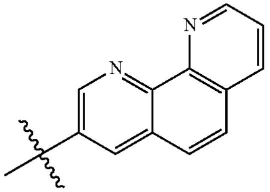 [SMILES: *c1cnc2c(ccc3cccnc32)c1] | 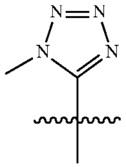 [SMILES: *c1nnnn1C] | |
| 1-305 | Cl | 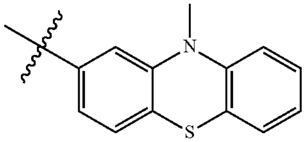 [SMILES: *c1ccc2c(c1)N(C)c1ccccc1S2] | 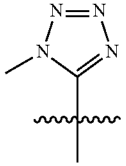 [SMILES: *c1nnnn1C] | |
| 1-306 | Cl | 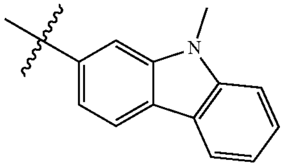 [SMILES: *c1ccc2c3ccccc3n(C)c2c1] | 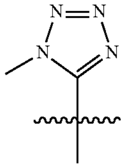 | |
| 1-307 | Cl | 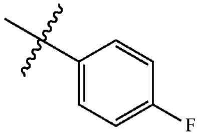 [SMILES: *c1ccc(F)cc1] | 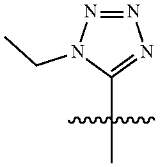 [SMILES: *c1nnnn1CC] | $^1$H NMR (500 MHz, DMSO-d6) δ 12.08 (s, 1H), 8.75 (d, J = 5.0 Hz, 1H), 7.65-7.57 (m, 2H), 7.25 (d, J = 5.0 Hz, 1H), 7.11-7.03 (m, 2H), 4.40-4.32 (m, 2H), 1.50 (t, J = 8.0 Hz, 3H). |
| 1-308 | Cl | 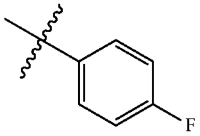 [SMILES: *c1ccc(F)cc1] | 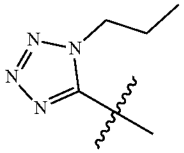 [SMILES: *c1nnnn1CCC] | $^1$H NMR (500 MHz, DMSO-$d_6$) δ 12.05 (s, 1H), 8.67 (d, J = 5.0 Hz, 1H), 8.05-7.97 (m, 2H), 7.53 (d, J = 5.0 Hz, 1H), 7.35-7.27 (m, 2H), 4.25 (t, J = 5.0 Hz, 2H), 1.74-1.70 (m, 2H), 0.89 (t, J = 8.0 Hz, 3H). |

TABLE A1-continued
| | | | | |
|---|---|---|---|---|
| 1-309 | Cl | 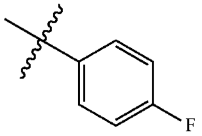 [SMILES: *c1ccc(F)cc1] | 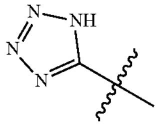 [SMILES: *c1nnn[nH]1] | $^1$H NMR (500 MHz, DMSO-$d_6$) δ 12.56 (s, 1H), 12.06 (s, 1H), 8.67 (d, J = 5.0 Hz, 1H), 8.05-7.97 (m, 2H), 7.52 (d, J = 5.0 Hz, 1H), 7.35-7.27 (m, 2H). |
| 1-310 | Cl | 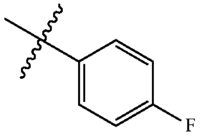 [SMILES: *c1ccc(F)cc1] | 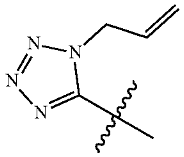 [SMILES: *c1nnnn1CC=C] | $^1$H NMR (500 MHz, DMSO-$d_6$) δ 12.06 (s, 1H), 8.67 (d, J = 5.0 Hz, 1H), 8.03-7.95 (m, 2H), 7.49 (d, J = 5.0 Hz, 1H), 7.35-7.27 (m, 2H), 6.07-6.04 (m, 1H), 5.41-5.32 (m, 1H), 5.27-5.16 (m, 1H), 4.43-4.37 (m, 2H). |
| 1-311 | Cl | 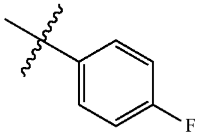 [SMILES: *c1ccc(F)cc1] | 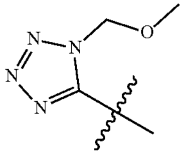 [SMILES: *c1nnnn1COC] | $^1$H NMR (500 MHz, DMSO-$d_6$) δ 12.09 (s, 1H), 8.67 (d, J = 5.0 Hz, 1H), 8.04-7.96 (m, 2H), 7.51 (d, J = 5.0 Hz, 1H), 7.35-7.27 (m, 2H), 5.57 (s, 2H), 3.35 (s, 3H). |
| 1-312 | Cl | 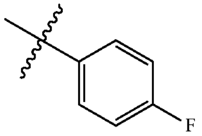 [SMILES: *c1ccc(F)cc1] | 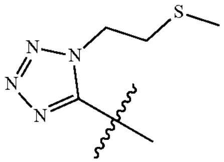 [SMILES: *c1nnnn1CCSC] | $^1$H NMR (500 MHz, DMSO-$d_6$) δ 12.08 (s, 1H), 8.68 (d, J = 5.0 Hz, 1H), 8.04-7.97 (m, 2H), 7.53 (d, J = 5.0 Hz, 1H), 7.35-7.27 (m, 2H), 4.10 (t, J = 8.0 Hz, 2H), 2.92 (t, J = 8.0 Hz, 2H), 2.09 (s, 3H). |
| 1-313 | Cl | 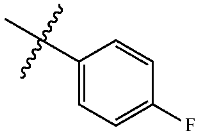 [SMILES: *c1ccc(F)cc1] | 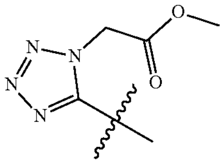 [SMILES: *c1nnnn1CC(=O)OC] | $^1$H NMR (500 MHz, DMSO-$d_6$) δ 12.06 (s, 1H), 8.67 (d, J = 5.0 Hz, 1H), 8.03-7.95 (m, 2H), 7.50 (d, J = 5.0 Hz, 1H), 7.35-7.27 (m, 2H), 5.05 (s, 2H), 3.78 (s, 3H). |
| 1-314 | Cl | 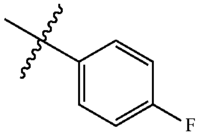 [SMILES: *c1ccc(F)cc1] | 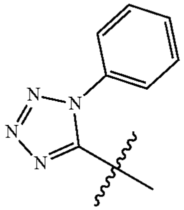 [SMILES: *c1nnnn1-c1ccccc1] | $^1$H NMR (500 MHz, DMSO-$d_6$) δ 12.07 (s, 1H), 8.88 (d, J = 5.0 Hz, 1H), 8.07-7.99 (m, 2H), 7.66 (d, J = 5.0 Hz, 1H), 7.59-7.53 (m, 4H), 7.52-7.49 (m, 1H), 7.35-7.27 (m, 2H). |

TABLE A1-continued
| | | | | |
|---|---|---|---|---|
| 1-315 | Cl | 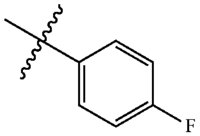 | 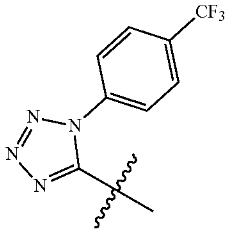 [SMILES: *c1nnnn1-c1ccc(C(F)(F)F)cc1] | $^1$H NMR (500 MHz, DMSO-$d_6$) δ 12.06 (s, 1H), 8.88 (d, J = 5.0 Hz, 1H), 8.06-7.99 (m, 2H), 7.69-7.60 (m, 3H), 7.57-7.54 (m, 2H), 7.35-7.27 (m, 2H). |
| 1-316 | Cl | 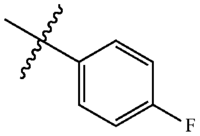 [SMILES: *c1ccc(F)cc1] | 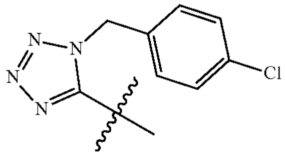 [SMILES: *c1nnnn1Cc1ccc(Cl)cc1] | $^1$H NMR (500 MHz, DMSO-$d_6$) δ 12.11 (s, 1H), 8.86 (d, J = 5.0 Hz, 1H), 8.05-7.98 (m, 2H), 7.59 (d, J = 5.0 Hz, 1H), 7.41 (dd, J = 7.5, 1.5 Hz, 2H), 7.35-7.27 (m, 2H), 7.08-7.02 (m, 2H), 5.45 (s, 2H). |
| 1-317 | Cl | $CH_3$ | 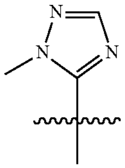 [SMILES: *c1ncnn1C] | |
| 1-318 | Cl | 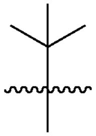 [SMILES: *C(C)(C)C] | 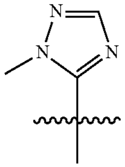 [SMILES: *c1ncnn1C] | |
| 1-319 | Cl | 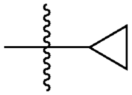 [SMILES: *C1CC1] | 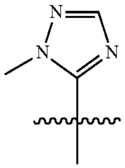 [SMILES: *c1ncnn1C] | |

TABLE A1-continued
| | | | | |
|---|---|---|---|---|
| 1-320 | Cl | 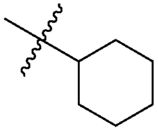 [SMILES: *C1CCCCC1] | 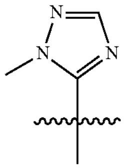 [SMILES: *c1ncnn1C] | |
| 1-321 | Cl | 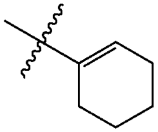 [SMILES: *C1=CCCCC1] | 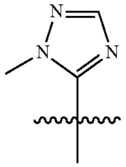 [SMILES: *c1ncnn1C] | |
| 1-322 | Cl | 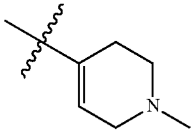 [SMILES: *C1=CCN(C)CC1] | 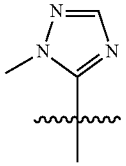 [SMILES: *c1ncnn1C] | $^{1}H$ NMR (500 MHz, DMSO-$d_6$) δ 12.24 (s, 1H), 8.67 (d, J = 5.0 Hz, 1H), 8.32 (s, 1H), 7.64 (d, J = 5.0 Hz, 1H), 6.14-6.07 (m, 1H), 3.91 (s, 3H), 3.36-3.30 (m, 2H), 3.05 (t, J = 7.0, Hz, 2H), 2.60 (t, J = 7.0 Hz, 2H), 2.20 (s, 3H). |
| 1-323 | Cl | 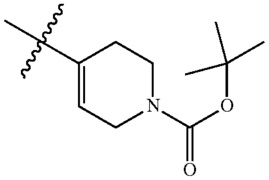 [SMILES: *C1=CCN(C(=O)OC(C)(C)C)CC1] | 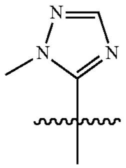 | |
| 1-324 | Cl | 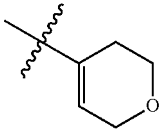 [SMILES: *C1=CCOCC1] | 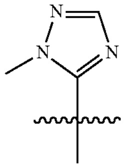 [SMILES: *c1ncnn1C] | |
| 1-325 | Cl | 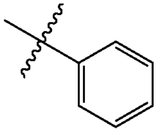 [SMILES: *c1ccccc1] | 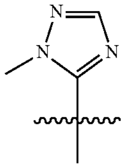 | |

TABLE A1-continued
| | | | |
|---|---|---|---|
| 1-326 | Cl | 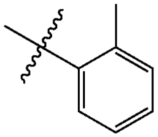 [SMILES: *c1ccccc1C] | 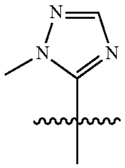 [SMILES: *c1ncnn1C] |
| 1-327 | Cl | 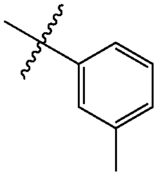 [SMILES: *c1cccc(C)c1] | 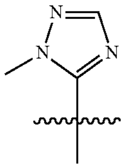 [SMILES: *c1ncnn1C] |
| 1-328 | Cl | 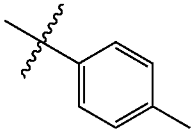 [SMILES: *c1ccc(C)cc1] | 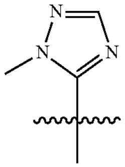 |
| 1-329 | Cl | 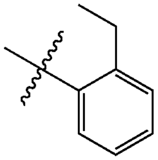 [SMILES: *c1ccccc1CC] | 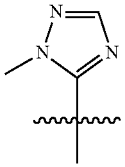 |
| 1-330 | Cl | 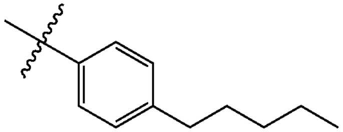 [SMILES: *c1ccc(CCCCC)cc1] | 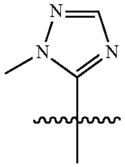 [SMILES: *c1ncnn1C] |

TABLE A1-continued
| | | | | |
|---|---|---|---|---|
| 1-331 | Cl | 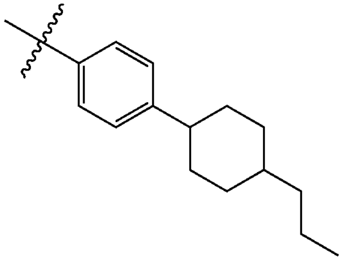 [SMILES: *c1ccc(C2CCC(CCC)CC2)cc1] | 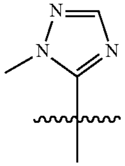 | |
| 1-332 | Cl | 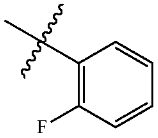 [SMILES: *c1ccccc1F] | 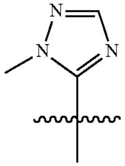 | |
| 1-333 | Cl | 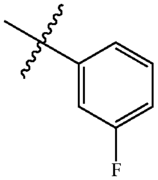 [SMILES: *c1cccc(F)c1] | 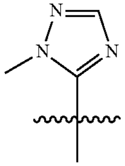 | |
| 1-334 | Cl | 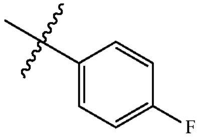 [SMILES: *c1ccc(F)cc1] | 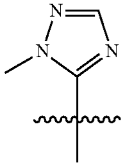 [SMILES: *c1ncnn1C] | $^{1}$H NMR (500 MHz, DMSO-d6) δ 12.03 (s, 1H), 8.75 (d, J = 5.0 Hz, 1H), 8.23 (s, 1H), 7.64-7.57 (m, 2H), 7.25 (d, J = 5.0 Hz, 1H), 7.11-7.03 (m, 2H), 3.95 (s, 3H). |
| 1-335 | Cl | 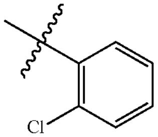 | 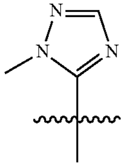 [SMILES: *c1ncnn1C] | |

TABLE A1-continued
| | | | |
|---|---|---|---|
| 1-336 | Cl | 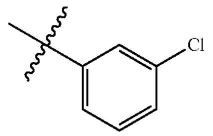 [SMILES: *c1cccc(Cl)c1] | 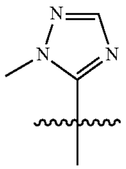 [SMILES: *c1ncnn1C] |
| 1-337 | Cl | 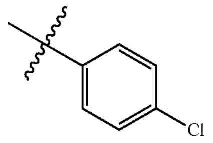 | 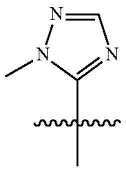 [SMILES: *c1ncnn1C] |
| 1-338 | Cl | 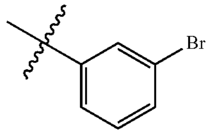 [SMILES: *c1cccc(Br)c1] | 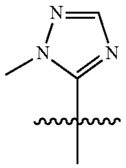 [SMILES: *c1ncnn1C] |
| 1-339 | Cl | 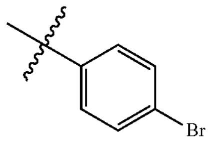 [SMILES: *c1ccc(Br)cc1] | 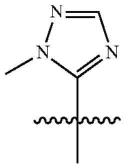 [SMILES: *c1ncnn1C] |
| 1-340 | Cl | 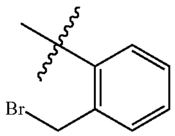 [SMILES: *c1ccccc1CBr] | 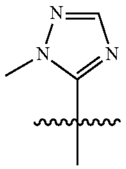 [SMILES: *c1ncnn1C] |
| 1-341 | Cl | 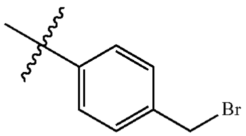 [SMILES: *c1ccc(CBr)cc1] | 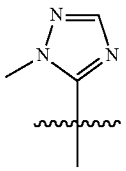 [SMILES: *c1ncnn1C] |

TABLE A1-continued
| | | | |
|---|---|---|---|
| 1-342 | Cl | 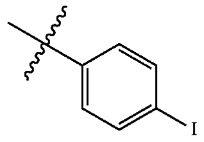 [SMILES: *c1ccc(I)cc1] | 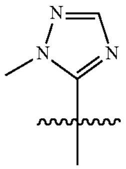 [SMILES: *c1ncnn1C] |
| 1-343 | Cl | 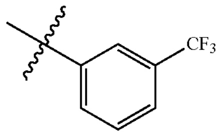 [SMILES: *c1cccc(C(F)(F)F)c1] | 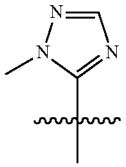 |
| 1-344 | Cl | 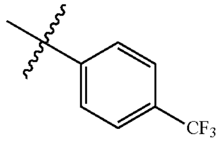 | 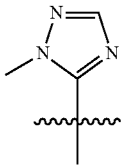 [SMILES: *c1ncnn1C] |
| 1-345 | Cl | 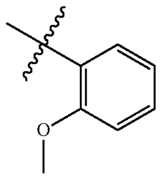 [SMILES: *c1ccccc1OC] | 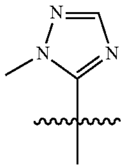 [SMILES: *c1ncnn1C] |
| 1-346 | Cl | 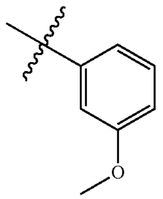 [SMILES: *c1cccc(OC)c1] | 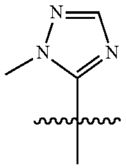 [SMILES: *c1ncnn1C] |

TABLE A1-continued
| | | | |
|---|---|---|---|
| 1-347 | Cl | 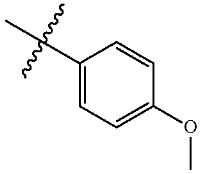 [SMILES: *c1ccc(OC)cc1] | 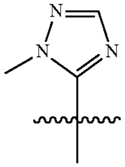 |
| 1-348 | Cl | 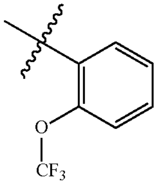 | 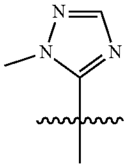 [SMILES: *c1ncnn1C] |
| 1-349 | Cl | 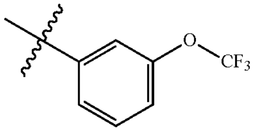 [SMILES: *c1cccc(OC(F)(F)F)c1] | 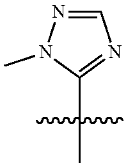 |
| 1-350 | Cl | 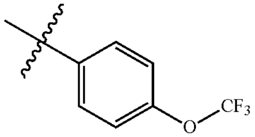 [SMILES: *c1ccc(OC(F)(F)F)cc1] | 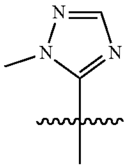 [SMILES: *c1ncnn1C] |
| 1-351 | Cl | 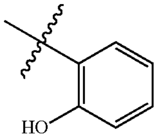 [SMILES: *c1ccccc1O] | 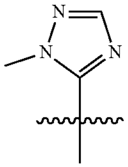 |
| 1-352 | Cl | 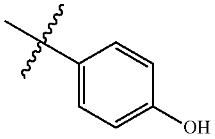 [SMILES: *c1ccc(O)cc1] | 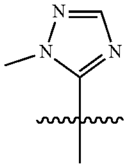 |

TABLE A1-continued
| | | | |
|---|---|---|---|
| 1-353 | Cl | 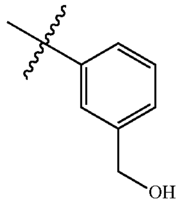 [SMILES: *c1cccc(CO)c1] | 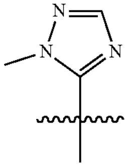 |
| 1-354 | Cl | 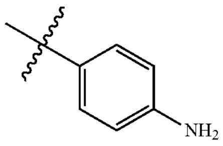 | 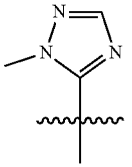 |
| 1-355 | Cl | 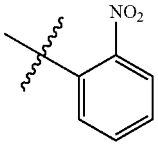 [SMILES: *c1ccccc1[N+](=O)[O-]] | 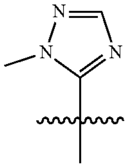 |
| 1-356 | Cl | 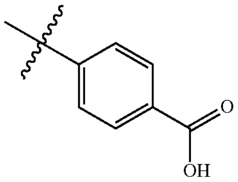 [SMILES: *c1ccc(C(=O)O)cc1] | 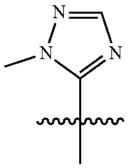 |
| 1-357 | Cl | 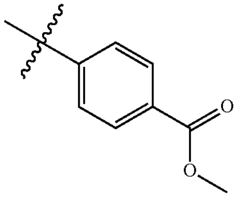 [SMILES: *c1ccc(C(=O)OC)cc1] | 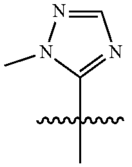 |

TABLE A1-continued
| | | | |
|---|---|---|---|
| 1-358 | Cl | 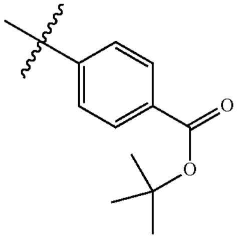 [SMILES: *c1ccc(C(=O)OC(C)(C)C)cc1] | 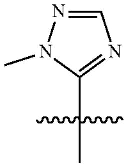 |
| 1-359 | Cl | 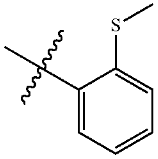 [SMILES: *c1ccccc1SC] | 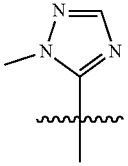 |
| 1-360 | Cl | 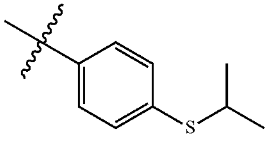 [SMILES: *c1ccc(SC(C)C)cc1] | 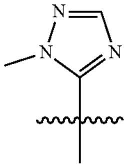 |
| 1-361 | Cl | 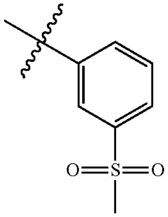 [SMILES: *c1cccc(S(C)(=O)=O)c1] | 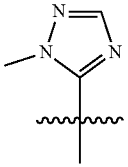 |
| 1-362 | Cl | 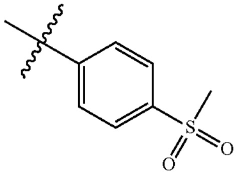 [SMILES: *c1ccc(S(C)(=O)=O)cc1] | 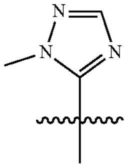 |

TABLE A1-continued
| | | | |
|---|---|---|---|
| 1-363 | Cl | 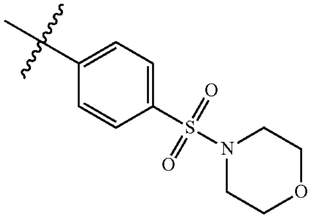 [SMILES: *c1ccc(S(=O)(=O)N2CCOCC2)cc1] | 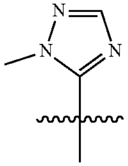 |
| 1-364 | Cl | 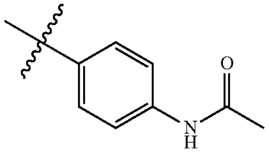 [SMILES: *c1ccc(NC(C)=O)cc1] | 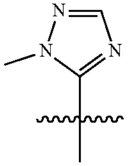 |
| 1-365 | Cl | 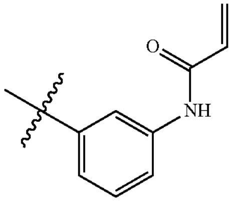 [SMILES: *c1cccc(NC(=O)C=C)c1] | 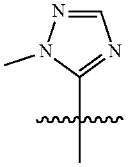 |
| 1-366 | Cl | 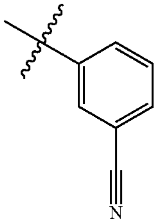 [SMILES: *c1cccc(C#N)c1] | 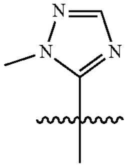 |
| 1-367 | Cl | 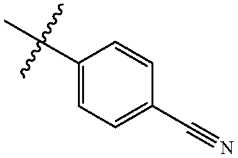 [SMILES: *c1ccc(C#N)cc1] | 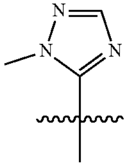 |

TABLE A1-continued
| | | | |
|---|---|---|---|
| 1-368 | Cl | 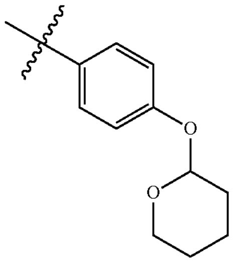 [SMILES: *c1ccc(OC2CCCCO2)cc1] | 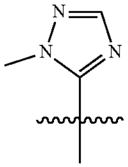 |
| 1-369 | Cl | 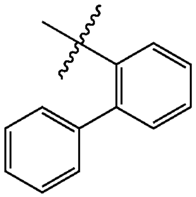 [SMILES: *c1ccccc1-c1ccccc1] | 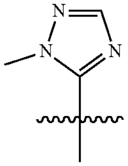 [SMILES: *c1ncnn1C] |
| 1-370 | Cl | 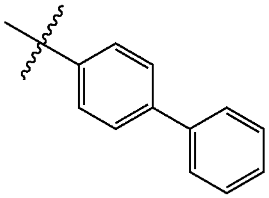 [SMILES: *c1ccc(-c2ccccc2)cc1] | 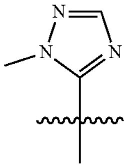 [SMILES: *c1ncnn1C] |
| 1-371 | Cl | 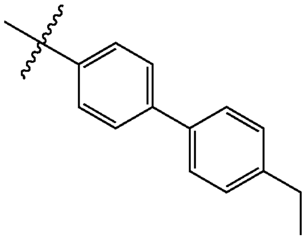 [SMILES: *c1ccc(-c2ccc(CC)cc2)cc1] | 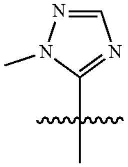 |

TABLE A1-continued
| | | | |
|---|---|---|---|
| 1-372 | Cl | 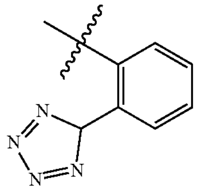 [SMILES: *c1ccccc1C1N=NN=N1] | 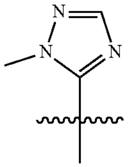 |
| 1-373 | Cl | 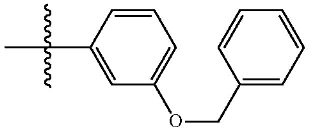 [SMILES: *c1cccc(OCc2ccccc2)c1] | 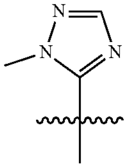 |
| 1-374 | Cl | 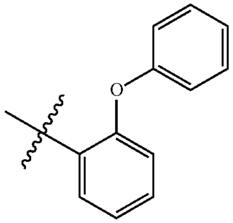 [SMILES: *c1ccccc1Oc1ccccc1] | 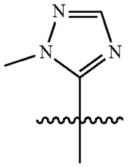 |
| 1-375 | Cl | 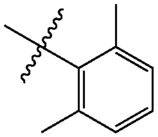 [SMILES: *c1c(C)cccc1C] | 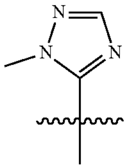 |
| 1-376 | Cl | 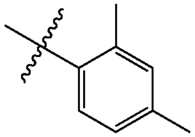 [SMILES: *c1ccc(C)cc1C] | 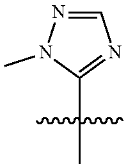 [SMILES: *c1ncnn1C] |

TABLE A1-continued
| | | | |
|---|---|---|---|
| 1-377 | Cl | 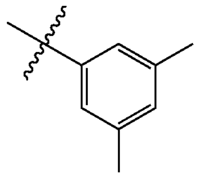 [SMILES: *c1cc(C)cc(C)c1] | 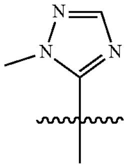 |
| 1-378 | Cl | 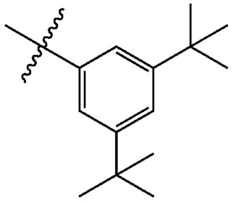 [SMILES: *c1cc(C(C)(C)C)cc(C(C)(C)C)c1] | 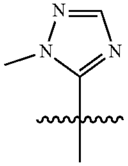 |
| 1-379 | Cl | 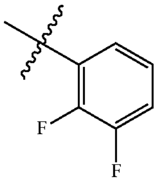 [SMILES: *c1cccc(F)c1F] | 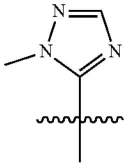 [SMILES: *c1ncnn1C] |
| 1-380 | Cl | 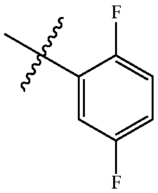 | 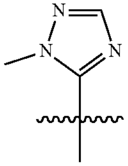 [SMILES: *c1ncnn1C] |
| 1-381 | Cl | 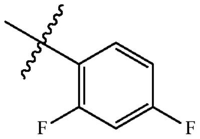 [SMILES: *c1ccc(F)cc1F] | 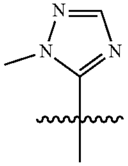 |

TABLE A1-continued
| | | | |
|---|---|---|---|
| 1-382 | Cl | 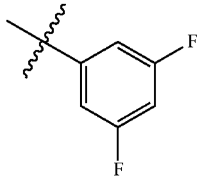 [SMILES: *c1cc(F)cc(F)c1] | 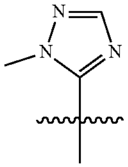 |
| 1-383 | Cl | 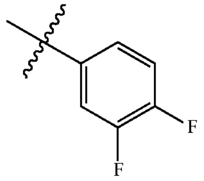 [SMILES: *c1ccc(F)c(F)c1] | 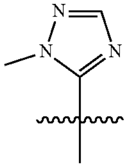 [SMILES: *c1ncnn1C] |
| 1-384 | Cl | 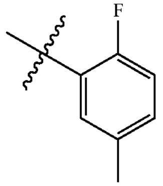 [SMILES: *c1cc(C)ccc1F] | 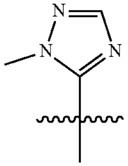 |
| 1-385 | Cl | 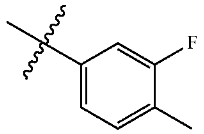 [SMILES: *c1ccc(C)c(F)c1] | 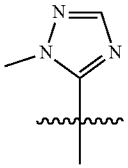 |
| 1-386 | Cl | 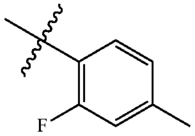 [SMILES: *c1ccc(C)cc1F] | 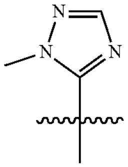 [SMILES: *c1ncnn1C] |

TABLE A1-continued
| | | | |
|---|---|---|---|
| 1-387 | Cl | 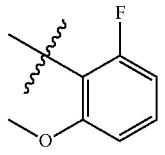 [SMILES: *c1c(F)cccc1OC] | 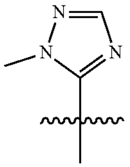 [SMILES: *c1ncnn1C] |
| 1-388 | Cl | 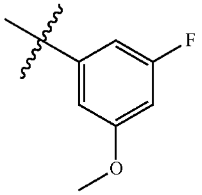 [SMILES: *c1cc(F)cc(OC)c1] | 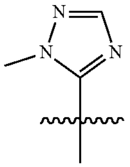 [SMILES: *c1ncnn1C] |
| 1-389 | Cl | 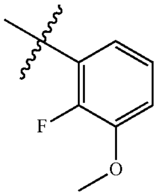 [SMILES: *c1cccc(OC)c1F] | 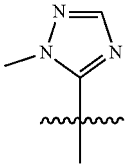 |
| 1-390 | Cl | 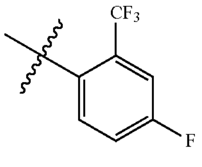 | 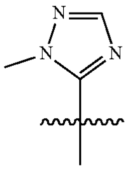 |
| 1-391 | Cl | 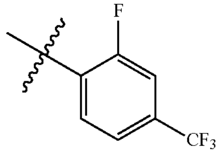 | 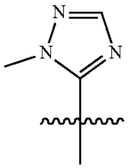 |

TABLE A1-continued
| | | | |
|---|---|---|---|
| 1-392 | Cl | 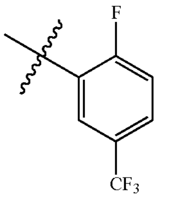 | 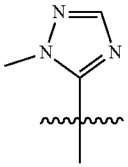 [SMILES: *c1ncnn1C] |
| 1-393 | Cl | 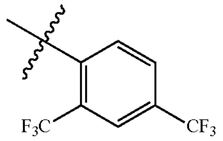 | 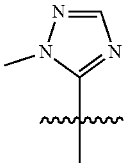 [SMILES: *c1ncnn1C] |
| 1-394 | Cl | 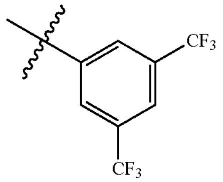 [SMILES: *c1cc(C(F)(F)F)cc(C(F)(F)F)c1] | 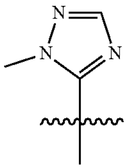 [SMILES: *c1ncnn1C] |
| 1-395 | Cl | 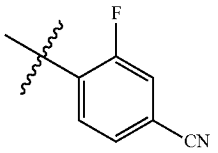 [SMILES: *c1ccc(C#N)cc1F] | 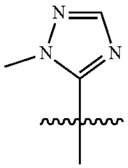 |
| 1-396 | Cl | 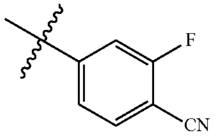 | 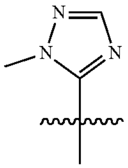 |

TABLE A1-continued
| | | | |
|---|---|---|---|
| 1-397 | Cl | 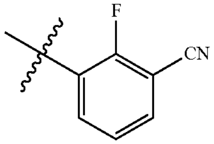 [SMILES: *c1cccc(C#N)c1F] | 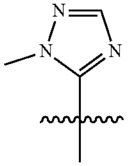 [SMILES: *c1ncnn1C] |
| 1-398 | Cl | 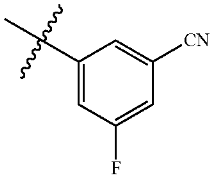 [SMILES: *c1cc(F)cc(C#N)c1] | 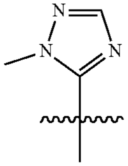 [SMILES: *c1ncnn1C] |
| 1-399 | Cl | 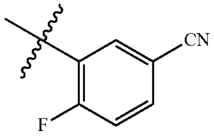 [SMILES: *c1cc(C#N)ccc1F] | 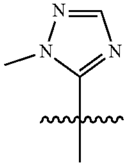 |
| 1-400 | Cl | 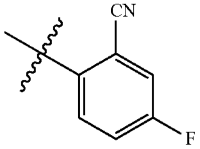 | 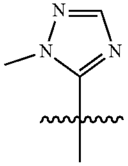 |
| 1-401 | Cl | 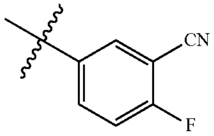 [SMILES: *c1ccc(F)c(C#N)c1] | 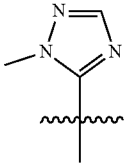 |

TABLE A1-continued
| | | | |
|---|---|---|---|
| 1-402 | Cl | 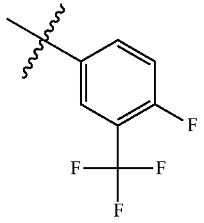 [SMILES: *c1ccc(F)c(C(F)(F)F)c1] | 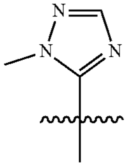 [SMILES: *c1ncnn1C] |
| 1-403 | Cl | 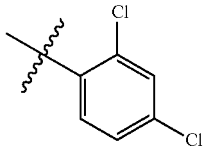 [SMILES: *c1ccc(Cl)cc1Cl] | 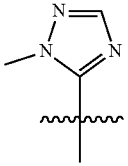 |
| 1-404 | Cl | 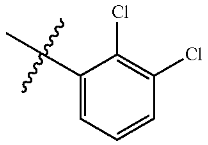 [SMILES: *c1cccc(Cl)c1Cl] | 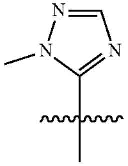 |
| 1-405 | Cl | 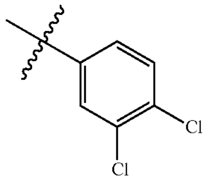 [SMILES: *c1ccc(Cl)c(Cl)c1] | 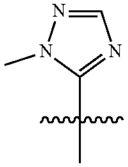 |
| 1-406 | Cl | 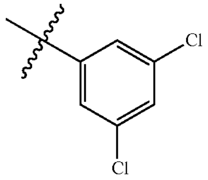 [SMILES: *c1cc(Cl)cc(Cl)c1] | 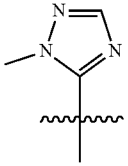 |

TABLE A1-continued
| | | | |
|---|---|---|---|
| 1-407 | Cl | 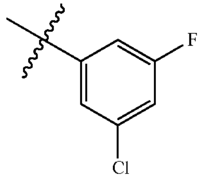 | 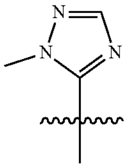 [SMILES: *c1ncnn1C] |
| 1-408 | Cl | 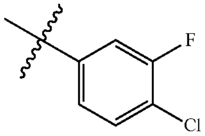 | 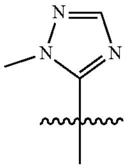 [SMILES: *c1ncnn1C] |
| 1-409 | Cl | 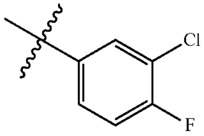 [SMILES: *c1ccc(F)c(Cl)c1] | 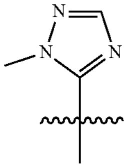 |
| 1-410 | Cl | 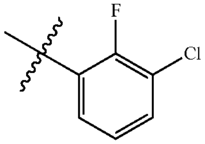 [SMILES: *c1cccc(Cl)c1F] | 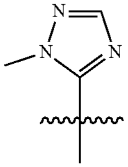 |
| 1-411 | Cl | 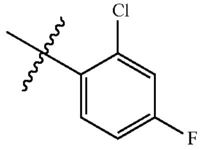 [SMILES: *c1ccc(F)cc1Cl] | 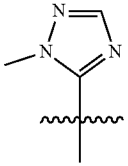 |
| 1-412 | Cl | 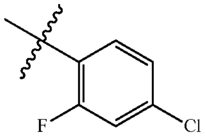 [SMILES: *c1ccc(Cl)cc1F] | 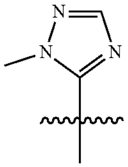 [SMILES: *c1ncnn1C] |

TABLE A1-continued
| | | | |
|---|---|---|---|
| 1-413 | Cl | 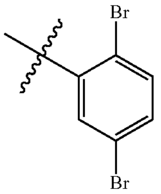 | 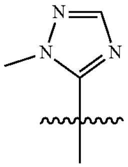 [SMILES: *c1ncnn1C] |
| 1-414 | Cl | 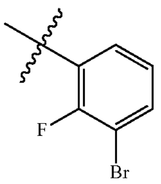 | 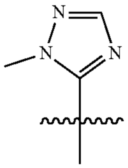 [SMILES: *c1ncnn1C] |
| 1-415 | Cl | 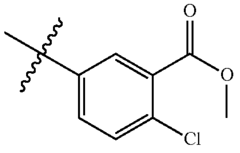 [SMILES: *c1ccc(Cl)c(C(=O)OC)c1] | 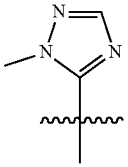 |
| 1-416 | Cl | 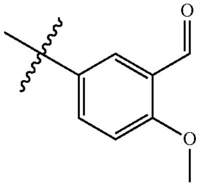 [SMILES: *c1ccc(OC)c(C=O)c1] | 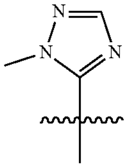 |
| 1-417 | Cl | 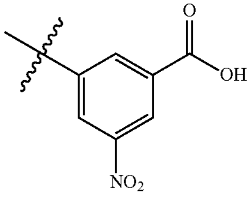 | 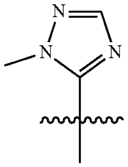 |

TABLE A1-continued
| | | | |
|---|---|---|---|
| 1-418 | Cl | 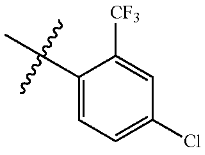 | 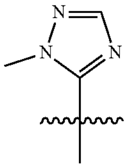 [SMILES: *c1ncnn1C] |
| 1-419 | Cl | 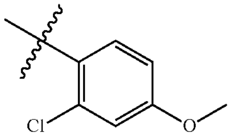 [SMILES: *c1ccc(OC)cc1Cl] | 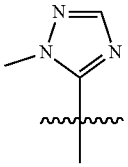 [SMILES: *c1ncnn1C] |
| 1-420 | Cl | 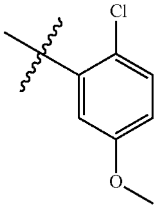 [SMILES: *c1cc(OC)ccc1Cl] | 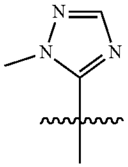 [SMILES: *c1ncnn1C] |
| 1-421 | Cl | 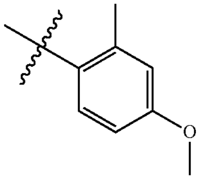 [SMILES: *c1ccc(OC)cc1C] | 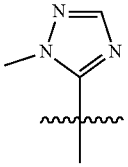 |
| 1-422 | Cl | 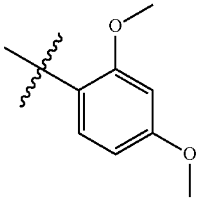 [SMILES: *c1ccc(OC)cc1OC] | 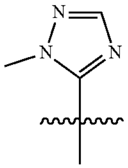 |

TABLE A1-continued
| | | | |
|---|---|---|---|
| 1-423 | Cl | 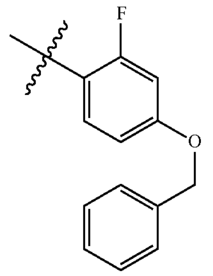 [SMILES: *c1ccc(OCc2ccccc2)cc1F] | 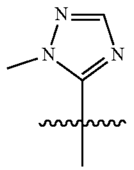 |
| 1-424 | Cl | 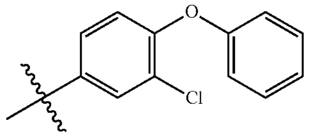 [SMILES: *c1ccc(Oc2ccccc2)c(Cl)c1] | 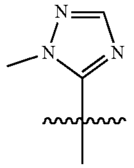 |
| 1-425 | Cl | 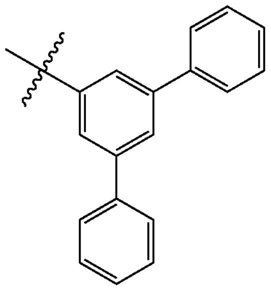 [SMILES: *c1cc(-c2ccccc2)cc(-c2ccccc2)c1] | 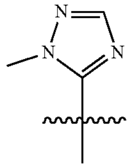 |
| 1-426 | Cl | 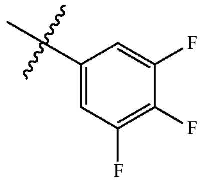 [SMILES: *c1cc(F)c(F)c(F)c1] | 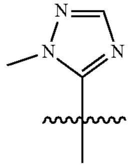 |

TABLE A1-continued
| | | | | |
|---|---|---|---|---|
| 1-427 | Cl | 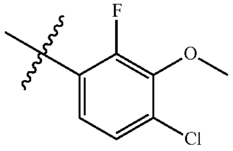 [SMILES: *c1ccc(Cl)c(OC)c1F] | 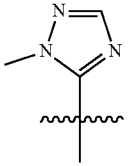 | |
| 1-428 | Cl | 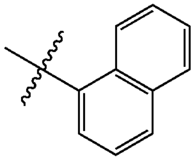 [SMILES: *c1cccc2ccccc12] | 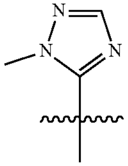 | $^1$H NMR (500 MHz, DMSO-$d_6$) δ 12.10 (s, 1H), 8.91 (d, J = 5.0 Hz, 1H), 8.38-8.35 (m, 2H), 8.18-8.07 (m, 2H), 8.03-8.00 (m, 1H), 7.90 (t, J = 8.5 Hz, 1H), 7.65 (d, J = 5.0 Hz, 1H), 7.59-7.56 (m, 1H), 7.52-7.50 (m, 1H), 4.31 (s, 3H). |
| 1-429 | Cl | 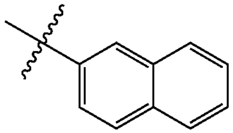 [SMILES: *c1ccc2ccccc2c1] | 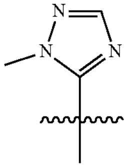 | |
| 1-430 | Cl | 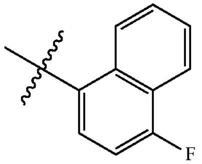 [SMILES: *c1ccc(F)c2ccccc12] | 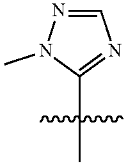 | |
| 1-431 | Cl | 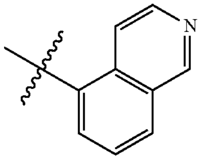 [SMILES: *c1cccc2cnccc12] | 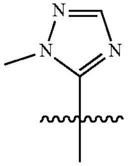 | $^1$H NMR (500 MHz, DMSO-$d_6$) δ 12.22 (s, 1H), 9.29 (s, 1H), 8.87 (d, J = 5.0 Hz, 1H), 8.59 (d, J = 5.0 Hz, 1H), 8.33 (s, 1H), 8.26-8.22 (m, 2H), 8.17-8.14 (m, 2H), 7.66 (d, J = 5.0 Hz, 1H), 3.92 (s, 3H). |
| 1-432 | Cl | 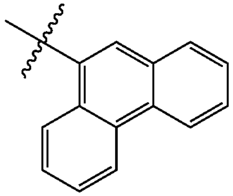 [SMILES: *c1cc2ccccc2c2ccccc12] | 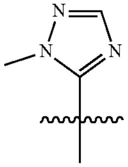 | $^1$H NMR (500 MHz, DMSO-$d_6$) δ 12.09 (s, 1H), 8.93-8.85 (m, 2H), 8.81-8.74 (m, 1H), 8.43-8.36 (m, 2H), 8.02-7.99 (m, 2H), 7.74-7.60 (m, 5H), 3.92 (s, 3H). |

TABLE A1-continued
| | | | | |
|---|---|---|---|---|
| 1-433 | Cl | 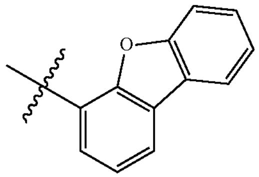 [SMILES: *c1cccc2c1oc1ccccc12] | 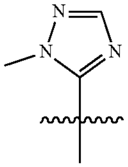 | $^1$H NMR (500 MHz, DMSO-$d_6$) δ 12.08 (s, 1H), 8.91 (d, J = 5.0 Hz, 1H), 8.51 (s, 1H), 8.20 (dd, J = 7.5, 2.0 Hz, 1H), 8.07-8.03 (m, 2H), 7.67 (d, J = 5.0 Hz, 1H), 7.65-7.58 (m, 2H), 7.44-7.41 (m, 1H), 7.35-7.32 (m, 1H), 3.96 (s, 3H). |
| 1-434 | Cl | 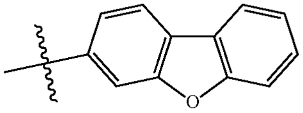 [SMILES: *c1ccc2c(c1)oc1ccccc12] | 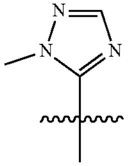 | |
| 1-435 | Cl | 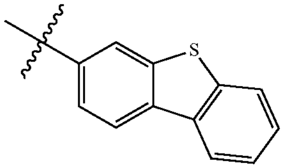 [SMILES: *c1ccc2c(c1)sc1ccccc12] | 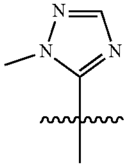 | $^1$H NMR (500 MHz, DMSO-$d_6$) δ 12.05 (s, 1H), 8.90 (d, J = 5.0 Hz, 1H), 8.55 (d, J = 2.0 Hz, 1H), 8.48 (dd, J = 7.5, 2.0 Hz, 1H), 8.39 (d, J = 7.5 Hz, 1H), 8.32 (s, 1H), 8.11-8.05 (m, 2H), 7.62 (d, J = 5.0 Hz, 1H), 7.56 (td, J = 7.5, 2.0 Hz, 1H), 7.48 (td, J = 7.5, 2.0 Hz, 1H), 3.92 (s, 3H). |
| 1-436 | Cl | 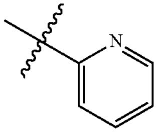 [SMILES: *c1ccccn1] | 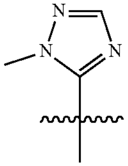 | $^1$H NMR (500 MHz, DMSO-$d_6$) δ 12.13 (s, 1H), 8.68 (d, J = 5.0 Hz, 1H), 8.58-8.48 (m, 2H), 8.29 (s, 1H), 7.74 (td, J = 7.5, 2.0 Hz, 1H), 7.58 (d, J = 5.0 Hz, 1H), 7.24-7.22 (m, 1H), 3.91 (s, 3H). |
| 1-437 | Cl | 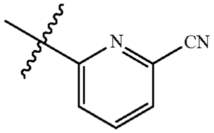 [SMILES: *c1cccc(C#N)n1] | 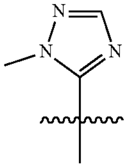 | |
| 1-438 | Cl | 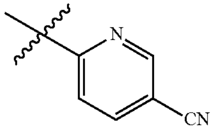 [SMILES: *c1ccc(C#N)cn1] | 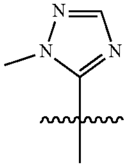 | |

TABLE A1-continued
| | | | |
|---|---|---|---|
| 1-439 | Cl | 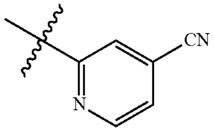 [SMILES: *c1cc(C#N)ccn1] | 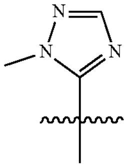 |
| 1-440 | Cl | 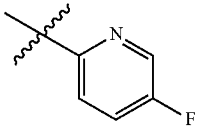 | 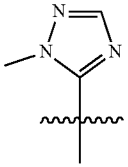 |
| 1-441 | Cl | 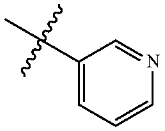 [SMILES: *c1cccnc1] | 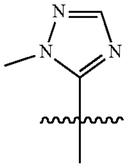 |
| 1-442 | Cl | 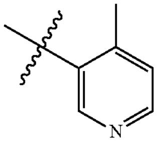 [SMILES: *c1cnccc1C] | 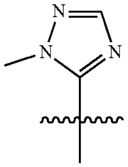 |
| 1-443 | Cl | 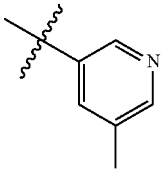 [SMILES: *c1cncc(C)c1] | 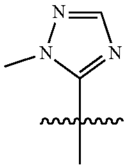 |
| 1-444 | Cl | 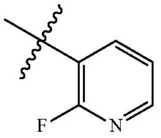 [SMILES: *c1cccnc1F] | 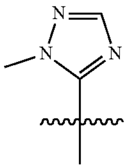 |

TABLE A1-continued
| | | | |
|---|---|---|---|
| 1-445 | Cl | 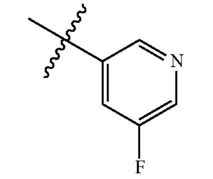 [SMILES: *c1cncc(F)c1] | 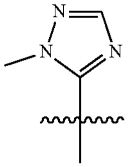 |
| 1-446 | Cl | 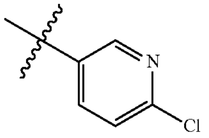 [SMILES: *c1ccc(Cl)nc1] | 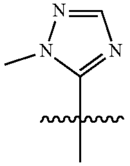 |
| 1-447 | Cl | 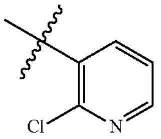 [SMILES: *c1cccnc1Cl] | 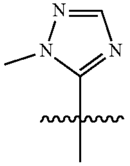 |
| 1-448 | Cl | 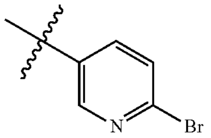 [SMILES: *c1ccc(Br)nc1] | 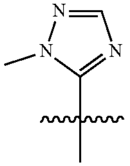 |
| 1-449 | Cl | 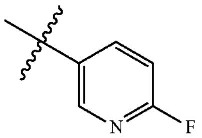 [SMILES: *c1ccc(F)nc1] | 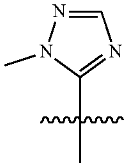 |
| 1-450 | Cl | 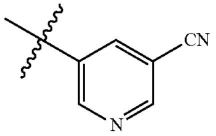 [SMILES: *c1cncc(C#N)c1] | 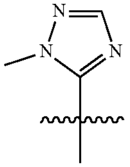 |

TABLE A1-continued
| | | | |
|---|---|---|---|
| 1-451 | Cl | 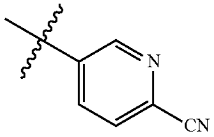 [SMILES: *c1ccc(C#N)nc1] | 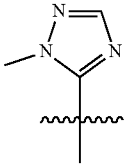 |
| 1-452 | Cl | 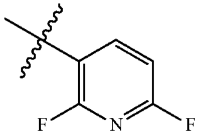 [SMILES: *c1ccc(F)nc1F] | 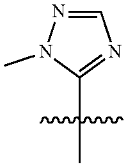 |
| 1-453 | Cl | 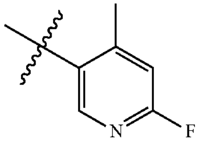 [SMILES: *c1cnc(F)cc1C] | 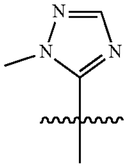 |
| 1-454 | Cl | 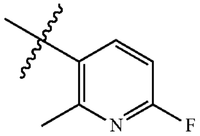 [SMILES: *c1ccc(F)nc1C] | 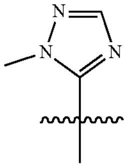 |
| 1-455 | Cl | 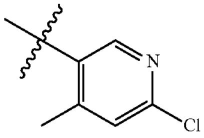 [SMILES: *c1cnc(Cl)cc1C] | 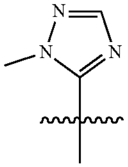 |
| 1-456 | Cl | 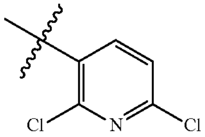 [SMILES: *c1ccc(Cl)nc1Cl] | 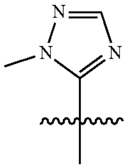 |

TABLE A1-continued
| | | | |
|---|---|---|---|
| 1-457 | Cl | 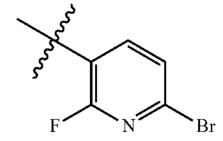 [SMILES: *c1ccc(Br)nc1F] | 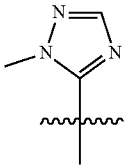 |
| 1-458 | Cl | 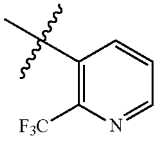 | 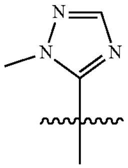 |
| 1-459 | Cl | 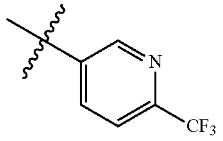 | 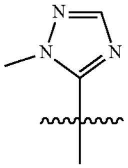 |
| 1-460 | Cl | 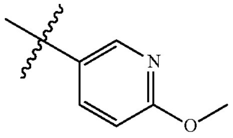 [SMILES: *c1ccc(OC)nc1] | 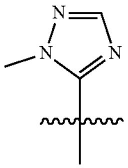 |
| 1-461 | Cl | 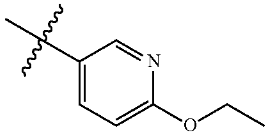 [SMILES: *c1ccc(OCC)nc1] | 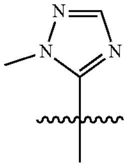 [SMILES: *c1ncnn1C] |
| 1-462 | Cl | 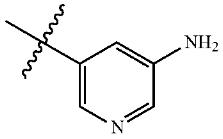 [SMILES: *c1cncc(N)c1] | 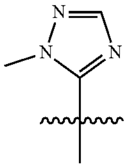 [SMILES: *c1ncnn1C] |

TABLE A1-continued
| | | | |
|---|---|---|---|
| 1-463 | Cl | 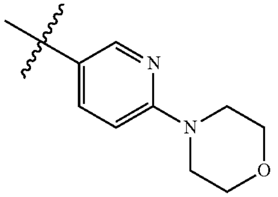 [SMILES: *c1ccc(N2CCOCC2)nc1] | 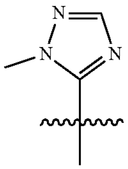 |
| 1-464 | Cl | 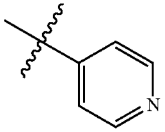 [SMILES: *c1ccncc1] | 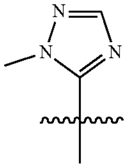 |
| 1-465 | Cl | 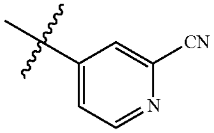 [SMILES: *c1ccnc(C#N)c1] | 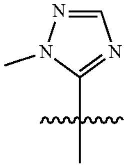 |
| 1-466 | Cl | 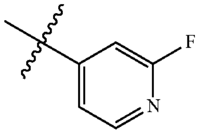 [SMILES: *c1ccnc(F)c1] | 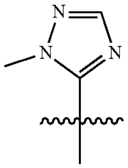 |
| 1-467 | Cl | 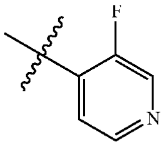 [SMILES: *c1ccncc1F] | 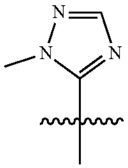 |
| 1-468 | Cl | 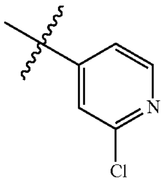 [SMILES: *c1ccnc(Cl)c1] | 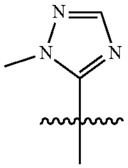 |

TABLE A1-continued
| | | | |
|---|---|---|---|
| 1-469 | Cl | 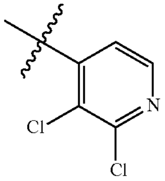 [SMILES: *c1ccnc(Cl)c1Cl] | 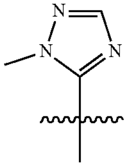 |
| 1-470 | Cl | 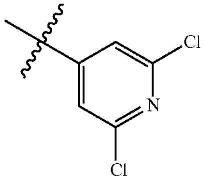 [SMILES: *c1cc(Cl)nc(Cl)c1] | 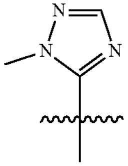 [SMILES: *c1ncnn1C] |
| 1-471 | Cl | 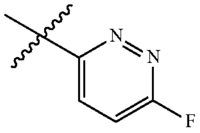 [SMILES: *c1ccc(F)nn1] | 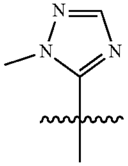 |
| 1-472 | Cl | 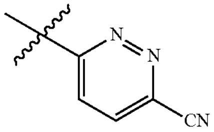 [SMILES: *c1ccc(C#N)nn1] | 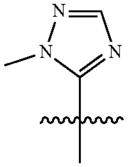 |
| 1-473 | Cl | 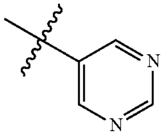 [SMILES: *c1cncnc1] | 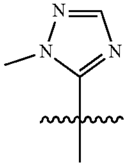 |

TABLE A1-continued
| | | | | |
|---|---|---|---|---|
| 1-474 | Cl | 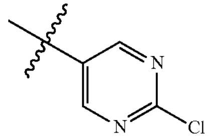 [SMILES: *c1cnc(Cl)nc1] | 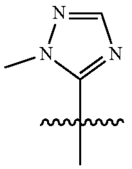 | |
| 1-475 | Cl | 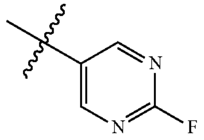 [SMILES: *c1cnc(F)nc1] | 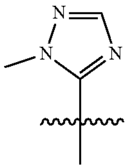 | |
| 1-476 | Cl | 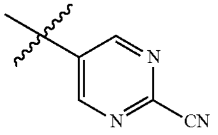 [SMILES: *c1cnc(C#N)nc1] | 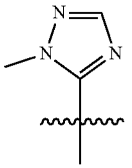 | |
| 1-477 | Cl | 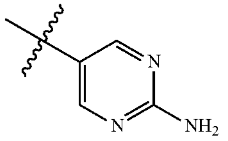 [SMILES: *c1cnc(N)nc1] | 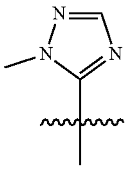 [SMILES: *c1ncnn1C] | |
| 1-478 | Cl | 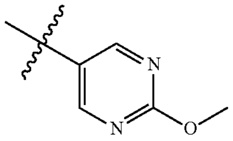 [SMILES: *c1cnc(OC)nc1] | 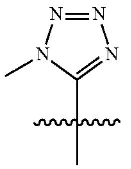 [SMILES: *c1nnnn1C] | $^1$H NMR (500 MHz, DMSO-$d_6$) δ 12.08 (s, 1H), 9.25 (s, 2H), 8.83 (d, J = 5.0 Hz, 1H), 8.31 (s, 1H), 7.75 (d, J = 5.0 Hz, 1H), 3.91 (s, 3H), 3.85 (s, 3H). |
| 1-479 | Cl | 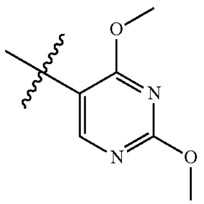 [SMILES: *c1cnc(OC)nc1OC] | 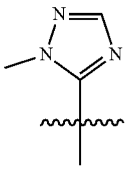 [SMILES: *c1ncnn1C] | |

TABLE A1-continued
| | | | |
|---|---|---|---|
| 1-480 | Cl | 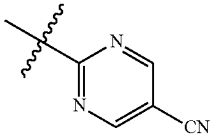 | 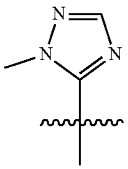 |
| 1-481 | Cl | 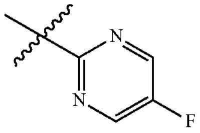 [SMILES: *c1ncc(F)cn1] | 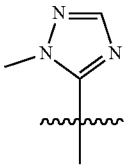 |
| 1-482 | Cl | 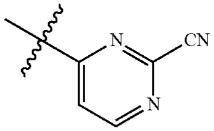 | 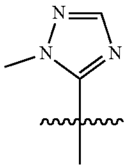 |
| 1-483 | Cl | 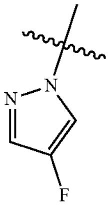 [SMILES: *n1cc(F)cn1] | 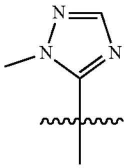 |
| 1-484 | Cl | 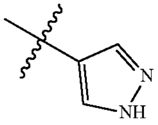 | 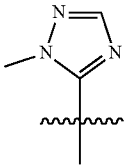 |

TABLE A1-continued
| | | | | |
|---|---|---|---|---|
| 1-485 | Cl | 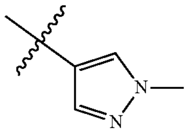 | 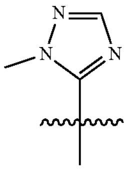 | |
| 1-486 | Cl | 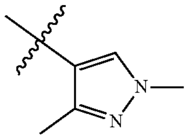 [SMILES: *c1cn(C)nc1C] | 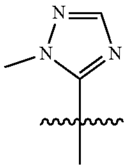 | $^1H$ NMR (500 MHz, DMSO-$d_6$) δ 12.10 (s, 1H), 8.91 (d, J = 5.0 Hz, 1H), 8.32 (s, 1H), 7.78 (d, J = 5.0 Hz, 1H), 6.87 (s, 1H), 3.93 (s, 3H), 3.92 (s, 3H), 2.41 (s, 3H). |
| 1-487 | Cl | 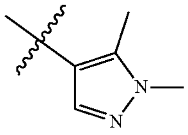 [SMILES: *c1cnn(C)c1C] | 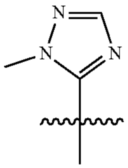 | |
| 1-488 | Cl | 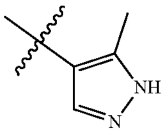 | 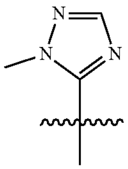 [SMILES: *c1ncnn1C] | |
| 1-489 | Cl | 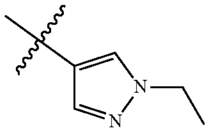 [SMILES: *c1cnn(CC)c1] | 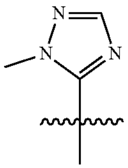 [SMILES: *c1ncnn1C] | |
| 1-490 | Cl | 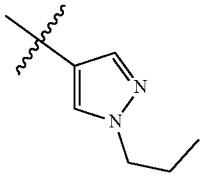 [SMILES: *c1cnn(CCC)c1] | 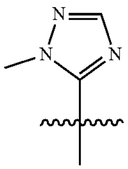 [SMILES: *c1ncnn1C] | |

TABLE A1-continued
| | | | |
|---|---|---|---|
| 1-491 | Cl | 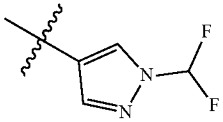 [SMILES: *c1cnn(C(F)F)c1] | 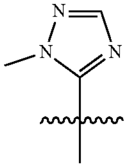 |
| 1-492 | Cl | 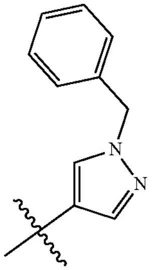 [SMILES: *c1cnn(Cc2ccccc2)c1] | 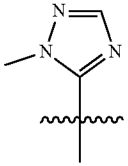 |
| 1-493 | Cl | 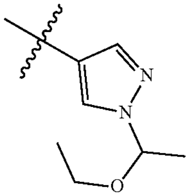 [SMILES: *c1cnn(C(C)OCC)c1] | 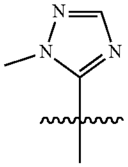 |
| 1-494 | Cl | 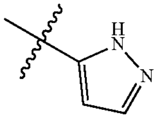 [SMILES: *c1ccn[nH]1] | 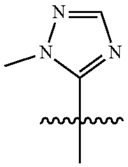 [SMILES: *c1ncnn1C] |
| 1-495 | Cl | 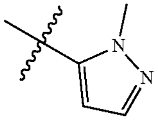 [SMILES: *c1ccnn1C] | 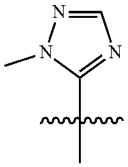 [SMILES: *c1ncnn1C] |

TABLE A1-continued
| | | | | |
|---|---|---|---|---|
| 1-496 | Cl | 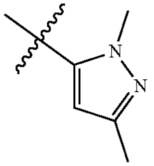 [SMILES: *c1cc(C)nn1C] | 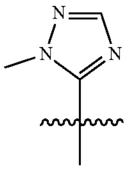 | |
| 1-497 | Cl | 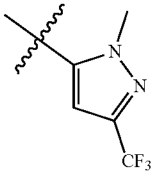 | 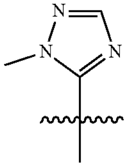 | |
| 1-498 | Cl | 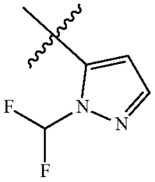 | 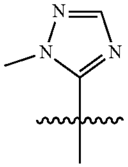 | |
| 1-499 | Cl | 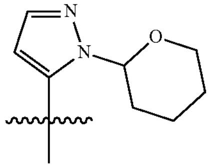 | 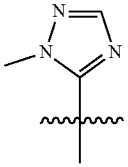 | |
| 1-500 | Cl | 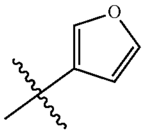 [SMILES: *c1ccoc1] | 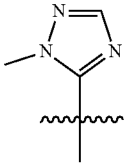 [SMILES: *c1ncnn1C] | $^1$H NMR (500 MHz, DMSO-$d_6$) δ 12.08 (s, 1H), 8.91 (d, J = 5.0 Hz, 1H), 8.37 (s, 1H), 7.92 (d, J = 5.0 Hz, 1H), 7.67 (s, 1H), 7.49 (d, J = 2.0 Hz, 1H), 6.69 (d, J = 2.0 Hz, 1H), 3.92 (s, 3H). |
| 1-501 | Cl | 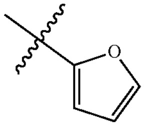 [SMILES: *c1ccco1] | 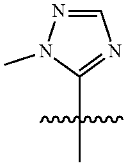 [SMILES: *c1ncnn1C] | |

TABLE A1-continued
| | | | | |
|---|---|---|---|---|
| 1-502 | Cl | 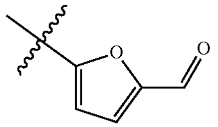 [SMILES: *c1ccc(C=O)o1] | 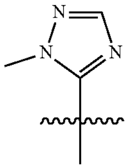 | |
| 1-503 | Cl | 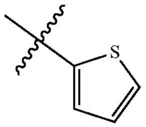 [SMILES: *c1cccs1] | 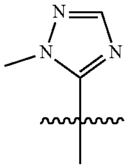 | |
| 1-504 | Cl | 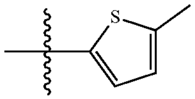 [SMILES: *c1ccc(C)s1] | 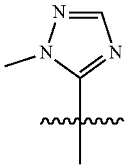 | |
| 1-505 | Cl | 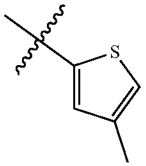 [SMILES: *c1cc(C)cs1] | 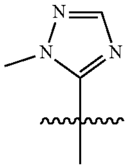 [SMILES: *c1ncnn1C] | |
| 1-506 | Cl | 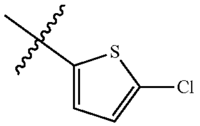 [SMILES: *c1ccc(Cl)s1] | 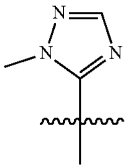 | $^1$H NMR (500 MHz, DMSO-$d_6$) δ 12.05 (s, 1H), 8.92 (d, J = 5.0 Hz, 1H), 8.37 (s, 1H), 7.94 (d, J = 5.0 Hz, 1H), 7.52 (d, J = 2.0 Hz, 1H), 7.13 (d, J = 2.0 Hz, 1H), 3.92 (s, 3H). |
| 1-507 | Cl | 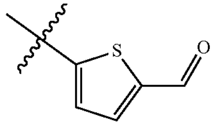 [SMILES: *c1ccc(C=O)s1] | 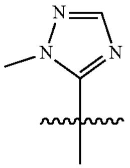 | |

TABLE A1-continued
| | | | | |
|---|---|---|---|---|
| 1-508 | Cl | 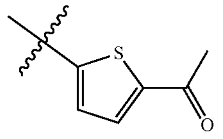 [SMILES: *c1ccc(C(C)=O)s1] | 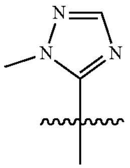 [SMILES: *c1ncnn1C] | |
| 1-509 | Cl | 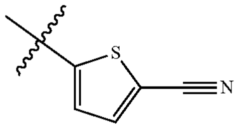 [SMILES: *c1ccc(C#N)s1] | 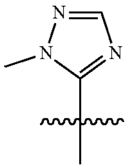 | |
| 1-510 | Cl | 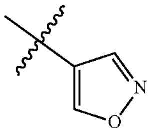 [SMILES: *c1cnoc1] | 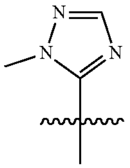 [SMILES: *c1ncnn1C] | |
| 1-511 | Cl | 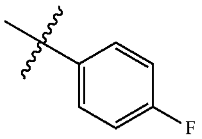 [SMILES: *c1ccc(F)cc1] | 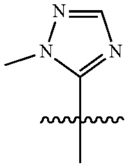 | $^{1}H$ NMR (500 MHz, DMSO-$d_6$) δ 12.07 (s, 1H), 8.58 (d, J = 5.0 Hz, 1H), 8.36 (s, 1H), 7.98-7.90 (m, 2H), 7.50 (d, J = 5.0 Hz, 1H), 7.35-7.27 (m, 2H), 4.33 (s, 3H), 2.52 (s, 3H). |
| 1-512 | F | 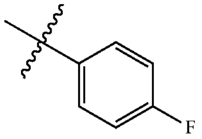 [SMILES: *c1ccc(F)cc1] | 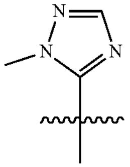 | |
| 1-513 | Br | 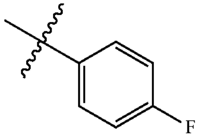 [SMILES: *c1ccc(F)cc1] | 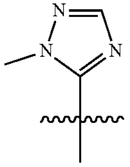 [SMILES: *c1ncnn1C] | |

TABLE A1-continued
| | | | | |
|---|---|---|---|---|
| 1-514 | 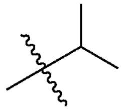 [SMILES: *C(C)C] | 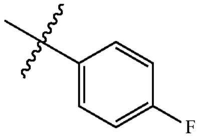 [SMILES: *c1ccc(F)cc1] | 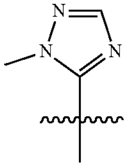 [SMILES: *c1ncnn1C] | |
| 1-515 | $CF_3$ | 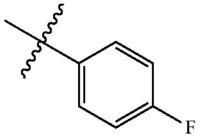 [SMILES: *c1ccc(F)cc1] | 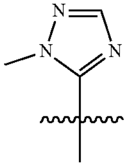 | $^1$H NMR (500 MHz, DMSO-$d_6$) δ 12.05 (s, 1H), 8.75 (d, J = 5.0 Hz, 1H), 8.36 (s, 1H), 8.02-7.95 (m, 2H), 7.58 (d, J = 5.0 Hz, 1H), 7.35-7.27 (m, 2H), 4.01 (s, 3H). |
| 1-516 | 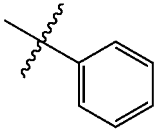 | 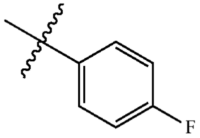 [SMILES: *c1ccc(F)cc1] | 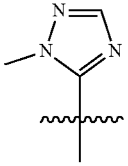 [SMILES: *c1ncnn1C] | $^1$H NMR (500 MHz, DMSO-$d_6$) δ 12.25 (s, 1H), 8.95 (d, J = 5.0 Hz, 1H), 8.34 (s, 1H), 8.00-7.93 (m, 2H), 7.69-7.60 (m, 3H), 7.47-7.35 (m, 3H), 7.35-7.27 (m, 2H), 3.83 (s, 3H). |
| 1-517 | 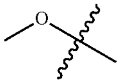 | 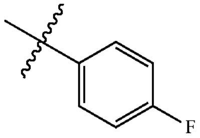 [SMILES: *c1ccc(F)cc1] | 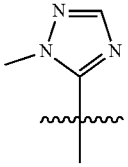 | $^1$H NMR (500 MHz, DMSO-$d_6$) δ 12.05 (s, 1H), 8.57 (d, J = 5.0 Hz, 1H), 8.32 (s, 1H), 8.09-8.01 (m, 2H), 7.50 (d, J = 5.0 Hz, 1H), 7.35-7.27 (m, 2H), 4.03 (s, 3H), 3.67 (s, 3H). |
| 1-518 | 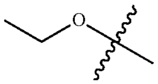 | 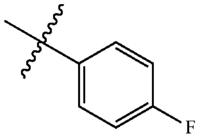 [SMILES: *c1ccc(F)cc1] | 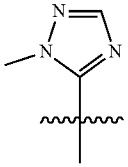 | |
| 1-519 | 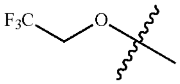 | 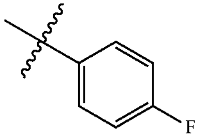 [SMILES: *c1ccc(F)cc1] | 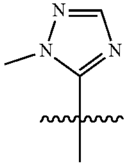 [SMILES: *c1ncnn1C] | |

TABLE A1-continued
| | | | | |
|---|---|---|---|---|
| 1-520 | 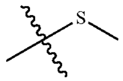 [SMILES: *SC] | 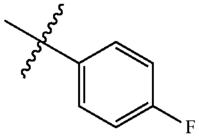 [SMILES: *c1ccc(F)cc1] | 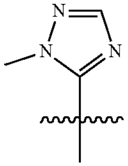 [SMILES: *c1ncnn1C] | |
| 1-521 | 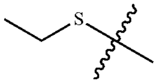 | 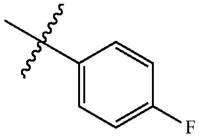 [SMILES: *c1ccc(F)cc1] | 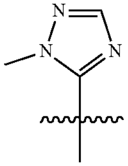 | $^1$H NMR (500 MHz, DMSO-$d_6$) δ 12.25 (s, 1H), 8.57 (d, J = 5.0 Hz, 1H), 8.33 (s, 1H), 8.04-7.97 (m, 2H), 7.47 (d, J = 5.0 Hz, 1H), 7.35-7.27 (m, 2H), 4.02 (s, 3H), 3.00 (q, J = 8.0 Hz, 2H), 1.19 (t, J = 8.0 Hz, 3H). |
| 1-522 | 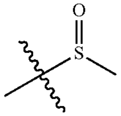 [SMILES: *S(C)=O] | 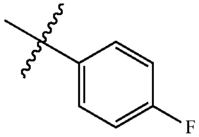 [SMILES: *c1ccc(F)cc1] | 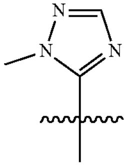 [SMILES: *c1ncnn1C] | |
| 1-523 | 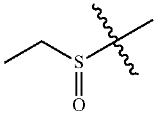 [SMILES: *S(=O)CC] | 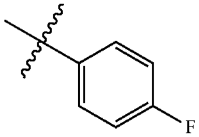 [SMILES: *c1ccc(F)cc1] | 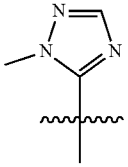 | $^1$H NMR (500 MHz, DMSO-$d_6$) δ 12.04 (s, 1H), 8.83 (d, J = 5.0 Hz, 1H), 8.31 (s, 1H), 8.04-7.97 (m, 2H), 7.55 (d, J = 5.0 Hz, 1H), 7.35-7.27 (m, 2H), 4.03 (s, 3H), 2.63-2.61 (m, 1H), 2.58-5.56 (m, 1H), 1.20 (t, J = 8.0 Hz, 3H). |
| 1-524 | 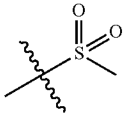 [SMILES: *S(C)(=O)=O] | 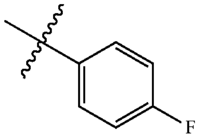 [SMILES: *c1ccc(F)cc1] | 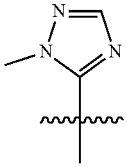 | |
| 1-525 | 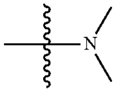 [SMILES: *N(C)C] | 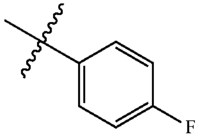 [SMILES: *c1ccc(F)cc1] | 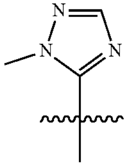 [SMILES: *c1ncnn1C] | $^1$H NMR (500 MHz, DMSO-$d_6$) δ 12.06 (s, 1H), 8.38 (d, J = 5.0 Hz, 1H), 8.33 (s, 1H), 8.06-7.98 (m, 2H), 7.46 (d, J = 5.0 Hz, 1H), 7.35-7.27 (m, 2H), 3.98 (s, 3H), 2.80 (s, 6H). |

TABLE A1-continued
| | | | | |
|---|---|---|---|---|
| 1-526 | 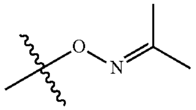 | 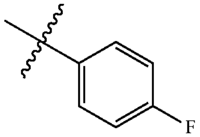 [SMILES: *c1ccc(F)cc1] | 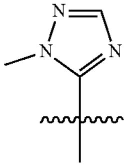 [SMILES: *c1ncnn1C] | |
| 1-527 | Et | 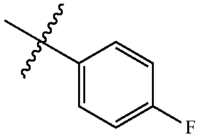 [SMILES: *c1ccc(F)cc1] | 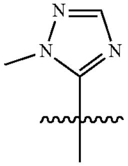 | |
| 1-528 | 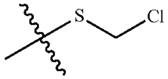 [SMILES: *SCCl] | 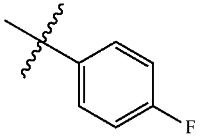 [SMILES: *c1ccc(F)cc1] | 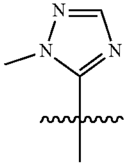 [SMILES: *c1ncnn1C] | |
| 1-529 | $NO_2$ | 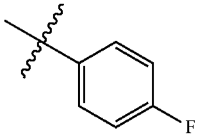 [SMILES: *c1ccc(F)cc1] | 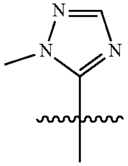 | $^1$H NMR (500 MHz, DMSO-$d_6$) δ 12.08 (s, 1H), 8.96 (d, J = 5.0 Hz, 1H), 8.35 (s, 1H), 7.98-7.91 (m, 2H), 7.72 (d, J = 5.0 Hz, 1H), 7.35-7.27 (m, 2H), 4.26 (s, 3H). |
| 1-530 | CN | 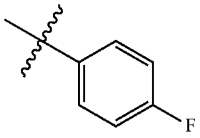 | 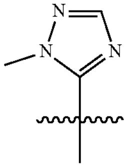 | $^1$H NMR (500 MHz, DMSO-$d_6$) δ 12.06 (s, 1H), 9.01 (d, J = 5.0 Hz, 1H), 8.33 (s, 1H), 8.05-7.97 (m, 2H), 7.70 (d, J = 5.0 Hz, 1H), 7.35-7.27 (m, 2H), 3.92 (s, 3H). |
| 1-531 | 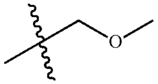 [SMILES: *COC] | 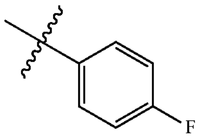 [SMILES: *c1ccc(F)cc1] | 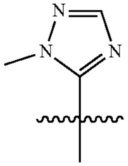 | $^1$H NMR (500 MHz, DMSO-$d_6$) δ 12.06 (s, 1H), 8.68 (d, J = 5.0 Hz, 1H), 8.37 (s, 1H), 8.03-7.95 (m, 2H), 7.65 (d, J = 5.0 Hz, 1H), 7.35-7.27 (m, 2H), 4.68 (s, 2H), 4.33 (s, 3H), 3.28 (s, 3H). |

TABLE A1-continued
| | | | | |
|---|---|---|---|---|
| 1-532 | 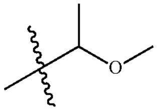 [SMILES: *C(C)OC] | 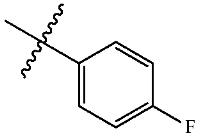 [SMILES: *c1ccc(F)cc1] | 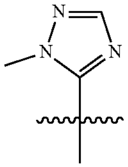 | |
| 1-533 | 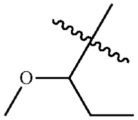 [SMILES: *C(CC)OC] | 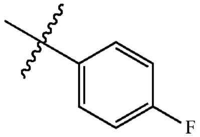 [SMILES: *c1ccc(F)cc1] | 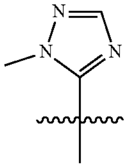 [SMILES: *c1ncnn1C] | |
| 1-534 | 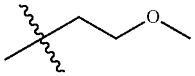 [SMILES: *CCOC] | 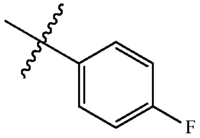 [SMILES: *c1ccc(F)cc1] | 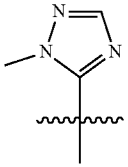 | |
| 1-535 | 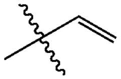 [SMILES: *C=C] | 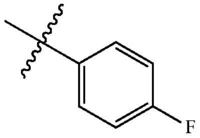 [SMILES: *c1ccc(F)cc1] | 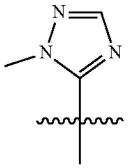 | $^1$H NMR (500 MHz, DMSO-$d_6$) δ 12.05 (s, 1H), 8.61 (d, J = 5.0 Hz, 1H), 8.03-7.96 (m, 2H), 7.35-7.25 (m, 3H), 6.53 (dd, J = 16.5, 10.0 Hz, 1H), 5.60-5.67 (m, 1H), 5.31 5.29 (m, 1H), 4.33 (s, 3H). |
| 1-536 | 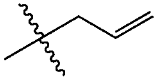 [SMILES: *CC=C] | 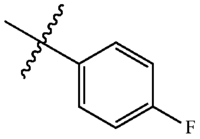 [SMILES: *c1ccc(F)cc1] | 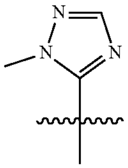 | |
| 1-537 | 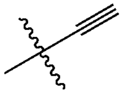 [SMILES: *C#C] | 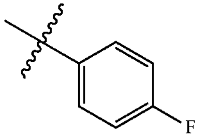 [SMILES: *c1ccc(F)cc1] | 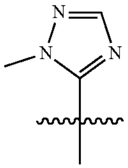 | $^1$H NMR (500 MHz, DMSO-$d_6$) δ 12.15 (s, 1H), 9.01 (d, J = 5.0 Hz, 1H), 8.33 (s, 1H), 8.05-7.97 (m, 2H), 7.70 (d, J = 5.0 Hz, 1H), 7.35-7.27 (m, 2H), 4.03 (s, 3H), 3.92 (s, 1H). |

TABLE A1-continued
| | | | |
|---|---|---|---|
| 1-538 | 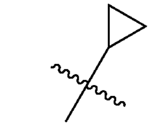 [SMILES: *C1CC1] | 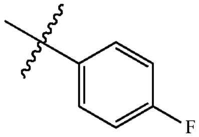 [SMILES: *c1ccc(F)cc1] | 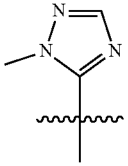 |
| 1-539 | 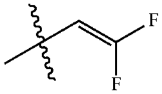 | 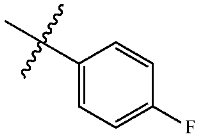 [SMILES: *c1ccc(F)cc1] | 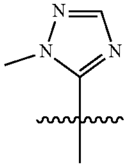 [SMILES: *c1ncnn1C] |
| 1-540 | 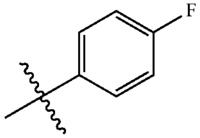 | 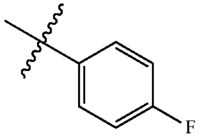 [SMILES: *c1ccc(F)cc1] | 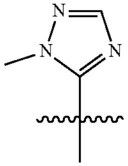 |
| 1-541 | Cl | 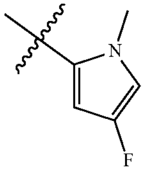 [SMILES: *c1cc(F)cn1C] | 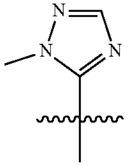 |
| 1-542 | Cl | 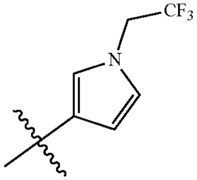 [SMILES: *c1ccn(CC(F)(F)F)c1] | 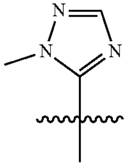 |
| 1-543 | Cl | 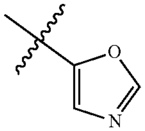 [SMILES: *c1cnco1] | 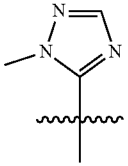 |

TABLE A1-continued
| | | | |
|---|---|---|---|
| 1-544 | Cl | 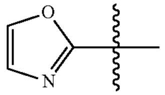 | 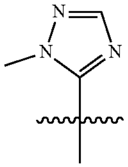 |
| 1-545 | Cl | 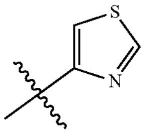 [SMILES: *c1cscn1] | 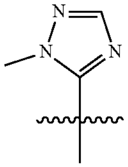 [SMILES: *c1ncnn1C] |
| 1-546 | Cl | 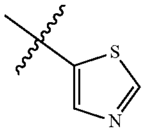 [SMILES: *c1cncs1] | 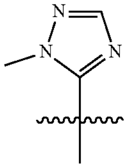 |
| 1-547 | Cl | 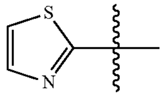 | 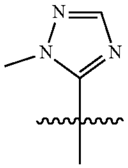 |
| 1-548 | Cl | 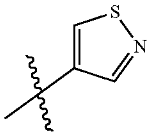 [SMILES: *c1cnsc1] | 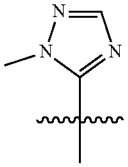 |
| 1-549 | Cl | 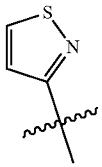 | 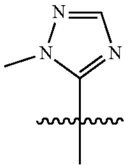 |

TABLE A1-continued
| | | | |
|---|---|---|---|
| 1-550 | Cl | 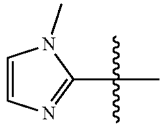 [SMILES: *c1nccn1C] | 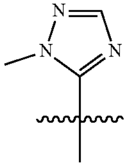 |
| 1-551 | Cl | 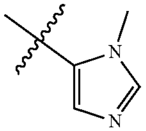 [SMILES: *c1cncn1C] | 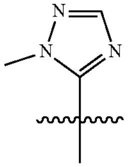 [SMILES: *c1ncnn1C] |
| 1-552 | Cl | 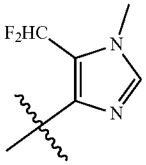 [SMILES: *c1ncn(C)c1C(F)F] | 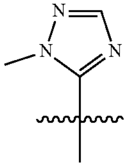 |
| 1-553 | Cl | 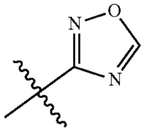 [SMILES: *c1ncon1] | 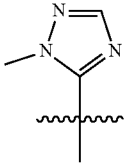 |
| 1-554 | Cl | 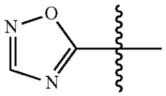 [SMILES: *c1ncno1] | 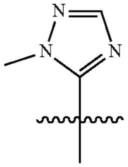 |
| 1-555 | Cl | 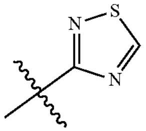 [SMILES: *c1ncsn1] | 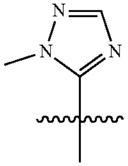 |

TABLE A1-continued
| | | | |
|---|---|---|---|
| 1-556 | Cl | 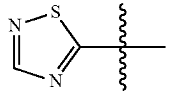 [SMILES: *c1ncns1] | 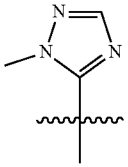 |
| 1-557 | Cl | 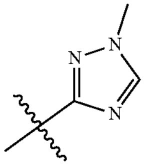 [SMILES: *c1ncn(C)n1] | 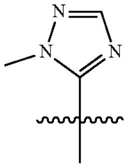 [SMILES: *c1ncnn1C] |
| 1-558 | Cl | 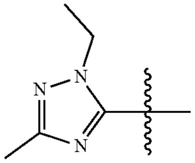 [SMILES: *c1nc(C)nn1CC] | 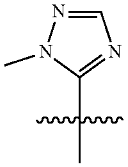 |
| 1-559 | Cl | 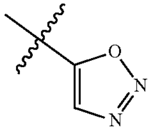 [SMILES: *c1cnno1] | 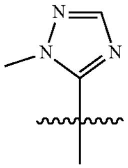 |
| 1-560 | Cl | 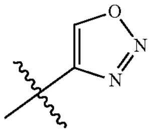 [SMILES: *c1conn1] | 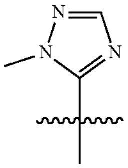 |
| 1-561 | Cl | 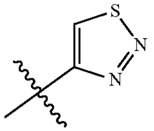 [SMILES: *c1csnn1] | 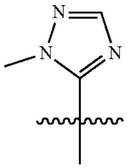 |

TABLE A1-continued
| | | | |
|---|---|---|---|
| 1-562 | Cl | 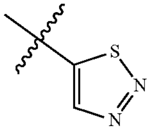 | 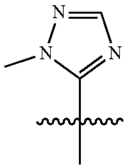 |
| 1-563 | Cl | 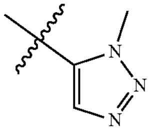 [SMILES: *c1cnnn1C] | 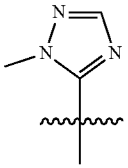 |
| 1-564 | Cl | 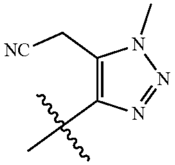 [SMILES: *c1nnn(C)c1CC#N] | 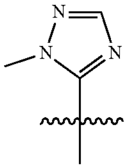 |
| 1-565 | Cl | 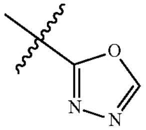 [SMILES: *c1nnco1] | 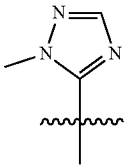 |
| 1-566 | Cl | 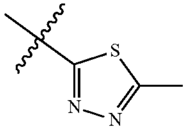 [SMILES: *c1nnc(C)s1] | 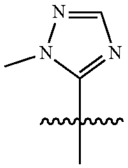 |
| 1-567 | Cl | 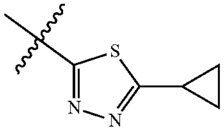 [SMILES: *c1nnc(C2CC2)s1] | 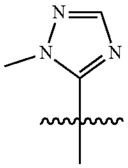 [SMILES: *c1ncnn1C] |

TABLE A1-continued
| | | | |
|---|---|---|---|
| 1-568 | Cl | 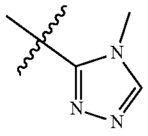 [SMILES: *c1nncn1C] | 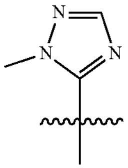 |
| 1-569 | Cl | 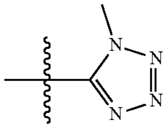 | 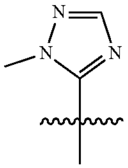 |
| 1-570 | Cl | 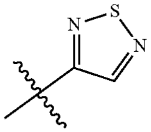 [SMILES: *c1cnsn1] | 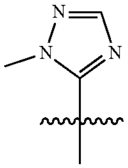 |
| 1-571 | Cl | 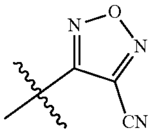 [SMILES: *c1nonc1C#N] | 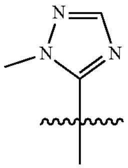 |
| 1-572 | Cl | 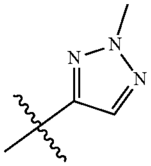 [SMILES: *c1cnn(C)n1] | 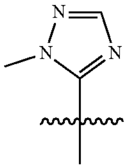 |
| 1-573 | Cl | 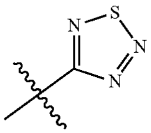 [SMILES: *c1nnsn1] | 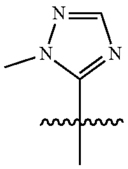 [SMILES: *c1ncnn1C] |

TABLE A1-continued
| | | | |
|---|---|---|---|
| 1-574 | Cl | 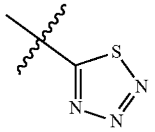 [SMILES: *c1nnns1] | 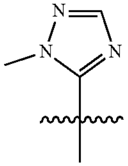 |
| 1-575 | Cl | 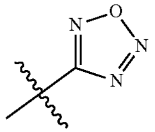 [SMILES: *c1nnon1] | 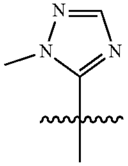 |
| 1-576 | Cl | 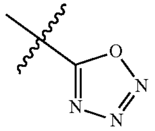 | 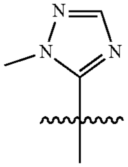 |
| 1-577 | Cl | 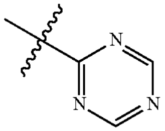 [SMILES: *c1ncncn1] | 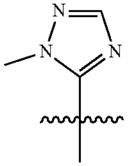 |
| 1-578 | Cl | 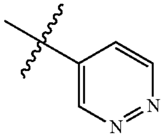 [SMILES: *c1ccnnc1] | 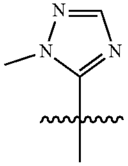 |
| 1-579 | Cl | 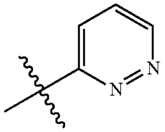 [SMILES: *c1cccnn1] | 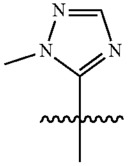 [SMILES: *c1ncnn1C] |

TABLE A1-continued
| | | | |
|---|---|---|---|
| 1-580 | Cl | 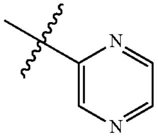 [SMILES: *c1cnccn1] | 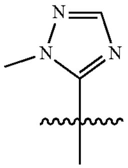 |
| 1-581 | Cl | 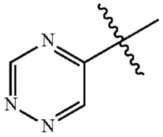 [SMILES: *c1cnncn1] | 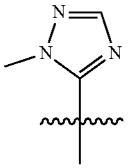 |
| 1-582 | Cl | 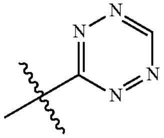 [SMILES: *c1nncnn1] | 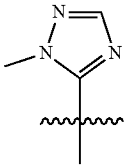 |
| 1-583 | Cl | 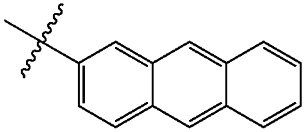 [SMILES: *c1ccc2cc3ccccc3cc2c1] | 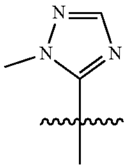 |
| 1-584 | Cl | 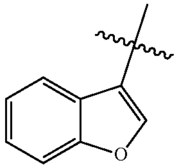 [SMILES: *c1coc2ccccc12] | 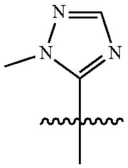 |
| 1-585 | Cl | 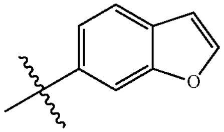 [SMILES: *c1ccc2ccoc2c1] | 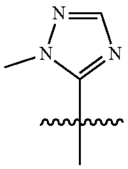 [SMILES: *c1ncnn1C] |

TABLE A1-continued
| | | | |
|---|---|---|---|
| 1-586 | Cl | 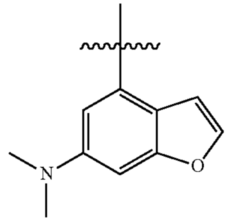 [SMILES: *c1cc(N(C)C)cc2occc12] | 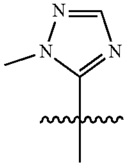 |
| 1-587 | Cl | 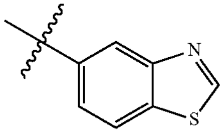 [SMILES: *c1ccc2scnc2c1] | 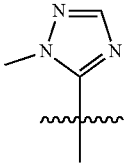 [SMILES: *c1ncnn1C] |
| 1-588 | Cl | 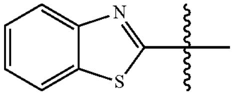 | 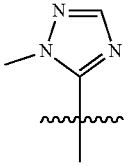 |
| 1-589 | Cl | 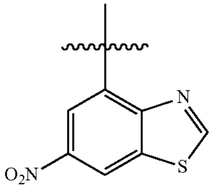 | 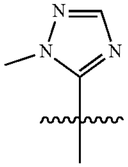 |
| 1-590 | Cl | 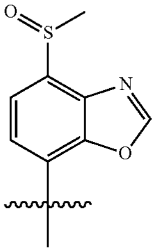 [SMILES: *c1ccc(S(C)=O)c2ncoc12] | 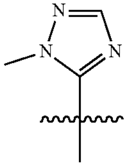 |

TABLE A1-continued
| | | | |
|---|---|---|---|
| 1-591 | Cl | 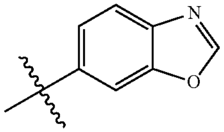 [SMILES: *c1ccc2ncoc2c1] | 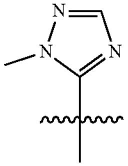 |
| 1-592 | Cl | 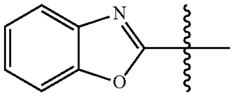 | 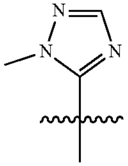 |
| 1-593 | Cl | 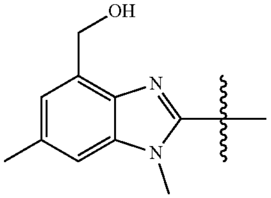 [SMILES: *c1nc2c(CO)cc(C)cc2n1C] | 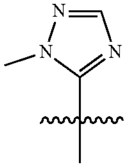 |
| 1-594 | Cl | 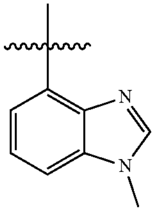 [SMILES: *c1cccc2c1ncn2C] | 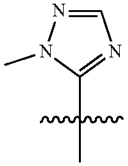 |
| 1-595 | Cl | 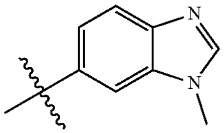 [SMILES: *c1ccc2ncn(C)c2c1] | 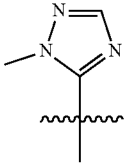 |

TABLE A1-continued
| | | | |
|---|---|---|---|
| 1-596 | Cl | 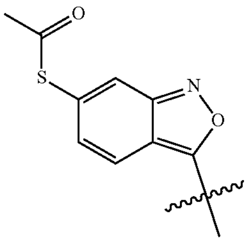 [SMILES: *c1onc2cc(SC(C)=O)ccc12] | 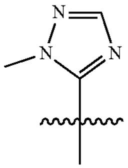 |
| 1-597 | Cl | 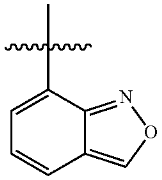 | 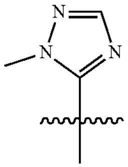 [SMILES: *c1ncnn1C] |
| 1-598 | Cl | 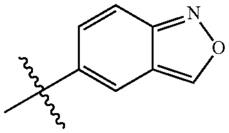 [SMILES: *c1ccc2nocc2c1] | 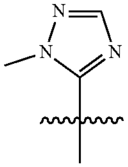 |
| 1-599 | Cl | 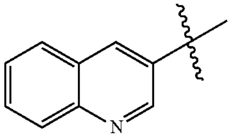 [SMILES: *c1cnc2ccccc2c1] | 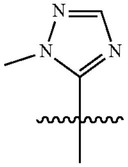 |
| 1-600 | Cl | 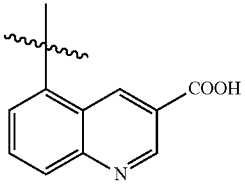 [SMILES: *c1cccc2ncc(C(=O)O)cc12] | 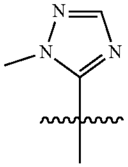 |

TABLE A1-continued
| | | | |
|---|---|---|---|
| 1-601 | Cl | 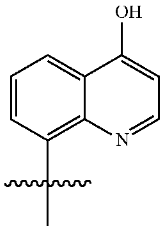 [SMILES: *c1cccc2c(O)ccnc12] | 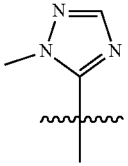 |
| 1-602 | Cl | 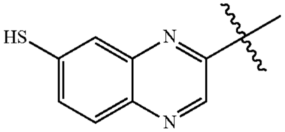 [SMILES: *c1cnc2ccc(S)cc2n1] | 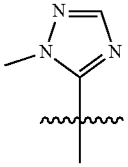 |
| 1-603 | Cl | 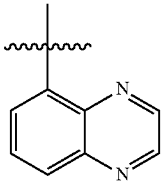 [SMILES: *c1cccc2nccnc12] | 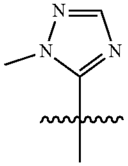 [SMILES: *c1ncnn1C] |
| 1-604 | Cl | 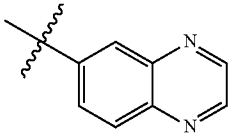 [SMILES: *c1ccc2nccnc2c1] | 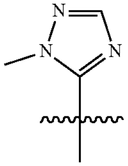 |
| 1-605 | Cl | 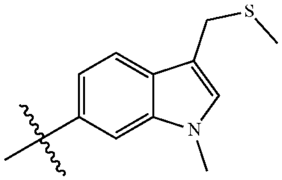 [SMILES: *c1ccc2c(CSC)cn(C)c2c1] | 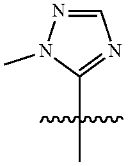 |

TABLE A1-continued
| | | | |
|---|---|---|---|
| 1-606 | Cl | 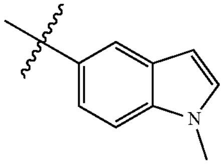 [SMILES: *c1ccc2c(ccn2C)c1] | 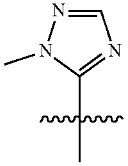 |
| 1-607 | Cl | 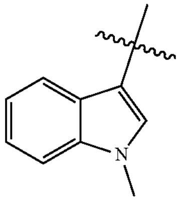 [SMILES: *c1cn(C)c2ccccc12] | 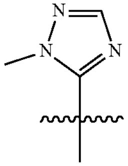 |
| 1-608 | Cl | 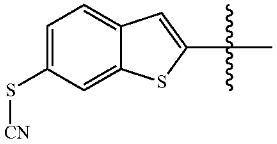 [SMILES: *c1cc2ccc(SC#N)cc2s1] | 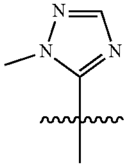 |
| 1-609 | Cl | 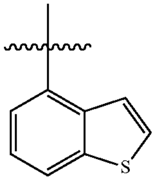 [SMILES: *c1cccc2sccc12] | 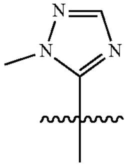 |
| 1-610 | Cl | 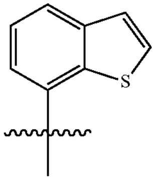 [SMILES: *c1cccc2ccsc12] | 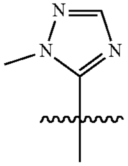 |

TABLE A1-continued
| | | | |
|---|---|---|---|
| 1-611 | Cl | 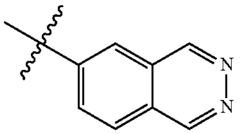 [SMILES: *c1ccc2cnncc2c1] | 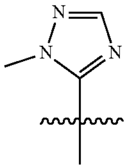 |
| 1-612 | Cl | 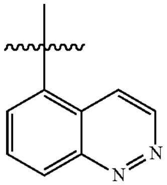 [SMILES: *c1cccc2nnccc12] | 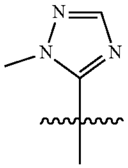 |
| 1-613 | Cl | 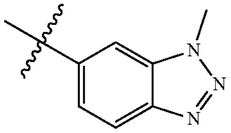 [SMILES: *c1ccc2nnn(C)c2c1] | 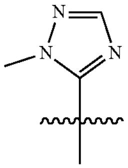 |
| 1-614 | Cl | 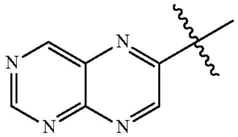 [SMILES: *c1cnc2ncncc2n1] | 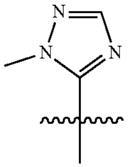 |
| 1-615 | Cl | 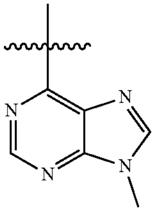 [SMILES: *c1ncnc2c1ncn2C] | 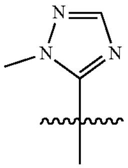 |

TABLE A1-continued
| | | | |
|---|---|---|---|
| 1-616 | Cl | 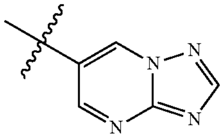 [SMILES: *c1cnc2ncnn2c1] | 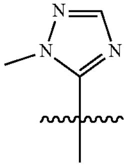 |
| 1-617 | Cl | 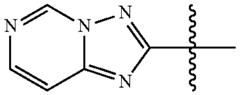 [SMILES: *c1nc2ccncn2n1] | 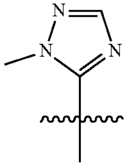 |
| 1-618 | Cl | 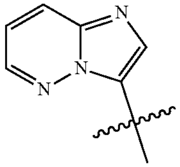 [SMILES: *c1cnc2cccnn12] | 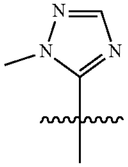 |
| 1-619 | Cl | 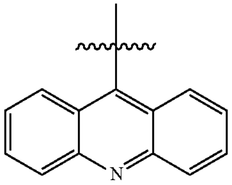 [SMILES: *c1c2ccccc2nc2ccccc12] | 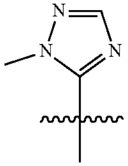 |
| 1-620 | Cl | 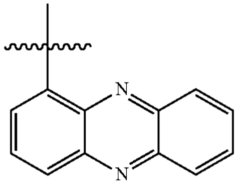 [SMILES: *c1cccc2nc3ccccc3nc12] | 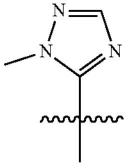 |

TABLE A1-continued
| | | | | |
|---|---|---|---|---|
| 1-621 | Cl | 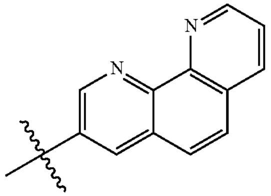 [SMILES: *c1cnc2c(ccc3cccnc32)c1] | 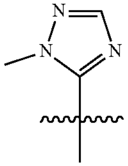 | |
| 1-622 | Cl | 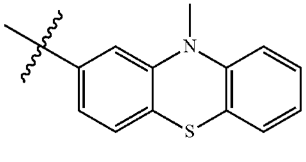 [SMILES: *c1ccc2c(c1)N(C)c1ccccc1S2] | 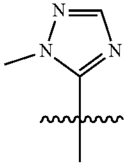 [SMILES: *c1ncnn1C] | |
| 1-623 | Cl | 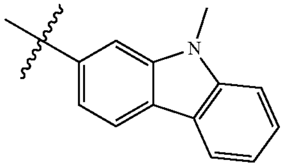 [SMILES: *c1ccc2c3ccccc3n(C)c2c1] | 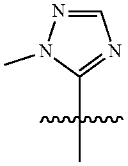 [SMILES: *c1ncnn1C] | |
| 1-624 | Cl | 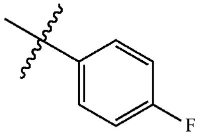 [SMILES: *c1ccc(F)cc1] | 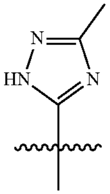 [SMILES: *c1nc(C)n[nH]1] | $^1$H NMR (500 MHz, DMSO-$d_6$) δ 12.16 (s, 1H), 10.08 (s, 1H), 8.68 (d, J = 5.0 Hz, 1H), 8.04-7.96 (m, 2H), 7.51 (d, J = 5.0 Hz, 1H), 7.35-7.27 (m, 2H), 2.45 (s, 3H). |
| 1-625 | Cl | 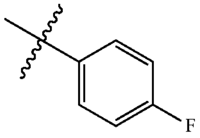 [SMILES: *c1ccc(F)cc1] | 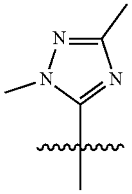 | |

TABLE A1-continued

| | | | | |
|---|---|---|---|---|
| 1-626 | Cl | 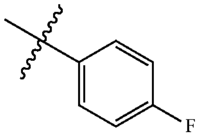 [SMILES: *c1ccc(F)cc1] | 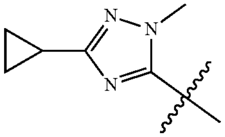 [SMILES: *c1nc(C2CC2)nn1C] | $^1$H NMR (500 MHz, DMSO-$d_6$) δ 12.11 (s, 1H), 8.95 (d, J = 5.0 Hz, 1H), 8.34-8.26 (m, 2H), 7.55 (d, J = 5.0 Hz, 1H), 7.35-7.27 (m, 2H), 3.61 (s, 3H), 2.18 (p, J = 7.0 Hz, 1H), 1.13 (m, 2H), 0.88 (m, 2H). |
| 1-627 | Cl | 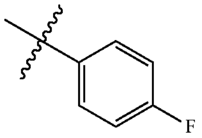 [SMILES: *c1ccc(F)cc1] | 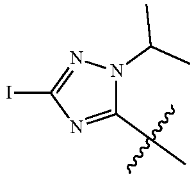 [SMILES: *c1nc(I)nn1C(C)C] | $^1$H NMR (500 MHz, DMSO-$d_6$) δ 12.06 (s, 1H), 8.95 (d, J = 5.0 Hz, 1H), 8.34-8.26 (m, 2H), 7.55 (d, J = 5.0 Hz, 1H), 7.35-7.27 (m, 2H), 4.46 (hept, J = 8.0 Hz, 1H), 1.65 (d, J = 8.0 Hz, 6H). |
| 1-628 | Cl | 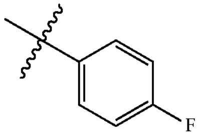 [SMILES: *c1ccc(F)cc1] | 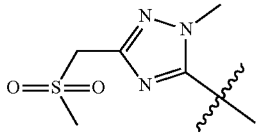 [SMILES: *c1nc(CS(C)(=O)=O)nn1C] | $^1$H NMR (500 MHz, DMSO-$d_6$) δ 12.08 (s, 1H), 8.69 (d, J = 5.0 Hz, 1H), 8.03-7.96 (m, 2H), 7.67 (d, J = 5.0 Hz, 1H), 7.35-7.27 (m, 2H), 4.32 (s, 2H), 3.94 (s, 3H), 2.99 (s, 3H). |
| 1-629 | Cl | 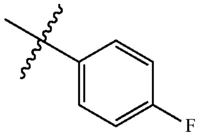 [SMILES: *c1ccc(F)cc1] | 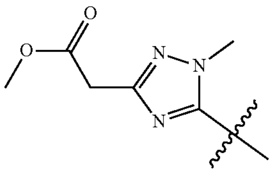 [SMILES: *c1nc(CC(=O)OC)nn1C] | $^1$H NMR (500 MHz, DMSO-$d_6$) δ 12.07 (s, 1H), 8.65 (d, J = 5.0 Hz, 1H), 8.08-8.00 (m, 2H), 7.46 (d, J = 5.0 Hz, 1H), 7.35-7.27 (m, 2H), 3.93 (s, 3H), 3.59 (s, 3H), 3.51 (s, 2H). |
| 1-630 | Cl | 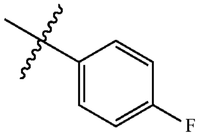 [SMILES: *c1ccc(F)cc1] | 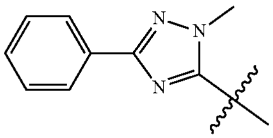 [SMILES: *c1nc(-c2ccccc2)nn1C] | $^1$H NMR (500 MHz, DMSO-$d_6$) δ 12.09 (s, 1H), 8.92 (d, J = 5.0 Hz, 1H), 8.11-8.02 (m, 4H), 7.65 (d, J = 5.0 Hz, 1H), 7.54-7.46 (m, 1H), 7.48-7.40 (m, 2H), 7.35-7.27 (m, 2H), 3.97 (s, 3H). |
| 1-631 | Cl | 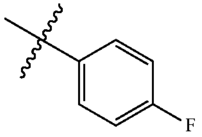 [SMILES: *c1ccc(F)cc1] | 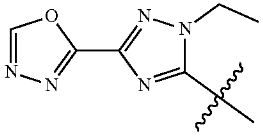 [SMILES: *c1nc(-c2nnco2)nn1CC] | $^1$H NMR (500 MHz, DMSO-$d_6$) δ 12.11 (s, 1H), 8.68 (d, J = 5.0 Hz, 1H), 8.04-7.96 (m, 2H), 7.89 (s, 1H), 7.65 (d, J = 5.0 Hz, 1H), 7.35-7.27 (m, 2H), 4.40 (q, J = 8.0 Hz, 2H), 1.49 (t, J = 8.0 Hz, 3H). |

TABLE A1-continued
| | | | | |
|---|---|---|---|---|
| 1-632 | Cl | 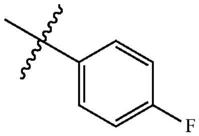 [SMILES: *c1ccc(F)cc1] | 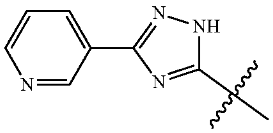 [SMILES: *c1nc(-c2cccnc2)n[nH]1] | $^1$H NMR (500 MHz, DMSO-$d_6$) δ 12.13 (s, 1H), 10.06 (s, 1H), 8.87 (d, J = 5.0 Hz, 1H), 8.70 (dd, J = 5.0, 2.0 Hz, 1H), 8.46-8.44 (m, 2H), 8.11-8.03 (m, 2H), 7.64 (d, J = 5.0 Hz, 1H), 7.57 (dd, J = 8.0, 2.0 Hz, 1H), 7.35-7.27 (m, 2H), . |
| 1-633 | Cl | 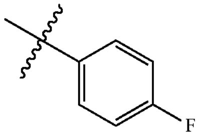 [SMILES: *c1ccc(F)cc1] | 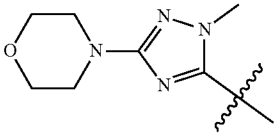 [SMILES: *c1nc(N2CCOCC2)nn1C] | $^1$H NMR (500 MHz, DMSO-$d_6$) δ 12.05 (s, 1H), 8.88 (d, J = 5.0 Hz, 1H), 8.08-8.00 (m, 2H), 7.63 (d, J = 5.0 Hz, 1H), 7.35-7.27 (m, 2H), 3.94 (s, 3H), 3.63 (t, J = 8.0 Hz, 4H), 3.36 (t, J = 8.0 Hz, 4H). |
| 1-634 | Cl | $CH_3$ | 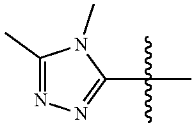 [SMILES: *c1nnc(C)n1C] | |
| 1-635 | Cl | 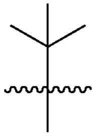 [SMILES: *C(C)(C)C] | 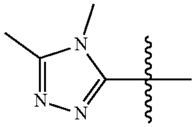 | |
| 1-636 | Cl | 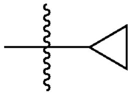 [SMILES: *C1CC1] | 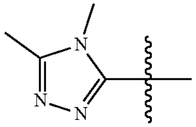 [SMILES: *c1nnc(C)n1C] | |
| 1-637 | Cl | 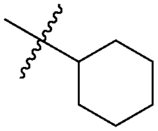 [SMILES: *C1CCCCC1] | 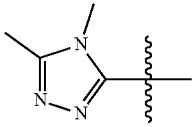 | |
| 1-638 | Cl | 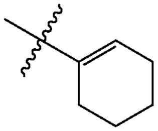 [SMILES: *C1=CCCCC1] | 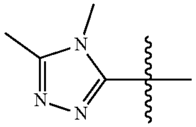 [SMILES: *c1nnc(C)n1C] | |

TABLE A1-continued
| | | | | |
|---|---|---|---|---|
| 1-639 | Cl | 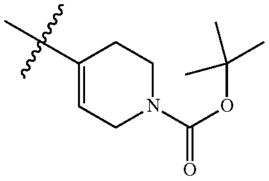 [SMILES: *C1=CCN(C(=O)OC(C)(C)C)CC1] | 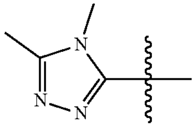 [SMILES: *c1nnc(C)n1C] | |
| 1-640 | Cl | 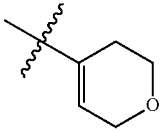 [SMILES: *C1=CCOCC1] | 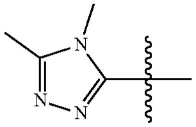 | $^1H$ NMR (500 MHz, DMSO-$d_6$) δ 12.12 (s, 1H), 8.74 (d, J = 5.0 Hz, 1H), 7.84 (d, J = 5.0 Hz, 1H), 6.26-6.19 (m, 1H), 4.23-4.17 (m, 2H), 3.86 (s, 3H), 3.79 (t, J = 5.0 Hz, 2H), 2.50 (s, 3H), 2.40 (t, J = 5.0, 2H). |
| 1-641 | Cl | 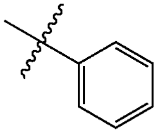 [SMILES: *c1ccccc1] | 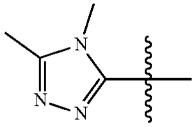 [SMILES: *c1nnc(C)n1C] | |
| 1-642 | Cl | 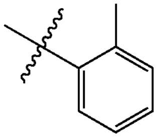 [SMILES: *c1ccccc1C] | 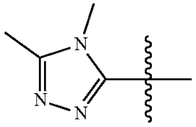 | |
| 1-643 | Cl | 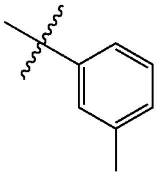 [SMILES: *c1cccc(C)c1] | 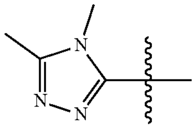 | |
| 1-644 | Cl | 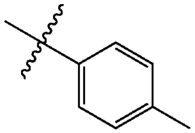 [SMILES: *c1ccc(C)cc1] | 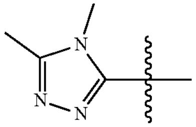 | |

TABLE A1-continued
| | | | | |
|---|---|---|---|---|
| 1-645 | Cl | 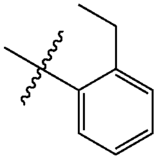 [SMILES: *c1ccccc1CC] | 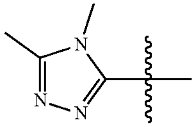 [SMILES: *c1nnc(C)n1C] | |
| 1-646 | Cl | 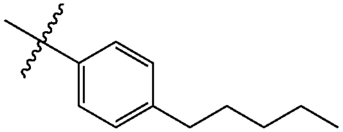 [SMILES: *c1ccc(CCCCC)cc1] | 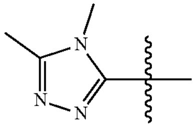 | |
| 1-647 | Cl | 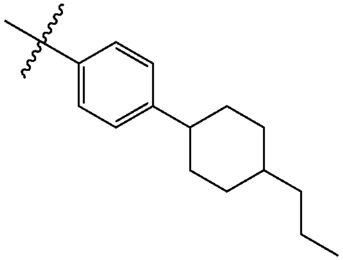 [SMILES: *c1ccc(C2CCC(CCC)CC2)cc1] | 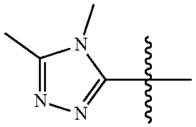 [SMILES: *c1nnc(C)n1C] | |
| 1-648 | Cl | 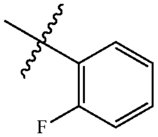 [SMILES: *c1ccccc1F] | 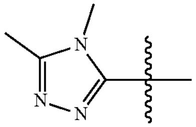 [SMILES: *c1nnc(C)n1C] | |
| 1-649 | Cl | 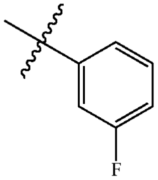 [SMILES: *c1cccc(F)c1] | 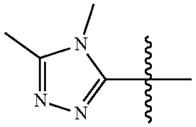 | |
| 1-650 | Cl | 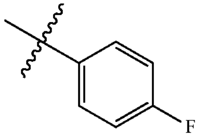 [SMILES: *c1ccc(F)cc1] | 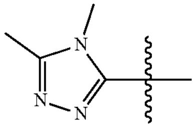 [SMILES: *c1nnc(C)n1C] | $^{1}$H NMR (500 MHz, DMSO-$d_6$) δ 12.12 (s, 1H), 8.68 (d, J = 5.0 Hz, 1H), 8.05-7.97 (m, 2H), 7.53 (d, J = 5.0 Hz, 1H), 7.35-7.27 (m, 2H), 3.88 (s, 3H), 2.50 (s, 3H). |

TABLE A1-continued
| | | | |
|---|---|---|---|
| 1-651 | Cl | 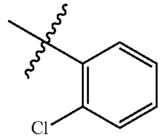 | 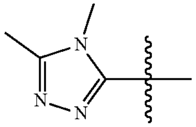 [SMILES: *c1nnc(C)n1C] |
| 1-652 | Cl | 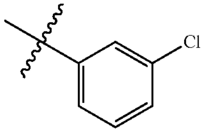 [SMILES: *c1cccc(Cl)c1] | 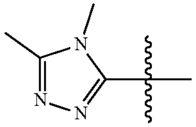 |
| 1-653 | Cl | 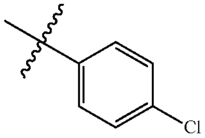 [SMILES: *c1ccc(Cl)cc1] | 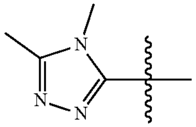 [SMILES: *c1nnc(C)n1C] |
| 1-654 | Cl | 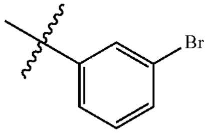 [SMILES: *c1cccc(Br)c1] | 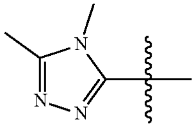 |
| 1-655 | Cl | 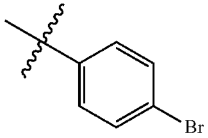 [SMILES: *c1ccc(Br)cc1] | 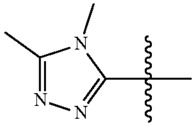 |
| 1-656 | Cl | 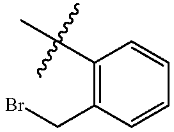 | 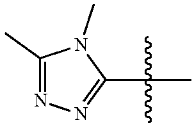 [SMILES: *c1nnc(C)n1C] |
| 1-657 | Cl | 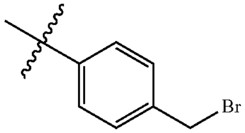 [SMILES: *c1ccc(CBr)cc1] | 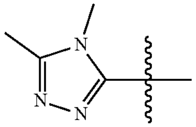 [SMILES: *c1nnc(C)n1C] |

TABLE A1-continued
| | | | |
|---|---|---|---|
| 1-658 | Cl | 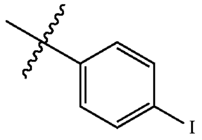 [SMILES: *c1ccc(I)cc1] | 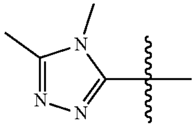 [SMILES: *c1nnc(C)n1C] |
| 1-659 | Cl | 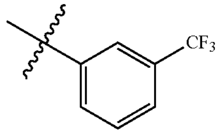 [SMILES: *c1cccc(C(F)(F)F)c1] | 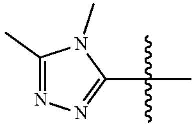 |
| 1-660 | Cl | 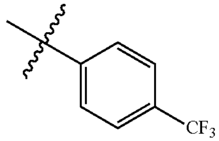 | 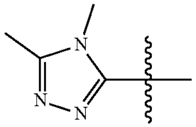 [SMILES: *c1nnc(C)n1C] |
| 1-661 | Cl | 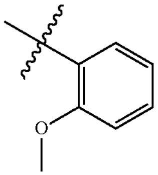 [SMILES: *c1ccccc1OC] | 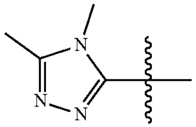 |
| 1-662 | Cl | 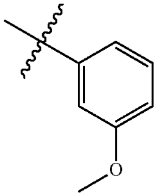 [SMILES: *c1cccc(OC)c1] | 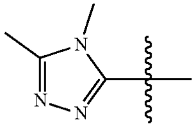 [SMILES: *c1nnc(C)n1C] |
| 1-663 | Cl | 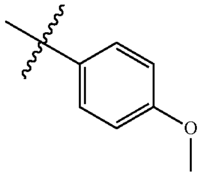 [SMILES: *c1ccc(OC)cc1] | 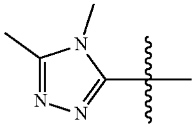 |

TABLE A1-continued
| | | | |
|---|---|---|---|
| 1-664 | Cl | 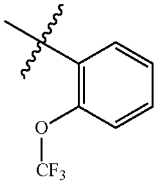 | 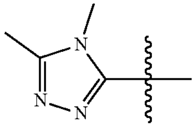 [SMILES: *c1nnc(C)n1C] |
| 1-665 | Cl | 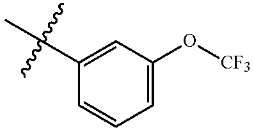 [SMILES: *c1cccc(OC(F)(F)F)c1] | 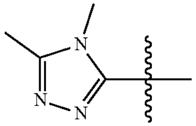 |
| 1-666 | Cl | 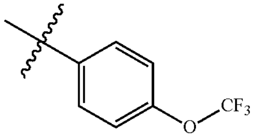 [SMILES: *c1ccc(OC(F)(F)F)cc1] | 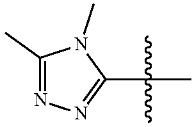 [SMILES: *c1nnc(C)n1C] |
| 1-667 | Cl | 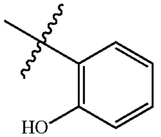 [SMILES: *c1ccccc1O] | 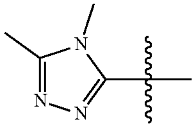 |
| 1-668 | Cl | 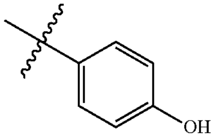 | 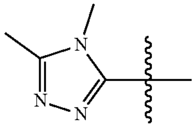 [SMILES: *c1nnc(C)n1C] |
| 1-669 | Cl | 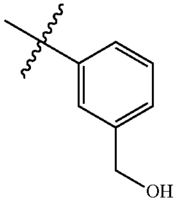 [SMILES: *c1cccc(CO)c1] | 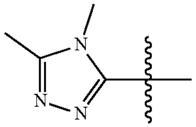 [SMILES: *c1nnc(C)n1C] |

TABLE A1-continued
| | | | |
|---|---|---|---|
| 1-670 | Cl | 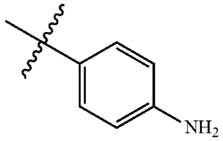 | 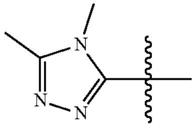 [SMILES: *c1nnc(C)n1C] |
| 1-671 | Cl | 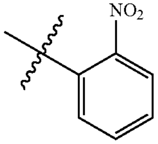 [SMILES: *c1ccccc1[N+](=O)[O-]] | 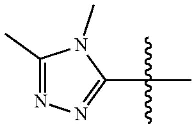 |
| 1-672 | Cl | 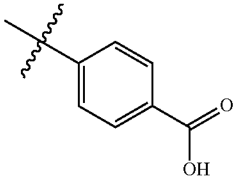 [SMILES: *c1ccc(C(=O)O)cc1] | 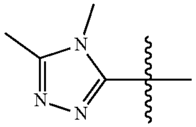 [SMILES: *c1nnc(C)n1C] |
| 1-673 | Cl | 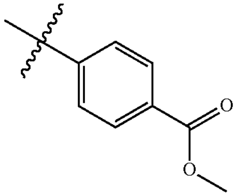 [SMILES: *c1ccc(C(=O)OC)cc1] | 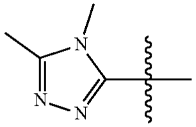 [SMILES: *c1nnc(C)n1C] |
| 1-674 | Cl | 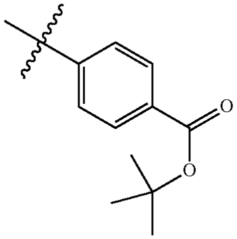 [SMILES: *c1ccc(C(=O)OC(C)(C)C)cc1] | 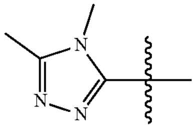 |

TABLE A1-continued
| | | | |
|---|---|---|---|
| 1-675 | Cl | 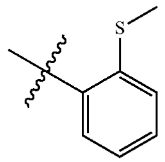 [SMILES: *c1ccccc1SC] | 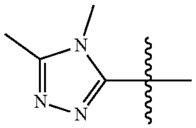 |
| 1-676 | Cl | 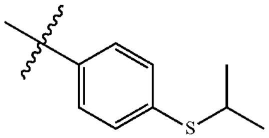 [SMILES: *c1ccc(SC(C)C)cc1] | 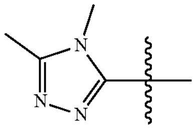 |
| 1-677 | Cl | 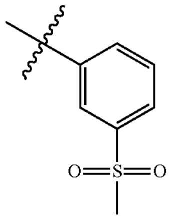 [SMILES: *c1cccc(S(C)(=O)=O)c1] | 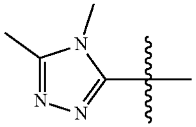 |
| 1-678 | Cl | 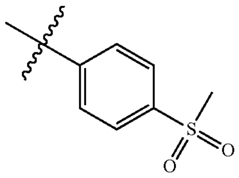 [SMILES: *c1ccc(S(C)(=O)=O)cc1] | 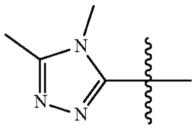 [SMILES: *c1nnc(C)n1C] |
| 1-679 | Cl | 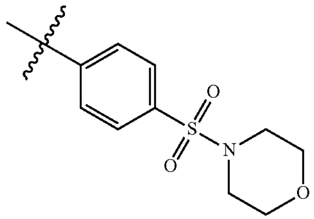 [SMILES: *c1ccc(S(=O)(=O)N2CCOCC2)cc1] | 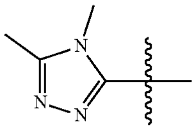 |

TABLE A1-continued
| | | | |
|---|---|---|---|
| 1-680 | Cl | 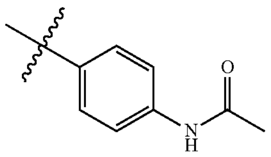 [SMILES: *c1ccc(NC(C)=O)cc1] | 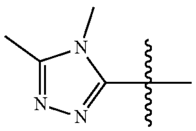 |
| 1-681 | Cl | 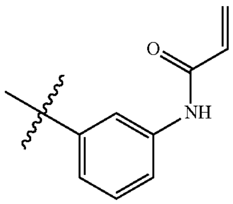 [SMILES: *c1cccc(NC(=O)C=C)c1] | 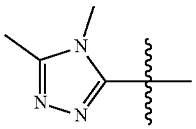 |
| 1-682 | Cl | 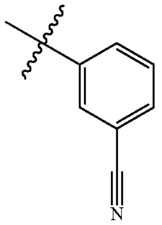 [SMILES: *c1cccc(C#N)c1] | 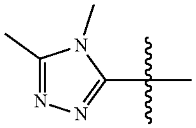 |
| 1-683 | Cl | 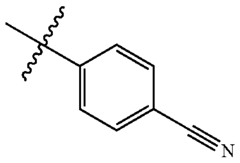 [SMILES: *c1ccc(C#N)cc1] | 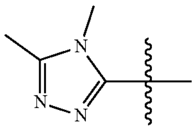 |
| 1-684 | Cl | 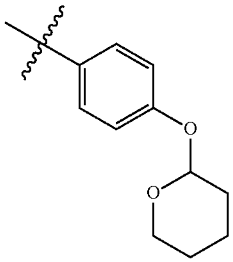 [SMILES: *c1ccc(OC2CCCCO2)cc1] | 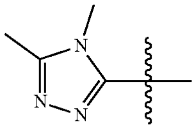 [SMILES: *c1nnc(C)n1C] |

TABLE A1-continued
| | | | |
|---|---|---|---|
| 1-685 | Cl | 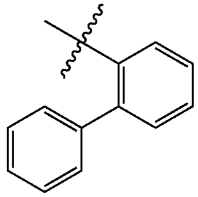 [SMILES: *c1ccccc1-c1ccccc1] | 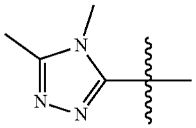 |
| 1-686 | Cl | 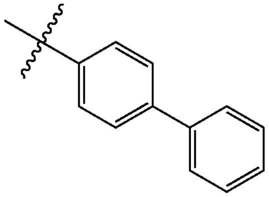 [SMILES: *c1ccc(-c2ccccc2)cc1] | 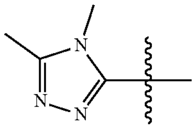 |
| 1-687 | Cl | 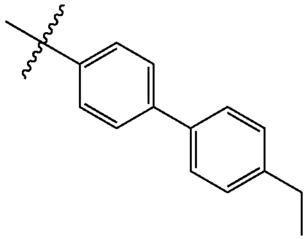 [SMILES: *c1ccc(-c2ccc(CC)cc2)cc1] | 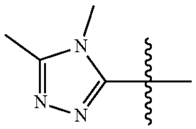 |
| 1-688 | Cl | 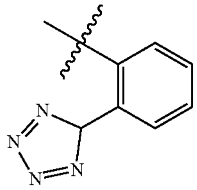 [SMILES: *c1ccccc1C1N=NN=N1] | 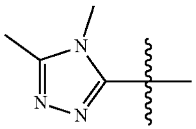 |
| 1-689 | Cl | 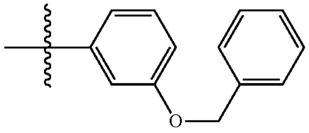 [SMILES: *c1cccc(OCc2ccccc2)c1] | 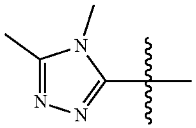 [SMILES: *c1nnc(C)n1C] |

TABLE A1-continued
| | | | |
|---|---|---|---|
| 1-690 | Cl | 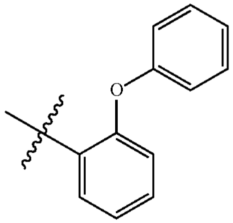 [SMILES: *c1ccccc1Oc1ccccc1] | 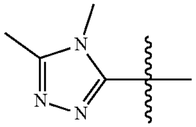 |
| 1-691 | Cl | 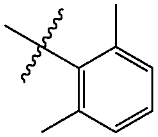 [SMILES: *c1c(C)cccc1C] | 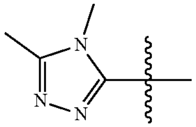 [SMILES: *c1nnc(C)n1C] |
| 1-692 | Cl | 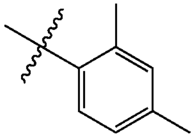 [SMILES: *c1ccc(C)cc1C] | 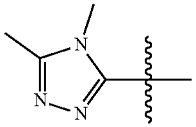 |
| 1-693 | Cl | 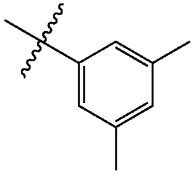 [SMILES: *c1cc(C)cc(C)c1] | 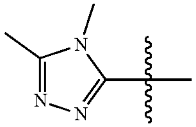 [SMILES: *c1nnc(C)n1C] |
| 1-694 | Cl | 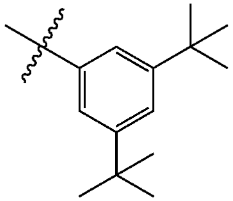 [SMILES: *c1cc(C(C)(C)C)cc(C(C)(C)C)c1] | 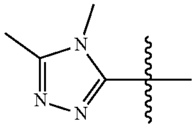 |

TABLE A1-continued
| | | | |
|---|---|---|---|
| 1-695 | Cl | 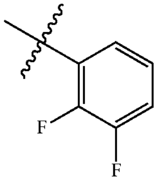 [SMILES: *c1cccc(F)c1F] | 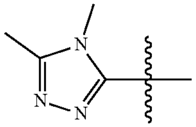 |
| 1-696 | Cl | 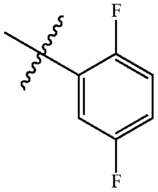 | 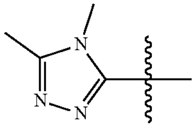 |
| 1-697 | Cl | 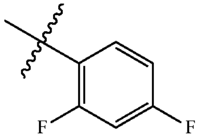 [SMILES: *c1ccc(F)cc1F] | 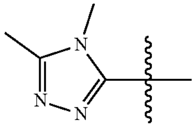 [SMILES: *c1nnc(C)n1C] |
| 1-698 | Cl | 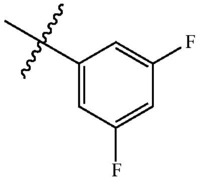 [SMILES: *c1cc(F)cc(F)c1] | 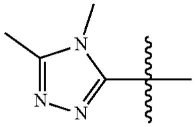 |
| 1-699 | Cl | 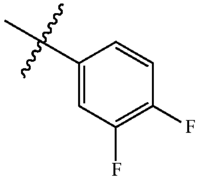 [SMILES: *c1ccc(F)c(F)c1] | 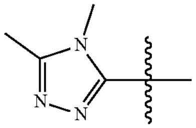 |

TABLE A1-continued
| | | | |
|---|---|---|---|
| 1-700 | Cl | 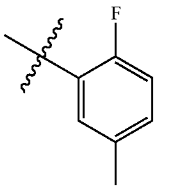 [SMILES: *c1cc(C)ccc1F] | 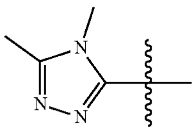 |
| 1-701 | Cl | 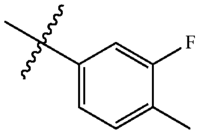 [SMILES: *c1ccc(C)c(F)c1] | 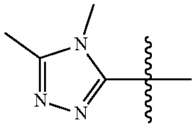 |
| 1-702 | Cl | 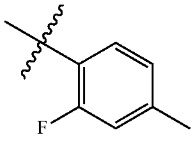 [SMILES: *c1ccc(C)cc1F] | 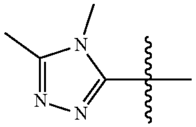 |
| 1-703 | Cl | 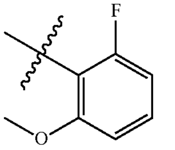 [SMILES: *c1c(F)cccc1OC] | 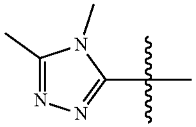 |
| 1-704 | Cl | 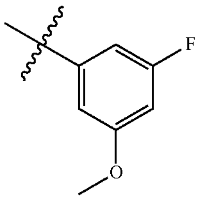 [SMILES: *c1cc(F)cc(OC)c1] | 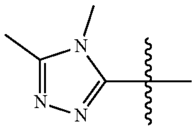 |
| 1-705 | Cl | 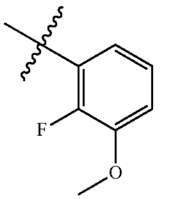 [SMILES: *c1cccc(OC)c1F] | 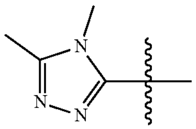 |

TABLE A1-continued
| | | | |
|---|---|---|---|
| 1-706 | Cl | 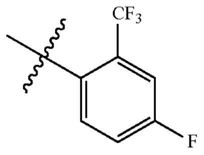 | 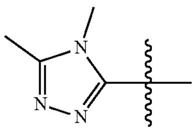 |
| 1-707 | Cl | 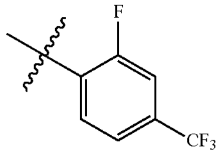 | 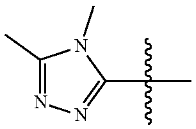 [SMILES: *c1nnc(C)n1C] |
| 1-708 | Cl | 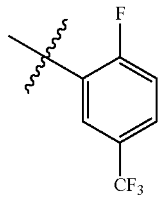 | 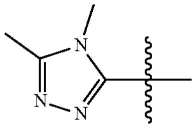 |
| 1-709 | Cl | 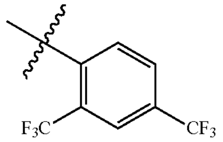 | 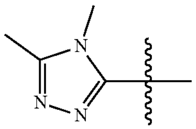 |
| 1-710 | Cl | 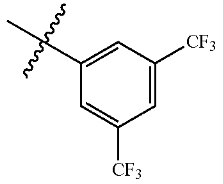 | 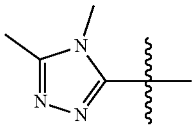 [SMILES: *c1nnc(C)n1C] |
| 1-711 | Cl | 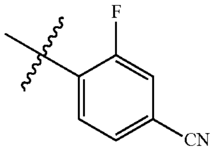 [SMILES: *c1ccc(C#N)cc1F] | 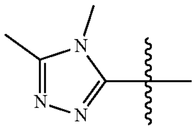 |

TABLE A1-continued
| | | | |
|---|---|---|---|
| 1-712 | Cl | 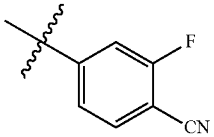 [SMILES: *c1ccc(C#N)c(F)c1] | 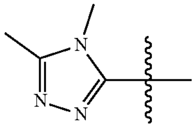 [SMILES: *c1nnc(C)n1C] |
| 1-713 | Cl | 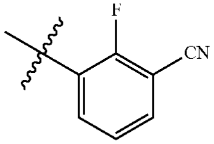 [SMILES: *c1cccc(C#N)c1F] | 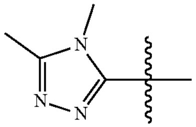 [SMILES: *c1nnc(C)n1C] |
| 1-714 | Cl | 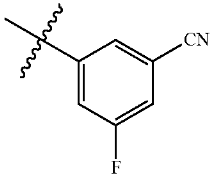 [SMILES: *c1cc(F)cc(C#N)c1] | 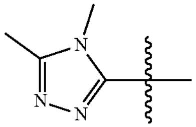 |
| 1-715 | Cl | 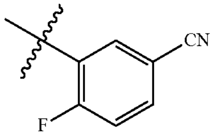 [SMILES: *c1cc(C#N)ccc1F] | 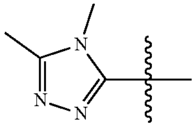 [SMILES: *c1nnc(C)n1C] |
| 1-716 | Cl | 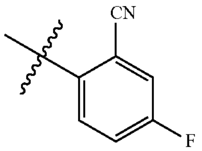 | 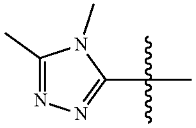 [SMILES: *c1nnc(C)n1C] |
| 1-717 | Cl | 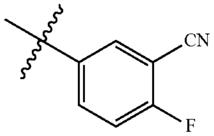 [SMILES: *c1ccc(F)c(C#N)c1] | 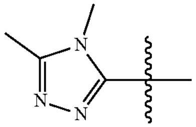 [SMILES: *c1nnc(C)n1C] |

TABLE A1-continued
| | | | |
|---|---|---|---|
| 1-718 | Cl | 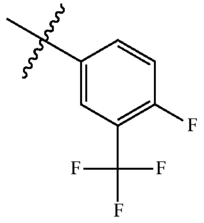 [SMILES: *c1ccc(F)c(C(F)(F)F)c1] | 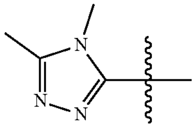 [SMILES: *c1nnc(C)n1C] |
| 1-719 | Cl | 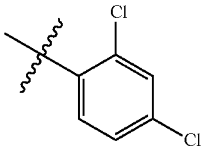 [SMILES: *c1ccc(Cl)cc1Cl] | 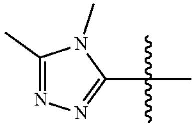 |
| 1-720 | Cl | 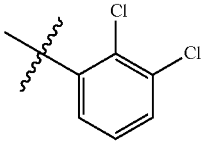 | 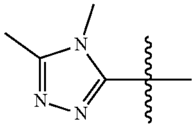 [SMILES: *c1nnc(C)n1C] |
| 1-721 | Cl | 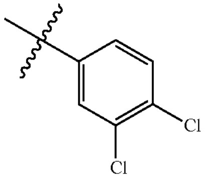 [SMILES: *c1ccc(Cl)c(Cl)c1] | 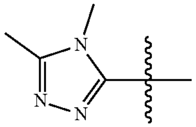 [SMILES: *c1nnc(C)n1C] |
| 1-722 | Cl | 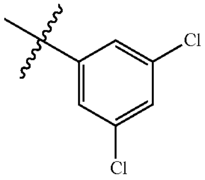 [SMILES: *c1cc(Cl)cc(Cl)c1] | 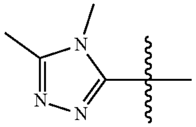 [SMILES: *c1nnc(C)n1C] |

TABLE A1-continued
| | | | |
|---|---|---|---|
| 1-723 | Cl | 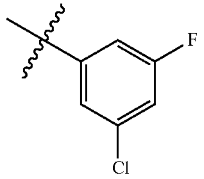 [SMILES: *c1cc(F)cc(Cl)c1] | 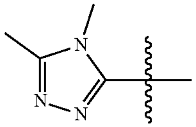 [SMILES: *c1nnc(C)n1C] |
| 1-724 | Cl | 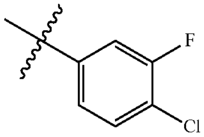 [SMILES: *c1ccc(Cl)c(F)c1] | 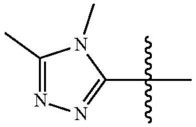 [SMILES: *c1nnc(C)n1C] |
| 1-725 | Cl | 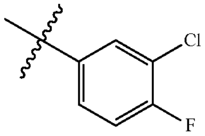 [SMILES: *c1ccc(F)c(Cl)c1] | 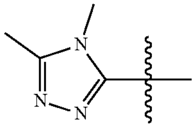 [SMILES: *c1nnc(C)n1C] |
| 1-726 | Cl | 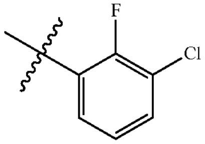 [SMILES: *c1cccc(Cl)c1F] | 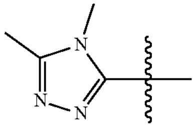 [SMILES: *c1nnc(C)n1C] |
| 1-727 | Cl | 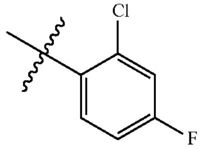 [SMILES: *c1ccc(F)cc1Cl] | 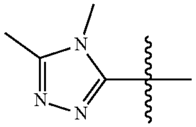 |
| 1-728 | Cl | 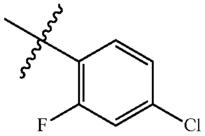 [SMILES: *c1ccc(Cl)cc1F] | 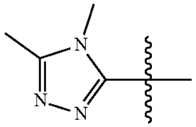 [SMILES: *c1nnc(C)n1C] |

TABLE A1-continued
| | | | |
|---|---|---|---|
| 1-729 | Cl | 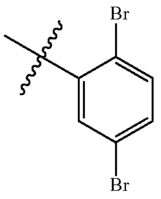 | 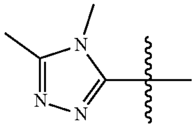 [SMILES: *c1nnc(C)n1C] |
| 1-730 | Cl | 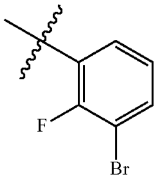 | 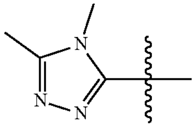 [SMILES: *c1nnc(C)n1C] |
| 1-731 | Cl | 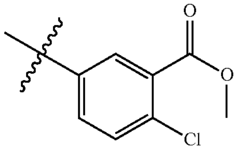 [SMILES: *c1ccc(Cl)c(C(=O)OC)c1] | 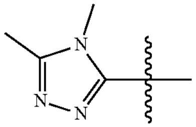 [SMILES: *c1nnc(C)n1C] |
| 1-732 | Cl | 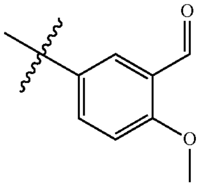 | 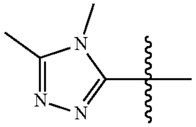 [SMILES: *c1nnc(C)n1C] |
| 1-733 | Cl | 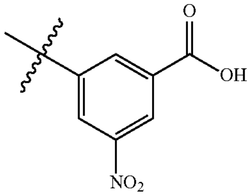 | 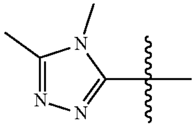 [SMILES: *c1nnc(C)n1C] |

TABLE A1-continued
| | | | |
|---|---|---|---|
| 1-734 | Cl | 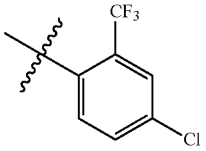 | 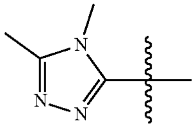 [SMILES: *c1nnc(C)n1C] |
| 1-735 | Cl | 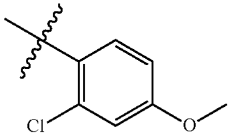 [SMILES: *c1ccc(OC)cc1Cl] | 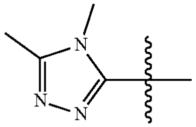 [SMILES: *c1nnc(C)n1C] |
| 1-736 | Cl | 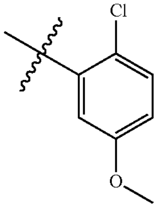 [SMILES: *c1cc(OC)ccc1Cl] | 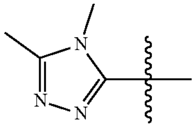 [SMILES: *c1nnc(C)n1C] |
| 1-737 | Cl | 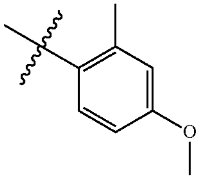 [SMILES: *c1ccc(OC)cc1C] | 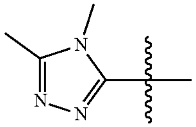 [SMILES: *c1nnc(C)n1C] |
| 1-738 | Cl | 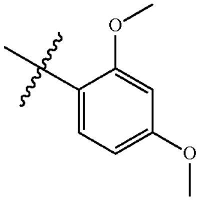 [SMILES: *c1ccc(OC)cc1OC] | 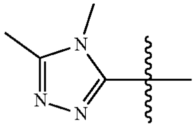 [SMILES: *c1nnc(C)n1C] |

TABLE A1-continued
| | | | |
|---|---|---|---|
| 1-739 | Cl | 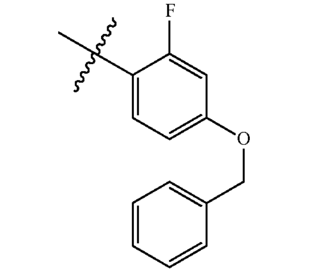 [SMILES: *c1ccc(OCc2ccccc2)cc1F] | 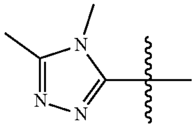 [SMILES: *c1nnc(C)n1C] |
| 1-740 | Cl | 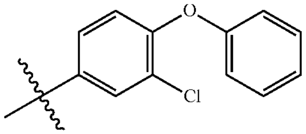 [SMILES: *c1ccc(Oc2ccccc2)c(Cl)c1] | 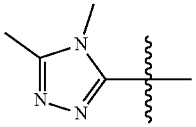 |
| 1-741 | Cl | 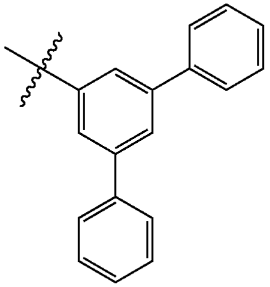 [SMILES: *c1cc(-c2ccccc2)cc(-c2ccccc2)c1] | 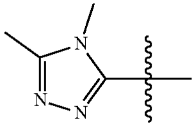 [SMILES: *c1nnc(C)n1C] |
| 1-742 | Cl | 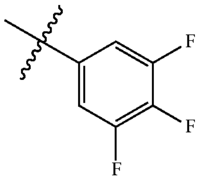 [SMILES: *c1cc(F)c(F)c(F)c1] | 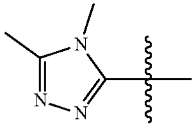 [SMILES: *c1nnc(C)n1C] |
| 1-743 | Cl | 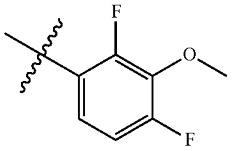 | 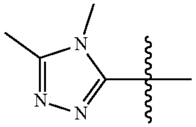 [SMILES: *c1nnc(C)n1C] |

TABLE A1-continued
| | | | | |
|---|---|---|---|---|
| 1-744 | Cl | 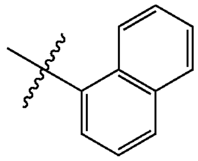 [SMILES: *c1cccc2ccccc12] | 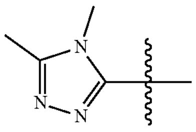 [SMILES: *c1nnc(C)n1C] | |
| 1-745 | Cl | 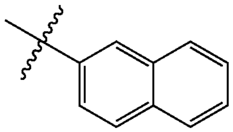 [SMILES: *c1ccc2ccccc2c1] | 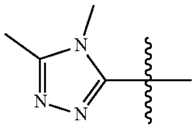 [SMILES: *c1nnc(C)n1C] | $^1$H NMR (500 MHz, DMSO-$d_6$) δ 12.09 (s, 1H), 8.98 (d, J = 5.0 Hz, 1H), 8.35 (dd, J = 7.5, 2.0 Hz, 1H), 8.13-8.10 (m, 2H), 8.04 (dt, J = 7.5, 2.0 Hz, 1H), 7.94-7.85 (m, 2H), 7.59 (td, J = 7.5, 2.0 Hz, 1H), 7.52 (td, J = 7.5, 2.00 Hz, 1H), 3.88 (s, 3H), 2.51 (s, 3H). |
| 1-746 | Cl | 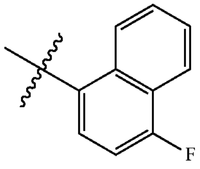 [SMILES: *c1ccc(F)c2ccccc12] | 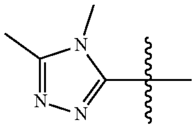 [SMILES: *c1nnc(C)n1C] | |
| 1-747 | Cl | 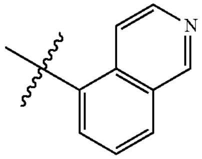 [SMILES: *c1cccc2cnccc12] | 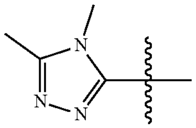 [SMILES: *c1nnc(C)n1C] | $^1$H NMR (500 MHz, DMSO-$d_6$) δ 12.08 (s, 1H), 9.28 (s, 1H), 8.93 (d, J = 5.0 Hz, 1H), 8.60 (d, J = 5.5 Hz, 1H), 8.20-8.17 (m, 2H), 7.89-7.78 (m, 3H), 3.87 (s, 3H), 2.51 (s, 3H). |
| 1-748 | Cl | 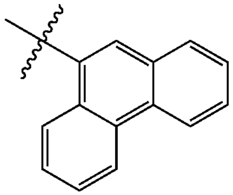 [SMILES: *c1cc2ccccc2c2ccccc12] | 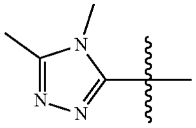 | $^1$H NMR (500 MHz, DMSO-$d_6$) δ 12.07 (s, 1H), 8.93-8.86 (m, 2H), 8.78 (dd, J = 8.0, 2.5 Hz, 1H), 8.38 (s, 1H), 8.05-7.94 (m, 2H), 7.83 (d, J = 5.0 Hz, 1H), 7.74-7.60 (m, 4H), 3.88 (s, 3H), 2.51 (s, 3H). |
| 1-749 | Cl | 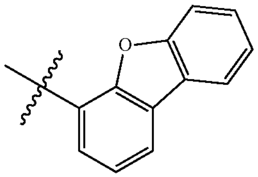 [SMILES: *c1cccc2c1oc1ccccc12] | 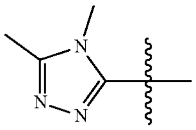 [SMILES: *c1nnc(C)n1C] | |

TABLE A1-continued
| | | | | |
|---|---|---|---|---|
| 1-750 | Cl | 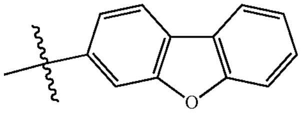 | 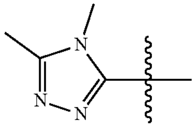 [SMILES: *c1nnc(C)n1C] | $^1$H NMR (500 MHz, DMSO-$d_6$) δ 12.08 (s, 1H), 8.97 (d, J = 5.0 Hz, 1H), 8.21 (dd, J = 7.5, 2.0 Hz, 1H), 8.05-8.03 (m, 2H), 7.85 (d, J = 5.0 Hz, 1H), 7.66-7.58 (m, 2H), 7.44 (td, J = 7.5, 2.0 Hz, 1H), 7.35 (td, J = 7.5, 2.0 Hz, 1H), 3.88 (s, 3H), 2.52 (s, 3H). |
| 1-751 | Cl | 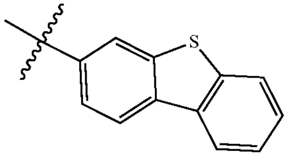 [SMILES: *c1ccc2c(c1)sc1ccccc12] | 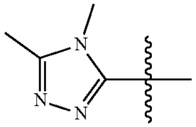 | |
| 1-752 | Cl | 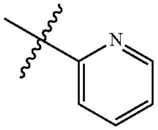 [SMILES: *c1ccccn1] | 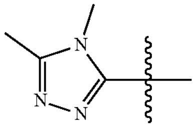 | |
| 1-753 | Cl | 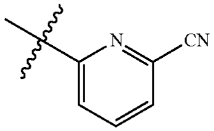 [SMILES: *c1cccc(C#N)n1] | 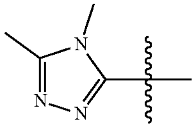 [SMILES: *c1nnc(C)n1C] | |
| 1-754 | Cl | 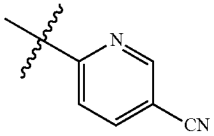 [SMILES: *c1ccc(C#N)cn1] | 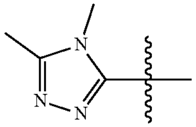 [SMILES: *c1nnc(C)n1C] | |
| 1-755 | Cl | 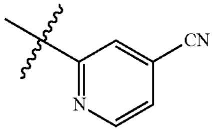 [SMILES: *c1cc(C#N)ccn1] | 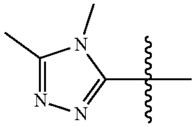 [SMILES: *c1nnc(C)n1C] | |
| 1-756 | Cl | 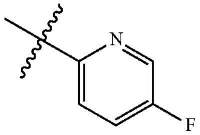 [SMILES: *c1ccc(F)cn1] | 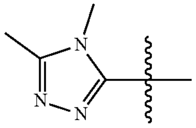 [SMILES: *c1nnc(C)n1C] | |

TABLE A1-continued
| | | | | |
|---|---|---|---|---|
| 1-757 | Cl | 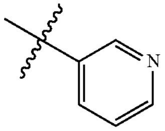 [SMILES: *c1cccnc1] | 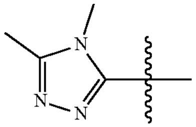 [SMILES: *c1nnc(C)n1C] | |
| 1-758 | Cl | 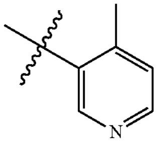 [SMILES: *c1cnccc1C] | 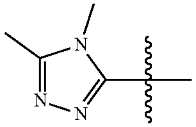 [SMILES: *c1nnc(C)n1C] | $^1H$ NMR (500 MHz, DMSO-$d_6$) δ 12.11 (s, 1H), 8.91 (s, 1H), 8.83 (d, J = 5.0 Hz, 1H), 8.45 (d, J = 5.0 Hz, 1H), 7.87 (d, J = 5.0 Hz, 1H), 7.43 (d, J = 5.0 Hz, 1H), 3.87 (s, 3H), 2.50 (s, 3H), 2.48 (s, 3H). |
| 1-759 | Cl | 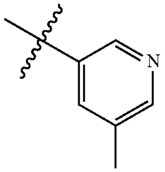 [SMILES: *c1cncc(C)c1] | 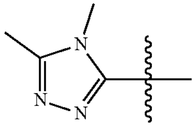 | |
| 1-760 | Cl | 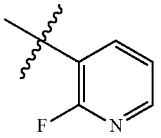 [SMILES: *c1cccnc1F] | 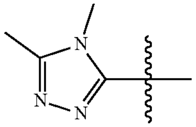 [SMILES: *c1nnc(C)n1C] | |
| 1-761 | Cl | 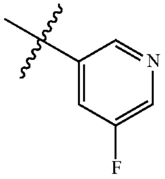 [SMILES: *c1cncc(F)c1] | 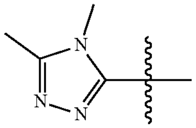 [SMILES: *c1nnc(C)n1C] | |
| 1-762 | Cl | 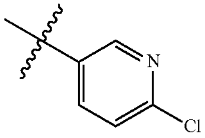 [SMILES: *c1ccc(Cl)nc1] | 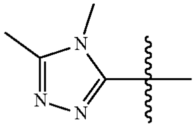 [SMILES: *c1nnc(C)n1C] | |

TABLE A1-continued
| | | | |
|---|---|---|---|
| 1-763 | Cl | 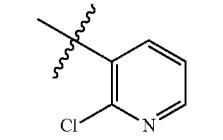 | 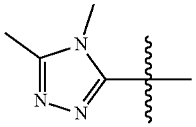 |
| 1-764 | Cl | 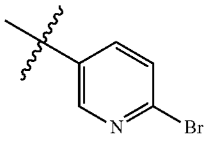 [SMILES: *c1ccc(Br)nc1] | 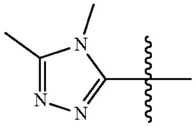 |
| 1-765 | Cl | 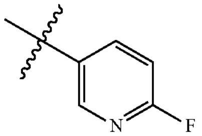 [SMILES: *c1ccc(F)nc1] | 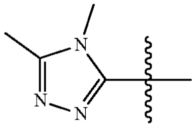 |
| 1-766 | Cl | 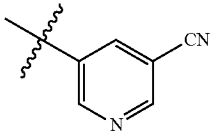 [SMILES: *c1cncc(C#N)c1] | 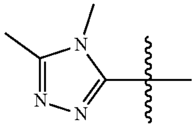 [SMILES: *c1nnc(C)n1C] |
| 1-767 | Cl | 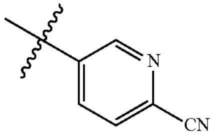 [SMILES: *c1ccc(C#N)nc1] | 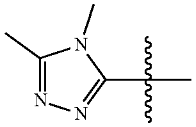 [SMILES: *c1nnc(C)n1C] |
| 1-768 | Cl | 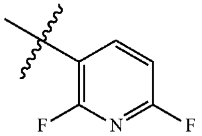 | 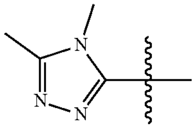 [SMILES: *c1nnc(C)n1C] |
| 1-769 | Cl | 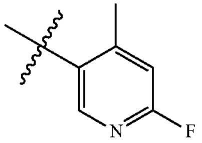 [SMILES: *c1cnc(F)cc1C] | 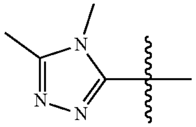 [SMILES: *c1nnc(C)n1C] |

TABLE A1-continued
| | | | |
|---|---|---|---|
| 1-770 | Cl | 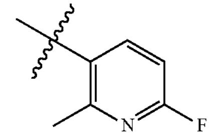 | 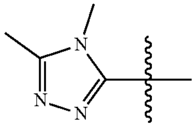 [SMILES: *c1nnc(C)n1C] |
| 1-771 | Cl | 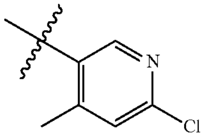 [SMILES: *c1cnc(Cl)cc1C] | 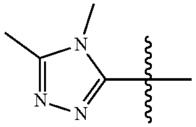 [SMILES: *c1nnc(C)n1C] |
| 1-772 | Cl | 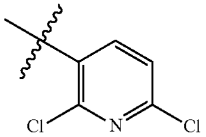 [SMILES: *c1ccc(Cl)nc1Cl] | 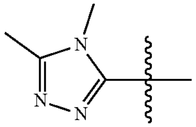 [SMILES: *c1nnc(C)n1C] |
| 1-773 | Cl | 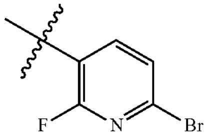 [SMILES: *c1ccc(Br)nc1F] | 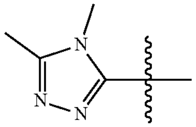 |
| 1-774 | Cl | 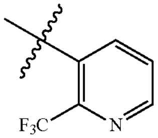 | 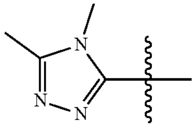 [SMILES: *c1nnc(C)n1C] |
| 1-775 | Cl | 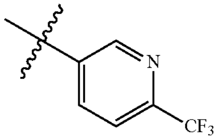 | 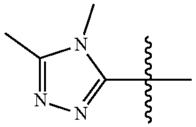 [SMILES: *c1nnc(C)n1C] |
| 1-776 | Cl | 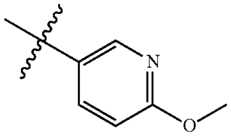 [SMILES: *c1ccc(OC)nc1] | 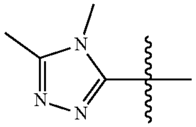 [SMILES: *c1nnc(C)n1C] |

TABLE A1-continued
| | | | |
|---|---|---|---|
| 1-777 | Cl | 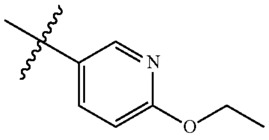 [SMILES: *c1ccc(OCC)nc1] | 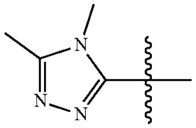 |
| 1-778 | Cl | 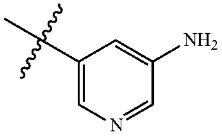 [SMILES: *c1cncc(N)c1] | 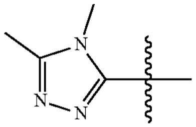 [SMILES: *c1nnc(C)n1C] |
| 1-779 | Cl | 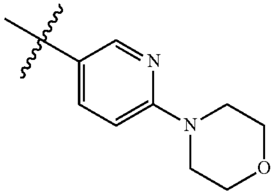 [SMILES: *c1ccc(N2CCOCC2)nc1] | 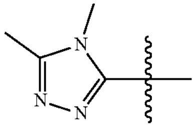 |
| 1-780 | Cl | 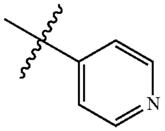 | 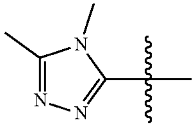 [SMILES: *c1nnc(C)n1C] |
| 1-781 | Cl | 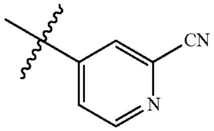 | 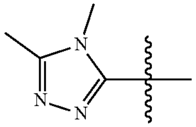 [SMILES: *c1nnc(C)n1C] |
| 1-782 | Cl | 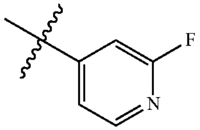 [SMILES: *c1ccnc(F)c1] | 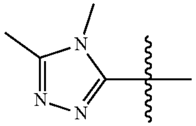 |
| 1-783 | Cl | 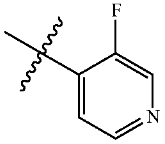 [SMILES: *c1ccncc1F] | 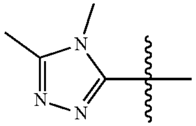 [SMILES: *c1nnc(C)n1C] |

TABLE A1-continued
| | | | |
|---|---|---|---|
| 1-784 | Cl | 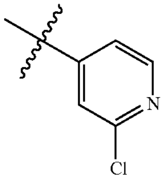 [SMILES: *c1ccnc(Cl)c1] | 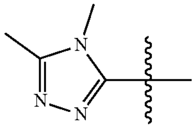 [SMILES: *c1nnc(C)n1C] |
| 1-785 | Cl | 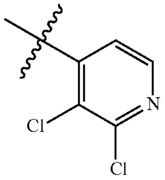 [SMILES: *c1ccnc(Cl)c1Cl] | 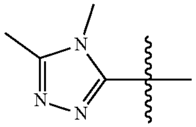 [SMILES: *c1nnc(C)n1C] |
| 1-786 | Cl | 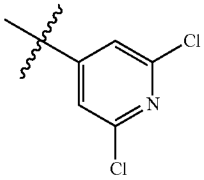 [SMILES: *c1cc(Cl)nc(Cl)c1] | 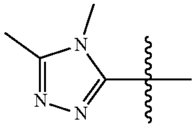 [SMILES: *c1nnc(C)n1C] |
| 1-787 | Cl | 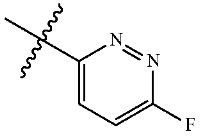 [SMILES: *c1ccc(F)nn1] | 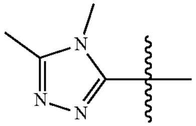 |
| 1-788 | Cl | 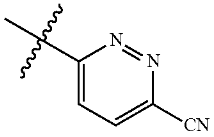 [SMILES: *c1ccc(C#N)nn1] | 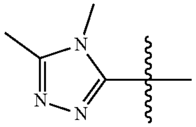 [SMILES: *c1nnc(C)n1C] |
| 1-789 | Cl | 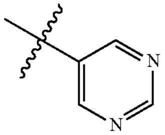 [SMILES: *c1cncnc1] | 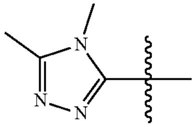 [SMILES: *c1nnc(C)n1C] |

TABLE A1-continued
| | | | |
|---|---|---|---|
| 1-790 | Cl | 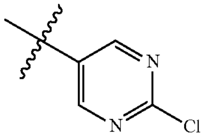 [SMILES: *c1cnc(Cl)nc1] | 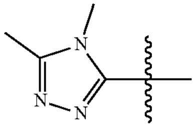 [SMILES: *c1nnc(C)n1C] |
| 1-791 | Cl | 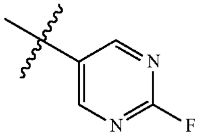 [SMILES: *c1cnc(F)nc1] | 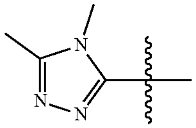 |
| 1-792 | Cl | 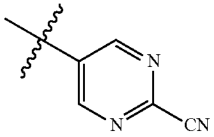 [SMILES: *c1cnc(C#N)nc1] | 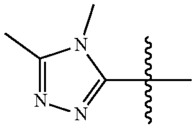 [SMILES: *c1nnc(C)n1C] |
| 1-793 | Cl | 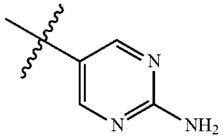 | 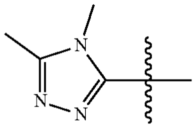 |
| 1-794 | Cl | 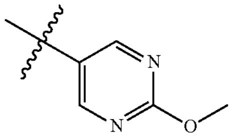 [SMILES: *c1cnc(OC)nc1] | 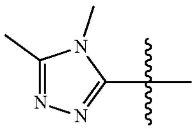 [SMILES: *c1nnc(C)n1C] |
| 1-795 | Cl | 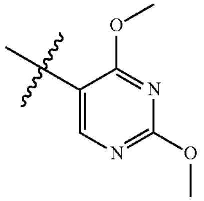 [SMILES: *c1cnc(OC)nc1OC] | 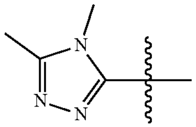 [SMILES: *c1nnc(C)n1C] |

TABLE A1-continued
| | | | | |
|---|---|---|---|---|
| 1-796 | Cl | 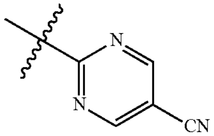 | 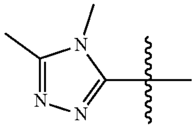 [SMILES: *c1nnc(C)n1C] | |
| 1-797 | Cl | 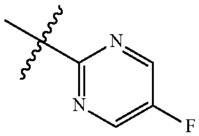 | 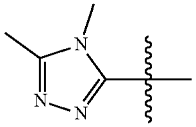 [SMILES: *c1nnc(C)n1C] | |
| 1-798 | Cl | 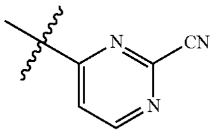 [SMILES: *c1ccnc(C#N)n1] | 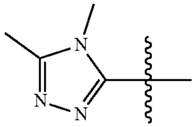 [SMILES: *c1nnc(C)n1C] | |
| 1-799 | Cl | 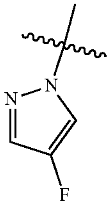 [SMILES: *n1cc(F)cn1] | 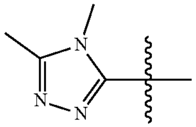 [SMILES: *c1nnc(C)n1C] | |
| 1-800 | Cl | 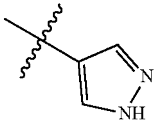 [SMILES: *c1cn[nH]c1] | 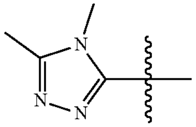 [SMILES: *c1nnc(C)n1C] | |
| 1-801 | Cl | 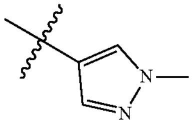 [SMILES: *c1cnn(C)c1] | 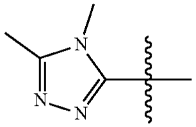 [SMILES: *c1nnc(C)n1C] | $^1$H NMR (500 MHz, DMSO-$d_6$) δ 12.05 (s, 1H), 8.96 (d, J = 5.0 Hz, 1H), 7.94 (d, J = 5.0 Hz, 1H), 7.80 (s, 1H), 6.97 (s, 1H), 3.92 (s, 3H), 3.87 (s, 3H), 2.51 (s, 3H). |
| 1-802 | Cl | 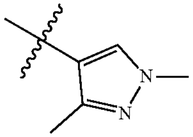 [SMILES: *c1cn(C)nc1C] | 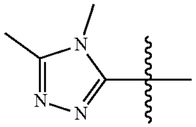 [SMILES: *c1nnc(C)n1C] | |

TABLE A1-continued
| | | | |
|---|---|---|---|
| 1-803 | Cl | 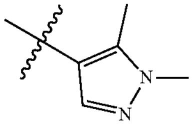 [SMILES: *c1cnn(C)c1C] | 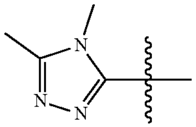 [SMILES: *c1nnc(C)n1C] |
| 1-804 | Cl | 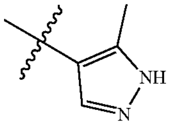 [SMILES: *c1cn[nH]c1C] | 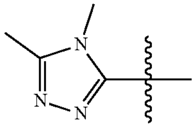 [SMILES: *c1nnc(C)n1C] |
| 1-805 | Cl | 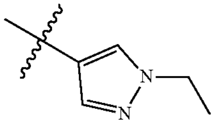 [SMILES: *c1cnn(CC)c1] | 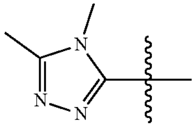 |
| 1-806 | Cl | 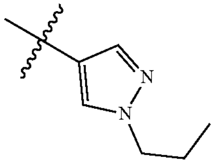 [SMILES: *c1cnn(CCC)c1] | 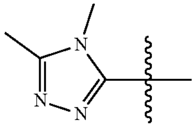 [SMILES: *c1nnc(C)n1C] |
| 1-807 | Cl | 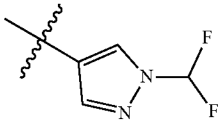 | 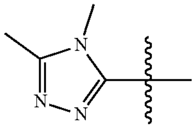 [SMILES: *c1nnc(C)n1C] |
| 1-808 | Cl | 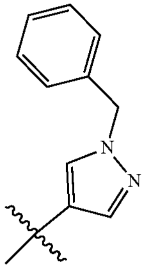 [SMILES: *c1cnn(Cc2ccccc2)c1] | 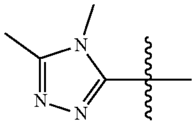 [SMILES: *c1nnc(C)n1C] |

TABLE A1-continued
| | | | |
|---|---|---|---|
| 1-809 | Cl | 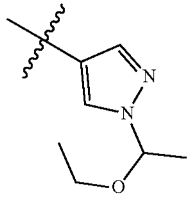 [SMILES: *c1cnn(C(C)OCC)c1] | 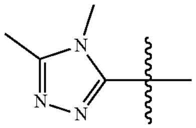 [SMILES: *c1nnc(C)n1C] |
| 1-810 | Cl | 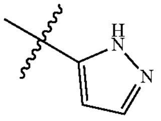 [SMILES: *c1ccn[nH]1] | 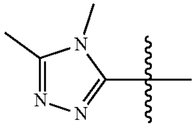 |
| 1-811 | Cl | 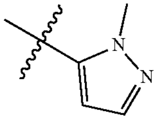 [SMILES: *c1ccnn1C] | 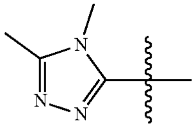 [SMILES: *c1nnc(C)n1C] |
| 1-812 | Cl | 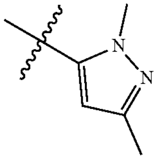 [SMILES: *c1cc(C)nn1C] | 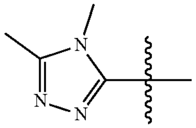 |
| 1-813 | Cl | 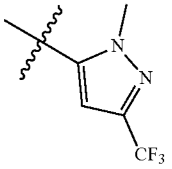 | 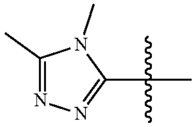 [SMILES: *c1nnc(C)n1C] |
| 1-814 | Cl | 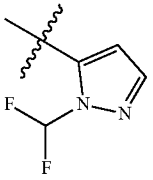 [SMILES: *c1ccnn1C(F)F] | 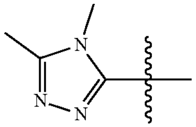 [SMILES: *c1nnc(C)n1C] |

TABLE A1-continued
| | | | | |
|---|---|---|---|---|
| 1-815 | Cl | 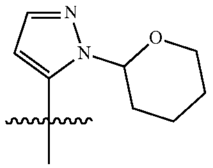 [SMILES: *c1ccnn1C1CCCCO1] | 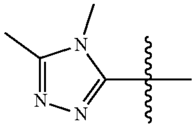 [SMILES: *c1nnc(C)n1C] | |
| 1-816 | Cl | 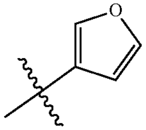 [SMILES: *c1ccoc1] | 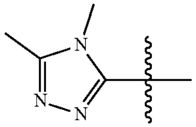 [SMILES: *c1nnc(C)n1C] | |
| 1-817 | Cl | 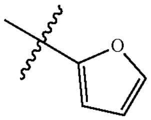 [SMILES: *c1ccco1] | 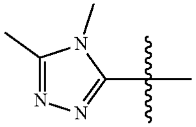 [SMILES: *c1nnc(C)n1C] | $^1$H NMR (500 MHz, DMSO-$d_6$) δ 12.11 (s, 1H), 8.95 (d, J = 5.0 Hz, 1H), 8.07 (d, J = 2.0 Hz, 1H), 7.94 (d, J = 5.0 Hz, 1H), 7.26 (d, J = 2.0 Hz, 1H), 6.98 (t, J = 2.0 Hz, 1H), 3.86 (s, 3H), 2.51 (s, 3H). |
| 1-818 | Cl | 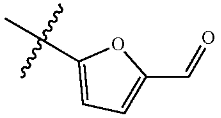 [SMILES: *c1ccc(C=O)o1] | 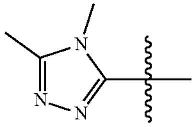 [SMILES: *c1nnc(C)n1C] | |
| 1-819 | Cl | 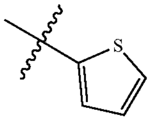 [SMILES: *c1cccs1] | 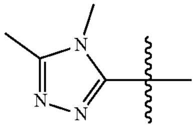 [SMILES: *c1nnc(C)n1C] | $^1$H NMR (500 MHz, DMSO-$d_6$) δ 12.23 (s, 1H), 8.98 (d, J = 5.0 Hz, 1H), 7.98 (d, J = 5.0 Hz, 1H), 7.58 (d, J = 2.0 Hz, 1H), 7.47 (d, J = 2.0 Hz, 1H), 7.15 (t, J = 2.0 Hz, 1H), 3.86 (s, 3H), 2.51 (s, 3H). |
| 1-820 | Cl | 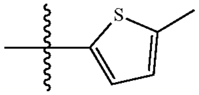 [SMILES: *c1ccc(C)s1] | 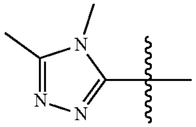 [SMILES: *c1nnc(C)n1C] | |
| 1-821 | Cl | 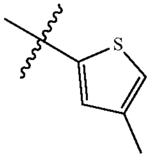 [SMILES: *c1cc(C)cs1] | 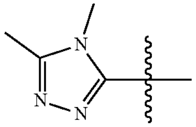 | |

TABLE A1-continued
| | | | |
|---|---|---|---|
| 1-822 | Cl | 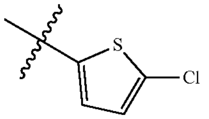 [SMILES: *c1ccc(Cl)s1] | 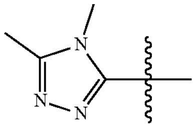 [SMILES: *c1nnc(C)n1C] |
| 1-823 | Cl | 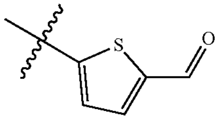 [SMILES: *c1ccc(C=O)s1] | 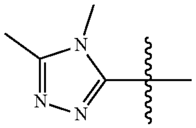 [SMILES: *c1nnc(C)n1C] |
| 1-824 | Cl | 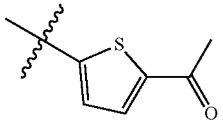 [SMILES: *c1ccc(C(C)=O)s1] | 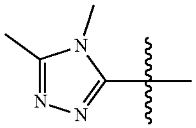 [SMILES: *c1nnc(C)n1C] |
| 1-825 | Cl | 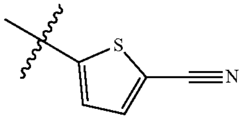 [SMILES: *c1ccc(C#N)s1] | 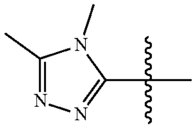 [SMILES: *c1nnc(C)n1C] |
| 1-826 | Cl | 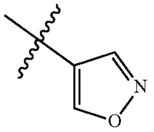 | 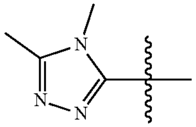 [SMILES: *c1nnc(C)n1C] |
| 1-827 | $CH_3$ | 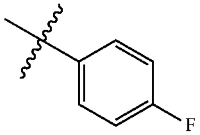 | 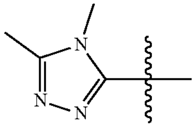 [SMILES: *c1nnc(C)n1C] |
| 1-828 | F | 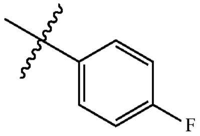 [SMILES: *c1ccc(F)cc1] | 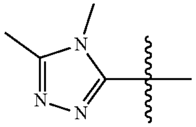 [SMILES: *c1nnc(C)n1C] |

TABLE A1-continued
| | | | | |
|---|---|---|---|---|
| 1-829 | Br | 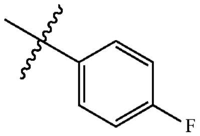 [SMILES: *c1ccc(F)cc1] | 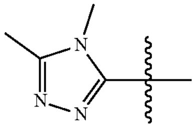 [SMILES: *c1nnc(C)n1C] | |
| 1-830 | 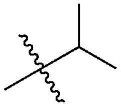 [SMILES: *C(C)C] | 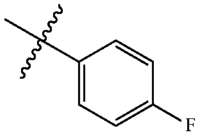 [SMILES: *c1ccc(F)cc1] | 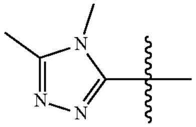 [SMILES: *c1nnc(C)n1C] | $^1$H NMR (500 MHz, DMSO-$d_6$) δ 12.11 (s, 1H), 8.57 (d, J = 5.0 Hz, 1H), 7.95-7.87 (m, 2H), 7.37 (d, J = 5.0 Hz, 1H), 7.35-7.27 (m, 2H), 3.87 (s, 3H), 2.85 (hept, J = 7.0 Hz, 1H), 2.50 (s, 3H), 1.11 (d, J = 7.0 Hz, 6H). |
| 1-831 | $CF_3$ | 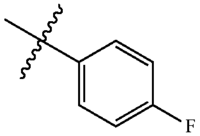 | 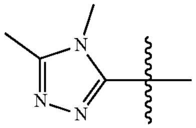 | $^1$H NMR (500 MHz, DMSO-$d_6$) δ 12.09 (s, 1H), 8.75 (d, J = 5.0 Hz, 1H), 8.05-7.97 (m, 2H), 7.58 (d, J = 5.0 Hz, 1H), 7.35-7.27 (m, 2H), 3.89 (s, 3H), 2.51 (s, 3H). |
| 1-832 | 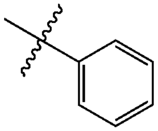 [SMILES: *c1ccccc1] | 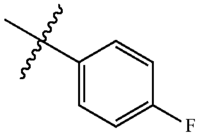 [SMILES: *c1ccc(F)cc1] | 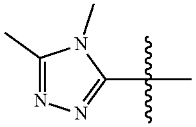 [SMILES: *c1nnc(C)n1C] | |
| 1-833 | 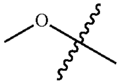 [SMILES: *OC] | 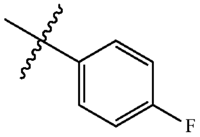 [SMILES: *c1ccc(F)cc1] | 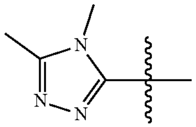 [SMILES: *c1nnc(C)n1C] | |
| 1-834 | 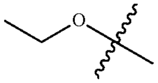 [SMILES: *OCC] | 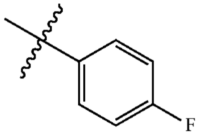 [SMILES: *c1ccc(F)cc1] | 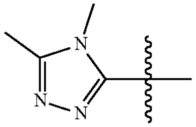 [SMILES: *c1nnc(C)n1C] | $^1$H NMR (500 MHz, DMSO-$d_6$) δ 12.33 (s, 1H), 8.59 (d, J = 5.0 Hz, 1H), 8.10-8.02 (m, 2H), 7.94 (d, J = 5.0 Hz, 1H), 7.35-7.27 (m, 2H), 4.10 (q, J = 8.0 Hz, 2H), 3.88 (s, 3H), 2.51 (s, 3H), 1.34 (t, J = 8.0 Hz, 3H). |
| 1-835 | 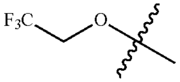 | 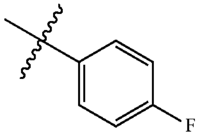 | 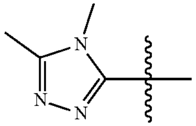 [SMILES: *c1nnc(C)n1C] | |

TABLE A1-continued
| | | | | |
|---|---|---|---|---|
| 1-836 | 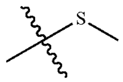 [SMILES: *SC] | 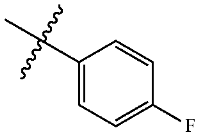 | 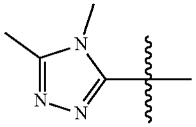 [SMILES: *c1nnc(C)n1C] | |
| 1-837 | 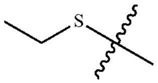 | 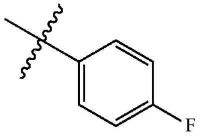 | 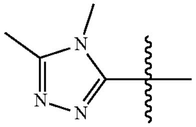 [SMILES: *c1nnc(C)n1C] | $^1$H NMR (500 MHz, DMSO-$d_6$) δ 12.06 (s, 1H), 8.56 (d, J = 5.0 Hz, 1H), 8.05-7.98 (m, 2H), 7.47 (d, J = 5.0 Hz, 1H), 7.35-7.27 (m, 2H), 3.88 (s, 3H), 3.00 (q, J = 8.0 Hz, 2H), 2.50 (s, 3H), 1.19 (t, J = 8.0 Hz, 3H). |
| 1-838 | 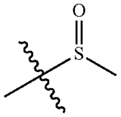 [SMILES: *S(C)=O] | 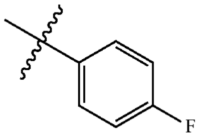 [SMILES: *c1ccc(F)cc1] | 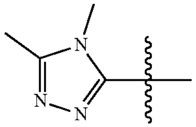 [SMILES: *c1nnc(C)n1C] | |
| 1-839 | 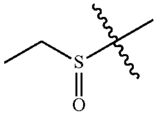 [SMILES: *S(=O)CC] | 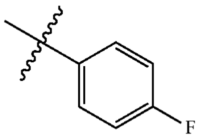 [SMILES: *c1ccc(F)cc1] | 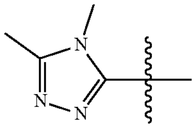 [SMILES: *c1nnc(C)n1C] | $^1$H NMR (500 MHz, DMSO-$d_6$) δ 12.08 (s, 1H), 8.83 (d, J = 5.0 Hz, 1H), 8.05-7.97 (m, 2H), 7.56 (d, J = 5.0 Hz, 1H), 7.35-7.27 (m, 2H), 3.87 (s, 3H), 2.61-2.59 (m, 1H), 2.57-2.55 (m, 1H) 2.50 (s, 3H), 1.20 (t, J = 8.0 Hz, 3H). |
| 1-840 | 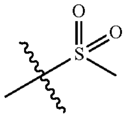 [SMILES: *S(C)(=O)=O] | 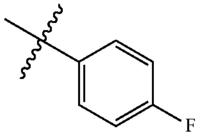 | 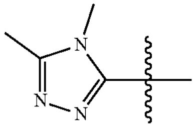 [SMILES: *c1nnc(C)n1C] | |
| 1-841 | 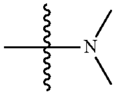 [SMILES: *N(C)C] | 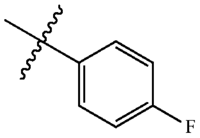 [SMILES: *c1ccc(F)cc1] | 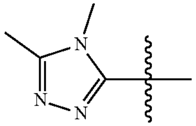 | $^1$H NMR (500 MHz, DMSO-$d_6$) δ 12.11 (s, 1H), 8.38 (d, J = 5.0 Hz, 1H), 8.07-8.00 (m, 2H), 7.46 (d, J = 5.0 Hz, 1H), 7.35-7.27 (m, 2H), 3.87 (s, 3H), 2.76 (s, 6H), 2.49 (s, 3H). |
| 1-842 | 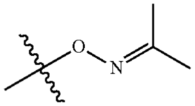 [SMILES: *ON=C(C)C] | 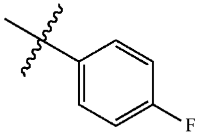 [SMILES: *c1ccc(F)cc1] | 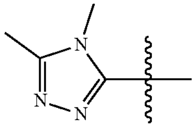 [SMILES: *c1nnc(C)n1C] | |

TABLE A1-continued
| | | | | |
|---|---|---|---|---|
| 1-843 | Et | 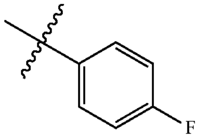 [SMILES: *c1ccc(F)cc1] | 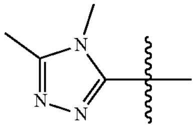 [SMILES: *c1nnc(C)n1C] | |
| 1-844 | 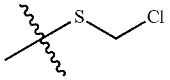 [SMILES: *SCCl] | 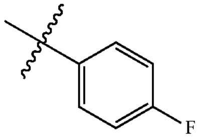 [SMILES: *c1ccc(F)cc1] | 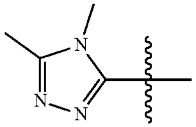 [SMILES: *c1nnc(C)n1C] | |
| 1-845 | $NO_2$ | 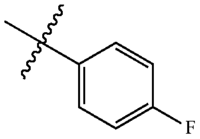 [SMILES: *c1ccc(F)cc1] | 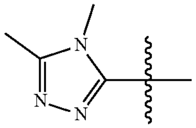 [SMILES: *c1nnc(C)n1C] | $^1$H NMR (500 MHz, DMSO-$d_6$) δ 12.09 (s, 1H), 8.96 (d, J = 5.0 Hz, 1H), 7.99-7.91 (m, 2H), 7.71 (d, J = 5.0 Hz, 1H), 7.35-7.27 (m, 2H), 3.89 (s, 3H), 2.52 (s, 3H). |
| 1-846 | CN | 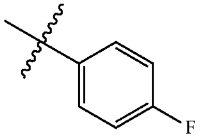 [SMILES: *c1ccc(F)cc1] | 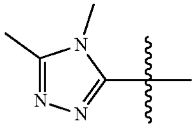 [SMILES: *c1nnc(C)n1C] | $^1$H NMR (500 MHz, DMSO-$d_6$) δ 12.08 (s, 1H), 9.02 (d, J = 5.0 Hz, 1H), 8.06-7.98 (m, 2H), 7.73 (d, J = 5.0 Hz, 1H), 7.35-7.27 (m, 2H), 3.89 (s, 3H), 2.51 (s, 3H). |
| 1-847 | 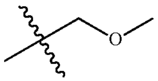 [SMILES: *COC] | 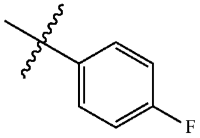 [SMILES: *c1ccc(F)cc1] | 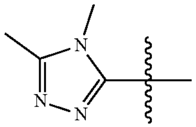 | $^1$H NMR (500 MHz, DMSO-$d_6$) δ 12.05 (s, 1H), 8.68 (d, J = 5.0 Hz, 1H), 8.04-7.97 (m, 2H), 7.55 (d, J = 5.0 Hz, 1H), 7.35-7.27 (m, 2H), 4.68 (s, 2H), 3.88 (s, 3H), 3.28 (s, 3H), 2.51 (s, 3H). |
| 1-848 | 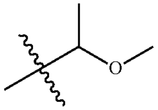 [SMILES: *C(C)OC] | 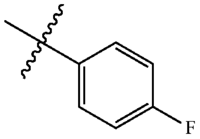 [SMILES: *c1ccc(F)cc1] | 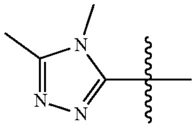 [SMILES: *c1nnc(C)n1C] | |
| 1-849 | 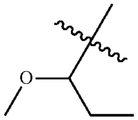 [SMILES: *C(CC)OC] | 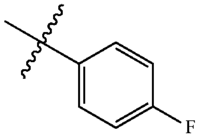 [SMILES: *c1ccc(F)cc1] | 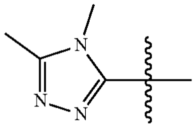 [SMILES: *c1nnc(C)n1C] | |

TABLE A1-continued
| | | | | |
|---|---|---|---|---|
| 1-850 | 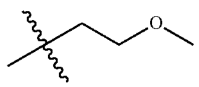 [SMILES: *CCOC] | 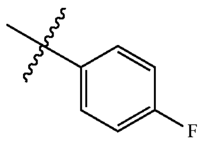 [SMILES: *c1ccc(F)cc1] | 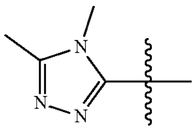 | |
| 1-851 | 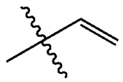 [SMILES: *C=C] | 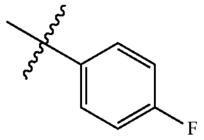 [SMILES: *c1ccc(F)cc1] | 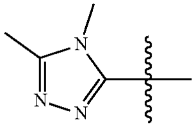 [SMILES: *c1nnc(C)n1C] | |
| 1-852 | 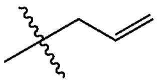 [SMILES: *CC=C] | 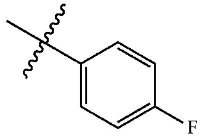 [SMILES: *c1ccc(F)cc1] | 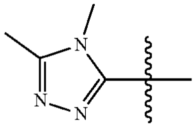 [SMILES: *c1nnc(C)n1C] | |
| 1-853 | 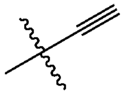 | 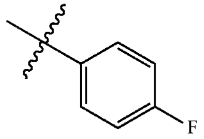 [SMILES: *c1ccc(F)cc1] | 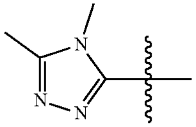 [SMILES: *c1nnc(C)n1C] | |
| 1-854 | 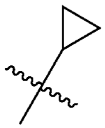 [SMILES: *C1CC1] | 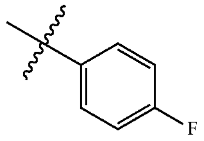 [SMILES: *c1ccc(F)cc1] | 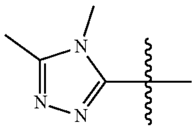 [SMILES: *c1nnc(C)n1C] | |
| 1-855 | 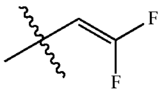 [SMILES: *C=C(F)F] | 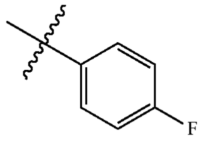 [SMILES: *c1ccc(F)cc1] | 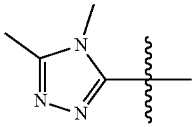 | |
| 1-856 | 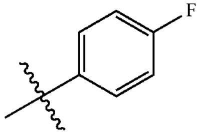 [SMILES: *c1ccc(F)cc1] | 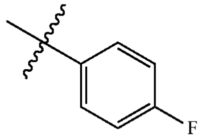 [SMILES: *c1ccc(F)cc1] | 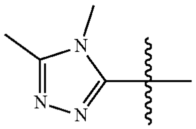 | $^1$H NMR (500 MHz, DMSO-$d_6$) δ 12.08 (s, 1H), 8.95 (d, J = 5.0 Hz, 1H), 8.01-7.93 (m, 2H), 7.62 (d, J = 5.0 Hz, 1H), 7.60-7.52 (m, 2H), 7.35-7.27 (m, 2H), 7.23-7.15 (m, 2H), 3.79 (s, 3H), 2.49 (s, 3H). |

TABLE A1-continued
| | | | |
|---|---|---|---|
| 1-857 | Cl | 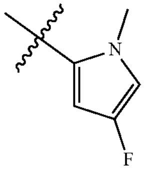 [SMILES: *c1cc(F)cn1C] | 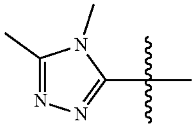 [SMILES: *c1nnc(C)n1C] |
| 1-858 | Cl | 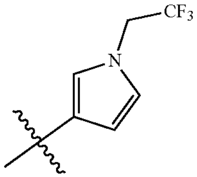 [SMILES: *c1ccn(CC(F)(F)F)c1] | 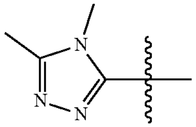 [SMILES: *c1nnc(C)n1C] |
| 1-859 | Cl | 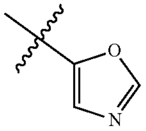 [SMILES: *c1cnco1] | 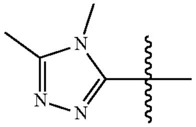 [SMILES: *c1nnc(C)n1C] |
| 1-860 | Cl | 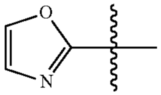 | 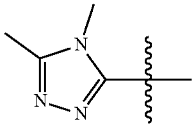 [SMILES: *c1nnc(C)n1C] |
| 1-861 | Cl | 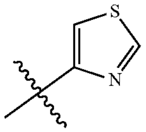 [SMILES: *c1cscn1] | 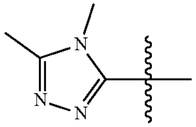 |
| 1-862 | Cl | 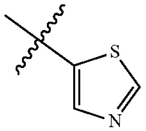 | 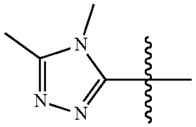 [SMILES: *c1nnc(C)n1C] |
| 1-863 | Cl | 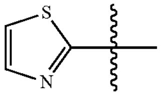 [SMILES: *c1nccs1] | 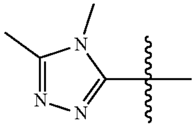 [SMILES: *c1nnc(C)n1C] |

TABLE A1-continued
| | | | |
|---|---|---|---|
| 1-864 | Cl | 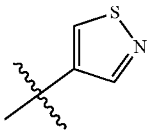 [SMILES: *c1cnsc1] | 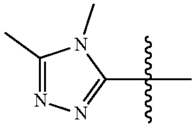 [SMILES: *c1nnc(C)n1C] |
| 1-865 | Cl | 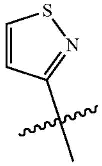 [SMILES: *c1ccsn1] | 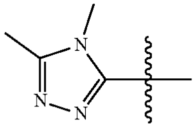 [SMILES: *c1nnc(C)n1C] |
| 1-866 | Cl | 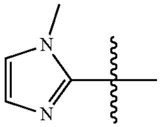 | 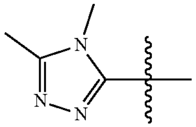 [SMILES: *c1nnc(C)n1C] |
| 1-867 | Cl | 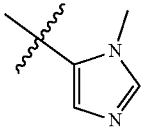 [SMILES: *c1cncn1C] | 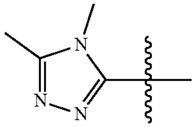 [SMILES: *c1nnc(C)n1C] |
| 1-868 | Cl | 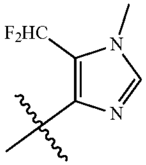 [SMILES: *c1ncn(C)c1C(F)F] | 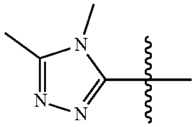 [SMILES: *c1nnc(C)n1C] |
| 1-869 | Cl | 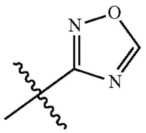 [SMILES: *c1ncon1] | 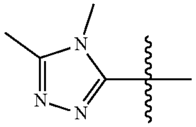 |
| 1-870 | Cl | 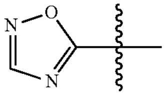 [SMILES: *c1ncno1] | 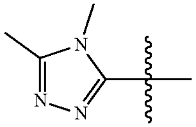 [SMILES: *c1nnc(C)n1C] |

TABLE A1-continued
| | | | |
|---|---|---|---|
| 1-871 | Cl | 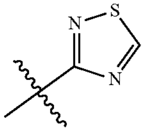 | 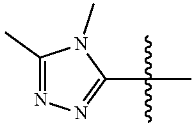 |
| 1-872 | Cl | 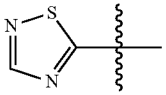 [SMILES: *c1ncns1] | 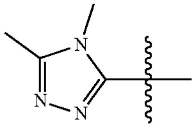 [SMILES: *c1nnc(C)n1C] |
| 1-873 | Cl | 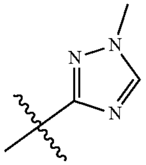 [SMILES: *c1ncn(C)n1] | 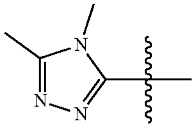 [SMILES: *c1nnc(C)n1C] |
| 1-874 | Cl | 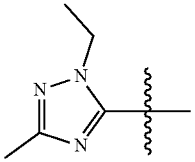 [SMILES: *c1nc(C)nn1CC] | 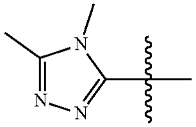 [SMILES: *c1nnc(C)n1C] |
| 1-875 | Cl | 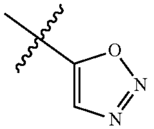 [SMILES: *c1cnno1] | 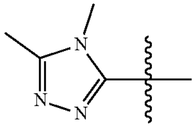 [SMILES: *c1nnc(C)n1C] |
| 1-876 | Cl | 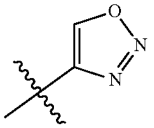 [SMILES: *c1conn1] | 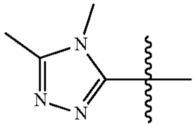 |
| 1-877 | Cl | 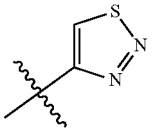 [SMILES: *c1csnn1] | 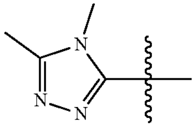 [SMILES: *c1nnc(C)n1C] |

TABLE A1-continued
| | | | |
|---|---|---|---|
| 1-878 | Cl | 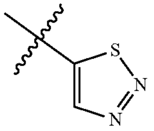 [SMILES: *c1cnns1] | 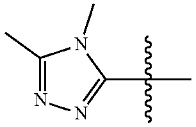 [SMILES: *c1nnc(C)n1C] |
| 1-879 | Cl | 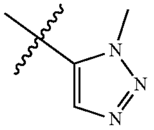 | 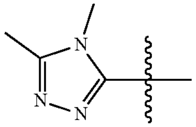 [SMILES: *c1nnc(C)n1C] |
| 1-880 | Cl | 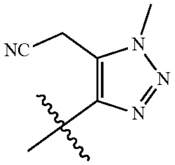 [SMILES: *c1nnn(C)c1CC#N] | 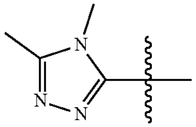 [SMILES: *c1nnc(C)n1C] |
| 1-881 | Cl | 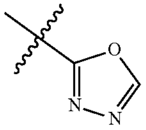 [SMILES: *c1nnco1] | 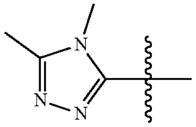 [SMILES: *c1nnc(C)n1C] |
| 1-882 | Cl | 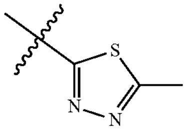 [SMILES: *c1nnc(C)s1] | 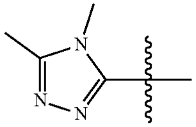 |
| 1-883 | Cl | 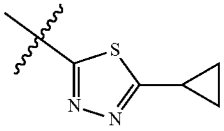 [SMILES: *c1nnc(C2CC2)s1] | 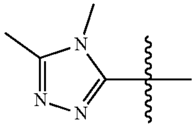 [SMILES: *c1nnc(C)n1C] |
| 1-884 | Cl | 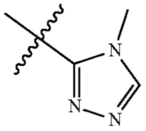 [SMILES: *c1nncn1C] | 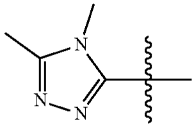 |

TABLE A1-continued
| | | | |
|---|---|---|---|
| 1-885 | Cl | 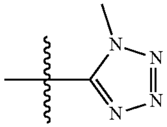 [SMILES: *c1nnnn1C] | 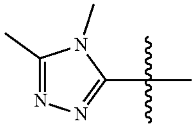 [SMILES: *c1nnc(C)n1C] |
| 1-886 | Cl | 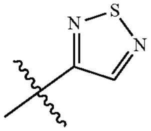 [SMILES: *c1cnsn1] | 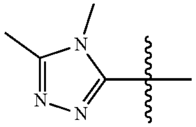 [SMILES: *c1nnc(C)n1C] |
| 1-887 | Cl | 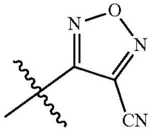 [SMILES: *c1nonc1C#N] | 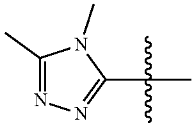 |
| 1-888 | Cl | 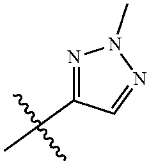 [SMILES: *c1cnn(C)n1] | 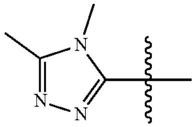 [SMILES: *c1nnc(C)n1C] |
| 1-889 | Cl | 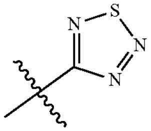 [SMILES: *c1nnsn1] | 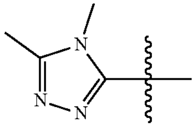 |
| 1-890 | Cl | 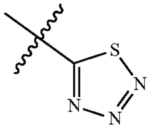 | 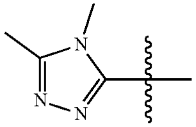 [SMILES: *c1nnc(C)n1C] |
| 1-891 | Cl | 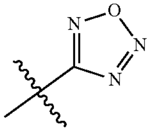 | 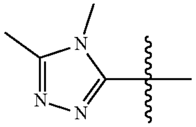 [SMILES: *c1nnc(C)n1C] |

TABLE A1-continued
| | | | |
|---|---|---|---|
| 1-892 | Cl | 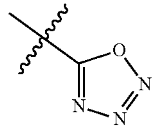 | 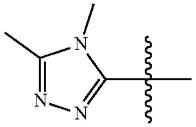 |
| 1-893 | Cl | 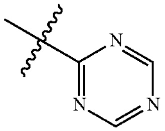 [SMILES: *c1ncncn1] | 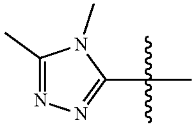 [SMILES: *c1nnc(C)n1C] |
| 1-894 | Cl | 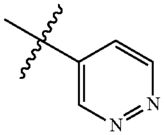 [SMILES: *c1ccnnc1] | 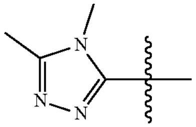 [SMILES: *c1nnc(C)n1C] |
| 1-895 | Cl | 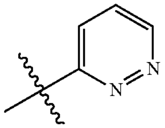 [SMILES: *c1cccnn1] | 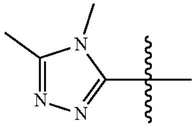 |
| 1-896 | Cl | 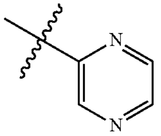 [SMILES: *c1cnccn1] | 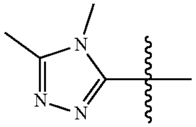 [SMILES: *c1nnc(C)n1C] |
| 1-897 | Cl | 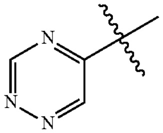 [SMILES: *c1cnncn1] | 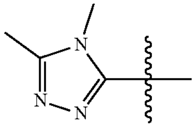 [SMILES: *c1nnc(C)n1C] |
| 1-898 | Cl | 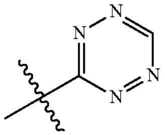 [SMILES: *c1nncnn1] | 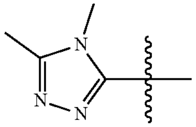 [SMILES: *c1nnc(C)n1C] |

TABLE A1-continued
| | | | |
|---|---|---|---|
| 1-899 | Cl | 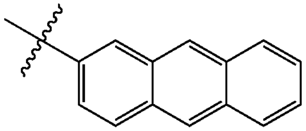 [SMILES: *c1ccc2cc3ccccc3cc2c1] | 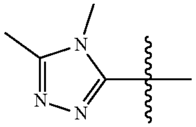 [SMILES: *c1nnc(C)n1C] |
| 1-900 | Cl | 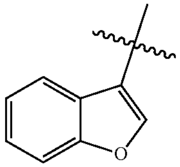 [SMILES: *c1coc2ccccc12] | 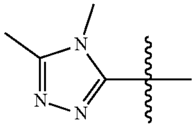 |
| 1-901 | Cl | 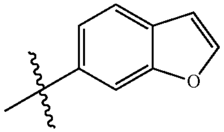 [SMILES: *c1ccc2ccoc2c1] | 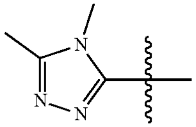 [SMILES: *c1nnc(C)n1C] |
| 1-902 | Cl | 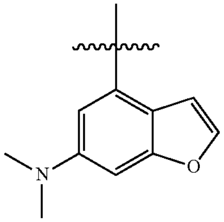 [SMILES: *c1cc(N(C)C)cc2occc12] | 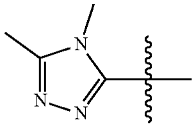 [SMILES: *c1nnc(C)n1C] |
| 1-903 | Cl | 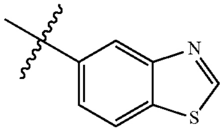 [SMILES: *c1ccc2scnc2c1] | 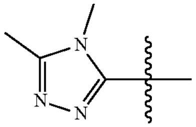 [SMILES: *c1nnc(C)n1C] |
| 1-904 | Cl | 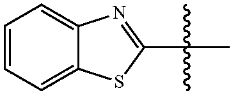 [SMILES: *c1nc2ccccc2s1] | 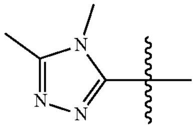 |

TABLE A1-continued
| | | | |
|---|---|---|---|
| 1-905 | Cl | 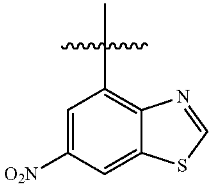 | 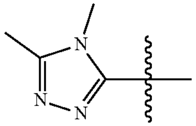 |
| 1-906 | Cl | 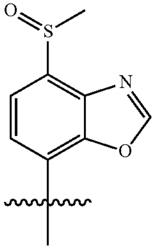 | 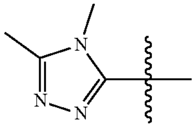 [SMILES: *c1nnc(C)n1C] |
| 1-907 | Cl | 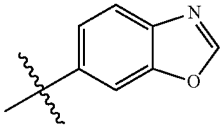 [SMILES: *c1ccc2ncoc2c1] | 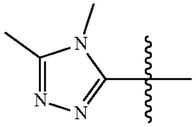 [SMILES: *c1nnc(C)n1C] |
| 1-908 | Cl | 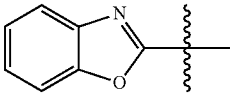 [SMILES: *c1nc2ccccc2o1] | 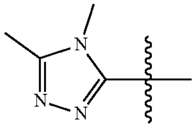 [SMILES: *c1nnc(C)n1C] |
| 1-909 | Cl | 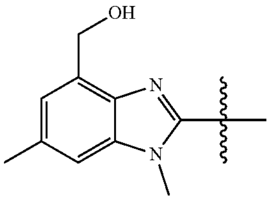 [SMILES: *c1nc2c(CO)cc(C)cc2n1C] | 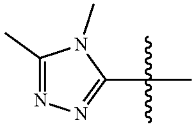 [SMILES: *c1nnc(C)n1C] |

TABLE A1-continued
| | | | |
|---|---|---|---|
| 1-910 | Cl | 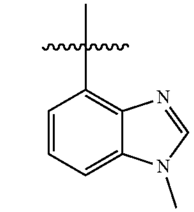 [SMILES: *c1cccc2c1ncn2C] | 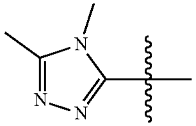 |
| 1-911 | Cl | 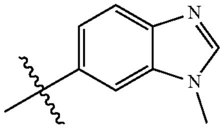 [SMILES: *c1ccc2ncn(C)c2c1] | 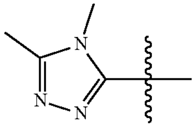 [SMILES: *c1nnc(C)n1C] |
| 1-912 | Cl | 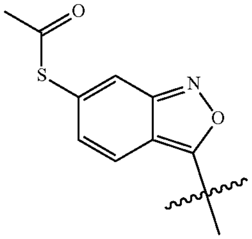 [SMILES: *c1onc2cc(SC(C)=O)ccc12] | 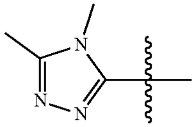 [SMILES: *c1nnc(C)n1C] |
| 1-913 | Cl | 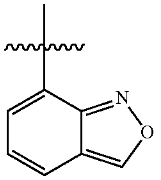 [SMILES: *c1cccc2conc12] | 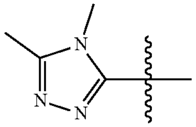 |
| 1-914 | Cl | 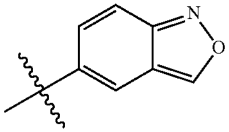 [SMILES: *c1ccc2nocc2c1] | 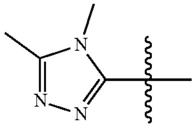 [SMILES: *c1nnc(C)n1C] |
| 1-915 | Cl | 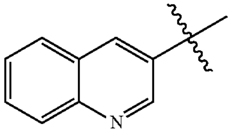 | 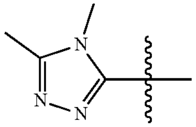 [SMILES: *c1nnc(C)n1C] |

TABLE A1-continued
| | | | |
|---|---|---|---|
| 1-916 | Cl | 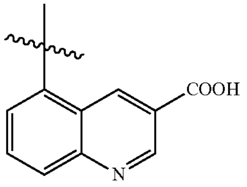 [SMILES: *c1cccc2ncc(C(=O)O)cc12] | 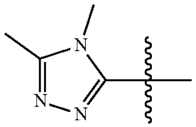 [SMILES: *c1nnc(C)n1C] |
| 1-917 | Cl | 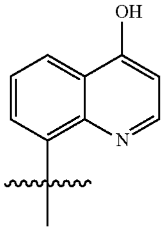 [SMILES: *c1cccc2c(O)ccnc12] | 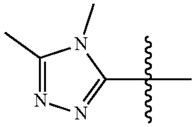 |
| 1-918 | Cl | 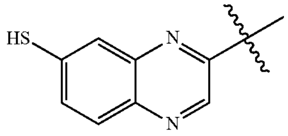 [SMILES: *c1cnc2ccc(S)cc2n1] | 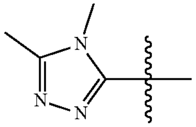 [SMILES: *c1nnc(C)n1C] |
| 1-919 | Cl | 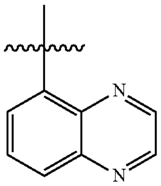 [SMILES: *c1cccc2nccnc12] | 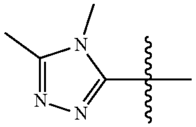 |
| 1-920 | Cl | 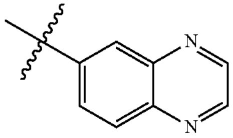 [SMILES: *c1ccc2nccnc2c1] | 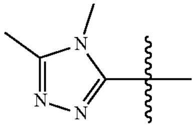 |

TABLE A1-continued
| | | | |
|---|---|---|---|
| 1-921 | Cl | 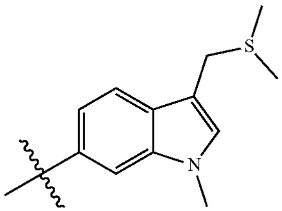 | 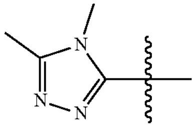 [SMILES: *c1nnc(C)n1C] |
| 1-922 | Cl | 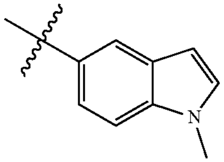 [SMILES: *c1ccc2c(ccn2C)c1] | 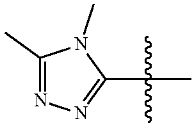 |
| 1-923 | Cl | 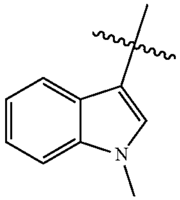 [SMILES: *c1cn(C)c2ccccc12] | 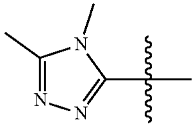 |
| 1-924 | Cl | 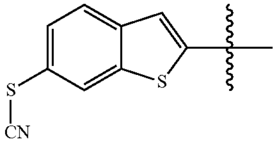 | 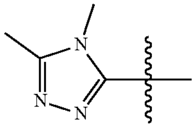 [SMILES: *c1nnc(C)n1C] |
| 1-925 | Cl | 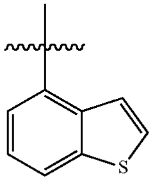 | 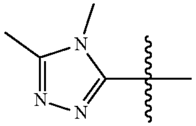 |

TABLE A1-continued
| | | | |
|---|---|---|---|
| 1-926 | Cl | 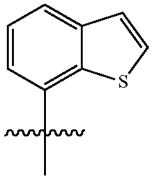 [SMILES: *c1cccc2ccsc12] | 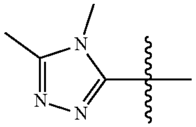 |
| 1-927 | Cl | 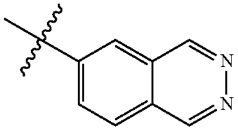 [SMILES: *c1ccc2cnncc2c1] | 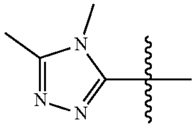 [SMILES: *c1nnc(C)n1C] |
| 1-928 | Cl | 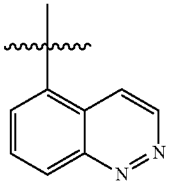 [SMILES: *c1cccc2nnccc12] | 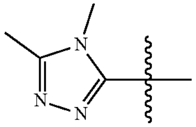 |
| 1-929 | Cl | 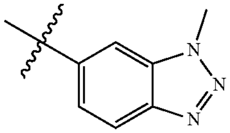 [SMILES: *c1ccc2nnn(C)c2c1] | 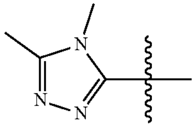 |
| 1-930 | Cl | 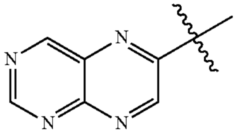 [SMILES: *c1cnc2ncncc2n1] | 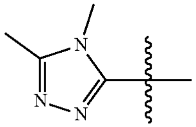 [SMILES: *c1nnc(C)n1C] |
| 1-931 | Cl | 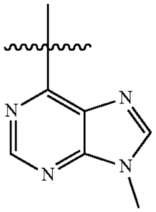 [SMILES: *c1ncnc2c1ncn2C] | 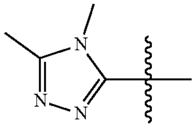 [SMILES: *c1nnc(C)n1C] |

TABLE A1-continued
| | | | |
|---|---|---|---|
| 1-932 | Cl | 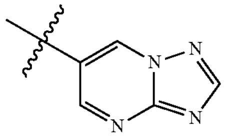 [SMILES: *c1cnc2ncnn2c1] | 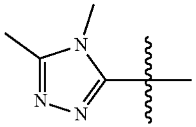 |
| 1-933 | Cl | 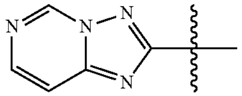 [SMILES: *c1nc2ccncn2n1] | 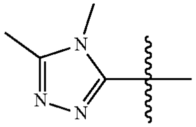 [SMILES: *c1nnc(C)n1C] |
| 1-934 | Cl | 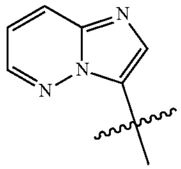 [SMILES: *c1cnc2cccnn12] | 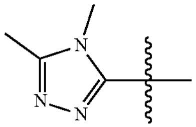 |
| 1-935 | Cl | 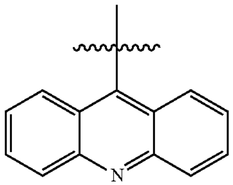 [SMILES: *c1c2ccccc2nc2ccccc12] | 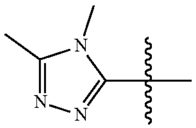 [SMILES: *c1nnc(C)n1C] |
| 1-936 | Cl | 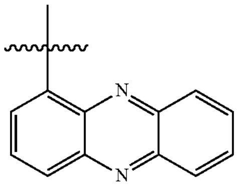 [SMILES: *c1cccc2nc3ccccc3nc12] | 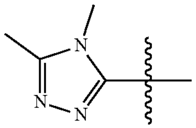 [SMILES: *c1nnc(C)n1C] |
| 1-937 | Cl | 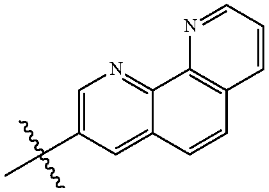 [SMILES: *c1cnc2c(ccc3cccnc32)c1] | 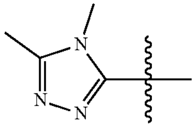 |

TABLE A1-continued
| | | | | |
|---|---|---|---|---|
| 1-938 | Cl | 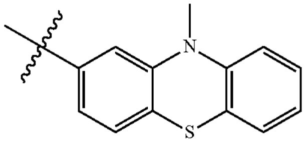 [SMILES: *c1ccc2c(c1)N(C)c1ccccc1S2] | 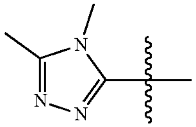 [SMILES: *c1nnc(C)n1C] | |
| 1-939 | Cl | 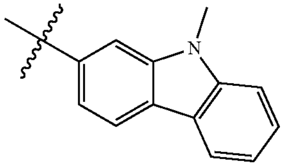 [SMILES: *c1ccc2c3ccccc3n(C)c2c1] | 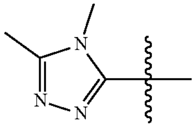 [SMILES: *c1nnc(C)n1C] | |
| 1-940 | Cl | 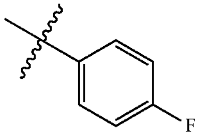 [SMILES: *c1ccc(F)cc1] | 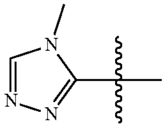 | $^1$H NMR (500 MHz, DMSO-$d_6$) δ 12.09 (s, 1H), 9.15 (s, 1H), 8.74 (d, J = 5.0 Hz, 1H), 8.03-7.95 (m, 2H), 7.70 (d, J = 5.0 Hz, 1H), 7.35-7.27 (m, 2H), 3.82 (s, 3H). |
| 1-941 | Cl | 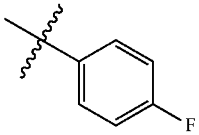 [SMILES: *c1ccc(F)cc1] | 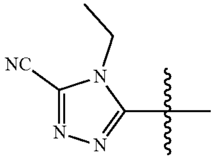 [SMILES: *c1nnc(C#N)n1CC] | $^1$H NMR (500 MHz, DMSO-$d_6$) δ 12.08 (s, 1H), 8.75 (d, J = 5.0 Hz, 1H), 8.02-7.95 (m, 2H), 7.74 (d, J = 5.0 Hz, 1H), 7.35-7.27 (m, 2H), 4.07 (q, J = 8.0 Hz, 2H), 1.29 (t, J = 8.0 Hz, 3H). |
| 1-942 | Cl | 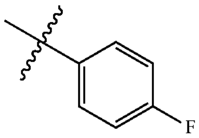 [SMILES: *c1ccc(F)cc1] | 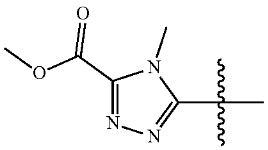 [SMILES: *c1nnc(C(=O)OC)n1C] | $^1$H NMR (500 MHz, DMSO-$d_6$) δ 12.07 (s, 1H), 8.74 (d, J = 5.0 Hz, 1H), 8.03-7.95 (m, 2H), 7.73 (d, J = 5.0 Hz, 1H), 7.35-7.27 (m, 2H), 4.01 (s, 3H), 3.88 (s, 3H). |
| 1-943 | Cl | 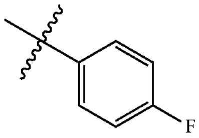 [SMILES: *c1ccc(F)cc1] | 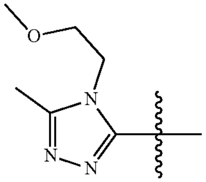 [SMILES: *c1nnc(C)n1CCOC] | $^1$H NMR (500 MHz, DMSO-$d_6$) δ 12.08 (s, 1H), 8.74 (d, J = 5.0 Hz, 1H), 8.03-7.95 (m, 2H), 7.68 (d, J = 5.0 Hz, 1H), 7.35-7.27 (m, 2H), 4.18 (t, J = 8.0 Hz, 2H), 3.96 (t, J = 8.0 Hz, 2H), 3.58 (s, 3H), 2.47 (s, 3H). |

TABLE A1-continued
| | | | | |
|---|---|---|---|---|
| 1-944 | Cl | 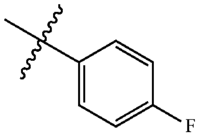 | 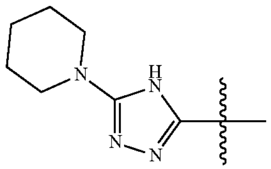 [SMILES: *c1nnc(N2CCCCC2)[nH]1] | $^1H$ NMR (500 MHz, DMSO-$d_6$) δ 12.10 (s, 1H), 10.40 (s, 1H), 8.94 (d, J = 5.0 Hz, 1H), 8.05-7.97 (m, 2H), 7.62 (d, J = 5.0 Hz, 1H), 7.35-7.27 (m, 2H), 3.36 (t, J = 5.5 Hz, 4H), 1.62-1.56 (m, 2H), 1.51 (p, J = 7.0 Hz, 4H). |
| 1-945 | Cl | 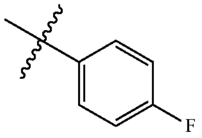 [SMILES: *c1ccc(F)cc1] | 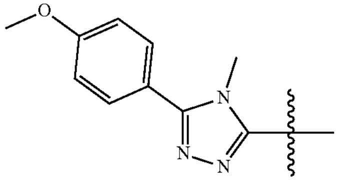 [SMILES: *c1nnc(-c2ccc(OC)cc2)n1C] | $^1H$ NMR (500 MHz, DMSO-$d_6$) δ 12.06 (s, 1H), 8.94 (d, J = 5.0 Hz, 1H), 8.05-7.93 (m, 4H), 7.83 (d, J = 5.0 Hz, 1H), 7.35-7.27 (m, 2H), 7.14-7.08 (m, 2H), 3.86 (s, 3H), 3.79 (s, 3H). |
| 1-946 | Cl | $CH_3$ | 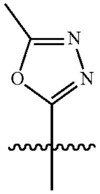 | $^1H$ NMR (500 MHz, DMSO-$d_6$) δ 12.94 (s, 1H), 8.64 (d, J = 5.0 Hz, 1H), 7.73 (d, J = 5.0 Hz, 1H), 2.59 (s, 3H), 2.46 (s, 3H). |
| 1-947 | Cl | 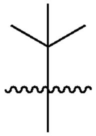 [SMILES: *C(C)(C)C] | 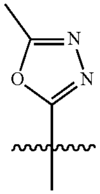 | |
| 1-948 | Cl | 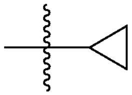 [SMILES: *C1CC1] | 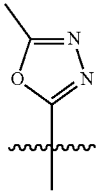 | |

TABLE A1-continued
| | | | | |
|---|---|---|---|---|
| 1-949 | Cl | 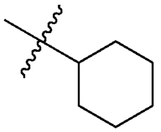 [SMILES: *C1CCCCC1] | 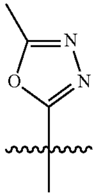 | |
| 1-950 | Cl | 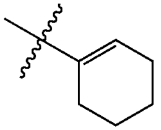 [SMILES: *C1=CCCCC1] | 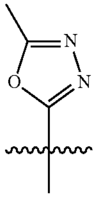 | $^1H$ NMR (500 MHz, DMSO-d6) δ 12.11 (s, 1H), 8.65 (d, J = 5.0 Hz, 1H), 7.66 (d, J = 5.0 Hz, 1H), 6.18 (t, J = 6.0 Hz, 1H), 2.44 (s, 3H), 2.13-1.92 (m, 4H), 1.76-1.58 (m, 2H), 1.48-1.35 (m, 2H). |
| 1-951 | Cl | 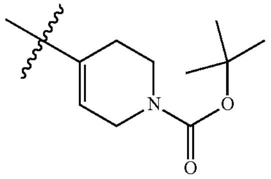 [SMILES: *C1=CCN(C(=O)OC(C)(C)C)CC1] | 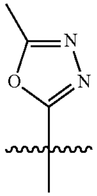 [SMILES: *c1nnc(C)o1] | |
| 1-952 | Cl | 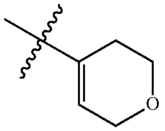 | 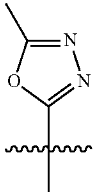 | |
| 1-953 | Cl | 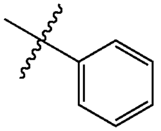 [SMILES: *c1ccccc1] | 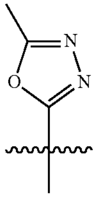 [SMILES: *c1nnc(C)o1] | |

TABLE A1-continued
| | | | |
|---|---|---|---|
| 1-954 | Cl | 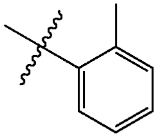 [SMILES: *c1ccccc1C] | 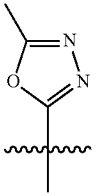 |
| 1-955 | Cl | 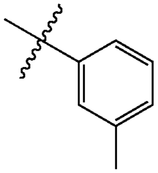 [SMILES: *c1cccc(C)c1] | 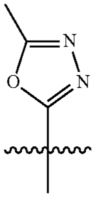 |
| 1-956 | Cl | 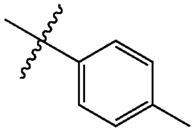 [SMILES: *c1ccc(C)cc1] | 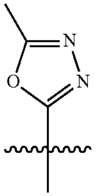 [SMILES: *c1nnc(C)o1] |
| 1-957 | Cl | 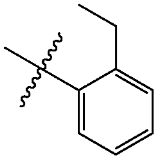 [SMILES: *c1ccccc1CC] | 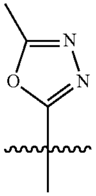 |
| 1-958 | Cl | 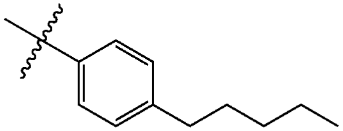 [SMILES: *c1ccc(CCCCC)cc1] | 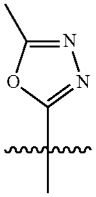 [SMILES: *c1nnc(C)o1] |

TABLE A1-continued
| | | | | |
|---|---|---|---|---|
| 1-959 | Cl | 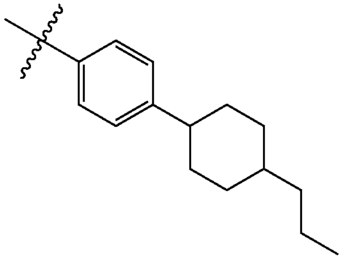 [SMILES: *c1ccc(C2CCC(CCC)CC2)cc1] | 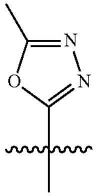 | |
| 1-960 | Cl | 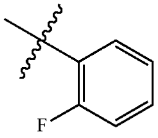 | 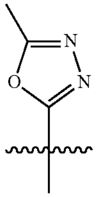 | |
| 1-961 | Cl | 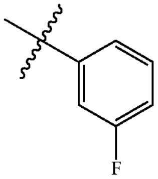 [SMILES: *c1cccc(F)c1] | 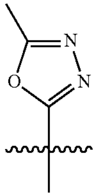 [SMILES: *c1nnc(C)o1] | |
| 1-962 | Cl | 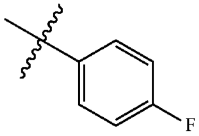 | 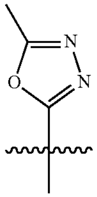 | $^1$H NMR (500 MHz, DMSO-d6) δ 12.09 (s, 1H), 8.72 (d, J = 5.0 Hz, 1H), 7.63-7.55 (m, 2H), 7.12-7.03 (m, 3H), 2.38 (s, 3H). |
| 1-963 | Cl | 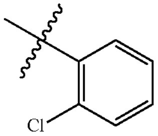 | 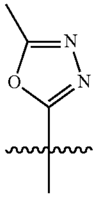 | |

TABLE A1-continued
| | | | |
|---|---|---|---|
| 1-964 | Cl | 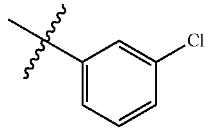 [SMILES: *c1cccc(Cl)c1] | 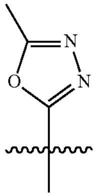 |
| 1-965 | Cl | 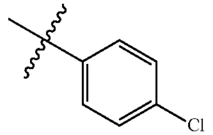 | 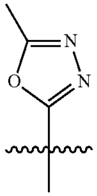 [SMILES: *c1nnc(C)o1] |
| 1-966 | Cl | 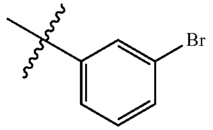 [SMILES: *c1cccc(Br)c1] | 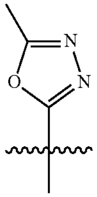 |
| 1-967 | Cl | 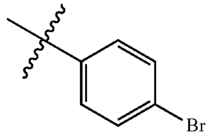 | 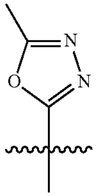 |
| 1-968 | Cl | 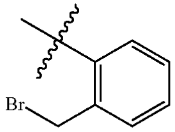 | 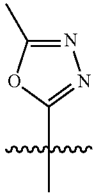 |

TABLE A1-continued
| | | | |
|---|---|---|---|
| 1-969 | Cl | 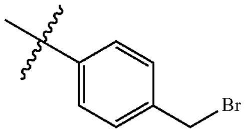 [SMILES: *c1ccc(CBr)cc1] | 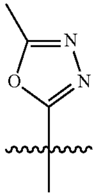 |
| 1-970 | Cl | 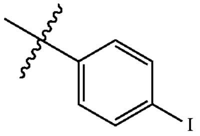 [SMILES: *c1ccc(I)cc1] | 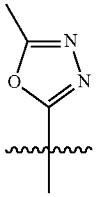 |
| 1-971 | Cl | 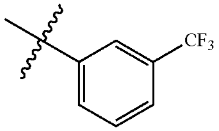 [SMILES: *c1cccc(C(F)(F)F)c1] | 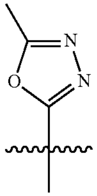 [SMILES: *c1nnc(C)o1] |
| 1-972 | Cl | 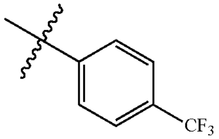 | 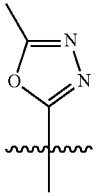 |
| 1-973 | Cl | 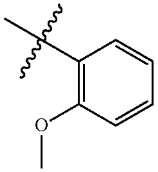 [SMILES: *c1ccccc1OC] | 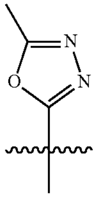 |

TABLE A1-continued
| | | | |
|---|---|---|---|
| 1-974 | Cl | 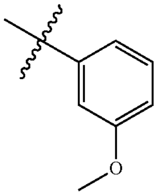 [SMILES: *c1cccc(OC)c1] | 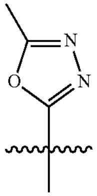 [SMILES: *c1nnc(C)o1] |
| 1-975 | Cl | 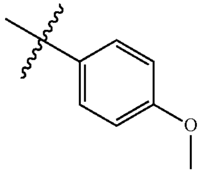 [SMILES: *c1ccc(OC)cc1] | 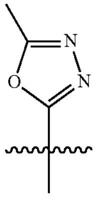 |
| 1-976 | Cl | 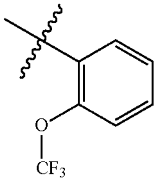 | 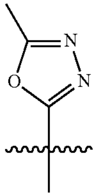 [SMILES: *c1nnc(C)o1] |
| 1-977 | Cl | 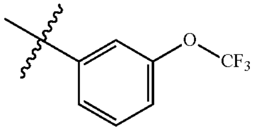 [SMILES: *c1cccc(OC(F)(F)F)c1] | 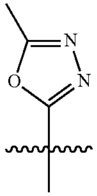 |
| 1-978 | Cl | 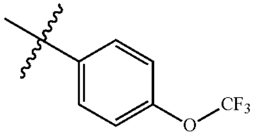 [SMILES: *c1ccc(OC(F)(F)F)cc1] | 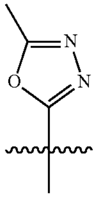 |

TABLE A1-continued
| | | | |
|---|---|---|---|
| 1-979 | Cl | 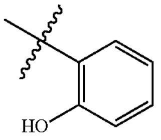 [SMILES: *c1ccccc1O] | 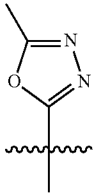 [SMILES: *c1nnc(C)o1] |
| 1-980 | Cl | 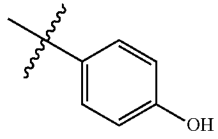 [SMILES: *c1ccc(O)cc1] | 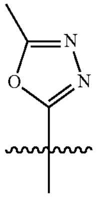 |
| 1-981 | Cl | 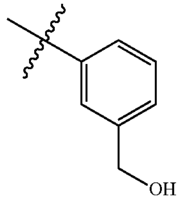 [SMILES: *c1cccc(CO)c1] | 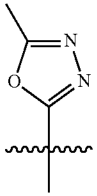 [SMILES: *c1nnc(C)o1] |
| 1-982 | Cl | 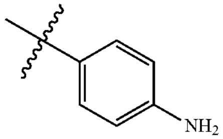 | 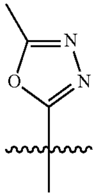 [SMILES: *c1nnc(C)o1] |
| 1-983 | Cl | 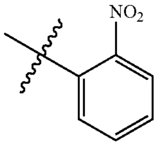 [SMILES: *c1ccccc1[N+](=O)[O-]] | 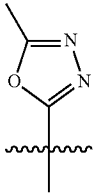 |

TABLE A1-continued
| | | | |
|---|---|---|---|
| 1-984 | Cl | 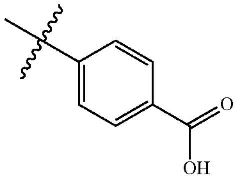 [SMILES: *c1ccc(C(=O)O)cc1] | 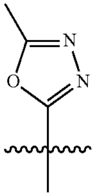 [SMILES: *c1nnc(C)o1] |
| 1-985 | Cl | 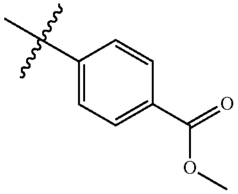 [SMILES: *c1ccc(C(=O)OC)cc1] | 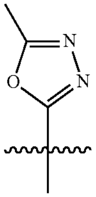 |
| 1-986 | Cl | 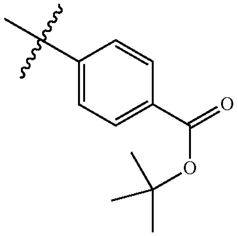 [SMILES: *c1ccc(C(=O)OC(C)(C)C)cc1] | 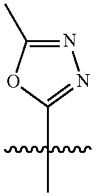 [SMILES: *c1nnc(C)o1] |
| 1-987 | Cl | 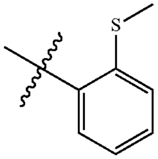 [SMILES: *c1ccccc1SC] | 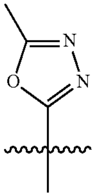 [SMILES: *c1nnc(C)o1] |
| 1-988 | Cl | 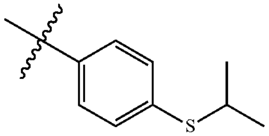 [SMILES: *c1ccc(SC(C)C)cc1] | 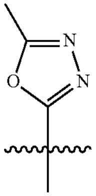 [SMILES: *c1nnc(C)o1] |

TABLE A1-continued
| | | | |
|---|---|---|---|
| 1-989 | Cl | 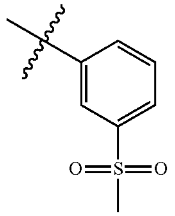 [SMILES: *c1cccc(S(C)(=O)=O)c1] | 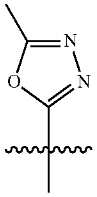 [SMILES: *c1nnc(C)o1] |
| 1-990 | Cl | 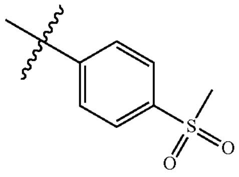 [SMILES: *c1ccc(S(C)(=O)=O)cc1] | 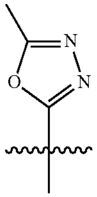 |
| 1-991 | Cl | 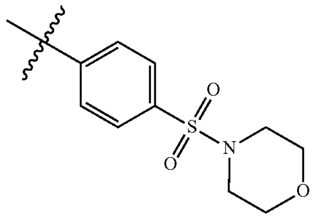 [SMILES: *c1ccc(S(=O)(=O)N2CCOCC2)cc1] | 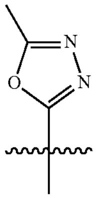 |
| 1-992 | Cl | 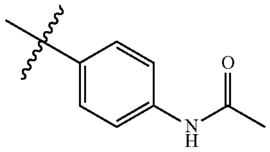 [SMILES: *c1ccc(NC(C)=O)cc1] | 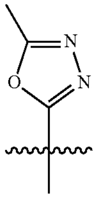 [SMILES: *c1nnc(C)o1] |
| 1-993 | Cl | 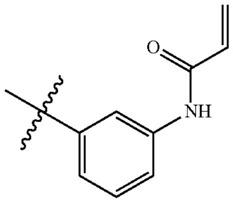 [SMILES: *c1cccc(NC(=O)C=C)c1] | 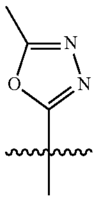 [SMILES: *c1nnc(C)o1] |

TABLE A1-continued
| | | | |
|---|---|---|---|
| 1-994 | Cl | 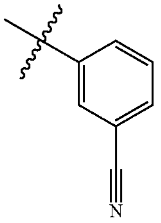 [SMILES: *c1cccc(C#N)c1] | 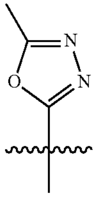 [SMILES: *c1nnc(C)o1] |
| 1-995 | Cl | 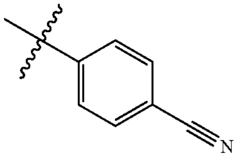 [SMILES: *c1ccc(C#N)cc1] | 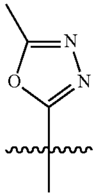 |
| 1-996 | Cl | 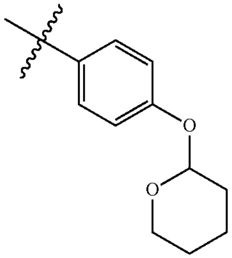 [SMILES: *c1ccc(OC2CCCCO2)cc1] | 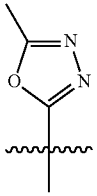 [SMILES: *c1nnc(C)o1] |
| 1-997 | Cl | 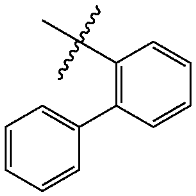 [SMILES: *c1ccccc1-c1ccccc1] | 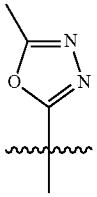 |

TABLE A1-continued
| | | | |
|---|---|---|---|
| 1-998 | Cl | 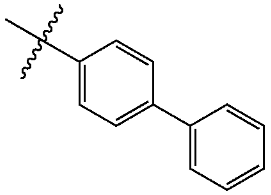 [SMILES: *c1ccc(-c2ccccc2)cc1] | 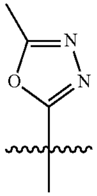 [SMILES: *c1nnc(C)o1] |
| 1-999 | Cl | 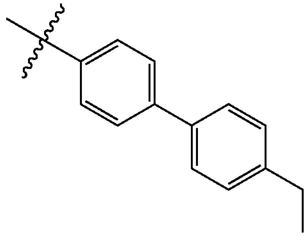 [SMILES: *c1ccc(-c2ccc(CC)cc2)cc1] | 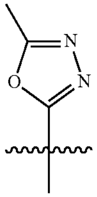 |
| 1-1000 | Cl | 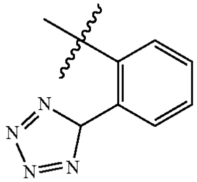 [SMILES: *c1ccccc1C1N=NN=N1] | 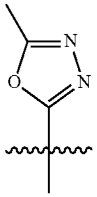 |
| 1-1001 | Cl | 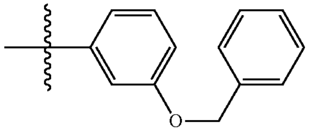 [SMILES: *c1cccc(OCc2ccccc2)c1] | 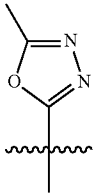 [SMILES: *c1nnc(C)o1] |
| 1-1002 | Cl | 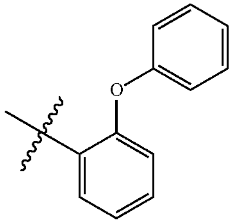 [SMILES: *c1ccccc1Oc1ccccc1] | 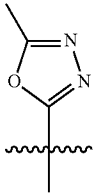 [SMILES: *c1nnc(C)o1] |

TABLE A1-continued
| | | | |
|---|---|---|---|
| 1-1003 | Cl | 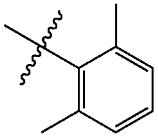 [SMILES: *c1c(C)cccc1C] | 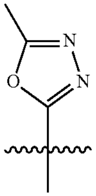 [SMILES: *c1nnc(C)o1] |
| 1-1004 | Cl | 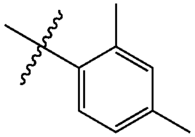 [SMILES: *c1ccc(C)cc1C] | 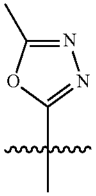 |
| 1-1005 | Cl | 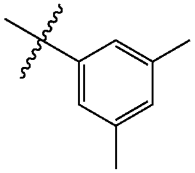 [SMILES: *c1cc(C)cc(C)c1] | 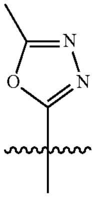 |
| 1-1006 | Cl | 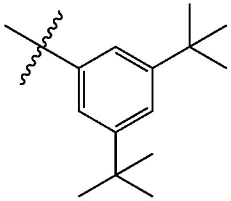 [SMILES: *c1cc(C(C)(C)C)cc(C(C)(C)C)c1] | 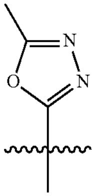 [SMILES: *c1nnc(C)o1] |
| 1-1007 | Cl | 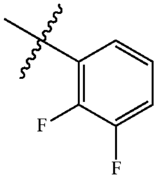 [SMILES: *c1cccc(F)c1F] | 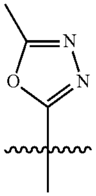 [SMILES: *c1nnc(C)o1] |

TABLE A1-continued
| | | | |
|---|---|---|---|
| 1-1008 | Cl | 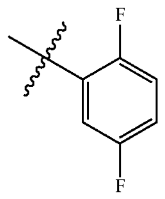 | 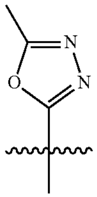 [SMILES: *c1nnc(C)o1] |
| 1-1009 | Cl | 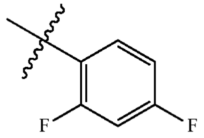 [SMILES: *c1ccc(F)cc1F] | 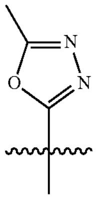 [SMILES: *c1nnc(C)o1] |
| 1-1010 | Cl | 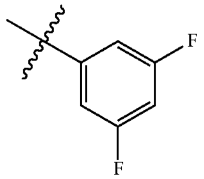 [SMILES: *c1cc(F)cc(F)c1] | 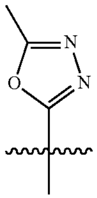 [SMILES: *c1nnc(C)o1] |
| 1-1011 | Cl | 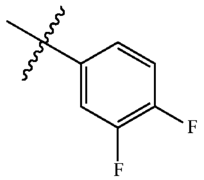 [SMILES: *c1ccc(F)c(F)c1] | 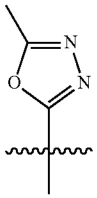 [SMILES: *c1nnc(C)o1] |
| 1-1012 | Cl | 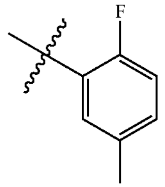 [SMILES: *c1cc(C)ccc1F] | 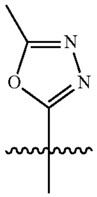 [SMILES: *c1nnc(C)o1] |

TABLE A1-continued
| | | | |
|---|---|---|---|
| 1-1013 | Cl | 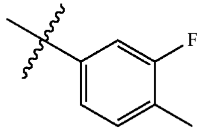 [SMILES: *c1ccc(C)c(F)c1] | 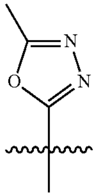 [SMILES: *c1nnc(C)o1] |
| 1-1014 | Cl | 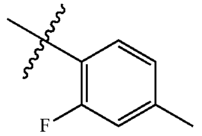 [SMILES: *c1ccc(C)cc1F] | 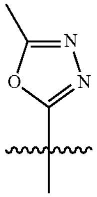 [SMILES: *c1nnc(C)o1] |
| 1-1015 | Cl | 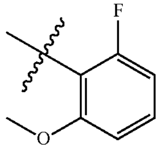 | 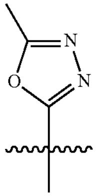 [SMILES: *c1nnc(C)o1] |
| 1-1016 | Cl | 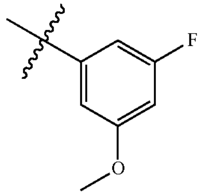 [SMILES: *c1cc(F)cc(OC)c1] | 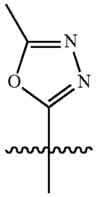 [SMILES: *c1nnc(C)o1] |
| 1-1017 | Cl | 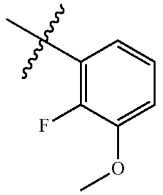 [SMILES: *c1cccc(OC)c1F] | 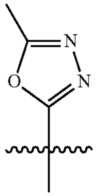 [SMILES: *c1nnc(C)o1] |

TABLE A1-continued
| | | | |
|---|---|---|---|
| 1-1018 | Cl | 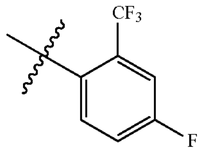 | 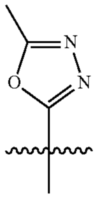 [SMILES: *c1nnc(C)o1] |
| 1-1019 | Cl | 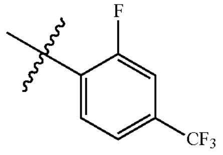 | 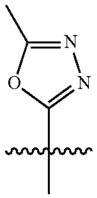 [SMILES: *c1nnc(C)o1] |
| 1-1020 | Cl | 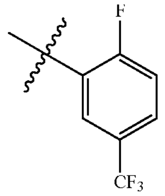 | 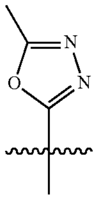 [SMILES: *c1nnc(C)o1] |
| 1-1021 | Cl | 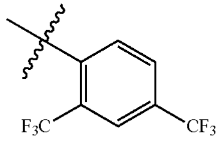 | 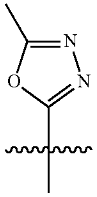 [SMILES: *c1nnc(C)o1] |
| 1-1022 | Cl | 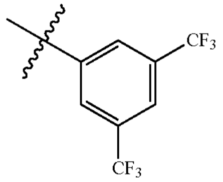 [SMILES: *c1cc(C(F)(F)F)cc(C(F)(F)F)c1] | 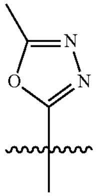 [SMILES: *c1nnc(C)o1] |

TABLE A1-continued
| | | | |
|---|---|---|---|
| 1-1023 | Cl | 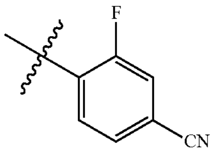 [SMILES: *c1ccc(C#N)cc1F] | 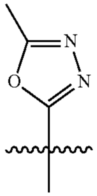 [SMILES: *c1nnc(C)o1] |
| 1-1024 | Cl | 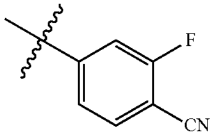 [SMILES: *c1ccc(C#N)c(F)c1] | 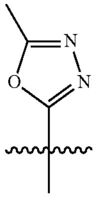 [SMILES: *c1nnc(C)o1] |
| 1-1025 | Cl | 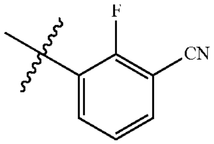 [SMILES: *c1cccc(C#N)c1F] | 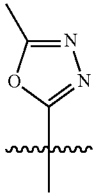 [SMILES: *c1nnc(C)o1] |
| 1-1026 | Cl | 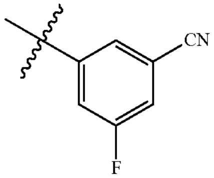 [SMILES: *c1cc(F)cc(C#N)c1] | 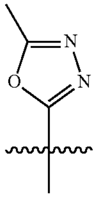 [SMILES: *c1nnc(C)o1] |
| 1-1027 | Cl | 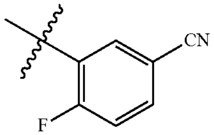 [SMILES: *c1cc(C#N)ccc1F] | 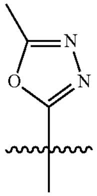 [SMILES: *c1nnc(C)o1] |

TABLE A1-continued
| | | | |
|---|---|---|---|
| 1-1028 | Cl | 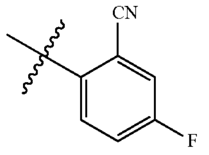 | 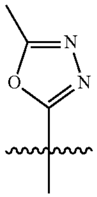 [SMILES: *c1nnc(C)o1] |
| 1-1029 | Cl | 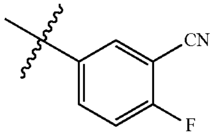 [SMILES: *c1ccc(F)c(C#N)c1] | 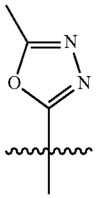 [SMILES: *c1nnc(C)o1] |
| 1-1030 | Cl | 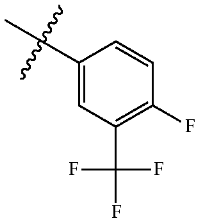 [SMILES: *c1ccc(F)c(C(F)(F)F)c1] | 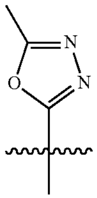 [SMILES: *c1nnc(C)o1] |
| 1-1031 | Cl | 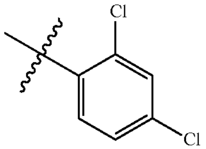 [SMILES: *c1ccc(Cl)cc1Cl] | 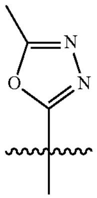 [SMILES: *c1nnc(C)o1] |
| 1-1032 | Cl | 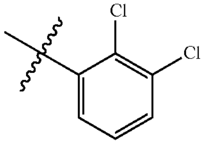 | 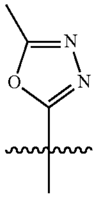 [SMILES: *c1nnc(C)o1] |

TABLE A1-continued
| | | | |
|---|---|---|---|
| 1-1033 | Cl | 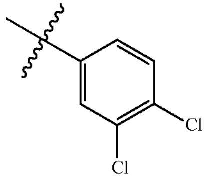 [SMILES: *c1ccc(Cl)c(Cl)c1] | 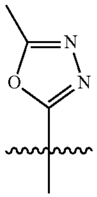 [SMILES: *c1nnc(C)o1] |
| 1-1034 | Cl | 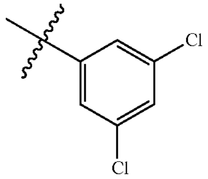 | 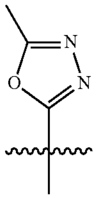 [SMILES: *c1nnc(C)o1] |
| 1-1035 | Cl | 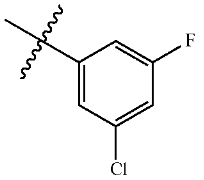 [SMILES: *c1cc(F)cc(Cl)c1] | 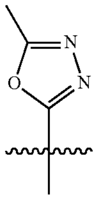 [SMILES: *c1nnc(C)o1] |
| 1-1036 | Cl | 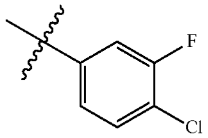 [SMILES: *c1ccc(Cl)c(F)c1] | 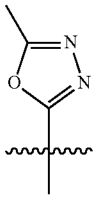 [SMILES: *c1nnc(C)o1] |
| 1-1037 | Cl | 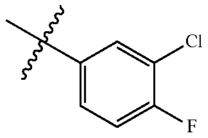 [SMILES: *c1ccc(F)c(Cl)c1] | 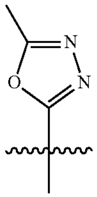 [SMILES: *c1nnc(C)o1] |

TABLE A1-continued
| | | | |
|---|---|---|---|
| 1-1038 | Cl | 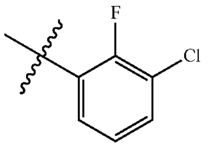 | 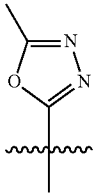 [SMILES: *c1nnc(C)o1] |
| 1-1039 | Cl | 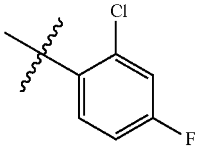 [SMILES: *c1ccc(F)cc1Cl] | 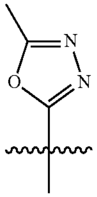 [SMILES: *c1nnc(C)o1] |
| 1-1040 | Cl | 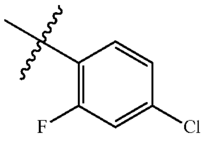 [SMILES: *c1ccc(Cl)cc1F] | 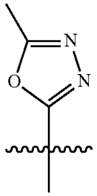 [SMILES: *c1nnc(C)o1] |
| 1-1041 | Cl | 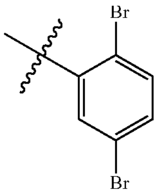 | 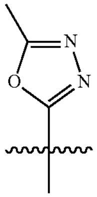 [SMILES: *c1nnc(C)o1] |
| 1-1042 | Cl | 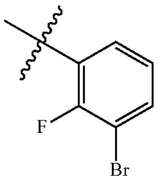 | 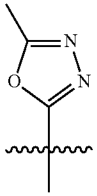 [SMILES: *c1nnc(C)o1] |

TABLE A1-continued
| | | | |
|---|---|---|---|
| 1-1043 | Cl | 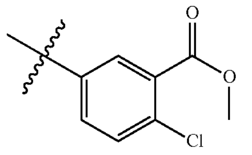 [SMILES: *c1ccc(Cl)c(C(=O)OC)c1] | 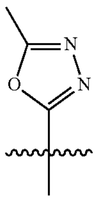 [SMILES: *c1nnc(C)o1] |
| 1-1044 | Cl | 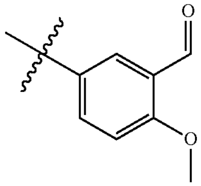 [SMILES: *c1ccc(OC)c(C=O)c1] | 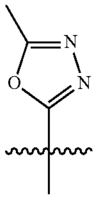 [SMILES: *c1nnc(C)o1] |
| 1-1045 | Cl | 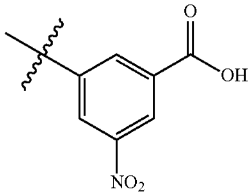 | 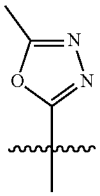 |
| 1-1046 | Cl | 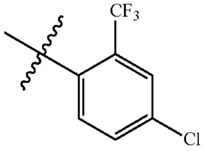 | 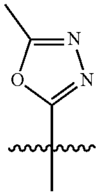 [SMILES: *c1nnc(C)o1] |
| 1-1047 | Cl | 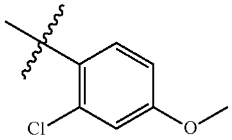 [SMILES: *c1ccc(OC)cc1Cl] | 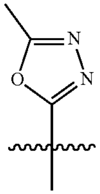 [SMILES: *c1nnc(C)o1] |

TABLE A1-continued
| | | | |
|---|---|---|---|
| 1-1048 | Cl | 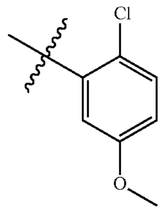 [SMILES: *c1cc(OC)ccc1Cl] | 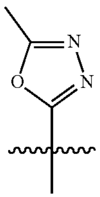 [SMILES: *c1nnc(C)o1] |
| 1-1049 | Cl | 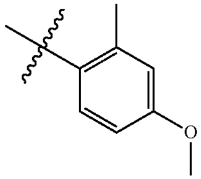 [SMILES: *c1ccc(OC)cc1C] | 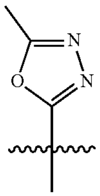 |
| 1-1050 | Cl | 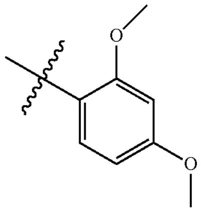 [SMILES: *c1ccc(OC)cc1OC] | 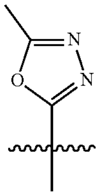 [SMILES: *c1nnc(C)o1] |
| 1-1051 | Cl | 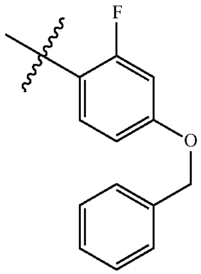 [SMILES: *c1ccc(OCc2ccccc2)cc1F] | 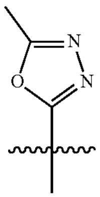 [SMILES: *c1nnc(C)o1] |

TABLE A1-continued
| | | | |
|---|---|---|---|
| 1-1052 | Cl | 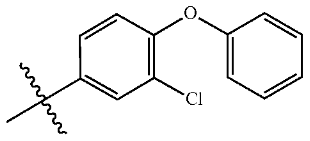 [SMILES: *c1ccc(Oc2ccccc2)c(Cl)c1] | 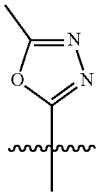 [SMILES: *c1nnc(C)o1] |
| 1-1053 | Cl | 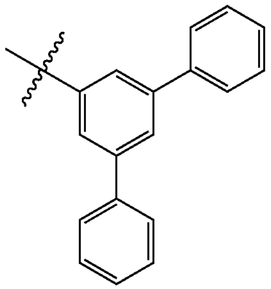 [SMILES: *c1cc(-c2ccccc2)cc(-c2ccccc2)c1] | 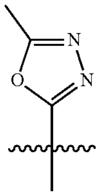 [SMILES: *c1nnc(C)o1] |
| 1-1054 | Cl | 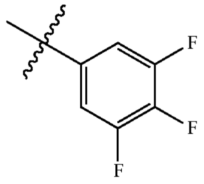 [SMILES: *c1cc(F)c(F)c(F)c1] | 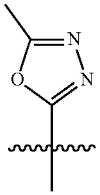 [SMILES: *c1nnc(C)o1] |
| 1-1055 | Cl | 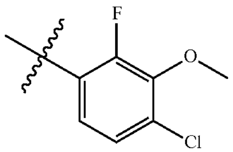 | 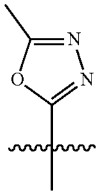 [SMILES: *c1nnc(C)o1] |

TABLE A1-continued
| | | | | |
|---|---|---|---|---|
| 1-1056 | Cl | 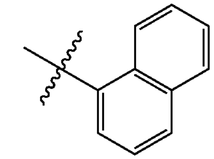 [SMILES: *c1cccc2ccccc12] | 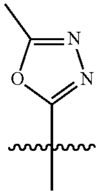 [SMILES: *c1nnc(C)o1] | |
| 1-1057 | Cl | 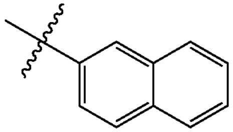 [SMILES: *c1ccc2ccccc2c1] | 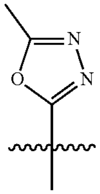 [SMILES: *c1nnc(C)o1] | $^1$H NMR (500 MHz, DMSO-d6) δ 12.09 (s, 1H), 8.86 (d, J = 5.0 Hz, 1H), 8.52 (d, J = 1.5 Hz, 1H), 8.17 (dd, J = 7.5, 1.5 Hz, 1H), 8.09-7.99 (m, 3H), 7.67-7.58 (m, 2H), 7.56 (d, J = 5.0 Hz, 1H), 2.44 (s, 3H). |
| 1-1058 | Cl | 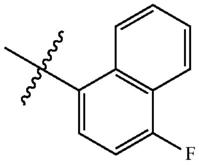 [SMILES: *c1ccc(F)c2ccccc12] | 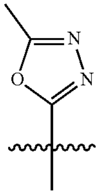 | |
| 1-1059 | Cl | 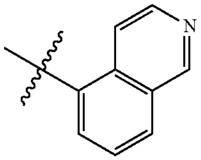 [SMILES: *c1cccc2cnccc12] | 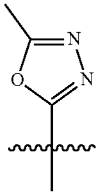 | $^1$H NMR (500 MHz, DMSO-d6) δ 12.09 (s, 1H), 9.26 (s, 1H), 8.84 (d, J = 5.0 Hz, 1H), 8.59 (d, J = 5.5 Hz, 1H), 8.22-8.13 (m, 2H), 7.86-7.79 (m, 2H), 7.60 (d, J = 5.0 Hz, 1H), 2.46 (s, 3H). |
| 1-1060 | Cl | 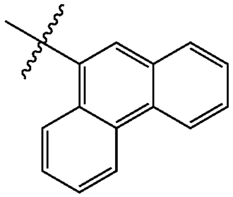 [SMILES: *c1cc2ccccc2c2ccccc12] | 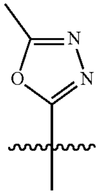 [SMILES: *c1nnc(C)o1] | $^1$H NMR (500 MHz, DMSO-d6) δ 12.08 (s, 1H), 8.90 (dd, J = 7.5, 1.5 Hz, 1H), 8.84 (d, J = 5.0 Hz, 1H), 8.81-8.73 (m, 1H), 8.38 (d, J = 1.5 Hz, 1H), 8.09-7.97 (m, 2H), 7.74-7.59 (m, 5H), 2.48 (s, 3H). |

TABLE A1-continued
| | | | | |
|---|---|---|---|---|
| 1-1061 | Cl | 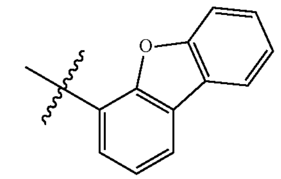 [SMILES: *c1cccc2c1oc1ccccc12] | 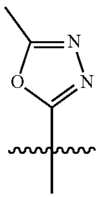 [SMILES: *c1nnc(C)o1] | $^1H$ NMR (500 MHz, DMSO-d6) δ 12.08 (s, 1H), 8.89 (d, J = 5.0 Hz, 1H), 8.20 (dd, J = 7.5, 1.5 Hz, 1H), 8.15-8.01 (m, 2H), 7.69 (d, J = 5.0 Hz, 1H), 7.64-7.57 (m, 2H), 7.48-7.41 (m, 1H), 7.39-7.26 (m, 1H), 2.45 (s, 3H). |
| 1-1062 | Cl | 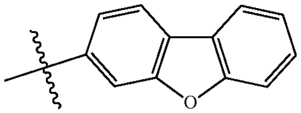 [SMILES: *c1ccc2c(c1)oc1ccccc12] | 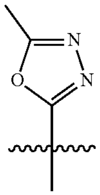 [SMILES: *c1nnc(C)o1] | |
| 1-1063 | Cl | 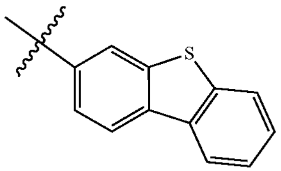 [SMILES: *c1ccc2c(c1)sc1ccccc12] | 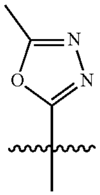 | $^1H$ NMR (500 MHz, DMSO-d6) δ 12.13 (s, 1H), 8.87 (d, J = 5.0 Hz, 1H), 8.52 (d, J = 1.5 Hz, 1H), 8.47 (dd, J = 7.5, 1.5 Hz, 1H), 8.38 (d, J = 7.5 Hz, 1H), 8.16-8.02 (m, 2H), 7.60-7.52 (m, 2H), 7.53-7.42 m, 1H), 2.44 (s, 3H). |
| 1-1064 | Cl | 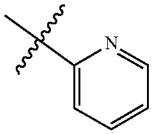 [SMILES: *c1ccccn1] | 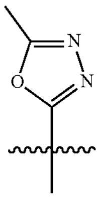 | |
| 1-1065 | Cl | 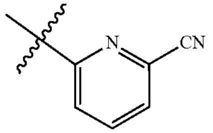 [SMILES: *c1cccc(C#N)n1] | 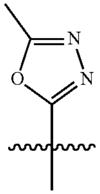 [SMILES: *c1nnc(C)o1] | |

TABLE A1-continued
| | | | |
|---|---|---|---|
| 1-1066 | Cl | 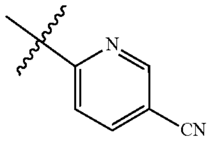 [SMILES: *c1ccc(C#N)cn1] | 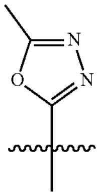 [SMILES: *c1nnc(C)o1] |
| 1-1067 | Cl | 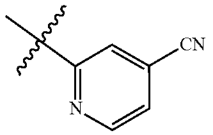 [SMILES: *c1cc(C#N)ccn1] | 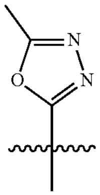 [SMILES: *c1nnc(C)o1] |
| 1-1068 | Cl | 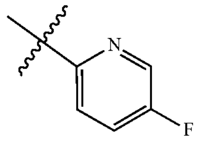 [SMILES: *c1ccc(F)cn1] | 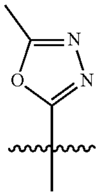 |
| 1-1069 | Cl | 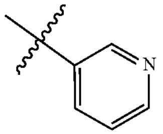 [SMILES: *c1cccnc1] | 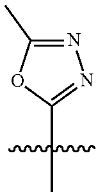 |
| 1-1070 | Cl | 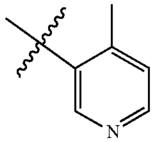 [SMILES: *c1cnccc1C] | 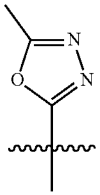 [SMILES: *c1nnc(C)o1] |

TABLE A1-continued
| | | | |
|---|---|---|---|
| 1-1071 | Cl | 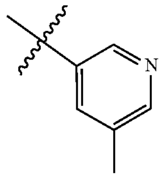 [SMILES: *c1cncc(C)c1] | 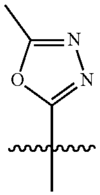 [SMILES: *c1nnc(C)o1] |
| 1-1072 | Cl | 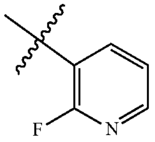 [SMILES: *c1cccnc1F] | 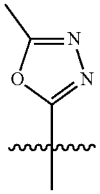 [SMILES: *c1nnc(C)o1] |
| 1-1073 | Cl | 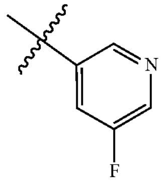 [SMILES: *c1cncc(F)c1] | 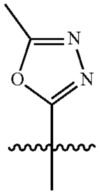 |
| 1-1074 | Cl | 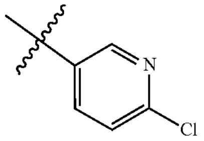 [SMILES: *c1ccc(Cl)nc1] | 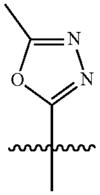 |
| 1-1075 | Cl | 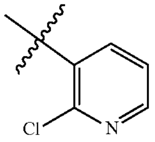 [SMILES: *c1cccnc1Cl] | 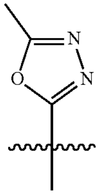 [SMILES: *c1nnc(C)o1] |

TABLE A1-continued
| | | | |
|---|---|---|---|
| 1-1076 | Cl | 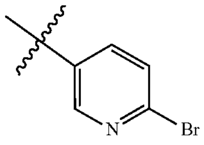 [SMILES: *c1ccc(Br)nc1] | 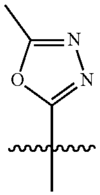 [SMILES: *c1nnc(C)o1] |
| 1-1077 | Cl | 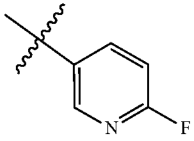 [SMILES: *c1ccc(F)nc1] | 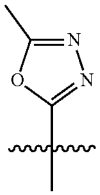 [SMILES: *c1nnc(C)o1] |
| 1-1078 | Cl | 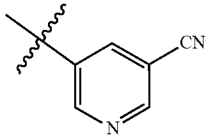 [SMILES: *c1cncc(C#N)c1] | 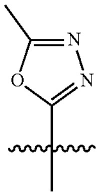 |
| 1-1079 | Cl | 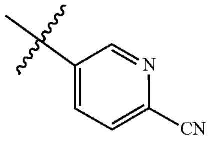 [SMILES: *c1ccc(C#N)nc1] | 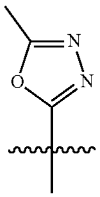 |
| 1-1080 | Cl | 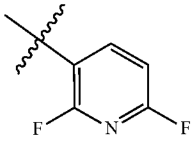 [SMILES: *c1ccc(F)nc1F] | 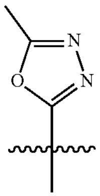 [SMILES: *c1nnc(C)o1] |

TABLE A1-continued
| | | | |
|---|---|---|---|
| 1-1081 | Cl | 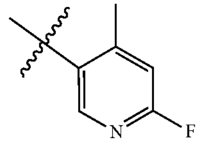 [SMILES: *c1cnc(F)cc1C] | 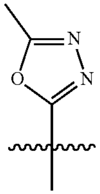 [SMILES: *c1nnc(C)o1] |
| 1-1082 | Cl | 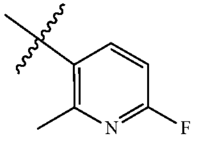 [SMILES: *c1ccc(F)nc1C] | 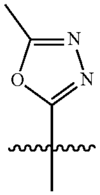 [SMILES: *c1nnc(C)o1] |
| 1-1083 | Cl | 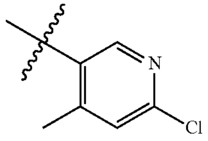 [SMILES: *c1cnc(Cl)cc1C] | 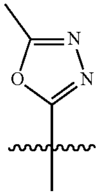 |
| 1-1084 | Cl | 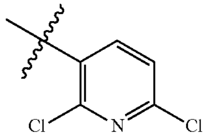 [SMILES: *c1ccc(Cl)nc1Cl] | 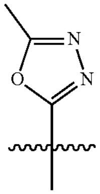 [SMILES: *c1nnc(C)o1] |
| 1-1085 | Cl | 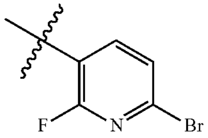 [SMILES: *c1ccc(Br)nc1F] | 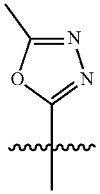 [SMILES: *c1nnc(C)o1] |

TABLE A1-continued
| | | | |
|---|---|---|---|
| 1-1086 | Cl | 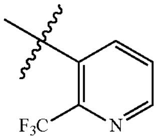 | 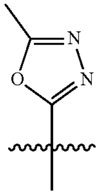 |
| 1-1087 | Cl | 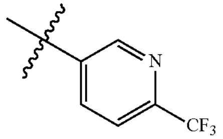 | 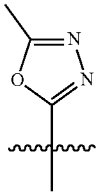 [SMILES: *c1nnc(C)o1] |
| 1-1088 | Cl | 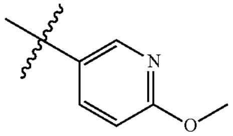 [SMILES: *c1ccc(OC)nc1] | 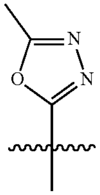 |
| 1-1089 | Cl | 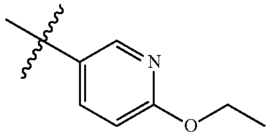 [SMILES: *c1ccc(OCC)nc1] | 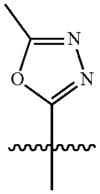 [SMILES: *c1nnc(C)o1] |
| 1-1090 | Cl | 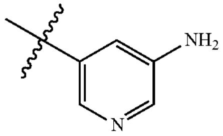 [SMILES: *c1cncc(N)c1] | 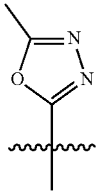 [SMILES: *c1nnc(C)o1] |

TABLE A1-continued
| | | | | |
|---|---|---|---|---|
| 1-1091 | Cl | 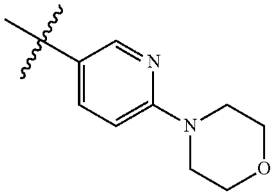 [SMILES: *c1ccc(N2CCOCC2)nc1] | 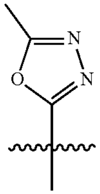 | |
| 1-1092 | Cl | 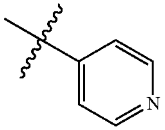 [SMILES: *c1ccncc1] | 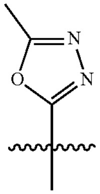 [SMILES: *c1nnc(C)o1] | |
| 1-1093 | Cl | 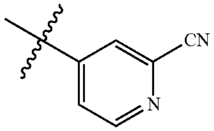 [SMILES: *c1ccnc(C#N)c1] | 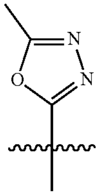 | |
| 1-1094 | Cl | 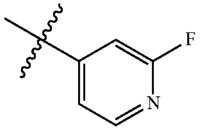 [SMILES: *c1ccnc(F)c1] | 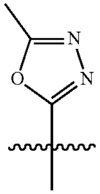 [SMILES: *c1nnc(C)o1] | $^1$H NMR (500 MHz, DMSO-d6) δ 12.13 (s, 1H), 8.76 (d, J = 5.0 Hz, 1H), 8.31 (dd, J = 5.5, 5.0 Hz, 1H), 8.16-8.01 (m, 1H), 7.88-7.85 (m, 1H), 7.73 (d, J = 5.0 Hz, 1H), 2.44 (s, 3H). |
| 1-1095 | Cl | 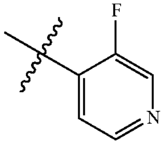 [SMILES: *c1ccncc1F] | 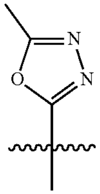 [SMILES: *c1nnc(C)o1] | |

TABLE A1-continued
| | | | |
|---|---|---|---|
| 1-1096 | Cl | 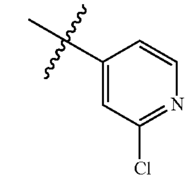 [SMILES: *c1ccnc(Cl)c1] | 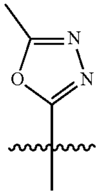 |
| 1-1097 | Cl | 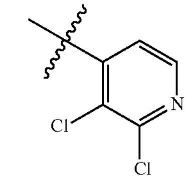 [SMILES: *c1ccnc(Cl)c1Cl] | 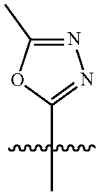 [SMILES: *c1nnc(C)o1] |
| 1-1098 | Cl | 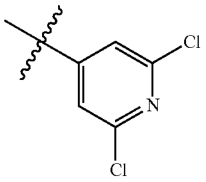 [SMILES: *c1cc(Cl)nc(Cl)c1] | 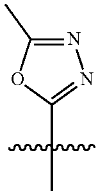 |
| 1-1099 | Cl | 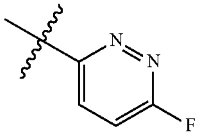 [SMILES: *c1ccc(F)nn1] | 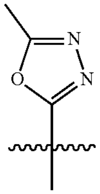 [SMILES: *c1nnc(C)o1] |
| 1-1100 | Cl | 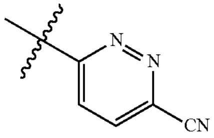 [SMILES: *c1ccc(C#N)nn1] | 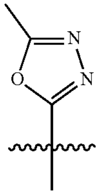 [SMILES: *c1nnc(C)o1] |

TABLE A1-continued
| | | | |
|---|---|---|---|
| 1-1101 | Cl | 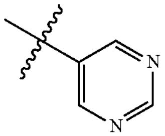 [SMILES: *c1cncnc1] | 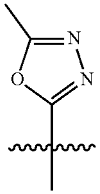 |
| 1-1102 | Cl | 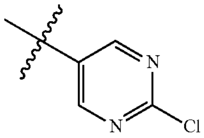 [SMILES: *c1cnc(Cl)nc1] | 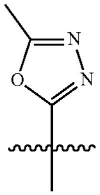 [SMILES: *c1nnc(C)o1] |
| 1-1103 | Cl | 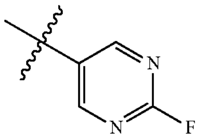 [SMILES: *c1cnc(F)nc1] | 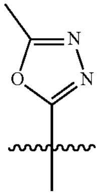 |
| 1-1104 | Cl | 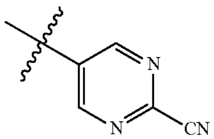 [SMILES: *c1cnc(C#N)nc1] | 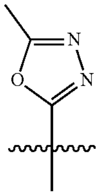 [SMILES: *c1nnc(C)o1] |
| 1-1105 | Cl | 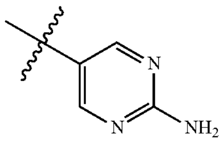 | 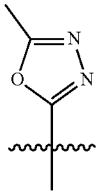 [SMILES: *c1nnc(C)o1] |

TABLE A1-continued
| | | | | |
|---|---|---|---|---|
| 1-1106 | Cl | 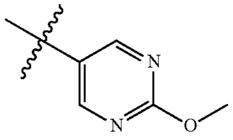 [SMILES: *c1cnc(OC)nc1] | 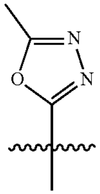 | $^1$H NMR (500 MHz, DMSO-d6) δ 12.11 (s, 1H), 9.48 (s, 2H), 8.80 (d, J = 5.0 Hz, 1H), 7.69 (d, J = 5.0 Hz, 1H), 3.85 (s, 3H), 2.44 (s, 3H). |
| 1-1107 | Cl | 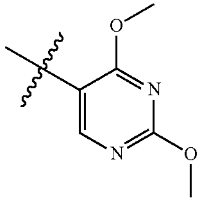 [SMILES: *c1cnc(OC)nc1OC] | 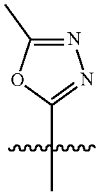 [SMILES: *c1nnc(C)o1] | |
| 1-1108 | Cl | 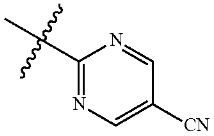 [SMILES: *c1ncc(C#N)cn1] | 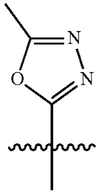 [SMILES: *c1nnc(C)o1] | |
| 1-1109 | Cl | 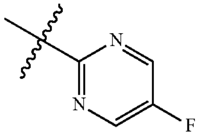 [SMILES: *c1ncc(F)cn1] | 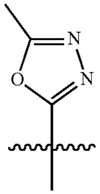 | |
| 1-1110 | Cl | 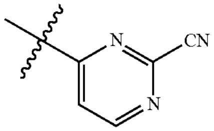 [SMILES: *c1ccnc(C#N)n1] | 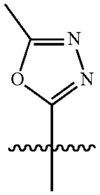 [SMILES: *c1nnc(C)o1] | |

TABLE A1-continued
| | | | |
|---|---|---|---|
| 1-1111 | Cl | 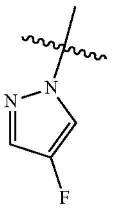 [SMILES: *n1cc(F)cn1] | 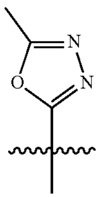 |
| 1-1112 | Cl | 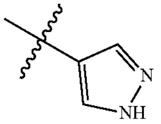 [SMILES: *c1cn[nH]c1] | 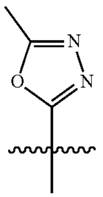 [SMILES: *c1nnc(C)o1] |
| 1-1113 | Cl | 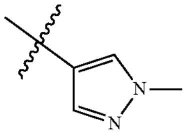 [SMILES: *c1cnn(C)c1] | 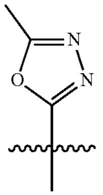 [SMILES: *c1nnc(C)o1] |
| 1-1114 | Cl | 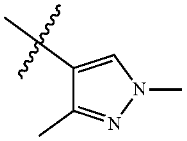 | 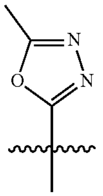 |
| 1-1115 | Cl | 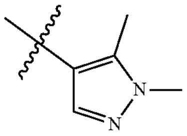 [SMILES: *c1cnn(C)c1C] | 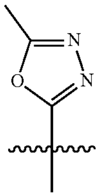 [SMILES: *c1nnc(C)o1] |

TABLE A1-continued
| | | | | |
|---|---|---|---|---|
| 1-1116 | Cl | 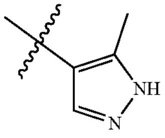 [SMILES: *c1cn[nH]c1C] | 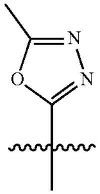 | |
| 1-1117 | Cl | 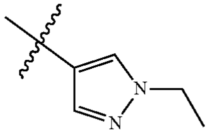 [SMILES: *c1cnn(CC)c1] | 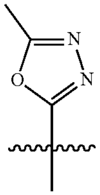 [SMILES: *c1nnc(C)o1] | |
| 1-1118 | Cl | 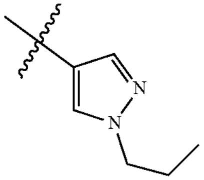 [SMILES: *c1cnn(CCC)c1] | 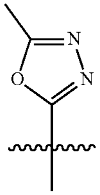 | |
| 1-1119 | Cl | 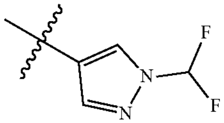 [SMILES: *c1cnn(C(F)F)c1] | 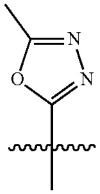 [SMILES: *c1nnc(C)o1] | |
| 1-1120 | Cl | 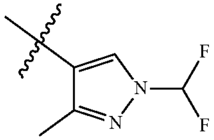 [SMILES: *c1cn(C(F)F)nc1C] | 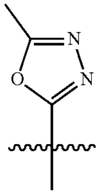 [SMILES: *c1nnc(C)o1] | $^1$H NMR (500 MHz, DMSO-d6) δ 12.25 (s, 1H), 8.88 (d, J = 5.0 Hz, 1H), 7.84 (t, J = 65.0 Hz, 1H), 7.65 (d, J = 5.0 Hz, 1H), 6.98 (s, 1H), 2.45 (s, 3H), 2.39 (s, 3H). |

TABLE A1-continued
| | | | |
|---|---|---|---|
| 1-1121 | Cl | 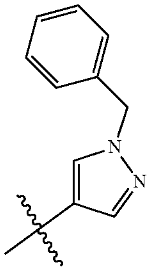 [SMILES: *c1cnn(Cc2ccccc2)c1] | 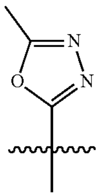 [SMILES: *c1nnc(C)o1] |
| 1-1122 | Cl | 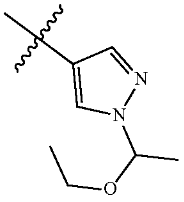 [SMILES: *c1cnn(C(C)OCC)c1] | 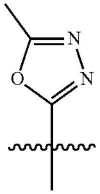 [SMILES: *c1nnc(C)o1] |
| 1-1123 | Cl | 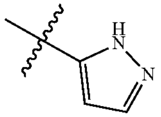 [SMILES: *c1ccn[nH]1] | 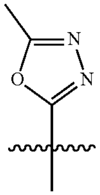 [SMILES: *c1nnc(C)o1] |
| 1-1124 | Cl | 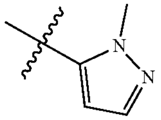 [SMILES: *c1ccnn1C] | 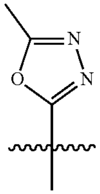 [SMILES: *c1nnc(C)o1] |
| 1-1125 | Cl | 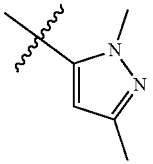 [SMILES: *c1cc(C)nn1C] | 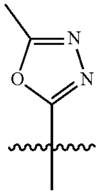 [SMILES: *c1nnc(C)o1] |

TABLE A1-continued
| | | | |
|---|---|---|---|
| 1-1126 | Cl | 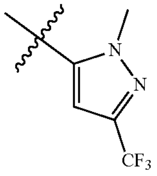 | 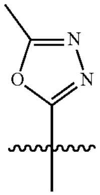 [SMILES: *c1nnc(C)o1] |
| 1-1127 | Cl | 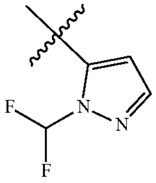 [SMILES: *c1ccnn1C(F)F] | 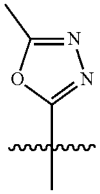 [SMILES: *c1nnc(C)o1] |
| 1-1128 | Cl | 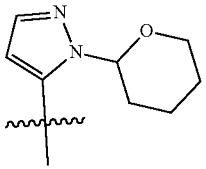 [SMILES: *c1ccnn1C1CCCCO1] | 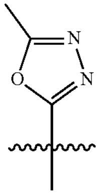 [SMILES: *c1nnc(C)o1] |
| 1-1129 | Cl | 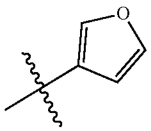 [SMILES: *c1ccoc1] | 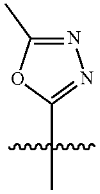 |
| 1-1130 | Cl | 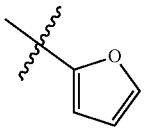 [SMILES: *c1ccco1] | 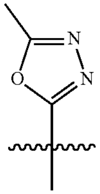 [SMILES: *c1nnc(C)o1] |

TABLE A1-continued
| | | | | |
|---|---|---|---|---|
| 1-1131 | Cl | 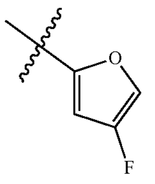 [SMILES: *c1cc(F)co1] | 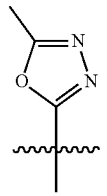 [SMILES: *c1nnc(C)o1] | $^1H$ NMR (500 MHz, DMSO-d6) δ 12.05 (s, 1H), 9.17 (d, J = 5.0 Hz, 1H), 8.05 (d, J = 5.0 Hz, 1H), 7.49-7.32 (m, 1H), 6.38-6.27 (m, 1H), 2.63 (s, 3H). |
| 1-1132 | Cl | 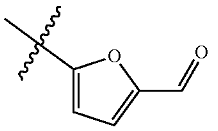 [SMILES: *c1ccc(C=O)o1] | 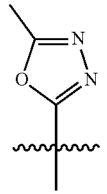 [SMILES: *c1nnc(C)o1] | |
| 1-1133 | Cl | 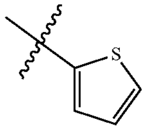 [SMILES: *c1cccs1] | 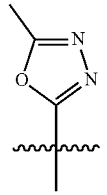 [SMILES: *c1nnc(C)o1] | |
| 1-1134 | Cl | 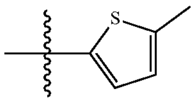 [SMILES: *c1ccc(C)s1] | 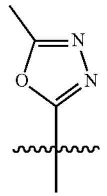 [SMILES: *c1nnc(C)o1] | |
| 1-1135 | Cl | 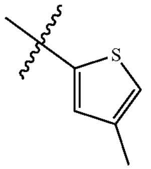 [SMILES: *c1cc(C)cs1] | 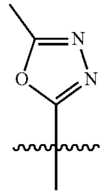 [SMILES: *c1nnc(C)o1] | |

TABLE A1-continued
| | | | |
|---|---|---|---|
| 1-1136 | Cl | 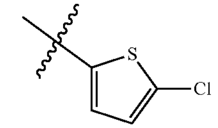 [SMILES: *c1ccc(Cl)s1] | 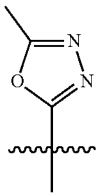 [SMILES: *c1nnc(C)o1] |
| 1-1137 | Cl | 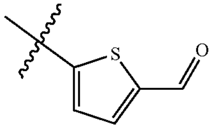 [SMILES: *c1ccc(C=O)s1] | 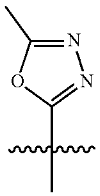 [SMILES: *c1nnc(C)o1] |
| 1-1138 | Cl | 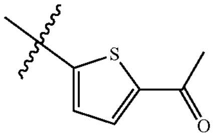 [SMILES: *c1ccc(C(C)=O)s1] | 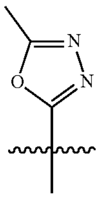 [SMILES: *c1nnc(C)o1] |
| 1-1139 | Cl | 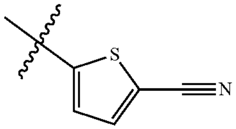 [SMILES: *c1ccc(C#N)s1] | 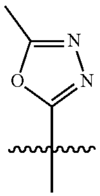 [SMILES: *c1nnc(C)o1] |
| 1-1140 | Cl | 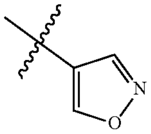 | 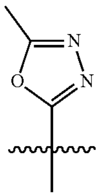 [SMILES: *c1nnc(C)o1] |

TABLE A1-continued
| | | | | |
|---|---|---|---|---|
| 1-1141 | $CH_3$ | 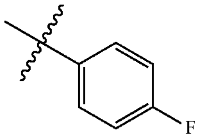 [SMILES: *c1ccc(F)cc1] | 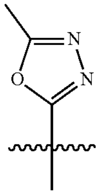 [SMILES: *c1nnc(C)o1] | |
| 1-1142 | F | 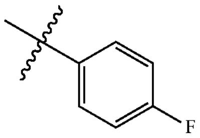 [SMILES: *c1ccc(F)cc1] | 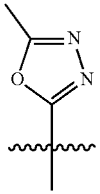 [SMILES: *c1nnc(C)o1] | |
| 1-1143 | Br | 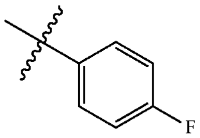 [SMILES: *c1ccc(F)cc1] | 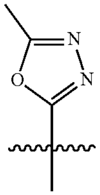 [SMILES: *c1nnc(C)o1] | |
| 1-1144 | 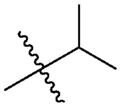 [SMILES: *C(C)C] | 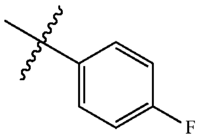 [SMILES: *c1ccc(F)cc1] | 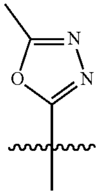 [SMILES: *c1nnc(C)o1] | |
| 1-1145 | $CF_3$ | 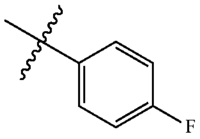 | 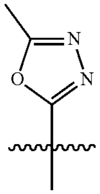 [SMILES: *c1nnc(C)o1] | $^1H$ NMR (500 MHz, DMSO-d6) δ 12.13 (s, 1H), 8.72 (d, J = 5.0 Hz, 1H), 8.00-7.93 (m, 2H), 7.48 (d, J = 5.0 Hz, 1H), 7.35-7.27 (m, 2H), 2.45 (s, 3H). |

TABLE A1-continued
| | | | | |
|---|---|---|---|---|
| 1-1146 | 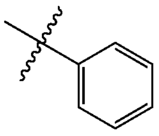 [SMILES: *c1ccccc1] | 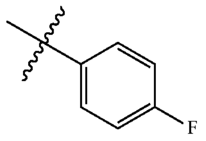 [SMILES: *c1ccc(F)cc1] | 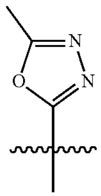 [SMILES: *c1nnc(C)o1] | |
| 1-1147 | 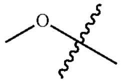 | 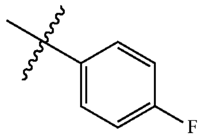 [SMILES: *c1ccc(F)cc1] | 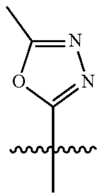 [SMILES: *c1nnc(C)o1] | $^1$H NMR (500 MHz, DMSO-d6) δ 12.11 (s, 1H), 8.53 (d, J = 5.0 Hz, 1H), 8.06-7.98 (m, 2H), 7.46 (d, J = 5.0 Hz, 1H), 7.35-7.27 (m, 2H), 3.64 (s, 3H), 2.45 (s, 3H). |
| 1-1148 | 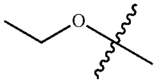 | 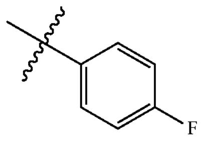 [SMILES: *c1ccc(F)cc1] | 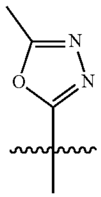 [SMILES: *c1nnc(C)o1] | |
| 1-1149 | 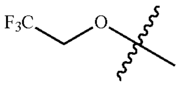 | 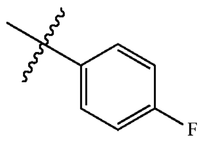 [SMILES: *c1ccc(F)cc1] | 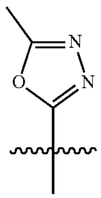 [SMILES: *c1nnc(C)o1] | |
| 1-1150 | 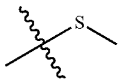 [SMILES: *SC] | 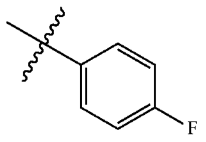 | 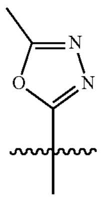 | $^1$H NMR (500 MHz, DMSO-d6) δ 12.60 (s, 1H), 8.54 (d, J = 5.0 Hz, 1H), 8.01-7.93 (m, 2H), 7.41 (d, J = 5.0 Hz, 1H), 7.35-7.27 (m, 2H), 2.45 (s, 3H), 2.20 (s, 3H). |

TABLE A1-continued
| | | | | |
|---|---|---|---|---|
| 1-1151 | 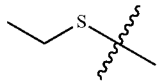 | 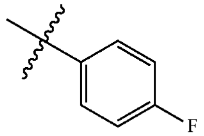 [SMILES: *c1ccc(F)cc1] | 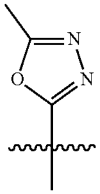 [SMILES: *c1nnc(C)o1] | |
| 1-1152 | 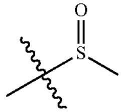 [SMILES: *S(C)=O] | 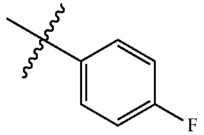 [SMILES: *c1ccc(F)cc1] | 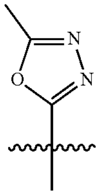 [SMILES: *c1nnc(C)o1] | $^1$H NMR (500 MHz, DMSO-d6) δ 12.03 (s, 1H), 8.88 (d, J = 5.0 Hz, 1H), 7.97-7.89 (m, 2H), 7.40 (d, J = 5.0 Hz, 1H), 7.35-7.27 (m, 2H), 2.45 (s, 3H), 2.37 (s, 3H). |
| 1-1153 | 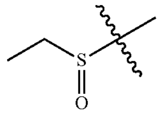 [SMILES: *S(=O)CC] | 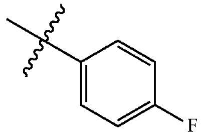 | 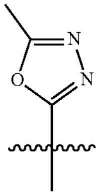 | |
| 1-1154 | 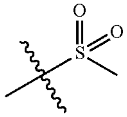 [SMILES: *S(C)(=O)=O] | 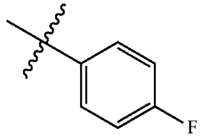 [SMILES: *c1ccc(F)cc1] | 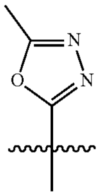 | |
| 1-1155 | 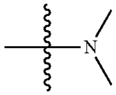 [SMILES: *N(C)C] | 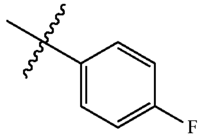 [SMILES: *c1ccc(F)cc1] | 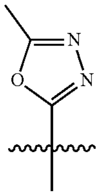 | $^1$H NMR (500 MHz, DMSO-d6) δ 12.08 (s, 1H), 8.35 (d, J = 5.0 Hz, 1H), 7.95-7.88 (m, 1H), 7.46 (d, J = 5.0 Hz, 1H), 7.35-7.27 (m, 2H), 2.72 (s, 6H), 2.44 (s, 3H). |

TABLE A1-continued
| | | | | |
|---|---|---|---|---|
| 1-1156 | 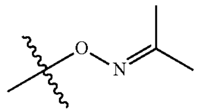 | 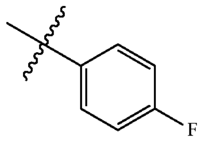 [SMILES: *c1ccc(F)cc1] | 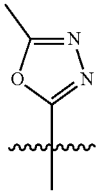 [SMILES: *c1nnc(C)o1] | |
| 1-1157 | Et | 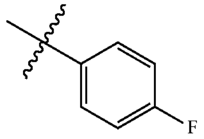 [SMILES: *c1ccc(F)cc1] | 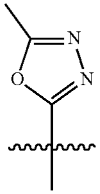 [SMILES: *c1nnc(C)o1] | $^1$H NMR (500 MHz, DMSO-d6) δ 12.08 (s, 1H), 8.54 (d, J = 5.0 Hz, 1H), 8.07-7.81 (m, 2H), 7.52-7.20 (m, 3H), 2.70 (q, J = 8.0 Hz, 2H), 2.45 (s, 3H), 1.07 (t, J = 8.0 Hz, 3H). |
| 1-1158 | 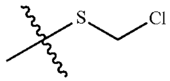 [SMILES: *SCCl] | 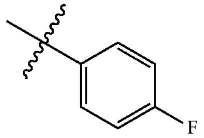 [SMILES: *c1ccc(F)cc1] | 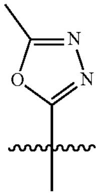 | |
| 1-1159 | $NO_2$ | 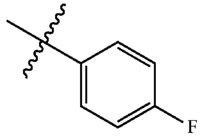 [SMILES: *c1ccc(F)cc1] | 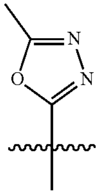 | $^1$H NMR (500 MHz, DMSO-d6) δ 12.12 (s, 1H), 8.92 (d, J = 5.0 Hz, 1H), 7.95-7.87 (m, 2H), 7.62 (d, J = 5.0 Hz, 1H), 7.35-7.27 (m, 2H), 2.47 (s, 3H). |
| 1-1160 | CN | 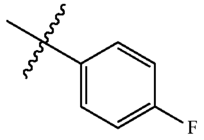 [SMILES: *c1ccc(F)cc1] | 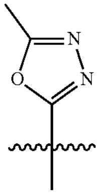 | $^1$H NMR (500 MHz, DMSO-d6) δ 12.06 (s, 1H), 8.98 (d, J = 5.0 Hz, 1H), 8.02-7.95 (m, 2H), 7.64 (d, J = 5.0 Hz, 1H), 7.35-7.27 (m, 2H), 2.46 (s, 3H). |

TABLE A1-continued
| | | | | |
|---|---|---|---|---|
| 1-1161 | 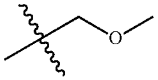 [SMILES: *COC] | 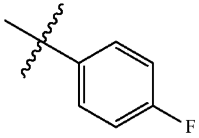 [SMILES: *c1ccc(F)cc1] | 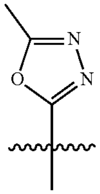 [SMILES: *c1nnc(C)o1] | |
| 1-1162 | 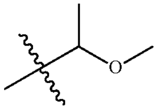 [SMILES: *C(C)OC] | 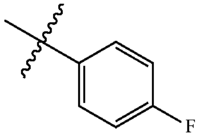 [SMILES: *c1ccc(F)cc1] | 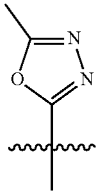 [SMILES: *c1nnc(C)o1] | |
| 1-1163 | 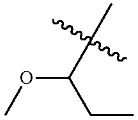 [SMILES: *C(CC)OC] | 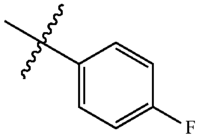 [SMILES: *c1ccc(F)cc1] | 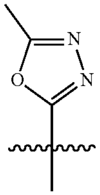 [SMILES: *c1nnc(C)o1] | |
| 1-1164 | 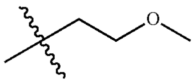 [SMILES: *CCOC] | 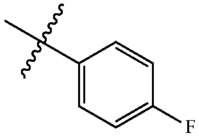 [SMILES: *c1ccc(F)cc1] | 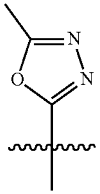 [SMILES: *c1nnc(C)o1] | |
| 1-1165 | 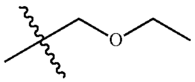 [SMILES: *COCC] | 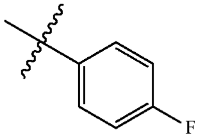 [SMILES: *c1ccc(F)cc1] | 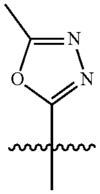 [SMILES: *c1nnc(C)o1] | $^1$H NMR (500 MHz, DMSO-d6) δ 12.06 (s, 1H), 8.65 (d, J = 5.0 Hz, 1H), 8.01-7.94 (m, 2H), 7.40 (d, J = 5.0 Hz, 1H), 7.35-7.27 (m, 2H), 4.68 (s, 2H), 3.58 (q, J = 8.0 Hz, 2H), 2.45 (s, 3H), 1.18 (t, J = 8.0 Hz, 3H). |

TABLE A1-continued
| | | | | |
|---|---|---|---|---|
| 1-1166 | 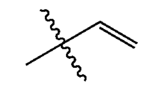 [SMILES: *C=C] | 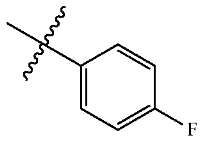 [SMILES: *c1ccc(F)cc1] | 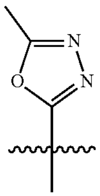 [SMILES: *c1nnc(C)o1] | $^1$H NMR (500 MHz, DMSO-d6) δ 12.06 (s, 1H), 8.58 (d, J = 5.0 Hz, 1H), 8.01-7.93 (m, 2H), 7.35-7.27 (m, 2H), 7.19 (d, J = 5.0 Hz, 1H), 6.62-6.48 (m, 1H), 5.48-5.36 (m, 1H), 5.30-5.22 (m, 1H), 2.43 (s, 3H). |
| 1-1167 | 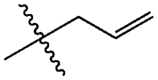 [SMILES: *CC=C] | 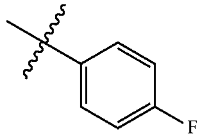 [SMILES: *c1ccc(F)cc1] | 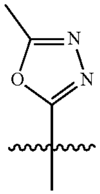 [SMILES: *c1nnc(C)o1] | |
| 1-1168 | 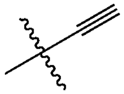 [SMILES: *C#C] | 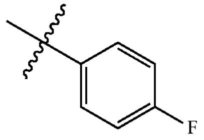 [SMILES: *c1ccc(F)cc1] | 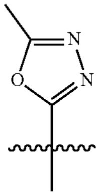 [SMILES: *c1nnc(C)o1] | |
| 1-1169 | 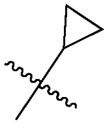 [SMILES: *C1CC1] | 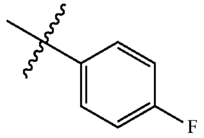 [SMILES: *c1ccc(F)cc1] | 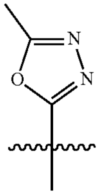 [SMILES: *c1nnc(C)o1] | |
| 1-1170 | 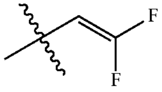 | 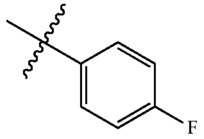 [SMILES: *c1ccc(F)cc1] | 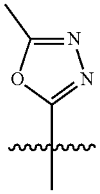 [SMILES: *c1nnc(C)o1] | |

TABLE A1-continued
| | | | | |
|---|---|---|---|---|
| 1-1171 | 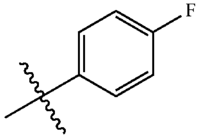 [SMILES: *c1ccc(F)cc1] | 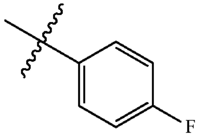 [SMILES: *c1ccc(F)cc1] | 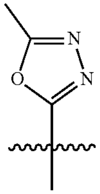 [SMILES: *c1nnc(C)o1] | $^1H$ NMR (500 MHz, DMSO-d6) δ 12.08 (s, 1H), 8.92 (d, J = 5.0 Hz, 1H), 7.98-7.91 (m, 2H), 7.57-7.47 (m, 3H), 7.35-7.27 (m, 2H), 7.23-7.15 (m, 2H), 2.43 (s, 3H). |
| 1-1172 | Cl | 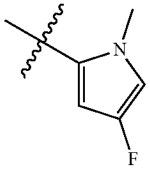 [SMILES: *c1cc(F)cn1C] | 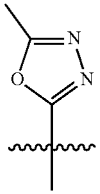 [SMILES: *c1nnc(C)o1] | |
| 1-1173 | Cl | 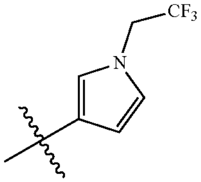 [SMILES: *c1ccn(CC(F)(F)F)c1] | 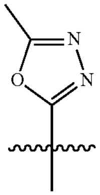 [SMILES: *c1nnc(C)o1] | |
| 1-1174 | Cl | 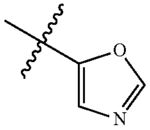 | 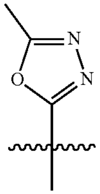 [SMILES: *c1nnc(C)o1] | |
| 1-1175 | Cl | 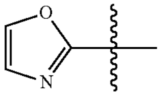 | 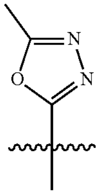 [SMILES: *c1nnc(C)o1] | |

TABLE A1-continued
| | | | |
|---|---|---|---|
| 1-1176 | Cl | 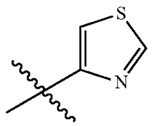 [SMILES: *c1cscn1] | 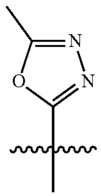 [SMILES: *c1nnc(C)o1] |
| 1-1177 | Cl | 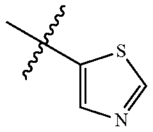 [SMILES: *c1cncs1] | 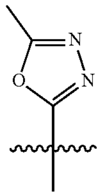 [SMILES: *c1nnc(C)o1] |
| 1-1178 | Cl | 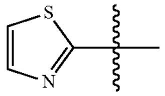 | 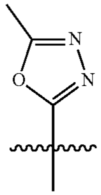 [SMILES: *c1nnc(C)o1] |
| 1-1179 | Cl | 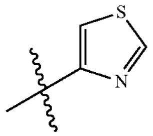 [SMILES: *c1cscn1] | 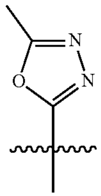 [SMILES: *c1nnc(C)o1] |
| 1-1180 | Cl | 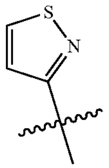 [SMILES: *c1ccsn1] | 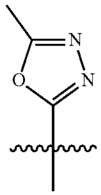 [SMILES: *c1nnc(C)o1] |

TABLE A1-continued
| | | | |
|---|---|---|---|
| 1-1181 | Cl | 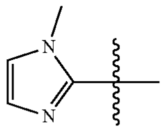 | 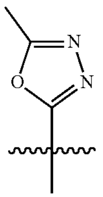 [SMILES: *c1nnc(C)o1] |
| 1-1182 | Cl | 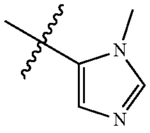 [SMILES: *c1cncn1C] | 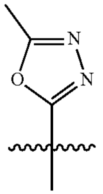 [SMILES: *c1nnc(C)o1] |
| 1-1183 | Cl | 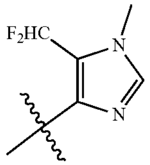 [SMILES: *c1ncn(C)c1C(F)F] | 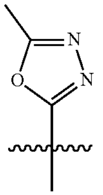 [SMILES: *c1nnc(C)o1] |
| 1-1184 | Cl | 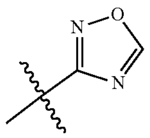 [SMILES: *c1ncon1] | 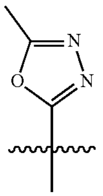 |
| 1-1185 | Cl | 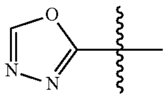 [SMILES: *c1nnco1] | 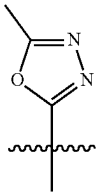 [SMILES: *c1nnc(C)o1] |

TABLE A1-continued
| | | | |
|---|---|---|---|
| 1-1186 | Cl | 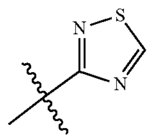 [SMILES: *c1ncsn1] | 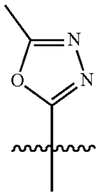 |
| 1-1187 | Cl | 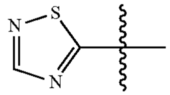 [SMILES: *c1ncns1] | 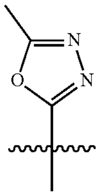 [SMILES: *c1nnc(C)o1] |
| 1-1188 | Cl | 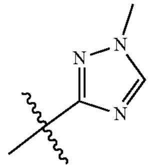 [SMILES: *c1ncn(C)n1] | 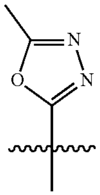 [SMILES: *c1nnc(C)o1] |
| 1-1189 | Cl | 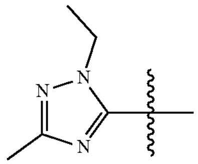 [SMILES: *c1nc(C)nn1CC] | 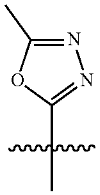 [SMILES: *c1nnc(C)o1] |
| 1-1190 | Cl | 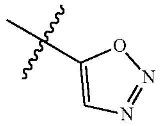 [SMILES: *c1cnno1] | 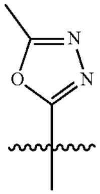 [SMILES: *c1nnc(C)o1] |

TABLE A1-continued
| | | | |
|---|---|---|---|
| 1-1191 | Cl | 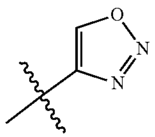 [SMILES: *c1conn1] | 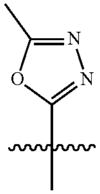 |
| 1-1192 | Cl | 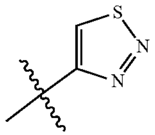 [SMILES: *c1csnn1] | 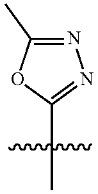 |
| 1-1193 | Cl | 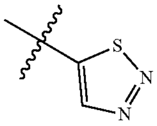 [SMILES: *c1cnns1] | 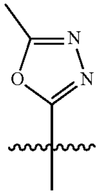 [SMILES: *c1nnc(C)o1] |
| 1-1194 | Cl | 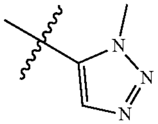 [SMILES: *c1cnnn1C] | 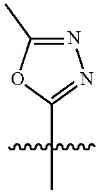 [SMILES: *c1nnc(C)o1] |
| 1-1195 | Cl | 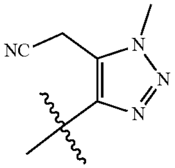 [SMILES: *c1nnn(C)c1CC#N] | 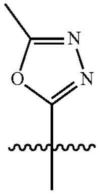 |

TABLE A1-continued
| | | | |
|---|---|---|---|
| 1-1196 | Cl | 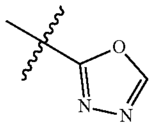 [SMILES: *c1nnco1] | 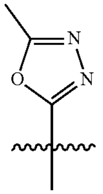 [SMILES: *c1nnc(C)o1] |
| 1-1197 | Cl | 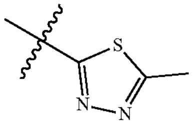 [SMILES: *c1nnc(C)s1] | 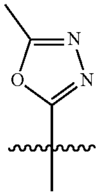 [SMILES: *c1nnc(C)o1] |
| 1-1198 | Cl | 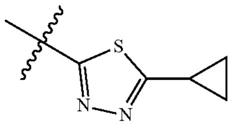 | 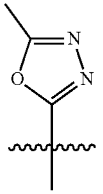 [SMILES: *c1nnc(C)o1] |
| 1-1199 | Cl | 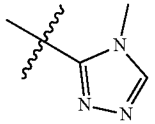 [SMILES: *c1nncn1C] | 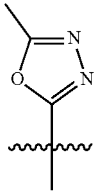 [SMILES: *c1nnc(C)o1] |
| 1-1200 | Cl | 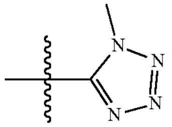 [SMILES: *c1nnnn1C] | 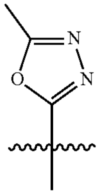 [SMILES: *c1nnc(C)o1] |

TABLE A1-continued
| | | | |
|---|---|---|---|
| 1-1201 | Cl | 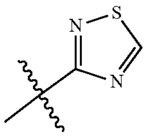 [SMILES: *c1ncsn1] | 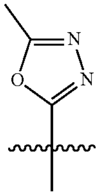 [SMILES: *c1nnc(C)o1] |
| 1-1202 | Cl | 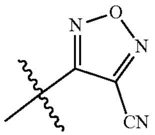 [SMILES: *c1nonc1C#N] | 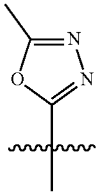 |
| 1-1203 | Cl | 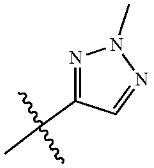 [SMILES: *c1cnn(C)n1] | 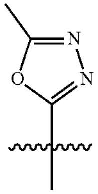 |
| 1-1204 | Cl | 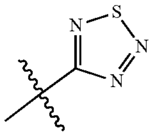 [SMILES: *c1nnsn1] | 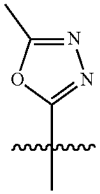 |
| 1-1205 | Cl | 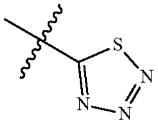 [SMILES: *c1nnns1] | 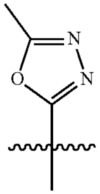 [SMILES: *c1nnc(C)o1] |

TABLE A1-continued
| | | | |
|---|---|---|---|
| 1-1206 | Cl | 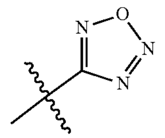 [SMILES: *c1nnon1] | 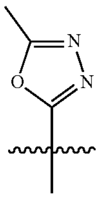 [SMILES: *c1nnc(C)o1] |
| 1-1207 | Cl | 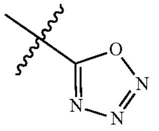 | 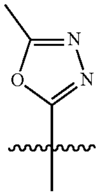 |
| 1-1208 | Cl | 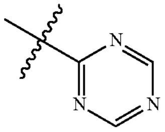 | 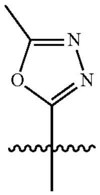 [SMILES: *c1nnc(C)o1] |
| 1-1209 | Cl | 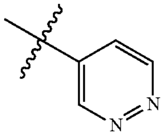 [SMILES: *c1ccnnc1] | 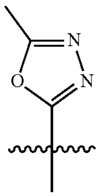 |
| 1-1210 | Cl | 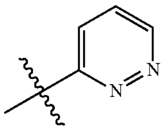 [SMILES: *c1cccnn1] | 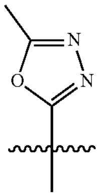 |

TABLE A1-continued
| | | | |
|---|---|---|---|
| 1-1211 | Cl | 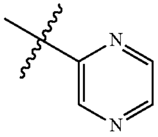 [SMILES: *c1cnccn1] | 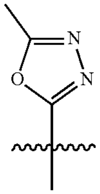 |
| 1-1212 | Cl | 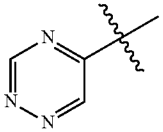 [SMILES: *c1cnncn1] | 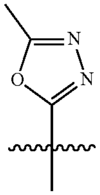 |
| 1-1213 | Cl | 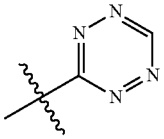 [SMILES: *c1nncnn1] | 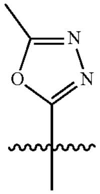 [SMILES: *c1nnc(C)o1] |
| 1-1214 | Cl | 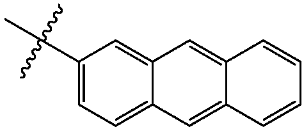 [SMILES: *c1ccc2cc3ccccc3cc2c1] | 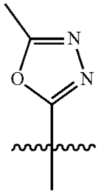 [SMILES: *c1nnc(C)o1] |
| 1-1215 | Cl | 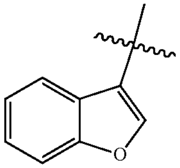 [SMILES: *c1coc2ccccc12] | 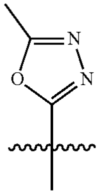 |

TABLE A1-continued
| | | | |
|---|---|---|---|
| 1-1216 | Cl | 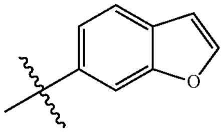 [SMILES: *c1ccc2ccoc2c1] | 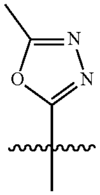 [SMILES: *c1nnc(C)o1] |
| 1-1217 | Cl | 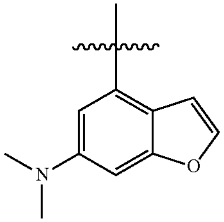 [SMILES: *c1cc(N(C)C)cc2occc12] | 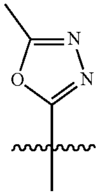 |
| 1-1218 | Cl | 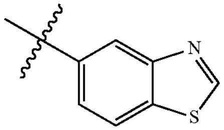 [SMILES: *c1ccc2scnc2c1] | 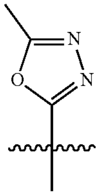 |
| 1-1219 | Cl | 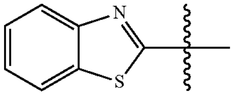 | 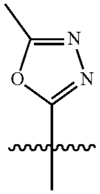 [SMILES: *c1nnc(C)o1] |
| 1-1220 | Cl | 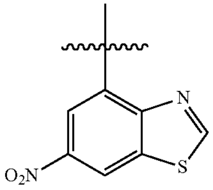 | 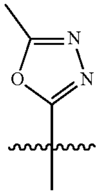 [SMILES: *c1nnc(C)o1] |

TABLE A1-continued
| | | | |
|---|---|---|---|
| 1-1221 | Cl | 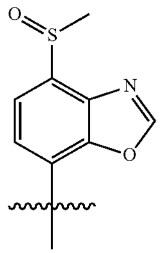 [SMILES: *c1ccc(S(C)=O)c2ncoc12] | 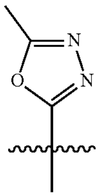 [SMILES: *c1nnc(C)o1] |
| 1-1222 | Cl | 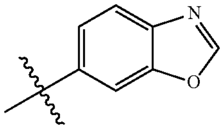 [SMILES: *c1ccc2ncoc2c1] | 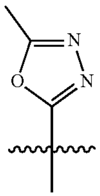 [SMILES: *c1nnc(C)o1] |
| 1-1223 | Cl | 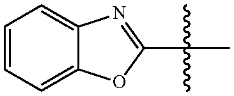 [SMILES: *c1nc2ccccc2o1] | 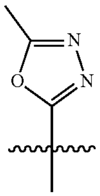 |
| 1-1224 | Cl | 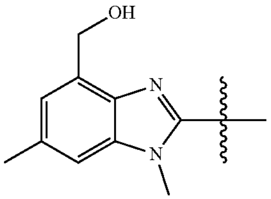 [SMILES: *c1nc2c(CO)cc(C)cc2n1C] | 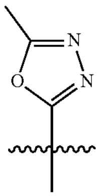 |
| 1-1225 | Cl | 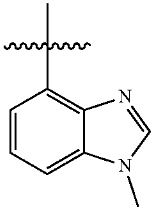 [SMILES: *c1cccc2c1ncn2C] | 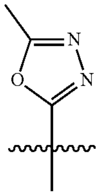 [SMILES: *c1nnc(C)o1] |

TABLE A1-continued
| | | | |
|---|---|---|---|
| 1-1226 | Cl | 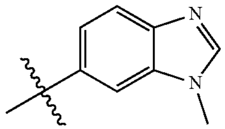 [SMILES: *c1ccc2ncn(C)c2c1] | 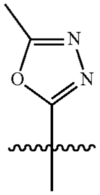 |
| 1-1227 | Cl | 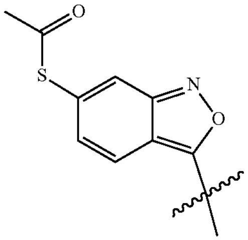 [SMILES: *c1onc2cc(SC(C)=O)ccc12] | 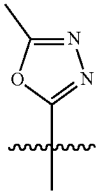 |
| 1-1228 | Cl | 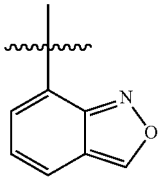 | 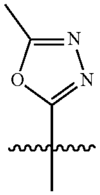 [SMILES: *c1nnc(C)o1] |
| 1-1229 | Cl | 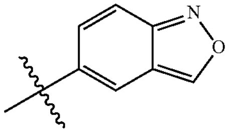 [SMILES: *c1ccc2nocc2c1] | 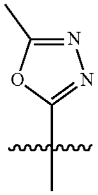 |
| 1-1230 | Cl | 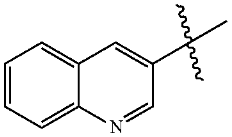 [SMILES: *c1cnc2ccccc2c1] | 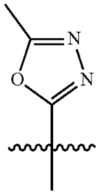 |

TABLE A1-continued
| | | | |
|---|---|---|---|
| 1-1231 | Cl | 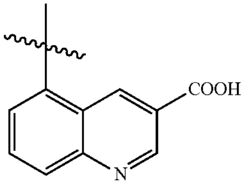 [SMILES: *c1cccc2ncc(C(=O)O)cc12] | 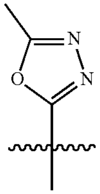 [SMILES: *c1nnc(C)o1] |
| 1-1232 | Cl | 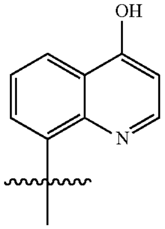 [SMILES: *c1cccc2c(O)ccnc12] | 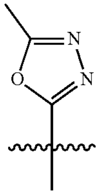 [SMILES: *c1nnc(C)o1] |
| 1-1233 | Cl | 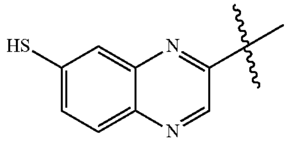 [SMILES: *c1cnc2ccc(S)cc2n1] | 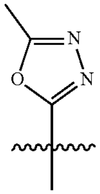 [SMILES: *c1nnc(C)o1] |
| 1-1234 | Cl | 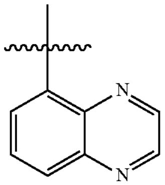 [SMILES: *c1cccc2nccnc12] | 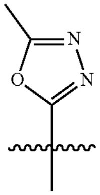 |
| 1-1235 | Cl | 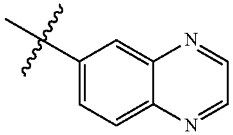 [SMILES: *c1ccc2nccnc2c1] | 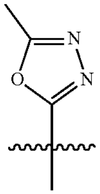 [SMILES: *c1nnc(C)o1] |

TABLE A1-continued
| | | | |
|---|---|---|---|
| 1-1236 | Cl | 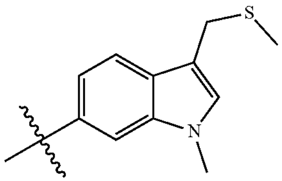 [SMILES: *c1ccc2c(CSC)cn(C)c2c1] | 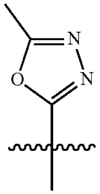 [SMILES: *c1nnc(C)o1] |
| 1-1237 | Cl | 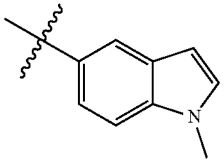 [SMILES: *c1ccc2c(ccn2C)c1] | 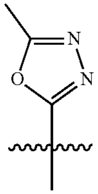 [SMILES: *c1nnc(C)o1] |
| 1-1238 | Cl | 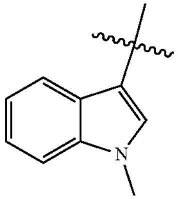 [SMILES: *c1cn(C)c2ccccc12] | 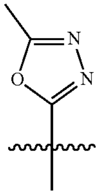 |
| 1-1239 | Cl | 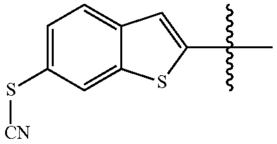 | 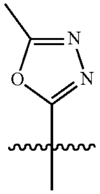 [SMILES: *c1nnc(C)o1] |
| 1-1240 | Cl | 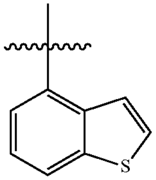 [SMILES: *c1cccc2sccc12] | 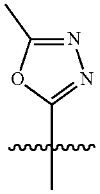 |

TABLE A1-continued
| | | | |
|---|---|---|---|
| 1-1241 | Cl | 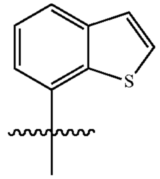 [SMILES: *c1cccc2ccsc12] | 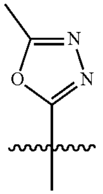 |
| 1-1242 | Cl | 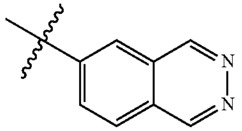 [SMILES: *c1ccc2cnncc2c1] | 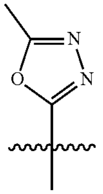 |
| 1-1243 | Cl | 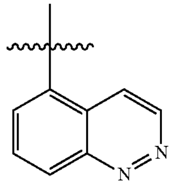 [SMILES: *c1cccc2nnccc12] | 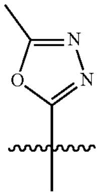 [SMILES: *c1nnc(C)o1] |
| 1-1244 | Cl | 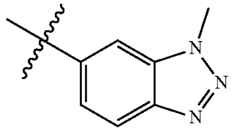 [SMILES: *c1ccc2nnn(C)c2c1] | 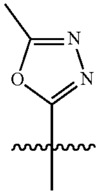 |
| 1-1245 | Cl | 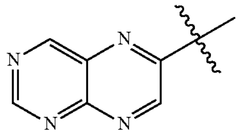 [SMILES: *c1cnc2ncncc2n1] | 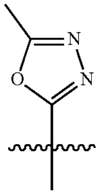 [SMILES: *c1nnc(C)o1] |

TABLE A1-continued
| | | | |
|---|---|---|---|
| 1-1246 | Cl | 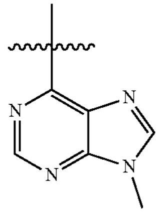 [SMILES: *c1ncnc2c1ncn2C] | 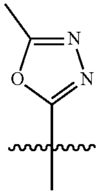 |
| 1-1247 | Cl | 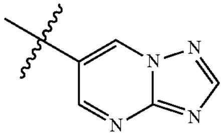 [SMILES: *c1cnc2ncnn2c1] | 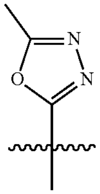 |
| 1-1248 | Cl | 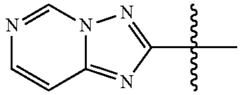 [SMILES: *c1nc2ccncn2n1] | 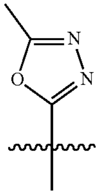 [SMILES: *c1nnc(C)o1] |
| 1-1249 | Cl | 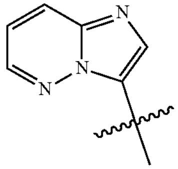 [SMILES: *c1cnc2cccnn12] | 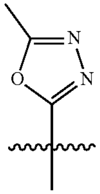 [SMILES: *c1nnc(C)o1] |
| 1-1250 | Cl | 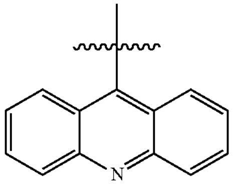 [SMILES: *c1c2ccccc2nc2ccccc12] | 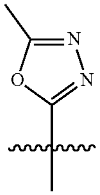 |

TABLE A1-continued
| | | | | |
|---|---|---|---|---|
| 1-1251 | Cl | 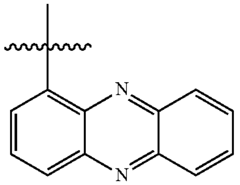 [SMILES: *c1cccc2nc3ccccc3nc12] | 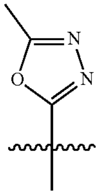 | |
| 1-1252 | Cl | 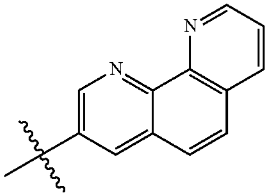 [SMILES: *c1cnc2c(ccc3cccnc32)c1] | 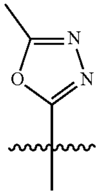 | |
| 1-1253 | Cl | 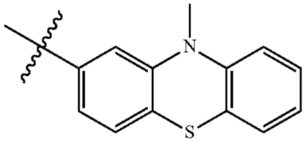 [SMILES: *c1ccc2c(c1)N(C)c1ccccc1S2] | 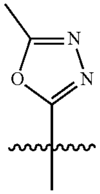 [SMILES: *c1nnc(C)o1] | |
| 1-1254 | Cl | 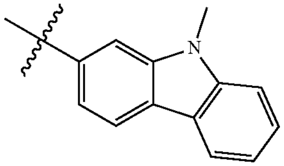 [SMILES: *c1ccc2c3ccccc3n(C)c2c1] | 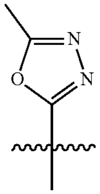 [SMILES: *c1nnc(C)o1] | |
| 1-1255 | Cl | 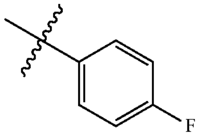 [SMILES: *c1ccc(F)cc1] | 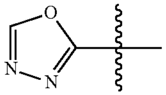 | $^1$H NMR (500 MHz, DMSO-$d_6$) δ 12.01 (s, 1H), 8.71 (d, J = 5.0 Hz, 1H), 8.01-7.93 (m, 2H), 7.76 (s, 1H), 7.60 (d, J = 5.0 Hz, 1H), 7.35-7.27 (m, 2H). |

TABLE A1-continued
| | | | | |
|---|---|---|---|---|
| 1-1256 | Cl | 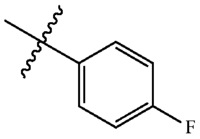 [SMILES: *c1ccc(F)cc1] | 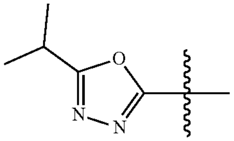 [SMILES: *c1nnc(C(C)C)o1] | $^{1}H$ NMR (500 MHz, DMSO-$d_6$) δ 12.02 (s, 1H), 8.73 (d, J = 5.0 Hz, 1H), 8.01-7.93 (m, 2H), 7.78 (d, J = 5.0 Hz, 1H), 7.35-7.27 (m, 2H), 3.08 (hept, J = 7.0 Hz, 1H), 1.26 (d, J = 7.0 Hz, 6H). |
| 1-1257 | Cl | 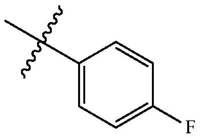 [SMILES: *c1ccc(F)cc1] | 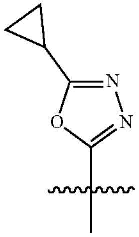 [SMILES: *c1nnc(C2CC2)o1] | $^{1}H$ NMR (500 MHz, DMSO-d6) δ 12.05 (s, 1H), 8.75 (d, J = 4.5 Hz, 1H), 7.68-7.60 (m, 2H), 7.11-7.03 (m, 2H), 6.79 (d, J = 4.5 Hz, 1H), 1.50-1.35 (m, 1H), 1.02-0.96 (m, 2H), 0.94-0.88 (m, 2H). |
| 1-1258 | Cl | 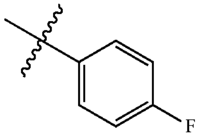 [SMILES: *c1ccc(F)cc1] | 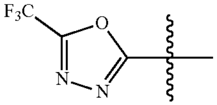 [SMILES: *c1nnc(C(F)(F)F)o1] | $^{1}H$ NMR (500 MHz, DMSO-$d_6$) δ 12.05 (s, 1H), 8.72 (d, J = 5.0 Hz, 1H), 8.01-7.93 (m, 2H), 7.70 (d, J = 5.0 Hz, 1H), 7.35-7.27 (m, 2H). |
| 1-1259 | Cl | 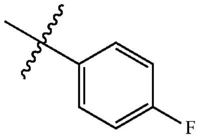 [SMILES: *c1ccc(F)cc1] | 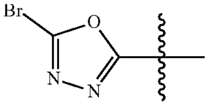 | $^{1}H$ NMR (500 MHz, DMSO-$d_6$) δ 12.04 (s, 1H), 8.95 (d, J = 5.0 Hz, 1H), 8.34-8.26 (m, 2H), 7.55 (d, J = 5.0 Hz, 1H), 7.35-7.27 (m, 2H). |
| 1-1260 | Cl | 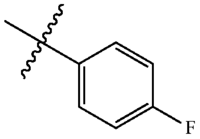 [SMILES: *c1ccc(F)cc1] | 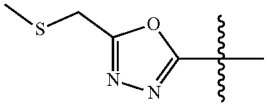 | $^{1}H$ NMR (500 MHz, DMSO-$d_6$) δ 12.04 (s, 1H), 8.73 (d, J = 5.0 Hz, 1H), 8.01-7.93 (m, 2H), 7.79 (d, J = 5.0 Hz, 1H), 7.35-7.27 (m, 2H), 3.70 (s, 2H), 2.10 (s, 3H). |
| 1-1261 | Cl | 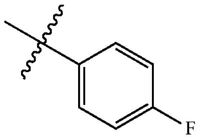 [SMILES: *c1ccc(F)cc1] | 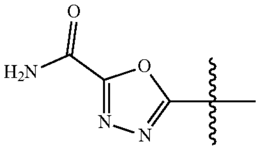 [SMILES: *c1nnc(C(N)=O)o1] | $^{1}H$ NMR (500 MHz, DMSO-$d_6$) δ 13.02 (s, 1H), 8.73 (d, J = 5.0 Hz, 1H), 8.15 (s, 2H), 8.01-7.93 (m, 2H), 7.80 (d, J = 5.0 Hz, 1H), 7.35-7.27 (m, 2H). |

TABLE A1-continued
| | | | | |
|---|---|---|---|---|
| 1-1262 | Cl | 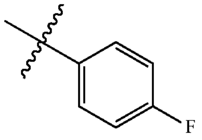 [SMILES: *c1ccc(F)cc1] | 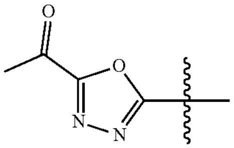 | $^1$H NMR (500 MHz, DMSO-$d_6$) δ 13.04 (s, 1H), 8.73 (d, J = 5.0 Hz, 1H), 8.01-7.93 (m, 2H), 7.81 (d, J = 5.0 Hz, 1H), 7.35-7.27 (m, 2H), 2.38 (s, 3H). |
| 1-1263 | Cl | 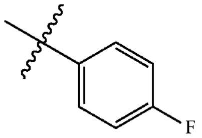 [SMILES: *c1ccc(F)cc1] | 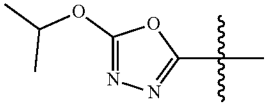 [SMILES: *c1nnc(OC(C)C)o1] | $^1$H NMR (500 MHz, DMSO-$d_6$) δ 12.04 (s, 1H), 8.73 (d, J = 5.0 Hz, 1H), 8.01-7.93 (m, 2H), 7.78 (d, J = 5.0 Hz, 1H), 7.35-7.27 (m, 2H), 4.48 (hept, J = 7.0 Hz, 1H), 1.21 (d, J = 7.0 Hz, 6H). |
| 1-1264 | Cl | 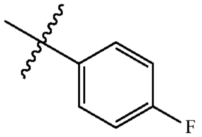 | 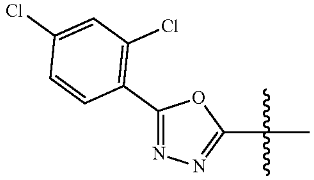 [SMILES: *c1nnc(-c2ccc(Cl)cc2Cl)o1] | $^1$H NMR (500 MHz, DMSO-$d_6$) δ 12.34 (s, 1H), 8.92 (d, J = 5.0 Hz, 1H), 8.03-7.95 (m, 2H), 7.89 (d, J = 5.0 Hz, 1H), 7.72 (s, 1H), 7.48 (d, J = 7.5 Hz, 1H), 7.42 (d, J = 7.5 Hz, 1H), 7.35-7.27 (m, 2H). |
| 1-1265 | Cl | 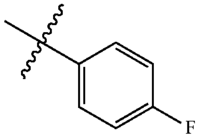 [SMILES: *c1ccc(F)cc1] | 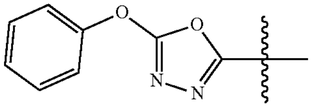 [SMILES: *c1nnc(Oc2ccccc2)o1] | $^1$H NMR (500 MHz, DMSO-d6) δ 12.21 (s, 1H), 8.89 (d, J = 5.0 Hz, 1H), 8.10-7.98 (m, 2H), 7.54 (d, J = 5.0 Hz, 1H), 7.37-7.19 (m, 4H), 6.72-6.95 (m, 1H), 6.90-6.80 (m, 2H). |
| 1-1266 | Cl | 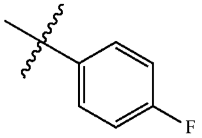 [SMILES: *c1ccc(F)cc1] | 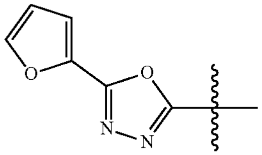 [SMILES: *c1nnc(-c2ccco2)o1] | $^1$H NMR (500 MHz, DMSO-d6) δ 12.14 (s, 1H), 8.65 (d, J = 5.0 Hz, 1H), 8.07-7.92 (m, 2H), 7.74-7.72 (m, 1H), 7.48 (d, J = 5.0 Hz, 1H), 7.37-7.25 (m, 2H), 6.84-6.82 (m, 1H), 6.68 (t, J = 7.5 Hz, 1H). |
| 1-1267 | Cl | 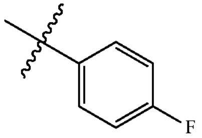 [SMILES: *c1ccc(F)cc1] | 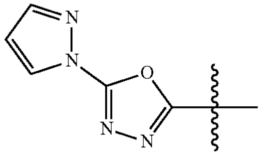 [SMILES: *c1nnc(-n2cccn2)o1] | $^1$H NMR (500 MHz, DMSO-d6) δ 12.15 (s, 1H), 8.65 (d, J = 5.0 Hz, 1H), 8.08-7.95 (m, 2H), 7.77 (d, J = 2.5, 1H), 7.66 (d, J = 2.5 Hz, 1H), 7.46 (d, J = 5.0 Hz, 1H), 7.37-7.25 (m, 2H), 6.66 (t, J = 2.5 Hz, 1H). |

TABLE A1-continued
| | | | | |
|---|---|---|---|---|
| 1-1268 | Cl | 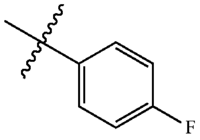 [SMILES: *c1ccc(F)cc1] | 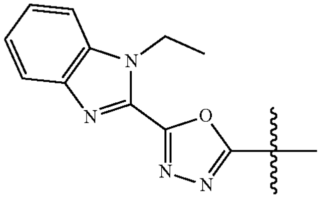 [SMILES: *c1nnc(-c2nc3ccccc3n2CC)o1] | $^1$H NMR (500 MHz, DMSO-d6) δ 12.05 (s, 1H), 8.85 (d, J = 5.0 Hz, 1H), 8.10-7.96 (m, 2H), 7.79-7.62 (m, 2H), 7.58 (d, J = 5.0 Hz, 1H), 7.38-7.20 (m, 4H), 4.07 (q, J = 8.0 Hz, 2H), 3.97 (t, J = 8.0 Hz, 3H). |
| 1-1269 | Cl | 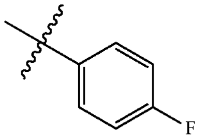 [SMILES: *c1ccc(F)cc1] | 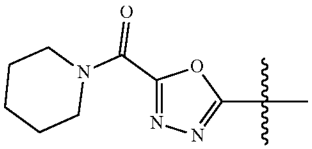 [SMILES: *c1nnc(C(=O)N2CCCCC2)o1] | $^1$H NMR (500 MHz, DMSO-d6) δ 12.06 (s, 1H), 8.84 (d, J = 5.0 Hz, 1H), 8.07-7.92 (m, 2H), 7.56 (d, J = 5.0 Hz, 1H), 7.40-7.24 (m, 2H), 3.58-3.40 (m, 4H), 1.81-1.68 (m, 4H), 1.59-1.43 (m, 2H). |
| 1-1270 | Cl | $CH_3$ | 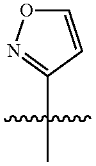 [SMILES: *c1ccon1] | |
| 1-1271 | Cl | 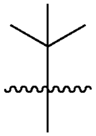 [SMILES: *C(C)(C)C] | 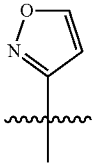 | |
| 1-1272 | Cl | 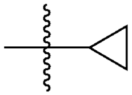 [SMILES: *C1CC1] | 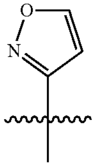 | |
| 1-1273 | Cl | 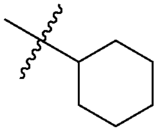 [SMILES: *C1CCCCC1] | 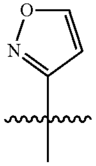 | |

TABLE A1-continued
| | | | |
|---|---|---|---|
| 1-1274 | Cl | 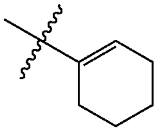 [SMILES: *C1=CCCCC1] | 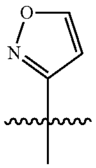 |
| 1-1275 | Cl | 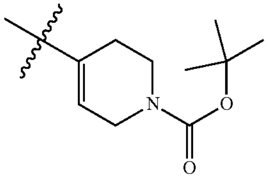 [SMILES: *C1=CCN(C(=O)OC(C)(C)C)CC1] | 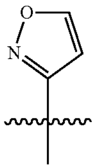 |
| 1-1276 | Cl | 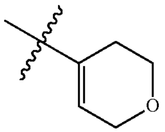 [SMILES: *C1=CCOCC1] | 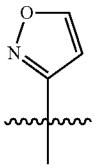 |
| 1-1277 | Cl | 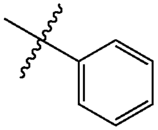 [SMILES: *c1ccccc1] | 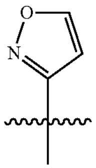 |
| 1-1278 | Cl | 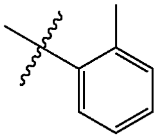 [SMILES: *c1ccccc1C] | 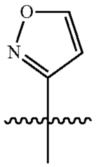 |
| 1-1279 | Cl | 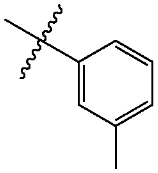 [SMILES: *c1cccc(C)c1] | 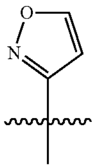 |

TABLE A1-continued
| | | | |
|---|---|---|---|
| 1-1280 | Cl | 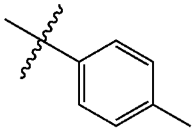 [SMILES: *c1ccc(C)cc1] | 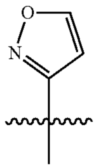 |
| 1-1281 | Cl | 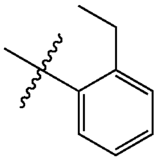 [SMILES: *c1ccccc1CC] | 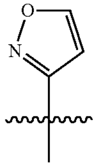 |
| 1-1282 | Cl | 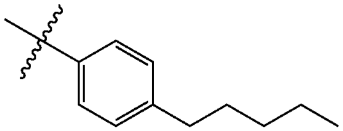 [SMILES: *c1ccc(CCCCC)cc1] | 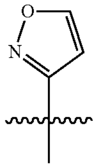 |
| 1-1283 | Cl | 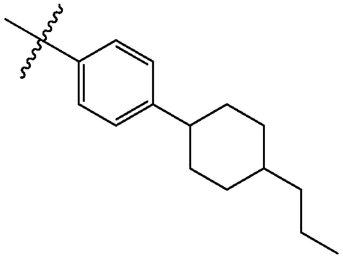 [SMILES: *c1ccc(C2CCC(CCC)CC2)cc1] | 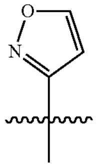 |
| 1-1284 | Cl | 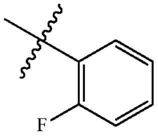 [SMILES: *c1ccccc1F] | 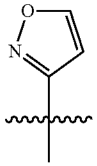 |

TABLE A1-continued
| | | | | |
|---|---|---|---|---|
| 1-1285 | Cl | 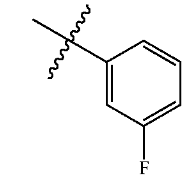 [SMILES: *c1cccc(F)c1] | 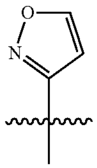 | |
| 1-1286 | Cl | 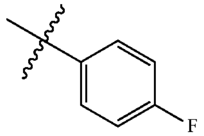 [SMILES: *c1ccc(F)cc1] | 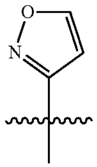 | $^1H$ NMR (500 MHz, DMSO-d6) δ 12.53 (s, 1H), 8.79-8.73 (m, 2H), 7.64-7.57 (m, 2H), 7.33 (d, J = 4.5 Hz, 1H), 7.11-7.03 (m, 2H), 6.77 (d, J = 2.5 Hz, 1H). |
| 1-1287 | Cl | 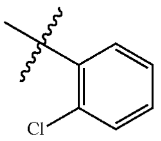 | 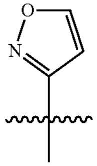 | |
| 1-1288 | Cl | 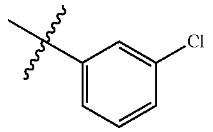 [SMILES: *c1cccc(Cl)c1] | 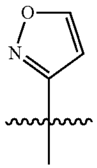 | |
| 1-1289 | Cl | 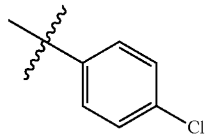 [SMILES: *c1ccc(Cl)cc1] | 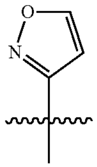 | |
| 1-1290 | Cl | 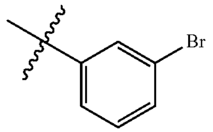 [SMILES: *c1cccc(Br)c1] | 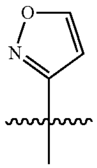 | |

TABLE A1-continued
| | | | |
|---|---|---|---|
| 1-1291 | Cl | 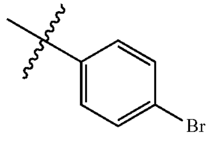 [SMILES: *c1ccc(Br)cc1] | 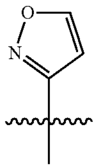 |
| 1-1292 | Cl | 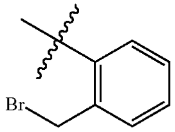 | 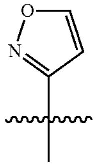 |
| 1-1293 | Cl | 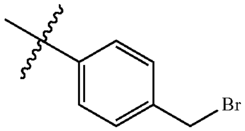 [SMILES: *c1ccc(CBr)cc1] | 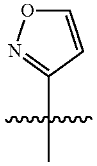 |
| 1-1294 | Cl | 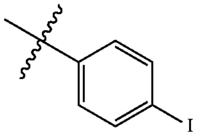 [SMILES: *c1ccc(I)cc1] | 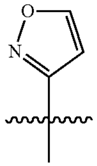 |
| 1-1295 | Cl | 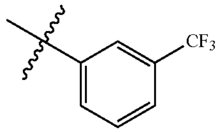 [SMILES: *c1cccc(C(F)(F)F)c1] | 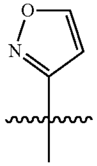 |
| 1-1296 | Cl | 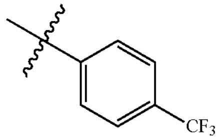 | 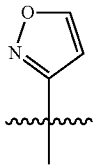 |

TABLE A1-continued
| | | | |
|---|---|---|---|
| 1-1297 | Cl | 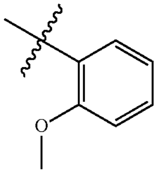 [SMILES: *c1ccccc1OC] | 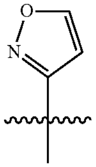 |
| 1-1298 | Cl | 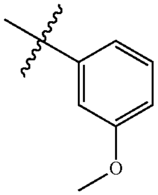 [SMILES: *c1cccc(OC)c1] | 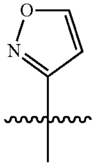 |
| 1-1299 | Cl | 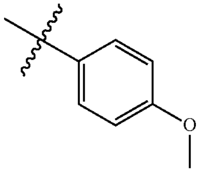 [SMILES: *c1ccc(OC)cc1] | 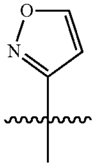 |
| 1-1300 | Cl | 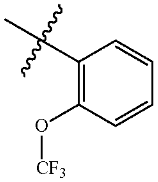 | 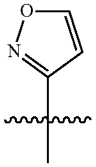 |
| 1-1301 | Cl | 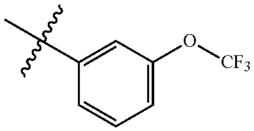 [SMILES: *c1cccc(OC(F)(F)F)c1] | 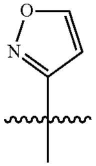 |

TABLE A1-continued
| | | | |
|---|---|---|---|
| 1-1302 | Cl | 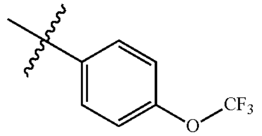 [SMILES: *c1ccc(OC(F)(F)F)cc1] | 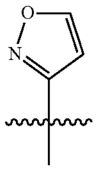 |
| 1-1303 | Cl | 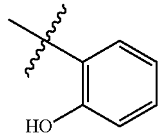 [SMILES: *c1ccccc1O] | 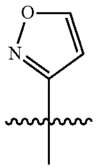 |
| 1-1304 | Cl | 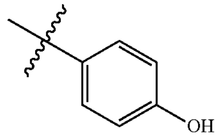 | 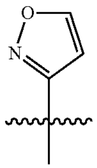 [SMILES: *c1ccon1] |
| 1-1305 | Cl | 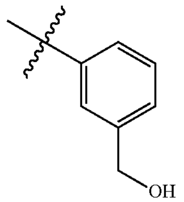 [SMILES: *c1cccc(CO)c1] | 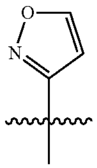 [SMILES: *c1ccon1] |
| 1-1306 | Cl | 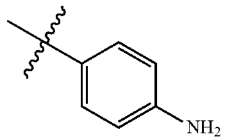 | 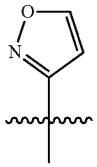 |
| 1-1307 | Cl | 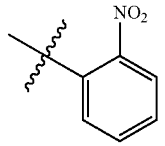 | 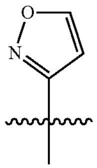 |

TABLE A1-continued
| | | | |
|---|---|---|---|
| 1-1308 | Cl | 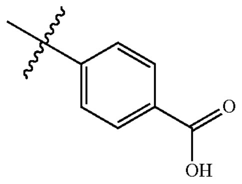 [SMILES: *c1ccc(C(=O)O)cc1] | 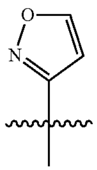 |
| 1-1309 | Cl | 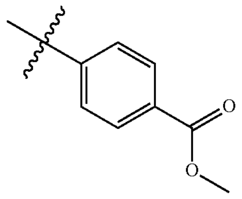 [SMILES: *c1ccc(C(=O)OC)cc1] | 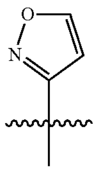 |
| 1-1310 | Cl | 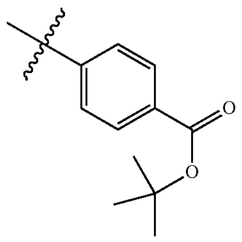 [SMILES: *c1ccc(C(=O)OC(C)(C)C)cc1] | 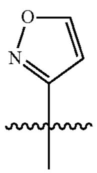 |
| 1-1311 | Cl | 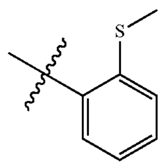 [SMILES: *c1ccccc1SC] | 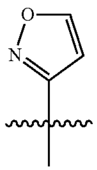 [SMILES: *c1ccon1] |
| 1-1312 | Cl | 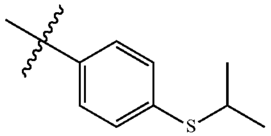 [SMILES: *c1ccc(SC(C)C)cc1] | 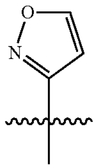 |

TABLE A1-continued
| | | | |
|---|---|---|---|
| 1-1313 | Cl | 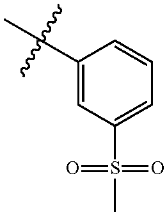 [SMILES: *c1cccc(S(C)(=O)=O)c1] | 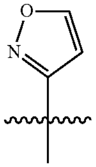 |
| 1-1314 | Cl | 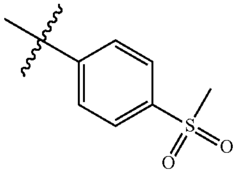 [SMILES: *c1ccc(S(C)(=O)=O)cc1] | 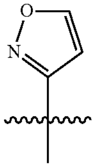 [SMILES: *c1ccon1] |
| 1-1315 | Cl | 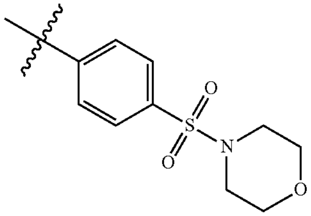 [SMILES: *c1ccc(S(=O)(=O)N2CCOCC2)cc1] | 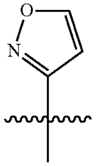 |
| 1-1316 | Cl | 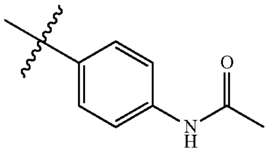 [SMILES: *c1ccc(NC(C)=O)cc1] | 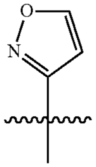 |
| 1-1317 | Cl | 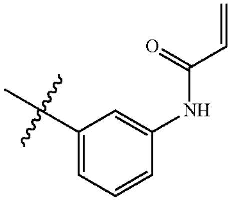 [SMILES: *c1cccc(NC(=O)C=C)c1] | 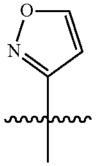 |

TABLE A1-continued
| | | | |
|---|---|---|---|
| 1-1318 | Cl | 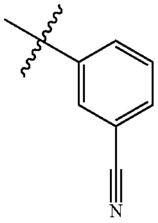 [SMILES: *c1cccc(C#N)c1] | 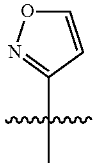 |
| 1-1319 | Cl | 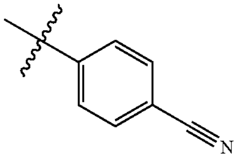 [SMILES: *c1ccc(C#N)cc1] | 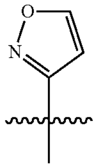 |
| 1-1320 | Cl | 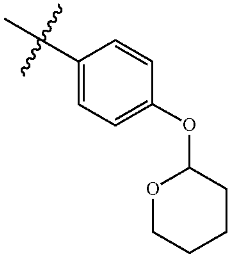 [SMILES: *c1ccc(OC2CCCCO2)cc1] | 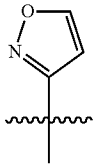 |
| 1-1321 | Cl | 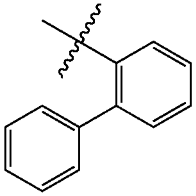 [SMILES: *c1ccccc1-c1ccccc1] | 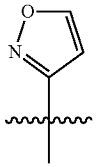 |
| 1-1322 | Cl | 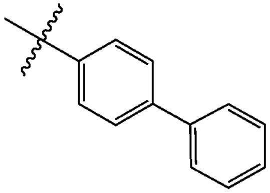 [SMILES: *c1ccc(-c2ccccc2)cc1] | 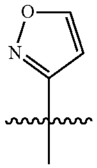 [SMILES: *c1ccon1] |

TABLE A1-continued
| | | | |
|---|---|---|---|
| 1-1323 | Cl | 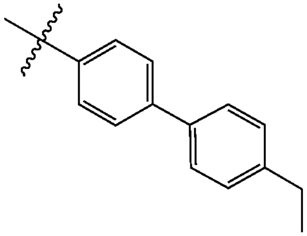 [SMILES: *c1ccc(-c2ccc(CC)cc2)cc1] | 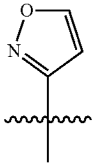 |
| 1-1324 | Cl | 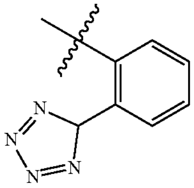 [SMILES: *c1ccccc1C1N=NN=N1] | 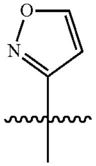 |
| 1-1325 | Cl | 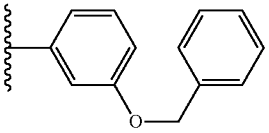 [SMILES: *c1cccc(OCc2ccccc2)c1] | 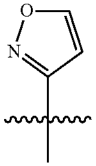 |
| 1-1326 | Cl | 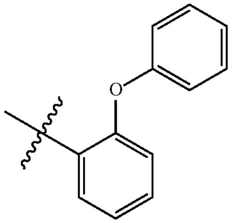 [SMILES: *c1ccccc1Oc1ccccc1] | 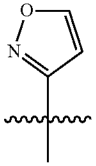 |
| 1-1327 | Cl | 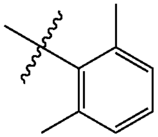 [SMILES: *c1c(C)cccc1C] | 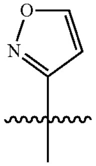 |

TABLE A1-continued
| | | | |
|---|---|---|---|
| 1-1328 | Cl | 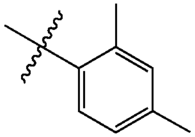 [SMILES: *c1ccc(C)cc1C] | 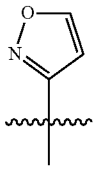 |
| 1-1329 | Cl | 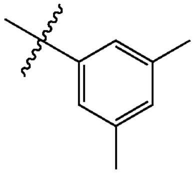 [SMILES: *c1cc(C)cc(C)c1] | 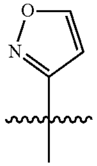 |
| 1-1330 | Cl | 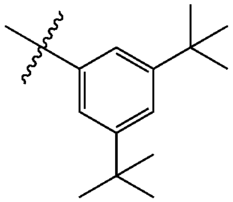 [SMILES: *c1cc(C(C)(C)C)cc(C(C)(C)C)c1] | 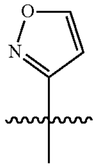 |
| 1-1331 | Cl | 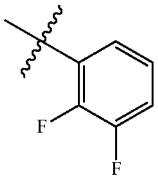 [SMILES: *c1cccc(F)c1F] | 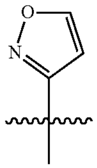 |
| 1-1332 | Cl | 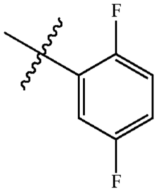 | 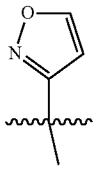 |

TABLE A1-continued
| | | | |
|---|---|---|---|
| 1-1333 | Cl | 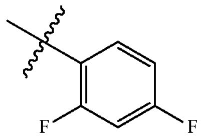 [SMILES: *c1ccc(F)cc1F] | 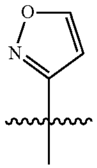 |
| 1-1334 | Cl | 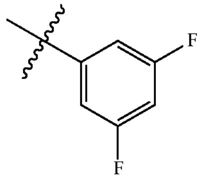 [SMILES: *c1cc(F)cc(F)c1] | 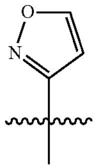 |
| 1-1335 | Cl | 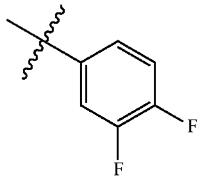 [SMILES: *c1ccc(F)c(F)c1] | 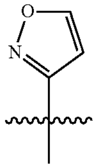 [SMILES: *c1ccon1] |
| 1-1336 | Cl | 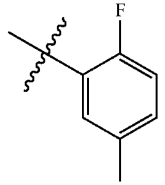 [SMILES: *c1cc(C)ccc1F] | 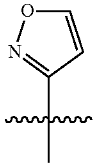 |
| 1-1337 | Cl | 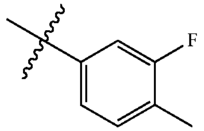 [SMILES: *c1ccc(C)c(F)c1] | 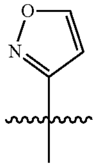 [SMILES: *c1ccon1] |

TABLE A1-continued
| | | | |
|---|---|---|---|
| 1-1338 | Cl | 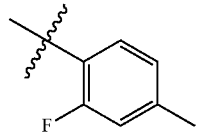 [SMILES: *c1ccc(C)cc1F] | 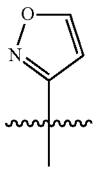 |
| 1-1339 | Cl | 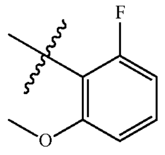 | 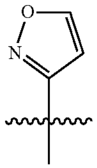 |
| 1-1340 | Cl | 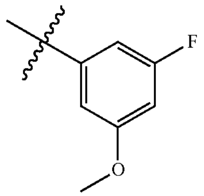 [SMILES: *c1cc(F)cc(OC)c1] | 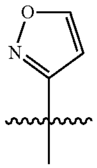 [SMILES: *c1ccon1] |
| 1-1341 | Cl | 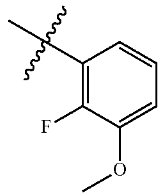 [SMILES: *c1cccc(OC)c1F] | 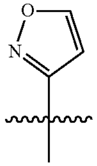 |
| 1-1342 | Cl | 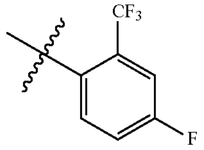 | 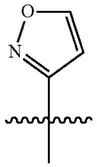 |

TABLE A1-continued
| | | | |
|---|---|---|---|
| 1-1343 | Cl | 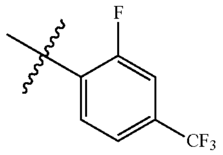 | 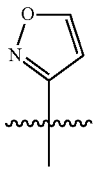 |
| 1-1344 | Cl | 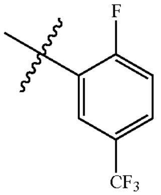 | 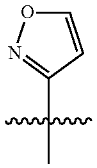 |
| 1-1345 | Cl | 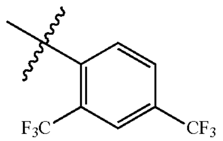 | 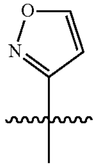 |
| 1-1346 | Cl | 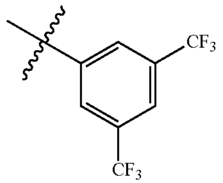 [SMILES: *c1cc(C(F)(F)F)cc(C(F)(F)F)c1] | 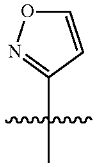 |
| 1-1347 | Cl | 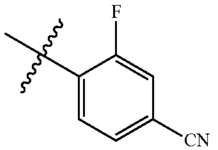 [SMILES: *c1ccc(C#N)cc1F] | 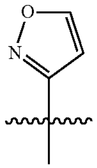 |

TABLE A1-continued
| | | | |
|---|---|---|---|
| 1-1348 | Cl | 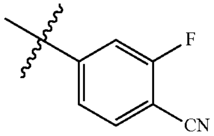 [SMILES: *c1ccc(C#N)c(F)c1] | 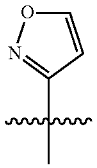 |
| 1-1349 | Cl | 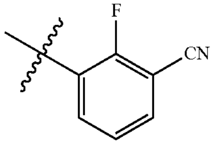 [SMILES: *c1cccc(C#N)c1F] | 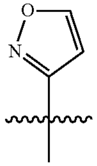 |
| 1-1350 | Cl | 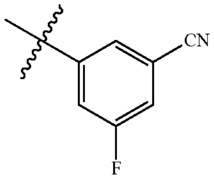 [SMILES: *c1cc(F)cc(C#N)c1] | 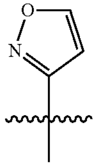 [SMILES: *c1ccon1] |
| 1-1351 | Cl | 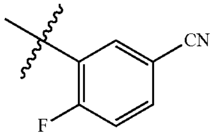 [SMILES: *c1cc(C#N)ccc1F] | 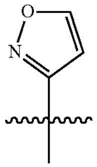 |
| 1-1352 | Cl | 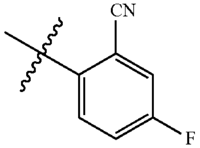 | 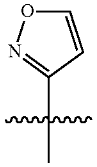 |
| 1-1353 | Cl | 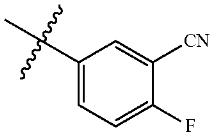 [SMILES: *c1ccc(F)c(C#N)c1] | 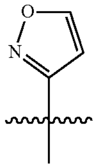 |

TABLE A1-continued
| | | | |
|---|---|---|---|
| 1-1354 | Cl | 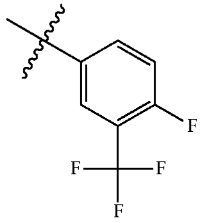 [SMILES: *c1ccc(F)c(C(F)(F)F)c1] | 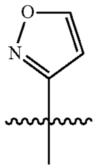 |
| 1-1355 | Cl | 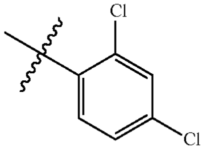 [SMILES: *c1ccc(Cl)cc1Cl] | 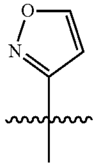 |
| 1-1356 | Cl | 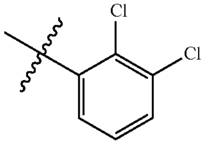 [SMILES: *c1cccc(Cl)c1Cl] | 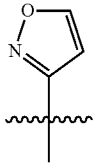 |
| 1-1357 | Cl | 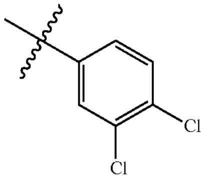 [SMILES: *c1ccc(Cl)c(Cl)c1] | 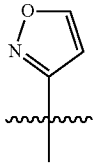 |
| 1-1358 | Cl | 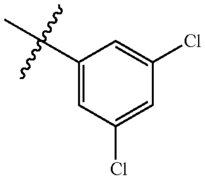 [SMILES: *c1cc(Cl)cc(Cl)c1] | 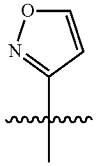 |

TABLE A1-continued
| | | | |
|---|---|---|---|
| 1-1359 | Cl | 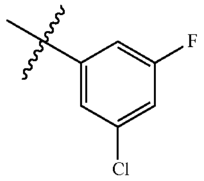 | 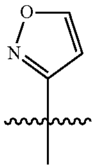 |
| 1-1360 | Cl | 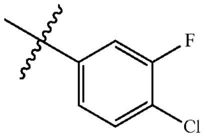 [SMILES: *c1ccc(Cl)c(F)c1] | 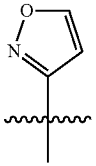 [SMILES: *c1ccon1] |
| 1-1361 | Cl | 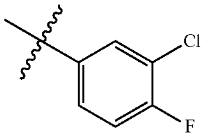 [SMILES: *c1ccc(F)c(Cl)c1] | 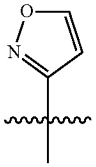 [SMILES: *c1ccon1] |
| 1-1362 | Cl | 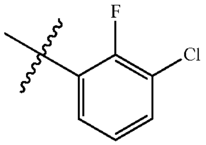 [SMILES: *c1cccc(Cl)c1F] | 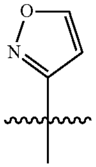 |
| 1-1363 | Cl | 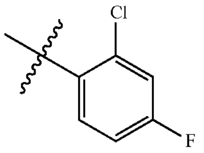 [SMILES: *c1ccc(F)cc1Cl] | 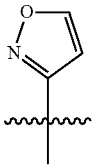 |
| 1-1364 | Cl | 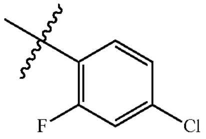 | 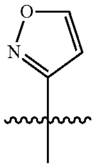 [SMILES: *c1ccon1] |

TABLE A1-continued
| | | | |
|---|---|---|---|
| 1-1365 | Cl | 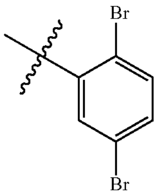 [SMILES: *c1cc(Br)ccc1Br] | 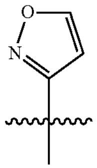 |
| 1-1366 | Cl | 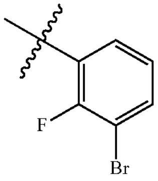 | 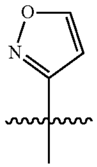 |
| 1-1367 | Cl | 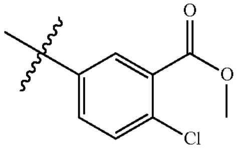 [SMILES: *c1ccc(Cl)c(C(=O)OC)c1] | 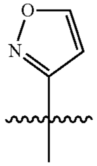 |
| 1-1368 | Cl | 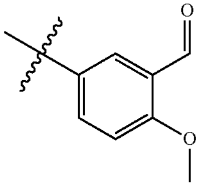 [SMILES: *c1ccc(OC)c(C=O)c1] | 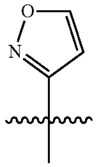 |
| 1-1369 | Cl | 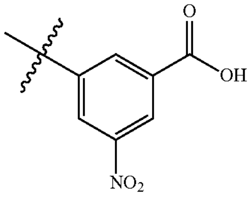 | 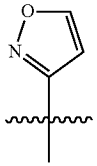 |

TABLE A1-continued
| | | | |
|---|---|---|---|
| 1-1370 | Cl | 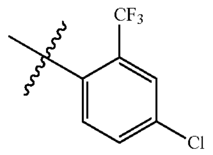 | 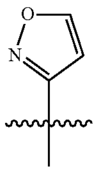 |
| 1-1371 | Cl | 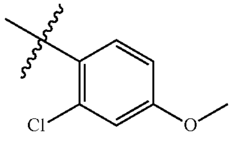 [SMILES: *c1ccc(OC)cc1Cl] | 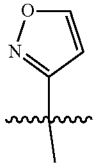 |
| 1-1372 | Cl | 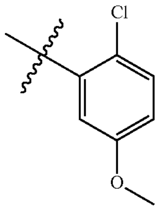 [SMILES: *c1cc(OC)ccc1Cl] | 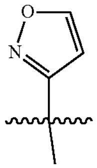 |
| 1-1373 | Cl | 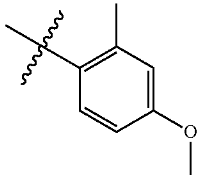 [SMILES: *c1ccc(OC)cc1C] | 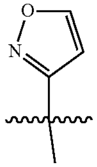 |
| 1-1374 | Cl | 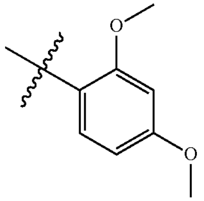 [SMILES: *c1ccc(OC)cc1OC] | 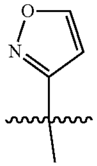 |

TABLE A1-continued
| | | | |
|---|---|---|---|
| 1-1375 | Cl | 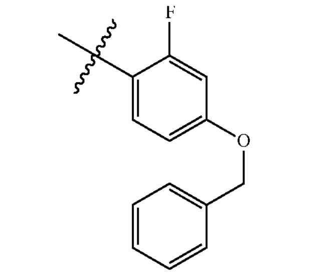 [SMILES: *c1ccc(OCc2ccccc2)cc1F] | 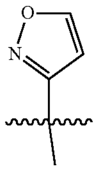 |
| 1-1376 | Cl | 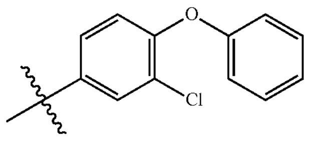 [SMILES: *c1ccc(Oc2ccccc2)c(Cl)c1] | 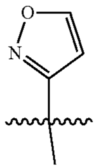 |
| 1-1377 | Cl | 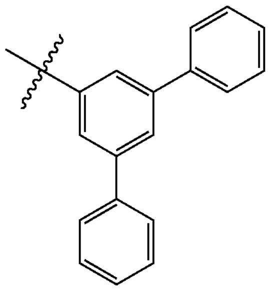 [SMILES: *c1cc(-c2ccccc2)cc(-c2ccccc2)c1] | 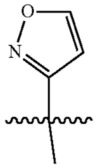 |
| 1-1378 | Cl | 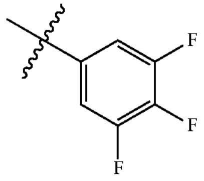 [SMILES: *c1cc(F)c(F)c(F)c1] | 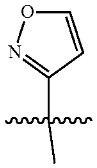 |

TABLE A1-continued
| | | | | |
|---|---|---|---|---|
| 1-1379 | Cl | 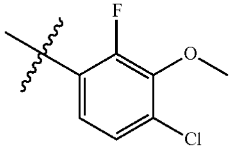 | 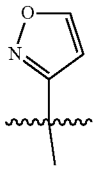 | |
| 1-1380 | Cl | 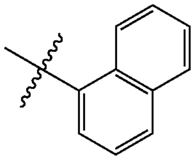 [SMILES: *c1cccc2ccccc12] | 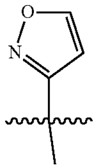 | |
| 1-1381 | Cl | 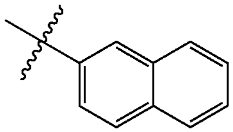 [SMILES: *c1ccc2ccccc2c1] | 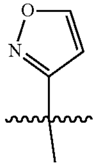 | $^1$H NMR (500 MHz, DMSO-d6) δ 12.24 (s, 1H), 8.91 (d, J = 5.0 Hz, 1H), 8.76 (d, J = 7.5 Hz, 1H), 8.54 (t, J = 1.5 Hz, 1H), 8.19 (dd, J = 7.5, 1.5 Hz, 1H), 8.14-7.92 (m, 3H), 7.88 (d, J = 5.0 Hz, 1H), 7.67-7.58 (m, 2H), 6.77 (d, J = 2.5 Hz, 1H). |
| 1-1382 | Cl | 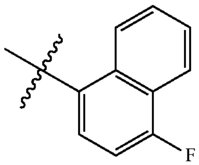 [SMILES: *c1ccc(F)c2ccccc12] | 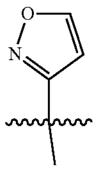 | |
| 1-1383 | Cl | 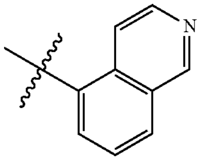 [SMILES: *c1cccc2cnccc12] | 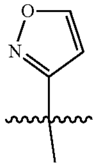 | $^1$H NMR (500 MHz, DMSO-d6) δ 12.09 (s, 1H), 9.26 (s, 1H), 8.87 (d, J = 5.0 Hz, 1H), 8.76 (d, J = 5.5 Hz, 1H), 8.60-8.58 (m, 1H), 8.23 (dd, J = 7.5, 1.5 Hz, 1H), 8.17-8.14 (m, 1H), 7.87-7.82 (m, 2H), 7.66 (d, J = 2.5 Hz, 1H), 6.77 (d, J = 2.5 Hz, 1H). |
| 1-1384 | Cl | 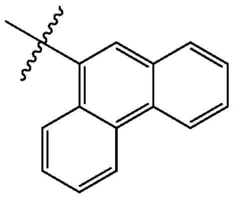 [SMILES: *c1cc2ccccc2c2ccccc12] | 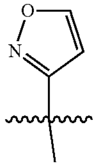 | $^1$H NMR (500 MHz, DMSO-d6) δ 12.21 (s, 1H), 8.94-8.85 (m, 2H), 8.81-8.73 (m, 2H), 8.40 (d, J = 1.5 Hz, 1H), 8.20-8.13 (m, 1H), 8.05-7.99 (m, 1H), 7.95-7.86 (m, 5H), 6.77 (d, J = 2.5 Hz, 1H). |

TABLE A1-continued
| | | | | |
|---|---|---|---|---|
| 1-1385 | Cl | 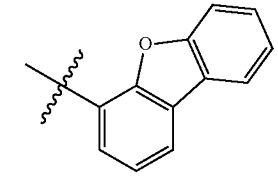 [SMILES: *c1cccc2c1oc1ccccc12] | 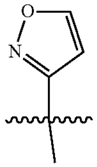 | $^1$H NMR (500 MHz, DMSO-d6) δ 12.09 (s, 1H), 8.92 (d, J = 5.0 Hz, 1H), 8.76 (d, J = 7.5 Hz, 1H), 8.21 (dd, J = 7.5, 1.5 Hz, 1H), 8.13-7.98 (m, 2H), 7.91 (d, J = 5.0 Hz, 1H), 7.66-7.58 (m, 2H), 7.44 (td, J = 7.5, 1.5 Hz, 1H), 7.38-7.22 (m, 1H), 6.77 (d, J = 7.5 Hz, 1H). |
| 1-1386 | Cl | 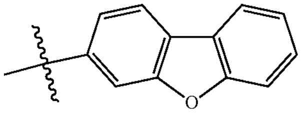 [SMILES: *c1ccc2c(c1)oc1ccccc12] | 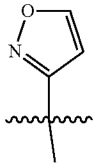 | |
| 1-1387 | Cl | 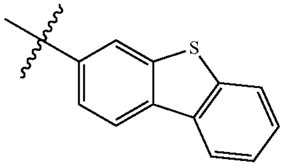 [SMILES: *c1ccc2c(c1)sc1ccccc12] | 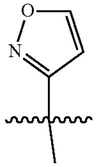 | |
| 1-1388 | Cl | 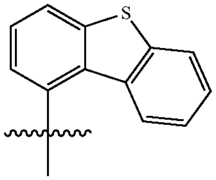 [SMILES: *c1cccc2sc3ccccc3c12] | 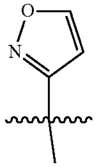 | $^1$H NMR (500 MHz, DMSO-d6) δ 12.21 (s, 1H), 8.92 (d, J = 5.0 Hz, 1H), 8.76 (d, J = 7.5 Hz, 1H), 8.25-8.12 (m, 2H), 8.05-7.88 (m, 2H), 7.72-7.62 (m, 2H), 7.60-7.55 (m, 1H), 7.48-7.21 (m, 1H), 6.77 (d, J = 2.5 Hz, 1H). |
| 1-1389 | Cl | 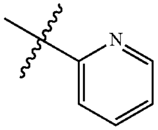 [SMILES: *c1ccccn1] | 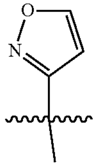 | |
| 1-1390 | Cl | 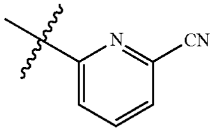 [SMILES: *c1cccc(C#N)n1] | 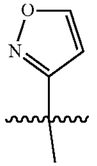 | |

TABLE A1-continued
| | | | | |
|---|---|---|---|---|
| 1-1391 | Cl | 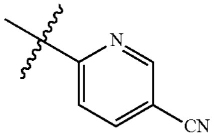 | 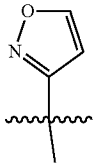 | |
| 1-1392 | Cl | 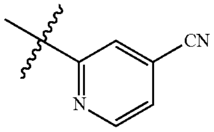 [SMILES: *c1cc(C#N)ccn1] | 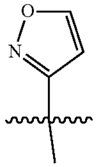 | |
| 1-1393 | Cl | 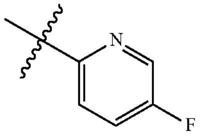 | 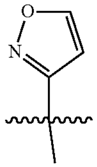 | |
| 1-1394 | Cl | 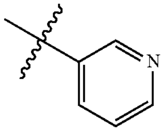 [SMILES: *c1cccnc1] | 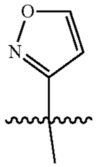 | |
| 1-1395 | Cl | 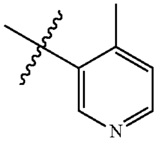 [SMILES: *c1cnccc1C] | 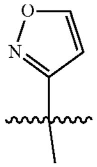 | $^1$H NMR (500 MHz, DMSO-d6) δ 12.18 (s, 1H), 8.90 (s, 1H), 8.77-8.61 (m, 2H), 8.46 (d, J = 5.0 Hz, 1H), 8.02 (d, J = 2.5 Hz, 1H), 7.43 (d, J = 5.0 Hz, 1H), 6.77 (d, J = 2.5 Hz, 1H), 2.42 (s, 3H). |
| 1-1396 | Cl | 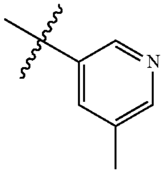 [SMILES: *c1cncc(C)c1] | 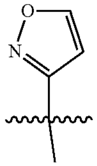 | |

TABLE A1-continued
| | | | |
|---|---|---|---|
| 1-1397 | Cl | 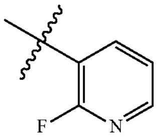 [SMILES: *c1cccnc1F] | 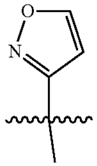 |
| 1-1398 | Cl | 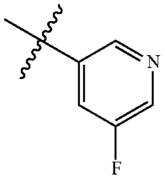 [SMILES: *c1cncc(F)c1] | 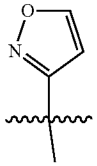 |
| 1-1399 | Cl | 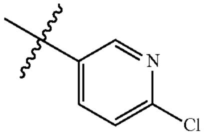 [SMILES: *c1ccc(Cl)nc1] | 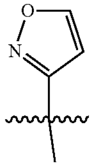 |
| 1-1400 | Cl | 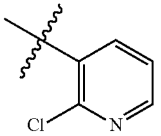 [SMILES: *c1cccnc1Cl] | 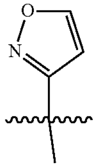 |
| 1-1401 | Cl | 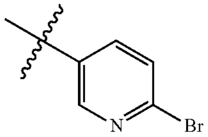 [SMILES: *c1ccc(Br)nc1] | 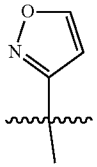 |
| 1-1402 | Cl | 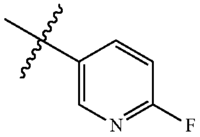 [SMILES: *c1ccc(F)nc1] | 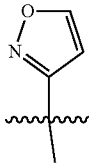 |

TABLE A1-continued
| | | | |
|---|---|---|---|
| 1-1403 | Cl | 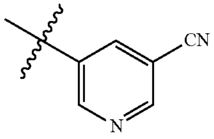 [SMILES: *c1cncc(C#N)c1] | 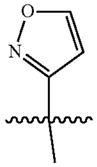 |
| 1-1404 | Cl | 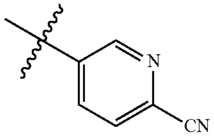 [SMILES: *c1ccc(C#N)nc1] | 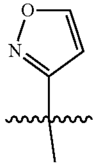 |
| 1-1405 | Cl | 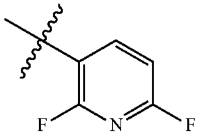 | 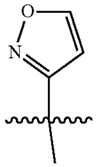 |
| 1-1406 | Cl | 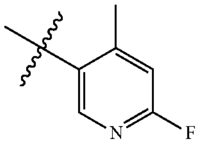 [SMILES: *c1cnc(F)cc1C] | 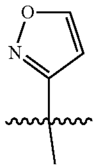 |
| 1-1407 | Cl | 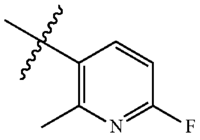 | 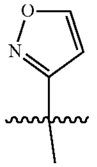 |
| 1-1408 | Cl | 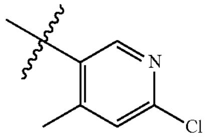 [SMILES: *c1cnc(Cl)cc1C] | 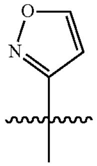 |

TABLE A1-continued
| | | | |
|---|---|---|---|
| 1-1409 | Cl | 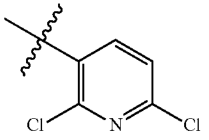 [SMILES: *c1ccc(Cl)nc1Cl] | 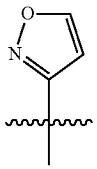 |
| 1-1410 | Cl | 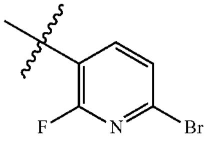 [SMILES: *c1ccc(Br)nc1F] | 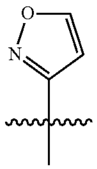 |
| 1-1411 | Cl | 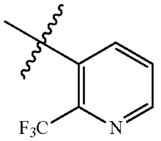 | 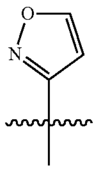 |
| 1-1412 | Cl | 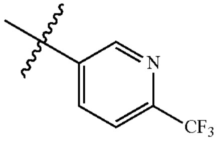 [SMILES: *c1ccc(C(F)(F)F)nc1] | 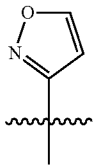 |
| 1-1413 | Cl | 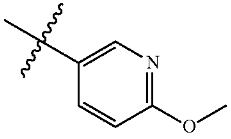 [SMILES: *c1ccc(OC)nc1] | 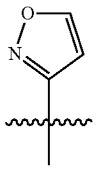 |
| 1-1414 | Cl | 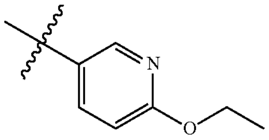 [SMILES: *c1ccc(OCC)nc1] | 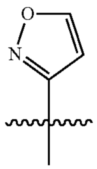 |

TABLE A1-continued
| | | | |
|---|---|---|---|
| 1-1415 | Cl | 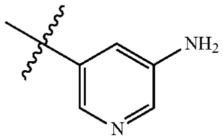 [SMILES: *c1cncc(N)c1] | 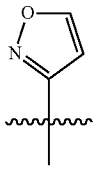 |
| 1-1416 | Cl | 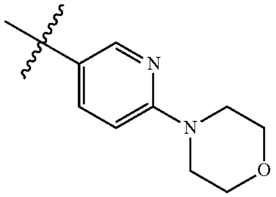 [SMILES: *c1ccc(N2CCOCC2)nc1] | 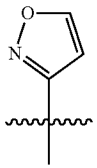 |
| 1-1417 | Cl | 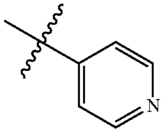 [SMILES: *c1ccncc1] | 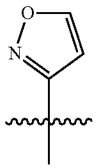 |
| 1-1418 | Cl | 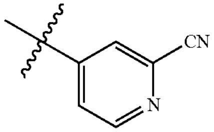 [SMILES: *c1ccnc(C#N)c1] | 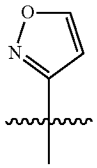 |
| 1-1419 | Cl | 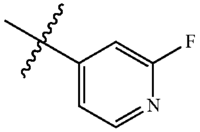 [SMILES: *c1ccnc(F)c1] | 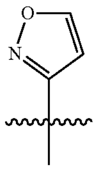 |
| 1-1420 | Cl | 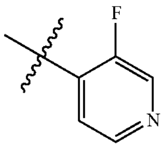 [SMILES: *c1ccncc1F] | 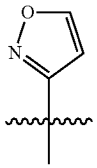 |

TABLE A1-continued
| | | | |
|---|---|---|---|
| 1-1421 | Cl | 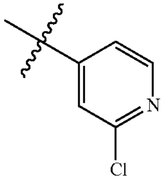 [SMILES: *c1ccnc(Cl)c1] | 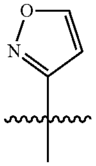 |
| 1-1422 | Cl | 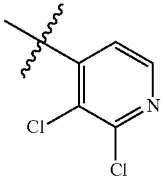 [SMILES: *c1ccnc(Cl)c1Cl] | 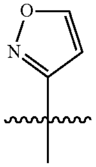 |
| 1-1423 | Cl | 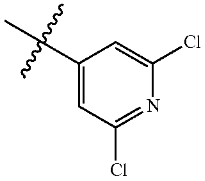 | 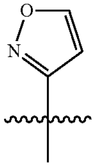 |
| 1-1424 | Cl | 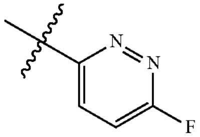 [SMILES: *c1ccc(F)nn1] | 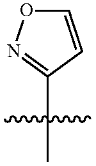 |
| 1-1425 | Cl | 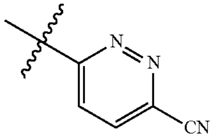 [SMILES: *c1ccc(C#N)nn1] | 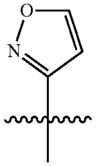 |

TABLE A1-continued
| | | | | |
|---|---|---|---|---|
| 1-1426 | Cl | 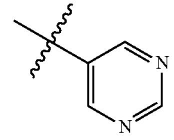 [SMILES: *c1cncnc1] | 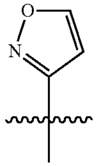 | $^1$H NMR (500 MHz, DMSO-d6) δ 12.14 (s, 1H), 9.37-9.33 (m, 3H), 8.83 (d, J = 5.0 Hz, 1H), 8.76 (d, J = 2.5 Hz, 1H), 7.99 (d, J = 5.0 Hz, 1H), 6.77 (d, J = 2.5 Hz, 1H). |
| 1-1427 | Cl | 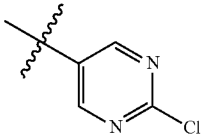 [SMILES: *c1cnc(Cl)nc1] | 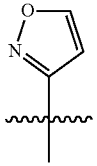 | |
| 1-1428 | Cl | 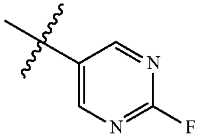 [SMILES: *c1cnc(F)nc1] | 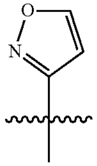 | |
| 1-1429 | Cl | 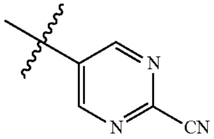 [SMILES: *c1cnc(C#N)nc1] | 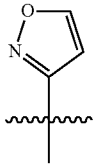 | |
| 1-1430 | Cl | 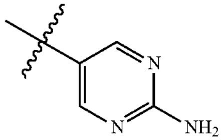 | 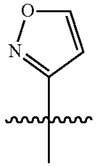 | |
| 1-1431 | Cl | 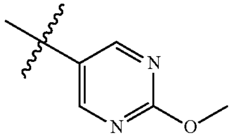 [SMILES: *c1cnc(OC)nc1] | 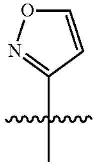 | |

TABLE A1-continued
| | | | |
|---|---|---|---|
| 1-1432 | Cl | 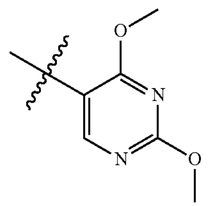 [SMILES: *c1cnc(OC)nc1OC] | 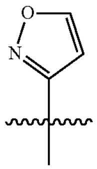 |
| 1-1433 | Cl | 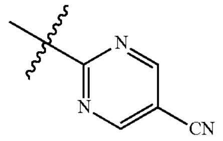 | 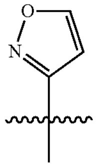 |
| 1-1434 | Cl | 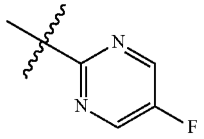 [SMILES: *c1ncc(F)cn1] | 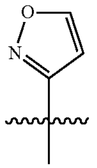 |
| 1-1435 | Cl | 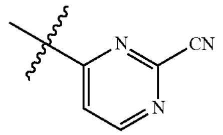 [SMILES: *c1ccnc(C#N)n1] | 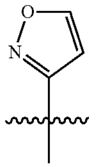 |
| 1-1436 | Cl | 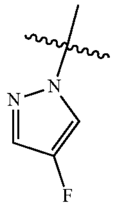 [SMILES: *n1cc(F)cn1] | 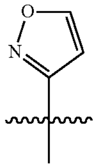 |

TABLE A1-continued
| | | | | |
|---|---|---|---|---|
| 1-1437 | Cl | 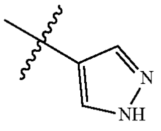 [SMILES: *c1cn[nH]c1] | 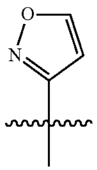 | |
| 1-1438 | Cl | 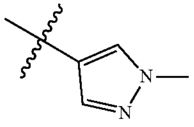 [SMILES: *c1cnn(C)c1] | 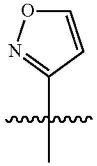 | |
| 1-1439 | Cl | 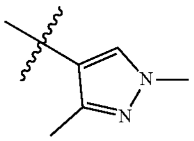 [SMILES: *c1cn(C)nc1C] | 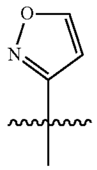 | |
| 1-1440 | Cl | 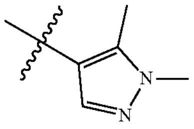 [SMILES: *c1cnn(C)c1C] | 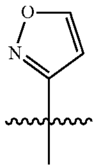 | |
| 1-1441 | Cl | 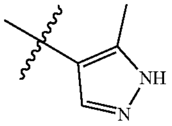 [SMILES: *c1cn[nH]c1C] | 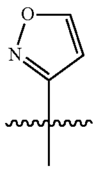 | |
| 1-1442 | Cl | 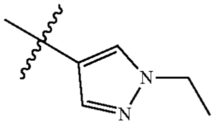 [SMILES: *c1cnn(CC)c1] | 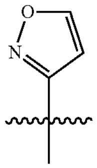 | $^1$H NMR (500 MHz, DMSO-d6) δ 12.17 (s, 1H), 8.91 (d, J = 5.0 Hz, 1H), 8.76 (d, J = 2.5 Hz, 1H), 7.97 (d, J = 5.0 Hz, 1H), 7.80 (s, 1H), 6.97 (s, 1H), 6.77 (d, J = 2.5 Hz, 1H), 4.29 (q, J = 8.0 Hz, 2H), 1.16 (t, J = 8.0 Hz, 3H). |

TABLE A1-continued
| | | | |
|---|---|---|---|
| 1-1443 | Cl | 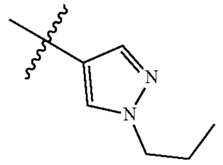 [SMILES: *c1cnn(CCC)c1] | 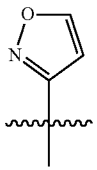 |
| 1-1444 | Cl | 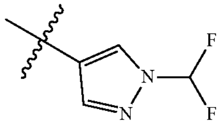 [SMILES: *c1cnn(C(F)F)c1] | 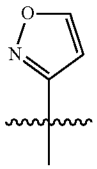 |
| 1-1445 | Cl | 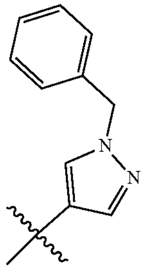 [SMILES: *c1cnn(Cc2ccccc2)c1] | 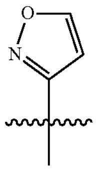 |
| 1-1446 | Cl | 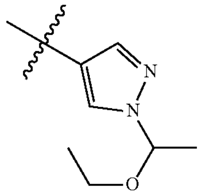 [SMILES: *c1cnn(C(C)OCC)c1] | 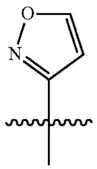 |
| 1-1447 | Cl | 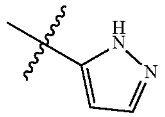 [SMILES: *c1ccn[nH]1] | 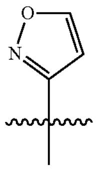 |

TABLE A1-continued
| | | | |
|---|---|---|---|
| 1-1448 | Cl | 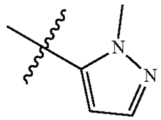 [SMILES: *c1ccnn1C] | 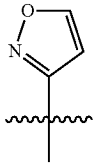 |
| 1-1449 | Cl | 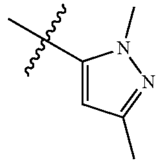 [SMILES: *c1cc(C)nn1C] | 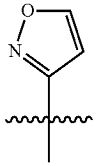 |
| 1-1450 | Cl | 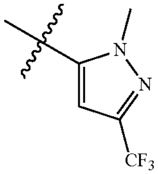 [SMILES: *c1cc(C(F)(F)F)nn1C] | 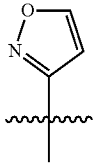 |
| 1-1451 | Cl | 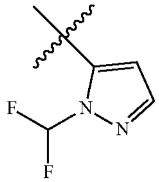 [SMILES: *c1ccnn1C(F)F] | 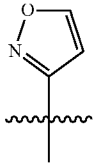 |
| 1-1452 | Cl | 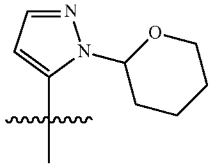 [SMILES: *c1ccnn1C1CCCCO1] | 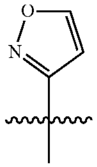 |
| 1-1453 | Cl | 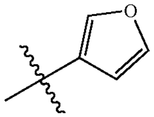 [SMILES: *c1ccoc1] | 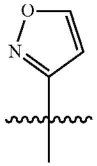 |

TABLE A1-continued
| | | | | |
|---|---|---|---|---|
| 1-1454 | Cl | 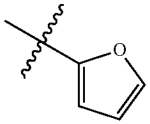 | 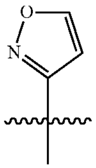 | |
| 1-1455 | Cl | 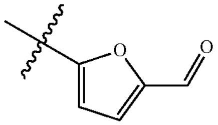 [SMILES: *c1ccc(C=O)o1] | 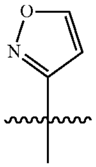 | |
| 1-1456 | Cl | 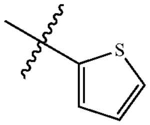 [SMILES: *c1cccs1] | 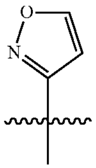 | $^1$H NMR (500 MHz, DMSO-d6) δ 12.12 (s, 1H), 8.93 (d, J = 5.0 Hz, 1H), 8.76 (d, J = 2.5 Hz, 1H), 8.03 (d, J = 5.0 Hz, 1H), 7.58 (d, J = 2.5 Hz, 1H), 7.47 (d, J = 4.0 Hz, 1H), 7.15-7.12 (m, 1H), 6.77 (d, J = 2.5 Hz, 1H). |
| 1-1457 | Cl | 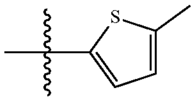 [SMILES: *c1ccc(C)s1] | 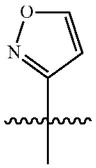 | |
| 1-1458 | Cl | 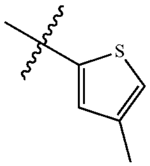 [SMILES: *c1cc(C)cs1] | 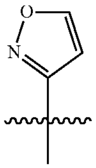 | |
| 1-1459 | Cl | 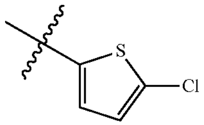 [SMILES: *c1ccc(Cl)s1] | 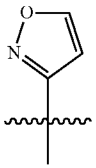 | |

TABLE A1-continued
| | | | | |
|---|---|---|---|---|
| 1-1460 | Cl | 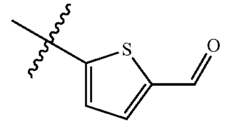 | 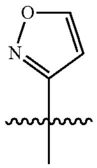 | |
| 1-1461 | Cl | 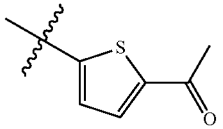 [SMILES: *c1ccc(C(C)=O)s1] | 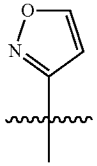 | |
| 1-1462 | Cl | 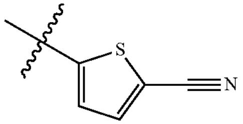 [SMILES: *c1ccc(C#N)s1] | 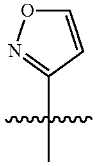 | |
| 1-1463 | Cl | 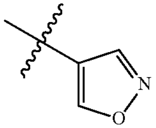 [SMILES: *c1cnoc1] | 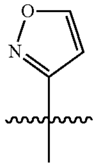 | |
| 1-1464 | $CH_3$ | 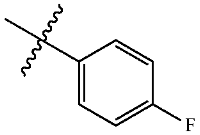 [SMILES: *c1ccc(F)cc1] | 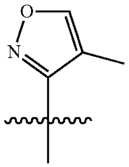 | $^1H$ NMR (500 MHz, DMSO-d6) δ 12.12 (s, 1H), 8.58 (d, J = 5.0 Hz, 1H), 7.98-7.90 (m, 2H), 7.85 (s, 1H), 7.49 (d, J = 5.0 Hz, 1H), 7.35-7.27 (m, 2H), 2.51 (s, 3H), 2.35 (s, 3H). |
| 1-1465 | F | 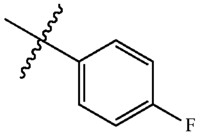 [SMILES: *c1ccc(F)cc1] | 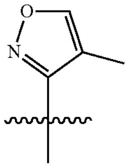 | |

TABLE A1-continued
| | | | | |
|---|---|---|---|---|
| 1-1466 | Br | 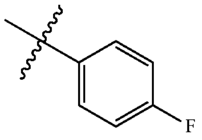 [SMILES: *c1ccc(F)cc1] | 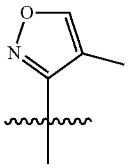 | |
| 1-1467 | 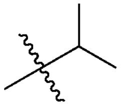 [SMILES: *C(C)C] | 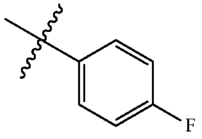 [SMILES: *c1ccc(F)cc1] | 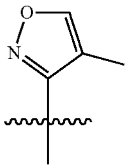 | |
| 1-1468 | $CF_3$ | 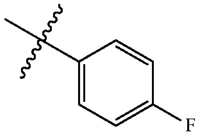 [SMILES: *c1ccc(F)cc1] | 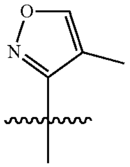 | $^1$H NMR (500 MHz, DMSO-d6) δ 12.09 (s, 1H), 8.75 (d, J = 5.0 Hz, 1H), 8.03-7.95 (m, 2H), 7.84 (s, 1H), 7.52 (d, J = 5.0 Hz, 1H), 7.35-7.27 (m, 2H), 2.31 (s, 3H). |
| 1-1469 | 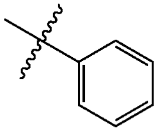 | 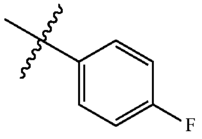 | 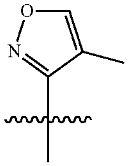 | $^1$H NMR (500 MHz, DMSO-d6) δ 12.15 (s, 1H), 8.95 (d, J = 5.0 Hz, 1H), 8.01-7.93 (m, 2H), 7.83 (s, 1H), 7.69-7.59 (m, 3H), 7.47-7.40 (m, 2H), 7.39-7.21 (m, 1H), 7.35-7.27 (m, 2H), 2.23 (s, 3H). |
| 1-1470 | 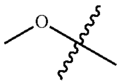 [SMILES: *OC] | 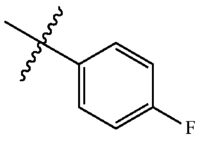 [SMILES: *c1ccc(F)cc1] | 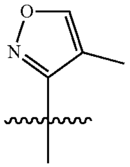 | $^1$H NMR (500 MHz, DMSO-d6) δ 12.12 (s, 1H), 8.56 (d, J = 5.0 Hz, 1H), 8.09-8.01 (m, 2H), 7.85 (s, 1H), 7.50 (d, J = 5.0 Hz, 1H), 7.35-7.27 (m, 2H), 3.67 (s, 3H), 2.31 (s, 3H). |
| 1-1471 | 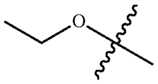 [SMILES: *OCC] | 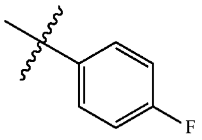 [SMILES: *c1ccc(F)cc1] | 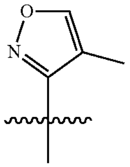 | |

TABLE A1-continued
| | | | | |
|---|---|---|---|---|
| 1-1472 | 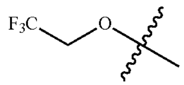 [SMILES: *OCC(F)(F)F] | 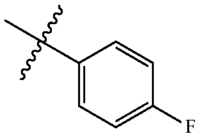 [SMILES: *c1ccc(F)cc1] | 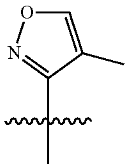 | |
| 1-1473 | 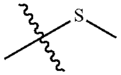 [SMILES: *SC] | 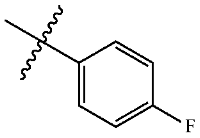 [SMILES: *c1ccc(F)cc1] | 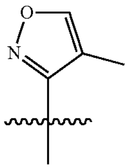 | |
| 1-1474 | 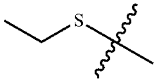 | 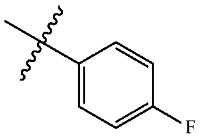 [SMILES: *c1ccc(F)cc1] | 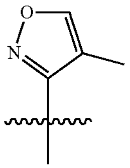 | $^1$H NMR (500 MHz, DMSO-d6) δ 12.05 (s, 1H), 8.58 (d, J = 4.9 Hz, 1H), 8.03-7.96 (m, 2H), 7.85 (s, 1H), 7.47 (d, J = 4.9 Hz, 1H), 7.35-7.27 (m, 2H), 3.00 (q, J = 8.0 Hz, 2H), 2.31 (s, 3H), 1.19 (t, J = 8.0 Hz, 3H). |
| 1-1475 | 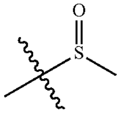 [SMILES: *S(C)=O] | 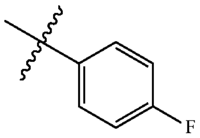 | 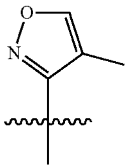 | |
| 1-1476 | 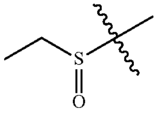 [SMILES: *S(=O)CC] | 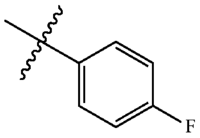 [SMILES: *c1ccc(F)cc1] | 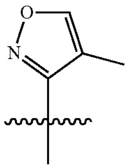 | $^1$H NMR (500 MHz, DMSO-d6) δ 12.06 (s, 1H), 8.83 (d, J = 5.0 Hz, 1H), 8.14-8.06 (m, 2H), 7.86 (s, 1H), 7.54 (d, J = 5.0 Hz, 1H), 7.35-7.27 (m, 2H), 2.63-2.61 (m, 1H), 2.59-2.56 (m, 1H), 2.31 (s, 3H), 1.22 (t, J = 8.0 Hz, 3H). |
| 1-1477 | 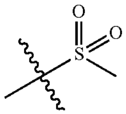 [SMILES: *S(C)(=O)=O] | 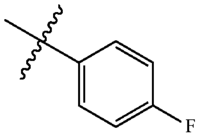 [SMILES: *c1ccc(F)cc1] | 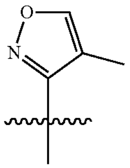 | |

TABLE A1-continued
| | | | | |
|---|---|---|---|---|
| 1-1478 | 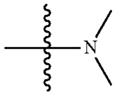 [SMILES: *N(C)C] | 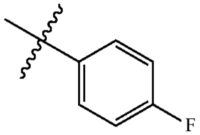 [SMILES: *c1ccc(F)cc1] | 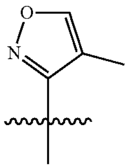 | 1H NMR (500 MHz, DMSO-d6) δ 12.07 (s, 1H), 8.38 (d, J = 5.0 Hz, 1H), 8.06-7.98 (m, 2H), 7.83 (s, 1H), 7.48 (d, J = 5.0 Hz, 1H), 7.35-7.27 (m, 2H), 2.75 (s, 6H), 2.30 (s, 3H). |
| 1-1479 | 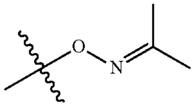 [SMILES: *ON=C(C)C] | 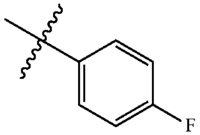 [SMILES: *c1ccc(F)cc1] | 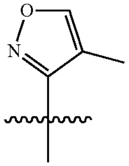 | |
| 1-1480 | Et | 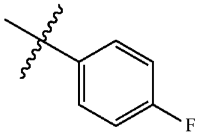 [SMILES: *c1ccc(F)cc1] | 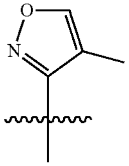 | |
| 1-1481 | 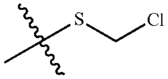 [SMILES: *SCCl] | 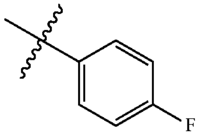 | 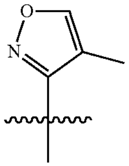 | |
| 1-1482 | $NO_2$ | 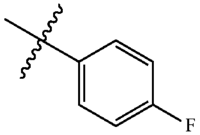 [SMILES: *c1ccc(F)cc1] | 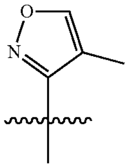 | 1H NMR (500 MHz, DMSO-d6) δ 12.09 (s, 1H), 8.96 (d, J = 5.0 Hz, 1H), 7.99-7.91 (m, 2H), 7.86 (s, 1H), 7.71 (d, J = 5.0 Hz, 1H), 7.35-7.27 (m, 2H), 2.31 (s, 3H). |
| 1-1483 | CN | 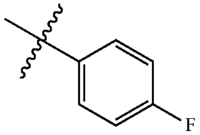 [SMILES: *c1ccc(F)cc1] | 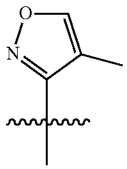 [SMILES: *c1nocc1C] | 1H NMR (500 MHz, DMSO-d6) δ 12.13 (s, 1H), 9.01 (d, J = 5.0 Hz, 1H), 8.05-7.97 (m, 2H), 7.84 (s, 1H), 7.69 (d, J = 5.0 Hz, 1H), 7.35-7.27 (m, 2H), 2.31 (s, 3H). |

TABLE A1-continued
| | | | | |
|---|---|---|---|---|
| 1-1484 | 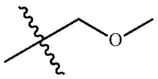 | 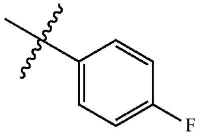 [SMILES: *c1ccc(F)cc1] | 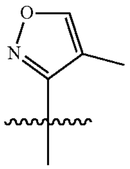 | 1H NMR (500 MHz, DMSO-d6) δ 12.09 (s, 1H), 8.68 (d, J = 5.0 Hz, 1H), 8.03-7.96 (m, 2H), 7.84 (s, 1H), 7.49 (d, J = 5.0 Hz, 1H), 7.35-7.27 (m, 2H), 4.68 (s, 2H), 3.28 (s, 3H), 2.30 (s, 3H). |
| 1-1485 | 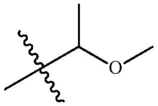 [SMILES: *C(C)OC] | 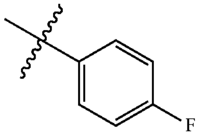 [SMILES: *c1ccc(F)cc1] | 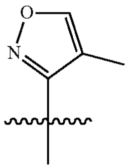 | |
| 1-1486 | 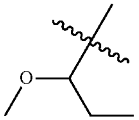 [SMILES: *C(CC)OC] | 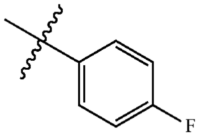 [SMILES: *c1ccc(F)cc1] | 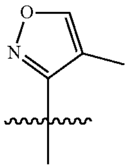 | |
| 1-1487 | 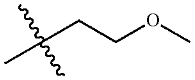 [SMILES: *CCOC] | 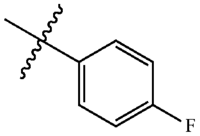 [SMILES: *c1ccc(F)cc1] | 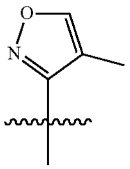 | |
| 1-1488 | 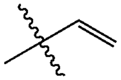 [SMILES: *C=C] | 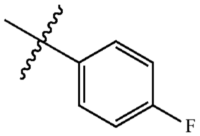 [SMILES: *c1ccc(F)cc1] | 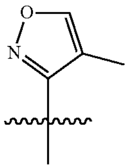 | |
| 1-1489 | 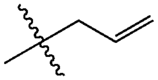 [SMILES: *CC=C] | 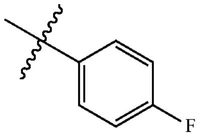 [SMILES: *c1ccc(F)cc1] | 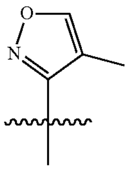 | |

TABLE A1-continued
| | | | | |
|---|---|---|---|---|
| 1-1490 | 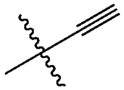 [SMILES: *C#C] | 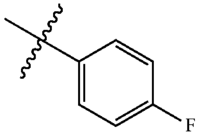 [SMILES: *c1ccc(F)cc1] | 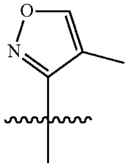 | 1H NMR (500 MHz, DMSO-d6) δ 12.08 (s, 1H), 8.69 (d, J = 5.0 Hz, 1H), 8.01-7.94 (m, 2H), 7.80 (s, 1H), 7.53 (d, J = 5.0 Hz, 1H), 7.35-7.27 (m, 2H), 4.31 (s, 1H), 2.39 (s, 3H). |
| 1-1491 | 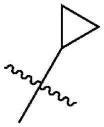 [SMILES: *C1CC1] | 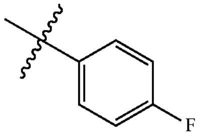 [SMILES: *c1ccc(F)cc1] | 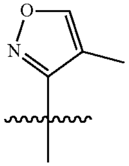 | |
| 1-1492 | 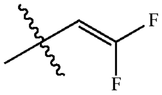 [SMILES: *C=C(F)F] | 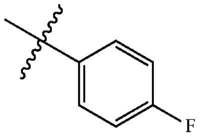 [SMILES: *c1ccc(F)cc1] | 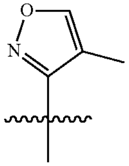 | |
| 1-1493 | 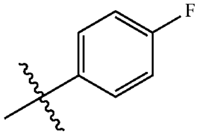 [SMILES: *c1ccc(F)cc1] | 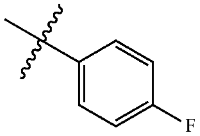 [SMILES: *c1ccc(F)cc1] | 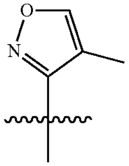 | |
| 1-1494 | Cl | 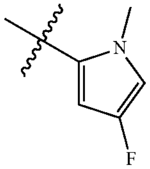 [SMILES: *c1cc(F)cn1C] | 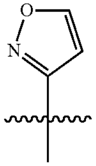 | |
| 1-1495 | Cl | 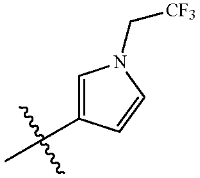 [SMILES: *c1ccn(CC(F)(F)F)c1] | 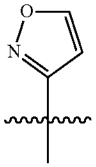 | |

TABLE A1-continued
| | | | |
|---|---|---|---|
| 1-1496 | Cl | 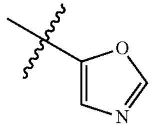 | 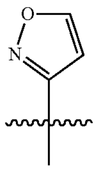 |
| 1-1497 | Cl | 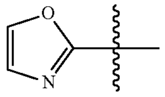 [SMILES: *c1ncco1] | 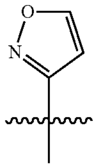 |
| 1-1498 | Cl | 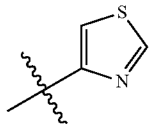 [SMILES: *c1cscn1] | 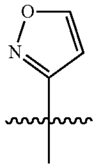 |
| 1-1499 | Cl | 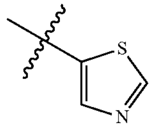 [SMILES: *c1cncs1] | 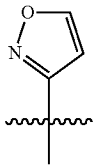 |
| 1-1500 | Cl | 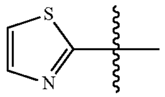 | 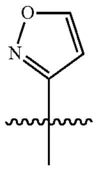 |
| 1-1501 | Cl | 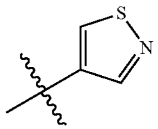 [SMILES: *c1cnsc1] | 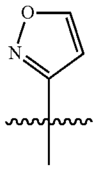 |

TABLE A1-continued
| | | | |
|---|---|---|---|
| 1-1502 | Cl | 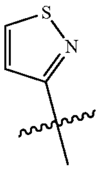 [SMILES: *c1ccsn1] | 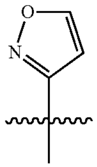 |
| 1-1503 | Cl | 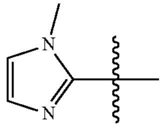 | 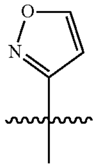 |
| 1-1504 | Cl | 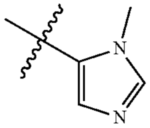 [SMILES: *c1cncn1C] | 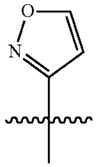 |
| 1-1505 | Cl | 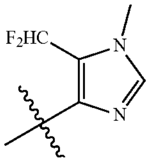 [SMILES: *c1ncn(C)c1C(F)F] | 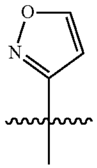 |
| 1-1506 | Cl | 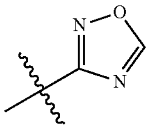 [SMILES: *c1ncon1] | 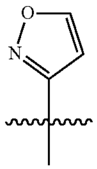 |
| 1-1507 | Cl | 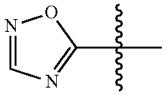 [SMILES: *c1ncno1] | 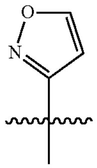 |

TABLE A1-continued
| | | | |
|---|---|---|---|
| 1-1508 | Cl | 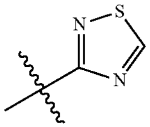 [SMILES: *c1ncsn1] | 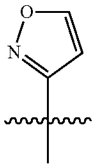 |
| 1-1509 | Cl | 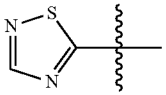 [SMILES: *c1ncns1] | 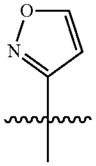 |
| 1-1510 | Cl | 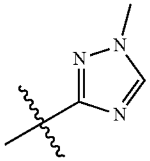 [SMILES: *c1ncn(C)n1] | 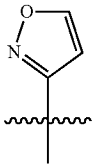 |
| 1-1511 | Cl | 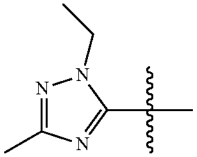 [SMILES: *c1nc(C)nn1CC] | 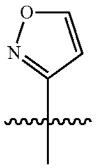 |
| 1-1512 | Cl | 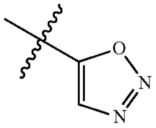 [SMILES: *c1cnno1] | 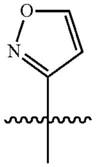 |
| 1-1513 | Cl | 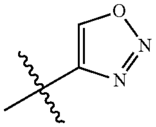 [SMILES: *c1conn1] | 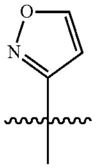 |

TABLE A1-continued
| | | | |
|---|---|---|---|
| 1-1514 | Cl | 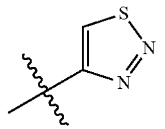 [SMILES: *c1csnn1] | 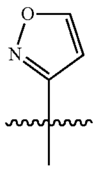 |
| 1-1515 | Cl | 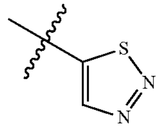 [SMILES: *c1cnns1] | 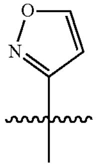 |
| 1-1516 | Cl | 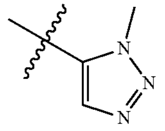 [SMILES: *c1cnnn1C] | 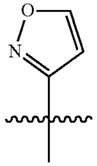 |
| 1-1517 | Cl | 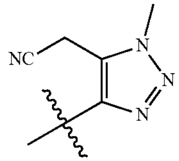 [SMILES: *c1nnn(C)c1CC#N] | 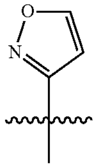 |
| 1-1518 | Cl | 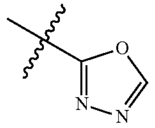 [SMILES: *c1nnco1] | 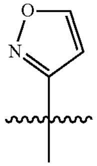 |
| 1-1519 | Cl | 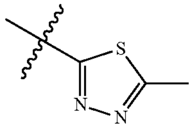 [SMILES: *c1nnc(C)s1] | 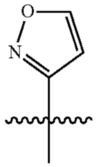 |

TABLE A1-continued
| | | | |
|---|---|---|---|
| 1-1520 | Cl | 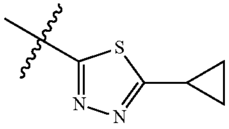 [SMILES: *c1nnc(C2CC2)s1] | 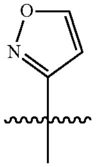 |
| 1-1521 | Cl | 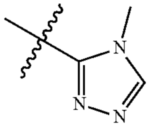 [SMILES: *c1nncn1C] | 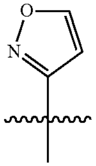 |
| 1-1522 | Cl | 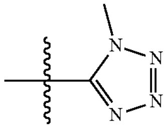 [SMILES: *c1nnnn1C] | 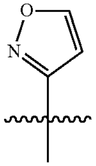 |
| 1-1523 | Cl | 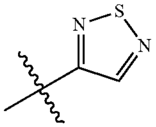 [SMILES: *c1cnsn1] | 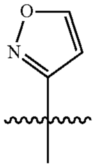 |
| 1-1524 | Cl | 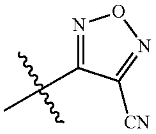 [SMILES: *c1nonc1C#N] | 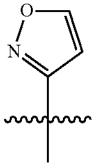 |
| 1-1525 | Cl | 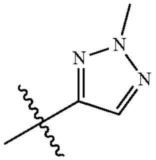 [SMILES: *c1cnn(C)n1] | 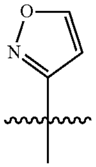 |

TABLE A1-continued
| | | | |
|---|---|---|---|
| 1-1526 | Cl | 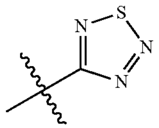 [SMILES: *c1nnsn1] | 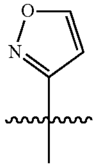 |
| 1-1527 | Cl | 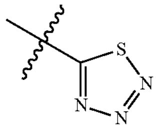 [SMILES: *c1nnns1] | 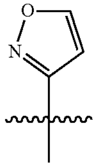 |
| 1-1528 | Cl | 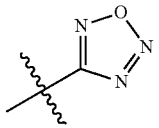 [SMILES: *c1nnon1] | 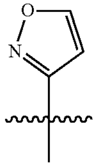 |
| 1-1529 | Cl | 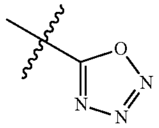 [SMILES: *c1nnno1] | 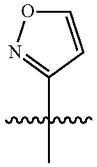 |
| 1-1530 | Cl | 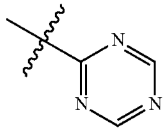 | 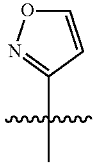 |
| 1-1531 | Cl | 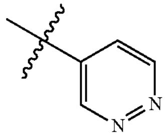 [SMILES: *c1ccnnc1] | 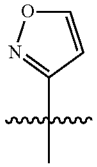 |

TABLE A1-continued
| | | | |
|---|---|---|---|
| 1-1532 | Cl | 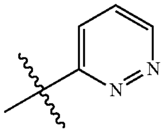 [SMILES: *c1cccnn1] | 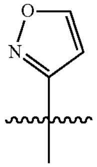 |
| 1-1533 | Cl | 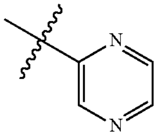 | 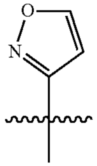 |
| 1-1534 | Cl | 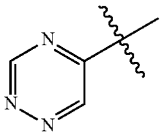 [SMILES: *c1cnncn1] | 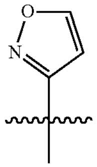 |
| 1-1535 | Cl | 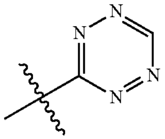 [SMILES: *c1nncnn1] | 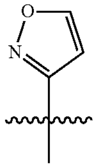 |
| 1-1536 | Cl | 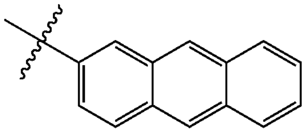 [SMILES: *c1ccc2cc3ccccc3cc2c1] | 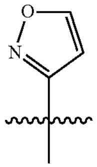 |
| 1-1537 | Cl | 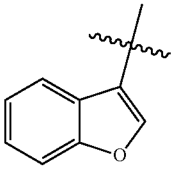 [SMILES: *c1coc2ccccc12] | 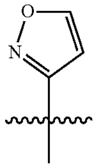 |

TABLE A1-continued
| | | | |
|---|---|---|---|
| 1-1538 | Cl | 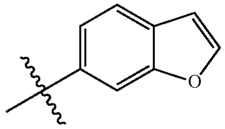 [SMILES: *c1ccc2ccoc2c1] | 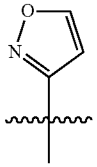 |
| 1-1539 | Cl | 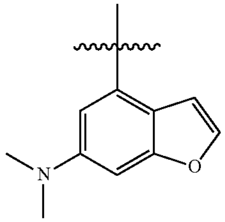 [SMILES: *c1cc(N(C)C)cc2occc12] | 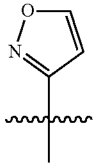 |
| 1-1540 | Cl | 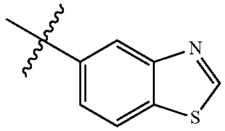 [SMILES: *c1ccc2scnc2c1] | 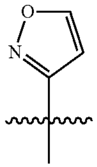 |
| 1-1541 | Cl | 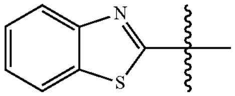 | 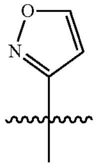 |
| 1-1542 | Cl | 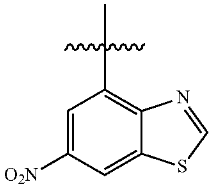 | 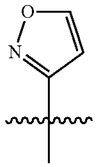 |

TABLE A1-continued
| | | | |
|---|---|---|---|
| 1-1543 | Cl | 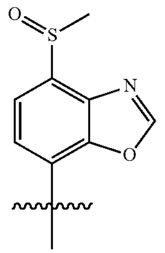 [SMILES: *c1ccc(S(C)=O)c2ncoc12] | 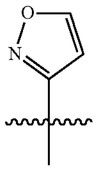 |
| 1-1544 | Cl | 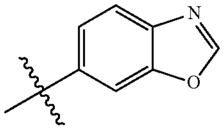 [SMILES: *c1ccc2ncoc2c1] | 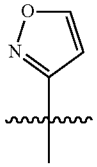 |
| 1-1545 | Cl | 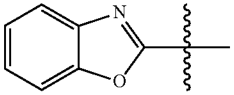 [SMILES: *c1nc2ccccc2o1] | 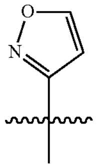 |
| 1-1546 | Cl | 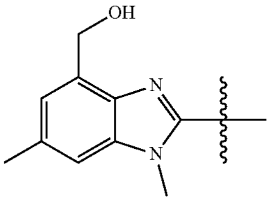 [SMILES: *c1nc2c(CO)cc(C)cc2n1C] | 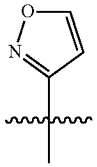 |
| 1-1547 | Cl | 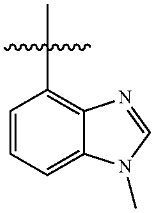 [SMILES: *c1cccc2c1ncn2C] | 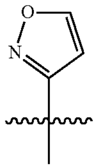 |

TABLE A1-continued
| | | | |
|---|---|---|---|
| 1-1548 | Cl | 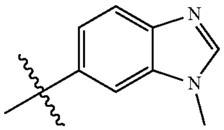 [SMILES: *c1ccc2ncn(C)c2c1] | 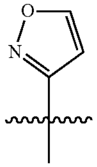 |
| 1-1549 | Cl | 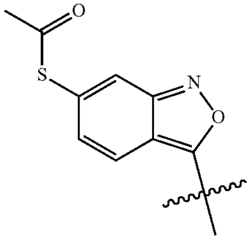 [SMILES: *c1onc2cc(SC(C)=O)ccc12] | 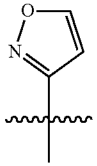 |
| 1-1550 | Cl | 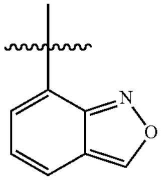 [SMILES: *c1cccc2conc12] | 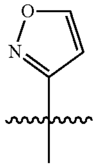 |
| 1-1551 | Cl | 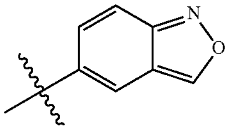 [SMILES: *c1ccc2nocc2c1] | 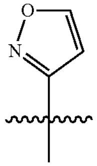 |
| 1-1552 | Cl | 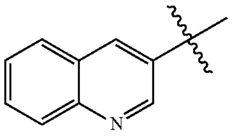 | 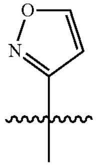 |

TABLE A1-continued
| | | | |
|---|---|---|---|
| 1-1553 | Cl | 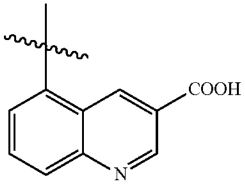 [SMILES: *c1cccc2ncc(C(=O)O)cc12] | 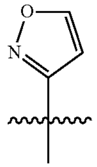 |
| 1-1554 | Cl | 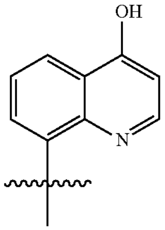 [SMILES: *c1cccc2c(O)ccnc12] | 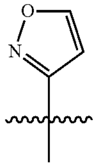 |
| 1-1555 | Cl | 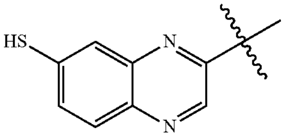 [SMILES: *c1cnc2ccc(S)cc2n1] | 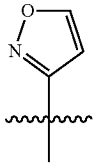 |
| 1-1556 | Cl | 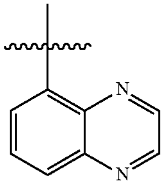 [SMILES: *c1cccc2nccnc12] | 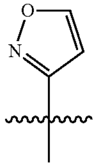 |
| 1-1557 | Cl | 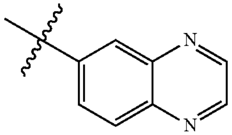 [SMILES: *c1ccc2nccnc2c1] | 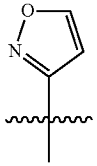 |

TABLE A1-continued
| | | | |
|---|---|---|---|
| 1-1558 | Cl | 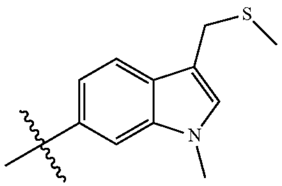 [SMILES: *c1ccc2c(CSC)cn(C)c2c1] | 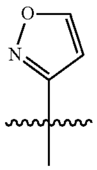 |
| 1-1559 | Cl | 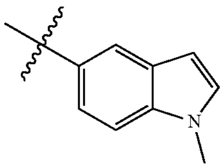 [SMILES: *c1ccc2c(ccn2C)c1] | 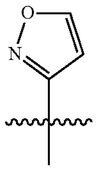 |
| 1-1560 | Cl | 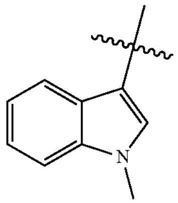 [SMILES: *c1cn(C)c2ccccc12] | 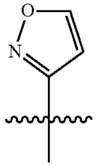 |
| 1-1561 | Cl | 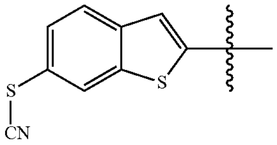 [SMILES: *c1cc2ccc(SC#N)cc2s1] | 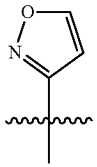 |
| 1-1562 | Cl | 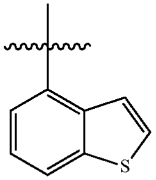 [SMILES: *c1cccc2sccc12] | 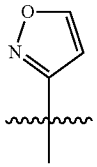 |

TABLE A1-continued
| | | | |
|---|---|---|---|
| 1-1563 | Cl | 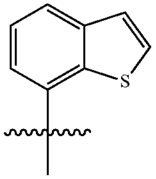 [SMILES: *c1cccc2ccsc12] | 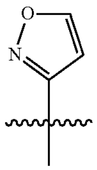 |
| 1-1564 | Cl | 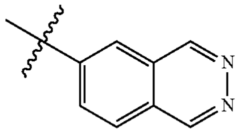 [SMILES: *c1ccc2cnncc2c1] | 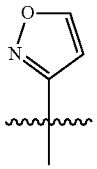 |
| 1-1565 | Cl | 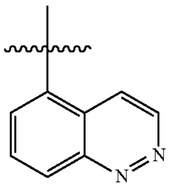 [SMILES: *c1cccc2nnccc12] | 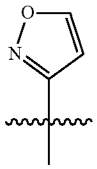 |
| 1-1566 | Cl | 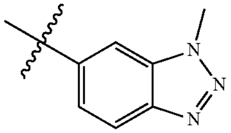 [SMILES: *c1ccc2nnn(C)c2c1] | 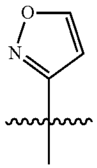 |
| 1-1567 | Cl | 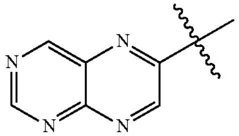 [SMILES: *c1cnc2ncncc2n1] | 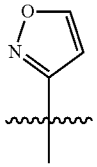 |

TABLE A1-continued
| | | | |
|---|---|---|---|
| 1-1568 | Cl | 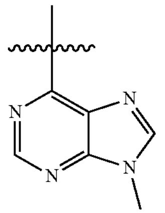 [SMILES: *c1ncnc2c1ncn2C] | 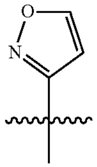 |
| 1-1569 | Cl | 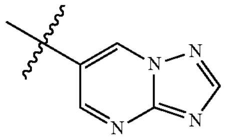 [SMILES: *c1cnc2ncnn2c1] | 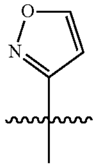 |
| 1-1570 | Cl | 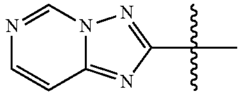 [SMILES: *c1nc2ccncn2n1] | 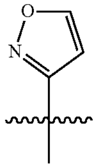 |
| 1-1571 | Cl | 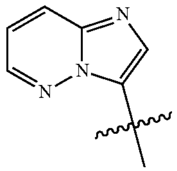 [SMILES: *c1cnc2cccnn12] | 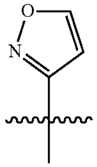 |
| 1-1572 | Cl | 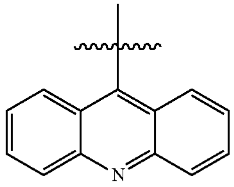 [SMILES: *c1c2ccccc2nc2ccccc12] | 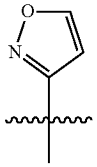 |

TABLE A1-continued
| | | | | |
|---|---|---|---|---|
| 1-1573 | Cl | 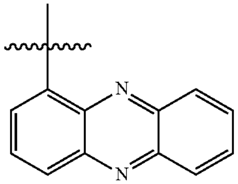 [SMILES: *c1cccc2nc3ccccc3nc12] | 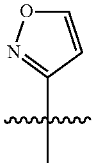 | |
| 1-1574 | Cl | 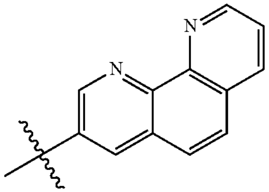 [SMILES: *c1cnc2c(ccc3cccnc32)c1] | 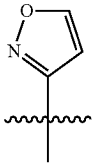 | |
| 1-1575 | Cl | 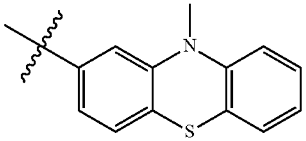 [SMILES: *c1ccc2c(c1)N(C)c1ccccc1S2] | 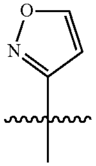 | |
| 1-1576 | Cl | 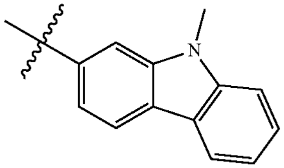 [SMILES: *c1ccc2c3ccccc3n(C)c2c1] | 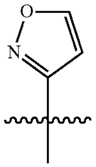 | |
| 1-1577 | Cl | 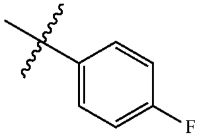 [SMILES: *c1ccc(F)cc1] | 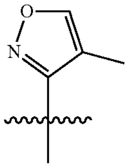 | $^1$H NMR (500 MHz, DMSO-d6) δ 12.06 (s, 1H), 8.76 (d, J = 5.0 Hz, 1H), 7.78 (s, 1H), 7.63-7.56 (m, 2H), 7.41 (d, J = 5.0 Hz, 1H), 7.11-7.03 (m, 2H), 2.31 (s, 3H). |

TABLE A1-continued
| | | | | |
|---|---|---|---|---|
| 1-1578 | Cl | 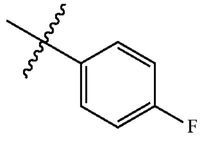 [SMILES: *c1ccc(F)cc1] | 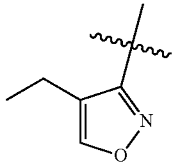 [SMILES: *c1nocc1CC] | 1H NMR (500 MHz, DMSO-d6) δ 12.08 (s, 1H), 8.68 (d, J = 5.0 Hz, 1H), 8.04-7.97 (m, 2H), 7.76 (s, 1H), 7.54 (d, J = 5.0 Hz, 1H), 7.35-7.27 (m, 2H), 2.70 (q, J = 8.0 Hz, 2H), 1.25 (t, J = 8.0 Hz, 3H). |
| 1-1579 | Cl | 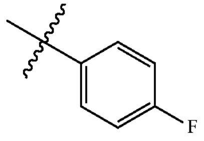 [SMILES: *c1ccc(F)cc1] | 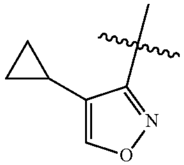 [SMILES: *c1nocc1C1CC1] | 1H NMR (500 MHz, DMSO-d6) δ 12.07 (s, 1H), 8.95 (d, J = 5.0 Hz, 1H), 8.34-8.26 (m, 2H), 8.10 (s, 1H), 7.55 (d, J = 5.0 Hz, 1H), 7.35-7.27 (m, 2H), 2.46-2.32 (m, 1H), 1.12-1.02 (m, 2H), 0.85-0.69 (m, 2H). |
| 1-1580 | Cl | 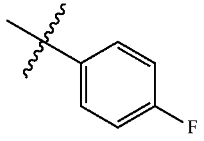 [SMILES: *c1ccc(F)cc1] | 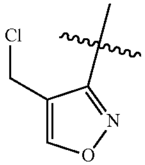 [SMILES: *c1nocc1CCl] | 1H NMR (500 MHz, DMSO-d6) δ 12.07 (s, 1H), 8.68 (d, J = 5.0 Hz, 1H), 8.04-7.97 (m, 2H), 7.85 (s, 1H), 7.50 (d, J = 5.0 Hz, 1H), 7.35-7.27 (m, 2H), 4.64 (s, 2H). |
| 1-1581 | Cl | 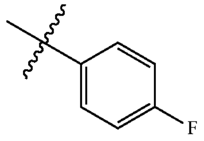 [SMILES: *c1ccc(F)cc1] | 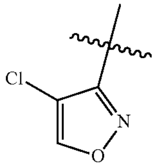 [SMILES: *c1nocc1Cl] | 1H NMR (500 MHz, DMSO-d6) δ 12.08 (s, 1H), 8.68 (d, J = 5.0 Hz, 1H), 8.04-7.97 (m, 3H), 7.52 (d, J = 5.0 Hz, 1H), 7.35-7.27 (m, 2H). |
| 1-1582 | Cl | 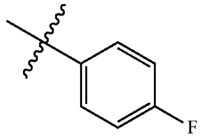 [SMILES: *c1ccc(F)cc1] | 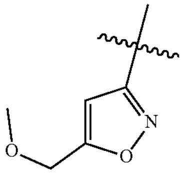 [SMILES: *c1cc(COC)on1] | 1H NMR (500 MHz, DMSO-d6) δ 11.99 (s, 1H), 8.68 (d, J = 5.0 Hz, 1H), 8.04-7.97 (m, 2H), 7.51 (d, J = 5.0 Hz, 1H), 7.35-7.27 (m, 2H), 6.82 (s, 1H), 4.63 (s, 2H), 3.33 (s, 3H). |
| 1-1583 | Cl | 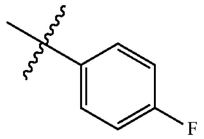 [SMILES: *c1ccc(F)cc1] | 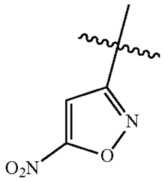 [SMILES: *c1cc([N+](=O)[O-])on1] | 1H NMR (500 MHz, DMSO-d6) δ 12.05 (s, 1H), 8.69 (d, J = 5.0 Hz, 1H), 8.04-7.97 (m, 2H), 7.72 (s, 1H), 7.52 (d, J = 5.0 Hz, 1H), 7.35-7.27 (m, 2H). |

TABLE A1-continued
| | | | | |
|---|---|---|---|---|
| 1-1584 | Cl | 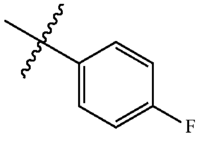 [SMILES: *c1ccc(F)cc1] | 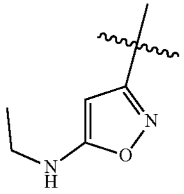 [SMILES: *c1cc(NCC)on1] | 1H NMR (500 MHz, DMSO-d6) δ 12.43 (s, 1H), 10.68 (s, 1H), 8.67 (d, J = 5.0 Hz, 1H), 8.04-7.96 (m, 2H), 7.50 (d, J = 5.0 Hz, 1H), 7.35-7.27 (m, 2H), 5.88 (s, 1H), 3.47 (q, J = 8.0 Hz, 2H), 1.07 (t, J = 8.0 Hz, 3H). |
| 1-1585 | Cl | 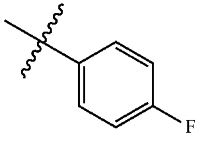 [SMILES: *c1ccc(F)cc1] | 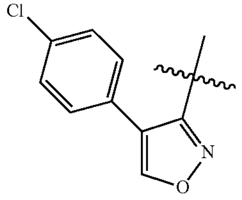 [SMILES: *c1nocc1-c1ccc(Cl)cc1] | 1H NMR (500 MHz, DMSO-d6) δ 12.08 (s, 1H), 8.88 (d, J = 5.0 Hz, 1H), 8.11 (s, 1H), 8.07-7.99 (m, 2H), 7.65-7.58 (m, 3H), 7.58-7.52 (m, 2H), 7.35-7.27 (m, 2H). |
| 1-1586 | Cl | 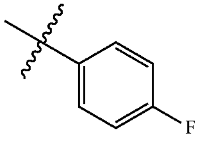 [SMILES: *c1ccc(F)cc1] | 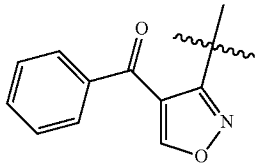 [SMILES: *c1nocc1C(=O)c1ccccc1] | 1H NMR (500 MHz, DMSO-d6) δ 12.06 (s, 1H), 9.00 (s, 1H), 8.88 (d, J = 5.0 Hz, 1H), 8.07-7.99 (m, 2H), 7.86-7.79 (m, 2H), 7.73-7.65 (m, 1H), 7.66-7.56 (m, 3H), 7.35-7.27 (m, 2H). |
| 1-1587 | Cl | 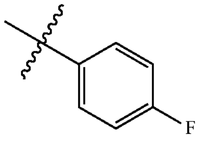 [SMILES: *c1ccc(F)cc1] | 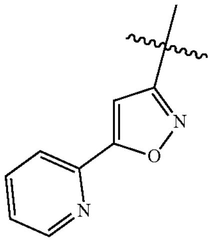 [SMILES: *c1cc(-c2ccccn2)on1] | 1H NMR (500 MHz, DMSO-d6) δ 12.24 (s, 1H), 8.83 (d, J = 5.0 Hz, 1H), 8.73-8.58 (m, 1H), 8.07-8.00 (m, 2H), 7.97 (dd, J = 8.0, 1.0 Hz, 1H), 7.86-7.69 (m, 1H), 7.63 (d, J = 5.0 Hz, 1H), 7.48-7.36 (m, 1H), 7.35-7.27 (m, 2H), 6.74 (s, 1H). |
| 1-1588 | Cl | 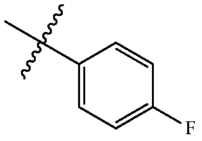 [SMILES: *c1ccc(F)cc1] | 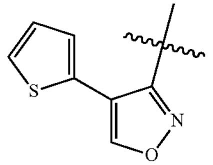 [SMILES: *c1nocc1-c1cccs1] | 1H NMR (500 MHz, DMSO-d6) δ 12.06 (s, 1H), 8.69 (d, J = 5.0 Hz, 1H), 8.30 (s, 1H), 8.05-7.97 (m, 2H), 7.70 (d, J = 2.0 Hz, 1H), 7.58 (d, J = 5.0 Hz, 1H), 7.35-7.27 (m, 2H), 7.19-7.09 (m, 2H). |

TABLE A1-continued
| | | | | |
|---|---|---|---|---|
| 1-1589 | Cl | 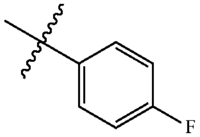 [SMILES: *c1ccc(F)cc1] | 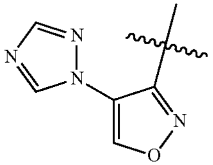 [SMILES: *c1nocc1-n1cncn1] | 1H NMR (500 MHz, DMSO-d6) δ 12.07 (s, 1H), 8.85 (s, 1H), 8.69 (d, J = 5.0 Hz, 1H), 8.32 (s, 1H), 8.28 (s, 1H), 8.05-7.98 (m, 2H), 7.53 (d, J = 5.0 Hz, 1H), 7.35-7.27 (m, 2H). |
| 1-1590 | Cl | $CH_3$ | 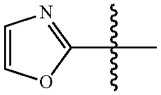 [SMILES: *c1ncco1] | |
| 1-1591 | Cl | 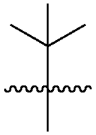 [SMILES: *C(C)(C)C] | 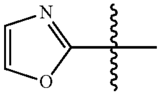 [SMILES: *c1ncco1] | |
| 1-1592 | Cl | 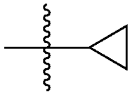 | 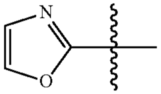 [SMILES: *c1ncco1] | |
| 1-1593 | Cl | 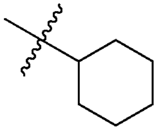 [SMILES: *C1CCCCC1] | 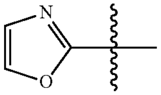 [SMILES: *c1ncco1] | |
| 1-1594 | Cl | 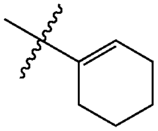 [SMILES: *C1=CCCCC1] | 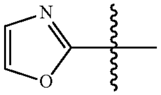 [SMILES: *c1ncco1] | |
| 1-1595 | Cl | 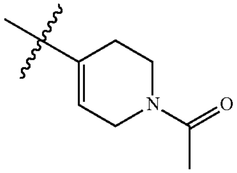 [SMILES: *C1=CCN(C(C)=O)CC1] | 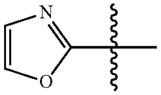 [SMILES: *c1ncco1] | $^{1}H$ NMR (500 MHz, DMSO-$d_6$) δ 12.09 (s, 1H), 8.66 (d, J = 5.0 Hz, 1H), 7.63 (d, J = 5.0 Hz, 1H), 7.44 (d, J = 2.5 Hz, 1H), 7.25 (d, J = 2.5 Hz, 1H), 6.42-6.36 (m, 1H), 4.34 (t, J = 6.0 Hz, 2H), 3.33-3.31 (m, 2H), 3.05-3.01 (m, 2H), 1.96 (s, 3H). |

TABLE A1-continued
| | | | |
|---|---|---|---|
| 1-1596 | Cl | 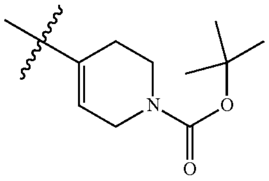 [SMILES: *C1=CCN(C(=O)OC(C)(C)C)CC1] | 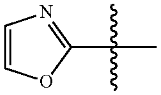 [SMILES: *c1ncco1] |
| 1-1597 | Cl | 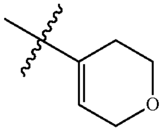 [SMILES: *C1=CCOCC1] | 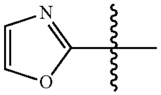 |
| 1-1598 | Cl | 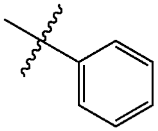 [SMILES: *c1ccccc1] | 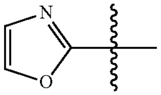 |
| 1-1599 | Cl | 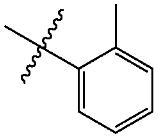 [SMILES: *c1ccccc1C] | 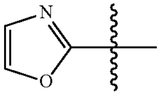 |
| 1-1600 | Cl | 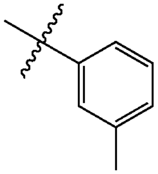 [SMILES: *c1cccc(C)c1] | 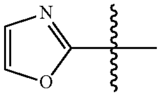 [SMILES: *c1ncco1] |
| 1-1601 | Cl | 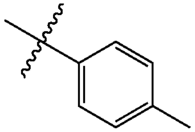 [SMILES: *c1ccc(C)cc1] | 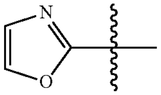 |

TABLE A1-continued
| | | | | |
|---|---|---|---|---|
| 1-1602 | Cl | 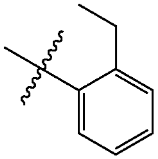 [SMILES: *c1ccccc1CC] | 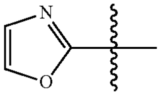 | |
| 1-1603 | Cl | 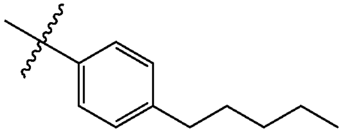 [SMILES: *c1ccc(CCCCC)cc1] | 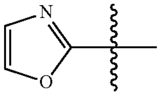 [SMILES: *c1ncco1] | |
| 1-1604 | Cl | 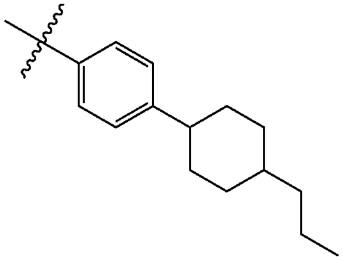 [SMILES: *c1ccc(C2CCC(CCC)CC2)cc1] | 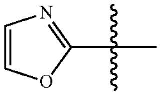 [SMILES: *c1ncco1] | |
| 1-1605 | Cl | 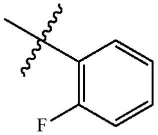 [SMILES: *c1ccccc1F] | 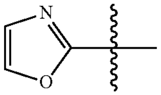 [SMILES: *c1ncco1] | |
| 1-1606 | Cl | 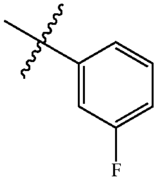 [SMILES: *c1cccc(F)c1] | 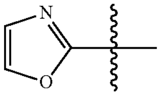 [SMILES: *c1ncco1] | |
| 1-1607 | Cl | 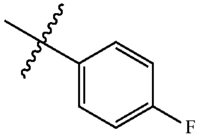 [SMILES: *c1ccc(F)cc1] | 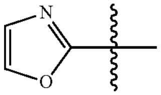 [SMILES: *c1ncco1] | 1H NMR (500 MHz, DMSO-d6) δ 12.24 (s, 1H), 8.67 (d, J = 5.0 Hz, 1H), 8.05-7.98 (m, 2H), 7.56-7.48 (m, 2H), 7.35-7.27 (m, 2H), 7.23 (d, J = 2.5 Hz, 1H). |

TABLE A1-continued
| | | | |
|---|---|---|---|
| 1-1608 | Cl | 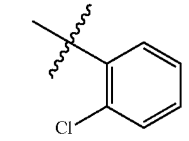 [SMILES: *c1ccccc1Cl] | 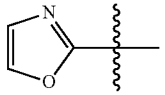 |
| 1-1609 | Cl | 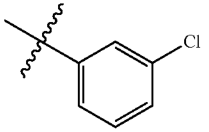 [SMILES: *c1cccc(Cl)c1] | 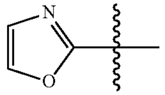 |
| 1-1610 | Cl | 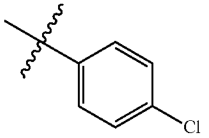 [SMILES: *c1ccc(Cl)cc1] | 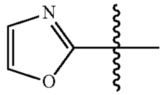 [SMILES: *c1ncco1] |
| 1-1611 | Cl | 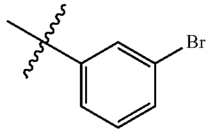 [SMILES: *c1cccc(Br)c1] | 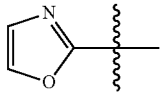 [SMILES: *c1ncco1] |
| 1-1612 | Cl | 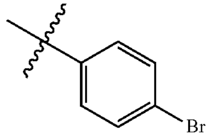 [SMILES: *c1ccc(Br)cc1] | 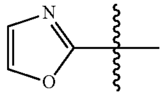 [SMILES: *c1ncco1] |
| 1-1613 | Cl | 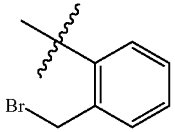 [SMILES: *c1ccccc1CBr] | 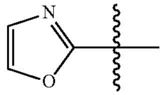 |
| 1-1614 | Cl | 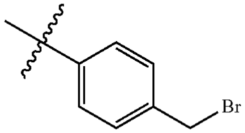 [SMILES: *c1ccc(CBr)cc1] | 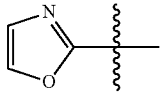 [SMILES: *c1ncco1] |

TABLE A1-continued
| | | | |
|---|---|---|---|
| 1-1615 | Cl | 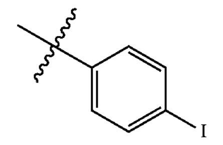 [SMILES: *c1ccc(I)cc1] | 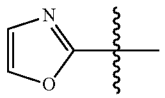 [SMILES: *c1ncco1] |
| 1-1616 | Cl | 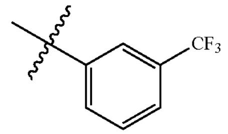 [SMILES: *c1cccc(C(F)(F)F)c1] | 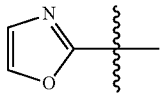 |
| 1-1617 | Cl | 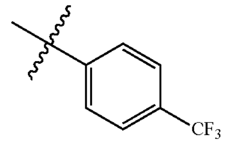 | 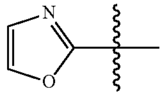 [SMILES: *c1ncco1] |
| 1-1618 | Cl | 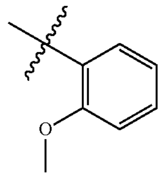 [SMILES: *c1ccccc1OC] | 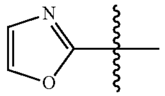 [SMILES: *c1ncco1] |
| 1-1619 | Cl | 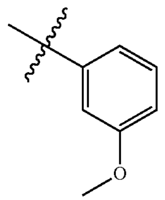 [SMILES: *c1cccc(OC)c1] | 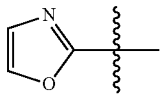 |
| 1-1620 | Cl | 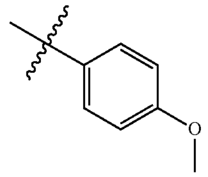 [SMILES: *c1ccc(OC)cc1] | 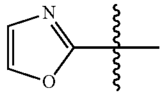 [SMILES: *c1ncco1] |

TABLE A1-continued
| | | | |
|---|---|---|---|
| 1-1621 | Cl | 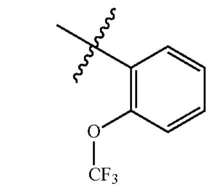 | 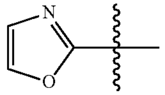 |
| 1-1622 | Cl | 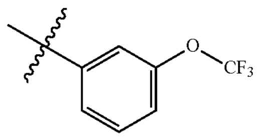 [SMILES: *c1cccc(OC(F)(F)F)c1] | 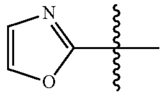 |
| 1-1623 | Cl | 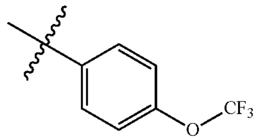 [SMILES: *c1ccc(OC(F)(F)F)cc1] | 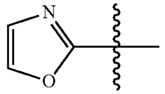 [SMILES: *c1ncco1] |
| 1-1624 | Cl | 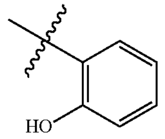 [SMILES: *c1ccccc1O] | 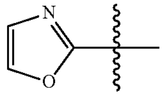 [SMILES: *c1ncco1] |
| 1-1625 | Cl | 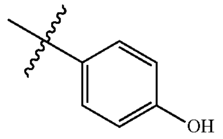 | 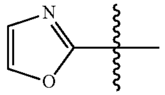 [SMILES: *c1ncco1] |
| 1-1626 | Cl | 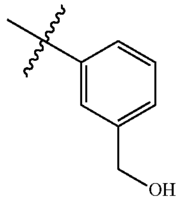 [SMILES: *c1cccc(CO)c1] | 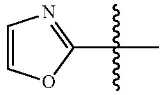 |

TABLE A1-continued
| | | | |
|---|---|---|---|
| 1-1627 | Cl | 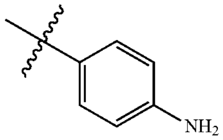 | 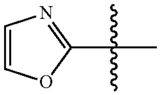 [SMILES: *c1ncco1] |
| 1-1628 | Cl | 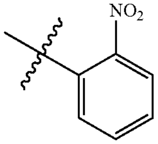 | 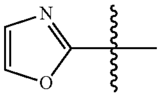 [SMILES: *c1ncco1] |
| 1-1629 | Cl | 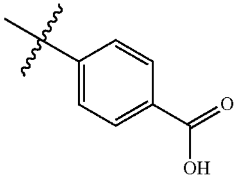 [SMILES: *c1ccc(C(=O)O)cc1] | 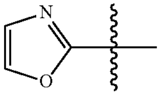 |
| 1-1630 | Cl | 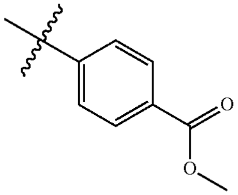 [SMILES: *c1ccc(C(=O)OC)cc1] | 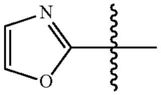 [SMILES: *c1ncco1] |
| 1-1631 | Cl | 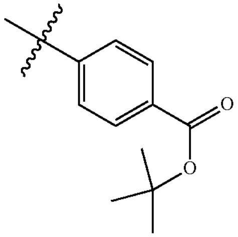 [SMILES: *c1ccc(C(=O)OC(C)(C)C)cc1] | 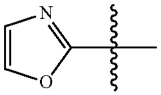 [SMILES: *c1ncco1] |

TABLE A1-continued
| | | | |
|---|---|---|---|
| 1-1632 | Cl | 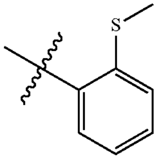 [SMILES: *c1ccccc1SC] | 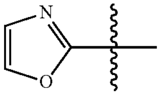 |
| 1-1633 | Cl | 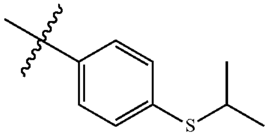 [SMILES: *c1ccc(SC(C)C)cc1] | 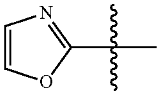 [SMILES: *c1ncco1] |
| 1-1634 | Cl | 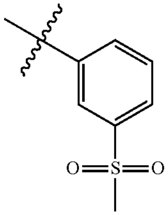 [SMILES: *c1cccc(S(C)(=O)=O)c1] | 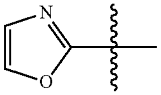 [SMILES: *c1ncco1] |
| 1-1635 | Cl | 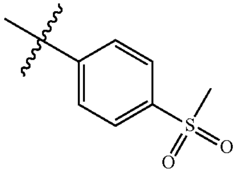 [SMILES: *c1ccc(S(C)(=O)=O)cc1] | 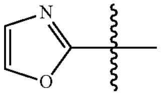 [SMILES: *c1ncco1] |
| 1-1636 | Cl | 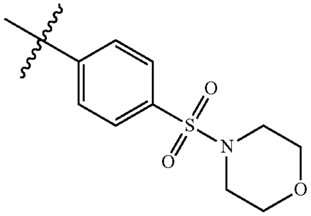 [SMILES: *c1ccc(S(=O)(=O)N2CCOCC2)cc1] | 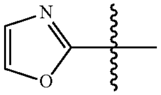 |

TABLE A1-continued
| | | | |
|---|---|---|---|
| 1-1637 | Cl | 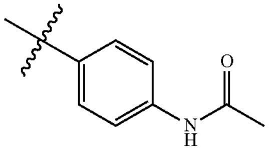 [SMILES: *c1ccc(NC(C)=O)cc1] | 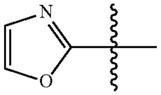 [SMILES: *c1ncco1] |
| 1-1638 | Cl | 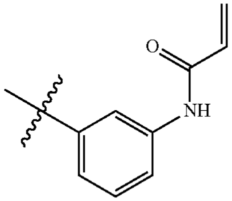 [SMILES: *c1cccc(NC(=O)C=C)c1] | 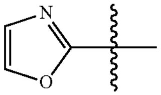 |
| 1-1639 | Cl | 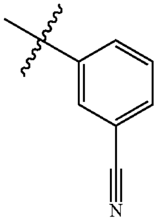 [SMILES: *c1cccc(C#N)c1] | 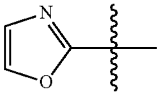 [SMILES: *c1ncco1] |
| 1-1640 | Cl | 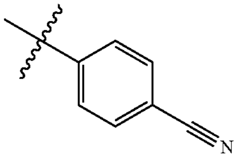 [SMILES: *c1ccc(C#N)cc1] | 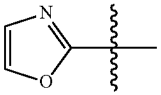 [SMILES: *c1ncco1] |
| 1-1641 | Cl | 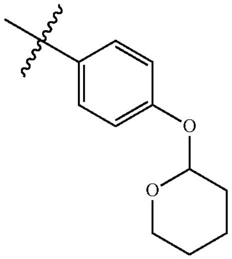 [SMILES: *c1ccc(OC2CCCCO2)cc1] | 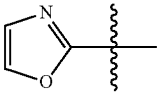 [SMILES: *c1ncco1] |

TABLE A1-continued
| | | | |
|---|---|---|---|
| 1-1642 | Cl | 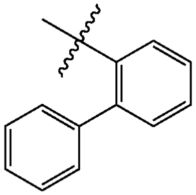 [SMILES: *c1ccccc1-c1ccccc1] | 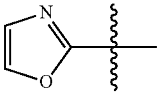 [SMILES: *c1ncco1] |
| 1-1643 | Cl | 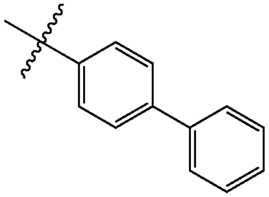 [SMILES: *c1ccc(-c2ccccc2)cc1] | 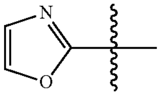 [SMILES: *c1ncco1] |
| 1-1644 | Cl | 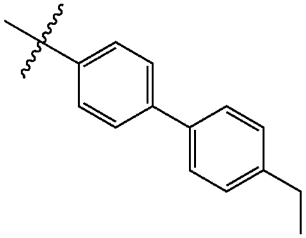 [SMILES: *c1ccc(-c2ccc(CC)cc2)cc1] | 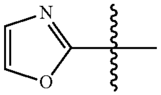 [SMILES: *c1ncco1] |
| 1-1645 | Cl | 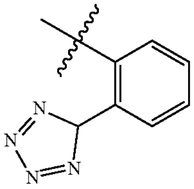 [SMILES: *c1ccccc1C1N=NN=N1] | 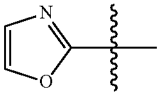 |
| 1-1646 | Cl | 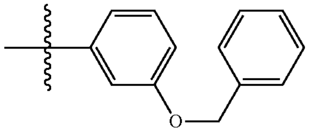 [SMILES: *c1cccc(OCc2ccccc2)c1] | 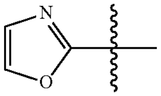 [SMILES: *c1ncco1] |

TABLE A1-continued
| | | | |
|---|---|---|---|
| 1-1647 | Cl | 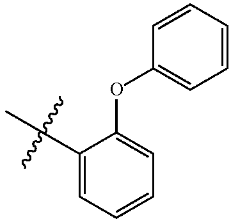 [SMILES: *c1ccccc1Oc1ccccc1] | 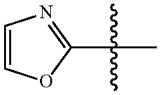 |
| 1-1648 | Cl | 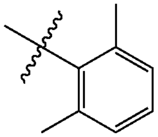 [SMILES: *c1c(C)cccc1C] | 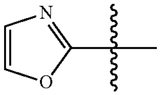 [SMILES: *c1ncco1] |
| 1-1649 | Cl | 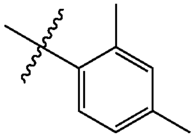 [SMILES: *c1ccc(C)cc1C] | 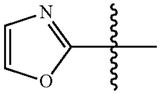 [SMILES: *c1ncco1] |
| 1-1650 | Cl | 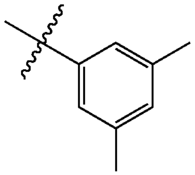 [SMILES: *c1cc(C)cc(C)c1] | 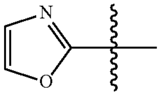 |
| 1-1651 | Cl | 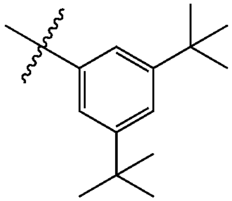 [SMILES: *c1cc(C(C)(C)C)cc(C(C)(C)C)c1] | 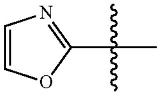 [SMILES: *c1ncco1] |

TABLE A1-continued
| | | | |
|---|---|---|---|
| 1-1652 | Cl | 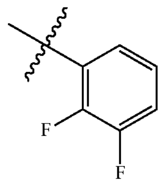 [SMILES: *c1cccc(F)c1F] | 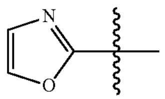 |
| 1-1653 | Cl | 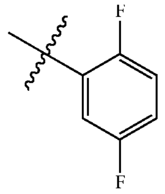 [SMILES: *c1cc(F)ccc1F] | 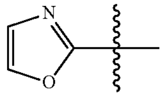 [SMILES: *c1ncco1] |
| 1-1654 | Cl | 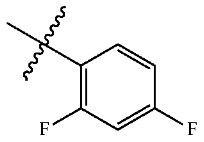 [SMILES: *c1ccc(F)cc1F] | 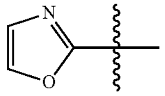 [SMILES: *c1ncco1] |
| 1-1655 | Cl | 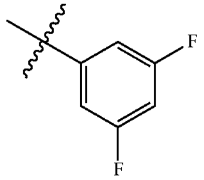 [SMILES: *c1cc(F)cc(F)c1] | 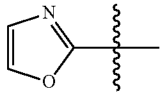 [SMILES: *c1ncco1] |
| 1-1656 | Cl | 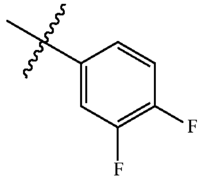 [SMILES: *c1ccc(F)c(F)c1] | 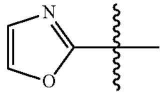 |

TABLE A1-continued
| | | | |
|---|---|---|---|
| 1-1657 | Cl | 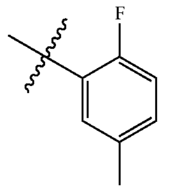 [SMILES: *c1cc(C)ccc1F] | 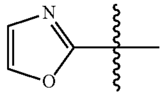 [SMILES: *c1ncco1] |
| 1-1658 | Cl | 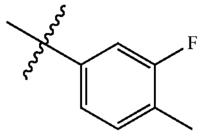 [SMILES: *c1ccc(C)c(F)c1] | 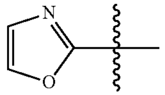 [SMILES: *c1ncco1] |
| 1-1659 | Cl | 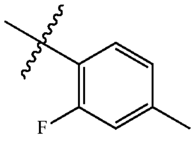 [SMILES: *c1ccc(C)cc1F] | 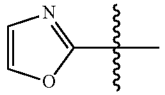 |
| 1-1660 | Cl | 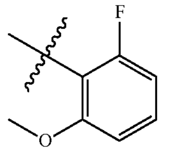 [SMILES: *c1c(F)cccc1OC] | 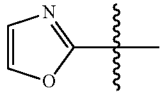 [SMILES: *c1ncco1] |
| 1-1661 | Cl | 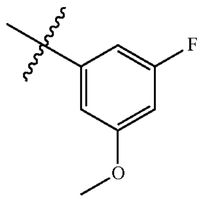 [SMILES: *c1cc(F)cc(OC)c1] | 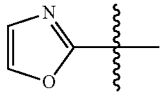 [SMILES: *c1ncco1] |
| 1-1662 | Cl | 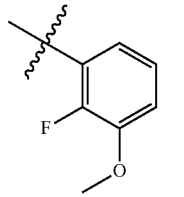 [SMILES: *c1cccc(OC)c1F] | 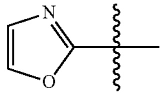 [SMILES: *c1ncco1] |

TABLE A1-continued
| | | | |
|---|---|---|---|
| 1-1663 | Cl | 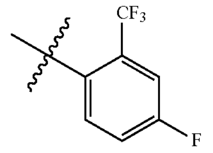 | 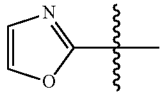 [SMILES: *c1ncco1] |
| 1-1664 | Cl | 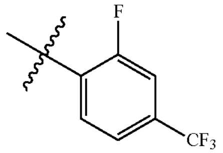 | 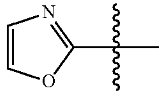 [SMILES: *c1ncco1] |
| 1-1665 | Cl | 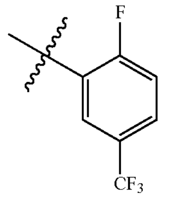 | 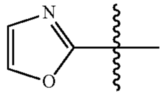 |
| 1-1666 | Cl | 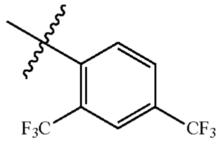 | 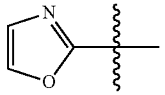 [SMILES: *c1ncco1] |
| 1-1667 | Cl | 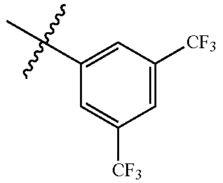 [SMILES: *c1cc(C(F)(F)F)cc(C(F)(F)F)c1] | 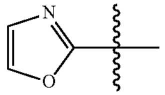 |
| 1-1668 | Cl | 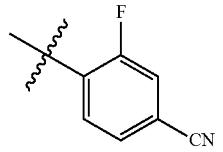 [SMILES: *c1ccc(C#N)cc1F] | 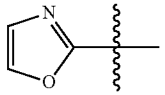 [SMILES: *c1ncco1] |

TABLE A1-continued
| | | | |
|---|---|---|---|
| 1-1669 | Cl | 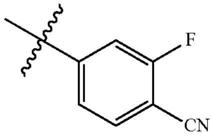 [SMILES: *c1ccc(C#N)c(F)c1] | 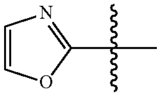 [SMILES: *c1ncco1] |
| 1-1670 | Cl | 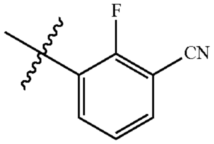 [SMILES: *c1cccc(C#N)c1F] | 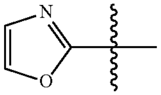 [SMILES: *c1ncco1] |
| 1-1671 | Cl | 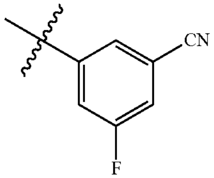 [SMILES: *c1cc(F)cc(C#N)c1] | 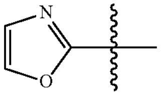 |
| 1-1672 | Cl | 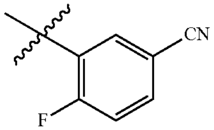 [SMILES: *c1cc(C#N)ccc1F] | 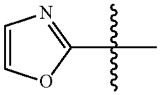 [SMILES: *c1ncco1] |
| 1-1673 | Cl | 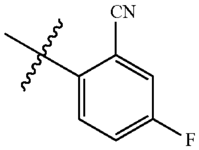 | 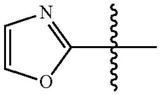 [SMILES: *c1ncco1] |
| 1-1674 | Cl | 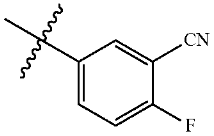 [SMILES: *c1ccc(F)c(C#N)c1] | 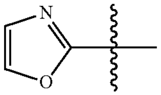 [SMILES: *c1ncco1] |

TABLE A1-continued
| | | | |
|---|---|---|---|
| 1-1675 | Cl | 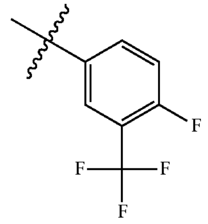 [SMILES: *c1ccc(F)c(C(F)(F)F)c1] | 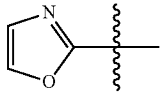 [SMILES: *c1ncco1] |
| 1-1676 | Cl | 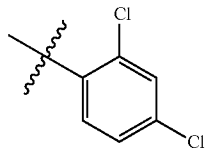 [SMILES: *c1ccc(Cl)cc1Cl] | 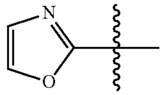 |
| 1-1677 | Cl | 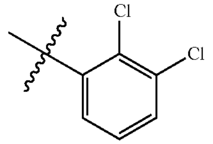 [SMILES: *c1cccc(Cl)c1Cl] | 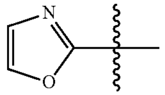 [SMILES: *c1ncco1] |
| 1-1678 | Cl | 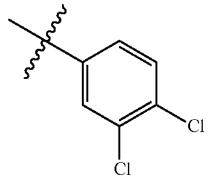 [SMILES: *c1ccc(Cl)c(Cl)c1] | 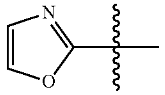 [SMILES: *c1ncco1] |
| 1-1679 | Cl | 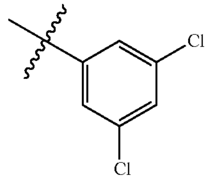 [SMILES: *c1cc(Cl)cc(Cl)c1] | 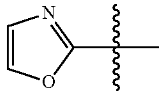 [SMILES: *c1ncco1] |

TABLE A1-continued
| | | | |
|---|---|---|---|
| 1-1680 | Cl | 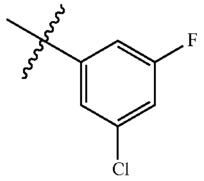 [SMILES: *c1cc(F)cc(Cl)c1] | 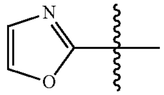 [SMILES: *c1ncco1] |
| 1-1681 | Cl | 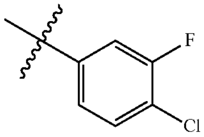 | 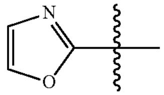 [SMILES: *c1ncco1] |
| 1-1682 | Cl | 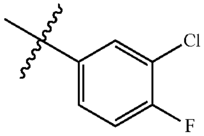 [SMILES: *c1ccc(F)c(Cl)c1] | 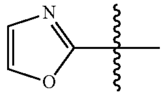 |
| 1-1683 | Cl | 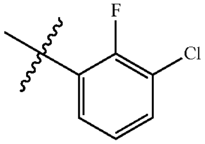 | 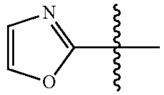 [SMILES: *c1ncco1] |
| 1-1684 | Cl | 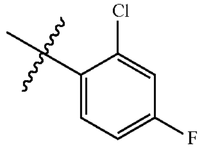 [SMILES: *c1ccc(F)cc1Cl] | 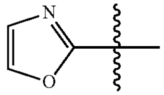 [SMILES: *c1ncco1] |
| 1-1685 | Cl | 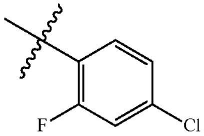 [SMILES: *c1ccc(Cl)cc1F] | 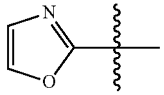 |

TABLE A1-continued
| | | | |
|---|---|---|---|
| 1-1686 | Cl | 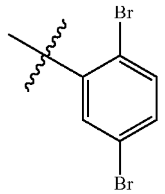 | 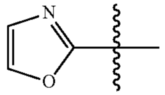 [SMILES: *c1ncco1] |
| 1-1687 | Cl | 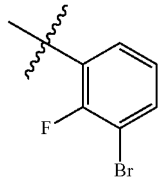 [SMILES: *c1cccc(Br)c1F] | 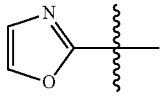 |
| 1-1688 | Cl | 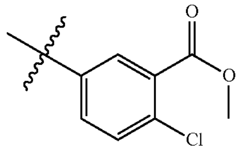 | 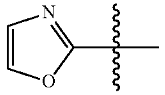 |
| 1-1689 | Cl | 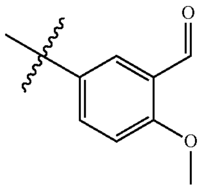 [SMILES: *c1ccc(OC)c(C=O)c1] | 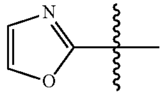 [SMILES: *c1ncco1] |
| 1-1690 | Cl | 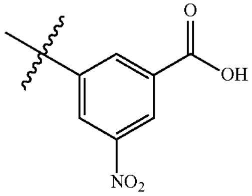 | 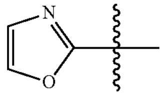 [SMILES: *c1ncco1] |

TABLE A1-continued
| | | | |
|---|---|---|---|
| 1-1691 | Cl | 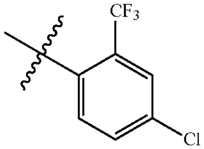 | 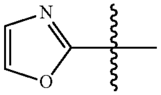 |
| 1-1692 | Cl | 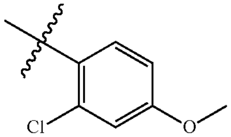 [SMILES: *c1ccc(OC)cc1Cl] | 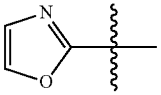 [SMILES: *c1ncco1] |
| 1-1693 | Cl | 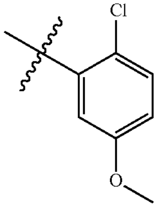 [SMILES: *c1cc(OC)ccc1Cl] | 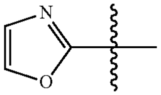 [SMILES: *c1ncco1] |
| 1-1694 | Cl | 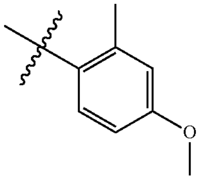 [SMILES: *c1ccc(OC)cc1C] | 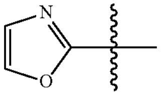 |
| 1-1695 | Cl | 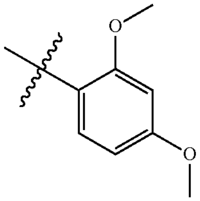 [SMILES: *c1ccc(OC)cc1OC] | 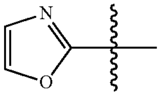 |

TABLE A1-continued
| | | | |
|---|---|---|---|
| 1-1696 | Cl | 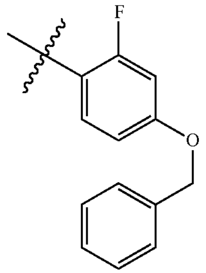 [SMILES: *c1ccc(OCc2ccccc2)cc1F] | 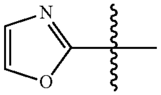 [SMILES: *c1ncco1] |
| 1-1697 | Cl | 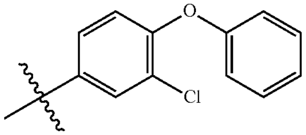 [SMILES: *c1ccc(Oc2ccccc2)c(Cl)c1] | 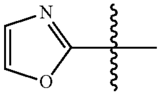 |
| 1-1698 | Cl | 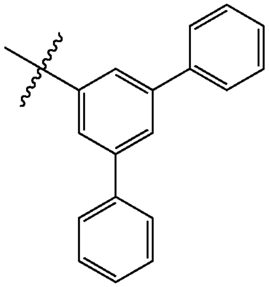 [SMILES: *c1cc(-c2ccccc2)cc(-c2ccccc2)c1] | 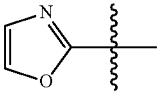 |
| 1-1699 | Cl | 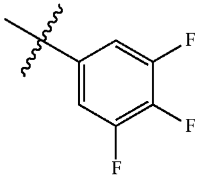 [SMILES: *c1cc(F)c(F)c(F)c1] | 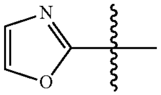 |
| 1-1700 | Cl | 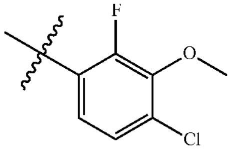 [SMILES: *c1ccc(Cl)c(OC)c1F] | 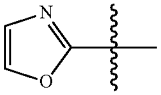 [SMILES: *c1ncco1] |

TABLE A1-continued
| | | | | |
|---|---|---|---|---|
| 1-1701 | Cl | 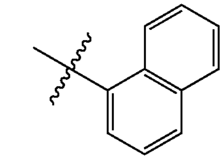 [SMILES: *c1cccc2ccccc12] | 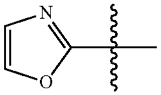 [SMILES: *c1ncco1] | $^1H$ NMR (500 MHz, DMSO-$d_6$) δ 12.12 (s, 1H), 8.89 (d, J = 5.0 Hz, 1H), 8.39 (dd, J = 7.5, 2.0 Hz, 1H), 8.15-8.07 (m, 2H), 8.03-8.01 (m, 1H), 7.90 (t, J = 7.5 Hz, 1H), 7.64 (d, J = 5.0 Hz, 1H), 7.60-7.56 (m, 1H), 7.52-7.50 (m, 1H), 7.47 (d, J = 2.0 Hz, 1H), 7.25 (d, J = 2.0 Hz, 1H). |
| 1-1702 | Cl | 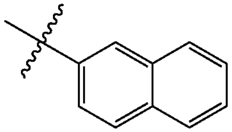 [SMILES: *c1ccc2ccccc2c1] | 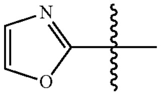 [SMILES: *c1ncco1] | |
| 1-1703 | Cl | 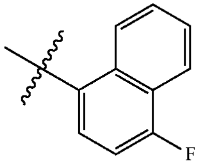 [SMILES: *c1ccc(F)c2ccccc12] | 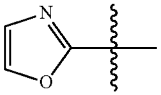 | |
| 1-1704 | Cl | 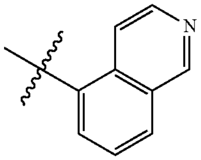 [SMILES: *c1cccc2cnccc12] | 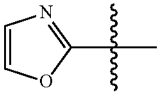 [SMILES: *c1ncco1] | |
| 1-1705 | Cl | 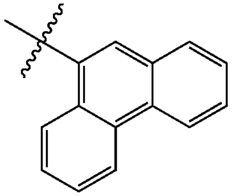 [SMILES: *c1cc2ccccc2c2ccccc12] | 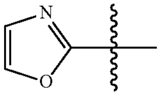 | |
| 1-1706 | Cl | 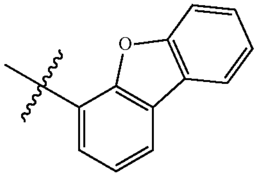 [SMILES: *c1cccc2c1oc1ccccc12] | 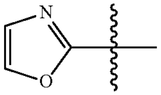 | |

TABLE A1-continued
| | | | | |
|---|---|---|---|---|
| 1-1707 | Cl | 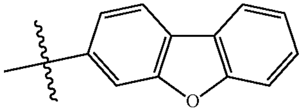 [SMILES: *c1ccc2c(c1)oc1ccccc12] | 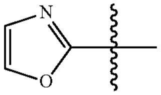 [SMILES: *c1ncco1] | |
| 1-1708 | Cl | 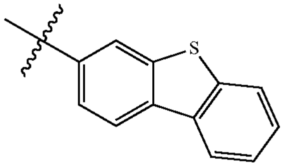 [SMILES: *c1ccc2c(c1)sc1ccccc12] | 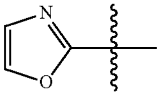 [SMILES: *c1ncco1] | |
| 1-1709 | Cl | 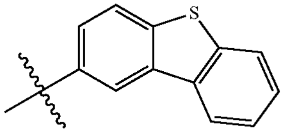 [SMILES: *c1ccc2sc3ccccc3c2c1] | 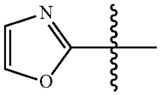 | $^1$H NMR (500 MHz, DMSO-$d_6$) δ 12.08 (s, 1H), 8.89 (d, J = 5.0 Hz, 1H), 8.63 (s, 1H), 8.48 (dd, J = 7.5, 2.0 Hz, 1H), 8.15-8.10 (m, 2H), 8.07-8.04 (m, 1H), 7.61 (d, J = 5.0 Hz, 1H), 7.56-7.54 (m, 1H), 7.49-7.46 (m, 1H), 7.45 (d, J = 2.5 Hz, 1H), 7.25 (d, J = 2.5 Hz, 1H). |
| 1-1710 | Cl | 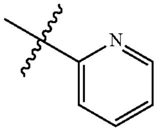 [SMILES: *c1ccccn1] | 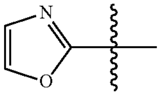 [SMILES: *c1ncco1] | |
| 1-1711 | Cl | 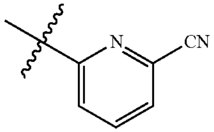 [SMILES: *c1cccc(C#N)n1] | 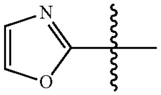 [SMILES: *c1ncco1] | |
| 1-1712 | Cl | 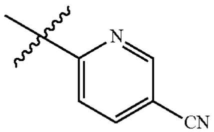 [SMILES: *c1ccc(C#N)cn1] | 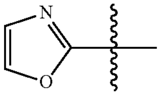 | |
| 1-1713 | Cl | 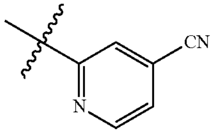 [SMILES: *c1cc(C#N)ccn1] | 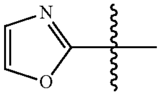 [SMILES: *c1ncco1] | |

TABLE A1-continued
| | | | |
|---|---|---|---|
| 1-1714 | Cl | 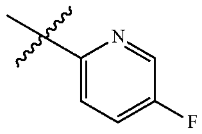 [SMILES: *c1ccc(F)cn1] | 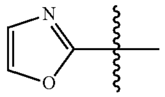 [SMILES: *c1ncco1] |
| 1-1715 | Cl | 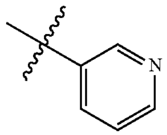 [SMILES: *c1cccnc1] | 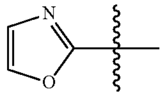 |
| 1-1716 | Cl | 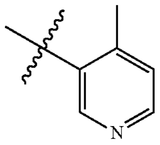 [SMILES: *c1cnccc1C] | 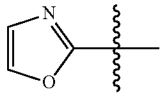 [SMILES: *c1ncco1] |
| 1-1717 | Cl | 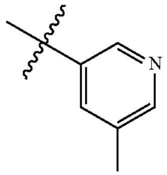 [SMILES: *c1cncc(C)c1] | 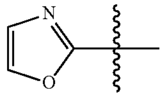 [SMILES: *c1ncco1] |
| 1-1718 | Cl | 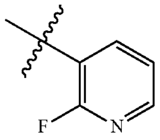 [SMILES: *c1cccnc1F] | 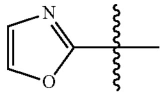 [SMILES: *c1ncco1] |
| 1-1719 | Cl | 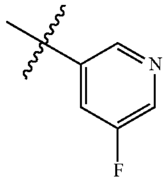 [SMILES: *c1cncc(F)c1] | 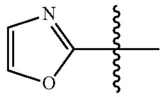 [SMILES: *c1ncco1] |

TABLE A1-continued
| | | | |
|---|---|---|---|
| 1-1720 | Cl | 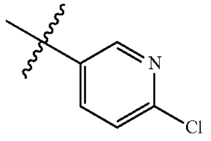 [SMILES: *c1ccc(Cl)nc1] | 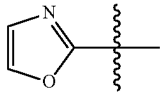 |
| 1-1721 | Cl | 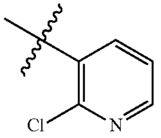 [SMILES: *c1cccnc1Cl] | 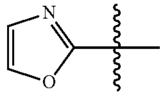 [SMILES: *c1ncco1] |
| 1-1722 | Cl | 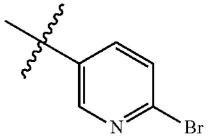 | 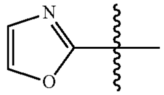 [SMILES: *c1ncco1] |
| 1-1723 | Cl | 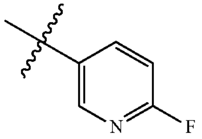 [SMILES: *c1ccc(F)nc1] | 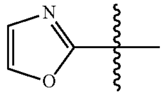 [SMILES: *c1ncco1] |
| 1-1724 | Cl | 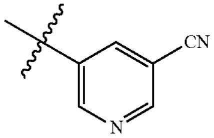 [SMILES: *c1cncc(C#N)c1] | 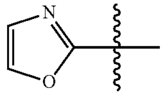 [SMILES: *c1ncco1] |
| 1-1725 | Cl | 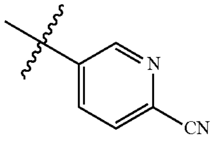 | 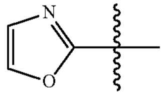 [SMILES: *c1ncco1] |
| 1-1726 | Cl | 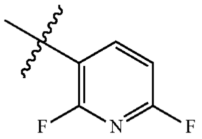 [SMILES: *c1ccc(F)nc1F] | 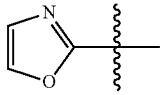 [SMILES: *c1ncco1] |

TABLE A1-continued
| | | | |
|---|---|---|---|
| 1-1727 | Cl | 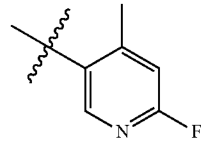 [SMILES: *c1cnc(F)cc1C] | 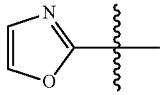 |
| 1-1728 | Cl | 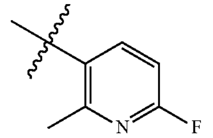 | 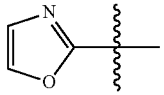 [SMILES: *c1ncco1] |
| 1-1729 | Cl | 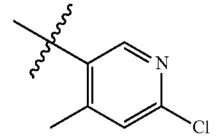 | 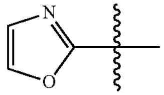 |
| 1-1730 | Cl | 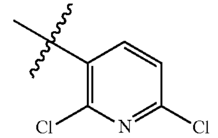 [SMILES: *c1ccc(Cl)nc1Cl] | 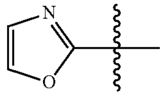 [SMILES: *c1ncco1] |
| 1-1731 | Cl | 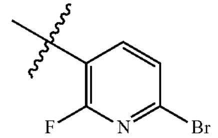 [SMILES: *c1ccc(Br)nc1F] | 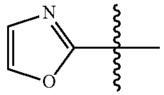 [SMILES: *c1ncco1] |
| 1-1732 | Cl | 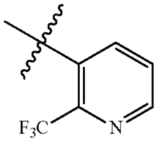 | 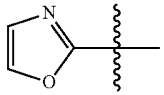 [SMILES: *c1ncco1] |
| 1-1733 | Cl | 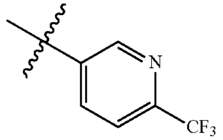 | 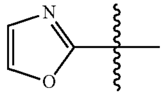 [SMILES: *c1ncco1] |

TABLE A1-continued
| | | | |
|---|---|---|---|
| 1-1734 | Cl | 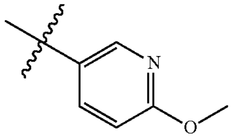 [SMILES: *c1ccc(OC)nc1] | 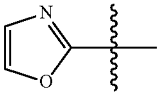 |
| 1-1735 | Cl | 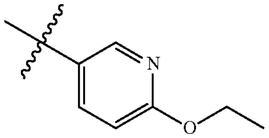 [SMILES: *c1ccc(OCC)nc1] | 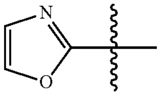 [SMILES: *c1ncco1] |
| 1-1736 | Cl | 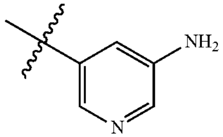 [SMILES: *c1cncc(N)c1] | 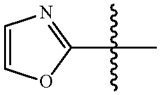 [SMILES: *c1ncco1] |
| 1-1737 | Cl | 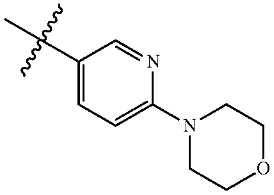 | 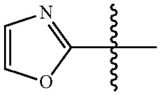 [SMILES: *c1ncco1] |
| 1-1738 | Cl | 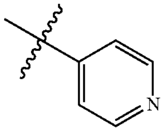 [SMILES: *c1ccncc1] | 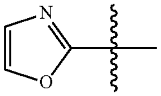 [SMILES: *c1ncco1] |
| 1-1739 | Cl | 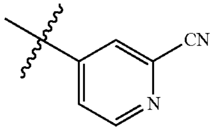 [SMILES: *c1ccnc(C#N)c1] | 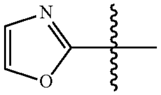 [SMILES: *c1ncco1] |
| 1-1740 | Cl | 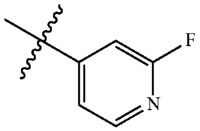 [SMILES: *c1ccnc(F)c1] | 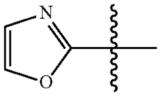 [SMILES: *c1ncco1] |

TABLE A1-continued
| | | | | |
|---|---|---|---|---|
| 1-1741 | Cl | 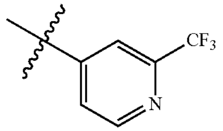 [SMILES: *c1ccnc(C(F)(F)F)c1] | 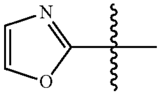 [SMILES: *c1ncco1] | $^1$H NMR (500 MHz, DMSO-$d_6$) δ 12.07 (s, 1H), 8.82 (d, J = 5.0 Hz, 1H), 8.77 (d, J = 5.0 Hz, 1H), 8.13 (s, 1H), 8.02 (d, J = 5.0 Hz, 1H), 7.76 (d, J = 5.0 Hz, 1H), 7.43 (d, J = 2.5 Hz, 1H), 7.24 (d, J = 2.5 Hz, 1H). |
| 1-1742 | Cl | 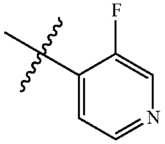 [SMILES: *c1ccncc1F] | 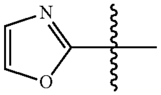 | |
| 1-1743 | Cl | 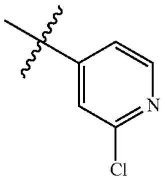 [SMILES: *c1ccnc(Cl)c1] | 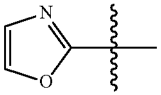 | |
| 1-1744 | Cl | 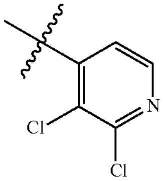 [SMILES: *c1ccnc(Cl)c1Cl] | 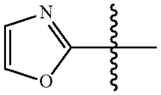 [SMILES: *c1ncco1] | |
| 1-1745 | Cl | 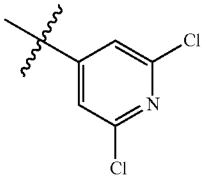 [SMILES: *c1cc(Cl)nc(Cl)c1] | 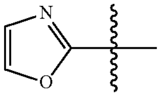 [SMILES: *c1ncco1] | |
| 1-1746 | Cl | 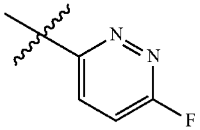 [SMILES: *c1ccc(F)nn1] | 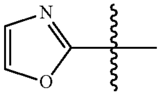 [SMILES: *c1ncco1] | |

TABLE A1-continued
| | | | |
|---|---|---|---|
| 1-1747 | Cl | 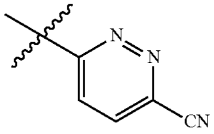 [SMILES: *c1ccc(C#N)nn1] | 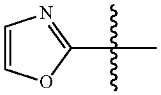 |
| 1-1748 | Cl | 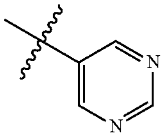 [SMILES: *c1cncnc1] | 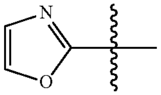 |
| 1-1749 | Cl | 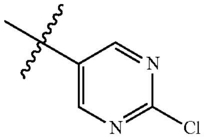 [SMILES: *c1cnc(Cl)nc1] | 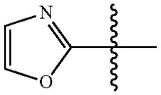 [SMILES: *c1ncco1] |
| 1-1750 | Cl | 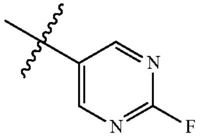 [SMILES: *c1cnc(F)nc1] | 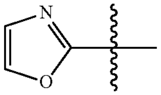 |
| 1-1751 | Cl | 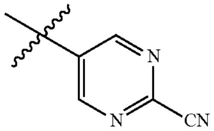 [SMILES: *c1cnc(C#N)nc1] | 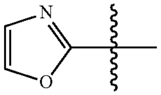 |
| 1-1752 | Cl | 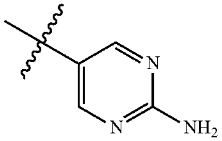 | 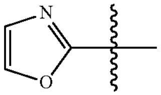 [SMILES: *c1ncco1] |
| 1-1753 | Cl | 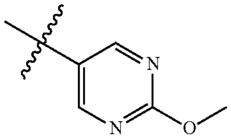 [SMILES: *c1cnc(OC)nc1] | 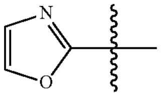 |

TABLE A1-continued
| | | | |
|---|---|---|---|
| 1-1754 | Cl | 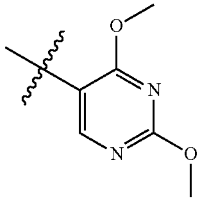 [SMILES: *c1cnc(OC)nc1OC] | 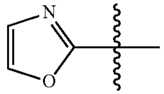 |
| 1-1755 | Cl | 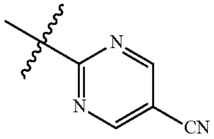 | 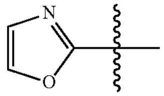 |
| 1-1756 | Cl | 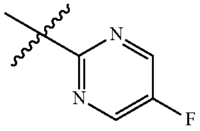 [SMILES: *c1ncc(F)cn1] | 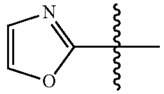 [SMILES: *c1ncco1] |
| 1-1757 | Cl | 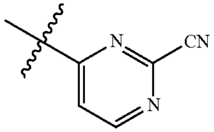 [SMILES: *c1ccnc(C#N)n1] | 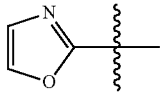 [SMILES: *c1ncco1] |
| 1-1758 | Cl | 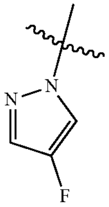 [SMILES: *n1cc(F)cn1] | 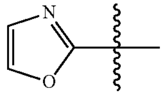 |
| 1-1759 | Cl | 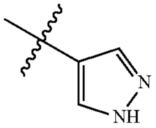 [SMILES: *c1cn[nH]c1] | 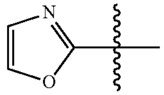 |

TABLE A1-continued
| | | | |
|---|---|---|---|
| 1-1760 | Cl | 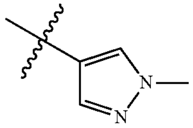 [SMILES: *c1cnn(C)c1] | 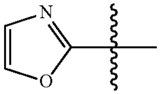 |
| 1-1761 | Cl | 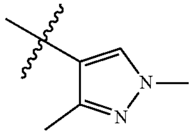 [SMILES: *c1cn(C)nc1C] | 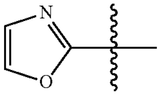 |
| 1-1762 | Cl | 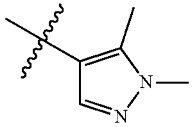 [SMILES: *c1cnn(C)c1C] | 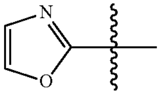 |
| 1-1763 | Cl | 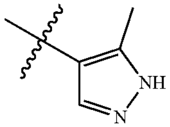 [SMILES: *c1cn[nH]c1C] | 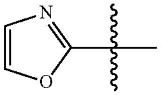 |
| 1-1764 | Cl | 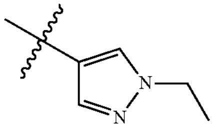 [SMILES: *c1cnn(CC)c1] | 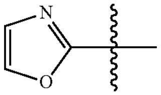 [SMILES: *c1ncco1] |
| 1-1765 | Cl | 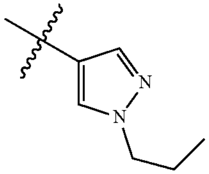 [SMILES: *c1cnn(CCC)c1] | 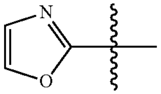 [SMILES: *c1ncco1] |
| 1-1766 | Cl | 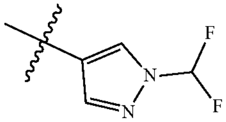 [SMILES: *c1cnn(C(F)F)c1] | 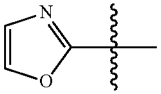 |

TABLE A1-continued
| | | | |
|---|---|---|---|
| 1-1767 | Cl | 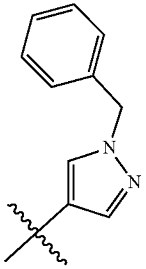 [SMILES: *c1cnn(Cc2ccccc2)c1] | 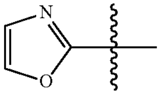 |
| 1-1768 | Cl | 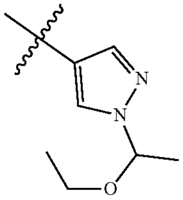 [SMILES: *c1cnn(C(C)OCC)c1] | 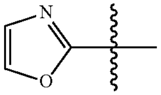 |
| 1-1769 | Cl | 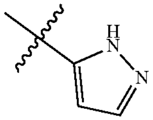 [SMILES: *c1ccn[nH]1] | 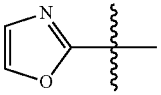 |
| 1-1770 | Cl | 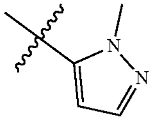 [SMILES: *c1ccnn1C] | 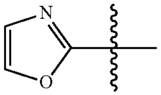 |
| 1-1771 | Cl | 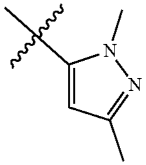 [SMILES: *c1cc(C)nn1C] | 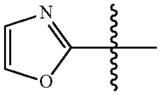 |

TABLE A1-continued
| | | | | |
|---|---|---|---|---|
| 1-1772 | Cl | 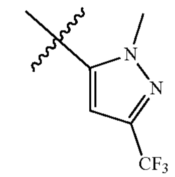 | 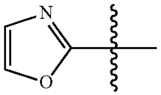 | |
| 1-1773 | Cl | 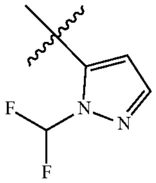 | 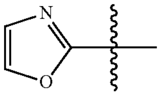 [SMILES: *c1ncco1] | |
| 1-1774 | Cl | 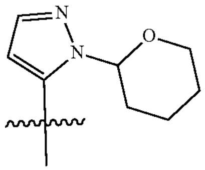 [SMILES: *c1ccnn1C1CCCCO1] | 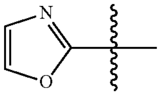 | |
| 1-1775 | Cl | 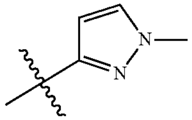 [SMILES: *c1ccn(C)n1] | 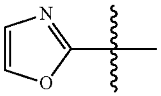 [SMILES: *c1ncco1] | $^1$H NMR (500 MHz, DMSO-$d_6$) δ 12.09 (s, 1H), 8.87 (d, J = 5.0 Hz, 1H), 7.75 (d, J = 5.0 Hz, 1H), 7.43 (d, J = 2.5 Hz, 1H), 7.26 (d, J = 2.5 Hz, 1H), 7.24 (d, J = 2.5 Hz, 1H), 6.69 (d, J = 2.5 Hz, 1H), 3.92 (s, 3H). |
| 1-1776 | Cl | 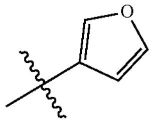 [SMILES: *c1ccoc1] | 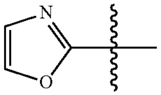 | |
| 1-1777 | Cl | 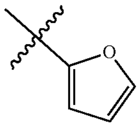 [SMILES: *c1ccco1] | 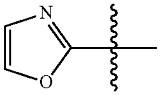 [SMILES: *c1ncco1] | $^1$H NMR (500 MHz, DMSO-$d_6$) δ 12.11 (s, 1H), 8.86 (d, J = 5.0 Hz, 1H), 8.07 (d, J = 2.0 Hz, 1H), 7.89 (d, J = 5.0 Hz, 1H), 7.50 (d, J = 2.5 Hz, 1H), 7.28-7.22 (m, 2H), 6.98 (t, J = 2.5 Hz, 1H). |

TABLE A1-continued
| | | | |
|---|---|---|---|
| 1-1778 | Cl | 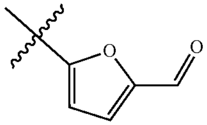 [SMILES: *c1ccc(C=O)o1] | 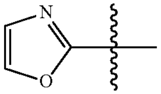 |
| 1-1779 | Cl | 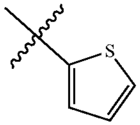 [SMILES: *c1cccs1] | 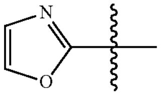 [SMILES: *c1ncco1] |
| 1-1780 | Cl | 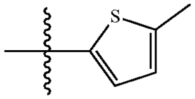 [SMILES: *c1ccc(C)s1] | 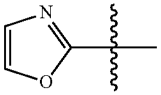 |
| 1-1781 | Cl | 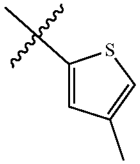 [SMILES: *c1cc(C)cs1] | 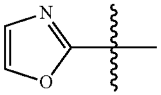 [SMILES: *c1ncco1] |
| 1-1782 | Cl | 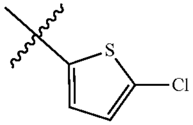 [SMILES: *c1ccc(Cl)s1] | 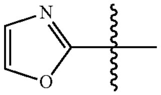 [SMILES: *c1ncco1] |
| 1-1783 | Cl | 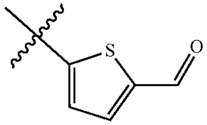 [SMILES: *c1ccc(C=O)s1] | 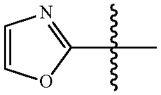 |
| 1-1784 | Cl | 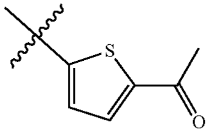 [SMILES: *c1ccc(C(C)=O)s1] | 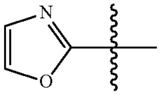 |

TABLE A1-continued
| | | | | |
|---|---|---|---|---|
| 1-1785 | Cl | 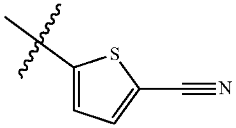 [SMILES: *c1ccc(C#N)s1] | 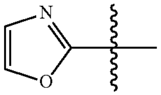 [SMILES: *c1ncco1] | |
| 1-1786 | Cl | 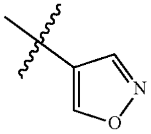 [SMILES: *c1cnoc1] | 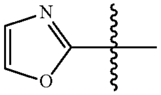 | |
| 1-1787 | $CH_3$ | 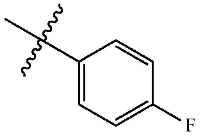 [SMILES: *c1ccc(F)cc1] | 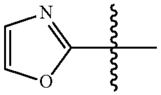 | $^{1}H$ NMR (500 MHz, DMSO-$d_6$) δ 12.07 (s, 1H), 8.57 (d, J = 5.0 Hz, 1H), 8.00-7.92 (m, 2H), 7.52 (d, J = 2.5 Hz, 1H), 7.38 (d, J = 5.0 Hz, 1H), 7.35-7.27 (m, 2H), 7.22 (d, J = 2.5 Hz, 1H), 2.44 (s, 3H). |
| 1-1788 | F | 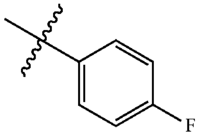 [SMILES: *c1ccc(F)cc1] | 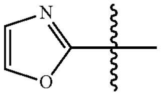 [SMILES: *c1ncco1] | |
| 1-1789 | Br | 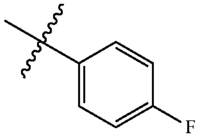 [SMILES: *c1ccc(F)cc1] | 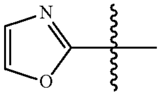 | |
| 1-1790 | 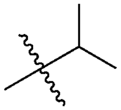 [SMILES: *C(C)C] | 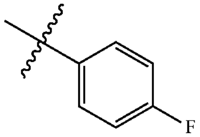 [SMILES: *c1ccc(F)cc1] | 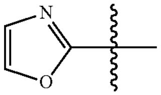 [SMILES: *c1ncco1] | |
| 1-1791 | $CF_3$ | 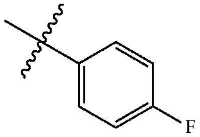 [SMILES: *c1ccc(F)cc1] | 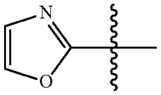 | $^{1}H$ NMR (500 MHz, DMSO-$d_6$) δ 12.11 (s, 1H), 8.74 (d, J = 5.0 Hz, 1H), 8.03-7.95 (m, 2H), 7.55-7.48 (m, 2H), 7.35-7.27 (m, 2H), 7.21 (d, J = 2.5 Hz, 1H). |

TABLE A1-continued
| | | | | |
|---|---|---|---|---|
| 1-1792 | 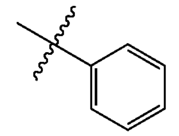 | 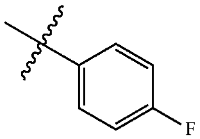 | 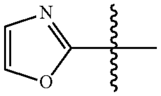 [SMILES: *c1ncco1] | $^1$H NMR (500 MHz, DMSO-$d_6$) δ 12.13 (s, 1H), 8.97 (d, J = 5.0 Hz, 1H), 8.01-7.93 (m, 2H), 7.67-7.61 (m, 3H), 7.49-7.35 (m, 4H), 7.35-7.27 (m, 2H), 7.23 (d, J = 2.5 Hz, 1H). |
| 1-1793 | 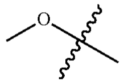 | 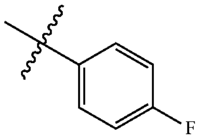 [SMILES: *c1ccc(F)cc1] | 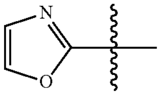 | |
| 1-1794 | 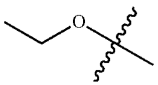 | 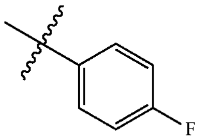 [SMILES: *c1ccc(F)cc1] | 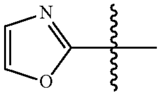 [SMILES: *c1ncco1] | |
| 1-1795 | 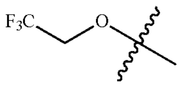 | 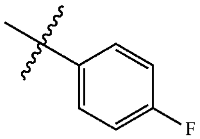 [SMILES: *c1ccc(F)cc1] | 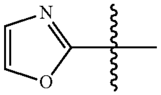 [SMILES: *c1ncco1] | $^1$H NMR (500 MHz, DMSO-$d_6$) δ 12.08 (s, 1H), 8.53 (d, J = 5.0 Hz, 1H), 8.10-8.02 (m, 2H), 7.52 (d, J = 2.5 Hz, 1H), 7.45 (d, J = 5.0 Hz, 1H), 7.35-7.27 (m, 2H), 7.21 (d, J = 2.5 Hz, 1H), 5.03 (s, 2H). |
| 1-1796 | 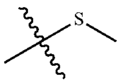 [SMILES: *SC] | 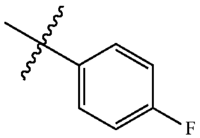 [SMILES: *c1ccc(F)cc1] | 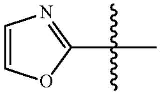 | |
| 1-1797 | 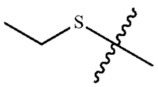 [SMILES: *SCC] | 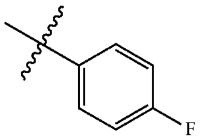 [SMILES: *c1ccc(F)cc1] | 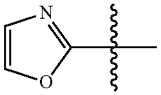 [SMILES: *c1ncco1] | $^1$H NMR (500 MHz, DMSO-$d_6$) δ 12.11 (s, 1H), 8.55 (d, J = 5.0 Hz, 1H), 8.03-7.95 (m, 2H), 7.46 (d, J = 5.0 Hz, 1H), 7.45 (d, J = 2.5 Hz, 1H), 7.35-7.27 (m, 2H), 7.25 (d, J = 2.5 Hz, 1H), 3.00 (q, J = 8.0 Hz, 2H), 1.19 (t, J = 8.0 Hz, 3H). |
| 1-1798 | 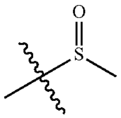 [SMILES: *S(C)=O] | 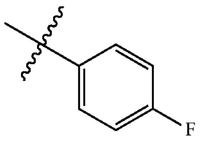 [SMILES: *c1ccc(F)cc1] | 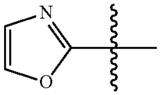 | |

TABLE A1-continued
| | | | | |
|---|---|---|---|---|
| 1-1799 | 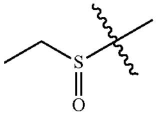 [SMILES: *S(=O)CC] | 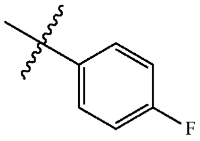 [SMILES: *c1ccc(F)cc1] | 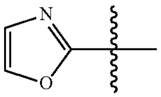 [SMILES: *c1ncco1] | $^1$H NMR (500 MHz, DMSO-$d_6$) δ 12.34 (s, 1H), 8.81 (d, J = 5.0 Hz, 1H), 8.04-7.96 (m, 2H), 7.52 (d, J = 5.0 Hz, 1H), 7.43 (d, J = 2.5 Hz, 1H), 7.35-7.27 (m, 2H), 7.24 (d, J = 7.5 Hz, 1H), 2.61-2.59 (m, 1H), 2.57-2.55 (m, 1H), 1.21 (t, J = 8.0 Hz, 3H). |
| 1-1800 | 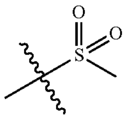 [SMILES: *S(C)(=O)=O] | 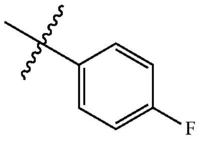 [SMILES: *c1ccc(F)cc1] | 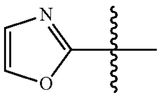 | |
| 1-1801 | 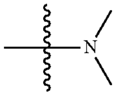 [SMILES: *N(C)C] | 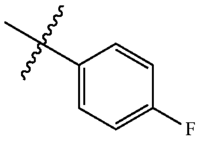 [SMILES: *c1ccc(F)cc1] | 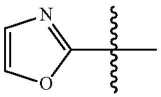 [SMILES: *c1ncco1] | $^1$H NMR (500 MHz, DMSO-$d_6$) δ 12.06 (s, 1H), 8.36 (d, J = 5.0 Hz, 1H), 8.07-8.00 (m, 2H), 7.47 (d, J = 5.0 Hz, 1H), 7.42 (d, J = 2.5 Hz, 1H), 7.35-7.27 (m, 2H), 7.24 (d, J = 2.5 Hz, 1H), 2.77 (s, 6H). |
| 1-1802 | 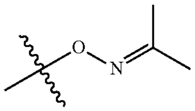 [SMILES: *ON=C(C)C] | 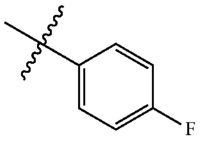 [SMILES: *c1ccc(F)cc1] | 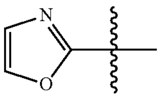 [SMILES: *c1ncco1] | $^1$H NMR (500 MHz, DMSO-$d_6$) δ 12.08 (s, 1H), 8.41 (d, J = 5.0 Hz, 1H), 8.04-7.97 (m, 2H), 7.93 (d, J = 5.0 Hz, 1H), 7.51 (d, J = 2.5 Hz, 1H), 7.35-7.27 (m, 2H), 7.26 (d, J = 2.5 Hz, 1H), 2.35 (s, 6H). |
| 1-1803 | Et | 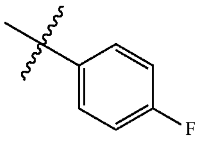 [SMILES: *c1ccc(F)cc1] | 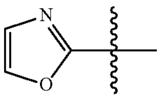 | |
| 1-1804 | 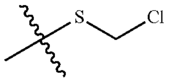 | 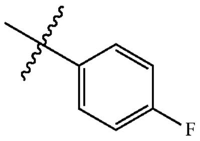 [SMILES: *c1ccc(F)cc1] | 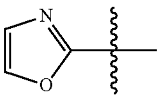 [SMILES: *c1ncco1] | |
| 1-1805 | $NO_2$ | 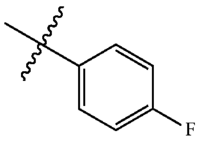 [SMILES: *c1ccc(F)cc1] | 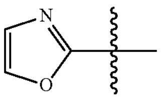 | $^1$H NMR (500 MHz, DMSO-$d_6$) δ 12.08 (s, 1H), 8.97 (d, J = 5.0 Hz, 1H), 8.01-7.93 (m, 2H), 7.73 (d, J = 5.0 Hz, 1H), 7.47 (d, J = 2.5 Hz, 1H), 7.34-7.29 (m, 2H), 7.27 (d, J = 2.5 Hz, 1H). |

TABLE A1-continued
| | | | | |
|---|---|---|---|---|
| 1-1806 | CN | 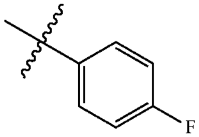 [SMILES: *c1ccc(F)cc1] | 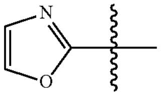 [SMILES: *c1ncco1] | $^1$H NMR (500 MHz, DMSO-$d_6$) δ 12.07 (s, 1H), 9.02 (d, J = 5.0 Hz, 1H), 8.05-7.98 (m, 2H), 7.69 (d, J = 5.0 Hz, 1H), 7.46 (d, J = 2.5 Hz, 1H), 7.37-7.27 (m, 2H), 7.25 (d, J = 2.5 Hz, 1H). |
| 1-1807 | 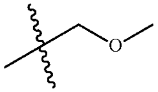 [SMILES: *COC] | 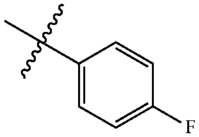 [SMILES: *c1ccc(F)cc1] | 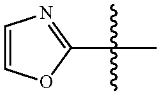 | $^1$H NMR (500 MHz, DMSO-$d_6$) δ 12.12 (s, 1H), 8.67 (d, J = 5.0 Hz, 1H), 8.04-7.96 (m, 2H), 7.51 (d, J = 2.5 Hz, 1H), 7.47 (d, J = 5.0 Hz, 1H), 7.35-7.27 (m, 2H), 7.20 (d, J = 2.5 Hz, 1H), 4.68 (s, 2H), 3.28 (s, 3H). |
| 1-1808 | 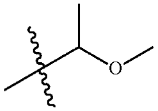 [SMILES: *C(C)OC] | 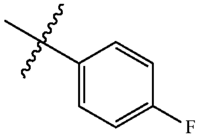 [SMILES: *c1ccc(F)cc1] | 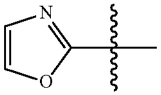 [SMILES: *c1ncco1] | |
| 1-1809 | 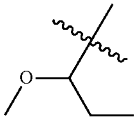 [SMILES: *C(CC)OC] | 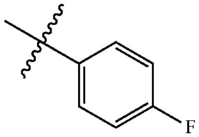 [SMILES: *c1ccc(F)cc1] | 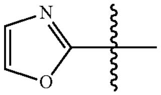 [SMILES: *c1ncco1] | |
| 1-1810 | 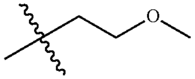 [SMILES: *CCOC] | 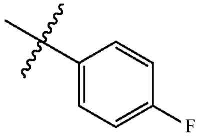 [SMILES: *c1ccc(F)cc1] | 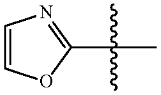 | |
| 1-1811 | 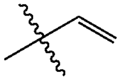 [SMILES: *C=C] | 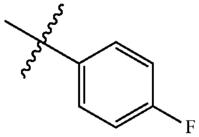 [SMILES: *c1ccc(F)cc1] | 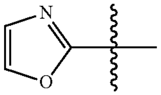 [SMILES: *c1ncco1] | |
| 1-1812 | 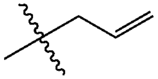 [SMILES: *CC=C] | 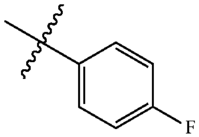 [SMILES: *c1ccc(F)cc1] | 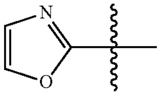 [SMILES: *c1ncco1] | |

TABLE A1-continued
| | | | |
|---|---|---|---|
| 1-1813 | 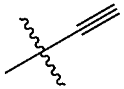 [SMILES: *C#C] | 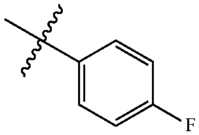 | 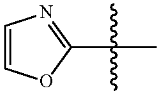 |
| 1-1814 | 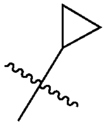 [SMILES: *C1CC1] | 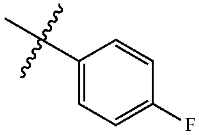 [SMILES: *c1ccc(F)cc1] | 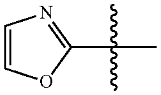 [SMILES: *c1ncco1] |
| 1-1815 | 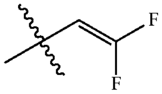 [SMILES: *C=C(F)F] | 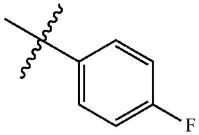 | 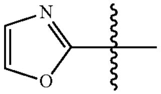 |
| 1-1816 | 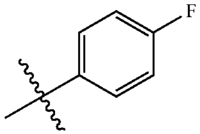 [SMILES: *c1ccc(F)cc1] | 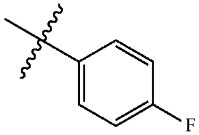 | 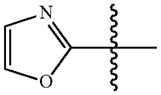 |
| 1-1817 | Cl | 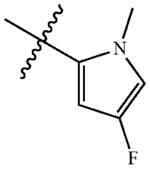 [SMILES: *c1cc(F)cn1C] | 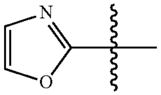 |
| 1-1818 | Cl | 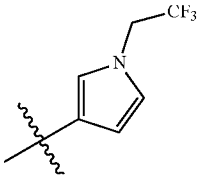 [SMILES: *c1ccn(CC(F)(F)F)c1] | 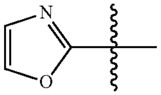 [SMILES: *c1ncco1] |

TABLE A1-continued
| | | | |
|---|---|---|---|
| 1-1819 | Cl | 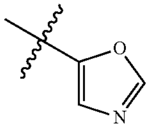 [SMILES: *c1cnco1] | 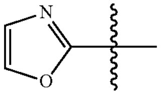 |
| 1-1820 | Cl | 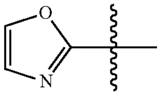 | 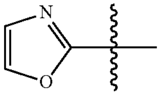 [SMILES: *c1ncco1] |
| 1-1821 | Cl | 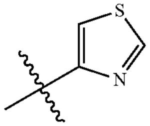 [SMILES: *c1cscn1] | 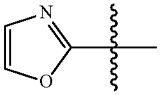 [SMILES: *c1ncco1] |
| 1-1822 | Cl | 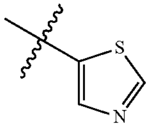 [SMILES: *c1cncs1] | 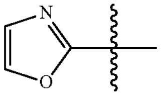 [SMILES: *c1ncco1] |
| 1-1823 | Cl | 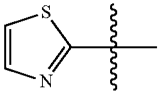 | 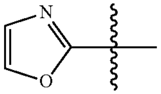 |
| 1-1824 | Cl | 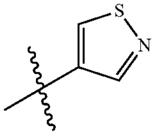 [SMILES: *c1cnsc1] | 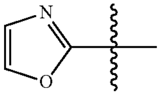 [SMILES: *c1ncco1] |
| 1-1825 | Cl | 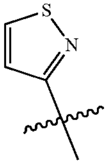 [SMILES: *c1ccsn1] | 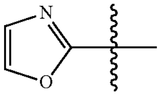 |
| 1-1826 | Cl | 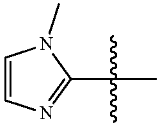 | 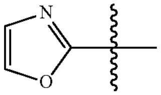 [SMILES: *c1ncco1] |

TABLE A1-continued
| | | | |
|---|---|---|---|
| 1-1827 | Cl | 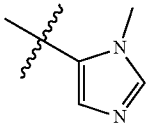 [SMILES: *c1cncn1C] | 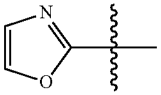 [SMILES: *c1ncco1] |
| 1-1828 | Cl | 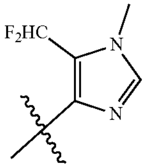 | 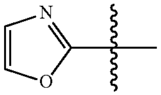 [SMILES: *c1ncco1] |
| 1-1829 | Cl | 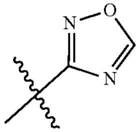 [SMILES: *c1ncon1] | 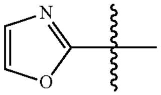 |
| 1-1830 | Cl | 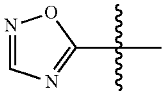 | 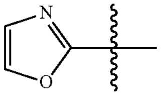 [SMILES: *c1ncco1] |
| 1-1831 | Cl | 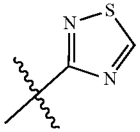 | 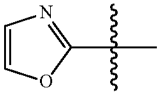 [SMILES: *c1ncco1] |
| 1-1832 | Cl | 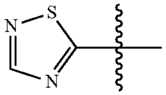 [SMILES: *c1ncns1] | 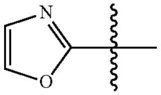 |
| 1-1833 | Cl | 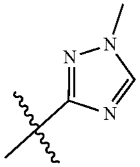 [SMILES: *c1ncn(C)n1] | 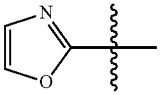 |

TABLE A1-continued
| | | | |
|---|---|---|---|
| 1-1834 | Cl | 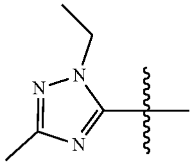 [SMILES: *c1nc(C)nn1CC] | 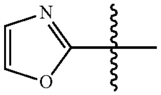 |
| 1-1835 | Cl | 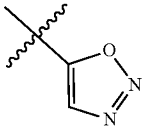 [SMILES: *c1cnno1] | 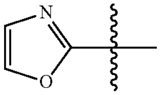 |
| 1-1836 | Cl | 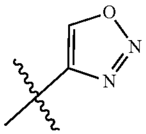 [SMILES: *c1conn1] | 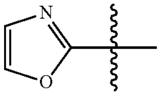 |
| 1-1837 | Cl | 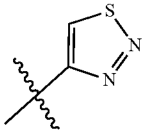 [SMILES: *c1csnn1] | 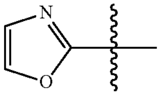 |
| 1-1838 | Cl | 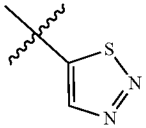 [SMILES: *c1cnns1] | 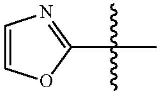 |
| 1-1839 | Cl | 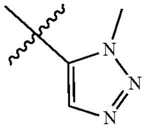 [SMILES: *c1cnnn1C] | 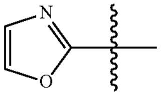 |
| 1-1840 | Cl | 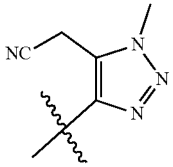 [SMILES: *c1nnn(C)c1CC#N] | 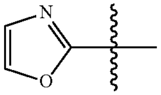 |

TABLE A1-continued
| | | | |
|---|---|---|---|
| 1-1841 | Cl | 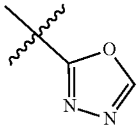 [SMILES: *c1nnco1] | 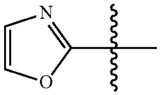 |
| 1-1842 | Cl | 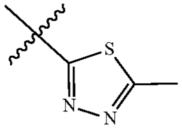 [SMILES: *c1nnc(C)s1] | 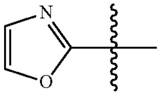 |
| 1-1843 | Cl | 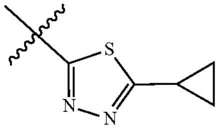 [SMILES: *c1nnc(C2CC2)s1] | 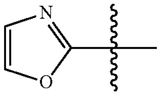 [SMILES: *c1ncco1] |
| 1-1844 | Cl | 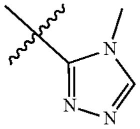 [SMILES: *c1nncn1C] | 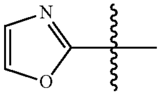 |
| 1-1845 | Cl | 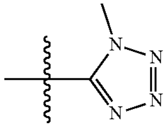 [SMILES: *c1nnnn1C] | 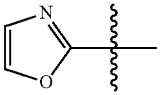 [SMILES: *c1ncco1] |
| 1-1846 | Cl | 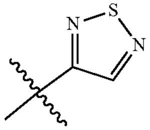 [SMILES: *c1cnsn1] | 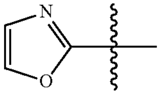 [SMILES: *c1ncco1] |
| 1-1847 | Cl | 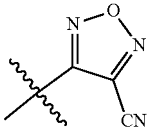 | 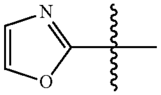 [SMILES: *c1ncco1] |

TABLE A1-continued
| | | | |
|---|---|---|---|
| 1-1848 | Cl | 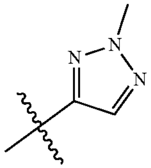 [SMILES: *c1cnn(C)n1] | 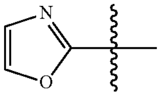 |
| 1-1849 | Cl | 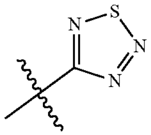 [SMILES: *c1nnsn1] | 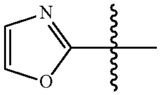 [SMILES: *c1ncco1] |
| 1-1850 | Cl | 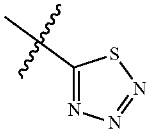 [SMILES: *c1nnns1] | 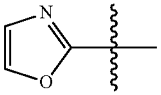 |
| 1-1851 | Cl | 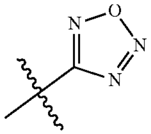 [SMILES: *c1nnon1] | 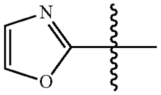 [SMILES: *c1ncco1] |
| 1-1852 | Cl | 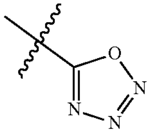 [SMILES: *c1nnno1] | 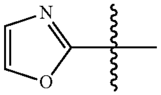 [SMILES: *c1ncco1] |
| 1-1853 | Cl | 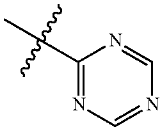 [SMILES: *c1ncncn1] | 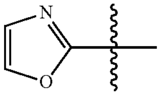 |
| 1-1854 | Cl | 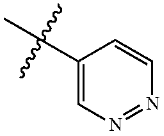 [SMILES: *c1ccnnc1] | 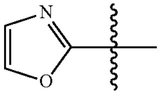 |

TABLE A1-continued
| | | | |
|---|---|---|---|
| 1-1855 | Cl | 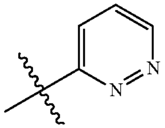 [SMILES: *c1cccnn1] | 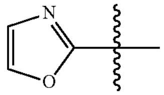 |
| 1-1856 | Cl | 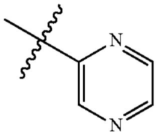 [SMILES: *c1cnccn1] | 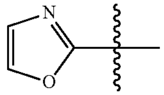 |
| 1-1857 | Cl | 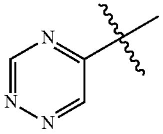 [SMILES: *c1cnncn1] | 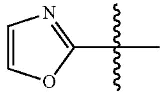 |
| 1-1858 | Cl | 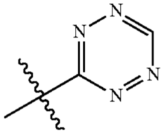 [SMILES: *c1nncnn1] | 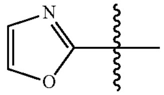 |
| 1-1859 | Cl | 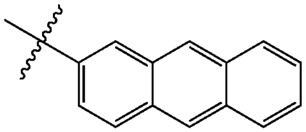 [SMILES: *c1ccc2cc3ccccc3cc2c1] | 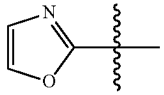 |
| 1-1860 | Cl | 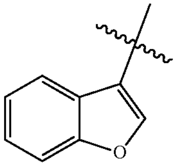 [SMILES: *c1coc2ccccc12] | 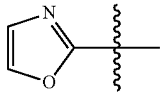 [SMILES: *c1ncco1] |
| 1-1861 | Cl | 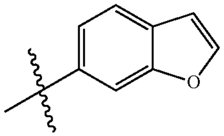 [SMILES: *c1ccc2ccoc2c1] | 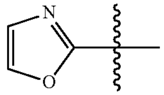 |

TABLE A1-continued
| | | | |
|---|---|---|---|
| 1-1862 | Cl | 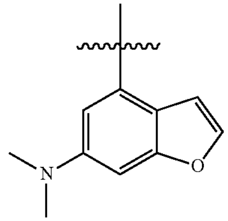 [SMILES: *c1cc(N(C)C)cc2occc12] | 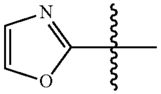 [SMILES: *c1ncco1] |
| 1-1863 | Cl | 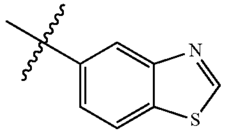 [SMILES: *c1ccc2scnc2c1] | 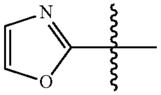 |
| 1-1864 | Cl | 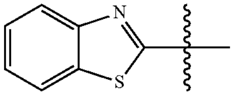 [SMILES: *c1nc2ccccc2s1] | 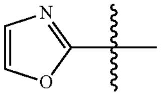 [SMILES: *c1ncco1] |
| 1-1865 | Cl | 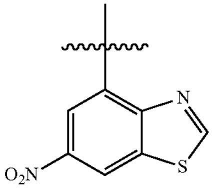 | 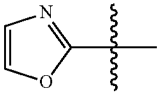 |
| 1-1866 | Cl | 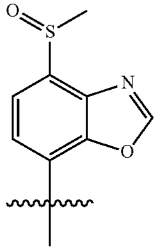 [SMILES: *c1ccc(S(C)=O)c2ncoc12] | 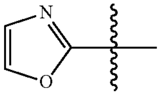 |
| 1-1867 | Cl | 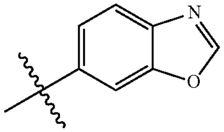 [SMILES: *c1ccc2ncoc2c1] | 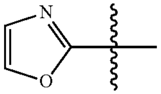 |

TABLE A1-continued
| | | | |
|---|---|---|---|
| 1-1868 | Cl | 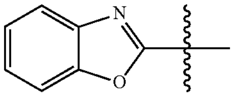 [SMILES: *c1nc2ccccc2o1] | 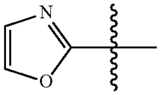 |
| 1-1869 | Cl | 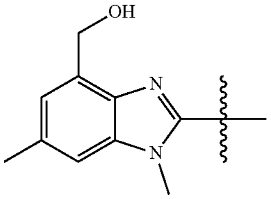 [SMILES: *c1nc2c(CO)cc(C)cc2n1C] | 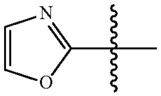 |
| 1-1870 | Cl | 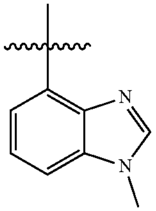 [SMILES: *c1cccc2c1ncn2C] | 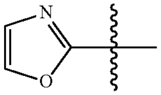 |
| 1-1871 | Cl | 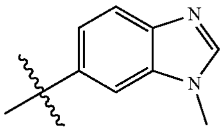 [SMILES: *c1ccc2ncn(C)c2c1] | 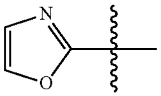 [SMILES: *c1ncco1] |
| 1-1872 | Cl | 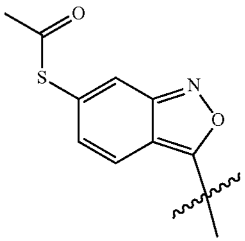 [SMILES: *c1onc2cc(SC(C)=O)ccc12] | 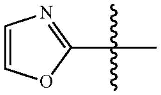 |

TABLE A1-continued
| | | | |
|---|---|---|---|
| 1-1873 | Cl | 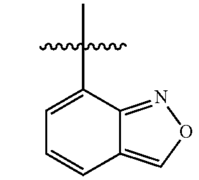 | 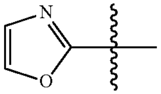 |
| 1-1874 | Cl | 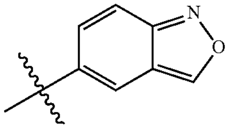 [SMILES: *c1ccc2nocc2c1] | 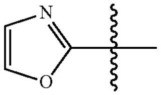 |
| 1-1875 | Cl | 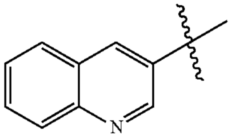 [SMILES: *c1cnc2ccccc2c1] | 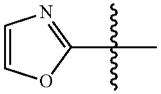 |
| 1-1876 | Cl | 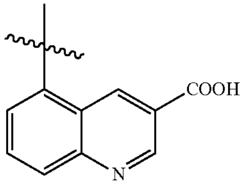 [SMILES: *c1cccc2ncc(C(=O)O)cc12] | 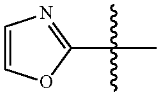 |
| 1-1877 | Cl | 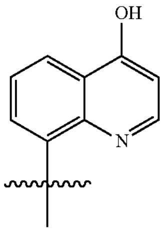 [SMILES: *c1cccc2c(O)ccnc12] | 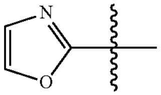 |
| 1-1878 | Cl | 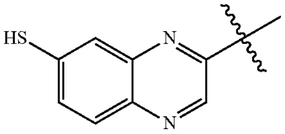 [SMILES: *c1cnc2ccc(S)cc2n1] | 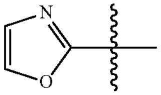 |

TABLE A1-continued
| | | | |
|---|---|---|---|
| 1-1879 | Cl | 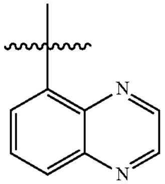 [SMILES: *c1cccc2nccnc12] | 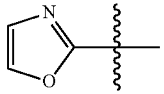 |
| 1-1880 | Cl | 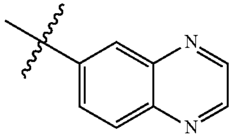 [SMILES: *c1ccc2nccnc2c1] | 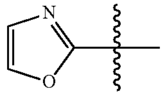 [SMILES: *c1ncco1] |
| 1-1881 | Cl | 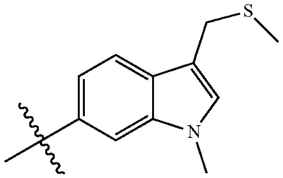 | 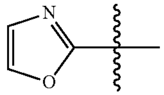 [SMILES: *c1ncco1] |
| 1-1882 | Cl | 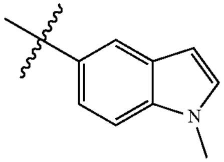 [SMILES: *c1ccc2c(ccn2C)c1] | 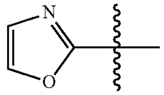 |
| 1-1883 | Cl | 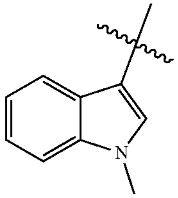 [SMILES: *c1cn(C)c2ccccc12] | 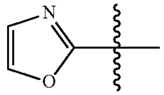 |
| 1-1884 | Cl | 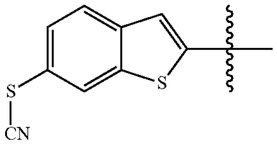 [SMILES: *c1cc2ccc(SC#N)cc2s1] | 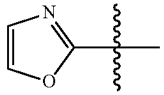 |

TABLE A1-continued
| | | | |
|---|---|---|---|
| 1-1885 | Cl | 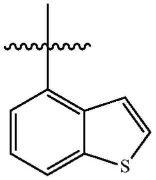 [SMILES: *c1cccc2sccc12] | 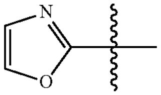 [SMILES: *c1ncco1] |
| 1-1886 | Cl | 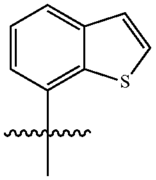 [SMILES: *c1cccc2ccsc12] | 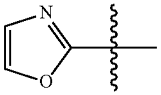 |
| 1-1887 | Cl | 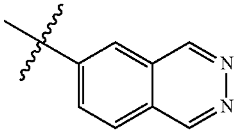 [SMILES: *c1ccc2cnncc2c1] | 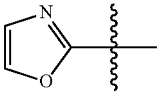 |
| 1-1888 | Cl | 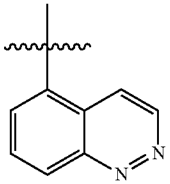 [SMILES: *c1cccc2nnccc12] | 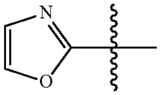 |
| 1-1889 | Cl | 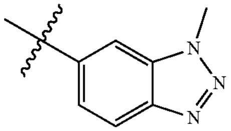 [SMILES: *c1ccc2nnn(C)c2c1] | 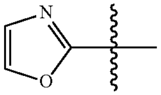 |
| 1-1890 | Cl | 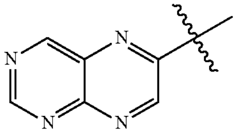 [SMILES: *c1cnc2ncncc2n1] | 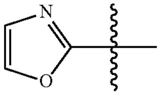 [SMILES: *c1ncco1] |

TABLE A1-continued
| | | | |
|---|---|---|---|
| 1-1891 | Cl | 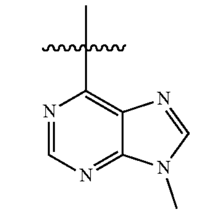 [SMILES: *c1ncnc2c1ncn2C] | 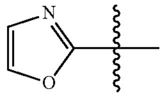 [SMILES: *c1ncco1] |
| 1-1892 | Cl | 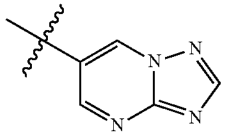 [SMILES: *c1cnc2ncnn2c1] | 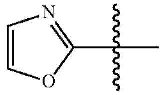 |
| 1-1893 | Cl | 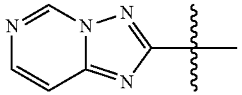 [SMILES: *c1nc2ccncn2n1] | 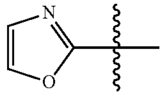 |
| 1-1894 | Cl | 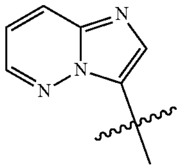 [SMILES: *c1cnc2cccnn12] | 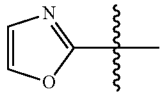 [SMILES: *c1ncco1] |
| 1-1895 | Cl | 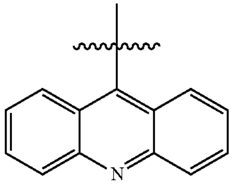 [SMILES: *c1c2ccccc2nc2ccccc12] | 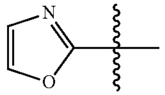 [SMILES: *c1ncco1] |
| 1-1896 | Cl | 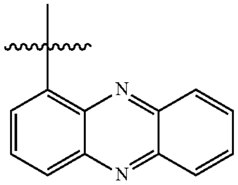 [SMILES: *c1cccc2nc3ccccc3nc12] | 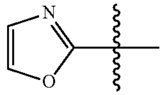 |

TABLE A1-continued
| | | | | |
|---|---|---|---|---|
| 1-1897 | Cl | 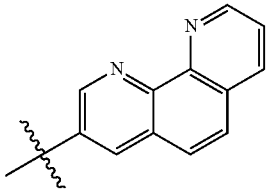 [SMILES: *c1cnc2c(ccc3cccnc32)c1] | 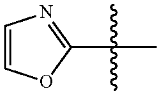 [SMILES: *c1ncco1] | |
| 1-1898 | Cl | 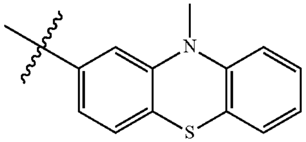 [SMILES: *c1ccc2c(c1)N(C)c1ccccc1S2] | 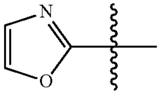 [SMILES: *c1ncco1] | |
| 1-1899 | Cl | 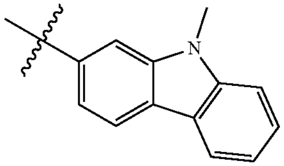 [SMILES: *c1ccc2c3ccccc3n(C)c2c1] | 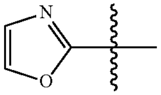 | |
| 1-1900 | Cl | 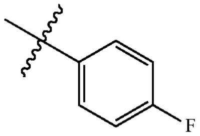 [SMILES: *c1ccc(F)cc1] | 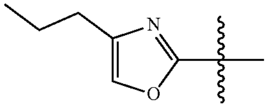 [SMILES: *c1nc(CCC)co1] | $^1$H NMR (500 MHz, DMSO-d6) δ 12.34 (s, 1H), 8.69 (d, J = 5.0 Hz, 1H), 8.04-7.97 (m, 2H), 7.54 (d, J = 5.0 Hz, 1H), 7.35-7.27 (m, 2H), 7.25 (s, 1H), 2.65 (t, J = 8.0 Hz, 2H), 1.70-1.48 (m, 2H), 0.92 (t, J = 8.0 Hz, 3H). |
| 1-1901 | Cl | 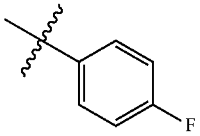 | 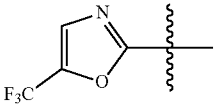 | $^1$H NMR (500 MHz, DMSO-d6) δ 12.14 (s, 1H), 8.69 (d, J = 5.0 Hz, 1H), 8.03-7.95 (m, 2H), 7.75 (d, J = 5.0 Hz, 1H), 7.36 (s, 1H), 7.35-7.27 (m, 2H). |
| 1-1902 | Cl | 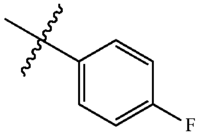 [SMILES: *c1ccc(F)cc1] | 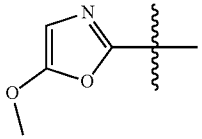 [SMILES: *c1ncc(OC)o1] | $^1$H NMR (500 MHz, DMSO-$d_6$) δ 12.14 (s, 1H), 8.71 (d, J = 5.0 Hz, 1H), 8.06-7.99 (m, 2H), 7.54 (d, J = 5.0 Hz, 1H), 7.35-7.27 (m, 2H), 6.81 (s, 1H), 3.81 (s, 3H). |

TABLE A1-continued
| | | | | |
|---|---|---|---|---|
| 1-1903 | Cl | 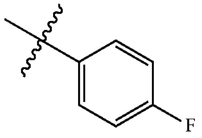 | 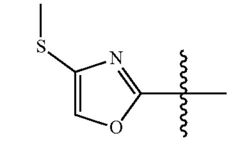 | $^1$H NMR (500 MHz, DMSO-$d_6$) δ 12.24 (s, 1H), 8.69 (d, J = 5.0 Hz, 1H), 8.03-7.95 (m, 2H), 7.70 (d, J = 5.0 Hz, 1H), 7.45 (s, 1H), 7.35-7.27 (m, 2H), 2.40 (s, 3H). |
| 1-1904 | Cl | 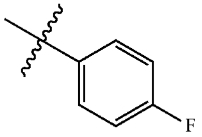 [SMILES: *c1ccc(F)cc1] | 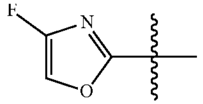 [SMILES: *c1nc(F)co1] | $^1$H NMR (500 MHz, DMSO-$d_6$) δ 12.04 (s, 1H), 8.95 (d, J = 5.0 Hz, 1H), 8.34-8.26 (m, 2H), 7.69 (d, J = 5.0 Hz, 1H), 7.55 (d, J = 5.0 Hz, 1H), 7.35-7.27 (m, 2H). |
| 1-1905 | Cl | 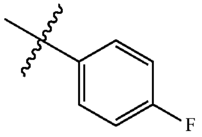 [SMILES: *c1ccc(F)cc1] | 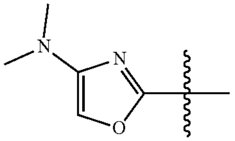 [SMILES: *c1nc(N(C)C)co1] | $^1$H NMR (500 MHz, DMSO-$d_6$) δ 12.08 (s, 1H), 8.69 (d, J = 5.0 Hz, 1H), 8.04-7.97 (m, 2H), 7.69 (s, 1H), 7.54 (d, J = 5.0 Hz, 1H), 7.35-7.27 (m, 2H), 3.20 (s, 6H). |
| 1-1906 | Cl | 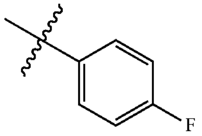 [SMILES: *c1ccc(F)cc1] | 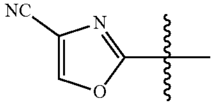 | $^1$H NMR (500 MHz, DMSO-$d_6$) δ 12.07 (s, 1H), 8.71 (d, J = 5.0 Hz, 1H), 8.04-7.96 (m, 2H), 7.74 (s, 1H), 7.55 (d, J = 5.0 Hz, 1H), 7.35-7.27 (m, 2H). |
| 1-1907 | Cl | 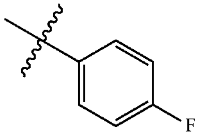 [SMILES: *c1ccc(F)cc1] | 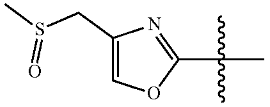 [SMILES: *c1nc(CS(C)=O)co1] | $^1$H NMR (500 MHz, DMSO-$d_6$) δ 12.09 (s, 1H), 8.70 (d, J = 5.0 Hz, 1H), 8.04-7.96 (m, 2H), 7.56 (d, J = 5.0 Hz, 1H), 7.46 (s, 1H), 7.35-7.27 (m, 2H), 3.83 (s, 2H), 2.60 (s, 3H). |
| 1-1908 | Cl | 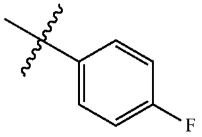 [SMILES: *c1ccc(F)cc1] | 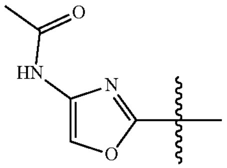 [SMILES: *c1nc(NC(C)=O)co1] | $^1$H NMR (500 MHz, DMSO-$d_6$) δ 12.11 (s, 1H), 10.52 (s, 1H), 8.70 (d, J = 5.0 Hz, 1H), 8.06-7.99 (m, 2H), 7.69 (s, 1H), 7.52 (d, J = 5.0 Hz, 1H), 7.35-7.27 (m, 2H), 2.13 (s, 3H). |

TABLE A1-continued
| | | | | |
|---|---|---|---|---|
| 1-1909 | Cl | 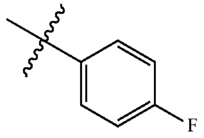 | 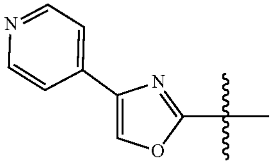 [SMILES: *c1nc(-c2ccncc2)co1] | $^1$H NMR (500 MHz, DMSO-$d_6$) δ 12.08 (s, 1H), 8.85 (d, J = 5.0 Hz, 1H), 8.66 (d, J = 5.5 Hz, 2H), 8.05-8.01 (m, 2H), 7.99 (d, J = 5.5, 2H), 7.79 (s, 1H), 7.71 (d, J = 5.0 H,z 1H), 7.35-7.27 (m, 2H). |
| 1-1910 | Cl | 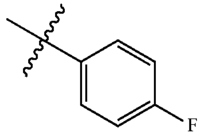 [SMILES: *c1ccc(F)cc1] | 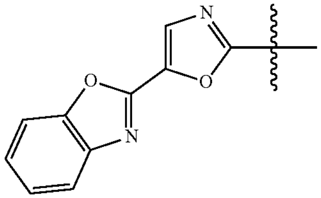 [SMILES: *c1ncc(-c2nc3ccccc3o2)o1] | $^1$H NMR (500 MHz, DMSO-$d_6$) δ 12.05 (s, 1H), 8.92 (d, J = 5.0 Hz, 1H), 8.20-8.13 (m, 2H), 7.90 (s, 1H), 7.66 (d, J = 5.0 Hz, 1H), 7.64-7.60 (m, 2H), 7.55-7.51 (m, 2H), 7.35-7.27 (m, 2H). |
| 1-1911 | Cl | 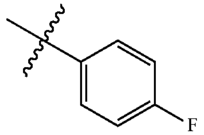 | 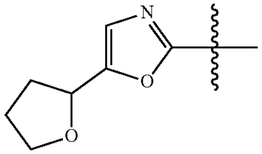 [SMILES: *c1ncc(C2CCCO2)o1] | $^1$H NMR (500 MHz, DMSO-$d_6$) δ 12.06 (s, 1H), 8.70 (d, J = 5.0 Hz, 1H), 8.05-7.98 (m, 2H), 7.54 (d, J = 5.0 Hz, 1H), 7.35-7.27 (m, 2H), 7.22 (s, 1H), 5.08 (t, J = 7.0 Hz, 1H), 3.90-3.79 (m, 2H), 2.26-2.11 (m, 2H), 1.88-1.76 (m, 2H). |
| 1-1912 | OMe | $CH_3$ | 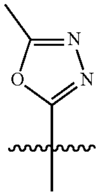 [SMILES: *c1nnc(C)o1] | $^1$H NMR (500 MHz, DMSO-$d_6$) δ 12.84 (s, 1H), 8.62 (d, J = 5.0 Hz, 1H), 7.90 (d, J = 5.0 Hz, 1H), 3.74 (s, 3H), 2.51 (s, 3H), 2.46 (s, 3H). |
| 1-1913 | Cl | 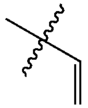 [SMILES: *C=C] | 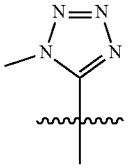 [SMILES: *c1nnnn1C] | $^1$H NMR (500 MHz, DMSO-$d_6$) δ 12.25 (s, 1H), 8.77 (d, J = 5.0 Hz, 1H), 7.78 (d, J = 5.0 Hz, 1H), 6.99-6.94 (m, 1H), 6.13-6.09 (m, 1H), 5.63-5.59 (m, 1H), 4.33 (s, 3H). |

TABLE A1-continued

| | | | | |
|---|---|---|---|---|
| 1-1914 | Cl | 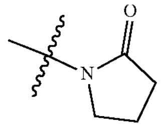 [SMILES: *N1CCCC1=O] | 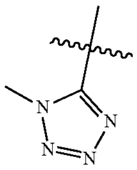 [SMILES: *c1nnnn1C] | $^1$H NMR (500 MHz, DMSO-$d_6$) δ 12.33 (s, 1H), 8.63 (d, J = 5.0 Hz, 1H), 7.77 (d, J = 5.0 Hz, 1H), 4.38 (s, 3H), 3.70 (t, J = 6.0 Hz, 2H), 2.43 (t, J = 7.5 Hz, 2H), 2.11-2.06 (m, 2H). |
| 1-1915 | Cl | 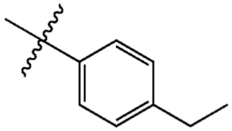 [SMILES: *c1ccc(CC)cc1] | 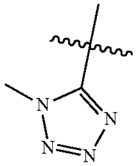 [SMILES: *c1nnnn1C] | $^1$H NMR (500 MHz, DMSO-$d_6$) δ 12.25 (s, 1H), 8.63 (d, J = 5.0 Hz, 1H), 7.74-7.70 (m, 2H), 7.49 (d, J = 5.0 Hz, 1H), 7.27-7.23 (m, 2H), 4.31 (s, 3H), 2.74-2.69 (m, 2H), 1.19 (t, J = 8.0 Hz, 3H). |
| 1-1916 | Cl | 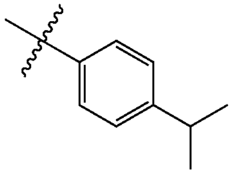 [SMILES: *c1ccc(C(C)C)cc1] | 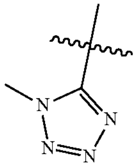 [SMILES: *c1nnnn1C] | $^1$H NMR (500 MHz, DMSO-$d_6$) δ 12.29 (s, 1H), 8.63 (d, J = 5.0 Hz, 1H), 7.72-7.69 (m, 2H), 7.47 (d, J = 5.0 Hz, 1H), 7.40-7.37 (m, 2H), 4.36 (s, 3H), 2.89-2.84 (m, 1H), 1.20 (d, J = 7.0 Hz, 6H). |
| 1-1917 | Cl | 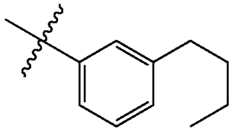 [SMILES: *c1cccc(CCCC)c1] | 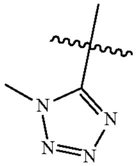 [SMILES: *c1nnnn1C] | $^1$H NMR (500 MHz, DMSO-$d_6$) δ 12.35 (s, 1H), 8.64 (d, J = 5.0 Hz, 1H), 7.88-7.85 (m, 1H), 7.81-7.79 (m, 1H), 7.63-7.60 (m, 1H), 7.47 (d, J = 5.0 Hz, 1H), 7.34-7.31 (m, 1H), 4.39 (s, 3H), 2.63 (t, J = 5.5 Hz, 2H), 1.56-1.51 (m, 2H), 1.32-1.28 (m, 2H), 0.89 (t, J = 8.0 Hz, 3H). |
| 1-1918 | Cl | 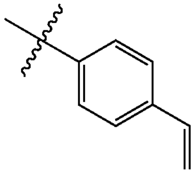 [SMILES: *c1ccc(C=C)cc1] | 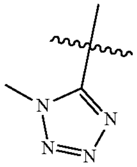 [SMILES: *c1nnnn1C] | $^1$H NMR (500 MHz, DMSO-$d_6$) δ 12.22 (s, 1H), 8.64 (d, J = 5.0 Hz, 1H), 7.71-7.68 (m, 2H), 7.48-7.45 (m, 3H), 6.73-6.70 (m, 1H), 5.96-5.93 (m, 1H), 5.71-5.68 (m, 1H), 4.32 (s, 3H). |
| 1-1919 | Cl | 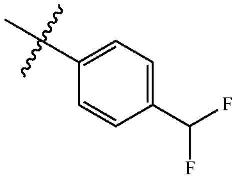 [SMILES: *c1ccc(C(F)F)cc1] | 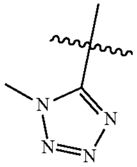 [SMILES: *c1nnnn1C] | $^1$H NMR (500 MHz, DMSO-$d_6$) δ 12.30 (s, 1H), 8.68 (d, J = 5.0 Hz, 1H), 7.81-7.75 (m, 2H), 7.65-7.59 (m, 2H), 7.52 (d, J = 5.0 Hz, 1H), 6.45 (t, J = 57.0 Hz, 1H), 4.32 (s, 3H). |

TABLE A1-continued
| | | | | |
|---|---|---|---|---|
| 1-1920 | Cl | 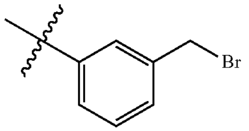 [SMILES: *c1cccc(CBr)c1] | 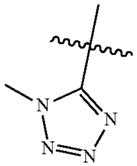 [SMILES: *c1nnnn1C] | $^1$H NMR (500 MHz, DMSO-$d_6$) δ 12.26 (s, 1H), 8.64 (d, J = 5.0 Hz, 1H), 8.02 (s, 1H), 7.88-7.85 (m, 1H), 7.68-7.65 (m, 1H), 7.59-7.57 (m, 1H), 7.48 (d, J = 5.0 Hz, 1H), 4.99 (s, 2H), 4.33 (s, 3H). |
| 1-1921 | Cl | 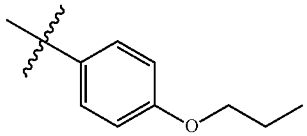 [SMILES: *c1ccc(OCCC)cc1] | 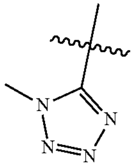 [SMILES: *c1nnnn1C] | $^1$H NMR (500 MHz, DMSO-$d_6$) δ 12.21 (s, 1H), 8.63 (d, J = 5.0 Hz, 1H), 7.80-7.77 (m, 2H), 7.48 (d, J = 5.0 Hz, 1H), 7.04-7.01 (m, 2H), 4.38 (s, 3H), 3.99 (t, J = 7.5 Hz, 2H), 1.78-1.71 (m, 2H), 0.98 (t, J = 8.0 Hz, 3H). |
| 1-1922 | Cl | 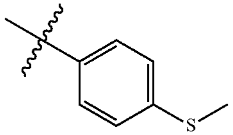 [SMILES: *c1ccc(SC)cc1] | 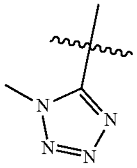 [SMILES: *c1nnnn1C] | $^1$H NMR (500 MHz, DMSO-$d_6$) δ 12.22 (s, 1H), 8.68 (d, J = 5.0 Hz, 1H), 7.85-7.79 (m, 2H), 7.55-7.49 (m, 3H), 4.39 (s, 3H), 2.45 (s, 3H). |
| 1-1923 | Cl | 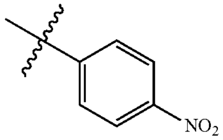 | 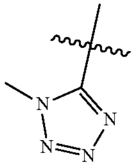 [SMILES: *c1nnnn1C] | $^1$H NMR (500 MHz, DMSO-$d_6$) δ 12.29 (s, 1H), 8.63 (d, J = 5.0 Hz, 1H), 7.68-7.65 (m, 2H), 7.47 (d, J = 5.0 Hz, 1H), 7.21-7.17 (m, 2H), 4.38 (s, 3H). |
| 1-1924 | Cl | 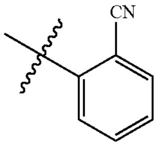 [SMILES: *c1ccccc1C#N] | 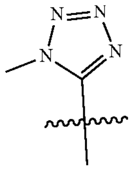 | |

TABLE A1-continued
| | | | | |
|---|---|---|---|---|
| 1-1925 | Cl | 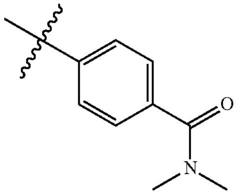 [SMILES: *c1ccc(C(=O)N(C)C)cc1] | 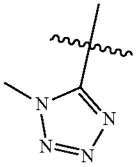 [SMILES: *c1nnnn1C] | $^1$H NMR (500 MHz, DMSO-$d_6$) δ 12.25 (s, 1H), 8.68 (d, J = 5.0 Hz, 1H), 7.89-7.82 (m, 2H), 7.54 (d, J = 5.0 Hz, 1H), 7.51-7.45 (m, 2H), 4.30 (s, 3H), 2.87 (s, 6H). |
| 1-1926 | Cl | 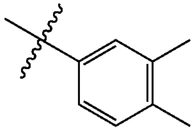 [SMILES: *c1ccc(C)c(C)c1] | 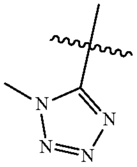 [SMILES: *c1nnnn1C] | $^1$H NMR (500 MHz, DMSO-$d_6$) δ 12.29 (s, 1H), 8.72 (d, J = 5.0 Hz, 1H), 7.73-7.70 (m, 2H), 7.53-7.50 (m, 1H), 7.16-7.14 (m, 1H), 4.31 (s, 3H), 2.27 (s, 3H), 2.23 (s, 3H). |
| 1-1927 | Cl | 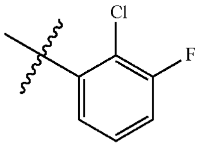 [SMILES: *c1cccc(F)c1Cl] | 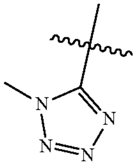 [SMILES: *c1nnnn1C] | $^1$H NMR (500 MHz, DMSO-$d_6$) δ 12.29 (s, 1H), 8.65 (d, J = 5.0 Hz, 1H), 7.65 (d, J = 5.0 Hz, 1H), 7.53-7.50 (m, 1H), 7.33-7.26 (m, 2H), 4.38 (s, 3H). |
| 1-1928 | Cl | 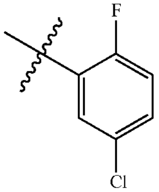 [SMILES: *c1cc(Cl)ccc1F] | 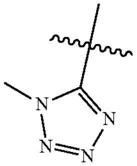 [SMILES: *c1nnnn1C] | $^1$H NMR (500 MHz, DMSO-$d_6$) δ 12.28 (s, 1H), 8.63 (d, J = 5.0 Hz, 1H), 7.88-7.85 (m, 1H), 7.56-7.53 (m, 1H), 7.47 (d, J = 5.0 Hz, 1H), 7.22-7.19 (m, 1H), 4.39 (s, 3H). |
| 1-1929 | Cl | 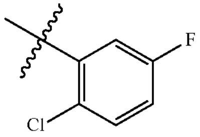 [SMILES: *c1cc(F)ccc1Cl] | 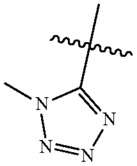 [SMILES: *c1nnnn1C] | $^1$H NMR (500 MHz, DMSO-$d_6$) δ 12.23 (s, 1H), 8.65 (d, J = 5.0 Hz, 1H), 7.65-7.62 (m, 2H), 7.54-7.51 (m, 1H), 7.27-7.23 (m, 1H), 4.38 (s, 3H). |

TABLE A1-continued
| | | | | |
|---|---|---|---|---|
| 1-1930 | Cl | 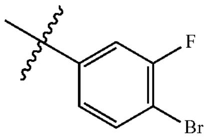 | 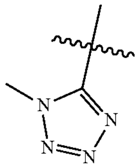 [SMILES: *c1nnnn1C] | $^1$H NMR (500 MHz, DMSO-$d_6$) δ 12.21 (s, 1H), 8.68 (d, J = 5.0 Hz, 1H), 7.69-7.62 (m, 2H), 7.62-7.59 (m, 1H), 7.53 (d, J = 5.0 Hz, 1H), 4.25 (s, 3H). |
| 1-1931 | Cl | 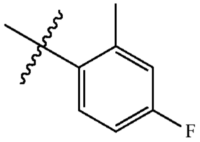 [SMILES: *c1ccc(F)cc1C] | 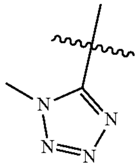 [SMILES: *c1nnnn1C] | $^1$H NMR (500 MHz, DMSO-$d_6$) δ 12.27 (s, 1H), 8.63 (d, J = 5.0 Hz, 1H), 7.60-7.57 (m, 1H), 7.49 (d, J = 5.0 Hz, 1H), 7.19-7.16 (m, 1H), 7.12-7.09 (m, 1H), 4.29 (s, 3H), 2.37 (s, 3H). |
| 1-1932 | Cl | 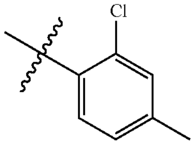 [SMILES: *c1ccc(C)cc1Cl] | 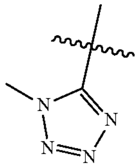 [SMILES: *c1nnnn1C] | $^1$H NMR (500 MHz, DMSO-$d_6$) δ 12.25 (s, 1H), 8.64 (d, J = 5.0 Hz, 1H), 7.74 (d, J = 7.5 Hz, 1H), 7.68 (d, J = 5.0 Hz, 1H), 7.56-7.53 (m, 1H), 7.10-7.07 (m, 1H), 4.30 (s, 3H), 2.31 (s, 3H). |
| 1-1933 | Cl | 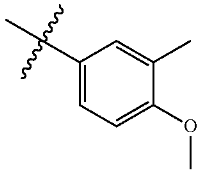 [SMILES: *c1ccc(OC)c(C)c1] | 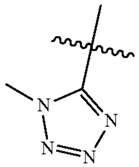 [SMILES: *c1nnnn1C] | $^1$H NMR (500 MHz, DMSO-$d_6$) δ 12.20 (s, 1H), 8.64 (d, J = 5.0 Hz, 1H), 7.75 (s, 1H), 7.67-7.64 (m, 2H), 6.94 (d, J = 7.5 Hz, 1H), 4.39 (s, 3H), 3.74 (s, 3H), 2.15 (s, 3H). |
| 1-1934 | Cl | 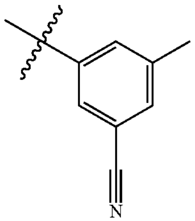 [SMILES: *c1cc(C)cc(C#N)c1] | 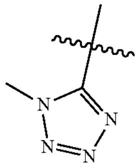 [SMILES: *c1nnnn1C] | $^1$H NMR (500 MHz, DMSO-$d_6$) δ 12.25 (s, 1H), 8.73 (d, J = 6.0 Hz, 1H), 8.10 (s, 1H), 8.02 (s, 1H), 7.75 (s, 1H), 7.56 (d, J = 5.0 Hz, 1H), 4.29 (s, 3H), 2.32 (s, 3H). |

TABLE A1-continued

| | | | | |
|---|---|---|---|---|
| 1-1935 | Cl | 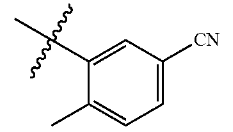 [SMILES: *c1cc(C#N)ccc1C] | 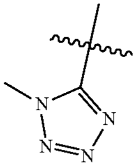 [SMILES: *c1nnnn1C] | $^1H$ NMR (500 MHz, DMSO-$d_6$) δ 12.26 (s, 1H), 8.69 (d, J = 5.0 Hz, 1H), 8.07 (d, J = 2.0 Hz, 1H), 7.72 (dd, J = 7.5, 2.0 Hz, 1H), 7.54 (d, J = 5.0 Hz, 1H), 7.38 (d, J = 7.5 Hz, 1H), 4.37 (s, 3H), 2.25 (s, 3H). |
| 1-1936 | Cl | 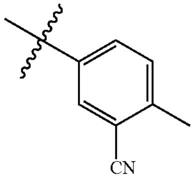 [SMILES: *c1ccc(C)c(C#N)c1] | 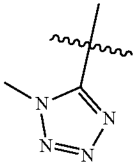 [SMILES: *c1nnnn1C] | $^1H$ NMR (500 MHz, DMSO-$d_6$) δ 12.33 (s, 1H), 8.69 (d, J = 5.0 Hz, 1H), 8.11 (d, J = 2.0 Hz, 1H), 7.96 (dd, J = 7.5, 2.0 Hz, 1H), 7.52 (d, J = 5.0 Hz, 1H), 7.45 (d, J = 7.5 Hz, 1H), 4.33 (s, 3H), 2.45 (s, 3H). |
| 1-1937 | Cl | 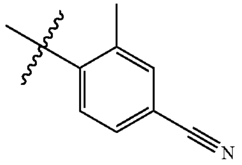 [SMILES: *c1ccc(C#N)cc1C] | 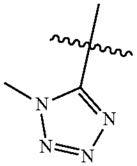 [SMILES: *c1nnnn1C] | $^1H$ NMR (500 MHz, DMSO-$d_6$) δ 12.28 (s, 1H), 8.71 (d, J = 5.0 Hz, 1H), 8.08 (d, J = 7.5 Hz, 1H), 7.76-7.72 (m, 1H), 7.61-7.55 (m, 2H), 4.29 (s, 3H), 2.39 (s, 3H). |
| 1-1938 | Cl | 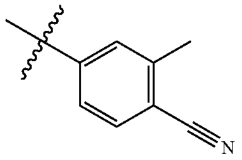 [SMILES: *c1ccc(C#N)c(C)c1] | 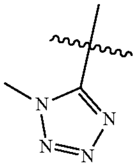 [SMILES: *c1nnnn1C] | $^1H$ NMR (500 MHz, DMSO-$d_6$) δ 12.23 (s, 1H), 8.73 (d, J = 5.0 Hz, 1H), 8.05-7.98 (m, 2H), 7.74 (d, J = 5.0 Hz, 1H), 7.71 (d, J = 7.5 Hz, 1H), 4.35 (s, 3H), 2.45 (s, 3H). |
| 1-1939 | Cl | 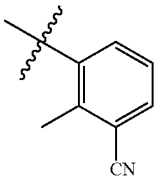 [SMILES: *c1cccc(C#N)c1C] | 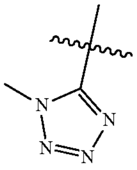 [SMILES: *c1nnnn1C] | $^1H$ NMR (500 MHz, DMSO-$d_6$) δ 12.25 (s, 1H), 8.72 (d, J = 5.0 Hz, 1H), 8.27 (dd, J = 7.5, 2.0 Hz, 1H), 7.74 (dd, J = 7.5, 2.0 Hz, 1H), 7.58 (d, J = 5.0 Hz, 1H), 7.40 (dd, J = 7.5, 7.5 Hz, 1H), 4.36 (s, 3H), 2.45 (s, 3H). |
| 1-1940 | Cl | 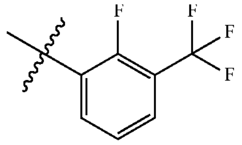 [SMILES: *c1cccc(C(F)(F)F)c1F] | 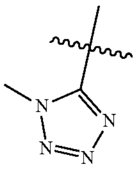 [SMILES: *c1nnnn1C] | $^1H$ NMR (500 MHz, DMSO-$d_6$) δ 12.27 (s, 1H), 8.63 (d, J = 5.0 Hz, 1H), 7.96-7.92 (m, 1H), 7.68-7.65 (m, 1H), 7.48-7.43 (m, 2H), 4.30 (s, 3H). |

TABLE A1-continued
| | | | | |
|---|---|---|---|---|
| 1-1941 | Cl | 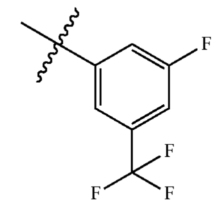 [SMILES: *c1cc(F)cc(C(F)(F)F)c1] | 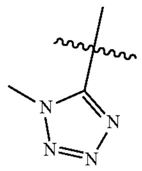 [SMILES: *c1nnnn1C] | $^1$H NMR (500 MHz, DMSO-$d_6$) δ 12.29 (s, 1H), 8.66 (d, J = 5.0 Hz, 1H), 7.91-7.87 (m, 2H), 7.65 (d, J = 5.0 Hz, 1H), 7.53-7.50 (m, 1H), 4.37 (s, 3H). |
| 1-1942 | Cl | 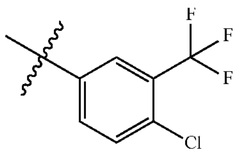 [SMILES: *c1ccc(Cl)c(C(F)(F)F)c1] | 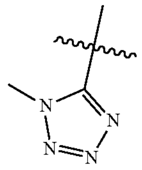 [SMILES: *c1nnnn1C] | $^1$H NMR (500 MHz, DMSO-$d_6$) δ 12.31 (s, 1H), 8.65 (d, J = 5.0 Hz, 1H), 8.20 (s, 1H), 8.06-8.03 (m, 1H), 7.66 (d, J = 5.0 Hz, 1H), 7.59 (d, J = 7.5 Hz, 1H), 4.35 (s, 3H). |
| 1-1943 | Cl | 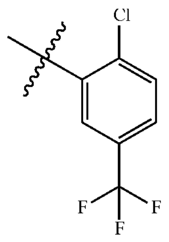 [SMILES: *c1cc(C(F)(F)F)ccc1Cl] | 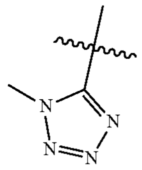 [SMILES: *c1nnnn1C] | $^1$H NMR (500 MHz, DMSO-$d_6$) δ 12.24 (s, 1H), 8.64 (d, J = 5.0 Hz, 1H), 8.17-8.14 (m, 1H), 7.61-7.55 (m, 2H), 7.49 (d, J = 5.0 Hz, 1H), 4.31 (s, 3H). |
| 1-1944 | Cl | 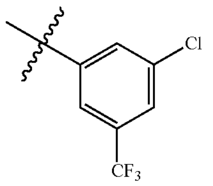 | 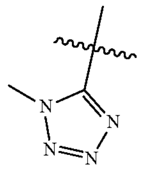 [SMILES: *c1nnnn1C] | $^1$H NMR (500 MHz, DMSO-$d_6$) δ 12.29 (s, 1H), 8.72 (d, J = 5.0 Hz, 1H), 7.88 (s, 1H), 7.74-7.70 (m, 2H), 7.59 (s, 1H), 4.35 (s, 3H). |
| 1-1945 | Cl | 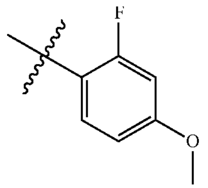 [SMILES: *c1ccc(OC)cc1F] | 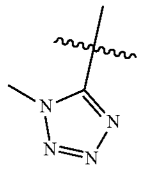 [SMILES: *c1nnnn1C] | $^1$H NMR (500 MHz, DMSO-$d_6$) δ 12.31 (s, 1H), 8.62 (d, J = 5.0 Hz, 1H), 7.81-7.78 (m, 1H), 7.46 (d, J = 5.0 Hz, 1H), 6.79-6.76 (m, 1H), 6.74-6.72 (m, 1H), 4.31 (s, 3H), 3.76 (s, 3H). |

TABLE A1-continued
| | | | | |
|---|---|---|---|---|
| 1-1946 | Cl | 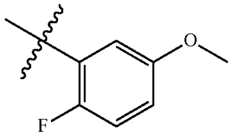 [SMILES: *c1cc(OC)ccc1F] | 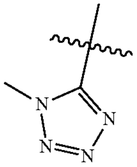 [SMILES: *c1nnnn1C] | $^1$H NMR (500 MHz, DMSO-$d_6$) δ 12.25 (s, 1H), 8.63 (d, J = 5.0 Hz, 1H), 7.47-7.44 (m, 2H), 7.25-7.22 (m, 2H), 4.35 (s, 3H), 3.80 (s, 3H). |
| 1-1947 | Cl | 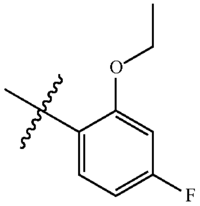 [SMILES: *c1ccc(F)cc1OCC] | 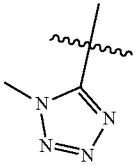 [SMILES: *c1nnnn1C] | $^1$H NMR (500 MHz, DMSO-$d_6$) δ 12.29 (s, 1H), 8.62 (d, J = 5.0 Hz, 1H), 7.78-7.75 (m, 1H), 7.63 (d, J = 5.0 Hz, 1H), 6.92-6.89 (m, 1H), 6.80-6.77 (m, 1H), 4.38 (q, J = 8.0 Hz, 2H), 4.35 (s, 3H), 1.45 (t, J = 8.0 Hz, 3H). |
| 1-1948 | Cl | 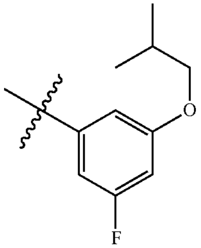 [SMILES: *c1cc(F)cc(OCC(C)C)c1] | 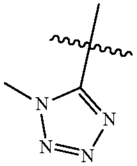 [SMILES: *c1nnnn1C] | $^1$H NMR (500 MHz, DMSO-$d_6$) δ 12.24 (s, 1H), 8.65 (d, J = 5.0 Hz, 1H), 7.48-7.44 (m, 2H), 7.05-7.01 (m, 1H), 6.90-6.87 (m, 1H), 4.39 (s, 3H), 3.70 (d, J = 7.0 Hz, 2H), 2.01-1.92 (m, 1H), 0.95 (d, J = 7.0 Hz, 6H). |
| 1-1949 | Cl | 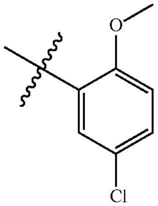 [SMILES: *c1cc(Cl)ccc1OC] | 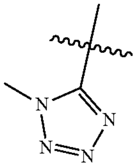 [SMILES: *c1nnnn1C] | $^1$H NMR (500 MHz, DMSO-$d_6$) δ 12.29 (s, 1H), 8.63 (d, J = 5.0 Hz, 1H), 7.94 (s, 1H), 7.65 (d, J = 5.0 Hz, 1H), 7.48 (d, J = 7.5 Hz, 1H), 6.93 (d, J = 7.5 Hz, 1H), 4.33 (s, 3H), 3.85 (s, 3H). |
| 1-1950 | Cl | 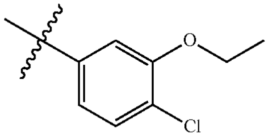 [SMILES: *c1ccc(Cl)c(OCC)c1] | 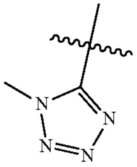 [SMILES: *c1nnnn1C] | $^1$H NMR (500 MHz, DMSO-$d_6$) δ 12.26 (s, 1H), 8.65 (d, J = 5.0 Hz, 1H), 7.79 (dd, J = 7.5, 2.0 Hz, 1H), 7.67-7.63 (m, 2H), 7.55 (d, J = 7.5 Hz, 1H), 4.31 (s, 3H), 4.10 (q, J = 8.0 Hz, 2H), 1.34 (t, J = 8.0 Hz, 3H). |

TABLE A1-continued
| | | | | |
|---|---|---|---|---|
| 1-1951 | Cl | 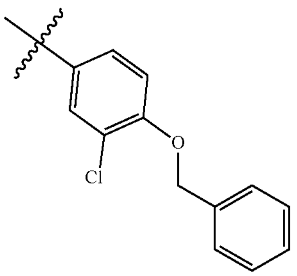 [SMILES: *c1ccc(OCc2ccccc2)c(Cl)c1] | 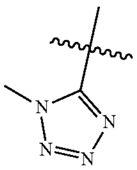 [SMILES: *c1nnnn1C] | $^1H$ NMR (500 MHz, DMSO-$d_6$) δ 12.27 (s, 1H), 8.88 (d, J = 5.0 Hz, 1H), 7.82 (s, 1H), 7.78 (d, J = 5.0 Hz, 1H), 7.65-7.62 (m, 1H), 7.48-7.44 (m, 2H), 7.39-7.35 (m, 2H), 7.32-7.29 (m, 2H), 5.15 (s, 2H), 4.35 (s, 3H). |
| 1-1952 | Cl | 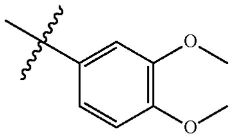 [SMILES: *c1ccc(OC)c(OC)c1] | 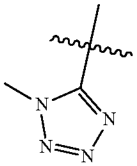 [SMILES: *c1nnnn1C] | $^1H$ NMR (500 MHz, DMSO-$d_6$) δ 12.28 (s, 1H), 8.72 (d, J = 5.0 Hz, 1H), 7.73-7.70 (m, 2H), 7.63 (dd, J = 7.5, 2.0 Hz, 1H), 7.22 (d, J = 7.5 Hz, 1H), 4.32 (s, 3H), 3.94 (s, 3H), 3.79 (s, 3H). |
| 1-1953 | Cl | 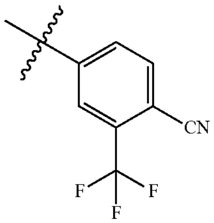 [SMILES: *c1ccc(C#N)c(C(F)(F)F)c1] | 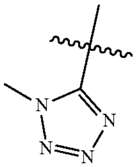 [SMILES: *c1nnnn1C] | $^1H$ NMR (500 MHz, DMSO-$d_6$) δ 12.31 (s, 1H), 8.70 (d, J = 5.0 Hz, 1H), 8.43 (d, J = 2.0 Hz, 1H), 8.32 (dd, J = 7.5, 2.0 Hz, 1H), 7.81 (d, J = 7.5 Hz, 1H), 7.54 (d, J = 5.0 Hz, 1H), 4.30 (s, 3H). |
| 1-1954 | Cl | 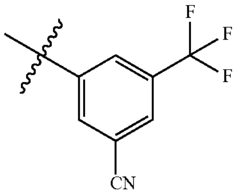 [SMILES: *c1cc(C#N)cc(C(F)(F)F)c1] | 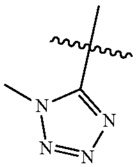 [SMILES: *c1nnnn1C] | $^1H$ NMR (500 MHz, DMSO-$d_6$) δ 12.27 (s, 1H), 8.70 (d, J = 5.0 Hz, 1H), 8.46 (s, 1H), 8.25-8.22 (m, 2H), 7.54 (d, J = 5.0 Hz, 1H), 4.39 (s, 3H). |
| 1-1955 | Cl | 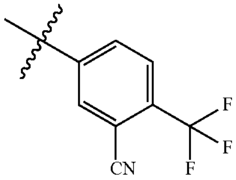 [SMILES: *c1ccc(C(F)(F)F)c(C#N)c1] | 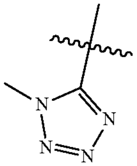 [SMILES: *c1nnnn1C] | $^1H$ NMR (500 MHz, DMSO-$d_6$) δ 12.29 (s, 1H), 8.70 (d, J = 5.0 Hz, 1H), 8.17 (d, J = 2.0 Hz, 1H), 8.04 (dd, J = 7.5, 2.0 Hz, 1H), 7.83 (d, J = 7.5 Hz, 1H), 7.55 (d, J = 5.0 Hz, 1H), 4.38 (s, 3H). |

TABLE A1-continued
| | | | | |
|---|---|---|---|---|
| 1-1956 | Cl | 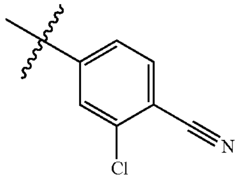 [SMILES: *c1ccc(C#N)c(Cl)c1] | 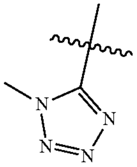 [SMILES: *c1nnnn1C] | $^1$H NMR (500 MHz, DMSO-$d_6$) δ 12.24 (s, 1H), 8.73 (d, J = 5.0 Hz, 1H), 8.09 (d, J = 2.0 Hz, 1H), 8.05 (dd, J = 7.5, 2.0 Hz, 1H), 7.74 (d, J = 7.5 Hz, 1H), 7.57 (d, J = 5.0 Hz, 1H), 4.38 (s, 3H). |
| 1-1957 | Cl | 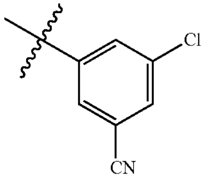 [SMILES: *c1cc(Cl)cc(C#N)c1] | 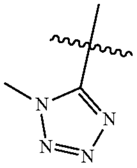 [SMILES: *c1nnnn1C] | $^1$H NMR (500 MHz, DMSO-$d_6$) δ 12.24 (s, 1H), 8.70 (d, J = 5.0 Hz, 1H), 8.25 (s, 1H), 7.98 (s, 1H), 7.92 (s, 1H), 7.69 (d, J = 5.0 Hz, 1H), 4.31 (s, 3H). |
| 1-1958 | Cl | 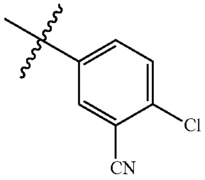 [SMILES: *c1ccc(Cl)c(C#N)c1] | 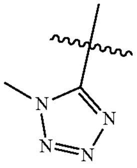 [SMILES: *c1nnnn1C] | $^1$H NMR (500 MHz, DMSO-$d_6$) δ 12.23 (s, 1H), 8.69 (d, J = 5.0 Hz, 1H), 8.18 (dd, J = 7.5, 2.0 Hz, 1H), 8.10 (d, J = 2.0 Hz, 1H), 7.70 (d, J = 7.5 Hz, 1H), 7.53 (d, J = 5.0 Hz, 1H), 4.33 (s, 3H). |
| 1-1959 | Cl | 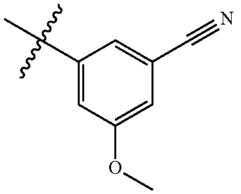 [SMILES: *c1cc(C#N)cc(OC)c1] | 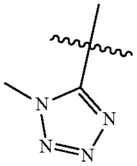 [SMILES: *c1nnnn1C] | $^1$H NMR (500 MHz, DMSO-$d_6$) δ 12.32 (s, 1H), 8.69 (d, J = 5.0 Hz, 1H), 7.78 (s, 1H), 7.53 (d, J = 5.0 Hz, 1H), 7.49 (s, 1H), 7.42 (s, 1H), 4.31 (s, 3H), 3.79 (s, 3H). |
| 1-1960 | Cl | 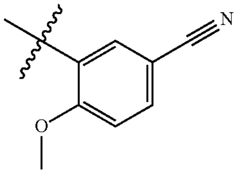 [SMILES: *c1cc(C#N)ccc1OC] | 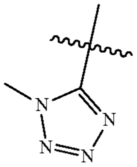 [SMILES: *c1nnnn1C] | $^1$H NMR (500 MHz, DMSO-$d_6$) δ 12.21 (s, 1H), 8.68 (d, J = 5.0 Hz, 1H), 8.01 (d, J = 2.0 Hz, 1H), 7.79 (dd, J = 7.5, 2.0 Hz, 1H), 7.70 (d, J = 5.0 Hz, 1H), 7.15 (d, J = 7.5 Hz, 1H), 4.39 (s, 3H), 3.85 (s, 3H). |

TABLE A1-continued
| | | | | |
|---|---|---|---|---|
| 1-1961 | Cl | 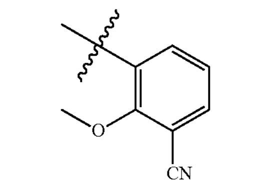 [SMILES: *c1cccc(C#N)c1OC] | 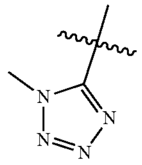 [SMILES: *c1nnnn1C] | $^1H$ NMR (500 MHz, DMSO-$d_6$) δ 12.19 (s, 1H), 8.68 (d, J = 5.0 Hz, 1H), 8.44 (dd, J = 7.5, 2.0 Hz, 1H), 7.82 (dd, J = 7.5, 2.0 Hz, 1H), 7.54 (d, J = 5.0 Hz, 1H), 7.37 (dd, J = 7.5, 7.5 Hz, 1H), 4.34 (s, 3H), 3.84 (s, 3H). |
| 1-1962 | Cl | 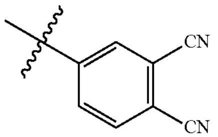 [SMILES: *c1ccc(C#N)c(C#N)c1] | 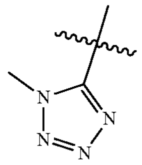 [SMILES: *c1nnnn1C] | $^1H$ NMR (500 MHz, DMSO-$d_6$) δ 12.26 (s, 1H), 8.71 (d, J = 5.0 Hz, 1H), 8.46 (dd, J = 7.5, 2.0 Hz, 1H), 8.34 (d, J = 2.0 Hz, 1H), 7.98 (d, J = 7.5 Hz, 1H), 7.71 (d, J = 5.0 Hz, 1H), 4.31 (s, 3H). |
| 1-1963 | Cl | 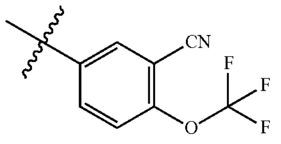 [SMILES: *c1ccc(OC(F)(F)F)c(C#N)c1] | 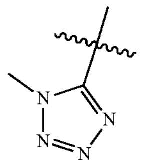 [SMILES: *c1nnnn1C] | $^1H$ NMR (500 MHz, DMSO-$d_6$) δ 12.29 (s, 1H), 8.69 (d, J = 5.0 Hz, 1H), 8.38 (d, J = 2.0 Hz, 1H), 8.11 (dd, J = 7.5, 2.0 Hz, 1H), 7.53 (d, J = 5.0 Hz, 1H), 7.36 (d, J = 7.5 Hz, 1H), 4.34 (s, 3H). |
| 1-1964 | Cl | 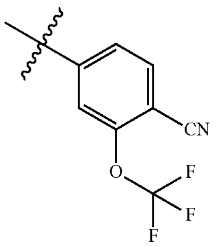 [SMILES: *c1ccc(C#N)c(OC(F)(F)F)c1] | 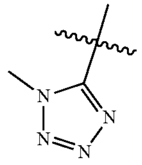 [SMILES: *c1nnnn1C] | $^1H$ NMR (500 MHz, DMSO-$d_6$) δ 12.29 (s, 1H), 8.70 (d, J = 5.0 Hz, 1H), 7.94 (dd, J = 7.5, 2.0 Hz, 1H), 7.87 (d, J = 2.0 Hz, 1H), 7.76 (d, J = 7.5 Hz, 1H), 7.54 (d, J = 5.0 Hz, 1H), 4.32 (s, 3H). |
| 1-1965 | Cl | 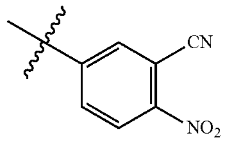 | 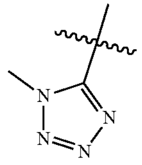 [SMILES: *c1nnnn1C] | $^1H$ NMR (500 MHz, DMSO-$d_6$) δ 12.23 (s, 1H), 8.68 (d, J = 5.0 Hz, 1H), 8.08 (d, J = 2.0 Hz, 1H), 7.89 (dd, J = 7.5, 2.0 Hz, 1H), 7.52 (d, J = 5.0 Hz, 1H), 7.43 (d, J = 7.5 Hz, 1H), 4.30 (s, 3H). |

TABLE A1-continued
| | | | | |
|---|---|---|---|---|
| 1-1966 | Cl | 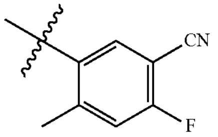 [SMILES: *c1cc(C#N)c(F)cc1C] | 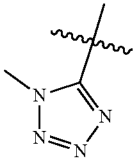 [SMILES: *c1nnnn1C] | $^1$H NMR (500 MHz, DMSO-$d_6$) δ 12.26 (s, 1H), 8.69 (d, J = 5.0 Hz, 1H), 8.16 (s, 1H), 7.54 (d, J = 5.0 Hz, 1H), 7.28 (s, 1H), 4.35 (s, 3H), 2.37 (s, 3H). |
| 1-1967 | Cl | 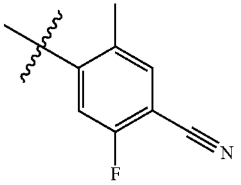 [SMILES: *c1cc(F)c(C#N)cc1C] | 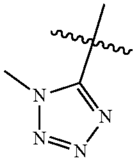 [SMILES: *c1nnnn1C] | $^1$H NMR (500 MHz, DMSO-$d_6$) δ 12.28 (s, 1H), 8.73 (d, J = 5.0 Hz, 1H), 7.88 (d, J = 10.0 Hz, 1H), 7.74 (d, J = 6.0 Hz, 1H), 7.58 (d, J = 5.0 Hz, 1H), 4.35 (s, 3H), 2.43 (s, 3H). |
| 1-1968 | Cl | 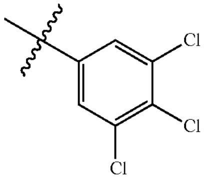 [SMILES: *c1cc(Cl)c(Cl)c(Cl)c1] | 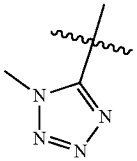 [SMILES: *c1nnnn1C] | $^1$H NMR (500 MHz, DMSO-$d_6$) δ 12.27 (s, 1H), 8.64 (d, J = 5.0 Hz, 1H), 7.87 (s, 2H), 7.49 (d, J = 5.0 Hz, 1H), 4.32 (s, 3H). |
| 1-1969 | Cl | 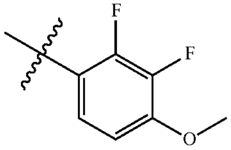 | 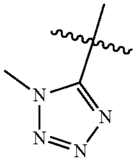 [SMILES: *c1nnnn1C] | $^1$H NMR (500 MHz, DMSO-$d_6$) δ 12.23 (s, 1H), 8.63 (d, J = 5.0 Hz, 1H), 7.64 (d, J = 5.0 Hz, 1H), 7.56-7.53 (m, 1H), 7.00-6.97 (m, 1H), 4.34 (s, 3H), 3.84 (s, 3H). |
| 1-1970 | Cl | 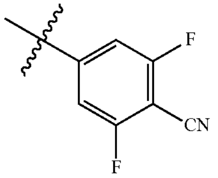 [SMILES: *c1cc(F)c(C#N)c(F)c1] | 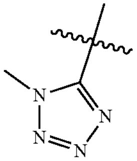 [SMILES: *c1nnnn1C] | $^1$H NMR (500 MHz, DMSO-$d_6$) δ 12.26 (s, 1H), 8.71 (d, J = 5.0 Hz, 1H), 7.71 (d, J = 5.0 Hz, 1H), 7.68-7.61 (m, 2H), 4.35 (s, 3H). |

TABLE A1-continued
| | | | | |
|---|---|---|---|---|
| 1-1971 | Cl | 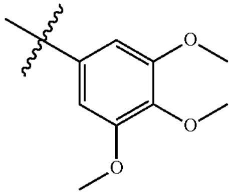 [SMILES: *c1cc(OC)c(OC)c(OC)c1] | 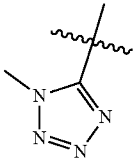 [SMILES: *c1nnnn1C] | $^1$H NMR (500 MHz, DMSO-$d_6$) δ 12.25 (s, 1H), 8.64 (d, J = 5.0 Hz, 1H), 7.50 (d, J = 5.0 Hz, 1H), 7.36 (s, 2H), 4.31 (s, 3H), 3.82 (s, 6H), 3.73 (s, 3H). |
| 1-1972 | Cl | 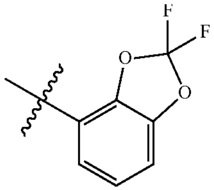 [SMILES: *c1cccc2c1OC(F)(F)O2] | 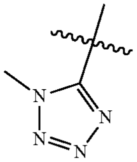 [SMILES: *c1nnnn1C] | $^1$H NMR (500 MHz, DMSO-$d_6$) δ 9.25 (s, 1H), 8.67 (d, J = 5.0 Hz, 1H), 7.86 (dd, J = 7.5, 2.0 Hz, 1H), 7.52 (d, J = 5.0 Hz, 1H), 7.13 (dd, J = 7.5, 2.0 Hz, 1H), 7.01-6.98 (m, 1H), 4.33 (s, 3H). |
| 1-1973 | Cl | 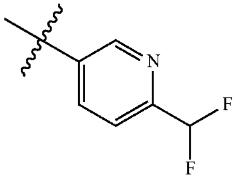 [SMILES: *c1ccc(C(F)F)nc1] | 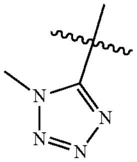 [SMILES: *c1nnnn1C] | |
| 1-1974 | Cl | 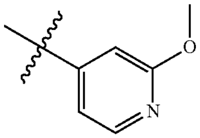 [SMILES: *c1ccnc(OC)c1] | 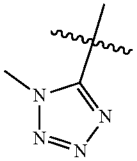 [SMILES: *c1nnnn1C] | $^1$H NMR (500 MHz, DMSO-$d_6$) δ 12.23 (s, 1H), 8.74 (d, J = 5.0 Hz, 1H), 7.95 (d, J = 5.0 Hz, 1H), 7.74 (d, J = 5.0 Hz, 1H), 7.60 (s, 1H), 7.28 (d, J = 5.0 Hz, 1H), 4.33 (s, 3H), 3.89 (s, 3H). |
| 1-1975 | Cl | 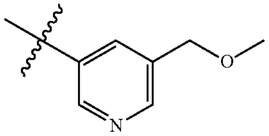 [SMILES: *c1cncc(COC)c1] | 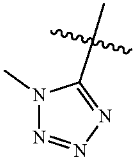 [SMILES: *c1nnnn1C] | |

TABLE A1-continued
| | | | |
|---|---|---|---|
| 1-1976 | Cl | 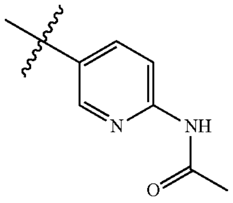 [SMILES: *c1ccc(NC(C)=O)nc1] | 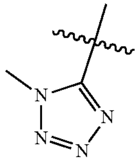 [SMILES: *c1nnnn1C] |
| 1-1977 | Cl | 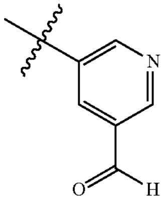 [SMILES: *c1cncc(C=O)c1] | 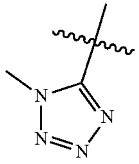 [SMILES: *c1nnnn1C] |
| 1-1978 | Cl | 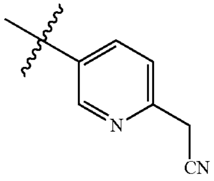 [SMILES: *c1ccc(CC#N)nc1] | 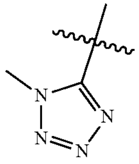 [SMILES: *c1nnnn1C] |
| 1-1979 | Cl | 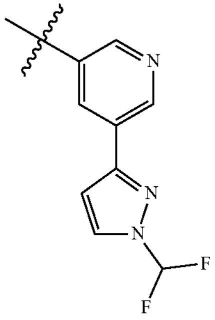 [SMILES: *c1cncc(-c2ccn(C(F)F)n2)c1] | 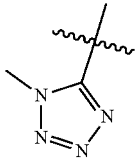 [SMILES: *c1nnnn1C] |

TABLE A1-continued
| | | | | |
|---|---|---|---|---|
| 1-1980 | Cl | 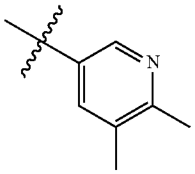 [SMILES: *c1cnc(C)c(C)c1] | 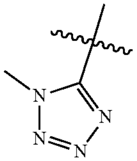 [SMILES: *c1nnnn1C] | |
| 1-1981 | Cl | 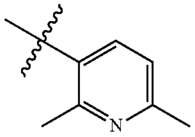 | 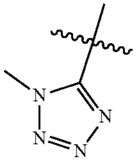 [SMILES: *c1nnnn1C] | |
| 1-1982 | Cl | 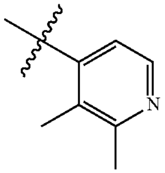 [SMILES: *c1ccnc(C)c1C] | 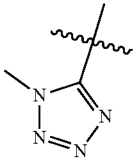 [SMILES: *c1nnnn1C] | $^{1}$H NMR (500 MHz, DMSO-$d_6$) δ 12.22 (s, 1H), 8.78 (d, J = 5.0 Hz, 1H), 8.58 (d, J = 5.0 Hz, 1H), 7.78 (d, J = 5.0 Hz, 1H), 7.63 (d, J = 5.0 Hz, 1H), 4.32 (s, 3H), 2.60 (s, 3H), 2.21 (s, 3H). |
| 1-1983 | Cl | 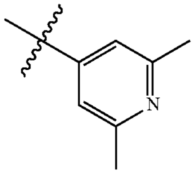 [SMILES: *c1cc(C)nc(C)c1] | 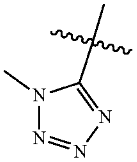 [SMILES: *c1nnnn1C] | $^{1}$H NMR (500 MHz, DMSO-$d_6$) δ 12.29 (s, 1H), 8.78 (d, J = 5.0 Hz, 1H), 7.79 (d, J = 5.0 Hz, 1H), 7.64 (s, 2H), 4.39 (s, 3H), 2.55 (s, 6H). |
| 1-1984 | Cl | 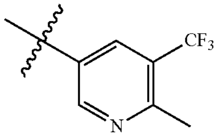 [SMILES: *c1cnc(C)c(C(F)(F)F)c1] | 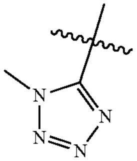 [SMILES: *c1nnnn1C] | |
| 1-1985 | Cl | 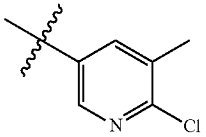 [SMILES: *c1cnc(Cl)c(C)c1] | 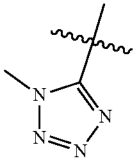 [SMILES: *c1nnnn1C] | $^{1}$H NMR (500 MHz, DMSO-$d_6$) δ 12.26 (s, 1H), 8.81 (s, 1H), 8.74 (d, J = 5.0 Hz, 1H), 8.18 (s, 1H), 7.87 (d, J = 5.0 Hz, 1H), 4.36 (s, 3H), 2.32 (s, 3H). |

TABLE A1-continued
| | | | | |
|---|---|---|---|---|
| 1-1986 | Cl | 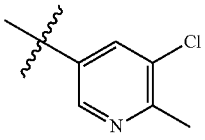 [SMILES: *c1cnc(C)c(Cl)c1] | 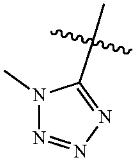 [SMILES: *c1nnnn1C] | |
| 1-1987 | Cl | 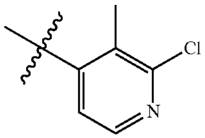 [SMILES: *c1ccnc(Cl)c1C] | 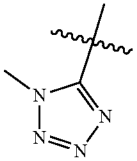 [SMILES: *c1nnnn1C] | $^1$H NMR (500 MHz, DMSO-$d_6$) δ 12.21 (s, 1H), 8.77 (d, J = 5.0 Hz, 1H), 8.26 (d, J = 5.0 Hz, 1H), 7.92 (d, J = 5.0 Hz, 1H), 7.79 (d, J = 5.0 Hz, 1H), 4.38 (s, 3H), 2.30 (s, 3H). |
| 1-1988 | Cl | 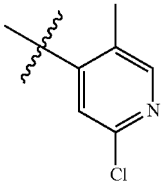 [SMILES: *c1cc(Cl)ncc1C] | 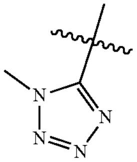 [SMILES: *c1nnnn1C] | $^1$H NMR (500 MHz, DMSO-$d_6$) δ 12.24 (s, 1H), 8.77 (d, J = 5.0 Hz, 1H), 8.42 (s, 1H), 8.33 (s, 1H), 7.78 (d, J = 5.0 Hz, 1H), 4.31 (s, 3H), 2.28 (s, 3H). |
| 1-1989 | Cl | 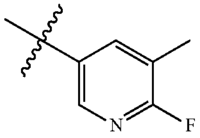 [SMILES: *c1cnc(F)c(C)c1] | 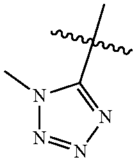 [SMILES: *c1nnnn1C] | $^1$H NMR (500 MHz, DMSO-$d_6$) δ 12.30 (s, 1H), 8.74 (d, J = 5.0 Hz, 1H), 8.62 (s, 1H), 8.25 (d, J = 5.0 Hz, 1H), 7.87 (d, J = 5.0 Hz, 1H), 4.35 (s, 3H), 2.30 (s, 3H). |
| 1-1990 | Cl | 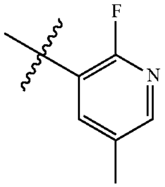 [SMILES: *c1cc(C)cnc1F] | 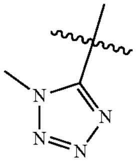 [SMILES: *c1nnnn1C] | |
| 1-1991 | Cl | 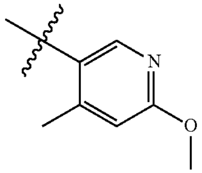 [SMILES: *c1cnc(OC)cc1C] | 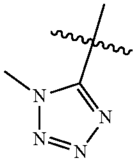 [SMILES: *c1nnnn1C] | |

TABLE A1-continued
| | | | |
|---|---|---|---|
| 1-1992 | Cl | 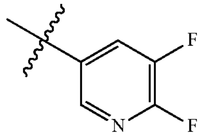 [SMILES: *c1cnc(F)c(F)c1] | 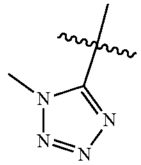 [SMILES: *c1nnnn1C] |
| 1-1993 | Cl | 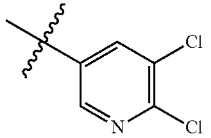 [SMILES: *c1cnc(Cl)c(Cl)c1] | 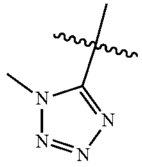 [SMILES: *c1nnnn1C] |
| 1-1994 | Cl | 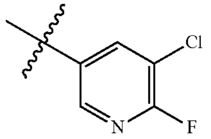 [SMILES: *c1cnc(F)c(Cl)c1] | 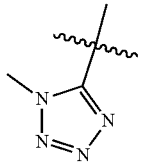 [SMILES: *c1nnnn1C] |
| 1-1995 | Cl | 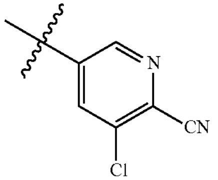 [SMILES: *c1cnc(C#N)c(Cl)c1] | 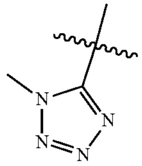 [SMILES: *c1nnnn1C] |
| 1-1996 | Cl | 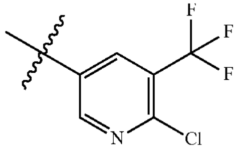 [SMILES: *c1cnc(Cl)c(C(F)(F)F)c1] | 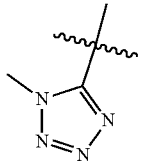 [SMILES: *c1nnnn1C] |
| 1-1997 | Cl | 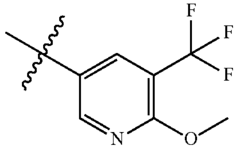 | 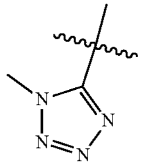 [SMILES: *c1nnnn1C] |

TABLE A1-continued
| | | | | |
|---|---|---|---|---|
| 1-1998 | Cl | 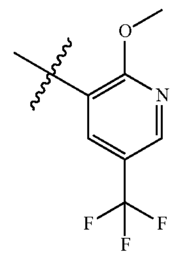 [SMILES: *c1cc(C(F)(F)F)cnc1OC] | 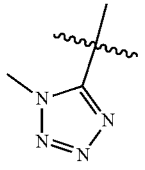 [SMILES: *c1nnnn1C] | |
| 1-1999 | Cl | 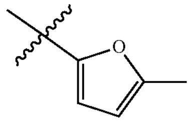 [SMILES: *c1ccc(C)o1] | 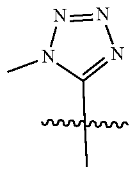 [SMILES: *c1nnnn1C] | $^1H$ NMR (500 MHz, DMSO-$d_6$) δ 12.27 (s, 1H), 8.85 (d, J = 5.0 Hz, 1H), 7.89 (d, J = 5.0 Hz, 1H), 6.80 (d, J = 4.5 Hz, 1H), 6.09 (d, J = 4.5 Hz, 1H), 4.35 (s, 3H), 2.35 (s, 3H). |
| 1-2000 | Cl | 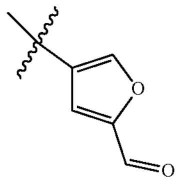 [SMILES: *c1coc(C=O)c1] | 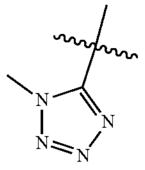 [SMILES: *c1nnnn1C] | $^1H$ NMR (500 MHz, DMSO-$d_6$) δ 12.25 (s, 1H), 9.25 (s, 1H), 8.93 (d, J = 5.0 Hz, 1H), 7.92 (d, J = 5.0 Hz, 1H), 7.67 (s, 1H), 6.88 (s, 1H), 4.33 (s, 3H). |
| 1-2001 | Cl | 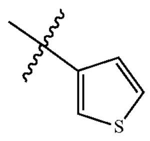 [SMILES: *c1ccsc1] | 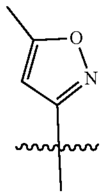 [SMILES: *c1cc(C)on1] | $^1H$ NMR (500 MHz, DMSO-$d_6$) δ 11.51 (s, 1H), 8.97 (d, J = 5.0 Hz, 1H), 8.04 (d, J = 5.0 Hz, 1H), 7.74-7.71 (m, 2H), 7.33 (d, J = 4.5 Hz, 1H), 6.74 (s, 1H), 2.41 (s, 3H). |
| 1-2002 | Cl | 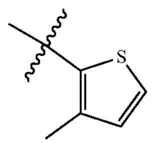 [SMILES: *c1sccc1C] | 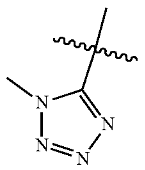 [SMILES: *c1nnnn1C] | $^1H$ NMR (500 MHz, DMSO-$d_6$) δ 12.28 (s, 1H), 8.91 (d, J = 5.0 Hz, 1H), 7.79 (d, J = 5.0 Hz, 1H), 7.60 (d, J = 4.5 Hz, 1H), 7.27 (d, J = 4.5 Hz, 1H), 4.33 (s, 3H), 2.31 (s, 3H). |

TABLE A1-continued

| | | | | |
|---|---|---|---|---|
| 1-2003 | Cl | 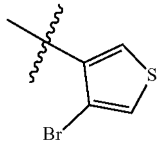 [SMILES: *c1cscc1Br] | 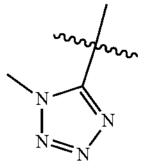 [SMILES: *c1nnnn1C] | $^1$H NMR (500 MHz, DMSO-$d_6$) δ 12.21 (s, 1H), 8.93 (d, J = 5.0 Hz, 1H), 8.10 (s, 1H), 7.80 (d, J = 5.0 Hz, 1H), 7.68 (s, 1H), 4.33 (s, 3H). |
| 1-2004 | Cl | 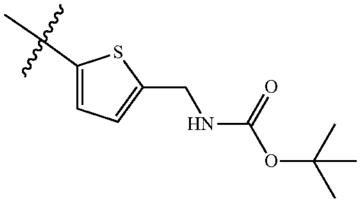 [SMILES: *c1ccc(CNC(=O)OC(C)(C)C)s1] | 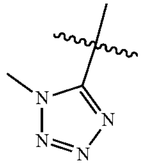 [SMILES: *c1nnnn1C] | $^1$H NMR (500 MHz, DMSO-$d_6$) δ 12.30 (s, 1H), 8.91 (d, J = 5.0 Hz, 1H), 7.96 (d, J = 5.0 Hz, 1H), 7.85 (s, 1H), 7.42 (d, J = 4.5 Hz, 1H), 7.18 (d, J = 4.5 Hz, 1H), 4.51 (s, 2H), 4.33 (s, 3H), 1.39 (s, 9H). |
| 1-2005 | Cl | 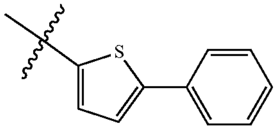 [SMILES: *c1ccc(-c2ccccc2)s1] | 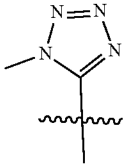 [SMILES: *c1nnnn1C] | $^1$H NMR (500 MHz, DMSO-$d_6$) δ 12.21 (s, 1H), 8.77 (d, J = 5.0 Hz, 1H), 7.94 (d, J = 5.0 Hz, 1H), 7.86-7.78 (m, 2H), 7.60 (d, J = 7.5 Hz, 1H), 7.51-7.45 (m, 3H), 7.34 (d, J = 7.5 Hz, 1H), 4.36 (s, 3H). |
| 1-2006 | Cl | 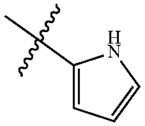 [SMILES: *c1ccc[nH]1] | 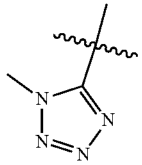 [SMILES: *c1nnnn1C] | $^1$H NMR (500 MHz, DMSO-$d_6$) δ 12.27 (s, 1H), 8.85 (d, J = 5.0 Hz, 1H), 7.72 (d, J = 5.0 Hz, 1H), 7.03 (d, J = 4.5 Hz, 1H), 6.81 (d, J = 4.5 Hz, 1H), 6.35-6.31 (m, 1H), 4.36 (s, 3H). |
| 1-2007 | Cl | 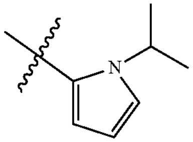 [SMILES: *c1cccn1C(C)C] | 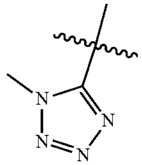 [SMILES: *c1nnnn1C] | $^1$H NMR (500 MHz, DMSO-$d_6$) δ 12.28 (s, 1H), 8.87 (d, J = 5.0 Hz, 1H), 7.74 (d, J = 5.0 Hz, 1H), 7.60 (d, J = 3.5 Hz, 1H), 6.69 (d, J = 3.5 Hz, 1H), 4.60-4.56 (m, 1H), 4.32 (s, 3H), 1.27 (d, J = 7.0 Hz, 6H). |
| 1-2008 | Cl | 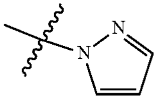 [SMILES: *n1cccn1] | 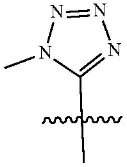 [SMILES: *c1nnnn1C] | $^1$H NMR (500 MHz, DMSO-$d_6$) δ 12.22 (s, 1H), 8.68 (d, J = 5.0 Hz, 1H), 7.91 (d, J = 4.5 Hz, 1H), 7.80 (d, J = 5.0 Hz, 1H), 7.59 (d, J = 4.5 Hz, 1H), 6.58-6.53 (m, 1H), 4.30 (s, 3H). |

TABLE A1-continued
| | | | | |
|---|---|---|---|---|
| 1-2009 | Cl | 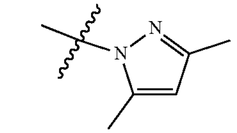 [SMILES: *n1nc(C)cc1C] | 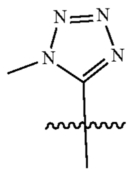 | $^1$H NMR (500 MHz, DMSO-$d_6$) δ 12.21 (s, 1H), 8.66 (d, J = 5.0 Hz, 1H), 7.80 (d, J = 5.0 Hz, 1H), 6.14 (s, 1H), 4.32 (s, 3H), 2.75 (s, 3H), 2.24 (s, 3H). |
| 1-2010 | Cl | 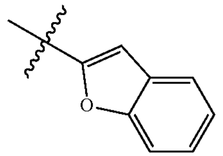 | 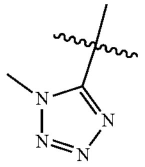 [SMILES: *c1nnnn1C] | $^1$H NMR (500 MHz, DMSO-$d_6$) δ 12.27 (s, 1H), 8.80 (d, J = 5.0 Hz, 1H), 7.75 (d, J = 5.0 Hz, 1H), 7.67 (dd, J = 7.5, 1.5 Hz, 1H), 7.61 (dd, J = 7.5, 1.5 Hz, 1H), 7.42-7.38 (m, 1H), 7.30-7.23 (m, 2H), 4.33 (s, 3H). |
| 1-2011 | Cl | 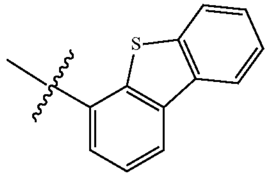 | 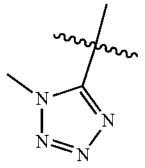 [SMILES: *c1nnnn1C] | $^1$H NMR (500 MHz, DMSO-$d_6$) δ 12.26 (s, 1H), 8.92 (d, J = 5.0 Hz, 1H), 8.58-8.56 (m, 1H), 8.49-8.47 (m, 1H), 8.10-8.07 (m, 1H), 8.05-8.02 (m, 1H), 7.83 (d, J = 5.0 Hz, 1H), 7.73-7.69 (m, 1H), 7.57-7.54 (m, 1H), 7.49-7.46 (m, 1H), 4.32 (s, 3H). |
| 1-2012 | F | $CH_3$ | 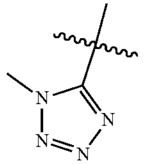 [SMILES: *c1nnnn1C] | $^1$H NMR (500 MHz, DMSO-$d_6$) δ 12.25 (s, 1H), 8.46 (d, J = 5.0 Hz, 1H), 7.50-7.47 (m, 1H), 4.33 (s, 3H), 2.54 (s, 3H). |
| 1-2013 | F | 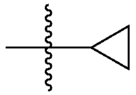 [SMILES: *C1CC1] | 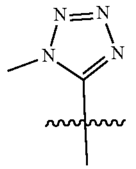 [SMILES: *c1nnnn1C] | $^1$H NMR (500 MHz, DMSO-$d_6$) δ 12.27 (s, 1H), 8.30 (d, J = 5.0 Hz, 1H), 7.82 (dd, J = 7.0, 5.0 Hz, 1H), 4.33 (s, 3H), 1.77-1.72 (m, 1H), 0.84-0.79 (m, 2H), 0.71-0.65 (m, 2H). |
| 1-2014 | F | 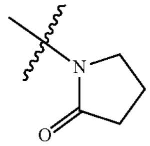 [SMILES: *N1CCCC1=O] | 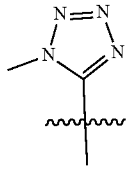 [SMILES: *c1nnnn1C] | $^1$H NMR (500 MHz, DMSO-$d_6$) δ 12.29 (s, 1H), 8.35 (d, J = 5.0 Hz, 1H), 7.81 (dd, J = 7.0, 5.0 Hz, 1H), 4.34 (s, 3H), 3.70 (t, J = 6.0 Hz, 2H), 2.43 (t, J = 7.0 Hz, 2H), 2.09-2.02 (m, 2H). |

TABLE A1-continued
| | | | | |
|---|---|---|---|---|
| 1-2015 | F | 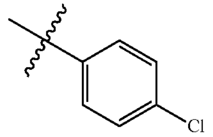 [SMILES: *c1ccc(Cl)cc1] | 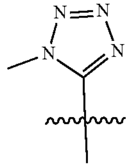 [SMILES: *c1nnnn1C] | $^1$H NMR (500 MHz, DMSO-$d_6$) δ 12.28 (s, 1H), 8.45 (d, J = 5.0 Hz, 1H), 7.95-7.89 (m, 2H), 7.81 (dd, J = 7.0, 5.0 Hz, 1H), 7.51-7.45 (m, 2H), 4.37 (s, 3H). |
| 1-2016 | F | 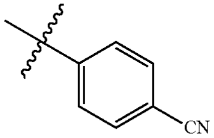 | 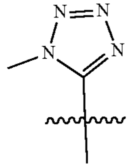 [SMILES: *c1nnnn1C] | $^1$H NMR (500 MHz, DMSO-$d_6$) δ 12.26 (s 1H), 8.47 (d, J = 5.0 Hz, 1H), 8.18-8.12 (m, 2H), 7.84 (dd, J = 6.0, 5.0 Hz, 1H), 7.77-7.71 (m, 2H), 4.38 (s, 3H). |
| 1-2017 | F | 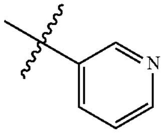 [SMILES: *c1cccnc1] | 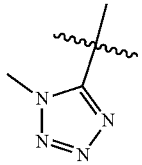 [SMILES: *c1nnnn1C] | $^1$H NMR (500 MHz, DMSO-$d_6$) δ 12.25 (s, 1H), 9.06 (s, 1H), 8.63 (d, J = 5.0 Hz, 1H), 8.41 (d, J = 5.0 Hz, 1H), 8.31 (d, J = 8.0 H,z 1H), 8.16 (d, J = 5.0 Hz, 1H), 7.46 (dd, J = 8.0, 5.0 Hz, 1H), 4.34 (s, 3H). |
| 1-2018 | F | 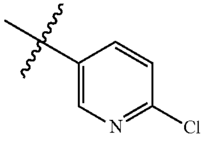 [SMILES: *c1ccc(Cl)nc1] | 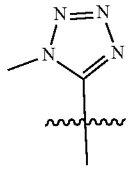 [SMILES: *c1nnnn1C] | $^1$H NMR (500 MHz, DMSO-$d_6$) δ 12.26 (s, 1H), 8.90 (s, 1H), 8.54 (d, J = 5.0 Hz, 1H), 8.09-8.01 (m, 2H), 7.47 (d, J = 8.0 Hz, 1H), 4.30 (s, 3H). |
| 1-2019 | F | 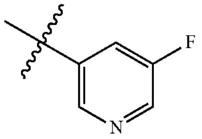 [SMILES: *c1cncc(F)c1] | 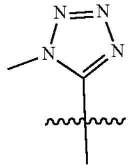 [SMILES: *c1nnnn1C] | $^1$H NMR (500 MHz, DMSO-$d_6$) δ 12.26 (s, 1H), 8.73 (s, 1H), 8.56 (d, J = 5.0 Hz, 1H), 8.37-8.28 (m, 2H), 8.07 (d, J = 7.0 Hz, 1H), 4.32 (s, 3H). |
| 1-2020 | F | 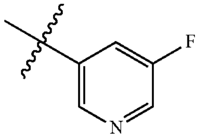 [SMILES: *c1cncc(F)c1] | 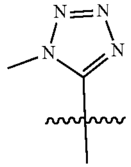 [SMILES: *c1nnnn1C] | $^1$H NMR (500 MHz, DMSO-$d_6$) δ 12.25 (s, 1H), 8.57 (d, J = 5.0 Hz, 1H), 8.22 (d, J = 5.0 Hz, 1H), 8.09 (dd, J = 7.0, 5.0 Hz, 1H), 7.96 (d, J = 8.0 Hz, 1H), 7.89 (d, J = 5.0 Hz, 1H), 4.32 (s, 3H). |

TABLE A1-continued
| | | | | |
|---|---|---|---|---|
| 1-2021 | F | 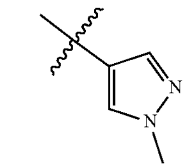 [SMILES: *c1cnn(C)c1] | 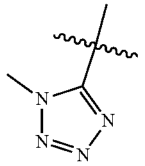 [SMILES: *c1nnnn1C] | $^1$H NMR (500 MHz, DMSO-$d_6$) δ 12.33 (s, 1H), 8.73 (d, J = 5.0 Hz, 1H), 8.14-8.10 (m, 1H), 7.90 (s, 1H), 7.00 (s, 1H), 4.35 (s, 3H), 3.93 (s, 3H). |
| 1-2022 | F | 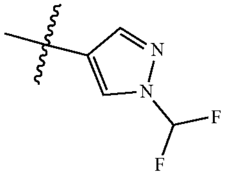 [SMILES: *c1cnn(C(F)F)c1] | 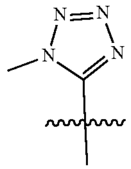 | $^1$H NMR (500 MHz, DMSO-$d_6$) δ 12.25 (s, 1H), 8.66 (d, J = 5.0 Hz, 1H), 8.05 (dd, J = 7.0, 5.0 Hz, 1H), 7.98-7.62 (m, 2H), 7.04 (s, 1H), 4.35 (s, 3H). |
| 1-2023 | OH | 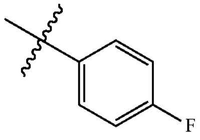 [SMILES: *c1ccc(F)cc1] | 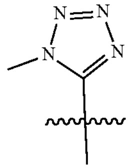 [SMILES: *c1nnnn1C] | $^1$H NMR (500 MHz, DMSO-$d_6$) δ 12.22 (s, 1H), 8.38 (d, J = 5.0 Hz, 1H), 7.89-7.86 (m, 3H), 7.35-7.27 (m, 2H), 4.38 (s, 3H). |
| 1-2024 | OMe | 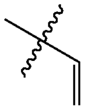 [SMILES: *C=C] | 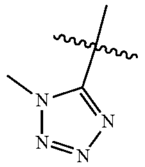 [SMILES: *c1nnnn1C] | $^1$H NMR (500 MHz, DMSO-$d_6$) δ 12.22 (s, 1H), 8.75 (d, J = 5.0 Hz, 1H), 8.05 (d, J = 5.0 Hz, 1H), 6.86-6.82 (m, 1H), 6.17-6.13 (m 1H), 5.68-5.64 (m, 1H), 4.32 (s, 3H), 3.79 (s, 3H). |
| 1-2025 | OMe | 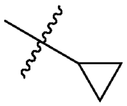 [SMILES: *C1CC1] | 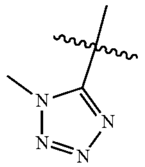 [SMILES: *c1nnnn1C] | $^1$H NMR (500 MHz, DMSO-$d_6$) δ 12.25 (s, 1H), 8.43 (d, J = 5.0 Hz, 1H), 7.89 (d, J = 5.0 Hz, 1H), 4.33 (s, 3H), 3.83 (s, 3H), 1.78-1.74 (m, 1H), 0.84-0.77 (m, 2H), 0.72-0.65 (m, 2H). |
| 1-2026 | OMe | 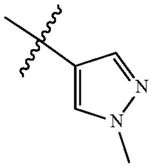 [SMILES: *c1cnn(C)c1] | 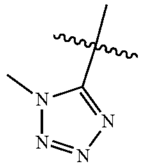 [SMILES: *c1nnnn1C] | $^1$H NMR (500 MHz, DMSO-$d_6$) δ 12.28 (s, 1H), 8.84 (d, J = 5.0 Hz, 1H), 8.16 (d, J = 5.0 Hz, 1H), 7.88 (s, 1H), 7.03 (s, 1H), 4.32 (s, 3H), 3.93 (s, 3H), 3.82 (s, 3H). |

TABLE A1-continued

| | | | | |
|---|---|---|---|---|
| 1-2027 | OMe | 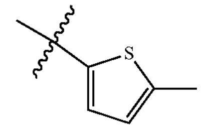 [SMILES: *c1ccc(C)s1] | 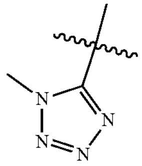 [SMILES: *c1nnnn1C] | $^1$H NMR (500 MHz, DMSO-$d_6$) δ 12.26 (s, 1H), 8.85 (d, J = 5.0 Hz, 1H), 8.18 (d, J = 5.0 Hz, 1H), 7.62 (d, J = 4.5 Hz, 1H), 7.12 (d, J = 4.5 Hz, 1H), 4.31 (s, 3H), 3.79 (s, 3H), 2.39 (s, 3H). |
| 1-2028 | OMe | 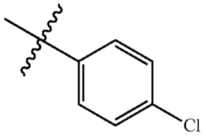 [SMILES: *c1ccc(Cl)cc1] | 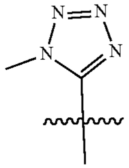 [SMILES: *c1nnnn1C] | $^1$H NMR (500 MHz, DMSO-$d_6$) δ 12.30 (s, 1H), 8.59 (d, J = 5.0 Hz, 1H), 7.84-7.78 (m, 2H), 7.51-7.42 (m, 3H), 4.35 (s, 3H), 3.68 (s, 3H). |
| 1-2029 | OMe | 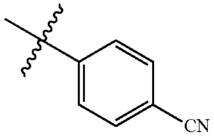 [SMILES: *c1ccc(C#N)cc1] | 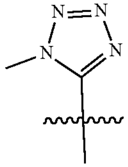 [SMILES: *c1nnnn1C] | $^1$H NMR (500 MHz, DMSO-$d_6$) δ 12.28 (s, 1H), 8.57 (d, J = 5.0 Hz, 1H), 8.17-8.10 (m, 2H), 7.87 (d, J = 5.0 Hz, 1H), 7.77-7.71 (m, 2H), 4.36 (s, 3H), 3.71 (s, 3H). |
| 1-2030 | OMe | 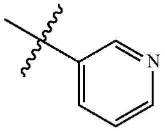 [SMILES: *c1cccnc1] | 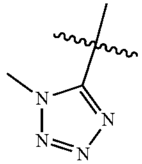 [SMILES: *c1nnnn1C] | $^1$H NMR (500 MHz, DMSO-$d_6$) δ 12.29 (s, 1H), 9.06 (s, 1H), 8.73 (d, J = 5.0 Hz, 1H), 8.41 (d, J = 5.0 Hz, 1H), 8.30 (d, J = 8.0 Hz, 1H), 8.18 (d, J = 5.0 Hz, 1H), 7.46 (dd, J = 8.0, 5.0 Hz, 1H), 4.33 (s, 3H), 3.72 (s, 3H). |
| 1-2031 | OMe | 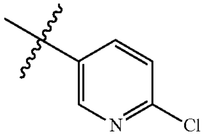 [SMILES: *c1ccc(Cl)nc1] | 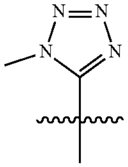 | $^1$H NMR (500 MHz, DMSO-$d_6$) δ 12.21 (s, 1H), 8.79 (s, 1H), 8.69 (d, J = 5.0 Hz, 1H), 7.93 (d, J = 8.0, Hz, 1H), 7.58 (d, J = 5.0 Hz, 1H), 7.45 (d, J = 8.0 Hz, 1H), 4.33 (s, 3H), 3.53 (s, 3H). |
| 1-2032 | OMe | 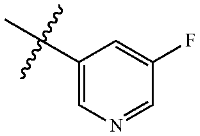 [SMILES: *c1cncc(F)c1] | 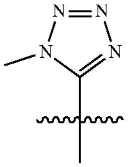 | $^1$H NMR (500 MHz, DMSO-$d_6$) δ 12.30 (s, 1H), 8.72-8.63 (m, 2H), 8.32 (d, J = 8.0 Hz, 1H), 8.20 (d, J = 9.0 Hz, 1H), 7.65 (d, J = 5.0 Hz, 1H), 4.38 (s, 3H), 3.58 (s, 3H). |

TABLE A1-continued
| | | | | |
|---|---|---|---|---|
| 1-2033 | OMe | 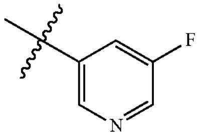 [SMILES: *c1cncc(F)c1] | 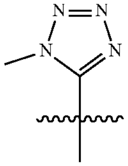 | |
| 1-2034 | OMe | 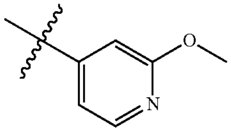 [SMILES: *c1ccnc(OC)c1] | 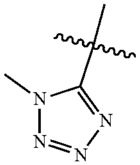 [SMILES: *c1nnnn1C] | |
| 1-2035 | OMe | 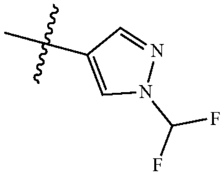 [SMILES: *c1cnn(C(F)F)c1] | 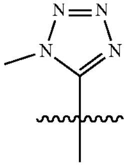 | $^1$H NMR (500 MHz, DMSO-$d_6$) δ 12.29 (s, 1H), 8.82 (d, J = 5.0 Hz, 1H), 7.83 (t, J = 57.0 Hz, 1H), 7.70 (s, 1H), 7.58 (d, J = 5.0 H, 1H), 6.96 (s, 1H), 4.33 (s, 3H), 2.59 (s, 3H). |
| 1-2036 | 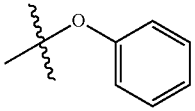 [SMILES: *Oc1ccccc1] | 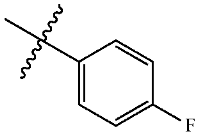 [SMILES: *c1ccc(F)cc1] | 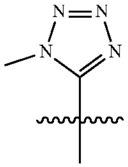 | |
| 1-2037 | 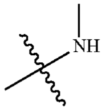 | 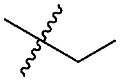 [SMILES: *CC] | 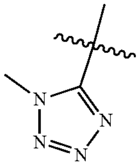 [SMILES: *c1nnnn1C] | |
| 1-2038 | 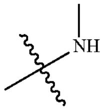 [SMILES: *NC] | 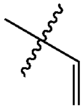 [SMILES: *C=C] | 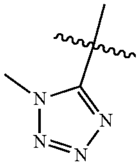 [SMILES: *c1nnnn1C] | $^1$H NMR (500 MHz, DMSO-$d_6$) δ 12.31 (s, 1H), 8.55 (d, J = 5.0 Hz, 1H), 8.12 (d, J = 5.0 Hz, 1H), 6.78 (dd, J = 17.0, 10.0 Hz, 1H), 6.06 (dd, J = 14.0, 10.0 Hz, 1H), 5.95 (s, 1H), 5.58 (dd, J = 17.0, 14.0 Hz, 1H), 4.33 (s, 3H), 2.71 (s, 3H). |

TABLE A1-continued

| | | | | |
|---|---|---|---|---|
| 1-2039 | 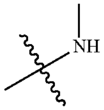 [SMILES: *NC] | 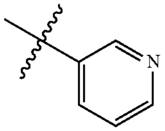 | 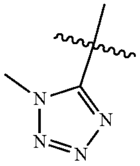 [SMILES: *c1nnnn1C] | $^1$H NMR (500 MHz, DMSO-$d_6$) δ 12.25 (s, 1H), 8.92 (s, 1H), 8.51 (d, J = 5.0 Hz, 1H), 8.41 (d, J = 5.0 Hz, 1H), 8.24 (d, J = 5.0 Hz, 1H), 8.20 (d, J = 8.0 Hz, 1H), 7.46 (dd, J = 8.0, 5.0 Hz, 1H), 5.95 (s, 1H), 4.29 (s, 3H), 2.64 (s, 3H). |
| 1-2040 | 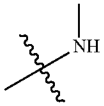 [SMILES: *NC] | 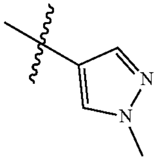 [SMILES: *c1cnn(C)c1] | 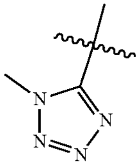 [SMILES: *c1nnnn1C] | $^1$H NMR (500 MHz, DMSO-$d_6$) δ 12.31 (s, 1H), 8.64 (d, J = 5.0 Hz, 1H), 8.24 (d, J = 5.0 Hz, 1H), 7.75 (s, 1H), 6.87 (s, 1H), 5.95 (s, 1H), 4.38 (s, 3H), 3.92 (s, 3H), 2.72 (s, 3H). |
| 1-2041 | 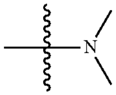 [SMILES: *N(C)C] | $CH_3$ | 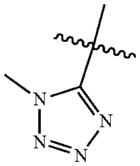 [SMILES: *c1nnnn1C] | $^1$H NMR (500 MHz, DMSO-$d_6$) δ 12.21 (s, 1H), 8.46 (d, J = 5.0 Hz, 1H), 8.04 (d, J = 5.0 Hz, 1H), 4.33 (s, 3H), 2.92 (s, 6H), 2.56 (s, 3H). |
| 1-2042 | 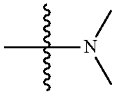 [SMILES: *N(C)C] | $CH_2CH_3$ | 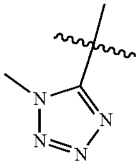 [SMILES: *c1nnnn1C] | $^1$H NMR (500 MHz, DMSO-$d_6$) δ 12.25 (s, 1H), 8.44 (d, J = 5.0 Hz, 1H), 8.08 (d, J = 5.0 Hz, 1H), 4.36 (s, 3H), 3.13 (q, J = 8.0 Hz, 2H), 2.89 (s, 6H), 1.18 (t, J = 8.0 Hz, 3H). |
| 1-2043 | 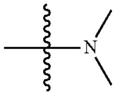 [SMILES: *N(C)C] | 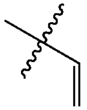 [SMILES: *C=C] | 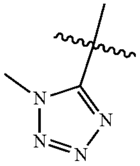 [SMILES: *c1nnnn1C] | $^1$H NMR (500 MHz, DMSO-$d_6$) δ 12.26 (s, 1H), 8.59 (d, J = 5.0 Hz, 1H), 8.17 (d, J = 5.0 Hz, 1H), 6.73 (dd, J = 17.0, 10.0 Hz, 1H), 6.10 (dd, J = 14.0, 10.0 Hz, 1H), 5.60 (dd, J = 17.0, 14.0 Hz, 1H), 4.33 (s, 3H), 2.91 (s, 6H). |
| 1-2044 | 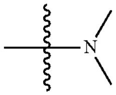 [SMILES: *N(C)C] | 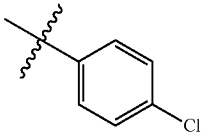 | 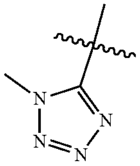 [SMILES: *c1nnnn1C] | $^1$H NMR (500 MHz, DMSO-$d_6$) δ 12.28 (s, 1H), 8.44 (d, J = 5.0 Hz, 1H), 8.01 (d, J = 5.0 Hz, 1H), 7.61-7.54 (m, 2H), 7.24-7.17 (m, 2H), 4.37 (s, 3H), 2.80 (s, 6H). |

TABLE A1-continued
| | | | | |
|---|---|---|---|---|
| 1-2045 | 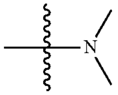 [SMILES: *N(C)C] | 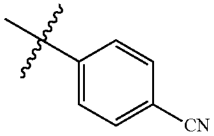 [SMILES: *c1ccc(C#N)cc1] | 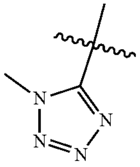 [SMILES: *c1nnnn1C] | $^1H$ NMR (500 MHz, DMSO-$d_6$) δ 12.26 (s, 1H), 8.88 (s, 1H), 8.54 (d, J = 5.0 Hz, 1H), 8.41 (d, J = 5.0 Hz, 1H), 8.25 (d, J = 5.0 Hz, 1H), 8.15 (d, J = 8.0 Hz, 1H), 7.46 (dd, J = 8.0, 5.0 Hz, 1H), 4.39 (s, 3H), 2.82 (s, 6H). |
| 1-2046 | 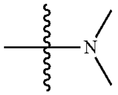 [SMILES: *N(C)C] | 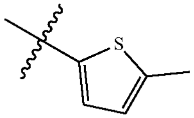 [SMILES: *c1ccc(C)s1] | 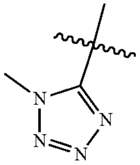 [SMILES: *c1nnnn1C] | $^1H$ NMR (500 MHz, DMSO-$d_6$) δ 12.91 (s, 1H), 8.68 (d, J = 5.0 Hz, 1H), 8.26 (d, J = 5.0 Hz, 1H), 7.48 (d, J = 7.5 Hz, 1H), 7.10 (d, J = 7.5 Hz, 1H), 4.35 (s, 3H), 2.93 (s, 6H), 2.38 (s, 3H). |
| 1-2047 | 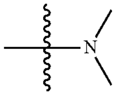 [SMILES: *N(C)C] | 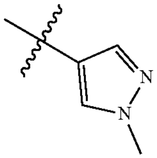 [SMILES: *c1cnn(C)c1] | 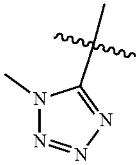 [SMILES: *c1nnnn1C] | $^1H$ NMR (500 MHz, DMSO-$d_6$) δ 12.26 (s, 1H), 8.68 (d, J = 5.0 Hz, 1H), 8.27 (d, J = 5.0 Hz, 1H), 7.70 (s, 1H), 6.82 (s, 1H), 4.33 (s, 3H), 3.92 (s, 3H), 2.95 (s, 6H). |
| 1-2048 | 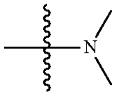 [SMILES: *N(C)C] | 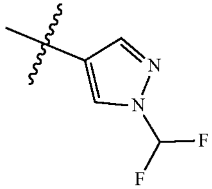 [SMILES: *c1cnn(C(F)F)c1] | 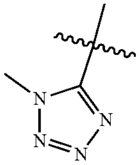 [SMILES: *c1nnnn1C] | $^1H$ NMR (500 MHz, DMSO-$d_6$) δ 12.33 (s, 1H), 8.68 (d, J = 5.0 Hz, 1H), 8.27 (d, J = 5.0 Hz, 1H), 7.97-7.72 (m, 2H), 6.97 (s, 1H), 4.33 (s, 3H), 2.94 (s, 6H). |
| 1-2049 | 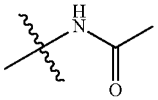 | 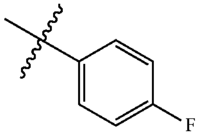 [SMILES: *c1ccc(F)cc1] | 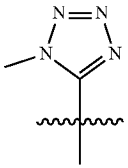 | |
| 1-2050 | 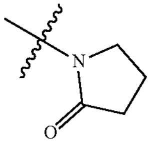 [SMILES: *N1CCCC1=O] | 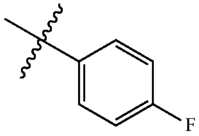 [SMILES: *c1ccc(F)cc1] | 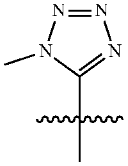 | |

TABLE A1-continued
| | | | | |
|---|---|---|---|---|
| 1-2051 | SMe | 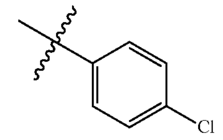 | 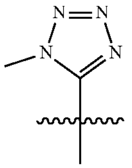 | $^1$H NMR (500 MHz, DMSO-$d_6$) δ 12.23 (s, 1H), 8.59 (d, J = 5.0 Hz, 1H), 7.84-7.78 (m, 2H), 7.51-7.42 (m, 3H), 4.37 (s, 3H), 2.48 (s, 3H). |
| 1-2052 | SMe | 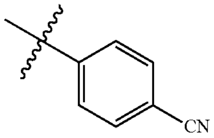 [SMILES: *c1ccc(C#N)cc1] | 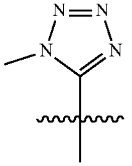 | $^1$H NMR (500 MHz, DMSO-$d_6$) δ 12.26 (s, 1H), 8.56 (d, J = 5.0 Hz, 1H), 8.11-8.04 (m, 2H), 7.77-7.71 (m, 2H), 7.66 (d, J = 5.0 Hz, 1H), 4.36 (s, 3H), 2.22 (s, 3H). |
| 1-2053 | SMe | 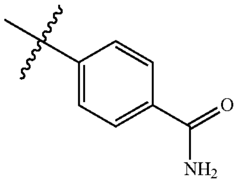 [SMILES: *c1ccc(C(N)=O)cc1] | 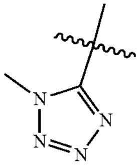 [SMILES: *c1nnnn1C] | $^1$H NMR (500 MHz, DMSO-$d_6$) δ 12.29 (s, 1H), 8.62 (d, J = 5.0 Hz, 1H), 7.89-7.83 (m, 2H), 7.72-7.66 (m, 2H), 7.52 (d, J = 5.0 Hz, 1H), 6.99 (s, 2H), 4.33 (s, 3H), 2.22 (s, 3H). |
| 1-2054 | SMe | 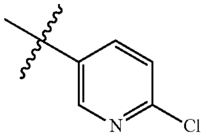 [SMILES: *c1ccc(Cl)nc1] | 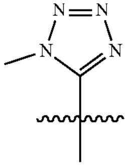 | $^1$H NMR (500 MHz, DMSO-$d_6$) δ 12.24 (s, 1H), 8.79 (s, 1H), 8.69 (d, J = 5.0 Hz, 1H), 7.93 (d, J = 8.0 Hz, 1H), 7.58 (d, J = 5.0 Hz, 1H), 7.45 (d, J = 8.0 Hz, 1H), 4.34 (s, 3H), 2.53 (s, 3H). |
| 1-2055 | SMe | 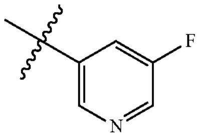 [SMILES: *c1cncc(F)c1] | 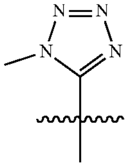 | $^1$H NMR (500 MHz, DMSO-$d_6$) δ 12.25 (s, 1H), 8.69 (d, J = 5.0 Hz, 1H), 8.62 (s, 1H), 8.31 (d, J = 8.0 Hz, 1H), 8.22 (d, J = 6.0 Hz, 1H), 7.59 (d, J = 5.0 Hz, 1H), 4.31 (s, 3H), 2.54 (s, 3H). |
| 1-2056 | SMe | 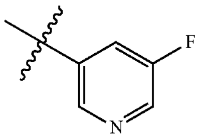 [SMILES: *c1cncc(F)c1] | 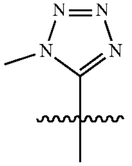 | |

TABLE A1-continued
| | | | | |
|---|---|---|---|---|
| 1-2057 | SMe | 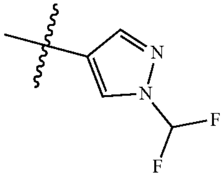 [SMILES: *c1cnn(C(F)F)c1] | 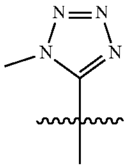 | $^1$H NMR (500 MHz, DMSO-$d_6$) δ 12.23 (s, 1H), 8.82 (d, J = 5.0 Hz, 1H), 7.83 (t, J = 57.0 Hz, 1H), 7.70 (s, 1H), 7.58 (d, J = 5.0 Hz, 1H), 6.96 (s, 1H), 4.34 (s, 3H), 2.59 (s, 3H). |
| 1-2058 | 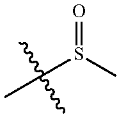 [SMILES: *S(C)=O] | $CH_3$ | 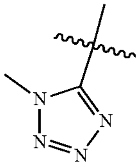 [SMILES: *c1nnnn1C] | $^1$H NMR (500 MHz, DMSO-$d_6$) δ 12.23 (s, 1H), 8.87 (d, J = 5.0 Hz, 1H), 7.57 (d, J = 5.0 Hz, 1H), 4.37 (s, 3H), 2.72 (s, 3H), 2.61 (s, 3H). |
| 1-2059 | 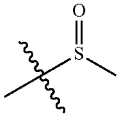 [SMILES: *S(C)=O] | 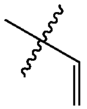 [SMILES: *C=C] | 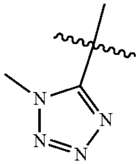 [SMILES: *c1nnnn1C] | $^1$H NMR (500 MHz, DMSO-$d_6$) δ 12.26 (s, 1H), 8.99 (d, J = 5.0 Hz, 1H), 7.88 (d, J = 5.0 Hz, 1H), 6.99 (dd, J = 17.0, 10.0 Hz, 1H), 6.10 (dd, J = 14.0, 10.0 Hz, 1H), 5.72 (dd, J = 17.0, 14.0 Hz, 1H), 4.31 (s, 3H), 2.66 (s, 3H). |
| 1-2060 | 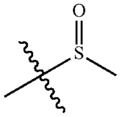 [SMILES: *S(C)=O] | 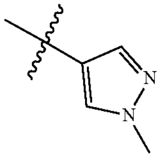 [SMILES: *c1cnn(C)c1] | 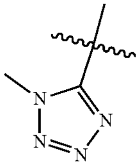 [SMILES: *c1nnnn1C] | $^1$H NMR (500 MHz, DMSO-$d_6$) δ 12.28 (s, 1H), 9.09 (d, J = 5.0 Hz, 1H), 7.94 (s, 1H), 7.82 (d, J = 5.0 Hz, 1H), 6.92 (s, 1H), 4.36 (s, 3H), 3.92 (s, 3H), 2.71 (s, 3H). |
| 1-2061 | Cl | OMe | 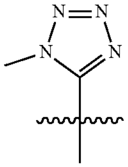 [SMILES: *c1nnnn1C] | $^1$H NMR (500 MHz, DMSO-$d_6$) δ 12.25 (s, 1H), 8.65 (d, J = 5.0 Hz, 1H), 7.70 (d, J = 5.0 Hz, 1H), 4.33 (s, 3H), 3.60 (s, 3H). |
| 1-2062 | Cl | 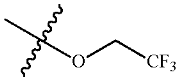 [SMILES: *OCC(F)(F)F] | 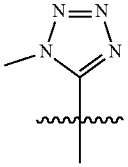 [SMILES: *c1nnnn1C] | $^1$H NMR (500 MHz, DMSO-$d_6$) δ 12.24 (s, 1H), 8.06 (d, J = 5.0 Hz, 1H), 7.22 (d, J = 5.0 Hz, 1H), 4.39 (s, 2H), 4.30 (s, 3H). |

TABLE A1-continued
| | | | | |
|---|---|---|---|---|
| 1-2063 | Cl | 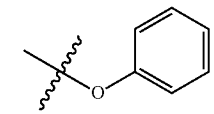 [SMILES: *Oc1ccccc1] | 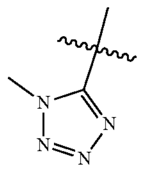 [SMILES: *c1nnnn1C] | $^1$H NMR (500 MHz, DMSO-$d_6$) δ 12.22 (s, 1H), 8.17 (d, J = 5.0 Hz, 1H), 7.47-7.39 (m, 2H), 7.32 (d, J = 5.0 Hz, 1H), 7.18-7.11 (m, 2H), 7.00-6.96 (m, 1H), 4.35 (s, 3H). |
| 1-2064 | Cl | 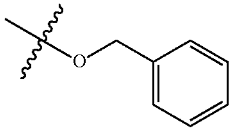 [SMILES: *OCc1ccccc1] | 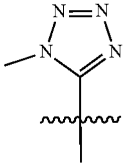 | $^1$H NMR (500 MHz, DMSO-$d_6$) δ 12.22 (s, 1H), 8.08 (d, J = 5.0 Hz, 1H), 7.43-7.27 (m, 5H), 7.22 (d, J = 5.0 Hz, 1H), 5.33 (s, 2H), 4.40 (s, 3H). |
| 1-2065 | Cl | SMe | 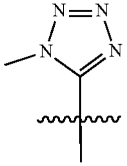 | $^1$H NMR (500 MHz, DMSO-$d_6$) δ 12.20 (s, 1H), 8.65 (d, J = 5.0 Hz, 1H), 7.70 (d, J = 5.0 Hz, 1H), 4.33 (s, 3H), 2.60 (s, 3H). |
| 1-2066 | Cl | 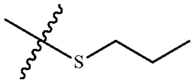 [SMILES: *SCCC] | 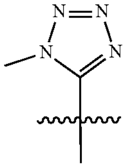 [SMILES: *c1nnnn1C] | $^1$H NMR (500 MHz, DMSO-$d_6$) δ 12.24 (s, 1H), 8.36 (d, J = 5.0 Hz, 1H), 7.58 (d, J = 5.0 Hz, 1H), 4.31 (s, 3H), 2.10 (t, J = 5.0 Hz, 2H), 1.68-1.64 (m, 2H), 1.02 (t, J = 8.0 Hz, 3H). |
| 1-2067 | Cl | 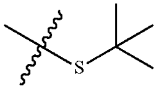 | 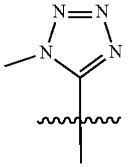 | $^1$H NMR (500 MHz, DMSO-$d_6$) δ 12.21 (s, 1H), 8.47 (d, J = 5.0 Hz, 1H), 7.69 (d, J = 5.0 Hz, 1H), 4.32 (s, 3H), 1.35 (s, 9H). |
| 1-2068 | Cl | 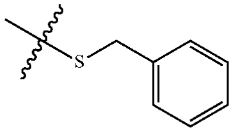 [SMILES: *SCc1ccccc1] | 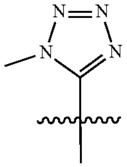 | $^1$H NMR (500 MHz, DMSO-$d_6$) δ 12.23 (s, 1H), 8.39 (d, J = 5.0 Hz, 1H), 7.58 (d, J = 5.0 Hz, 1H), 7.36-7.30 (m, 3H), 7.28-7.21 (m, 2H), 4.55 (s, 2H), 4.33 (s, 3H). |

TABLE A1-continued
| | | | | |
|---|---|---|---|---|
| 1-2069 | Cl | 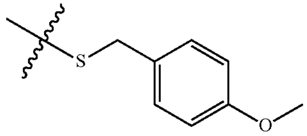 [SMILES: *SCc1ccc(OC)cc1] | 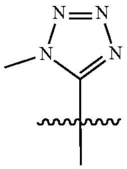 [SMILES: *c1nnnn1C] | $^1$H NMR (500 MHz, DMSO-$d_6$) δ 12.23 (s, 1H), 8.48 (d, J = 5.0 Hz, 1H), 7.66 (d, J = 5.0 Hz, 1H), 7.17 (d, J = 7.0 Hz, 2H), 7.12-7.06 (m, 2H), 4.53 (s, 2H), 4.39 (s, 3H), 3.51 (s, 3H). |
| 1-2070 | Cl | 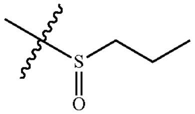 | 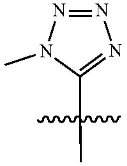 | $^1$H NMR (500 MHz, DMSO-$d_6$) δ 12.28 (s, 1H), 8.84 (d, J = 5.0 Hz, 1H), 8.00 (d, J = 5.0 Hz, 1H), 4.30 (s, 3H), 2.83 (t, J = 5.0 Hz, 1H), 2.55 (t, J = 5.0 Hz, 1H), 1.47-1.42 (m, 2H), 0.93 (t, J = 8.0 Hz, 3H). |
| 1-2071 | Cl | 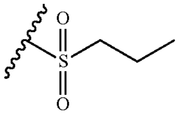 [SMILES: *S(=O)(=O)CCC] | 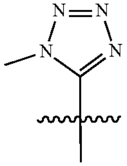 | $^1$H NMR (500 MHz, DMSO-$d_6$) δ 12.29 (s, 1H), 8.96 (d, J = 5.0 Hz, 1H), 8.16 (d, J = 5.0 Hz, 1H), 4.33 (s, 3H), 3.13 (t, J = 8.0 Hz, 2H), 1.56-1.48 (m, 2H), 0.90 (t, J = 8.0 Hz, 3H). |
| 1-2072 | Cl | $NH_2$ | 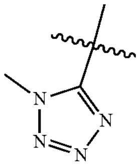 [SMILES: *c1nnnn1C] | $^1$H NMR (500 MHz, DMSO-$d_6$) δ 12.31 (s, 1H), 8.39 (d, J = 5.0 Hz, 1H), 7.45 (d, J = 5.0 Hz, 1H), 6.30 (s, 2H), 4.33 (s, 3H). |
| 1-2073 | Cl | 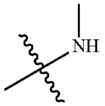 | 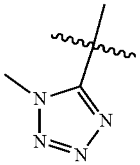 [SMILES: *c1nnnn1C] | $^1$H NMR (500 MHz, DMSO-$d_6$) δ 12.27 (s, 1H), 9.25 (s, 1H), 8.42 (d, J = 5.0 Hz, 1H), 7.44 (d, J = 5.0 Hz, 1H), 4.37 (s, 3H), 3.04 (s, 3H). |
| 1-2074 | Cl | 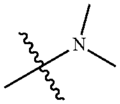 [SMILES: *N(C)C] | 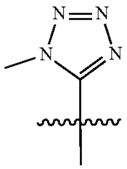 | $^1$H NMR (500 MHz, DMSO-$d_6$) δ 12.27 (s, 1H), 8.34 (d, J = 5.0 Hz, 1H), 7.40 (d, J = 5.0 Hz, 1H), 4.33 (s, 3H), 3.19 (s, 6H). |

TABLE A1-continued

| | | | | |
|---|---|---|---|---|
| 1-2075 | Cl | 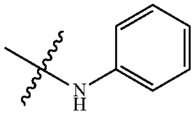 [SMILES: *Nc1ccccc1] | 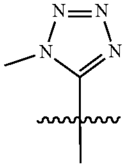 [SMILES: *c1nnnn1C] | $^1$H NMR (500 MHz, DMSO-$d_6$) δ 12.31 (s, 1H), 10.22 (s, 1H), 8.41 (d, J = 5.0 Hz, 1H), 7.78-7.72 (m, 2H), 7.42 (d, J = 5.0 Hz, 1H), 7.33-7.28 (m, 2H), 7.02-6.99 (m, 1H), 4.33 (s, 3H). |
| 1-2076 | Cl | 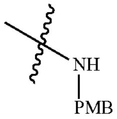 | 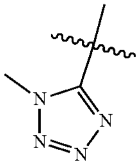 [SMILES: *c1nnnn1C] | $^1$H NMR (500 MHz, DMSO-$d_6$) δ 12.23 (s, 1H), 8.99 (s, 1H), 8.37 (d, J = 5.0 Hz, 1H), 7.35 (d, J = 5.0 Hz, 1H), 7.21-7.15 (m, 2H), 6.92-6.86 (m, 2H), 4.62 (s, 2H), 4.30 (s, 3H), 3.79 (s, 3H). |
| 1-2077 | F | OMe | 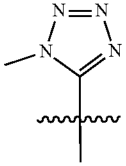 | $^1$H NMR (500 MHz, DMSO-$d_6$) δ 12.28 (s, 1H), 8.45 (d, J = 5.0 Hz, 1H), 7.83 (d, J = 5.0 Hz, 1H), 4.30 (s, 3H), 3.55 (s, 3H). |
| 1-2078 | F | 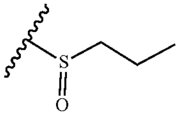 [SMILES: *S(=O)CCC] | 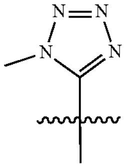 [SMILES: *c1nnnn1C] | $^1$H NMR (500 MHz, DMSO-$d_6$) δ 12.28 (s, 1H), 8.66 (d, J = 5.0 Hz, 1H), 8.15 (dd, J = 8.0, 5.0 Hz, 1H), 4.33 (s, 3H), 2.81 (t, J = 5.0 Hz, 1H), 2.54 (t, J = 5.0 Hz, 1H), 1.47-1.41 (m, 2H), 0.92 (t, J = 8.0 Hz, 3H). |
| 1-2079 | OMe | OMe | 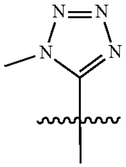 | $^1$H NMR (500 MHz, DMSO-$d_6$) δ 12.25 (s, 1H), 8.59 (d, J = 5.0 Hz, 1H), 7.38 (d, J = 5.0 Hz, 1H), 4.32 (s, 3H), 3.62 (s, 3H), 3.45 (s, 3H). |
| 1-2080 | OMe | 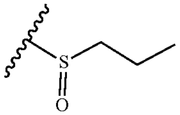 [SMILES: *S(=O)CCC] | 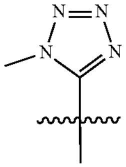 | $^1$H NMR (500 MHz, DMSO-$d_6$) δ 12.29 (s, 1H), 8.77 (d, J = 5.0 Hz, 1H), 7.73 (d, J = 5.0 Hz, 1H), 4.33 (s, 3H), 3.39 (s, 3H), 2.81 (t, J = 5.0 Hz, 1H), 2.54 (t, J = 5.0 Hz, 1H), 1.47-1.41 (m, 2H), 0.93 (t, J = 8.0 Hz, 3H). |

TABLE A1-continued
| | | | | |
|---|---|---|---|---|
| 1-2081 | OMe | $NH_2$ | 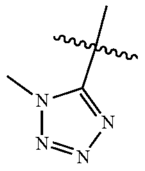 [SMILES: *c1nnnn1C] | $^1H$ NMR (500 MHz, DMSO-$d_6$) δ 12.27 (s, 1H), 8.23 (d, J = 5.0 Hz, 1H), 7.61 (d, J = 5.0 Hz, 1H), 4.33 (s, 3H), 4.21 (s, 2H), 3.81 (s, 3H). |
| 1-2082 | SMe | OMe | 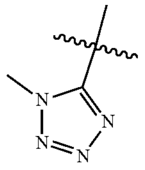 [SMILES: *c1nnnn1C] | $^1H$ NMR (500 MHz, DMSO-$d_6$) δ 12.24 (s, 1H), 8.02 (d, J = 5.0 Hz, 1H), 7.28 (d, J = 5.0 Hz, 1H), 4.33 (s, 3H), 3.92 (s, 3H), 2.31 (s, 3H). |
| 1-2083 | SMe | SMe | 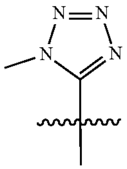 | $^1H$ NMR (500 MHz, DMSO-$d_6$) δ 12.25 (s, 1H), 8.59 (d, J = 5.0 Hz, 1H), 7.38 (d, J = 5.0 Hz, 1H), 4.31 (s, 3H), 2.62 (s, 3H), 2.20 (s, 3H). |
| 1-2084 | SMe | 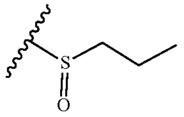 [SMILES: *S(=O)CCC] | 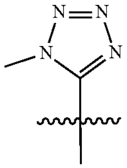 | $^1H$ NMR (500 MHz, DMSO-$d_6$) δ 12.33 (s, 1H), 8.77 (d, J = 5.0 Hz, 1H), 7.73 (d, J = 5.0 Hz, 1H), 4.33 (s, 3H), 2.85 (t, J = 5.0 Hz, 1H), 2.55 (t, J = 5.0 Hz, 1H), 2.39 (s, 3H), 1.46-1.40 (m, 2H), 0.92 (t, J = 8.0 Hz, 3H). |
| 1-2085 | 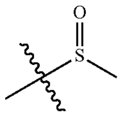 | OMe | 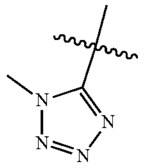 [SMILES: *c1nnnn1C] | $^1H$ NMR (500 MHz, DMSO-$d_6$) δ 12.29 (s, 1H), 8.28 (d, J = 5.0 Hz, 1H), 7.14 (d, J = 5.0 Hz, 1H), 4.35 (s, 3H), 3.92 (s, 3H), 2.86 (s, 3H). |
| 1-2086 | 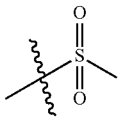 [SMILES: *S(C)(=O)=O] | OMe | 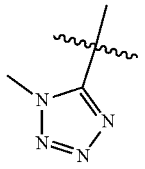 [SMILES: *c1nnnn1C] | $^1H$ NMR (500 MHz, DMSO-$d_6$) δ 12.23 (s, 1H), 8.45 (d, J = 5.0 Hz, 1H), 7.34 (d, J = 5.0 Hz, 1H), 4.33 (s, 3H), 3.95 (s, 3H), 3.24 (s, 3H). |

TABLE A1-continued
| | | | | |
|---|---|---|---|---|
| 1-2087 | $NH_2$ | 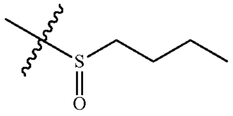 [SMILES: *S(=O)CCCC] | 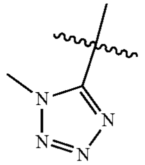 [SMILES: *c1nnnn1C] | $^1$H NMR (500 MHz, DMSO-$d_6$) δ 12.20 (s, 1H), 8.45 (d, J = 5.0 Hz, 1H), 7.80 (d, J = 5.0 Hz, 1H), 5.83 (s, 2H), 4.33 (s, 3H), 2.76 (t, J = 8.0 Hz, 1H), 2.53 (t, J = 8.0 Hz, 1H), 1.47-1.42 (m, 2H), 0.88 (t, J = 8.0 Hz, 3H). |
| 1-2088 | 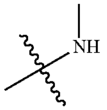 | 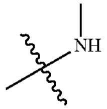 | 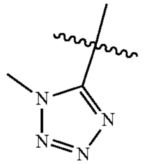 [SMILES: *c1nnnn1C] | $^1$H NMR (500 MHz, DMSO-$d_6$) δ 12.21 (s, 1H), 7.98 (d, J = 5.0 Hz, 1H), 7.58 (d, J = 5.0 Hz, 1H), 6.58 (s, 1H), 5.95 (s, 1H), 4.30 (s, 3H), 2.73 (s, 3H), 2.68 (s, 3H). |
| 1-2089 | 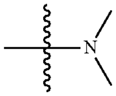 [SMILES: *N(C)C] | OMe | 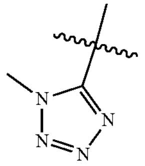 [SMILES: *c1nnnn1C] | $^1$H NMR (500 MHz, DMSO-$d_6$) δ 12.35 (s, 1H), 7.87 (d, J = 5.0 Hz, 1H), 7.57 (d, J = 5.0 Hz, 1H), 4.30 (s, 3H), 3.83 (s, 3H), 2.91 (s, 6H). |
| 1-2090 | 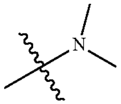 [SMILES: *N(C)C] | 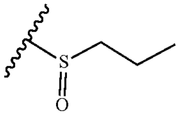 [SMILES: *S(=O)CCC] | 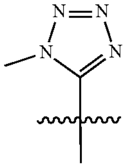 [SMILES: *c1nnnn1C] | $^1$H NMR (500 MHz, DMSO-$d_6$) δ 12.26 (s, 1H), 8.58 (d, J = 5.0 Hz, 1H), 8.28 (d, J = 5.0 Hz, 1H), 4.33 (s, 3H), 2.93 (s, 6H), 2.82 (t, J = 5.0 Hz, 1H), 2.54 (t, J = 5.0 Hz, 1H), 1.47-1.41 (m, 2H), 0.92 (t, J = 7.9 Hz, 3H). |
| 1-2091 | 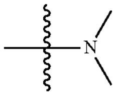 | 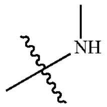 | 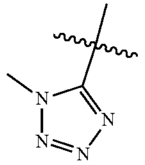 [SMILES: *c1nnnn1C] | $^1$H NMR (500 MHz, DMSO-$d_6$) δ 12.33 (s, 1H), 8.09 (d, J = 5.0 Hz, 1H), 7.19 (d, J = 5.0 Hz, 1H), 6.50 (s, 1H), 4.36 (s, 3H), 2.81 (s, 6H), 2.73 (s, 3H). |
| 1-2092 | 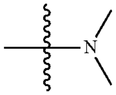 [SMILES: *N(C)C] | 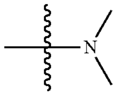 [SMILES: *N(C)C] | 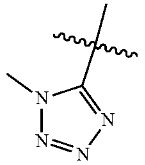 [SMILES: *c1nnnn1C] | $^1$H NMR (500 MHz, DMSO-$d_6$) δ 12.28 (s, 1H), 8.19 (d, J = 5.0 Hz, 1H), 7.80 (d, J = 5.0 Hz, 1H), 4.36 (s, 3H), 3.18 (s, 6H), 2.93 (s, 6H). |

TABLE A1-continued
| | | | | |
|---|---|---|---|---|
| 1-2093 | 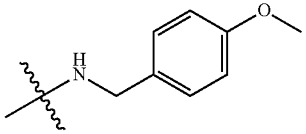 [SMILES: *NCc1ccc(OC)cc1] | 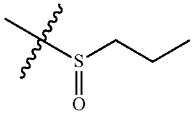 [SMILES: *S(=O)CCC] | 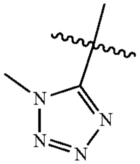 [SMILES: *c1nnnn1C] | $^1$H NMR (500 MHz, DMSO-$d_6$) δ 12.31 (s, 1H), 8.62 (d, J = 5.0 Hz, 1H), 7.87 (d, J = 5.0 Hz, 1H), 7.38-7.32 (m, 2H), 6.92-6.86 (m, 2H), 6.22 (s, 1H), 4.34-4.31 (m, 5H), 3.79 (s, 3H), 2.75 (t, J = 5.0 Hz, 1H), 2.55 (t, J = 5.0 Hz, 1H), 1.50-1.44 (m, 2H), 0.95 (t, J = 8.0 Hz, 3H). |
| 1-2094 | 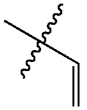 [SMILES: *C=C] | OMe | 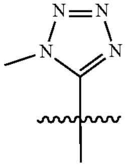 | $^1$H NMR (500 MHz, DMSO-$d_6$) δ 12.25 (s, 1H), 8.63 (d, J = 5.0 Hz, 1H), 7.55 (d, J = 5.0 Hz, 1H), 6.69-6.64 (m, 1H), 5.74-5.70 (m, 1H), 5.46-5.42 (m, 1H), 4.33 (s, 3H), 3.63 (s, 3H). |
| 1-2095 | 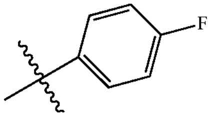 [SMILES: *c1ccc(F)cc1] | OMe | 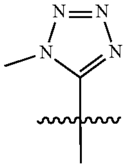 | $^1$H NMR (500 MHz, DMSO-$d_6$) δ 12.31 (s, 1H), 8.64 (d, J = 5.0 Hz, 1H), 7.56 (d, J = 5.0 Hz, 1H), 7.23-7.13 (m, 4H), 4.33 (s, 3H), 3.80 (s, 3H). |
| 1-2096 | 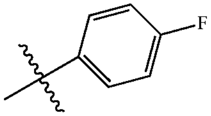 [SMILES: *c1ccc(F)cc1] | 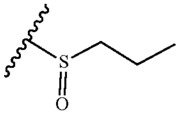 [SMILES: *S(=O)CCC] | 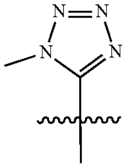 [SMILES: *c1nnnn1C] | |
| 1-2097 | 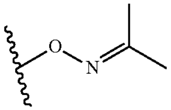 [SMILES: *ON=C(C)C] | 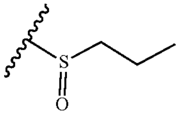 [SMILES: *S(=O)CCC] | 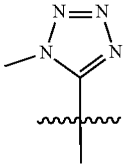 | $^1$H NMR (500 MHz, DMSO-$d_6$) δ 12.22 (s, 1H), 8.60 (d, J = 5.0 Hz, 1H), 8.23 (d, J = 5.0 Hz, 1H), 4.33 (s, 3H), 2.85 (t, J = 8.0 Hz, 1H), 2.65 (t, J = 8.0 Hz, 1H), 2.48 (s, 3H), 2.40 (s, 3H) 1.47-1.41 (m, 2H), 0.91 (t, J = 8.0 Hz, 3H). |

The method for preparing the compound of the invention will be explained in detail in the following program and embodiment. The material is commercial available or prepared through known method reported in the literature or shown in the route. Those skilled in the art should understand that the compound of the invention can also be synthesized by other synthetic route. Although the detailed material and reaction condition in the synthetic route have been explicated in the following text, it is still easy to be replaced by other similar material and condition. Isomer of the compound, for example, that produced with the variation of the preparation method of the present invention is included in the scope of the present invention. In addition, the following preparation method can be further modified according to the disclosures of the present invention by using common chemical method known to those skilled in the art, for example, protection of suitable group in the process of the reaction, etc.

The following method of application can be used to improve further understanding of the preparation method of the present invention. The specific material, class and condition have been determined to be further explication of the present invention, not to be any limit of the reasonable scope thereof. Reagents of the following synthetic compound showed in the table can either be purchased from the market or easily prepared by those skilled in the art.

Examples of representative compounds are as follows, the synthetic methods of other compounds are similar, and will not be described in detail here.

1. Synthesis of Compound 1-1

(1) To a 50 mL single-necked eggplant-shaped flask, 1.0 equivalent of compound a, 3.0 equivalents of sodium hydroxide, and 1.2 equivalents of 1-1-1 were charged sequentially at room temperature. After dissolved with 10:1 dioxane-water (10V), nitrogen replacement was performed three times under stirring, the catalyst 1,1'-bis(diphenylphosphino)ferrocene dichloride palladium(II) dichloromethane complex (1%) was added, nitrogen replacement was performed three times, then heated to 120° C., and reacted at this temperature for 16-24 hours. The reaction solution was sampled and when the remaining raw materials were less than 5% according to LC-MS detection, the reaction was terminated. After the reaction was completed, 10V water was added, the insolubles were removed by filtration, and the mother liquor was adjusted to pH 1-2 with 2M hydrochloric acid solution, then extracted three times with ethyl acetate (5V). The organic phases were combined and distilled under reduced pressure to remove ethyl acetate. The product 1-1-2 was obtained by reverse-phase purification with yield of 78%.

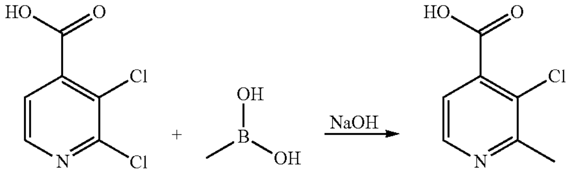

a 1-1-1 1-1-2

(2) To a 50 mL single-necked eggplant-shaped flask, 1.0 equivalent of compound 1-1-2 was charged at room temperature. After dissolved with dichloromethane (10V), 1.1 equivalent of N,N'-carbonyldiimidazole (CDI) was added, and reacted at 30-40° C. for 1 hour under stirring. After stirring, 1.2 equivalent of b and 1.0 equivalent of 1,8-diazabicycloundec-7-ene (DBU) were added, and continued to react at 30-40° C. for 16-24 hours under stirring. The reaction solution was sampled and when the remaining raw materials were less than 5% according to LC-MS detection, the reaction was terminated. After the reaction was completed, 10V water was added to the reaction system, stirred, extracted, and the organic phase was poured into the waste liquid. The water phase was adjusted to pH 5-6 with 2M hydrochloric acid solution, and a large amount of solid was precipitated out at this time. After stirring for 15-30 minutes, the solid was filtered to obtain the product, and the product was dried to remove water with yield of about 72%.

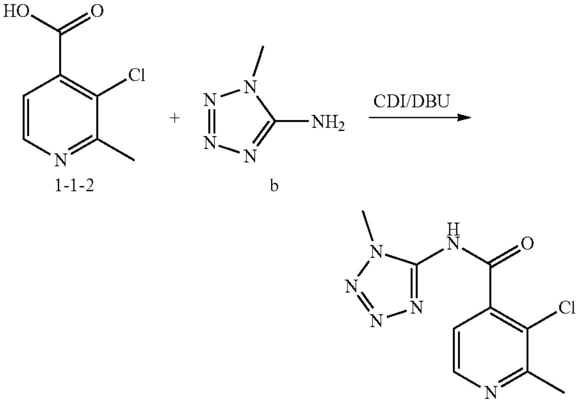

1-1

2. Synthesis of Compound 1-17

It can be prepared by referring to the above method for preparing compound 1-1; or it can be prepared by the following method:

(1) To a 50 mL single-necked eggplant-shaped flask, 1.0 equivalent of compound a was charged at room temperature. After dissolved with dichloromethane (10V), 1.1 equivalent of N,N'-carbonyldiimidazole (CDI) was added, and reacted at 30-40° C. for 1 hour under stirring. After stirring, 1.2 equivalent of b and 1.0 equivalent of 1,8-diazabicycloundec-7-ene (DBU) were added, and continued to react at 30-40° C. for 16-24 hours under stirring. The reaction solution was sampled and when the remaining raw materials were less than 5% according to LC-MS detection, the reaction was terminated. After the reaction was completed, 10V water was added to the reaction system, stirred, extracted, and the organic phase was poured into the waste liquid. The water phase was adjusted to pH 5-6 with 2M hydrochloric acid solution, and a large amount of solid was precipitated out at this time. After stirring for 15-30 minutes, the solid was filtered to obtain the product, and the product was dried to remove water with yield of about 75%,

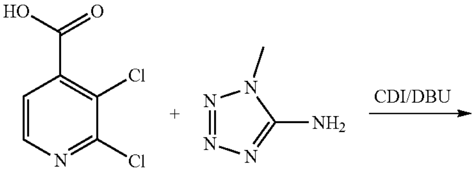

a b

-continued

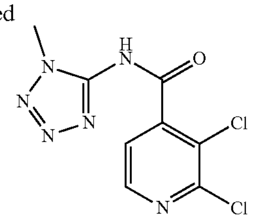

1-17-1

(2) To a 50 mL single-necked eggplant-shaped flask, 1.0 equivalent of compound 1-17-1, 3.0 equivalents of potassium carbonate, and 1.2 equivalents of c were charged sequentially at room temperature. After dissolved with 10:1 dioxane-water (10V), nitrogen replacement was performed three times under stirring, the catalyst 1,1'-bis(diphenylphosphino)ferrocene dichloride palladium(II) dichloromethane complex (1%) was added, nitrogen replacement was performed three times, then heated to 110° C., and reacted at this temperature for 16-24 hours. The reaction solution was sampled and when the remaining raw materials were less than 5% according to LC-MS detection, the reaction was terminated. After the reaction was completed, 10V water was added, the insolubles were removed by filtration, and the mother liquor was adjusted to pH 5-6 with 2M hydrochloric acid solution, then extracted three times with ethyl acetate (5V). The organic phases were combined and distilled under reduced pressure to remove ethyl acetate. The product was obtained by reverse-phase purification with yield of 50%.

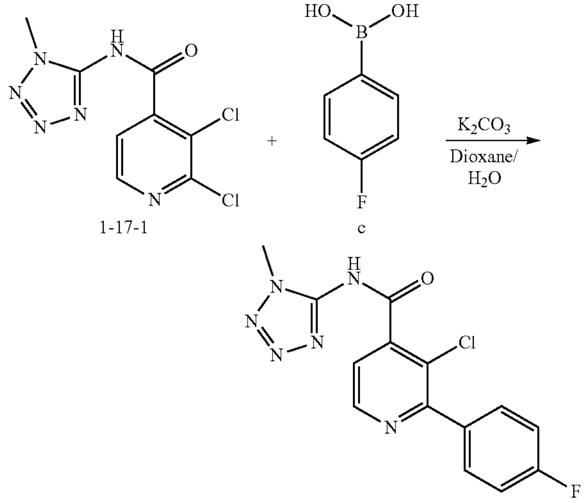

1-17-1 c 1-17

3. Synthesis of Compounds 1-203 and 1-205

(1) To a 50 mL single-necked eggplant-shaped flask, 1.0 equivalent of compound 1-203-1 (It can be prepared by referring to the above method for preparing compound 1-17) was charged at room temperature. After dissolved with N,N-dimethylformamide (10V), 1.0 equivalent of sodium thiomethoxide aqueous solution (20% content) was added, and reacted at 50-60° C. for 6-8 hours under stirring. The reaction solution was sampled and when the remaining raw materials were less than 2% according to LC-MS detection, the reaction was terminated. After the reaction was completed, 10V water was added, and adjusted to pH 5-6 with 2M hydrochloric acid solution, and the solid was precipitated out at this time, the insolubles were removed by filtration. The mother liquor was distilled under reduced pressure to remove the solvent, and the compound 1-203 was obtained by reverse-phase purification with yield of about 62%.

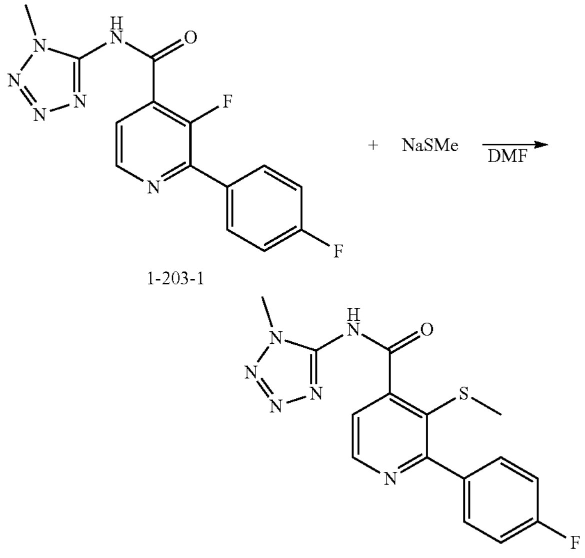

1-203-1 1-203

(2) To a 50 mL single-necked eggplant-shaped flask, 1.0 equivalent of compound 1-203 was charged at room temperature. After dissolved with dichloromethane (10V), 1.0 equivalent of 1-205-1 (85% content) was added, and reacted at 10-20° C. for 15-30 minutes under stirring. The reaction solution was sampled and when the remaining raw materials were less than 1% according to LC-MS detection, the reaction was terminated. After the reaction was completed, sodium thiosulfate aqueous solution was added to quench the reaction, the insolubles were removed by filtration, distilled under reduced pressure to remove the solvent, and the compound 1-205 was obtained by reverse-phase purification with yield of about 50%.

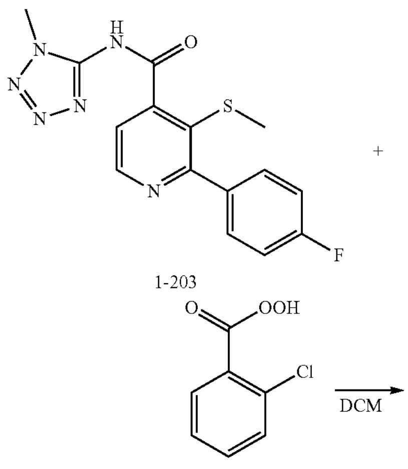

1-203 1-205-1

-continued

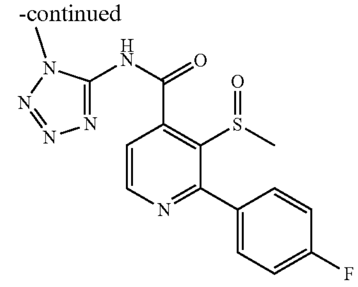

1-205

Or

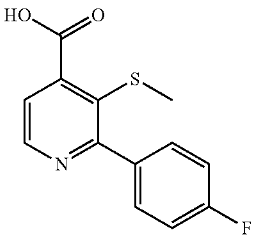 [SMILES: CSc1c(C(=O)O)ccnc1-c1ccc(F)cc1]

can be prepared from

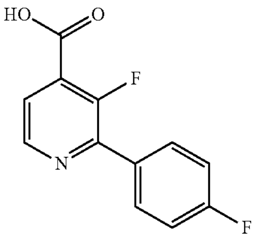 [SMILES: O=C(O)c1ccnc(-c2ccc(F)cc2)c1F]

by referring to the above preparation method, then

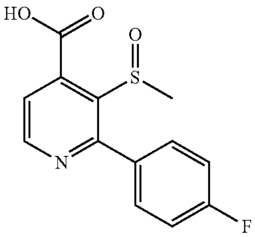 [SMILES: CS(=O)c1c(C(=O)O)ccnc1-c1ccc(F)cc1]

can be prepared, and reacts with

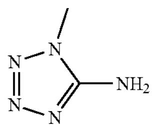

b respectively to obtain compound 1-203 and compound 1-205 by referring to the synthesis step (2) of the above compound 1-1.

4. Synthesis of Compound 1-223

(1) To a 50 mL single-necked eggplant-shaped flask, 1.0 equivalent of compound a, 3.0 equivalents of sodium hydroxide, and 2.5 equivalents of c were charged sequentially at room temperature. After dissolved with 10:1 dioxane-water (10V), nitrogen replacement was performed three times under stirring, the catalyst 1,1'-bis(diphenylphosphino)ferrocene dichloride palladium(II) dichloromethane complex (1%) was added, nitrogen replacement was performed three times, then heated to 120° C., and reacted at this temperature for 16-24 hours. The reaction solution was sampled and when the remaining raw materials were less than 5% according to LC-MS detection, the reaction was terminated. After the reaction was completed, 10V water was added, the insolubles were removed by filtration, and the mother liquor was adjusted to pH 1-2 with 2M hydrochloric acid solution, then extracted three times with ethyl acetate (5V). The organic phases were combined and distilled under reduced pressure to remove ethyl acetate. The product 1-223-1 was obtained by reverse-phase purification with yield of 45%.

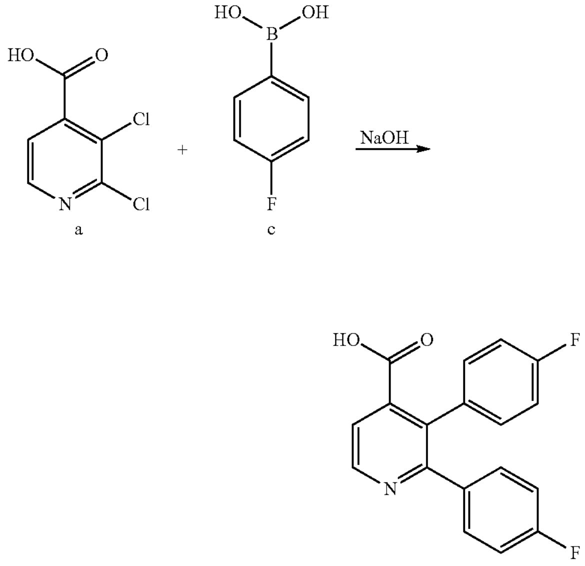

1-223-1

(2) To a 50 mL single-necked eggplant-shaped flask, 1.0 equivalent of compound 1-223-1 was charged at 10-20° C. After dissolved with pyridine (10V), 10% 4-dimethylaminopyridine (DMAP) and 1.2 equivalents of compound b were charged sequentially, and 3.0 equivalents of thionyl chloride was added in a dropwise manner at 10-20° C. under stirring, then heated to 30-40° C., and reacted for 2 hours under stirring. The reaction solution was sampled and when the remaining raw materials were less than 5% according to LC-MS detection, the reaction was terminated. After the reaction was completed, the pyridine was removed by distillation under reduced pressure, dissolved with 10V water, adjusted to pH 2-3 with 1M hydrochloric acid, then extracted three times with dichloromethane (5V). The organic phases were combined and distilled under reduced pressure to remove the solvent. The product 1-223 was obtained by reverse-phase purification with yield of about 52%.

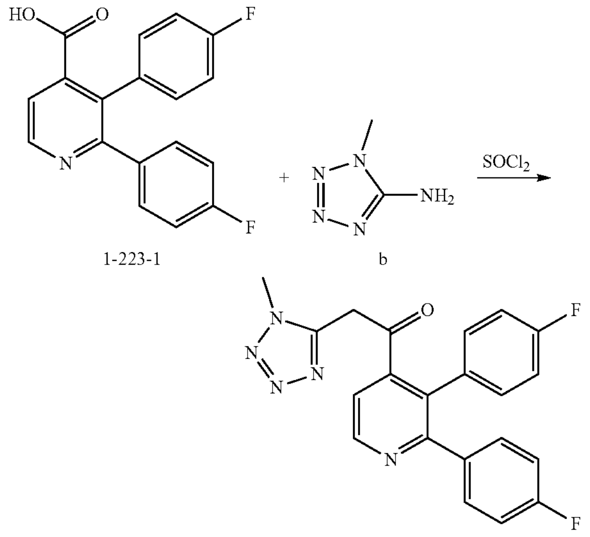

1-223-1 b 1-223

5. Synthesis of Compound 1-249

It can be prepared by referring to the above method for preparing compound 1-1; or it can be prepared by the following method:

To a 50 mL single-necked eggplant-shaped flask, 1.0 equivalent of compound 1-17-1, 3.0 equivalents of potassium carbonate, and 1.2 equivalents of 1-249-1 were charged sequentially at room temperature. After dissolved with 10:1 dioxane-water (10V), nitrogen replacement was performed three times under stirring, the catalyst 1,1'-bis (diphenylphosphino)ferrocene dichloride palladium(II) dichloromethane complex (1%) was added, nitrogen replacement was performed three times, then heated to 110° C., and reacted at this temperature for 16-24 hours. The reaction solution was sampled and when the remaining raw materials were less than 5% according to LC-MS detection, the reaction was terminated. After the reaction was completed, 10V water was added, the insolubles were removed by filtration, and the mother liquor was adjusted to pH 5-6 with 2M hydrochloric acid solution, then extracted three times with ethyl acetate (5V). The organic phases were combined and distilled under reduced pressure to remove ethyl acetate. The product was obtained by reverse-phase purification with yield of 50%.

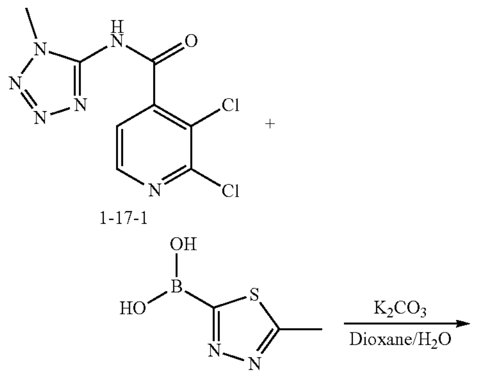

1-17-1 1-249-1

-continued

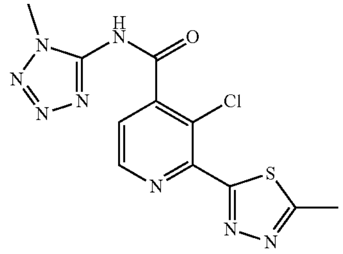

1-249

6. Synthesis of Compound 1-962

(1) To a 50 mL single-necked eggplant-shaped flask, 1.0 equivalent of compound a, 3.0 equivalents of potassium carbonate, and 1.1 equivalents of c were charged sequentially at room temperature. After dissolved with 10:1 dioxane-water (10V), nitrogen replacement was performed three times under stirring, the catalyst 1,1'-bis(diphenylphosphino)ferrocene dichloride palladium(II) dichloromethane complex (1%) was added, nitrogen replacement was performed three times, then heated to 120° C., and reacted at this temperature for 16-24 hours. The reaction solution was sampled and when the remaining raw materials were less than 1% according to LC-MS detection, the reaction was terminated. After the reaction was completed, 10V water was added, the insolubles were removed by filtration, extracted two times with ethyl acetate (5V), and the water phases were adjusted to pH 2-3 with 2M hydrochloric acid solution, then the solid was precipitated out, filtered and dried to obtain the product 1-962-1 with yield of 82%.

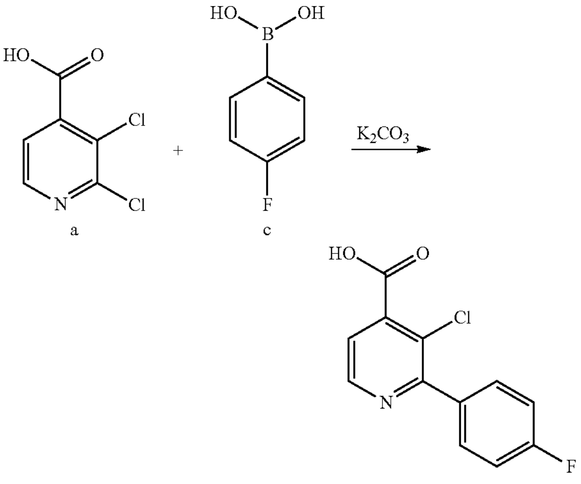

a c 1-962-1

(2) To a 50 mL single-necked eggplant-shaped flask, 1.0 equivalent of compound 1-962-1 was charged at room temperature. After dissolved with dichloromethane (10V), 1.1 equivalent of N,N'-carbonyldiimidazole (CDI) was added, and reacted at 30-40° C. for 1 hour under stirring. After stirring, 1.2 equivalent of d and 1.0 equivalent of 1,8-diazabicycloundec-7-ene (DBU) were added, and continued to react at 30-40° C. for 5-8 hours under stirring. The reaction solution was sampled and when the remaining raw materials were less than 5% according to LC-MS detection, the reaction was terminated. After the reaction was completed, 10V water was added to the reaction system, stirred, extracted, and the organic phase was poured into the waste liquid. The water phase was adjusted to pH 5-6 with 2M hydrochloric acid solution, and a large amount of solid was precipitated out at this time. After stirring for 15-30 minutes, the solid was filtered to obtain the product, and the product was dried to remove water with yield of about 69%.

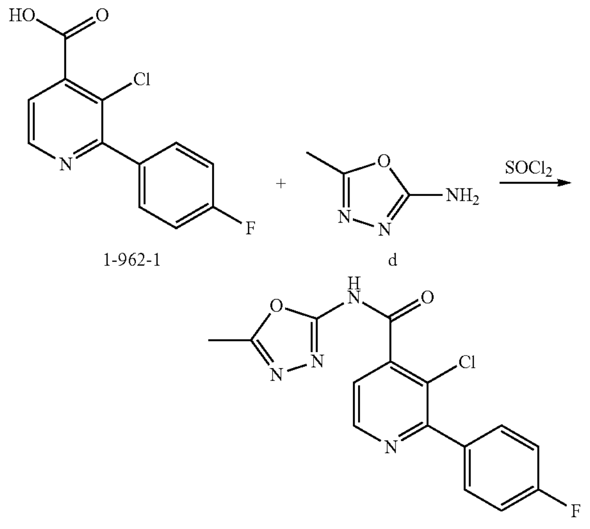

1-962-1 d 1-962

Biological Activity Evaluation:

The activity level criteria for plant damage (i.e., growth control rate) are as follows:

Level 5: growth control rate is above 85%;

Level 4: growth control rate is greater than or equal to 60% and less than 85%;

Level 3: growth control rate is greater than or equal to 40% and less than 60%;

Level 2: growth control rate is greater than or equal to 20% and less than 40%;

Level 1: growth control rate is greater than or equal to 5% and less than 20%;

Level 0: growth control rate is less than 5%.

The above growth control rates are fresh weight control rates.

Experiment on weeding effect in post-emergence stage: monocotyledonous and dicotyledonous weed seeds and major crop seeds (wheat, corn, rice, soybean, cotton, oilseed rape, millet, *sorghum*) were placed in plastic pots filled with soil, then covered with 0.5-2 cm of soil, allowed to grow in a good greenhouse environment. After 2 weeks of sowing, the test plants were treated in the 2-3 leaf stage. The tested compounds of the present invention were respectively dissolved in acetone at the dosage of 2000, 1000, 500, 250, 125 g/ha, then added with Tween 80 and 1.5 liter/ha of emulsifiable concentrate of methyl oleate as synergist, diluted with a certain amount of water to obtain a solution with a certain concentration, and sprayed with a spray tower onto the plants. After the application, the plants were cultured for 3 weeks in the greenhouse, and then the experimental results were listed in Table 1.

TABLE 1

| Results on weeding effect in post-emergence stage | | | | |
|---|---|---|---|---|
| Compound No. | *Descurainia sophia* | *Abutilon theophrasti* | *Amaranthus retroflexus* L. | *Chenopodium album* |
| 1-1 | 5 | 5 | 5 | 5 |
| 1-2 | 5 | 5 | 5 | 5 |
| 1-3 | 5 | 5 | 5 | 5 |
| 1-4 | 5 | 5 | 5 | 5 |
| 1-5 | 5 | 5 | 5 | 5 |
| 1-6 | 5 | 5 | 5 | 5 |
| 1-7 | 5 | 5 | 5 | 5 |
| 1-8 | 5 | 5 | 5 | 5 |
| 1-9 | 5 | 5 | 5 | 5 |
| 1-10 | 5 | 5 | 5 | 5 |
| 1-11 | 5 | 5 | 5 | 5 |
| 1-12 | 5 | 5 | 5 | 5 |
| 1-13 | 5 | 5 | 5 | 5 |
| 1-14 | 5 | 5 | 5 | 5 |
| 1-15 | 5 | 5 | 5 | 5 |
| 1-16 | 5 | 5 | 5 | 5 |
| 1-17 | 5 | 5 | 5 | 5 |
| 1-18 | 5 | 5 | 5 | 5 |
| 1-19 | 5 | 5 | 5 | 5 |
| 1-20 | 5 | 5 | 5 | 5 |
| 1-21 | 5 | 5 | 5 | 5 |
| 1-22 | 5 | 5 | 5 | 5 |
| 1-23 | 5 | 5 | 5 | 5 |
| 1-24 | 5 | 5 | 5 | 5 |
| 1-25 | 5 | 5 | 5 | 5 |
| 1-26 | 5 | 5 | 5 | 5 |
| 1-27 | 5 | 5 | 5 | 5 |
| 1-28 | 5 | 5 | 5 | 5 |
| 1-29 | 5 | 5 | 5 | 5 |
| 1-30 | 5 | 5 | 5 | 5 |
| 1-31 | 5 | 5 | 5 | 5 |
| 1-32 | 5 | 5 | 5 | 5 |
| 1-33 | 5 | 5 | 5 | 5 |
| 1-34 | 5 | 5 | 5 | 5 |
| 1-35 | 5 | 5 | 5 | 5 |
| 1-36 | 5 | 5 | 5 | 5 |
| 1-37 | 5 | 5 | 5 | 5 |
| 1-38 | 5 | 5 | 5 | 5 |
| 1-39 | 5 | 5 | 5 | 5 |
| 1-40 | 5 | 5 | 5 | 5 |
| 1-41 | 5 | 5 | 5 | 5 |
| 1-42 | 5 | 5 | 5 | 5 |
| 1-43 | 5 | 5 | 5 | 5 |
| 1-44 | 5 | 5 | 5 | 5 |
| 1-45 | 5 | 5 | 5 | 5 |
| 1-46 | 5 | 5 | 5 | 5 |
| 1-47 | 5 | 5 | 5 | 5 |
| 1-48 | 5 | 5 | 5 | 5 |
| 1-49 | 5 | 5 | 5 | 5 |
| 1-50 | 5 | 5 | 5 | 5 |
| 1-51 | 5 | 5 | 5 | 5 |
| 1-52 | 5 | 5 | 5 | 5 |
| 1-53 | 5 | 5 | 5 | 5 |
| 1-54 | 5 | 5 | 5 | 5 |
| 1-55 | 5 | 5 | 5 | 5 |
| 1-56 | 5 | 5 | 5 | 5 |
| 1-57 | 5 | 5 | 5 | 5 |
| 1-58 | 5 | 5 | 5 | 5 |
| 1-59 | 5 | 5 | 5 | 5 |
| 1-60 | 5 | 5 | 5 | 5 |
| 1-61 | 5 | 5 | 5 | 5 |
| 1-62 | 5 | 5 | 5 | 5 |
| 1-63 | 5 | 5 | 5 | 5 |
| 1-64 | 5 | 5 | 5 | 5 |
| 1-65 | 5 | 5 | 5 | 5 |
| 1-66 | 5 | 5 | 5 | 5 |
| 1-67 | 5 | 5 | 5 | 5 |
| 1-68 | 5 | 5 | 5 | 5 |
| 1-69 | 5 | 5 | 5 | 5 |
| 1-70 | 5 | 5 | 5 | 5 |
| 1-71 | 5 | 5 | 5 | 5 |
| 1-72 | 5 | 5 | 5 | 5 |
| 1-73 | 5 | 5 | 5 | 5 |
| 1-74 | 5 | 5 | 5 | 5 |
| 1-75 | 5 | 5 | 5 | 5 |

TABLE 1-continued

| Results on weeding effect in post-emergence stage | | | | |
|---|---|---|---|---|
| Compound No. | *Descurainia sophia* | *Abutilon theophrasti* | *Amaranthus retroflexus* L. | *Chenopodium album* |
| 1-76 | 5 | 5 | 5 | 5 |
| 1-77 | 5 | 5 | 5 | 5 |
| 1-78 | 5 | 5 | 5 | 5 |
| 1-79 | 5 | 5 | 5 | 5 |
| 1-80 | 5 | 5 | 5 | 5 |
| 1-81 | 5 | 5 | 5 | 5 |
| 1-82 | 5 | 5 | 5 | 5 |
| 1-83 | 5 | 5 | 5 | 5 |
| 1-84 | 5 | 5 | 5 | 5 |
| 1-85 | 5 | 5 | 5 | 5 |
| 1-86 | 5 | 5 | 5 | 5 |
| 1-87 | 5 | 5 | 5 | 5 |
| 1-88 | 5 | 5 | 5 | 5 |
| 1-89 | 5 | 5 | 5 | 5 |
| 1-90 | 5 | 5 | 5 | 5 |
| 1-91 | 5 | 5 | 5 | 5 |
| 1-92 | 5 | 5 | 5 | 5 |
| 1-93 | 5 | 5 | 5 | 5 |
| 1-94 | 5 | 5 | 5 | 5 |
| 1-95 | 5 | 5 | 5 | 5 |
| 1-96 | 5 | 5 | 5 | 5 |
| 1-97 | 5 | 5 | 5 | 5 |
| 1-98 | 5 | 5 | 5 | 5 |
| 1-99 | 5 | 5 | 5 | 5 |
| 1-100 | 5 | 5 | 5 | 5 |
| 1-101 | 5 | 5 | 5 | 5 |
| 1-102 | 5 | 5 | 5 | 5 |
| 1-103 | 5 | 5 | 5 | 5 |
| 1-104 | 5 | 5 | 5 | 5 |
| 1-105 | 5 | 5 | 5 | 5 |
| 1-106 | 5 | 5 | 5 | 5 |
| 1-107 | 5 | 5 | 5 | 5 |
| 1-108 | 5 | 5 | 5 | 5 |
| 1-109 | 5 | 5 | 5 | 5 |
| 1-110 | 5 | 5 | 5 | 5 |
| 1-111 | 5 | 5 | 5 | 5 |
| 1-112 | 5 | 5 | 5 | 5 |
| 1-113 | 5 | 5 | 5 | 5 |
| 1-114 | 5 | 5 | 5 | 5 |
| 1-115 | 5 | 5 | 5 | 5 |
| 1-116 | 5 | 5 | 5 | 5 |
| 1-117 | 5 | 5 | 5 | 5 |
| 1-118 | 5 | 5 | 5 | 5 |
| 1-119 | 5 | 5 | 5 | 5 |
| 1-120 | 5 | 5 | 5 | 5 |
| 1-121 | 5 | 5 | 5 | 5 |
| 1-122 | 5 | 5 | 5 | 5 |
| 1-123 | 5 | 5 | 5 | 5 |
| 1-124 | 5 | 5 | 5 | 5 |
| 1-125 | 5 | 5 | 5 | 5 |
| 1-126 | 5 | 5 | 5 | 5 |
| 1-127 | 5 | 5 | 5 | 5 |
| 1-128 | 5 | 5 | 5 | 5 |
| 1-129 | 5 | 5 | 5 | 5 |
| 1-130 | 5 | 5 | 5 | 5 |
| 1-131 | 5 | 5 | 5 | 5 |
| 1-132 | 5 | 5 | 5 | 5 |
| 1-133 | 5 | 5 | 5 | 5 |
| 1-134 | 5 | 5 | 5 | 5 |
| 1-135 | 5 | 5 | 5 | 5 |
| 1-136 | 5 | 5 | 5 | 5 |
| 1-137 | 5 | 5 | 5 | 5 |
| 1-138 | 5 | 5 | 5 | 5 |
| 1-139 | 5 | 5 | 5 | 5 |
| 1-140 | 5 | 5 | 5 | 5 |
| 1-141 | 5 | 5 | 5 | 5 |
| 1-142 | 5 | 5 | 5 | 5 |
| 1-143 | 5 | 5 | 5 | 5 |
| 1-144 | 5 | 5 | 5 | 5 |
| 1-145 | 5 | 5 | 5 | 5 |
| 1-146 | 5 | 5 | 5 | 5 |
| 1-147 | 5 | 5 | 5 | 5 |
| 1-148 | 5 | 5 | 5 | 5 |
| 1-149 | 5 | 5 | 5 | 5 |
| 1-150 | 5 | 5 | 5 | 5 |

TABLE 1-continued

| Results on weeding effect in post-emergence stage | | | | |
|---|---|---|---|---|
| Compound No. | *Descurainia sophia* | *Abutilon theophrasti* | *Amaranthus retroflexus* L. | *Chenopodium album* |
| 1-151 | 5 | 5 | 5 | 5 |
| 1-152 | 5 | 5 | 5 | 5 |
| 1-153 | 5 | 5 | 5 | 5 |
| 1-154 | 5 | 5 | 5 | 5 |
| 1-155 | 5 | 5 | 5 | 5 |
| 1-156 | 5 | 5 | 5 | 5 |
| 1-157 | 5 | 5 | 5 | 5 |
| 1-158 | 5 | 5 | 5 | 5 |
| 1-159 | 5 | 5 | 5 | 5 |
| 1-160 | 5 | 5 | 5 | 5 |
| 1-161 | 5 | 5 | 5 | 5 |
| 1-162 | 5 | 5 | 5 | 5 |
| 1-163 | 5 | 5 | 5 | 5 |
| 1-164 | 5 | 5 | 5 | 5 |
| 1-165 | 5 | 5 | 5 | 5 |
| 1-166 | 5 | 5 | 5 | 5 |
| 1-167 | 5 | 5 | 5 | 5 |
| 1-168 | 5 | 5 | 5 | 5 |
| 1-169 | 5 | 5 | 5 | 5 |
| 1-170 | 5 | 5 | 5 | 5 |
| 1-171 | 5 | 5 | 5 | 5 |
| 1-172 | 5 | 5 | 5 | 5 |
| 1-173 | 5 | 5 | 5 | 5 |
| 1-174 | 5 | 5 | 5 | 5 |
| 1-175 | 5 | 5 | 5 | 5 |
| 1-176 | 5 | 5 | 5 | 5 |
| 1-177 | 5 | 5 | 5 | 5 |
| 1-178 | 5 | 5 | 5 | 5 |
| 1-179 | 5 | 5 | 5 | 5 |
| 1-180 | 5 | 5 | 5 | 5 |
| 1-181 | 5 | 5 | 5 | 5 |
| 1-182 | 5 | 5 | 5 | 5 |
| 1-183 | 5 | 5 | 5 | 5 |
| 1-184 | 5 | 5 | 5 | 5 |
| 1-185 | 5 | 5 | 5 | 5 |
| 1-186 | 5 | 5 | 5 | 5 |
| 1-187 | 5 | 5 | 5 | 5 |
| 1-188 | 5 | 5 | 5 | 5 |
| 1-189 | 5 | 5 | 5 | 5 |
| 1-190 | 5 | 5 | 5 | 5 |
| 1-191 | 5 | 5 | 5 | 5 |
| 1-192 | 5 | 5 | 5 | 5 |
| 1-193 | 5 | 5 | 5 | 5 |
| 1-194 | 5 | 5 | 5 | 5 |
| 1-195 | 5 | 5 | 5 | 5 |
| 1-196 | 5 | 5 | 5 | 5 |
| 1-197 | 5 | 5 | 5 | 5 |
| 1-198 | 5 | 5 | 5 | 5 |
| 1-199 | 5 | 5 | 5 | 5 |
| 1-200 | 5 | 5 | 5 | 5 |
| 1-201 | 5 | 5 | 5 | 5 |
| 1-202 | 5 | 5 | 5 | 5 |
| 1-203 | 5 | 5 | 5 | 5 |
| 1-204 | 5 | 5 | 5 | 5 |
| 1-205 | 5 | 5 | 5 | 5 |
| 1-206 | 5 | 5 | 5 | 5 |
| 1-207 | 5 | 5 | 5 | 5 |
| 1-208 | 5 | 5 | 5 | 5 |
| 1-209 | 5 | 5 | 5 | 5 |
| 1-210 | 5 | 5 | 5 | 5 |
| 1-211 | 5 | 5 | 5 | 5 |
| 1-212 | 5 | 5 | 5 | 5 |
| 1-213 | 5 | 5 | 5 | 5 |
| 1-214 | 5 | 5 | 5 | 5 |
| 1-215 | 5 | 5 | 5 | 5 |
| 1-216 | 5 | 5 | 5 | 5 |
| 1-217 | 5 | 5 | 5 | 5 |
| 1-218 | 5 | 5 | 5 | 5 |
| 1-219 | 5 | 5 | 5 | 5 |
| 1-220 | 5 | 5 | 5 | 5 |
| 1-221 | 5 | 5 | 5 | 5 |
| 1-222 | 5 | 5 | 5 | 5 |
| 1-223 | 5 | 5 | 5 | 5 |
| 1-228 | 5 | 5 | 5 | 5 |
| 1-229 | 5 | 5 | 5 | 5 |

TABLE 1-continued

| Results on weeding effect in post-emergence stage | | | | |
|---|---|---|---|---|
| Compound No. | *Descurainia sophia* | *Abutilon theophrasti* | *Amaranthus retroflexus* L. | *Chenopodium album* |
| 1-230 | 5 | 5 | 5 | 5 |
| 1-233 | 5 | 5 | 5 | 5 |
| 1-234 | 5 | 5 | 5 | 5 |
| 1-249 | 5 | 5 | 5 | 5 |
| 1-307 | 5 | 5 | 5 | 5 |
| 1-334 | 5 | 5 | 5 | 5 |
| 1-650 | 5 | 5 | 5 | 5 |
| 1-962 | 5 | 5 | 5 | 5 |
| 1-1257 | 5 | 5 | 5 | 5 |
| 1-1286 | 5 | 5 | 5 | 5 |
| 1-1577 | 5 | 5 | 5 | 5 |
| 1-1607 | 5 | 5 | 5 | 5 |
| 1-1918 | 5 | 5 | 5 | 5 |
| 1-1925 | 5 | 5 | 5 | 5 |
| 1-1972 | 5 | 5 | 5 | 5 |
| 1-2004 | 5 | 5 | 5 | 5 |
| 1-2006 | 5 | 5 | 5 | 5 |
| 1-2010 | 5 | 5 | 5 | 5 |
| 1-2016 | 5 | 5 | 5 | 5 |
| 1-2029 | 5 | 5 | 5 | 5 |
| 1-2044 | 5 | 5 | 5 | 5 |
| 1-2052 | 5 | 5 | 5 | 5 |
| 1-2053 | 5 | 5 | 5 | 5 |
| 1-2061 | 5 | 5 | 5 | 5 |
| 1-2062 | 5 | 5 | 5 | 5 |
| 1-2063 | 5 | 5 | 5 | 5 |
| 1-2064 | 5 | 5 | 5 | 5 |
| 1-2065 | 5 | 5 | 5 | 5 |
| 1-2069 | 5 | 5 | 5 | 5 |
| 1-2070 | 5 | 5 | 5 | 5 |
| 1-2071 | 5 | 5 | 5 | 5 |
| 1-2075 | 5 | 5 | 5 | 5 |

Note:
The application dose was active ingredient 2000 g/ha.

In addition, under the active ingredient of 250 g/ha, many compounds also show good crop selectivity and excellent control effect on key weeds. For example, see Table 2:

amount of water to reach a certain concentration, and sprayed immediately after sowing. The obtained seeds were incubated for 4 weeks in the greenhouse after spraying and the test results were observed. It was observed that the herbicide mostly had excellent effect at the application rate of 2000 g a.i./ha, especially to weeds such as *Echinochloa crusgalli, Digitaria sanguinalis, Abutilon theophrasti*, etc. And many compounds had good selectivity for corn, wheat, rice, soybean, oilseed rape, etc.

It is indicated from the experiment that the compounds of the present invention generally have good weed control efficacy, especially for the major cyperaceae weeds like *Echinochloa crusgalli, Digitaria sanguinalis*, and *Setaria viridis*, etc., and the major broad-leaved weeds like *Abutilon theophrasti, Rorippa* indica, and *Bidens pilosa* L., etc., which are widely occurring in corn, rice, and wheat fields, and have excellent commercial value. Above all, it is noted that they have extremely high activity to weeds, which are resistant to ALS inhibitor, like *Rorippa* indica, *Descurainia sophia, Capsella bursa-pastoris, Lithospermum arvense, Galium aparine* L., *Stellaria media, Setaria viridis, Echinochloa crusgalli, Digitaria sanguinalis, Alopecurus aequalis, Beckmannia syzigachne*, etc.

Transplanted rice safety evaluation and weed control effect evaluation in rice field:

Rice field soil was loaded into a 1/1,000,000 ha pot. The seeds of *Echinochloa crusgalli, Scirpus juncoides, Bidens tripartita* L., *Sagittaria trifolia*, and *Monochoria vaginalis* were sowed and gently covered with soil, then left to stand still in greenhouse in the state of 0.5-1 cm of water storage. The tuber of *Sagittaria trifolia* was planted in the next day or 2 days later. It was kept at 3-4 cm of water storage thereafter. The weeds were treated by dripping the WP or SC water diluents prepared according to the common preparation method of the compounds of the present invention with pipette homogeneously to achieve specified effective amount when *Echinochloa crusgalli, Scirpus juncoides,*

TABLE 2

| Test results | | | | | | |
|---|---|---|---|---|---|---|
| No. | *Alopecurus aequalis* | *Beckmannia syzigachne* | *Alopecurus myosuroides* | *Sclerochloa dura* | *Descurainia sophia* | Wheat |
| 1-15 | 5 | 5 | 5 | 5 | 5 | 0 |
| 1-17 | 5 | 5 | 5 | 5 | 5 | 0 |
| Control compound A | 0 | 0 | 0 | 0 | 0 | 0 |

Control Compound A:

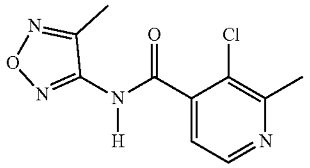 [SMILES: Cc1nonc1NC(=O)c1ccnc(C)c1Cl]

Experiment on Weed Effect in Pre-Emergence Stage

Seeds of monocotyledonous and dicotyledonous weeds and main crops (e.g. wheat, corn, rice, soybean, cotton, oilseed rape, millet and *sorghum*) were put into a plastic pot loaded with soil and covered with 0.5-2 cm soil. The test compounds of the present invention was dissolved with acetone, then added with tween 80, diluted by a certain

*Bidens tripartita* L., and *Monochoria vaginalis* reached 0.5 leaf stage and *Sagittaria trifolia* reached the time point of primary leaf stage.

In addition, the rice field soil that loaded into the 1/1,000,000 ha pot was leveled to keep water storage at 3-4 cm depth. The 3 leaf stage rice (*japonica* rice) was transplanted at 3 cm of transplanting depth the next day. The compound of the present invention was treated by the same way after 5 days of transplantation.

The fertility condition of *Echinochloa crusgalli, Scirpus juncoides, Bidens tripartita* L., *Sagittaria trifolia* and *Monochoria vaginalis* 14 days after the treatment of the compound of the invention and the fertility condition of rice 21 days after the treatment of the compound of the invention respectively with the naked eye. Evaluate the weed control effect with the above 0-5 activity standard level, many compounds show excellent activity and selectivity. Wherein, the seeds of *Echinochloa crusgali, Scirpus juncoides, Bidens tripartita, Sagittaria trifolia* and *Monochoria vaginalis* were collected from Heilongjiang Province of China. The tests indicated that the weeds were resistant to the common doses of Pyrazosulfuron-ethyl and Penoxsulam.

It could be seen from this experiment that the compound of the present invention has excellent activity against the anti-ALS weeds which is a serious challenge in the production, and could solve the increasingly serious problem of resistance.

At the same time, it is found after several tests that the compound of the present invention and its composition have good selectivity to many gramineae grass such as *Zoysia japonica*, bermuda grass, tall fescue, bluegrass, ryegrass and seashore *paspalum* etc, and is able to control many important grass weeds and broadleaf weeds. The compound also shows excellent selectivity and commercial value in the tests on wheat, corn, rice, sugarcane, soybean, cotton, oil sunflower, potato, orchards and vegetables in different herbicide application methods.

The invention claimed is:

1. A 4-pyridinyl formamide herbicidal compound or derivative thereof, as shown in Formula I:

I

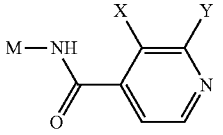

wherein, X, and Y each independently represent nitro, halogen, cyano, formyl, thiocyano, mercapto; alkyl, alkenyl, alkynyl, cycloalkyl, cycloalkenyl, cycloalkylalkyl, or cycloalkenylalkyl, which is with or without halogen; $OR^1$, $COR^1$, $COOR^1$, $OCOR^1$, $OCOOR^1$, $NR^3SO_2R^2$, $OSO_2R^2$, $S(O)_mR^2$, $NR^3COR^1$, $NR^3COOR^1$, $C(O)NR^3OR^1$, $SO_2OR^1$, $C(O)NR^4R^5$, $NR^3C(O)NR^4R^5$, $OC(O)NR^4R^5$, $SO_2NR^4R^5$, $C(S)R^1$, $C(S)OR^1$, $C(S)SR^2$, $C(O)SR^2$, $SC(O)R^1$, $SC(S)R^1$, $OC(S)R^1$, -alkyl-$C(S)R^1$, -alkyl-$C(S)OR^1$, -alkyl-C(O)$SR^1$, -alkyl-$C(S)SR^1$, -alkyl-$SC(O)R^1$, -alkyl-OC(S)$R^1$, -alkyl-$SC(S)R^1$, —O— alkyl-$NR^4R^5$, —S-alkyl-$NR^4R^5$, -alkyl-O-alkyl-$NR^4R^5$, -alkyl-S-alkyl-$NR^4R^5$, -alkyl-$(C{=}S)_n$—$NR^4R^5$, —NH-alkyl-$NR^4R^5$, -alkyl-$OR^1$, -alkyl-$COR^1$, -alkyl-$CO_2R^1$, -alkyl-$OCOR^1$, -alkyl-$NR^3COR^1$, -alkyl-$SO_2OR'$, -alkyl-$NR^3SO_2R^2$, -alkyl-$OSO_2R^2$, -alkyl-$S(O)_mR^2$, -alkyl-$CONR^4R^5$, -alkyl-$SO_2NR^4R^5$, $NR^4R^5$,

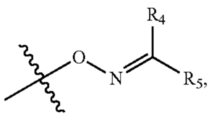

$P(O)(OR^6)_2$, $CH_2P(O)(OR^6)_2$, $SO_2NR^4R^5$-alkyl-$S(O)_mR^2$, -alkyl-CN, -alkylaryl, -alkylheteroaryl, -alkylheterocyclyl, aryl, heteroaryl, or heterocyclyl;

$R^1$, $R^3$, $R^4$, and $R^5$ each independently represent hydrogen, aryl, arylalkyl, heteroaryl, heteroarylalkyl, alkyl, halogenated alkyl, alkenyl, halogenated alkenyl, alkynyl, halogenated alkynyl, cycloalkyl, halogenated cycloalkyl, alkoxyalkyl, or cycloalkylalkyl, wherein the last 10 groups as mentioned are each substituted by s groups selected from the group consisting of cyano, halogen, nitro, thiocyano, $OR^7$, $S(O)_mR^9$, $NR^7R^8$, $NR^8OR^7$, $COR^7$, $OCOR^7$, $SCOR^7$, $NR^8COR^7$, $CO_2R^7$, $COSR^7$, $CONR^7R^8$, and alkoxyalkoxycarbonyl;

$R^2$ represents aryl, arylalkyl, heteroaryl, heteroarylalkyl, alkyl, alkenyl, alkynyl, cycloalkyl, or cycloalkylalkyl, wherein the last 5 groups as mentioned are each substituted by s groups selected from the group consisting of cyano, halogen, nitro, thiocyano, $OR^7$, $S(O)_mR^9$, $NR^7R^8$, $NR^8OR^7$, $COR^7$, $OCOR^7$, $SCOR^7$, $NR^8COR^7$, $CO_2R^7$, $COSR^7$, $CONR^7R^8$, and alkoxyalkoxycarbonyl;

$R^6$ represents methyl, or ethyl;

$R^7$, and $R^8$ each independently represent hydrogen, alkyl, alkenyl, or alkynyl;

$R^9$ represents alkyl, alkenyl, or alkynyl;

M represents

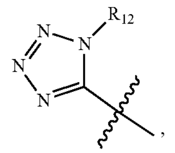

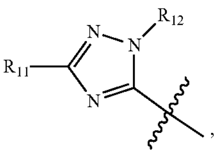

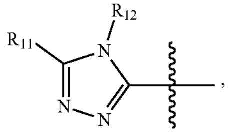

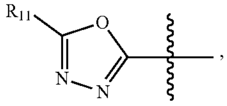

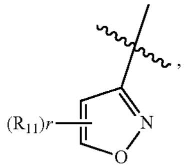

or

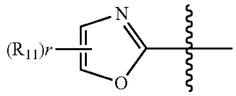

which is unsubstituted or substituted;

$R_{11}$ represents hydrogen, halogen, cyano, nitro, alkyl which is unsubstituted or substituted with a substituent selected from $R_{13}$, cycloalkyl which is unsubstituted or substituted with a substituent selected from $R_{14}$, alkenyl, halogenated alkenyl, alkynyl, halogenated alkynyl, cycloalkenyl, $NH_2$, aminoacyl, carboxyl, alkoxyalkoxycarbonyl, $OR_{15}$, -alkyl-$OR_{15}$, $C(O)R_{16}$, -alkyl-$C(O)R_{16}$, $C(O)OR_{16}$, -alkyl-$C(O)OR_{16}$, $S(O)_mR_{16}$, -alkyl-$S(O)_mR_{16}$, —$N(R_{16})_2$, —$NHR_{16}$, —C(O)$NHR_{16}$, —$C(O)N(R_{16})_2$, —$NHC(O)R_{17}$, heterocyclyl, heterocyclylalkyl, heterocyclyloxy, heterocyclylcarbonyl, aryl, arylalkyl, aryloxy, arylcarbonyl, heteroaryl, heteroarylalkyl, heteroaryloxy, or heteroarylcarbonyl;

$R_{12}$ represents hydrogen, alkyl which is unsubstituted or substituted with a substituent selected from $R_{18}$, cycloalkyl, halogenated cycloalkyl, alkenyl, halogenated alkenyl, alkynyl, halogenated alkynyl, cycloalkenyl, alkoxyalkyl, alkylthioalkyl, alkoxycarbonylalkyl, aryl, or arylalkyl;

when M is

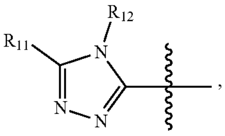

—$(CH_2)_4$— or —CH═CH—CH═CH— formed by $R_{11}$ and $R_{12}$, the nitrogen atom bound to $R_{12}$ and the carbon atom bound to $R_{11}$ together form a 6-membered ring;

$R_{15}$ represents alkyl which is unsubstituted or substituted with a substituent selected from $R_{21}$, cycloalkyl, halogenated cycloalkyl, alkenyl, halogenated alkenyl, alkynyl, halogenated alkynyl, cycloalkenyl, or phenyl;

$R_{16}$ represents alkyl, halogenated alkyl, cycloalkyl, alkenyl, halogenated alkenyl, alkynyl, halogenated alkynyl, or cycloalkenyl;

$R_{21}$ represents halogen, cyano, cycloalkyl, hydroxy, mercapto, alkoxy, $C(O)R_{22}$, carboxyl, alkoxycarbonyl, alkoxyalkoxycarbonyl, —$S(O)_m$-alkyl, heteroaryl, heterocyclyl, or phenyl which is unsubstituted or substituted with one or more groups selected from $R_{23}$;

$R_{17}$, and $R_{22}$ each independently represent hydrogen, alkyl, or $N(R_{24})R_{25}$;

$R_{23}$ represents halogen, cyano, nitro, alkyl, alkyl which is unsubstituted or substituted with a substituent selected from $R_{31}$, cycloalkyl, halogenated cycloalkyl, alkenyl, halogenated alkenyl, alkynyl, halogenated alkynyl, cycloalkenyl, alkylcarbonyl, cycloalkylcarbonyl, halogenated alkylcarbonyl, halogenated cycloalkylcarbonyl, alkoxycarbonyl, halogenated alkoxycarbonyl, alkylaminocarbonyl, halogenated alkylaminocarbonyl, bis(alkyl)aminocarbonyl, $OR_{32}$, $S(O)_mR_{33}$, alkylaminosulfonyl, bis(alkyl)aminosulfonyl, $NH_2$, alkylamino, bis(alkyl)amino, aryl, heteroaryl, or heterocyclyl;

$R_{24}$, and $R_{25}$ each independently represent hydrogen, alkyl, or phenyl; or, alkylidene chain formed by $R_{24}$ and $R_{25}$, and the nitrogen atom(s) bound to $R_{24}$ and $R_{25}$ together form a 3-7-membered ring, said alkylidene chain optionally contains one O, S, S(O), $S(O)_2$, NH, or N-alkyl and optionally substituted by oxo or thio group;

$R_{13}$, $R_{14}$, $R_{18}$, and $R_{31}$ each independently represent halogen, cyano, nitro, carboxyl, alkoxycarbonyl, alkoxyalkoxycarbonyl, $S(O)_mR_{41}$, $OR_{42}$, aryl, heteroaryl, or heterocyclyl;

$R_{32}$ represents hydrogen, alkyl, halogenated alkyl, cycloalkyl, halogenated cycloalkyl, alkenyl, halogenated alkenyl, alkynyl, halogenated alkynyl, or cycloalkenyl;

$R_{33}$ represents alkyl, halogenated alkyl, cycloalkyl, alkenyl, halogenated alkenyl, alkynyl, halogenated alkynyl, or cycloalkenyl;

$R_{41}$, and $R_{42}$ each independently represent hydrogen, alkyl, halogenated alkyl, cycloalkyl, halogenated cycloalkyl, alkenyl, halogenated alkenyl, alkynyl, halogenated alkynyl, cycloalkenyl, or phenyl;

r represents 1 or 2;

m represents 0, 1 or 2;

n represents 0, or 1;

s represents 0, 1, 2 or 3.

2. The 4-pyridinyl formamide compound or derivative thereof according to claim 1, wherein:

X, and Y each independently represent nitro, halogen, cyano, formyl, thiocyano, mercapto: C1-C8 alkyl, C2-C8 alkenyl, C2-C8 alkynyl, C3-C8 cycloalkyl, C3-C8 cycloalkenyl, C3-C8 cycloalkyl-C1-C6 alkyl, or C3-C8 cycloalkenyl-C1-C6 alkyl, which is with or without halogen; $OR^1$, $COR^1$, $COOR^1$, $OCOR^1$, $OCOOR^1$, $NR^3SO_2R^2$, $OSO_2R^2$, $S(O)_mR^2$, $NR^3COR^1$, $NR^3COOR^1$, $C(O)NR^3OR^1$, $SO_2OR'$, $C(O)NR^4R^5$, $NR^3C(O)NR^4R^5$, $OC(O)NR^4R^5$, $SO_2NR^4R^5$, $C(S)R^1$, $C(S)OR^1$, $C(S)SR^2$, $C(O)SR^2$, $SC(O)R^1$, $SC(S)R^1$, $OC(S)R^1$, —(C1-C6)alkyl-$C(S)R^1$, —(C1-C6)alkyl-$C(S)OR^1$, —(C1-C6)alkyl-$C(O)SR^1$, —(C1-C6)alkyl-$C(S)SR^1$, —(C1-C6)alkyl-$SC(O)R^1$, —(C1-C6)alkyl-$OC(S)R^1$, —(C1-C6)alkyl-$SC(S)R^1$, —O—(C1-C6) alkyl-$NR^4R^5$, —S—(C1-C6)alkyl-$NR^4R^5$, —(C1-C6) alkyl-O—(C1-C6)alkyl-$NR^4R^5$, —(C1-C6)alkyl-S—(C1-C6)alkyl-$NR^4R^5$, —(C1-C6)alkyl-$(C{=}S)_n$-$NR^4R^5$, —NH—(C1-C6)alkyl-$NR^4R^5$, —(C1-C6) alkyl-$OR^1$, —(C1-C6)alkyl-$COR^1$, —(C1-C6)alkyl-$CO_2R^1$, —(C1-C6)alkyl-$OCOR^1$, —(C1-C6)alkyl-$NR^3COR^1$, —(C1-C6)alkyl-$SO_2OR^1$, —(C1-C6)alkyl-$NR^3SO_2R^2$, —(C1-C6)alkyl-$OSO_2R^2$, -alkyl-$S(O)_mR^2$, —(C1-C6)alkyl-$CONR^4R^5$, —(C1-C6)alkyl-$SO_2NR^4R^5$, $NR^4R^5$,

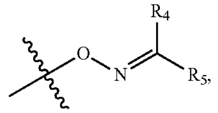

$P(O)(OR^6)_2$, $CH_2P(O)(OR^6)_2$, $SO_2NR^4R^5$—(C1-C6)alkyl-$S(O)_mR^2$, —(C1-C6)alkyl-CN, —(C1-C6)alkylaryl, —(C1-C6)alkylheteroaryl, —(C1-C6)alkylheterocyclyl, aryl, heteroaryl, or heterocyclyl;

$R^1$, $R^3$, $R^4$, and $R^5$ each independently represent hydrogen, aryl, aryl-C1-C6 alkyl, heteroaryl, heteroaryl-C1-C6 alkyl, C1-C8 alkyl, halogenated C1-C8 alkyl, C2-C8 alkenyl, halogenated C2-C8 alkenyl, C2-C8 alkynyl, halogenated C2-C8 alkynyl, C3-C8 cycloalkyl, halogenated C3-C8 cycloalkyl, C1-C8 alkoxy-C1-C6 alkyl, or C3-C8 cycloalkyl-C1-C6 alkyl, wherein the last 10 groups as mentioned are each substituted by s groups selected from the group consisting of cyano, halogen, nitro, thiocyano, $OR^7$, $S(O)_mR^9$, $NR^7R^8$, $NR^8OR^7$, $COR^7$, $OCOR^7$, $SCOR^7$, $NR^8COR^7$, $CO_2R^7$, $COSR^7$, $CONR^7R^8$, and C1-C8 alkoxy-C1-C6 alkoxycarbonyl;

$R^2$ represents aryl, aryl-C1-C6 alkyl, heteroaryl, heteroaryl-C1-C6 alkyl, C1-C8 alkyl, C2-C8 alkenyl, C2-C8 alkynyl, C3-C8 cycloalkyl, or C3-C8 cycloalkyl-C1-C6 alkyl, wherein the last 5 groups as mentioned are each substituted by s groups selected from the group consisting of cyano, halogen, nitro, thiocyano, $OR^7$, $S(O)_mR^9$, $NR^7R^8$, $NR^8OR^7$, $COR^7$, $OCOR^7$, $SCOR^7$, $NR^8COR^7$, $CO_2R^7$, $COSR^7$, $CONR^7R^8$, and C1-C8 alkoxy-C1-C6 alkoxycarbonyl;

$R^6$ represents methyl, or ethyl;

$R^7$, and $R^8$ each independently represent hydrogen, C1-C8 alkyl, C2-C8 alkenyl, or C2-C8 alkynyl;

$R^9$ represents C1-C8 alkyl, C2-C8 alkenyl, or C2-C8 alkynyl;

M represents

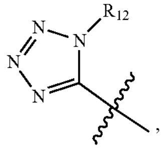

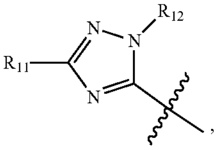

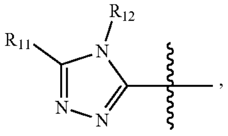

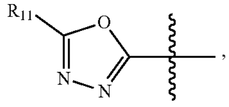

-continued

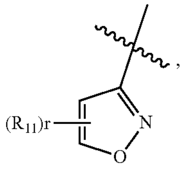, or 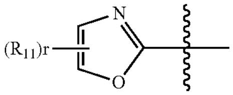, which is unsubstituted or substituted;

$R_{11}$ represents hydrogen, halogen, cyano, nitro, C1-C8 alkyl which is unsubstituted or substituted with a substituent selected from $R_{13}$, C3-C8 cycloalkyl which is unsubstituted or substituted with a substituent selected from $R_{14}$, C2-C8 alkenyl, halogenated C2-C8 alkenyl, C2-C8 alkynyl, halogenated C2-C8 alkynyl, C3-C8 cycloalkenyl, $NH_2$, aminoacyl, carboxyl, C1-C8 alkoxy-C1-C6 alkoxycarbonyl, $OR_{15}$, —(C1-C6)alkyl-$OR_{15}$, C(O)$R_{16}$, —(C1-C6)alkyl-C(O)$R_{16}$, C(O)O$R_{16}$, —(C1-C6)alkyl-C(O)O$R_{16}$, $S(O)_mR_{16}$, —(C1-C6)alkyl-$S(O)_mR_{16}$, —$N(R_{16})_2$, —$NHR_{16}$, —C(O)N$HR_{16}$, -nitro, C1-C8 alkyl which is C(O)$N(R_{16})_2$, —NHC(O)$R_{17}$, heterocyclyl, heterocyclyl-C1-C6 alkyl, heterocyclyloxy, heterocyclylcarbonyl, aryl, aryl-C1-C6 alkyl, aryloxy, arylcarbonyl, heteroaryl, heteroaryl-C1-C6 alkyl, heteroaryloxy, or heteroarylcarbonyl;

$R_{12}$ represents hydrogen, C1-C8 alkyl which is unsubstituted or substituted with a substituent selected from $R_{18}$, C3-C8 cycloalkyl, halogenated C3-C8 cycloalkyl, C2-C8 alkenyl, halogenated C2-C8 alkenyl, C2-C8 alkynyl, halogenated C2-C8 alkynyl, C3-C8 cycloalkenyl, C1-C8 alkoxy-C1-C6 alkyl, C1-C8 alkylthio-C1-C6 alkyl, C1-C8 alkoxycarbonyl-C1-C6 alkyl, aryl, or aryl-C1-C6 alkyl;

when M is

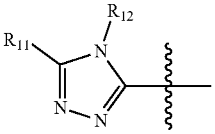,

—$(CH_2)_4$— or —CH═CH—CH═CH— formed by $R_{11}$ and $R_{12}$, the nitrogen atom bound to $R_{12}$ and the carbon atom bound to $R_{11}$ together form a 6-membered ring;

$R_{15}$ represents C1-C8 alkyl which is unsubstituted or substituted with a substituent selected from $R_{21}$, C3-C8 cycloalkyl, halogenated C3-C8 cycloalkyl, C2-C8 alkenyl, halogenated C2-C8 alkenyl, C2-C8 alkynyl, halogenated C2-C8 alkynyl, C3-C8 cycloalkenyl, or phenyl;

$R_{16}$ represents C1-C8 alkyl, halogenated C1-C8 alkyl, C3-C8 cycloalkyl, C2-C8 alkenyl, halogenated C2-C8 alkenyl, C2-C8 alkynyl, halogenated C2-C8 alkynyl, or C3-C8 cycloalkenyl;

$R_{21}$ represents halogen, cyano, C3-C8 cycloalkyl, hydroxy, mercapto, C1-C8 alkoxy, C(O)$R_{22}$, carboxyl, C1-C8 alkoxycarbonyl, C1-C8 alkoxy-C1-C6 alkoxycarbonyl, —$S(O)_m$—(C1-C8)alkyl, heteroaryl, heterocyclyl, or phenyl which is unsubstituted or substituted with one or more groups selected from $R_{23}$;

$R_{17}$, and $R_{22}$ each independently represent hydrogen, C1-C8 alkyl, or $N(R_{24})R_{25}$;

$R_{23}$ represents halogen, cyano, nitro, C1-C8 alkyl, C1-C8 alkyl which is unsubstituted or substituted with a substituent selected from $R_{31}$, C3-C8 cycloalkyl, halogenated C3-C8 cycloalkyl, C2-C8 alkenyl, halogenated C2-C8 alkenyl, C2-C8 alkynyl, halogenated C2-C8 alkynyl, C3-C8 cycloalkenyl, C1-C8 alkylcarbonyl, C3-C8 cycloalkylcarbonyl, halogenated C1-C8 alkylcarbonyl, halogenated C3-C8 cycloalkylcarbonyl, C1-C8 alkoxycarbonyl, halogenated C1-C8 alkoxycarbonyl, C1-C8 alkylaminocarbonyl, halogenated C1-C8 alkylaminocarbonyl, bis(C1-C8 alkyl)aminocarbonyl, $OR_{32}$, $S(O)_mR_{33}$, C1-C8 alkylaminosulfonyl, bis(C1-C8 alkyl)aminosulfonyl, $NH_2$, C1-C8 alkylamino, bis(C1-C8 alkyl)amino, aryl, heteroaryl, or heterocyclyl;

$R_{24}$, and $R_{25}$ each independently represent hydrogen, C1-C8 alkyl, or phenyl; or, C2-C8 alkylidene chain formed by $R_{24}$ and $R_{25}$, and the nitrogen atom(s) bound to $R_{24}$ and $R_{25}$ together form a 3-7-membered ring, said C2-C8 alkylidene chain optionally contains one O, S, S(O), $S(O)_2$, NH, or N-alkyl and optionally substituted by oxo or thio group;

$R_{13}$, $R_{14}$, $R_{18}$, and $R_{31}$ each independently represent halogen, cyano, nitro, carboxyl, C1-C8 alkoxycarbonyl, C1-C8 alkoxy-C1-C8 alkoxycarbonyl, $S(O)_mR_{41}$, $OR_{42}$, aryl, heteroaryl, or heterocyclyl;

$R_{32}$ represents hydrogen, C1-C8 alkyl, halogenated C1-C8 alkyl, C3-C8 cycloalkyl, halogenated C3-C8 cycloalkyl, C2-C8 alkenyl, halogenated C2-C8 alkenyl, C2-C8 alkynyl, halogenated C2-C8 alkynyl, or C3-C8 cycloalkenyl;

$R_{33}$ represents C1-C8 alkyl, halogenated C1-C8 alkyl, C3-C8 cycloalkyl, C2-C8 alkenyl, halogenated C2-C8 alkenyl, C2-C8 alkynyl, halogenated C2-C8 alkynyl, or C3-C8 cycloalkenyl;

$R_{41}$, and $R_{42}$ each independently represent hydrogen, C1-C8 alkyl, halogenated C1-C8 alkyl, C3-C8 cycloalkyl, halogenated C3-C8 cycloalkyl, C2-C8 alkenyl, halogenated C2-C8 alkenyl, C2-C8 alkynyl, halogenated C2-C8 alkynyl, C3-C8 cycloalkenyl, or phenyl;

r represents 1, or 2;

m represents 0, 1, or 2;

n represents 0, or 1;

s represents 0, 1, 2, or 3;

wherein, the "heterocyclyl" is

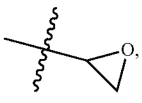, 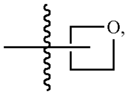, 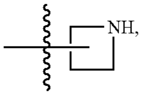,

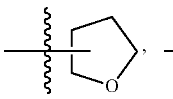, 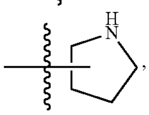, 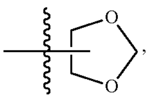,

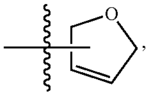, 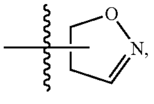, 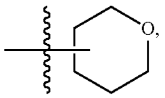,

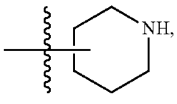, 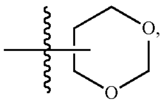, 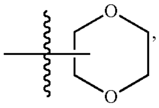,

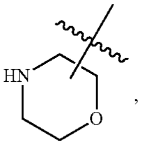, 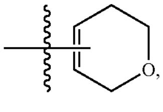, or 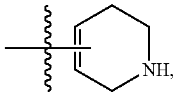, which has 0, 1, or 2 oxo groups; the "aryl" is phenyl, naphthyl,
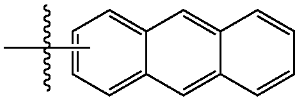
, or
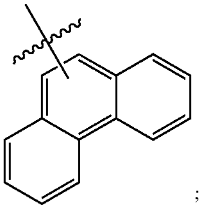
;
the "heteroaryl" is
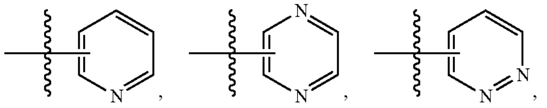
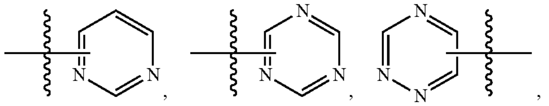
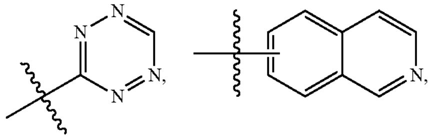
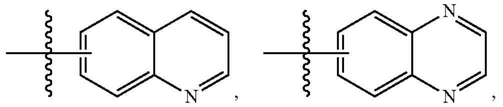
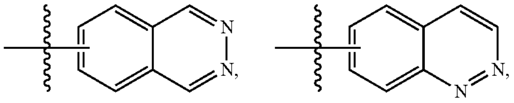
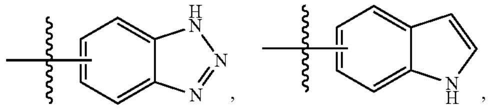
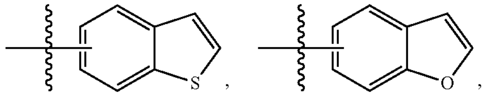
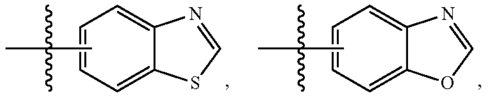
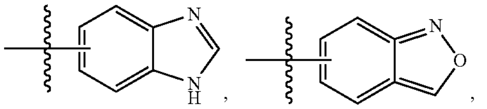
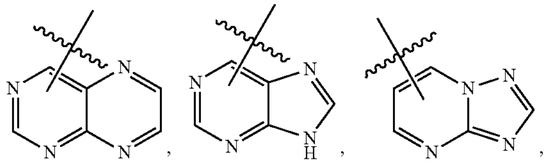
-continued
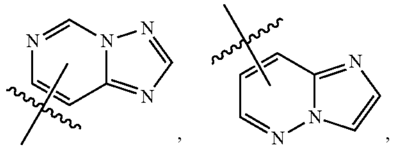
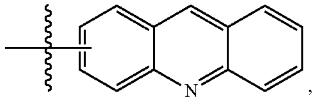
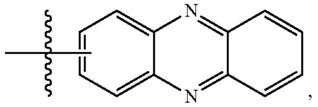
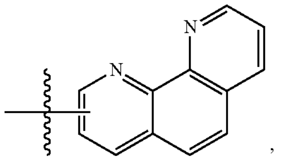
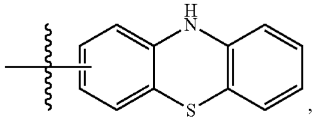
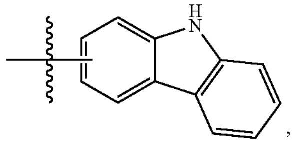
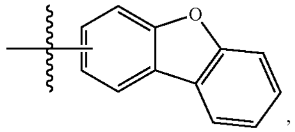
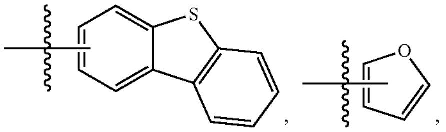
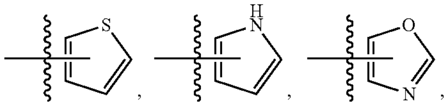
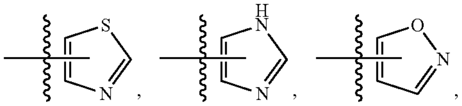
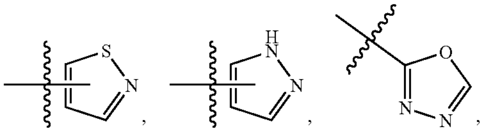
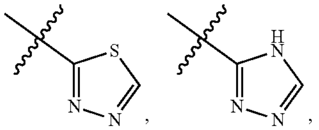
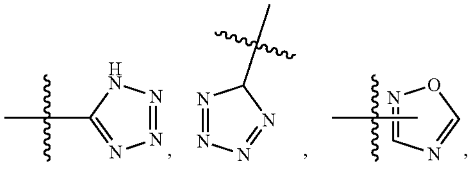

-continued

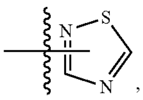, 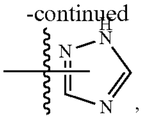, 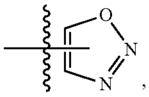,

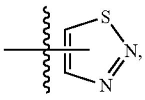 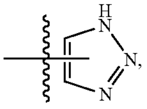 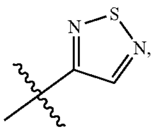

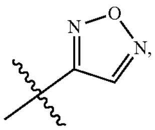 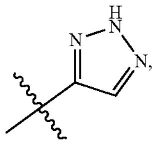 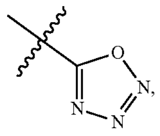

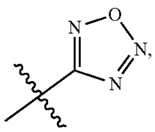 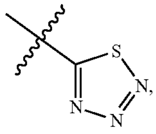 or 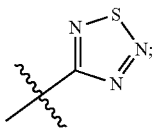

the above-mentioned groups are respectively unsubstituted or substituted by at least one group selected from: halogen, nitro, cyano, thiocyano, cyanoalkyl, mercapto, hydroxy, hydroxyalkyl, carboxyl, formyl, trialkylsilyl, dialkylphosphonyl; heterocyclyl, heterocyclylalkyl, aryl, arylalkyl, heteroaryl, or heteroarylalkyl, which is unsubstituted or substituted; alkyl, alkenyl, alkynyl, cycloalkyl, cycloalkenyl, cycloalkylalkyl, cycloalkyl substituted by alkyl, OR", SR", -alkyl-OR", —O-alkyl-OR", -alkyl-SR", COR", -alkyl-COR", —O-alkyl-COR", COOR", -alkyl-COOR", —O-alkyl-COOR", COSR", SOR", $SO_2R$", —O—$SO_2R$", -alkyl-$SO_2R$", OCOR", -alkyl-OCOR", or SCOR" group, which is with or without halogen; and amino, aminoalkyl, aminocarbonyl, aminocarbonylalkyl, or aminosulfonyl group which is unsubstituted or substituted by one or two groups selected from R", COR", COOR", $SO_2R$", and OR", wherein the R", COR", COOR", $SO_2R$", or OR" is with or without halogen; or, two adjacent substitutable positions of the above-mentioned "heterocyclyl", "aryl", "heteroaryl" groups are linked with —$OCH_2CH_2$—, —$OCH_2O$—, —$OCH_2CH_2O$— or —CH═CH—CH═CH— group to form a ring, wherein the —$OCH_2CH_2$—, —$OCH_2O$—, —$OCH_2CH_2O$— or —CH═CH—CH═CH— group is with or without halogen;

R" each independently represents alkyl, alkenyl, alkynyl, cycloalkyl, cycloalkylalkyl, cycloalkenyl; or heterocyclyl, heterocyclylalkyl, aryl, arylalkyl, heteroaryl, or heteroarylalkyl, which is unsubstituted or substituted.

3. The 4-pyridinyl formamide compound or derivative thereof according to claim 1, wherein:

X represents nitro, halogen, cyano, formyl, thiocyano, mercapto; C1-C6 alkyl, C2-C6 alkenyl, C2-C6 alkynyl, C3-C6 cycloalkyl, C3-C6 cycloalkenyl, C3-C6 cycloalkyl-C1-C3 alkyl, or C3-C6 cycloalkenyl-C1-C3 alkyl, which is with or without halogen; $OR^1$, $COR^1$, $COOR^1$, $OCOR^1$, $OCOOR^1$, $NR^3SO_2R^2$, $OSO_2R^2$, $S(O)_mR^2$, $NR^3COR^1$, $NR^3COOR^1$, $C(O)NR^3OR^1$, $SO_2OR^1$, $C(O)NR^4R^5$, $NR^3C(O)NR^4R^5$, $OC(O)NR^4R^5$, $SO_2NR^4R^5$, $C(S)R^1$, $C(S)OR^1$, $C(S)SR^2$, $C(O)SR^2$, $SC(O)R^1$, $SC(S)R^1$, $OC(S)R^1$, —(C1-C3)alkyl-C(S)$R^1$, —(C1-C3)alkyl-C(S)$OR^1$, —(C1-C3)alkyl-C(O)$SR^1$, —(C1-C3)alkyl-C(S)$SR^1$, —(C1-C3)alkyl-SC(O)$R^1$, —(C1-C3)alkyl-OC(S)$R^1$, —(C1-C3)alkyl-SC(S)$R^1$, —O—(C1-C3)alkyl-$NR^4R^5$, —S—(C1-C3)alkyl-$NR^4R^5$, —(C1-C3)alkyl-*O*—(C1-C3)alkyl-$NR^4R^5$, —(C1-C3)alkyl-S—(C1-C3)alkyl-$NR^4R^5$, —(C1-C3) alkyl-(C═S)$_n$—$NR^4R^5$, —NH—(C1-C3)alkyl-$NR^4R^5$, —(C1-C3)alkyl-$OR^1$, —(C1-C3)alkyl-$COR^1$, —(C1-C3)alkyl-$CO_2R'$, —(C1-C3)alkyl-$OCOR^1$, —(C1-C3)alkyl-$NR^3COR^1$, —(C1-C3)alkyl-$SO_2OR'$, —(C1-C3)alkyl-$NR^3SO_2R^2$, —(C1-C3)alkyl-$OSO_2R^2$, -alkyl-$S(O)_mR^2$, —(C1-C3)alkyl-$CONR^4R^5$, —(C1-C3)alkyl-$SO_2NR^4R^5$, $NR^4R^5$,

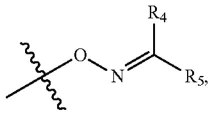

$P(O)(OR^6)_2$, $CH_2P(O)(OR^6)_2$, $SO_2NR^4R^5$—(C1-C3)alkyl-S$(O)_mR^2$, —(C1-C3)alkyl-CN, —(C1-C3)alkylaryl, —(C1-C3)alkylheteroaryl, —(C1-C3)alkylheterocyclyl, aryl, heteroaryl, or heterocyclyl;

Y represents C1-C6 alkyl, C2-C6 alkenyl, C2-C6 alkynyl, C3-C6 cycloalkyl, or C3-C6 cycloalkenyl, which is with or without halogen; $OR^1$, $S(O)_mR^2$, $NR^4R^5$, heterocyclyl, aryl, or heteroaryl;

$R^1$, $R^3$, $R^4$, and $R^5$ each independently represent hydrogen, aryl, aryl-C1-C3 alkyl, heteroaryl, heteroaryl-C1-C3 alkyl, C1-C6 alkyl, halogenated C1-C6 alkyl, C2-C6 alkenyl, halogenated C2-C6 alkenyl, C2-C6 alkynyl, halogenated C2-C6 alkynyl, C3-C6 cycloalkyl, halogenated C3-C6 cycloalkyl, C1-C6 alkoxy-C1-C3 alkyl, or C3-C6 cycloalkyl-C1-C3 alkyl, wherein the last 10 groups as mentioned are each substituted by s groups selected from the group consisting of cyano, halogen, nitro, thiocyano, $OR^7$, $S(O)_mR^9$, $NR^7R^8$, $NR^8OR^7$, $COR^7$, $OCOR^7$, $SCOR^7$, $NR^8COR^7$, $CO_2R^7$, $COSR^7$, $CONR^7R^8$, and C1-C6 alkoxy-C1-C3 alkoxycarbonyl;

$R^2$ represents aryl, aryl-C1-C3 alkyl, heteroaryl, heteroaryl-C1-C3 alkyl, C1-C6 alkyl, C2-C6 alkenyl, C2-C6 alkynyl, C3-C6 cycloalkyl, or C3-C6 cycloalkyl-C1-C3 alkyl, wherein the last 5 groups as mentioned are each substituted by s groups selected from the group consisting of cyano, halogen, nitro, thiocyano, $OR^7$, $S(O)_mR^9$, $NR^7R^8$, $NR^8OR^7$, $COR^7$, $OCOR^7$, $SCOR^7$, $NR^8COR^7$, $CO_2R^7$, $COSR^7$, $CONR^7R^8$, and C1-C6 alkoxy-C1-C3 alkoxycarbonyl;

$R^6$ represents methyl, or ethyl;

$R^7$, and $R^8$ each independently represent hydrogen, C1-C6 alkyl, C2-C6 alkenyl, or C2-C6 alkynyl;

$R^9$ represents C1-C6 alkyl, C2-C6 alkenyl, or C2-C6 alkynyl;

M represents

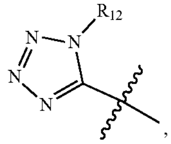, 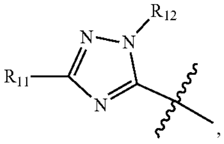,

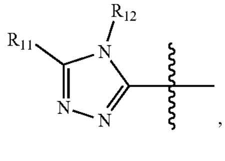, 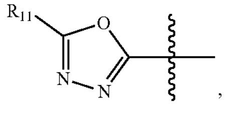,

-continued

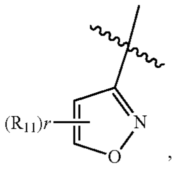
, or
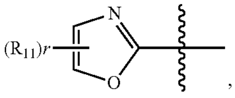
, which is unsubstituted or substituted;

$R_{11}$ represents hydrogen, halogen, cyano, nitro, C1-C6 alkyl which is unsubstituted or substituted with a substituent selected from $R_{13}$, C3-C6 cycloalkyl which is unsubstituted or substituted with a substituent selected from $R_{14}$, C2-C6 alkenyl, halogenated C2-C6 alkenyl, C2-C6 alkynyl, halogenated C2-C6 alkynyl, C3-C6 cycloalkenyl, $NH_2$, aminoacyl, carboxyl, C1-C6 alkoxy-C1-C3 alkoxycarbonyl, $OR_{15}$, —(C1-C3)alkyl-$OR_{15}$, $C(O)R_{16}$, —(C1-C3)alkyl-$C(O)R_{16}$, $C(O)OR_{16}$, —(C1-C3)alkyl-$C(O)OR_{16}$, $S(O)_mR_{16}$, —(C1-C3)alkyl-$S(O)_mR_{16}$, —$N(R_{16})_2$, —$NHR_{16}$, —$C(O)NHR_{16}$, —$C(O)N(R_{16})_2$, —$NHC(O)R_{17}$, heterocyclyl, heterocyclyl-C1-C3 alkyl, heterocyclyloxy, heterocyclylcarbonyl, aryl, aryl-C1-C3 alkyl, aryloxy, arylcarbonyl, heteroaryl, heteroaryl-C1-C3 alkyl, heteroaryloxy, or heteroarylcarbonyl;

$R_{12}$ represents hydrogen, C1-C6 alkyl which is unsubstituted or substituted with a substituent selected from $R_{18}$, C3-C6 cycloalkyl, halogenated C3-C6 cycloalkyl, C2-C6 alkenyl, halogenated C2-C6 alkenyl, C2-C6 alkynyl, halogenated C2-C6 alkynyl, C3-C6 cycloalkenyl, C1-C6 alkoxy-C1-C3 alkyl, C1-C6 alkylthio-C1-C3 alkyl, C1-C6 alkoxycarbonyl-C1-C3 alkyl, aryl, or aryl-C1-C3 alkyl;

when M is

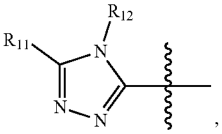
,

—$(CH_2)_4$— or —CH=CH—CH=CH— formed by $R_{11}$ and $R_{12}$, the nitrogen atom bound to $R_{12}$ and the carbon atom bound to $R_{11}$ together form a 6-membered ring;

$R_{15}$ represents C1-C6 alkyl which is unsubstituted or substituted with a substituent selected from $R_{21}$, C3-C6 cycloalkyl, halogenated C3-C6 cycloalkyl, C2-C6 alkenyl, halogenated C2-C6 alkenyl, C2-C6 alkynyl, halogenated C2-C6 alkynyl, C3-C6 cycloalkenyl, or phenyl;

$R_{16}$ represents C1-C6 alkyl, halogenated C1-C6 alkyl, C3-C6 cycloalkyl, C2-C6 alkenyl, halogenated C2-C6 alkenyl, C2-C6 alkynyl, halogenated C2-C6 alkynyl, or C3-C6 cycloalkenyl;

$R_{21}$ represents halogen, cyano, C3-C6 cycloalkyl, hydroxy, mercapto, C1-C6 alkoxy, $C(O)R_{22}$, carboxyl, C1-C6 alkoxycarbonyl, C1-C6 alkoxy-C1-C3 alkoxycarbonyl, —$S(O)_m$—(C1-C6)alkyl, heteroaryl, heterocyclyl, or phenyl which is unsubstituted or substituted with 1-3 groups selected from $R_{23}$;

$R_{17}$, and $R_{22}$ each independently represent hydrogen, C1-C6 alkyl, or $N(R_{24})R_{25}$;

$R_{23}$ represents halogen, cyano, nitro, C1-C6 alkyl, C1-C6 alkyl which is unsubstituted or substituted with a substituent selected from $R_{31}$, C3-C6 cycloalkyl, halogenated C3-C6 cycloalkyl, C2-C6 alkenyl, halogenated C2-C6 alkenyl, C2-C6 alkynyl, halogenated C2-C6 alkynyl, C3-C6 cycloalkenyl, C1-C6 alkylcarbonyl, C3-C6 cycloalkylcarbonyl, halogenated C1-C6 alkylcarbonyl, halogenated C3-C6 cycloalkylcarbonyl, C1-C6 alkoxycarbonyl, halogenated C1-C6 alkoxycarbonyl, C1-C6 alkylaminocarbonyl, halogenated C1-C6 alkylaminocarbonyl, bis(C1-C6 alkyl)aminocarbonyl, $OR_{32}$, $S(O)_mR_{33}$, C1-C6 alkylaminosulfonyl, bis(C1-C6 alkyl)aminosulfonyl, $NH_2$, C1-C6 alkylamino, bis(C1-C6 alkyl)amino, aryl, heteroaryl, or heterocyclyl;

$R_{24}$, and $R_{25}$ each independently represent hydrogen, C1-C6 alkyl, or phenyl; or, C2-C6 alkylidene chain formed by $R_{24}$ and $R_{25}$, and the nitrogen atom(s) bound to $R_{24}$ and $R_{25}$ together form a 3-7-membered ring, said C2-C6 alkylidene chain optionally contains one O, S, S(O), $S(O)_2$, NH, or N-alkyl and optionally substituted by oxo or thio group;

$R_{13}$, $R_{14}$, $R_{18}$, and $R_{31}$ each independently represent halogen, cyano, nitro, carboxyl, C1-C6 alkoxycarbonyl, C1-C6 alkoxy-C1-C6 alkoxycarbonyl, $S(O)_mR_{41}$, $OR_{42}$, aryl, heteroaryl, or heterocyclyl;

$R_{32}$ represents hydrogen, C1-C6 alkyl, halogenated C1-C6 alkyl, C3-C6 cycloalkyl, halogenated C3-C6 cycloalkyl, C2-C6 alkenyl, halogenated C2-C6 alkenyl, C2-C6 alkynyl, halogenated C2-C6 alkynyl, or C3-C6 cycloalkenyl;

$R_{33}$ represents C1-C6 alkyl, halogenated C1-C6 alkyl, C3-C6 cycloalkyl, C2-C6 alkenyl, halogenated C2-C6 alkenyl, C2-C6 alkynyl, halogenated C2-C6 alkynyl, or $R_{41}$, and $R_{42}$ each independently represent hydrogen, C1-C6 alkyl, halogenated C1-C6 alkyl, C3-C6 cycloalkyl, halogenated C3-C6 cycloalkyl, C2-C6 alkenyl, halogenated C2-C6 alkenyl, C2-C6 alkynyl, halogenated C2-C6 alkynyl, C3-C6 cycloalkenyl, or phenyl;

r represents 1, or 2;

m represents 0, 1, or 2;

n represents 0, or 1;

s represents 0, 1, 2, or 3;

wherein, the "heterocyclyl" is

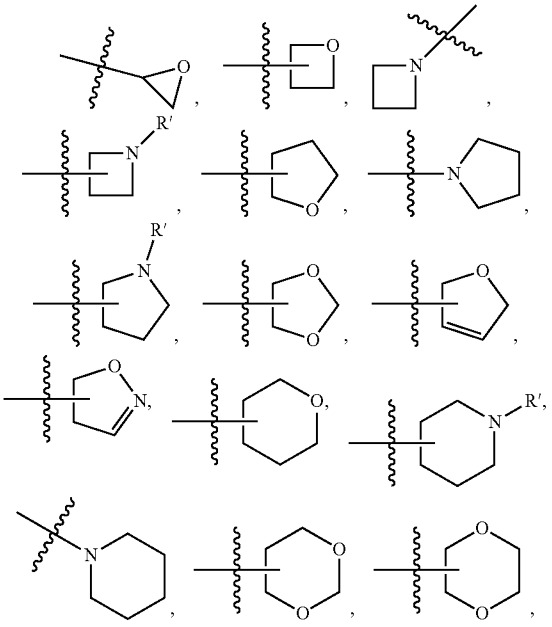

-continued
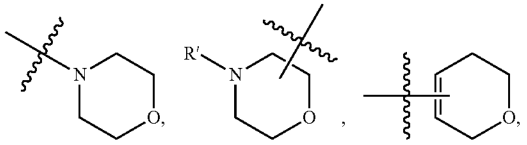
or
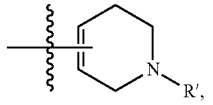
which has 0, 1, or 2 oxo groups; the "aryl" is phenyl, napthyhl,
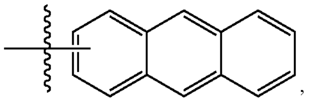
or
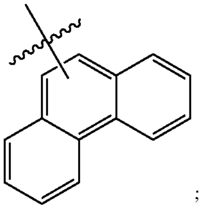
;
the "heteroaryl" is
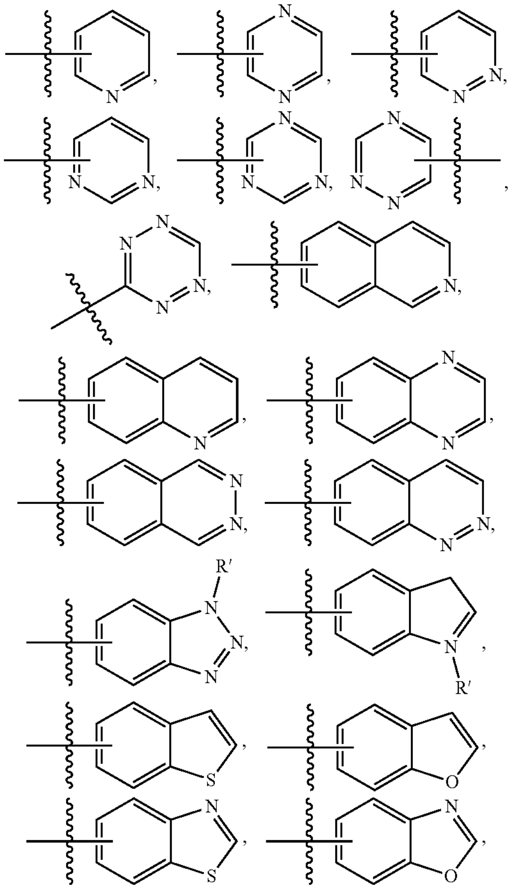
-continued
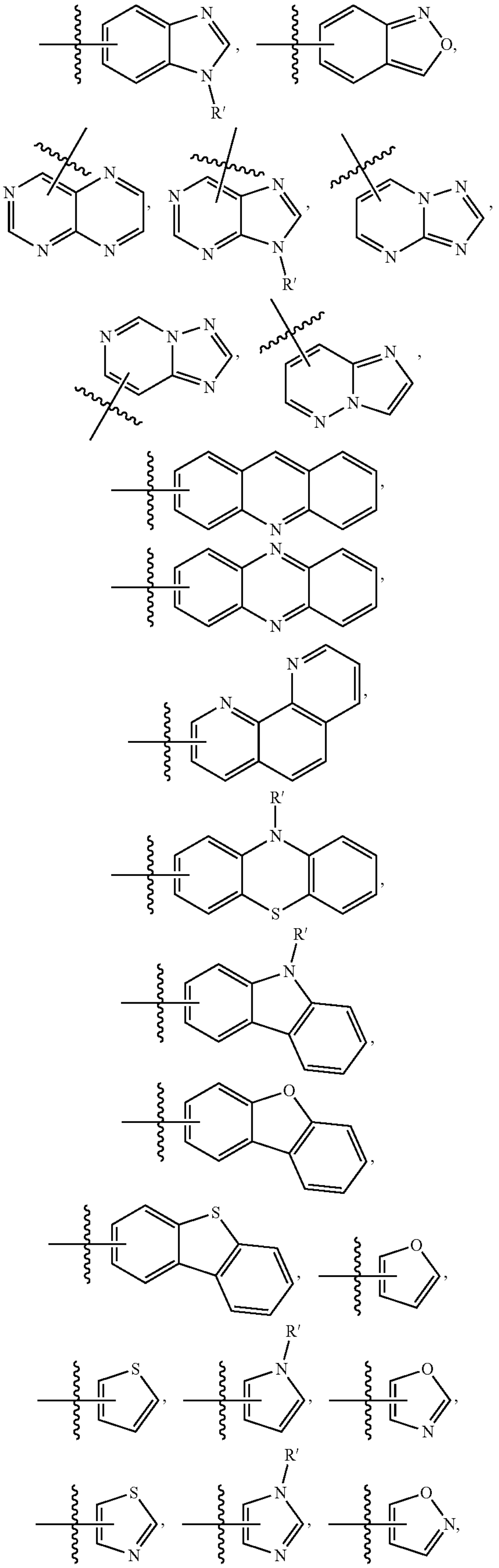

-continued

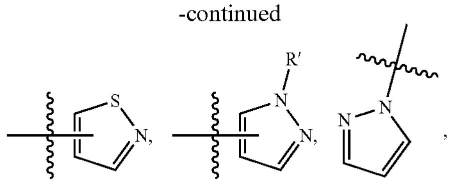

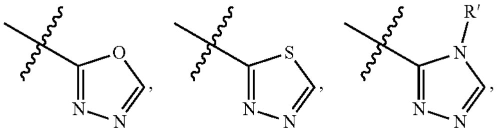

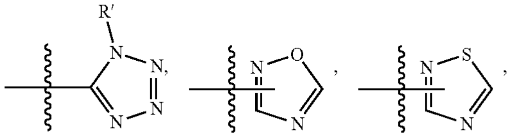

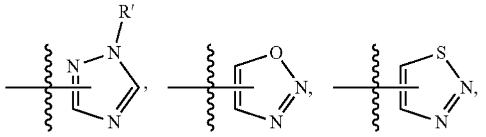

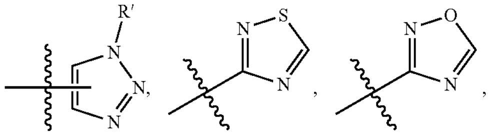

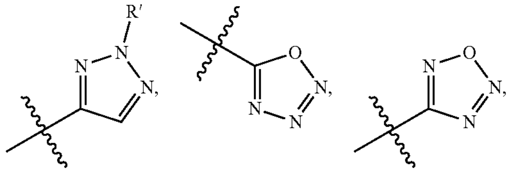

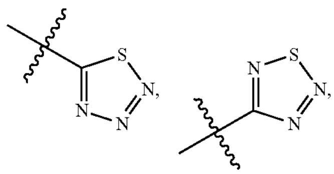

or

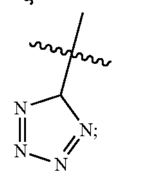

above-mentioned groups are respectively unsubstituted or substituted by 1-3 groups selected from: halogen, nitro, cyano, thiocyano, cyano C1-C6 alkyl, mercapto, hydroxy, hydroxy C1-C6 alkyl, carboxyl, formyl;

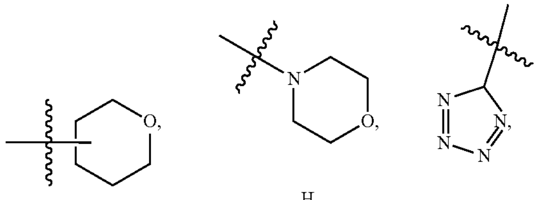

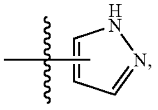

phenyl, or benzyl group, which is unsubstituted or substituted by 1-3 groups selected from halogen, hydroxy, nitro, cyano, amino, carboxyl, C1-C6 alkyl with or without halogen, C2-C6 alkenyl with or without halogen, C2-C6 alkynyl with or without halogen, C3-C6 cycloalkyl with or without halogen, C1-C6 alkoxy with or without halogen, C1-C6 alkoxycarbonyl with or without halogen, C1-C6 alkylacyl with or without halogen, C1-C6 alkylacyloxy with or without halogen, C1-C6 alkylamino with or without halogen, and C1-C6 alkylsulfonyl with or without halogen; C1-C6 alkyl, C2-C6 alkenyl, C2-C6 alkynyl, C3-C6 cycloalkyl, C3-C6 cycloalkyl-C1-C6 alkyl, C3-C6 cycloalkyl substituted by C1-C6 alkyl, OR", SR", —(C1-C6) alkyl —OR", —O—(C1-C6) alkyl —OR", —(C1-C6) alkyl —SR", COR", —(C1-C6) alkyl —COR", —O—(C1-C6) alkyl —COR", COOR", —(C1-C6) alkyl —COOR", —O—(C1-C6) alkyl —COOR", COSR", SOR", $SO_2R$", —O—$SO_2R$", —(C1-C6) alkyl —$SO_2R$", OCOR", —(C1-C6) alkyl —OCOR", or SCOR" group, which is with or without halogen; and amino, aminoalkyl, aminocarbonyl, or aminosulfonyl group, which is unsubstituted or substituted by one or two groups selected from R", COR", COOR", $SO_2R$", and OR", wherein the R", COR", COOR", $SO_2R$", or OR" is with or without halogen; or, two adjacent substitutable positions of the above-mentioned "heterocyclyl", "aryl", "heteroaryl" groups are linked with —$OCH_2CH_2$—, —$OCH_2O$—, —$OCH_2CH_2O$—, or —CH═CH—CH═CH— group to form a ring, wherein the —$OCH_2CH_2$—, —$OCH_2O$—, —$OCH_2CH_2O$—, or —CH═CH—CH═CH— group is with or without halogen;

R' each independently represents hydrogen, nitro, hydroxy, amino; C1-C6 alkyl, C2-C6 alkenyl, C2-C6 alkynyl, C3-C6 cycloalkyl, C3-C6 cycloalkenyl, C3-C6 cycloalkyl-C1-C6 alkyl,

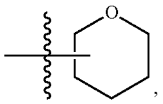

C1-C6 alkoxy, C2-C6 alkenyloxy, C2-C6 alkynyloxy, C3-C6 cycloalkyloxy, C1-C6 alkoxy-C1-C6 alkyl, C1-C6 alkoxycarbonyl, C1-C6 alkyithiocarbonyl, C1-C6 alkylsulfonyl, C1-C6 alkylsulfonyl-C1-C6 alkyl, C1-C6 alkylcarbonyl, C1-C6 alkylcarbonyl-C1-C6 alkyl, C1-C6 alkylacyloxy, C1-C6 alkylamino, C1-C6 alkylaminocarbonyl, C1-C6 alkoxyaminocarbonyl, C1-C6 alkoxycarbonyl-C1-C6 alkyl, C1-C6 alkylaminocarbonyl-C1-C6 alkyl, tri (C1-C6 alkyl)silyl, or di(C1-C6 alkyl)phosphonyl, which is with or without halogen; or phenyl, or benzyl which is unsubstituted or substituted by 1-3 groups selected from halogen, hydroxy, nitro, cyano, amino, carboxyl, C1-C6 alkyl with or without halogen, C2-C6 alkenyl with or without halogen, C2-C6 alkynyl with or without halogen, C3-C6 cycloalkyl with or without halogen, C1-C6 alkoxy with or without halogen, C1-C6 alkoxycarbonyl with or without halogen, C1-C6 alkylacyl with or without halogen, C1-C6 alkylacyloxy with or without halogen, C1-C6 alkylamino with or without halogen, and C1-C6 alkylsulfonyl with or without halogen;

R" each independently represents C1-C6 alkyl, C2-C6 alkenyl, C2-C6 alkynyl, C3—C6 cycloalkyl, C3-C6 cycloalkyl-C1-C6 alkyl, C3-C6 cycloalkenyl; or

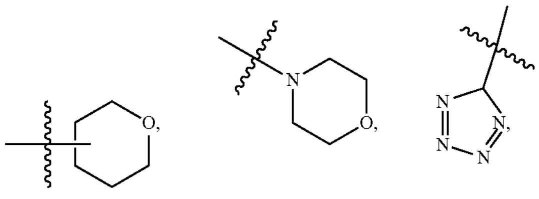

phenyl, or benzyl which is unsubstituted or substituted by 1-3 groups selected from halogen, hydroxy, nitro, cyano, amino, carboxyl, C1-C6 alkyl with or without halogen, C2-C6 alkenyl with or without halogen, C2-C6 alkynyl with or without halogen, C3-C6 cycloalkyl with or without halogen, C1-C6 alkoxy with or without halogen, C1-C6 alkoxycarbonyl with or without halogen, C1-C6 alkylacyl with or without halogen, C1-C6 alkylacyloxy with or without halogen, C1-C6 alkylamino with or without halogen, and C1-C6 alkylsulfonyl with or without halogen.

4. The 4-pyridinyl formamide compound or derivative thereof according to claim 1, wherein:

X represents halogen, nitro, cyano, $OR^1$, $S(O)_mR^2$, $NR^3COR^1$, $NR^4R^5$,

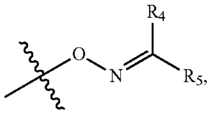

C1-C6 alkoxy-C1-C3 alkyl; C1-C6 alkyl, C2-C6 alkenyl, C2-C6 alkynyl, or C3-C6 cycloalkyl, which is with or without halogen;

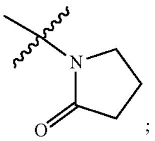 [SMILES: *N1CCCC1=O]

;

or phenyl which is unsubstituted or substituted with 1, 2, or 3 groups selected from halogen, and C1-C6 alkoxy;

Y represents C1-C6 alkyl, C2-C6 alkenyl, C2-C6 alkynyl, C3-C6 cycloalkyl, or C3-C6 cycloalkenyl, which is with or without halogen; $OR^1$, $S(O)_mR^2$, $NR^4R^5$, heterocyclyl, aryl, or heteroaryl;

$R^1$, $R^3$, $R^4$, and $R^5$ each independently represent hydrogen, C1-C6 alkyl, halogenated C1-C6 alkyl, phenyl; or benzyl which is unsubstituted or substituted with 1, 2, or 3 groups selected from halogen, and C1-C6 alkoxy;

$R^2$ represents C1-C6 alkyl, or halogenated C1-C6 alkyl;

M represents

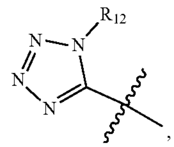
,
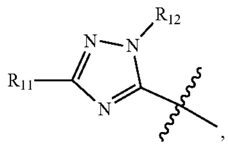
,
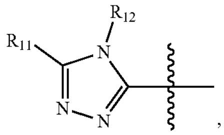
,
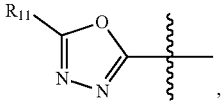
,
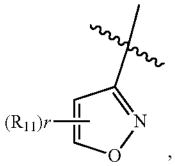
, or
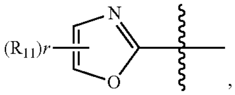
, which is unsubstituted or substituted;

$R_{11}$ represents hydrogen, C1-C6 alkyl, C3-C6 cycloalkyl, halogenated C1-C6 alkyl, C1-C6 alkoxy, C1-C6 alkylthio, halogen, C1-C6 alkylamino, bis(C1-C6 alkyl) amino, cyano, nitro, C1-C6 alkylcarbonyl, C1-C6 alkoxycarbonyl, C1-C6 alkoxycarbonyl-C1-C3 alkyl, aminocarbonyl, C1-C6 alkylcarbonylamino, C1-C6 alkoxy-C1-C3 alkyl, C1-C6 alkylthio-C1-C3 alkyl, C1-C6 alkylsulfinyl-C1-C3 alkyl, C1-C6 alkylsulfonyl-C1-C3 alkyl; or benzyl, phenoxy, benzoyl, pyridyl,

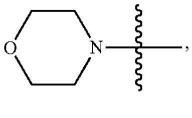
,
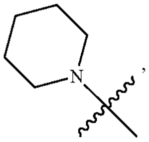
,
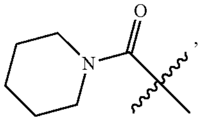
,
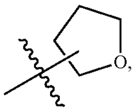
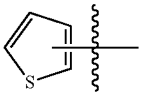
,
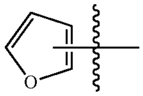
,
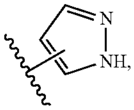
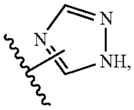
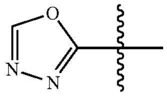
,
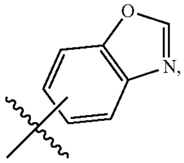
or
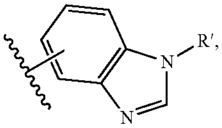

which is unsubstituted or substituted with 1, 2, or 3 groups selected from halogen, and C1-C6 alkoxy;

$R_{12}$ represents hydrogen, C1-C6 alkyl, C2-C6 alkenyl, C1-C6 alkoxy-C1-C3 alkyl, C1-C6 alkylthio-C1-C3 alkyl, C1-C6 alkoxycarbonyl-C1-C3 alkyl; or phenyl, or benzyl which is unsubstituted or substituted with at least one group selected from halogen, and halogenated C1-C6 alkyl;

r represents 1, or 2;

m represents 0, 1, or 2;

wherein, the "heterocyclyl" is

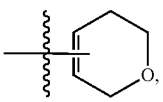
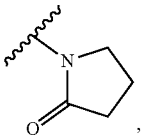
, or
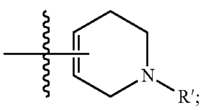

the aryl is phenyl, naphthyl, or
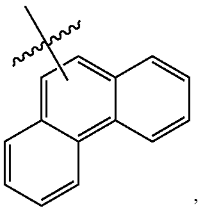
which is unsubstituted or substituted; the "heteroaryl" is
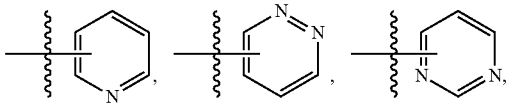
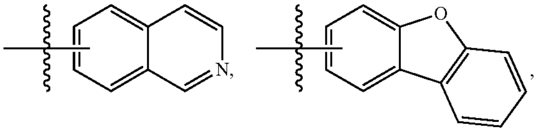
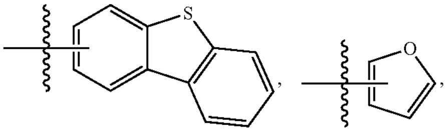
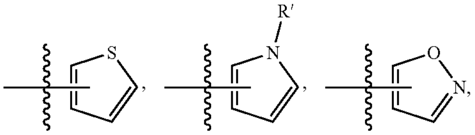
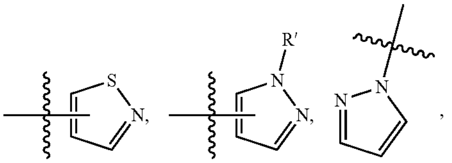
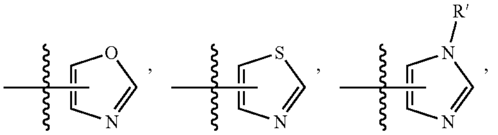
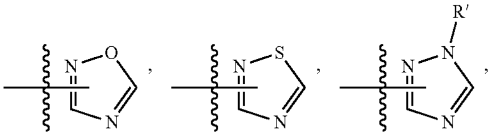
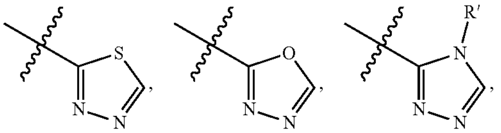
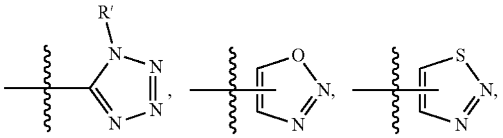
-continued
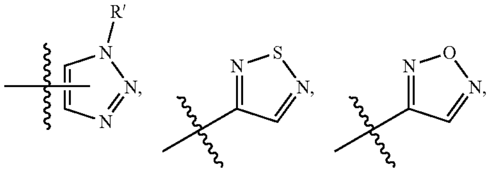
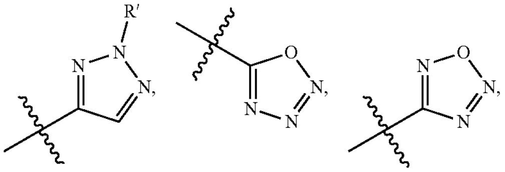
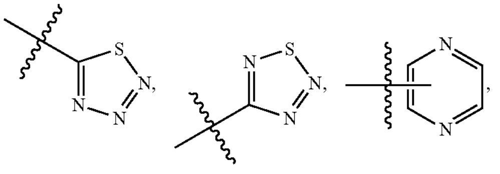
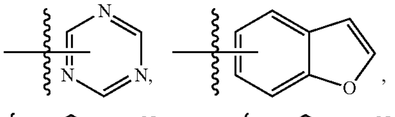
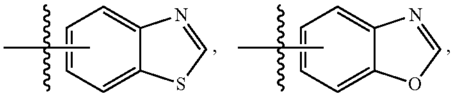
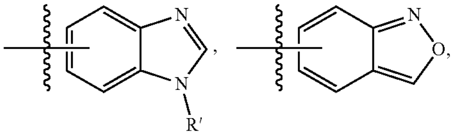
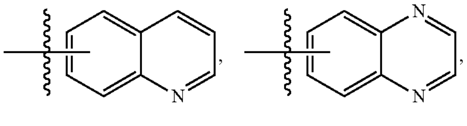
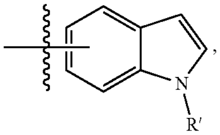
or
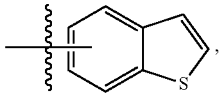
which is unsubstituted or substituted; the aforementioned "substituted" respectively refers to being substituted by 1-3 groups selected from: halogen, nitro, cyano, thiocyano, cyano C1-C3 alkyl, hydroxy, hydroxy C1-C3 alkyl, mercapto, carboxyl, formyl,
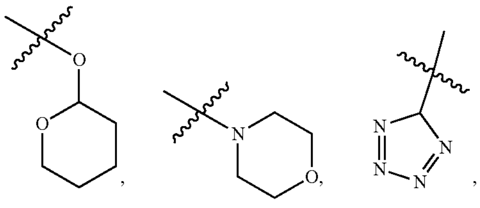

-continued

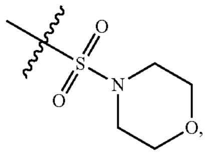

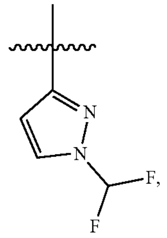

phenyl, phenyl substituted by C1-C6 alkyl, phenoxy, benzyloxy; amino, aminoalkyl, or aminocarbonyl group which is unsubstituted or substituted by one or two groups selected from C1-C6 alkyl, COR", and COOR"; and C1-C6 alkyl, C2-C6 alkenyl, C3-C6 cycloalkyl, C1-C6 alkoxy-C1-C3 alkyl, C1-C6 alkylthio-C1-C3 alkyl, C1-C6 alkylcarbonylthio, C3-C6 cycloalkyl substituted with C1-C6 alkyl, OR", SR", SOR", COR", COOR", or $SO_2R$", which is with or without halogen; or, two adjacent substitutable positions of the above-mentioned "heterocyclyl", "aryl", "heteroaryl" groups are linked with $—OCH_2CH_2—$, $—OCH_2O—$, $—OCH_2CH_2O—$, or —CH═CH—CH═CH— group to form a ring, wherein the $—OCH_2CH_2—$, $—OCH_2O—$, $—OCH_2CH_2O—$, or —CH═CH—CH═CH— group, which is with or without halogen;

R' each independently represents hydrogen, C1-C6 alkyl, C1-C6 alkylcarbonyl, halogenated C1-C6 alkyl,

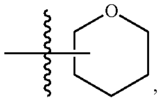

C1-C6 alkoxycarbonyl, C1-C6 alkoxy-C1-C3 alkyl, or benzyl;

R" each independently represents C1-C6 alkyl, or C2-C6 alkenyl;

wherein, when X is fluorine, Y is not amino, monomethylamino, monoethylamino and monopropylamino; when M is

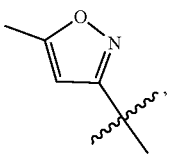 [SMILES: *c1cc(C)on1]

X and Y are not methyl at the same time.

5. The 4-pyridinyl formamide compound or derivative thereof according to claim 1, wherein:

X represents chlorine, fluorine, bromine, methyl, ethyl, isopropyl, vinyl, allyl, ethynyl, cyclopropyl, trifluoromethyl,

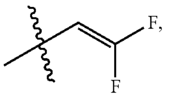 [SMILES: *C=C(F)F]

hydroxy, methoxy, ethyloxy, methylthio, ethylthio,

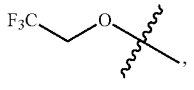

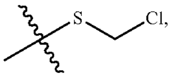

nitro, cyano, methylsulfinyl, ethylsulfinyl, methylsulfonyl, amino, monomethylamino, dimethylamino, acetamido,

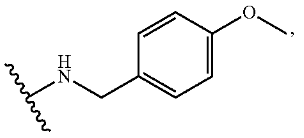

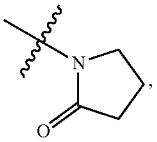

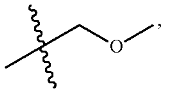

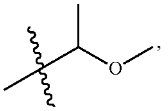

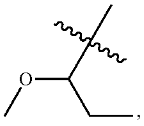

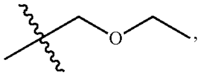

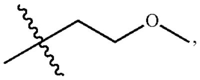

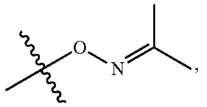

phenyl, phenoxy, or 4-fluorophenyl;

Y represents methyl, ethyl, vinyl, methoxy,

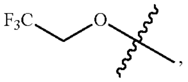

phenoxy, benzyloxy, methylthio, propylthio, tert-butylthio, benzylthio, 4-methoxybenzylthiol, propylsulfinyl, amino, monomethylamino, dimethylamino, anilino, p-methoxybenzylamino, tert-butyl, cyclopropyl, cyclohexyl,

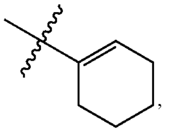 [SMILES: *C1=CCCCC1]

heterocyclyl, aryl, or heteroaryl;

M represents

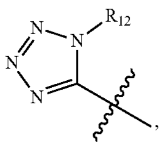

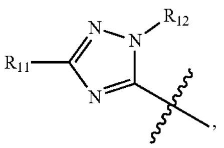

-continued

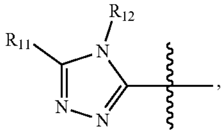, 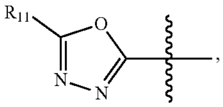,

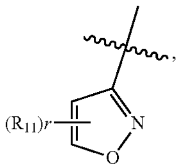, or 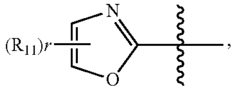, which is unsubstituted or substituted;

$R_{11}$ each independently represents hydrogen, methyl, ethyl, n-propyl, isopropyl, cyclopropyl, monochloromethyl, trifluoromethyl, methoxy, isopropyloxy, methylthio, fluorine, chlorine, bromine, iodine, dimethylamino, ethylamino, cyano, nitro, acetyl, methoxycarbonyl; phenyl which is unsubstituted or substituted by 1, 2, or 3 groups selected from chlorine, and methoxy; pyridyl,

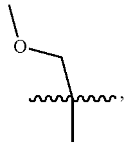, 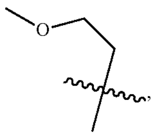, 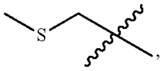,

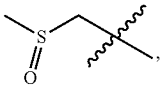, 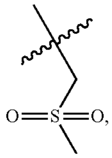, 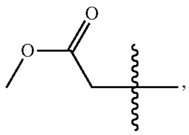,

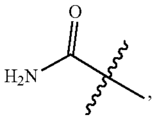, 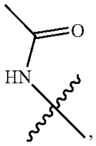, 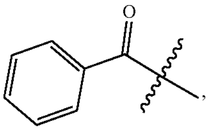,

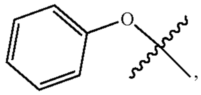, 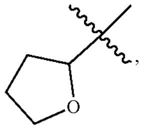, 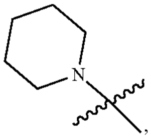,

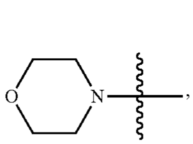, 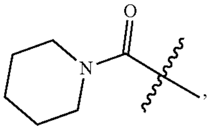, 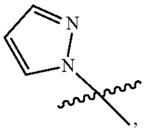,

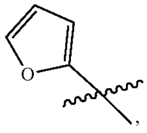, 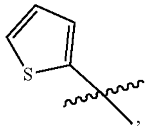, 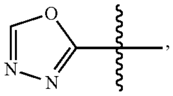,

-continued

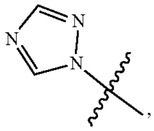, 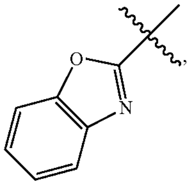, or

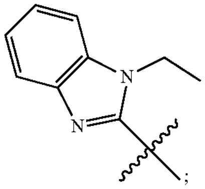;

$R_{12}$ each independently represents hydrogen, methyl, ethyl, n-propyl, isopropyl, allyl,

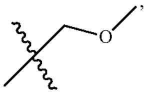, 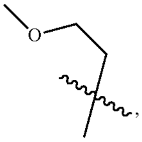, 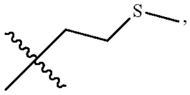,

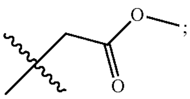;

or phenyl, or benzyl which is unsubstituted or substituted by 1, 2, or 3 groups selected from chlorine, and trifluoromethyl;

r represents 1, or 2;

wherein, the "heterocyclyl" is

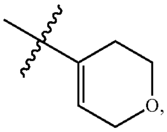, 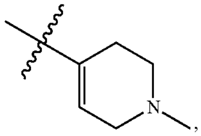,

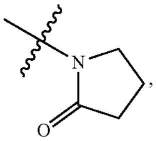, 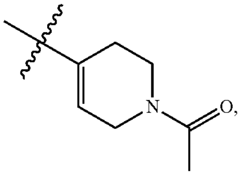, or

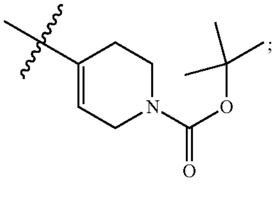;

the "aryl" is phenyl, naphthyl, or

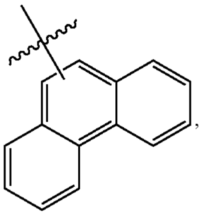, which is unsubstituted or substituted; the "heteroaryl" is

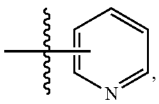, 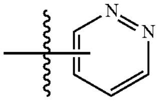, 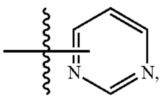,

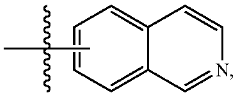, 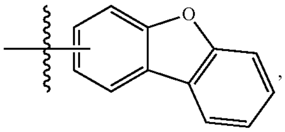,

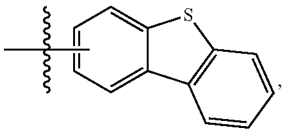, 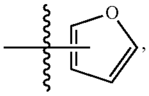,

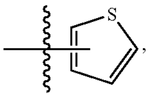, 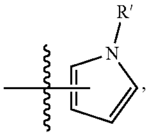, 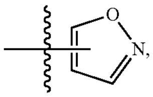,

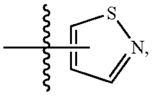, 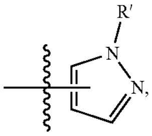, 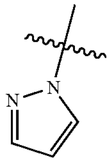,

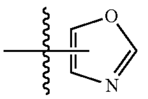, 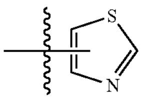, 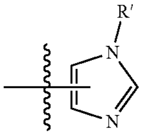,

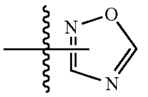, 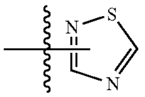, 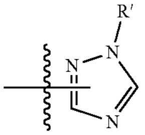,

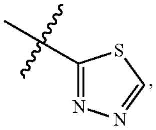, 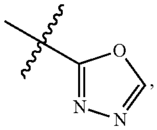, 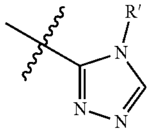,

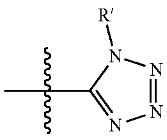, 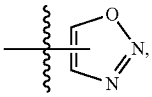, 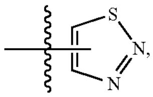,

-continued

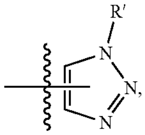, 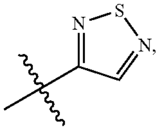, 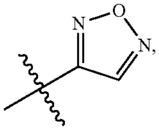,

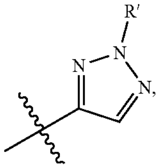, 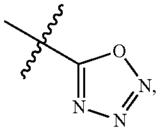, 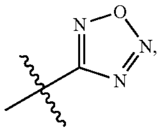,

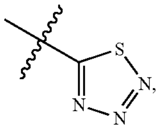, 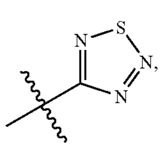, 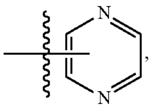,

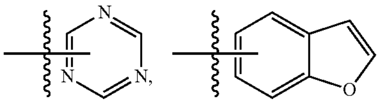,

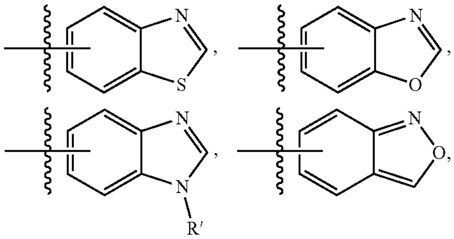,

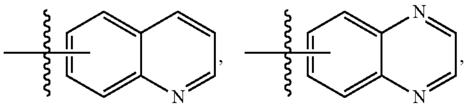,

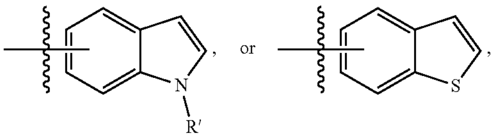, which is unsubstituted or substituted; the aforementioned "substituted" refers to being substituted by 1, 2, or 3 groups selected from: methyl, ethyl, isopropyl, n-butyl, tert-butyl, n-pentyl, vinyl, cyclopropyl,

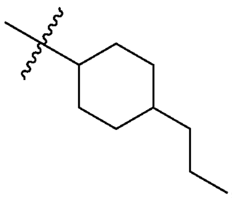, fluorine, chlorine, bromine, iodine, monobromomethyl, difluoromethyl, trifluoromethyl, methoxy, ethoxy, propoxy, butoxy, trifluoromethoxy, hydroxyl, hydroxymethyl, amino, cyano, cyanomethyl, thiocyano, mercapto, nitro, carboxy, formyl, acetyl, methoxycarbonyl, tert-butyloxycarbonyl, methylthio, isopropylthio, methylsulfinyl, methylsulfonyl,

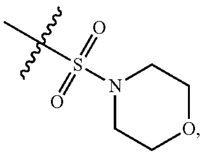 [SMILES: *S(=O)(=O)N1CCOCC1]

dimethylamino, aminocarbonyl, dimethylaminocarbonyl, acetylamino,

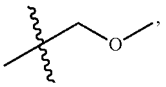
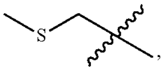
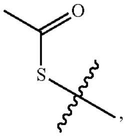
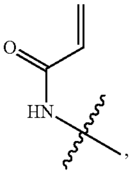
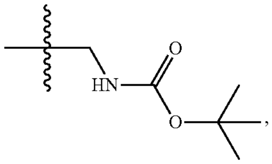
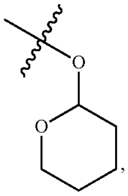
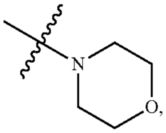
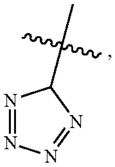
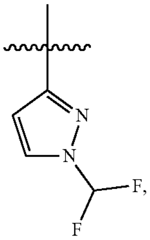

phenyl, 4-ethylphenyl, phenoxy, and benzyloxy; or, two adjacent substitutable positions of the above-mentioned “aryl”, “heteroaryl” groups are linked with —$OCH_2CH_2$—, —$OCH_2O$—, —$OCH_2CH_2O$—, or —CH═CH—CH═CH— group to form a ring, wherein the —$OCH_2CH_2$—, —$OCH_2O$—, —$OCH_2CH_2O$—, or —CH═CH—CH═CH— group is with or without halogen;

R' each independently represents hydrogen, methyl, ethyl, n-propyl, isopropyl, difluoromethyl, 3,3,3-trifluoroethyl, benzyl,

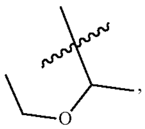
or
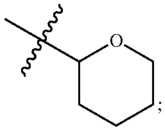

wherein, when X is fluorine, Y is not amino and monomethylamino; when M is

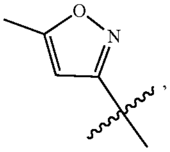 [SMILES: *c1cc(C)on1]

X and Y are not methyl at the same time.

6. The 4-pyridinyl formamide compound or derivative thereof according to claim 1, wherein the compound is selected from the follows:

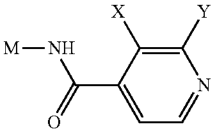

I

| NO. | X | Y | M |
|---|---|---|---|
| 1-1 | Cl | $CH_3$ | 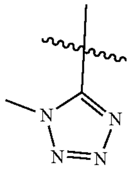 [SMILES: *c1nnnn1C] |

-continued
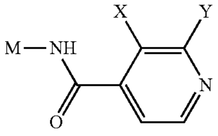
I
| NO. | X | Y | M |
|---|---|---|---|
| 1-2 | Cl | 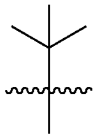 | 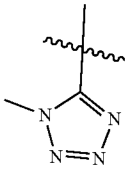 [SMILES: *c1nnnn1C] |
| 1-3 | Cl | 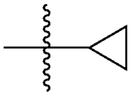 [SMILES: *C1CC1] | 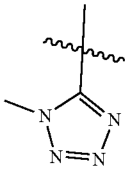 [SMILES: *c1nnnn1C] |
| 1-4 | Cl | 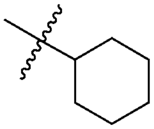 [SMILES: *C1CCCCC1] | 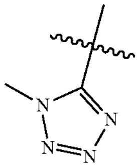 [SMILES: *c1nnnn1C] |
| 1-5 | Cl | 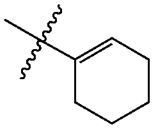 [SMILES: *C1=CCCCC1] | 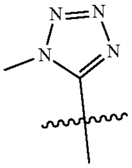 [SMILES: *c1nnnn1C] |
| 1-6 | Cl | 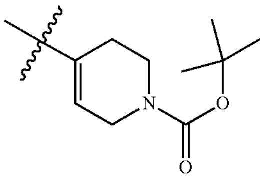 [SMILES: *C1=CCN(C(=O)OC(C)(C)C)CC1] | 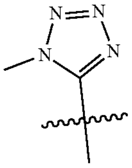 [SMILES: *c1nnnn1C] |
| 1-7 | Cl | 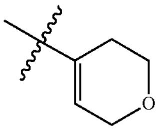 [SMILES: *C1=CCOCC1] | 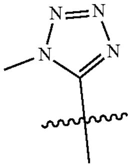 [SMILES: *c1nnnn1C] |
| 1-8 | Cl | 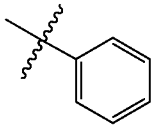 [SMILES: *c1ccccc1] | 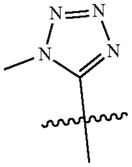 [SMILES: *c1nnnn1C] |

-continued
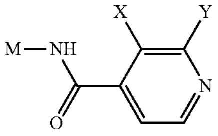
I
| NO. | X | Y | M |
|---|---|---|---|
| 1-9 | Cl | 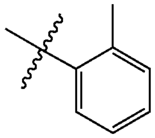 [SMILES: *c1ccccc1C] | 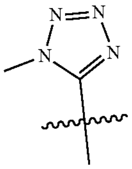 [SMILES: *c1nnnn1C] |
| 1-10 | Cl | 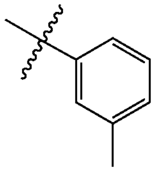 [SMILES: *c1cccc(C)c1] | 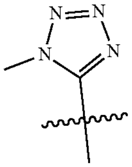 [SMILES: *c1nnnn1C] |
| 1-11 | Cl | 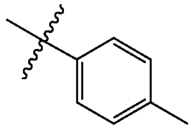 [SMILES: *c1ccc(C)cc1] | 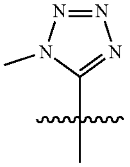 [SMILES: *c1nnnn1C] |
| 1-12 | Cl | 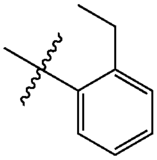 [SMILES: *c1ccccc1CC] | 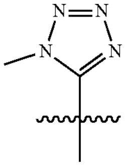 [SMILES: *c1nnnn1C] |
| 1-13 | Cl | 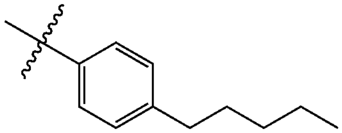 [SMILES: *c1ccc(CCCCC)cc1] | 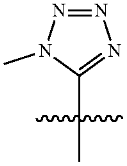 [SMILES: *c1nnnn1C] |
| 1-14 | Cl | 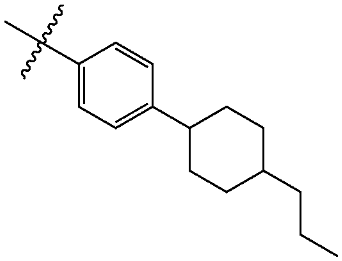 [SMILES: *c1ccc(C2CCC(CCC)CC2)cc1] | 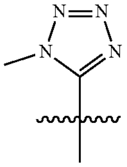 [SMILES: *c1nnnn1C] |
| 1-15 | Cl | 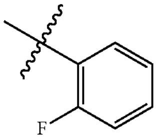 [SMILES: *c1ccccc1F] | 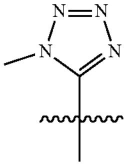 [SMILES: *c1nnnn1C] |

-continued
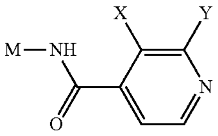
I
| NO. | X | Y | M |
|---|---|---|---|
| 1-16 | Cl | 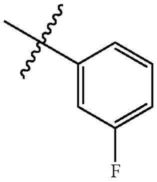 [SMILES: *c1cccc(F)c1] | 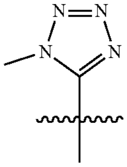 [SMILES: *c1nnnn1C] |
| 1-17 | Cl | 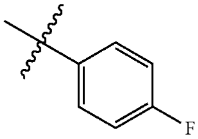 [SMILES: *c1ccc(F)cc1] | 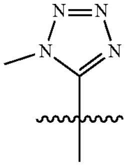 [SMILES: *c1nnnn1C] |
| 1-18 | Cl | 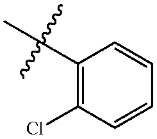 [SMILES: *c1ccccc1Cl] | 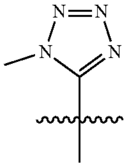 [SMILES: *c1nnnn1C] |
| 1-19 | Cl | 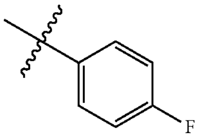 [SMILES: *c1ccc(F)cc1] | 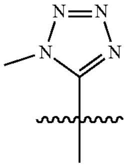 [SMILES: *c1nnnn1C] |
| 1-20 | Cl | 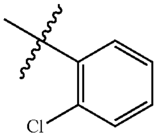 [SMILES: *c1ccccc1Cl] | 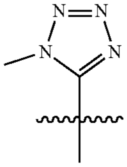 [SMILES: *c1nnnn1C] |
| 1-21 | Cl | 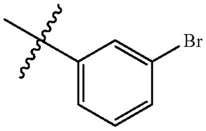 [SMILES: *c1cccc(Br)c1] | 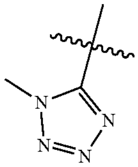 [SMILES: *c1nnnn1C] |
| 1-22 | Cl | 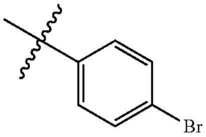 [SMILES: *c1ccc(Br)cc1] | 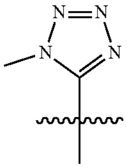 [SMILES: *c1nnnn1C] |

-continued
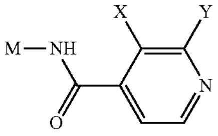
I
| NO. | X | Y | M |
|---|---|---|---|
| 1-23 | Cl | 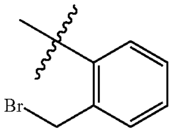 [SMILES: *c1ccccc1CBr] | 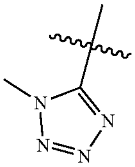 [SMILES: *c1nnnn1C] |
| 1-24 | Cl | 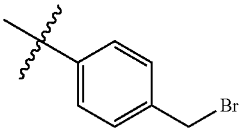 [SMILES: *c1ccc(CBr)cc1] | 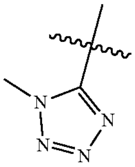 [SMILES: *c1nnnn1C] |
| 1-25 | Cl | 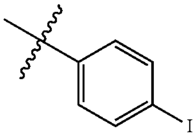 [SMILES: *c1ccc(I)cc1] | 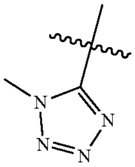 [SMILES: *c1nnnn1C] |
| 1-26 | Cl | 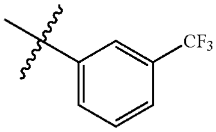 [SMILES: *c1cccc(C(F)(F)F)c1] | 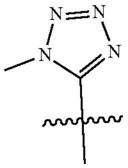 [SMILES: *c1nnnn1C] |
| 1-27 | Cl | 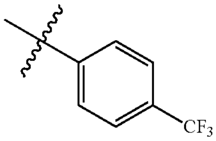 | 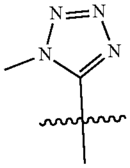 [SMILES: *c1nnnn1C] |
| 1-28 | Cl | 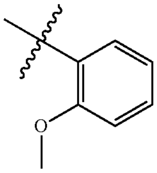 [SMILES: *c1ccccc1OC] | 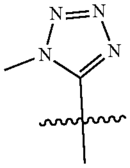 [SMILES: *c1nnnn1C] |
| 1-29 | Cl | 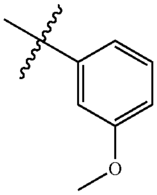 [SMILES: *c1cccc(OC)c1] | 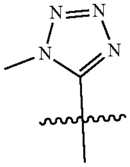 [SMILES: *c1nnnn1C] |

-continued
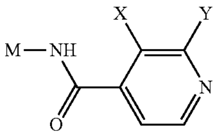
I
| NO. | X | Y | M |
|---|---|---|---|
| 1-30 | Cl | 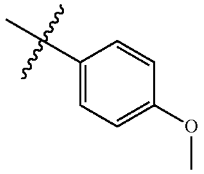 [SMILES: *c1ccc(OC)cc1] | 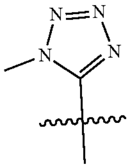 [SMILES: *c1nnnn1C] |
| 1-31 | Cl | 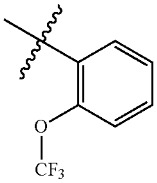 [SMILES: *c1ccccc1OC(F)(F)F] | 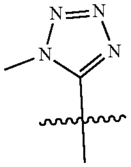 [SMILES: *c1nnnn1C] |
| 1-32 | Cl | 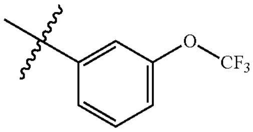 [SMILES: *c1cccc(OC(F)(F)F)c1] | 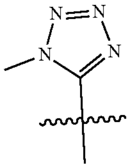 [SMILES: *c1nnnn1C] |
| 1-33 | Cl | 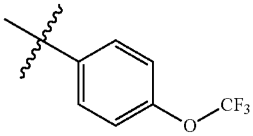 [SMILES: *c1ccc(OC(F)(F)F)cc1] | 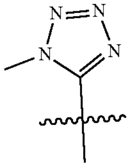 [SMILES: *c1nnnn1C] |
| 1-34 | Cl | 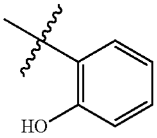 [SMILES: *c1ccccc1O] | 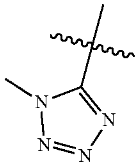 [SMILES: *c1nnnn1C] |
| 1-35 | Cl | 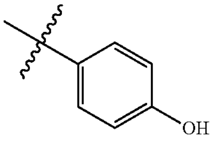 | 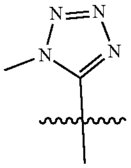 [SMILES: *c1nnnn1C] |
| 1-36 | Cl | 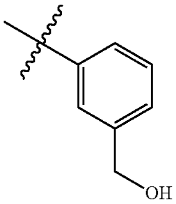 [SMILES: *c1cccc(CO)c1] | 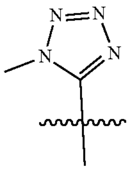 [SMILES: *c1nnnn1C] |

-continued
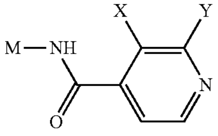
I
| NO. | X | Y | M |
|---|---|---|---|
| 1-37 | Cl | 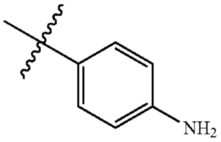 | 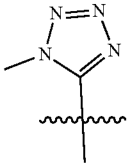 [SMILES: *c1nnnn1C] |
| 1-38 | Cl | 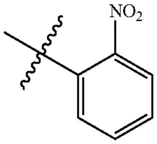 [SMILES: *c1ccccc1[N+](=O)[O-]] | 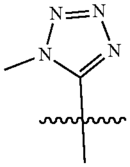 [SMILES: *c1nnnn1C] |
| 1-39 | Cl | 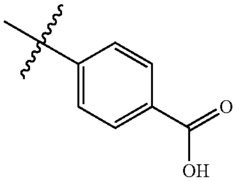 [SMILES: *c1ccc(C(=O)O)cc1] | 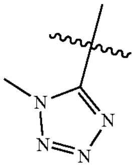 [SMILES: *c1nnnn1C] |
| 1-40 | Cl | 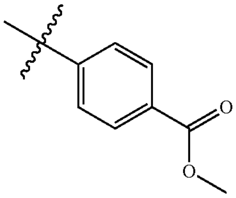 [SMILES: *c1ccc(C(=O)OC)cc1] | 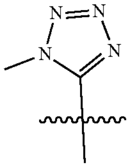 [SMILES: *c1nnnn1C] |
| 1-41 | Cl | 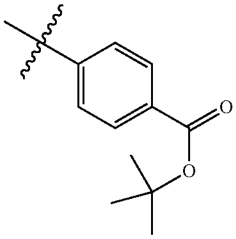 [SMILES: *c1ccc(C(=O)OC(C)(C)C)cc1] | 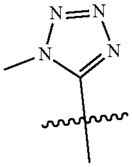 [SMILES: *c1nnnn1C] |
| 1-42 | Cl | 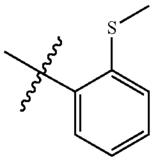 [SMILES: *c1ccccc1SC] | 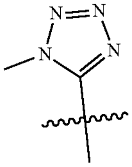 [SMILES: *c1nnnn1C] |
| 1-43 | Cl | 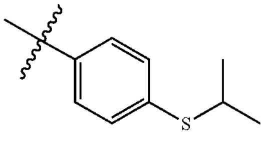 [SMILES: *c1ccc(SC(C)C)cc1] | 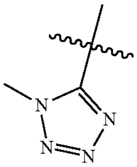 [SMILES: *c1nnnn1C] |

-continued
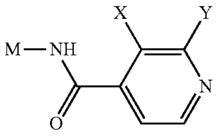
I
| NO. | X | Y | M |
|---|---|---|---|
| 1-44 | Cl | 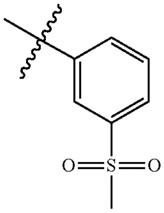 [SMILES: *c1cccc(S(C)(=O)=O)c1] | 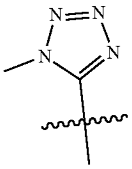 [SMILES: *c1nnnn1C] |
| 1-45 | Cl | 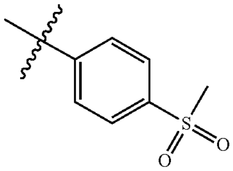 [SMILES: *c1ccc(S(C)(=O)=O)cc1] | 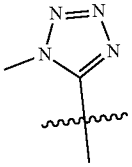 [SMILES: *c1nnnn1C] |
| 1-46 | Cl | 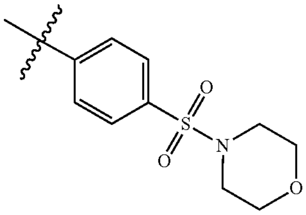 [SMILES: *c1ccc(S(=O)(=O)N2CCOCC2)cc1] | 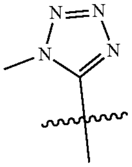 [SMILES: *c1nnnn1C] |
| 1-47 | Cl | 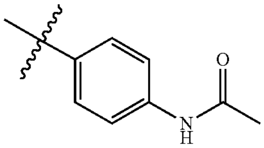 [SMILES: *c1ccc(NC(C)=O)cc1] | 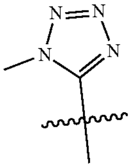 [SMILES: *c1nnnn1C] |
| 1-48 | Cl | 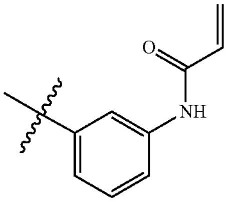 [SMILES: *c1cccc(NC(=O)C=C)c1] | 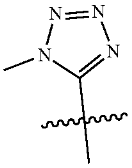 [SMILES: *c1nnnn1C] |
| 1-49 | Cl | 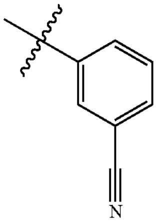 [SMILES: *c1cccc(C#N)c1] | 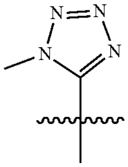 [SMILES: *c1nnnn1C] |

-continued
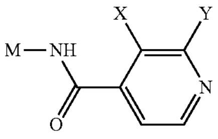
I
| NO. | X | Y | M |
|---|---|---|---|
| 1-50 | Cl | 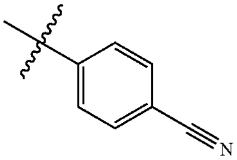 [SMILES: *c1ccc(C#N)cc1] | 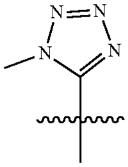 [SMILES: *c1nnnn1C] |
| 1-51 | Cl | 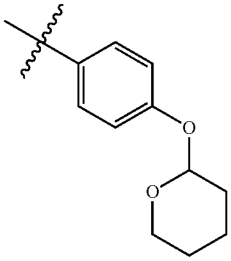 [SMILES: *c1ccc(OC2CCCCO2)cc1] | 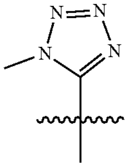 [SMILES: *c1nnnn1C] |
| 1-52 | Cl | 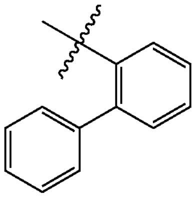 [SMILES: *c1ccccc1-c1ccccc1] | 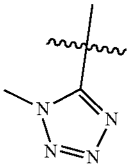 [SMILES: *c1nnnn1C] |
| 1-53 | Cl | 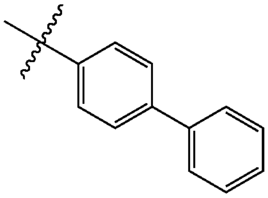 [SMILES: *c1ccc(-c2ccccc2)cc1] | 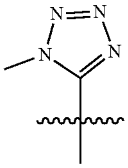 [SMILES: *c1nnnn1C] |
| 1-54 | Cl | 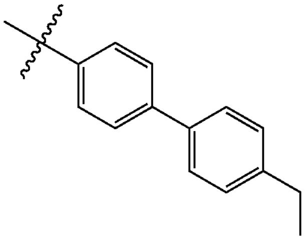 [SMILES: *c1ccc(-c2ccc(CC)cc2)cc1] | 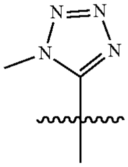 [SMILES: *c1nnnn1C] |
| 1-55 | Cl | 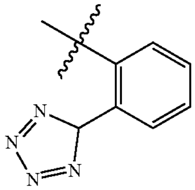 [SMILES: *c1ccccc1C1N=NN=N1] | 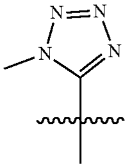 [SMILES: *c1nnnn1C] |

-continued
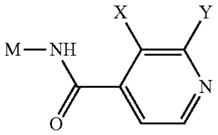
I
| NO. | X | Y | M |
|---|---|---|---|
| 1-56 | Cl | 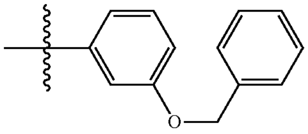 [SMILES: *c1cccc(OCc2ccccc2)c1] | 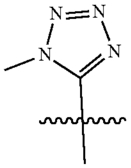 [SMILES: *c1nnnn1C] |
| 1-57 | Cl | 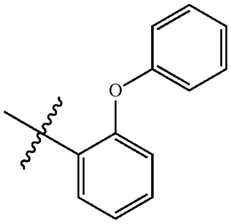 [SMILES: *c1ccccc1Oc1ccccc1] | 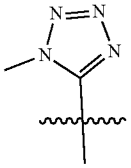 [SMILES: *c1nnnn1C] |
| 1-58 | Cl | 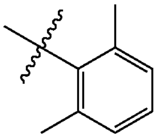 [SMILES: *c1c(C)cccc1C] | 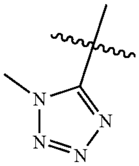 [SMILES: *c1nnnn1C] |
| 1-59 | Cl | 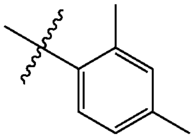 [SMILES: *c1ccc(C)cc1C] | 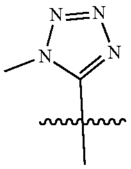 [SMILES: *c1nnnn1C] |
| 1-60 | Cl | 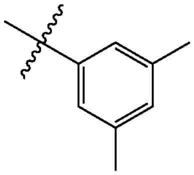 [SMILES: *c1cc(C)cc(C)c1] | 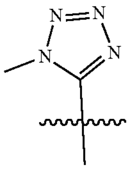 [SMILES: *c1nnnn1C] |
| 1-61 | Cl | 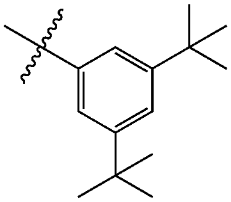 [SMILES: *c1cc(C(C)(C)C)cc(C(C)(C)C)c1] | 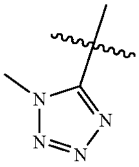 [SMILES: *c1nnnn1C] |
| 1-62 | Cl | 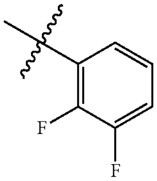 [SMILES: *c1cccc(F)c1F] | 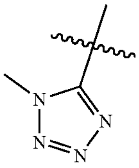 [SMILES: *c1nnnn1C] |

-continued
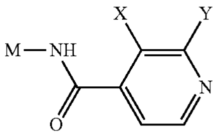
I
| NO. | X | Y | M |
|---|---|---|---|
| 1-63 | Cl | 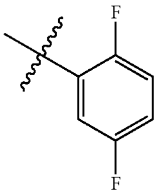 [SMILES: *c1cc(F)ccc1F] | 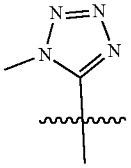 [SMILES: *c1nnnn1C] |
| 1-64 | Cl | 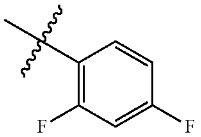 [SMILES: *c1ccc(F)cc1F] | 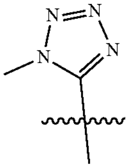 [SMILES: *c1nnnn1C] |
| 1-65 | Cl | 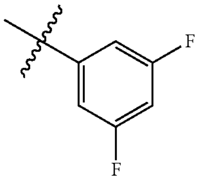 [SMILES: *c1cc(F)cc(F)c1] | 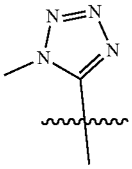 [SMILES: *c1nnnn1C] |
| 1-66 | Cl | 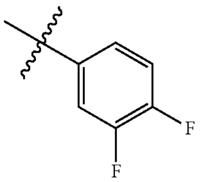 [SMILES: *c1ccc(F)c(F)c1] | 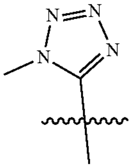 [SMILES: *c1nnnn1C] |
| 1-67 | Cl | 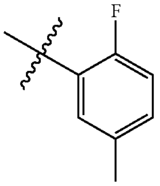 [SMILES: *c1cc(C)ccc1F] | 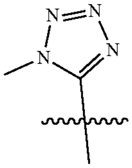 [SMILES: *c1nnnn1C] |
| 1-68 | Cl | 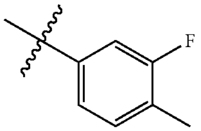 [SMILES: *c1ccc(C)c(F)c1] | 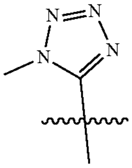 [SMILES: *c1nnnn1C] |
| 1-69 | Cl | 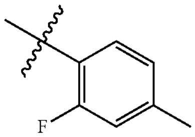 [SMILES: *c1ccc(C)cc1F] | 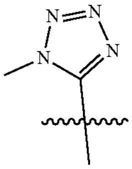 [SMILES: *c1nnnn1C] |

-continued
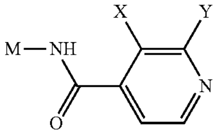
I
| NO. | X | Y | M |
|---|---|---|---|
| 1-70 | Cl | 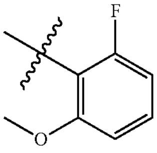 [SMILES: *c1c(F)cccc1OC] | 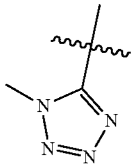 [SMILES: *c1nnnn1C] |
| 1-71 | Cl | 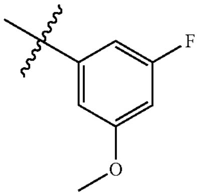 [SMILES: *c1cc(F)cc(OC)c1] | 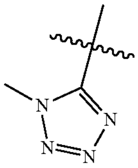 [SMILES: *c1nnnn1C] |
| 1-72 | Cl | 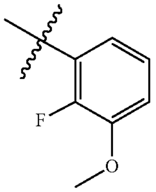 [SMILES: *c1cccc(OC)c1F] | 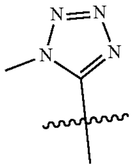 [SMILES: *c1nnnn1C] |
| 1-73 | Cl | 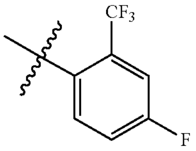 [SMILES: *c1ccc(F)cc1C(F)(F)F] | 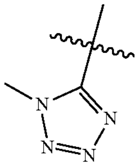 [SMILES: *c1nnnn1C] |
| 1-74 | Cl | 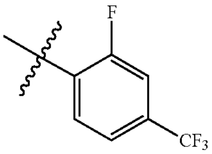 [SMILES: *c1ccc(C(F)(F)F)cc1F] | 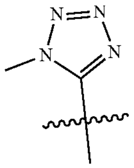 [SMILES: *c1nnnn1C] |
| 1-75 | Cl | 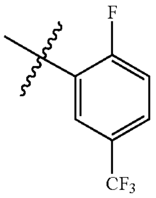 [SMILES: *c1cc(C(F)(F)F)ccc1F] | 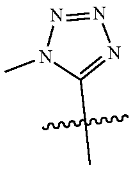 [SMILES: *c1nnnn1C] |
| 1-76 | Cl | 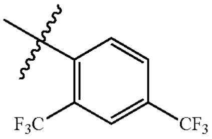 [SMILES: *c1ccc(C(F)(F)F)cc1C(F)(F)F] | 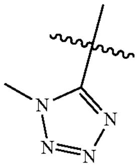 [SMILES: *c1nnnn1C] |

-continued
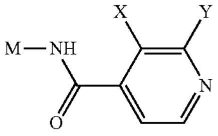
I
| NO. | X | Y | M |
|---|---|---|---|
| 1-77 | Cl | 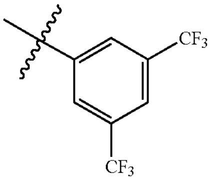 [SMILES: *c1cc(C(F)(F)F)cc(C(F)(F)F)c1] | 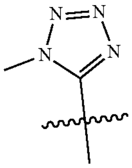 [SMILES: *c1nnnn1C] |
| 1-78 | Cl | 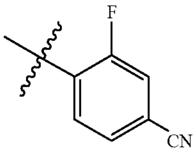 | 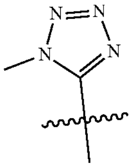 [SMILES: *c1nnnn1C] |
| 1-79 | Cl | 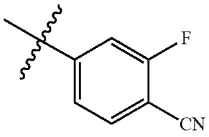 [SMILES: *c1ccc(C#N)c(F)c1] | 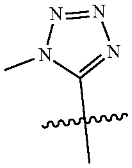 [SMILES: *c1nnnn1C] |
| 1-80 | Cl | 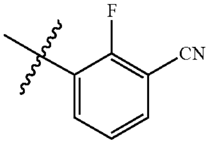 [SMILES: *c1cccc(C#N)c1F] | 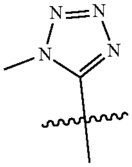 [SMILES: *c1nnnn1C] |
| 1-81 | Cl | 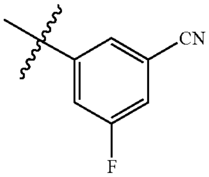 [SMILES: *c1cc(F)cc(C#N)c1] | 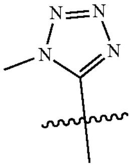 [SMILES: *c1nnnn1C] |
| 1-82 | Cl | 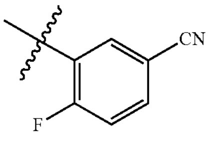 [SMILES: *c1cc(C#N)ccc1F] | 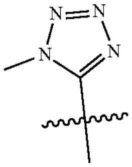 [SMILES: *c1nnnn1C] |
| 1-83 | Cl | 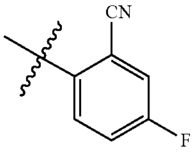 [SMILES: *c1ccc(F)cc1C#N] | 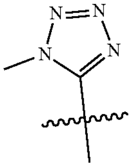 [SMILES: *c1nnnn1C] |

-continued
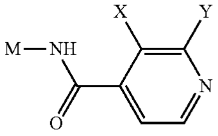
I
| NO. | X | Y | M |
|---|---|---|---|
| 1-84 | Cl | 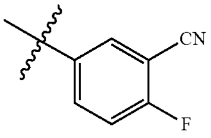 [SMILES: *c1ccc(F)c(C#N)c1] | 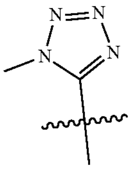 [SMILES: *c1nnnn1C] |
| 1-85 | Cl | 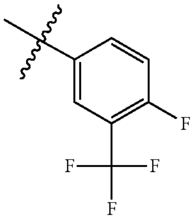 [SMILES: *c1ccc(F)c(C(F)(F)F)c1] | 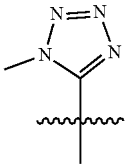 [SMILES: *c1nnnn1C] |
| 1-86 | Cl | 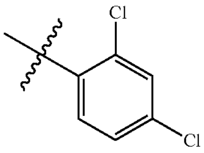 [SMILES: *c1ccc(Cl)cc1Cl] | 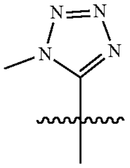 [SMILES: *c1nnnn1C] |
| 1-87 | Cl | 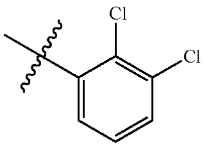 [SMILES: *c1cccc(Cl)c1Cl] | 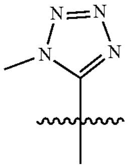 [SMILES: *c1nnnn1C] |
| 1-88 | Cl | 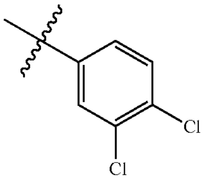 [SMILES: *c1ccc(Cl)c(Cl)c1] | 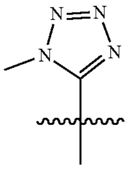 [SMILES: *c1nnnn1C] |
| 1-89 | Cl | 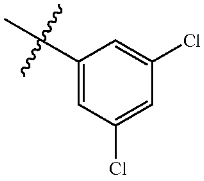 [SMILES: *c1cc(Cl)cc(Cl)c1] | 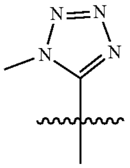 [SMILES: *c1nnnn1C] |
| 1-90 | Cl | 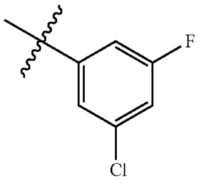 [SMILES: *c1cc(F)cc(Cl)c1] | 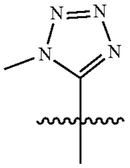 [SMILES: *c1nnnn1C] |

-continued
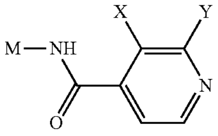
I
| NO. | X | Y | M |
| --- | --- | --- | --- |
| 1-91 | Cl | 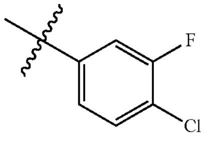 [SMILES: *c1ccc(Cl)c(F)c1] | 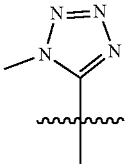 [SMILES: *c1nnnn1C] |
| 1-92 | Cl | 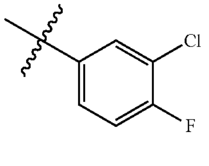 [SMILES: *c1ccc(F)c(Cl)c1] | 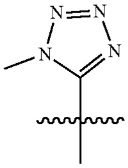 [SMILES: *c1nnnn1C] |
| 1-93 | Cl | 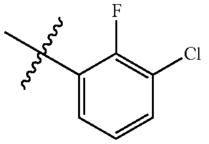 [SMILES: *c1cccc(Cl)c1F] | 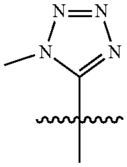 |
| 1-94 | Cl | 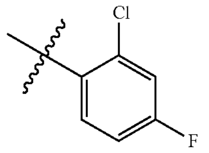 [SMILES: *c1ccc(F)cc1Cl] | 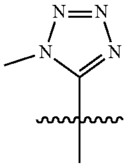 |
| 1-95 | Cl | 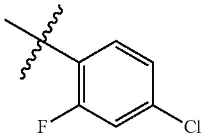 [SMILES: *c1ccc(Cl)cc1F] | 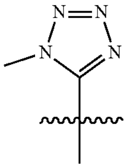 [SMILES: *c1nnnn1C] |
| 1-96 | Cl | 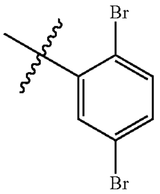 [SMILES: *c1cc(Br)ccc1Br] | 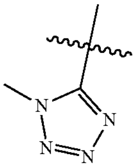 [SMILES: *c1nnnn1C] |
| 1-97 | Cl | 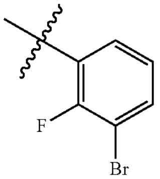 [SMILES: *c1cccc(Br)c1F] | 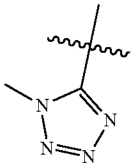 [SMILES: *c1nnnn1C] |

-continued
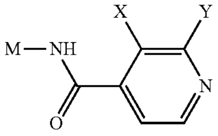
I
| NO. | X | Y | M |
|---|---|---|---|
| 1-98 | Cl | 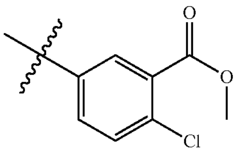 [SMILES: *c1ccc(Cl)c(C(=O)OC)c1] | 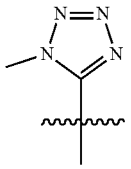 [SMILES: *c1nnnn1C] |
| 1-99 | Cl | 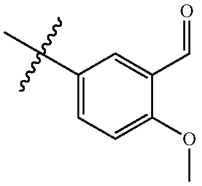 [SMILES: *c1ccc(OC)c(C=O)c1] | 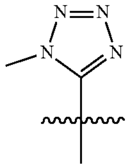 [SMILES: *c1nnnn1C] |
| 1-100 | Cl | 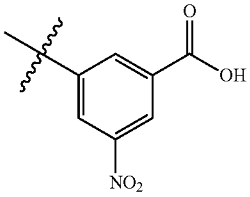 [SMILES: *c1cc(C(=O)O)cc([N+](=O)[O-])c1] | 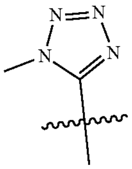 [SMILES: *c1nnnn1C] |
| 1-101 | Cl | 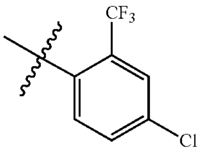 [SMILES: *c1ccc(Cl)cc1C(F)(F)F] | 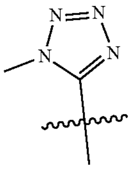 [SMILES: *c1nnnn1C] |
| 1-102 | Cl | 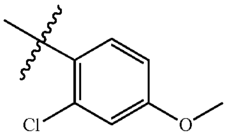 [SMILES: *c1ccc(OC)cc1Cl] | 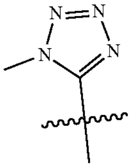 [SMILES: *c1nnnn1C] |
| 1-103 | Cl | 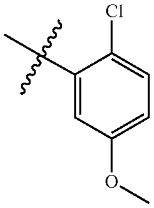 [SMILES: *c1cc(OC)ccc1Cl] | 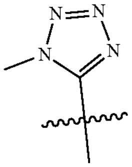 [SMILES: *c1nnnn1C] |
| 1-104 | Cl | 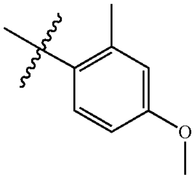 [SMILES: *c1ccc(OC)cc1C] | 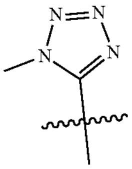 [SMILES: *c1nnnn1C] |

-continued
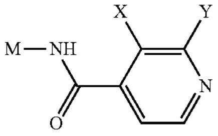
I
| NO. | X | Y | M |
| --- | --- | --- | --- |
| 1-105 | Cl | 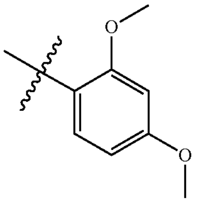 [SMILES: *c1ccc(OC)cc1OC] | 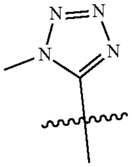 [SMILES: *c1nnnn1C] |
| 1-106 | Cl | 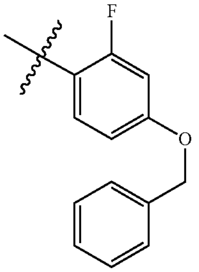 [SMILES: *c1ccc(OCc2ccccc2)cc1F] | 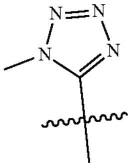 [SMILES: *c1nnnn1C] |
| 1-107 | Cl | 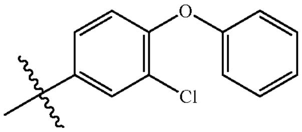 [SMILES: *c1ccc(Oc2ccccc2)c(Cl)c1] | 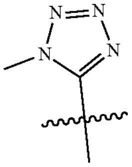 [SMILES: *c1nnnn1C] |
| 1-108 | Cl | 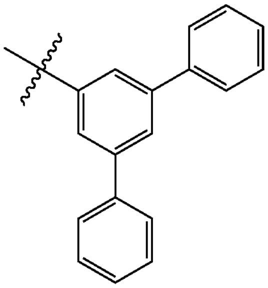 [SMILES: *c1cc(-c2ccccc2)cc(-c2ccccc2)c1] | 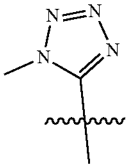 [SMILES: *c1nnnn1C] |
| 1-109 | Cl | 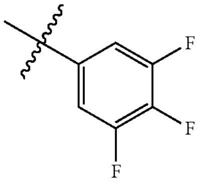 [SMILES: *c1cc(F)c(F)c(F)c1] | 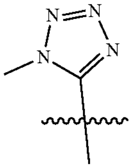 [SMILES: *c1nnnn1C] |
| 1-110 | Cl | 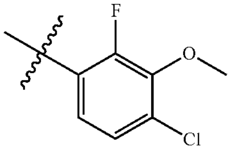 [SMILES: *c1ccc(Cl)c(OC)c1F] | 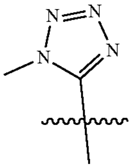 [SMILES: *c1nnnn1C] |

-continued
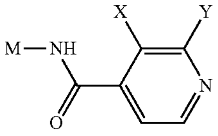
I
| NO. | X | Y | M |
| --- | --- | --- | --- |
| 1-111 | Cl | 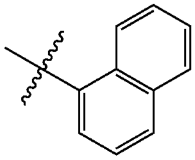 [SMILES: *c1cccc2ccccc12] | 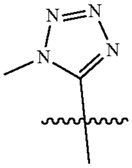 [SMILES: *c1nnnn1C] |
| 1-112 | Cl | 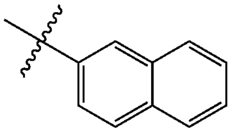 [SMILES: *c1ccc2ccccc2c1] | 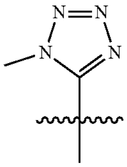 [SMILES: *c1nnnn1C] |
| 1-113 | Cl | 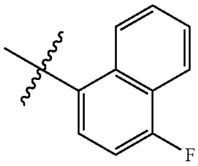 [SMILES: *c1ccc(F)c2ccccc12] | 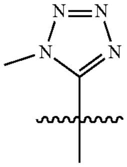 [SMILES: *c1nnnn1C] |
| 1-114 | Cl | 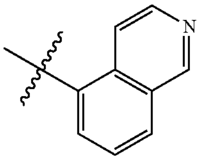 [SMILES: *c1cccc2cnccc12] | 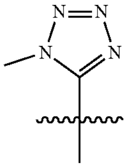 [SMILES: *c1nnnn1C] |
| 1-115 | Cl | 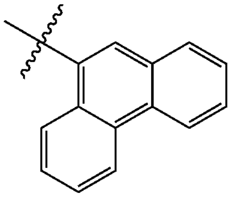 [SMILES: *c1cc2ccccc2c2ccccc12] | 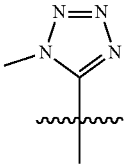 [SMILES: *c1nnnn1C] |
| 1-116 | Cl | 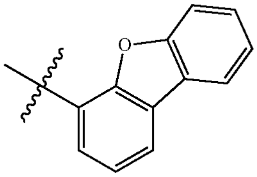 [SMILES: *c1cccc2c1oc1ccccc12] | 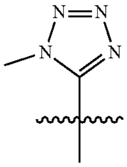 [SMILES: *c1nnnn1C] |
| 1-117 | Cl | 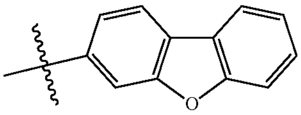 [SMILES: *c1ccc2c(c1)oc1ccccc12] | 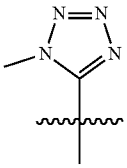 [SMILES: *c1nnnn1C] |

-continued
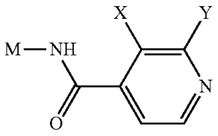
I
| NO. | X | Y | M |
|---|---|---|---|
| 1-118 | Cl | 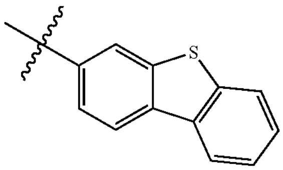 [SMILES: *c1ccc2c(c1)sc1ccccc12] | 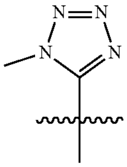 [SMILES: *c1nnnn1C] |
| 1-119 | Cl | 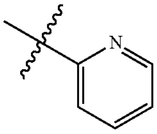 [SMILES: *c1ccccn1] | 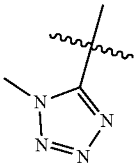 [SMILES: *c1nnnn1C] |
| 1-120 | Cl | 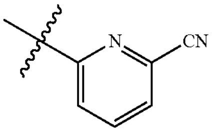 [SMILES: *c1cccc(C#N)n1] | 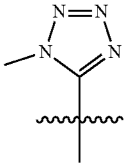 [SMILES: *c1nnnn1C] |
| 1-121 | Cl | 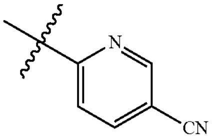 [SMILES: *c1ccc(C#N)cn1] | 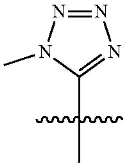 [SMILES: *c1nnnn1C] |
| 1-122 | Cl | 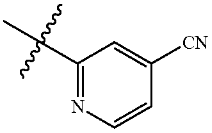 [SMILES: *c1cc(C#N)ccn1] | 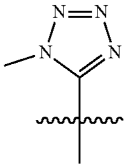 [SMILES: *c1nnnn1C] |
| 1-123 | Cl | 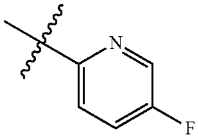 [SMILES: *c1ccc(F)cn1] | 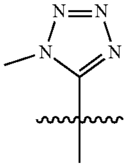 [SMILES: *c1nnnn1C] |
| 1-124 | Cl | 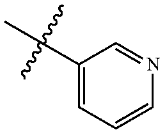 [SMILES: *c1cccnc1] | 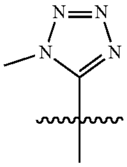 [SMILES: *c1nnnn1C] |

-continued
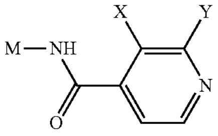
I
| NO. | X | Y | M |
|---|---|---|---|
| 1-125 | Cl | 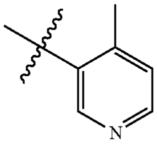 [SMILES: *c1cnccc1C] | 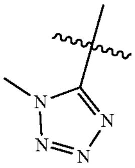 [SMILES: *c1nnnn1C] |
| 1-126 | Cl | 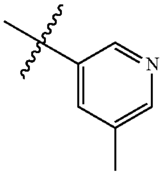 [SMILES: *c1cncc(C)c1] | 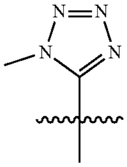 [SMILES: *c1nnnn1C] |
| 1-127 | Cl | 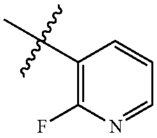 [SMILES: *c1cccnc1F] | 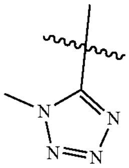 [SMILES: *c1nnnn1C] |
| 1-128 | Cl | 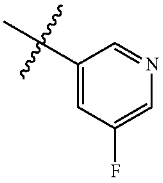 [SMILES: *c1cncc(F)c1] | 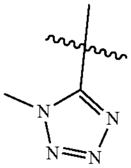 [SMILES: *c1nnnn1C] |
| 1-129 | Cl | 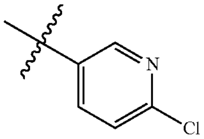 [SMILES: *c1ccc(Cl)nc1] | 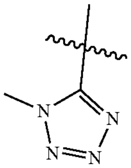 [SMILES: *c1nnnn1C] |
| 1-130 | Cl | 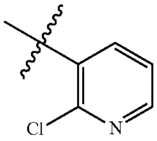 [SMILES: *c1cccnc1Cl] | 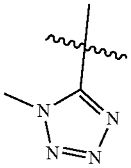 [SMILES: *c1nnnn1C] |
| 1-131 | Cl | 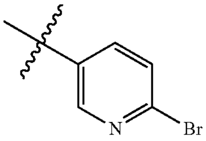 | 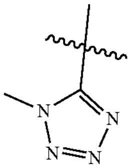 [SMILES: *c1nnnn1C] |

-continued
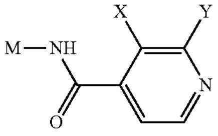
I
| NO. | X | Y | M |
|---|---|---|---|
| 1-132 | Cl | 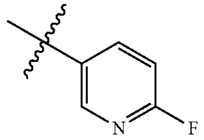 [SMILES: *c1ccc(F)nc1] | 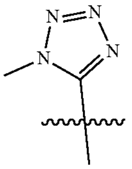 [SMILES: *c1nnnn1C] |
| 1-133 | Cl | 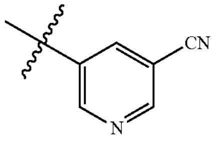 [SMILES: *c1cncc(C#N)c1] | 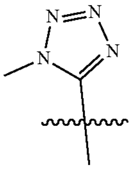 [SMILES: *c1nnnn1C] |
| 1-134 | Cl | 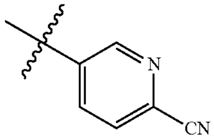 [SMILES: *c1ccc(C#N)nc1] | 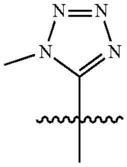 [SMILES: *c1nnnn1C] |
| 1-135 | Cl | 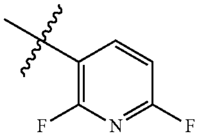 [SMILES: *c1ccc(F)nc1F] | 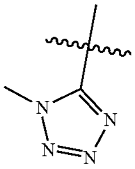 [SMILES: *c1nnnn1C] |
| 1-136 | Cl | 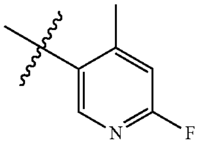 [SMILES: *c1cnc(F)cc1C] | 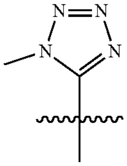 [SMILES: *c1nnnn1C] |
| 1-137 | Cl | 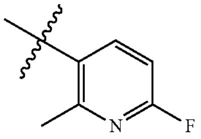 [SMILES: *c1ccc(F)nc1C] | 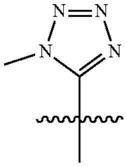 [SMILES: *c1nnnn1C] |
| 1-138 | Cl | 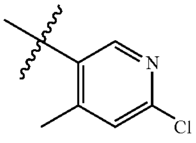 [SMILES: *c1cnc(Cl)cc1C] | 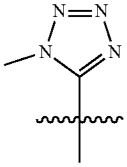 [SMILES: *c1nnnn1C] |

-continued
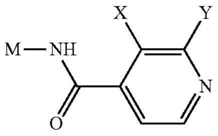
I
| NO. | X | Y | M |
| --- | --- | --- | --- |
| 1-139 | Cl | 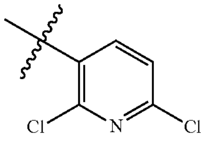 [SMILES: *c1ccc(Cl)nc1Cl] | 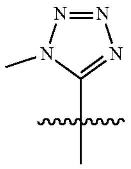 [SMILES: *c1nnnn1C] |
| 1-140 | Cl | 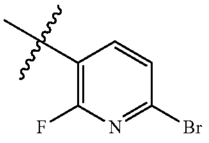 [SMILES: *c1ccc(Br)nc1F] | 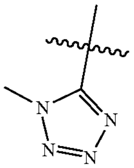 [SMILES: *c1nnnn1C] |
| 1-141 | Cl | 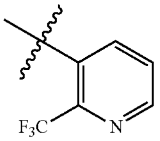 [SMILES: *c1cccnc1C(F)(F)F] | 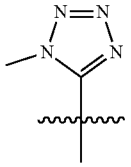 [SMILES: *c1nnnn1C] |
| 1-142 | Cl | 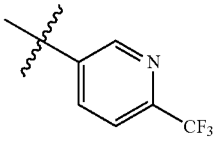 | 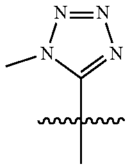 [SMILES: *c1nnnn1C] |
| 1-143 | Cl | 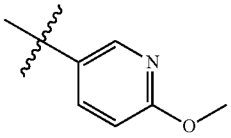 [SMILES: *c1ccc(OC)nc1] | 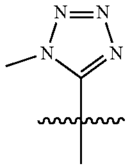 [SMILES: *c1nnnn1C] |
| 1-144 | Cl | 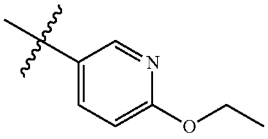 [SMILES: *c1ccc(OCC)nc1] | 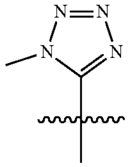 [SMILES: *c1nnnn1C] |
| 1-145 | Cl | 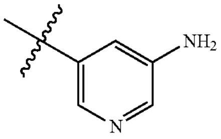 [SMILES: *c1cncc(N)c1] | 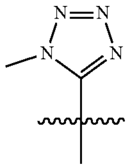 [SMILES: *c1nnnn1C] |

-continued
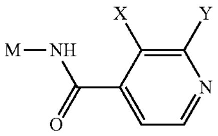
I
| NO. | X | Y | M |
| --- | --- | --- | --- |
| 1-146 | Cl | 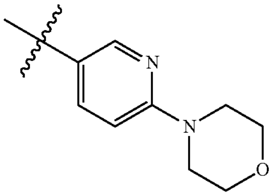 | 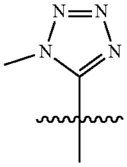 [SMILES: *c1nnnn1C] |
| 1-147 | Cl | 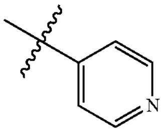 [SMILES: *c1ccncc1] | 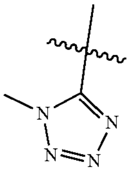 [SMILES: *c1nnnn1C] |
| 1-148 | Cl | 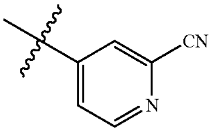 [SMILES: *c1ccnc(C#N)c1] | 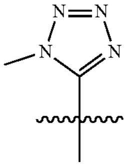 [SMILES: *c1nnnn1C] |
| 1-149 | Cl | 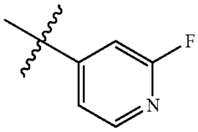 [SMILES: *c1ccnc(F)c1] | 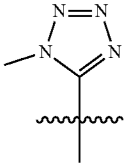 [SMILES: *c1nnnn1C] |
| 1-150 | Cl | 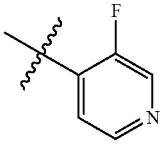 [SMILES: *c1ccncc1F] | 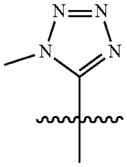 [SMILES: *c1nnnn1C] |
| 1-151 | Cl | 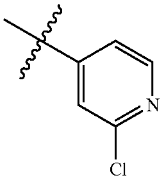 [SMILES: *c1ccnc(Cl)c1] | 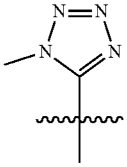 [SMILES: *c1nnnn1C] |
| 1-152 | Cl | 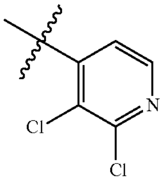 [SMILES: *c1ccnc(Cl)c1Cl] | 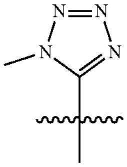 [SMILES: *c1nnnn1C] |

-continued
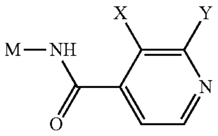
I
| NO. | X | Y | M |
|---|---|---|---|
| 1-153 | Cl | 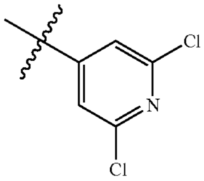 [SMILES: *c1cc(Cl)nc(Cl)c1] | 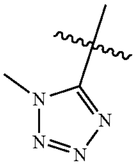 [SMILES: *c1nnnn1C] |
| 1-154 | Cl | 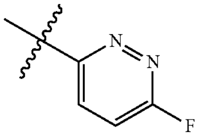 [SMILES: *c1ccc(F)nn1] | 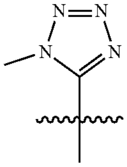 [SMILES: *c1nnnn1C] |
| 1-155 | Cl | 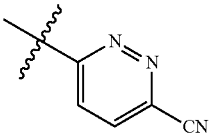 [SMILES: *c1ccc(C#N)nn1] | 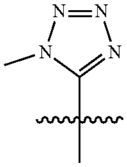 [SMILES: *c1nnnn1C] |
| 1-156 | Cl | 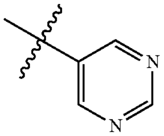 [SMILES: *c1cncnc1] | 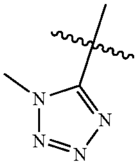 [SMILES: *c1nnnn1C] |
| 1-157 | Cl | 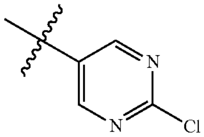 [SMILES: *c1cnc(Cl)nc1] | 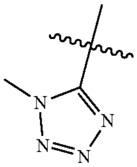 [SMILES: *c1nnnn1C] |
| 1-158 | Cl | 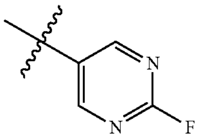 [SMILES: *c1cnc(F)nc1] | 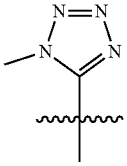 [SMILES: *c1nnnn1C] |
| 1-159 | Cl | 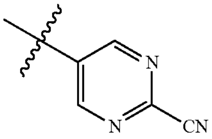 [SMILES: *c1cnc(C#N)nc1] | 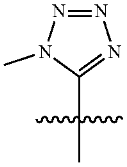 [SMILES: *c1nnnn1C] |

-continued
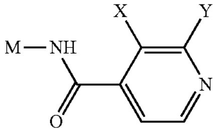
I
| NO. | X | Y | M |
|---|---|---|---|
| 1-160 | Cl | 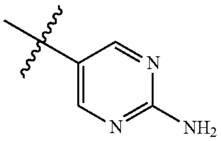 | 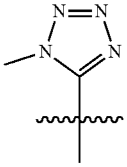 [SMILES: *c1nnnn1C] |
| 1-161 | Cl | 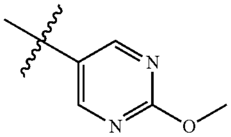 [SMILES: *c1cnc(OC)nc1] | 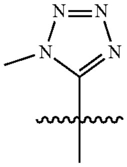 [SMILES: *c1nnnn1C] |
| 1-162 | Cl | 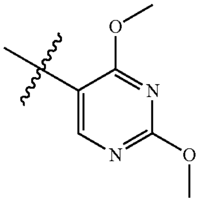 [SMILES: *c1cnc(OC)nc1OC] | 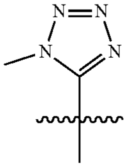 [SMILES: *c1nnnn1C] |
| 1-163 | Cl | 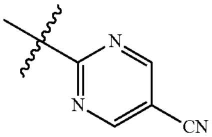 [SMILES: *c1ncc(C#N)cn1] | 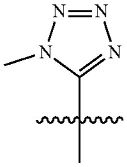 [SMILES: *c1nnnn1C] |
| 1-164 | Cl | 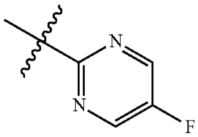 [SMILES: *c1ncc(F)cn1] | 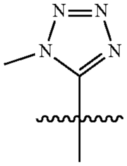 [SMILES: *c1nnnn1C] |
| 1-165 | Cl | 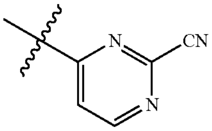 [SMILES: *c1ccnc(C#N)n1] | 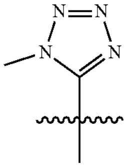 [SMILES: *c1nnnn1C] |
| 1-166 | Cl | 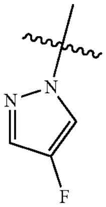 [SMILES: *n1cc(F)cn1] | 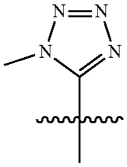 [SMILES: *c1nnnn1C] |

-continued
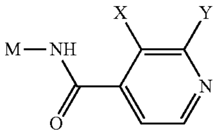
I
| NO. | X | Y | M |
|---|---|---|---|
| 1-167 | Cl | 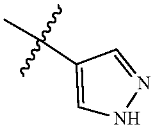 [SMILES: *c1cn[nH]c1] | 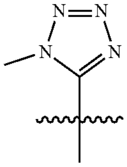 [SMILES: *c1nnnn1C] |
| 1-168 | Cl | 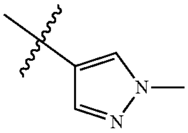 [SMILES: *c1cnn(C)c1] | 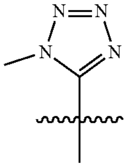 [SMILES: *c1nnnn1C] |
| 1-169 | Cl | 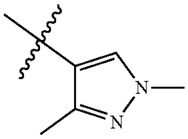 [SMILES: *c1cn(C)nc1C] | 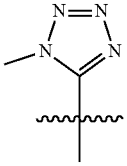 [SMILES: *c1nnnn1C] |
| 1-170 | Cl | 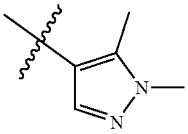 [SMILES: *c1cnn(C)c1C] | 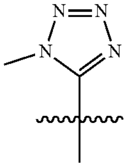 [SMILES: *c1nnnn1C] |
| 1-171 | Cl | 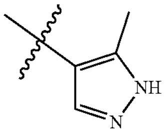 [SMILES: *c1cn[nH]c1C] | 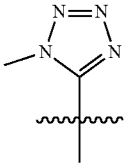 [SMILES: *c1nnnn1C] |
| 1-172 | Cl | 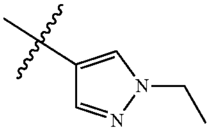 [SMILES: *c1cnn(CC)c1] | 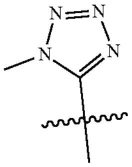 [SMILES: *c1nnnn1C] |
| 1-173 | Cl | 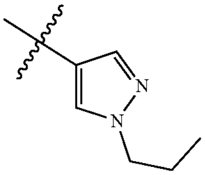 [SMILES: *c1cnn(CCC)c1] | 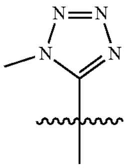 [SMILES: *c1nnnn1C] |

-continued
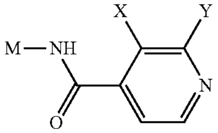
I
| NO. | X | Y | M |
| --- | --- | --- | --- |
| 1-174 | Cl | 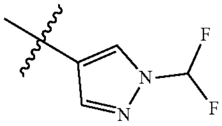 [SMILES: *c1cnn(C(F)F)c1] | 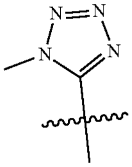 [SMILES: *c1nnnn1C] |
| 1-175 | Cl | 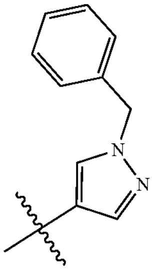 [SMILES: *c1cnn(Cc2ccccc2)c1] | 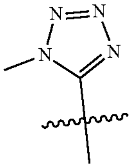 [SMILES: *c1nnnn1C] |
| 1-176 | Cl | 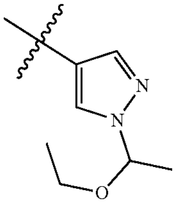 [SMILES: *c1cnn(C(C)OCC)c1] | 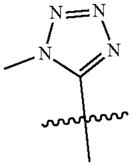 [SMILES: *c1nnnn1C] |
| 1-177 | Cl | 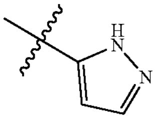 [SMILES: *c1ccn[nH]1] | 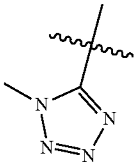 [SMILES: *c1nnnn1C] |
| 1-178 | Cl | 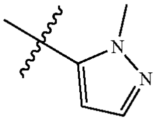 [SMILES: *c1ccnn1C] | 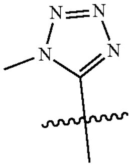 [SMILES: *c1nnnn1C] |
| 1-179 | Cl | 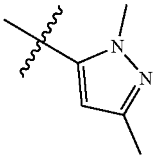 [SMILES: *c1cc(C)nn1C] | 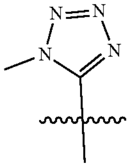 [SMILES: *c1nnnn1C] |
| 1-180 | Cl | 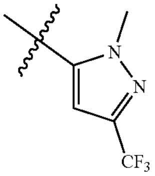 [SMILES: *c1cc(C(F)(F)F)nn1C] | 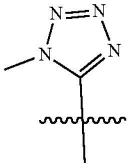 [SMILES: *c1nnnn1C] |

-continued
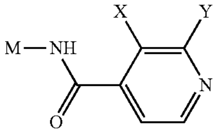
I
| NO. | X | Y | M |
|---|---|---|---|
| 1-181 | Cl | 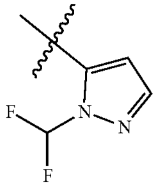 [SMILES: *c1ccnn1C(F)F] | 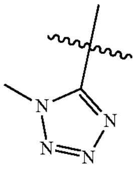 [SMILES: *c1nnnn1C] |
| 1-182 | Cl | 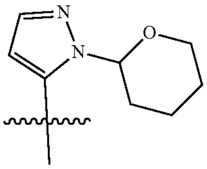 [SMILES: *c1ccnn1C1CCCCO1] | 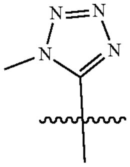 [SMILES: *c1nnnn1C] |
| 1-183 | Cl | 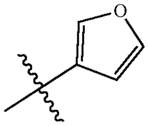 [SMILES: *c1ccoc1] | 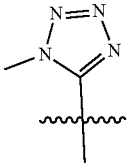 [SMILES: *c1nnnn1C] |
| 1-184 | Cl | 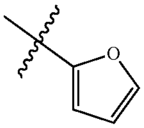 | 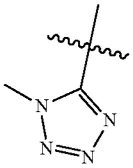 [SMILES: *c1nnnn1C] |
| 1-185 | Cl | 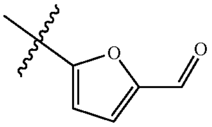 [SMILES: *c1ccc(C=O)o1] | 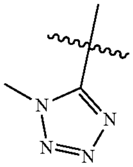 [SMILES: *c1nnnn1C] |
| 1-186 | Cl | 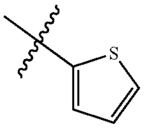 | 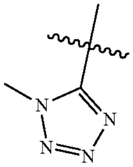 [SMILES: *c1nnnn1C] |
| 1-187 | Cl | 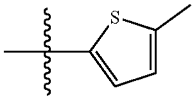 [SMILES: *c1ccc(C)s1] | 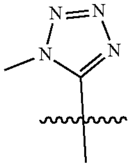 [SMILES: *c1nnnn1C] |

-continued
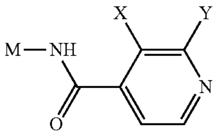
I
| NO. | X | Y | M |
| --- | --- | --- | --- |
| 1-188 | Cl | 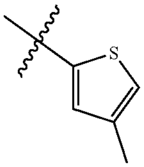 [SMILES: *c1cc(C)cs1] | 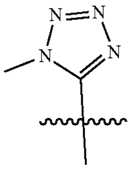 [SMILES: *c1nnnn1C] |
| 1-189 | Cl | 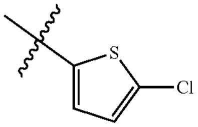 [SMILES: *c1ccc(Cl)s1] | 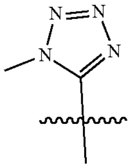 [SMILES: *c1nnnn1C] |
| 1-190 | Cl | 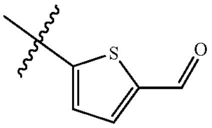 [SMILES: *c1ccc(C=O)s1] | 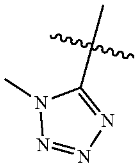 [SMILES: *c1nnnn1C] |
| 1-191 | Cl | 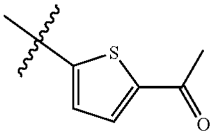 [SMILES: *c1ccc(C(C)=O)s1] | 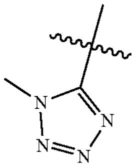 [SMILES: *c1nnnn1C] |
| 1-192 | Cl | 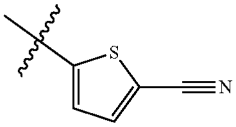 [SMILES: *c1ccc(C#N)s1] | 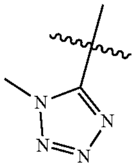 [SMILES: *c1nnnn1C] |
| 1-193 | Cl | 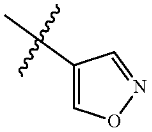 [SMILES: *c1cnoc1] | 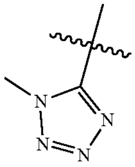 [SMILES: *c1nnnn1C] |
| 1-194 | $CH_3$ | 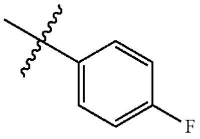 [SMILES: *c1ccc(F)cc1] | 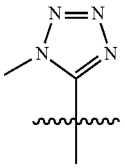 [SMILES: *c1nnnn1C] |

-continued
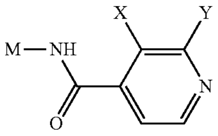
I
| NO. | X | Y | M |
|---|---|---|---|
| 1-195 | F | 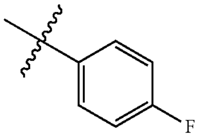 [SMILES: *c1ccc(F)cc1] | 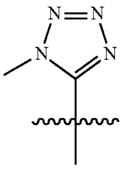 |
| 1-196 | Br | 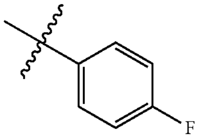 [SMILES: *c1ccc(F)cc1] | 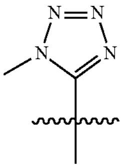 [SMILES: *c1nnnn1C] |
| 1-197 | 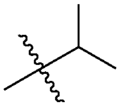 [SMILES: *C(C)C] | 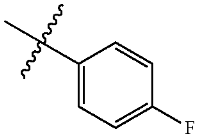 [SMILES: *c1ccc(F)cc1] | 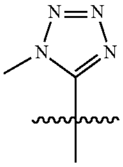 |
| 1-198 | $CF_3$ | 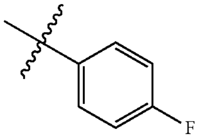 [SMILES: *c1ccc(F)cc1] | 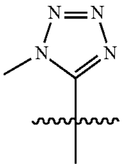 [SMILES: *c1nnnn1C] |
| 1-199 | 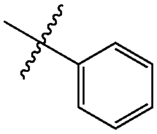 [SMILES: *c1ccccc1] | 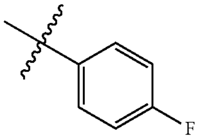 [SMILES: *c1ccc(F)cc1] | 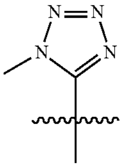 |
| 1-200 | 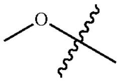 [SMILES: *OC] | 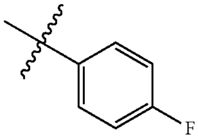 [SMILES: *c1ccc(F)cc1] | 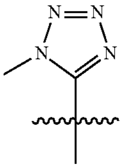 [SMILES: *c1nnnn1C] |
| 1-201 | 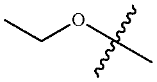 [SMILES: *OCC] | 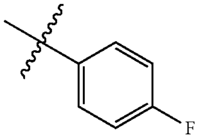 [SMILES: *c1ccc(F)cc1] | 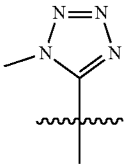 [SMILES: *c1nnnn1C] |

-continued
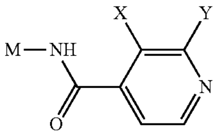
I
| NO. | X | Y | M |
|---|---|---|---|
| 1-202 | 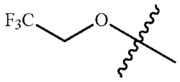 [SMILES: *OCC(F)(F)F] | 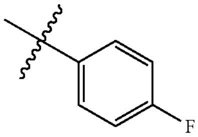 [SMILES: *c1ccc(F)cc1] | 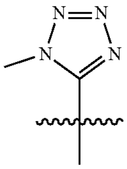 [SMILES: *c1nnnn1C] |
| 1-203 | 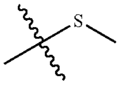 [SMILES: *SC] | 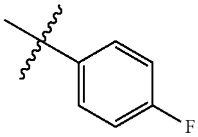 [SMILES: *c1ccc(F)cc1] | 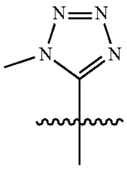 [SMILES: *c1nnnn1C] |
| 1-204 | 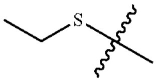 | 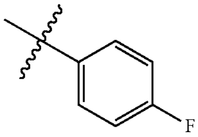 [SMILES: *c1ccc(F)cc1] | 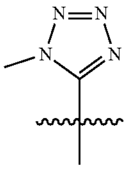 [SMILES: *c1nnnn1C] |
| 1-205 | 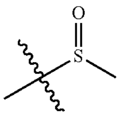 [SMILES: *S(C)=O] | 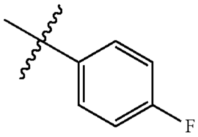 [SMILES: *c1ccc(F)cc1] | 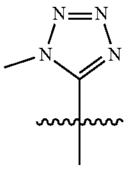 [SMILES: *c1nnnn1C] |
| 1-206 | 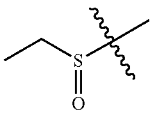 [SMILES: *S(=O)CC] | 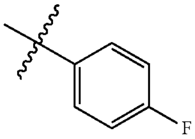 [SMILES: *c1ccc(F)cc1] | 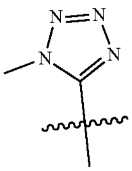 [SMILES: *c1nnnn1C] |
| 1-207 | 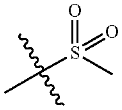 [SMILES: *S(C)(=O)=O] | 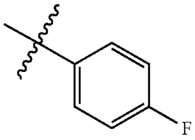 [SMILES: *c1ccc(F)cc1] | 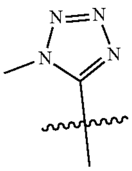 [SMILES: *c1nnnn1C] |
| 1-208 | 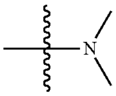 [SMILES: *N(C)C] | 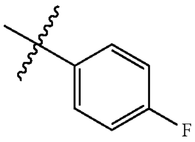 [SMILES: *c1ccc(F)cc1] | 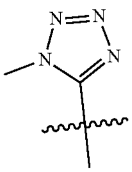 [SMILES: *c1nnnn1C] |

-continued
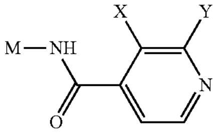
I
| NO. | X | Y | M |
|---|---|---|---|
| 1-209 | 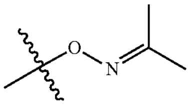 [SMILES: *ON=C(C)C] | 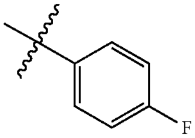 [SMILES: *c1ccc(F)cc1] | 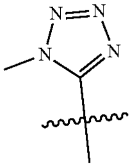 [SMILES: *c1nnnn1C] |
| 1-210 | Et | 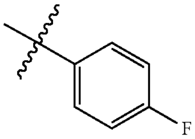 | 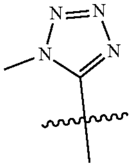 [SMILES: *c1nnnn1C] |
| 1-211 | 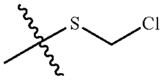 [SMILES: *SCCl] | 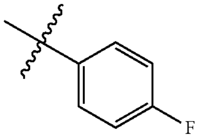 [SMILES: *c1ccc(F)cc1] | 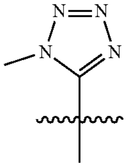 [SMILES: *c1nnnn1C] |
| 1-212 | $NO_2$ | 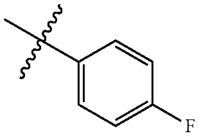 [SMILES: *c1ccc(F)cc1] | 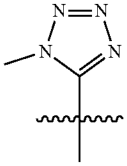 [SMILES: *c1nnnn1C] |
| 1-213 | CN | 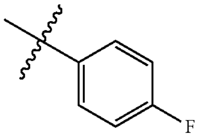 [SMILES: *c1ccc(F)cc1] | 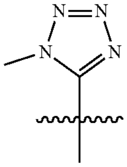 [SMILES: *c1nnnn1C] |
| 1-214 | 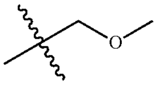 [SMILES: *COC] | 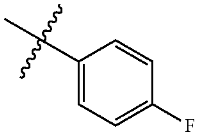 [SMILES: *c1ccc(F)cc1] | 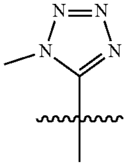 [SMILES: *c1nnnn1C] |
| 1-215 | 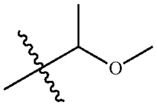 [SMILES: *C(C)OC] | 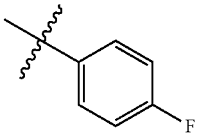 [SMILES: *c1ccc(F)cc1] | 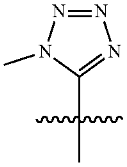 [SMILES: *c1nnnn1C] |

-continued
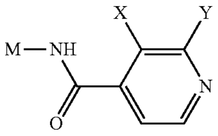
I
| NO. | X | Y | M |
|---|---|---|---|
| 1-216 | 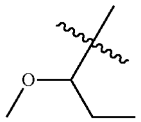 [SMILES: *C(CC)OC] | 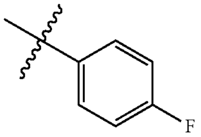 [SMILES: *c1ccc(F)cc1] | 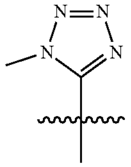 [SMILES: *c1nnnn1C] |
| 1-217 | 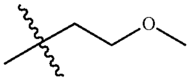 [SMILES: *CCOC] | 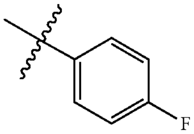 [SMILES: *c1ccc(F)cc1] | 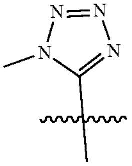 [SMILES: *c1nnnn1C] |
| 1-218 | 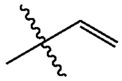 [SMILES: *C=C] | 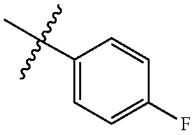 [SMILES: *c1ccc(F)cc1] | 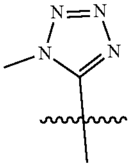 [SMILES: *c1nnnn1C] |
| 1-219 | 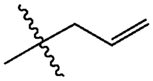 [SMILES: *CC=C] | 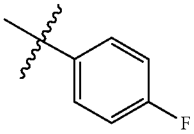 [SMILES: *c1ccc(F)cc1] | 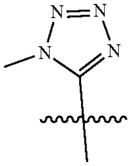 [SMILES: *c1nnnn1C] |
| 1-220 | 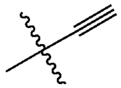 | 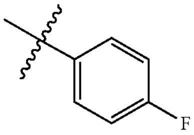 [SMILES: *c1ccc(F)cc1] | 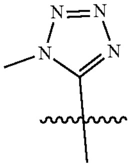 [SMILES: *c1nnnn1C] |
| 1-221 | 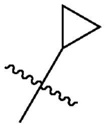 [SMILES: *C1CC1] | 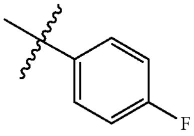 [SMILES: *c1ccc(F)cc1] | 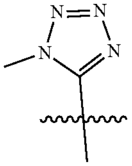 [SMILES: *c1nnnn1C] |
| 1-222 | 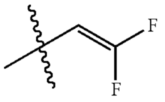 [SMILES: *C=C(F)F] | 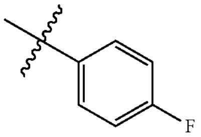 [SMILES: *c1ccc(F)cc1] | 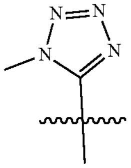 [SMILES: *c1nnnn1C] |

-continued
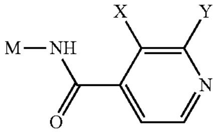
I
| NO. | X | Y | M |
|---|---|---|---|
| 1-223 | 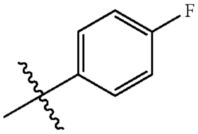 [SMILES: *c1ccc(F)cc1] | 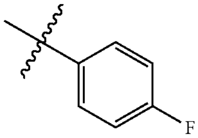 | 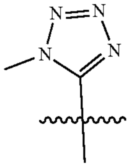 [SMILES: *c1nnnn1C] |
| 1-224 | Cl | 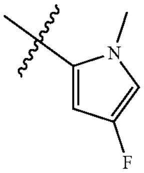 [SMILES: *c1cc(F)cn1C] | 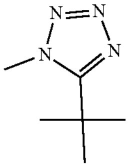 |
| 1-225 | Cl | 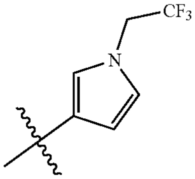 [SMILES: *c1ccn(CC(F)(F)F)c1] | 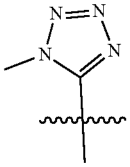 [SMILES: *c1nnnn1C] |
| 1-226 | Cl | 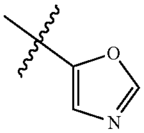 [SMILES: *c1cnco1] | 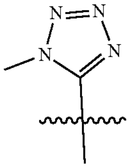 [SMILES: *c1nnnn1C] |
| 1-227 | Cl | 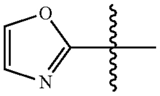 | 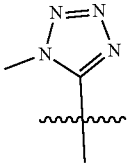 [SMILES: *c1nnnn1C] |
| 1-228 | Cl | 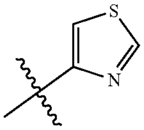 [SMILES: *c1cscn1] | 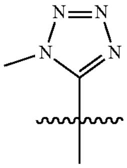 [SMILES: *c1nnnn1C] |
| 1-229 | Cl | 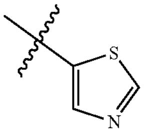 [SMILES: *c1cncs1] | 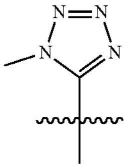 [SMILES: *c1nnnn1C] |

-continued
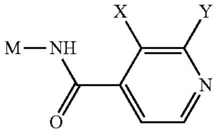
I
| NO. | X | Y | M |
|---|---|---|---|
| 1-230 | Cl | 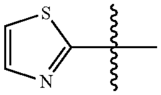 | 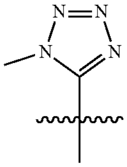 [SMILES: *c1nnnn1C] |
| 1-231 | Cl | 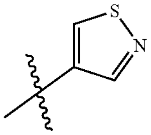 [SMILES: *c1cnsc1] | 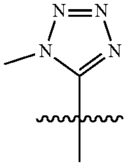 [SMILES: *c1nnnn1C] |
| 1-232 | Cl | 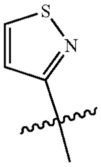 [SMILES: *c1ccsn1] | 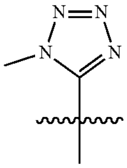 [SMILES: *c1nnnn1C] |
| 1-233 | Cl | 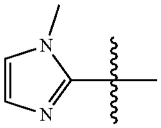 [SMILES: *c1nccn1C] | 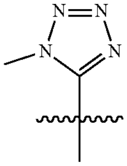 [SMILES: *c1nnnn1C] |
| 1-234 | Cl | 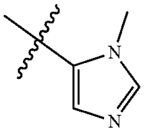 [SMILES: *c1cncn1C] | 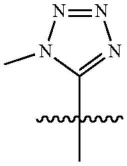 [SMILES: *c1nnnn1C] |
| 1-235 | Cl | 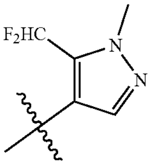 [SMILES: *c1cnn(C)c1C(F)F] | 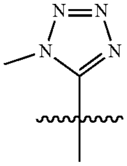 [SMILES: *c1nnnn1C] |
| 1-236 | Cl | 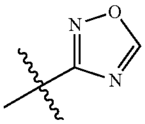 [SMILES: *c1ncon1] | 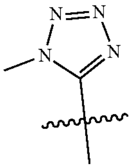 [SMILES: *c1nnnn1C] |

-continued
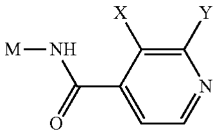
I
| NO. | X | Y | M |
|---|---|---|---|
| 1-237 | Cl | 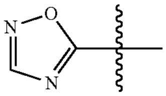 | 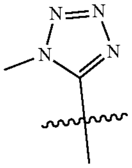 [SMILES: *c1nnnn1C] |
| 1-238 | Cl | 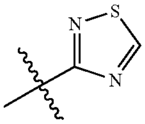 [SMILES: *c1ncsn1] | 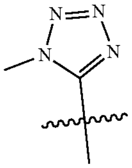 [SMILES: *c1nnnn1C] |
| 1-239 | Cl | 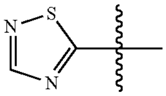 [SMILES: *c1ncns1] | 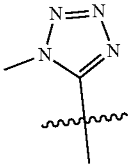 [SMILES: *c1nnnn1C] |
| 1-240 | Cl | 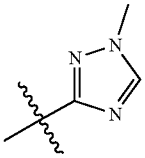 [SMILES: *c1ncn(C)n1] | 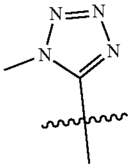 [SMILES: *c1nnnn1C] |
| 1-241 | Cl | 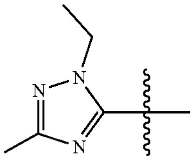 [SMILES: *c1nc(C)nn1CC] | 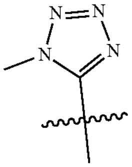 [SMILES: *c1nnnn1C] |
| 1-242 | Cl | 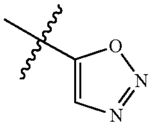 [SMILES: *c1cnno1] | 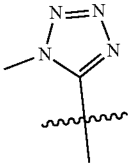 [SMILES: *c1nnnn1C] |
| 1-243 | Cl | 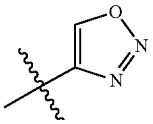 [SMILES: *c1conn1] | 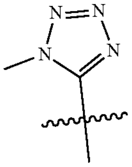 [SMILES: *c1nnnn1C] |

-continued
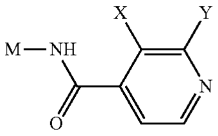
I
| NO. | X | Y | M |
| --- | --- | --- | --- |
| 1-244 | Cl | 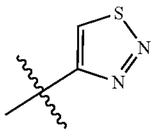 [SMILES: *c1csnn1] | 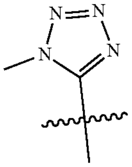 [SMILES: *c1nnnn1C] |
| 1-245 | Cl | 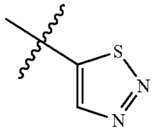 [SMILES: *c1cnns1] | 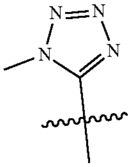 [SMILES: *c1nnnn1C] |
| 1-246 | Cl | 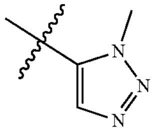 [SMILES: *c1cnnn1C] | 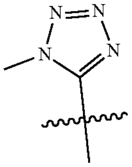 [SMILES: *c1nnnn1C] |
| 1-247 | Cl | 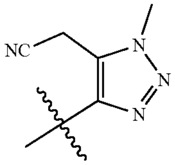 [SMILES: *c1nnn(C)c1CC#N] | 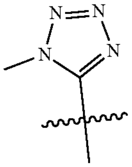 [SMILES: *c1nnnn1C] |
| 1-248 | Cl | 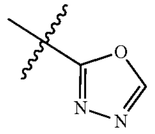 [SMILES: *c1nnco1] | 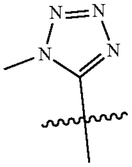 [SMILES: *c1nnnn1C] |
| 1-249 | Cl | 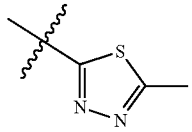 [SMILES: *c1nnc(C)s1] | 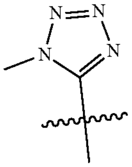 [SMILES: *c1nnnn1C] |
| 1-250 | Cl | 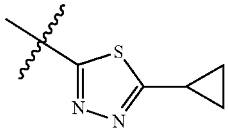 [SMILES: *c1nnc(C2CC2)s1] | 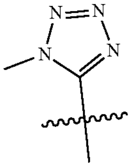 [SMILES: *c1nnnn1C] |

-continued
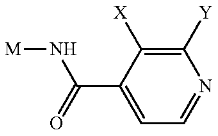
I
| NO. | X | Y | M |
|---|---|---|---|
| 1-251 | Cl | 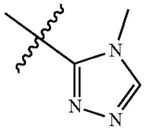 [SMILES: *c1nncn1C] | 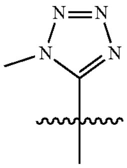 [SMILES: *c1nnnn1C] |
| 1-252 | Cl | 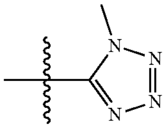 [SMILES: *c1nnnn1C] | 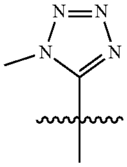 [SMILES: *c1nnnn1C] |
| 1-253 | Cl | 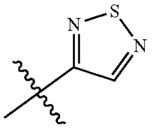 [SMILES: *c1cnsn1] | 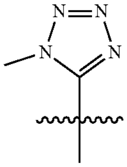 [SMILES: *c1nnnn1C] |
| 1-254 | Cl | 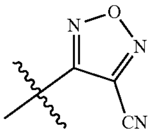 [SMILES: *c1nonc1C#N] | 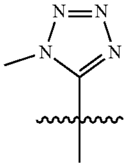 [SMILES: *c1nnnn1C] |
| 1-255 | Cl | 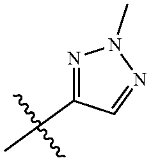 [SMILES: *c1cnn(C)n1] | 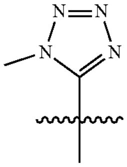 [SMILES: *c1nnnn1C] |
| 1-256 | Cl | 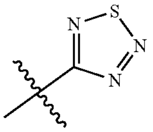 [SMILES: *c1nnsn1] | 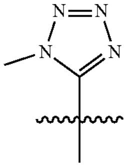 [SMILES: *c1nnnn1C] |
| 1-257 | Cl | 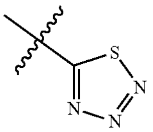 | 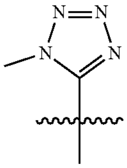 [SMILES: *c1nnnn1C] |

-continued
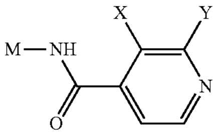
I
| NO. | X | Y | M |
|---|---|---|---|
| 1-258 | Cl | 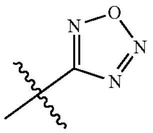 [SMILES: *c1nnon1] | 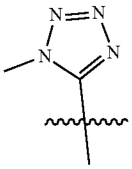 [SMILES: *c1nnnn1C] |
| 1-259 | Cl | 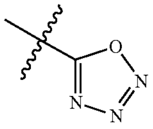 [SMILES: *c1nnno1] | 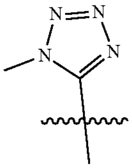 [SMILES: *c1nnnn1C] |
| 1-260 | Cl | 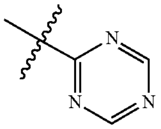 [SMILES: *c1ncncn1] | 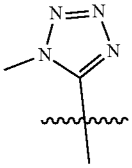 [SMILES: *c1nnnn1C] |
| 1-261 | Cl | 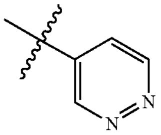 [SMILES: *c1ccnnc1] | 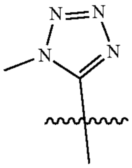 [SMILES: *c1nnnn1C] |
| 1-262 | Cl | 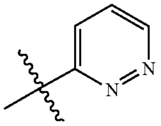 [SMILES: *c1cccnn1] | 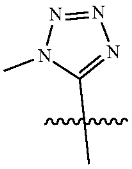 [SMILES: *c1nnnn1C] |
| 1-263 | Cl | 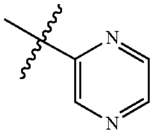 [SMILES: *c1cnccn1] | 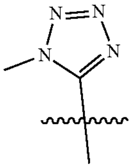 [SMILES: *c1nnnn1C] |
| 1-264 | Cl | 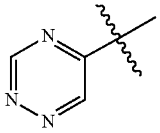 | 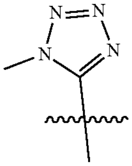 [SMILES: *c1nnnn1C] |

-continued
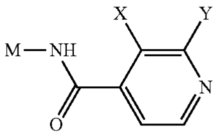
I
| NO. | X | Y | M |
| --- | --- | --- | --- |
| 1-265 | Cl | 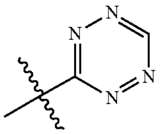 [SMILES: *c1nncnn1] | 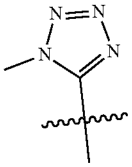 [SMILES: *c1nnnn1C] |
| 1-266 | Cl | 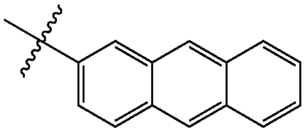 [SMILES: *c1ccc2cc3ccccc3cc2c1] | 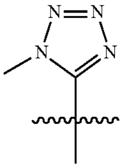 [SMILES: *c1nnnn1C] |
| 1-267 | Cl | 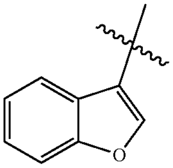 [SMILES: *c1coc2ccccc12] | 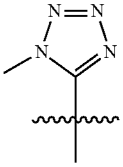 |
| 1-268 | Cl | 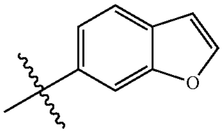 [SMILES: *c1ccc2ccoc2c1] | 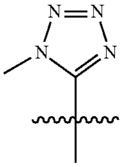 [SMILES: *c1nnnn1C] |
| 1-269 | Cl | 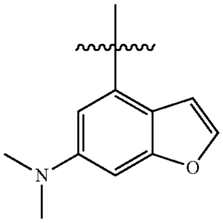 [SMILES: *c1cc(N(C)C)cc2occc12] | 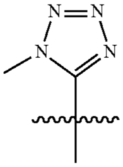 [SMILES: *c1nnnn1C] |
| 1-270 | Cl | 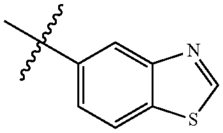 [SMILES: *c1ccc2scnc2c1] | 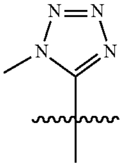 |
| 1-271 | Cl | 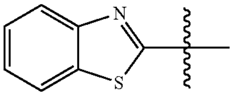 | 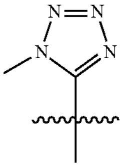 [SMILES: *c1nnnn1C] |

-continued
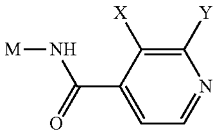
I
| NO. | X | Y | M |
| --- | --- | --- | --- |
| 1-272 | Cl | 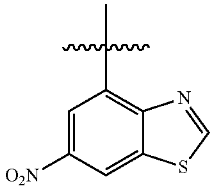 [SMILES: *c1cc([N+](=O)[O-])cc2scnc12] | 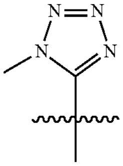 [SMILES: *c1nnnn1C] |
| 1-273 | Cl | 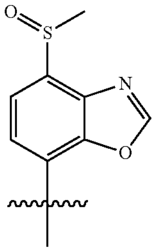 [SMILES: *c1ccc(S(C)=O)c2ncoc12] | 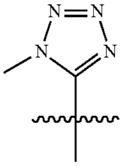 [SMILES: *c1nnnn1C] |
| 1-274 | Cl | 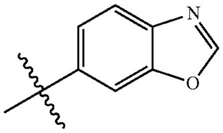 [SMILES: *c1ccc2ncoc2c1] | 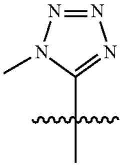 [SMILES: *c1nnnn1C] |
| 1-275 | Cl | 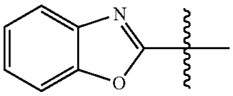 | 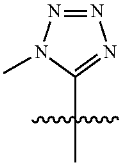 [SMILES: *c1nnnn1C] |
| 1-276 | Cl | 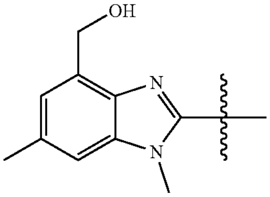 [SMILES: *c1nc2c(CO)cc(C)cc2n1C] | 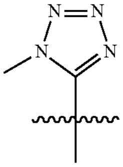 |
| 1-277 | Cl | 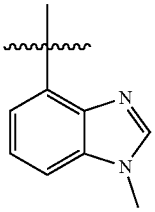 [SMILES: *c1cccc2c1ncn2C] | 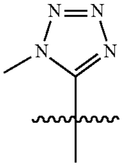 [SMILES: *c1nnnn1C] |

-continued
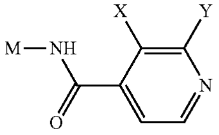
I
| NO. | X | Y | M |
|---|---|---|---|
| 1-278 | Cl | 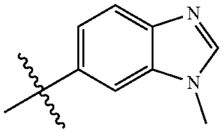 [SMILES: *c1ccc2ncn(C)c2c1] | 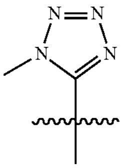 |
| 1-279 | Cl | 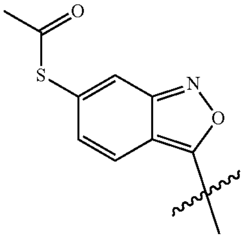 [SMILES: *c1onc2cc(SC(C)=O)ccc12] | 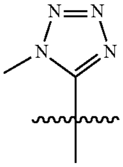 [SMILES: *c1nnnn1C] |
| 1-280 | Cl | 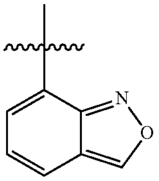 [SMILES: *c1cccc2conc12] | 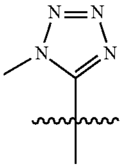 [SMILES: *c1nnnn1C] |
| 1-281 | Cl | 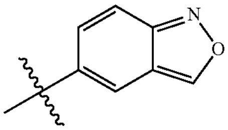 [SMILES: *c1ccc2nocc2c1] | 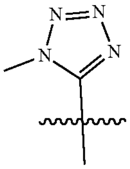 [SMILES: *c1nnnn1C] |
| 1-282 | Cl | 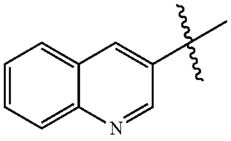 [SMILES: *c1cnc2ccccc2c1] | 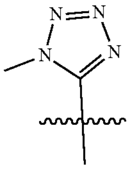 [SMILES: *c1nnnn1C] |
| 1-283 | Cl | 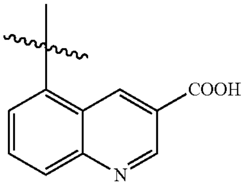 [SMILES: *c1cccc2ncc(C(=O)O)cc12] | 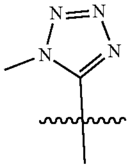 [SMILES: *c1nnnn1C] |
| 1-284 | Cl | 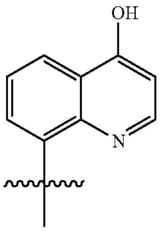 [SMILES: *c1cccc2c(O)ccnc12] | 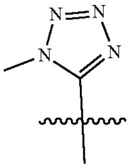 [SMILES: *c1nnnn1C] |

-continued
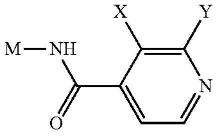
I
| NO. | X | Y | M |
|---|---|---|---|
| 1-285 | Cl | 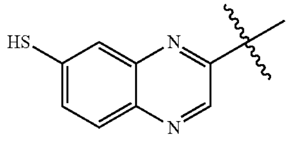 [SMILES: *c1cnc2ccc(S)cc2n1] | 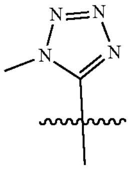 [SMILES: *c1nnnn1C] |
| 1-286 | Cl | 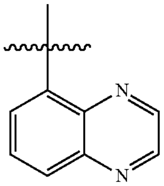 [SMILES: *c1cccc2nccnc12] | 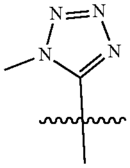 [SMILES: *c1nnnn1C] |
| 1-287 | Cl | 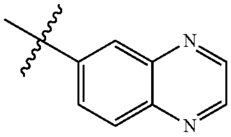 [SMILES: *c1ccc2nccnc2c1] | 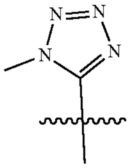 [SMILES: *c1nnnn1C] |
| 1-288 | Cl | 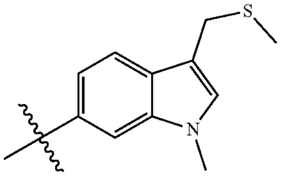 [SMILES: *c1ccc2c(CSC)cn(C)c2c1] | 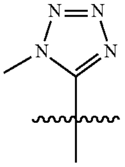 [SMILES: *c1nnnn1C] |
| 1-289 | Cl | 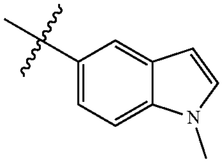 [SMILES: *c1ccc2c(ccn2C)c1] | 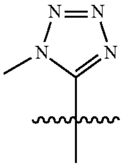 [SMILES: *c1nnnn1C] |
| 1-290 | Cl | 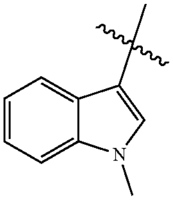 [SMILES: *c1cn(C)c2ccccc12] | 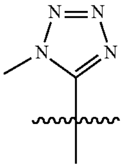 |
| 1-291 | Cl | 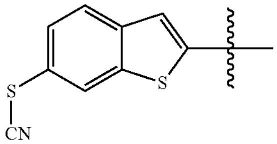 [SMILES: *c1cc2ccc(SC#N)cc2s1] | 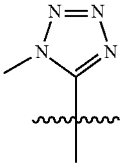 [SMILES: *c1nnnn1C] |

-continued
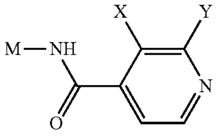
I
| NO. | X | Y | M |
|---|---|---|---|
| 1-292 | Cl | 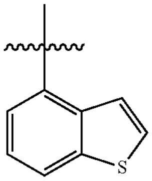 [SMILES: *c1cccc2sccc12] | 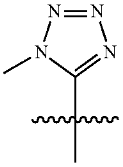 [SMILES: *c1nnnn1C] |
| 1-293 | Cl | 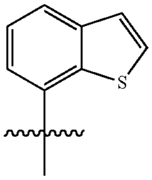 [SMILES: *c1cccc2ccsc12] | 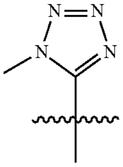 |
| 1-294 | Cl | 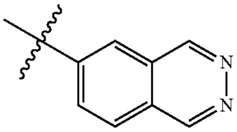 [SMILES: *c1ccc2cnncc2c1] | 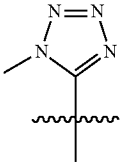 [SMILES: *c1nnnn1C] |
| 1-295 | Cl | 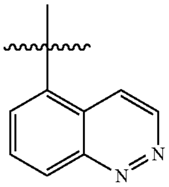 | 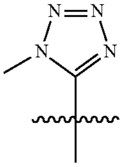 |
| 1-296 | Cl | 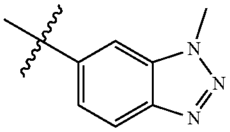 [SMILES: *c1ccc2nnn(C)c2c1] | 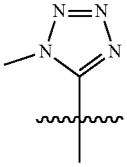 [SMILES: *c1nnnn1C] |
| 1-297 | Cl | 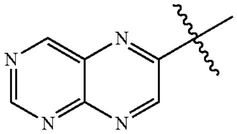 [SMILES: *c1cnc2ncncc2n1] | 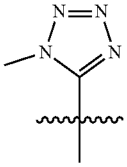 [SMILES: *c1nnnn1C] |
| 1-298 | Cl | 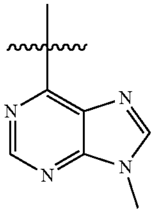 [SMILES: *c1ncnc2c1ncn2C] | 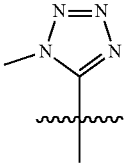 [SMILES: *c1nnnn1C] |

-continued
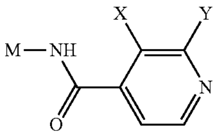
I
| NO. | X | Y | M |
|---|---|---|---|
| 1-299 | Cl | 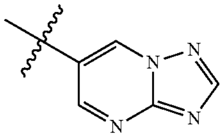 [SMILES: *c1cnc2ncnn2c1] | 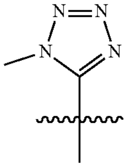 [SMILES: *c1nnnn1C] |
| 1-300 | Cl | 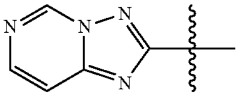 [SMILES: *c1nc2ccncn2n1] | 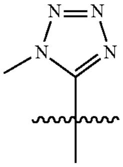 [SMILES: *c1nnnn1C] |
| 1-301 | Cl | 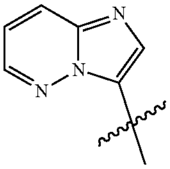 [SMILES: *c1cnc2cccnn12] | 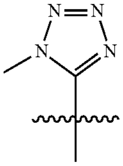 [SMILES: *c1nnnn1C] |
| 1-302 | Cl | 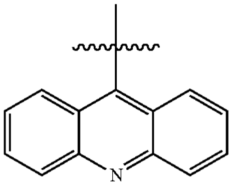 [SMILES: *c1c2ccccc2nc2ccccc12] | 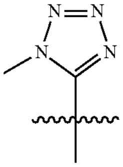 [SMILES: *c1nnnn1C] |
| 1-303 | Cl | 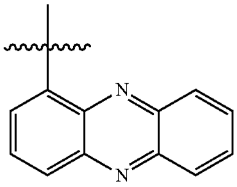 [SMILES: *c1cccc2nc3ccccc3nc12] | 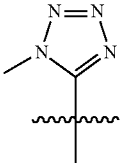 [SMILES: *c1nnnn1C] |
| 1-304 | Cl | 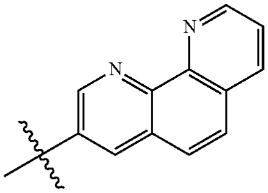 [SMILES: *c1cnc2c(ccc3cccnc32)c1] | 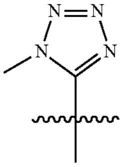 |
| 1-305 | Cl | 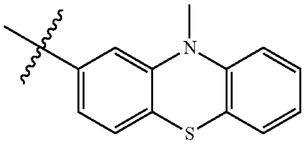 [SMILES: *c1ccc2c(c1)N(C)c1ccccc1S2] | 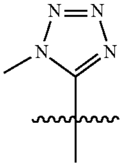 [SMILES: *c1nnnn1C] |

-continued
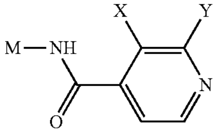
I
| NO. | X | Y | M |
|---|---|---|---|
| 1-306 | Cl | 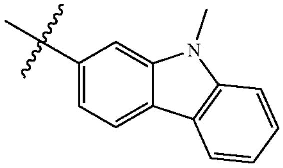 [SMILES: *c1ccc2c3ccccc3n(C)c2c1] | 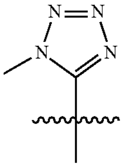 [SMILES: *c1nnnn1C] |
| 1-307 | Cl | 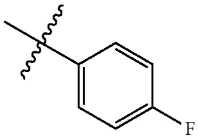 [SMILES: *c1ccc(F)cc1] | 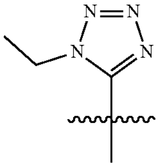 [SMILES: *c1nnnn1CC] |
| 1-308 | Cl | 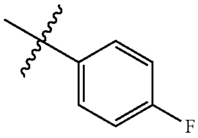 [SMILES: *c1ccc(F)cc1] | 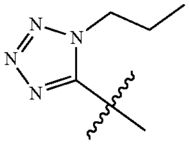 [SMILES: *c1nnnn1CCC] |
| 1-309 | Cl | 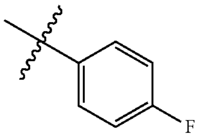 [SMILES: *c1ccc(F)cc1] | 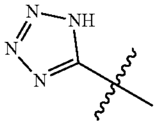 [SMILES: *c1nnn[nH]1] |
| 1-310 | Cl | 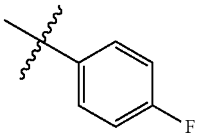 [SMILES: *c1ccc(F)cc1] | 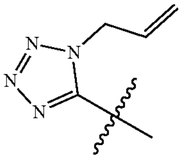 [SMILES: *c1nnnn1CC=C] |
| 1-311 | Cl | 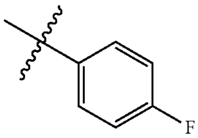 [SMILES: *c1ccc(F)cc1] | 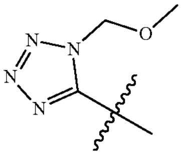 [SMILES: *c1nnnn1COC] |
| 1-312 | Cl | 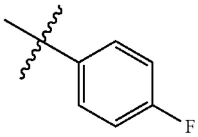 [SMILES: *c1ccc(F)cc1] | 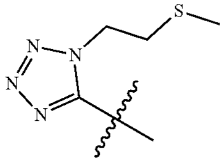 [SMILES: *c1nnnn1CCSC] |
| 1-313 | Cl | 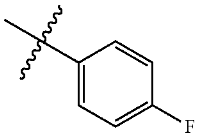 [SMILES: *c1ccc(F)cc1] | 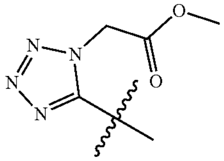 [SMILES: *c1nnnn1CC(=O)OC] |

-continued
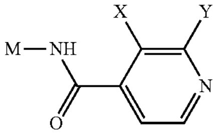
I
| NO. | X | Y | M |
|---|---|---|---|
| 1-314 | Cl | 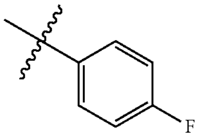 [SMILES: *c1ccc(F)cc1] | 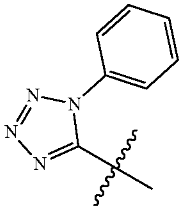 [SMILES: *c1nnnn1-c1ccccc1] |
| 1-315 | Cl | 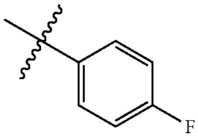 [SMILES: *c1ccc(F)cc1] | 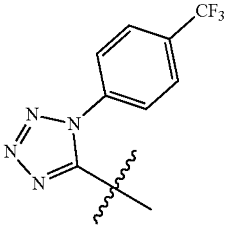 [SMILES: *c1nnnn1-c1ccc(C(F)(F)F)cc1] |
| 1-316 | Cl | 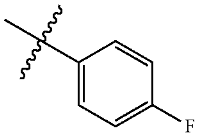 [SMILES: *c1ccc(F)cc1] | 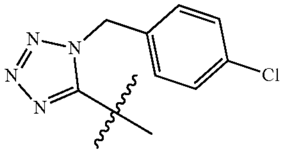 [SMILES: *c1nnnn1Cc1ccc(Cl)cc1] |
| 1-317 | Cl | $CH_3$ | 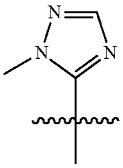 |
| 1-318 | Cl | 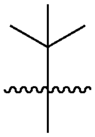 | 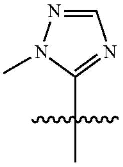 [SMILES: *c1ncnn1C] |
| 1-319 | Cl | 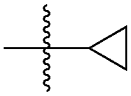 [SMILES: *C1CC1] | 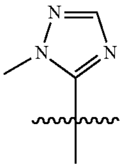 |
| 1-320 | Cl | 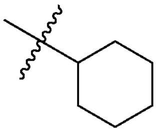 [SMILES: *C1CCCCC1] | 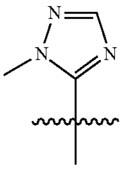 [SMILES: *c1ncnn1C] |

-continued
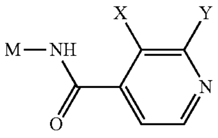
I
| NO. | X | Y | M |
|---|---|---|---|
| 1-321 | Cl | 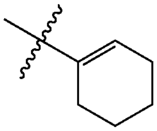 [SMILES: *C1=CCCCC1] | 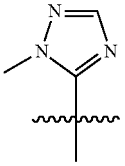 |
| 1-322 | Cl | 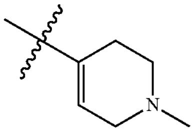 [SMILES: *C1=CCN(C)CC1] | 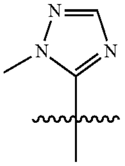 [SMILES: *c1ncnn1C] |
| 1-323 | Cl | 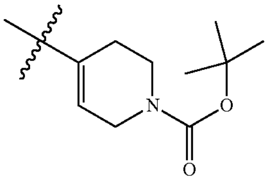 [SMILES: *C1=CCN(C(=O)OC(C)(C)C)CC1] | 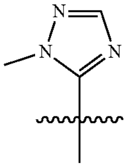 [SMILES: *c1ncnn1C] |
| 1-324 | Cl | 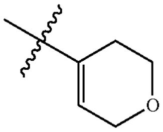 [SMILES: *C1=CCOCC1] | 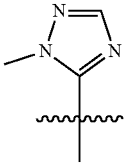 [SMILES: *c1ncnn1C] |
| 1-325 | Cl | 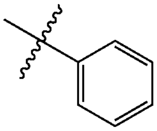 | 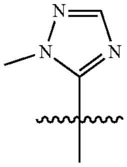 |
| 1-326 | Cl | 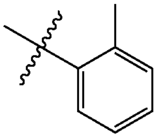 [SMILES: *c1ccccc1C] | 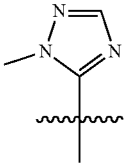 [SMILES: *c1ncnn1C] |
| 1-327 | Cl | 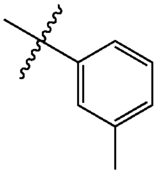 [SMILES: *c1cccc(C)c1] | 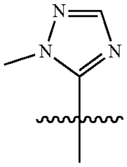 [SMILES: *c1ncnn1C] |

-continued
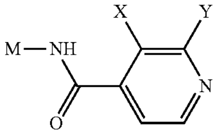
I
| NO. | X | Y | M |
|---|---|---|---|
| 1-328 | Cl | 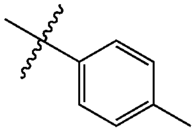 [SMILES: *c1ccc(C)cc1] | 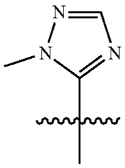 |
| 1-329 | Cl | 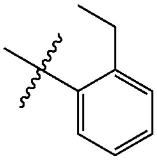 [SMILES: *c1ccccc1CC] | 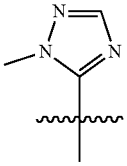 [SMILES: *c1ncnn1C] |
| 1-330 | Cl | 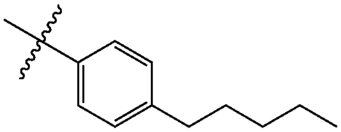 [SMILES: *c1ccc(CCCCC)cc1] | 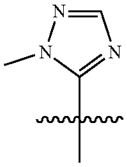 [SMILES: *c1ncnn1C] |
| 1-331 | Cl | 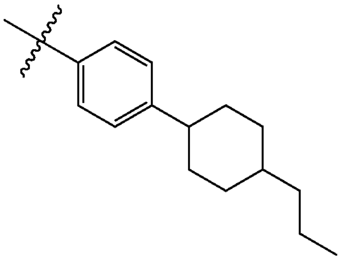 [SMILES: *c1ccc(C2CCC(CCC)CC2)cc1] | 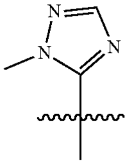 [SMILES: *c1ncnn1C] |
| 1-332 | Cl | 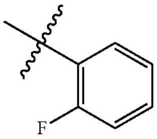 [SMILES: *c1ccccc1F] | 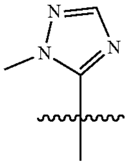 [SMILES: *c1ncnn1C] |
| 1-333 | Cl | 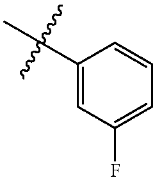 [SMILES: *c1cccc(F)c1] | 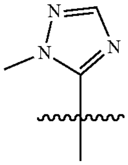 [SMILES: *c1ncnn1C] |
| 1-334 | Cl | 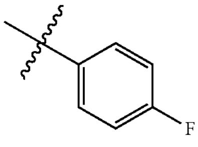 [SMILES: *c1ccc(F)cc1] | 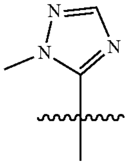 [SMILES: *c1ncnn1C] |

-continued
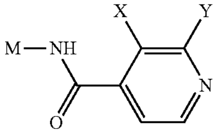
I
| NO. | X | Y | M |
|---|---|---|---|
| 1-335 | Cl | 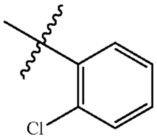 [SMILES: *c1ccccc1Cl] | 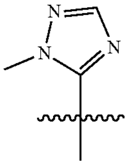 [SMILES: *c1ncnn1C] |
| 1-336 | Cl | 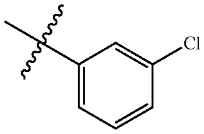 [SMILES: *c1cccc(Cl)c1] | 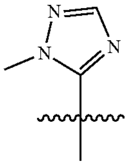 [SMILES: *c1ncnn1C] |
| 1-337 | Cl | 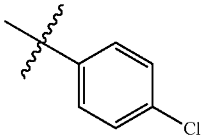 | 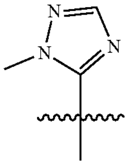 [SMILES: *c1ncnn1C] |
| 1-338 | Cl | 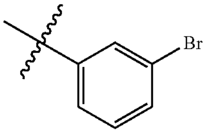 [SMILES: *c1cccc(Br)c1] | 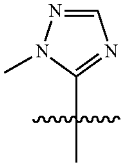 |
| 1-339 | Cl | 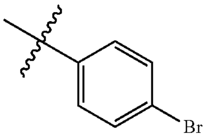 | 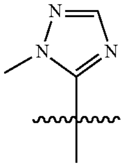 |
| 1-340 | Cl | 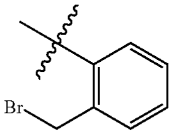 [SMILES: *c1ccccc1CBr] | 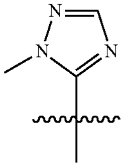 |
| 1-341 | Cl | 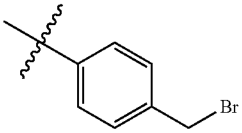 [SMILES: *c1ccc(CBr)cc1] | 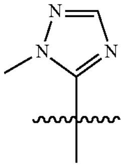 |
| 1-342 | Cl | 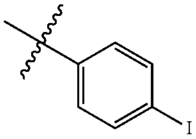 [SMILES: *c1ccc(I)cc1] | 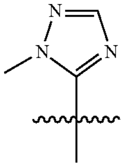 [SMILES: *c1ncnn1C] |

-continued
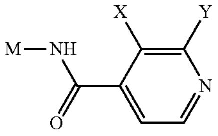
I
| NO. | X | Y | M |
|---|---|---|---|
| 1-343 | Cl | 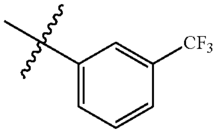 [SMILES: *c1cccc(C(F)(F)F)c1] | 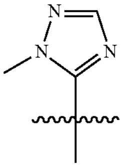 |
| 1-344 | Cl | 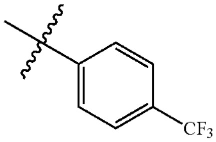 [SMILES: *c1ccc(C(F)(F)F)cc1] | 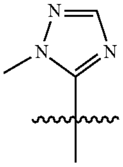 [SMILES: *c1ncnn1C] |
| 1-345 | Cl | 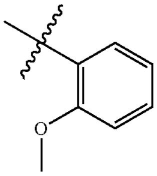 [SMILES: *c1ccccc1OC] | 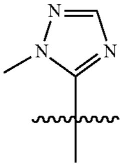 |
| 1-346 | Cl | 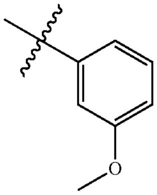 [SMILES: *c1cccc(OC)c1] | 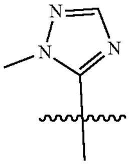 [SMILES: *c1ncnn1C] |
| 1-347 | Cl | 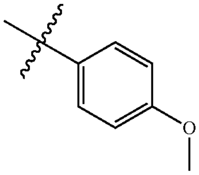 [SMILES: *c1ccc(OC)cc1] | 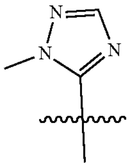 [SMILES: *c1ncnn1C] |
| 1-348 | Cl | 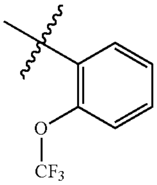 [SMILES: *c1ccccc1OC(F)(F)F] | 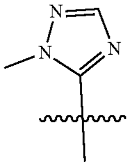 [SMILES: *c1ncnn1C] |
| 1-349 | Cl | 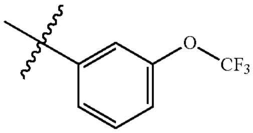 [SMILES: *c1cccc(OC(F)(F)F)c1] | 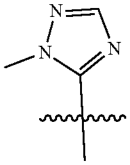 [SMILES: *c1ncnn1C] |

-continued
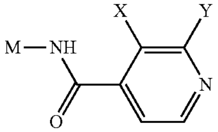
I
| NO. | X | Y | M |
|---|---|---|---|
| 1-350 | Cl | 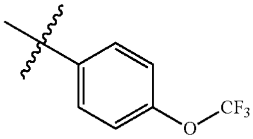 [SMILES: *c1ccc(OC(F)(F)F)cc1] | 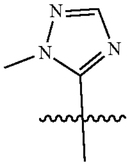 [SMILES: *c1ncnn1C] |
| 1-351 | Cl | 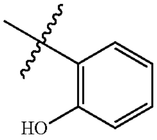 [SMILES: *c1ccccc1O] | 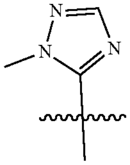 [SMILES: *c1ncnn1C] |
| 1-352 | Cl | 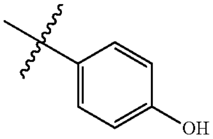 | 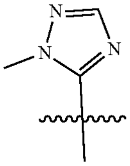 [SMILES: *c1ncnn1C] |
| 1-353 | Cl | 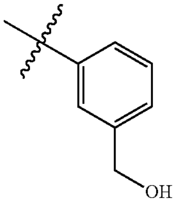 [SMILES: *c1cccc(CO)c1] | 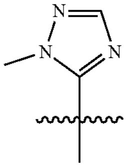 [SMILES: *c1ncnn1C] |
| 1-354 | Cl | 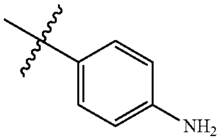 | 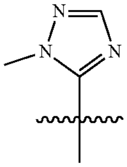 [SMILES: *c1ncnn1C] |
| 1-355 | Cl | 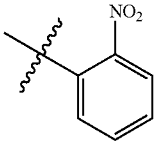 [SMILES: *c1ccccc1[N+](=O)[O-]] | 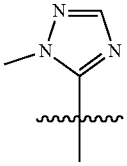 [SMILES: *c1ncnn1C] |
| 1-356 | Cl | 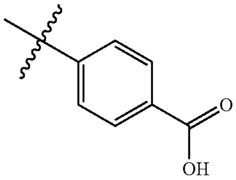 [SMILES: *c1ccc(C(=O)O)cc1] | 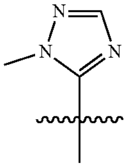 [SMILES: *c1ncnn1C] |

-continued
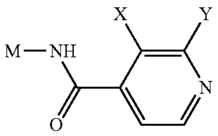
I
| NO. | X | Y | M |
|---|---|---|---|
| 1-357 | Cl | 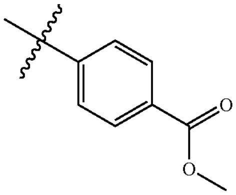 [SMILES: *c1ccc(C(=O)OC)cc1] | 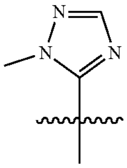 [SMILES: *c1ncnn1C] |
| 1-358 | Cl | 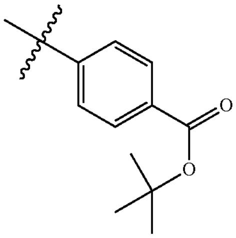 [SMILES: *c1ccc(C(=O)OC(C)(C)C)cc1] | 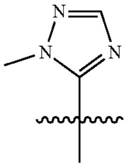 |
| 1-359 | Cl | 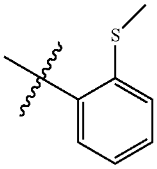 [SMILES: *c1ccccc1SC] | 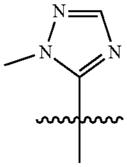 [SMILES: *c1ncnn1C] |
| 1-360 | Cl | 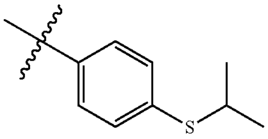 [SMILES: *c1ccc(SC(C)C)cc1] | 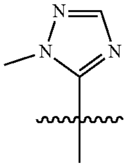 [SMILES: *c1ncnn1C] |
| 1-361 | Cl | 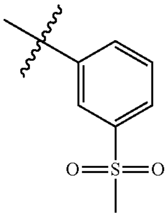 [SMILES: *c1cccc(S(C)(=O)=O)c1] | 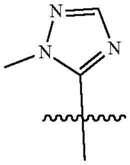 [SMILES: *c1ncnn1C] |
| 1-362 | Cl | 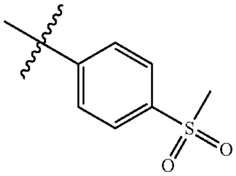 [SMILES: *c1ccc(S(C)(=O)=O)cc1] | 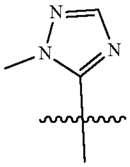 [SMILES: *c1ncnn1C] |

-continued
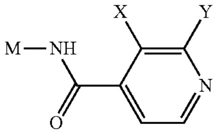
I
| NO. | X | Y | M |
| --- | --- | --- | --- |
| 1-363 | Cl | 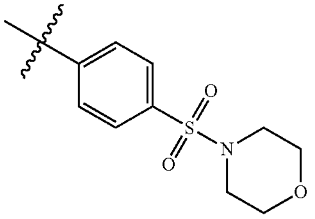 [SMILES: *c1ccc(S(=O)(=O)N2CCOCC2)cc1] | 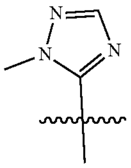 [SMILES: *c1ncnn1C] |
| 1-364 | Cl | 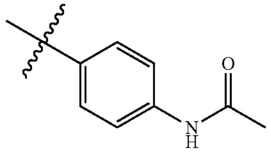 [SMILES: *c1ccc(NC(C)=O)cc1] | 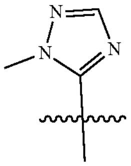 [SMILES: *c1ncnn1C] |
| 1-365 | Cl | 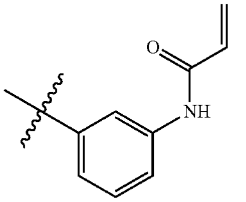 [SMILES: *c1cccc(NC(=O)C=C)c1] | 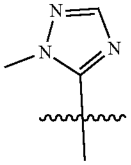 [SMILES: *c1ncnn1C] |
| 1-366 | Cl | 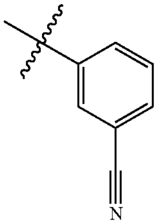 [SMILES: *c1cccc(C#N)c1] | 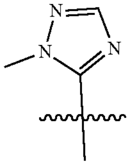 [SMILES: *c1ncnn1C] |
| 1-367 | Cl | 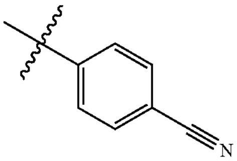 [SMILES: *c1ccc(C#N)cc1] | 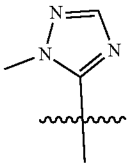 [SMILES: *c1ncnn1C] |
| 1-368 | Cl | 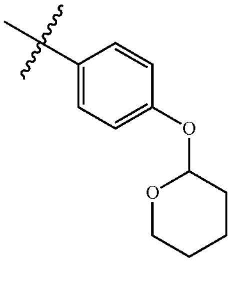 [SMILES: *c1ccc(OC2CCCCO2)cc1] | 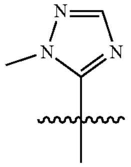 [SMILES: *c1ncnn1C] |

-continued
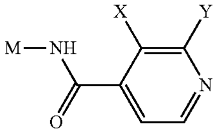
I
| NO. | X | Y | M |
|---|---|---|---|
| 1-369 | Cl | 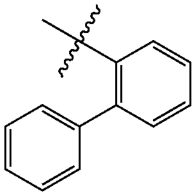 [SMILES: *c1ccccc1-c1ccccc1] | 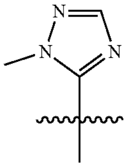 [SMILES: *c1ncnn1C] |
| 1-370 | Cl | 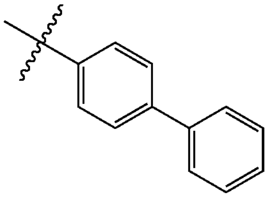 [SMILES: *c1ccc(-c2ccccc2)cc1] | 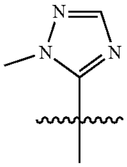 [SMILES: *c1ncnn1C] |
| 1-371 | Cl | 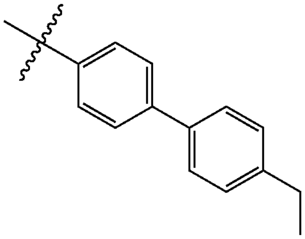 [SMILES: *c1ccc(-c2ccc(CC)cc2)cc1] | 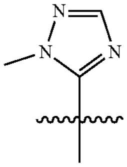 [SMILES: *c1ncnn1C] |
| 1-372 | Cl | 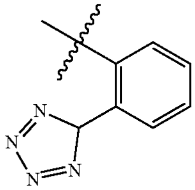 [SMILES: *c1ccccc1C1N=NN=N1] | 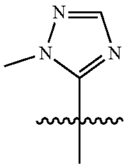 [SMILES: *c1ncnn1C] |
| 1-373 | Cl | 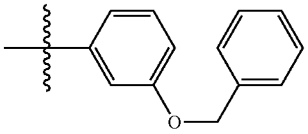 [SMILES: *c1cccc(OCc2ccccc2)c1] | 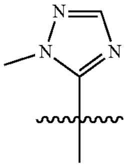 [SMILES: *c1ncnn1C] |
| 1-374 | Cl | 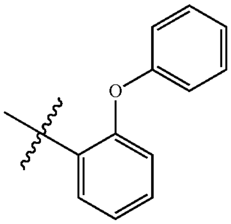 [SMILES: *c1ccccc1Oc1ccccc1] | 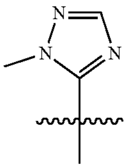 [SMILES: *c1ncnn1C] |

-continued
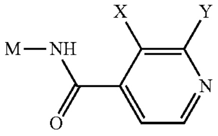
I
| NO. | X | Y | M |
|---|---|---|---|
| 1-375 | Cl | 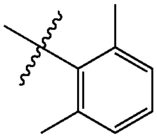 [SMILES: *c1c(C)cccc1C] | 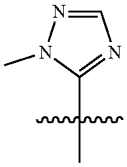 [SMILES: *c1ncnn1C] |
| 1-376 | Cl | 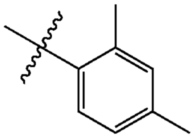 [SMILES: *c1ccc(C)cc1C] | 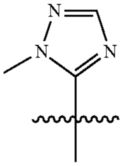 [SMILES: *c1ncnn1C] |
| 1-377 | Cl | 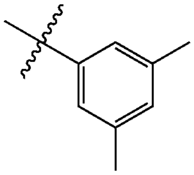 [SMILES: *c1cc(C)cc(C)c1] | 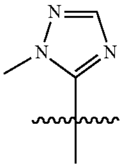 |
| 1-378 | Cl | 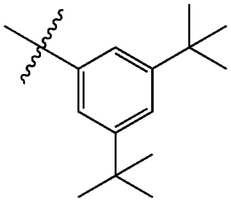 [SMILES: *c1cc(C(C)(C)C)cc(C(C)(C)C)c1] | 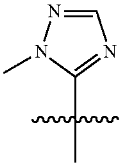 |
| 1-379 | Cl | 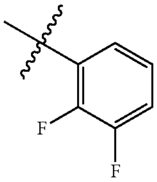 [SMILES: *c1cccc(F)c1F] | 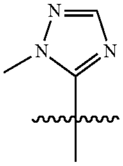 [SMILES: *c1ncnn1C] |
| 1-380 | Cl | 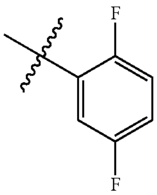 [SMILES: *c1cc(F)ccc1F] | 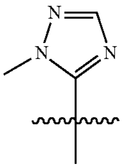 |
| 1-381 | Cl | 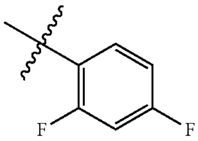 [SMILES: *c1ccc(F)cc1F] | 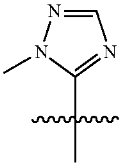 |

-continued
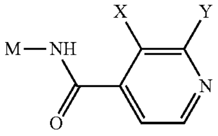
I
| NO. | X | Y | M |
|---|---|---|---|
| 1-382 | Cl | 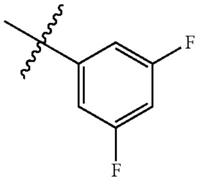 [SMILES: *c1cc(F)cc(F)c1] | 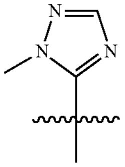 |
| 1-383 | Cl | 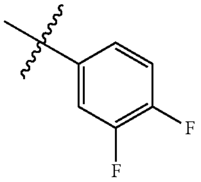 [SMILES: *c1ccc(F)c(F)c1] | 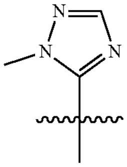 [SMILES: *c1ncnn1C] |
| 1-384 | Cl | 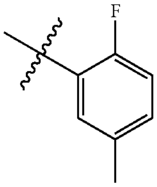 [SMILES: *c1cc(C)ccc1F] | 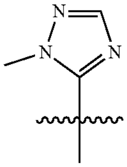 [SMILES: *c1ncnn1C] |
| 1-385 | Cl | 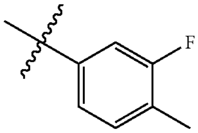 [SMILES: *c1ccc(C)c(F)c1] | 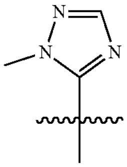 [SMILES: *c1ncnn1C] |
| 1-386 | Cl | 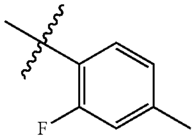 [SMILES: *c1ccc(C)cc1F] | 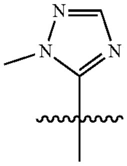 [SMILES: *c1ncnn1C] |
| 1-387 | Cl | 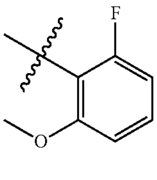 [SMILES: *c1c(F)cccc1OC] | 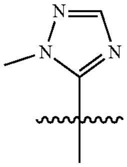 [SMILES: *c1ncnn1C] |
| 1-388 | Cl | 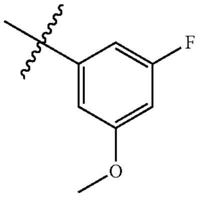 [SMILES: *c1cc(F)cc(OC)c1] | 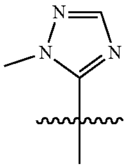 [SMILES: *c1ncnn1C] |

-continued
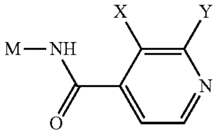
I
| NO. | X | Y | M |
| --- | --- | --- | --- |
| 1-389 | Cl | 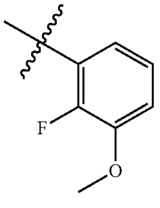 [SMILES: *c1cccc(OC)c1F] | 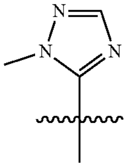 [SMILES: *c1ncnn1C] |
| 1-390 | Cl | 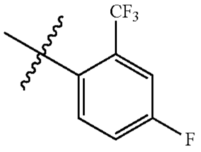 | 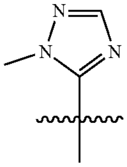 |
| 1-391 | Cl | 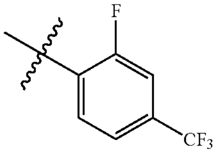 | 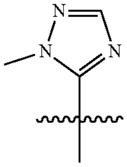 [SMILES: *c1ncnn1C] |
| 1-392 | Cl | 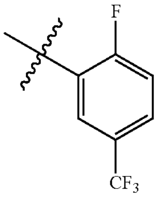 [SMILES: *c1cc(C(F)(F)F)ccc1F] | 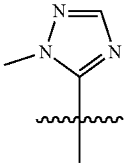 [SMILES: *c1ncnn1C] |
| 1-393 | Cl | 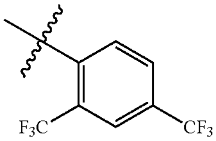 | 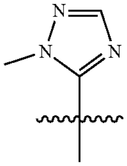 [SMILES: *c1ncnn1C] |
| 1-394 | Cl | 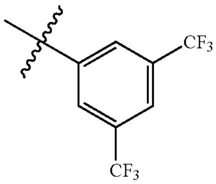 [SMILES: *c1cc(C(F)(F)F)cc(C(F)(F)F)c1] | 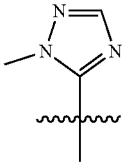 [SMILES: *c1ncnn1C] |
| 1-395 | Cl | 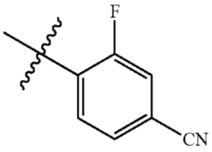 [SMILES: *c1ccc(C#N)cc1F] | 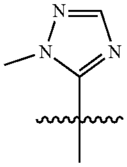 [SMILES: *c1ncnn1C] |

-continued
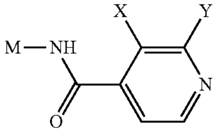
I
| NO. | X | Y | M |
|---|---|---|---|
| 1-396 | Cl | 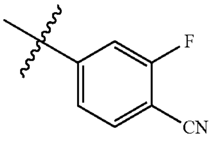 [SMILES: *c1ccc(C#N)c(F)c1] | 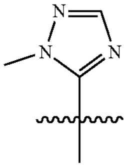 [SMILES: *c1ncnn1C] |
| 1-397 | Cl | 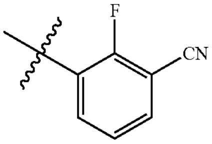 [SMILES: *c1cccc(C#N)c1F] | 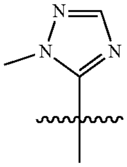 [SMILES: *c1ncnn1C] |
| 1-398 | Cl | 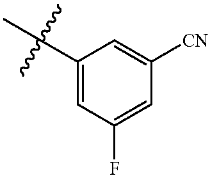 [SMILES: *c1cc(F)cc(C#N)c1] | 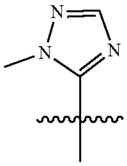 [SMILES: *c1ncnn1C] |
| 1-399 | Cl | 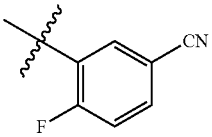 [SMILES: *c1cc(C#N)ccc1F] | 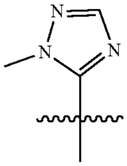 [SMILES: *c1ncnn1C] |
| 1-400 | Cl | 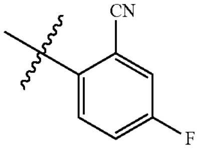 [SMILES: *c1ccc(F)cc1C#N] | 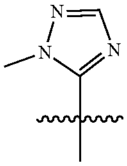 [SMILES: *c1ncnn1C] |
| 1-401 | Cl | 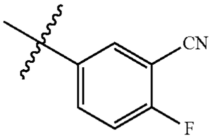 [SMILES: *c1ccc(F)c(C#N)c1] | 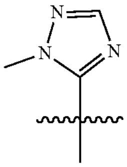 [SMILES: *c1ncnn1C] |
| 1-402 | Cl | 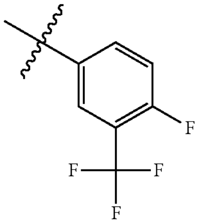 [SMILES: *c1ccc(F)c(C(F)(F)F)c1] | 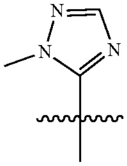 [SMILES: *c1ncnn1C] |

-continued
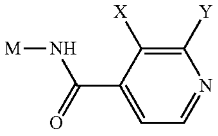
I
| NO. | X | Y | M |
|---|---|---|---|
| 1-403 | Cl | 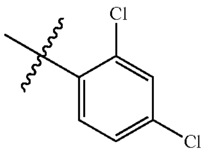 | 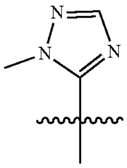 [SMILES: *c1ncnn1C] |
| 1-404 | Cl | 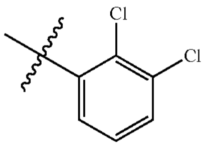 | 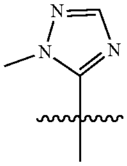 [SMILES: *c1ncnn1C] |
| 1-405 | Cl | 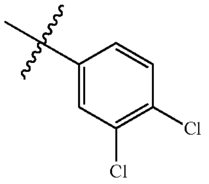 [SMILES: *c1ccc(Cl)c(Cl)c1] | 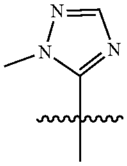 [SMILES: *c1ncnn1C] |
| 1-406 | Cl | 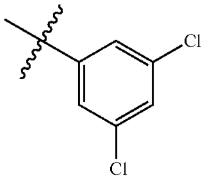 | 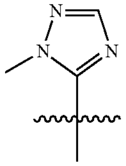 [SMILES: *c1ncnn1C] |
| 1-407 | Cl | 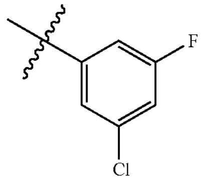 [SMILES: *c1cc(F)cc(Cl)c1] | 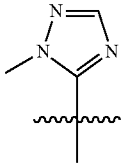 |
| 1-408 | Cl | 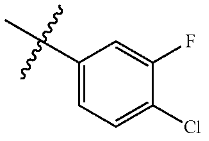 | 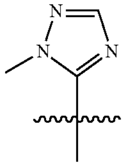 |
| 1-409 | Cl | 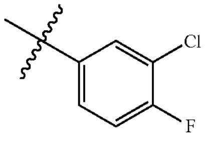 [SMILES: *c1ccc(F)c(Cl)c1] | 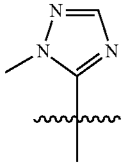 [SMILES: *c1ncnn1C] |

-continued
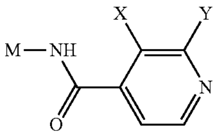
I
| NO. | X | Y | M |
|---|---|---|---|
| 1-410 | Cl | 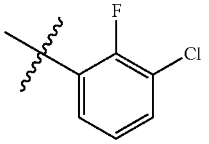 | 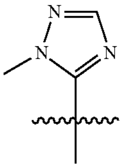 [SMILES: *c1ncnn1C] |
| 1-411 | Cl | 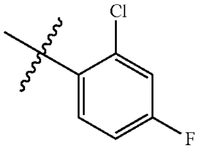 [SMILES: *c1ccc(F)cc1Cl] | 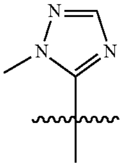 |
| 1-412 | Cl | 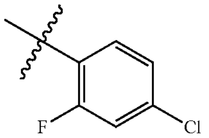 [SMILES: *c1ccc(Cl)cc1F] | 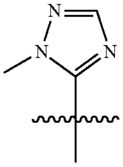 [SMILES: *c1ncnn1C] |
| 1-413 | Cl | 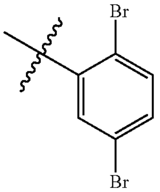 [SMILES: *c1cc(Br)ccc1Br] | 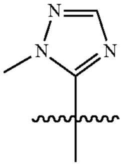 |
| 1-414 | Cl | 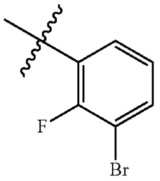 [SMILES: *c1cccc(Br)c1F] | 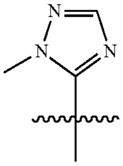 |
| 1-415 | Cl | 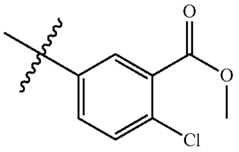 [SMILES: *c1ccc(Cl)c(C(=O)OC)c1] | 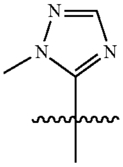 [SMILES: *c1ncnn1C] |
| 1-416 | Cl | 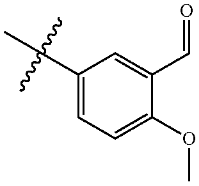 [SMILES: *c1ccc(OC)c(C=O)c1] | 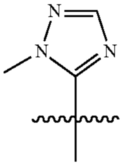 [SMILES: *c1ncnn1C] |

-continued
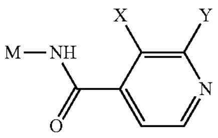
I
| NO. | X | Y | M |
|---|---|---|---|
| 1-417 | Cl | 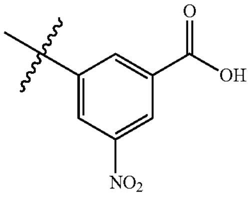 [SMILES: *c1cc(C(=O)O)cc([N+](=O)[O-])c1] | 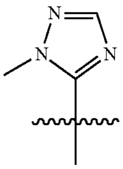 [SMILES: *c1ncnn1C] |
| 1-418 | Cl | 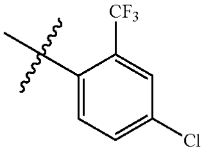 | 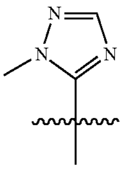 [SMILES: *c1ncnn1C] |
| 1-419 | Cl | 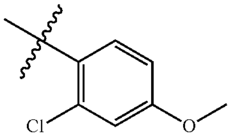 [SMILES: *c1ccc(OC)cc1Cl] | 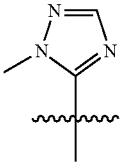 [SMILES: *c1ncnn1C] |
| 1-420 | Cl | 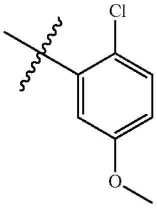 [SMILES: *c1cc(OC)ccc1Cl] | 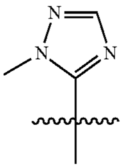 [SMILES: *c1ncnn1C] |
| 1-421 | Cl | 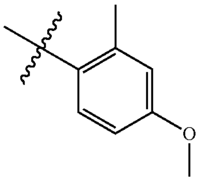 [SMILES: *c1ccc(OC)cc1C] | 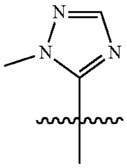 [SMILES: *c1ncnn1C] |
| 1-422 | Cl | 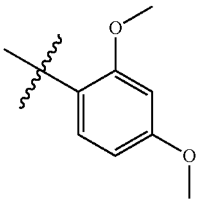 [SMILES: *c1ccc(OC)cc1OC] | 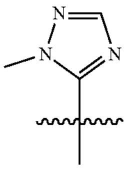 [SMILES: *c1ncnn1C] |

-continued
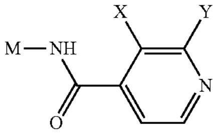
I
| NO. | X | Y | M |
|---|---|---|---|
| 1-423 | Cl | 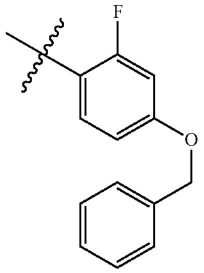 [SMILES: *c1ccc(OCc2ccccc2)cc1F] | 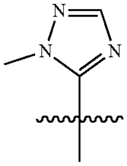 [SMILES: *c1ncnn1C] |
| 1-424 | Cl | 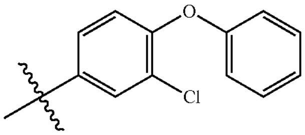 [SMILES: *c1ccc(Oc2ccccc2)c(Cl)c1] | 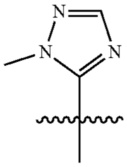 [SMILES: *c1ncnn1C] |
| 1-425 | Cl | 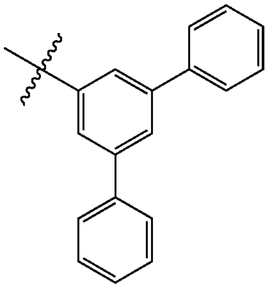 [SMILES: *c1cc(-c2ccccc2)cc(-c2ccccc2)c1] | 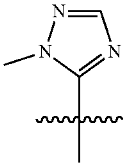 [SMILES: *c1ncnn1C] |
| 1-426 | Cl | 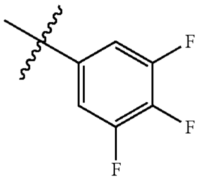 [SMILES: *c1cc(F)c(F)c(F)c1] | 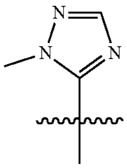 [SMILES: *c1ncnn1C] |
| 1-427 | Cl | 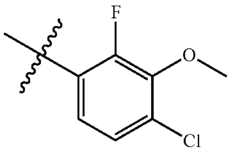 [SMILES: *c1ccc(Cl)c(OC)c1F] | 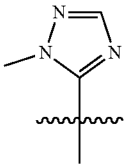 [SMILES: *c1ncnn1C] |
| 1-428 | Cl | 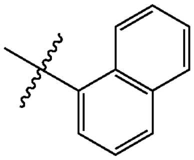 [SMILES: *c1cccc2ccccc12] | 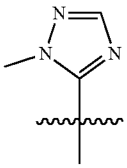 [SMILES: *c1ncnn1C] |

-continued
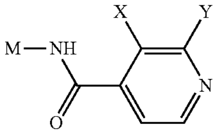
I
| NO. | X | Y | M |
|---|---|---|---|
| 1-429 | Cl | 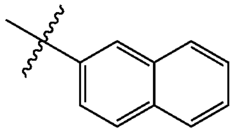 [SMILES: *c1ccc2ccccc2c1] | 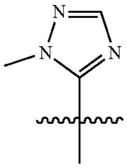 [SMILES: *c1ncnn1C] |
| 1-430 | Cl | 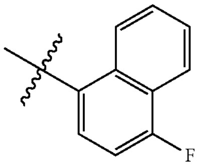 [SMILES: *c1ccc(F)c2ccccc12] | 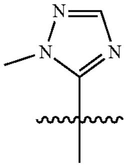 [SMILES: *c1ncnn1C] |
| 1-431 | Cl | 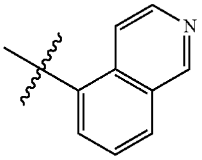 [SMILES: *c1cccc2cnccc12] | 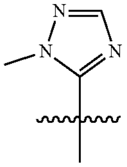 [SMILES: *c1ncnn1C] |
| 1-432 | Cl | 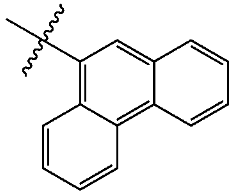 [SMILES: *c1cc2ccccc2c2ccccc12] | 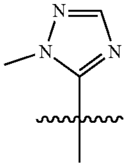 [SMILES: *c1ncnn1C] |
| 1-433 | Cl | 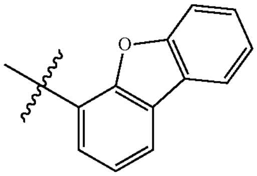 [SMILES: *c1cccc2c1oc1ccccc12] | 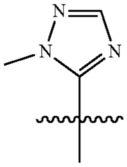 [SMILES: *c1ncnn1C] |
| 1-434 | Cl | 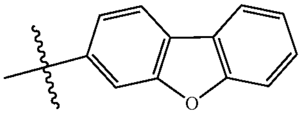 [SMILES: *c1ccc2c(c1)oc1ccccc12] | 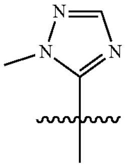 [SMILES: *c1ncnn1C] |
| 1-435 | Cl | 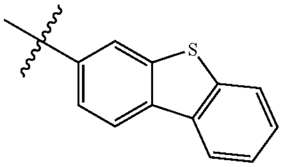 [SMILES: *c1ccc2c(c1)sc1ccccc12] | 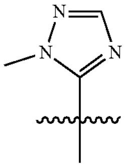 [SMILES: *c1ncnn1C] |

-continued
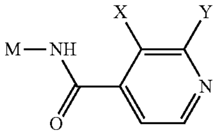
I
| NO. | X | Y | M |
|---|---|---|---|
| 1-436 | Cl | 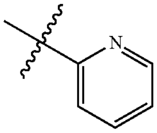 [SMILES: *c1ccccn1] | 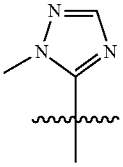 [SMILES: *c1ncnn1C] |
| 1-437 | Cl | 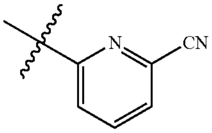 [SMILES: *c1cccc(C#N)n1] | 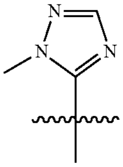 |
| 1-438 | Cl | 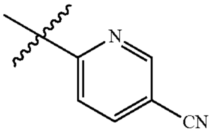 [SMILES: *c1ccc(C#N)cn1] | 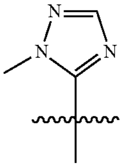 |
| 1-439 | Cl | 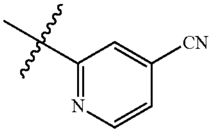 [SMILES: *c1cc(C#N)ccn1] | 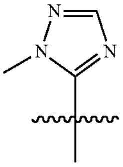 |
| 1-440 | Cl | 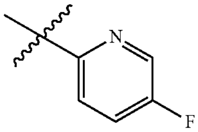 | 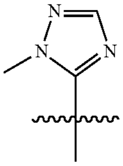 |
| 1-441 | Cl | 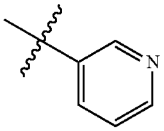 [SMILES: *c1cccnc1] | 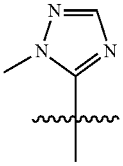 [SMILES: *c1ncnn1C] |
| 1-442 | Cl | 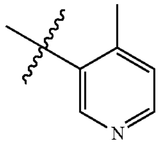 [SMILES: *c1cnccc1C] | 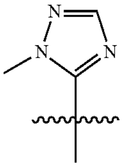 [SMILES: *c1ncnn1C] |
| 1-443 | Cl | 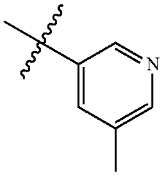 [SMILES: *c1cncc(C)c1] | 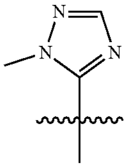 [SMILES: *c1ncnn1C] |

-continued
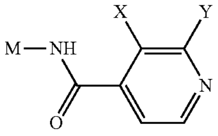
I
| NO. | X | Y | M |
|---|---|---|---|
| 1-444 | Cl | 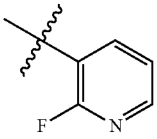 [SMILES: *c1cccnc1F] | 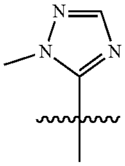 [SMILES: *c1ncnn1C] |
| 1-445 | Cl | 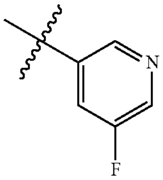 [SMILES: *c1cncc(F)c1] | 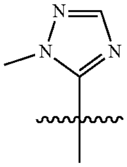 [SMILES: *c1ncnn1C] |
| 1-446 | Cl | 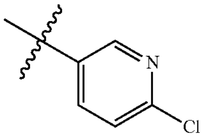 [SMILES: *c1ccc(Cl)nc1] | 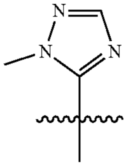 [SMILES: *c1ncnn1C] |
| 1-447 | Cl | 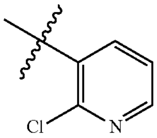 [SMILES: *c1cccnc1Cl] | 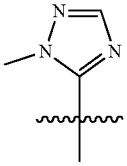 [SMILES: *c1ncnn1C] |
| 1-448 | Cl | 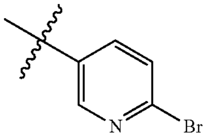 [SMILES: *c1ccc(Br)nc1] | 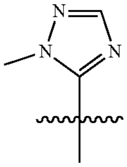 |
| 1-449 | Cl | 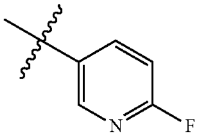 [SMILES: *c1ccc(F)nc1] | 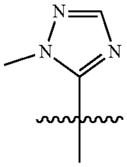 [SMILES: *c1ncnn1C] |
| 1-450 | Cl | 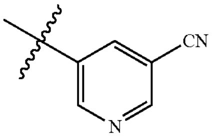 [SMILES: *c1cncc(C#N)c1] | 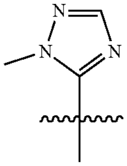 [SMILES: *c1ncnn1C] |

-continued
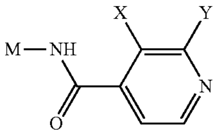
I
| NO. | X | Y | M |
| --- | --- | --- | --- |
| 1-451 | Cl | 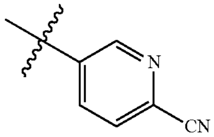 [SMILES: *c1ccc(C#N)nc1] | 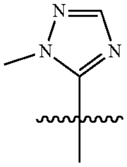 [SMILES: *c1ncnn1C] |
| 1-452 | Cl | 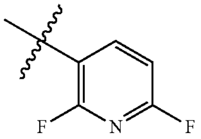 [SMILES: *c1ccc(F)nc1F] | 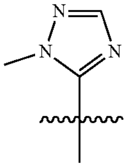 [SMILES: *c1ncnn1C] |
| 1-453 | Cl | 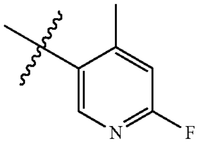 [SMILES: *c1cnc(F)cc1C] | 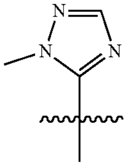 [SMILES: *c1ncnn1C] |
| 1-454 | Cl | 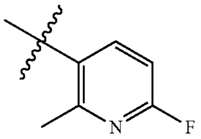 [SMILES: *c1ccc(F)nc1C] | 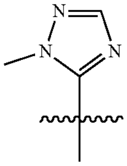 |
| 1-455 | Cl | 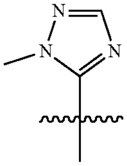 | 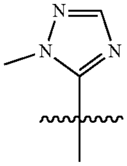 [SMILES: *c1ncnn1C] |
| 1-456 | Cl | 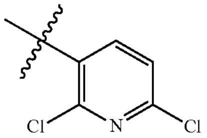 [SMILES: *c1ccc(Cl)nc1Cl] | 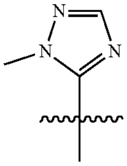 |
| 1-457 | Cl | 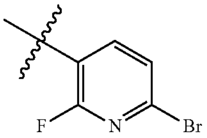 [SMILES: *c1ccc(Br)nc1F] | 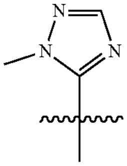 [SMILES: *c1ncnn1C] |

-continued
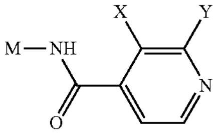
I
| NO. | X | Y | M |
|---|---|---|---|
| 1-458 | Cl | 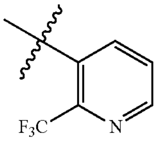 [SMILES: *c1cccnc1C(F)(F)F] | 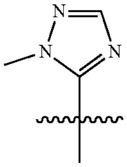 [SMILES: *c1ncnn1C] |
| 1-459 | Cl | 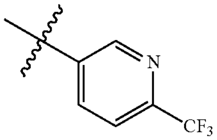 | 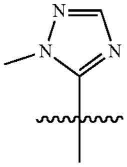 [SMILES: *c1ncnn1C] |
| 1-460 | Cl | 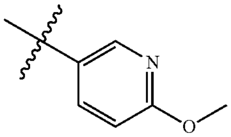 [SMILES: *c1ccc(OC)nc1] | 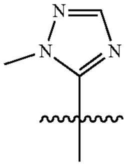 [SMILES: *c1ncnn1C] |
| 1-461 | Cl | 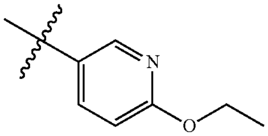 [SMILES: *c1ccc(OCC)nc1] | 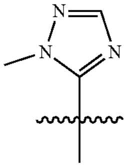 [SMILES: *c1ncnn1C] |
| 1-462 | Cl | 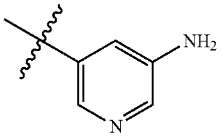 [SMILES: *c1cncc(N)c1] | 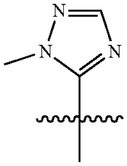 [SMILES: *c1ncnn1C] |
| 1-463 | Cl | 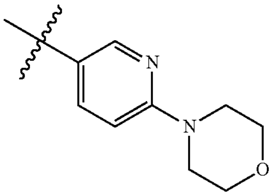 | 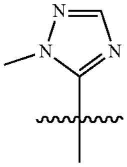 [SMILES: *c1ncnn1C] |
| 1-464 | Cl | 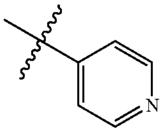 [SMILES: *c1ccncc1] | 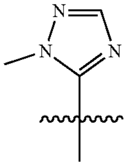 [SMILES: *c1ncnn1C] |

-continued
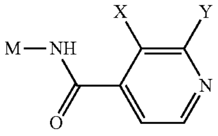
I
| NO. | X | Y | M |
|---|---|---|---|
| 1-465 | Cl | 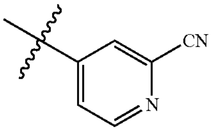 | 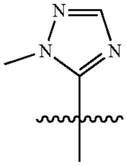 [SMILES: *c1ncnn1C] |
| 1-466 | Cl | 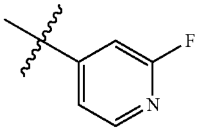 [SMILES: *c1ccnc(F)c1] | 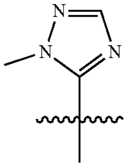 [SMILES: *c1ncnn1C] |
| 1-467 | Cl | 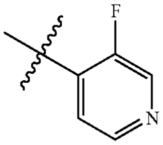 [SMILES: *c1ccncc1F] | 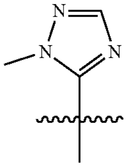 [SMILES: *c1ncnn1C] |
| 1-468 | Cl | 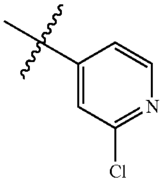 [SMILES: *c1ccnc(Cl)c1] | 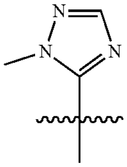 [SMILES: *c1ncnn1C] |
| 1-469 | Cl | 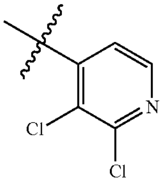 [SMILES: *c1ccnc(Cl)c1Cl] | 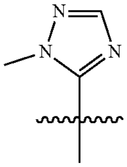 [SMILES: *c1ncnn1C] |
| 1-470 | Cl | 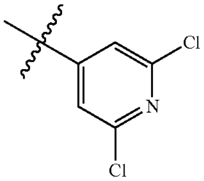 [SMILES: *c1cc(Cl)nc(Cl)c1] | 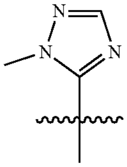 [SMILES: *c1ncnn1C] |
| 1-471 | Cl | 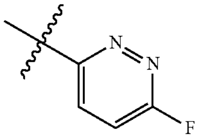 [SMILES: *c1ccc(F)nn1] | 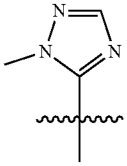 [SMILES: *c1ncnn1C] |

-continued
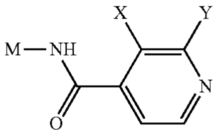
I
| NO. | X | Y | M |
|---|---|---|---|
| 1-472 | Cl | 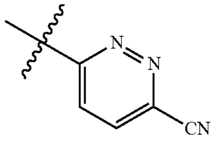 [SMILES: *c1ccc(C#N)nn1] | 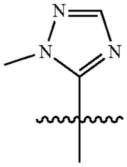 [SMILES: *c1ncnn1C] |
| 1-473 | Cl | 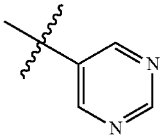 [SMILES: *c1cncnc1] | 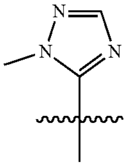 [SMILES: *c1ncnn1C] |
| 1-474 | Cl | 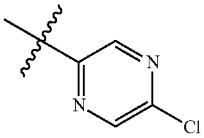 | 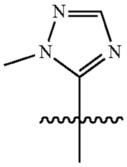 [SMILES: *c1ncnn1C] |
| 1-475 | Cl | 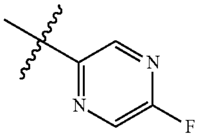 [SMILES: *c1cnc(F)cn1] | 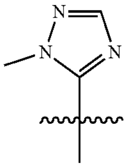 [SMILES: *c1ncnn1C] |
| 1-476 | Cl | 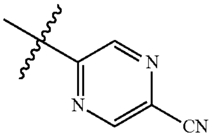 | 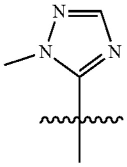 [SMILES: *c1ncnn1C] |
| 1-477 | Cl | 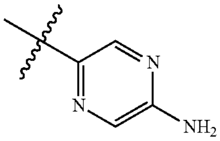 | 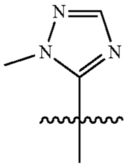 [SMILES: *c1ncnn1C] |
| 1-478 | Cl | 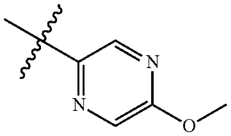 [SMILES: *c1cnc(OC)cn1] | 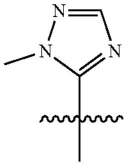 [SMILES: *c1ncnn1C] |

-continued
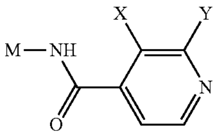
I
| NO. | X | Y | M |
|---|---|---|---|
| 1-479 | Cl | 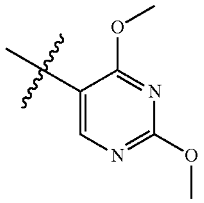 [SMILES: *c1cnc(OC)nc1OC] | 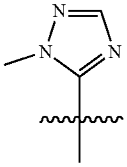 [SMILES: *c1ncnn1C] |
| 1-480 | Cl | 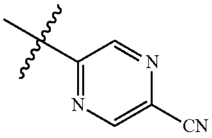 | 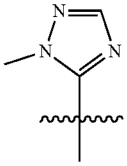 [SMILES: *c1ncnn1C] |
| 1-481 | Cl | 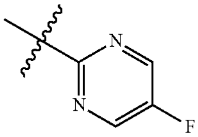 | 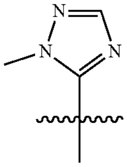 [SMILES: *c1ncnn1C] |
| 1-482 | Cl | 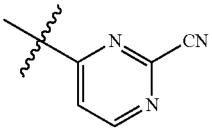 [SMILES: *c1ccnc(C#N)n1] | 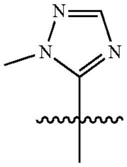 [SMILES: *c1ncnn1C] |
| 1-483 | Cl | 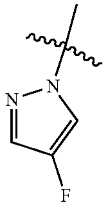 [SMILES: *n1cc(F)cn1] | 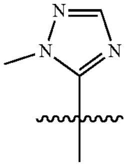 [SMILES: *c1ncnn1C] |
| 1-484 | Cl | 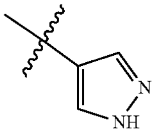 [SMILES: *c1cn[nH]c1] | 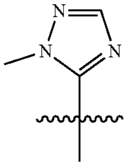 [SMILES: *c1ncnn1C] |
| 1-485 | Cl | 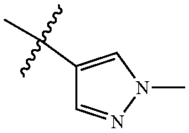 [SMILES: *c1cnn(C)c1] | 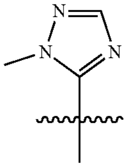 [SMILES: *c1ncnn1C] |

-continued
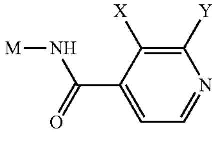
I
| NO. | X | Y | M |
|---|---|---|---|
| 1-486 | Cl | 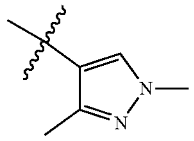 [SMILES: *c1cn(C)nc1C] | 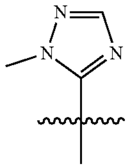 [SMILES: *c1ncnn1C] |
| 1-487 | Cl | 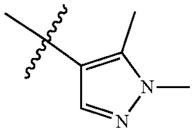 [SMILES: *c1cnn(C)c1C] | 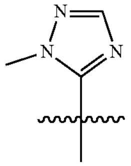 [SMILES: *c1ncnn1C] |
| 1-488 | Cl | 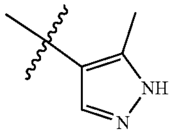 [SMILES: *c1cn[nH]c1C] | 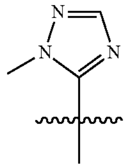 |
| 1-489 | Cl | 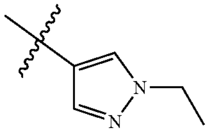 [SMILES: *c1cnn(CC)c1] | 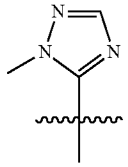 [SMILES: *c1ncnn1C] |
| 1-490 | Cl | 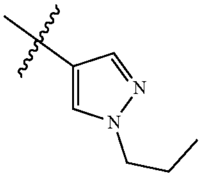 [SMILES: *c1cnn(CCC)c1] | 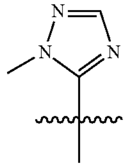 [SMILES: *c1ncnn1C] |
| 1-491 | Cl | 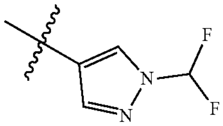 [SMILES: *c1cnn(C(F)F)c1] | 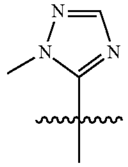 |
| 1-492 | Cl | 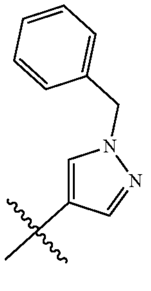 [SMILES: *c1cnn(Cc2ccccc2)c1] | 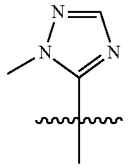 |

-continued
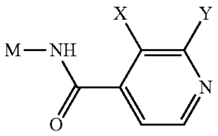
I
| NO. | X | Y | M |
|---|---|---|---|
| 1-493 | Cl | 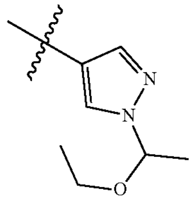 [SMILES: *c1cnn(C(C)OCC)c1] | 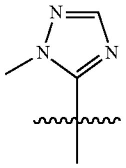 |
| 1-494 | Cl | 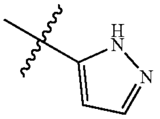 [SMILES: *c1ccn[nH]1] | 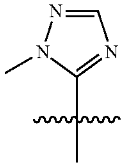 [SMILES: *c1ncnn1C] |
| 1-495 | Cl | 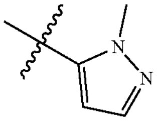 [SMILES: *c1ccnn1C] | 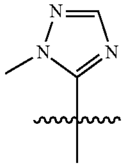 |
| 1-496 | Cl | 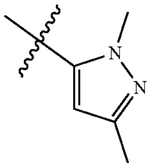 [SMILES: *c1cc(C)nn1C] | 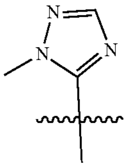 [SMILES: *c1ncnn1C] |
| 1-497 | Cl | 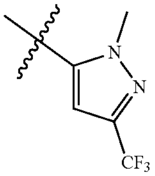 [SMILES: *c1cc(C(F)(F)F)nn1C] | 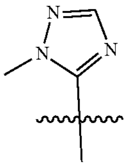 [SMILES: *c1ncnn1C] |
| 1-498 | Cl | 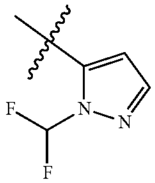 [SMILES: *c1ccnn1C(F)F] | 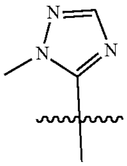 [SMILES: *c1ncnn1C] |
| 1-499 | Cl | 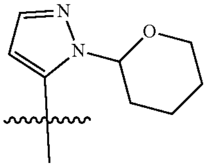 [SMILES: *c1ccnn1C1CCCCO1] | 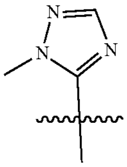 [SMILES: *c1ncnn1C] |

-continued
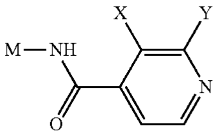
I
| NO. | X | Y | M |
|---|---|---|---|
| 1-500 | Cl | 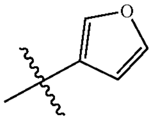 [SMILES: *c1ccoc1] | 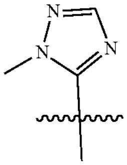 [SMILES: *c1ncnn1C] |
| 1-501 | Cl | 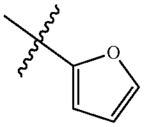 [SMILES: *c1ccco1] | 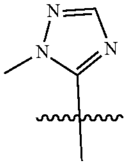 [SMILES: *c1ncnn1C] |
| 1-502 | Cl | 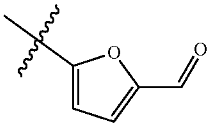 [SMILES: *c1ccc(C=O)o1] | 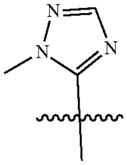 [SMILES: *c1ncnn1C] |
| 1-503 | Cl | 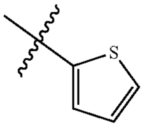 [SMILES: *c1cccs1] | 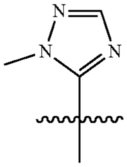 [SMILES: *c1ncnn1C] |
| 1-504 | Cl | 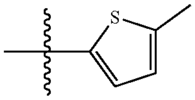 [SMILES: *c1ccc(C)s1] | 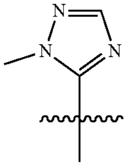 [SMILES: *c1ncnn1C] |
| 1-505 | Cl | 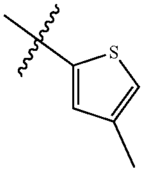 [SMILES: *c1cc(C)cs1] | 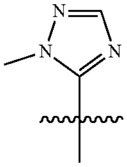 [SMILES: *c1ncnn1C] |
| 1-506 | Cl | 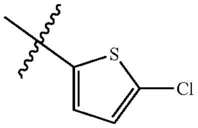 [SMILES: *c1ccc(Cl)s1] | 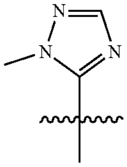 [SMILES: *c1ncnn1C] |

-continued
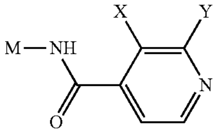
I
| NO. | X | Y | M |
|---|---|---|---|
| 1-507 | Cl | 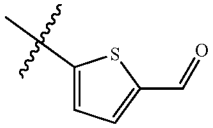 [SMILES: *c1ccc(C=O)s1] | 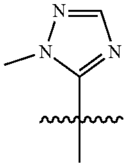 [SMILES: *c1ncnn1C] |
| 1-508 | Cl | 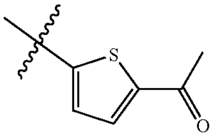 [SMILES: *c1ccc(C(C)=O)s1] | 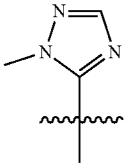 [SMILES: *c1ncnn1C] |
| 1-509 | Cl | 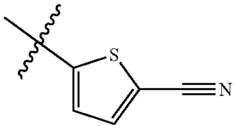 [SMILES: *c1ccc(C#N)s1] | 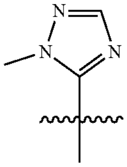 [SMILES: *c1ncnn1C] |
| 1-510 | Cl | 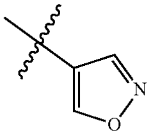 [SMILES: *c1cnoc1] | 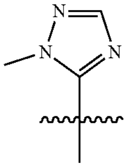 [SMILES: *c1ncnn1C] |
| 1-511 | $CH_3$ | 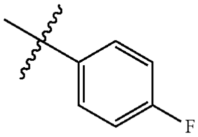 [SMILES: *c1ccc(F)cc1] | 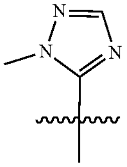 [SMILES: *c1ncnn1C] |
| 1-512 | F | 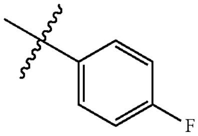 [SMILES: *c1ccc(F)cc1] | 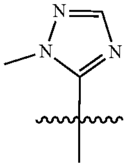 [SMILES: *c1ncnn1C] |
| 1-513 | Br | 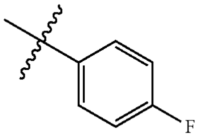 [SMILES: *c1ccc(F)cc1] | 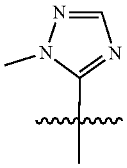 [SMILES: *c1ncnn1C] |

-continued
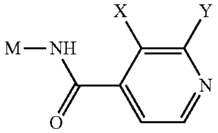
I
| NO. | X | Y | M |
|---|---|---|---|
| 1-514 | 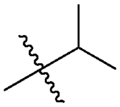 [SMILES: *C(C)C] | 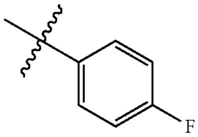 [SMILES: *c1ccc(F)cc1] | 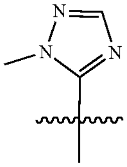 [SMILES: *c1ncnn1C] |
| 1-515 | $CF_3$ | 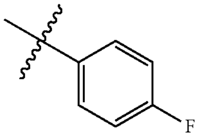 [SMILES: *c1ccc(F)cc1] | 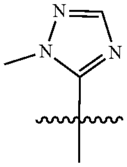 [SMILES: *c1ncnn1C] |
| 1-516 | 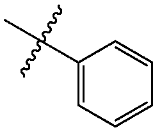 [SMILES: *c1ccccc1] | 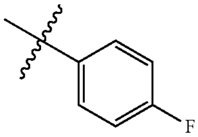 [SMILES: *c1ccc(F)cc1] | 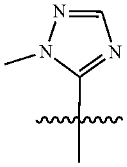 [SMILES: *c1ncnn1C] |
| 1-517 | 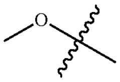 [SMILES: *OC] | 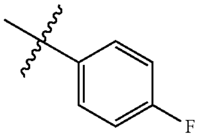 [SMILES: *c1ccc(F)cc1] | 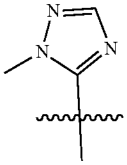 [SMILES: *c1ncnn1C] |
| 1-518 | 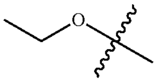 [SMILES: *OCC] | 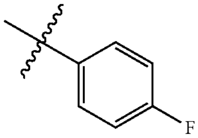 [SMILES: *c1ccc(F)cc1] | 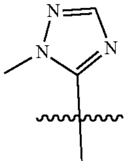 [SMILES: *c1ncnn1C] |
| 1-519 | 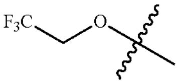 [SMILES: *OCC(F)(F)F] | 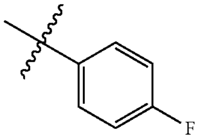 [SMILES: *c1ccc(F)cc1] | 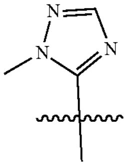 [SMILES: *c1ncnn1C] |
| 1-520 | 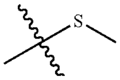 | 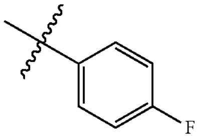 [SMILES: *c1ccc(F)cc1] | 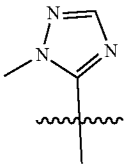 [SMILES: *c1ncnn1C] |
| 1-521 | 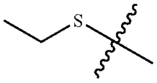 | 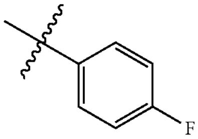 [SMILES: *c1ccc(F)cc1] | 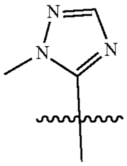 [SMILES: *c1ncnn1C] |

-continued
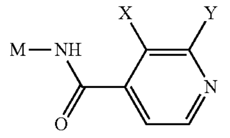
I
| NO. | X | Y | M |
|---|---|---|---|
| 1-522 | 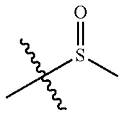 [SMILES: *S(C)=O] | 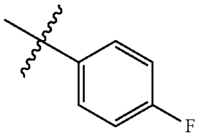 [SMILES: *c1ccc(F)cc1] | 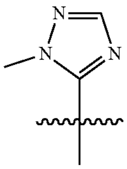 [SMILES: *c1ncnn1C] |
| 1-523 | 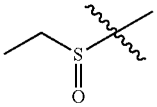 [SMILES: *S(=O)CC] | 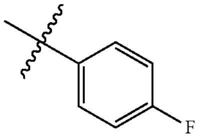 [SMILES: *c1ccc(F)cc1] | 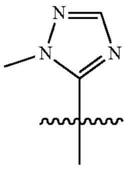 [SMILES: *c1ncnn1C] |
| 1-524 | 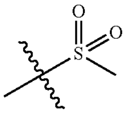 [SMILES: *S(C)(=O)=O] | 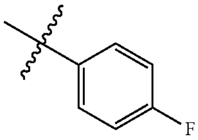 [SMILES: *c1ccc(F)cc1] | 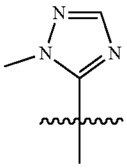 [SMILES: *c1ncnn1C] |
| 1-525 | 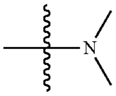 [SMILES: *N(C)C] | 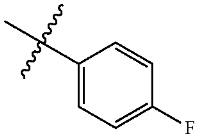 [SMILES: *c1ccc(F)cc1] | 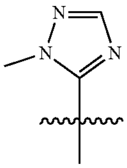 [SMILES: *c1ncnn1C] |
| 1-526 | 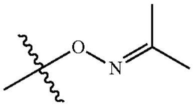 [SMILES: *ON=C(C)C] | 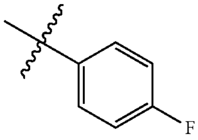 [SMILES: *c1ccc(F)cc1] | 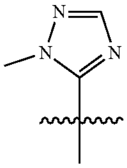 [SMILES: *c1ncnn1C] |
| 1-527 | Et | 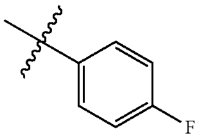 [SMILES: *c1ccc(F)cc1] | 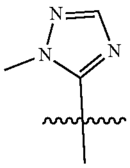 [SMILES: *c1ncnn1C] |
| 1-528 | 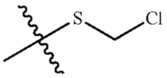 [SMILES: *SCCl] | 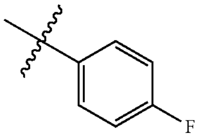 [SMILES: *c1ccc(F)cc1] | 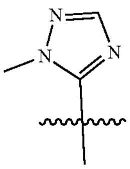 [SMILES: *c1ncnn1C] |

-continued
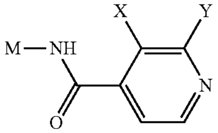
I
| NO. | X | Y | M |
|---|---|---|---|
| 1-529 | $NO_2$ | 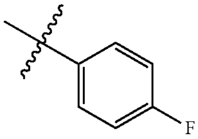 | 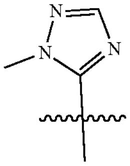 [SMILES: *c1ncnn1C] |
| 1-530 | CN | 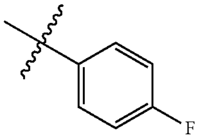 [SMILES: *c1ccc(F)cc1] | 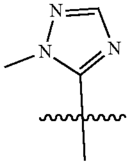 [SMILES: *c1ncnn1C] |
| 1-531 | 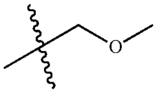 [SMILES: *COC] | 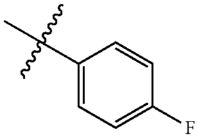 [SMILES: *c1ccc(F)cc1] | 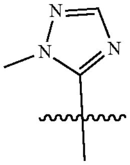 [SMILES: *c1ncnn1C] |
| 1-532 | 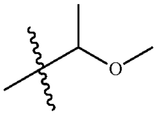 [SMILES: *C(C)OC] | 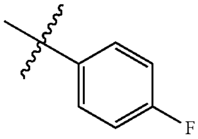 | 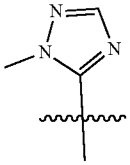 [SMILES: *c1ncnn1C] |
| 1-533 | 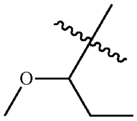 [SMILES: *C(CC)OC] | 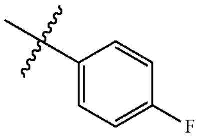 [SMILES: *c1ccc(F)cc1] | 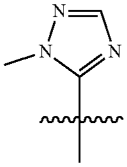 |
| 1-534 | 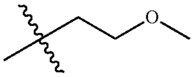 [SMILES: *CCOC] | 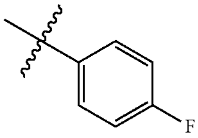 | 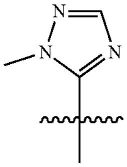 |
| 1-535 | 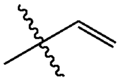 | 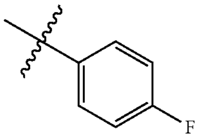 [SMILES: *c1ccc(F)cc1] | 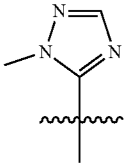 |
| 1-536 | 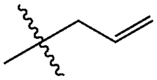 [SMILES: *CC=C] | 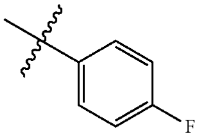 [SMILES: *c1ccc(F)cc1] | 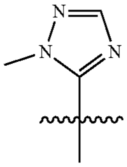 |

-continued
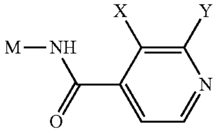
I
| NO. | X | Y | M |
|---|---|---|---|
| 1-537 | 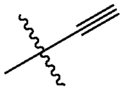 [SMILES: *C#C] | 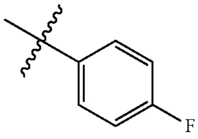 [SMILES: *c1ccc(F)cc1] | 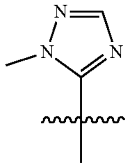 [SMILES: *c1ncnn1C] |
| 1-538 | 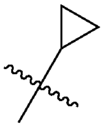 [SMILES: *C1CC1] | 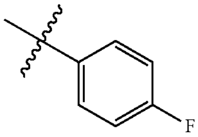 [SMILES: *c1ccc(F)cc1] | 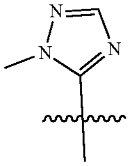 [SMILES: *c1ncnn1C] |
| 1-539 | 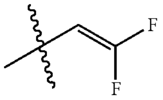 [SMILES: *C=C(F)F] | 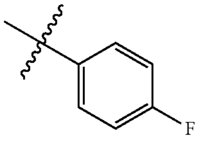 [SMILES: *c1ccc(F)cc1] | 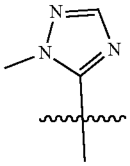 [SMILES: *c1ncnn1C] |
| 1-540 | 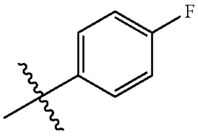 [SMILES: *c1ccc(F)cc1] | 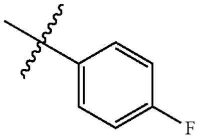 | 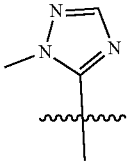 [SMILES: *c1ncnn1C] |
| 1-541 | Cl | 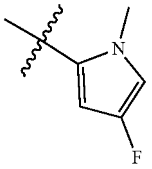 [SMILES: *c1cc(F)cn1C] | 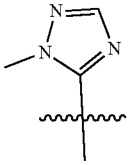 [SMILES: *c1ncnn1C] |
| 1-542 | Cl | 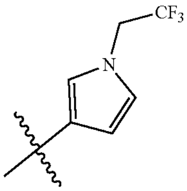 [SMILES: *c1ccn(CC(F)(F)F)c1] | 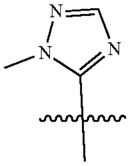 [SMILES: *c1ncnn1C] |
| 1-543 | Cl | 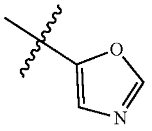 [SMILES: *c1cnco1] | 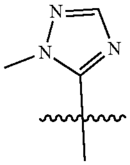 [SMILES: *c1ncnn1C] |

-continued
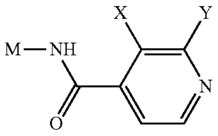
I
| NO. | X | Y | M |
|---|---|---|---|
| 1-544 | Cl | 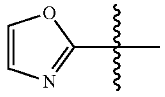 [SMILES: *c1ncco1] | 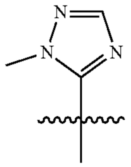 [SMILES: *c1ncnn1C] |
| 1-545 | Cl | 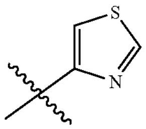 [SMILES: *c1cscn1] | 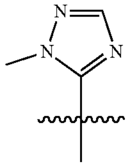 [SMILES: *c1ncnn1C] |
| 1-546 | Cl | 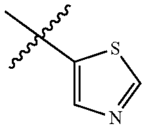 [SMILES: *c1cncs1] | 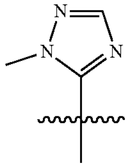 [SMILES: *c1ncnn1C] |
| 1-547 | Cl | 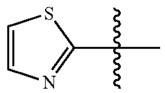 [SMILES: *c1nccs1] | 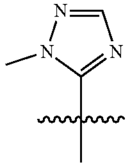 [SMILES: *c1ncnn1C] |
| 1-548 | Cl | 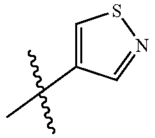 [SMILES: *c1cnsc1] | 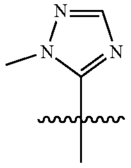 [SMILES: *c1ncnn1C] |
| 1-549 | Cl | 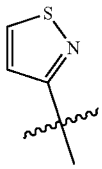 [SMILES: *c1ccsn1] | 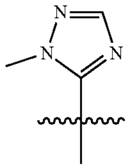 [SMILES: *c1ncnn1C] |
| 1-550 | Cl | 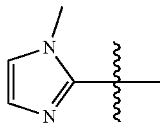 [SMILES: *c1nccn1C] | 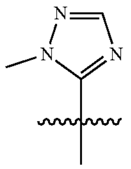 [SMILES: *c1ncnn1C] |

-continued
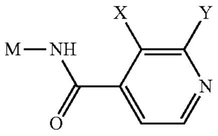
I
| NO. | X | Y | M |
|---|---|---|---|
| 1-551 | Cl | 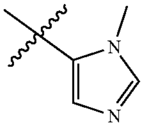 [SMILES: *c1cncn1C] | 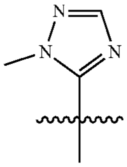 [SMILES: *c1ncnn1C] |
| 1-552 | Cl | 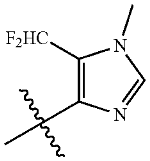 [SMILES: *c1ncn(C)c1C(F)F] | 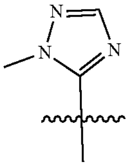 [SMILES: *c1ncnn1C] |
| 1-553 | Cl | 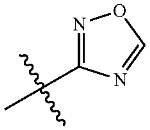 [SMILES: *c1ncon1] | 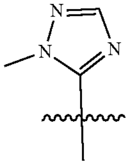 [SMILES: *c1ncnn1C] |
| 1-554 | Cl | 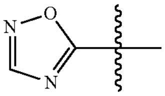 [SMILES: *c1ncno1] | 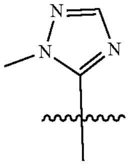 [SMILES: *c1ncnn1C] |
| 1-555 | Cl | 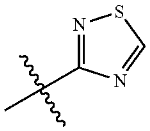 [SMILES: *c1ncsn1] | 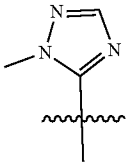 [SMILES: *c1ncnn1C] |
| 1-556 | Cl | 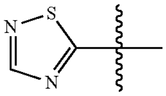 [SMILES: *c1ncns1] | 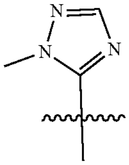 [SMILES: *c1ncnn1C] |
| 1-557 | Cl | 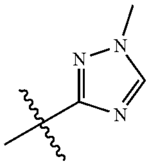 [SMILES: *c1ncn(C)n1] | 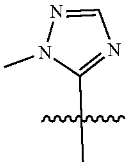 [SMILES: *c1ncnn1C] |

-continued
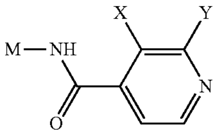
I
| NO. | X | Y | M |
|---|---|---|---|
| 1-558 | Cl | 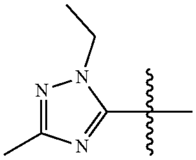 [SMILES: *c1nc(C)nn1CC] | 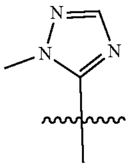 [SMILES: *c1ncnn1C] |
| 1-559 | Cl | 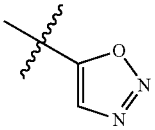 [SMILES: *c1cnno1] | 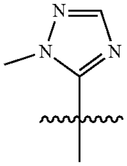 [SMILES: *c1ncnn1C] |
| 1-560 | Cl | 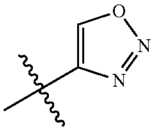 [SMILES: *c1conn1] | 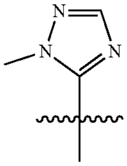 [SMILES: *c1ncnn1C] |
| 1-561 | Cl | 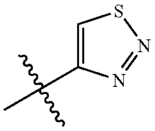 | 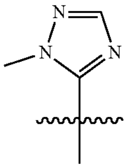 [SMILES: *c1ncnn1C] |
| 1-562 | Cl | 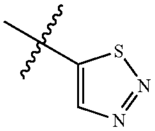 [SMILES: *c1cnns1] | 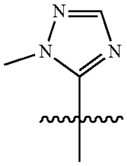 [SMILES: *c1ncnn1C] |
| 1-563 | Cl | 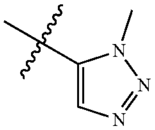 | 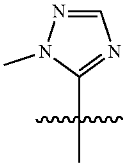 [SMILES: *c1ncnn1C] |
| 1-564 | Cl | 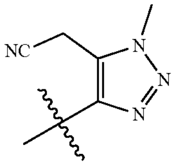 [SMILES: *c1nnn(C)c1CC#N] | 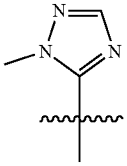 [SMILES: *c1ncnn1C] |

-continued
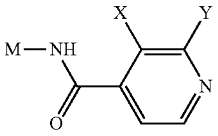
I
| NO. | X | Y | M |
|---|---|---|---|
| 1-565 | Cl | 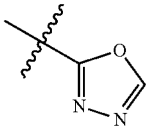 | 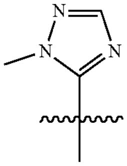 [SMILES: *c1ncnn1C] |
| 1-566 | Cl | 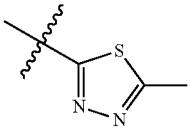 [SMILES: *c1nnc(C)s1] | 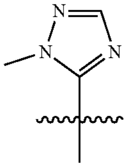 [SMILES: *c1ncnn1C] |
| 1-567 | Cl | 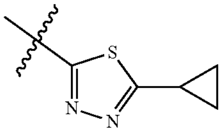 [SMILES: *c1nnc(C2CC2)s1] | 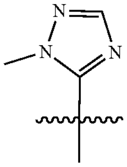 [SMILES: *c1ncnn1C] |
| 1-568 | Cl | 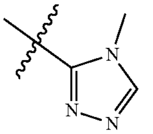 [SMILES: *c1nncn1C] | 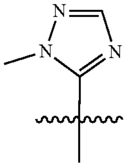 [SMILES: *c1ncnn1C] |
| 1-569 | Cl | 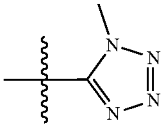 [SMILES: *c1nnnn1C] | 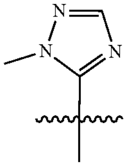 [SMILES: *c1ncnn1C] |
| 1-570 | Cl | 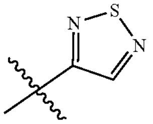 [SMILES: *c1cnsn1] | 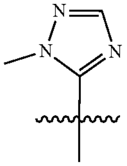 [SMILES: *c1ncnn1C] |
| 1-571 | Cl | 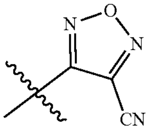 [SMILES: *c1nonc1C#N] | 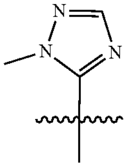 [SMILES: *c1ncnn1C] |

-continued
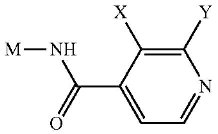
I
| NO. | X | Y | M |
|---|---|---|---|
| 1-572 | Cl | 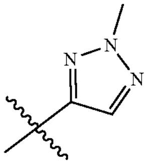 [SMILES: *c1cnn(C)n1] | 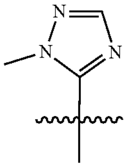 [SMILES: *c1ncnn1C] |
| 1-573 | Cl | 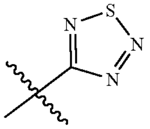 [SMILES: *c1nnsn1] | 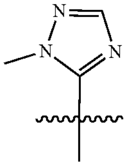 [SMILES: *c1ncnn1C] |
| 1-574 | Cl | 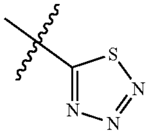 [SMILES: *c1nnns1] | 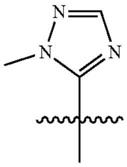 [SMILES: *c1ncnn1C] |
| 1-575 | Cl | 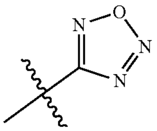 [SMILES: *c1nnon1] | 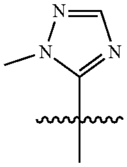 [SMILES: *c1ncnn1C] |
| 1-576 | Cl | 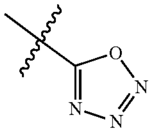 [SMILES: *c1nnno1] | 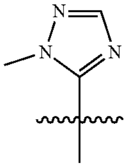 [SMILES: *c1ncnn1C] |
| 1-577 | Cl | 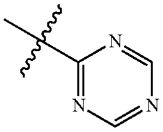 [SMILES: *c1ncncn1] | 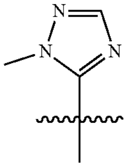 [SMILES: *c1ncnn1C] |
| 1-578 | Cl | 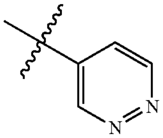 [SMILES: *c1ccnnc1] | 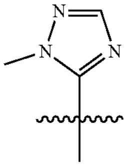 [SMILES: *c1ncnn1C] |
| 1-579 | Cl | 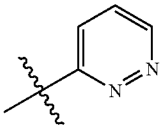 [SMILES: *c1cccnn1] | 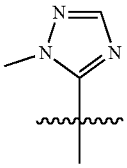 [SMILES: *c1ncnn1C] |

-continued
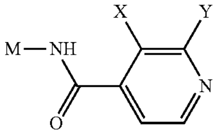
I
| NO. | X | Y | M |
|---|---|---|---|
| 1-580 | Cl | 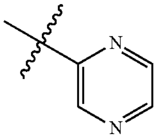 [SMILES: *c1cnccn1] | 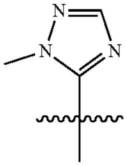 [SMILES: *c1ncnn1C] |
| 1-581 | Cl | 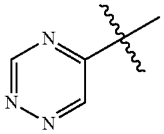 [SMILES: *c1cnncn1] | 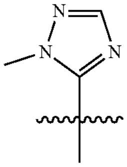 [SMILES: *c1ncnn1C] |
| 1-582 | Cl | 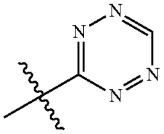 [SMILES: *c1nncnn1] | 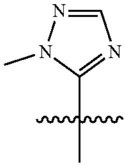 [SMILES: *c1ncnn1C] |
| 1-583 | Cl | 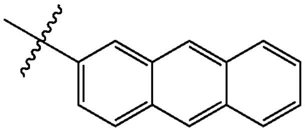 [SMILES: *c1ccc2cc3ccccc3cc2c1] | 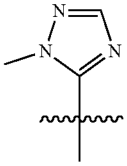 [SMILES: *c1ncnn1C] |
| 1-584 | Cl | 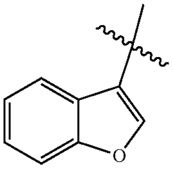 [SMILES: *c1coc2ccccc12] | 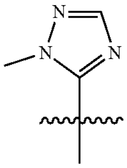 [SMILES: *c1ncnn1C] |
| 1-585 | Cl | 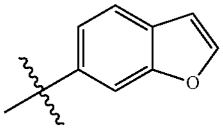 [SMILES: *c1ccc2ccoc2c1] | 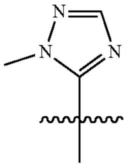 [SMILES: *c1ncnn1C] |
| 1-586 | Cl | 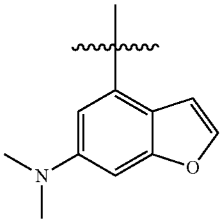 [SMILES: *c1cc(N(C)C)cc2occc12] | 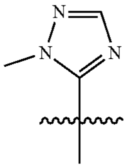 [SMILES: *c1ncnn1C] |

-continued
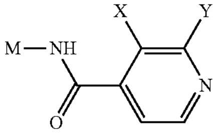
I
| NO. | X | Y | M |
|---|---|---|---|
| 1-587 | Cl | 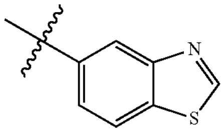 [SMILES: *c1ccc2scnc2c1] | 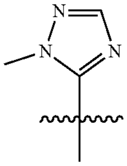 [SMILES: *c1ncnn1C] |
| 1-588 | Cl | 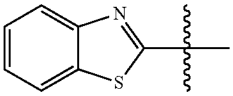 | 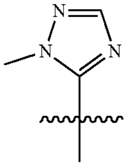 [SMILES: *c1ncnn1C] |
| 1-589 | Cl | 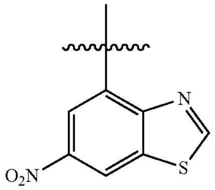 | 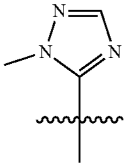 [SMILES: *c1ncnn1C] |
| 1-590 | Cl | 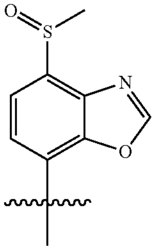 [SMILES: *c1ccc(S(C)=O)c2ncoc12] | 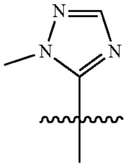 |
| 1-591 | Cl | 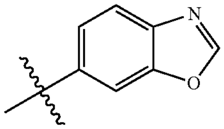 [SMILES: *c1ccc2ncoc2c1] | 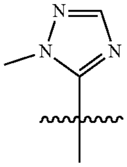 [SMILES: *c1ncnn1C] |
| 1-592 | Cl | 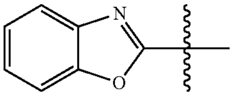 | 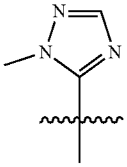 [SMILES: *c1ncnn1C] |
| 1-593 | Cl | 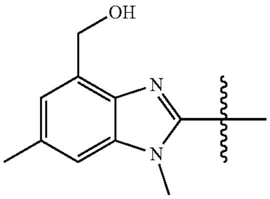 [SMILES: *c1nc2c(CO)cc(C)cc2n1C] | 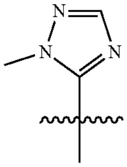 [SMILES: *c1ncnn1C] |

-continued
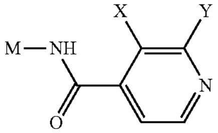
I
| NO. | X | Y | M |
| --- | --- | --- | --- |
| 1-594 | Cl | 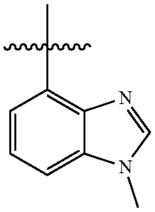 [SMILES: *c1cccc2c1ncn2C] | 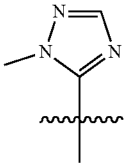 [SMILES: *c1ncnn1C] |
| 1-595 | Cl | 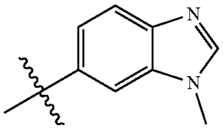 [SMILES: *c1ccc2ncn(C)c2c1] | 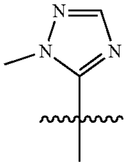 [SMILES: *c1ncnn1C] |
| 1-596 | Cl | 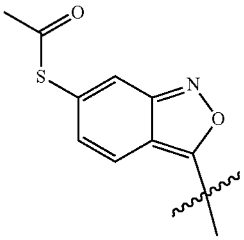 [SMILES: *c1onc2cc(SC(C)=O)ccc12] | 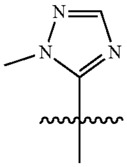 [SMILES: *c1ncnn1C] |
| 1-597 | Cl | 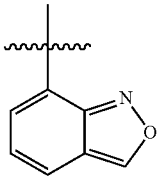 [SMILES: *c1cccc2conc12] | 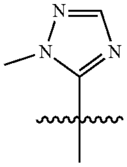 [SMILES: *c1ncnn1C] |
| 1-598 | Cl | 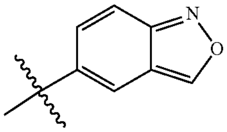 [SMILES: *c1ccc2nocc2c1] | 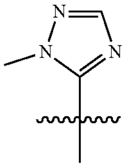 [SMILES: *c1ncnn1C] |
| 1-599 | Cl | 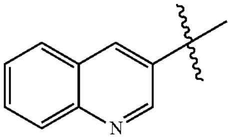 [SMILES: *c1cnc2ccccc2c1] | 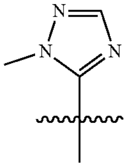 [SMILES: *c1ncnn1C] |
| 1-600 | Cl | 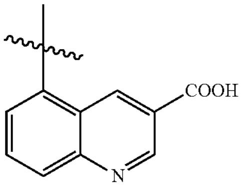 [SMILES: *c1cccc2ncc(C(=O)O)cc12] | 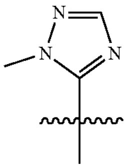 [SMILES: *c1ncnn1C] |

-continued
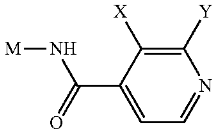
I
| NO. | X | Y | M |
|---|---|---|---|
| 1-601 | Cl | 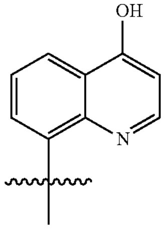 [SMILES: *c1cccc2c(O)ccnc12] | 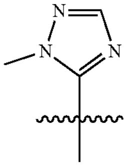 [SMILES: *c1ncnn1C] |
| 1-602 | Cl | 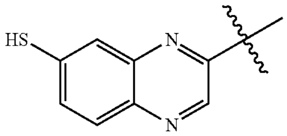 [SMILES: *c1cnc2ccc(S)cc2n1] | 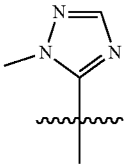 [SMILES: *c1ncnn1C] |
| 1-603 | Cl | 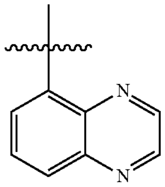 [SMILES: *c1cccc2nccnc12] | 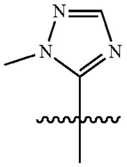 [SMILES: *c1ncnn1C] |
| 1-604 | Cl | 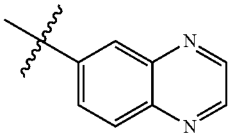 [SMILES: *c1ccc2nccnc2c1] | 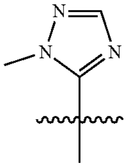 [SMILES: *c1ncnn1C] |
| 1-605 | Cl | 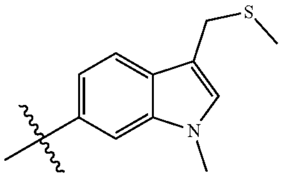 [SMILES: *c1ccc2c(CSC)cn(C)c2c1] | 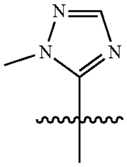 [SMILES: *c1ncnn1C] |
| 1-606 | Cl | 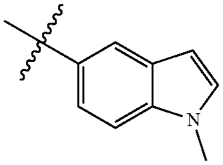 [SMILES: *c1ccc2c(ccn2C)c1] | 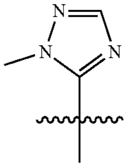 [SMILES: *c1ncnn1C] |
| 1-607 | Cl | 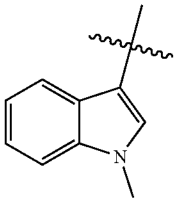 [SMILES: *c1cn(C)c2ccccc12] | 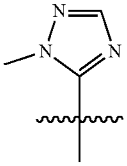 [SMILES: *c1ncnn1C] |

-continued
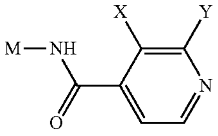
I
| NO. | X | Y | M |
|---|---|---|---|
| 1-608 | Cl | 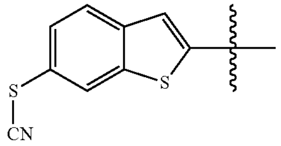 [SMILES: *c1cc2ccc(SC#N)cc2s1] | 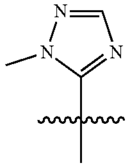 [SMILES: *c1ncnn1C] |
| 1-609 | Cl | 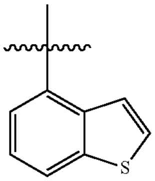 [SMILES: *c1cccc2sccc12] | 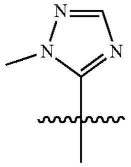 [SMILES: *c1ncnn1C] |
| 1-610 | Cl | 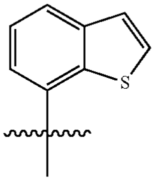 [SMILES: *c1cccc2ccsc12] | 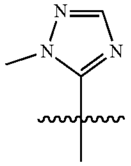 [SMILES: *c1ncnn1C] |
| 1-611 | Cl | 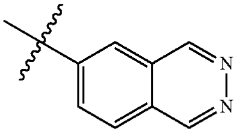 [SMILES: *c1ccc2cnncc2c1] | 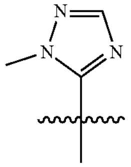 [SMILES: *c1ncnn1C] |
| 1-612 | Cl | 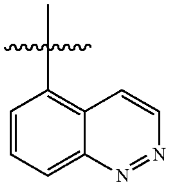 [SMILES: *c1cccc2nnccc12] | 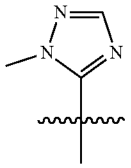 |
| 1-613 | Cl | 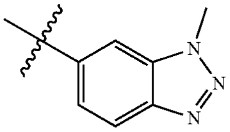 [SMILES: *c1ccc2nnn(C)c2c1] | 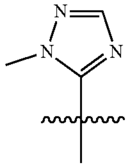 [SMILES: *c1ncnn1C] |
| 1-614 | Cl | 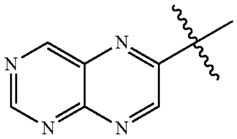 [SMILES: *c1cnc2ncncc2n1] | 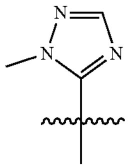 [SMILES: *c1ncnn1C] |

-continued
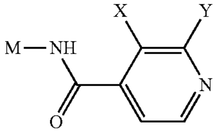
I
| NO. | X | Y | M |
|---|---|---|---|
| 1-615 | Cl | 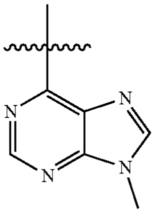 [SMILES: *c1ncnc2c1ncn2C] | 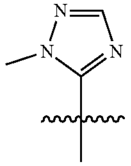 [SMILES: *c1ncnn1C] |
| 1-616 | Cl | 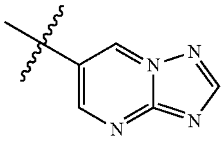 | 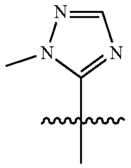 [SMILES: *c1ncnn1C] |
| 1-617 | Cl | 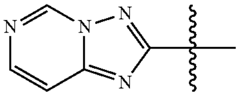 [SMILES: *c1nc2ccncn2n1] | 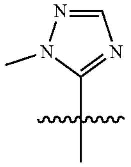 [SMILES: *c1ncnn1C] |
| 1-618 | Cl | 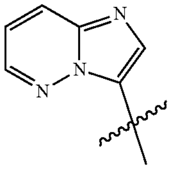 [SMILES: *c1cnc2cccnn12] | 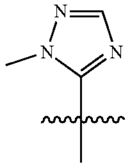 [SMILES: *c1ncnn1C] |
| 1-619 | Cl | 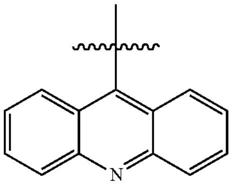 [SMILES: *c1c2ccccc2nc2ccccc12] | 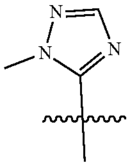 [SMILES: *c1ncnn1C] |
| 1-620 | Cl | 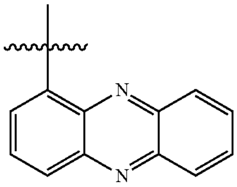 [SMILES: *c1cccc2nc3ccccc3nc12] | 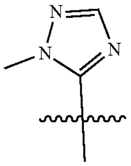 [SMILES: *c1ncnn1C] |
| 1-621 | Cl | 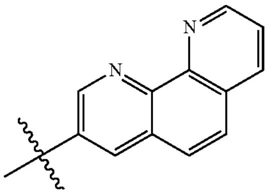 [SMILES: *c1cnc2c(ccc3cccnc32)c1] | 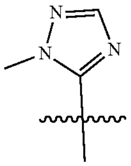 [SMILES: *c1ncnn1C] |

-continued
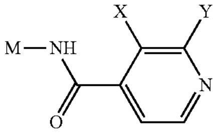
I
| NO. | X | Y | M |
|---|---|---|---|
| 1-622 | Cl | 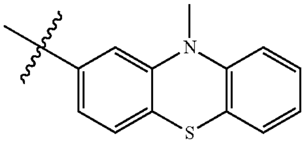 [SMILES: *c1ccc2c(c1)N(C)c1ccccc1S2] | 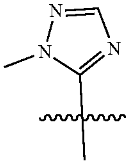 [SMILES: *c1ncnn1C] |
| 1-623 | Cl | 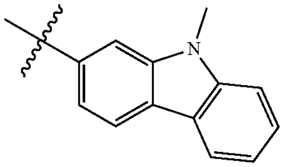 [SMILES: *c1ccc2c3ccccc3n(C)c2c1] | 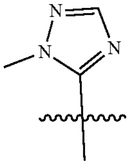 [SMILES: *c1ncnn1C] |
| 1-624 | Cl | 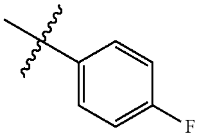 | 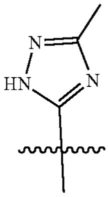 [SMILES: *c1nc(C)n[nH]1] |
| 1-625 | Cl | 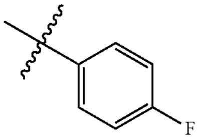 | 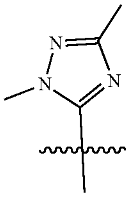 |
| 1-626 | Cl | 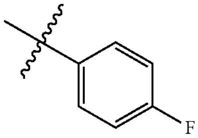 [SMILES: *c1ccc(F)cc1] | 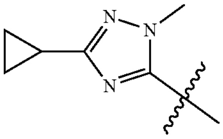 [SMILES: *c1nc(C2CC2)nn1C] |
| 1-627 | Cl | 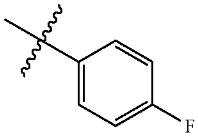 | 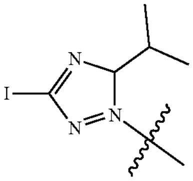 |
| 1-628 | Cl | 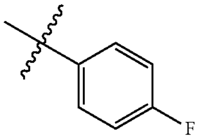 [SMILES: *c1ccc(F)cc1] | 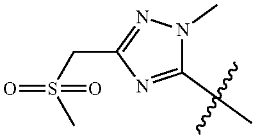 [SMILES: *c1nc(CS(C)(=O)=O)nn1C] |

-continued
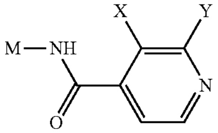
I
| NO. | X | Y | M |
|---|---|---|---|
| 1-629 | Cl | 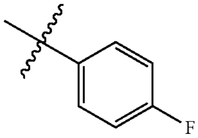 | 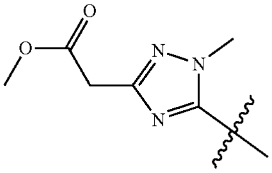 [SMILES: *c1nc(CC(=O)OC)nn1C] |
| 1-630 | Cl | 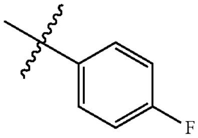 [SMILES: *c1ccc(F)cc1] | 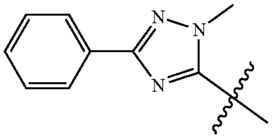 [SMILES: *c1nc(-c2ccccc2)nn1C] |
| 1-631 | Cl | 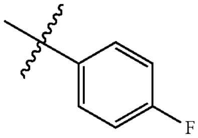 [SMILES: *c1ccc(F)cc1] | 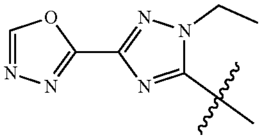 [SMILES: *c1nc(-c2nnco2)nn1CC] |
| 1-632 | Cl | 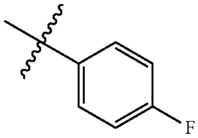 [SMILES: *c1ccc(F)cc1] | 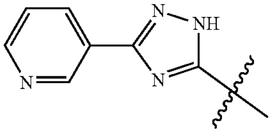 [SMILES: *c1nc(-c2cccnc2)n[nH]1] |
| 1-633 | Cl | 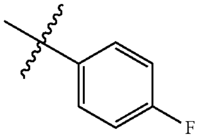 [SMILES: *c1ccc(F)cc1] | 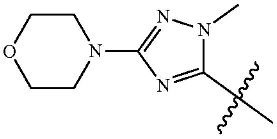 [SMILES: *c1nc(N2CCOCC2)nn1C] |
| 1-634 | Cl | $CH_3$ | 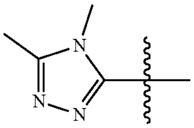 [SMILES: *c1nnc(C)n1C] |
| 1-635 | Cl | 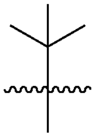 | 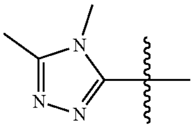 [SMILES: *c1nnc(C)n1C] |
| 1-636 | Cl | 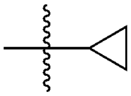 [SMILES: *C1CC1] | 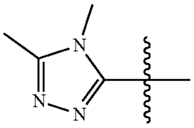 [SMILES: *c1nnc(C)n1C] |
| 1-637 | Cl | 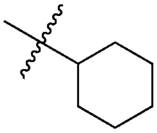 [SMILES: *C1CCCCC1] | 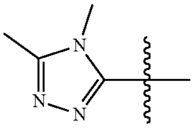 [SMILES: *c1nnc(C)n1C] |

-continued
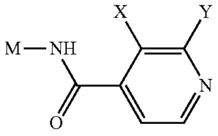
I
| NO. | X | Y | M |
|---|---|---|---|
| 1-638 | Cl | 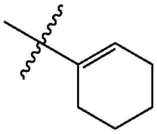 [SMILES: *C1=CCCCC1] | 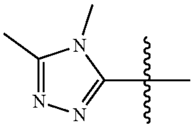 [SMILES: *c1nnc(C)n1C] |
| 1-639 | Cl | 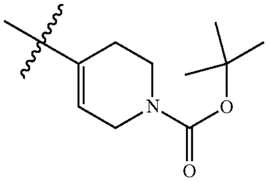 [SMILES: *C1=CCN(C(=O)OC(C)(C)C)CC1] | 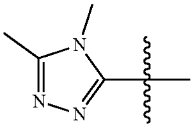 [SMILES: *c1nnc(C)n1C] |
| 1-640 | Cl | 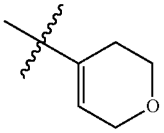 [SMILES: *C1=CCOCC1] | 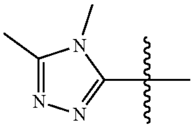 [SMILES: *c1nnc(C)n1C] |
| 1-641 | Cl | 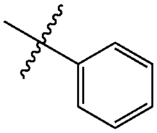 [SMILES: *c1ccccc1] | 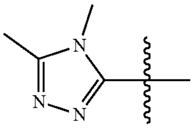 [SMILES: *c1nnc(C)n1C] |
| 1-642 | Cl | 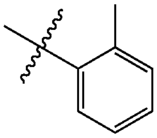 [SMILES: *c1ccccc1C] | 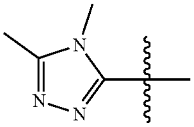 [SMILES: *c1nnc(C)n1C] |
| 1-643 | Cl | 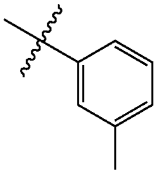 [SMILES: *c1cccc(C)c1] | 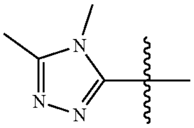 [SMILES: *c1nnc(C)n1C] |
| 1-644 | Cl | 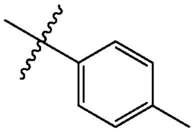 [SMILES: *c1ccc(C)cc1] | 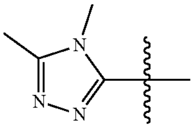 [SMILES: *c1nnc(C)n1C] |
| 1-645 | Cl | 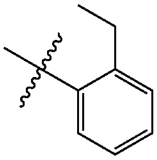 [SMILES: *c1ccccc1CC] | 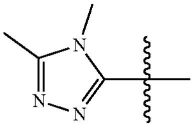 [SMILES: *c1nnc(C)n1C] |

-continued
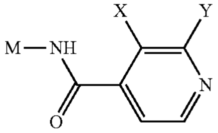
I
| NO. | X | Y | M |
|---|---|---|---|
| 1-646 | Cl | 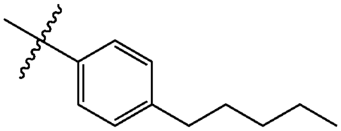 [SMILES: *c1ccc(CCCCC)cc1] | 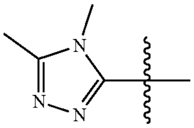 [SMILES: *c1nnc(C)n1C] |
| 1-647 | Cl | 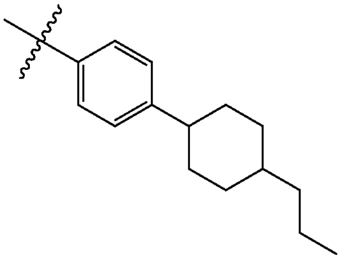 [SMILES: *c1ccc(C2CCC(CCC)CC2)cc1] | 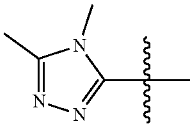 [SMILES: *c1nnc(C)n1C] |
| 1-648 | Cl | 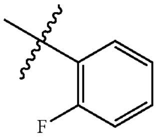 | 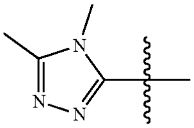 [SMILES: *c1nnc(C)n1C] |
| 1-649 | Cl | 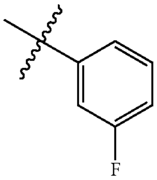 [SMILES: *c1cccc(F)c1] | 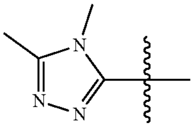 [SMILES: *c1nnc(C)n1C] |
| 1-650 | Cl | 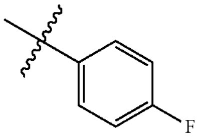 [SMILES: *c1ccc(F)cc1] | 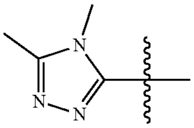 [SMILES: *c1nnc(C)n1C] |
| 1-651 | Cl | 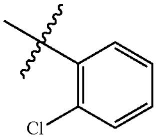 [SMILES: *c1ccccc1Cl] | 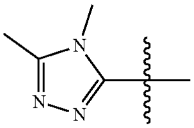 [SMILES: *c1nnc(C)n1C] |
| 1-652 | Cl | 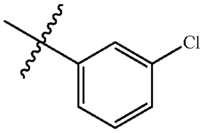 [SMILES: *c1cccc(Cl)c1] | 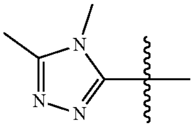 [SMILES: *c1nnc(C)n1C] |
| 1-653 | Cl | 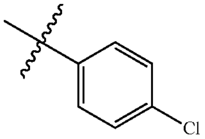 [SMILES: *c1ccc(Cl)cc1] | 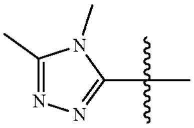 [SMILES: *c1nnc(C)n1C] |

-continued
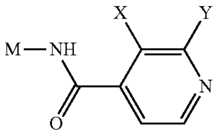
I
| NO. | X | Y | M |
|---|---|---|---|
| 1-654 | Cl | 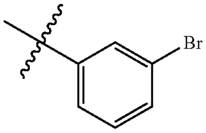 [SMILES: *c1cccc(Br)c1] | 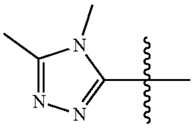 [SMILES: *c1nnc(C)n1C] |
| 1-655 | Cl | 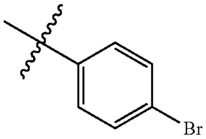 | 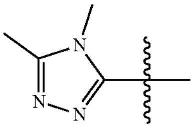 [SMILES: *c1nnc(C)n1C] |
| 1-656 | Cl | 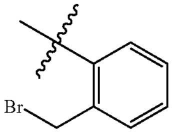 [SMILES: *c1ccccc1CBr] | 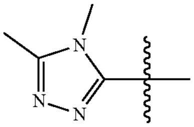 [SMILES: *c1nnc(C)n1C] |
| 1-657 | Cl | 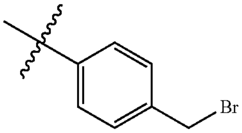 [SMILES: *c1ccc(CBr)cc1] | 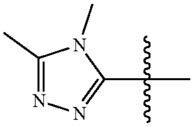 [SMILES: *c1nnc(C)n1C] |
| 1-658 | Cl | 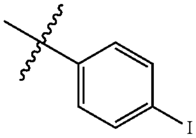 [SMILES: *c1ccc(I)cc1] | 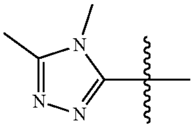 [SMILES: *c1nnc(C)n1C] |
| 1-659 | Cl | 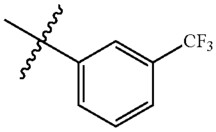 [SMILES: *c1cccc(C(F)(F)F)c1] | 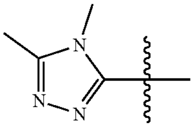 [SMILES: *c1nnc(C)n1C] |
| 1-660 | Cl | 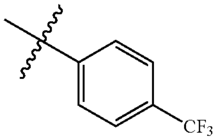 | 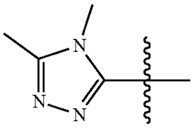 [SMILES: *c1nnc(C)n1C] |
| 1-661 | Cl | 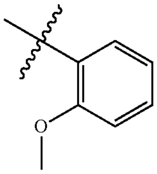 [SMILES: *c1ccccc1OC] | 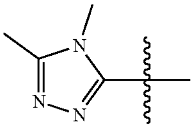 [SMILES: *c1nnc(C)n1C] |

-continued
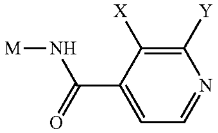
I
| NO. | X | Y | M |
|---|---|---|---|
| 1-662 | Cl | 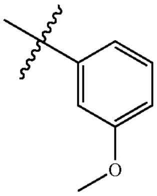 [SMILES: *c1cccc(OC)c1] | 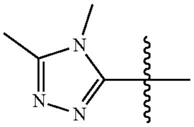 [SMILES: *c1nnc(C)n1C] |
| 1-663 | Cl | 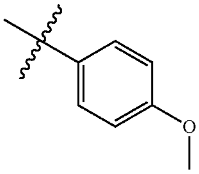 [SMILES: *c1ccc(OC)cc1] | 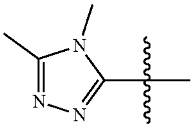 [SMILES: *c1nnc(C)n1C] |
| 1-664 | Cl | 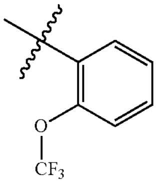 [SMILES: *c1ccccc1OC(F)(F)F] | 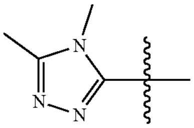 [SMILES: *c1nnc(C)n1C] |
| 1-665 | Cl | 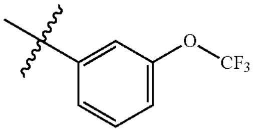 [SMILES: *c1cccc(OC(F)(F)F)c1] | 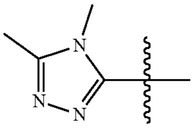 [SMILES: *c1nnc(C)n1C] |
| 1-666 | Cl | 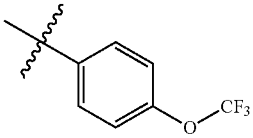 [SMILES: *c1ccc(OC(F)(F)F)cc1] | 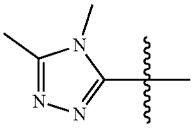 [SMILES: *c1nnc(C)n1C] |
| 1-667 | Cl | 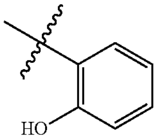 [SMILES: *c1ccccc1O] | 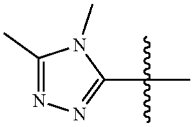 [SMILES: *c1nnc(C)n1C] |
| 1-668 | Cl | 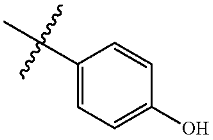 | 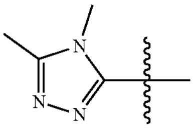 [SMILES: *c1nnc(C)n1C] |
| 1-669 | Cl | 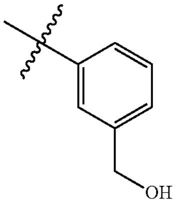 [SMILES: *c1cccc(CO)c1] | 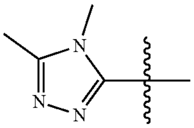 [SMILES: *c1nnc(C)n1C] |

-continued
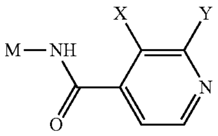
I
| NO. | X | Y | M |
|---|---|---|---|
| 1-670 | Cl | 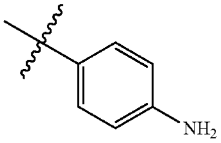 [SMILES: *c1ccc(N)cc1] | 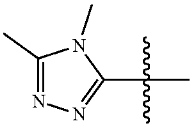 [SMILES: *c1nnc(C)n1C] |
| 1-671 | Cl | 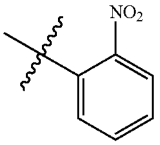 [SMILES: *c1ccccc1[N+](=O)[O-]] | 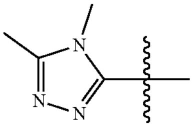 [SMILES: *c1nnc(C)n1C] |
| 1-672 | Cl | 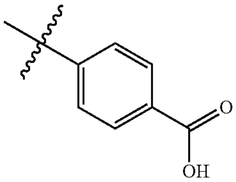 [SMILES: *c1ccc(C(=O)O)cc1] | 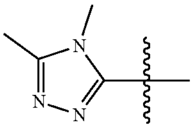 [SMILES: *c1nnc(C)n1C] |
| 1-673 | Cl | 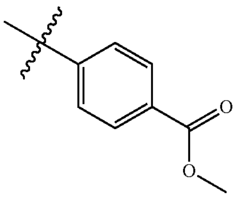 [SMILES: *c1ccc(C(=O)OC)cc1] | 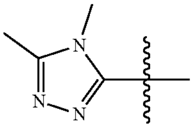 [SMILES: *c1nnc(C)n1C] |
| 1-674 | Cl | 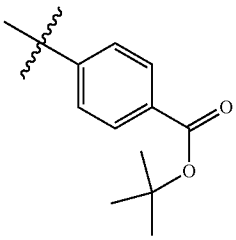 [SMILES: *c1ccc(C(=O)OC(C)(C)C)cc1] | 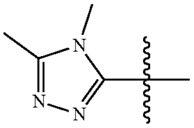 [SMILES: *c1nnc(C)n1C] |
| 1-675 | Cl | 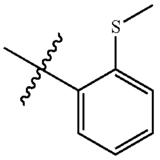 [SMILES: *c1ccccc1SC] | 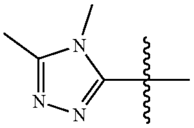 [SMILES: *c1nnc(C)n1C] |
| 1-676 | Cl | 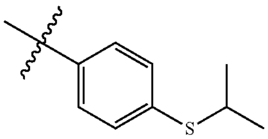 [SMILES: *c1ccc(SC(C)C)cc1] | 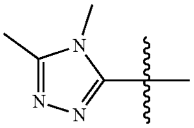 [SMILES: *c1nnc(C)n1C] |

-continued
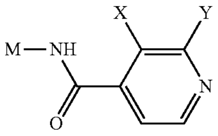
I
| NO. | X | Y | M |
|---|---|---|---|
| 1-677 | Cl | 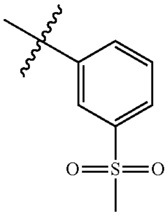 [SMILES: *c1cccc(S(C)(=O)=O)c1] | 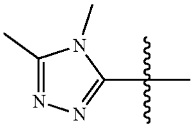 [SMILES: *c1nnc(C)n1C] |
| 1-678 | Cl | 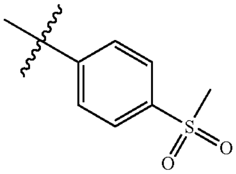 [SMILES: *c1ccc(S(C)(=O)=O)cc1] | 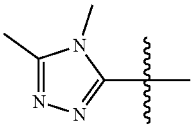 [SMILES: *c1nnc(C)n1C] |
| 1-679 | Cl | 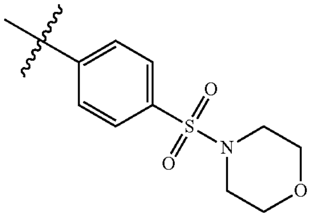 [SMILES: *c1ccc(S(=O)(=O)N2CCOCC2)cc1] | 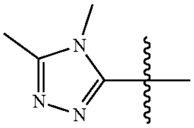 [SMILES: *c1nnc(C)n1C] |
| 1-680 | Cl | 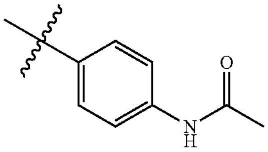 [SMILES: *c1ccc(NC(C)=O)cc1] | 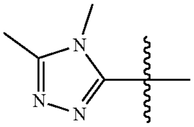 [SMILES: *c1nnc(C)n1C] |
| 1-681 | Cl | 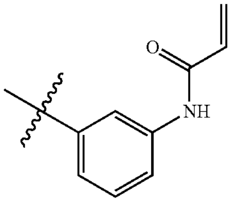 [SMILES: *c1cccc(NC(=O)C=C)c1] | 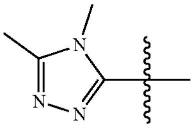 [SMILES: *c1nnc(C)n1C] |
| 1-682 | Cl | 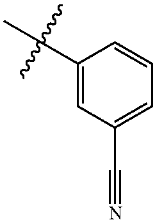 [SMILES: *c1cccc(C#N)c1] | 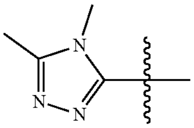 [SMILES: *c1nnc(C)n1C] |

-continued
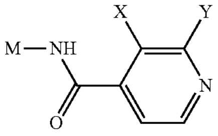
I
| NO. | X | Y | M |
|---|---|---|---|
| 1-683 | Cl | 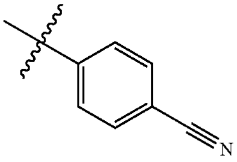 [SMILES: *c1ccc(C#N)cc1] | 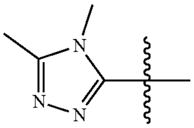 [SMILES: *c1nnc(C)n1C] |
| 1-684 | Cl | 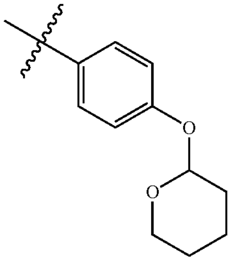 [SMILES: *c1ccc(OC2CCCCO2)cc1] | 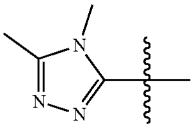 [SMILES: *c1nnc(C)n1C] |
| 1-685 | Cl | 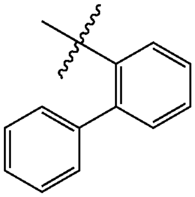 [SMILES: *c1ccccc1-c1ccccc1] | 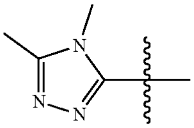 [SMILES: *c1nnc(C)n1C] |
| 1-686 | Cl | 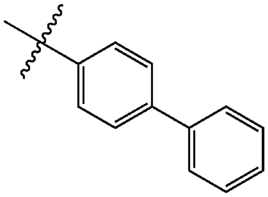 [SMILES: *c1ccc(-c2ccccc2)cc1] | 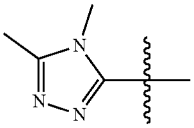 [SMILES: *c1nnc(C)n1C] |
| 1-687 | Cl | 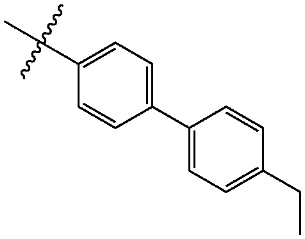 [SMILES: *c1ccc(-c2ccc(CC)cc2)cc1] | 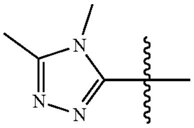 [SMILES: *c1nnc(C)n1C] |
| 1-688 | Cl | 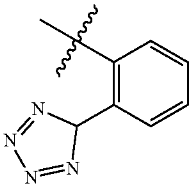 [SMILES: *c1ccccc1C1N=NN=N1] | 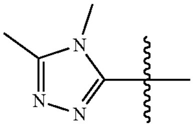 [SMILES: *c1nnc(C)n1C] |

-continued
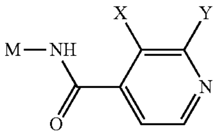
I
| NO. | X | Y | M |
|---|---|---|---|
| 1-689 | Cl | 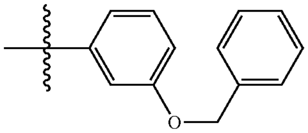 [SMILES: *c1cccc(OCc2ccccc2)c1] | 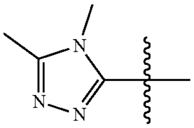 [SMILES: *c1nnc(C)n1C] |
| 1-690 | Cl | 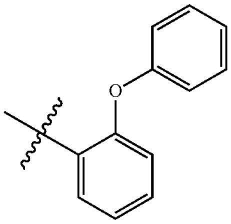 [SMILES: *c1ccccc1Oc1ccccc1] | 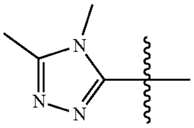 [SMILES: *c1nnc(C)n1C] |
| 1-691 | Cl | 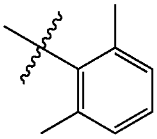 [SMILES: *c1c(C)cccc1C] | 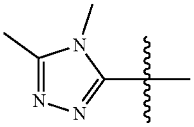 [SMILES: *c1nnc(C)n1C] |
| 1-692 | Cl | 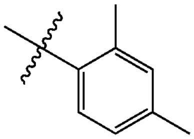 [SMILES: *c1ccc(C)cc1C] | 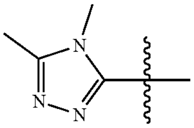 [SMILES: *c1nnc(C)n1C] |
| 1-693 | Cl | 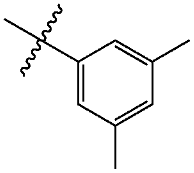 [SMILES: *c1cc(C)cc(C)c1] | 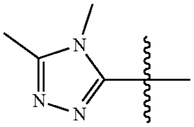 [SMILES: *c1nnc(C)n1C] |
| 1-694 | Cl | 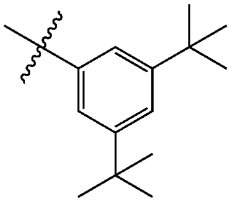 [SMILES: *c1cc(C(C)(C)C)cc(C(C)(C)C)c1] | 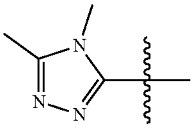 [SMILES: *c1nnc(C)n1C] |
| 1-695 | Cl | 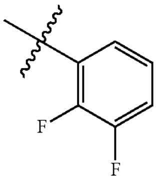 | 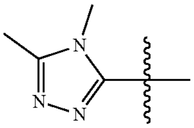 [SMILES: *c1nnc(C)n1C] |

-continued
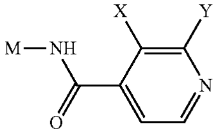
I
| NO. | X | Y | M |
|---|---|---|---|
| 1-696 | Cl | 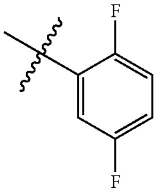 [SMILES: *c1cc(F)ccc1F] | 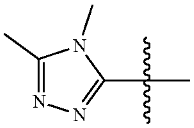 [SMILES: *c1nnc(C)n1C] |
| 1-697 | Cl | 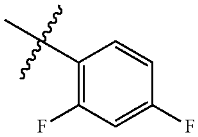 [SMILES: *c1ccc(F)cc1F] | 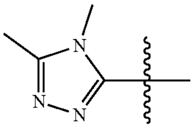 [SMILES: *c1nnc(C)n1C] |
| 1-698 | Cl | 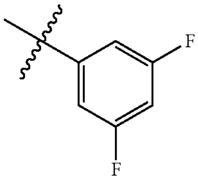 | 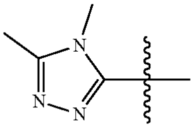 [SMILES: *c1nnc(C)n1C] |
| 1-699 | Cl | 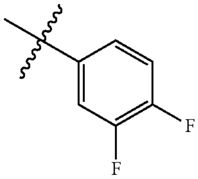 [SMILES: *c1ccc(F)c(F)c1] | 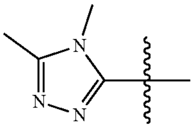 [SMILES: *c1nnc(C)n1C] |
| 1-700 | Cl | 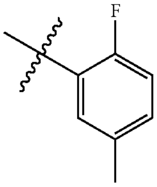 [SMILES: *c1cc(C)ccc1F] | 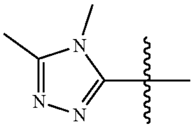 [SMILES: *c1nnc(C)n1C] |
| 1-701 | Cl | 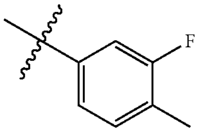 [SMILES: *c1ccc(C)c(F)c1] | 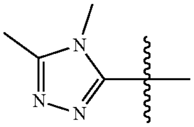 [SMILES: *c1nnc(C)n1C] |
| 1-702 | Cl | 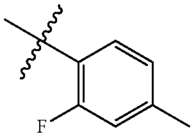 [SMILES: *c1ccc(C)cc1F] | 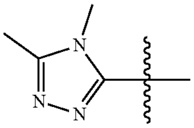 [SMILES: *c1nnc(C)n1C] |
| 1-703 | Cl | 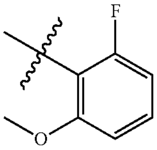 [SMILES: *c1c(F)cccc1OC] | 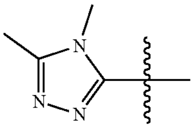 [SMILES: *c1nnc(C)n1C] |

-continued
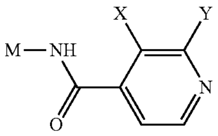
I
| NO. | X | Y | M |
|---|---|---|---|
| 1-704 | Cl | 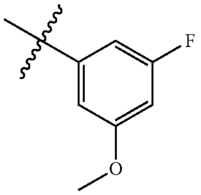 [SMILES: *c1cc(F)cc(OC)c1] | 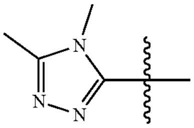 [SMILES: *c1nnc(C)n1C] |
| 1-705 | Cl | 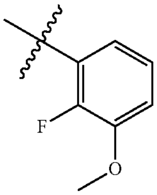 [SMILES: *c1cccc(OC)c1F] | 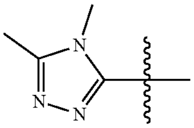 [SMILES: *c1nnc(C)n1C] |
| 1-706 | Cl | 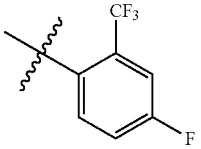 | 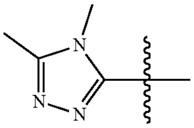 [SMILES: *c1nnc(C)n1C] |
| 1-707 | Cl | 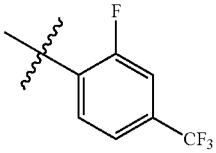 [SMILES: *c1ccc(C(F)(F)F)cc1F] | 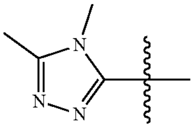 [SMILES: *c1nnc(C)n1C] |
| 1-708 | Cl | 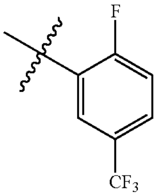 [SMILES: *c1cc(C(F)(F)F)ccc1F] | 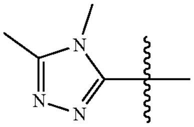 [SMILES: *c1nnc(C)n1C] |
| 1-709 | Cl | 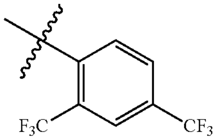 [SMILES: *c1ccc(C(F)(F)F)cc1C(F)(F)F] | 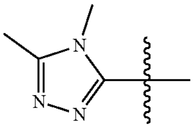 [SMILES: *c1nnc(C)n1C] |
| 1-710 | Cl | 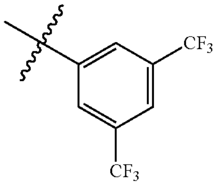 [SMILES: *c1cc(C(F)(F)F)cc(C(F)(F)F)c1] | 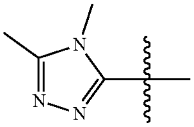 [SMILES: *c1nnc(C)n1C] |

-continued
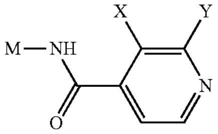
I
| NO. | X | Y | M |
|---|---|---|---|
| 1-711 | Cl | 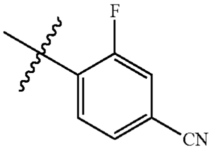 [SMILES: *c1ccc(C#N)cc1F] | 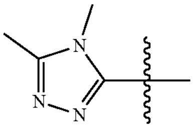 [SMILES: *c1nnc(C)n1C] |
| 1-712 | Cl | 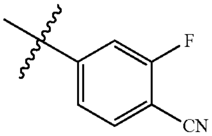 [SMILES: *c1ccc(C#N)c(F)c1] | 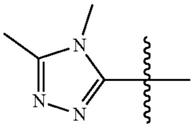 [SMILES: *c1nnc(C)n1C] |
| 1-713 | Cl | 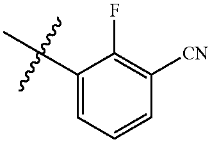 [SMILES: *c1cccc(C#N)c1F] | 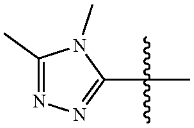 [SMILES: *c1nnc(C)n1C] |
| 1-714 | Cl | 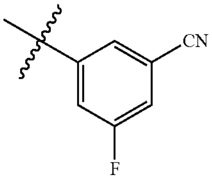 [SMILES: *c1cc(F)cc(C#N)c1] | 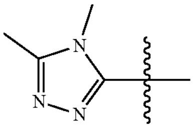 [SMILES: *c1nnc(C)n1C] |
| 1-715 | Cl | 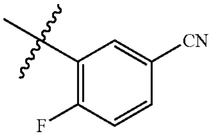 [SMILES: *c1cc(C#N)ccc1F] | 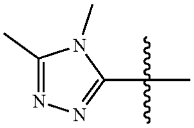 [SMILES: *c1nnc(C)n1C] |
| 1-716 | Cl | 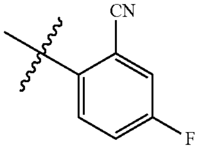 [SMILES: *c1ccc(F)cc1C#N] | 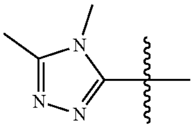 [SMILES: *c1nnc(C)n1C] |
| 1-717 | Cl | 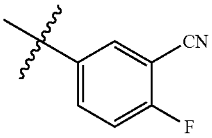 [SMILES: *c1ccc(F)c(C#N)c1] | 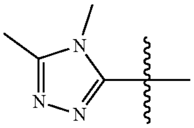 [SMILES: *c1nnc(C)n1C] |
| 1-718 | Cl | 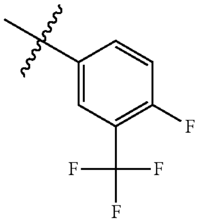 [SMILES: *c1ccc(F)c(C(F)(F)F)c1] | 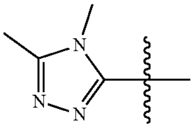 [SMILES: *c1nnc(C)n1C] |

-continued
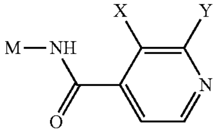
I
| NO. | X | Y | M |
|---|---|---|---|
| 1-719 | Cl | 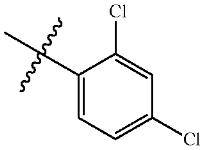 [SMILES: *c1ccc(Cl)cc1Cl] | 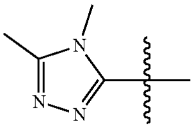 [SMILES: *c1nnc(C)n1C] |
| 1-720 | Cl | 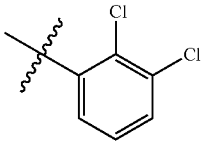 [SMILES: *c1cccc(Cl)c1Cl] | 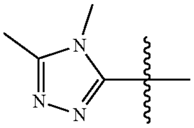 [SMILES: *c1nnc(C)n1C] |
| 1-721 | Cl | 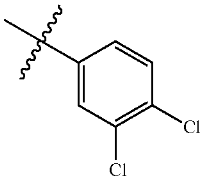 [SMILES: *c1ccc(Cl)c(Cl)c1] | 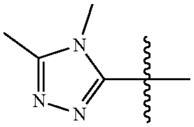 [SMILES: *c1nnc(C)n1C] |
| 1-722 | Cl | 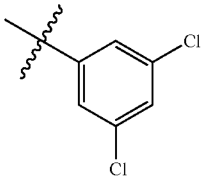 [SMILES: *c1cc(Cl)cc(Cl)c1] | 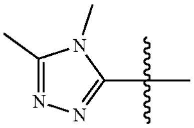 [SMILES: *c1nnc(C)n1C] |
| 1-723 | Cl | 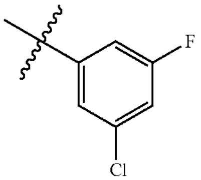 | 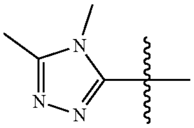 [SMILES: *c1nnc(C)n1C] |
| 1-724 | Cl | 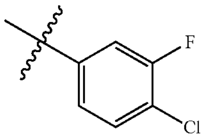 [SMILES: *c1ccc(Cl)c(F)c1] | 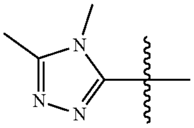 [SMILES: *c1nnc(C)n1C] |
| 1-725 | Cl | 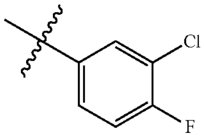 [SMILES: *c1ccc(F)c(Cl)c1] | 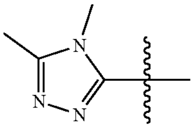 [SMILES: *c1nnc(C)n1C] |
| 1-726 | Cl | 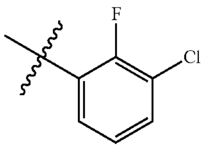 | 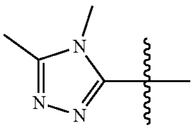 [SMILES: *c1nnc(C)n1C] |

-continued
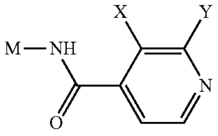
I
| NO. | X | Y | M |
|---|---|---|---|
| 1-727 | Cl | 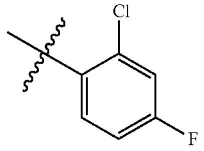 [SMILES: *c1ccc(F)cc1Cl] | 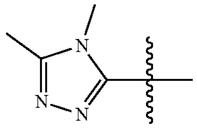 [SMILES: *c1nnc(C)n1C] |
| 1-728 | Cl | 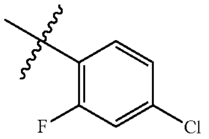 [SMILES: *c1ccc(Cl)cc1F] | 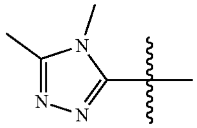 [SMILES: *c1nnc(C)n1C] |
| 1-729 | Cl | 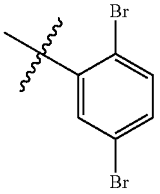 [SMILES: *c1cc(Br)ccc1Br] | 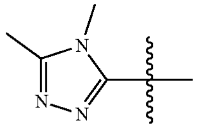 [SMILES: *c1nnc(C)n1C] |
| 1-730 | Cl | 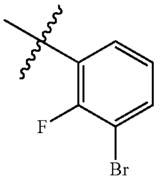 [SMILES: *c1cccc(Br)c1F] | 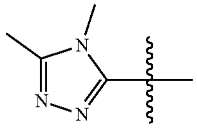 [SMILES: *c1nnc(C)n1C] |
| 1-731 | Cl | 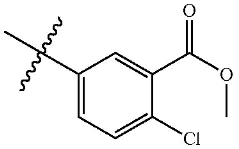 [SMILES: *c1ccc(Cl)c(C(=O)OC)c1] | 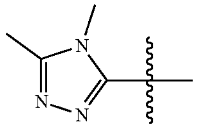 [SMILES: *c1nnc(C)n1C] |
| 1-732 | Cl | 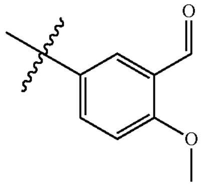 [SMILES: *c1ccc(OC)c(C=O)c1] | 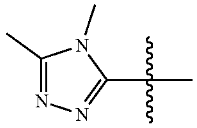 [SMILES: *c1nnc(C)n1C] |
| 1-733 | Cl | 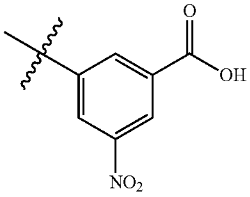 [SMILES: *c1cc(C(=O)O)cc([N+](=O)[O-])c1] | 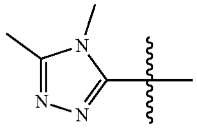 [SMILES: *c1nnc(C)n1C] |

-continued
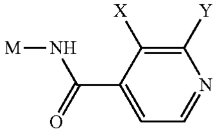
I
| NO. | X | Y | M |
|---|---|---|---|
| 1-734 | Cl | 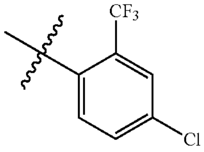 | 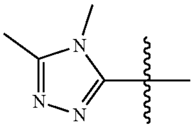 [SMILES: *c1nnc(C)n1C] |
| 1-735 | Cl | 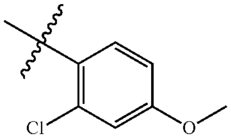 [SMILES: *c1ccc(OC)cc1Cl] | 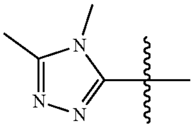 [SMILES: *c1nnc(C)n1C] |
| 1-736 | Cl | 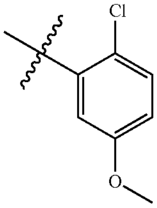 [SMILES: *c1cc(OC)ccc1Cl] | 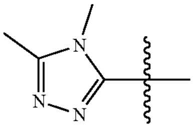 [SMILES: *c1nnc(C)n1C] |
| 1-737 | Cl | 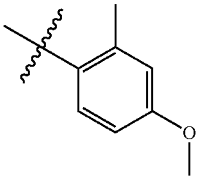 [SMILES: *c1ccc(OC)cc1C] | 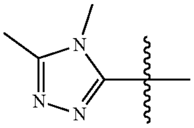 [SMILES: *c1nnc(C)n1C] |
| 1-738 | Cl | 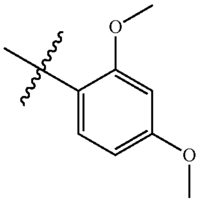 [SMILES: *c1ccc(OC)cc1OC] | 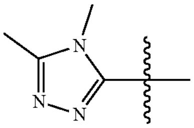 [SMILES: *c1nnc(C)n1C] |
| 1-739 | Cl | 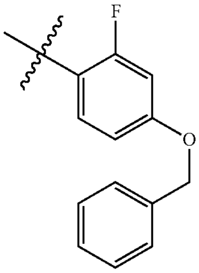 [SMILES: *c1ccc(OCc2ccccc2)cc1F] | 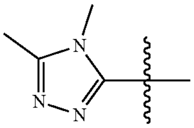 [SMILES: *c1nnc(C)n1C] |
| 1-740 | Cl | 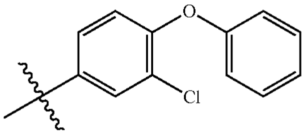 [SMILES: *c1ccc(Oc2ccccc2)c(Cl)c1] | 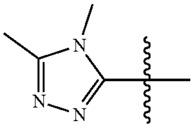 [SMILES: *c1nnc(C)n1C] |

-continued
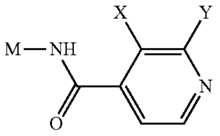
I
| NO. | X | Y | M |
| --- | --- | --- | --- |
| 1-741 | Cl | 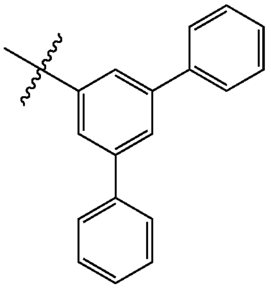 [SMILES: *c1cc(-c2ccccc2)cc(-c2ccccc2)c1] | 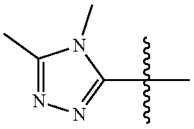 [SMILES: *c1nnc(C)n1C] |
| 1-742 | Cl | 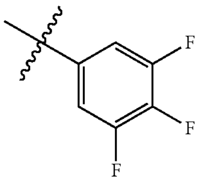 [SMILES: *c1cc(F)c(F)c(F)c1] | 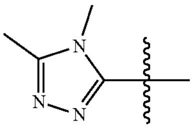 [SMILES: *c1nnc(C)n1C] |
| 1-743 | Cl | 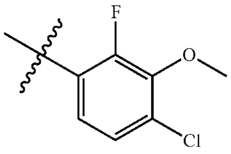 [SMILES: *c1ccc(Cl)c(OC)c1F] | 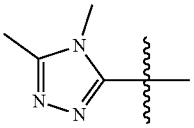 [SMILES: *c1nnc(C)n1C] |
| 1-744 | Cl | 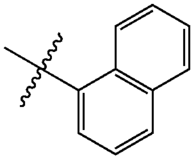 [SMILES: *c1cccc2ccccc12] | 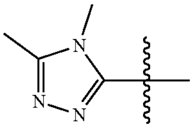 [SMILES: *c1nnc(C)n1C] |
| 1-745 | Cl | 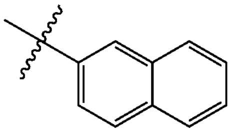 [SMILES: *c1ccc2ccccc2c1] | 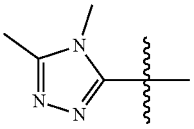 [SMILES: *c1nnc(C)n1C] |
| 1-746 | Cl | 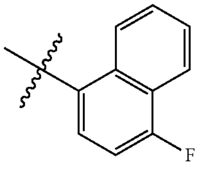 [SMILES: *c1ccc(F)c2ccccc12] | 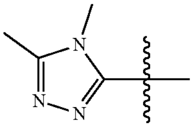 [SMILES: *c1nnc(C)n1C] |
| 1-747 | Cl | 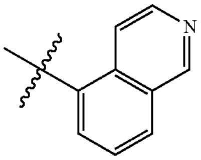 [SMILES: *c1cccc2cnccc12] | 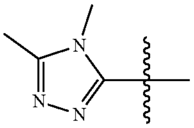 [SMILES: *c1nnc(C)n1C] |

-continued
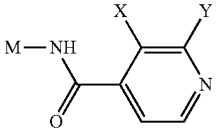
I
| NO. | X | Y | M |
| --- | --- | --- | --- |
| 1-748 | Cl | 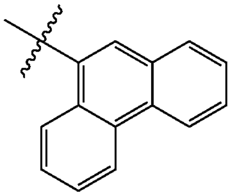 [SMILES: *c1cc2ccccc2c2ccccc12] | 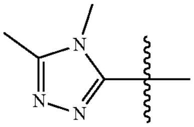 [SMILES: *c1nnc(C)n1C] |
| 1-749 | Cl | 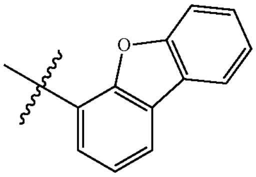 [SMILES: *c1cccc2c1oc1ccccc12] | 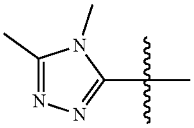 [SMILES: *c1nnc(C)n1C] |
| 1-750 | Cl | 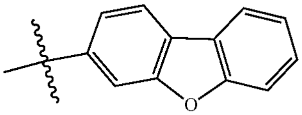 [SMILES: *c1ccc2c(c1)oc1ccccc12] | 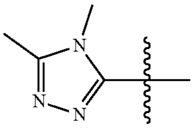 [SMILES: *c1nnc(C)n1C] |
| 1-751 | Cl | 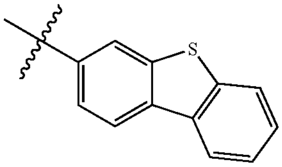 [SMILES: *c1ccc2c(c1)sc1ccccc12] | 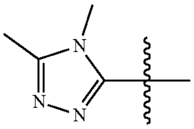 [SMILES: *c1nnc(C)n1C] |
| 1-752 | Cl | 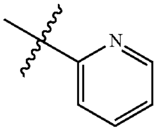 [SMILES: *c1ccccn1] | 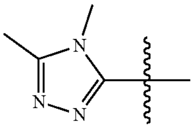 [SMILES: *c1nnc(C)n1C] |
| 1-753 | Cl | 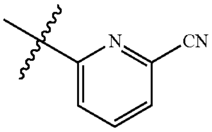 [SMILES: *c1cccc(C#N)n1] | 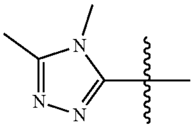 [SMILES: *c1nnc(C)n1C] |
| 1-754 | Cl | 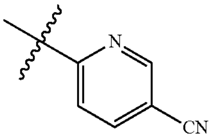 [SMILES: *c1ccc(C#N)cn1] | 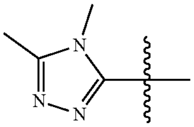 [SMILES: *c1nnc(C)n1C] |
| 1-755 | Cl | 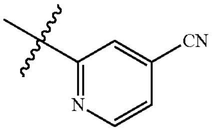 [SMILES: *c1cc(C#N)ccn1] | 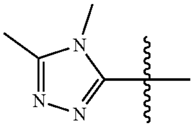 [SMILES: *c1nnc(C)n1C] |

-continued
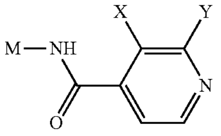
I
| NO. | X | Y | M |
| --- | --- | --- | --- |
| 1-756 | Cl | 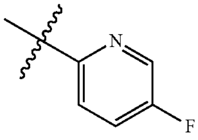 [SMILES: *c1ccc(F)cn1] | 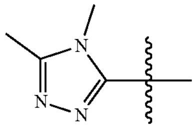 [SMILES: *c1nnc(C)n1C] |
| 1-757 | Cl | 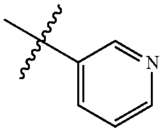 [SMILES: *c1cccnc1] | 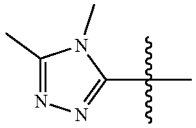 [SMILES: *c1nnc(C)n1C] |
| 1-758 | Cl | 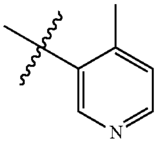 [SMILES: *c1cnccc1C] | 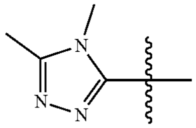 [SMILES: *c1nnc(C)n1C] |
| 1-759 | Cl | 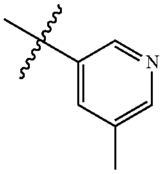 [SMILES: *c1cncc(C)c1] | 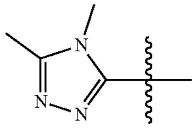 [SMILES: *c1nnc(C)n1C] |
| 1-760 | Cl | 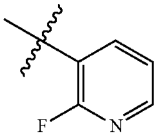 | 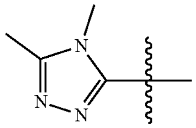 [SMILES: *c1nnc(C)n1C] |
| 1-761 | Cl | 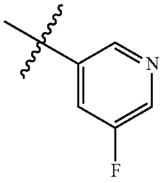 [SMILES: *c1cncc(F)c1] | 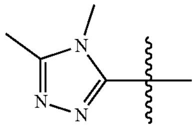 [SMILES: *c1nnc(C)n1C] |
| 1-762 | Cl | 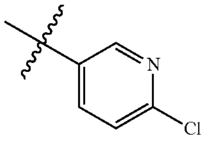 [SMILES: *c1ccc(Cl)nc1] | 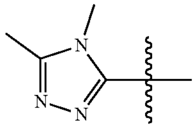 [SMILES: *c1nnc(C)n1C] |
| 1-763 | Cl | 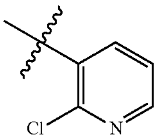 [SMILES: *c1cccnc1Cl] | 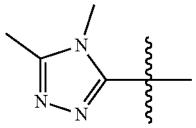 [SMILES: *c1nnc(C)n1C] |

-continued
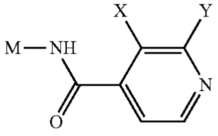
I
| NO. | X | Y | M |
|---|---|---|---|
| 1-764 | Cl | 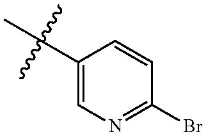 [SMILES: *c1ccc(Br)nc1] | 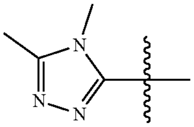 [SMILES: *c1nnc(C)n1C] |
| 1-765 | Cl | 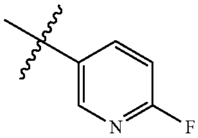 [SMILES: *c1ccc(F)nc1] | 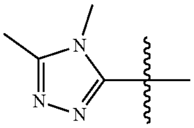 [SMILES: *c1nnc(C)n1C] |
| 1-766 | Cl | 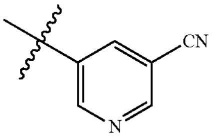 [SMILES: *c1cncc(C#N)c1] | 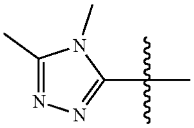 [SMILES: *c1nnc(C)n1C] |
| 1-767 | Cl | 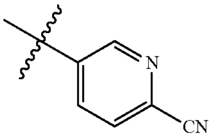 [SMILES: *c1ccc(C#N)nc1] | 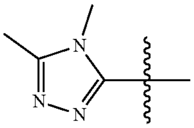 [SMILES: *c1nnc(C)n1C] |
| 1-768 | Cl | 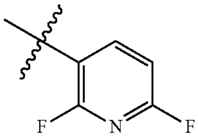 [SMILES: *c1ccc(F)nc1F] | 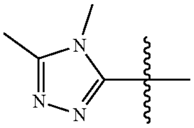 [SMILES: *c1nnc(C)n1C] |
| 1-769 | Cl | 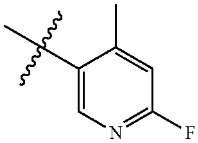 [SMILES: *c1cnc(F)cc1C] | 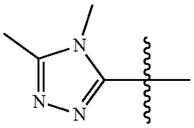 [SMILES: *c1nnc(C)n1C] |
| 1-770 | Cl | 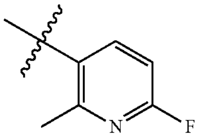 [SMILES: *c1ccc(F)nc1C] | 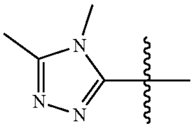 [SMILES: *c1nnc(C)n1C] |
| 1-771 | Cl | 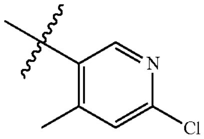 [SMILES: *c1cnc(Cl)cc1C] | 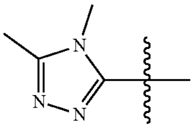 [SMILES: *c1nnc(C)n1C] |
| 1-772 | Cl | 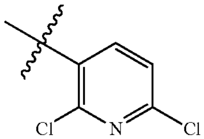 [SMILES: *c1ccc(Cl)nc1Cl] | 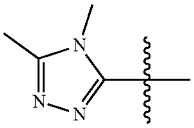 [SMILES: *c1nnc(C)n1C] |

-continued
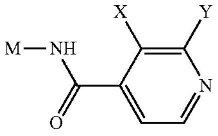
I
| NO. | X | Y | M |
|---|---|---|---|
| 1-773 | Cl | 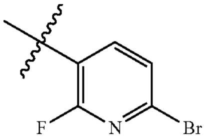 [SMILES: *c1ccc(Br)nc1F] | 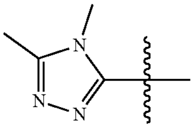 [SMILES: *c1nnc(C)n1C] |
| 1-774 | Cl | 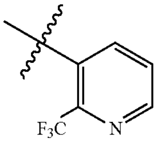 | 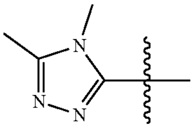 [SMILES: *c1nnc(C)n1C] |
| 1-775 | Cl | 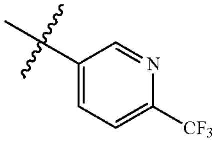 | 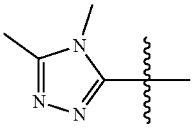 [SMILES: *c1nnc(C)n1C] |
| 1-776 | Cl | 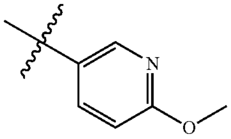 [SMILES: *c1ccc(OC)nc1] | 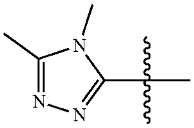 [SMILES: *c1nnc(C)n1C] |
| 1-777 | Cl | 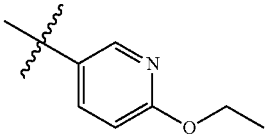 [SMILES: *c1ccc(OCC)nc1] | 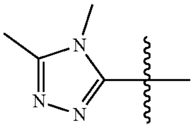 [SMILES: *c1nnc(C)n1C] |
| 1-778 | Cl | 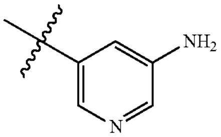 [SMILES: *c1cncc(N)c1] | 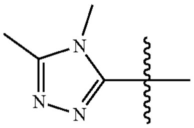 [SMILES: *c1nnc(C)n1C] |
| 1-779 | Cl | 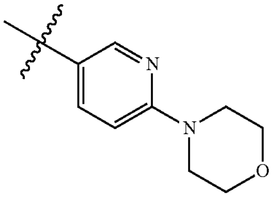 [SMILES: *c1ccc(N2CCOCC2)nc1] | 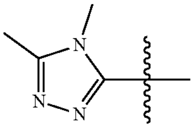 [SMILES: *c1nnc(C)n1C] |
| 1-780 | Cl | 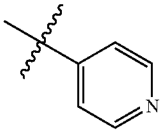 [SMILES: *c1ccncc1] | 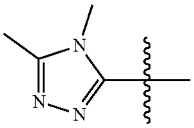 [SMILES: *c1nnc(C)n1C] |

-continued
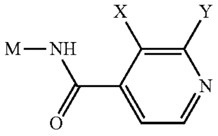
I
| NO. | X | Y | M |
|---|---|---|---|
| 1-781 | Cl | 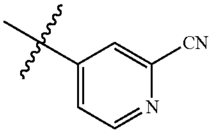 [SMILES: *c1ccnc(C#N)c1] | 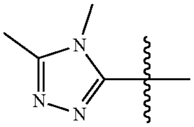 [SMILES: *c1nnc(C)n1C] |
| 1-782 | Cl | 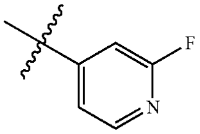 [SMILES: *c1ccnc(F)c1] | 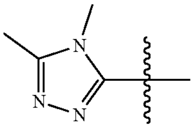 [SMILES: *c1nnc(C)n1C] |
| 1-783 | Cl | 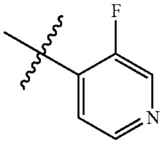 [SMILES: *c1ccncc1F] | 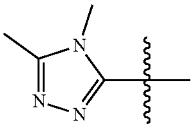 [SMILES: *c1nnc(C)n1C] |
| 1-784 | Cl | 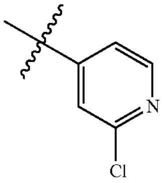 [SMILES: *c1ccnc(Cl)c1] | 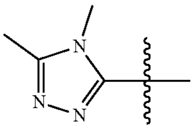 [SMILES: *c1nnc(C)n1C] |
| 1-785 | Cl | 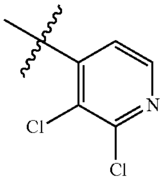 [SMILES: *c1ccnc(Cl)c1Cl] | 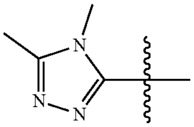 [SMILES: *c1nnc(C)n1C] |
| 1-786 | Cl | 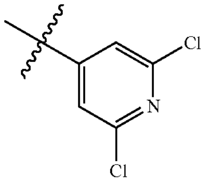 [SMILES: *c1cc(Cl)nc(Cl)c1] | 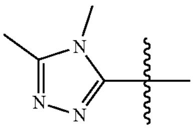 [SMILES: *c1nnc(C)n1C] |
| 1-787 | Cl | 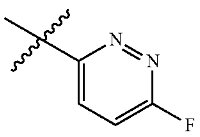 [SMILES: *c1ccc(F)nn1] | 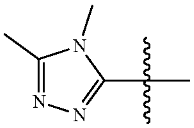 [SMILES: *c1nnc(C)n1C] |
| 1-788 | Cl | 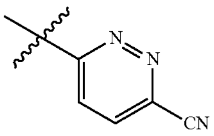 | 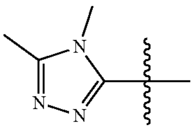 [SMILES: *c1nnc(C)n1C] |

-continued
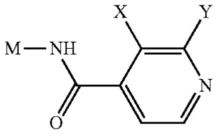
I
| NO. | X | Y | M |
|---|---|---|---|
| 1-789 | Cl | 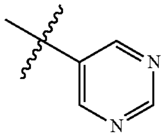 [SMILES: *c1cncnc1] | 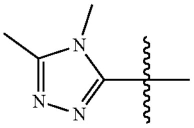 [SMILES: *c1nnc(C)n1C] |
| 1-790 | Cl | 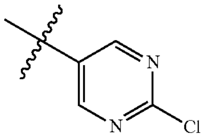 [SMILES: *c1cnc(Cl)nc1] | 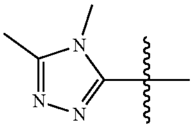 [SMILES: *c1nnc(C)n1C] |
| 1-791 | Cl | 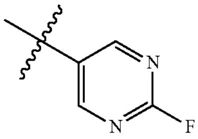 [SMILES: *c1cnc(F)nc1] | 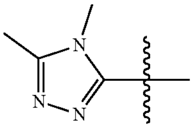 [SMILES: *c1nnc(C)n1C] |
| 1-792 | Cl | 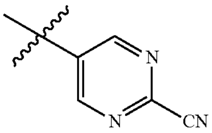 [SMILES: *c1cnc(C#N)nc1] | 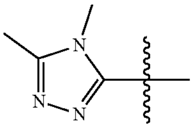 [SMILES: *c1nnc(C)n1C] |
| 1-793 | Cl | 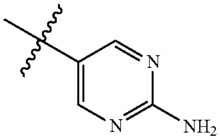 [SMILES: *c1cnc(N)nc1] | 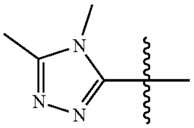 [SMILES: *c1nnc(C)n1C] |
| 1-794 | Cl | 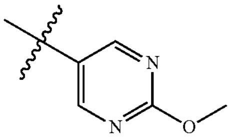 [SMILES: *c1cnc(OC)nc1] | 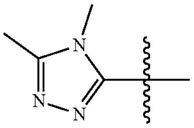 [SMILES: *c1nnc(C)n1C] |
| 1-795 | Cl | 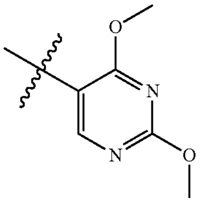 [SMILES: *c1cnc(OC)nc1OC] | 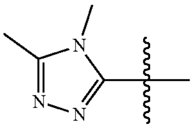 [SMILES: *c1nnc(C)n1C] |
| 1-796 | Cl | 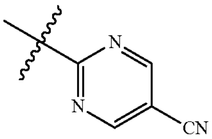 [SMILES: *c1ncc(C#N)cn1] | 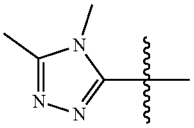 [SMILES: *c1nnc(C)n1C] |

-continued
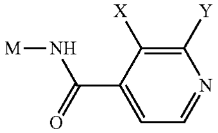
I
| NO. | X | Y | M |
| --- | --- | --- | --- |
| 1-797 | Cl | 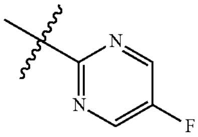 [SMILES: *c1ncc(F)cn1] | 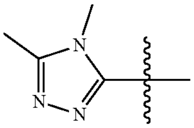 [SMILES: *c1nnc(C)n1C] |
| 1-798 | Cl | 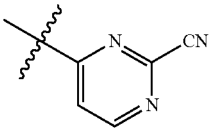 | 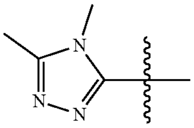 [SMILES: *c1nnc(C)n1C] |
| 1-799 | Cl | 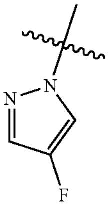 [SMILES: *n1cc(F)cn1] | 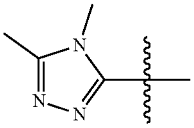 [SMILES: *c1nnc(C)n1C] |
| 1-800 | Cl | 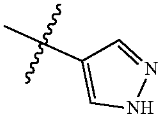 [SMILES: *c1cn[nH]c1] | 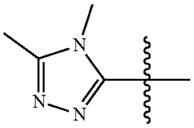 [SMILES: *c1nnc(C)n1C] |
| 1-801 | Cl | 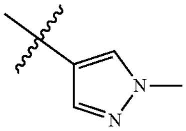 [SMILES: *c1cnn(C)c1] | 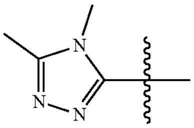 [SMILES: *c1nnc(C)n1C] |
| 1-802 | Cl | 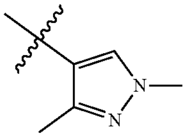 [SMILES: *c1cn(C)nc1C] | 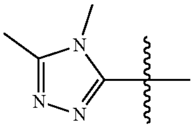 [SMILES: *c1nnc(C)n1C] |
| 1-803 | Cl | 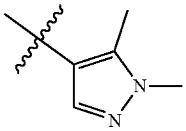 [SMILES: *c1cnn(C)c1C] | 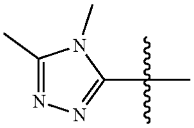 [SMILES: *c1nnc(C)n1C] |
| 1-804 | Cl | 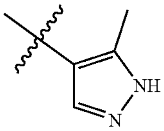 [SMILES: *c1cn[nH]c1C] | 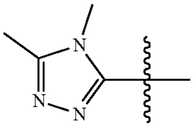 [SMILES: *c1nnc(C)n1C] |
| 1-805 | Cl | 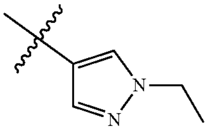 [SMILES: *c1cnn(CC)c1] | 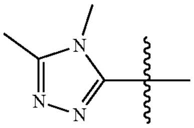 [SMILES: *c1nnc(C)n1C] |

-continued
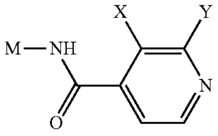
I
| NO. | X | Y | M |
|---|---|---|---|
| 1-806 | Cl | 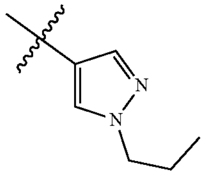 [SMILES: *c1cnn(CCC)c1] | 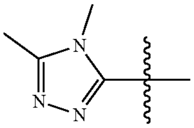 [SMILES: *c1nnc(C)n1C] |
| 1-807 | Cl | 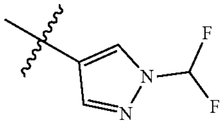 [SMILES: *c1cnn(C(F)F)c1] | 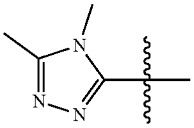 [SMILES: *c1nnc(C)n1C] |
| 1-808 | Cl | 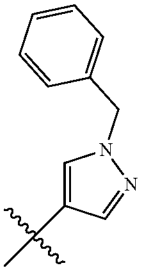 [SMILES: *c1cnn(Cc2ccccc2)c1] | 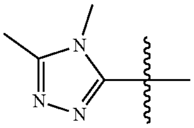 [SMILES: *c1nnc(C)n1C] |
| 1-809 | Cl | 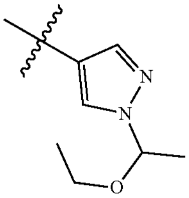 [SMILES: *c1cnn(C(C)OCC)c1] | 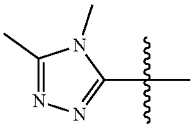 [SMILES: *c1nnc(C)n1C] |
| 1-810 | Cl | 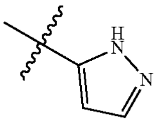 [SMILES: *c1ccn[nH]1] | 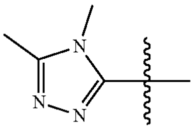 [SMILES: *c1nnc(C)n1C] |
| 1-811 | Cl | 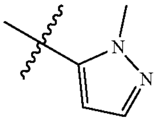 [SMILES: *c1ccnn1C] | 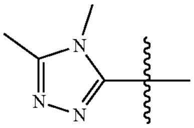 [SMILES: *c1nnc(C)n1C] |
| 1-812 | Cl | 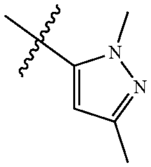 [SMILES: *c1cc(C)nn1C] | 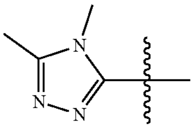 [SMILES: *c1nnc(C)n1C] |

-continued
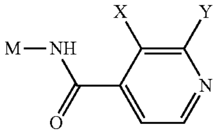
I
| NO. | X | Y | M |
|---|---|---|---|
| 1-813 | Cl | 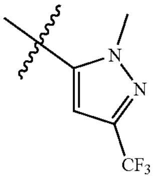 | 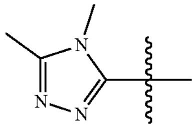 [SMILES: *c1nnc(C)n1C] |
| 1-814 | Cl | 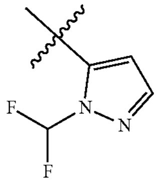 [SMILES: *c1ccnn1C(F)F] | 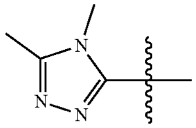 [SMILES: *c1nnc(C)n1C] |
| 1-815 | Cl | 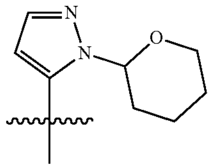 [SMILES: *c1ccnn1C1CCCCO1] | 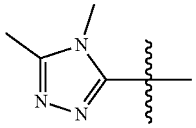 [SMILES: *c1nnc(C)n1C] |
| 1-816 | Cl | 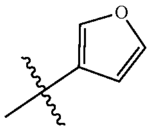 [SMILES: *c1ccoc1] | 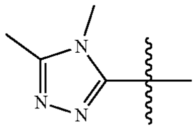 [SMILES: *c1nnc(C)n1C] |
| 1-817 | Cl | 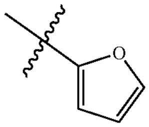 [SMILES: *c1ccco1] | 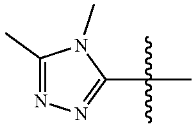 [SMILES: *c1nnc(C)n1C] |
| 1-818 | Cl | 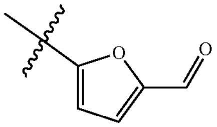 [SMILES: *c1ccc(C=O)o1] | 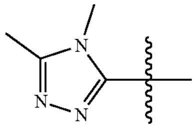 [SMILES: *c1nnc(C)n1C] |
| 1-819 | Cl | 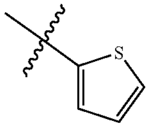 [SMILES: *c1cccs1] | 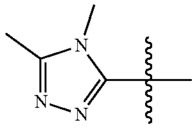 [SMILES: *c1nnc(C)n1C] |
| 1-820 | Cl | 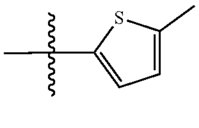 [SMILES: *c1ccc(C)s1] | 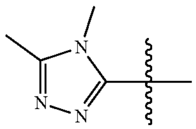 [SMILES: *c1nnc(C)n1C] |

-continued
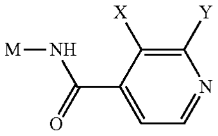
I
| NO. | X | Y | M |
|---|---|---|---|
| 1-821 | Cl | 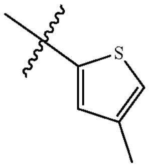 [SMILES: *c1cc(C)cs1] | 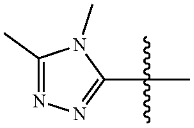 [SMILES: *c1nnc(C)n1C] |
| 1-822 | Cl | 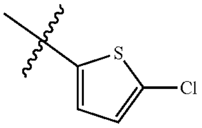 [SMILES: *c1ccc(Cl)s1] | 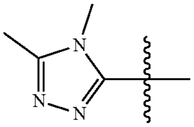 [SMILES: *c1nnc(C)n1C] |
| 1-823 | Cl | 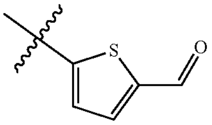 [SMILES: *c1ccc(C=O)s1] | 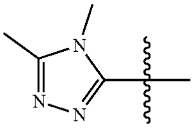 [SMILES: *c1nnc(C)n1C] |
| 1-824 | Cl | 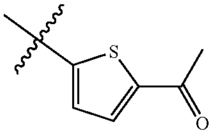 [SMILES: *c1ccc(C(C)=O)s1] | 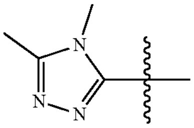 [SMILES: *c1nnc(C)n1C] |
| 1-825 | Cl | 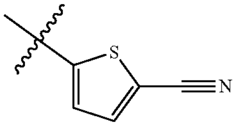 [SMILES: *c1ccc(C#N)s1] | 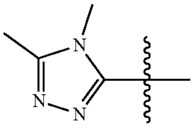 [SMILES: *c1nnc(C)n1C] |
| 1-826 | Cl | 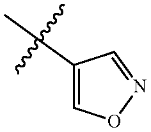 [SMILES: *c1cnoc1] | 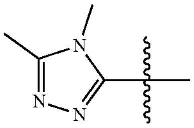 [SMILES: *c1nnc(C)n1C] |
| 1-827 | $CH_3$ | 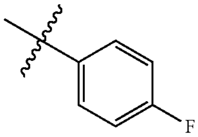 [SMILES: *c1ccc(F)cc1] | 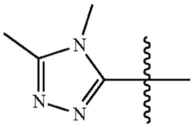 [SMILES: *c1nnc(C)n1C] |
| 1-828 | F | 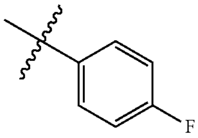 [SMILES: *c1ccc(F)cc1] | 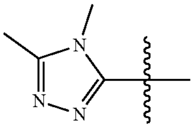 [SMILES: *c1nnc(C)n1C] |
| 1-829 | Br | 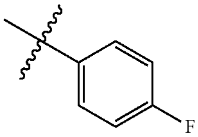 [SMILES: *c1ccc(F)cc1] | 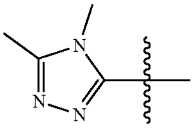 [SMILES: *c1nnc(C)n1C] |

-continued
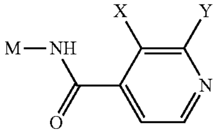
I
| NO. | X | Y | M |
|---|---|---|---|
| 1-830 | 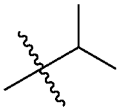 [SMILES: *C(C)C] | 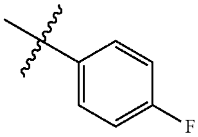 [SMILES: *c1ccc(F)cc1] | 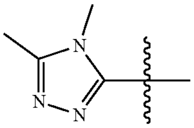 [SMILES: *c1nnc(C)n1C] |
| 1-831 | $CF_3$ | 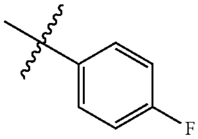 [SMILES: *c1ccc(F)cc1] | 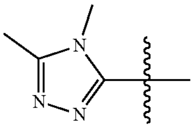 [SMILES: *c1nnc(C)n1C] |
| 1-832 | 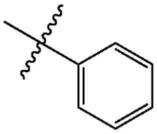 [SMILES: *c1ccccc1] | 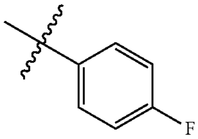 | 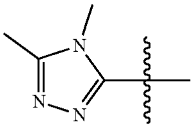 [SMILES: *c1nnc(C)n1C] |
| 1-833 | 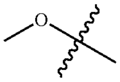 [SMILES: *OC] | 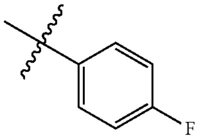 [SMILES: *c1ccc(F)cc1] | 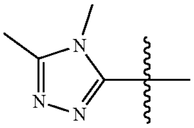 [SMILES: *c1nnc(C)n1C] |
| 1-834 | 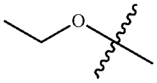 [SMILES: *OCC] | 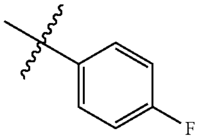 [SMILES: *c1ccc(F)cc1] | 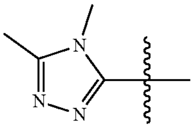 [SMILES: *c1nnc(C)n1C] |
| 1-835 | 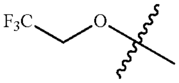 [SMILES: *OCC(F)(F)F] | 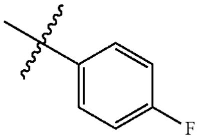 [SMILES: *c1ccc(F)cc1] | 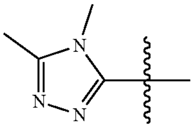 [SMILES: *c1nnc(C)n1C] |
| 1-836 | 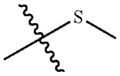 [SMILES: *SC] | 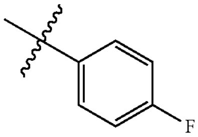 [SMILES: *c1ccc(F)cc1] | 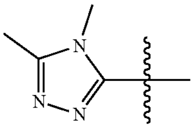 [SMILES: *c1nnc(C)n1C] |
| 1-837 | 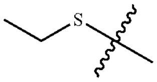 | 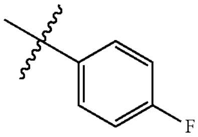 [SMILES: *c1ccc(F)cc1] | 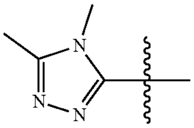 [SMILES: *c1nnc(C)n1C] |
| 1-838 | 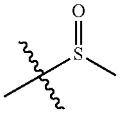 [SMILES: *S(C)=O] | 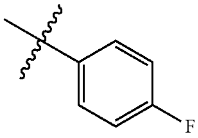 [SMILES: *c1ccc(F)cc1] | 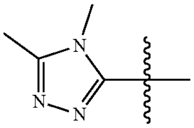 [SMILES: *c1nnc(C)n1C] |

-continued
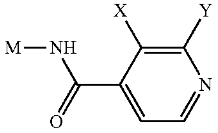
I
| NO. | X | Y | M |
|---|---|---|---|
| 1-839 | 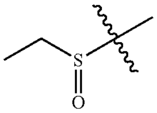 [SMILES: *S(=O)CC] | 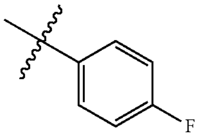 [SMILES: *c1ccc(F)cc1] | 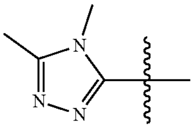 [SMILES: *c1nnc(C)n1C] |
| 1-840 | 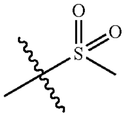 [SMILES: *S(C)(=O)=O] | 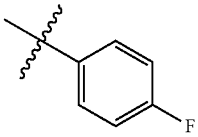 [SMILES: *c1ccc(F)cc1] | 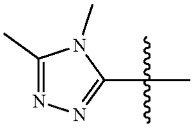 [SMILES: *c1nnc(C)n1C] |
| 1-841 | 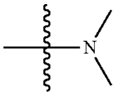 [SMILES: *N(C)C] | 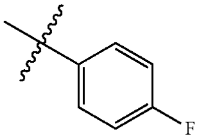 [SMILES: *c1ccc(F)cc1] | 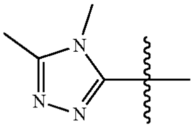 [SMILES: *c1nnc(C)n1C] |
| 1-842 | 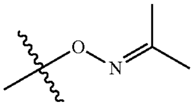 [SMILES: *ON=C(C)C] | 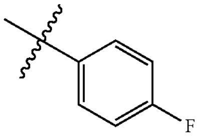 [SMILES: *c1ccc(F)cc1] | 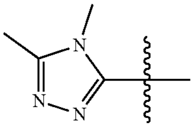 [SMILES: *c1nnc(C)n1C] |
| 1-843 | Et | 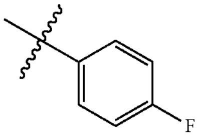 [SMILES: *c1ccc(F)cc1] | 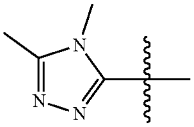 [SMILES: *c1nnc(C)n1C] |
| 1-844 | 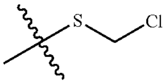 [SMILES: *SCCl] | 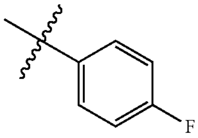 [SMILES: *c1ccc(F)cc1] | 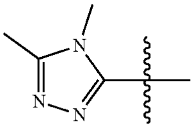 [SMILES: *c1nnc(C)n1C] |
| 1-845 | $NO_2$ | 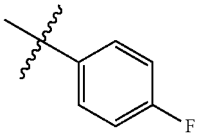 [SMILES: *c1ccc(F)cc1] | 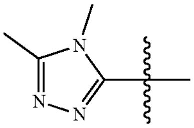 [SMILES: *c1nnc(C)n1C] |
| 1-846 | CN | 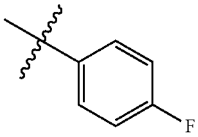 [SMILES: *c1ccc(F)cc1] | 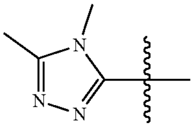 [SMILES: *c1nnc(C)n1C] |
| 1-847 | 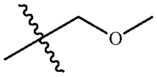 [SMILES: *COC] | 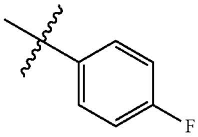 [SMILES: *c1ccc(F)cc1] | 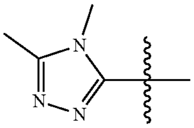 [SMILES: *c1nnc(C)n1C] |

-continued
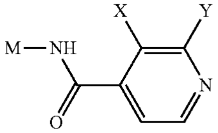
I
| NO. | X | Y | M |
|---|---|---|---|
| 1-848 | 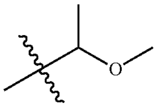 [SMILES: *C(C)OC] | 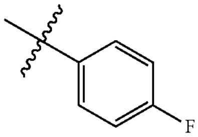 [SMILES: *c1ccc(F)cc1] | 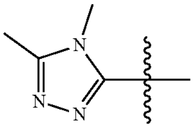 [SMILES: *c1nnc(C)n1C] |
| 1-849 | 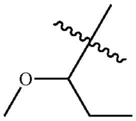 [SMILES: *C(CC)OC] | 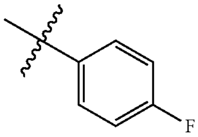 [SMILES: *c1ccc(F)cc1] | 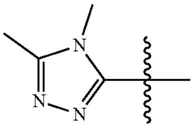 [SMILES: *c1nnc(C)n1C] |
| 1-850 | 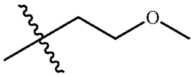 [SMILES: *CCOC] | 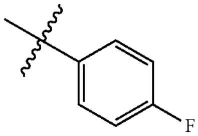 [SMILES: *c1ccc(F)cc1] | 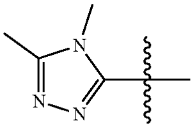 [SMILES: *c1nnc(C)n1C] |
| 1-851 | 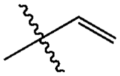 | 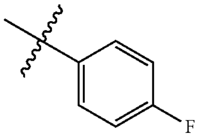 [SMILES: *c1ccc(F)cc1] | 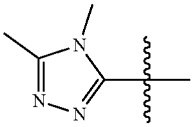 [SMILES: *c1nnc(C)n1C] |
| 1-852 | 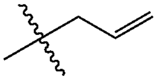 [SMILES: *CC=C] | 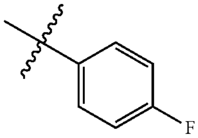 [SMILES: *c1ccc(F)cc1] | 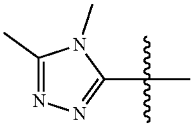 [SMILES: *c1nnc(C)n1C] |
| 1-853 | 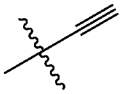 [SMILES: *C#C] | 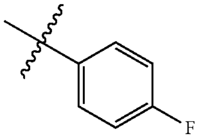 [SMILES: *c1ccc(F)cc1] | 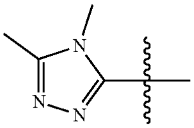 [SMILES: *c1nnc(C)n1C] |
| 1-854 | 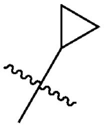 [SMILES: *C1CC1] | 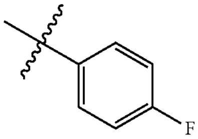 [SMILES: *c1ccc(F)cc1] | 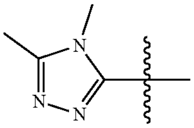 [SMILES: *c1nnc(C)n1C] |
| 1-855 | 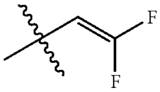 | 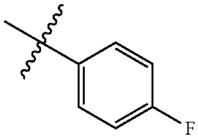 [SMILES: *c1ccc(F)cc1] | 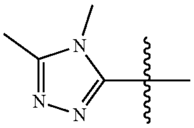 [SMILES: *c1nnc(C)n1C] |
| 1-856 | 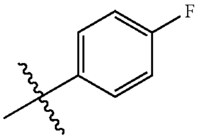 [SMILES: *c1ccc(F)cc1] | 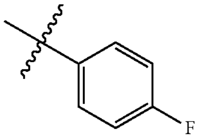 [SMILES: *c1ccc(F)cc1] | 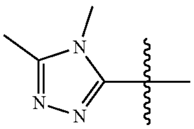 [SMILES: *c1nnc(C)n1C] |

-continued
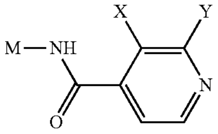
I
| NO. | X | Y | M |
|---|---|---|---|
| 1-857 | Cl | 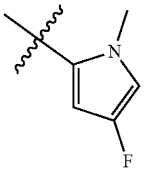 [SMILES: *c1cc(F)cn1C] | 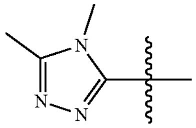 [SMILES: *c1nnc(C)n1C] |
| 1-858 | Cl | 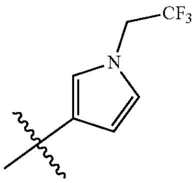 [SMILES: *c1ccn(CC(F)(F)F)c1] | 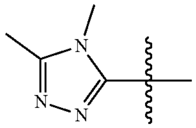 [SMILES: *c1nnc(C)n1C] |
| 1-859 | Cl | 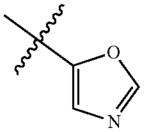 [SMILES: *c1cnco1] | 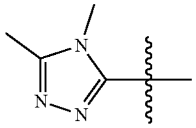 [SMILES: *c1nnc(C)n1C] |
| 1-860 | Cl | 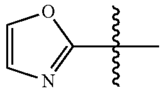 | 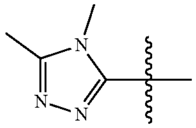 [SMILES: *c1nnc(C)n1C] |
| 1-861 | Cl | 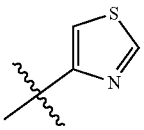 [SMILES: *c1cscn1] | 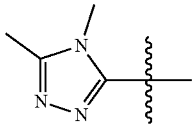 [SMILES: *c1nnc(C)n1C] |
| 1-862 | Cl | 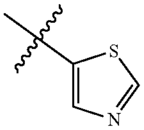 [SMILES: *c1cncs1] | 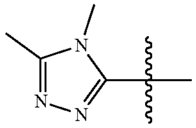 [SMILES: *c1nnc(C)n1C] |
| 1-863 | Cl | 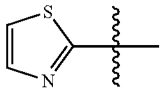 | 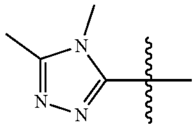 [SMILES: *c1nnc(C)n1C] |
| 1-864 | Cl | 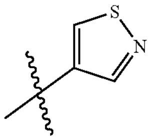 [SMILES: *c1cnsc1] | 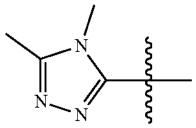 [SMILES: *c1nnc(C)n1C] |

-continued
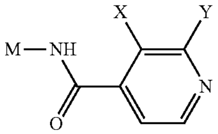
I
| NO. | X | Y | M |
| --- | --- | --- | --- |
| 1-865 | Cl | 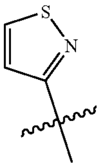 [SMILES: *c1ccsn1] | 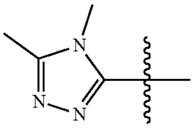 [SMILES: *c1nnc(C)n1C] |
| 1-866 | Cl | 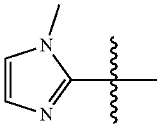 [SMILES: *c1nccn1C] | 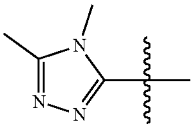 [SMILES: *c1nnc(C)n1C] |
| 1-867 | Cl | 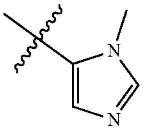 [SMILES: *c1cncn1C] | 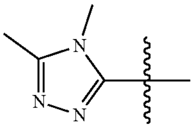 [SMILES: *c1nnc(C)n1C] |
| 1-868 | Cl | 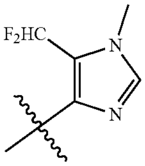 [SMILES: *c1ncn(C)c1C(F)F] | 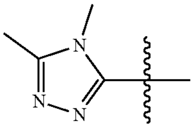 [SMILES: *c1nnc(C)n1C] |
| 1-869 | Cl | 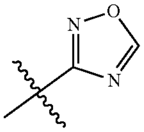 [SMILES: *c1ncon1] | 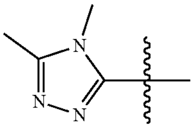 [SMILES: *c1nnc(C)n1C] |
| 1-870 | Cl | 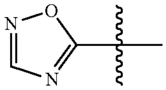 | 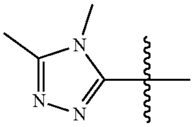 [SMILES: *c1nnc(C)n1C] |
| 1-871 | Cl | 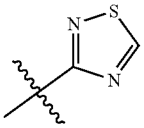 [SMILES: *c1ncsn1] | 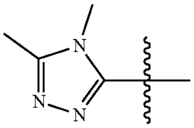 [SMILES: *c1nnc(C)n1C] |
| 1-872 | Cl | 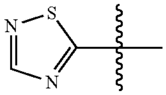 | 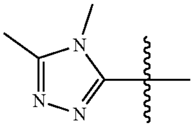 [SMILES: *c1nnc(C)n1C] |
| 1-873 | Cl | 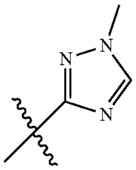 [SMILES: *c1ncn(C)n1] | 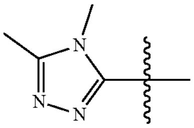 [SMILES: *c1nnc(C)n1C] |

-continued
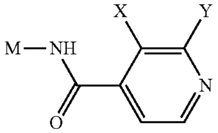
I
| NO. | X | Y | M |
|---|---|---|---|
| 1-874 | Cl | 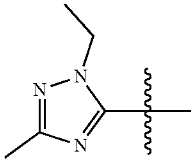 [SMILES: *c1nc(C)nn1CC] | 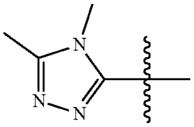 [SMILES: *c1nnc(C)n1C] |
| 1-875 | Cl | 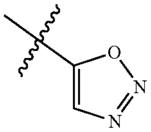 [SMILES: *c1cnno1] | 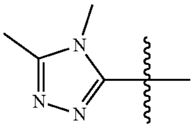 [SMILES: *c1nnc(C)n1C] |
| 1-876 | Cl | 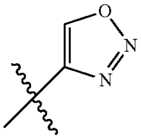 [SMILES: *c1conn1] | 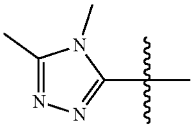 [SMILES: *c1nnc(C)n1C] |
| 1-877 | Cl | 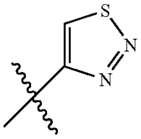 [SMILES: *c1csnn1] | 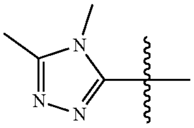 [SMILES: *c1nnc(C)n1C] |
| 1-878 | Cl | 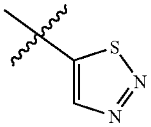 [SMILES: *c1cnns1] | 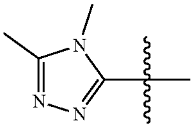 [SMILES: *c1nnc(C)n1C] |
| 1-879 | Cl | 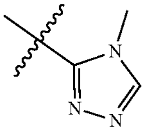 [SMILES: *c1nncn1C] | 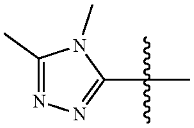 [SMILES: *c1nnc(C)n1C] |
| 1-880 | Cl | 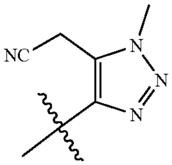 [SMILES: *c1nnn(C)c1CC#N] | 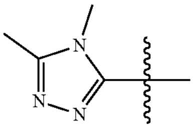 [SMILES: *c1nnc(C)n1C] |
| 1-881 | Cl | 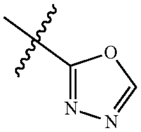 [SMILES: *c1nnco1] | 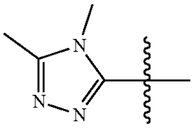 [SMILES: *c1nnc(C)n1C] |
| 1-882 | Cl | 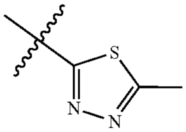 [SMILES: *c1nnc(C)s1] | 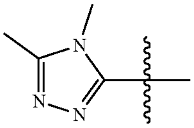 [SMILES: *c1nnc(C)n1C] |

-continued
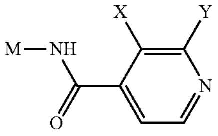
I
| NO. | X | Y | M |
|---|---|---|---|
| 1-883 | Cl | 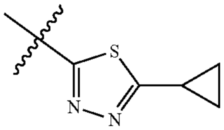 [SMILES: *c1nnc(C2CC2)s1] | 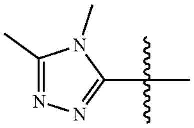 [SMILES: *c1nnc(C)n1C] |
| 1-884 | Cl | 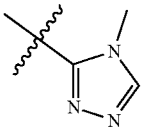 [SMILES: *c1nncn1C] | 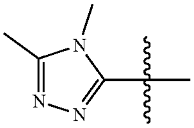 [SMILES: *c1nnc(C)n1C] |
| 1-885 | Cl | 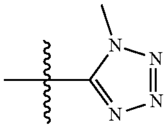 [SMILES: *c1nnnn1C] | 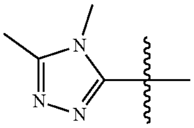 [SMILES: *c1nnc(C)n1C] |
| 1-886 | Cl | 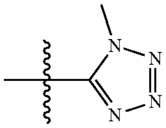 [SMILES: *c1nnnn1C] | 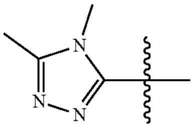 [SMILES: *c1nnc(C)n1C] |
| 1-887 | Cl | 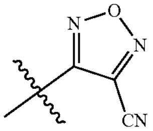 [SMILES: *c1nonc1C#N] | 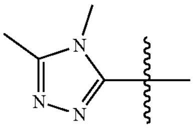 [SMILES: *c1nnc(C)n1C] |
| 1-888 | Cl | 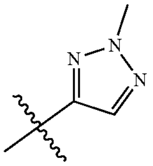 [SMILES: *c1cnn(C)n1] | 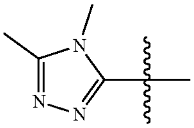 [SMILES: *c1nnc(C)n1C] |
| 1-889 | Cl | 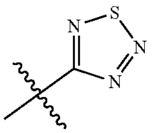 [SMILES: *c1nnsn1] | 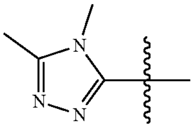 [SMILES: *c1nnc(C)n1C] |
| 1-890 | Cl | 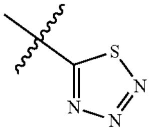 [SMILES: *c1nnns1] | 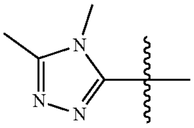 [SMILES: *c1nnc(C)n1C] |
| 1-891 | Cl | 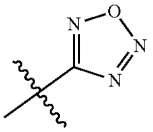 [SMILES: *c1nnon1] | 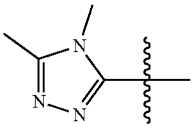 [SMILES: *c1nnc(C)n1C] |

-continued
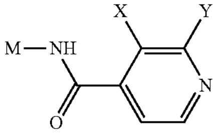
I
| NO. | X | Y | M |
|---|---|---|---|
| 1-892 | Cl | 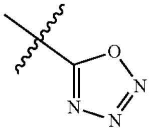 [SMILES: *c1nnno1] | 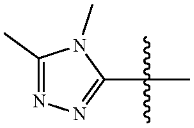 [SMILES: *c1nnc(C)n1C] |
| 1-893 | Cl | 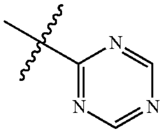 [SMILES: *c1ncncn1] | 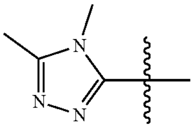 [SMILES: *c1nnc(C)n1C] |
| 1-894 | Cl | 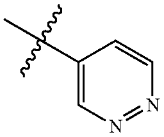 [SMILES: *c1ccnnc1] | 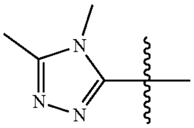 [SMILES: *c1nnc(C)n1C] |
| 1-895 | Cl | 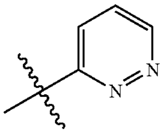 [SMILES: *c1cccnn1] | 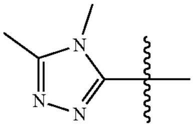 [SMILES: *c1nnc(C)n1C] |
| 1-896 | Cl | 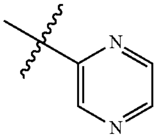 [SMILES: *c1cnccn1] | 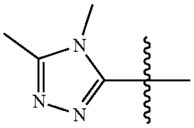 [SMILES: *c1nnc(C)n1C] |
| 1-897 | Cl | 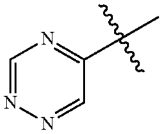 [SMILES: *c1cnncn1] | 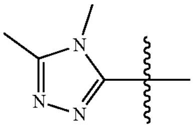 [SMILES: *c1nnc(C)n1C] |
| 1-898 | Cl | 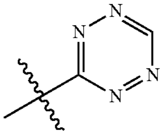 [SMILES: *c1nncnn1] | 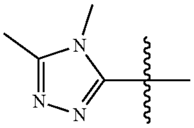 [SMILES: *c1nnc(C)n1C] |
| 1-899 | Cl | 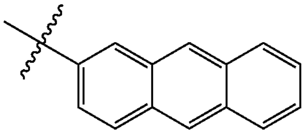 [SMILES: *c1ccc2cc3ccccc3cc2c1] | 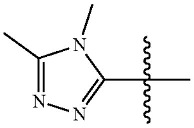 [SMILES: *c1nnc(C)n1C] |
| 1-900 | Cl | 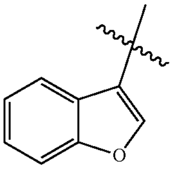 [SMILES: *c1coc2ccccc12] | 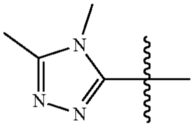 [SMILES: *c1nnc(C)n1C] |

-continued
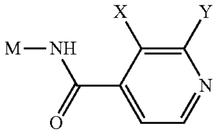
I
| NO. | X | Y | M |
|---|---|---|---|
| 1-901 | Cl | 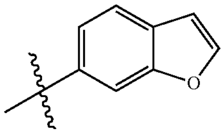 [SMILES: *c1ccc2ccoc2c1] | 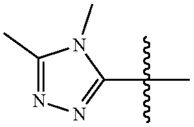 [SMILES: *c1nnc(C)n1C] |
| 1-902 | Cl | 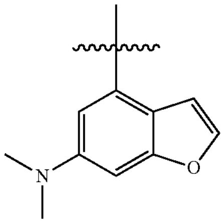 [SMILES: *c1cc(N(C)C)cc2occc12] | 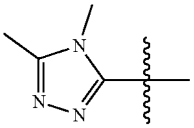 [SMILES: *c1nnc(C)n1C] |
| 1-903 | Cl | 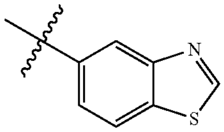 [SMILES: *c1ccc2scnc2c1] | 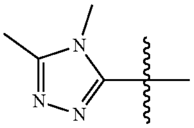 [SMILES: *c1nnc(C)n1C] |
| 1-904 | Cl | 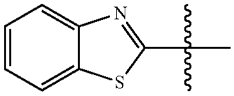 | 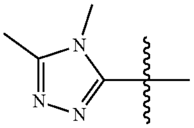 [SMILES: *c1nnc(C)n1C] |
| 1-905 | Cl | 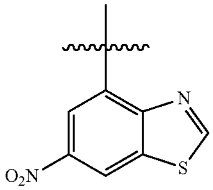 [SMILES: *c1cc([N+](=O)[O-])cc2scnc12] | 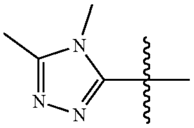 [SMILES: *c1nnc(C)n1C] |
| 1-906 | Cl | 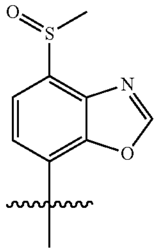 [SMILES: *c1ccc(S(C)=O)c2ncoc12] | 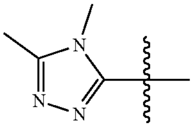 [SMILES: *c1nnc(C)n1C] |
| 1-907 | Cl | 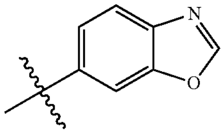 [SMILES: *c1ccc2ncoc2c1] | 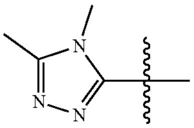 [SMILES: *c1nnc(C)n1C] |

-continued
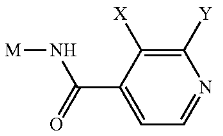
I
| NO. | X | Y | M |
| --- | --- | --- | --- |
| 1-908 | Cl | 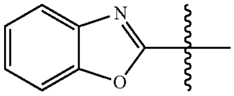 | 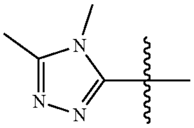 [SMILES: *c1nnc(C)n1C] |
| 1-909 | Cl | 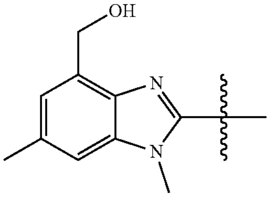 [SMILES: *c1nc2c(CO)cc(C)cc2n1C] | 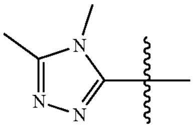 [SMILES: *c1nnc(C)n1C] |
| 1-910 | Cl | 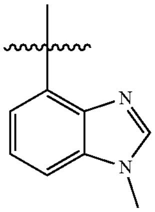 [SMILES: *c1cccc2c1ncn2C] | 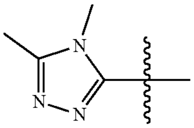 [SMILES: *c1nnc(C)n1C] |
| 1-911 | Cl | 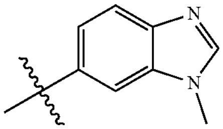 [SMILES: *c1ccc2ncn(C)c2c1] | 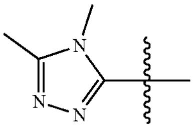 [SMILES: *c1nnc(C)n1C] |
| 1-912 | Cl | 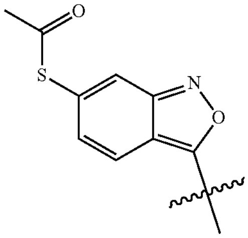 [SMILES: *c1onc2cc(SC(C)=O)ccc12] | 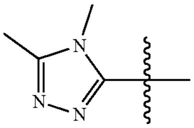 [SMILES: *c1nnc(C)n1C] |
| 1-913 | Cl | 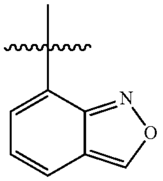 [SMILES: *c1cccc2conc12] | 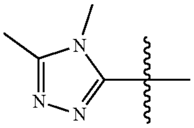 [SMILES: *c1nnc(C)n1C] |
| 1-914 | Cl | 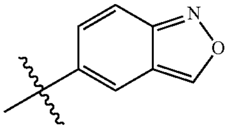 [SMILES: *c1ccc2nocc2c1] | 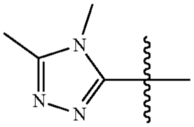 [SMILES: *c1nnc(C)n1C] |

-continued
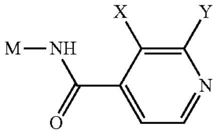
I
| NO. | X | Y | M |
|---|---|---|---|
| 1-915 | Cl | 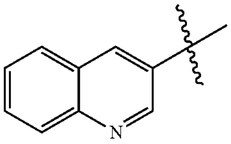 [SMILES: *c1cnc2ccccc2c1] | 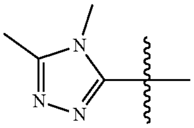 [SMILES: *c1nnc(C)n1C] |
| 1-916 | Cl | 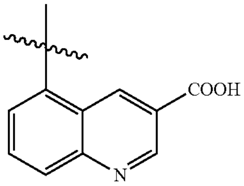 [SMILES: *c1cccc2ncc(C(=O)O)cc12] | 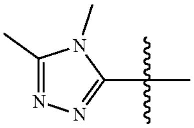 [SMILES: *c1nnc(C)n1C] |
| 1-917 | Cl | 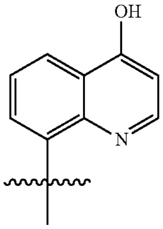 [SMILES: *c1cccc2c(O)ccnc12] | 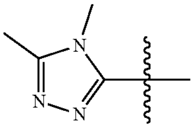 [SMILES: *c1nnc(C)n1C] |
| 1-918 | Cl | 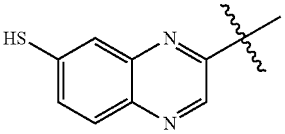 [SMILES: *c1cnc2ccc(S)cc2n1] | 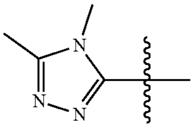 [SMILES: *c1nnc(C)n1C] |
| 1-919 | Cl | 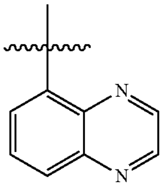 [SMILES: *c1cccc2nccnc12] | 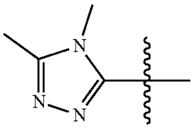 [SMILES: *c1nnc(C)n1C] |
| 1-920 | Cl | 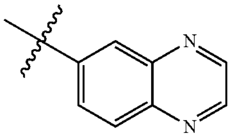 [SMILES: *c1ccc2nccnc2c1] | 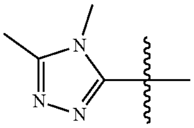 [SMILES: *c1nnc(C)n1C] |
| 1-921 | Cl | 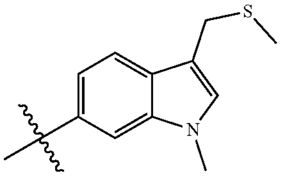 [SMILES: *c1ccc2c(CSC)cn(C)c2c1] | 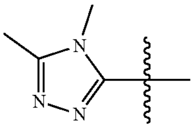 [SMILES: *c1nnc(C)n1C] |

-continued
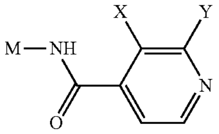
I
| NO. | X | Y | M |
|---|---|---|---|
| 1-922 | Cl | 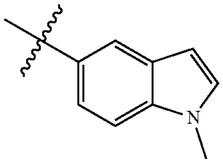 [SMILES: *c1ccc2c(ccn2C)c1] | 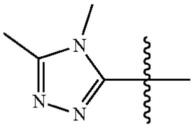 [SMILES: *c1nnc(C)n1C] |
| 1-923 | Cl | 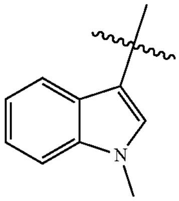 [SMILES: *c1cn(C)c2ccccc12] | 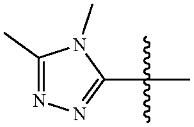 [SMILES: *c1nnc(C)n1C] |
| 1-924 | Cl | 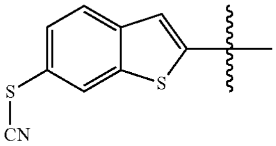 [SMILES: *c1cc2ccc(SC#N)cc2s1] | 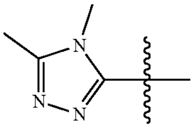 [SMILES: *c1nnc(C)n1C] |
| 1-925 | Cl | 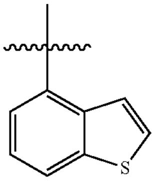 [SMILES: *c1cccc2sccc12] | 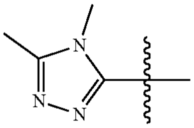 [SMILES: *c1nnc(C)n1C] |
| 1-926 | Cl | 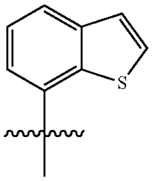 [SMILES: *c1cccc2ccsc12] | 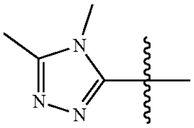 [SMILES: *c1nnc(C)n1C] |
| 1-927 | Cl | 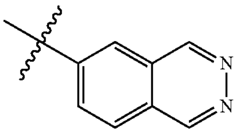 [SMILES: *c1ccc2cnncc2c1] | 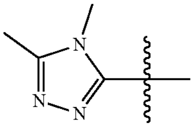 [SMILES: *c1nnc(C)n1C] |
| 1-928 | Cl | 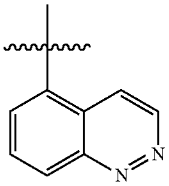 [SMILES: *c1cccc2nnccc12] | 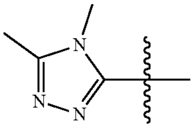 [SMILES: *c1nnc(C)n1C] |

-continued
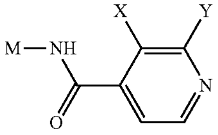
I
| NO. | X | Y | M |
|---|---|---|---|
| 1-929 | Cl | 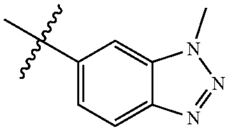 [SMILES: *c1ccc2nnn(C)c2c1] | 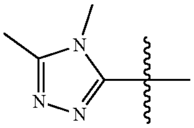 [SMILES: *c1nnc(C)n1C] |
| 1-930 | Cl | 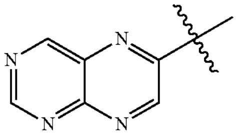 [SMILES: *c1cnc2ncncc2n1] | 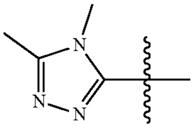 [SMILES: *c1nnc(C)n1C] |
| 1-931 | Cl | 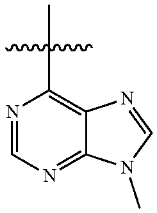 [SMILES: *c1ncnc2c1ncn2C] | 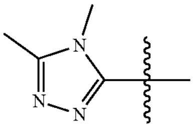 [SMILES: *c1nnc(C)n1C] |
| 1-932 | Cl | 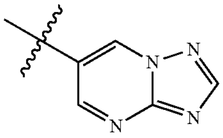 [SMILES: *c1cnc2ncnn2c1] | 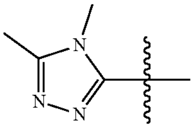 [SMILES: *c1nnc(C)n1C] |
| 1-933 | Cl | 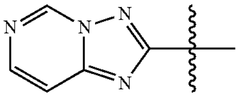 [SMILES: *c1nc2ccncn2n1] | 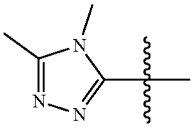 [SMILES: *c1nnc(C)n1C] |
| 1-934 | Cl | 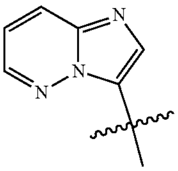 [SMILES: *c1cnc2cccnn12] | 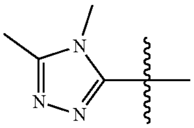 [SMILES: *c1nnc(C)n1C] |
| 1-935 | Cl | 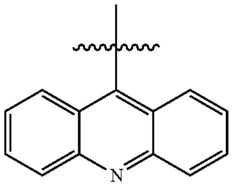 [SMILES: *c1c2ccccc2nc2ccccc12] | 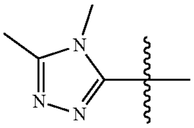 [SMILES: *c1nnc(C)n1C] |
| 1-936 | Cl | 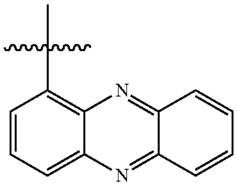 [SMILES: *c1cccc2nc3ccccc3nc12] | 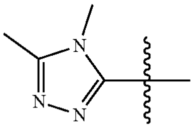 [SMILES: *c1nnc(C)n1C] |

-continued
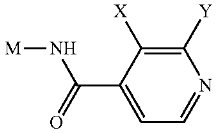
I
| NO. | X | Y | M |
|---|---|---|---|
| 1-937 | Cl | 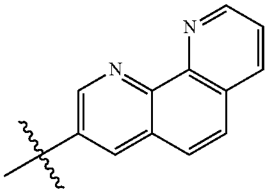 [SMILES: *c1cnc2c(ccc3cccnc32)c1] | 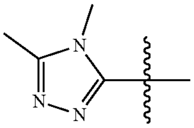 [SMILES: *c1nnc(C)n1C] |
| 1-938 | Cl | 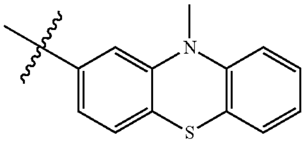 [SMILES: *c1ccc2c(c1)N(C)c1ccccc1S2] | 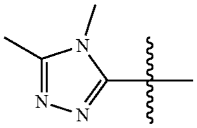 [SMILES: *c1nnc(C)n1C] |
| 1-939 | Cl | 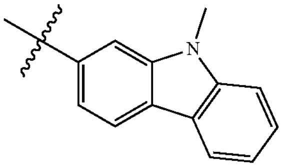 [SMILES: *c1ccc2c3ccccc3n(C)c2c1] | 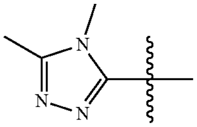 |
| 1-940 | Cl | 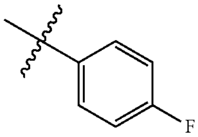 [SMILES: *c1ccc(F)cc1] | 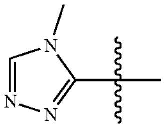 [SMILES: *c1nncn1C] |
| 1-941 | Cl | 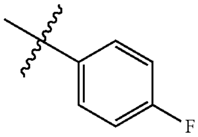 [SMILES: *c1ccc(F)cc1] | 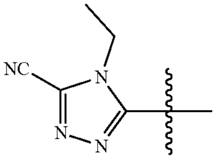 [SMILES: *c1nnc(C#N)n1CC] |
| 1-942 | Cl | 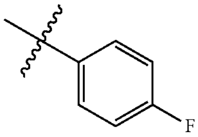 [SMILES: *c1ccc(F)cc1] | 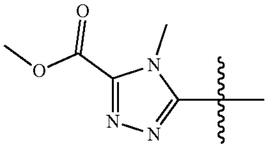 [SMILES: *c1nnc(C(=O)OC)n1C] |
| 1-943 | Cl | 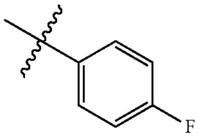 [SMILES: *c1ccc(F)cc1] | 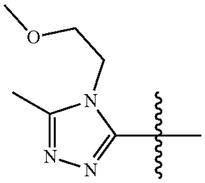 [SMILES: *c1nnc(C)n1CCOC] |
| 1-944 | Cl | 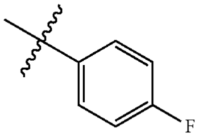 [SMILES: *c1ccc(F)cc1] | 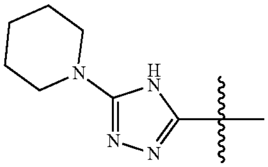 [SMILES: *c1nnc(N2CCCCC2)[nH]1] |

-continued
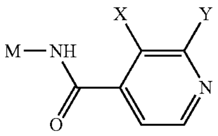
I
| NO. | X | Y | M |
|---|---|---|---|
| 1-945 | Cl | 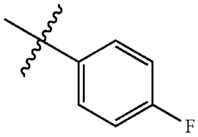 [SMILES: *c1ccc(F)cc1] | 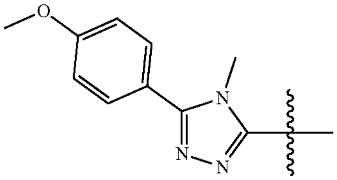 [SMILES: *c1nnc(-c2ccc(OC)cc2)n1C] |
| 1-946 | Cl | $CH_3$ | 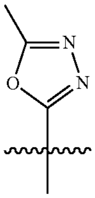 |
| 1-947 | Cl | 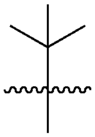 | 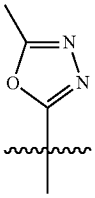 |
| 1-948 | Cl | 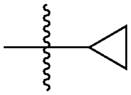 [SMILES: *C1CC1] | 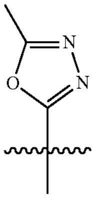 [SMILES: *c1nnc(C)o1] |
| 1-949 | Cl | 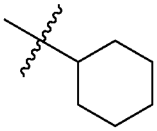 [SMILES: *C1CCCCC1] | 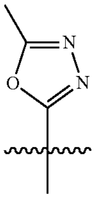 |
| 1-950 | Cl | 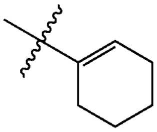 | 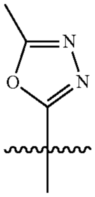 |

-continued
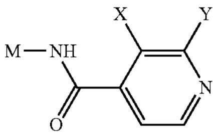
I
| NO. | X | Y | M |
| --- | --- | --- | --- |
| 1-951 | Cl | 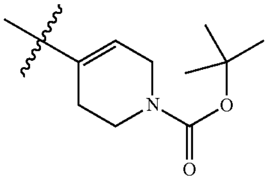 [SMILES: *C1=CCN(C(=O)OC(C)(C)C)CC1] | 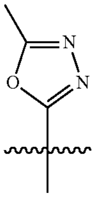 |
| 1-952 | Cl | 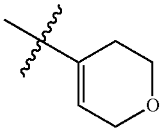 | 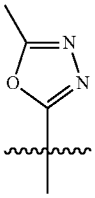 [SMILES: *c1nnc(C)o1] |
| 1-953 | Cl | 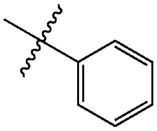 [SMILES: *c1ccccc1] | 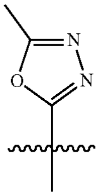 [SMILES: *c1nnc(C)o1] |
| 1-954 | Cl | 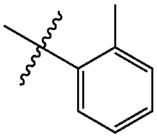 [SMILES: *c1ccccc1C] | 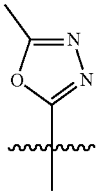 [SMILES: *c1nnc(C)o1] |
| 1-955 | Cl | 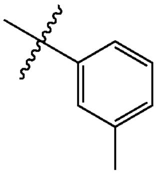 [SMILES: *c1cccc(C)c1] | 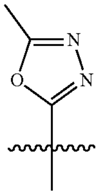 [SMILES: *c1nnc(C)o1] |
| 1-956 | Cl | 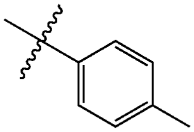 [SMILES: *c1ccc(C)cc1] | 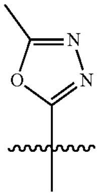 [SMILES: *c1nnc(C)o1] |

-continued
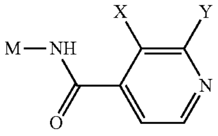
I
| NO. | X | Y | M |
| --- | --- | --- | --- |
| 1-957 | Cl | 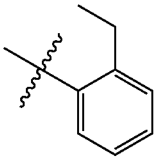 [SMILES: *c1ccccc1CC] | 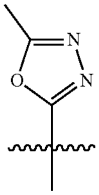 [SMILES: *c1nnc(C)o1] |
| 1-958 | Cl | 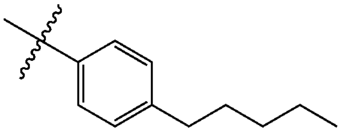 [SMILES: *c1ccc(CCCCC)cc1] | 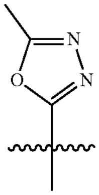 [SMILES: *c1nnc(C)o1] |
| 1-959 | Cl | 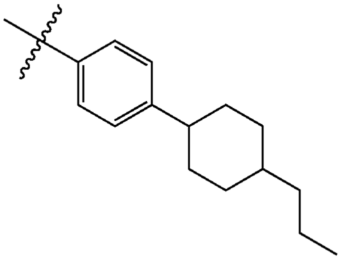 [SMILES: *c1ccc(C2CCC(CCC)CC2)cc1] | 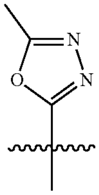 [SMILES: *c1nnc(C)o1] |
| 1-960 | Cl | 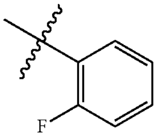 | 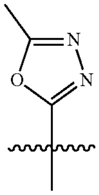 [SMILES: *c1nnc(C)o1] |
| 1-961 | Cl | 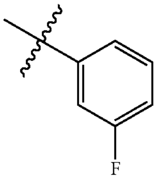 [SMILES: *c1cccc(F)c1] | 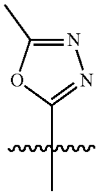 [SMILES: *c1nnc(C)o1] |
| 1-962 | Cl | 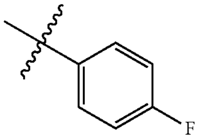 [SMILES: *c1ccc(F)cc1] | 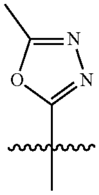 [SMILES: *c1nnc(C)o1] |

-continued
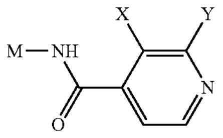
I
| NO. | X | Y | M |
|---|---|---|---|
| 1-963 | Cl | 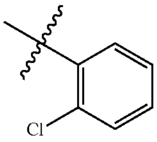 [SMILES: *c1ccccc1Cl] | 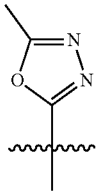 [SMILES: *c1nnc(C)o1] |
| 1-964 | Cl | 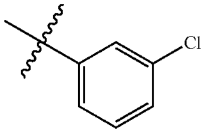 [SMILES: *c1cccc(Cl)c1] | 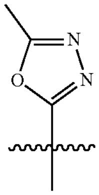 [SMILES: *c1nnc(C)o1] |
| 1-965 | Cl | 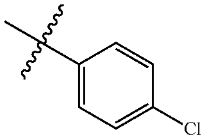 [SMILES: *c1ccc(Cl)cc1] | 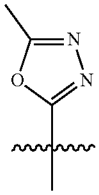 [SMILES: *c1nnc(C)o1] |
| 1-966 | Cl | 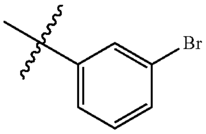 [SMILES: *c1cccc(Br)c1] | 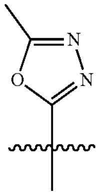 [SMILES: *c1nnc(C)o1] |
| 1-967 | Cl | 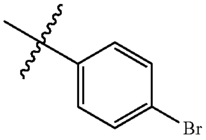 [SMILES: *c1ccc(Br)cc1] | 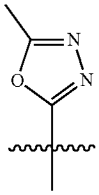 [SMILES: *c1nnc(C)o1] |
| 1-968 | Cl | 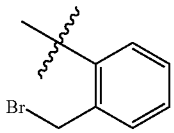 [SMILES: *c1ccccc1CBr] | 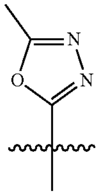 [SMILES: *c1nnc(C)o1] |

-continued
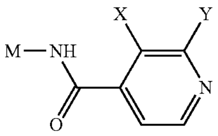
I
| NO. | X | Y | M |
|---|---|---|---|
| 1-969 | Cl | 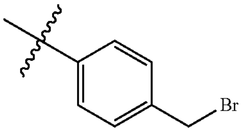 [SMILES: *c1ccc(CBr)cc1] | 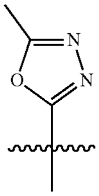 [SMILES: *c1nnc(C)o1] |
| 1-970 | Cl | 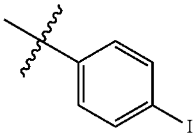 [SMILES: *c1ccc(I)cc1] | 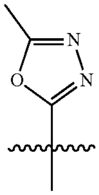 [SMILES: *c1nnc(C)o1] |
| 1-971 | Cl | 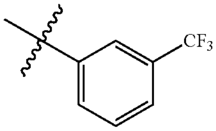 [SMILES: *c1cccc(C(F)(F)F)c1] | 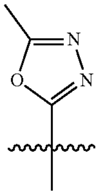 [SMILES: *c1nnc(C)o1] |
| 1-972 | Cl | 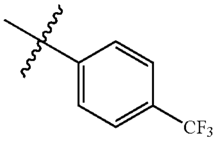 [SMILES: *c1ccc(C(F)(F)F)cc1] | 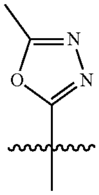 [SMILES: *c1nnc(C)o1] |
| 1-973 | Cl | 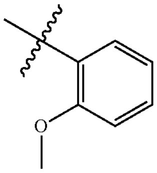 [SMILES: *c1ccccc1OC] | 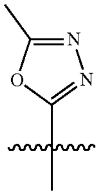 [SMILES: *c1nnc(C)o1] |
| 1-974 | Cl | 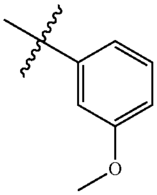 [SMILES: *c1cccc(OC)c1] | 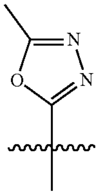 [SMILES: *c1nnc(C)o1] |

-continued
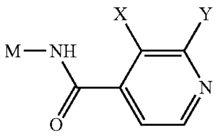
I
| NO. | X | Y | M |
|---|---|---|---|
| 1-975 | Cl | 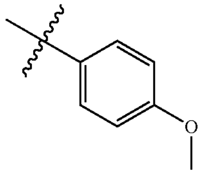 [SMILES: *c1ccc(OC)cc1] | 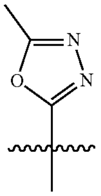 [SMILES: *c1nnc(C)o1] |
| 1-976 | Cl | 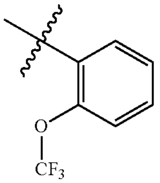 [SMILES: *c1ccccc1OC(F)(F)F] | 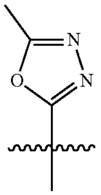 [SMILES: *c1nnc(C)o1] |
| 1-977 | Cl | 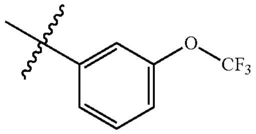 [SMILES: *c1cccc(OC(F)(F)F)c1] | 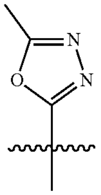 [SMILES: *c1nnc(C)o1] |
| 1-978 | Cl | 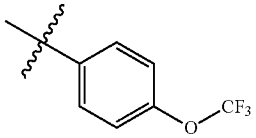 [SMILES: *c1ccc(OC(F)(F)F)cc1] | 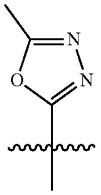 [SMILES: *c1nnc(C)o1] |
| 1-979 | Cl | 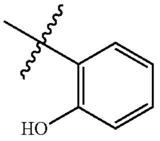 [SMILES: *c1ccccc1O] | 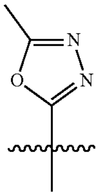 [SMILES: *c1nnc(C)o1] |
| 1-980 | Cl | 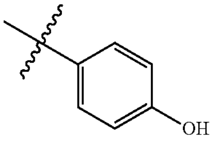 [SMILES: *c1ccc(O)cc1] | 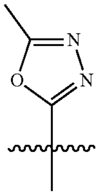 [SMILES: *c1nnc(C)o1] |

-continued
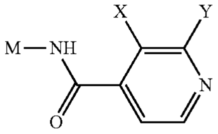
I
| NO. | X | Y | M |
|---|---|---|---|
| 1-981 | Cl | 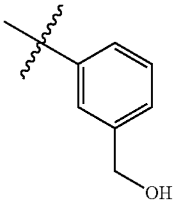 [SMILES: *c1cccc(CO)c1] | 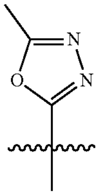 [SMILES: *c1nnc(C)o1] |
| 1-982 | Cl | 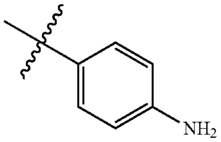 | 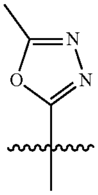 [SMILES: *c1nnc(C)o1] |
| 1-983 | Cl | 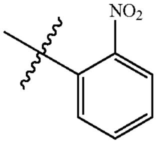 [SMILES: *c1ccccc1[N+](=O)[O-]] | 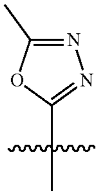 [SMILES: *c1nnc(C)o1] |
| 1-984 | Cl | 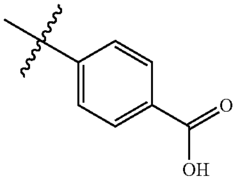 [SMILES: *c1ccc(C(=O)O)cc1] | 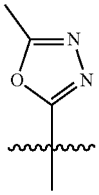 [SMILES: *c1nnc(C)o1] |
| 1-985 | Cl | 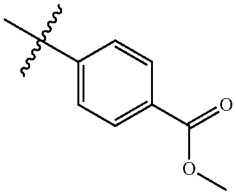 [SMILES: *c1ccc(C(=O)OC)cc1] | 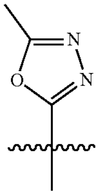 [SMILES: *c1nnc(C)o1] |
| 1-986 | Cl | 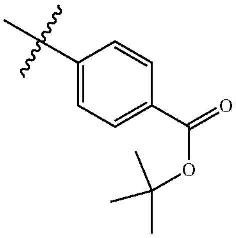 [SMILES: *c1ccc(C(=O)OC(C)(C)C)cc1] | 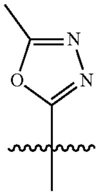 [SMILES: *c1nnc(C)o1] |

-continued
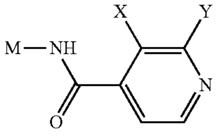
I
| NO. | X | Y | M |
|---|---|---|---|
| 1-987 | Cl | 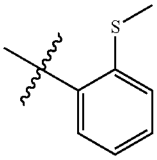 [SMILES: *c1ccccc1SC] | 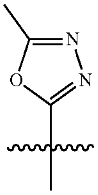 [SMILES: *c1nnc(C)o1] |
| 1-988 | Cl | 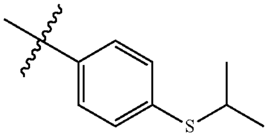 [SMILES: *c1ccc(SC(C)C)cc1] | 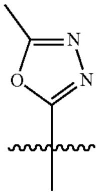 [SMILES: *c1nnc(C)o1] |
| 1-989 | Cl | 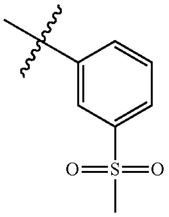 [SMILES: *c1cccc(S(C)(=O)=O)c1] | 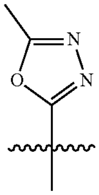 [SMILES: *c1nnc(C)o1] |
| 1-990 | Cl | 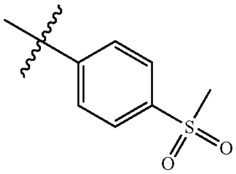 [SMILES: *c1ccc(S(C)(=O)=O)cc1] | 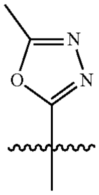 [SMILES: *c1nnc(C)o1] |
| 1-991 | Cl | 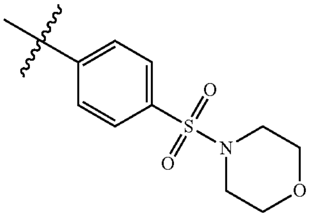 [SMILES: *c1ccc(S(=O)(=O)N2CCOCC2)cc1] | 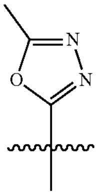 [SMILES: *c1nnc(C)o1] |
| 1-992 | Cl | 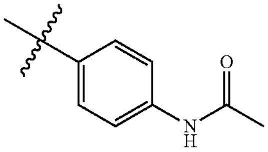 [SMILES: *c1ccc(NC(C)=O)cc1] | 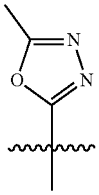 [SMILES: *c1nnc(C)o1] |

-continued
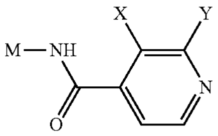
I
| NO. | X | Y | M |
|---|---|---|---|
| 1-993 | Cl | 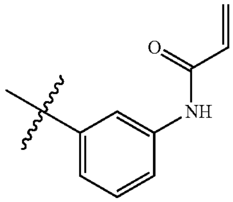 [SMILES: *c1cccc(NC(=O)C=C)c1] | 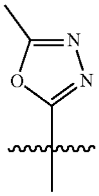 [SMILES: *c1nnc(C)o1] |
| 1-994 | Cl | 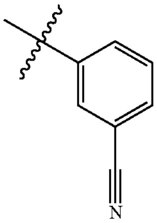 [SMILES: *c1cccc(C#N)c1] | 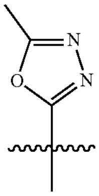 [SMILES: *c1nnc(C)o1] |
| 1-995 | Cl | 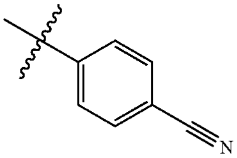 [SMILES: *c1ccc(C#N)cc1] | 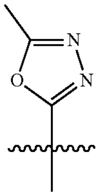 [SMILES: *c1nnc(C)o1] |
| 1-996 | Cl | 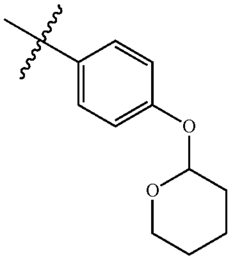 [SMILES: *c1ccc(OC2CCCCO2)cc1] | 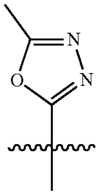 [SMILES: *c1nnc(C)o1] |
| 1-997 | Cl | 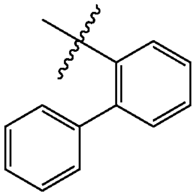 [SMILES: *c1ccccc1-c1ccccc1] | 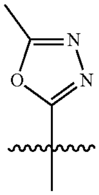 [SMILES: *c1nnc(C)o1] |
| 1-998 | Cl | 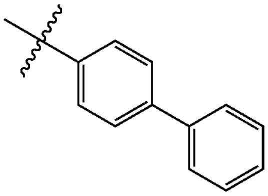 [SMILES: *c1ccc(-c2ccccc2)cc1] | 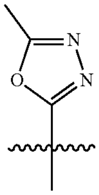 [SMILES: *c1nnc(C)o1] |

-continued
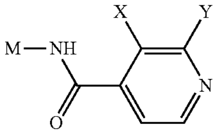
I
| NO. | X | Y | M |
|---|---|---|---|
| 1-999 | Cl | 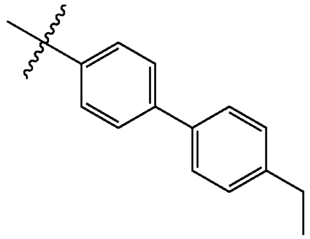 [SMILES: *c1ccc(-c2ccc(CC)cc2)cc1] | 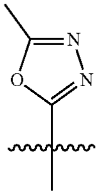 [SMILES: *c1nnc(C)o1] |
| 1-1000 | Cl | 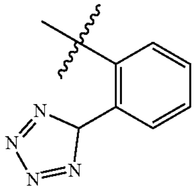 [SMILES: *c1ccccc1C1N=NN=N1] | 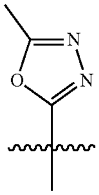 [SMILES: *c1nnc(C)o1] |
| 1-1001 | Cl | 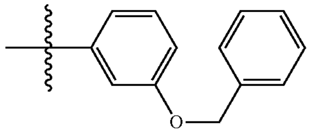 [SMILES: *c1cccc(OCc2ccccc2)c1] | 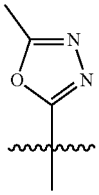 [SMILES: *c1nnc(C)o1] |
| 1-1002 | Cl | 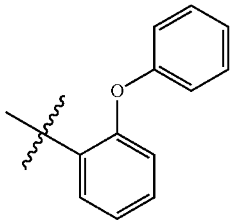 [SMILES: *c1ccccc1Oc1ccccc1] | 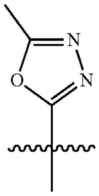 [SMILES: *c1nnc(C)o1] |
| 1-1003 | Cl | 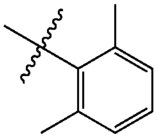 [SMILES: *c1c(C)cccc1C] | 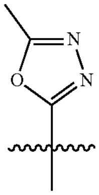 [SMILES: *c1nnc(C)o1] |
| 1-1004 | Cl | 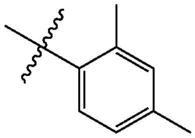 [SMILES: *c1ccc(C)cc1C] | 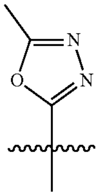 [SMILES: *c1nnc(C)o1] |

-continued
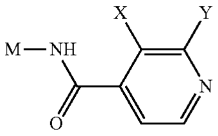
I
| NO. | X | Y | M |
|---|---|---|---|
| 1-1005 | Cl | 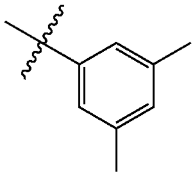 [SMILES: *c1cc(C)cc(C)c1] | 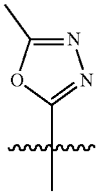 [SMILES: *c1nnc(C)o1] |
| 1-1006 | Cl | 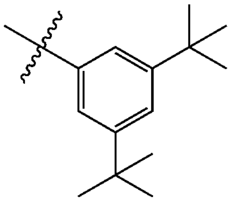 [SMILES: *c1cc(C(C)(C)C)cc(C(C)(C)C)c1] | 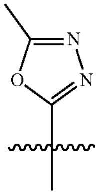 [SMILES: *c1nnc(C)o1] |
| 1-1007 | Cl | 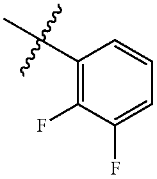 [SMILES: *c1cccc(F)c1F] | 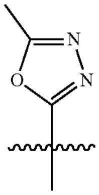 [SMILES: *c1nnc(C)o1] |
| 1-1008 | Cl | 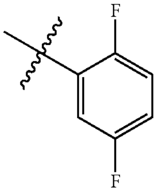 [SMILES: *c1cc(F)ccc1F] | 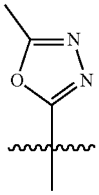 [SMILES: *c1nnc(C)o1] |
| 1-1009 | Cl | 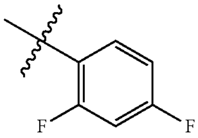 [SMILES: *c1ccc(F)cc1F] | 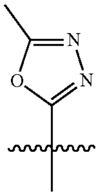 [SMILES: *c1nnc(C)o1] |
| 1-1010 | Cl | 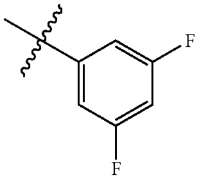 | 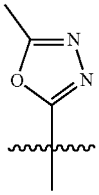 [SMILES: *c1nnc(C)o1] |

-continued
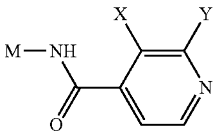
I
| NO. | X | Y | M |
|---|---|---|---|
| 1-1011 | Cl | 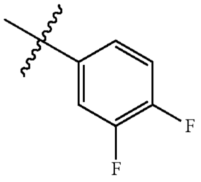 [SMILES: *c1ccc(F)c(F)c1] | 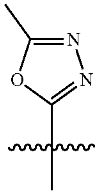 [SMILES: *c1nnc(C)o1] |
| 1-1012 | Cl | 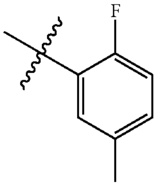 [SMILES: *c1cc(C)ccc1F] | 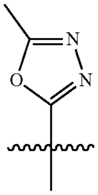 [SMILES: *c1nnc(C)o1] |
| 1-1013 | Cl | 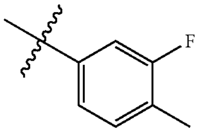 [SMILES: *c1ccc(C)c(F)c1] | 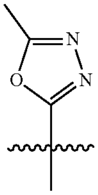 [SMILES: *c1nnc(C)o1] |
| 1-1014 | Cl | 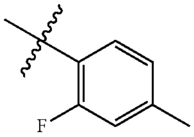 [SMILES: *c1ccc(C)cc1F] | 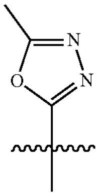 [SMILES: *c1nnc(C)o1] |
| 1-1015 | Cl | 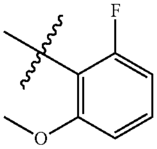 [SMILES: *c1c(F)cccc1OC] | 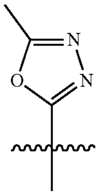 [SMILES: *c1nnc(C)o1] |
| 1-1016 | Cl | 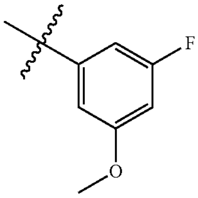 [SMILES: *c1cc(F)cc(OC)c1] | 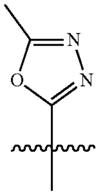 [SMILES: *c1nnc(C)o1] |

-continued
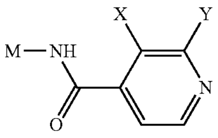
I
| NO. | X | Y | M |
|---|---|---|---|
| 1-1017 | Cl | 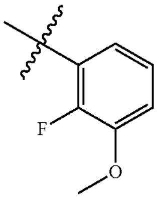 [SMILES: *c1cccc(OC)c1F] | 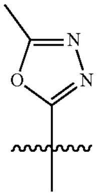 [SMILES: *c1nnc(C)o1] |
| 1-1018 | Cl | 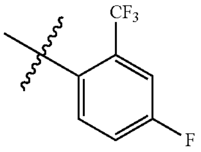 | 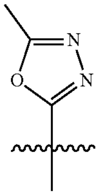 [SMILES: *c1nnc(C)o1] |
| 1-1019 | Cl | 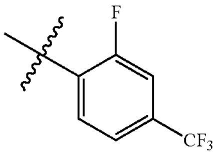 [SMILES: *c1ccc(C(F)(F)F)cc1F] | 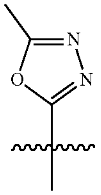 [SMILES: *c1nnc(C)o1] |
| 1-1020 | Cl | 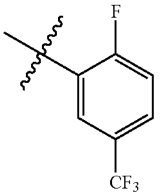 [SMILES: *c1cc(C(F)(F)F)ccc1F] | 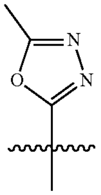 [SMILES: *c1nnc(C)o1] |
| 1-1021 | Cl | 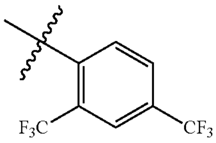 [SMILES: *c1ccc(C(F)(F)F)cc1C(F)(F)F] | 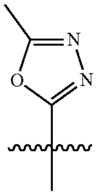 [SMILES: *c1nnc(C)o1] |
| 1-1022 | Cl | 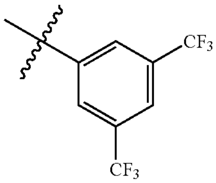 [SMILES: *c1cc(C(F)(F)F)cc(C(F)(F)F)c1] | 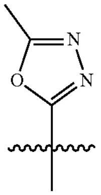 [SMILES: *c1nnc(C)o1] |

-continued
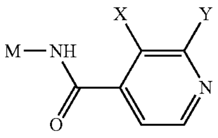
I
| NO. | X | Y | M |
| --- | --- | --- | --- |
| 1-1023 | Cl | 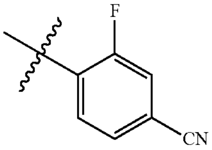 [SMILES: *c1ccc(C#N)cc1F] | 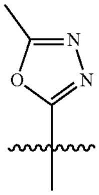 [SMILES: *c1nnc(C)o1] |
| 1-1024 | Cl | 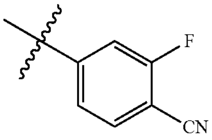 [SMILES: *c1ccc(C#N)c(F)c1] | 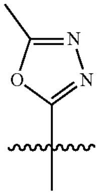 [SMILES: *c1nnc(C)o1] |
| 1-1025 | Cl | 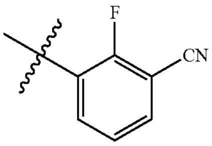 [SMILES: *c1cccc(C#N)c1F] | 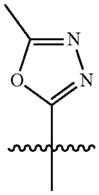 [SMILES: *c1nnc(C)o1] |
| 1-1026 | Cl | 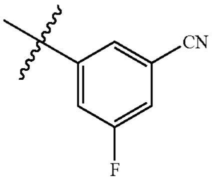 [SMILES: *c1cc(F)cc(C#N)c1] | 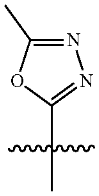 [SMILES: *c1nnc(C)o1] |
| 1-1027 | Cl | 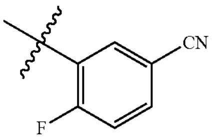 [SMILES: *c1cc(C#N)ccc1F] | 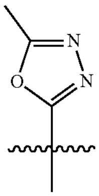 [SMILES: *c1nnc(C)o1] |
| 1-1028 | Cl | 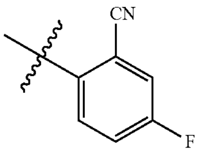 [SMILES: *c1ccc(F)cc1C#N] | 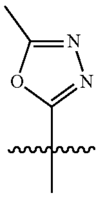 [SMILES: *c1nnc(C)o1] |

-continued
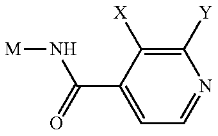
I
| NO. | X | Y | M |
|---|---|---|---|
| 1-1029 | Cl | 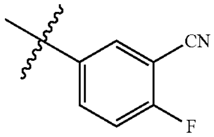 [SMILES: *c1ccc(F)c(C#N)c1] | 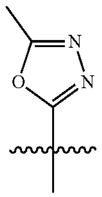 [SMILES: *c1nnc(C)o1] |
| 1-1030 | Cl | 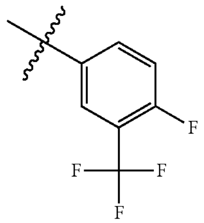 [SMILES: *c1ccc(F)c(C(F)(F)F)c1] | 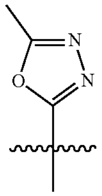 [SMILES: *c1nnc(C)o1] |
| 1-1031 | Cl | 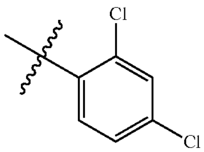 | 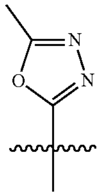 [SMILES: *c1nnc(C)o1] |
| 1-1032 | Cl | 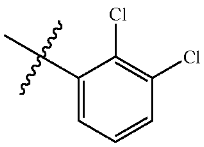 | 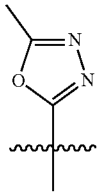 [SMILES: *c1nnc(C)o1] |
| 1-1033 | Cl | 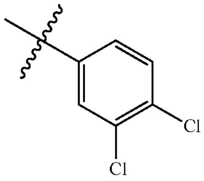 [SMILES: *c1ccc(Cl)c(Cl)c1] | 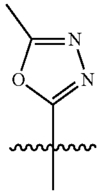 [SMILES: *c1nnc(C)o1] |
| 1-1034 | Cl | 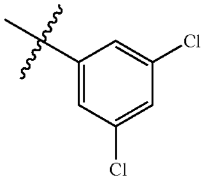 | 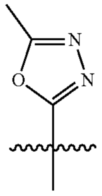 [SMILES: *c1nnc(C)o1] |

-continued
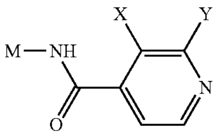
I
| NO. | X | Y | M |
|---|---|---|---|
| 1-1035 | Cl | 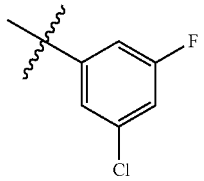 [SMILES: *c1cc(F)cc(Cl)c1] | 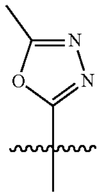 [SMILES: *c1nnc(C)o1] |
| 1-1036 | Cl | 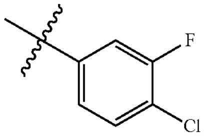 [SMILES: *c1ccc(Cl)c(F)c1] | 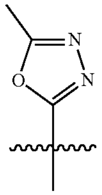 [SMILES: *c1nnc(C)o1] |
| 1-1037 | Cl | 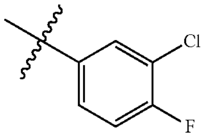 [SMILES: *c1ccc(F)c(Cl)c1] | 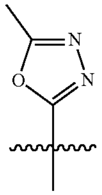 [SMILES: *c1nnc(C)o1] |
| 1-1038 | Cl | 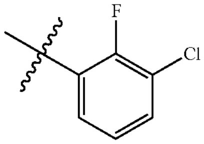 [SMILES: *c1cccc(Cl)c1F] | 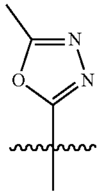 [SMILES: *c1nnc(C)o1] |
| 1-1039 | Cl | 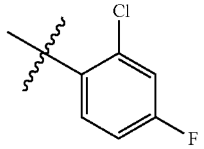 | 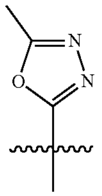 [SMILES: *c1nnc(C)o1] |
| 1-1040 | Cl | 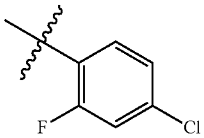 [SMILES: *c1ccc(Cl)cc1F] | 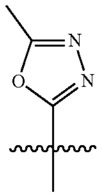 [SMILES: *c1nnc(C)o1] |

-continued
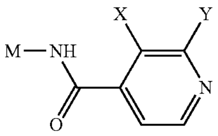
I
| NO. | X | Y | M |
|---|---|---|---|
| 1-1041 | Cl | 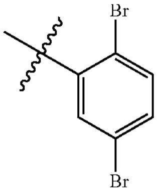 [SMILES: *c1cc(Br)ccc1Br] | 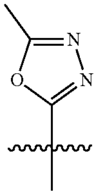 [SMILES: *c1nnc(C)o1] |
| 1-1042 | Cl | 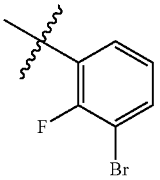 | 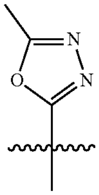 [SMILES: *c1nnc(C)o1] |
| 1-1043 | Cl | 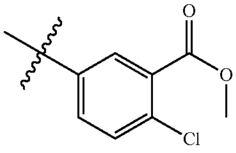 [SMILES: *c1ccc(Cl)c(C(=O)OC)c1] | 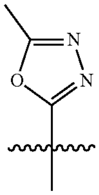 [SMILES: *c1nnc(C)o1] |
| 1-1044 | Cl | 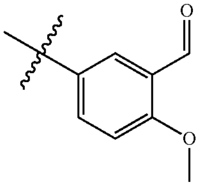 [SMILES: *c1ccc(OC)c(C=O)c1] | 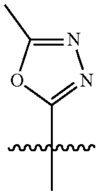 [SMILES: *c1nnc(C)o1] |
| 1-1045 | Cl | 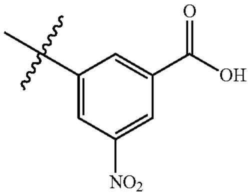 [SMILES: *c1cc(C(=O)O)cc([N+](=O)[O-])c1] | 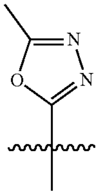 [SMILES: *c1nnc(C)o1] |
| 1-1046 | Cl | 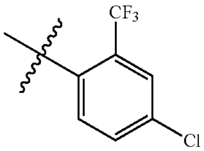 | 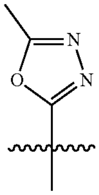 [SMILES: *c1nnc(C)o1] |

-continued
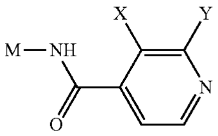
I
| NO. | X | Y | M |
|---|---|---|---|
| 1-1047 | Cl | 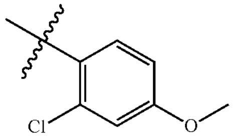 [SMILES: *c1ccc(OC)cc1Cl] | 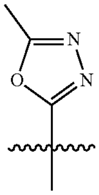 [SMILES: *c1nnc(C)o1] |
| 1-1048 | Cl | 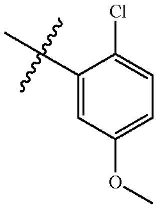 [SMILES: *c1cc(OC)ccc1Cl] | 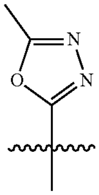 [SMILES: *c1nnc(C)o1] |
| 1-1049 | Cl | 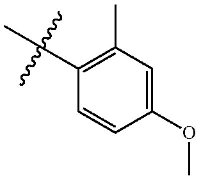 [SMILES: *c1ccc(OC)cc1C] | 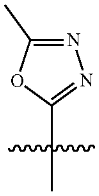 [SMILES: *c1nnc(C)o1] |
| 1-1050 | Cl | 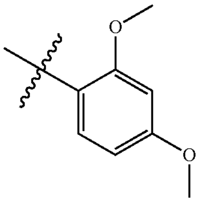 [SMILES: *c1ccc(OC)cc1OC] | 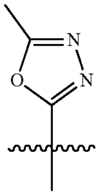 [SMILES: *c1nnc(C)o1] |
| 1-1051 | Cl | 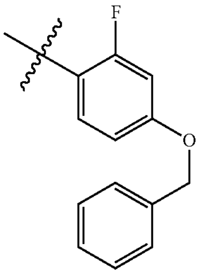 [SMILES: *c1ccc(OCc2ccccc2)cc1F] | 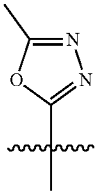 [SMILES: *c1nnc(C)o1] |
| 1-1052 | Cl | 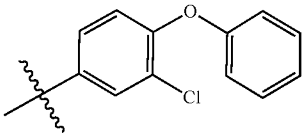 [SMILES: *c1ccc(Oc2ccccc2)c(Cl)c1] | 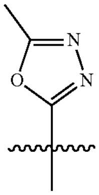 [SMILES: *c1nnc(C)o1] |

-continued
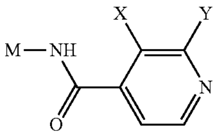
I
| NO. | X | Y | M |
|---|---|---|---|
| 1-1053 | Cl | 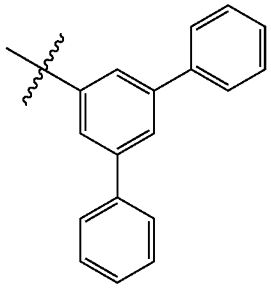 [SMILES: *c1cc(-c2ccccc2)cc(-c2ccccc2)c1] | 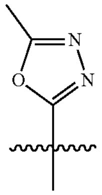 [SMILES: *c1nnc(C)o1] |
| 1-1054 | Cl | 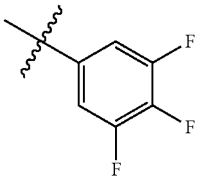 [SMILES: *c1cc(F)c(F)c(F)c1] | 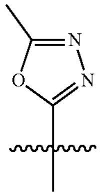 [SMILES: *c1nnc(C)o1] |
| 1-1055 | Cl | 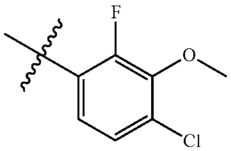 [SMILES: *c1ccc(Cl)c(OC)c1F] | 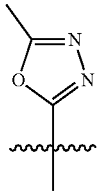 [SMILES: *c1nnc(C)o1] |
| 1-1056 | Cl | 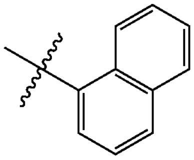 [SMILES: *c1cccc2ccccc12] | 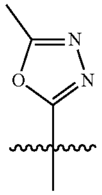 [SMILES: *c1nnc(C)o1] |
| 1-1057 | Cl | 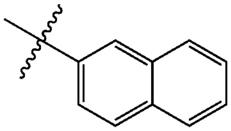 [SMILES: *c1ccc2ccccc2c1] | 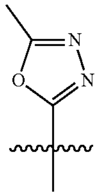 [SMILES: *c1nnc(C)o1] |
| 1-1058 | Cl | 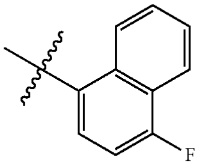 [SMILES: *c1ccc(F)c2ccccc12] | 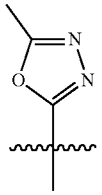 [SMILES: *c1nnc(C)o1] |

-continued
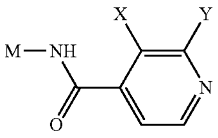
I
| NO. | X | Y | M |
|---|---|---|---|
| 1-1059 | Cl | 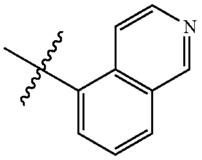 [SMILES: *c1cccc2cnccc12] | 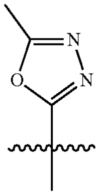 [SMILES: *c1nnc(C)o1] |
| 1-1060 | Cl | 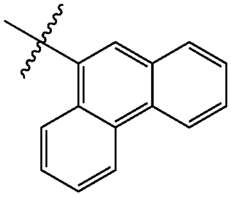 [SMILES: *c1cc2ccccc2c2ccccc12] | 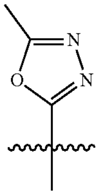 [SMILES: *c1nnc(C)o1] |
| 1-1061 | Cl | 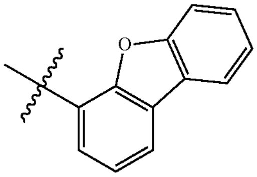 [SMILES: *c1cccc2c1oc1ccccc12] | 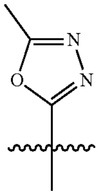 [SMILES: *c1nnc(C)o1] |
| 1-1062 | Cl | 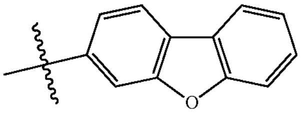 [SMILES: *c1ccc2c(c1)oc1ccccc12] | 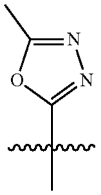 [SMILES: *c1nnc(C)o1] |
| 1-1063 | Cl | 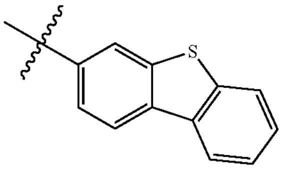 [SMILES: *c1ccc2c(c1)sc1ccccc12] | 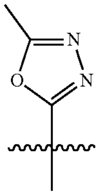 [SMILES: *c1nnc(C)o1] |
| 1-1064 | Cl | 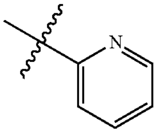 [SMILES: *c1ccccn1] | 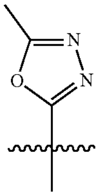 [SMILES: *c1nnc(C)o1] |

-continued
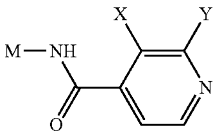
I
| NO. | X | Y | M |
|---|---|---|---|
| 1-1065 | Cl | 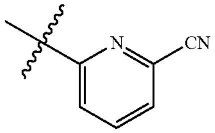 [SMILES: *c1cccc(C#N)n1] | 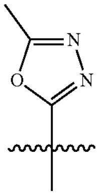 [SMILES: *c1nnc(C)o1] |
| 1-1066 | Cl | 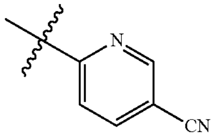 [SMILES: *c1ccc(C#N)cn1] | 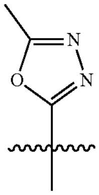 [SMILES: *c1nnc(C)o1] |
| 1-1067 | Cl | 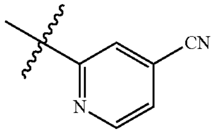 [SMILES: *c1cc(C#N)ccn1] | 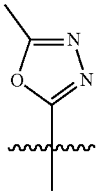 [SMILES: *c1nnc(C)o1] |
| 1-1068 | Cl | 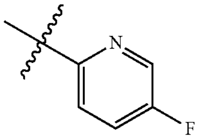 [SMILES: *c1ccc(F)cn1] | 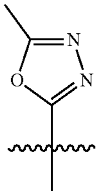 [SMILES: *c1nnc(C)o1] |
| 1-1069 | Cl | 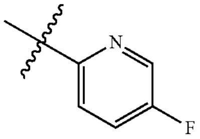 [SMILES: *c1ccc(F)cn1] | 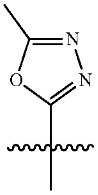 [SMILES: *c1nnc(C)o1] |
| 1-1070 | Cl | 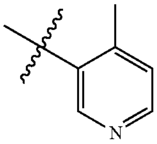 [SMILES: *c1cnccc1C] | 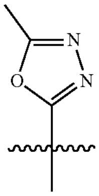 [SMILES: *c1nnc(C)o1] |

-continued
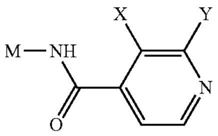
I
| NO. | X | Y | M |
|---|---|---|---|
| 1-1071 | Cl | 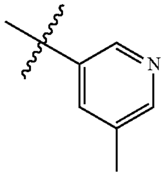 [SMILES: *c1cncc(C)c1] | 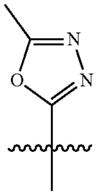 [SMILES: *c1nnc(C)o1] |
| 1-1072 | Cl | 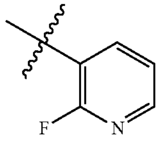 | 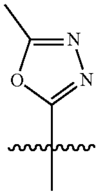 [SMILES: *c1nnc(C)o1] |
| 1-1073 | Cl | 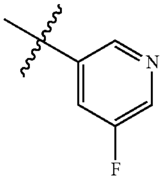 [SMILES: *c1cncc(F)c1] | 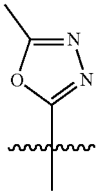 [SMILES: *c1nnc(C)o1] |
| 1-1074 | Cl | 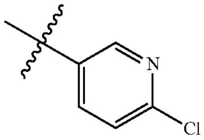 [SMILES: *c1ccc(Cl)nc1] | 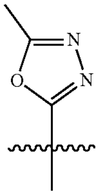 [SMILES: *c1nnc(C)o1] |
| 1-1075 | Cl | 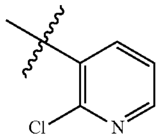 [SMILES: *c1cccnc1Cl] | 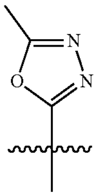 [SMILES: *c1nnc(C)o1] |
| 1-1076 | Cl | 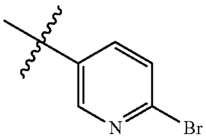 [SMILES: *c1ccc(Br)nc1] | 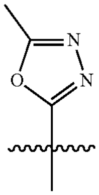 [SMILES: *c1nnc(C)o1] |

-continued
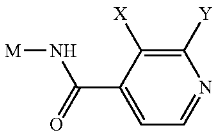
I
| NO. | X | Y | M |
| --- | --- | --- | --- |
| 1-1077 | Cl | 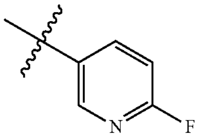 [SMILES: *c1ccc(F)nc1] | 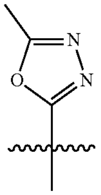 [SMILES: *c1nnc(C)o1] |
| 1-1078 | Cl | 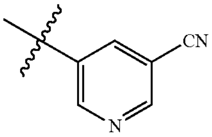 [SMILES: *c1cncc(C#N)c1] | 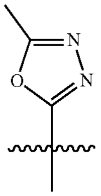 [SMILES: *c1nnc(C)o1] |
| 1-1079 | Cl | 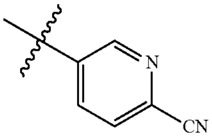 [SMILES: *c1ccc(C#N)nc1] | 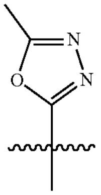 [SMILES: *c1nnc(C)o1] |
| 1-1080 | Cl | 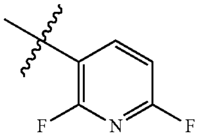 | 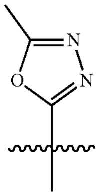 [SMILES: *c1nnc(C)o1] |
| 1-1081 | Cl | 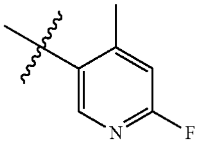 [SMILES: *c1cnc(F)cc1C] | 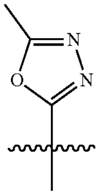 [SMILES: *c1nnc(C)o1] |
| 1-1082 | Cl | 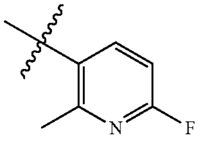 [SMILES: *c1ccc(F)nc1C] | 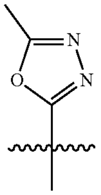 [SMILES: *c1nnc(C)o1] |

-continued
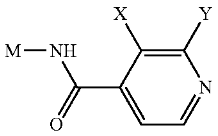
I
| NO. | X | Y | M |
|---|---|---|---|
| 1-1083 | Cl | 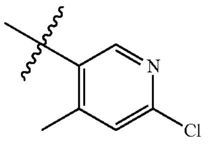 [SMILES: *c1cnc(Cl)cc1C] | 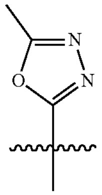 [SMILES: *c1nnc(C)o1] |
| 1-1084 | Cl | 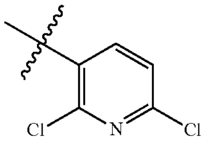 [SMILES: *c1ccc(Cl)nc1Cl] | 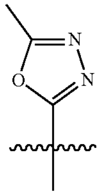 [SMILES: *c1nnc(C)o1] |
| 1-1085 | Cl | 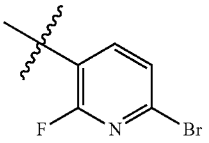 [SMILES: *c1ccc(Br)nc1F] | 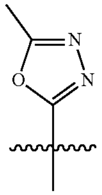 [SMILES: *c1nnc(C)o1] |
| 1-1086 | Cl | 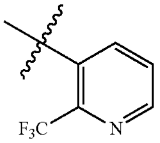 [SMILES: *c1cccnc1C(F)(F)F] | 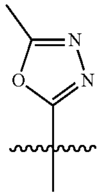 [SMILES: *c1nnc(C)o1] |
| 1-1087 | Cl | 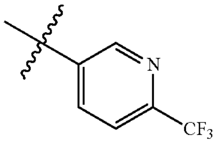 [SMILES: *c1ccc(C(F)(F)F)nc1] | 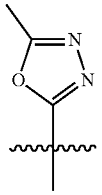 [SMILES: *c1nnc(C)o1] |
| 1-1088 | Cl | 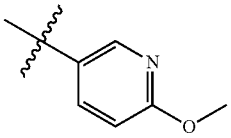 [SMILES: *c1ccc(OC)nc1] | 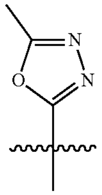 [SMILES: *c1nnc(C)o1] |

-continued
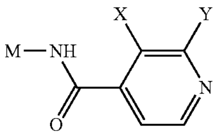
I
| NO. | X | Y | M |
|---|---|---|---|
| 1-1089 | Cl | 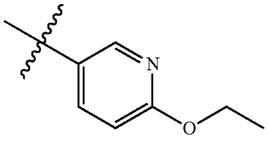 [SMILES: *c1ccc(OCC)nc1] | 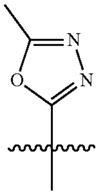 [SMILES: *c1nnc(C)o1] |
| 1-1090 | Cl | 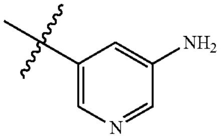 [SMILES: *c1cncc(N)c1] | 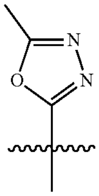 [SMILES: *c1nnc(C)o1] |
| 1-1091 | Cl | 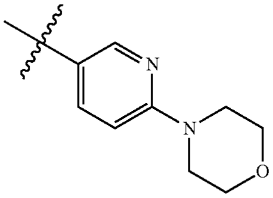 [SMILES: *c1ccc(N2CCOCC2)nc1] | 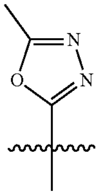 [SMILES: *c1nnc(C)o1] |
| 1-1092 | Cl | 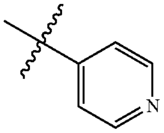 [SMILES: *c1ccncc1] | 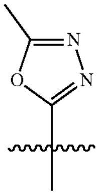 [SMILES: *c1nnc(C)o1] |
| 1-1093 | Cl | 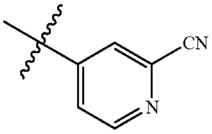 [SMILES: *c1ccnc(C#N)c1] | 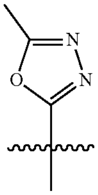 [SMILES: *c1nnc(C)o1] |
| 1-1094 | Cl | 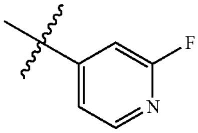 [SMILES: *c1ccnc(F)c1] | 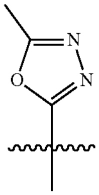 [SMILES: *c1nnc(C)o1] |

-continued
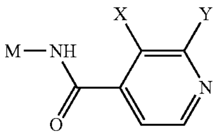
I
| NO. | X | Y | M |
|---|---|---|---|
| 1-1095 | Cl | 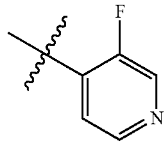 [SMILES: *c1ccncc1F] | 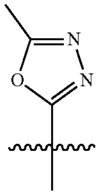 [SMILES: *c1nnc(C)o1] |
| 1-1096 | Cl | 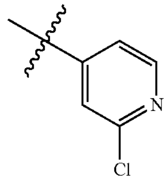 [SMILES: *c1ccnc(Cl)c1] | 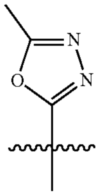 [SMILES: *c1nnc(C)o1] |
| 1-1097 | Cl | 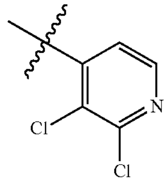 [SMILES: *c1ccnc(Cl)c1Cl] | 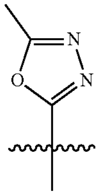 [SMILES: *c1nnc(C)o1] |
| 1-1098 | Cl | 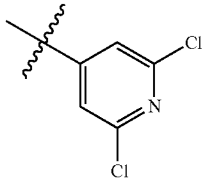 [SMILES: *c1cc(Cl)nc(Cl)c1] | 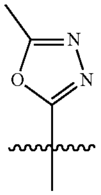 [SMILES: *c1nnc(C)o1] |
| 1-1099 | Cl | 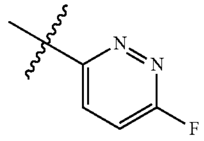 [SMILES: *c1ccc(F)nn1] | 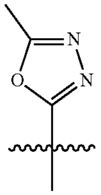 [SMILES: *c1nnc(C)o1] |
| 1-1100 | Cl | 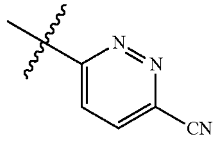 [SMILES: *c1ccc(C#N)nn1] | 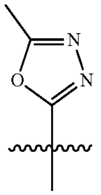 [SMILES: *c1nnc(C)o1] |

-continued
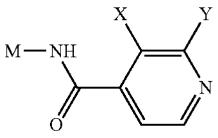
I
| NO. | X | Y | M |
|---|---|---|---|
| 1-1101 | Cl | 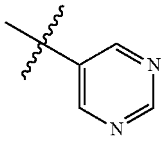 [SMILES: *c1cncnc1] | 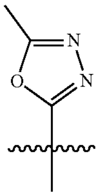 [SMILES: *c1nnc(C)o1] |
| 1-1102 | Cl | 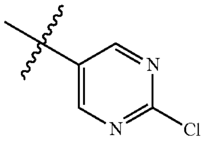 [SMILES: *c1cnc(Cl)nc1] | 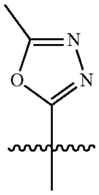 [SMILES: *c1nnc(C)o1] |
| 1-1103 | Cl | 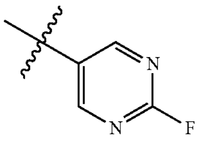 [SMILES: *c1cnc(F)nc1] | 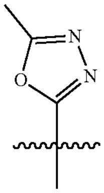 [SMILES: *c1nnc(C)o1] |
| 1-1104 | Cl | 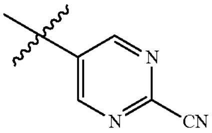 | 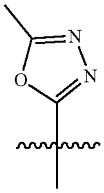 [SMILES: *c1nnc(C)o1] |
| 1-1105 | Cl | 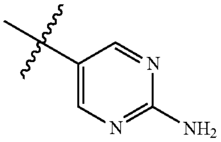 [SMILES: *c1cnc(N)nc1] | 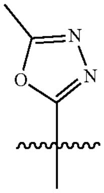 [SMILES: *c1nnc(C)o1] |
| 1-1106 | Cl | 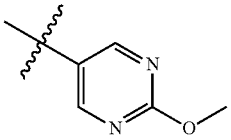 [SMILES: *c1cnc(OC)nc1] | 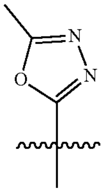 [SMILES: *c1nnc(C)o1] |

-continued
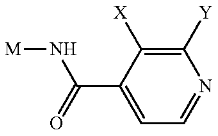
I
| NO. | X | Y | M |
| --- | --- | --- | --- |
| 1-1107 | Cl | 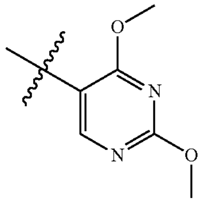 [SMILES: *c1cnc(OC)nc1OC] | 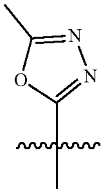 [SMILES: *c1nnc(C)o1] |
| 1-1108 | Cl | 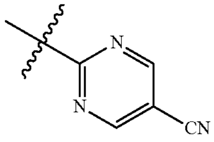 | 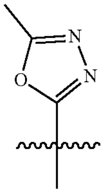 [SMILES: *c1nnc(C)o1] |
| 1-1109 | Cl | 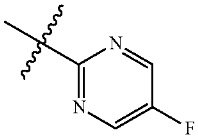 [SMILES: *c1ncc(F)cn1] | 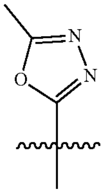 [SMILES: *c1nnc(C)o1] |
| 1-1110 | Cl | 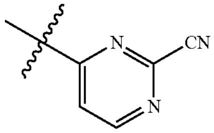 | 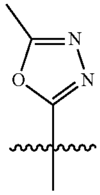 [SMILES: *c1nnc(C)o1] |
| 1-1111 | Cl | 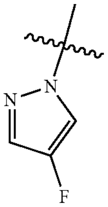 [SMILES: *n1cc(F)cn1] | 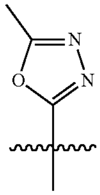 [SMILES: *c1nnc(C)o1] |
| 1-1112 | Cl | 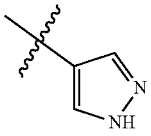 [SMILES: *c1cn[nH]c1] | 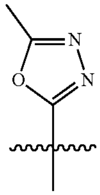 [SMILES: *c1nnc(C)o1] |

-continued
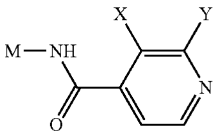
I
| NO. | X | Y | M |
|---|---|---|---|
| 1-1113 | Cl | 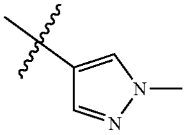 [SMILES: *c1cnn(C)c1] | 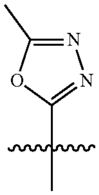 [SMILES: *c1nnc(C)o1] |
| 1-1114 | Cl | 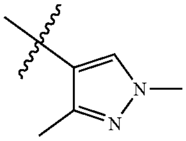 | 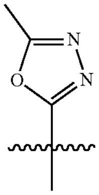 [SMILES: *c1nnc(C)o1] |
| 1-1115 | Cl | 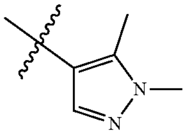 [SMILES: *c1cnn(C)c1C] | 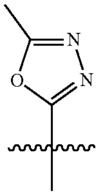 [SMILES: *c1nnc(C)o1] |
| 1-1116 | Cl | 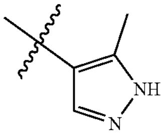 [SMILES: *c1cn[nH]c1C] | 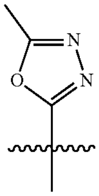 [SMILES: *c1nnc(C)o1] |
| 1-1117 | Cl | 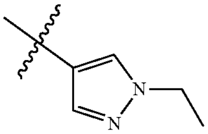 [SMILES: *c1cnn(CC)c1] | 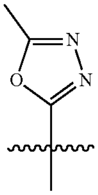 [SMILES: *c1nnc(C)o1] |
| 1-1118 | Cl | 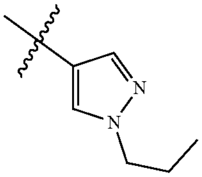 [SMILES: *c1cnn(CCC)c1] | 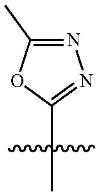 [SMILES: *c1nnc(C)o1] |

-continued
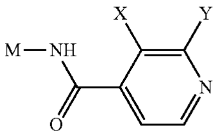
I
| NO. | X | Y | M |
| --- | --- | --- | --- |
| 1-1119 | Cl | 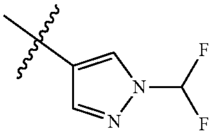 [SMILES: *c1cnn(C(F)F)c1] | 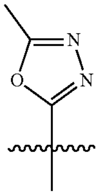 [SMILES: *c1nnc(C)o1] |
| 1-1120 | Cl | 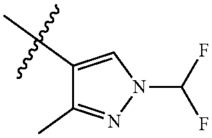 [SMILES: *c1cn(C(F)F)nc1C] | 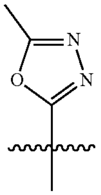 [SMILES: *c1nnc(C)o1] |
| 1-1121 | Cl | 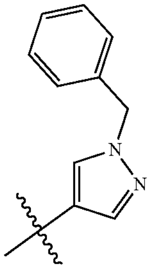 [SMILES: *c1cnn(Cc2ccccc2)c1] | 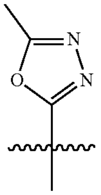 [SMILES: *c1nnc(C)o1] |
| 1-1122 | Cl | 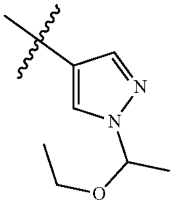 [SMILES: *c1cnn(C(C)OCC)c1] | 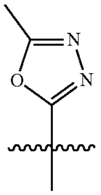 [SMILES: *c1nnc(C)o1] |
| 1-1123 | Cl | 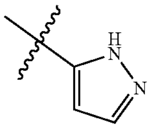 [SMILES: *c1ccn[nH]1] | 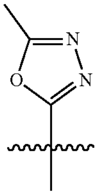 [SMILES: *c1nnc(C)o1] |
| 1-1124 | Cl | 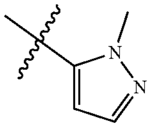 [SMILES: *c1ccnn1C] | 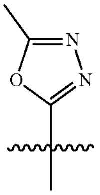 [SMILES: *c1nnc(C)o1] |

-continued
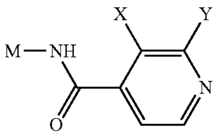
I
| NO. | X | Y | M |
|---|---|---|---|
| 1-1125 | Cl | 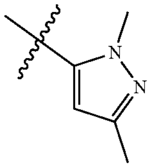 [SMILES: *c1cc(C)nn1C] | 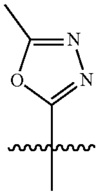 [SMILES: *c1nnc(C)o1] |
| 1-1126 | Cl | 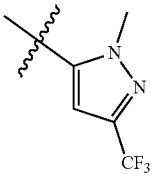 [SMILES: *c1cc(C(F)(F)F)nn1C] | 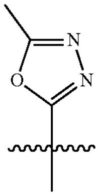 [SMILES: *c1nnc(C)o1] |
| 1-1127 | Cl | 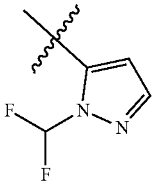 [SMILES: *c1ccnn1C(F)F] | 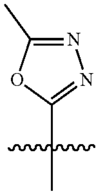 [SMILES: *c1nnc(C)o1] |
| 1-1128 | Cl | 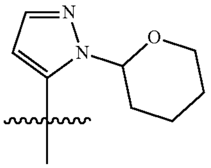 [SMILES: *c1ccnn1C1CCCCO1] | 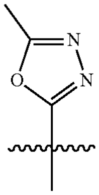 [SMILES: *c1nnc(C)o1] |
| 1-1129 | Cl | 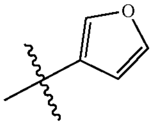 [SMILES: *c1ccoc1] | 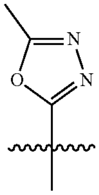 [SMILES: *c1nnc(C)o1] |
| 1-1130 | Cl | 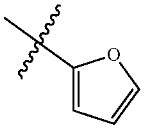 [SMILES: *c1ccco1] | 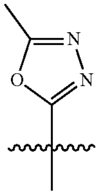 [SMILES: *c1nnc(C)o1] |

-continued
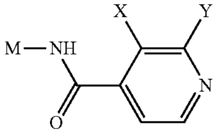
I
| NO. | X | Y | M |
|---|---|---|---|
| 1-1131 | Cl | 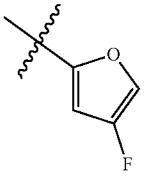 [SMILES: *c1cc(F)co1] | 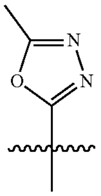 [SMILES: *c1nnc(C)o1] |
| 1-1132 | Cl | 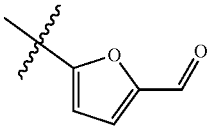 [SMILES: *c1ccc(C=O)o1] | 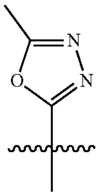 [SMILES: *c1nnc(C)o1] |
| 1-1133 | Cl | 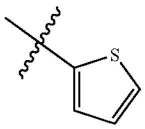 [SMILES: *c1cccs1] | 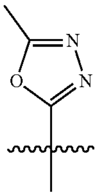 [SMILES: *c1nnc(C)o1] |
| 1-1134 | Cl | 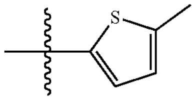 [SMILES: *c1ccc(C)s1] | 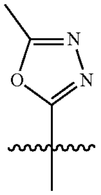 [SMILES: *c1nnc(C)o1] |
| 1-1135 | Cl | 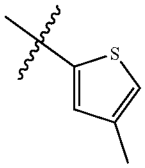 [SMILES: *c1cc(C)cs1] | 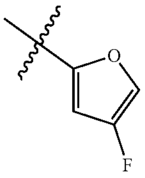 [SMILES: *c1cc(F)co1] |
| 1-1136 | Cl | 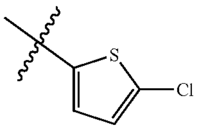 [SMILES: *c1ccc(Cl)s1] | 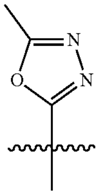 [SMILES: *c1nnc(C)o1] |
| 1-1137 | Cl | 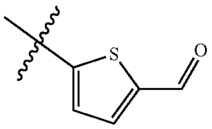 [SMILES: *c1ccc(C=O)s1] | 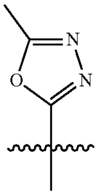 [SMILES: *c1nnc(C)o1] |

-continued
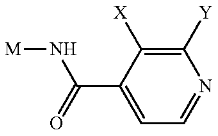
I
| NO. | X | Y | M |
|---|---|---|---|
| 1-1138 | Cl | 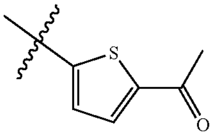 [SMILES: *c1ccc(C(C)=O)s1] | 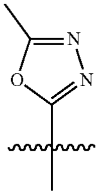 [SMILES: *c1nnc(C)o1] |
| 1-1139 | Cl | 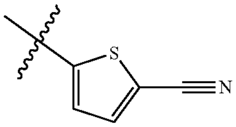 [SMILES: *c1ccc(C#N)s1] | 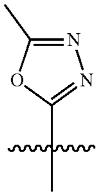 [SMILES: *c1nnc(C)o1] |
| 1-1140 | Cl | 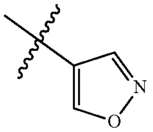 [SMILES: *c1cnoc1] | 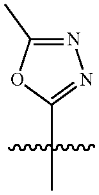 [SMILES: *c1nnc(C)o1] |
| 1-1141 | $CH_3$ | 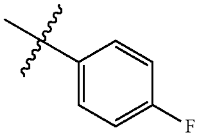 [SMILES: *c1ccc(F)cc1] | 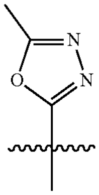 [SMILES: *c1nnc(C)o1] |
| 1-1142 | F | 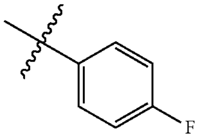 [SMILES: *c1ccc(F)cc1] | 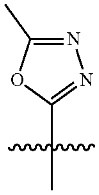 [SMILES: *c1nnc(C)o1] |
| 1-1143 | Br | 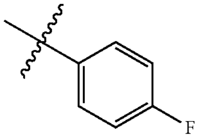 [SMILES: *c1ccc(F)cc1] | 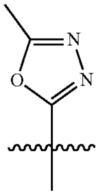 [SMILES: *c1nnc(C)o1] |

-continued
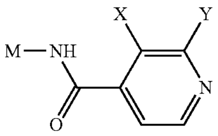
I
| NO. | X | Y | M |
| --- | --- | --- | --- |
| 1-1144 | 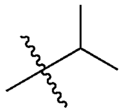 | 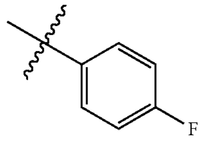 [SMILES: *c1ccc(F)cc1] | 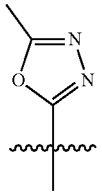 [SMILES: *c1nnc(C)o1] |
| 1-1145 | $CF_3$ | 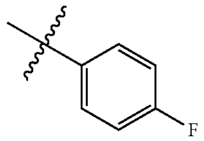 [SMILES: *c1ccc(F)cc1] | 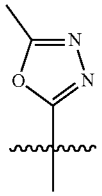 [SMILES: *c1nnc(C)o1] |
| 1-1146 | 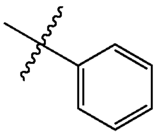 [SMILES: *c1ccccc1] | 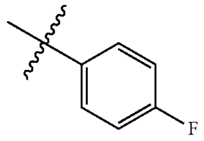 [SMILES: *c1ccc(F)cc1] | 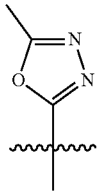 [SMILES: *c1nnc(C)o1] |
| 1-1147 | 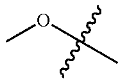 | 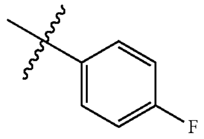 [SMILES: *c1ccc(F)cc1] | 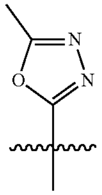 [SMILES: *c1nnc(C)o1] |
| 1-1148 | 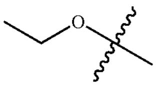 [SMILES: *OCC] | 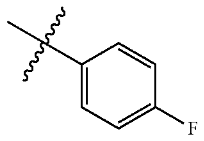 [SMILES: *c1ccc(F)cc1] | 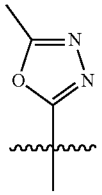 [SMILES: *c1nnc(C)o1] |
| 1-1149 | 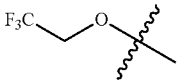 [SMILES: *OCC(F)(F)F] | 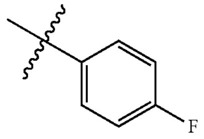 [SMILES: *c1ccc(F)cc1] | 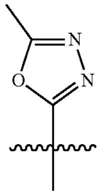 [SMILES: *c1nnc(C)o1] |

-continued
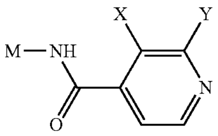
I
| NO. | X | Y | M |
|---|---|---|---|
| 1-1150 | 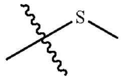 [SMILES: *SC] | 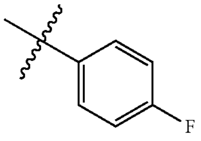 [SMILES: *c1ccc(F)cc1] | 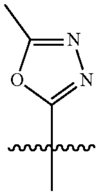 [SMILES: *c1nnc(C)o1] |
| 1-1151 | 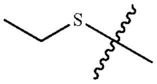 | 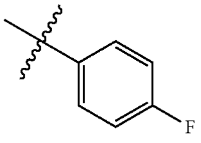 [SMILES: *c1ccc(F)cc1] | 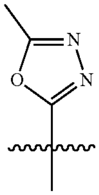 [SMILES: *c1nnc(C)o1] |
| 1-1152 | 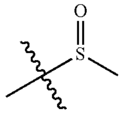 [SMILES: *S(C)=O] | 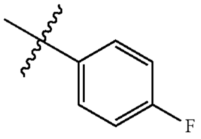 [SMILES: *c1ccc(F)cc1] | 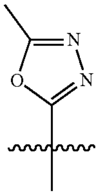 [SMILES: *c1nnc(C)o1] |
| 1-1153 | 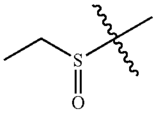 [SMILES: *S(=O)CC] | 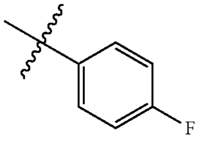 [SMILES: *c1ccc(F)cc1] | 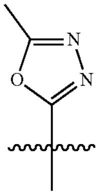 [SMILES: *c1nnc(C)o1] |
| 1-1154 | 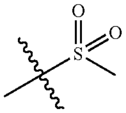 | 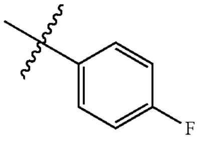 [SMILES: *c1ccc(F)cc1] | 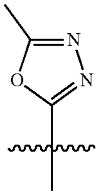 [SMILES: *c1nnc(C)o1] |
| 1-1155 | 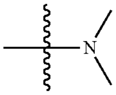 | 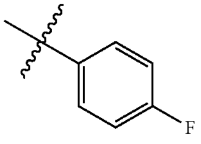 [SMILES: *c1ccc(F)cc1] | 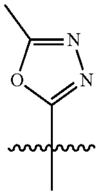 [SMILES: *c1nnc(C)o1] |

-continued
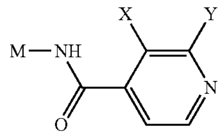
I
| NO. | X | Y | M |
|---|---|---|---|
| 1-1156 | 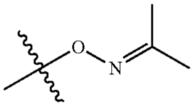 [SMILES: *ON=C(C)C] | 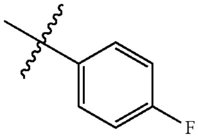 [SMILES: *c1ccc(F)cc1] | 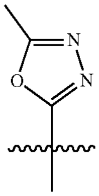 [SMILES: *c1nnc(C)o1] |
| 1-1157 | Et | 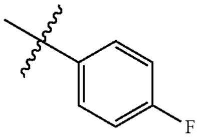 [SMILES: *c1ccc(F)cc1] | 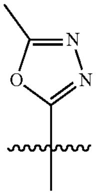 [SMILES: *c1nnc(C)o1] |
| 1-1158 | 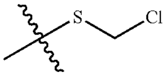 [SMILES: *SCCl] | 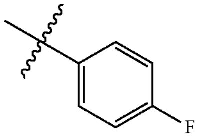 [SMILES: *c1ccc(F)cc1] | 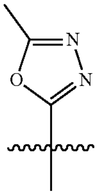 [SMILES: *c1nnc(C)o1] |
| 1-1159 | $NO_2$ | 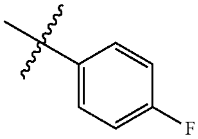 | 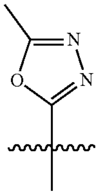 [SMILES: *c1nnc(C)o1] |
| 1-1160 | CN | 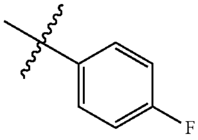 [SMILES: *c1ccc(F)cc1] | 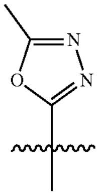 [SMILES: *c1nnc(C)o1] |
| 1-1161 | 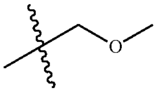 [SMILES: *COC] | 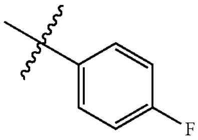 [SMILES: *c1ccc(F)cc1] | 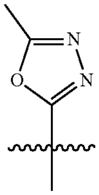 [SMILES: *c1nnc(C)o1] |

-continued
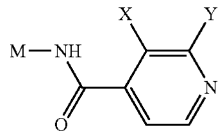
I
| NO. | X | Y | M |
|---|---|---|---|
| 1-1162 | 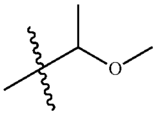 [SMILES: *C(C)OC] | 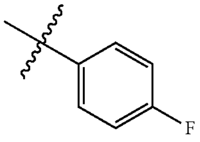 [SMILES: *c1ccc(F)cc1] | 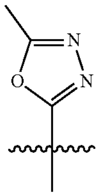 [SMILES: *c1nnc(C)o1] |
| 1-1163 | 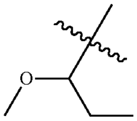 [SMILES: *C(CC)OC] | 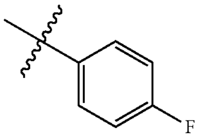 [SMILES: *c1ccc(F)cc1] | 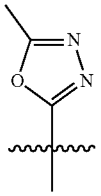 [SMILES: *c1nnc(C)o1] |
| 1-1164 | 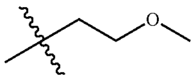 [SMILES: *CCOC] | 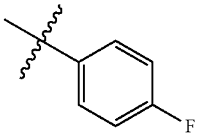 [SMILES: *c1ccc(F)cc1] | 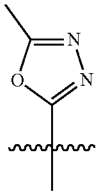 [SMILES: *c1nnc(C)o1] |
| 1-1165 | 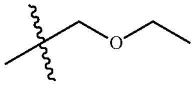 [SMILES: *COCC] | 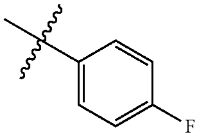 [SMILES: *c1ccc(F)cc1] | 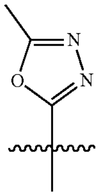 [SMILES: *c1nnc(C)o1] |
| 1-1166 | 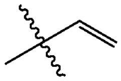 [SMILES: *C=C] | 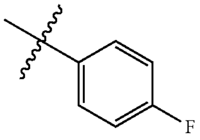 [SMILES: *c1ccc(F)cc1] | 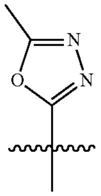 [SMILES: *c1nnc(C)o1] |
| 1-1167 | 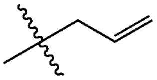 [SMILES: *CC=C] | 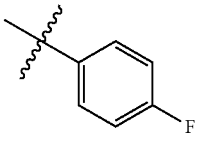 [SMILES: *c1ccc(F)cc1] | 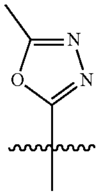 [SMILES: *c1nnc(C)o1] |

-continued
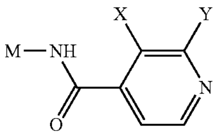
I
| NO. | X | Y | M |
| --- | --- | --- | --- |
| 1-1168 | 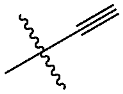 [SMILES: *C#C] | 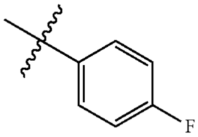 [SMILES: *c1ccc(F)cc1] | 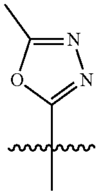 [SMILES: *c1nnc(C)o1] |
| 1-1169 | 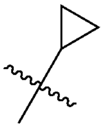 [SMILES: *C1CC1] | 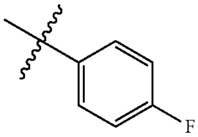 [SMILES: *c1ccc(F)cc1] | 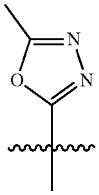 [SMILES: *c1nnc(C)o1] |
| 1-1170 | 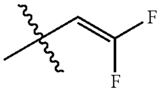 | 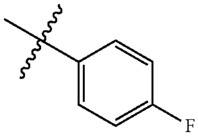 [SMILES: *c1ccc(F)cc1] | 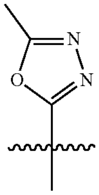 [SMILES: *c1nnc(C)o1] |
| 1-1171 | 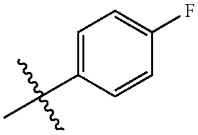 [SMILES: *c1ccc(F)cc1] | 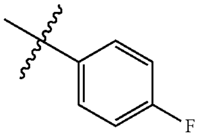 [SMILES: *c1ccc(F)cc1] | 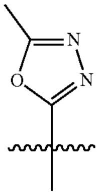 [SMILES: *c1nnc(C)o1] |
| 1-1172 | Cl | 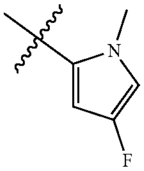 [SMILES: *c1cc(F)cn1C] | 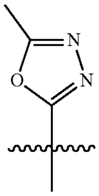 [SMILES: *c1nnc(C)o1] |
| 1-1173 | Cl | 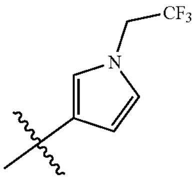 [SMILES: *c1ccn(CC(F)(F)F)c1] | 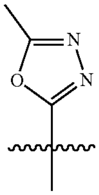 [SMILES: *c1nnc(C)o1] |

-continued
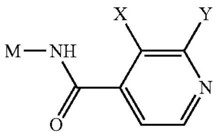
I
| NO. | X | Y | M |
|---|---|---|---|
| 1-1174 | Cl | 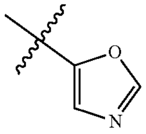 [SMILES: *c1cnco1] | 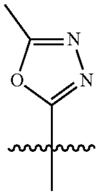 [SMILES: *c1nnc(C)o1] |
| 1-1175 | Cl | 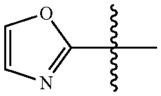 [SMILES: *c1ncco1] | 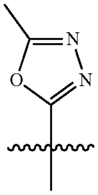 [SMILES: *c1nnc(C)o1] |
| 1-1176 | Cl | 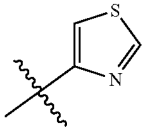 [SMILES: *c1cscn1] | 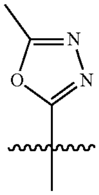 [SMILES: *c1nnc(C)o1] |
| 1-1177 | Cl | 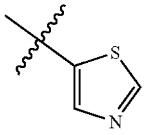 | 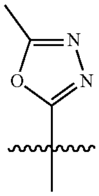 [SMILES: *c1nnc(C)o1] |
| 1-1178 | Cl | 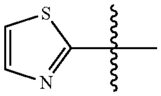 [SMILES: *c1nccs1] | 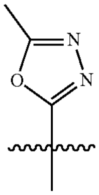 [SMILES: *c1nnc(C)o1] |
| 1-1179 | Cl | 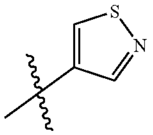 [SMILES: *c1cnsc1] | 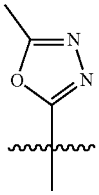 [SMILES: *c1nnc(C)o1] |

-continued
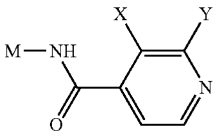
I
| NO. | X | Y | M |
|---|---|---|---|
| 1-1180 | Cl | 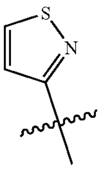 [SMILES: *c1ccsn1] | 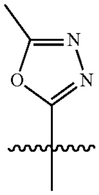 [SMILES: *c1nnc(C)o1] |
| 1-1181 | Cl | 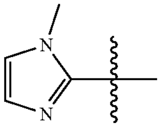 [SMILES: *c1nccn1C] | 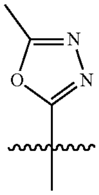 [SMILES: *c1nnc(C)o1] |
| 1-1182 | Cl | 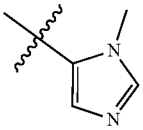 [SMILES: *c1cncn1C] | 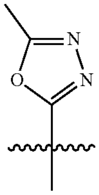 [SMILES: *c1nnc(C)o1] |
| 1-1183 | Cl | 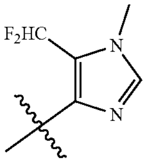 | 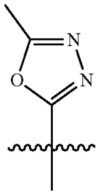 [SMILES: *c1nnc(C)o1] |
| 1-1184 | Cl | 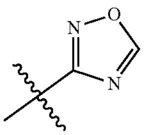 [SMILES: *c1ncon1] | 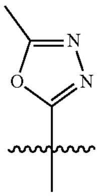 [SMILES: *c1nnc(C)o1] |
| 1-1185 | Cl | 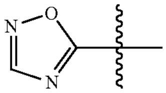 [SMILES: *c1ncno1] | 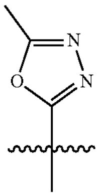 [SMILES: *c1nnc(C)o1] |

-continued
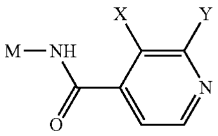
I
| NO. | X | Y | M |
|---|---|---|---|
| 1-1186 | Cl | 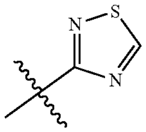 [SMILES: *c1ncsn1] | 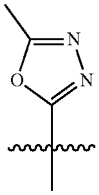 [SMILES: *c1nnc(C)o1] |
| 1-1187 | Cl | 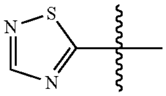 [SMILES: *c1ncns1] | 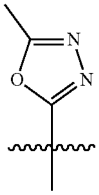 [SMILES: *c1nnc(C)o1] |
| 1-1188 | Cl | 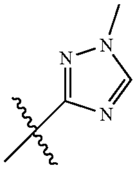 [SMILES: *c1ncn(C)n1] | 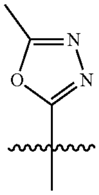 [SMILES: *c1nnc(C)o1] |
| 1-1189 | Cl | 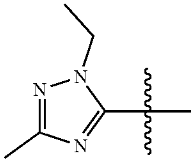 [SMILES: *c1nc(C)nn1CC] | 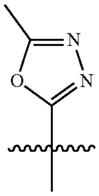 [SMILES: *c1nnc(C)o1] |
| 1-1190 | Cl | 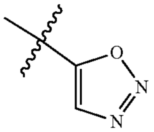 [SMILES: *c1cnno1] | 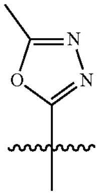 [SMILES: *c1nnc(C)o1] |
| 1-1191 | Cl | 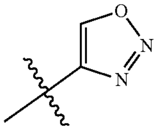 [SMILES: *c1conn1] | 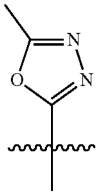 [SMILES: *c1nnc(C)o1] |

-continued
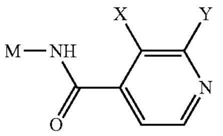
I
| NO. | X | Y | M |
|---|---|---|---|
| 1-1192 | Cl | 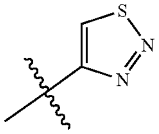 [SMILES: *c1csnn1] | 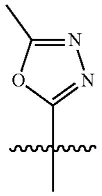 [SMILES: *c1nnc(C)o1] |
| 1-1193 | Cl | 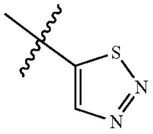 [SMILES: *c1cnns1] | 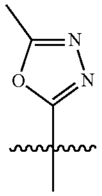 [SMILES: *c1nnc(C)o1] |
| 1-1194 | Cl | 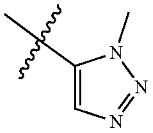 [SMILES: *c1cnnn1C] | 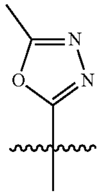 [SMILES: *c1nnc(C)o1] |
| 1-1195 | Cl | 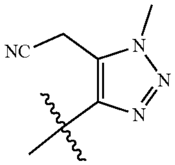 [SMILES: *c1nnn(C)c1CC#N] | 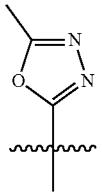 [SMILES: *c1nnc(C)o1] |
| 1-1196 | Cl | 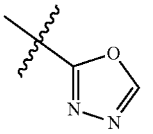 [SMILES: *c1nnco1] | 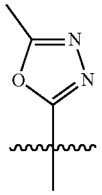 [SMILES: *c1nnc(C)o1] |
| 1-1197 | Cl | 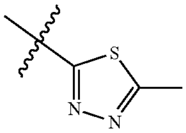 [SMILES: *c1nnc(C)s1] | 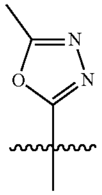 [SMILES: *c1nnc(C)o1] |

-continued
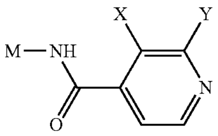
I
| NO. | X | Y | M |
|---|---|---|---|
| 1-1198 | Cl | 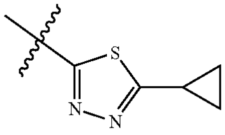 [SMILES: *c1nnc(C2CC2)s1] | 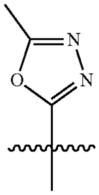 [SMILES: *c1nnc(C)o1] |
| 1-1199 | Cl | 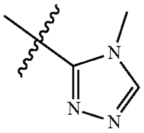 [SMILES: *c1nncn1C] | 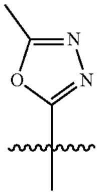 [SMILES: *c1nnc(C)o1] |
| 1-1200 | Cl | 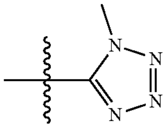 [SMILES: *c1nnnn1C] | 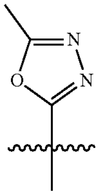 [SMILES: *c1nnc(C)o1] |
| 1-1201 | Cl | 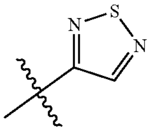 [SMILES: *c1cnsn1] | 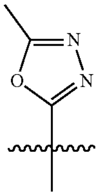 [SMILES: *c1nnc(C)o1] |
| 1-1202 | Cl | 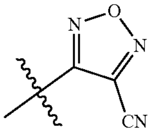 [SMILES: *c1nonc1C#N] | 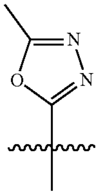 [SMILES: *c1nnc(C)o1] |
| 1-1203 | Cl | 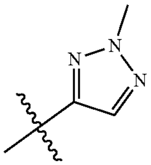 [SMILES: *c1cnn(C)n1] | 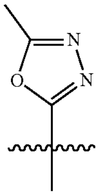 [SMILES: *c1nnc(C)o1] |

-continued
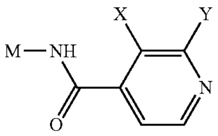
I
| NO. | X | Y | M |
| --- | --- | --- | --- |
| 1-1204 | Cl | 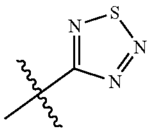 | 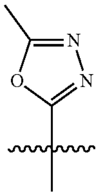 [SMILES: *c1nnc(C)o1] |
| 1-1205 | Cl | 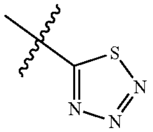 [SMILES: *c1nnns1] | 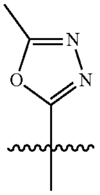 [SMILES: *c1nnc(C)o1] |
| 1-1206 | Cl | 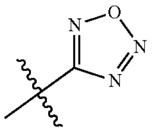 [SMILES: *c1nnon1] | 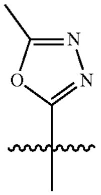 [SMILES: *c1nnc(C)o1] |
| 1-1207 | Cl | 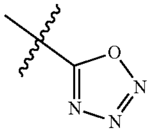 | 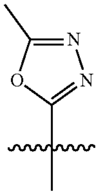 [SMILES: *c1nnc(C)o1] |
| 1-1208 | Cl | 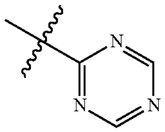 [SMILES: *c1ncncn1] | 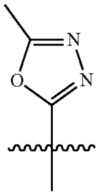 [SMILES: *c1nnc(C)o1] |
| 1-1209 | Cl | 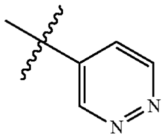 [SMILES: *c1ccnnc1] | 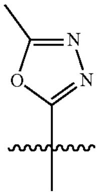 [SMILES: *c1nnc(C)o1] |

-continued
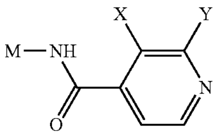
I
| NO. | X | Y | M |
|---|---|---|---|
| 1-1210 | Cl | 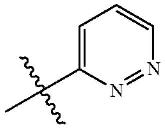 [SMILES: *c1cccnn1] | 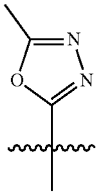 [SMILES: *c1nnc(C)o1] |
| 1-1211 | Cl | 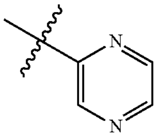 [SMILES: *c1cnccn1] | 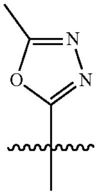 [SMILES: *c1nnc(C)o1] |
| 1-1212 | Cl | 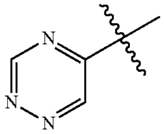 [SMILES: *c1cnncn1] | 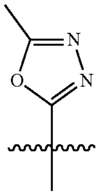 [SMILES: *c1nnc(C)o1] |
| 1-1213 | Cl | 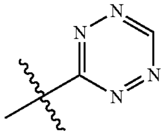 [SMILES: *c1nncnn1] | 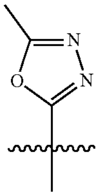 [SMILES: *c1nnc(C)o1] |
| 1-1214 | Cl | 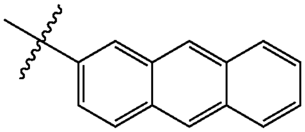 [SMILES: *c1ccc2cc3ccccc3cc2c1] | 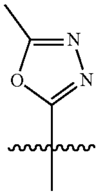 [SMILES: *c1nnc(C)o1] |
| 1-1215 | Cl | 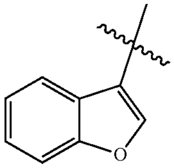 [SMILES: *c1coc2ccccc12] | 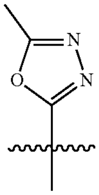 [SMILES: *c1nnc(C)o1] |

-continued
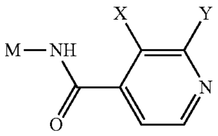
I
| NO. | X | Y | M |
|---|---|---|---|
| 1-1216 | Cl | 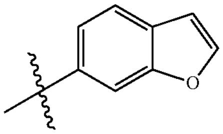 [SMILES: *c1ccc2ccoc2c1] | 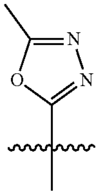 [SMILES: *c1nnc(C)o1] |
| 1-1217 | Cl | 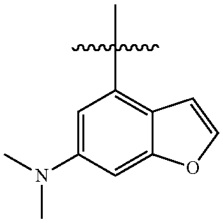 [SMILES: *c1cc(N(C)C)cc2occc12] | 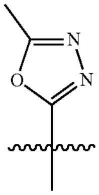 [SMILES: *c1nnc(C)o1] |
| 1-1218 | Cl | 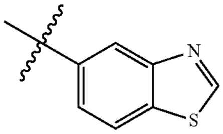 [SMILES: *c1ccc2scnc2c1] | 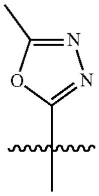 [SMILES: *c1nnc(C)o1] |
| 1-1219 | Cl | 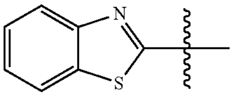 [SMILES: *c1nc2ccccc2s1] | 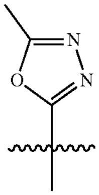 [SMILES: *c1nnc(C)o1] |
| 1-1220 | Cl | 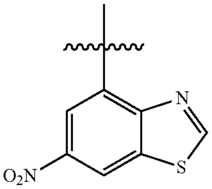 | 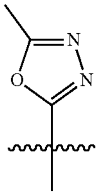 [SMILES: *c1nnc(C)o1] |
| 1-1221 | Cl | 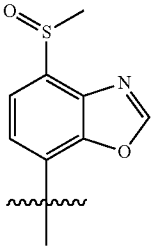 [SMILES: *c1ccc(S(C)=O)c2ncoc12] | 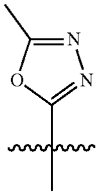 [SMILES: *c1nnc(C)o1] |

-continued
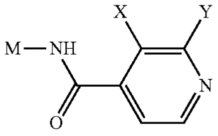
I
| NO. | X | Y | M |
|---|---|---|---|
| 1-1222 | Cl | 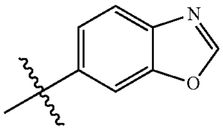 [SMILES: *c1ccc2ncoc2c1] | 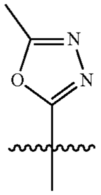 [SMILES: *c1nnc(C)o1] |
| 1-1223 | Cl | 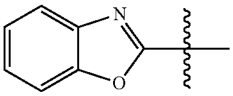 | 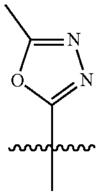 [SMILES: *c1nnc(C)o1] |
| 1-1224 | Cl | 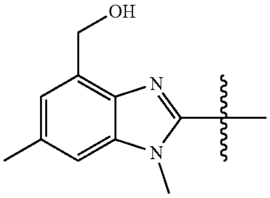 [SMILES: *c1nc2c(CO)cc(C)cc2n1C] | 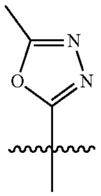 [SMILES: *c1nnc(C)o1] |
| 1-1225 | Cl | 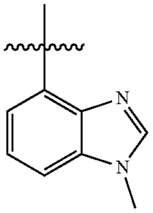 [SMILES: *c1cccc2c1ncn2C] | 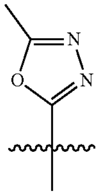 [SMILES: *c1nnc(C)o1] |
| 1-1226 | Cl | 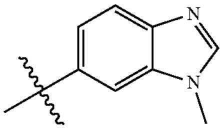 [SMILES: *c1ccc2ncn(C)c2c1] | 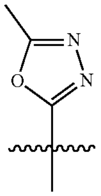 [SMILES: *c1nnc(C)o1] |
| 1-1227 | Cl | 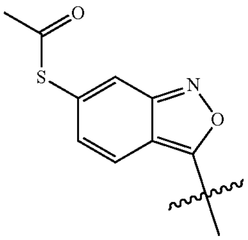 [SMILES: *c1onc2cc(SC(C)=O)ccc12] | 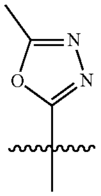 [SMILES: *c1nnc(C)o1] |

-continued
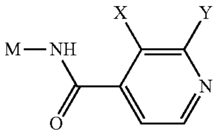
I
| NO. | X | Y | M |
|---|---|---|---|
| 1-1228 | Cl | 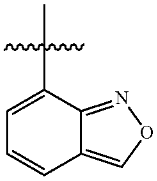 [SMILES: *c1cccc2conc12] | 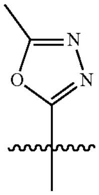 [SMILES: *c1nnc(C)o1] |
| 1-1229 | Cl | 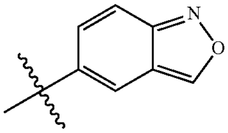 [SMILES: *c1ccc2nocc2c1] | 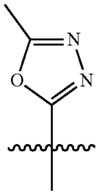 [SMILES: *c1nnc(C)o1] |
| 1-1230 | Cl | 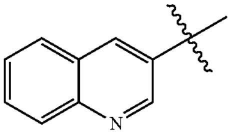 [SMILES: *c1cnc2ccccc2c1] | 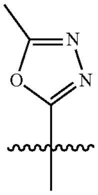 [SMILES: *c1nnc(C)o1] |
| 1-1231 | Cl | 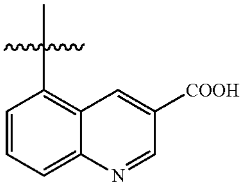 [SMILES: *c1cccc2ncc(C(=O)O)cc12] | 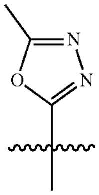 [SMILES: *c1nnc(C)o1] |
| 1-1232 | Cl | 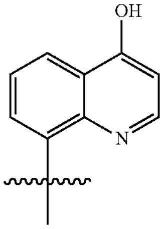 [SMILES: *c1cccc2c(O)ccnc12] | 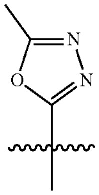 [SMILES: *c1nnc(C)o1] |
| 1-1233 | Cl | 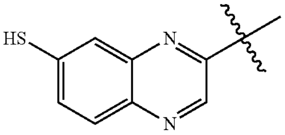 [SMILES: *c1cnc2ccc(S)cc2n1] | 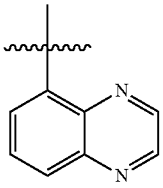 [SMILES: *c1cccc2nccnc12] |

-continued
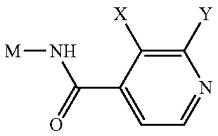
I
| NO. | X | Y | M |
|---|---|---|---|
| 1-1234 | Cl | 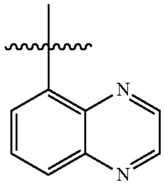 [SMILES: *c1cccc2nccnc12] | 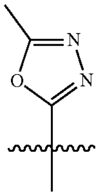 [SMILES: *c1nnc(C)o1] |
| 1-1235 | Cl | 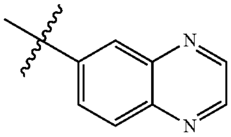 [SMILES: *c1ccc2nccnc2c1] | 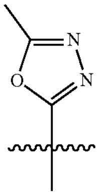 [SMILES: *c1nnc(C)o1] |
| 1-1236 | Cl | 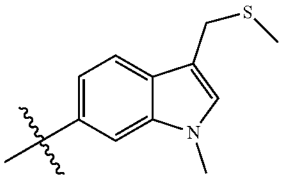 [SMILES: *c1ccc2c(CSC)cn(C)c2c1] | 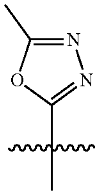 [SMILES: *c1nnc(C)o1] |
| 1-1237 | Cl | 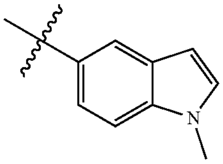 [SMILES: *c1ccc2c(ccn2C)c1] | 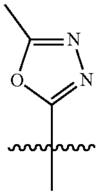 [SMILES: *c1nnc(C)o1] |
| 1-1238 | Cl | 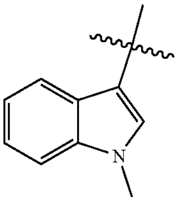 [SMILES: *c1cn(C)c2ccccc12] | 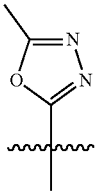 [SMILES: *c1nnc(C)o1] |
| 1-1239 | Cl | 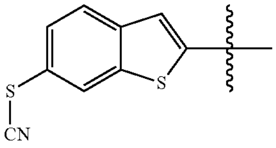 [SMILES: *c1cc2ccc(SC#N)cc2s1] | 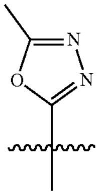 [SMILES: *c1nnc(C)o1] |

-continued
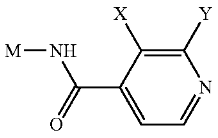
I
| NO. | X | Y | M |
|---|---|---|---|
| 1-1240 | Cl | 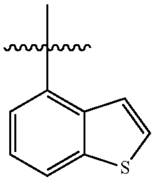 [SMILES: *c1cccc2sccc12] | 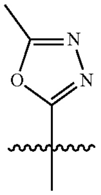 [SMILES: *c1nnc(C)o1] |
| 1-1241 | Cl | 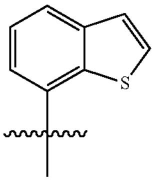 [SMILES: *c1cccc2ccsc12] | 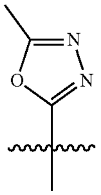 [SMILES: *c1nnc(C)o1] |
| 1-1242 | Cl | 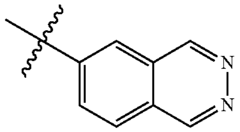 [SMILES: *c1ccc2cnncc2c1] | 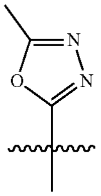 [SMILES: *c1nnc(C)o1] |
| 1-1243 | Cl | 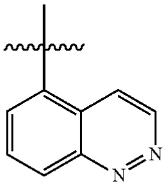 | 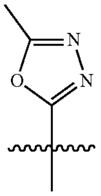 [SMILES: *c1nnc(C)o1] |
| 1-1244 | Cl | 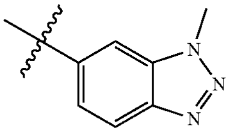 [SMILES: *c1ccc2nnn(C)c2c1] | 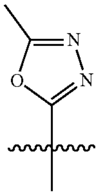 [SMILES: *c1nnc(C)o1] |
| 1-1245 | Cl | 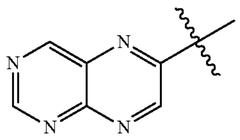 [SMILES: *c1cnc2ncncc2n1] | 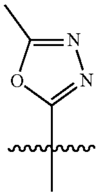 [SMILES: *c1nnc(C)o1] |

-continued
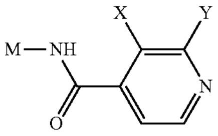
I
| NO. | X | Y | M |
|---|---|---|---|
| 1-1246 | Cl | 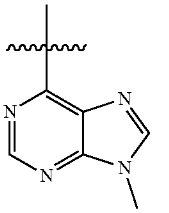 [SMILES: *c1ncnc2c1ncn2C] | 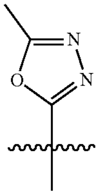 [SMILES: *c1nnc(C)o1] |
| 1-1247 | Cl | 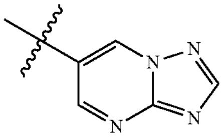 [SMILES: *c1cnc2ncnn2c1] | 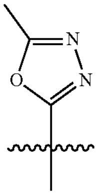 [SMILES: *c1nnc(C)o1] |
| 1-1248 | Cl | 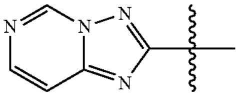 [SMILES: *c1nc2ccncn2n1] | 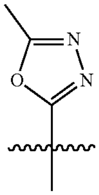 [SMILES: *c1nnc(C)o1] |
| 1-1249 | Cl | 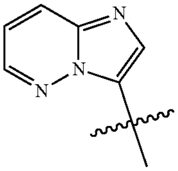 [SMILES: *c1cnc2cccnn12] | 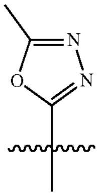 [SMILES: *c1nnc(C)o1] |
| 1-1250 | Cl | 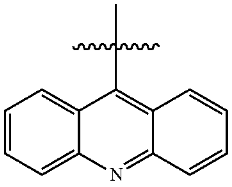 [SMILES: *c1c2ccccc2nc2ccccc12] | 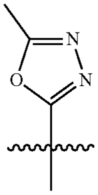 [SMILES: *c1nnc(C)o1] |
| 1-1251 | Cl | 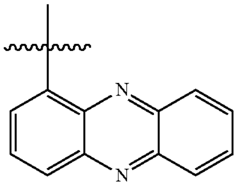 [SMILES: *c1cccc2nc3ccccc3nc12] | 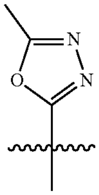 [SMILES: *c1nnc(C)o1] |

-continued
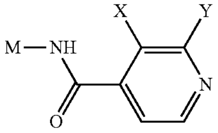
I
| NO. | X | Y | M |
|---|---|---|---|
| 1-1252 | Cl | 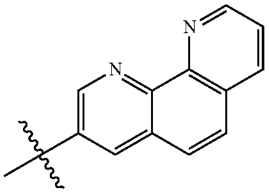 [SMILES: *c1cnc2c(ccc3cccnc32)c1] | 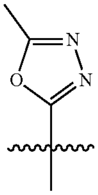 [SMILES: *c1nnc(C)o1] |
| 1-1253 | Cl | 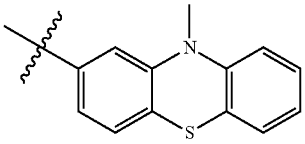 [SMILES: *c1ccc2c(c1)N(C)c1ccccc1S2] | 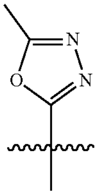 [SMILES: *c1nnc(C)o1] |
| 1-1254 | Cl | 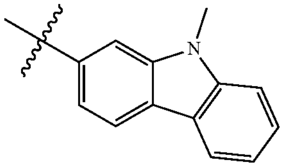 [SMILES: *c1ccc2c3ccccc3n(C)c2c1] | 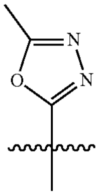 [SMILES: *c1nnc(C)o1] |
| 1-1255 | Cl | 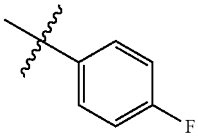 [SMILES: *c1ccc(F)cc1] | 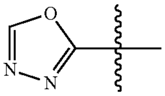 |
| 1-1256 | Cl | 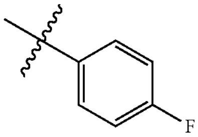 [SMILES: *c1ccc(F)cc1] | 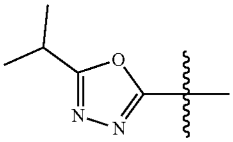 [SMILES: *c1nnc(C(C)C)o1] |
| 1-1257 | Cl | 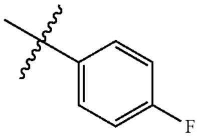 [SMILES: *c1ccc(F)cc1] | 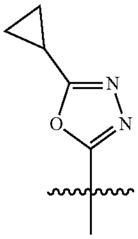 [SMILES: *c1nnc(C2CC2)o1] |
| 1-1258 | Cl | 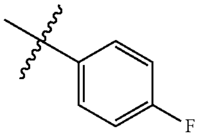 | 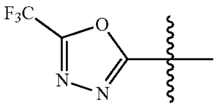 [SMILES: *c1nnc(C(F)(F)F)o1] |

-continued
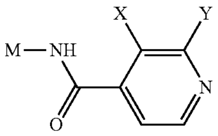
I
| NO. | X | Y | M |
|---|---|---|---|
| 1-1259 | Cl | 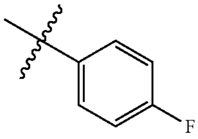 [SMILES: *c1ccc(F)cc1] | 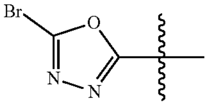 [SMILES: *c1nnc(Br)o1] |
| 1-1260 | Cl | 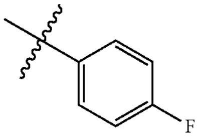 [SMILES: *c1ccc(F)cc1] | 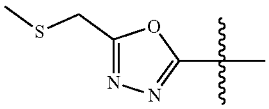 [SMILES: *c1nnc(CSC)o1] |
| 1-1261 | Cl | 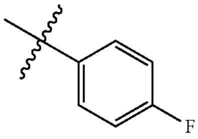 [SMILES: *c1ccc(F)cc1] | 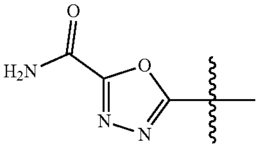 [SMILES: *c1nnc(C(N)=O)o1] |
| 1-1262 | Cl | 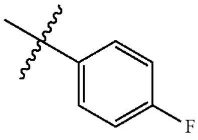 [SMILES: *c1ccc(F)cc1] | 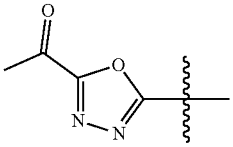 [SMILES: *c1nnc(C(C)=O)o1] |
| 1-1263 | Cl | 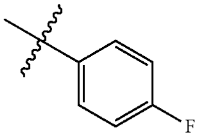 [SMILES: *c1ccc(F)cc1] | 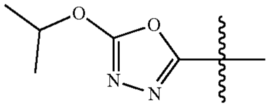 [SMILES: *c1nnc(OC(C)C)o1] |
| 1-1264 | Cl | 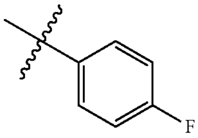 [SMILES: *c1ccc(F)cc1] | 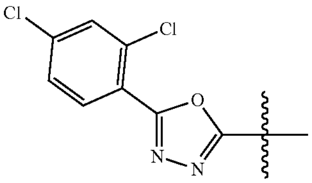 [SMILES: *c1nnc(-c2ccc(Cl)cc2Cl)o1] |
| 1-1265 | Cl | 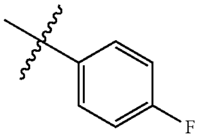 [SMILES: *c1ccc(F)cc1] | 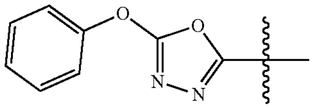 [SMILES: *c1nnc(Oc2ccccc2)o1] |
| 1-1266 | Cl | 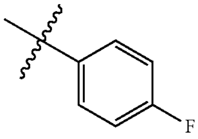 [SMILES: *c1ccc(F)cc1] | 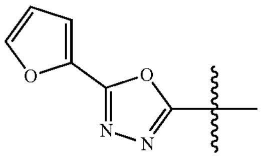 [SMILES: *c1nnc(-c2ccco2)o1] |

-continued
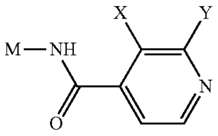
I
| NO. | X | Y | M |
|---|---|---|---|
| 1-1267 | Cl | 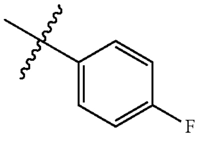 [SMILES: *c1ccc(F)cc1] | 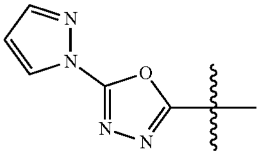 [SMILES: *c1nnc(-n2cccn2)o1] |
| 1-1268 | Cl | 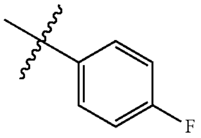 [SMILES: *c1ccc(F)cc1] | 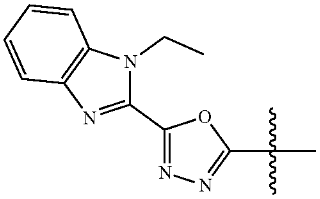 [SMILES: *c1nnc(-c2nc3ccccc3n2CC)o1] |
| 1-1269 | Cl | 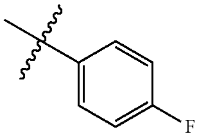 [SMILES: *c1ccc(F)cc1] | 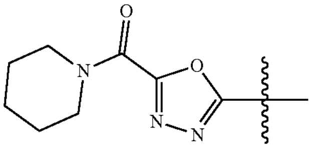 [SMILES: *c1nnc(C(=O)N2CCCCC2)o1] |
| 1-1270 | Cl | $CH_3$ | 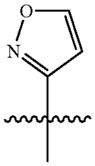 |
| 1-1271 | Cl | 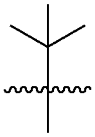 | 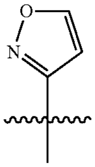 |
| 1-1272 | Cl | 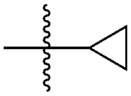 [SMILES: *C1CC1] | 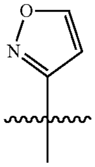 |
| 1-1273 | Cl | 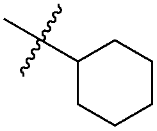 [SMILES: *C1CCCCC1] | 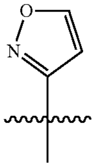 |

-continued
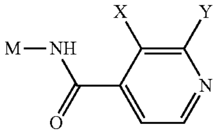
I
| NO. | X | Y | M |
|---|---|---|---|
| 1-1274 | Cl | 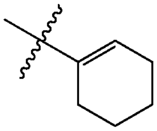 [SMILES: *C1=CCCCC1] | 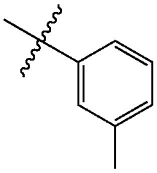 [SMILES: *c1cccc(C)c1] |
| 1-1275 | Cl | 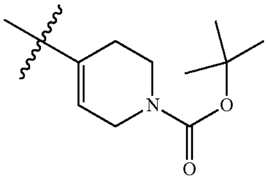 [SMILES: *C1=CCN(C(=O)OC(C)(C)C)CC1] | 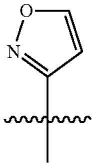 |
| 1-1276 | Cl | 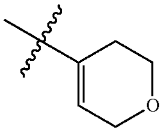 [SMILES: *C1=CCOCC1] | 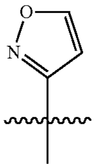 |
| 1-1277 | Cl | 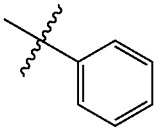 [SMILES: *c1ccccc1] | 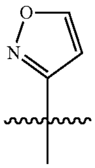 |
| 1-1278 | Cl | 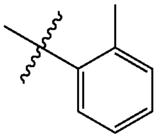 [SMILES: *c1ccccc1C] | 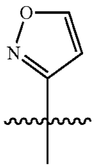 [SMILES: *c1ccon1] |
| 1-1279 | Cl | 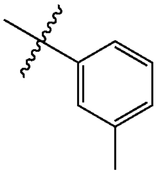 [SMILES: *c1cccc(C)c1] | 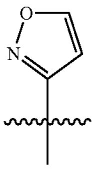 |
| 1-1280 | Cl | 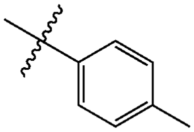 [SMILES: *c1ccc(C)cc1] | 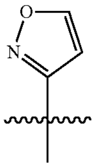 |

-continued
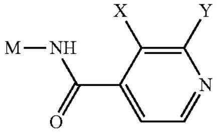
I
| NO. | X | Y | M |
|---|---|---|---|
| 1-1281 | Cl | 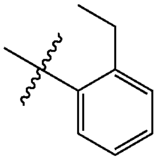 [SMILES: *c1ccccc1CC] | 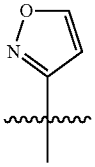 |
| 1-1282 | Cl | 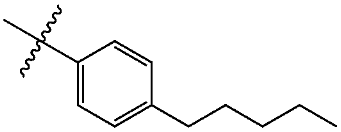 [SMILES: *c1ccc(CCCCC)cc1] | 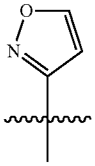 |
| 1-1283 | Cl | 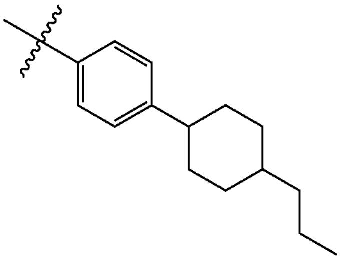 [SMILES: *c1ccc(C2CCC(CCC)CC2)cc1] | 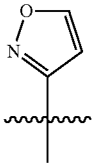 |
| 1-1284 | Cl | 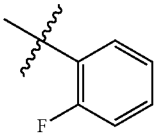 [SMILES: *c1ccccc1F] | 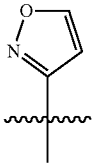 |
| 1-1285 | Cl | 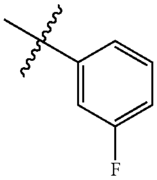 [SMILES: *c1cccc(F)c1] | 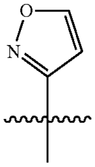 |
| 1-1286 | Cl | 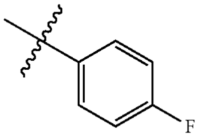 [SMILES: *c1ccc(F)cc1] | 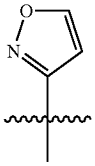 |
| 1-1287 | Cl | 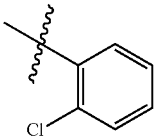 [SMILES: *c1ccccc1Cl] | 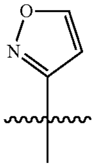 |

-continued
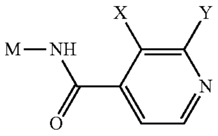
I
| NO. | X | Y | M |
|---|---|---|---|
| 1-1288 | Cl | 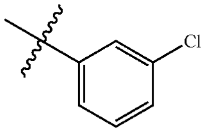 [SMILES: *c1cccc(Cl)c1] | 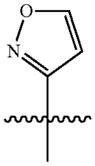 |
| 1-1289 | Cl | 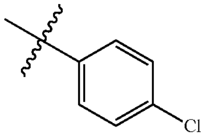 [SMILES: *c1ccc(Cl)cc1] | 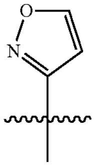 |
| 1-1290 | Cl | 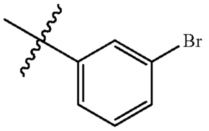 [SMILES: *c1cccc(Br)c1] | 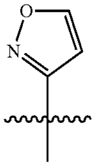 |
| 1-1291 | Cl | 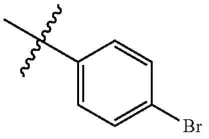 | 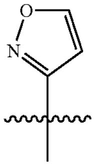 |
| 1-1292 | Cl | 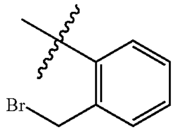 [SMILES: *c1ccccc1CBr] | 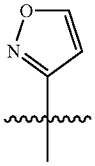 |
| 1-1293 | Cl | 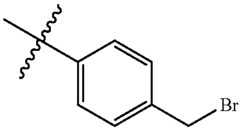 [SMILES: *c1ccc(CBr)cc1] | 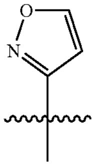 |
| 1-1294 | Cl | 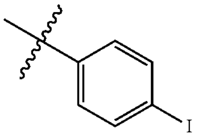 [SMILES: *c1ccc(I)cc1] | 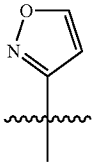 |

-continued
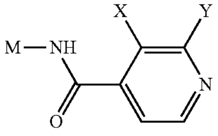
I
| NO. | X | Y | M |
|---|---|---|---|
| 1-1295 | Cl | 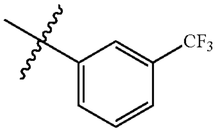 | 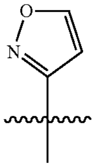 |
| 1-1296 | Cl | 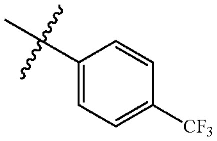 | 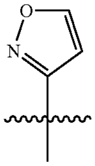 |
| 1-1297 | Cl | 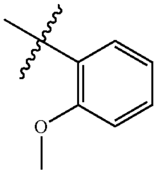 [SMILES: *c1ccccc1OC] | 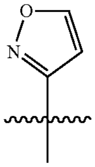 |
| 1-1298 | Cl | 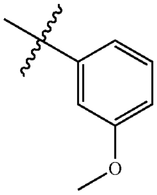 [SMILES: *c1cccc(OC)c1] | 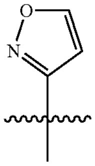 |
| 1-1299 | Cl | 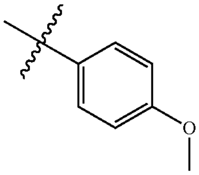 [SMILES: *c1ccc(OC)cc1] | 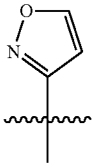 |
| 1-1300 | Cl | 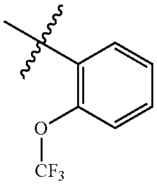 [SMILES: *c1ccccc1OC(F)(F)F] | 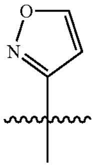 |
| 1-1301 | Cl | 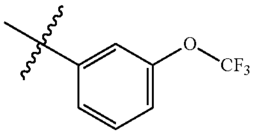 [SMILES: *c1cccc(OC(F)(F)F)c1] | 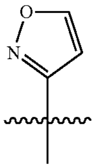 |

-continued
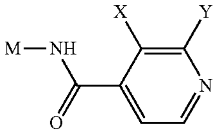
I
| NO. | X | Y | M |
|---|---|---|---|
| 1-1302 | Cl | 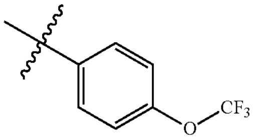 [SMILES: *c1ccc(OC(F)(F)F)cc1] | 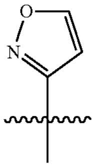 |
| 1-1303 | Cl | 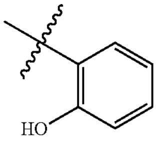 [SMILES: *c1ccccc1O] | 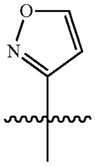 |
| 1-1304 | Cl | 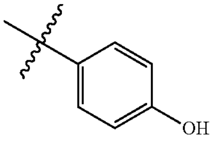 [SMILES: *c1ccc(O)cc1] | 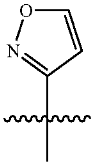 |
| 1-1305 | Cl | 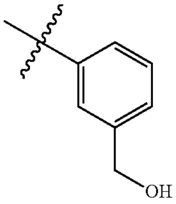 [SMILES: *c1cccc(CO)c1] | 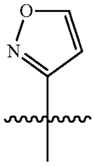 |
| 1-1306 | Cl | 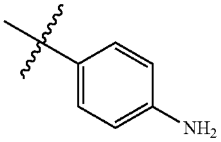 [SMILES: *c1ccc(N)cc1] | 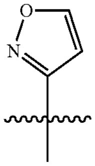 |
| 1-1307 | Cl | 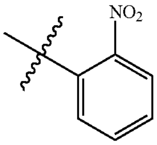 [SMILES: *c1ccccc1[N+](=O)[O-]] | 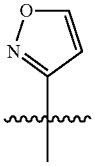 |
| 1-1308 | Cl | 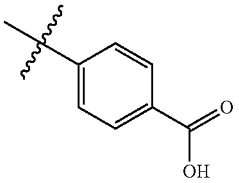 [SMILES: *c1ccc(C(=O)O)cc1] | 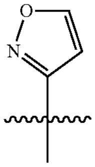 |

-continued
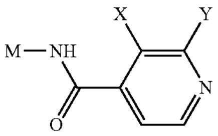
I
| NO. | X | Y | M |
| --- | --- | --- | --- |
| 1-1309 | Cl | 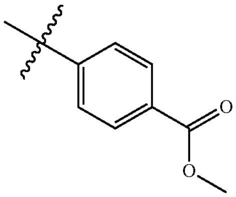 [SMILES: *c1ccc(C(=O)OC)cc1] | 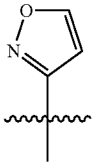 |
| 1-1310 | Cl | 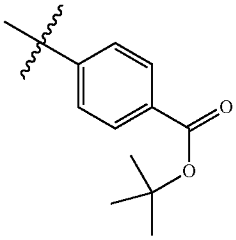 [SMILES: *c1ccc(C(=O)OC(C)(C)C)cc1] | 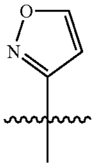 |
| 1-1311 | Cl | 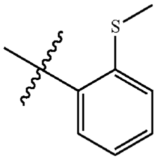 [SMILES: *c1ccccc1SC] | 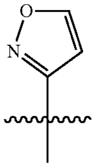 |
| 1-1312 | Cl | 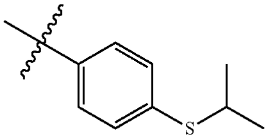 [SMILES: *c1ccc(SC(C)C)cc1] | 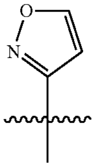 |
| 1-1313 | Cl | 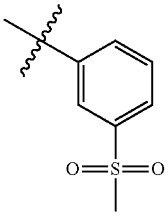 [SMILES: *c1cccc(S(C)(=O)=O)c1] | 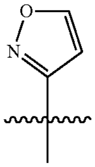 |
| 1-1314 | Cl | 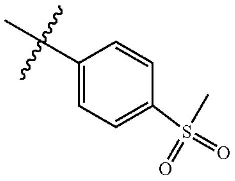 [SMILES: *c1ccc(S(C)(=O)=O)cc1] | 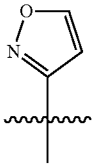 |

-continued
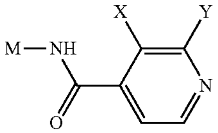
I
| NO. | X | Y | M |
|---|---|---|---|
| 1-1315 | Cl | 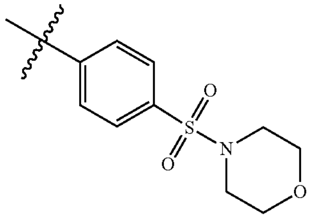 [SMILES: *c1ccc(S(=O)(=O)N2CCOCC2)cc1] | 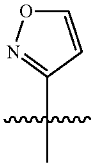 |
| 1-1316 | Cl | 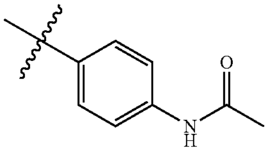 [SMILES: *c1ccc(NC(C)=O)cc1] | 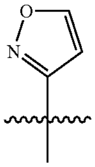 |
| 1-1317 | Cl | 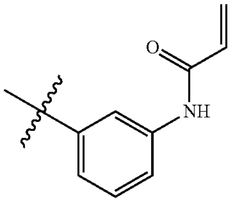 [SMILES: *c1cccc(NC(=O)C=C)c1] | 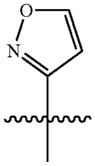 |
| 1-1318 | Cl | 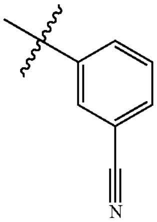 [SMILES: *c1cccc(C#N)c1] | 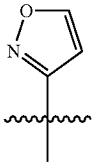 |
| 1-1319 | Cl | 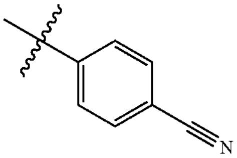 [SMILES: *c1ccc(C#N)cc1] | 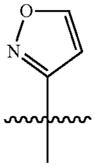 |
| 1-1320 | Cl | 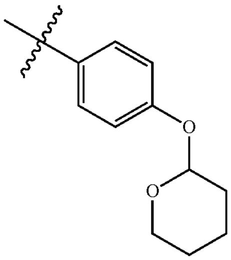 [SMILES: *c1ccc(OC2CCCCO2)cc1] | 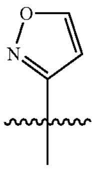 |

-continued
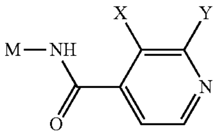
I
| NO. | X | Y | M |
|---|---|---|---|
| 1-1321 | Cl | 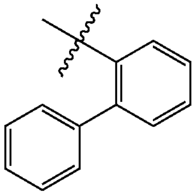 [SMILES: *c1ccccc1-c1ccccc1] | 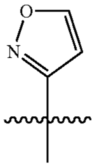 |
| 1-1322 | Cl | 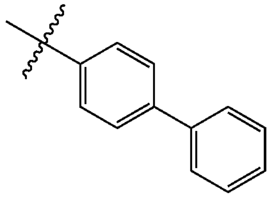 [SMILES: *c1ccc(-c2ccccc2)cc1] | 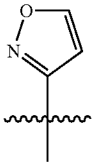 |
| 1-1323 | Cl | 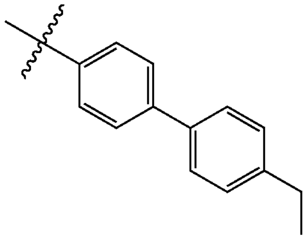 [SMILES: *c1ccc(-c2ccc(CC)cc2)cc1] | 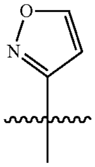 |
| 1-1324 | Cl | 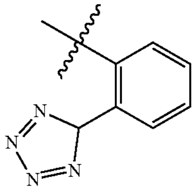 [SMILES: *c1ccccc1C1N=NN=N1] | 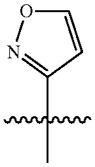 |
| 1-1325 | Cl | 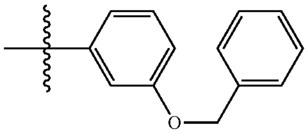 [SMILES: *c1cccc(OCc2ccccc2)c1] | 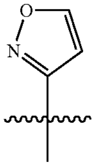 |
| 1-1326 | Cl | 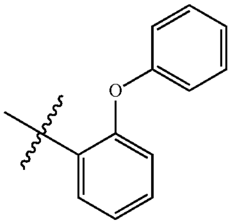 [SMILES: *c1ccccc1Oc1ccccc1] | 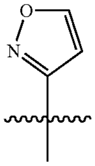 |

-continued
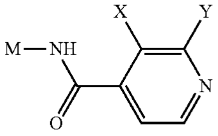
I
| NO. | X | Y | M |
|---|---|---|---|
| 1-1327 | Cl | 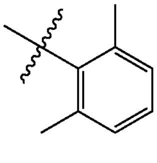 [SMILES: *c1c(C)cccc1C] | 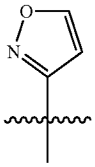 |
| 1-1328 | Cl | 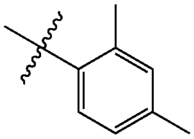 [SMILES: *c1ccc(C)cc1C] | 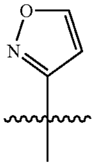 [SMILES: *c1ccon1] |
| 1-1329 | Cl | 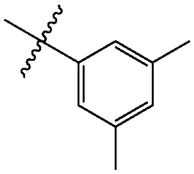 [SMILES: *c1cc(C)cc(C)c1] | 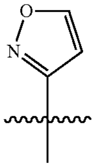 [SMILES: *c1ccon1] |
| 1-1330 | Cl | 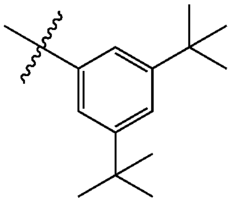 [SMILES: *c1cc(C(C)(C)C)cc(C(C)(C)C)c1] | 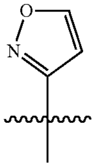 [SMILES: *c1ccon1] |
| 1-1331 | Cl | 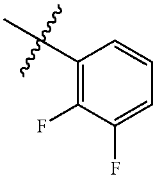 [SMILES: *c1cccc(F)c1F] | 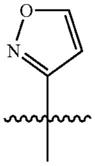 [SMILES: *c1ccon1] |
| 1-1332 | Cl | 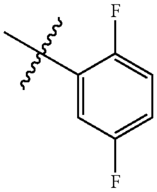 [SMILES: *c1cc(F)ccc1F] | 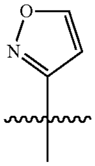 [SMILES: *c1ccon1] |
| 1-1333 | Cl | 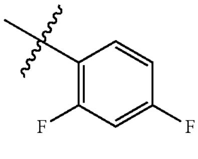 | 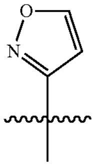 |

-continued
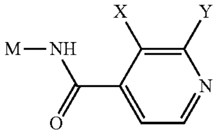
I
| NO. | X | Y | M |
|---|---|---|---|
| 1-1334 | Cl | 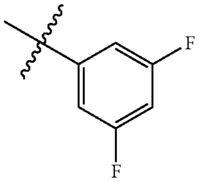 [SMILES: *c1cc(F)cc(F)c1] | 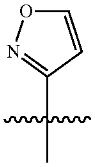 [SMILES: *c1ccon1] |
| 1-1335 | Cl | 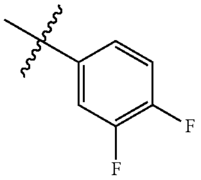 [SMILES: *c1ccc(F)c(F)c1] | 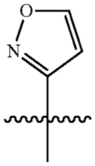 |
| 1-1336 | Cl | 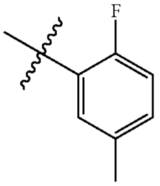 [SMILES: *c1cc(C)ccc1F] | 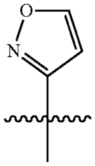 |
| 1-1337 | Cl | 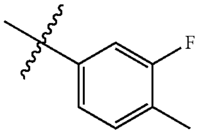 | 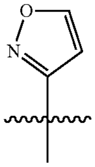 [SMILES: *c1ccon1] |
| 1-1338 | Cl | 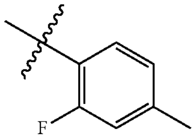 [SMILES: *c1ccc(C)cc1F] | 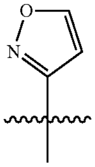 |
| 1-1339 | Cl | 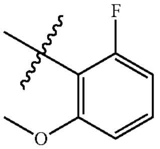 [SMILES: *c1c(F)cccc1OC] | 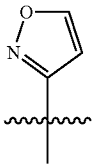 |
| 1-1340 | Cl | 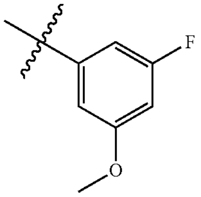 [SMILES: *c1cc(F)cc(OC)c1] | 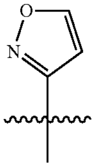 |

-continued
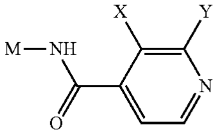
I
| NO. | X | Y | M |
|---|---|---|---|
| 1-1341 | Cl | 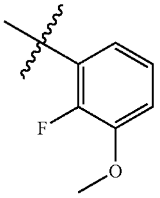 [SMILES: *c1cccc(OC)c1F] | 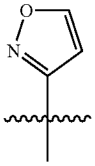 |
| 1-1342 | Cl | 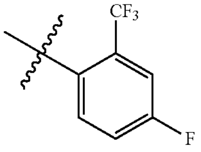 [SMILES: *c1ccc(F)cc1C(F)(F)F] | 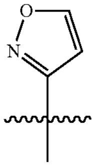 |
| 1-1343 | Cl | 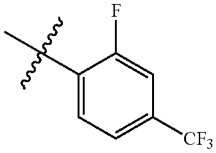 [SMILES: *c1ccc(C(F)(F)F)cc1F] | 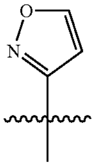 |
| 1-1344 | Cl | 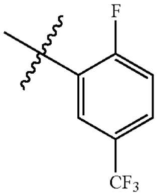 [SMILES: *c1cc(C(F)(F)F)ccc1F] | 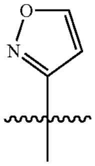 |
| 1-1345 | Cl | 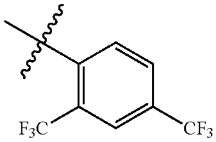 | 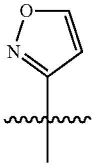 |
| 1-1346 | Cl | 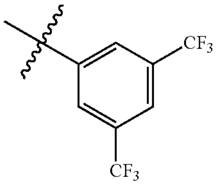 [SMILES: *c1cc(C(F)(F)F)cc(C(F)(F)F)c1] | 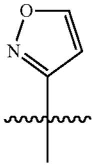 |
| 1-1347 | Cl | 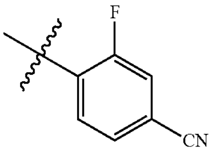 [SMILES: *c1ccc(C#N)cc1F] | 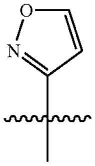 |

-continued
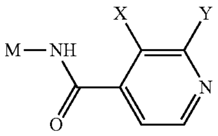
I
| NO. | X | Y | M |
|---|---|---|---|
| 1-1348 | Cl | 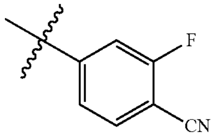 [SMILES: *c1ccc(C#N)c(F)c1] | 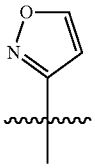 |
| 1-1349 | Cl | 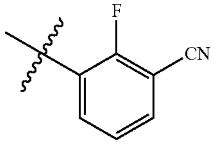 [SMILES: *c1cccc(C#N)c1F] | 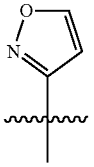 |
| 1-1350 | Cl | 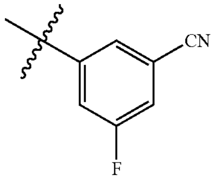 [SMILES: *c1cc(F)cc(C#N)c1] | 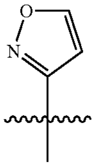 |
| 1-1351 | Cl | 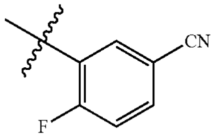 [SMILES: *c1cc(C#N)ccc1F] | 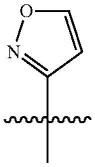 |
| 1-1352 | Cl | 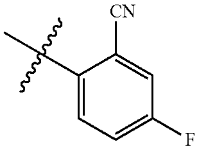 [SMILES: *c1ccc(F)cc1C#N] | 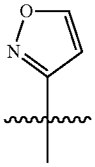 |
| 1-1353 | Cl | 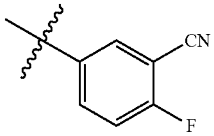 [SMILES: *c1ccc(F)c(C#N)c1] | 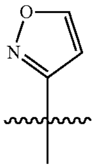 |
| 1-1354 | Cl | 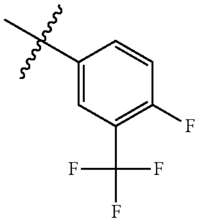 [SMILES: *c1ccc(F)c(C(F)(F)F)c1] | 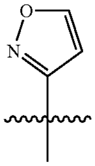 |

-continued
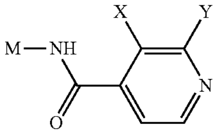
I
| NO. | X | Y | M |
|---|---|---|---|
| 1-1355 | Cl | 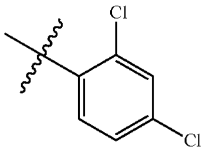 [SMILES: *c1ccc(Cl)cc1Cl] | 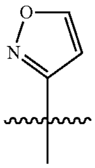 |
| 1-1356 | Cl | 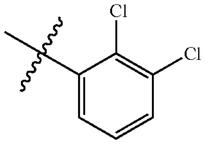 [SMILES: *c1cccc(Cl)c1Cl] | 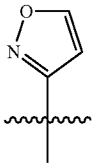 |
| 1-1357 | Cl | 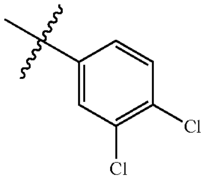 [SMILES: *c1ccc(Cl)c(Cl)c1] | 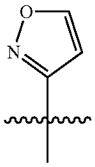 |
| 1-1358 | Cl | 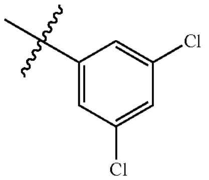 [SMILES: *c1cc(Cl)cc(Cl)c1] | 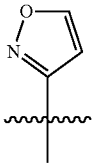 |
| 1-1359 | Cl | 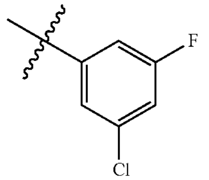 [SMILES: *c1cc(F)cc(Cl)c1] | 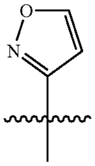 |
| 1-1360 | Cl | 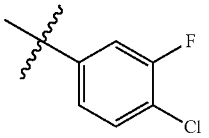 [SMILES: *c1ccc(Cl)c(F)c1] | 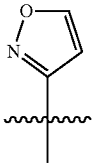 |
| 1-1361 | Cl | 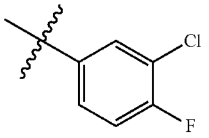 [SMILES: *c1ccc(F)c(Cl)c1] | 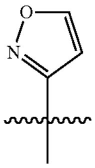 |

-continued
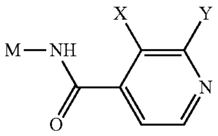
I
| NO. | X | Y | M |
|---|---|---|---|
| 1-1362 | Cl | 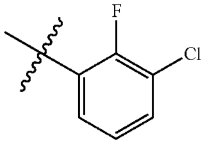 [SMILES: *c1cccc(Cl)c1F] | 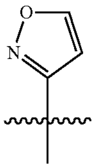 |
| 1-1363 | Cl | 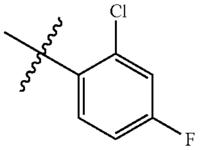 | 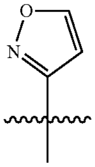 |
| 1-1364 | Cl | 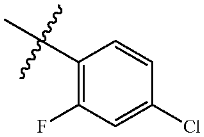 [SMILES: *c1ccc(Cl)cc1F] | 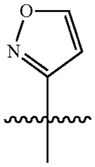 |
| 1-1365 | Cl | 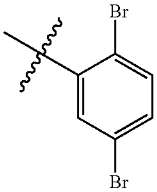 [SMILES: *c1cc(Br)ccc1Br] | 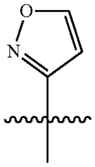 |
| 1-1366 | Cl | 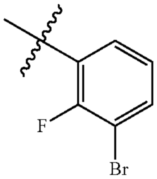 [SMILES: *c1cccc(Br)c1F] | 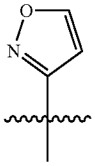 |
| 1-1367 | Cl | 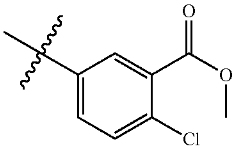 [SMILES: *c1ccc(Cl)c(C(=O)OC)c1] | 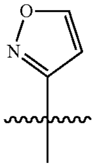 |
| 1-1368 | Cl | 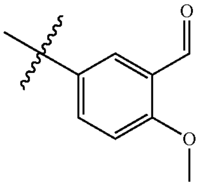 [SMILES: *c1ccc(OC)c(C=O)c1] | 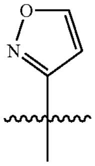 |

-continued
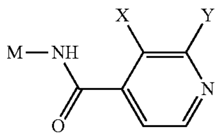
I
| NO. | X | Y | M |
|---|---|---|---|
| 1-1369 | Cl | 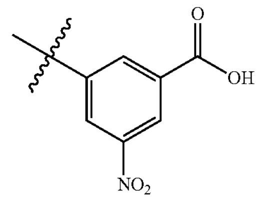 [SMILES: *c1cc(C(=O)O)cc([N+](=O)[O-])c1] | 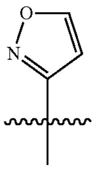 |
| 1-1370 | Cl | 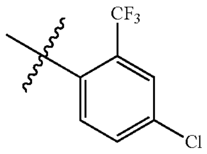 [SMILES: *c1ccc(Cl)cc1C(F)(F)F] | 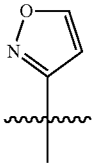 |
| 1-1371 | Cl | 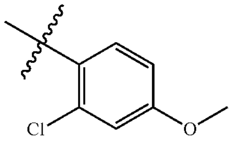 [SMILES: *c1ccc(OC)cc1Cl] | 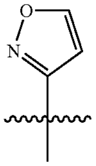 |
| 1-1372 | Cl | 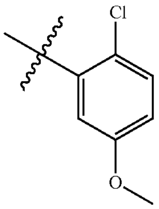 [SMILES: *c1cc(OC)ccc1Cl] | 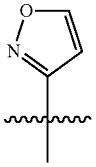 |
| 1-1373 | Cl | 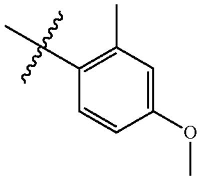 [SMILES: *c1ccc(OC)cc1C] | 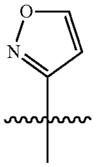 |
| 1-1374 | Cl | 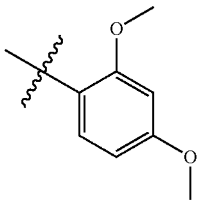 [SMILES: *c1ccc(OC)cc1OC] | 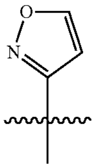 |

-continued
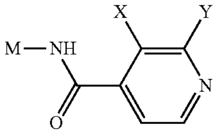
I
| NO. | X | Y | M |
|---|---|---|---|
| 1-1375 | Cl | 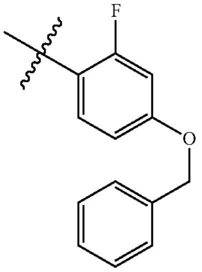 [SMILES: *c1ccc(OCc2ccccc2)cc1F] | 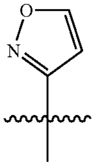 |
| 1-1376 | Cl | 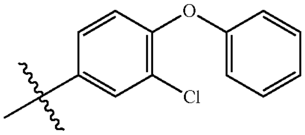 [SMILES: *c1ccc(Oc2ccccc2)c(Cl)c1] | 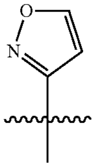 |
| 1-1377 | Cl | 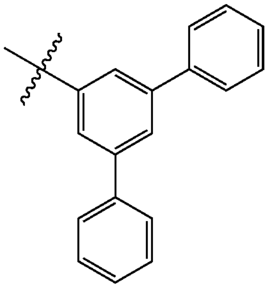 [SMILES: *c1cc(-c2ccccc2)cc(-c2ccccc2)c1] | 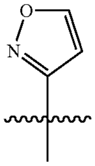 |
| 1-1378 | Cl | 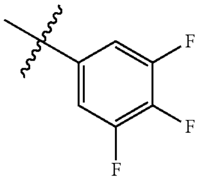 [SMILES: *c1cc(F)c(F)c(F)c1] | 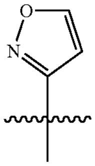 |
| 1-1379 | Cl | 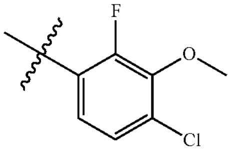 [SMILES: *c1ccc(Cl)c(OC)c1F] | 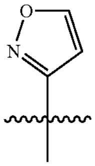 |
| 1-1380 | Cl | 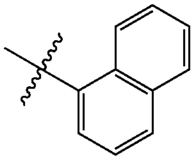 [SMILES: *c1cccc2ccccc12] | 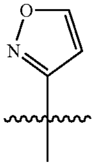 |

-continued
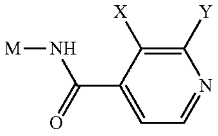
I
| NO. | X | Y | M |
| --- | --- | --- | --- |
| 1-1381 | Cl | 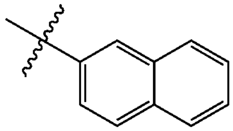 [SMILES: *c1ccc2ccccc2c1] | 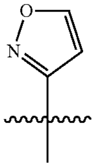 |
| 1-1382 | Cl | 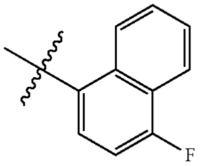 [SMILES: *c1ccc(F)c2ccccc12] | 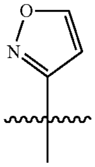 |
| 1-1383 | Cl | 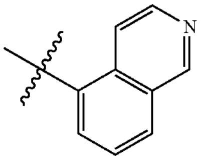 [SMILES: *c1cccc2cnccc12] | 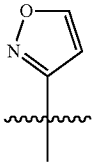 |
| 1-1384 | Cl | 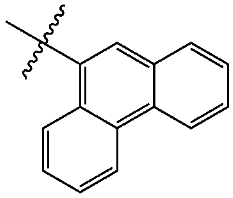 [SMILES: *c1cc2ccccc2c2ccccc12] | 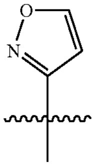 |
| 1-1385 | Cl | 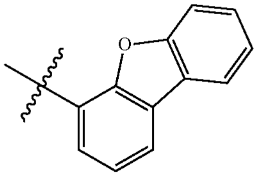 [SMILES: *c1cccc2c1oc1ccccc12] | 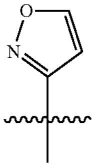 |
| 1-1386 | Cl | 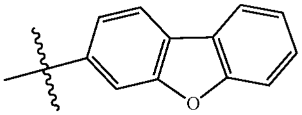 [SMILES: *c1ccc2c(c1)oc1ccccc12] | 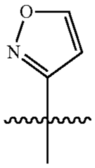 |
| 1-1387 | Cl | 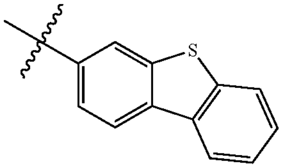 [SMILES: *c1ccc2c(c1)sc1ccccc12] | 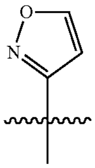 |

-continued
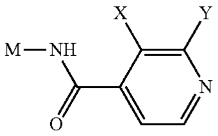
I
| NO. | X | Y | M |
| --- | --- | --- | --- |
| 1-1388 | Cl | 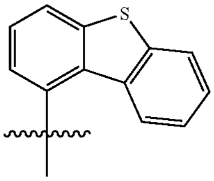 [SMILES: *c1cccc2sc3ccccc3c12] | 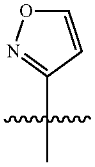 [SMILES: *c1ccon1] |
| 1-1389 | Cl | 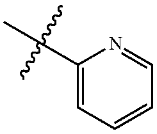 [SMILES: *c1ccccn1] | 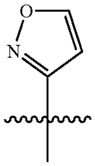 [SMILES: *c1ccon1] |
| 1-1390 | Cl | 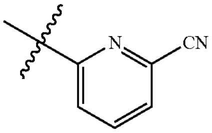 [SMILES: *c1cccc(C#N)n1] | 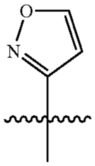 [SMILES: *c1ccon1] |
| 1-1391 | Cl | 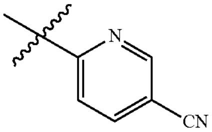 [SMILES: *c1ccc(C#N)cn1] | 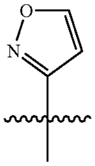 [SMILES: *c1ccon1] |
| 1-1392 | Cl | 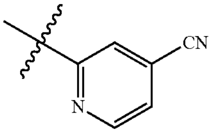 [SMILES: *c1cc(C#N)ccn1] | 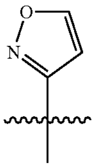 [SMILES: *c1ccon1] |
| 1-1393 | Cl | 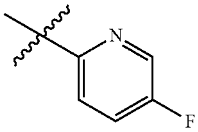 [SMILES: *c1ccc(F)cn1] | 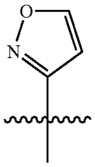 [SMILES: *c1ccon1] |
| 1-1394 | Cl | 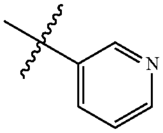 [SMILES: *c1cccnc1] | 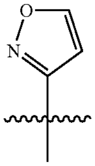 [SMILES: *c1ccon1] |

-continued
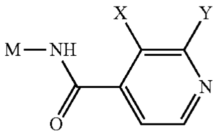
I
| NO. | X | Y | M |
|---|---|---|---|
| 1-1395 | Cl | 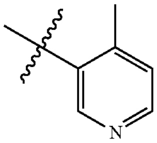 [SMILES: *c1cnccc1C] | 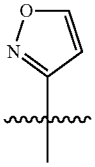 |
| 1-1396 | Cl | 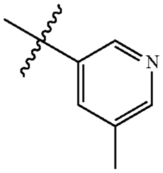 [SMILES: *c1cncc(C)c1] | 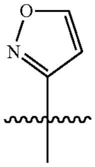 |
| 1-1397 | Cl | 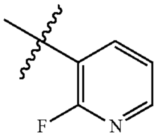 [SMILES: *c1cccnc1F] | 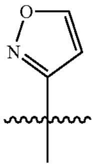 |
| 1-1398 | Cl | 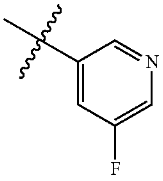 [SMILES: *c1cncc(F)c1] | 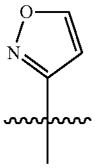 |
| 1-1399 | Cl | 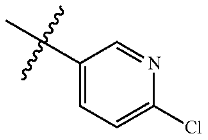 [SMILES: *c1ccc(Cl)nc1] | 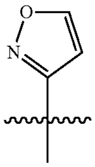 |
| 1-1400 | Cl | 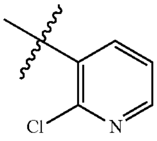 | 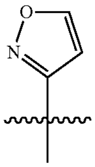 |
| 1-1401 | Cl | 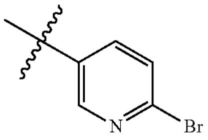 | 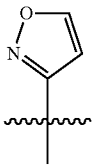 |

-continued
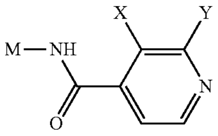
I
| NO. | X | Y | M |
|---|---|---|---|
| 1-1402 | Cl | 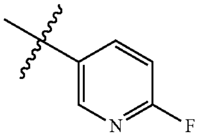 [SMILES: *c1ccc(F)nc1] | 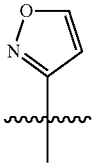 |
| 1-1403 | Cl | 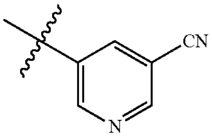 [SMILES: *c1cncc(C#N)c1] | 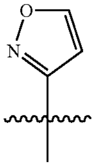 |
| 1-1404 | Cl | 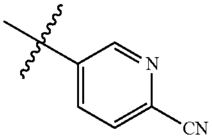 [SMILES: *c1ccc(C#N)nc1] | 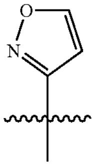 |
| 1-1405 | Cl | 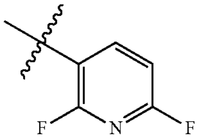 [SMILES: *c1ccc(F)nc1F] | 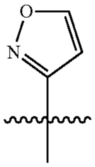 |
| 1-1406 | Cl | 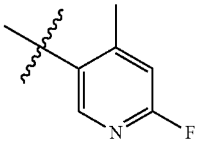 [SMILES: *c1cnc(F)cc1C] | 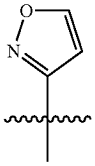 |
| 1-1407 | Cl | 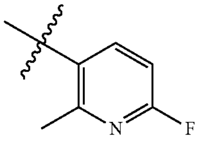 [SMILES: *c1ccc(F)nc1C] | 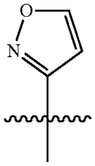 |
| 1-1408 | Cl | 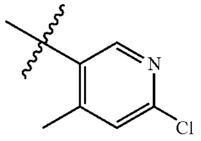 [SMILES: *c1cnc(Cl)cc1C] | 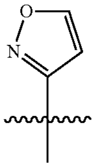 |

-continued
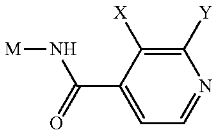
I
| NO. | X | Y | M |
|---|---|---|---|
| 1-1409 | Cl | 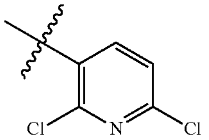 [SMILES: *c1ccc(Cl)nc1Cl] | 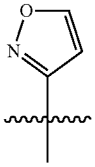 |
| 1-1410 | Cl | 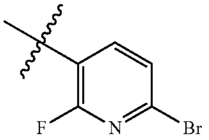 [SMILES: *c1ccc(Br)nc1F] | 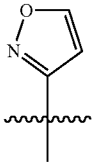 |
| 1-1411 | Cl | 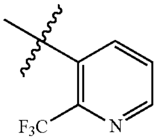 | 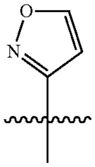 |
| 1-1412 | Cl | 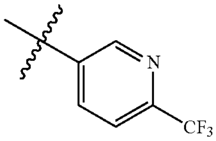 | 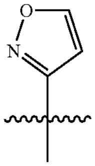 |
| 1-1413 | Cl | 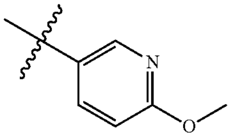 [SMILES: *c1ccc(OC)nc1] | 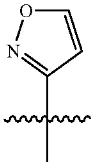 [SMILES: *c1ccon1] |
| 1-1414 | Cl | 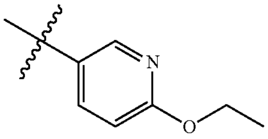 [SMILES: *c1ccc(OCC)nc1] | 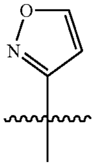 |
| 1-1415 | Cl | 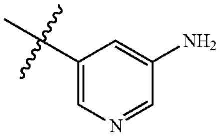 [SMILES: *c1cncc(N)c1] | 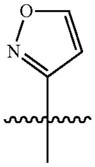 |

-continued
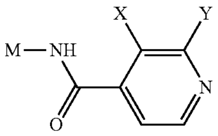
I
| NO. | X | Y | M |
|---|---|---|---|
| 1-1416 | Cl | 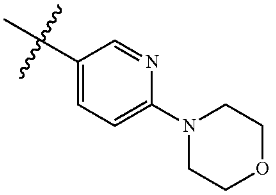 [SMILES: *c1ccc(N2CCOCC2)nc1] | 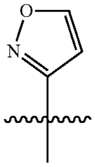 |
| 1-1417 | Cl | 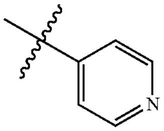 [SMILES: *c1ccncc1] | 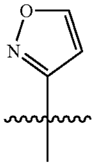 |
| 1-1418 | Cl | 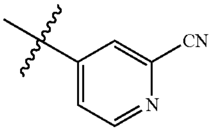 [SMILES: *c1ccnc(C#N)c1] | 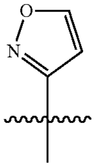 |
| 1-1419 | Cl | 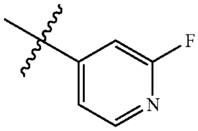 [SMILES: *c1ccnc(F)c1] | 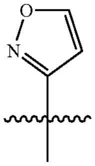 |
| 1-1420 | Cl | 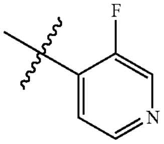 [SMILES: *c1ccncc1F] | 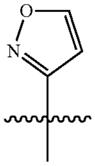 |
| 1-1421 | Cl | 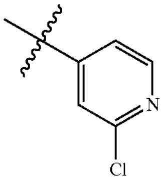 [SMILES: *c1ccnc(Cl)c1] | 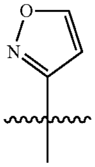 |
| 1-1422 | Cl | 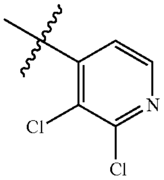 [SMILES: *c1ccnc(Cl)c1Cl] | 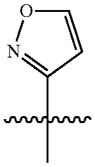 |

-continued
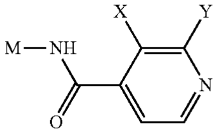
I
| NO. | X | Y | M |
| --- | --- | --- | --- |
| 1-1423 | Cl | 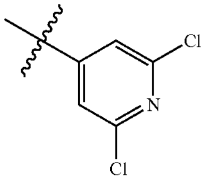 [SMILES: *c1cc(Cl)nc(Cl)c1] | 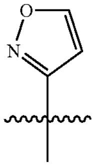 |
| 1-1424 | Cl | 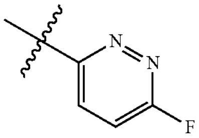 [SMILES: *c1ccc(F)nn1] | 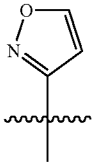 |
| 1-1425 | Cl | 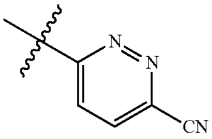 [SMILES: *c1ccc(C#N)nn1] | 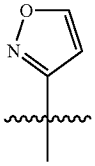 |
| 1-1426 | Cl | 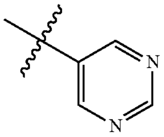 [SMILES: *c1cncnc1] | 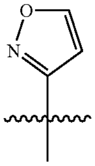 |
| 1-1427 | Cl | 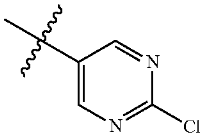 [SMILES: *c1cnc(Cl)nc1] | 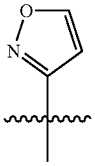 |
| 1-1428 | Cl | 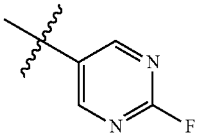 [SMILES: *c1cnc(F)nc1] | 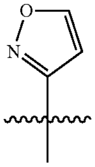 |
| 1-1429 | Cl | 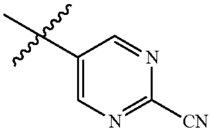 [SMILES: *c1cnc(C#N)nc1] | 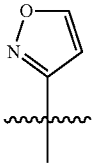 |

-continued
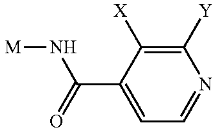
I
| NO. | X | Y | M |
|---|---|---|---|
| 1-1430 | Cl | 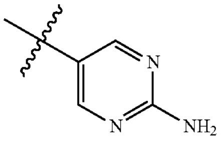 | 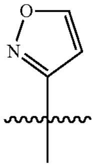 |
| 1-1431 | Cl | 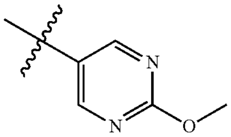 [SMILES: *c1cnc(OC)nc1] | 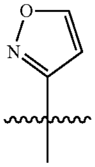 |
| 1-1432 | Cl | 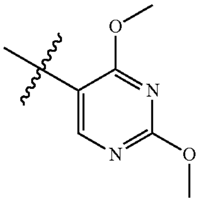 [SMILES: *c1cnc(OC)nc1OC] | 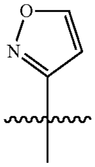 |
| 1-1433 | Cl | 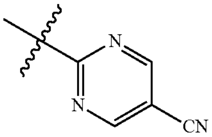 [SMILES: *c1ncc(C#N)cn1] | 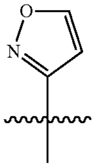 |
| 1-1434 | Cl | 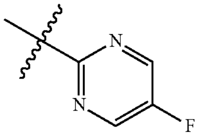 [SMILES: *c1ncc(F)cn1] | 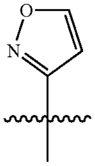 |
| 1-1435 | Cl | 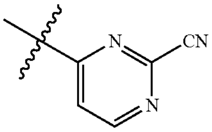 [SMILES: *c1ccnc(C#N)n1] | 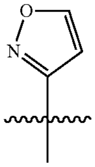 |
| 1-1436 | Cl | 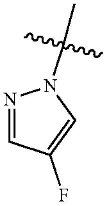 [SMILES: *n1cc(F)cn1] | 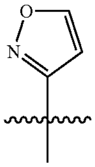 |

-continued
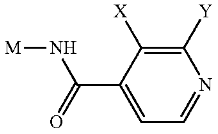
I
| NO. | X | Y | M |
|---|---|---|---|
| 1-1437 | Cl | 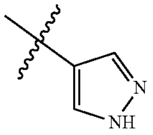 [SMILES: *c1cn[nH]c1] | 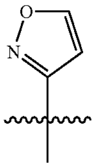 |
| 1-1438 | Cl | 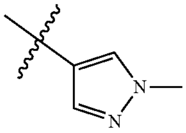 [SMILES: *c1cnn(C)c1] | 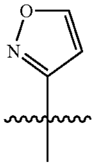 |
| 1-1439 | Cl | 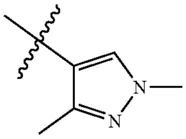 [SMILES: *c1cn(C)nc1C] | 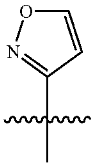 |
| 1-1440 | Cl | 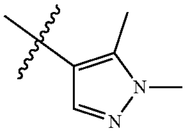 [SMILES: *c1cnn(C)c1C] | 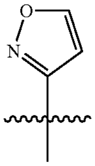 |
| 1-1441 | Cl | 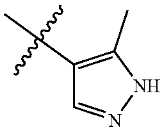 [SMILES: *c1cn[nH]c1C] | 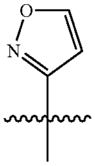 |
| 1-1442 | Cl | 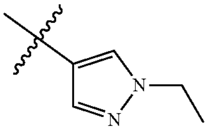 [SMILES: *c1cnn(CC)c1] | 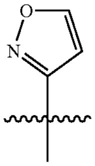 |
| 1-1443 | Cl | 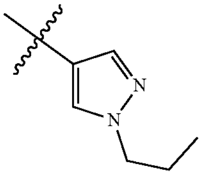 [SMILES: *c1cnn(CCC)c1] | 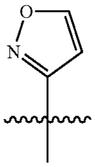 |

-continued
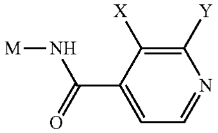
I
| NO. | X | Y | M |
|---|---|---|---|
| 1-1444 | Cl | 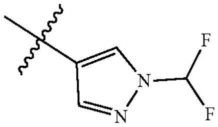 [SMILES: *c1cnn(C(F)F)c1] | 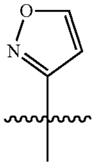 |
| 1-1445 | Cl | 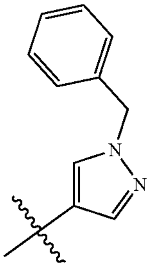 [SMILES: *c1cnn(Cc2ccccc2)c1] | 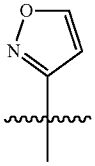 |
| 1-1446 | Cl | 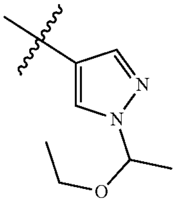 [SMILES: *c1cnn(C(C)OCC)c1] | 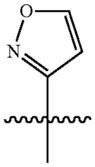 |
| 1-1447 | Cl | 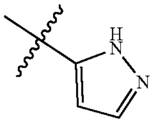 [SMILES: *c1ccn[nH]1] | 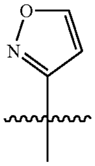 |
| 1-1448 | Cl | 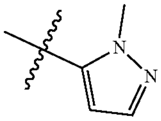 [SMILES: *c1ccnn1C] | 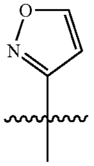 [SMILES: *c1ccon1] |
| 1-1449 | Cl | 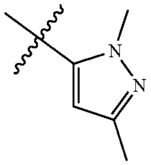 [SMILES: *c1cc(C)nn1C] | 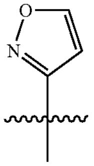 [SMILES: *c1ccon1] |
| 1-1450 | Cl | 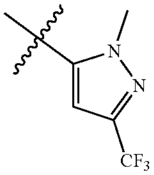 | 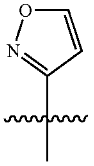 |

-continued
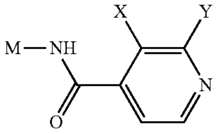
I
| NO. | X | Y | M |
|---|---|---|---|
| 1-1451 | Cl | 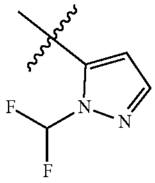 [SMILES: *c1ccnn1C(F)F] | 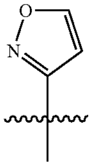 |
| 1-1452 | Cl | 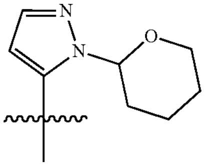 [SMILES: *c1ccnn1C1CCCCO1] | 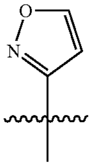 |
| 1-1453 | Cl | 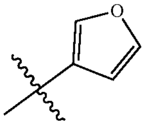 [SMILES: *c1ccoc1] | 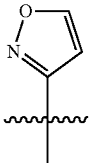 |
| 1-1454 | Cl | 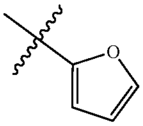 [SMILES: *c1ccco1] | 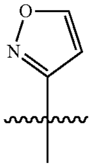 |
| 1-1455 | Cl | 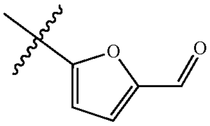 [SMILES: *c1ccc(C=O)o1] | 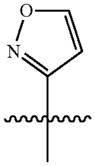 [SMILES: *c1ccon1] |
| 1-1456 | Cl | 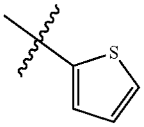 | 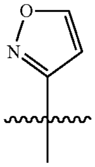 |
| 1-1457 | Cl | 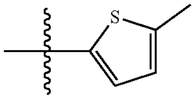 [SMILES: *c1ccc(C)s1] | 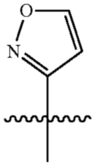 [SMILES: *c1ccon1] |

-continued
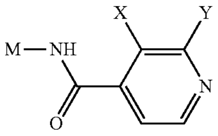
I
| NO. | X | Y | M |
|---|---|---|---|
| 1-1458 | Cl | 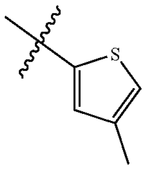 [SMILES: *c1cc(C)cs1] | 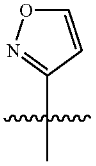 [SMILES: *c1ccon1] |
| 1-1459 | Cl | 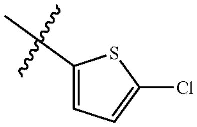 [SMILES: *c1ccc(Cl)s1] | 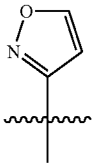 [SMILES: *c1ccon1] |
| 1-1460 | Cl | 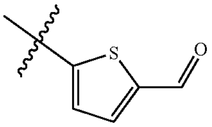 | 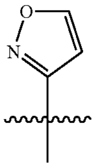 [SMILES: *c1ccon1] |
| 1-1461 | Cl | 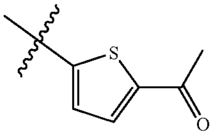 [SMILES: *c1ccc(C(C)=O)s1] | 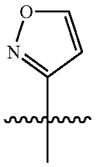 [SMILES: *c1ccon1] |
| 1-1462 | Cl | 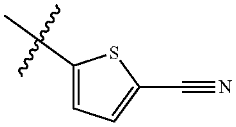 | 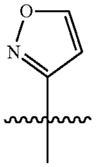 [SMILES: *c1ccon1] |
| 1-1463 | Cl | 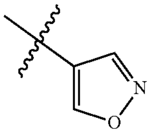 [SMILES: *c1cnoc1] | 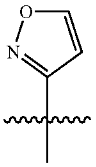 [SMILES: *c1ccon1] |
| 1-1464 | $CH_3$ | 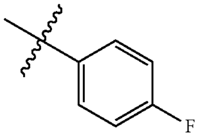 [SMILES: *c1ccc(F)cc1] | 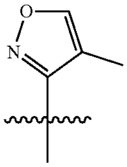 |

-continued
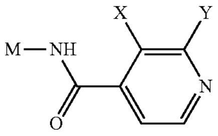
I
| NO. | X | Y | M |
|---|---|---|---|
| 1-1465 | F | 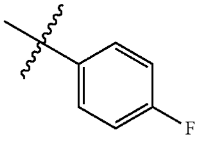 [SMILES: *c1ccc(F)cc1] | 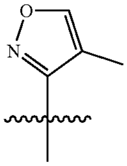 [SMILES: *c1nocc1C] |
| 1-1466 | Br | 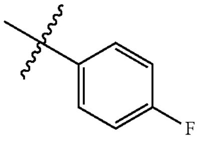 [SMILES: *c1ccc(F)cc1] | 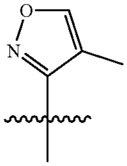 [SMILES: *c1nocc1C] |
| 1-1467 | 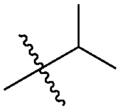 [SMILES: *C(C)C] | 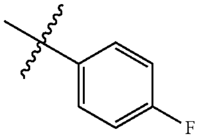 [SMILES: *c1ccc(F)cc1] | 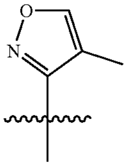 [SMILES: *c1nocc1C] |
| 1-1468 | $CF_3$ | 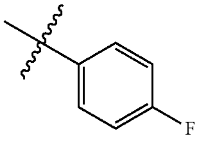 [SMILES: *c1ccc(F)cc1] | 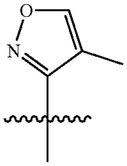 [SMILES: *c1nocc1C] |
| 1-1469 | 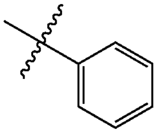 [SMILES: *c1ccccc1] | 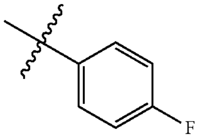 [SMILES: *c1ccc(F)cc1] | 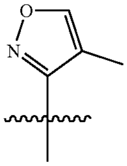 [SMILES: *c1nocc1C] |
| 1-1470 | 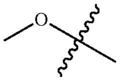 [SMILES: *OC] | 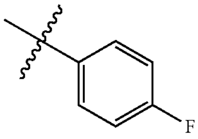 [SMILES: *c1ccc(F)cc1] | 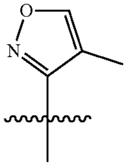 [SMILES: *c1nocc1C] |
| 1-1471 | 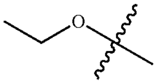 [SMILES: *OCC] | 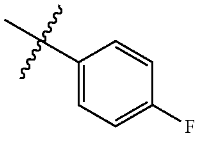 [SMILES: *c1ccc(F)cc1] | 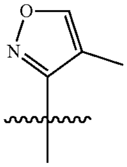 [SMILES: *c1nocc1C] |

-continued
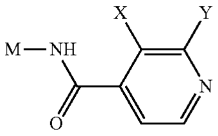
I
| NO. | X | Y | M |
| --- | --- | --- | --- |
| 1-1472 | 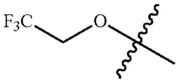 [SMILES: *OCC(F)(F)F] | 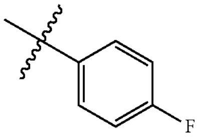 [SMILES: *c1ccc(F)cc1] | 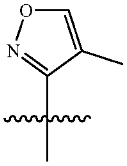 [SMILES: *c1nocc1C] |
| 1-1473 | 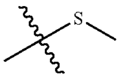 [SMILES: *SC] | 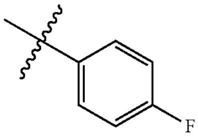 [SMILES: *c1ccc(F)cc1] | 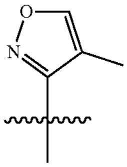 [SMILES: *c1nocc1C] |
| 1-1474 | 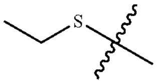 [SMILES: *SCC] | 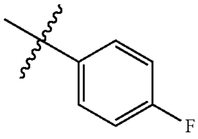 [SMILES: *c1ccc(F)cc1] | 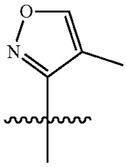 |
| 1-1475 | 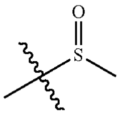 [SMILES: *S(C)=O] | 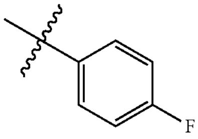 [SMILES: *c1ccc(F)cc1] | 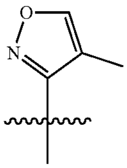 [SMILES: *c1nocc1C] |
| 1-1476 | 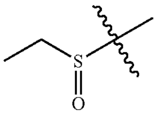 [SMILES: *S(=O)CC] | 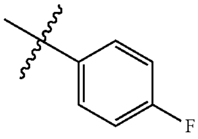 [SMILES: *c1ccc(F)cc1] | 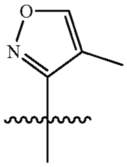 |
| 1-1477 | 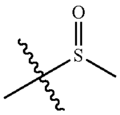 [SMILES: *S(C)=O] | 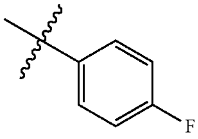 [SMILES: *c1ccc(F)cc1] | 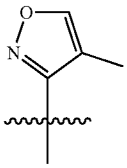 [SMILES: *c1nocc1C] |
| 1-1478 | 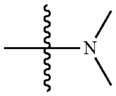 [SMILES: *N(C)C] | 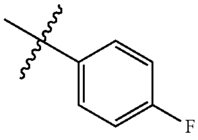 [SMILES: *c1ccc(F)cc1] | 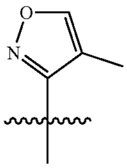 |

-continued
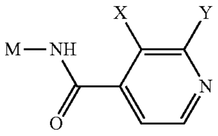
I
| NO. | X | Y | M |
|---|---|---|---|
| 1-1479 | 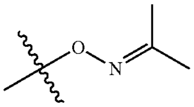 [SMILES: *ON=C(C)C] | 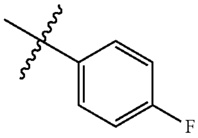 [SMILES: *c1ccc(F)cc1] | 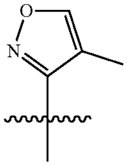 |
| 1-1480 | Et | 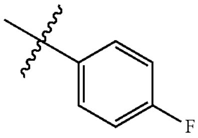 | 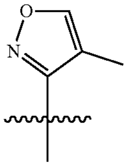 [SMILES: *c1nocc1C] |
| 1-1481 | 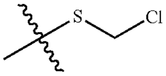 [SMILES: *SCCl] | 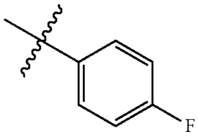 [SMILES: *c1ccc(F)cc1] | 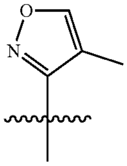 [SMILES: *c1nocc1C] |
| 1-1482 | $NO_2$ | 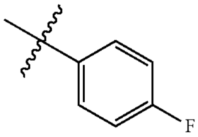 | 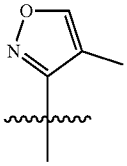 [SMILES: *c1nocc1C] |
| 1-1483 | CN | 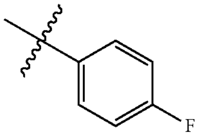 [SMILES: *c1ccc(F)cc1] | 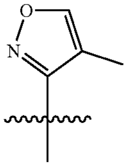 [SMILES: *c1nocc1C] |
| 1-1484 | 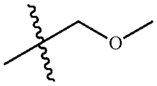 [SMILES: *COC] | 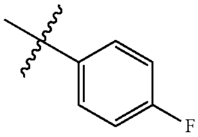 [SMILES: *c1ccc(F)cc1] | 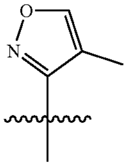 [SMILES: *c1nocc1C] |
| 1-1485 | 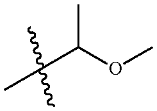 [SMILES: *C(C)OC] | 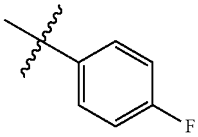 [SMILES: *c1ccc(F)cc1] | 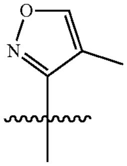 [SMILES: *c1nocc1C] |

-continued
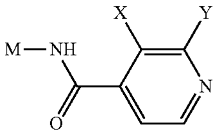
I
| NO. | X | Y | M |
|---|---|---|---|
| 1-1486 | 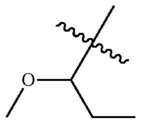 [SMILES: *C(CC)OC] | 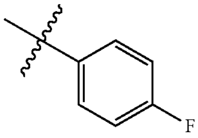 [SMILES: *c1ccc(F)cc1] | 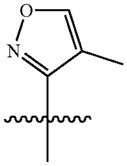 [SMILES: *c1nocc1C] |
| 1-1487 | 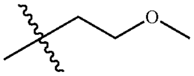 [SMILES: *CCOC] | 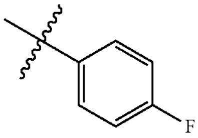 [SMILES: *c1ccc(F)cc1] | 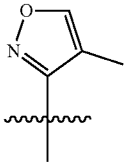 [SMILES: *c1nocc1C] |
| 1-1488 | 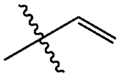 [SMILES: *C=C] | 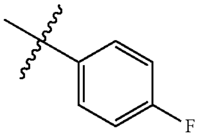 [SMILES: *c1ccc(F)cc1] | 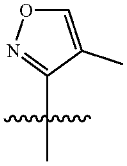 |
| 1-1489 | 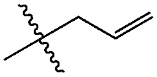 [SMILES: *CC=C] | 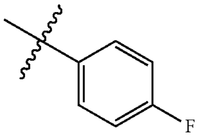 [SMILES: *c1ccc(F)cc1] | 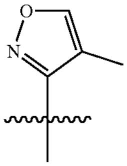 [SMILES: *c1nocc1C] |
| 1-1490 | 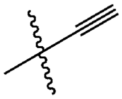 [SMILES: *C#C] | 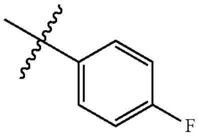 [SMILES: *c1ccc(F)cc1] | 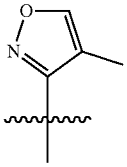 |
| 1-1491 | 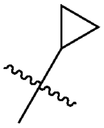 [SMILES: *C1CC1] | 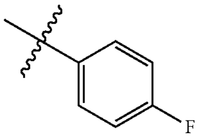 [SMILES: *c1ccc(F)cc1] | 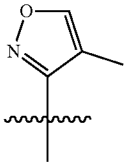 [SMILES: *c1nocc1C] |
| 1-1492 | 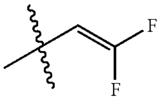 [SMILES: *C=C(F)F] | 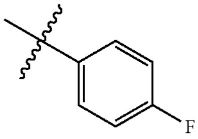 [SMILES: *c1ccc(F)cc1] | 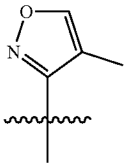 [SMILES: *c1nocc1C] |

-continued
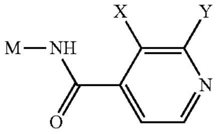
I
| NO. | X | Y | M |
|---|---|---|---|
| 1-1493 | 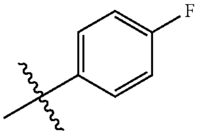 [SMILES: *c1ccc(F)cc1] | 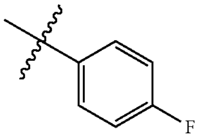 [SMILES: *c1ccc(F)cc1] | 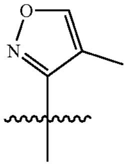 |
| 1-1494 | Cl | 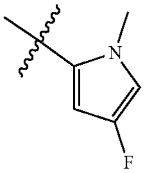 [SMILES: *c1cc(F)cn1C] | 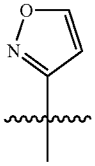 |
| 1-1495 | Cl | 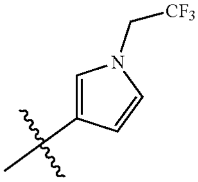 [SMILES: *c1ccn(CC(F)(F)F)c1] | 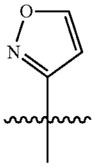 |
| 1-1496 | Cl | 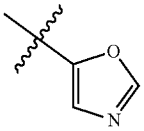 [SMILES: *c1cnco1] | 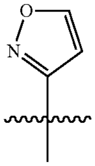 |
| 1-1497 | Cl | 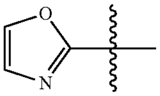 | 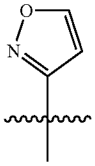 |
| 1-1498 | Cl | 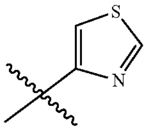 [SMILES: *c1cscn1] | 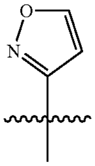 |
| 1-1499 | Cl | 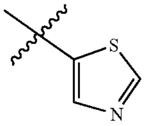 [SMILES: *c1cncs1] | 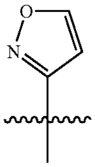 |

-continued
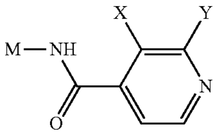
I
| NO. | X | Y | M |
|---|---|---|---|
| 1-1500 | Cl | 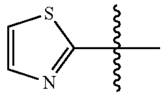 | 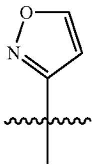 |
| 1-1501 | Cl | 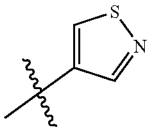 [SMILES: *c1cnsc1] | 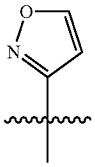 |
| 1-1502 | Cl | 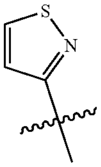 [SMILES: *c1ccsn1] | 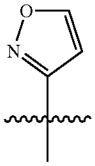 |
| 1-1503 | Cl | 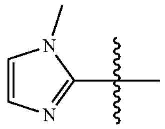 [SMILES: *c1nccn1C] | 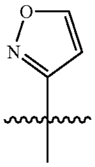 |
| 1-1504 | Cl | 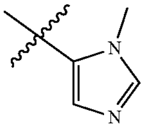 [SMILES: *c1cncn1C] | 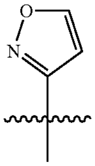 |
| 1-1505 | Cl | 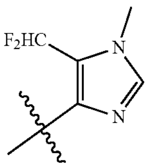 [SMILES: *c1ncn(C)c1C(F)F] | 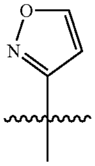 |
| 1-1506 | Cl | 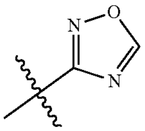 [SMILES: *c1ncon1] | 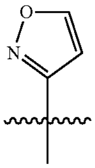 |

-continued
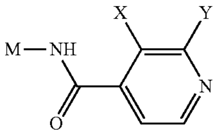
I
| NO. | X | Y | M |
|---|---|---|---|
| 1-1507 | Cl | 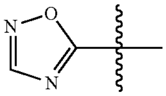 | 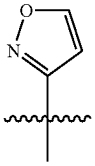 |
| 1-1508 | Cl | 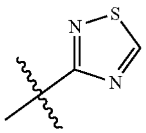 [SMILES: *c1ncsn1] | 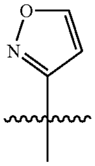 |
| 1-1509 | Cl | 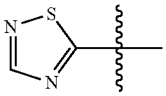 | 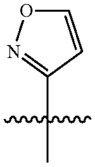 |
| 1-1510 | Cl | 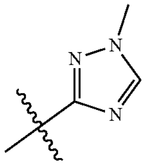 [SMILES: *c1ncn(C)n1] | 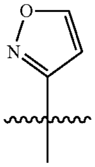 |
| 1-1511 | Cl | 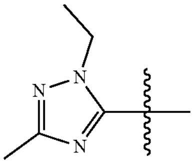 [SMILES: *c1nc(C)nn1CC] | 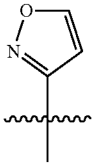 |
| 1-1512 | Cl | 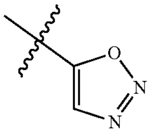 [SMILES: *c1cnno1] | 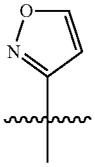 |
| 1-1513 | Cl | 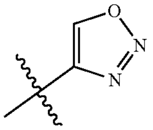 [SMILES: *c1conn1] | 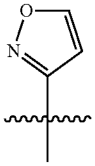 |

-continued
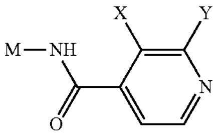
I
| NO. | X | Y | M |
|---|---|---|---|
| 1-1514 | Cl | 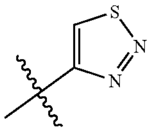 [SMILES: *c1csnn1] | 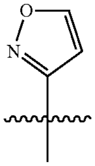 |
| 1-1515 | Cl | 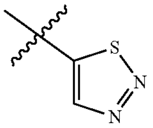 [SMILES: *c1cnns1] | 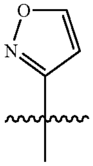 [SMILES: *c1ccon1] |
| 1-1516 | Cl | 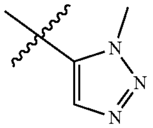 [SMILES: *c1cnnn1C] | 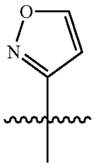 |
| 1-1517 | Cl | 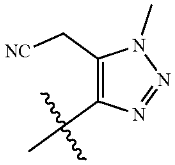 [SMILES: *c1nnn(C)c1CC#N] | 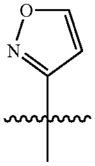 |
| 1-1518 | Cl | 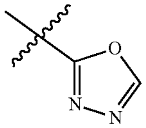 [SMILES: *c1nnco1] | 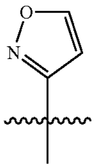 |
| 1-1519 | Cl | 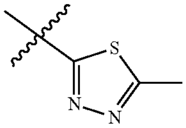 [SMILES: *c1nnc(C)s1] | 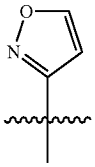 |
| 1-1520 | Cl | 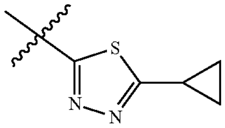 [SMILES: *c1nnc(C2CC2)s1] | 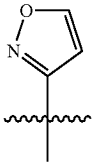 |

-continued
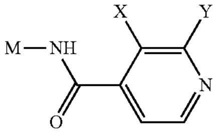
I
| NO. | X | Y | M |
|---|---|---|---|
| 1-1521 | Cl | 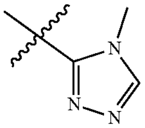 [SMILES: *c1nncn1C] | 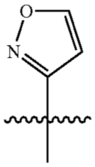 |
| 1-1522 | Cl | 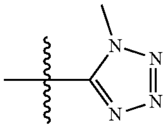 [SMILES: *c1nnnn1C] | 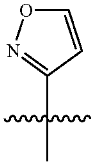 |
| 1-1523 | Cl | 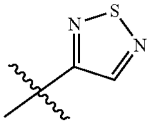 [SMILES: *c1cnsn1] | 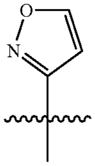 |
| 1-1524 | Cl | 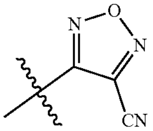 [SMILES: *c1nonc1C#N] | 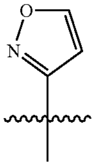 |
| 1-1525 | Cl | 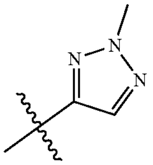 [SMILES: *c1cnn(C)n1] | 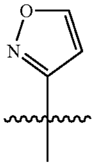 |
| 1-1526 | Cl | 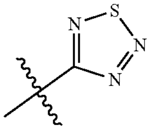 [SMILES: *c1nnsn1] | 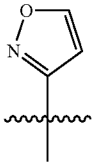 |
| 1-1527 | Cl | 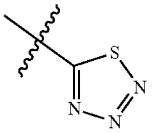 [SMILES: *c1nnns1] | 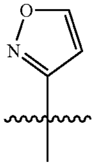 |

-continued
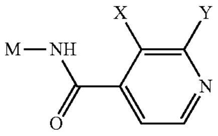
I
| NO. | X | Y | M |
|---|---|---|---|
| 1-1528 | Cl | 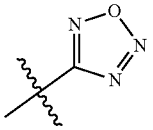 [SMILES: *c1nnon1] | 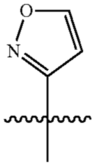 |
| 1-1529 | Cl | 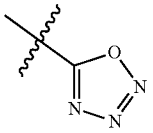 [SMILES: *c1nnno1] | 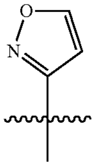 |
| 1-1530 | Cl | 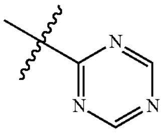 | 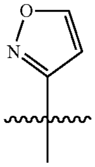 |
| 1-1531 | Cl | 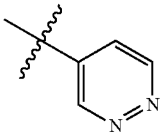 [SMILES: *c1ccnnc1] | 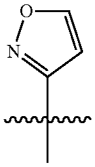 |
| 1-1532 | Cl | 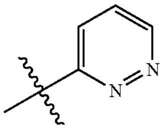 [SMILES: *c1cccnn1] | 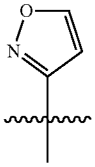 |
| 1-1533 | Cl | 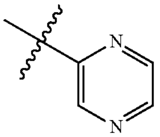 [SMILES: *c1cnccn1] | 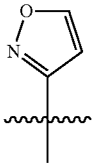 |
| 1-1534 | Cl | 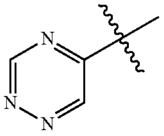 [SMILES: *c1cnncn1] | 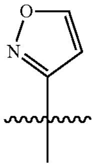 |

-continued
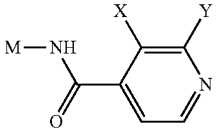
I
| NO. | X | Y | M |
| --- | --- | --- | --- |
| 1-1535 | Cl | 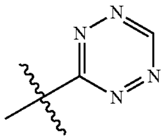 [SMILES: *c1nncnn1] | 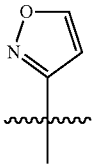 |
| 1-1536 | Cl | 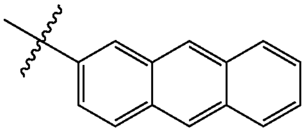 [SMILES: *c1ccc2cc3ccccc3cc2c1] | 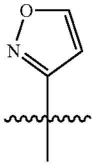 |
| 1-1537 | Cl | 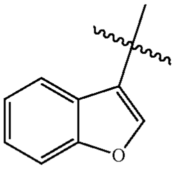 [SMILES: *c1coc2ccccc12] | 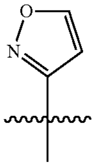 |
| 1-1538 | Cl | 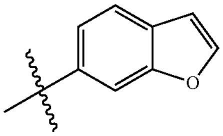 [SMILES: *c1ccc2ccoc2c1] | 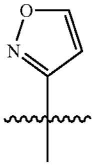 |
| 1-1539 | Cl | 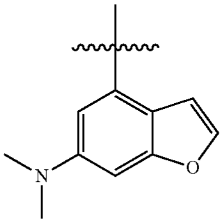 [SMILES: *c1cc(N(C)C)cc2occc12] | 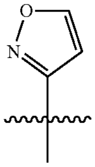 |
| 1-1540 | Cl | 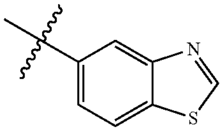 [SMILES: *c1ccc2scnc2c1] | 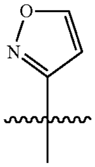 |
| 1-1541 | Cl | 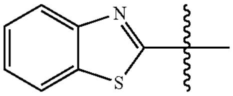 | 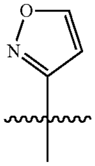 |

-continued
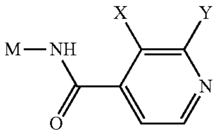
I
| NO. | X | Y | M |
|---|---|---|---|
| 1-1542 | Cl | 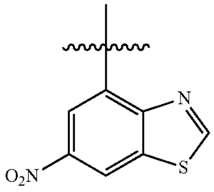 [SMILES: *c1cc([N+](=O)[O-])cc2scnc12] | 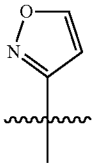 |
| 1-1543 | Cl | 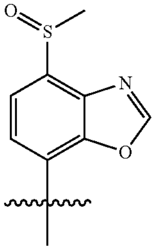 [SMILES: *c1ccc(S(C)=O)c2ncoc12] | 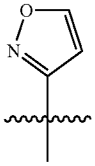 |
| 1-1544 | Cl | 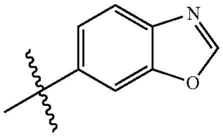 [SMILES: *c1ccc2ncoc2c1] | 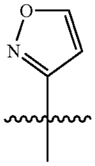 |
| 1-1545 | Cl | 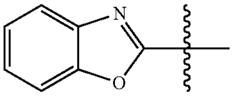 | 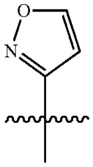 [SMILES: *c1ccon1] |
| 1-1546 | Cl | 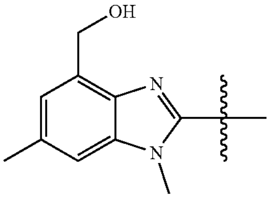 [SMILES: *c1nc2c(CO)cc(C)cc2n1C] | 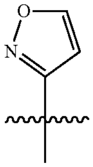 |
| 1-1547 | Cl | 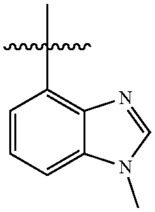 [SMILES: *c1cccc2c1ncn2C] | 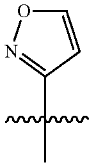 |

-continued
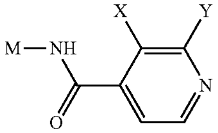
I
| NO. | X | Y | M |
|---|---|---|---|
| 1-1548 | Cl | 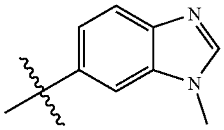 [SMILES: *c1ccc2ncn(C)c2c1] | 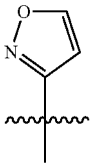 [SMILES: *c1ccon1] |
| 1-1549 | Cl | 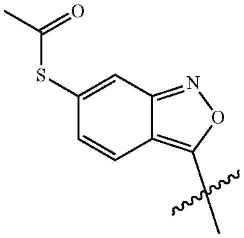 [SMILES: *c1onc2cc(SC(C)=O)ccc12] | 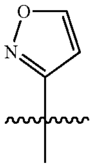 [SMILES: *c1ccon1] |
| 1-1550 | Cl | 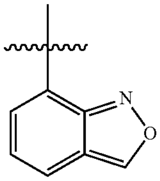 | 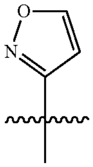 [SMILES: *c1ccon1] |
| 1-1551 | Cl | 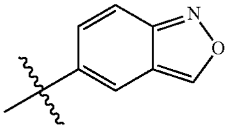 [SMILES: *c1ccc2nocc2c1] | 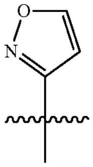 |
| 1-1552 | Cl | 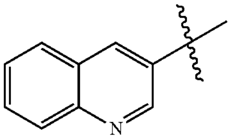 [SMILES: *c1cnc2ccccc2c1] | 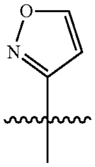 |
| 1-1553 | Cl | 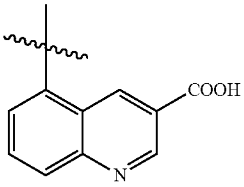 [SMILES: *c1cccc2ncc(C(=O)O)cc12] | 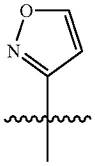 |
| 1-1554 | Cl | 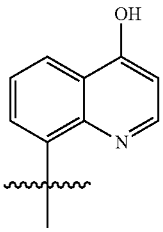 [SMILES: *c1cccc2c(O)ccnc12] | 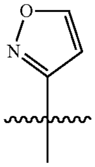 |

-continued
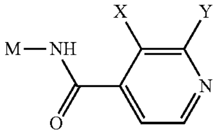
I
| NO. | X | Y | M |
|---|---|---|---|
| 1-1555 | Cl | 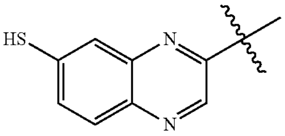 [SMILES: *c1cnc2ccc(S)cc2n1] | 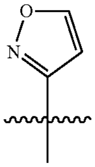 |
| 1-1556 | Cl | 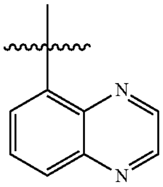 [SMILES: *c1cccc2nccnc12] | 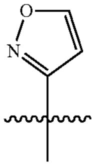 |
| 1-1557 | Cl | 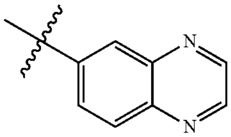 [SMILES: *c1ccc2nccnc2c1] | 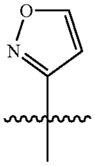 |
| 1-1558 | Cl | 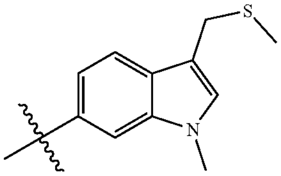 [SMILES: *c1ccc2c(CSC)cn(C)c2c1] | 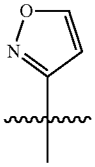 |
| 1-1559 | Cl | 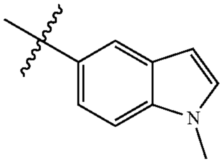 [SMILES: *c1ccc2c(ccn2C)c1] | 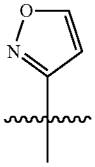 |
| 1-1560 | Cl | 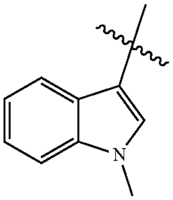 [SMILES: *c1cn(C)c2ccccc12] | 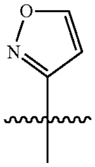 [SMILES: *c1ccon1] |
| 1-1561 | Cl | 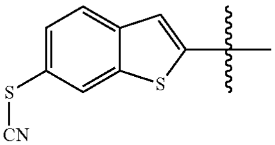 [SMILES: *c1cc2ccc(SC#N)cc2s1] | 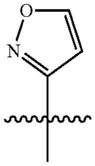 [SMILES: *c1ccon1] |

-continued
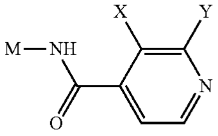
I
| NO. | X | Y | M |
|---|---|---|---|
| 1-1562 | Cl | 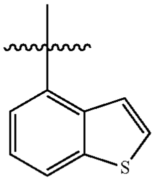 [SMILES: *c1cccc2sccc12] | 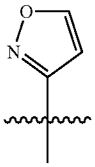 [SMILES: *c1ccon1] |
| 1-1563 | Cl | 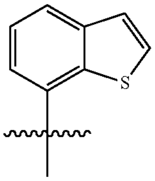 [SMILES: *c1cccc2ccsc12] | 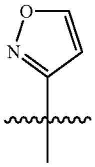 [SMILES: *c1ccon1] |
| 1-1564 | Cl | 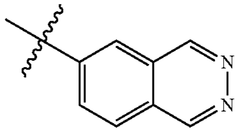 [SMILES: *c1ccc2cnncc2c1] | 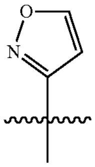 [SMILES: *c1ccon1] |
| 1-1565 | Cl | 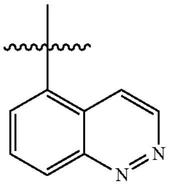 [SMILES: *c1cccc2nnccc12] | 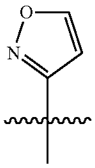 |
| 1-1566 | Cl | 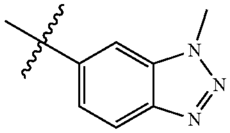 [SMILES: *c1ccc2nnn(C)c2c1] | 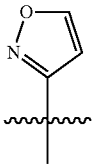 [SMILES: *c1ccon1] |
| 1-1567 | Cl | 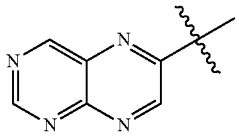 [SMILES: *c1cnc2ncncc2n1] | 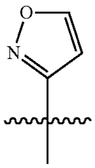 |
| 1-1568 | Cl | 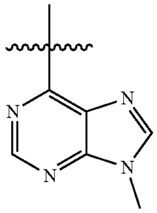 [SMILES: *c1ncnc2c1ncn2C] | 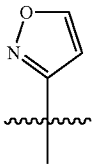 |

-continued
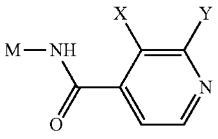
I
| NO. | X | Y | M |
|---|---|---|---|
| 1-1569 | Cl | 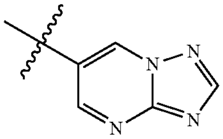 [SMILES: *c1cnc2ncnn2c1] | 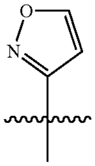 |
| 1-1570 | Cl | 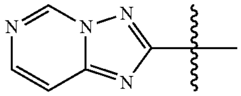 [SMILES: *c1nc2ccncn2n1] | 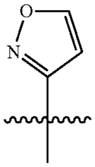 |
| 1-1571 | Cl | 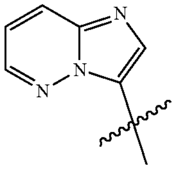 [SMILES: *c1cnc2cccnn12] | 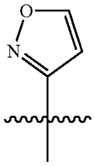 |
| 1-1572 | Cl | 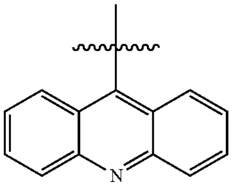 [SMILES: *c1c2ccccc2nc2ccccc12] | 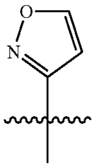 |
| 1-1573 | Cl | 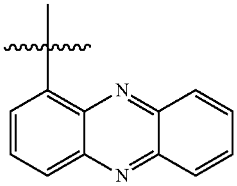 [SMILES: *c1cccc2nc3ccccc3nc12] | 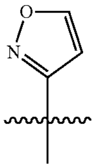 |
| 1-1574 | Cl | 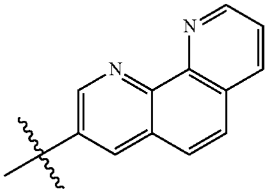 [SMILES: *c1cnc2c(ccc3cccnc32)c1] | 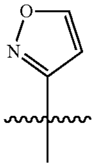 |
| 1-1575 | Cl | 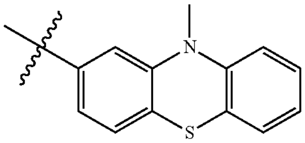 [SMILES: *c1ccc2c(c1)N(C)c1ccccc1S2] | 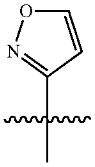 |

-continued
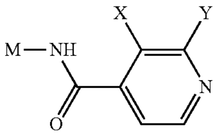
I
| NO. | X | Y | M |
|---|---|---|---|
| 1-1576 | Cl | 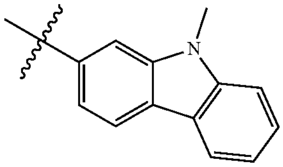 [SMILES: *c1ccc2c3ccccc3n(C)c2c1] | 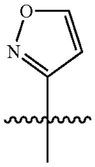 |
| 1-1577 | Cl | 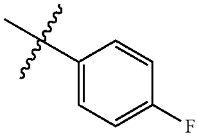 [SMILES: *c1ccc(F)cc1] | 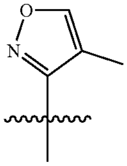 [SMILES: *c1nocc1C] |
| 1-1578 | Cl | 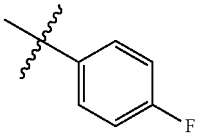 [SMILES: *c1ccc(F)cc1] | 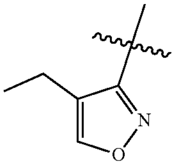 [SMILES: *c1nocc1CC] |
| 1-1579 | Cl | 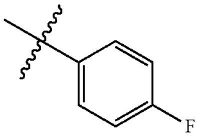 [SMILES: *c1ccc(F)cc1] | 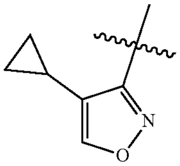 [SMILES: *c1nocc1C1CC1] |
| 1-1580 | Cl | 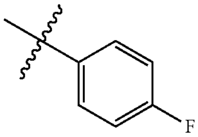 [SMILES: *c1ccc(F)cc1] | 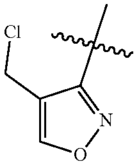 [SMILES: *c1nocc1CCl] |
| 1-1581 | Cl | 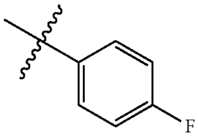 [SMILES: *c1ccc(F)cc1] | 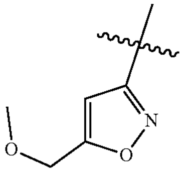 [SMILES: *c1cc(COC)on1] |
| 1-1582 | Cl | 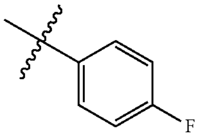 [SMILES: *c1ccc(F)cc1] | 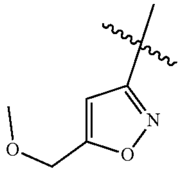 [SMILES: *c1cc(COC)on1] |

-continued
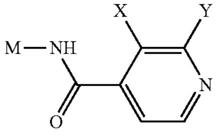
I
| NO. | X | Y | M |
| --- | --- | --- | --- |
| 1-1583 | Cl | 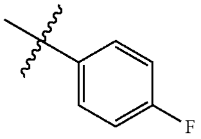 [SMILES: *c1ccc(F)cc1] | 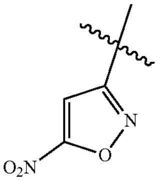 [SMILES: *c1cc([N+](=O)[O-])on1] |
| 1-1584 | Cl | 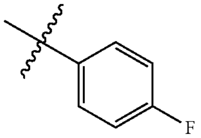 [SMILES: *c1ccc(F)cc1] | 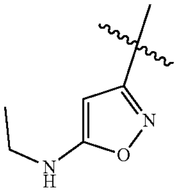 [SMILES: *c1cc(NCC)on1] |
| 1-1585 | Cl | 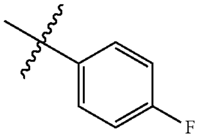 [SMILES: *c1ccc(F)cc1] | 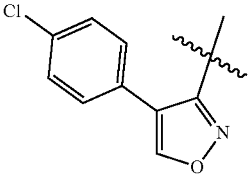 [SMILES: *c1nocc1-c1ccc(Cl)cc1] |
| 1-1586 | Cl | 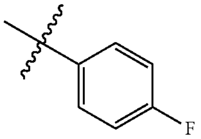 [SMILES: *c1ccc(F)cc1] | 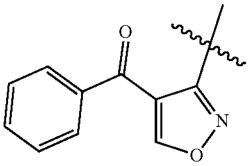 [SMILES: *c1nocc1C(=O)c1ccccc1] |
| 1-1587 | Cl | 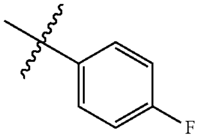 [SMILES: *c1ccc(F)cc1] | 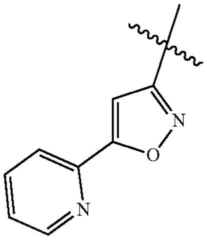 [SMILES: *c1cc(-c2ccccn2)on1] |
| 1-1588 | Cl | 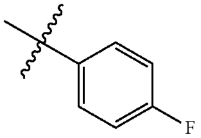 [SMILES: *c1ccc(F)cc1] | 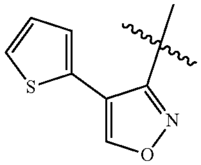 [SMILES: *c1nocc1-c1cccs1] |
| 1-1589 | Cl | 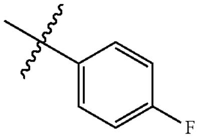 [SMILES: *c1ccc(F)cc1] | 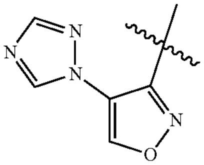 [SMILES: *c1nocc1-n1cncn1] |

-continued
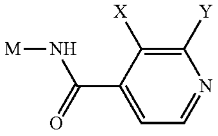
I
| NO. | X | Y | M |
| --- | --- | --- | --- |
| 1-1590 | Cl | $CH_3$ | 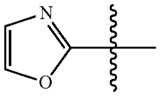 [SMILES: *c1ncco1] |
| 1-1591 | Cl | 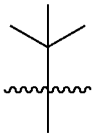 | 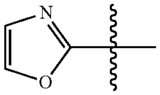 [SMILES: *c1ncco1] |
| 1-1592 | Cl | 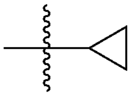 [SMILES: *C1CC1] | 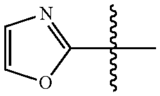 [SMILES: *c1ncco1] |
| 1-1593 | Cl | 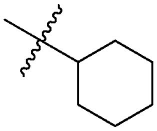 [SMILES: *C1CCCCC1] | 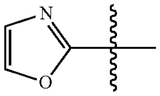 [SMILES: *c1ncco1] |
| 1-1594 | Cl | 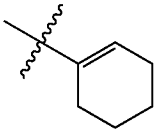 [SMILES: *C1=CCCCC1] | 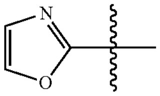 [SMILES: *c1ncco1] |
| 1-1595 | Cl | 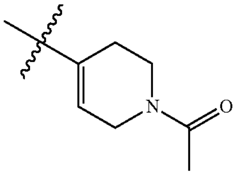 [SMILES: *C1=CCN(C(C)=O)CC1] | 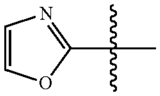 [SMILES: *c1ncco1] |
| 1-1596 | Cl | 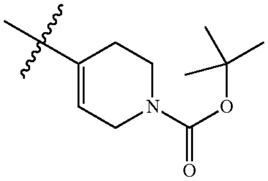 [SMILES: *C1=CCN(C(=O)OC(C)(C)C)CC1] | 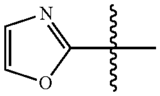 [SMILES: *c1ncco1] |
| 1-1597 | Cl | 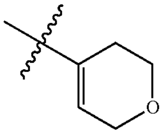 [SMILES: *C1=CCOCC1] | 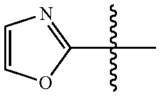 [SMILES: *c1ncco1] |
| 1-1598 | Cl | 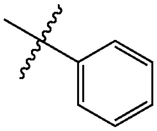 | 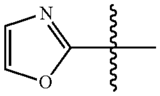 [SMILES: *c1ncco1] |

-continued
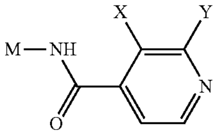
I
| NO. | X | Y | M |
|---|---|---|---|
| 1-1599 | Cl | 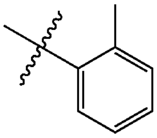 [SMILES: *c1ccccc1C] | 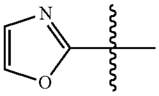 [SMILES: *c1ncco1] |
| 1-1600 | Cl | 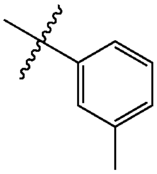 [SMILES: *c1cccc(C)c1] | 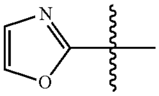 |
| 1-1601 | Cl | 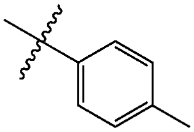 [SMILES: *c1ccc(C)cc1] | 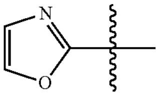 |
| 1-1602 | Cl | 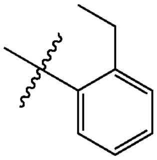 [SMILES: *c1ccccc1CC] | 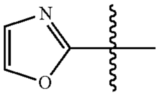 |
| 1-1603 | Cl | 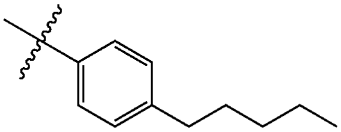 [SMILES: *c1ccc(CCCCC)cc1] | 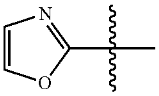 |
| 1-1604 | Cl | 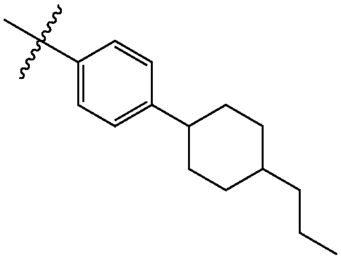 [SMILES: *c1ccc(C2CCC(CCC)CC2)cc1] | 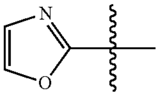 |
| 1-1605 | Cl | 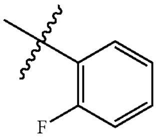 [SMILES: *c1ccccc1F] | 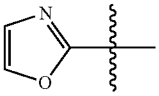 [SMILES: *c1ncco1] |
| 1-1606 | Cl | 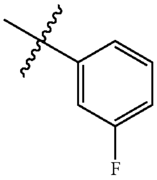 [SMILES: *c1cccc(F)c1] | 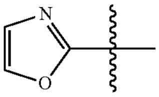 |

-continued
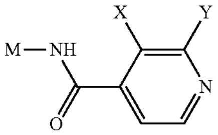
I
| NO. | X | Y | M |
|---|---|---|---|
| 1-1607 | Cl | 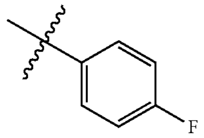 [SMILES: *c1ccc(F)cc1] | 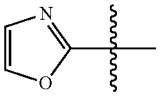 [SMILES: *c1ncco1] |
| 1-1608 | Cl | 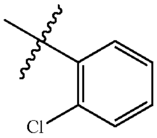 [SMILES: *c1ccccc1Cl] | 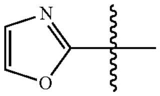 |
| 1-1609 | Cl | 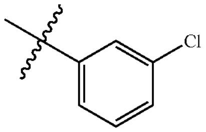 [SMILES: *c1cccc(Cl)c1] | 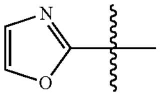 |
| 1-1610 | Cl | 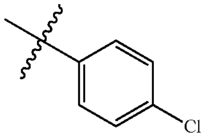 [SMILES: *c1ccc(Cl)cc1] | 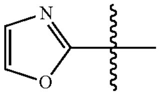 |
| 1-1611 | Cl | 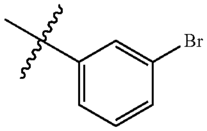 [SMILES: *c1cccc(Br)c1] | 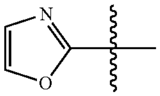 [SMILES: *c1ncco1] |
| 1-1612 | Cl | 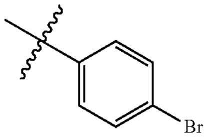 | 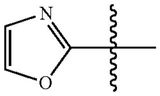 [SMILES: *c1ncco1] |
| 1-1613 | Cl | 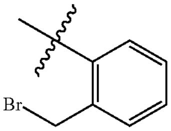 [SMILES: *c1ccccc1CBr] | 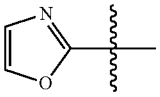 [SMILES: *c1ncco1] |
| 1-1614 | Cl | 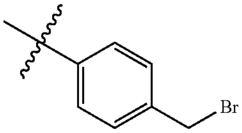 [SMILES: *c1ccc(CBr)cc1] | 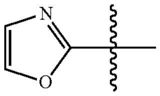 |
| 1-1615 | Cl | 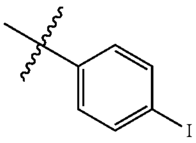 [SMILES: *c1ccc(I)cc1] | 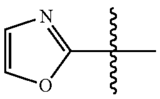 [SMILES: *c1ncco1] |

-continued
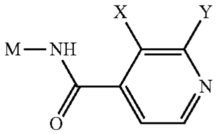
I
| NO. | X | Y | M |
|---|---|---|---|
| 1-1616 | Cl | 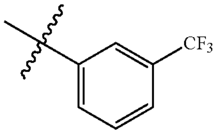 [SMILES: *c1cccc(C(F)(F)F)c1] | 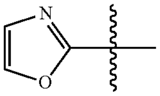 [SMILES: *c1ncco1] |
| 1-1617 | Cl | 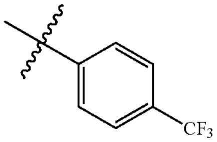 | 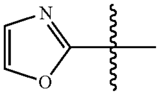 [SMILES: *c1ncco1] |
| 1-1618 | Cl | 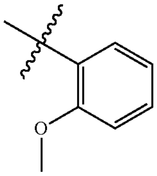 [SMILES: *c1ccccc1OC] | 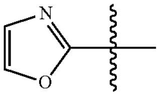 [SMILES: *c1ncco1] |
| 1-1619 | Cl | 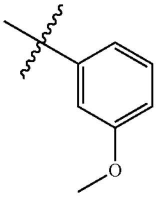 [SMILES: *c1cccc(OC)c1] | 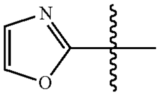 |
| 1-1620 | Cl | 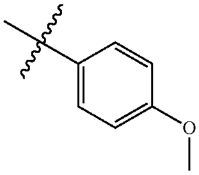 [SMILES: *c1ccc(OC)cc1] | 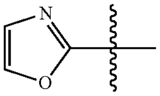 [SMILES: *c1ncco1] |
| 1-1621 | Cl | 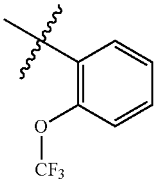 [SMILES: *c1ccccc1OC(F)(F)F] | 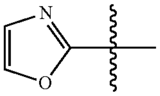 [SMILES: *c1ncco1] |
| 1-1622 | Cl | 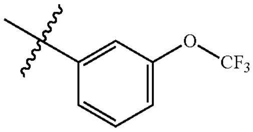 [SMILES: *c1cccc(OC(F)(F)F)c1] | 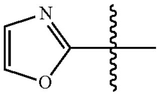 [SMILES: *c1ncco1] |
| 1-1623 | Cl | 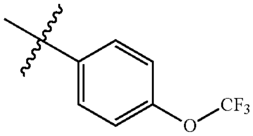 [SMILES: *c1ccc(OC(F)(F)F)cc1] | 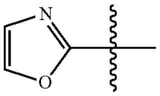 [SMILES: *c1ncco1] |

-continued
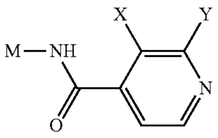
I
| NO. | X | Y | M |
|---|---|---|---|
| 1-1624 | Cl | 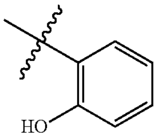 | 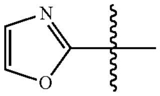 |
| 1-1625 | Cl | 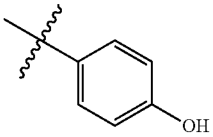 [SMILES: *c1ccc(O)cc1] | 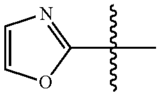 [SMILES: *c1ncco1] |
| 1-1626 | Cl | 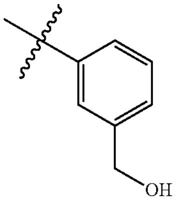 [SMILES: *c1cccc(CO)c1] | 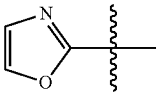 |
| 1-1627 | Cl | 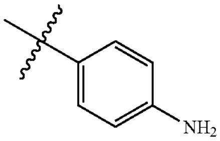 | 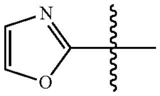 |
| 1-1628 | Cl | 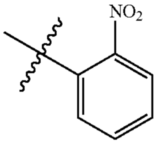 [SMILES: *c1ccccc1[N+](=O)[O-]] | 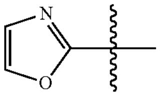 [SMILES: *c1ncco1] |
| 1-1629 | Cl | 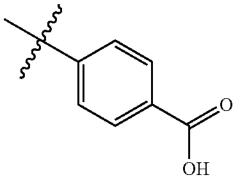 [SMILES: *c1ccc(C(=O)O)cc1] | 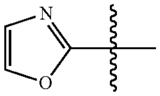 [SMILES: *c1ncco1] |
| 1-1630 | Cl | 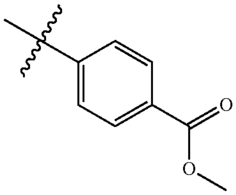 [SMILES: *c1ccc(C(=O)OC)cc1] | 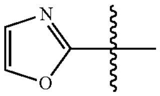 [SMILES: *c1ncco1] |

-continued
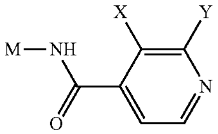
I
| NO. | X | Y | M |
|---|---|---|---|
| 1-1631 | Cl | 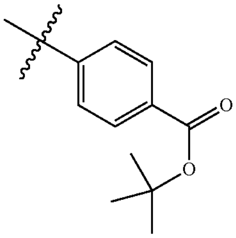 [SMILES: *c1ccc(C(=O)OC(C)(C)C)cc1] | 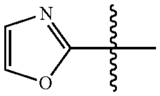 [SMILES: *c1ncco1] |
| 1-1632 | Cl | 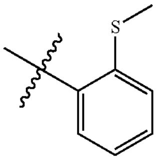 [SMILES: *c1ccccc1SC] | 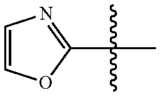 [SMILES: *c1ncco1] |
| 1-1633 | Cl | 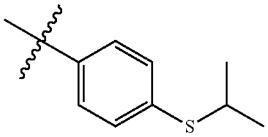 [SMILES: *c1ccc(SC(C)C)cc1] | 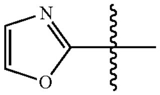 [SMILES: *c1ncco1] |
| 1-1634 | Cl | 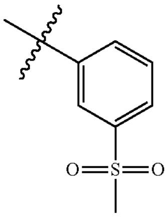 [SMILES: *c1cccc(S(C)(=O)=O)c1] | 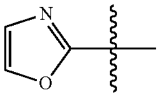 [SMILES: *c1ncco1] |
| 1-1635 | Cl | 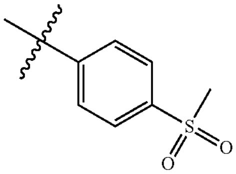 [SMILES: *c1ccc(S(C)(=O)=O)cc1] | 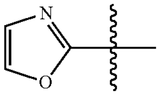 |
| 1-1636 | Cl | 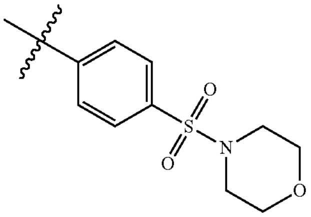 [SMILES: *c1ccc(S(=O)(=O)N2CCOCC2)cc1] | 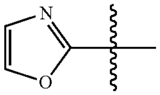 [SMILES: *c1ncco1] |
| 1-1637 | Cl | 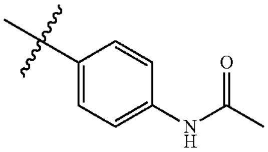 [SMILES: *c1ccc(NC(C)=O)cc1] | 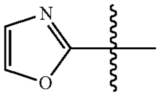 [SMILES: *c1ncco1] |

-continued
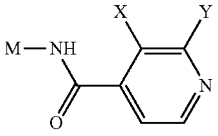
I
| NO. | X | Y | M |
|---|---|---|---|
| 1-1638 | Cl | 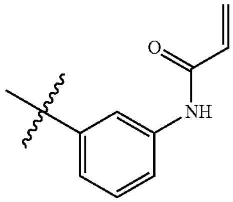 [SMILES: *c1cccc(NC(=O)C=C)c1] | 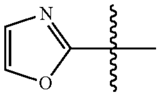 [SMILES: *c1ncco1] |
| 1-1639 | Cl | 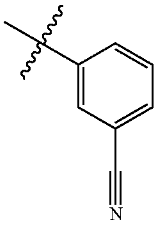 [SMILES: *c1cccc(C#N)c1] | 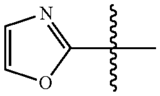 |
| 1-1640 | Cl | 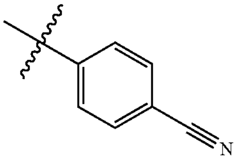 [SMILES: *c1ccc(C#N)cc1] | 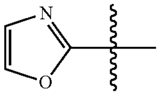 [SMILES: *c1ncco1] |
| 1-1641 | Cl | 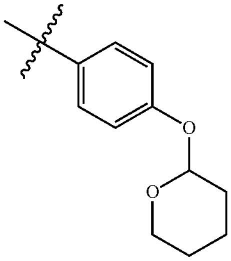 [SMILES: *c1ccc(OC2CCCCO2)cc1] | 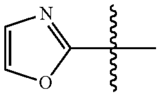 [SMILES: *c1ncco1] |
| 1-1642 | Cl | 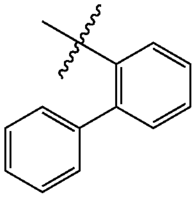 [SMILES: *c1ccccc1-c1ccccc1] | 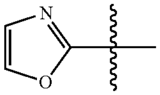 [SMILES: *c1ncco1] |
| 1-1643 | Cl | 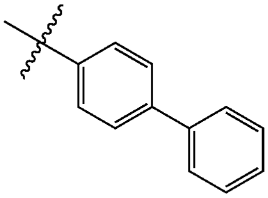 [SMILES: *c1ccc(-c2ccccc2)cc1] | 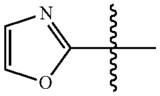 [SMILES: *c1ncco1] |

-continued
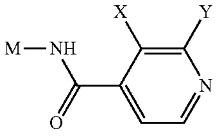
I
| NO. | X | Y | M |
|---|---|---|---|
| 1-1644 | Cl | 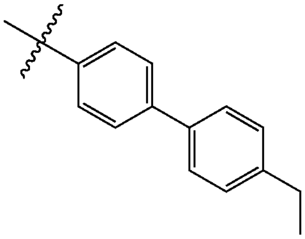 [SMILES: *c1ccc(-c2ccc(CC)cc2)cc1] | 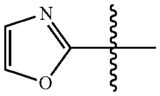 [SMILES: *c1ncco1] |
| 1-1645 | Cl | 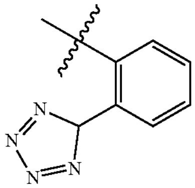 [SMILES: *c1ccccc1C1N=NN=N1] | 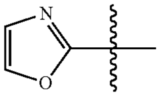 [SMILES: *c1ncco1] |
| 1-1646 | Cl | 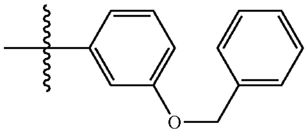 [SMILES: *c1cccc(OCc2ccccc2)c1] | 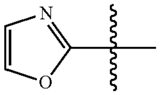 [SMILES: *c1ncco1] |
| 1-1647 | Cl | 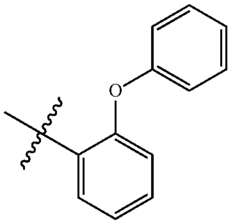 [SMILES: *c1ccccc1Oc1ccccc1] | 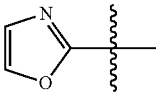 [SMILES: *c1ncco1] |
| 1-1648 | Cl | 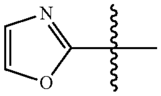 | 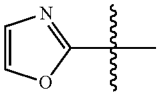 [SMILES: *c1ncco1] |
| 1-1649 | Cl | 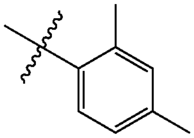 [SMILES: *c1ccc(C)cc1C] | 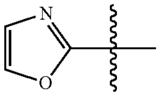 [SMILES: *c1ncco1] |
| 1-1650 | Cl | 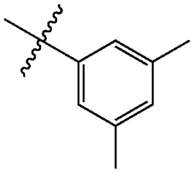 [SMILES: *c1cc(C)cc(C)c1] | 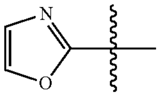 [SMILES: *c1ncco1] |

-continued
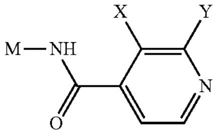
I
| NO. | X | Y | M |
|---|---|---|---|
| 1-1651 | Cl | 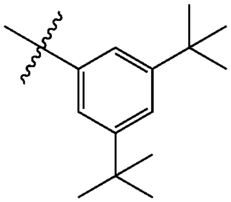 [SMILES: *c1cc(C(C)(C)C)cc(C(C)(C)C)c1] | 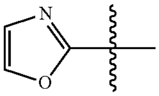 [SMILES: *c1ncco1] |
| 1-1652 | Cl | 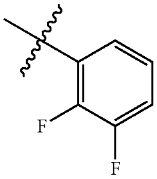 [SMILES: *c1cccc(F)c1F] | 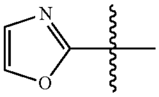 [SMILES: *c1ncco1] |
| 1-1653 | Cl | 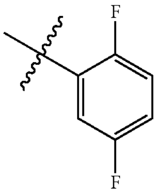 [SMILES: *c1cc(F)ccc1F] | 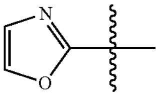 [SMILES: *c1ncco1] |
| 1-1654 | Cl | 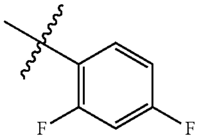 [SMILES: *c1ccc(F)cc1F] | 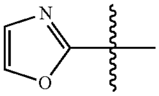 [SMILES: *c1ncco1] |
| 1-1655 | Cl | 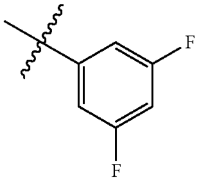 [SMILES: *c1cc(F)cc(F)c1] | 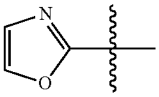 [SMILES: *c1ncco1] |
| 1-1656 | Cl | 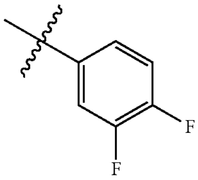 [SMILES: *c1ccc(F)c(F)c1] | 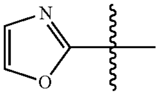 [SMILES: *c1ncco1] |
| 1-1657 | Cl | 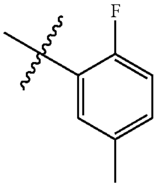 [SMILES: *c1cc(C)ccc1F] | 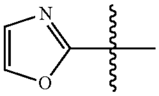 [SMILES: *c1ncco1] |

-continued
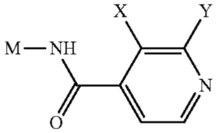
I
| NO. | X | Y | M |
|---|---|---|---|
| 1-1658 | Cl | 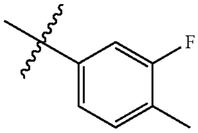 [SMILES: *c1ccc(C)c(F)c1] | 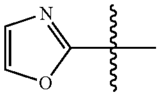 |
| 1-1659 | Cl | 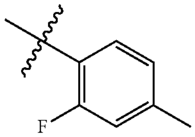 [SMILES: *c1ccc(C)cc1F] | 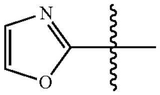 [SMILES: *c1ncco1] |
| 1-1660 | Cl | 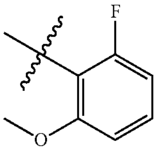 [SMILES: *c1c(F)cccc1OC] | 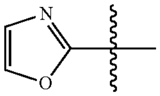 [SMILES: *c1ncco1] |
| 1-1661 | Cl | 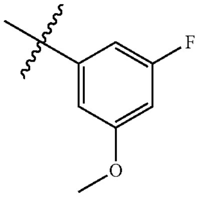 [SMILES: *c1cc(F)cc(OC)c1] | 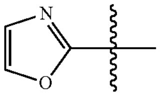 |
| 1-1662 | Cl | 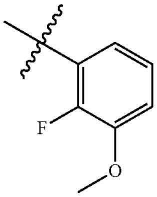 [SMILES: *c1cccc(OC)c1F] | 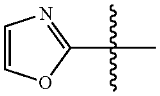 [SMILES: *c1ncco1] |
| 1-1663 | Cl | 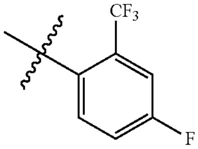 [SMILES: *c1ccc(F)cc1C(F)(F)F] | 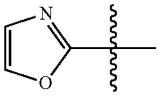 [SMILES: *c1ncco1] |
| 1-1664 | Cl | 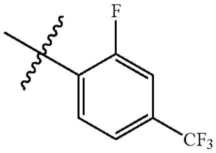 | 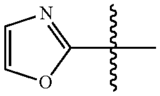 [SMILES: *c1ncco1] |
| 1-1665 | Cl | 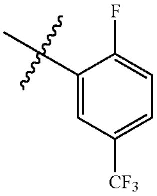 [SMILES: *c1cc(C(F)(F)F)ccc1F] | 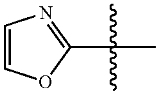 [SMILES: *c1ncco1] |

-continued
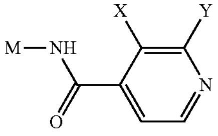
I
| NO. | X | Y | M |
|---|---|---|---|
| 1-1666 | Cl | 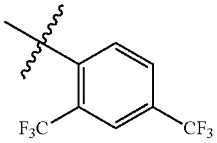 | 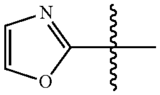 |
| 1-1667 | Cl | 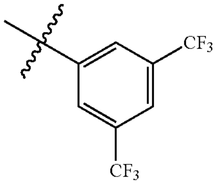 [SMILES: *c1cc(C(F)(F)F)cc(C(F)(F)F)c1] | 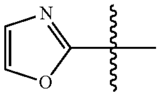 [SMILES: *c1ncco1] |
| 1-1668 | Cl | 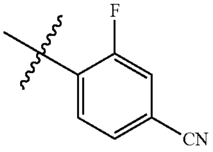 [SMILES: *c1ccc(C#N)cc1F] | 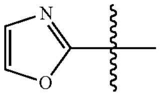 [SMILES: *c1ncco1] |
| 1-1669 | Cl | 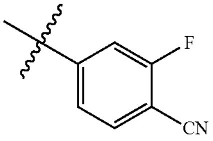 [SMILES: *c1ccc(C#N)c(F)c1] | 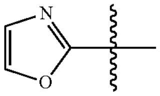 [SMILES: *c1ncco1] |
| 1-1670 | Cl | 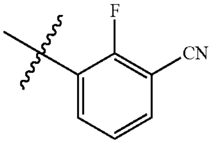 [SMILES: *c1cccc(C#N)c1F] | 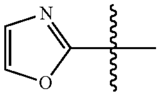 [SMILES: *c1ncco1] |
| 1-1671 | Cl | 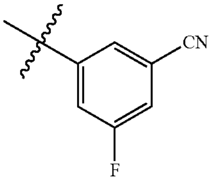 [SMILES: *c1cc(F)cc(C#N)c1] | 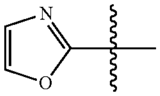 [SMILES: *c1ncco1] |
| 1-1672 | Cl | 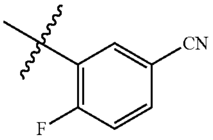 [SMILES: *c1cc(C#N)ccc1F] | 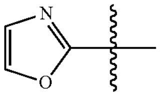 [SMILES: *c1ncco1] |
| 1-1673 | Cl | 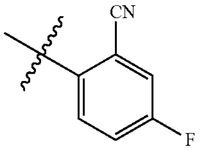 [SMILES: *c1ccc(F)cc1C#N] | 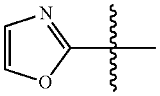 |

-continued
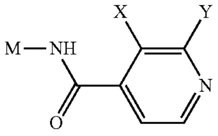
I
| NO. | X | Y | M |
|---|---|---|---|
| 1-1674 | Cl | 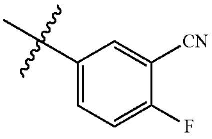 [SMILES: *c1ccc(F)c(C#N)c1] | 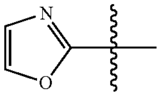 [SMILES: *c1ncco1] |
| 1-1675 | Cl | 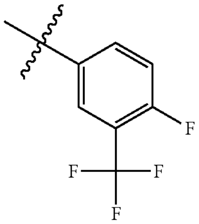 [SMILES: *c1ccc(F)c(C(F)(F)F)c1] | 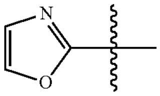 |
| 1-1676 | Cl | 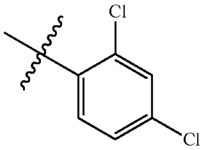 | 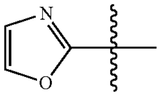 [SMILES: *c1ncco1] |
| 1-1677 | Cl | 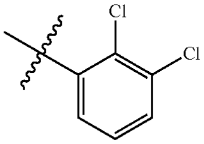 | 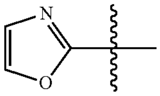 [SMILES: *c1ncco1] |
| 1-1678 | Cl | 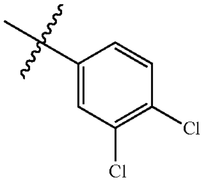 [SMILES: *c1ccc(Cl)c(Cl)c1] | 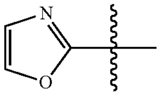 [SMILES: *c1ncco1] |
| 1-1679 | Cl | 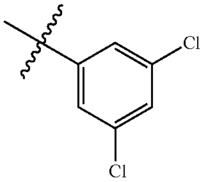 [SMILES: *c1cc(Cl)cc(Cl)c1] | 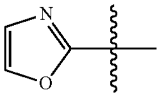 [SMILES: *c1ncco1] |
| 1-1680 | Cl | 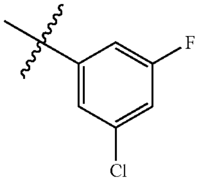 [SMILES: *c1cc(F)cc(Cl)c1] | 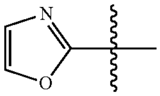 [SMILES: *c1ncco1] |

-continued
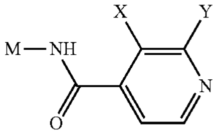
I
| NO. | X | Y | M |
|---|---|---|---|
| 1-1681 | Cl | 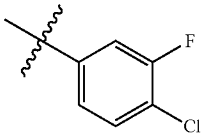 [SMILES: *c1ccc(Cl)c(F)c1] | 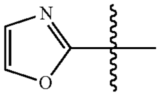 |
| 1-1682 | Cl | 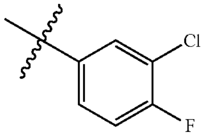 [SMILES: *c1ccc(F)c(Cl)c1] | 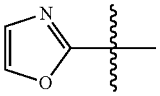 [SMILES: *c1ncco1] |
| 1-1683 | Cl | 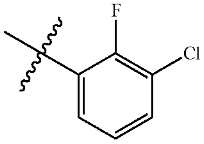 [SMILES: *c1cccc(Cl)c1F] | 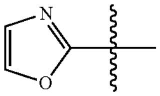 [SMILES: *c1ncco1] |
| 1-1684 | Cl | 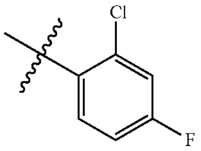 [SMILES: *c1ccc(F)cc1Cl] | 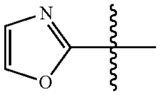 [SMILES: *c1ncco1] |
| 1-1685 | Cl | 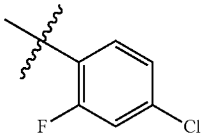 [SMILES: *c1ccc(Cl)cc1F] | 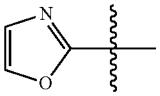 [SMILES: *c1ncco1] |
| 1-1686 | Cl | 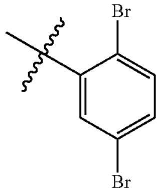 [SMILES: *c1cc(Br)ccc1Br] | 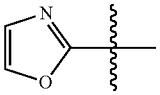 [SMILES: *c1ncco1] |
| 1-1687 | Cl | 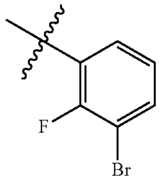 | 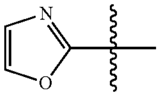 [SMILES: *c1ncco1] |
| 1-1688 | Cl | 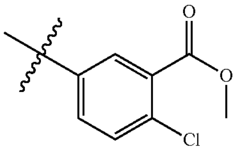 [SMILES: *c1ccc(Cl)c(C(=O)OC)c1] | 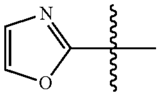 [SMILES: *c1ncco1] |

-continued
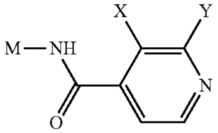
I
| NO. | X | Y | M |
|---|---|---|---|
| 1-1689 | Cl | 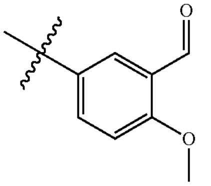 [SMILES: *c1ccc(OC)c(C=O)c1] | 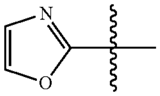 [SMILES: *c1ncco1] |
| 1-1690 | Cl | 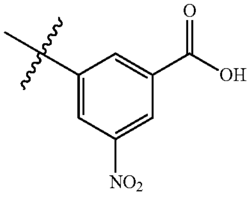 [SMILES: *c1cc(C(=O)O)cc([N+](=O)[O-])c1] | 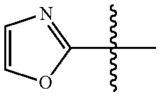 |
| 1-1691 | Cl | 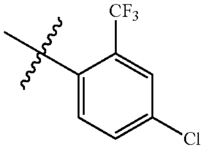 | 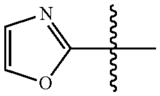 [SMILES: *c1ncco1] |
| 1-1692 | Cl | 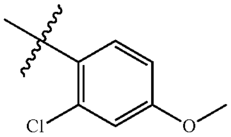 [SMILES: *c1ccc(OC)cc1Cl] | 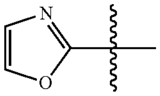 [SMILES: *c1ncco1] |
| 1-1693 | Cl | 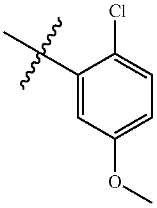 [SMILES: *c1cc(OC)ccc1Cl] | 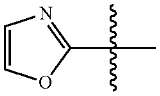 [SMILES: *c1ncco1] |
| 1-1694 | Cl | 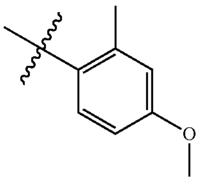 [SMILES: *c1ccc(OC)cc1C] | 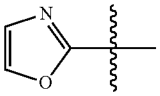 [SMILES: *c1ncco1] |
| 1-1695 | Cl | 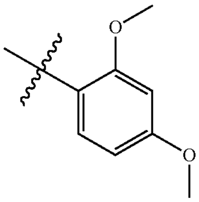 [SMILES: *c1ccc(OC)cc1OC] | 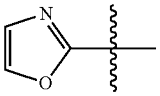 [SMILES: *c1ncco1] |

-continued
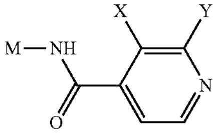
I
| NO. | X | Y | M |
|---|---|---|---|
| 1-1696 | Cl | 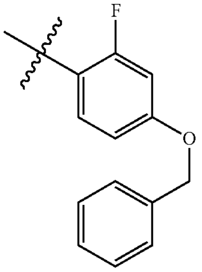 [SMILES: *c1ccc(OCc2ccccc2)cc1F] | 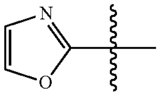 [SMILES: *c1ncco1] |
| 1-1697 | Cl | 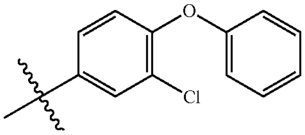 [SMILES: *c1ccc(Oc2ccccc2)c(Cl)c1] | 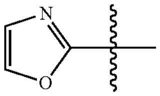 [SMILES: *c1ncco1] |
| 1-1698 | Cl | 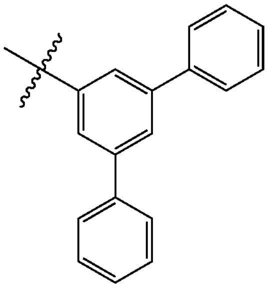 [SMILES: *c1cc(-c2ccccc2)cc(-c2ccccc2)c1] | 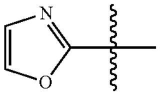 [SMILES: *c1ncco1] |
| 1-1699 | Cl | 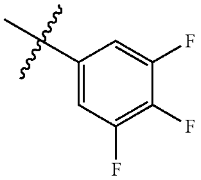 [SMILES: *c1cc(F)c(F)c(F)c1] | 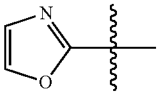 [SMILES: *c1ncco1] |
| 1-1700 | Cl | 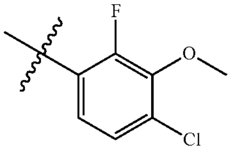 [SMILES: *c1ccc(Cl)c(OC)c1F] | 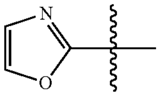 [SMILES: *c1ncco1] |
| 1-1701 | Cl | 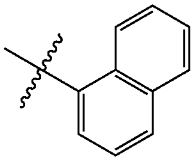 [SMILES: *c1cccc2ccccc12] | 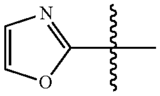 [SMILES: *c1ncco1] |
| 1-1702 | Cl | 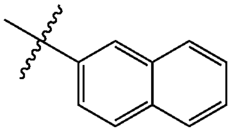 [SMILES: *c1ccc2ccccc2c1] | 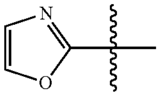 [SMILES: *c1ncco1] |

-continued
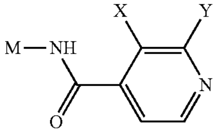
I
| NO. | X | Y | M |
|---|---|---|---|
| 1-1703 | Cl | 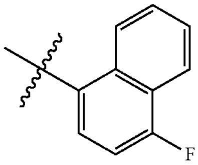 [SMILES: *c1ccc(F)c2ccccc12] | 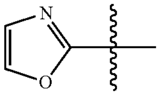 |
| 1-1704 | Cl | 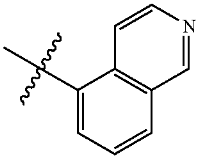 [SMILES: *c1cccc2cnccc12] | 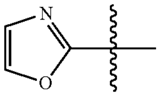 [SMILES: *c1ncco1] |
| 1-1705 | Cl | 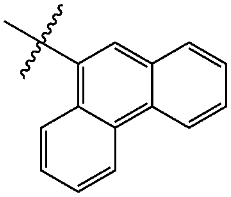 [SMILES: *c1cc2ccccc2c2ccccc12] | 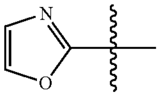 |
| 1-1706 | Cl | 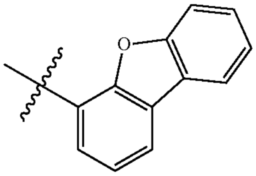 [SMILES: *c1cccc2c1oc1ccccc12] | 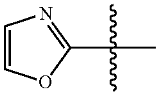 [SMILES: *c1ncco1] |
| 1-1707 | Cl | 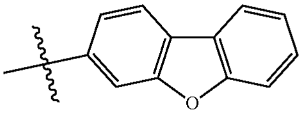 [SMILES: *c1ccc2c(c1)oc1ccccc12] | 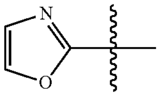 [SMILES: *c1ncco1] |
| 1-1708 | Cl | 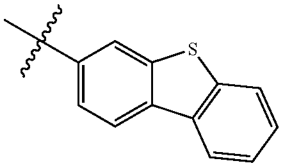 [SMILES: *c1ccc2c(c1)sc1ccccc12] | 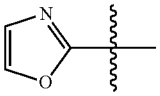 [SMILES: *c1ncco1] |
| 1-1709 | Cl | 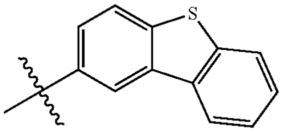 [SMILES: *c1ccc2sc3ccccc3c2c1] | 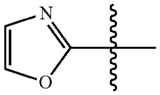 [SMILES: *c1ncco1] |
| 1-1710 | Cl | 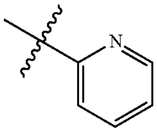 [SMILES: *c1ccccn1] | 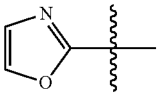 [SMILES: *c1ncco1] |

-continued
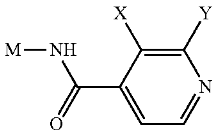
I
| NO. | X | Y | M |
|---|---|---|---|
| 1-1711 | Cl | 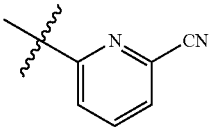 [SMILES: *c1cccc(C#N)n1] | 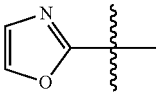 |
| 1-1712 | Cl | 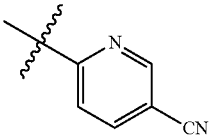 | 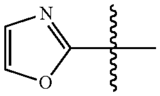 [SMILES: *c1ncco1] |
| 1-1713 | Cl | 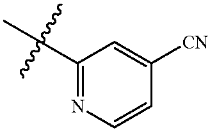 [SMILES: *c1cc(C#N)ccn1] | 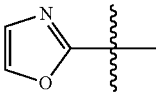 [SMILES: *c1ncco1] |
| 1-1714 | Cl | 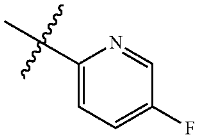 [SMILES: *c1ccc(F)cn1] | 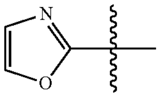 [SMILES: *c1ncco1] |
| 1-1715 | Cl | 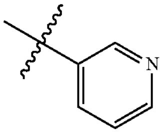 [SMILES: *c1cccnc1] | 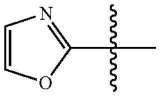 [SMILES: *c1ncco1] |
| 1-1716 | Cl | 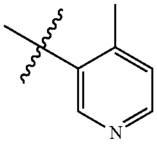 [SMILES: *c1cnccc1C] | 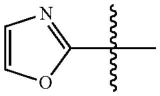 [SMILES: *c1ncco1] |
| 1-1717 | Cl | 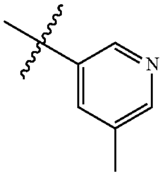 [SMILES: *c1cncc(C)c1] | 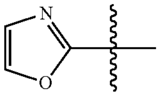 [SMILES: *c1ncco1] |
| 1-1718 | Cl | 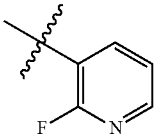 [SMILES: *c1cccnc1F] | 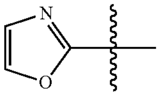 [SMILES: *c1ncco1] |

-continued
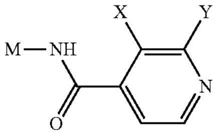
I
| NO. | X | Y | M |
|---|---|---|---|
| 1-1719 | Cl | 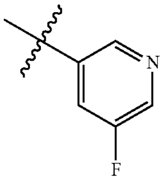 [SMILES: *c1cncc(F)c1] | 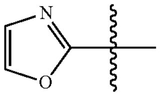 [SMILES: *c1ncco1] |
| 1-1720 | Cl | 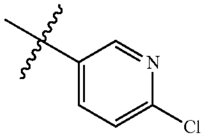 [SMILES: *c1ccc(Cl)nc1] | 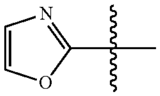 [SMILES: *c1ncco1] |
| 1-1721 | Cl | 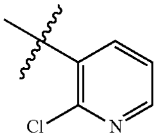 [SMILES: *c1cccnc1Cl] | 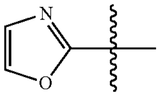 [SMILES: *c1ncco1] |
| 1-1722 | Cl | 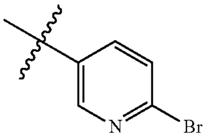 [SMILES: *c1ccc(Br)nc1] | 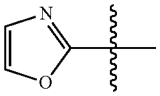 [SMILES: *c1ncco1] |
| 1-1723 | Cl | 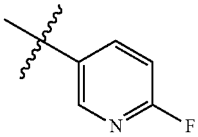 [SMILES: *c1ccc(F)nc1] | 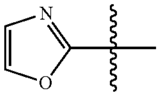 [SMILES: *c1ncco1] |
| 1-1724 | Cl | 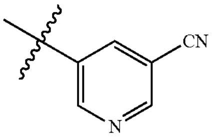 [SMILES: *c1cncc(C#N)c1] | 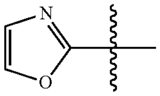 [SMILES: *c1ncco1] |
| 1-1725 | Cl | 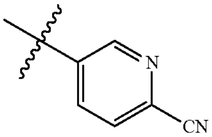 [SMILES: *c1ccc(C#N)nc1] | 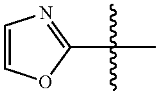 [SMILES: *c1ncco1] |
| 1-1726 | Cl | 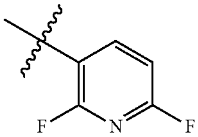 | 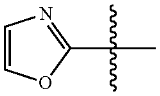 |
| 1-1727 | Cl | 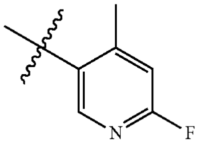 [SMILES: *c1cnc(F)cc1C] | 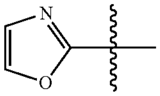 [SMILES: *c1ncco1] |

-continued
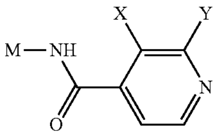
I
| NO. | X | Y | M |
|---|---|---|---|
| 1-1728 | Cl | 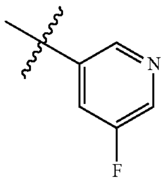 [SMILES: *c1cncc(F)c1] | 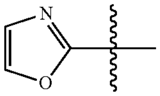 |
| 1-1729 | Cl | 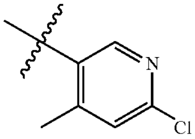 [SMILES: *c1cnc(Cl)cc1C] | 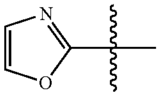 |
| 1-1730 | Cl | 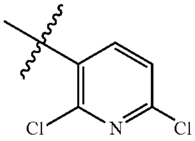 [SMILES: *c1ccc(Cl)nc1Cl] | 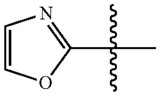 [SMILES: *c1ncco1] |
| 1-1731 | Cl | 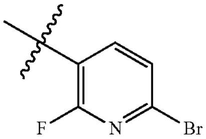 [SMILES: *c1ccc(Br)nc1F] | 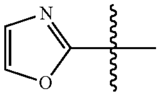 [SMILES: *c1ncco1] |
| 1-1732 | Cl | 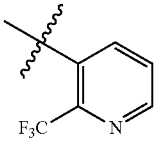 [SMILES: *c1cccnc1C(F)(F)F] | 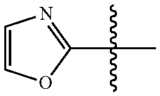 [SMILES: *c1ncco1] |
| 1-1733 | Cl | 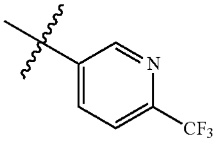 | 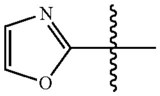 [SMILES: *c1ncco1] |
| 1-1734 | Cl | 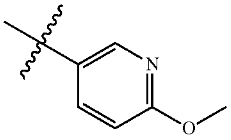 [SMILES: *c1ccc(OC)nc1] | 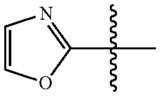 |
| 1-1735 | Cl | 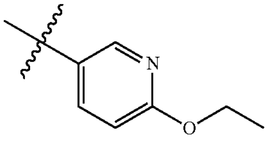 [SMILES: *c1ccc(OCC)nc1] | 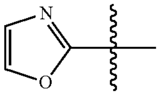 |

-continued
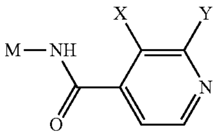
I
| NO. | X | Y | M |
|---|---|---|---|
| 1-1736 | Cl | 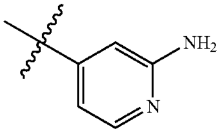 [SMILES: *c1ccnc(N)c1] | 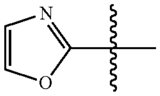 |
| 1-1737 | Cl | 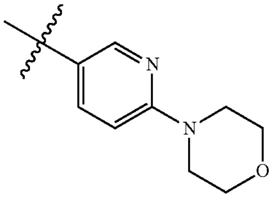 [SMILES: *c1ccc(N2CCOCC2)nc1] | 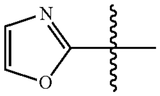 [SMILES: *c1ncco1] |
| 1-1738 | Cl | 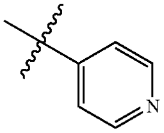 [SMILES: *c1ccncc1] | 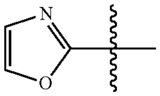 |
| 1-1739 | Cl | 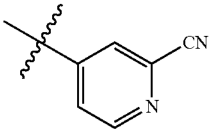 [SMILES: *c1ccnc(C#N)c1] | 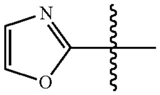 |
| 1-1740 | Cl | 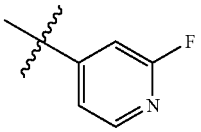 [SMILES: *c1ccnc(F)c1] | 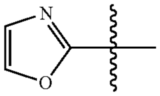 [SMILES: *c1ncco1] |
| 1-1741 | Cl | 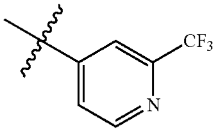 [SMILES: *c1ccnc(C(F)(F)F)c1] | 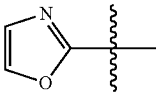 [SMILES: *c1ncco1] |
| 1-1742 | Cl | 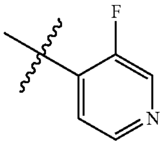 [SMILES: *c1ccncc1F] | 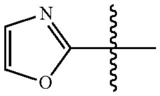 [SMILES: *c1ncco1] |
| 1-1743 | Cl | 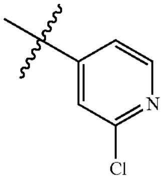 [SMILES: *c1ccnc(Cl)c1] | 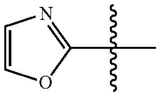 |

-continued
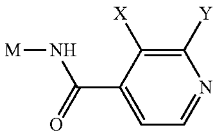
I
| NO. | X | Y | M |
| --- | --- | --- | --- |
| 1-1744 | Cl | 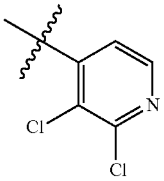 [SMILES: *c1ccnc(Cl)c1Cl] | 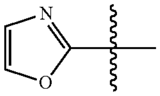 [SMILES: *c1ncco1] |
| 1-1745 | Cl | 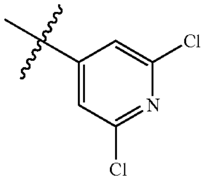 [SMILES: *c1cc(Cl)nc(Cl)c1] | 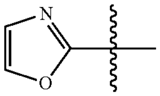 [SMILES: *c1ncco1] |
| 1-1746 | Cl | 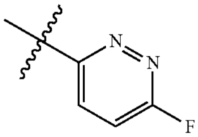 [SMILES: *c1ccc(F)nn1] | 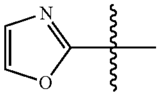 [SMILES: *c1ncco1] |
| 1-1747 | Cl | 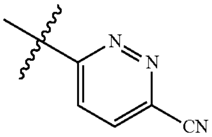 [SMILES: *c1ccc(C#N)nn1] | 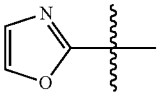 |
| 1-1748 | Cl | 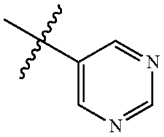 [SMILES: *c1cncnc1] | 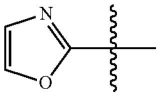 [SMILES: *c1ncco1] |
| 1-1749 | Cl | 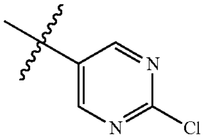 [SMILES: *c1cnc(Cl)nc1] | 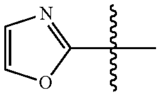 |
| 1-1750 | Cl | 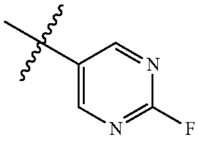 [SMILES: *c1cnc(F)nc1] | 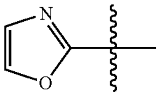 [SMILES: *c1ncco1] |
| 1-1751 | Cl | 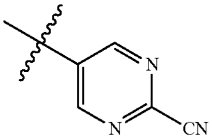 [SMILES: *c1cnc(C#N)nc1] | 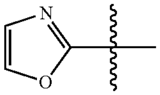 [SMILES: *c1ncco1] |

-continued
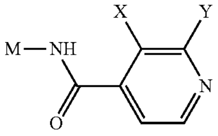
I
| NO. | X | Y | M |
|---|---|---|---|
| 1-1752 | Cl | 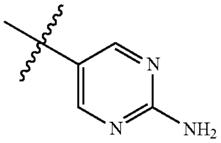 | 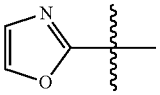 [SMILES: *c1ncco1] |
| 1-1753 | Cl | 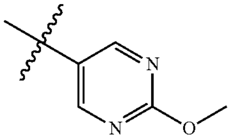 [SMILES: *c1cnc(OC)nc1] | 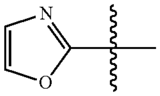 [SMILES: *c1ncco1] |
| 1-1754 | Cl | 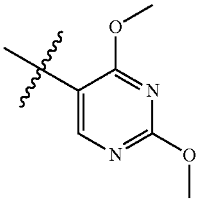 [SMILES: *c1cnc(OC)nc1OC] | 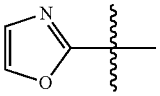 |
| 1-1755 | Cl | 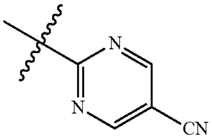 | 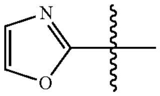 |
| 1-1756 | Cl | 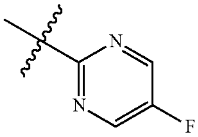 | 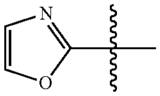 [SMILES: *c1ncco1] |
| 1-1757 | Cl | 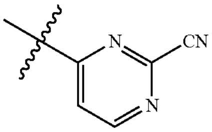 [SMILES: *c1ccnc(C#N)n1] | 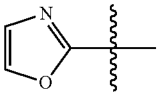 [SMILES: *c1ncco1] |
| 1-1758 | Cl | 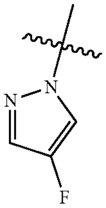 [SMILES: *n1cc(F)cn1] | 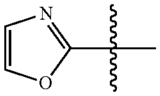 [SMILES: *c1ncco1] |
| 1-1759 | Cl | 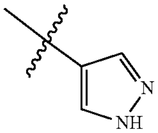 [SMILES: *c1cn[nH]c1] | 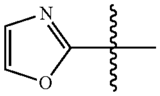 [SMILES: *c1ncco1] |

-continued
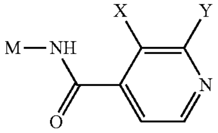
I
| NO. | X | Y | M |
|---|---|---|---|
| 1-1760 | Cl | 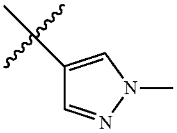 [SMILES: *c1cnn(C)c1] | 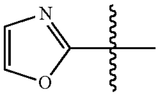 |
| 1-1761 | Cl | 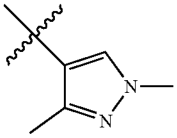 | 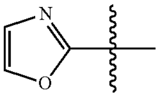 |
| 1-1762 | Cl | 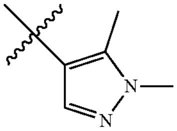 [SMILES: *c1cnn(C)c1C] | 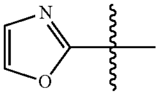 [SMILES: *c1ncco1] |
| 1-1763 | Cl | 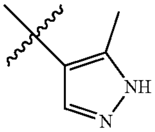 [SMILES: *c1cn[nH]c1C] | 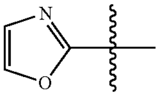 [SMILES: *c1ncco1] |
| 1-1764 | Cl | 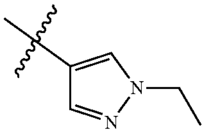 [SMILES: *c1cnn(CC)c1] | 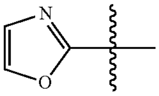 [SMILES: *c1ncco1] |
| 1-1765 | Cl | 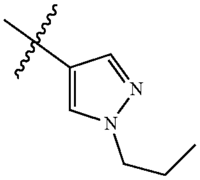 [SMILES: *c1cnn(CCC)c1] | 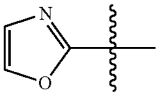 [SMILES: *c1ncco1] |
| 1-1766 | Cl | 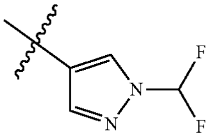 [SMILES: *c1cnn(C(F)F)c1] | 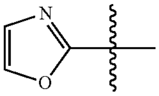 [SMILES: *c1ncco1] |
| 1-1767 | Cl | 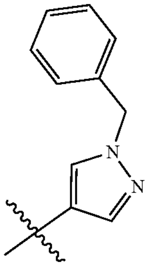 [SMILES: *c1cnn(Cc2ccccc2)c1] | 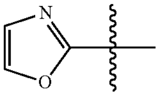 [SMILES: *c1ncco1] |

-continued
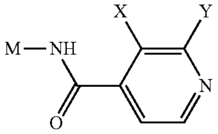
I
| NO. | X | Y | M |
|---|---|---|---|
| 1-1768 | Cl | 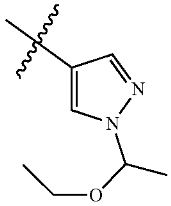 [SMILES: *c1cnn(C(C)OCC)c1] | 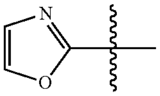 [SMILES: *c1ncco1] |
| 1-1769 | Cl | 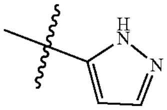 [SMILES: *c1ccn[nH]1] | 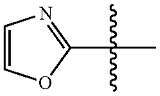 [SMILES: *c1ncco1] |
| 1-1770 | Cl | 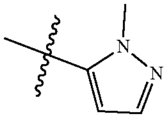 [SMILES: *c1ccnn1C] | 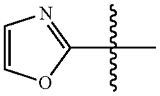 [SMILES: *c1ncco1] |
| 1-1771 | Cl | 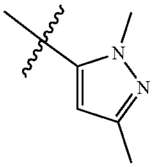 [SMILES: *c1cc(C)nn1C] | 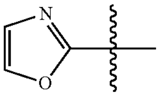 |
| 1-1772 | Cl | 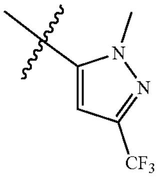 [SMILES: *c1cc(C(F)(F)F)nn1C] | 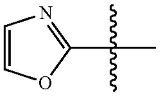 [SMILES: *c1ncco1] |
| 1-1773 | Cl | 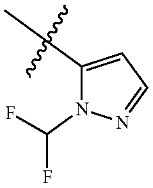 [SMILES: *c1ccnn1C(F)F] | 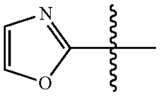 |
| 1-1774 | Cl | 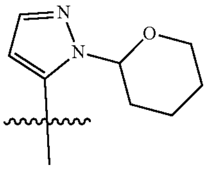 [SMILES: *c1ccnn1C1CCCCO1] | 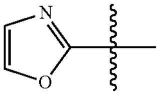 |
| 1-1775 | Cl | 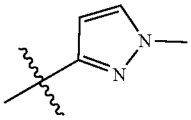 [SMILES: *c1ccn(C)n1] | 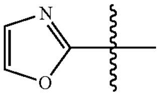 [SMILES: *c1ncco1] |

-continued
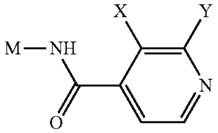
I
| NO. | X | Y | M |
| --- | --- | --- | --- |
| 1-1776 | Cl | 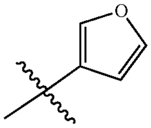 [SMILES: *c1ccoc1] | 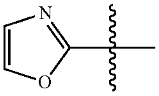 |
| 1-1777 | Cl | 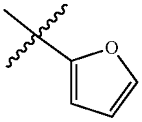 [SMILES: *c1ccco1] | 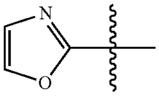 |
| 1-1778 | Cl | 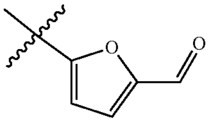 [SMILES: *c1ccc(C=O)o1] | 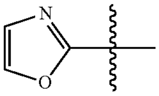 [SMILES: *c1ncco1] |
| 1-1779 | Cl | 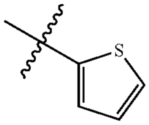 [SMILES: *c1cccs1] | 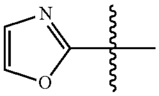 [SMILES: *c1ncco1] |
| 1-1780 | Cl | 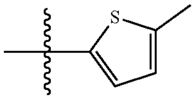 | 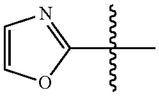 [SMILES: *c1ncco1] |
| 1-1781 | Cl | 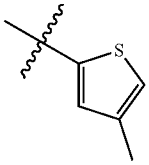 [SMILES: *c1cc(C)cs1] | 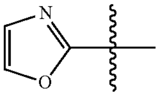 [SMILES: *c1ncco1] |
| 1-1782 | Cl | 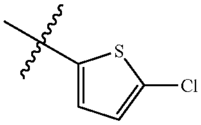 [SMILES: *c1ccc(Cl)s1] | 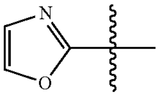 [SMILES: *c1ncco1] |
| 1-1783 | Cl | 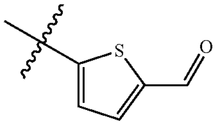 [SMILES: *c1ccc(C=O)s1] | 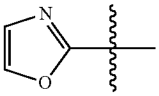 [SMILES: *c1ncco1] |
| 1-1784 | Cl | 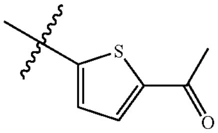 [SMILES: *c1ccc(C(C)=O)s1] | 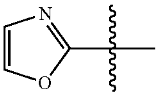 [SMILES: *c1ncco1] |
| 1-1785 | Cl | 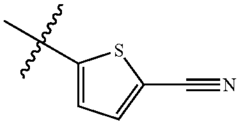 | 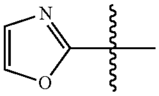 |

-continued
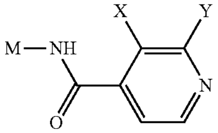
I
| NO. | X | Y | M |
|---|---|---|---|
| 1-1786 | Cl | 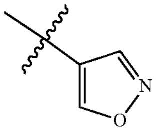 [SMILES: *c1cnoc1] | 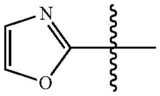 [SMILES: *c1ncco1] |
| 1-1787 | $CH_3$ | 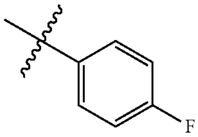 [SMILES: *c1ccc(F)cc1] | 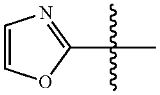 |
| 1-1788 | F | 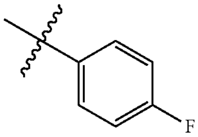 [SMILES: *c1ccc(F)cc1] | 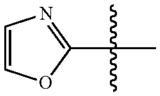 [SMILES: *c1ncco1] |
| 1-1789 | Br | 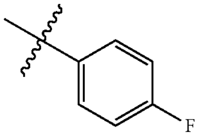 [SMILES: *c1ccc(F)cc1] | 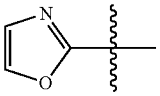 [SMILES: *c1ncco1] |
| 1-1790 | 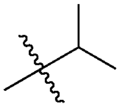 [SMILES: *C(C)C] | 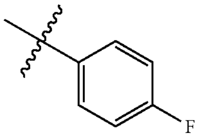 [SMILES: *c1ccc(F)cc1] | 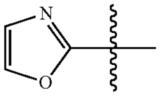 [SMILES: *c1ncco1] |
| 1-1791 | $CF_3$ | 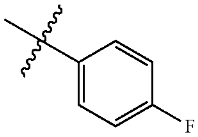 | 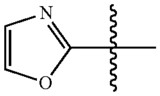 [SMILES: *c1ncco1] |
| 1-1792 | 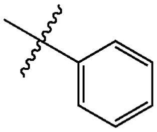 [SMILES: *c1ccccc1] | 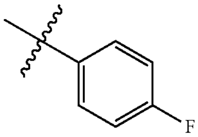 [SMILES: *c1ccc(F)cc1] | 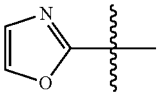 [SMILES: *c1ncco1] |
| 1-1793 | 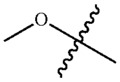 [SMILES: *OC] | 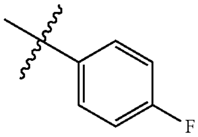 [SMILES: *c1ccc(F)cc1] | 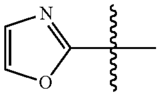 |
| 1-1794 | 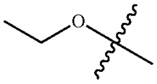 [SMILES: *OCC] | 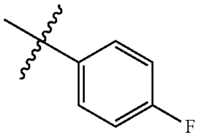 [SMILES: *c1ccc(F)cc1] | 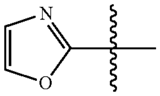 |

-continued
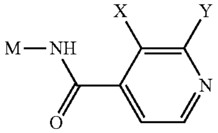
I
| NO. | X | Y | M |
|---|---|---|---|
| 1-1795 | 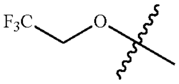 [SMILES: *OCC(F)(F)F] | 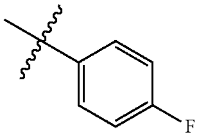 [SMILES: *c1ccc(F)cc1] | 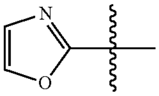 |
| 1-1796 | 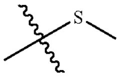 [SMILES: *SC] | 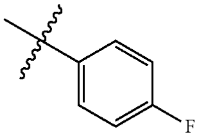 [SMILES: *c1ccc(F)cc1] | 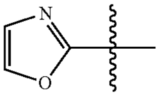 [SMILES: *c1ncco1] |
| 1-1797 | 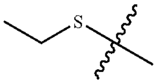 | 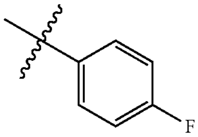 [SMILES: *c1ccc(F)cc1] | 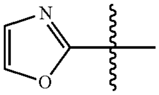 [SMILES: *c1ncco1] |
| 1-1798 | 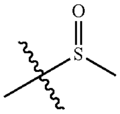 [SMILES: *S(C)=O] | 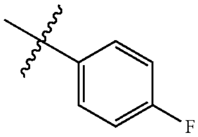 [SMILES: *c1ccc(F)cc1] | 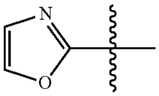 [SMILES: *c1ncco1] |
| 1-1799 | 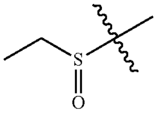 [SMILES: *S(=O)CC] | 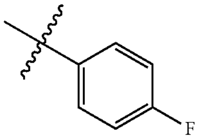 [SMILES: *c1ccc(F)cc1] | 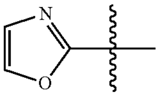 |
| 1-1800 | 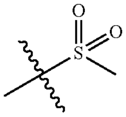 | 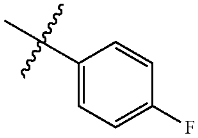 [SMILES: *c1ccc(F)cc1] | 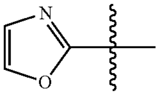 [SMILES: *c1ncco1] |
| 1-1801 | 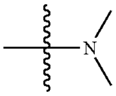 [SMILES: *N(C)C] | 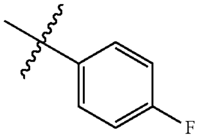 [SMILES: *c1ccc(F)cc1] | 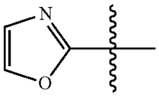 |
| 1-1802 | 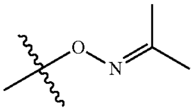 [SMILES: *ON=C(C)C] | 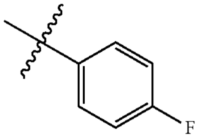 [SMILES: *c1ccc(F)cc1] | 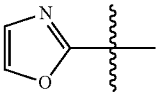 [SMILES: *c1ncco1] |
| 1-1803 | Et | 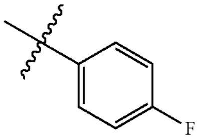 [SMILES: *c1ccc(F)cc1] | 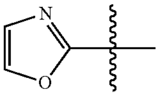 [SMILES: *c1ncco1] |

-continued
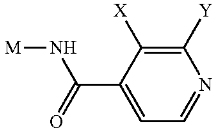
I
| NO. | X | Y | M |
|---|---|---|---|
| 1-1804 | 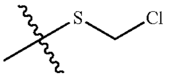 [SMILES: *SCCl] | 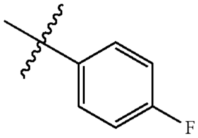 [SMILES: *c1ccc(F)cc1] | 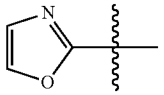 [SMILES: *c1ncco1] |
| 1-1805 | $NO_2$ | 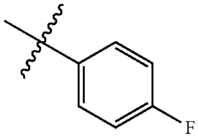 [SMILES: *c1ccc(F)cc1] | 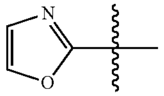 [SMILES: *c1ncco1] |
| 1-1806 | CN | 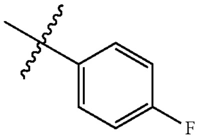 [SMILES: *c1ccc(F)cc1] | 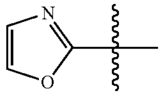 [SMILES: *c1ncco1] |
| 1-1807 | 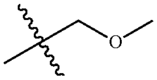 [SMILES: *COC] | 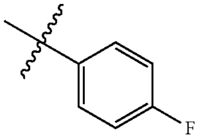 [SMILES: *c1ccc(F)cc1] | 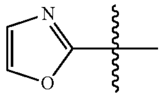 [SMILES: *c1ncco1] |
| 1-1808 | 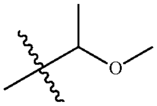 [SMILES: *C(C)OC] | 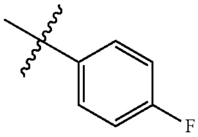 [SMILES: *c1ccc(F)cc1] | 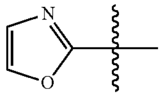 [SMILES: *c1ncco1] |
| 1-1809 | 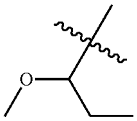 | 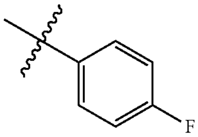 [SMILES: *c1ccc(F)cc1] | 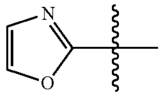 [SMILES: *c1ncco1] |
| 1-1810 | 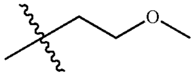 [SMILES: *CCOC] | 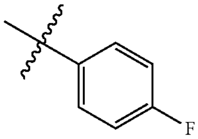 [SMILES: *c1ccc(F)cc1] | 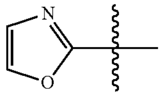 [SMILES: *c1ncco1] |
| 1-1811 | 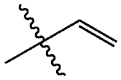 [SMILES: *C=C] | 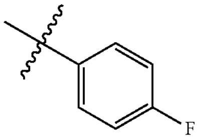 [SMILES: *c1ccc(F)cc1] | 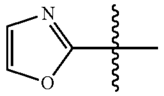 [SMILES: *c1ncco1] |
| 1-1812 | 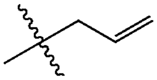 [SMILES: *CC=C] | 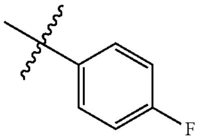 [SMILES: *c1ccc(F)cc1] | 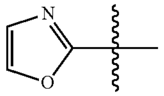 [SMILES: *c1ncco1] |

-continued
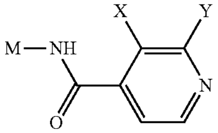
I
| NO. | X | Y | M |
|---|---|---|---|
| 1-1813 | 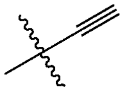 [SMILES: *C#C] | 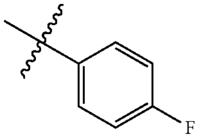 [SMILES: *c1ccc(F)cc1] | 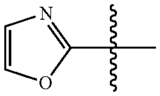 [SMILES: *c1ncco1] |
| 1-1814 | 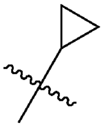 [SMILES: *C1CC1] | 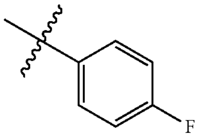 [SMILES: *c1ccc(F)cc1] | 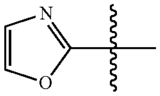 [SMILES: *c1ncco1] |
| 1-1815 | 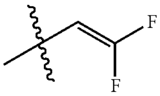 [SMILES: *C=C(F)F] | 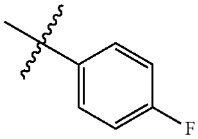 [SMILES: *c1ccc(F)cc1] | 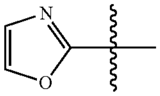 [SMILES: *c1ncco1] |
| 1-1816 | 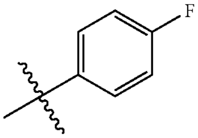 [SMILES: *c1ccc(F)cc1] | 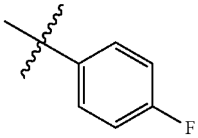 [SMILES: *c1ccc(F)cc1] | 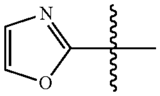 [SMILES: *c1ncco1] |
| 1-1817 | Cl | 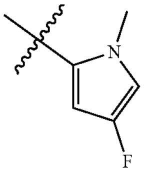 [SMILES: *c1cc(F)cn1C] | 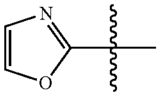 [SMILES: *c1ncco1] |
| 1-1818 | Cl | 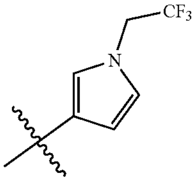 [SMILES: *c1ccn(CC(F)(F)F)c1] | 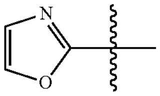 [SMILES: *c1ncco1] |
| 1-1819 | Cl | 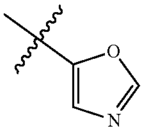 [SMILES: *c1cnco1] | 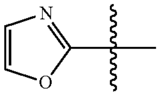 [SMILES: *c1ncco1] |
| 1-1820 | Cl | 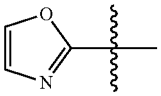 | 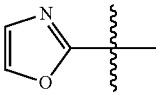 [SMILES: *c1ncco1] |
| 1-1821 | Cl | 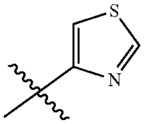 [SMILES: *c1cscn1] | 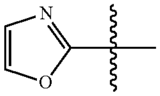 [SMILES: *c1ncco1] |

-continued
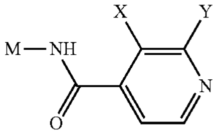
I
| NO. | X | Y | M |
| --- | --- | --- | --- |
| 1-1822 | Cl | 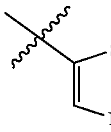 | 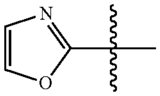 [SMILES: *c1ncco1] |
| 1-1823 | Cl | 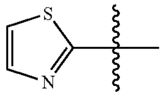 | 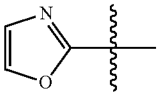 [SMILES: *c1ncco1] |
| 1-1824 | Cl | 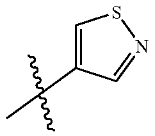 [SMILES: *c1cnsc1] | 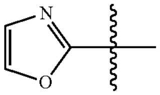 [SMILES: *c1ncco1] |
| 1-1825 | Cl | 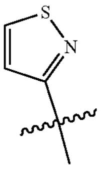 [SMILES: *c1ccsn1] | 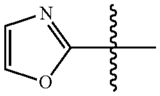 [SMILES: *c1ncco1] |
| 1-1826 | Cl | 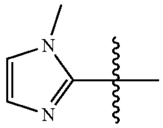 [SMILES: *c1nccn1C] | 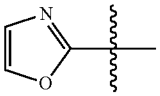 [SMILES: *c1ncco1] |
| 1-1827 | Cl | 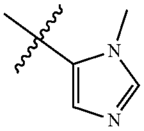 [SMILES: *c1cncn1C] | 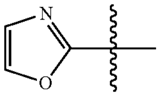 [SMILES: *c1ncco1] |
| 1-1828 | Cl | 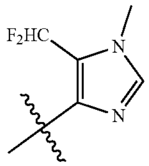 [SMILES: *c1ncn(C)c1C(F)F] | 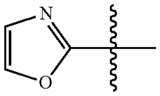 [SMILES: *c1ncco1] |
| 1-1829 | Cl | 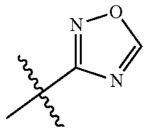 [SMILES: *c1ncon1] | 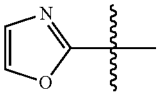 [SMILES: *c1ncco1] |
| 1-1830 | Cl | 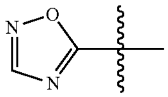 | 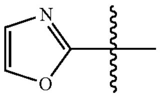 |

-continued
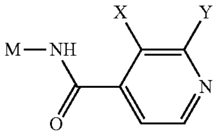
I
| NO. | X | Y | M |
|---|---|---|---|
| 1-1831 | Cl | 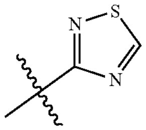 [SMILES: *c1ncsn1] | 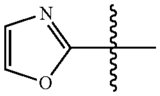 [SMILES: *c1ncco1] |
| 1-1832 | Cl | 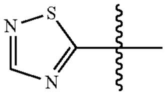 | 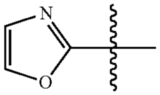 |
| 1-1833 | Cl | 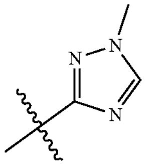 [SMILES: *c1ncn(C)n1] | 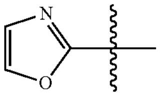 [SMILES: *c1ncco1] |
| 1-1834 | Cl | 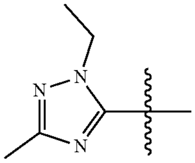 [SMILES: *c1nc(C)nn1CC] | 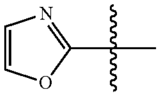 [SMILES: *c1ncco1] |
| 1-1835 | Cl | 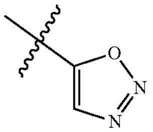 [SMILES: *c1cnno1] | 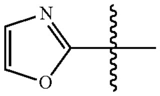 [SMILES: *c1ncco1] |
| 1-1836 | Cl | 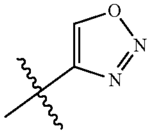 [SMILES: *c1conn1] | 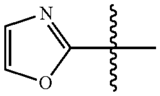 [SMILES: *c1ncco1] |
| 1-1837 | Cl | 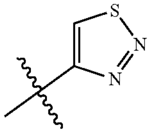 [SMILES: *c1csnn1] | 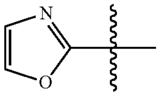 [SMILES: *c1ncco1] |
| 1-1838 | Cl | 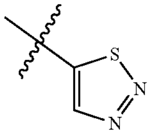 [SMILES: *c1cnns1] | 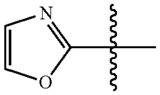 [SMILES: *c1ncco1] |
| 1-1839 | Cl | 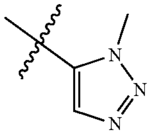 [SMILES: *c1cnnn1C] | 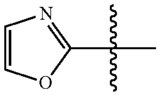 [SMILES: *c1ncco1] |

-continued
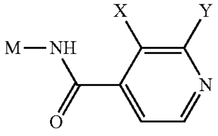
I
| NO. | X | Y | M |
| --- | --- | --- | --- |
| 1-1840 | Cl | 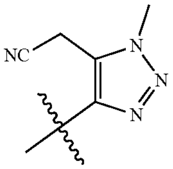 [SMILES: *c1nnn(C)c1CC#N] | 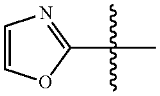 [SMILES: *c1ncco1] |
| 1-1841 | Cl | 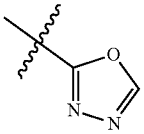 [SMILES: *c1nnco1] | 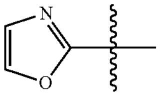 [SMILES: *c1ncco1] |
| 1-1842 | Cl | 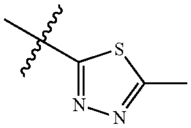 [SMILES: *c1nnc(C)s1] | 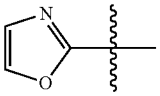 |
| 1-1843 | Cl | 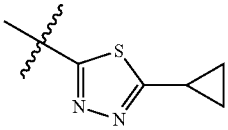 [SMILES: *c1nnc(C2CC2)s1] | 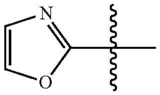 |
| 1-1844 | Cl | 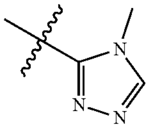 [SMILES: *c1nncn1C] | 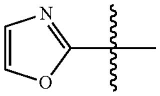 [SMILES: *c1ncco1] |
| 1-1845 | Cl | 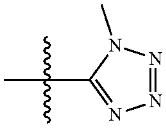 [SMILES: *c1nnnn1C] | 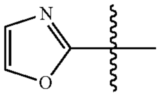 [SMILES: *c1ncco1] |
| 1-1846 | Cl | 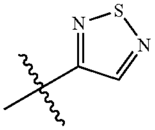 [SMILES: *c1cnsn1] | 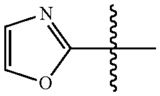 [SMILES: *c1ncco1] |
| 1-1847 | Cl | 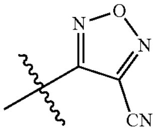 [SMILES: *c1nonc1C#N] | 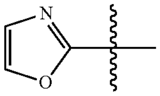 [SMILES: *c1ncco1] |
| 1-1848 | Cl | 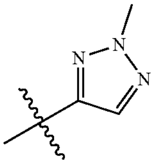 [SMILES: *c1cnn(C)n1] | 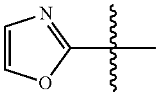 [SMILES: *c1ncco1] |

-continued
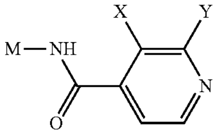
I
| NO. | X | Y | M |
|---|---|---|---|
| 1-1849 | Cl | 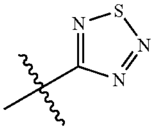 [SMILES: *c1nnsn1] | 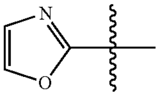 [SMILES: *c1ncco1] |
| 1-1850 | Cl | 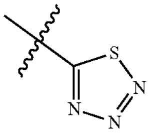 [SMILES: *c1nnns1] | 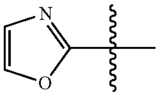 [SMILES: *c1ncco1] |
| 1-1851 | Cl | 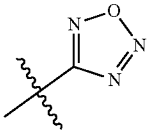 [SMILES: *c1nnon1] | 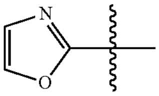 [SMILES: *c1ncco1] |
| 1-1852 | Cl | 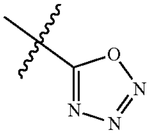 [SMILES: *c1nnno1] | 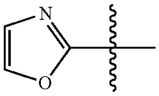 [SMILES: *c1ncco1] |
| 1-1853 | Cl | 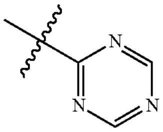 [SMILES: *c1ncncn1] | 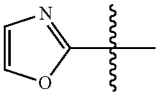 [SMILES: *c1ncco1] |
| 1-1854 | Cl | 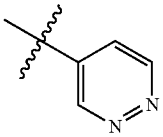 [SMILES: *c1ccnnc1] | 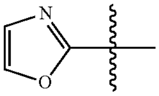 [SMILES: *c1ncco1] |
| 1-1855 | Cl | 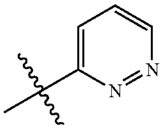 [SMILES: *c1cccnn1] | 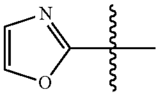 [SMILES: *c1ncco1] |
| 1-1856 | Cl | 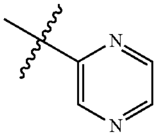 [SMILES: *c1cnccn1] | 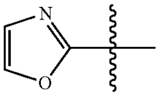 [SMILES: *c1ncco1] |
| 1-1857 | Cl | 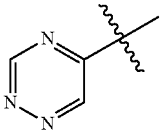 [SMILES: *c1cnncn1] | 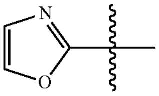 |

-continued
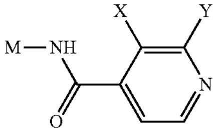
I
| NO. | X | Y | M |
|---|---|---|---|
| 1-1858 | Cl | 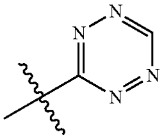 [SMILES: *c1nncnn1] | 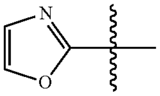 [SMILES: *c1ncco1] |
| 1-1859 | Cl | 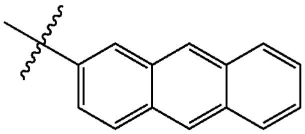 [SMILES: *c1ccc2cc3ccccc3cc2c1] | 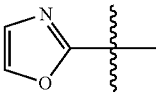 [SMILES: *c1ncco1] |
| 1-1860 | Cl | 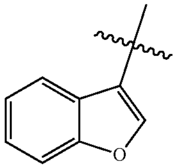 [SMILES: *c1coc2ccccc12] | 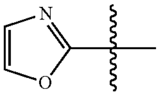 [SMILES: *c1ncco1] |
| 1-1861 | Cl | 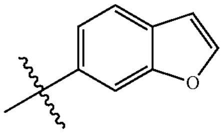 [SMILES: *c1ccc2ccoc2c1] | 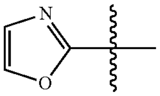 |
| 1-1862 | Cl | 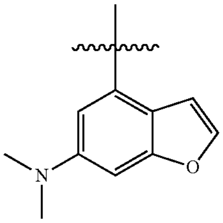 [SMILES: *c1cc(N(C)C)cc2occc12] | 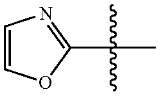 [SMILES: *c1ncco1] |
| 1-1863 | Cl | 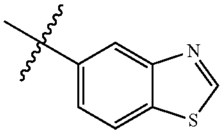 [SMILES: *c1ccc2scnc2c1] | 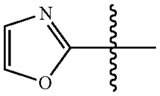 [SMILES: *c1ncco1] |
| 1-1864 | Cl | 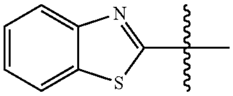 | 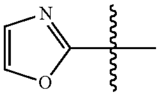 |
| 1-1865 | Cl | 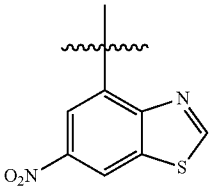 [SMILES: *c1cc([N+](=O)[O-])cc2scnc12] | 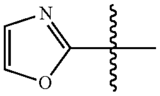 |

-continued
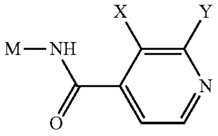
I
| NO. | X | Y | M |
|---|---|---|---|
| 1-1866 | Cl | 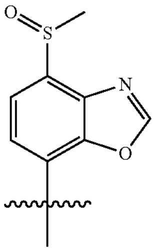 [SMILES: *c1ccc(S(C)=O)c2ncoc12] | 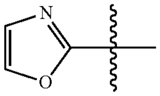 [SMILES: *c1ncco1] |
| 1-1867 | Cl | 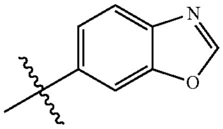 [SMILES: *c1ccc2ncoc2c1] | 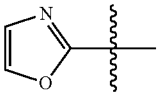 [SMILES: *c1ncco1] |
| 1-1868 | Cl | 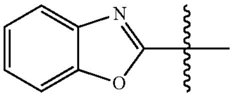 | 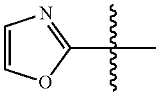 [SMILES: *c1ncco1] |
| 1-1869 | Cl | 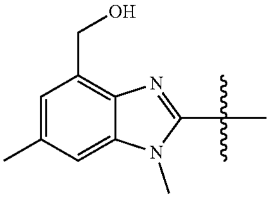 [SMILES: *c1nc2c(CO)cc(C)cc2n1C] | 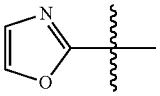 |
| 1-1870 | Cl | 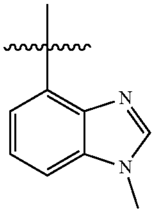 [SMILES: *c1cccc2c1ncn2C] | 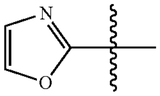 [SMILES: *c1ncco1] |
| 1-1871 | Cl | 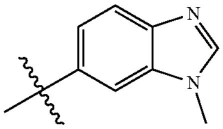 [SMILES: *c1ccc2ncn(C)c2c1] | 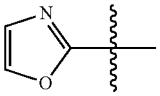 |
| 1-1872 | Cl | 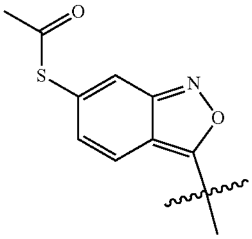 [SMILES: *c1onc2cc(SC(C)=O)ccc12] | 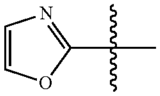 [SMILES: *c1ncco1] |

-continued
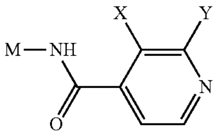
I
| NO. | X | Y | M |
| --- | --- | --- | --- |
| 1-1873 | Cl | 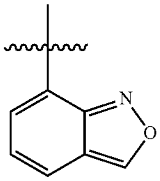 [SMILES: *c1cccc2conc12] | 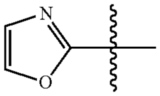 [SMILES: *c1ncco1] |
| 1-1874 | Cl | 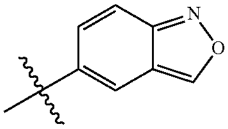 [SMILES: *c1ccc2nocc2c1] | 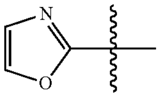 |
| 1-1875 | Cl | 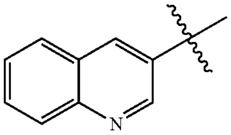 [SMILES: *c1cnc2ccccc2c1] | 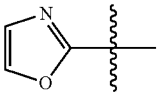 [SMILES: *c1ncco1] |
| 1-1876 | Cl | 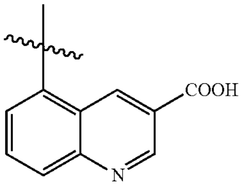 [SMILES: *c1cccc2ncc(C(=O)O)cc12] | 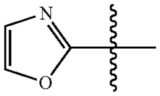 [SMILES: *c1ncco1] |
| 1-1877 | Cl | 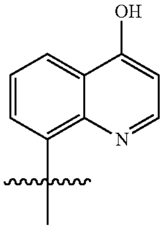 [SMILES: *c1cccc2c(O)ccnc12] | 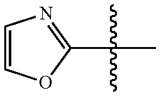 [SMILES: *c1ncco1] |
| 1-1878 | Cl | 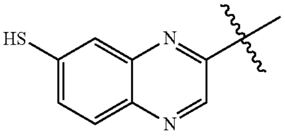 [SMILES: *c1cnc2ccc(S)cc2n1] | 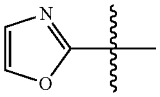 |
| 1-1879 | Cl | 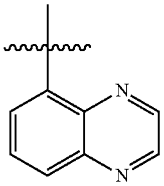 [SMILES: *c1cccc2nccnc12] | 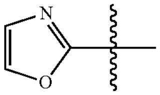 |

-continued
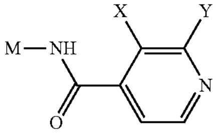
I
| NO. | X | Y | M |
| --- | --- | --- | --- |
| 1-1880 | Cl | 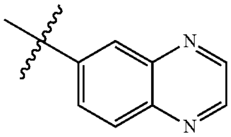 [SMILES: *c1ccc2nccnc2c1] | 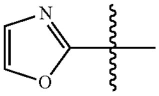 |
| 1-1881 | Cl | 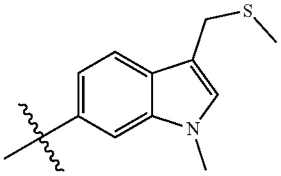 [SMILES: *c1ccc2c(CSC)cn(C)c2c1] | 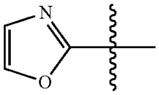 [SMILES: *c1ncco1] |
| 1-1882 | Cl | 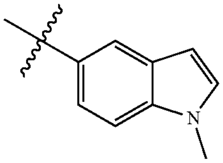 [SMILES: *c1ccc2c(ccn2C)c1] | 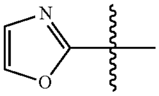 |
| 1-1883 | Cl | 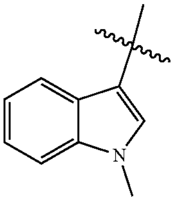 [SMILES: *c1cn(C)c2ccccc12] | 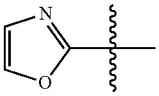 |
| 1-1884 | Cl | 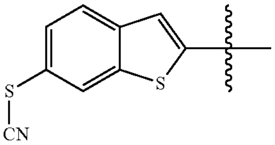 [SMILES: *c1cc2ccc(SC#N)cc2s1] | 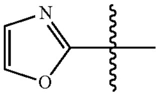 [SMILES: *c1ncco1] |
| 1-1885 | Cl | 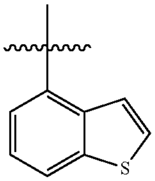 [SMILES: *c1cccc2sccc12] | 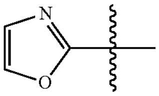 |
| 1-1886 | Cl | 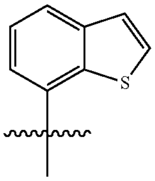 [SMILES: *c1cccc2ccsc12] | 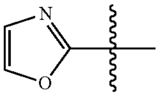 [SMILES: *c1ncco1] |
| 1-1887 | Cl | 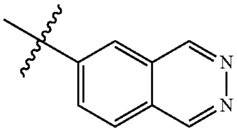 [SMILES: *c1ccc2cnncc2c1] | 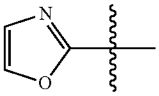 [SMILES: *c1ncco1] |

-continued
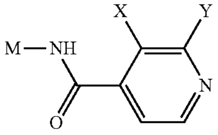
I
| NO. | X | Y | M |
|---|---|---|---|
| 1-1888 | Cl | 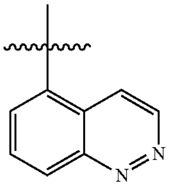 [SMILES: *c1cccc2nnccc12] | 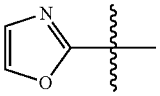 [SMILES: *c1ncco1] |
| 1-1889 | Cl | 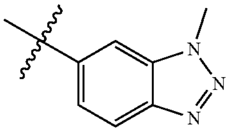 [SMILES: *c1ccc2nnn(C)c2c1] | 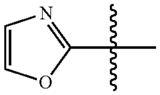 [SMILES: *c1ncco1] |
| 1-1890 | Cl | 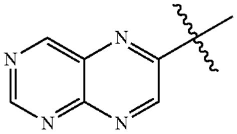 [SMILES: *c1cnc2ncncc2n1] | 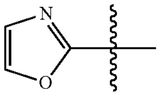 [SMILES: *c1ncco1] |
| 1-1891 | Cl | 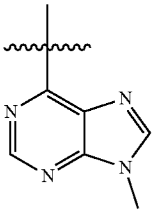 [SMILES: *c1ncnc2c1ncn2C] | 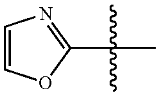 [SMILES: *c1ncco1] |
| 1-1892 | Cl | 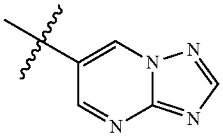 [SMILES: *c1cnc2ncnn2c1] | 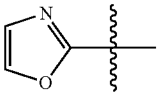 [SMILES: *c1ncco1] |
| 1-1893 | Cl | 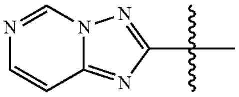 [SMILES: *c1nc2ccncn2n1] | 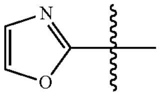 [SMILES: *c1ncco1] |
| 1-1894 | Cl | 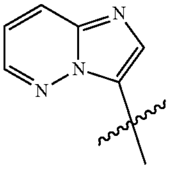 [SMILES: *c1cnc2cccnn12] | 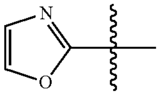 [SMILES: *c1ncco1] |
| 1-1895 | Cl | 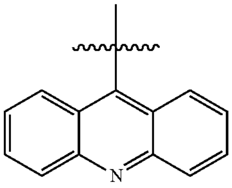 [SMILES: *c1c2ccccc2nc2ccccc12] | 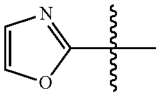 [SMILES: *c1ncco1] |

-continued
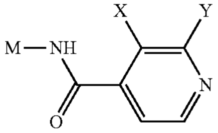
I
| NO. | X | Y | M |
|---|---|---|---|
| 1-1896 | Cl | 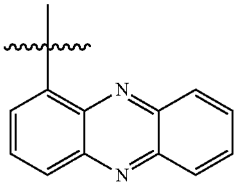 [SMILES: *c1cccc2nc3ccccc3nc12] | 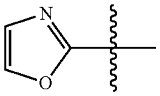 [SMILES: *c1ncco1] |
| 1-1897 | Cl | 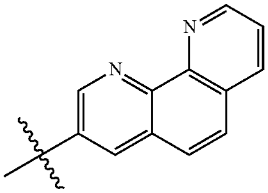 [SMILES: *c1cnc2c(ccc3cccnc32)c1] | 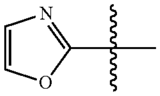 [SMILES: *c1ncco1] |
| 1-1898 | Cl | 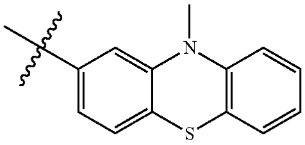 [SMILES: *c1ccc2c(c1)N(C)c1ccccc1S2] | 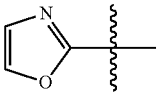 [SMILES: *c1ncco1] |
| 1-1899 | Cl | 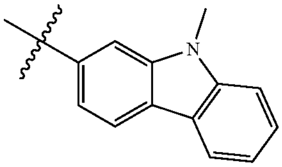 [SMILES: *c1ccc2c3ccccc3n(C)c2c1] | 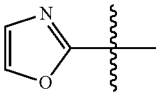 [SMILES: *c1ncco1] |
| 1-1900 | Cl | 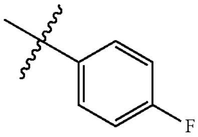 [SMILES: *c1ccc(F)cc1] | 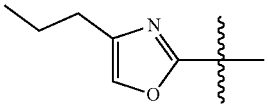 [SMILES: *c1nc(CCC)co1] |
| 1-1901 | Cl | 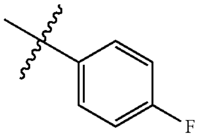 [SMILES: *c1ccc(F)cc1] | 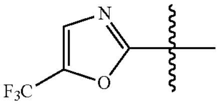 |
| 1-1902 | Cl | 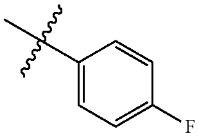 [SMILES: *c1ccc(F)cc1] | 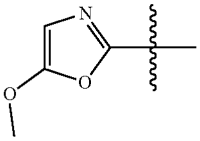 [SMILES: *c1ncc(OC)o1] |
| 1-1903 | Cl | 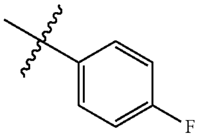 [SMILES: *c1ccc(F)cc1] | 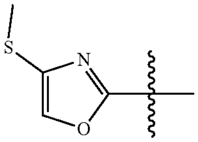 [SMILES: *c1nc(SC)co1] |

-continued
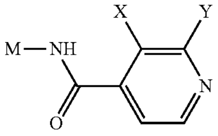
I
| NO. | X | Y | M |
|---|---|---|---|
| 1-1904 | Cl | 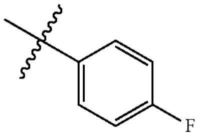 [SMILES: *c1ccc(F)cc1] | 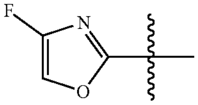 [SMILES: *c1nc(F)co1] |
| 1-1905 | Cl | 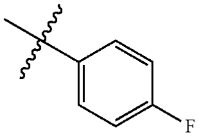 [SMILES: *c1ccc(F)cc1] | 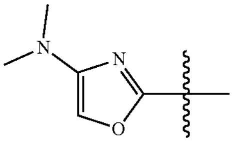 [SMILES: *c1nc(N(C)C)co1] |
| 1-1906 | Cl | 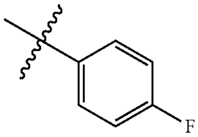 [SMILES: *c1ccc(F)cc1] | 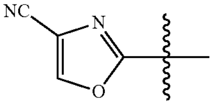 [SMILES: *c1nc(C#N)co1] |
| 1-1907 | Cl | 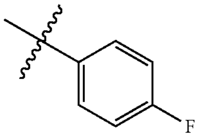 [SMILES: *c1ccc(F)cc1] | 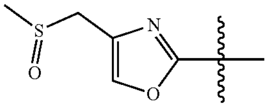 [SMILES: *c1nc(CS(C)=O)co1] |
| 1-1908 | Cl | 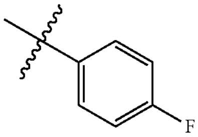 [SMILES: *c1ccc(F)cc1] | 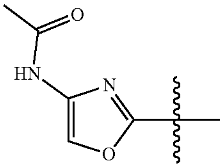 [SMILES: *c1nc(NC(C)=O)co1] |
| 1-1909 | Cl | 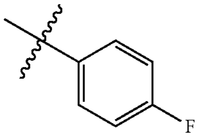 [SMILES: *c1ccc(F)cc1] | 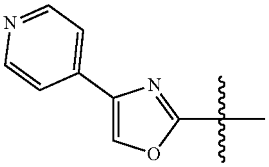 [SMILES: *c1nc(-c2ccncc2)co1] |
| 1-1910 | Cl | 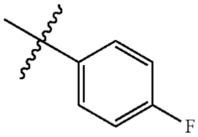 [SMILES: *c1ccc(F)cc1] | 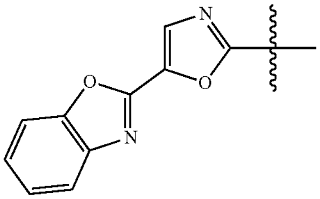 [SMILES: *c1ncc(-c2nc3ccccc3o2)o1] |
| 1-1911 | Cl | 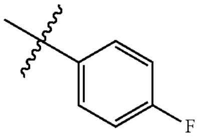 [SMILES: *c1ccc(F)cc1] | 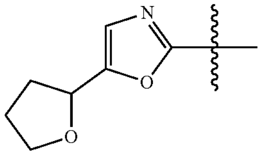 [SMILES: *c1ncc(C2CCCO2)o1] |

-continued
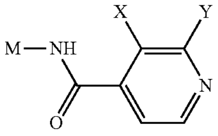
I
| NO. | X | Y | M |
|---|---|---|---|
| 1-1912 | OMe | $CH_3$ | 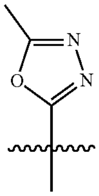 [SMILES: *c1nnc(C)o1] |
| 1-1913 | Cl | 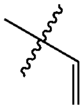 [SMILES: *C=C] | 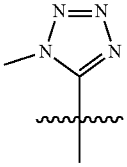 [SMILES: *c1nnnn1C] |
| 1-1914 | Cl | 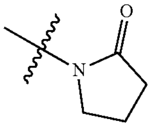 [SMILES: *N1CCCC1=O] | 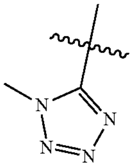 [SMILES: *c1nnnn1C] |
| 1-1915 | Cl | 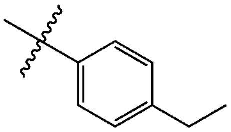 [SMILES: *c1ccc(CC)cc1] | 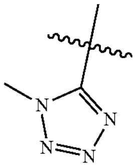 [SMILES: *c1nnnn1C] |
| 1-1916 | Cl | 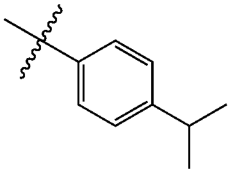 [SMILES: *c1ccc(C(C)C)cc1] | 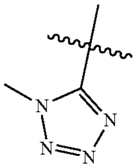 [SMILES: *c1nnnn1C] |
| 1-1917 | Cl | 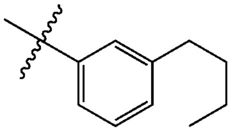 [SMILES: *c1cccc(CCCC)c1] | 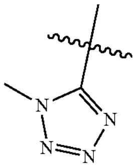 [SMILES: *c1nnnn1C] |
| 1-1918 | Cl | 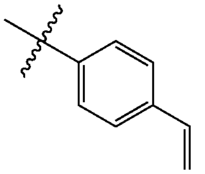 [SMILES: *c1ccc(C=C)cc1] | 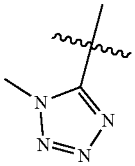 [SMILES: *c1nnnn1C] |

-continued
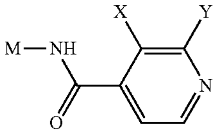
I
| NO. | X | Y | M |
|---|---|---|---|
| 1-1919 | Cl | 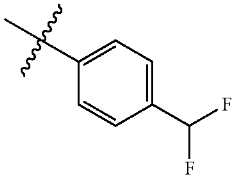 [SMILES: *c1ccc(C(F)F)cc1] | 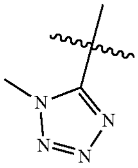 [SMILES: *c1nnnn1C] |
| 1-1920 | Cl | 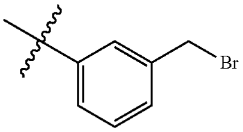 [SMILES: *c1cccc(CBr)c1] | 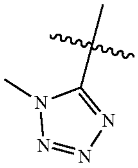 [SMILES: *c1nnnn1C] |
| 1-1921 | Cl | 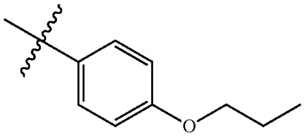 [SMILES: *c1ccc(OCCC)cc1] | 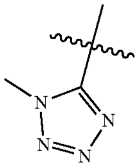 [SMILES: *c1nnnn1C] |
| 1-1922 | Cl | 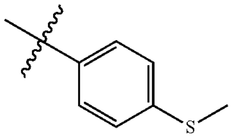 [SMILES: *c1ccc(SC)cc1] | 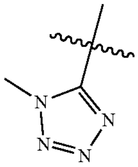 [SMILES: *c1nnnn1C] |
| 1-1923 | Cl | 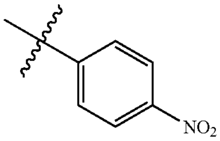 | 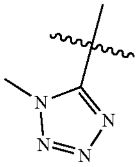 [SMILES: *c1nnnn1C] |
| 1-1924 | Cl | 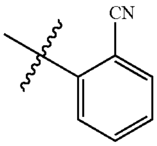 [SMILES: *c1ccccc1C#N] | 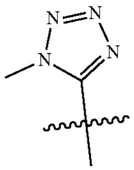 [SMILES: *c1nnnn1C] |
| 1-1925 | Cl | 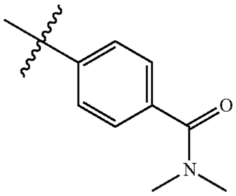 [SMILES: *c1ccc(C(=O)N(C)C)cc1] | 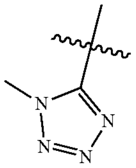 [SMILES: *c1nnnn1C] |

-continued
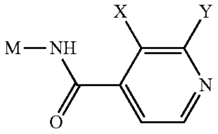
I
| NO. | X | Y | M |
|---|---|---|---|
| 1-1926 | Cl | 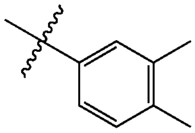 [SMILES: *c1ccc(C)c(C)c1] | 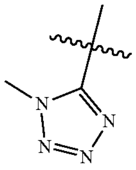 [SMILES: *c1nnnn1C] |
| 1-1927 | Cl | 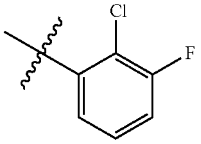 | 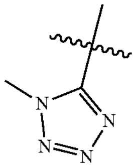 [SMILES: *c1nnnn1C] |
| 1-1928 | Cl | 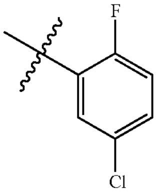 [SMILES: *c1cc(Cl)ccc1F] | 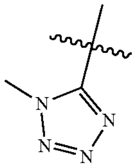 [SMILES: *c1nnnn1C] |
| 1-1929 | Cl | 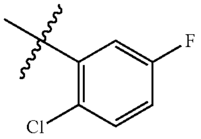 [SMILES: *c1cc(F)ccc1Cl] | 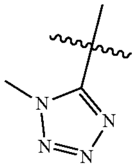 [SMILES: *c1nnnn1C] |
| 1-1930 | Cl | 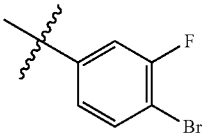 [SMILES: *c1ccc(Br)c(F)c1] | 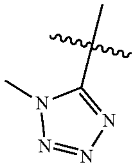 [SMILES: *c1nnnn1C] |
| 1-1931 | Cl | 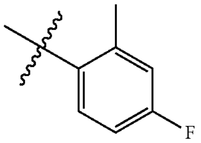 [SMILES: *c1ccc(F)cc1C] | 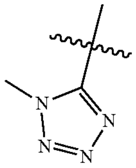 [SMILES: *c1nnnn1C] |
| 1-1932 | Cl | 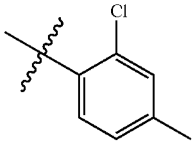 [SMILES: *c1ccc(C)cc1Cl] | 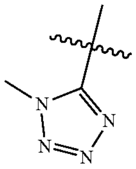 [SMILES: *c1nnnn1C] |

-continued
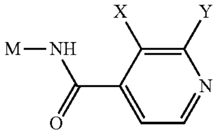
I
| NO. | X | Y | M |
|---|---|---|---|
| 1-1933 | Cl | 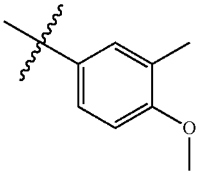 [SMILES: *c1ccc(OC)c(C)c1] | 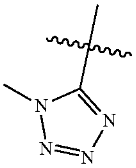 [SMILES: *c1nnnn1C] |
| 1-1934 | Cl | 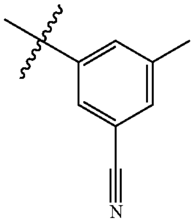 [SMILES: *c1cc(C)cc(C#N)c1] | 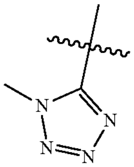 [SMILES: *c1nnnn1C] |
| 1-1935 | Cl | 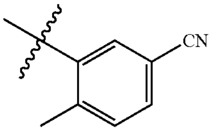 [SMILES: *c1cc(C#N)ccc1C] | 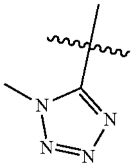 [SMILES: *c1nnnn1C] |
| 1-1936 | Cl | 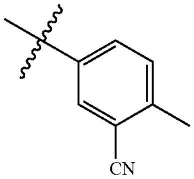 [SMILES: *c1ccc(C)c(C#N)c1] | 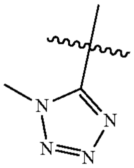 [SMILES: *c1nnnn1C] |
| 1-1937 | Cl | 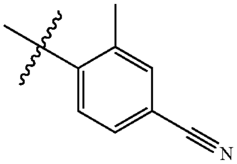 [SMILES: *c1ccc(C#N)cc1C] | 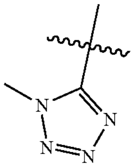 [SMILES: *c1nnnn1C] |
| 1-1938 | Cl | 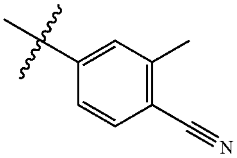 [SMILES: *c1ccc(C#N)c(C)c1] | 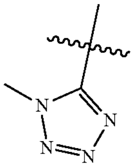 [SMILES: *c1nnnn1C] |
| 1-1939 | Cl | 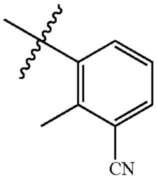 [SMILES: *c1cccc(C#N)c1C] | 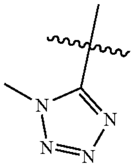 [SMILES: *c1nnnn1C] |

-continued
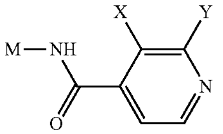
I
| NO. | X | Y | M |
| --- | --- | --- | --- |
| 1-1940 | Cl | 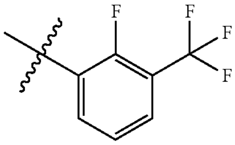 [SMILES: *c1cccc(C(F)(F)F)c1F] | 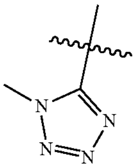 [SMILES: *c1nnnn1C] |
| 1-1941 | Cl | 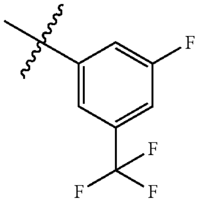 [SMILES: *c1cc(F)cc(C(F)(F)F)c1] | 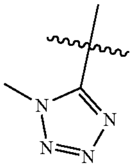 [SMILES: *c1nnnn1C] |
| 1-1942 | Cl | 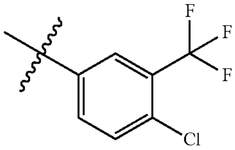 [SMILES: *c1ccc(Cl)c(C(F)(F)F)c1] | 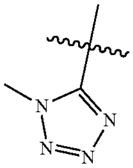 [SMILES: *c1nnnn1C] |
| 1-1943 | Cl | 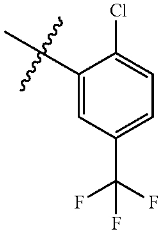 [SMILES: *c1cc(C(F)(F)F)ccc1Cl] | 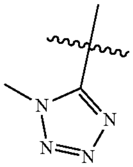 [SMILES: *c1nnnn1C] |
| 1-1944 | Cl | 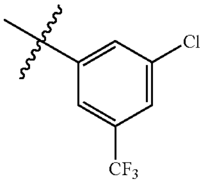 [SMILES: *c1cc(Cl)cc(C(F)(F)F)c1] | 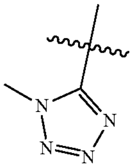 [SMILES: *c1nnnn1C] |
| 1-1945 | Cl | 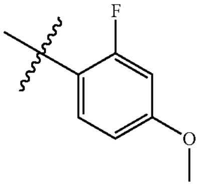 [SMILES: *c1ccc(OC)cc1F] | 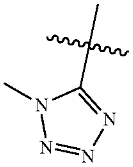 [SMILES: *c1nnnn1C] |
| 1-1946 | Cl | 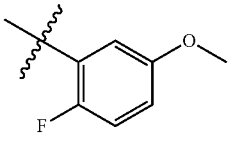 [SMILES: *c1cc(OC)ccc1F] | 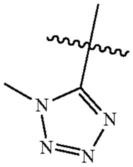 [SMILES: *c1nnnn1C] |

-continued
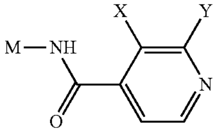
I
| NO. | X | Y | M |
|---|---|---|---|
| 1-1947 | Cl | 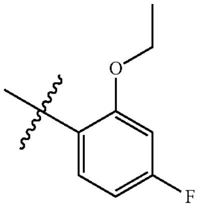 [SMILES: *c1ccc(F)cc1OCC] | 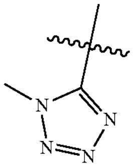 [SMILES: *c1nnnn1C] |
| 1-1948 | Cl | 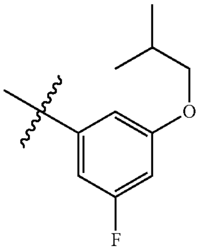 [SMILES: *c1cc(F)cc(OCC(C)C)c1] | 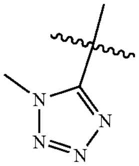 |
| 1-1949 | Cl | 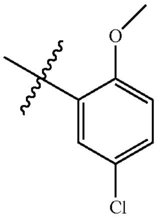 [SMILES: *c1cc(Cl)ccc1OC] | 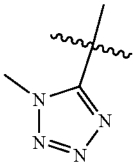 [SMILES: *c1nnnn1C] |
| 1-1950 | Cl | 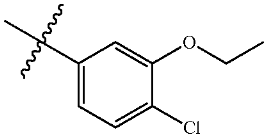 [SMILES: *c1ccc(Cl)c(OCC)c1] | 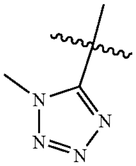 [SMILES: *c1nnnn1C] |
| 1-1951 | Cl | 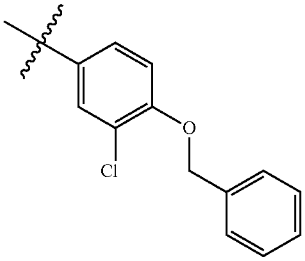 [SMILES: *c1ccc(OCc2ccccc2)c(Cl)c1] | 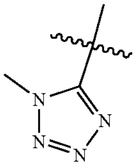 [SMILES: *c1nnnn1C] |
| 1-1952 | Cl | 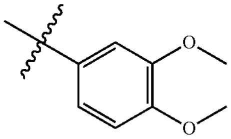 [SMILES: *c1ccc(OC)c(OC)c1] | 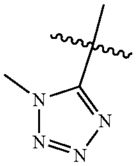 [SMILES: *c1nnnn1C] |

-continued
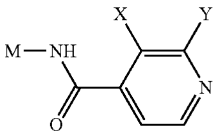
I
| NO. | X | Y | M |
|---|---|---|---|
| 1-1953 | Cl | 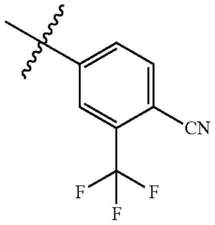 [SMILES: *c1ccc(C#N)c(C(F)(F)F)c1] | 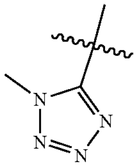 [SMILES: *c1nnnn1C] |
| 1-1954 | Cl | 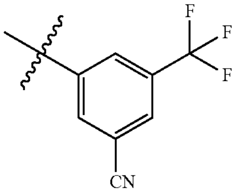 [SMILES: *c1cc(C#N)cc(C(F)(F)F)c1] | 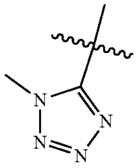 [SMILES: *c1nnnn1C] |
| 1-1955 | Cl | 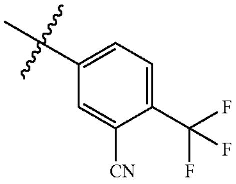 [SMILES: *c1ccc(C(F)(F)F)c(C#N)c1] | 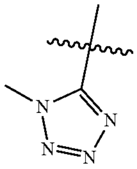 [SMILES: *c1nnnn1C] |
| 1-1956 | Cl | 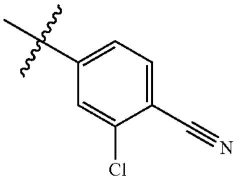 [SMILES: *c1ccc(C#N)c(Cl)c1] | 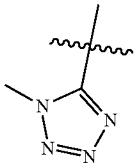 [SMILES: *c1nnnn1C] |
| 1-1957 | Cl | 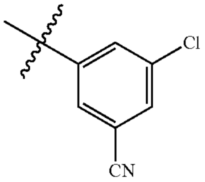 [SMILES: *c1cc(Cl)cc(C#N)c1] | 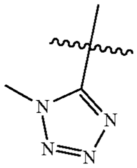 [SMILES: *c1nnnn1C] |
| 1-1958 | Cl | 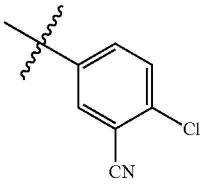 [SMILES: *c1ccc(Cl)c(C#N)c1] | 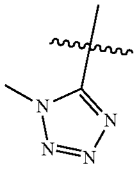 [SMILES: *c1nnnn1C] |

-continued
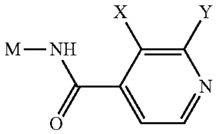
I
| NO. | X | Y | M |
|---|---|---|---|
| 1-1959 | Cl | 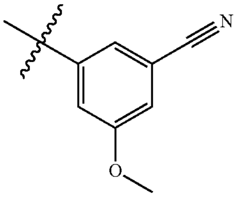 [SMILES: *c1cc(C#N)cc(OC)c1] | 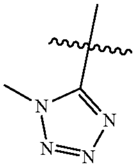 [SMILES: *c1nnnn1C] |
| 1-1960 | Cl | 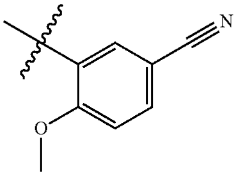 [SMILES: *c1cc(C#N)ccc1OC] | 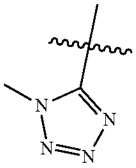 [SMILES: *c1nnnn1C] |
| 1-1961 | Cl | 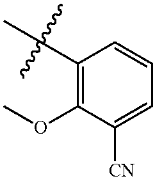 [SMILES: *c1cccc(C#N)c1OC] | 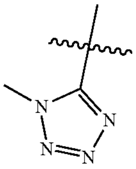 [SMILES: *c1nnnn1C] |
| 1-1962 | Cl | 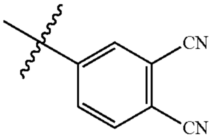 [SMILES: *c1ccc(C#N)c(C#N)c1] | 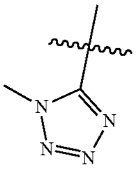 [SMILES: *c1nnnn1C] |
| 1-1963 | Cl | 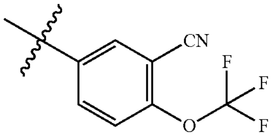 [SMILES: *c1ccc(OC(F)(F)F)c(C#N)c1] | 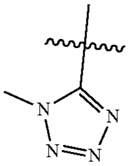 [SMILES: *c1nnnn1C] |
| 1-1964 | Cl | 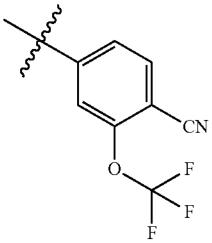 [SMILES: *c1ccc(C#N)c(OC(F)(F)F)c1] | 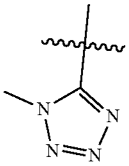 [SMILES: *c1nnnn1C] |
| 1-1965 | Cl | 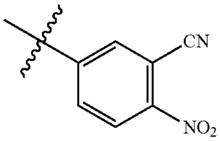 [SMILES: *c1ccc([N+](=O)[O-])c(C#N)c1] | 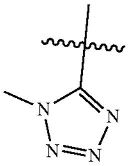 [SMILES: *c1nnnn1C] |

-continued
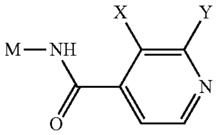
I
| NO. | X | Y | M |
|---|---|---|---|
| 1-1966 | Cl | 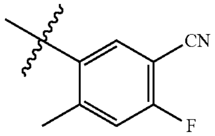 [SMILES: *c1cc(C#N)c(F)cc1C] | 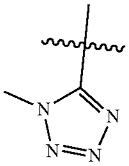 [SMILES: *c1nnnn1C] |
| 1-1967 | Cl | 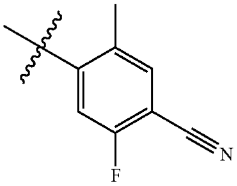 [SMILES: *c1cc(F)c(C#N)cc1C] | 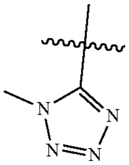 [SMILES: *c1nnnn1C] |
| 1-1968 | Cl | 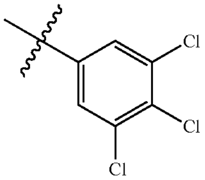 [SMILES: *c1cc(Cl)c(Cl)c(Cl)c1] | 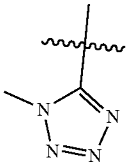 [SMILES: *c1nnnn1C] |
| 1-1969 | Cl | 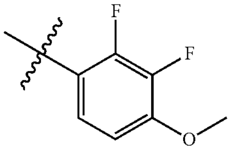 [SMILES: *c1ccc(OC)c(F)c1F] | 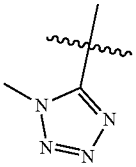 [SMILES: *c1nnnn1C] |
| 1-1970 | Cl | 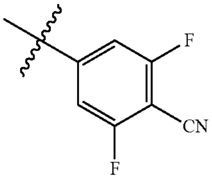 [SMILES: *c1cc(F)c(C#N)c(F)c1] | 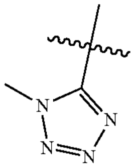 [SMILES: *c1nnnn1C] |
| 1-1971 | Cl | 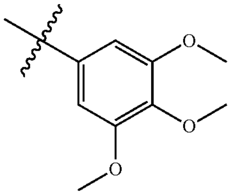 [SMILES: *c1cc(OC)c(OC)c(OC)c1] | 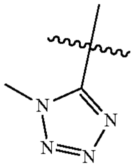 [SMILES: *c1nnnn1C] |
| 1-1972 | Cl | 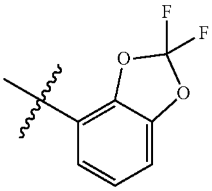 [SMILES: *c1cccc2c1OC(F)(F)O2] | 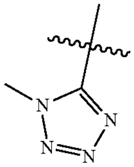 [SMILES: *c1nnnn1C] |

-continued
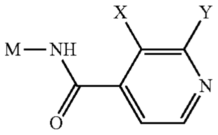
I
| NO. | X | Y | M |
|---|---|---|---|
| 1-1973 | Cl | 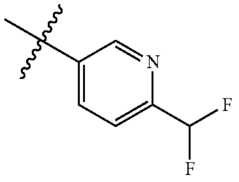 [SMILES: *c1ccc(C(F)F)nc1] | 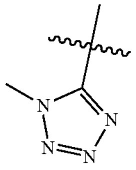 [SMILES: *c1nnnn1C] |
| 1-1974 | Cl | 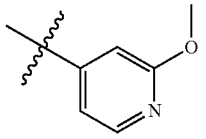 [SMILES: *c1ccnc(OC)c1] | 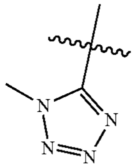 [SMILES: *c1nnnn1C] |
| 1-1975 | Cl | 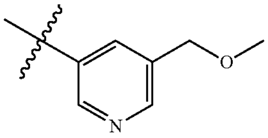 [SMILES: *c1cncc(COC)c1] | 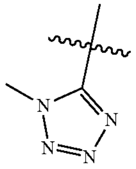 [SMILES: *c1nnnn1C] |
| 1-1976 | Cl | 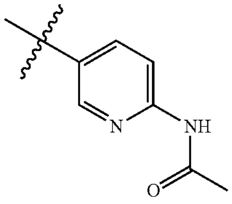 [SMILES: *c1ccc(NC(C)=O)nc1] | 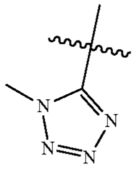 [SMILES: *c1nnnn1C] |
| 1-1977 | Cl | 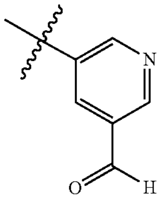 [SMILES: *c1cncc(C=O)c1] | 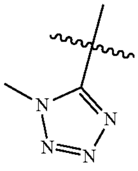 [SMILES: *c1nnnn1C] |
| 1-1978 | Cl | 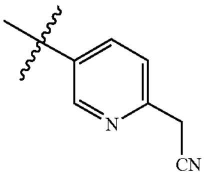 [SMILES: *c1ccc(CC#N)nc1] | 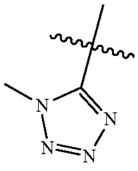 [SMILES: *c1nnnn1C] |

-continued
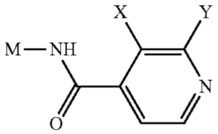
I
| NO. | X | Y | M |
|---|---|---|---|
| 1-1979 | Cl | 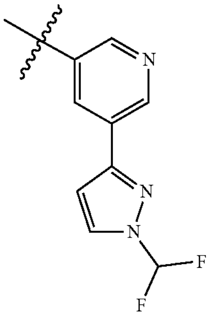 [SMILES: *c1cncc(-c2ccn(C(F)F)n2)c1] | 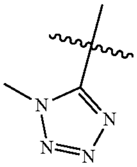 [SMILES: *c1nnnn1C] |
| 1-1980 | Cl | 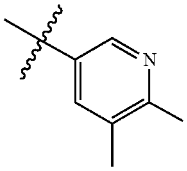 [SMILES: *c1cnc(C)c(C)c1] | 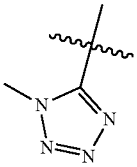 [SMILES: *c1nnnn1C] |
| 1-1981 | Cl | 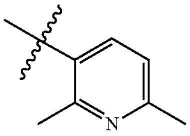 | 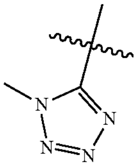 [SMILES: *c1nnnn1C] |
| 1-1982 | Cl | 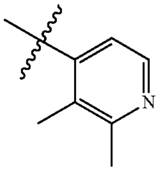 [SMILES: *c1ccnc(C)c1C] | 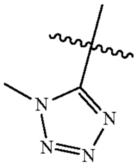 [SMILES: *c1nnnn1C] |
| 1-1983 | Cl | 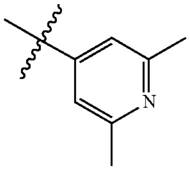 [SMILES: *c1cc(C)nc(C)c1] | 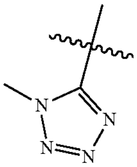 [SMILES: *c1nnnn1C] |
| 1-1984 | Cl | 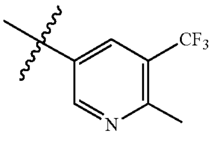 [SMILES: *c1cnc(C)c(C(F)(F)F)c1] | 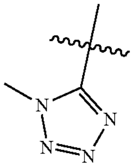 [SMILES: *c1nnnn1C] |
| 1-1985 | Cl | 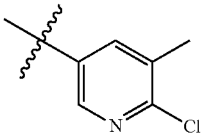 [SMILES: *c1cnc(Cl)c(C)c1] | 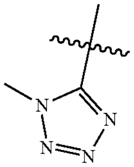 [SMILES: *c1nnnn1C] |

-continued
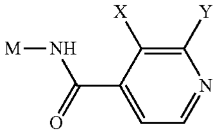
I
| NO. | X | Y | M |
|---|---|---|---|
| 1-1986 | Cl | 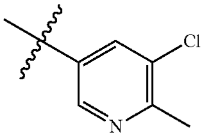 [SMILES: *c1cnc(C)c(Cl)c1] | 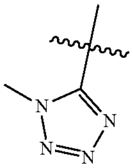 [SMILES: *c1nnnn1C] |
| 1-1987 | Cl | 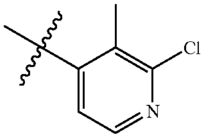 [SMILES: *c1ccnc(Cl)c1C] | 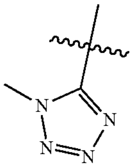 [SMILES: *c1nnnn1C] |
| 1-1988 | Cl | 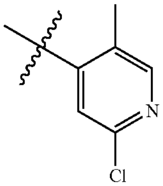 [SMILES: *c1cc(Cl)ncc1C] | 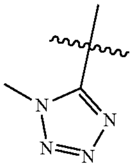 [SMILES: *c1nnnn1C] |
| 1-1989 | Cl | 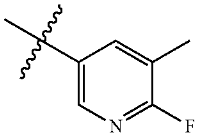 [SMILES: *c1cnc(F)c(C)c1] | 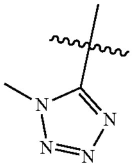 [SMILES: *c1nnnn1C] |
| 1-1990 | Cl | 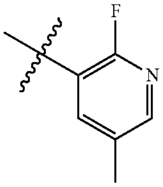 | 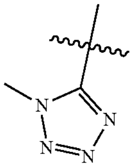 [SMILES: *c1nnnn1C] |
| 1-1991 | Cl | 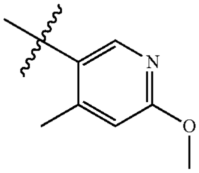 [SMILES: *c1cnc(OC)cc1C] | 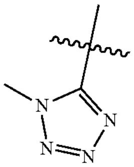 [SMILES: *c1nnnn1C] |
| 1-1992 | Cl | 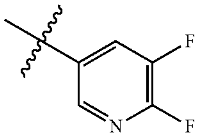 [SMILES: *c1cnc(F)c(F)c1] | 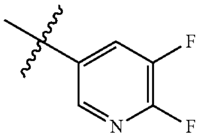 [SMILES: *c1cnc(F)c(F)c1] |

-continued
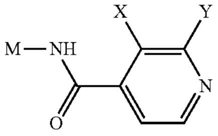
I
| NO. | X | Y | M |
|---|---|---|---|
| 1-1993 | Cl | 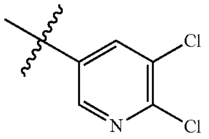 [SMILES: *c1cnc(Cl)c(Cl)c1] | 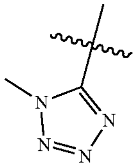 [SMILES: *c1nnnn1C] |
| 1-1994 | Cl | 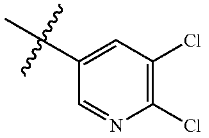 [SMILES: *c1cnc(Cl)c(Cl)c1] | 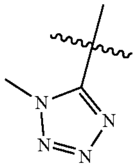 [SMILES: *c1nnnn1C] |
| 1-1995 | Cl | 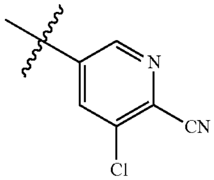 [SMILES: *c1cnc(C#N)c(Cl)c1] | 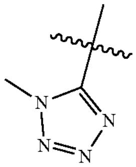 [SMILES: *c1nnnn1C] |
| 1-1996 | Cl | 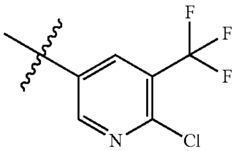 [SMILES: *c1cnc(Cl)c(C(F)(F)F)c1] | 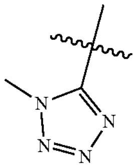 [SMILES: *c1nnnn1C] |
| 1-1997 | Cl | 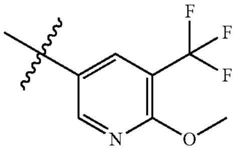 [SMILES: *c1cnc(OC)c(C(F)(F)F)c1] | 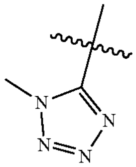 [SMILES: *c1nnnn1C] |
| 1-1998 | Cl | 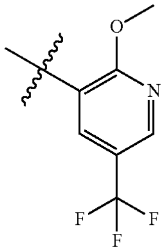 | 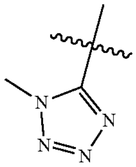 [SMILES: *c1nnnn1C] |
| 1-1999 | Cl | 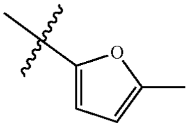 [SMILES: *c1ccc(C)o1] | 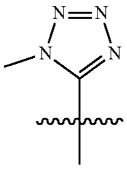 |

-continued
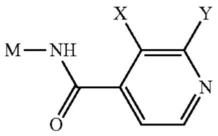
I
| NO. | X | Y | M |
|---|---|---|---|
| 1-2000 | Cl | 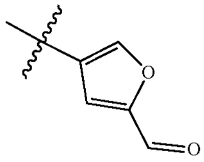 [SMILES: *c1coc(C=O)c1] | 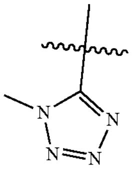 [SMILES: *c1nnnn1C] |
| 1-2001 | Cl | 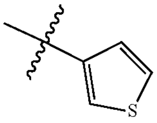 [SMILES: *c1ccsc1] | 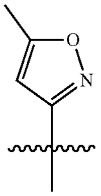 [SMILES: *c1cc(C)on1] |
| 1-2002 | Cl | 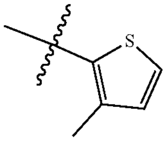 [SMILES: *c1sccc1C] | 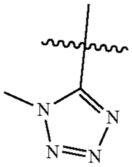 [SMILES: *c1nnnn1C] |
| 1-2003 | Cl | 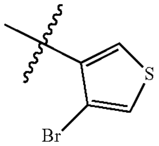 [SMILES: *c1cscc1Br] | 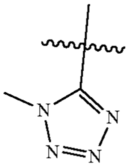 [SMILES: *c1nnnn1C] |
| 1-2004 | Cl | 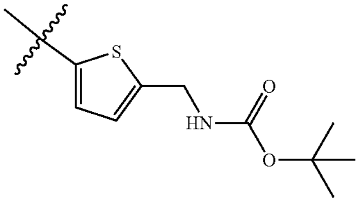 [SMILES: *c1ccc(CNC(=O)OC(C)(C)C)s1] | 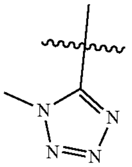 [SMILES: *c1nnnn1C] |
| 1-2005 | Cl | 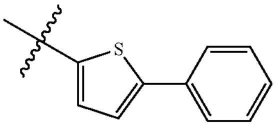 [SMILES: *c1ccc(-c2ccccc2)s1] | 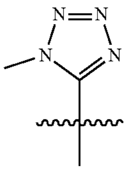 |
| 1-2006 | Cl | 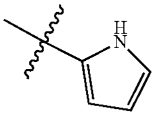 [SMILES: *c1ccc[nH]1] | 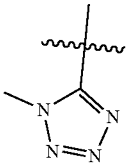 [SMILES: *c1nnnn1C] |

-continued
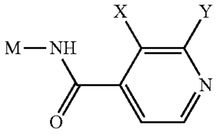
I
| NO. | X | Y | M |
|---|---|---|---|
| 1-2007 | Cl | 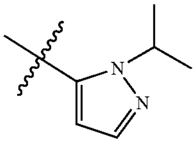 [SMILES: *c1ccnn1C(C)C] | 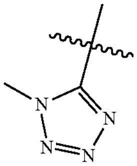 [SMILES: *c1nnnn1C] |
| 1-2008 | Cl | 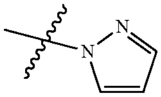 [SMILES: *n1cccn1] | 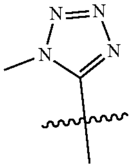 [SMILES: *c1nnnn1C] |
| 1-2009 | Cl | 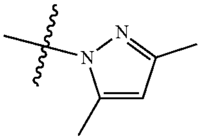 [SMILES: *n1nc(C)cc1C] | 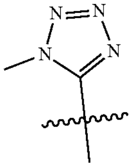 [SMILES: *c1nnnn1C] |
| 1-2010 | Cl | 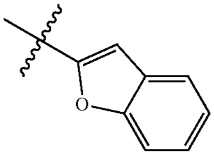 [SMILES: *c1cc2ccccc2o1] | 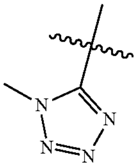 [SMILES: *c1nnnn1C] |
| 1-2011 | Cl | 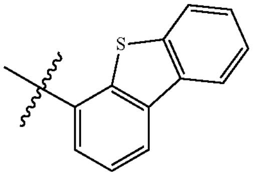 [SMILES: *c1cccc2c1sc1ccccc12] | 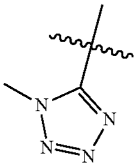 [SMILES: *c1nnnn1C] |
| 1-2012 | F | $CH_3$ | 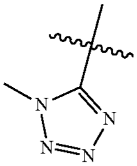 [SMILES: *c1nnnn1C] |
| 1-2013 | F | 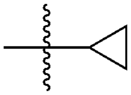 [SMILES: *C1CC1] | 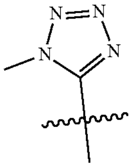 [SMILES: *c1nnnn1C] |

-continued
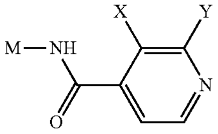
I
| NO. | X | Y | M |
|---|---|---|---|
| 1-2014 | F | 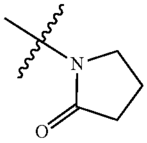 [SMILES: *N1CCCC1=O] | 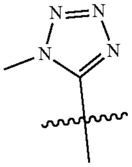 [SMILES: *c1nnnn1C] |
| 1-2015 | F | 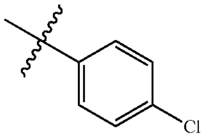 [SMILES: *c1ccc(Cl)cc1] | 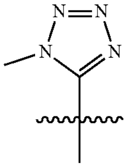 [SMILES: *c1nnnn1C] |
| 1-2016 | F | 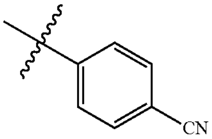 [SMILES: *c1ccc(C#N)cc1] | 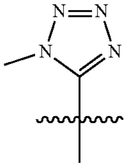 [SMILES: *c1nnnn1C] |
| 1-2017 | F | 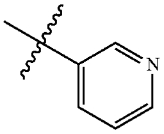 [SMILES: *c1cccnc1] | 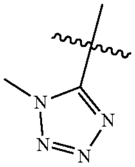 [SMILES: *c1nnnn1C] |
| 1-2018 | F | 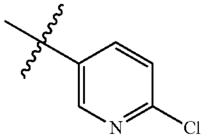 [SMILES: *c1ccc(Cl)nc1] | 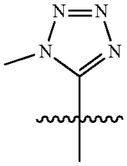 [SMILES: *c1nnnn1C] |
| 1-2019 | F | 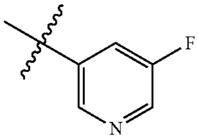 [SMILES: *c1cncc(F)c1] | 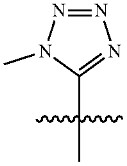 [SMILES: *c1nnnn1C] |
| 1-2020 | F | 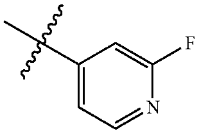 [SMILES: *c1ccnc(F)c1] | 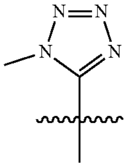 [SMILES: *c1nnnn1C] |

-continued
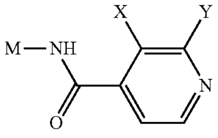
I
| NO. | X | Y | M |
|---|---|---|---|
| 1-2021 | F | 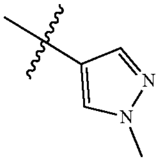 [SMILES: *c1cnn(C)c1] | 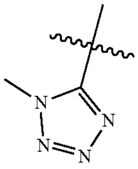 [SMILES: *c1nnnn1C] |
| 1-2022 | F | 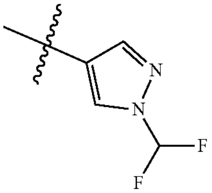 [SMILES: *c1cnn(C(F)F)c1] | 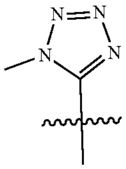 [SMILES: *c1nnnn1C] |
| 1-2023 | OH | 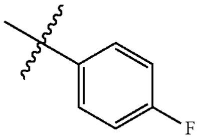 [SMILES: *c1ccc(F)cc1] | 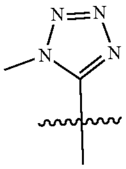 [SMILES: *c1nnnn1C] |
| 1-2024 | OMe | 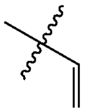 [SMILES: *C=C] | 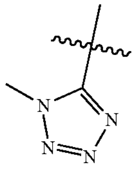 [SMILES: *c1nnnn1C] |
| 1-2025 | OMe | 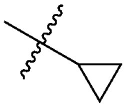 [SMILES: *C1CC1] | 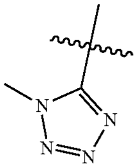 [SMILES: *c1nnnn1C] |
| 1-2026 | OMe | 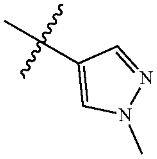 [SMILES: *c1cnn(C)c1] | 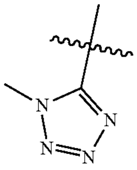 [SMILES: *c1nnnn1C] |
| 1-2027 | OMe | 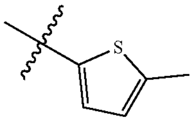 [SMILES: *c1ccc(C)s1] | 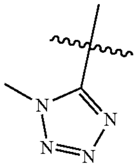 [SMILES: *c1nnnn1C] |

-continued
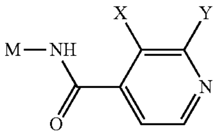
I
| NO. | X | Y | M |
|---|---|---|---|
| 1-2028 | OMe | 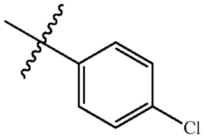 [SMILES: *c1ccc(Cl)cc1] | 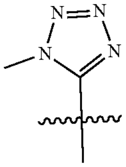 [SMILES: *c1nnnn1C] |
| 1-2029 | OMe | 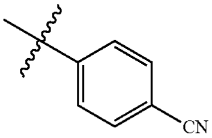 | 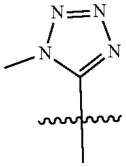 [SMILES: *c1nnnn1C] |
| 1-2030 | OMe | 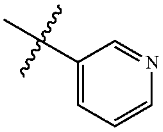 [SMILES: *c1cccnc1] | 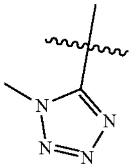 [SMILES: *c1nnnn1C] |
| 1-2031 | OMe | 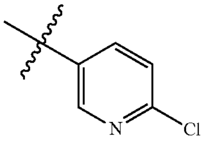 [SMILES: *c1ccc(Cl)nc1] | 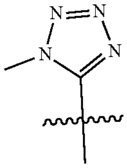 [SMILES: *c1nnnn1C] |
| 1-2032 | OMe | 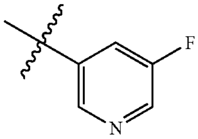 [SMILES: *c1cncc(F)c1] | 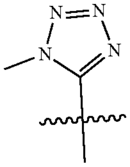 [SMILES: *c1nnnn1C] |
| 1-2033 | OMe | 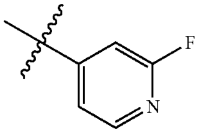 [SMILES: *c1ccnc(F)c1] | 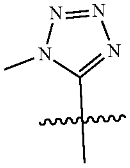 [SMILES: *c1nnnn1C] |
| 1-2034 | OMe | 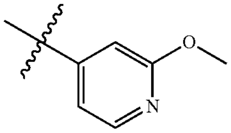 [SMILES: *c1ccnc(OC)c1] | 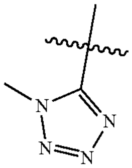 [SMILES: *c1nnnn1C] |

-continued
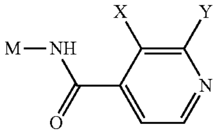
I
| NO. | X | Y | M |
|---|---|---|---|
| 1-2035 | OMe | 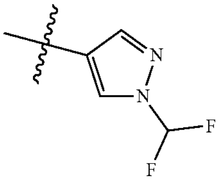 [SMILES: *c1cnn(C(F)F)c1] | 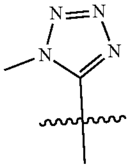 [SMILES: *c1nnnn1C] |
| 1-2036 | 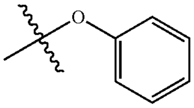 [SMILES: *Oc1ccccc1] | 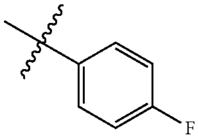 [SMILES: *c1ccc(F)cc1] | 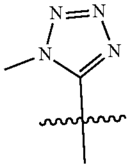 [SMILES: *c1nnnn1C] |
| 1-2037 | 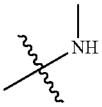 [SMILES: *NC] | 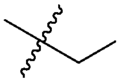 [SMILES: *CC] | 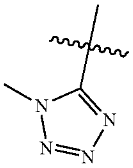 [SMILES: *c1nnnn1C] |
| 1-2038 | 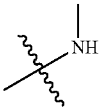 | 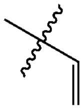 [SMILES: *C=C] | 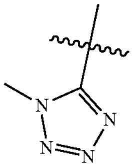 [SMILES: *c1nnnn1C] |
| 1-2039 | 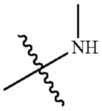 [SMILES: *NC] | 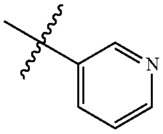 [SMILES: *c1cccnc1] | 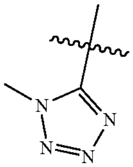 [SMILES: *c1nnnn1C] |
| 1-2040 | 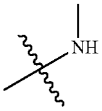 | 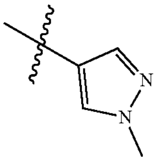 [SMILES: *c1cnn(C)c1] | 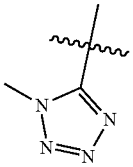 [SMILES: *c1nnnn1C] |
| 1-2041 | 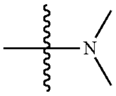 [SMILES: *N(C)C] | $CH_3$ | 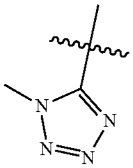 [SMILES: *c1nnnn1C] |

-continued
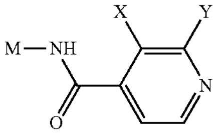
I
| NO. | X | Y | M |
|---|---|---|---|
| 1-2042 | 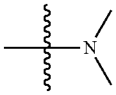 [SMILES: *N(C)C] | $CH_2CH_3$ | 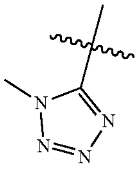 [SMILES: *c1nnnn1C] |
| 1-2043 | 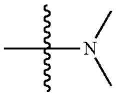 [SMILES: *N(C)C] | 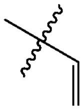 | 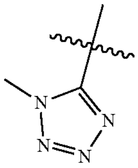 [SMILES: *c1nnnn1C] |
| 1-2044 | 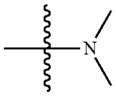 [SMILES: *N(C)C] | 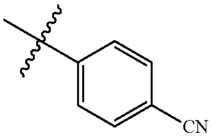 | 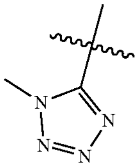 [SMILES: *c1nnnn1C] |
| 1-2045 | 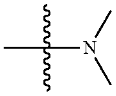 [SMILES: *N(C)C] | 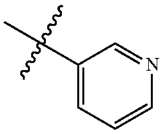 [SMILES: *c1cccnc1] | 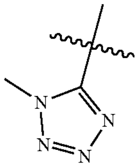 [SMILES: *c1nnnn1C] |
| 1-2046 | 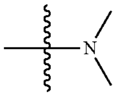 [SMILES: *N(C)C] | 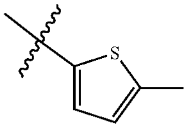 [SMILES: *c1ccc(C)s1] | 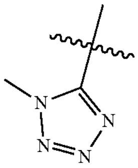 [SMILES: *c1nnnn1C] |
| 1-2047 | 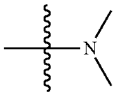 [SMILES: *N(C)C] | 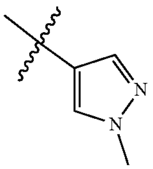 [SMILES: *c1cnn(C)c1] | 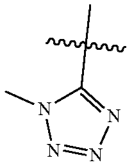 [SMILES: *c1nnnn1C] |
| 1-2048 | 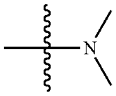 [SMILES: *N(C)C] | 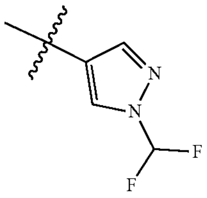 [SMILES: *c1cnn(C(F)F)c1] | 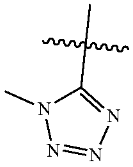 [SMILES: *c1nnnn1C] |

-continued
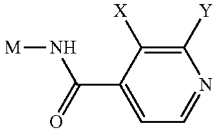
I
| NO. | X | Y | M |
| --- | --- | --- | --- |
| 1-2049 | 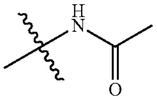 [SMILES: *NC(C)=O] | 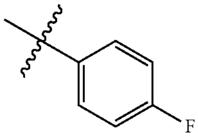 [SMILES: *c1ccc(F)cc1] | 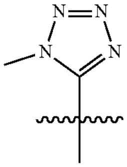 |
| 1-2050 | 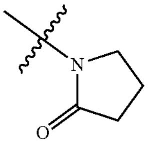 [SMILES: *N1CCCC1=O] | 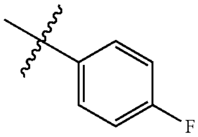 [SMILES: *c1ccc(F)cc1] | 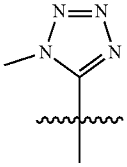 |
| 1-2051 | SMe | 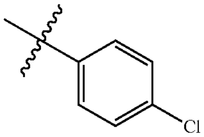 [SMILES: *c1ccc(Cl)cc1] | 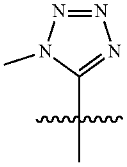 |
| 1-2052 | SMe | 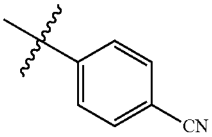 [SMILES: *c1ccc(C#N)cc1] | 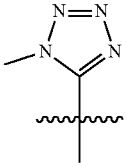 |
| 1-2053 | SMe | 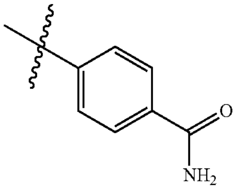 [SMILES: *c1ccc(C(N)=O)cc1] | 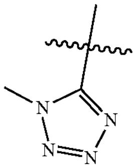 [SMILES: *c1nnnn1C] |
| 1-2054 | SMe | 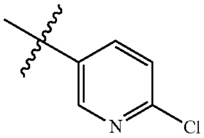 [SMILES: *c1ccc(Cl)nc1] | 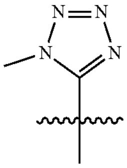 [SMILES: *c1nnnn1C] |
| 1-2055 | SMe | 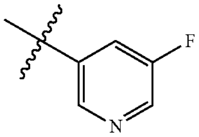 [SMILES: *c1cncc(F)c1] | 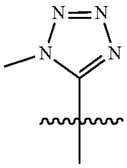 [SMILES: *c1nnnn1C] |

-continued
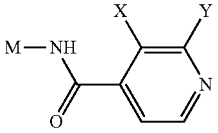
I
| NO. | X | Y | M |
|---|---|---|---|
| 1-2056 | SMe | 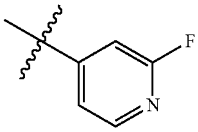 [SMILES: *c1ccnc(F)c1] | 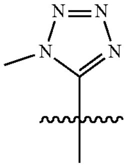 [SMILES: *c1nnnn1C] |
| 1-2057 | SMe | 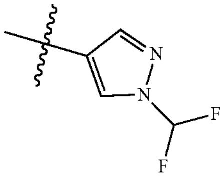 [SMILES: *c1cnn(C(F)F)c1] | 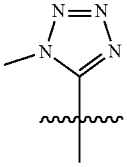 [SMILES: *c1nnnn1C] |
| 1-2058 | 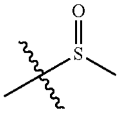 [SMILES: *S(C)=O] | $CH_3$ | 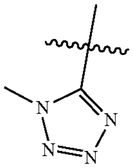 [SMILES: *c1nnnn1C] |
| 1-2059 | 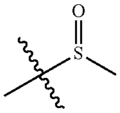 [SMILES: *S(C)=O] | 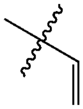 [SMILES: *C=C] | 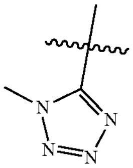 [SMILES: *c1nnnn1C] |
| 1-2060 | 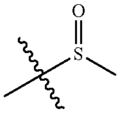 [SMILES: *S(C)=O] | 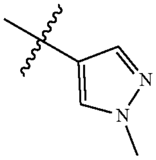 [SMILES: *c1cnn(C)c1] | 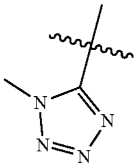 [SMILES: *c1nnnn1C] |
| 1-2061 | Cl | OMe | 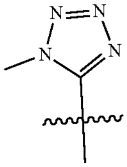 [SMILES: *c1nnnn1C] |
| 1-2062 | Cl | 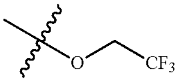 [SMILES: *OCC(F)(F)F] | 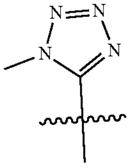 [SMILES: *c1nnnn1C] |

-continued
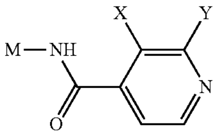
I
| NO. | X | Y | M |
|---|---|---|---|
| 1-2063 | Cl | 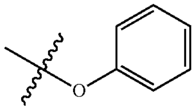 [SMILES: *Oc1ccccc1] | 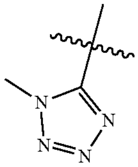 [SMILES: *c1nnnn1C] |
| 1-2064 | Cl | 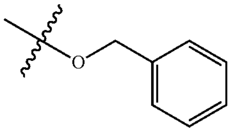 [SMILES: *OCc1ccccc1] | 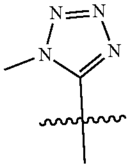 [SMILES: *c1nnnn1C] |
| 1-2065 | Cl | SMe | 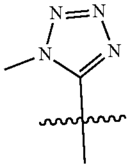 [SMILES: *c1nnnn1C] |
| 1-2066 | Cl | 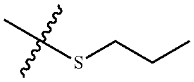 [SMILES: *SCCC] | 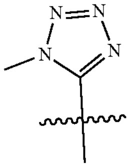 [SMILES: *c1nnnn1C] |
| 1-2067 | Cl | 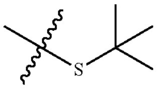 [SMILES: *SC(C)(C)C] | 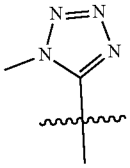 [SMILES: *c1nnnn1C] |
| 1-2068 | Cl | 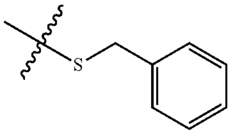 [SMILES: *SCc1ccccc1] | 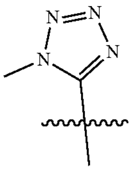 [SMILES: *c1nnnn1C] |
| 1-2069 | Cl | 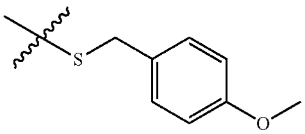 [SMILES: *SCc1ccc(OC)cc1] | 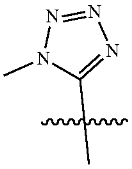 [SMILES: *c1nnnn1C] |

-continued
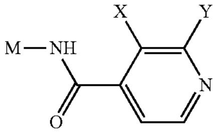
I
| NO. | X | Y | M |
|---|---|---|---|
| 1-2070 | Cl | 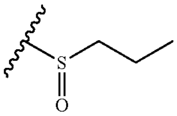 [SMILES: *S(=O)CCC] | 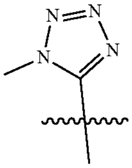 [SMILES: *c1nnnn1C] |
| 1-2071 | Cl | 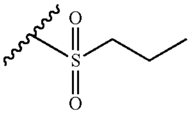 [SMILES: *S(=O)(=O)CCC] | 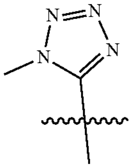 [SMILES: *c1nnnn1C] |
| 1-2072 | Cl | $NH_2$ | 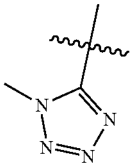 [SMILES: *c1nnnn1C] |
| 1-2073 | Cl | 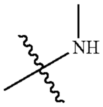 | 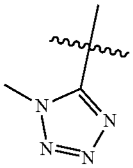 [SMILES: *c1nnnn1C] |
| 1-2074 | Cl | 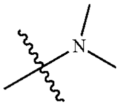 [SMILES: *N(C)C] | 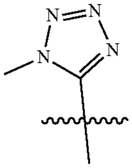 [SMILES: *c1nnnn1C] |
| 1-2075 | Cl | 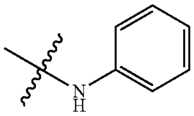 [SMILES: *Nc1ccccc1] | 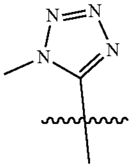 [SMILES: *c1nnnn1C] |
| 1-2076 | Cl | 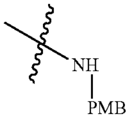 | 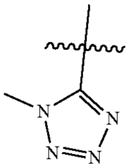 [SMILES: *c1nnnn1C] |

-continued
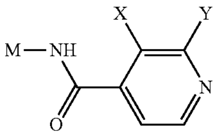
I
| NO. | X | Y | M |
|---|---|---|---|
| 1-2077 | F | OMe | 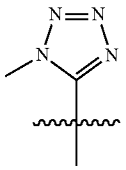 [SMILES: *c1nnnn1C] |
| 1-2078 | F | 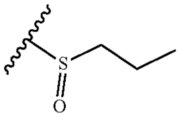 [SMILES: *S(=O)CCC] | 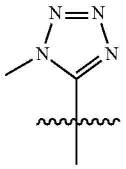 [SMILES: *c1nnnn1C] |
| 1-2079 | OMe | OMe | 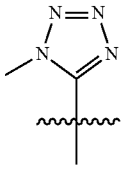 [SMILES: *c1nnnn1C] |
| 1-2080 | OMe | 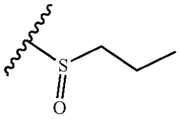 [SMILES: *S(=O)CCC] | 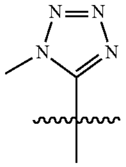 [SMILES: *c1nnnn1C] |
| 1-2081 | OMe | $NH_2$ | 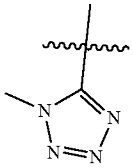 [SMILES: *c1nnnn1C] |
| 1-2082 | SMe | OMe | 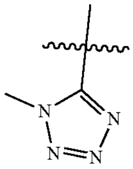 [SMILES: *c1nnnn1C] |
| 1-2083 | SMe | SMe | 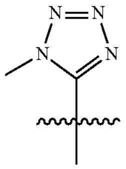 [SMILES: *c1nnnn1C] |

-continued
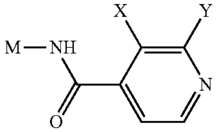
I
| NO. | X | Y | M |
| --- | --- | --- | --- |
| 1-2084 | SMe | 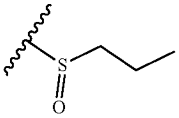 [SMILES: *S(=O)CCC] | 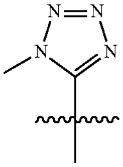 [SMILES: *c1nnnn1C] |
| 1-2085 | 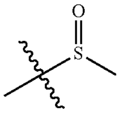 [SMILES: *S(C)=O] | OMe | 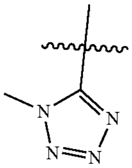 [SMILES: *c1nnnn1C] |
| 1-2086 | 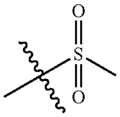 [SMILES: *S(C)(=O)=O] | OMe | 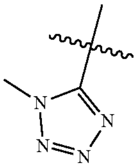 [SMILES: *c1nnnn1C] |
| 1-2087 | $NH_2$ | 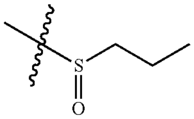 [SMILES: *S(=O)CCC] | 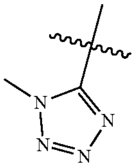 [SMILES: *c1nnnn1C] |
| 1-2088 | 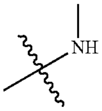 [SMILES: *NC] | 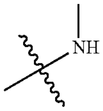 | 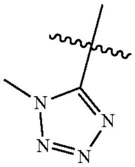 [SMILES: *c1nnnn1C] |
| 1-2089 | 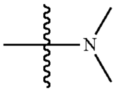 [SMILES: *N(C)C] | OMe | 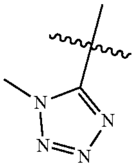 [SMILES: *c1nnnn1C] |
| 1-2090 | 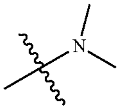 [SMILES: *N(C)C] | 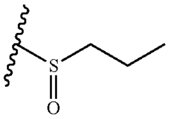 [SMILES: *S(=O)CCC] | 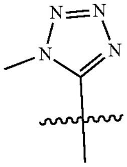 [SMILES: *c1nnnn1C] |

-continued
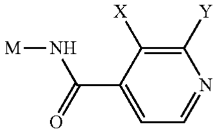
I
| NO. | X | Y | M |
|---|---|---|---|
| 1-2091 | 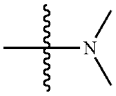 | 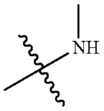 | 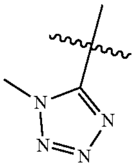 [SMILES: *c1nnnn1C] |
| 1-2092 | 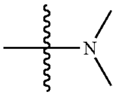 [SMILES: *N(C)C] | 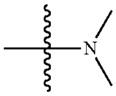 | 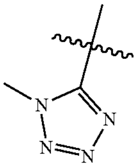 [SMILES: *c1nnnn1C] |
| 1-2093 | 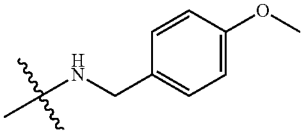 [SMILES: *NCc1ccc(OC)cc1] | 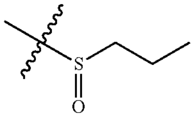 [SMILES: *S(=O)CCC] | 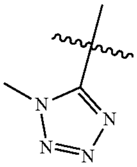 [SMILES: *c1nnnn1C] |
| 1-2094 | 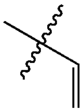 [SMILES: *C=C] | OMe | 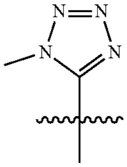 [SMILES: *c1nnnn1C] |
| 1-2095 | 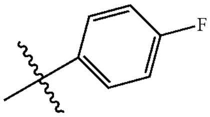 [SMILES: *c1ccc(F)cc1] | OMe | 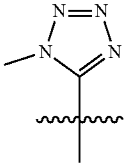 [SMILES: *c1nnnn1C] |
| 1-2096 | 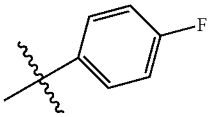 [SMILES: *c1ccc(F)cc1] | 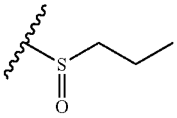 | 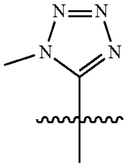 [SMILES: *c1nnnn1C] |
| 1-2097 | 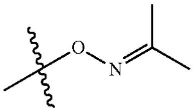 [SMILES: *ON=C(C)C] | 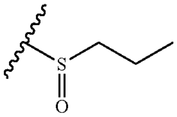 [SMILES: *S(=O)CCC] | 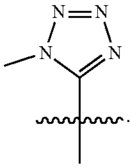 [SMILES: *c1nnnn1C] |

7. A herbicidal composition, comprising (i) the 4-pyridinyl formamide compound or derivative thereof of claim 1; optionally further comprising (ii) at least one additional herbicide and/or safener, and/or (iii) at least one agrochemically acceptable formulation auxiliary.

8. A method for controlling a weed, comprising applying a herbicidally effective amount of at least one 4-pyridinyl formamide compound or derivative thereof of claim 1 on a plant or in a weed area.

9. A method for preventing and/or controlling a weed in a useful crop, comprising applying at least one 4-pyridinyl formamide compound or derivative thereof of claim 1 on the useful crop or in a weed area.

10. The method of claim 9, wherein the useful crop is a transgenic crop, or a crop treated by gene editing technique.

11. A method for controlling a weed, comprising applying a herbicidally effective amount of at least one herbicidal composition of claim 7 on a plant or in a weed area.

12. A method for preventing and/or controlling a weed in a useful crop, comprising applying at least one herbicidal composition of claim 7 on the useful crop or in a weed area.

13. The method of claim 12, wherein the useful crop is a transgenic crop, or a crop treated by gene editing technique.

* * * * *